US012703873B2

(12) United States Patent
Graybuck et al.

(10) Patent No.: US 12,703,873 B2
(45) Date of Patent: Aug. 11, 2026

(54) ARTIFICIAL EXPRESSION CONSTRUCTS FOR SELECTIVELY MODULATING GENE EXPRESSION IN EXCITATORY CORTICAL NEURONS

(71) Applicant: Allen Institute, Seattle, WA (US)

(72) Inventors: Lucas T. Graybuck, Seattle, WA (US); Bosiljka Tasic, Seattle, WA (US); Tanya Daigle, Lake Forest Park, WA (US); Jonathan Ting, Lake Forest Park, WA (US); Hongkui Zeng, Seattle, WA (US); Brian Edward Kalmbach, Poulsbo, WA (US); John K. Mich, Seattle, WA (US); Erik Hess, Issaquah, WA (US); Edward Sebastian Lein, Mercer Island, WA (US); Boaz P. Levi, Seattle, WA (US)

(73) Assignee: Allen Institute, Seattle, WA (US)

( * ) Notice: Subject to any disclaimer, the term of this patent is extended or adjusted under 35 U.S.C. 154(b) by 1123 days.

(21) Appl. No.: 17/291,584

(22) PCT Filed: Nov. 5, 2019

(86) PCT No.: PCT/US2019/059927
§ 371 (c)(1),
(2) Date: May 5, 2021

(87) PCT Pub. No.: WO2020/097121
PCT Pub. Date: May 14, 2020

(65) Prior Publication Data

US 2021/0395780 A1 Dec. 23, 2021

Related U.S. Application Data

(60) Provisional application No. 62/872,021, filed on Jul. 9, 2019, provisional application No. 62/806,684, filed on Feb. 15, 2019, provisional application No. 62/806,600, filed on Feb. 15, 2019, provisional application No. 62/755,988, filed on Nov. 5, 2018.

(51) Int. Cl.
*C12N 15/86* (2006.01)
*A01K 67/0275* (2024.01)

(52) U.S. Cl.
CPC .......... *C12N 15/86* (2013.01); *A01K 67/0275* (2013.01); *A01K 2217/05* (2013.01); *A01K 2227/105* (2013.01); *A01K 2267/0393* (2013.01); *C12N 2750/14143* (2013.01); *C12N 2830/008* (2013.01)

(58) Field of Classification Search
CPC .......... C12N 15/86; C12N 2750/14143; C12N 2830/008; A01K 67/0275; A01K 2217/05
See application file for complete search history.

(56) References Cited

U.S. PATENT DOCUMENTS

| | | | |
|---|---|---|---|
| 5,552,157 A | 9/1996 | Yagi et al. | |
| 5,565,213 A | 10/1996 | Nakamori et al. | |
| 5,567,434 A | 10/1996 | Szoka, Jr. | |
| 5,738,868 A | 4/1998 | Shinkarenko | |
| 5,795,587 A | 8/1998 | Gao et al. | |
| 9,579,399 B2 | 2/2017 | Roska et al. | |
| 2007/0037165 A1 | 2/2007 | Venter et al. | |
| 2009/0186002 A1 | 7/2009 | Flotte et al. | |
| 2010/0166720 A1* | 7/2010 | Vanderhaeghen ... | C12N 5/0623 435/325 |
| 2012/0308530 A1 | 12/2012 | Hu et al. | |
| 2012/0329714 A1 | 12/2012 | Shingo et al. | |
| 2015/0044187 A1 | 2/2015 | Visel et al. | |
| 2015/0354009 A1* | 12/2015 | Sadanandam .... | G01N 33/57419 435/7.1 |
| 2016/0281107 A1 | 9/2016 | Marengo et al. | |
| 2017/0044550 A1 | 2/2017 | Lee et al. | |
| 2017/0239373 A1 | 8/2017 | Chen et al. | |
| 2017/0360961 A1 | 12/2017 | Hetz Flores et al. | |
| 2018/0078658 A1 | 3/2018 | Fishell et al. | |
| 2018/0155716 A1 | 6/2018 | Zhang et al. | |
| 2019/0024118 A1* | 1/2019 | Tagliatela .......... | C12N 15/8645 |
| 2022/0249703 A1 | 8/2022 | Ting et al. | |

FOREIGN PATENT DOCUMENTS

| | | |
|---|---|---|
| WO | WO2015191780 A2 | 12/2015 |
| WO | WO2017100671 A1 | 6/2017 |
| WO | WO2020097121 A1 | 5/2020 |

OTHER PUBLICATIONS

Kim, Jin Hee, et al. "High cleavage efficiency of a 2A peptide derived from porcine teschovirus-1 in human cell lines, zebrafish and mice." PloS one 6.4 (2011): e18556. (Year: 2011).*
Chan, Ken Y., et al. "Engineered AAVs for efficient noninvasive gene delivery to the central and peripheral nervous systems." Nature neuroscience 20.8 (2017): 1172-1179. (Year: 2017).*
https://www.addgene.org/browse/sequence/190876/; last accessed Jan. 3, 2025 (Year: 2025).*
Hariprakash, Judith Mary, and Francesco Ferrari. "Computational Biology Solutions to Identify Enhancers-target Gene Pairs." Computational and structural biotechnology journal vol. 17 821-831. Jun. 14, 2019, doi:10.1016/j.csbj.2019.06.012 (Year: 2019).*

(Continued)

*Primary Examiner* — Robert M Kelly
*Assistant Examiner* — Allison Marie Johnson
(74) *Attorney, Agent, or Firm* — C. Rachal Winger; Chrystal Quisenberry; Lee & Hayes PC

(57) ABSTRACT

Artificial expression constructs for selectively modulating gene expression in selected central nervous system cell types are described. The artificial expression constructs can be used to selectively express synthetic genes or modify gene expression in excitatory cortical neurons, such as primarily within cortical layers 2/3, 4, 5, and 6 and including those with extratelencephalic (ET) projections, intratelencephalic (IT) projections, and pyramidal tract (PT) projections, among others.

19 Claims, 210 Drawing Sheets
(97 of 210 Drawing Sheet(s) Filed in Color)

Specification includes a Sequence Listing.

(56) References Cited

OTHER PUBLICATIONS

Mo, et al., "Epigenomic Signatures of Neuronal Diversity in the Mammalian Brain", Neuron, vol. 86, No. 6, 2015, pp. 1369-1384.
Anonymous, "CAS2295008194_1", retreived from internet on Jul. 11, 2022, <<http://ibis.internal.epo.org/exam/dbfetch.isp?id=CAS2:295008194_1>>, Oct. 12, 2000, 1 page.
Dimidschstein, et al., "A viral strategy for targeting and manipulating interneurons across vertebrate species", Nature Neuroscience, vol. 19, No. 12, 2016, pp. 1743-1749.
Partial European Search Report Dated Jul. 21, 2022 for European Patent Application No. 19881101.0, 15 pages.
Graybuck, et al., "Prospective, brain-wide labeling of neuronal subclasses with enhancer-driven AAVs", bioRxiv, 2019, 41 pages.
"1M0256H11R Mouse 10kb plasmid UUGC1M library Mus musculus genomic clone UUGB1M0256H11 R, genomic survey sequence", GenBank Accession No. AZ454624.1, retrieved on Feb. 6, 2020 at <<https://www.ncbi.nlm.nih.gov/nuccore/AZ454624>>, 12 pages.
"Cloning vector pAAV-CW3B-EGFP, complete sequence", GenBank Accession No. KJ411912.1, retrieved on Feb. 6, 2020 at <<https://www.ncbi.nlm.nih.gov/nuccore/KJ411912>>, 12 pages.
Invitation to Pay Additional Fees Dated Jan. 13, 2020 for International Application No. PCT/US19/59927, 2 pages.
Invitation to Pay Additional Fees Dated Jun. 4, 2020 for International Application No. PCT/US2020/018416, 3 pages.
"Mus musculus chromosome 15, clone RP23-108H23, complete sequence", GenBank Accession No. AC164597, retrieved on Feb. 6, 2020 at <<https://www.ncbi.nlm.nih.gov/nuccore/AC164597>>, 2 pages.
"Mus musculus domesticus DNA, BAC clone: B6Ng01-146G01, 3' end, genomic survery sequence", GenBank Accession No. DH943539.1, retrieved on Feb. 6, 2020 at <<https://www.ncbi.nlm.nih.gov/nuccore/DH943539>>, 1 page.
Search Report and Written Opinion Dated Mar. 18, 2020 for International Application No. PCT/US19/59927, 12 pages.
Search Report and Written Opinion Dated Jul. 29, 2020 for International Application No. PCT/US2020/018416, 12 pages.
Choi, et al., "Optimization of AAV expression cassettes to improve packaging capacity and transgene expression on neurons", Molecular brain, vol. 7, No. 17, 2014, 10 pages.
Office Action for Japanese Application No. 2021-547404, Dated May 21, 2024, 7 pages.
Office Action for Canadian Application No. 3,118,689, Dated Dec. 3, 2024, 7 pages.
Database EMBL, "CH240_399014.TV CHORI-240 Bos taurus genomic clone CH240_39o14, genomic survey sequence", retrieved from EBI accession No. EM_GSS:BZ950206, 1 page.
Partial European Search Report Dated Dec. 21, 2022 for European Patent Application No. 20756018.6, 15 pages.
Extended European Search Report Dated Dec. 22, 2022 for European Patent Application No. 19881101.0, 17 pages.
Extended European Search Report Dated Apr. 18, 2023 for European Patent Application No. 20756018.6, 16 pages.
Office Action for Japanese Application No. 2021-523074, Dated Apr. 23, 2024, 7 pages.
European Office Action mailed on Oct. 17, 2023 for European Patent Application No. 3,118,689, a foreign counterpart to U.S. Appl. No. 17/291,584, 4 pages.
Japanese Office Action mailed Nov. 7, 2023 for Japanese Application No. 2021-523074, a foreign counterpart to U.S. Appl. No. 17/291,584, 9 pages.
Anney, et al., "Meta-analysis of GWAS of over 16,000 individuals with autism spectrum disorder highlights a novel locus at 10q24.32 and a significant over lap with schizophrenia," Molecular Autism, vol. 8, No. 21, 2017, 17 pages.
Baker, et al., "Specialized Subpopulations of Deep-Layer Pyramidal Neurons in the Neocortex: Bridging Cellular Properties to Functional Consequences," J. Neurosci., vol. 38, No. 24, 2018, pp. 5441-5455.
Buenrostro, et al., "Single-cell chromatin accessibility reveals principles of regulatory variation," Nature, vol. 523, No. 7561, 2015, pp. 486-490.
Bulik-Sullivan, et al., "LD Score regression distinguishes confounding from polygenicity in genome-wide association studies," Nat. Genet., vol. 47, No. 3, 2015, pp. 291-295.
Chen, et al., "ATAC-see reveals the accessible genome by transposase-mediated imaging and sequencing," Nat. Methods., vol. 13, No. 12, pp. 1013-1020.
Cusanovich, et al., "A Single-Cell Atlas of In Vivo Mammalian Chromatin Accessibility," Cell., vol. 174, No. 5, 2018, pp. 1309-1324.
Cusanovich, et al., "Multiplex single cell profiling of chromatin accessibility by combinatorial cellular indexing," Science, 2015, vol. 348, No. 6237, pp. 910-914.
Daigle, et al., "A Suite of Transgenic Driver and Reporter Mouse Lines with Enhanced Brain-Cell-Type Targeting and Functionality," Cell., vol. 174, No. 2, 2018, pp. 465-480.
De Lange, et al., "Genome-wide association study implicates immune activation of multiple integrin genes in inflammatory bowel disease," Nat. Genet., vol. 49, No. 2, 2017, pp. 256-261.
Demontis, et al., "Discovery of the first genome-wide significant risk loci for attention deficit/hyperactivity disorder," Nat. Genet., vol. 51, No. 1, 2019, pp. 63-75.
Dimidschstein, et al., "A viral strategy for targeting and manipulating interneurons across vertebrate species," Nat. Neurosci., vol. 19, No. 12, 2016, pp. 1743-1749.
Dobin, et al., "STAR: ultrafast universal RNA-seq aligner," Bioinformatics, vol. 29, No. 1, 2013, pp. 15-21.
Allen Brain Atlas, Data Portal, "Cell Types: Overview of the Data", Documentation section of the Allen Institute data portal at http://celltypes.brain-map.org/.
Duncan, et al., "Largest GWAS of PTSD (N=20 070) yields genetic overlap with schizophrenia and sex differences in heritability," Mol. Psychiatry., vol. 23, No. 3, 2018, pp. 666-673.
Duncan, et al., "Significant Locus and Metabolic Genetic Correlations Revealed in Genome-Wide Association Study of Anorexia Nervosa," Am. J. Psychiatry, vol. 174, No. 9, 2017, pp. 850-858.
ENCODE Project Consortium, "An integrated encyclopedia of DNA elements in the human genome," Nature, vol. 489, No. 7414, 2012, pp. 57-74.
ENCSR000EIK.
ENCSR000EIY.
Finucane, et al., "Partitioning heritability by functional annotation using genome-wide association summary statistics," Nat. Genet., vol. 47, No. 11, 2015, pp. 1228-1235.
Nucleotide [Internet]. Bethesda (MD): National Library of Medicine (US), National Center for Biotechnology Information; [1988]—Accession No. NM_008077, Mus musculus glutamate decarboxylase 1 (Gad1), transcript variant 1, mRNA; [cited Feb. 17, 2022]. Available from: https://www.ncbi.nlm.nih.gov/nuccore/NM_008077.
Gao, et al., "Genome-Wide Association Study of Loneliness Demonstrates a Role for Common Variation," Neuropsychopharmacology, vol. 42, No. 4, 2017, pp. 811-821.
Girdhar, et al., "Cell-specific histone modification maps in the human frontal lobe link schizophrenia risk to the neuronal epigenome," Nat. Neurosci., vol. 21, No. 8, 2018, pp. 1126-1136.
Gong, et al., "Targeting Cre recombinase to specific neuron populations with bacterial artificial chromosome constructs," J. Neurosci., vol. 27, No. 37, 2007, pp. 98177-9823.
Gouwens, et al., "Classification of electrophysiological and morphological neuron types in the mouse visual cortex," Nat. Neurosci., vol. 22, No. 7, 2019, pp. 1182-1195.
Gray, et al., "Layer-specific chromatin accessibility landscapes reveal regulatory networks in adult mouse visual cortex," Elife, vol. 6, 2017, 30 pages.
Graybuck, et al., "Prospective, brain-wide labeling of neuronal subclasses with enhancer-driven AAVs," BioRxiv, vol. 525014, 2019, 71 pages.
Harris, et al., "The organization of intracortical connections by layer and cell class in the mouse brain," BioRxiv, 2018, 40 pages.

(56) References Cited

OTHER PUBLICATIONS

Heinz, et al., "Simple combinations of lineage-determining transcription factors prime cis-regulatory elements required for macrophage and B cell identities," Mol. Cell, vol. 38, No. 4, 2010, pp. 576-589.

Hnasko, et al., "Cre recombinase-mediated restoration of nigrostriatal dopamine in dopamine-deficient mice reverses hypophagia and bradykinesia," PNAS, vol. 103, No. 23, pp. 8858-8863.

Hodge, et al., "Conserved cell types with divergent features in human versus mouse cortex," Nature, vol. 573, 2019, pp. 61-68.

Huang, et al., "Statistical Significance of Clustering using Soft Thresholding," J. Comput. Graph. Stat., vol. 2015, No. 4, 2015, pp. 975-993.

International Obsessive Compulsive Disorder Foundation Genetics Collaborative (IOCDF-GC) and OCD Collaborative Genetics Association Studies (OCGAS), Mol. Psychiatry. 23, 118✐ 1188, 2018.

Tan G (2017). JASPAR2018: Data package for JASPAR 2018. R package version 1.1.1, http://jaspar.genereg.net/.

Karolchik, et al., "The UCSC Table Browser data retrieval tool," Nucleic Acids Res., vol. 31, 2004, 4 pages.

King, et al., "Evaluation of Differences in Temporal Synchrony Between Brain Regions in Individuals With Autism and Typical Development," JAMA Netw Open, vol. 1, No. 7, 2018, 20 pages.

Korbelin, et al., "A brain microvasculature endothelial cell-specific viral vector with the potential to treat neurovascular and neurological diseases," EMBO. Mol. Med., vol. 8, No. 6, 2016, pp. 608-625.

Kremers, et al., "Cyan and yellow super fluorescent proteins with improved brightness, protein folding, and FRET Förster radius," Biochemistry, vol. 45, No. 21, 2006, pp. 6570-6580.

Lambert, et al., "Meta-analysis of 74,046 individuals identifies 11 new susceptibility loci for Alzheimer's disease," Nat. Genet., vol. 45, No. 12, 2013, pp. 1452-1458.

Nucleotide [Internet]. Bethesda (MD): National Library of Medicine (US), National Center for Biotechnology Information; [1988]—Accession No. NM_029530.2, Mus musculus lysosomal-associated membrane protein family, member 5 (Lamp5), mRNA; [cited Feb. 17, 2022]. Available from: https://www.ncbi.nlm.nih.gov/nuccore/NM_029530.2?report=GenBank.

Lee, et al., "Gene discovery and polygenic prediction from a genome-wide association study of educational attainment in 1.1 million individuals," Nat. Genet., vol. 50, No. 8, 2018, pp. 1112-1121.

Levine, et al., "Data-driven phenotypic dissection of AML reveals progenitor-like cells that correlate with prognosis," Cell, vol. 162, No. 1, 2016, pp. 184-197.

Lister, et al., "Global epigenomic reconfiguration during mammalian brain development," Science, vol. 341, No. 6146, 2013, 21 pages.

Liu, et al., "Association analyses identify 38 susceptibility loci for inflammatory bowel disease and highlight shared genetic risk across populations," Nat Genet., vol. 47, No. 9, 2015, pp. 979-986.

Luo, et al., "Single-cell methylomes identify neuronal subtypes and regulatory elements in mammalian cortex," Science, vol. 357, No. 6351, 2017, pp. 600-604.

Madisen, et al., "A robust and high-throughput Cre reporting and characterization system for the whole mouse brain," Nat. Neurosci., vol. 13, No. 1, 2010, pp. 133-140.

Madisen, et al., "Transgenic mice for intersectional targeting of neural sensors and effectors with high specificity and performance," Neuron, vol. 85, No. 5, 2015, pp. 942-958.

Major Depressive Disorder Working Group of the Psychiatric GWAS Consortium et al., "A mega-analysis of genome-wide association studies for major depressive disorder," Mol. Psychiatry, vol. 18, No. 4, 2013, pp. 497-511.

Marioni, et al., "GWAS on family history of Alzheimer's disease," Transl Psychiatry., vol. 8, No. 1, 2018, pp. 1-7.

Naso, et al., "Adeno-Associated Virus (AAV) as a Vector for Gene Therapy," BioDrugs, vol. 31, No. 4, 2017, pp. 317-334.

Chodl chondrolectin (NCBI, Gene ID: 246048). (Year: 2024).

Gabrg1 gamma-aminobutyric acid type A receptor subunit gamma 1 (NCBI, Gene ID: 14405). (Year: 2024).

Mus musculus BAC clone RP24-349O21 from 16 ( NCBI, Accession: AC114925, Jan. 28, 2005) (Year: 2005).

Mus musculus chromosome 5, clone RP23-14J20 (NCBI, Accession AC092716, Nov. 17, 2004) (Year: 2004).

* cited by examiner

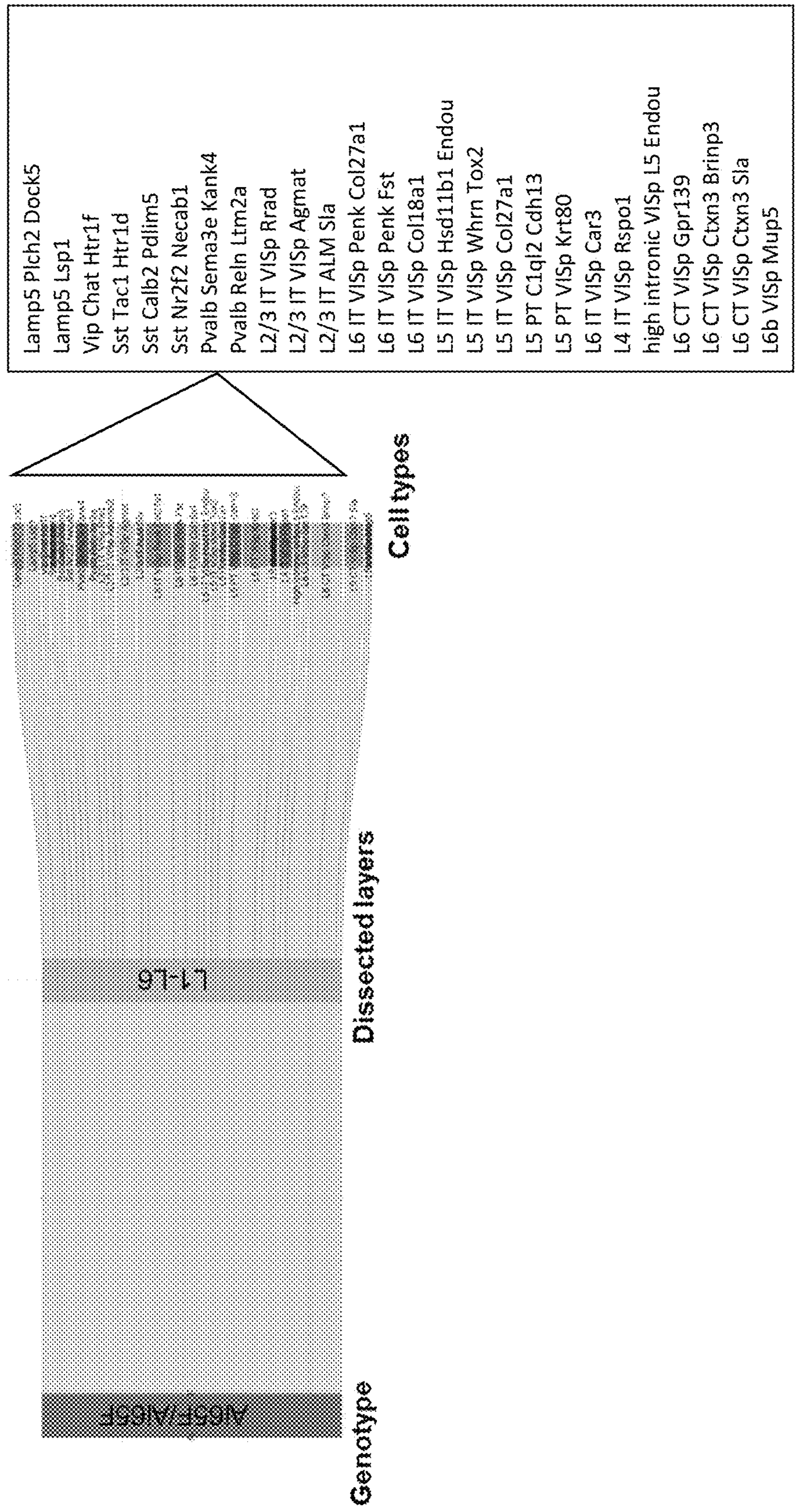

FIG. 13B
Genotype
Ai65F/Ai65F
Dissected layers
L1-L6
Cell types
Lamp5 Plch2 Dock5
Lamp5 Lsp1
Vip Chat Htr1f
Sst Tac1 Htr1d
Sst Calb2 Pdlim5
Sst Nr2f2 Necab1
Pvalb Sema3e Kank4
Pvalb Reln Ltm2a
L2/3 IT VISp Rrad
L2/3 IT VISp Agmat
L2/3 IT ALM Sla
L6 IT VISp Penk Col27a1
L6 IT VISp Penk Fst
L6 IT VISp Col18a1
L5 IT VISp Hsd11b1 Endou
L5 IT VISp Whrn Tox2
L5 IT VISp Col27a1
L5 PT C1ql2 Cdh13
L5 PT VISp Krt80
L6 IT VISp Car3
L4 IT VISp Rspo1
high intronic VISp L5 Endou
L6 CT VISp Gpr139
L6 CT VISp Ctxn3 Brinp3
L6 CT VISp Ctxn3 Sla
L6b VISp Mup5 n =
4706
4031
17
115
473
62
1
7
Distance to Pia (μm)
0
400
800
1200
All Cells
Unlabeled
Off-target
On-target
Off-target
SYFP2+
Fam84b+
Rorb+
Image Position (ventral−dorsal, μm)
Image Position (lateral-medial, μm)
Pia
Pia + 1200 μm
0
500
1000
1500
2000

| Population | #Events | %Parent | %Total |
| --- | --- | --- | --- |
| All Events | 137,448 | #### | 100.0 |
| P1 | 64,525 | 46.9 | 46.9 |
| Morphology | 15,730 | 11.4 | 11.4 |
| SC-F3C | 14,012 | 92.9 | 10.6 |
| SC-SSC | 14,200 | 97.2 | 10.3 |
| P2 | 65 | 0.5 | 0.0 |

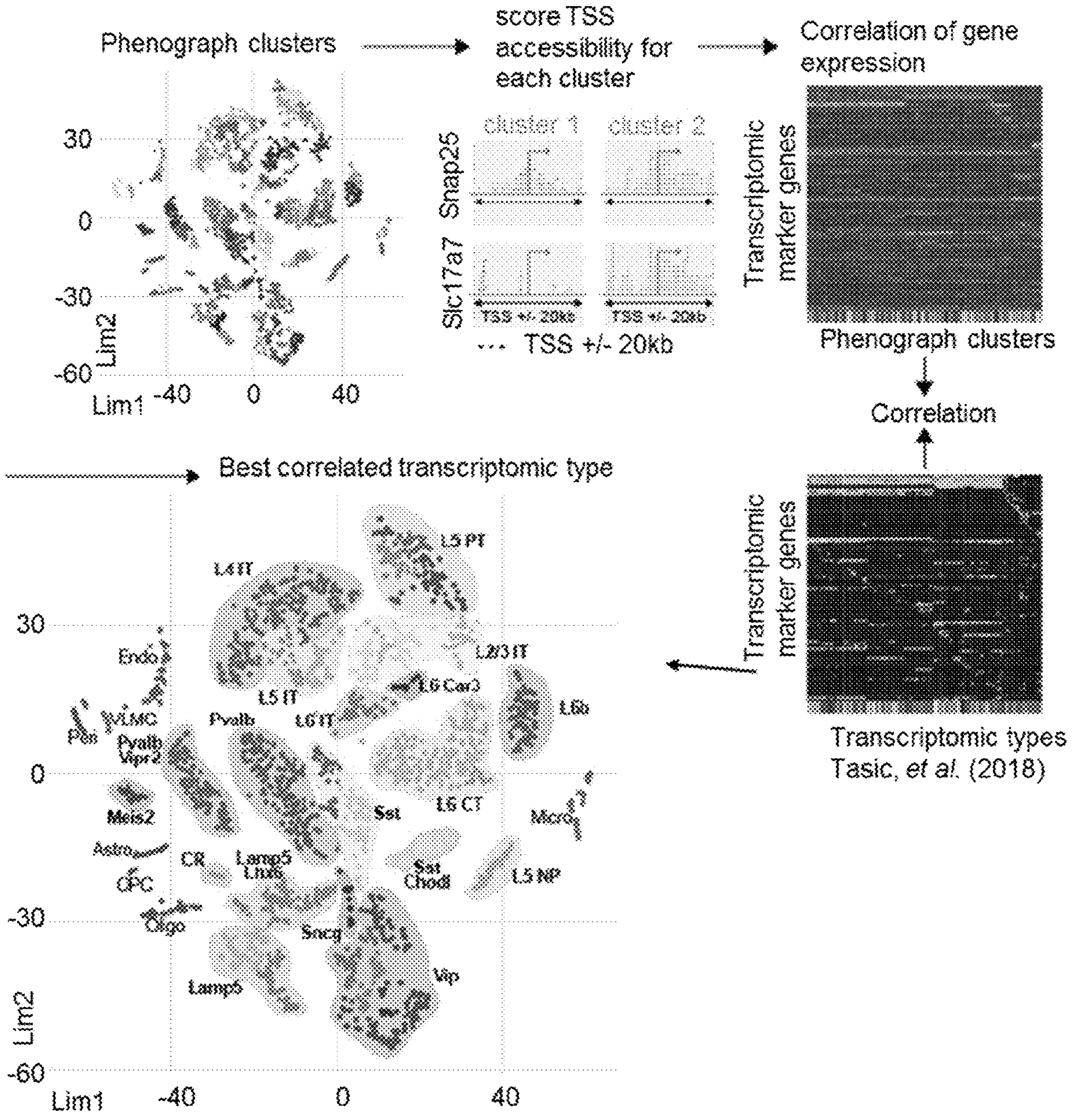

FIG. 45

Phenograph clusters score TSS accessibility for each cluster

Correlation of gene expression cluster 1 cluster 2

Snap25

Slc17a7

TSS +/- 20kb

Transcriptomic marker genes

Phenograph clusters

Correlation

Transcriptomic marker genes

Transcriptomic types Tasic, *et al.* (2018)

Best correlated transcriptomic type

L5 PT
L4 IT
L2/3 IT
Endo
L6 Car3
L5 IT
L6b
VLMC
Pvalb
L6 IT
Peri
Pvalb Vipr2
Meis2
Sst
L6 CT
Micro
Astro
CR
Lamp5 Lhx6
Sst Chodl
L5 NP
OPC
Oligo
Sncg
Vip
Lamp5

Lim1 Lim2

113 kb downstream
Fam84b TSS
mscRE4
Gad2
Slc17a7
Rbp4
Deptor
Fam84b
Lamp5
Sncg
Serpinf1
Vip
Sst
Pvalb
L2/3 IT
L4
L5 IT
L6 IT
L5 PT
NP
L6 CT
L6b
Meis2
CR
Fraction
0.01
0.25
0.50
0.75
1.00
log10(CPM + 1)
3.78
0

FIG. 47

| Enhancer | Population Target | Gene Target | Size (bp) | 5' Cloning Primer<br>MluI Restriction Site (Underlined)<br>**Genomic Target Sequence (Bold)** | 3' Cloning Primer<br>SacI Restriction Site (Underlined)<br>**Genomic Target Sequence (Bold)** |
|---|---|---|---|---|---|
| Mscre1 | L5b | Glra3 | 564 | GGTGGAGTCGTGACCTAGGACGCG **TTTCTAATCATGAATTCTTTTGTGG** (SEQ ID NO: 1) | CTTTTATGCCCAGCCCGAGCTC**AA TGTTCTTGAACTTACCAATCAGG** (SEQ ID NO: 12) |
| Mscre2 | L5b | Depdc7 | 498 | GGTGGAGTCGTGACCTAGGACGCGT **CTGATTGTACAGCAGGCACTC** (SEQ ID NO: 2) | CTTTTATGCCCAGCCCGAGCTC**ATGCC GTGAAGTAATCCAGTG** (SEQ ID NO: 13) |
| Mscre3 | L5b | Bcl6 | 563 | GGTGGAGTCGTGACCTAGGACGCGT **ACCTTTCCAGCCTGGCTTAC** (SEQ ID NO: 3) | CTTTTATGCCCAGCCCGAGCTC**CGG TGGTTGAAATAAACAAGAAC** (SEQ ID NO: 14) |
| Mscre4 | L5b | Fam84b | 558 | GGTGGAGTCGTGACCTAGGACGCGT **ATAAGCCTTGGGGGCAATC** (SEQ ID NO: 4) | CTTTTATGCCCAGCCCGAGCTC**AT TTGTCCTGTGCATAGCATTG** (SEQ ID NO: 15) |
| Mscre10 | L6 IT Car3 | Car3 | 595 | CGTACACGCGT**ATGTGTCTTTTAC TCTGATCCTCC** (SEQ ID NO: 5) | CGTACGAGCTC**TGTTGCTACACTA GACTCAATGG** (SEQ ID NO: 16) |
| Mscre11 | L6 IT Car3 | Car1 | 578 | CGTACACGCGT**CAGTAGTGTTAAT GACAGAGTCAG** (SEQ ID NO: 6) | CGTACGAGCTC**GGCTTGAGTATAG ACAAACCACTC** (SEQ ID NO: 17) |
| Mscre12 | L6 IT Car3 | Nr2f2 | 598 | CGTACACGCGT**CCTTTTCCAA CCGTTCCTTC** (SEQ ID NO: 7) | CGTACGAGCTC**TGCTCAGGAACCAAA GGAG** (SEQ ID NO: 18) |
| Mscre13 | L6 IT | Osr1 | 583 | CGTACACGCGT**GTCCCATAG GCAGTTTGTGG** (SEQ ID NO: 8) | CGTACGAGCTC**AGACCTTACCAC TGCATTCTGA** (SEQ ID NO: 19) |
| Mscre14 | L6 IT | Penk | 596 | CGTACACGCGT**AGCCGCTCTCAC CTTCTATA** (SEQ ID NO: 9) | CGTACGAGCTC**CTGGGATGAACGGA ATTGTGT** (SEQ ID NO: 20) |
| Mscre15 | L5 IT | Deptor | 598 | CGTACACGCGT**GAGCTGGGCAT CATCACATC** (SEQ ID NO: 10) | CGTACGAGCTC**TGCCGTCTGATTT GCATACT** (SEQ ID NO: 21) |
| Mscre16 | L5 IT | Hsd11b1 | 599 | CGTACACGCGT**AGGGTGCAGGAG AAATGTGA** (SEQ ID NO: 11) | CGTACGAGCTC**CTTGCCCATGAACGT TCTGT** (SEQ ID NO: 22) |

Stereotaxic Injection (50nL)
rAAV-mscRE4-EGFP (Fam84b)

Stereotaxic Injection (250nL)
rAAV-mscRE4-EGFP (Fam84b)

Stereotaxic Injection (50nL)
scAAV-mscRE4-SYFP2 (Fam84b)

Stereotaxic Injection (250nL)
scAAV-mscRE4-SYFP2 (Fam84b)

rAAV-FlpO
enh * FlpO WPRE3 pA rAAV-dgCre
enh * dgCre WPRE3 pA rAAV-iCre
enh * iCre WPRE3 pA rAAV-tTA2
enh * tTA2 WPRE3 pA

* Indicates pBGmin

Retro-orbital
rAAV-FlpO + mscRE4; Ai65F

Retro-orbital
rAAV-dgCre + mscRE4; Ai14

Retro-orbital
rAAV-iCre + mscRE4; Ai14

Retro-orbital
rAAV-tTA2 + mscRE4; Ai63

FIG. 57A
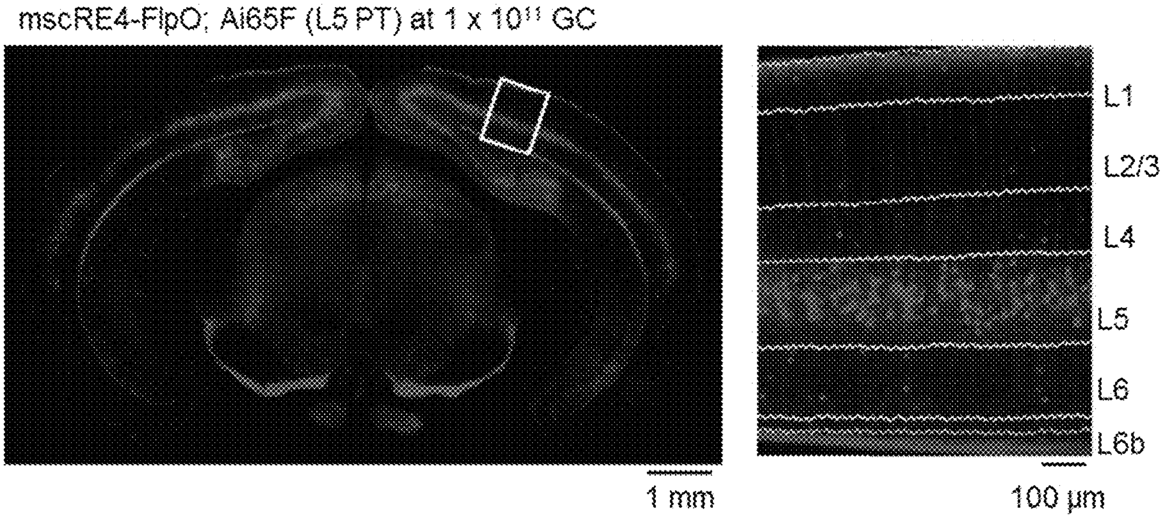
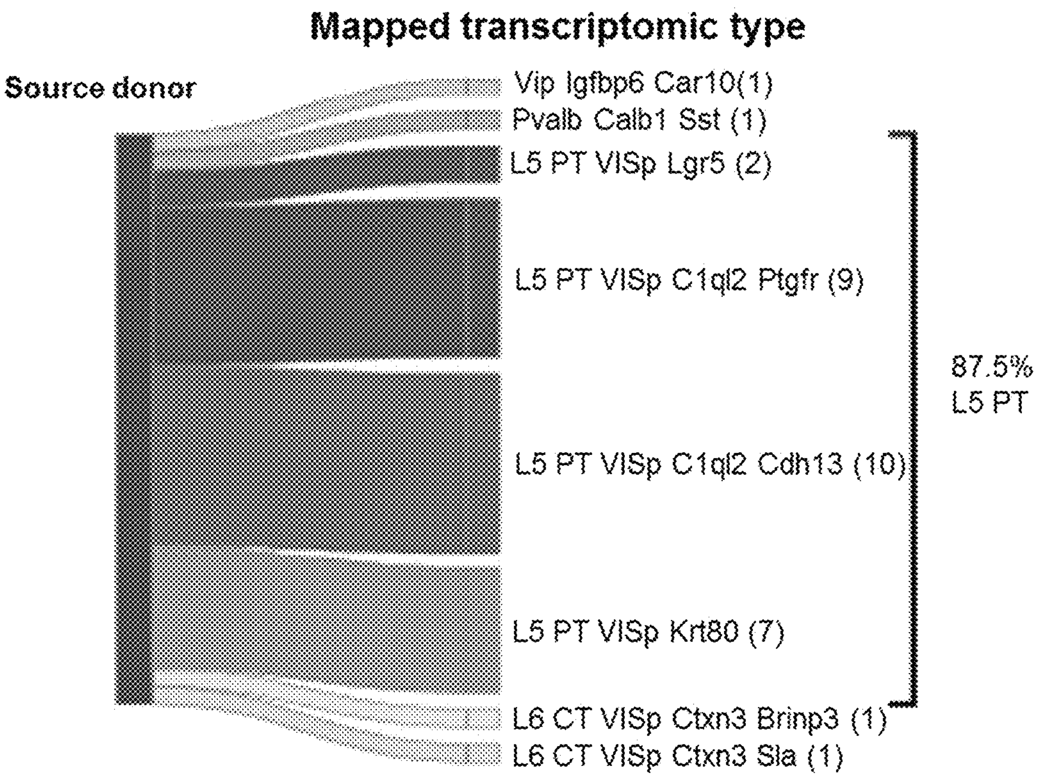

FIG. 57C
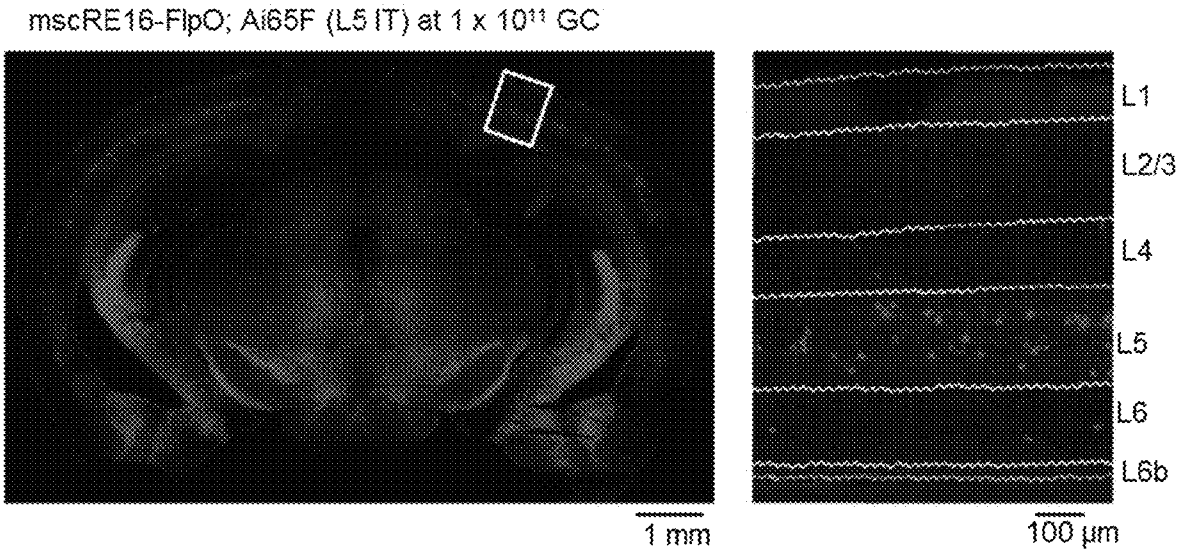
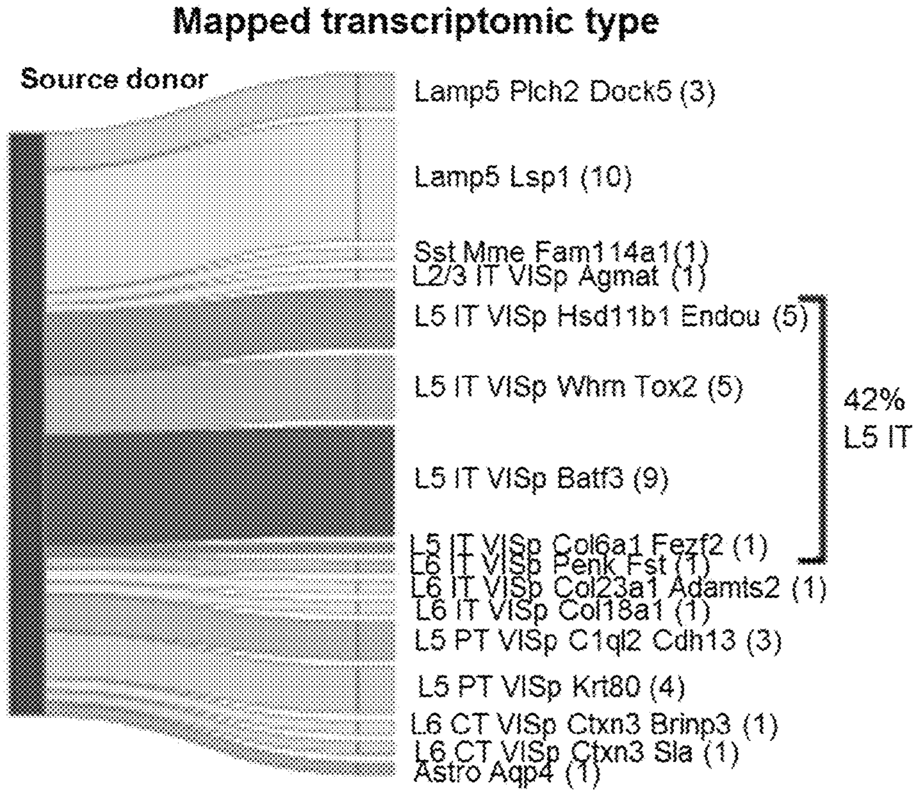

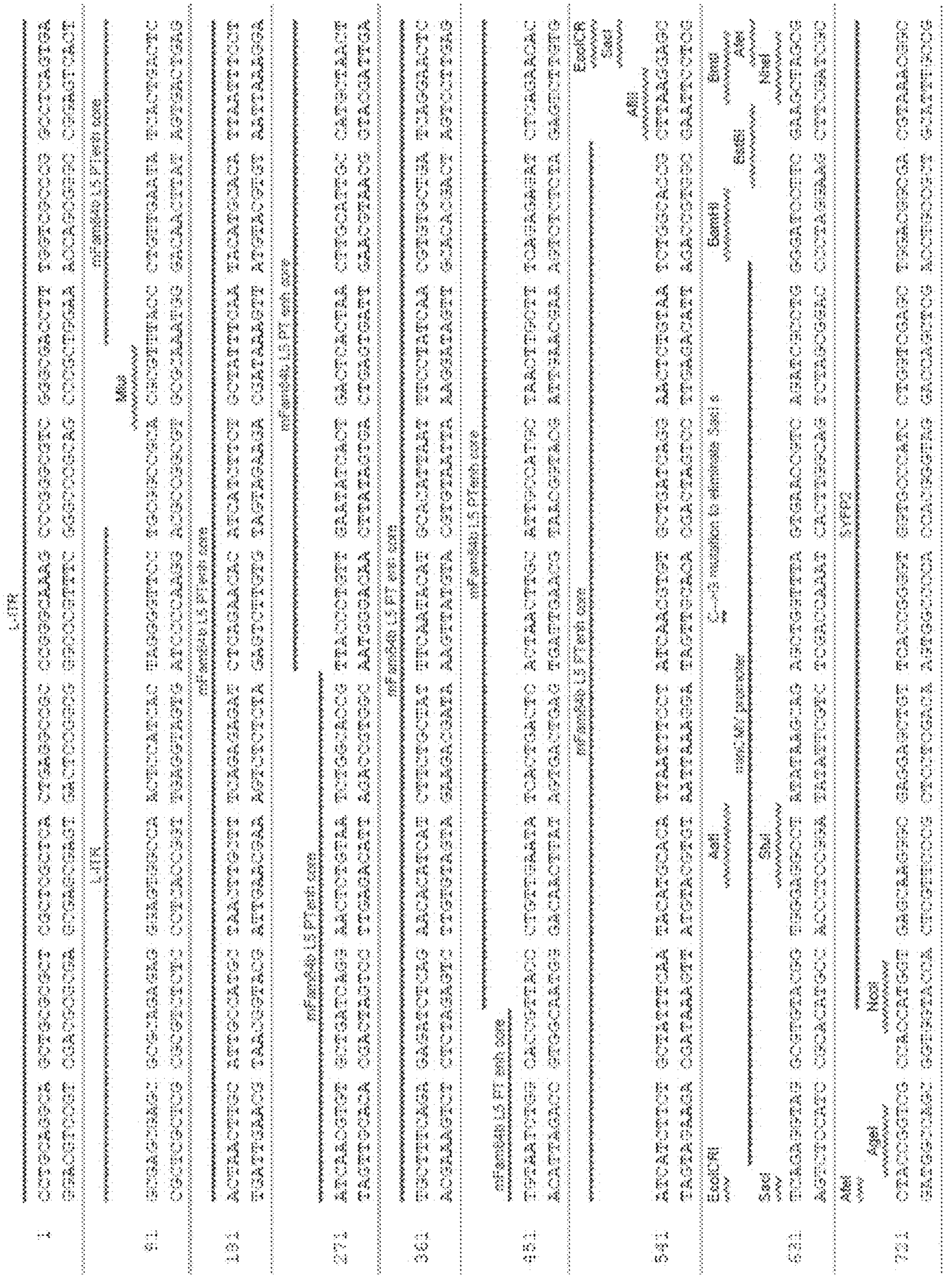

FIG. 62

```
                                    L-ITR
1    CCTGCAGGCA GCTGCGCGCT CGCTCGCTCA CTGAGGCCGC CCGGGCAAAG CCCGGGCGTC GGGCGACCTT TGGTCGCCCG GCCTCAGTGA
     GGACGTCCGT CGACGCGCGA GCGAGCGAGT GACTCCGGCG GGCCCGTTTC GGGCCCGCAG CCCGCTGGAA ACCAGCGGGC CGGAGTCACT

                 L-ITR                                                   mFam84b L5 PTenh core
                                                        MluI
91   GCGAGCGAGC GCGCAGAGAG GGAGTGGCCA ACTCCATCAC TAGGGGTTCC TGCGGCCGCA CGCGTTTACC CTGTTGAATA TCACTGACTC
     CGCTCGCTCG CGCGTCTCTC CCTCACCGGT TGAGGTAGTG ATCCCCAAGG ACGCCGGCGT GCGCAAATGG GACAACTTAT AGTGACTGAG

                                    mFam84b L5 PTenh core
181  ACTAACTTGC ATTGCCATGC TAACTTGCTT TCAGAGAGAT CTCAGAACAC ATCATCTTCT GCTATTTCAA TACATGCACA TTAATTTCCT
     TGATTGAACG TAACGGTACG ATTGAACGAA AGTCTCTCTA GAGTCTTGTG TAGTAGAAGA CGATAAAGTT ATGTACGTGT AATTAAAGGA

                                                          mFam84b L5 PT enh core
            mFam84b L5 PTenh core
271  ATCAACGTGT GCTGATCAGG AACTCTGTAA TCTGGCACCG TTACCCTGTT GAATATCACT GACTCACTAA CTTGCATTGC CATGCTAACT
     TAGTTGCACA CGACTAGTCC TTGAGACATT AGACCGTGGC AATGGGACAA CTTATAGTGA CTGAGTGATT GAACGTAACG GTACGATTGA

                                    mFam84b L5 PT enh core
361  TGCTTTCAGA GAGATCTCAG AACACATCAT CTTCTGCTAT TTCAATACAT GCACATTAAT TTCCTATCAA CGTGTGCTGA TCAGGAACTC
     ACGAAAGTCT CTCTAGAGTC TTGTGTAGTA GAAGACGATA AAGTTATGTA CGTGTAATTA AAGGATAGTT GCACACGACT AGTCCTTGAG

                                          mFam84b L5 PTenh core
     mFam84b L5 PT enh core
451  TGTAATCTGG CACCGTTACC CTGTTGAATA TCACTGACTC ACTAACTTGC ATTGCCATGC TAACTTGCTT TCAGAGAGAT CTCAGAACAC
     ACATTAGACC GTGGCAATGG GACAACTTAT AGTGACTGAG TGATTGAACG TAACGGTACG ATTGAACGAA AGTCTCTCTA GAGTCTTGTG

                                 mFam84b L5 PTenh core                                          EcoICRI
                                                                                                SacI
                                                                                          AflII
541  ATCATCTTCT GCTATTTCAA TACATGCACA TTAATTTCCT ATCAACGTGT GCTGATCAGG AACTCTGTAA TCTGGCACCG CTTAAGGAGC
     TAGTAGAAGA CGATAAAGTT ATGTACGTGT AATTAAAGGA TAGTTGCACA CGACTAGTCC TTGAGACATT AGACCGTGGC GAATTCCTCG

     EcoICRI               AatII                C-->G mutation to eliminate SacI s    BamHI      BmtI
                              minCMV promoter                                             BstBI   AfeI
     SacI                  StuI                                                                  NheI
631  TCAGAGGTAG GCGTGTACGG TGGGAGGCCT ATATAAGCAG AGCTGGTTTA GTGAACCGTC AGATCGCCTG GGGATCCTTC GAAGCTAGCG
     AGTCTCCATC CGCACATGCC ACCCTCCGGA TATATTCGTC TCGACCAAAT CACTTGGCAG TCTAGCGGAC CCCTAGGAAG CTTCGATCGC

     AfeI                                       SYFP2
        AgeI       NcoI
721  CTACCGGTCG CCACCATGGT GAGCAAGGGC GAGGAGCTGT TCACCGGGGT GGTGCCCATC CTGGTCGAGC TGGACGGCGA CGTAAACGGC
     GATGGCCAGC GGTGGTACCA CTCGTTCCCG CTCCTCGACA AGTGGCCCCA CCACGGGTAG GACCAGCTCG ACCTGCCGCT GCATTTGCCG
```

FIG. 62 cont'd

```
                                                      SYFP2
811   CACAAGTTCA GCGTGTCCGG CGAGGGCGAG GGCGATGCCA CCTACGGCAA GCTGACCCTG AAGCTGATCT GCACCACCGG CAAGCTGCCC
      GTGTTCAAGT CGCACAGGCC GCTCCCGCTC CCGCTACGGT GGATGCCGTT CGACTGGGAC TTCGACTAGA CGTGGTGGCC GTTCGACGGG

                                                      SYFP2
901   GTGCCCTGGC CCACCCTCGT GACCACCCTG GGCTACGGCG TGCAGTGCTT CGCCCGCTAC CCCGACCACA TGAAGCAGCA CGACTTCTTC
      CACGGGACCG GGTGGGAGCA CTGGTGGGAC CCGATGCCGC ACGTCACGAA GCGGGCGATG GGGCTGGTGT ACTTCGTCGT GCTGAAGAAG

                                                      SYFP2
991   AAGTCCGCCA TGCCCGAAGG CTACGTCCAG GAGCGCACCA TCTTCTTCAA GGACGACGGC AACTACAAGA CCCGCGCCGA GGTGAAGTTC
      TTCAGGCGGT ACGGGCTTCC GATGCAGGTC CTCGCGTGGT AGAAGAAGTT CCTGCTGCCG TTGATGTTCT GGGCGCGGCT CCACTTCAAG

                                                      SYFP2
1081  GAGGGCGACA CCCTGGTGAA CCGCATCGAG CTGAAGGGCA TCGACTTCAA GGAGGACGGC AACATCCTGG GGCACAAGCT GGAGTACAAC
      CTCCCGCTGT GGGACCACTT GGCGTAGCTC GACTTCCCGT AGCTGAAGTT CCTCCTGCCG TTGTAGGACC CCGTGTTCGA CCTCATGTTG

                                                      SYFP2
1171  TACAACAGCC ACAACGTCTA TATCACCGCC GACAAGCAGA AGAACGGCAT CAAGGCCAAC TTCAAGATCC GCCACAACAT CGAGGACGGC
      ATGTTGTCGG TGTTGCAGAT ATAGTGGCGG CTGTTCGTCT TCTTGCCGTA GTTCC[illegible]TTG AAGTTCTAGG CGGTGTTGTA GCTCCTGCCG

                                                      SYFP2
1261  GGCGTGCAGC TCGCCGACCA CTACCAGCAG AACACCCCCA TCGGCGACGG CCCCGTGCTG CTGCCCGACA ACCACTACCT GAGCTACCAG
      CCGCACGTCG AGCGGCTGGT GATGGTCGTC TTGTGGGGGT AGCCGCTGCC GGGGCACGAC GACGGGCTGT TGGTGATGGA CTCGATGGTC

                                                      SYFP2
              BlpI
1351  TCCAAGCTGA GCAAAGACCC CAACGAGAAG CGCGATCACA TGGTCCTGCT GGAGTTCGTG ACCGCCGCCG GGATCACTCT CGGCATGGAC
      AGGTTCGACT CGTTTCTGGG GTTGCTCTTC GCGCTAGTGT ACCAGGACGA CCTCAAGCAC TGGCGGCGGC CCTAGTGAGA GCCGTACCTG

          SYFP2                 AscI                                                WPRE3
                        SalI                                    EcoRV
          BsrGI         AccI               SacII       EcoRI
1441  GAGCTGTACA AGTAAGTCGA CGGCGCGCCG CGGCCGCGAA TTCGATATCA TAATCAACCT CTGGATTACA AAATTTGTGA AAGATTGACT
      CTCGACATGT TCATTCAGCT GCCGCGCGGC GCCGGCGCTT AAGCTATAGT ATTAGTTGGA GACCTAATGT TTTAAACACT TTCTAACTGA

                                                      WPRE3
1531  GGTATTCTTA ACTATGTTGC TCCTTTTACG CTATGTGGAT ACGCTGCTTT AATGCCTTTG TATCATGCTA TTGCTTCCCG TATGGCTTTC
      CCATAAGAAT TGATACAACG AGGAAAATGC GATACACCTA TGCGACGAAA TTACGGAAAC ATAGTACGAT AACGAAGGGC ATACCGAAAG

                                                      WPRE3
1621  ATTTTCTCCT CCTTGTATAA ATCCTGGTTA GTTCTTGCCA CGGCGGAACT CATCGCCGCC TGCCTTGCCC GCTGCTGGAC AGGGGCTCGG
      TAAAAGAGGA GGAACATATT TAGGACCAAT CAAGAACGGT GCCGCCTTGA GTAGCGGCGG ACGGAACGGG CGACGACCTG TCCCCGAGCC
```

FIG. 62 cont'd

```
             WPRE3                                                   BGH-pA
                                 XhoI
                                 SalI
1711  CTGTTGGGCA CTGACAATTC CGTGGCTCGA GAGATCTTCG ACTGTGCCTT CTAGTTGCCA GCCATCTGTT GTTTGCCCCT CCCCCGTGCC
      GACAACCCGT GACTGTTAAG GCACCGAGCT CTCTAGAAGC TGACACGGAA GATCAACGGT CGGTAGACAA CAAACGGGGA GGGGGCACGG

                                               BGH-pA
1801  TTCCTTGACC CTGGAAGGTG CCACTCCCAC TGTCCTTTCC TAATAAAATG AGGAAATTGC ATCGCATTGT CTGAGTAGGT GTCATTCTAT
      AAGGAACTGG GACCTTCCAC GGTGAGGGTG ACAGGAAAGG ATTATTTTAC TCCTTTAACG TAGCGTAACA GACTCATCCA CAGTAAGATA
                                                                        BGH-R

                            BGH-pA                                                         R-ITR
                                               BbsI         SphI
                                               Bbr7I             PmlI
1891  TCTGGGGGGT GGGGTGGGGC AGGACAGCAA GGGGGAGGAT TGGGAAGACA ATAGCAGGCA TGCACGTGCG GACCGAGCGG CCGCAGGAAC
      AGACCCCCCA CCCCACCCCG TCCTGTCGTT CCCCCTCCTA ACCCTTCTGT TATCGTCCGT ACGTGCACGC CTGGCTCGCC GGCGTCCTTG

                                               R-ITR
1981  CCCTAGTGAT GGAGTTGGCC ACTCCCTCTC TGCGCGCTCG CTCGCTCACT GAGGCCGGGC GACCAAAGGT CGCCCGACGC CCGGGCTTTG
      GGGATCACTA CCTCAACCGG TGAGGGAGAG ACGCGCGAGC GAGCGAGTGA CTCCGGCCCG CTGGTTTCCA GCGGGCTGCG GGCCCGAAAC

                       R-ITR
                                                   KasI
                                                   NarI
                                                   SfoI
                                                   PluTI
2071  CCCGGGCGGC CTCAGTGAGC GAGCGAGCGC GCAGCTGCCT GCAGGGGCGC CTGATGCGGT ATTTTCTCCT TACGCATCTG TGCGGTATTT
      GGGCCCGCCG GAGTCACTCG CTCGCTCGCG CGTCGACGGA CGTCCCCGCG GACTACGCCA TAAAAGAGGA ATGCGTAGAC ACGCCATAAA

                                                                  f1 Origin
2161  CACACCGCAT ACGTCAAAGC AACCATAGTA CGCGCCCTGT AGCGGCGCAT TAAGCGCGGC GGGTGTGGTG GTTACGCGCA GCGTGACCGC
      GTGTGGCGTA TGCAGTTTCG TTGGTATCAT GCGCGGGACA TCGCCGCGTA ATTCGCGCCG CCCACACCAC CAATGCGCGT CGCACTGGCG

                                               f1 Origin
                                                                      NgoMIV
                                                                      NaeI
2251  TACACTTGCC AGCGCCCTAG CGCCCGCTCC TTTCGCTTTC TTCCCTTCCT TTCTCGCCAC GTTCGCCGGC TTTCCCCGTC AAGCTCTAAA
      ATGTGAACGG TCGCGGGATC GCGGGCGAGG AAAGCGAAAG AAGGGAAGGA AAGAGCGGTG CAAGCGGCCG AAAGGGGCAG TTCGAGATTT

                                               f1 Origin
2341  TCGGGGGCTC CCTTTAGGGT TCCGATTTAG TGCTTTACGG CACCTCGACC CCAAAAAACT TGATTTGGGT GATGGTTCAC GTAGTGGGCC
      AGCCCCCGAG GGAAATCCCA AGGCTAAATC ACGAAATGCC GTGGAGCTGG GGTTTTTTGA ACTAAACCCA CTACCAAGTG CATCACCCGG
```

FIG. 62 cont'd

```
                                                            f1 Origin
2431  ATCGCCCTGA TAGACGGTTT TTCGCCCTTT GACGTTGGAG TCCACGTTCT TTAATAGTGG ACTCTTGTTC CAAACTGGAA CAACACTCAA
      TAGCGGGACT ATCTGCCAAA AAGCGGGAAA CTGCAACCTC AGGTGCAAGA AATTATCACC TGAGAACAAG GTTTGACCTT GTTGTGAGTT

                              PsiI
2521  CCCTATCTCG GGCTATTCTT TTGATTTATA AGGGATTTTG CCGATTTCGG CCTATTGGTT AAAAAATGAG CTGATTTAAC AAAAATTTAA
      GGGATAGAGC CCGATAAGAA AACTAAATAT TCCCTAAAAC GGCTAAAGCC GGATAACCAA TTTTTTACTC GACTAAATTG TTTTTAAATT

2611  CGCGAATTTT AACAAAATAT TAACGTTTAC AATTTTATGG TGCACTCTCA GTACAATCTG CTCTGATGCC GCATAGTTAA GCCAGCCCCG
      GCGCTTAAAA TTGTTTTATA ATTGCAAATG TTAAAATACC ACGTGAGAGT CATGTTAGAC GAGACTACGG CGTATCAATT CGGTCGGGGC

2701  ACACCCGCCA ACACCCGCTG ACGCGCCCTG ACGGGCTTGT CTGCTCCCGG CATCCGCTTA CAGACAAGCT GTGACCGTCT CCGGGAGCTG
      TGTGGGCGGT TGTGGGCGAC TGCGCGGGAC TGCCCGAACA GACGAGGGCC GTAGGCGAAT GTCTGTTCGA CACTGGCAGA GGCCCTCGAC

                                                       EcoO109I
2791  CATGTGTCAG AGGTTTTCAC CGTCATCACC GAAACGCGCG AGACGAAAGG GCCTCGTGAT ACGCCTATTT TTATAGGTTA ATGTCATGAT
      GTACACAGTC TCCAAAAGTG GCAGTAGTGG CTTTGCGCGC TCTGCTTTCC CGGAGCACTA TGCGGATAAA AATATCCAAT TACAGTACTA

                   ZraI
                   AatII
2881  AATAATGGTT TCTTAGACGT CAGGTGGCAC TTTTCGGGGA AATGTGCGCG GAACCCCTAT TTGTTTATTT TTCTAAATAC ATTCAAATAT
      TTATTACCAA AGAATCTGCA GTCCACCGTG AAAAGCCCCT TTACACGCGC CTTGGGGATA AACAAATAAA AAGATTTATG TAAGTTTATA

                                                                                 AmpR
2971  GTATCCGCTC ATGAGACAAT AACCCTGATA AATGCTTCAA TAATATTGAA AAAGGAAGAG TATGAGTATT CAACATTTCC GTGTCGCCCT
      CATAGGCGAG TACTCTGTTA TTGGGACTAT TTACGAAGTT ATTATAACTT TTTCCTTCTC ATACTCATAA GTTGTAAAGG CACAGCGGGA
                                                                 EarI

                                                    AmpR
3061  TATTCCCTTT TTTGCGGCAT TTTGCCTTCC TGTTTTTGCT CACCCAGAAA CGCTGGTGAA AGTAAAAGAT GCTGAAGATC AGTTGGGTGC
      ATAAGGGAAA AAACGCCGTA AAACGGAAGG ACAAAAACGA GTGGGTCTTT GCGACCACTT TCATTTTCTA CGACTTCTAG TCAACCCACG

                                                    AmpR
3151  ACGAGTGGGT TACATCGAAC TGGATCTCAA CAGCGGTAAG ATCCTTGAGA GTTTTCGCCC CGAAGAACGT TTTCCAATGA TGAGCACTTT
      TGCTCACCCA ATGTAGCTTG ACCTAGAGTT GTCGCCATTC TAGGAACTCT CAAAAGCGGG GCTTCTTGCA AAAGGTTACT ACTCGTGAAA

                                                    AmpR
3241  TAAAGTTCTG CTATGTGGCG CGGTATTATC CCGTATTGAC GCCGGGCAAG AGCAACTCGG TCGCCGCATA CACTATTCTC AGAATGACTT
      ATTTCAAGAC GATACACCGC GCCATAATAG GGCATAACTG CGGCCCGTTC TCGTTGAGCC AGCGGCGTAT GTGATAAGAG TCTTACTGAA

                                                    AmpR
         ScaI
3331  GGTTGAGTAC TCACCAGTCA CAGAAAAGCA TCTTACGGAT GGCATGACAG TAAGAGAATT ATGCAGTGCT GCCATAACCA TGAGTGATAA
      CCAACTCATG AGTGGTCAGT GTCTTTTCGT AGAATGCCTA CCGTACTGTC ATTCTCTTAA TACGTCACGA CGGTATTGGT ACTCACTATT
```

FIG. 62 cont'd

AmpR
PvuI

```
3421 CACTGCGGCC AACTTACTTC TGACAACGAT CGGAGGACCG AAGGAGCTAA CCGCTTTTTT GCACAACATG GGGGATCATG TAACTCGCCT
     GTGACGCCGG TTGAATGAAG ACTGTTGCTA GCCTCCTGGC TTCCTCGATT GGCGAAAAAA CGTGTTGTAC CCCCTAGTAC ATTGAGCGGA
```

AmpR
FspI

```
3511 TGATCGTTGG GAACCGGAGC TGAATGAAGC CATACCAAAC GACGAGCGTG ACACCACGAT GCCTGTAGCA ATGGCAACAA CGTTGCGCAA
     ACTAGCAACC CTTGGCCTCG ACTTACTTCG GTATGGTTTG CTGCTCGCAC TGTGGTGCTA CGGACATCGT TACCGTTGTT GCAACGCGTT
```

AmpR

```
3601 ACTATTAACT GGCGAACTAC TTACTCTAGC TTCCCGGCAA CAATTAATAG ACTGGATGGA GGCGGATAAA GTTGCAGGAC CACTTCTGCG
     TGATAATTGA CCGCTTGATG AATGAGATCG AAGGGCCGTT GTTAATTATC TGACCTACCT CCGCCTATTT CAACGTCCTG GTGAAGACGC
```

AmpR
BsaI
BmrI

```
3691 CTCGGCCCTT CCGGCTGGCT GGTTTATTGC TGATAAATCT GGAGCCGGTG AGCGTGGGTC TCGCGGTATC ATTGCAGCAC TGGGGCCAGA
     GAGCCGGGAA GGCCGACCGA CCAAATAACG ACTATTTAGA CCTCGGCCAC TCGCACCCAG AGCGCCATAG TAACGTCGTG ACCCCGGTCT
```

AmpR

```
3781 TGGTAAGCCC TCCCGTATCG TAGTTATCTA CACGACGGGG AGTCAGGCAA CTATGGATGA ACGAAATAGA CAGATCGCTG AGATAGGTGC
     ACCATTCGGG AGGGCATAGC ATCAATAGAT GTGCTGCCCC TCAGTCCGTT GATACCTACT TGCTTTATCT GTCTAGCGAC TCTATCCACG
```

AmpR

```
3871 CTCACTGATT AAGCATTGGT AACTGTCAGA CCAAGTTTAC TCATATATAC TTTAGATTGA TTTAAAACTT CATTTTTAAT TTAAAAGGAT
     GAGTGACTAA TTCGTAACCA TTGACAGTCT GGTTCAAATG AGTATATATG AAATCTAACT AAATTTTGAA GTAAAAATTA AATTTTCCTA
```

pUC ori

```
3961 CTAGGTGAAG ATCCTTTTTG ATAATCTCAT GACCAAAATC CCTTAACGTG AGTTTTCGTT CCACTGAGCG TCAGACCCCG TAGAAAAGAT
     GATCCACTTC TAGGAAAAAC TATTAGAGTA CTGGTTTTAG GGAATTGCAC TCAAAAGCAA GGTGACTCGC AGTCTGGGGC ATCTTTTCTA
```

pUC ori

```
4051 CAAAGGATCT TCTTGAGATC CTTTTTTTCT GCGCGTAATC TGCTGCTTGC AAACAAAAAA ACCACCGCTA CCAGCGGTGG TTTGTTTGCC
     GTTTCCTAGA AGAACTCTAG GAAAAAAAGA CGCGCATTAG ACGACGAACG TTTGTTTTTT TGGTGGCGAT GGTCGCCACC AAACAAACGG
```

pUC ori

```
4141 GGATCAAGAG CTACCAACTC TTTTTCCGAA GGTAACTGGC TTCAGCAGAG CGCAGATACC AAATACTGTC CTTCTAGTGT AGCCGTAGTT
     CCTAGTTCTC GATGGTTGAG AAAAAGGCTT CCATTGACCG AAGTCGTCTC GCGTCTATGG TTTATGACAG GAAGATCACA TCGGCATCAA
```

pUC ori

```
4231 AGGCCACCAC TTCAAGAACT CTGTAGCACC GCCTACATAC CTCGCTCTGC TAATCCTGTT ACCAGTGGCT GCTGCCAGTG GCGATAAGTC
     TCCGGTGGTG AAGTTCTTGA GACATCGTGG CGGATGTATG GAGCGAGACG ATTAGGACAA TGGTCACCGA CGACGGTCAC CGCTATTCAG
```

FIG. 62 cont'd

```
                                              pUC ori
                                                                                                   BseYI
4321  GTGTCTTACC GGGTTGGACT CAAGACGATA GTTACCGGAT AAGGCGCAGC GGTCGGGCTG AACGGGGGGT TCGTGCACAC AGCCCAGCTT
      CACAGAATGG CCCAACCTGA GTTCTGCTAT CAATGGCCTA TTCCGCGTCG CCAGCCCGAC TTGCCCCCCA AGCACGTGTG TCGGGTCGAA
                                              pUC ori
4411  GGAGCGAACG ACCTACACCG AACTGAGATA CCTACAGCGT GAGCTATGAG AAAGCGCCAC GCTTCCCGAA GGGAGAAAGG CGGACAGGTA
      CCTCGCTTGC TGGATGTGGC TTGACTCTAT GGATGTCGCA CTCGATACTC TTTCGCGGTG CGAAGGGCTT CCCTCTTTCC GCCTGTCCAT
                                              pUC ori
4501  TCCGGTAAGC GGCAGGGTCG GAACAGGAGA GCGCACGAGG GAGCTTCCAG GGGGAAACGC CTGGTATCTT TATAGTCCTG TCGGGTTTCG
      AGGCCATTCG CCGTCCCAGC CTTGTCCTCT CGCGTGCTCC CTCGAAGGTC CCCCTTTGCG GACCATAGAA ATATCAGGAC AGCCCAAAGC
                                              pUC ori
4591  CCACCTCTGA CTTGAGCGTC GATTTTTGTG ATGCTCGTCA GGGGGGCGGA GCCTATGGAA AAACGCCAGC AACGCGGCCT TTTTACGGTT
      GGTGGAGACT GAACTCGCAG CTAAAAACAC TACGAGCAGT CCCCCCGCCT CGGATACCTT TTTGCGGTCG TTGCGCCGGA AAAATGCCAA
                  pUC ori
                                   PciI
4681  CCTGGCCTTT TGCTGGCCTT TTGCTCACAT GT          (SEQ ID NO: 23)
      GGACCGGAAA ACGACCGGAA AACGAGTGTA CA          (SEQ ID NO: 24)
```

CN1818 – rAAV-mFam84b(3x core)-minCMV-SYFP2-WPRE3-BGHpA

Cell type-specific enhancer-driven virus
enh
Cre
Viral injection
Constitutive promoter
Fluor
lox-STOP-lox
Viral incubation
Off-target cells
enh
Cre
Fluor
On-target cells
enh
Cre
Fluor

FIG. 70

| Enhancer ID | Labeled types/classes | Validation |
|---|---|---|
| Grik1_enhScnn1a-2 | Excitatory Layer 4 | Fluorescence microscopy |
| mscRE1 | Excitatory Layer 5 PT and IT | Fluorescence microscopy; scRNA-seq |
| mscRE3 | Excitatory Layer L2/3 and Layer 5 | Fluorescence microscopy |
| mscRE10 | Excitatory Layer 6 CT, 2/3 IT, 5 IT, 6b | Fluorescence microscopy; scRNA-seq |
| mscRE11 | Excitatory Layer 5 IT and PT | Fluorescence microscopy |
| mscRE13 | Excitatory Layer 6 IT | Fluorescence microscopy |

FIG. 71

| Sequence Name | Sequence Length (bp) | Enhancer ID & Promoter | Product Class | Primary Product | Other Components |
|---|---|---|---|---|---|
| T502-050 | 5902 | Grik1_enhScnn1a-2 Hsp68 | Fluoro-phore | EGFP | WPRE3; bGHpA |
| T502-054 | 5102 | Grik1_enhScnn1a-2 pBGmin | Fluoro-phore | EGFP | WPRE3; bGHpA |
| vAi1.0 | 4862 | mscRE1 pBGmin | Fluoro-phore | SYFP2 | WPRE3; bGHpA |
| T502-057 | 4856 | mscRE4 pBGmin | Fluoro-phore | SYFP2 | WPRE3; bGHpA |
| T502-059 | 4861 | mscRE3 pBGmin | Fluoro-phore | SYFP2 | WPRE3; bGHpA |
| TG975 | 6587 | mscRE4 pBGmin | Recombi-nase | FlpO | IRES2; WPRE3; bGHpA |
| TG978 | 5969 | mscRE4 pBGmin | Recombi-nase | FlpO | WPRE3; bGHpA |
| TG979 | 5343 | mscRE4 pBGmin | Recombi-nase | FlpO | bGHpA |
| TG981 | 5321 | mscRE4 pBGmin | Fluoro-phore | EGFP | WPRE3; bGHpA |
| TG982 | 5717 | mscRE4 pBGmin | Recombi-nase | iCre | IRES2 ; bGHpA |
| TG987 | 5408 | mscRE4 pBGmin | Trans-activator | tTA2 | IRES2; bGHpA |
| TG988 | 4806 | mscRE4 pBGmin | Trans-activator | tTA2 | bGHpA |
| TG995 | 5432 | mscRE10 pBGmin | Fluoro-phore | EGFP | WPRE3; bGHpA |
| TG996 | 5411 | mscRE11 pBGmin | Fluoro-phore | EGFP | WPRE3; bGHpA |

FIG. 71 cont'd

| Sequence Name | Sequence Length (bp) | Enhancer ID & Promoter | Product Class | Primary Product | Other Components |
|---|---|---|---|---|---|
| TG997 | 5442 | mscRE12 pBGmin | Fluoro-phore | EGFP | WPRE3; bGHpA |
| TG999 | 5427 | mscRE13 pBGmin | Fluoro-phore | EGFP | WPRE3; bGHpA |
| TG1002 | 5432 | mscRE16 pBGmin | Fluoro-phore | EGFP | WPRE3; bGHpA |
| TG1009 | 6932 | mscRE4 pBGmin | Recomb-inase | dgCre | WPRE3; bGHpA |
| TG1010 | 5727 | mscRE4 pBGmin | Recombi-nase | iCre | WPRE3; bGHpA |
| TG1011 | 5417 | mscRE4 pBGmin | Trans-activator | tTA2 | IRES2; WPRE3; bGHpA |
| TG1021 | 5716 | mscRE4 pBGmin | Recombi-nase | Cre | WPRE3; bGHpA |
| TG1022 | 5806 | mscRE4 pBGmin | Recombi-nase | Cre-i-Cre | WPRE3; bGHpA |
| TG1036 | 6010 | mscRE10 pBGmin | Recombi-nase | FlpO | WPRE3; bGHpA |
| TG1037 | 5994 | mscRE13 pBGmin | Recombi-nase | FlpO | WPRE3; bGHpA |
| TG1038 | 6010 | mscRE16 pBGmin | Recombi-nase | FlpO | WPRE3; bGHpA |
| TG1045 | 5779 | mscRE10 pBGmin | Recombi-nase | iCre | WPRE3; bGHpA |
| TG1046 | 5752 | mscRE13 pBGmin | Recombi-nase | iCre | WPRE3; bGHpA |
| TG1047 | 5768 | mscRE16 pBGmin | Recombi-nase | iCre | WPRE3; bGHpA |
| TG1048 | 5470 | mscRE10 pBGmin | Driver | tTA2 | WPRE3; bGHpA |
| TG1049 | 5443 | mscRE13 pBGmin | Driver | tTA2 | WPRE3; bGHpA |
| TG1050 | 5459 | mscRE16 pBGmin | Trans-activator | tTA2 | WPRE3; bGHpA |
| TG1052 | 7292 | 4XmscRE16 pBGmin | Fluoro-phore | EGFP | WPRE3; bGHpA |
| CN1818 | 4718 | 3XmscRE4 core minCMV | Fluoro-phore | SYFP2 | WPRE3; bGHpA |
| CN1402 | 4798 | eHGT_058h minBglobin | Fluoro-phore | SYFP2 | WPRE3; BGHpA |
| CN1457 | 4802 | eHGT_078h minBglobin | Fluoro-phore | SYFP2 | WPRE3; BGHpA |
| vAi34.0 | 3695 | Grik1_enhScnn1a pBGmin | Recombi-nase | FlpO | WPRE3 |

FIG. 71 cont'd

| Sequence Name | Sequence Length (bp) | Enhancer ID & Promoter | Product Class | Primary Product | Other Components |
|---|---|---|---|---|---|
| vAi33.2 | 3116 | Grik1_enhScnn1a pBGmin | Fluoro-phore | EGFP | WPRE3 |
| vAi45.0 | 5912 | mscRE12 | Recombi-nase | FlpO | WPRE3 |
| CN1416 | 4953 | eHGT_058m minBglobin | Fluoro-phore | SYFP2 | WPRE3; BGHpA |
| CN1452 | 5018 | eHGT_073h minBglobin | Fluoro-phore | SYFP2 | WPRE3; BGHpA |
| CN1461 | 4949 | eHGT_073m minBglobin | Fluoro-phore | SYFP2 | WPRE3; BGHpA |
| CN1454 | 4831 | eHGT_075h minBglobin | Fluoro-phore | SYFP2 | WPRE3; BGHpA |
| CN1456 | 4904 | eHGT_077h minBglobin | Fluoro-phore | SYFP2 | WPRE3; BGHpA |
| CN1772 | 5124 | eHGT_254h minRho | Fluoro-phore | SYFP2 | WPRE3; BGHpA |
| CN2014 | 4810 | mscRE4 minCMV | Fluoro-phore | SYFP2 | WPRE3; BGHpA |
| CN1427 | 6938 | 4XmscRE4 minBglobin | Fluoro-phore | tdTomato | WPRE3; BGHpA |
| CN1466 | 4751 | eHGT_078m minBglobin | Fluoro-phore | SYFP2 | WPRE3; BGHpA |
| CN1954 | 5498 | eHGT_078h(3xCore) minRho | Fluoro-phore | SYFP2 | WPRE3; BGHpA |
| CN1955 | 5771 | eHGT_078m(3xCore) minRho | Fluoro-phore | SYFP2 | WPRE3; BGHpA |
| CN2137 | 4600 | eHGT_440h minBglobin | Fluoro-phore | SYFP2 | WPRE3; BGHpA |
| CN2139 | 4623 | eHGT_439m minBglobin | Fluoro-phore | SYFP2 | WPRE3; BGHpA |

FIG. 72

| Class ID No. | Class Label | Subclass ID No. | Subclass Label | Cluster ID No. | Cluster Label |
|---|---|---|---|---|---|
| 1 | GABAergic Neuron | 1 | Lamp5 | 1 | Lamp5 Krt73 |
| 1 | GABAergic Neuron | 1 | Lamp5 | 2 | Lamp5 Fam19a1 Pax6 |
| 1 | GABAergic Neuron | 1 | Lamp5 | 3 | Lamp5 Fam19a1 Tmem182 |
| 1 | GABAergic Neuron | 1 | Lamp5 | 4 | Lamp5 Ntn1 Npy2r |
| 1 | GABAergic Neuron | 1 | Lamp5 | 5 | Lamp5 Plch2 Dock5 |
| 1 | GABAergic Neuron | 1 | Lamp5 | 6 | Lamp5 Lsp1 |
| 1 | GABAergic Neuron | 1 | Lamp5 | 7 | Lamp5 Lhx6 |
| 1 | GABAergic Neuron | 2 | Sncg | 8 | Sncg Slc17a8 |
| 1 | GABAergic Neuron | 2 | Sncg | 9 | Sncg Vip Nptx2 |
| 1 | GABAergic Neuron | 2 | Sncg | 10 | Sncg Gpr50 |
| 1 | GABAergic Neuron | 2 | Sncg | 11 | Sncg Vip Itih5 |
| 1 | GABAergic Neuron | 3 | Serpinf1 | 12 | Serpinf1 Clrn1 |
| 1 | GABAergic Neuron | 3 | Serpinf1 | 13 | Serpinf1 Aqp5 Vip |
| 1 | GABAergic Neuron | 4 | Vip | 14 | Vip Igfbp6 Car10 |
| 1 | GABAergic Neuron | 4 | Vip | 15 | Vip Igfbp6 Pltp |
| 1 | GABAergic Neuron | 4 | Vip | 16 | Vip Igfbp4 Mab21l1 |
| 1 | GABAergic Neuron | 4 | Vip | 17 | Vip Arhgap36 Hmcn1 |
| 1 | GABAergic Neuron | 4 | Vip | 18 | Vip Gpc3 Slc18a3 |
| 1 | GABAergic Neuron | 4 | Vip | 19 | Vip Lmo1 Fam159b |
| 1 | GABAergic Neuron | 4 | Vip | 20 | Vip Lmo1 Myl1 |
| 1 | GABAergic Neuron | 4 | Vip | 21 | Vip Ptprt Pkp2 |
| 1 | GABAergic Neuron | 4 | Vip | 22 | Vip Rspo4 Rxfp1 Chat |
| 1 | GABAergic Neuron | 4 | Vip | 23 | Vip Lect1 Oxtr |
| 1 | GABAergic Neuron | 4 | Vip | 24 | Vip Rspo1 Itga4 |
| 1 | GABAergic Neuron | 4 | Vip | 25 | Vip Chat Htr1f |
| 1 | GABAergic Neuron | 4 | Vip | 26 | Vip Pygm C1ql1 |
| 1 | GABAergic Neuron | 4 | Vip | 27 | Vip Crispld2 Htr2c |
| 1 | GABAergic Neuron | 4 | Vip | 28 | Vip Crispld2 Kcne4 |
| 1 | GABAergic Neuron | 4 | Vip | 29 | Vip Col15a1 Pde1a |
| 1 | GABAergic Neuron | 5 | Sst | 30 | Sst Chodl |
| 1 | GABAergic Neuron | 5 | Sst | 31 | Sst Mme Fam114a1 |
| 1 | GABAergic Neuron | 5 | Sst | 32 | Sst Tac1 Htr1d |
| 1 | GABAergic Neuron | 5 | Sst | 33 | Sst Tac1 Tacr3 |
| 1 | GABAergic Neuron | 5 | Sst | 34 | Sst Calb2 Necab1 |
| 1 | GABAergic Neuron | 5 | Sst | 35 | Sst Calb2 Pdlim5 |
| 1 | GABAergic Neuron | 5 | Sst | 36 | Sst Nr2f2 Necab1 |

FIG. 72 cont'd

| Class ID No. | Class Label | Subclass ID No. | Subclass Label | Cluster ID No. | Cluster Label |
|---|---|---|---|---|---|
| 1 | GABAergic Neuron | 5 | Sst | 37 | Sst Myh8 Etv1 |
| 1 | GABAergic Neuron | 5 | Sst | 38 | Sst Myh8 Fibin |
| 1 | GABAergic Neuron | 5 | Sst | 39 | Sst Chrna2 Glra3 |
| 1 | GABAergic Neuron | 5 | Sst | 40 | Sst Chrna2 Ptgdr |
| 1 | GABAergic Neuron | 5 | Sst | 41 | Sst Tac2 Myh4 |
| 1 | GABAergic Neuron | 5 | Sst | 42 | Sst Hpse Sema3c |
| 1 | GABAergic Neuron | 5 | Sst | 43 | Sst Hpse Cbln4 |
| 1 | GABAergic Neuron | 5 | Sst | 44 | Sst Crhr2 Efemp1 |
| 1 | GABAergic Neuron | 5 | Sst | 45 | Sst Crh 4930553C11Rik |
| 1 | GABAergic Neuron | 5 | Sst | 46 | Sst Esm1 |
| 1 | GABAergic Neuron | 5 | Sst | 47 | Sst Tac2 Tacstd2 |
| 1 | GABAergic Neuron | 5 | Sst | 48 | Sst Rxfp1 Eya1 |
| 1 | GABAergic Neuron | 5 | Sst | 49 | Sst Rxfp1 Prdm8 |
| 1 | GABAergic Neuron | 5 | Sst | 50 | Sst Nts |
| 1 | GABAergic Neuron | 6 | Pvalb | 51 | Pvalb Gabrg1 |
| 1 | GABAergic Neuron | 6 | Pvalb | 52 | Pvalb Th Sst |
| 1 | GABAergic Neuron | 6 | Pvalb | 53 | Pvalb Akr1c18 Ntf3 |
| 1 | GABAergic Neuron | 6 | Pvalb | 54 | Pvalb Calb1 Sst |
| 1 | GABAergic Neuron | 6 | Pvalb | 55 | Pvalb Sema3e Kank4 |
| 1 | GABAergic Neuron | 6 | Pvalb | 56 | Pvalb Gpr149 Islr |
| 1 | GABAergic Neuron | 6 | Pvalb | 57 | Pvalb Reln Tac1 |
| 1 | GABAergic Neuron | 6 | Pvalb | 58 | Pvalb Reln Itm2a |
| 1 | GABAergic Neuron | 6 | Pvalb | 59 | Pvalb Tpbg |
| 1 | GABAergic Neuron | 6 | Pvalb | 60 | Pvalb Vipr2 |
| 2 | Glutamatergic Neuron | 7 | L2/3 IT | 61 | L2/3 IT VISp Rrad |
| 2 | Glutamatergic Neuron | 7 | L2/3 IT | 62 | L2/3 IT VISp Adamts2 |
| 2 | Glutamatergic Neuron | 7 | L2/3 IT | 63 | L2/3 IT VISp Agmat |
| 2 | Glutamatergic Neuron | 7 | L2/3 IT | 64 | L2/3 IT ALM Sla |
| 2 | Glutamatergic Neuron | 7 | L2/3 IT | 65 | L2/3 IT ALM Ptrf |
| 2 | Glutamatergic Neuron | 7 | L2/3 IT | 66 | L2/3 IT ALM Macc1 Lrg1 |
| 2 | Glutamatergic Neuron | 8 | L4 | 67 | L4 IT VISp Rspo1 |
| 2 | Glutamatergic Neuron | 9 | L5 IT | 68 | L5 IT VISp Hsd11b1 Endou |
| 2 | Glutamatergic Neuron | 9 | L5 IT | 69 | L5 IT VISp Whrn Tox2 |
| 2 | Glutamatergic Neuron | 9 | L5 IT | 70 | L5 IT VISp Batf3 |
| 2 | Glutamatergic Neuron | 9 | L5 IT | 71 | L5 IT VISp Col6a1 Fezf2 |
| 2 | Glutamatergic Neuron | 9 | L5 IT | 72 | L5 IT VISp Col27a1 |
| 2 | Glutamatergic Neuron | 9 | L5 IT | 73 | L5 IT ALM Npw |

FIG. 72 cont'd

| Class ID No. | Class Label | Subclass ID No. | Subclass Label | Cluster ID No. | Cluster Label |
|---|---|---|---|---|---|
| 2 | Glutamatergic Neuron | 9 | L5 IT | 74 | L5 IT ALM Pld5 |
| 2 | Glutamatergic Neuron | 9 | L5 IT | 75 | L5 IT ALM Cbln4 Fezf2 |
| 2 | Glutamatergic Neuron | 9 | L5 IT | 76 | L5 IT ALM Lypd1 Gpr88 |
| 2 | Glutamatergic Neuron | 9 | L5 IT | 77 | L5 IT ALM Tnc |
| 2 | Glutamatergic Neuron | 9 | L5 IT | 78 | L5 IT ALM Tmem163 Dmrtb1 |
| 2 | Glutamatergic Neuron | 9 | L5 IT | 79 | L5 IT ALM Tmem163 Arhgap25 |
| 2 | Glutamatergic Neuron | 9 | L5 IT | 80 | L5 IT ALM Cpa6 Gpr88 |
| 2 | Glutamatergic Neuron | 9 | L5 IT | 81 | L5 IT ALM Gkn1 Pcdh19 |
| 2 | Glutamatergic Neuron | 10 | L6 IT | 82 | L6 IT ALM Tgfb1 |
| 2 | Glutamatergic Neuron | 10 | L6 IT | 83 | L6 IT ALM Oprk1 |
| 2 | Glutamatergic Neuron | 10 | L6 IT | 84 | L6 IT VISp Penk Col27a1 |
| 2 | Glutamatergic Neuron | 10 | L6 IT | 85 | L6 IT VISp Penk Fst |
| 2 | Glutamatergic Neuron | 10 | L6 IT | 86 | L6 IT VISp Col23a1 Adamts2 |
| 2 | Glutamatergic Neuron | 10 | L6 IT | 87 | L6 IT VISp Col18a1 |
| 2 | Glutamatergic Neuron | 10 | L6 IT | 88 | L6 IT VISp Car3 |
| 2 | Glutamatergic Neuron | 11 | L5 PT | 89 | L5 PT VISp Chrna6 |
| 2 | Glutamatergic Neuron | 11 | L5 PT | 90 | L5 PT VISp Lgr5 |
| 2 | Glutamatergic Neuron | 11 | L5 PT | 91 | L5 PT VISp C1ql2 Ptgfr |
| 2 | Glutamatergic Neuron | 11 | L5 PT | 92 | L5 PT VISp C1ql2 Cdh13 |
| 2 | Glutamatergic Neuron | 11 | L5 PT | 93 | L5 PT VISp Krt80 |
| 2 | Glutamatergic Neuron | 11 | L5 PT | 94 | L5 PT ALM Slco2a1 |
| 2 | Glutamatergic Neuron | 11 | L5 PT | 95 | L5 PT ALM Npsr1 |
| 2 | Glutamatergic Neuron | 11 | L5 PT | 96 | L5 PT ALM Hpgd |
| 2 | Glutamatergic Neuron | 12 | NP | 97 | L5 NP VISp Trhr Cpne7 |
| 2 | Glutamatergic Neuron | 12 | NP | 98 | L5 NP ALM Trhr Nefl |
| 2 | Glutamatergic Neuron | 12 | NP | 99 | L5 NP VISp Trhr Met |
| 2 | Glutamatergic Neuron | 12 | NP | 100 | L6 NP ALM Trh |
| 2 | Glutamatergic Neuron | 13 | L6 CT | 101 | L6 CT ALM Cpa6 |
| 2 | Glutamatergic Neuron | 13 | L6 CT | 102 | L6 CT Nxph2 Sla |
| 2 | Glutamatergic Neuron | 13 | L6 CT | 103 | L6 CT VISp Nxph2 Wls |
| 2 | Glutamatergic Neuron | 13 | L6 CT | 104 | L6 CT VISp Gpr139 |
| 2 | Glutamatergic Neuron | 13 | L6 CT | 105 | L6 CT VISp Ctxn3 Brinp3 |
| 2 | Glutamatergic Neuron | 13 | L6 CT | 106 | L6 CT VISp Ctxn3 Sla |
| 2 | Glutamatergic Neuron | 13 | L6 CT | 107 | L6 CT VISp Krt80 Sla |
| 2 | Glutamatergic Neuron | 14 | L6b | 108 | L6b Col8a1 Rprm |
| 2 | Glutamatergic Neuron | 14 | L6b | 109 | L6b VISp Mup5 |

FIG. 72 cont'd

| Class ID No. | Class Label | Subclass ID No. | Subclass Label | Cluster ID No. | Cluster Label |
|---|---|---|---|---|---|
| 2 | Glutamatergic Neuron | 14 | L6b | 110 | L6b VISp Col8a1 Rxfp1 |
| 2 | Glutamatergic Neuron | 14 | L6b | 111 | L6b ALM Olfr111 Spon1 |
| 2 | Glutamatergic Neuron | 14 | L6b | 112 | L6b ALM Olfr111 Nxph1 |
| 2 | Glutamatergic Neuron | 14 | L6b | 113 | L6b P2ry12 |
| 2 | Glutamatergic Neuron | 14 | L6b | 114 | L6b VISp Crh |
| 2 | Glutamatergic Neuron | 14 | L6b | 115 | L6b Hsd17b2 |
| 1 | GABAergic Neuron | 15 | Meis2 | 116 | Meis2 Adamts19 |
| 2 | Glutamatergic Neuron | 16 | CR | 117 | CR Lhx5 |
| 3 | Non-Neuronal | 17 | Astro | 118 | Astro Aqp4 |
| 3 | Non-Neuronal | 18 | Oligo | 119 | OPC Pdgfra Grm5 |
| 3 | Non-Neuronal | 18 | Oligo | 120 | OPC Pdgfra Ccnb1 |
| 3 | Non-Neuronal | 18 | Oligo | 121 | Oligo Rassf10 |
| 3 | Non-Neuronal | 18 | Oligo | 122 | Oligo Serpinb1a |
| 3 | Non-Neuronal | 18 | Oligo | 123 | Oligo Synpr |
| 3 | Non-Neuronal | 19 | VLMC | 124 | VLMC Osr1 Cd74 |
| 3 | Non-Neuronal | 19 | VLMC | 125 | VLMC Osr1 Mc5r |
| 3 | Non-Neuronal | 19 | VLMC | 126 | VLMC Spp1 Hs3st6 |
| 3 | Non-Neuronal | 19 | VLMC | 127 | VLMC Spp1 Col15a1 |
| 4 | Non-Neuronal | 20 | Peri | 128 | Peri Kcnj8 |
| 4 | Non-Neuronal | 21 | SMC | 129 | SMC Acta2 |
| 4 | Non-Neuronal | 22 | Endo | 130 | Endo Ctla2a |
| 4 | Non-Neuronal | 22 | Endo | 131 | Endo Cytl1 |
| 3 | Non-Neuronal | 23 | Macrophage | 132 | PVM Mrc1 |
| 3 | Non-Neuronal | 23 | Macrophage | 133 | Microglia Siglech |

FIG. 73A

| | | | GABAergic Neuron | | | | | |
|---|---|---|---|---|---|---|---|---|
| Enhancer ID | Labeled types/classes | Validation | Lamp5 | Sncg | Vip | Sst | Pvalb | Meis2 |
| Grik1_enhScnn1a-2 | Layer 4 | FM | | | | | | |
| mscRE1 | Layer 5 PT | FM; scRNA-seq | 3% | | 1% | 15% | 3% | |
| mscRE3 | Layer L2/3 and Layer 5 | FM | | | | | | |
| mscRE10 | Layer 6 CT | FM; scRNA-seq | 2% | | 2% | | | |
| mscRE11 | Layer 5 | FM | | | | | | |
| mscRE12 | (Broad) | FM | | | | | | |
| mscRE13 | Layer 6 | FM | | | | | | |

| | Glutamatergic Neuron | | | | | | | | Non-neuronal | | | | | | | |
|---|---|---|---|---|---|---|---|---|---|---|---|---|---|---|---|---|
| Enhancer ID | L2/3 IT | L4 IT | L5 IT | L5 PT | L6 IT | L5/6 NP | L6 CT | L6b | Cajal Retzius | Astrocyte | Oligodendrocyte | VLMC | Pericyte | Smooth Muscle | Endothelial | Macrophage |
| Grik1_enhScnn1a-2 | | + | | | | | | | | | | | | | | |
| mscRE1 | | 1% | 4% | 37% | 13% | 1% | 4% | 2% | 1% | 2% | 1% | | | | | 9% |
| mscRE3 | + | | + | | | | | | | | | | | | | |
| mscRE10 | 6% | | 6% | | 8% | | 69% | 6% | | | | | | | | |
| mscRE11 | | | + | + | | | | | | | | | | | | |
| mscRE12 | + | + | + | + | + | + | + | + | | | | | | | | |
| mscRE13 | | | | | + | | | | | | | | | | | |

FIG. 73B

| Vector Name (Plasmid ID) | Enhancer Name (Enhancer ID) | Glutamatergic | L2/3 IT | L4 IT | L5 IT | L6 IT | L5 PT | L6 CT | L5 NP | L6b | CR | GABAergic |
|---|---|---|---|---|---|---|---|---|---|---|---|---|
| N/A (vAi1.0) | mscRE1 (eAi1.0) | S | | | A | | A | | | | | |
| T502-059 (vAi2.0) | mscRE3 (eAi2.0) | S | | | | | | | | | | |
| T502-057 (vAi3.0) | mscRE4 (eAi3.0) | S* | | | | | A* | | | | | |
| TG975 (vAi4.0) | mscRE4 (eAi3.0) | S | | | | | A | | | | | |
| TG978 (vAi4.1) | mscRE4 (eAi3.0) | S~ | | | | | S~ | | | | | |
| TG979 (vAi4.2) | mscRE4 (eAi3.0) | S | | | | | A | | | | | |
| TG981 (vAi5.0) | mscRE4 (eAi3.0) | S | | | | | A | | | | | |
| TG982 (vAi6.0) | mscRE4 (eAi3.0) | S | | | | | A | | | | | |
| TG987 (vAi7.0) | mscRE4 (eAi3.0) | S | | | | | A | | | | | |
| TG988 (vAi7.1) | mscRE4 (eAi3.0) | S | | | | | A | | | | | |
| TG1009 (vAi8.0dgCre) | mscRE4 (eAi3.0) | S | | | | | A | | | | | |
| TG1010 (vAi6.1) | mscRE4 (eAi3.0) | S | | | | | A | | | | | |
| TG1011 (vAi7.2) | mscRE4 (eAi3.0) | S | | | | | A | | | | | |
| TG1021 (vAi8.0Cre) | mscRE4 (eAi3.0) | S | | | | | A | | | | | |

FIG. 73B cont'd

| Vector Name (Plasmid ID) | Enhancer Name (Enhancer ID) | Glutamatergic | L2/3 IT | L4 IT | L5 IT | L6 IT | L5 PT | L6 CT | L5 NP | L6b | CR | GABAergic |
|---|---|---|---|---|---|---|---|---|---|---|---|---|
| TG1022 (vAi9.0) | mscRE4 (eAi3.0) | S | | | | | A | | | | | |
| TG1052 (vAi10.0) | 4XmscRE16 (eAi11.1) | S | | | | | A | | | | | |
| TG995 (vAi15.0) | mscRE10 (eAi6.0) | S | | | | | | S | | | | |
| TG1036 (vAi16.0) | mscRE10 (eAi6.0) | S* | | | | | | S* | | | | |
| TG1045 (vAi17.0) | mscRE10 (eAi6.0) | S | | | | | | S | | | | |
| TG1048 (vAi18.0) | mscRE10 (eAi6.0) | S | | | | | | S | | | | |
| TG996 (vAi19.0) | mscRE11 (eAi7.0) | S | | | A | | A | | | | | |
| TG997 (vAi20.0) | mscRE12 (eAi8.0) | S | | | | | | | | | | S |
| TG999 (vAi21.0) | mscRE13 (eAi9.0) | S | | | | A | | | | | | |
| TG1037 (vAi22.0) | mscRE13 (eAi9.0) | S | | | | A | | | | | | |
| TG1046 (vAi23.0) | mscRE13 (eAi9.0) | S | | | | A | | | | | | |
| TG1049 (vAi24.0) | mscRE13 (eAi9.0) | S | | | | A | | | | | | |
| TG1002 (vAi26.0) | mscRE16 (eAi11.0) | S | | | A | | S | | | | | |
| TG1038 (vAi27.0) | mscRE16 (eAi11.0) | S* | | | A* | | S* | | | | | |

FIG. 73B cont'd

| Vector Name (Plasmid ID) | Enhancer Name (Enhancer ID) | Glutamatergic | L2/3 IT | L4 IT | L5 IT | L6 IT | L5 PT | L6 CT | L5 NP | L6b | CR | GABAergic |
|---|---|---|---|---|---|---|---|---|---|---|---|---|
| TG1047 (vAi28.0) | mscRE16 (eAi11.0) | S | | | A | | S | | | | | |
| TG1050 (vAi29.0) | mscRE16 (eAi11.0) | S | | | A | | S | | | | | |
| T502-050 (vAi33.0) | Grik1-enhSCnn1a-2 (eAi14.0) | S | | A | | | | | | | | |
| T502-055 (vAi33.1) | Grik1-enhSCnn1a-2 (eAi14.0) | S | | A | | | | | | | | |
| (vAi34.0) | Grik1-enhSCnn1a-2 (eAi14.0) | S | | | | | | | | | | |
| (vAi33.2) | Grik1-enhSCnn1a-2 (eAi14.0) | S | | | | | | | | | | |
| (vAi45.0) | mscRE12 (eAi8.0) | S | | | | | | | | | | S |
| CN1402 (vAi106.0) | eHGT_058h (eAi106.0) | S* | | A* | | | | | | | | |
| CN1457 (vAi107.0) | eHGT_078h (eAi107.0) | S* | A* | A* | A* | A* | A* | | | | A* | |
| CN1416 (vAi108.0) | eHGT_058m (eAi108.0) | S | | A | | | | | | | | |
| CN1452 (vAi111.0) | eHGT_073h (eAi111.0) | A | A | A | A | A | A | A | A | A | A | |
| CN1461 (vAi112.0) | eHGT_073m (eAi112.0) | A | A | A | A | A | A | A | A | A | A | |
| CN1454 (vAi113.0) | eHGT_075h (eAi113.0) | S | A | | | | | | | | | |
| CN1456 (vAi114.0) | eHGT_077h (eAi114.0) | A | A | A | A | A | A | A | A | A | A | |

FIG. 73B cont'd

| Vector Name (Plasmid ID) | Enhancer Name (Enhancer ID) | Glutamatergic | L2/3 IT | L4 IT | L5 IT | L6 IT | L5 PT | L6 CT | L5 NP | L6b | CR | GABAergic |
|---|---|---|---|---|---|---|---|---|---|---|---|---|
| CN1772 (vAi127.0) | eHGT_254h (eAi127.0) | S | | A | | | | | | | | |
| CN1818 (vAi128.0) | 3xmFam84b (eAi3.2) | S | | | | | A | | | | | |
| CN2014 (vAi129.0) | mscRE4 (eAi3.0) | S | | | | | A | | | | | |
| CN1427 (vAi130.0) | mscRE4(4x) (eAi3.1) | S | | | | | A | | | | | |
| CN1466 (vAi131.0) | eHGT_078m (eAi128.0) | A | A | A | A | A | A | A | A | A | A | |
| CN1954 (vAi132.0) | eHGT_078h(3xCore) (eAi129.0) | A | A | A | A | A | A | A | A | A | A | |
| CN1955 (vAi133.0) | eHGT_078m(3xCore) (eAi130.0) | A | A | A | A | A | A | A | A | A | A | |
| CN2137 (vAi135.0) | eHGT_440h (eAi131.0) | S | | | | | | | | S | | |
| CN2139 (vAi134.0) | eHGT_439m (eAi132.0) | A | | A | | | | | | | | |

Human single neuron epigenetic characterization at the Allen Institute for Brain Science and Seattle surgeon network

FIG. 79

Enhancer Grik1-enhScnn1a-1 nucleotide sequence (255 bp) Short Form:
CTCCAAATTTCTTCAACCAAGTAGAGAAAAATGAGAGAGAAGGAAAGAAAAAAAGAGGTAT
GGGGAGAAGAGAAAGAAGGCAACTTGTTAAAAATCTCAGTCAAACTTACATACTATATAGAA
CAGCATGGTGAATTTAGGGCACATGGATATAAAATGGAAGTTTCTTATTCAGTAGCAGCAA
CTTGTGGGCACAGGAGTTGGCAAAGATAAAAATGTCCAAAGTCACAAATACAATGTATAGT
TAGTCATAGG (SEQ ID NO: 188)

Enhancer Grik1-enhScnn1a-1 nucleotide sequence (854 bp):
CTCCAAATTTCTTCAACCAAGTAGAGAAAAATGAGAGAGAAGGAAAGAAAAAAAGAGGTAT
GGGGAGAAGAGAAAGAAGGCAACTTGTTAAAAATCTCAGTCAAACTTACATACTATATAGAA
CAGCATGGTGAATTTAGGGCACATGGATATAAAATGGAAGTTTCTTATTCAGTAGCAGCAA
CTTGTGGGCACAGGAGTTGGCAAAGATAAAAATGTCCAAAGTCACAAATACAATGTATAGT
TAGTCATAGGTGCTGTTATTTGCCTCAAAAAATAGACTTTTATTTTGCCTTTCTTTTCTTTAAC
CACACTCAAAATTAGAGAACAGAGACAAAACCCAGCAGGAAATAGCACAGAAAGCCCACA
GAATCAAAGACGTGTTCAAACAGCCAGCTGAATTCATTGCACATTTCAACCACAGAAATATT
TTCAGGTGATTCTGTTGTTTGACAAAACGTGGGAACCACAGGATCTACAACACTTGCAAGC
AAAACTCAACAGCTCTAATAATAGTTACAGAAGTGAAAGCCAATTTGGATAAAATAAGACAT
TGACTCAAGTCCTCTCAGAAGAGTTTTGAAAGCAAAGTTTACAAAAGTCTGGTTTGTCCTTT
GGGATTTACAGACCTTTCAGCCCCTTGATTCATTTTTTTTTTTTTGGATTTCTTCATCACTGG
GAGAATTCCCATGCATTATTTCTCCCCTGCTTCAAAATCATCAAATGTGAAACATTTTTCACT
CTTTTCTTCTGTATATAGTGATAAAATAGCTATTGGCTTTTGGCTAAATGTGCTACTTTGAGC
CCACCCACACAAGGGAGAAATGGGGGCAGACATGAGTTTGGGCATGAGT (SEQ ID NO: 25)

Enhancer mscRE1 nucleotide sequence (565 bp):
TTCTAATCATGAATTCTTTTGTGGTATTTTAGATTTTCAGTTTGTTCTGTATCAATTCTCTCTC
ATTCAAAGAATATGATAGTGAGGTAGATGAAGCTGCCTAAGCCACAGGAAGAAACATCTTC
AGTCTGTCGTAAATGCACTTCAGATACAGCACCTTGCACTGCACATAAAAATTCATAGTCAC
CTAAGTGGGAATAGCTATGAAAATCTGAGTATCGCCATGCTGTTGACTCAGTGCTATTTATA
AAACTCAGTTTTAATGTTTCCAATTTAAATTCTCTGCACATATCTCTCCTGCACTAAAGACTT
GAGATACCAGTGCTTTACCCTAAAATATCTTGCTTTTATATCTTGACTCTTATGTTGAGAATT
TATTATTTTTAAAATATACTTTAAAACATGCATTGGTACAAAATTAGTCAAAACAGCAACCAG
TGAATTCAAAGTAAATTAGTATTATTAATGCTGTGTATAATTTTGGTGAATTTTACTATTAAAT
TATAAATAAAAAGTCCTTCCAGGTAGTCATGTTCACTCCTGATTGGTAAGTTCAAGAACATT
(SEQ ID NO: 26)

Enhancer mscRE3 nucleotide sequence (563 bp):
CCTTTCCAGCCTGGCTTACAGGCTTTTTTCACCACAGTACCAATTGCCCATGCTCTGCTCAT
TAATTTAAATGGCAATGACTATCTGGGTTTTAAAATAGAGAAGTGTCAGGATGGGAACACG
CAATCATTTGGCTTTTTGCGTTCCAGCACTGTTTTGAATAGCAGGGTTTTCACTTCCTATGA
AACCTTAGCAGGAGGAAAAGCGGAAACTAAACCATAAAGTGAGAGGGATGAGGGGAGGGA
GGGACTTGAGTATTTGTAAACTCAGGGTGGCTGGCCCTGCCTACCAGGCTGCTCTCTACC
ACCGGAGGCTAGGAGTGGAAAAACTTGATTTACGTGTTGTGCCTGCCTTTTTTTTTTCTTCT
TCTTCTTCTTCTTCTTCTTCGTCTCCACACCACCTTCTGTACACCTGACTCTGCATAAGCCT
ATCTGAAGCTGGCTTGGTGGCAGGGATAGCTGGAGAACAGAAGAATGTGCGGAGGGAGG
GAGGGAGGAAGGGAGGGCTGGTACTTTTCCATTCACATCTCCACAGTGGCTGTTCTTGTTT
ATTTCAACCACCG (SEQ ID NO: 27)

FIG. 79 cont'd

Enhancer mscRE4 nucleotide sequence (555 bp):
AGCCTTGGGGGCAATCAAACTATTACATTGAGTCCTTGGATTTGCTACAAATTACATTTTAA
ATGCAATCATTTTATAAAAGCTTCAACACTCACACTTGGAAGCGTTACCCTGTTGAATATCA
CTGACTCACTAACTTGCATTGCCATGCTAACTTGCTTTCAGAGAGATCTCAGAACACATCAT
CTTCTGCTATTTCAATACATGCACATTAATTTCCTATCAACGTGTGCTGATCAGGAACTCTG
TAATCTGGCACCGGTGTTTATTTTTATTCCTGTCTATTCCTGTTGGCTCACGAAAAGATTGTT
TGAGCAAGTGTTTTATGGTGAGTTGTATCATATGTACATTGATTTAATCTGCCCACATTCAG
TTCTACAAGCGGAGCCAAAAAAATAGAGACAAGCATAATTTTCATTCAACATGAGCCCCTCA
ATGCAAGCCAAGTACCTCATCTGGTGCTCAGCTAAAGCAACAGCAATCTGTTCCACCCTGG
AGACACAACTGGCCACAGAAAACTTAGTGAAAAGAGGCAATGCTATGCACAGGACAAAT
(SEQ ID NO: 28)

Mouse Fam84b L5 PT enhancer core (mscRE4 core) (155 bp):
TTACCCTGTTGAATATCACTGACTCACTAACTTGCATTGCCATGCTAACTTGCTTTCAGAGA
GATCTCAGAACACATCATCTTCTGCTATTTCAATACATGCACATTAATTTCCTATCAACGTGT
GCTGATCAGGAACTCTGTAATCTGGCACCG (SEQ ID NO: 29)

3x(core) mouse Fam84b L5 PT enhancer (465 bp):
TTACCCTGTTGAATATCACTGACTCACTAACTTGCATTGCCATGCTAACTTGCTTTCAGAGA
GATCTCAGAACACATCATCTTCTGCTATTTCAATACATGCACATTAATTTCCTATCAACGTGT
GCTGATCAGGAACTCTGTAATCTGGCACCGTTACCCTGTTGAATATCACTGACTCACTAACT
TGCATTGCCATGCTAACTTGCTTTCAGAGAGATCTCAGAACACATCATCTTCTGCTATTTCA
ATACATGCACATTAATTTCCTATCAACGTGTGCTGATCAGGAACTCTGTAATCTGGCACCGT
TACCCTGTTGAATATCACTGACTCACTAACTTGCATTGCCATGCTAACTTGCTTTCAGAGAG
ATCTCAGAACACATCATCTTCTGCTATTTCAATACATGCACATTAATTTCCTATCAACGTGTG
CTGATCAGGAACTCTGTAATCTGGCACCG (SEQ ID NO: 30)

FIG. 79 cont'd

Enhancer mscRE4 (4x) nucleotide sequence (2000 bp):
CCTTGGATTTGCTACAAATTACATTTTAAATGCAATCATTTTATAAAAGCTTCAACACTCACA
CTTGGAAGCGTTACCCTGTTGAATATCACTGACTCACTAACTTGCATTGCCATGCTAACTTG
CTTTCAGAGAGATCTCAGAACACATCATCTTCTGCTATTTCAATACATGCACATTAATTTCCT
ATCAACGTGTGCTGATCAGGAACTCTGTAATCTGGCACCGGTGTTTATTTTTATTCCTGTCT
ATTCCTGTTGGCTCACGAAAAGATTGTTTGAGCAAGTGTTTTATGGTGAGTTGTATCATATG
TACATTGATTTAATCTGCCCACATTCAGTTCTACAAGCGGAGCCAAAAAAATAGAGACAAGC
ATAATTTTCATTCAACATGAGCCCCTCAATGCAAGCCAAGTACCTCATCTGGTGCTCAGCTA
AAGCAACAGCAATCTGTTCCACCCTGGAGACACAACTGGCCACAGAAAACTTAGTGAAAAG
AGGCCTTGGATTTGCTACAAATTACATTTTAAATGCAATCATTTTATAAAAGCTTCAACACTC
ACACTTGGAAGCGTTACCCTGTTGAATATCACTGACTCACTAACTTGCATTGCCATGCTAAC
TTGCTTTCAGAGAGATCTCAGAACACATCATCTTCTGCTATTTCAATACATGCACATTAATTT
CCTATCAACGTGTGCTGATCAGGAACTCTGTAATCTGGCACCGGTGTTTATTTTTATTCCTG
TCTATTCCTGTTGGCTCACGAAAAGATTGTTTGAGCAAGTGTTTTATGGTGAGTTGTATCAT
ATGTACATTGATTTAATCTGCCCACATTCAGTTCTACAAGCGGAGCCAAAAAAATAGAGACA
AGCATAATTTTCATTCAACATGAGCCCCTCAATGCAAGCCAAGTACCTCATCTGGTGCTCA
GCTAAAGCAACAGCAATCTGTTCCACCCTGGAGACACAACTGGCCACAGAAAACTTAGTGA
AAAGAGGCCTTGGATTTGCTACAAATTACATTTTAAATGCAATCATTTTATAAAAGCTTCAAC
ACTCACACTTGGAAGCGTTACCCTGTTGAATATCACTGACTCACTAACTTGCATTGCCATGC
TAACTTGCTTTCAGAGAGATCTCAGAACACATCATCTTCTGCTATTTCAATACATGCACATTA
ATTTCCTATCAACGTGTGCTGATCAGGAACTCTGTAATCTGGCACCGGTGTTTATTTTTATT
CCTGTCTATTCCTGTTGGCTCACGAAAAGATTGTTTGAGCAAGTGTTTTATGGTGAGTTGTA
TCATATGTACATTGATTTAATCTGCCCACATTCAGTTCTACAAGCGGAGCCAAAAAAATAGA
GACAAGCATAATTTTCATTCAACATGAGCCCCTCAATGCAAGCCAAGTACCTCATCTGGTG
CTCAGCTAAAGCAACAGCAATCTGTTCCACCCTGGAGACACAACTGGCCACAGAAAACTTA
GTGAAAAGAGGCCTTGGATTTGCTACAAATTACATTTTAAATGCAATCATTTTATAAAAGCTT
CAACACTCACACTTGGAAGCGTTACCCTGTTGAATATCACTGACTCACTAACTTGCATTGCC
ATGCTAACTTGCTTTCAGAGAGATCTCAGAACACATCATCTTCTGCTATTTCAATACATGCA
CATTAATTTCCTATCAACGTGTGCTGATCAGGAACTCTGTAATCTGGCACCGGTGTTTATTT
TTATTCCTGTCTATTCCTGTTGGCTCACGAAAAGATTGTTTGAGCAAGTGTTTTATGGTGAG
TTGTATCATATGTACATTGATTTAATCTGCCCACATTCAGTTCTACAAGCGGAGCCAAAAAA
ATAGAGACAAGCATAATTTTCATTCAACATGAGCCCCTCAATGCAAGCCAAGTACCTCATCT
GGTGCTCAGCTAAAGCAACAGCAATCTGTTCCACCCTGGAGACACAACTGGCCACAGAAA
ACTTAGTGAAAAGAGG (SEQ ID NO: 31)

Enhancer mscRE10 nucleotide sequence (501 bp):
CACTGTGCATAGCATCATTACAATGTTATAGTTTTTCACACTATGCCTTGACTTTTTGGAAAG
GCAAACCACCTCTTGGATTTCTCCTTCCTTCTCTATCTCTCTCTCTCTCTCTTCCTCCCTCC
GTCCCTCCATCTCTTCCTCCTTCCCATTTTCTTCTCTCCCTATTTGGACACAATATAAAATAA
TTTAGATGAGGTGAGTTAAATTGTGAACAAAGTATGTGCCTATACATGGTTGTAAATCAGCT
TATCAAAGTGTAATATTAGAAGAATTTATAAAAATGATAAAATTCATACTCAAAGTTCTGTGT
AAAGCAATAATAGCTTTATCTCCTTTTAGTTATCTTGAGTCTTTCTATGACTAACAACTCCCT
CATAGGCATCTTAAAGAGCAGTAAGCATAAGTAGATTCCAAATGGGAAGGGAGAAGTGTGA
ACCATCACTTTCATCCAGACTTGTAGATATATCTGCTGCATTTTCAGAAACCAGAAACAGAC
AG (SEQ ID NO: 32)

FIG. 79 cont'd

Enhancer mscRE11 nucleotide sequence (501 bp):
AAAATGTTCATTTTGCCAATATGATCACCAATAAAACCATTTGTGTAGACTATCCACCTTAAT
CCCCCTATAATACAATAGCACAGAGGTGAGTCAGTTTGATTTTGATACTAGGTTTATTTTATA
GGAGCTATTAAAGTTTCAGAATTTTGCTGAGTCACCAGGCTCTTCATTTTGTGGCAAATCCA
TCACTACAGTTTAAGGAGAGAAGAAACAGACCCCCCCCTACCCTCTGAAAAATAAAAATAA
AAACTTGTTTCAGGCAGGCTAGCGATTCACTAATAATGAGAAAACTCCAGTTTTAAGACTTA
ATTTCACCATAAATACTCTTTCATTCTAAGCTCTGGGACATCATGAGCCAGAGAACAGCAGA
GTGAATAATACAGTTACAGAGCTGATGAGCAATGCCAGTCACTGTAAAAAATACAGAATCC
CATCCAAAGGACATCTGTAAAAGTGTCTTTAACATCTACTCAGCCCTTCTGTGTAAAGGTCA
GCACG (SEQ ID NO: 33)

Enhancer mscRE12 nucleotide sequence (598 bp) Long Form:
CCTTTTCCAACCGTTCCTTCATGACATCAAGGCTTCAGACTGCTAAGCTTTGGGCACTACCT
GGGGTCAGTCTGCATCAAAATGTAAGGCTCAAATGTGTAATTGTAAGTACTGTTTTGCTGA
GCTGGAAGGGCTCCTTTGAAGCCCACGTTTTAATTTTAATTTAGCCACACAGAGTGGCAAA
GACAAATAGATTTATCCAAAATACATTTGGTAACAGATTTTTTGAGTCAGTTATTAATTTTATT
TGAGGGGTTCCTCTTTTTATTTTTTATAAACTGTGAAACTCAAGAGGAAGCAGGATCCCATG
CAATGCCTTTTATTGATGGCCTGCTATGTGCCAAGAAAGGTGTTAAATGTTTTCCAATGCTG
CCTCATTTATCCTGATCTTACAGACAAGCAAAAGGAGGTGTGAAGAGGTGAAGTTTCTCAC
CCAGCTGGAAAGTGGCAAAGTCATTCACAGATCTGCCTCCGCTCAAAAAAATTGCTTTATG
CAACTCTTTGGAAGCTAACTTCATGGGAGCTACATGCAGCTTCTCAATGAACCTTGTTTTGC
TGGCCTGCAGCCAGAAGTTACTACTCCTTTGGTTCCTGAGCA (SEQ ID NO: 34)

Enhancer mscre12 nucleotide sequence (501 bp):
GACTGCTAAGCTTTGGGCACTACCTGGGGTCAGTCTGCATCAAAATGTAAGGCTCAAATGT
GTAATTGTAAGTACTGTTTTGCTGAGCTGGAAGGGCTCCTTTGAAGCCCACGTTTTAATTTT
AATTTAGCCACACAGAGTGGCAAAGACAAATAGATTTATCCAAAATACATTTGGTAACAGAT
TTTTTGAGTCAGTTATTAATTTTATTTGAGGGGTTCCTCTTTTTATTTTTTATAAACTGTGAAA
CTCAAGAGGAAGCAGGATCCCATGCAATGCCTTTTATTGATGGCCTGCTATGTGCCAAGAA
AGGTGTTAAATGTTTTCCAATGCTGCCTCATTTATCCTGATCTTACAGACAAGCAAAAGGAG
GTGTGAAGAGGTGAAGTTTCTCACCCAGCTGGAAAGTGGCAAAGTCATTCACAGATCTGCC
TCCGCTCAAAAAAATTGCTTTATGCAACTCTTTGGAAGCTAACTTCATGGGAGCTACATGCA
GCTTCT (SEQ ID NO: 35)

Enhancer mscRE13 nucleotide sequence (501 bp):
GGTGGGCTATGTTACTGAGGGTCTCTGGGTGTTAGGAAAACAGGGCCCAGGAGTCTGGCT
GCTCGTATGCTGGCCCAGGCTCTTGTTTTTCTTGAGCTGACTTGCTGGAGAAGTGAGCTAA
GTCAGAAACAAAATGCCACATTGCACGCCCACTGAAGTCTGGGCTCAAGGGAAAGAAGAG
AGATTGCCAGAGCGTTAGCTGTTCCCAATCCACTCCTGGACCTTAAGCTGTCTTGAACAGA
GTTGCCAATCAGCTTGGTAGGGACTGGCCTTTGAGGAGGGGAGGGGGTGTAGGCAGGGG
AGGGGGAGAGAAGGGAGCAGTCTGCGCTCCATCTTAATTACCTCATCAGAAACAGCTCCC
TTCCCGCAAAGCTCTGGTGTCTTCTACAAGAGGGTGAGTCTTTGGCTTTACATGTGAACTT
GTGCCATTTGCCTGCGTATATAAACATGAAGGGTCGTCTGGGTTCAGAGCTGAAATCTTTC
ACTTGTGACTTAGCTGGG (SEQ ID NO: 36)

FIG. 79 cont'd

Enhancer mscRE16 nucleotide sequence (501 bp):
CTGTGCTCAGCAATTTACCAGGACACCCCCACCCCACATGTCTTGACCACTGTCTGGATAA
CTGGTATGCAGGACCACACTAGGCTTACTCACAGTGTAAACTCTCATAACCATCACTGGAG
CCCATCCTGCCTGGTAGACAAGGATTCAACCATGACTCATTGTACTTTAGTGGTGCCATGC
TTAGTCATCAGGTGCCCTGTGCTCTGACAGCCGAGGGTCAGAGCTGGAATCACACTCTTG
TTGTCTTTTAATCTCTCCCTCCCTTTCTTCCTTCTTTCTTCACTCTGTTGTGATTGCTCATGG
AACAGATCCTAGCTGGTCTCCCTGGCAACCTACATGATTTGAGCCCAACAGATGGATAATG
GGGACATCGACTTCCAATGTCATTCAACAGAATCATTGCCAAGGGAGTCTGATGAGCAGGC
AACTGAGATGACACCCTTATCAATATAGCTTCATTTTGGCAATCTGGAGTAGGTGTTTCAAA
AGGAGAGCCCC (SEQ ID NO: 37)

FIG. 79 cont'd

Enhancer 4XmscRE16 nucleotide sequence (2372 bp):
CTGTGCTCAGCAATTTACCAGGACACCCCCACCCCACATGTCTTGACCACTGTCTGGATAA
CTGGTATGCAGGACCACACTAGGCTTACTCACAGTGTAAACTCTCATAACCATCACTGGAG
CCCATCCTGCCTGGTAGACAAGGATTCAACCATGACTCATTGTACTTTAGTGGTGCCATGC
TTAGTCATCAGGTGCCCTGTGCTCTGACAGCCGAGGGTCAGAGCTGGAATCACACTCTTG
TTGTCTTTTAATCTCTCCCTCCCTTTCTTCCTTCTTTCTTCACTCTGTTGTGATTGCTCATGG
AACAGATCCTAGCTGGTCTCCCTGGCAACCTACATGATTTGAGCCCAACAGATGGATAATG
GGGACATCGACTTCCAATGTCATTCAACAGAATCATTGCCAAGGGAGTCTGATGAGCAGGC
AACTGAGATGACACCCTTATCAATATAGCTTCATTTTGGCAATCTGGAGTAGGTGTTTCAAA
AGGAGAGCCCCCACTGATGCCAGCAATACAGAACGTTCATGGGCAAGTGACATAGCGATA
GACAGATTCGACTCGGTACCAGGGTGCAGGAGAAATGTGACCTCAAAGTCTTGTTCTATAA
CTGTTGGACCTTAGGAGAGATCTGTGCTCAGCAATTTACCAGGACACCCCCACCCCACATG
TCTTGACCACTGTCTGGATAACTGGTATGCAGGACCACACTAGGCTTACTCACAGTGTAAA
CTCTCATAACCATCACTGGAGCCCATCCTGCCTGGTAGACAAGGATTCAACCATGACTCAT
TGTACTTTAGTGGTGCCATGCTTAGTCATCAGGTGCCCTGTGCTCTGACAGCCGAGGGTCA
GAGCTGGAATCACACTCTTGTTGTCTTTTAATCTCTCCCTCCCTTTCTTCCTTCTTTCTTCAC
TCTGTTGTGATTGCTCATGGAACAGATCCTAGCTGGTCTCCCTGGCAACCTACATGATTTG
AGCCCAACAGATGGATAATGGGGACATCGACTTCCAATGTCATTCAACAGAATCATTGCCA
AGGGAGTCTGATGAGCAGGCAACTGAGATGACACCCTTATCAATATAGCTTCATTTTGGCA
ATCTGGAGTAGGTGTTTCAAAAGGAGAGCCCCCACTGATGCCAGCAATACAGAACGTTCAT
GGGCAAGGATGATGGCATCATTGAGTAGCATGATCTCAATTGAGGGTGCAGGAGAAATGT
GACCTCAAAGTCTTGTTCTATAACTGTTGGACCTTAGGAGAGATCTGTGCTCAGCAATTTAC
CAGGACACCCCCACCCCACATGTCTTGACCACTGTCTGGATAACTGGTATGCAGGACCAC
ACTAGGCTTACTCACAGTGTAAACTCTCATAACCATCACTGGAGCCCATCCTGCCTGGTAG
ACAAGGATTCAACCATGACTCATTGTACTTTAGTGGTGCCATGCTTAGTCATCAGGTGCCC
TGTGCTCTGACAGCCGAGGGTCAGAGCTGGAATCACACTCTTGTTGTCTTTTAATCTCTCC
CTCCCTTTCTTCCTTCTTTCTTCACTCTGTTGTGATTGCTCATGGAACAGATCCTAGCTGGT
CTCCCTGGCAACCTACATGATTTGAGCCCAACAGATGGATAATGGGGACATCGACTTCCAA
TGTCATTCAACAGAATCATTGCCAAGGGAGTCTGATGAGCAGGCAACTGAGATGACACCCT
TATCAATATAGCTTCATTTTGGCAATCTGGAGTAGGTGTTTCAAAAGGAGAGCCCCCACTG
ATGCCAGCAATACAGAACGTTCATGGGCAAGGAGCTCAGGGTGCAGGAGAAATGTGACCT
CAAAGTCTTGTTCTATAACTGTTGGACCTTAGGAGAGATCTGTGCTCAGCAATTTACCAGGA
CACCCCCACCCCACATGTCTTGACCACTGTCTGGATAACTGGTATGCAGGACCACACTAG
GCTTACTCACAGTGTAAACTCTCATAACCATCACTGGAGCCCATCCTGCCTGGTAGACAAG
GATTCAACCATGACTCATTGTACTTTAGTGGTGCCATGCTTAGTCATCAGGTGCCCTGTGC
TCTGACAGCCGAGGGTCAGAGCTGGAATCACACTCTTGTTGTCTTTTAATCTCTCCCTCCC
TTTCTTCCTTCTTTCTTCACTCTGTTGTGATTGCTCATGGAACAGATCCTAGCTGGTCTCCC
TGGCAACCTACATGATTTGAGCCCAACAGATGGATAATGGGGACATCGACTTCCAATGTCA
TTCAACAGAATCATTGCCAAGGGAGTCTGATGAGCAGGCAACTGAGATGACACCCTTATCA
ATATAGCTTCATTTTGGCAATCTGGAGTAGGTGTTTCAAAAGGAGAGCCCC (SEQ ID NO:
38)

FIG. 79 cont'd

Enhancer eHGT_078h nucleotide sequence (536 bp):
TAGTCTGCCTCAGGTACACACTGAGAAACTGCTTTAATGTAACCTGACCCACGGTTATTAGT
GAAAATATCACTTTTGTTGTTACCTTATTCCCAACAAATTCATTTCTGCTTTAATGGAAAAGA
TCCGGGTTCACACTAATCAGGCCCAACGGAAGGCCATATTAGCAATTTGGCAGGTACCCG
AGGGCCATACCTAATCTGCATAAAATGAAGCAGATTGCAACCGCCCTCATCTTTTTTATTTT
TAAACTGGTTTTTGAAGCAGAGCATAAAATCTCAGAGGGAGAGACAGAAGATGCTAGTGCA
TACATTTTCCTTCATGCCTTTATTTTCATTCTTTTTGCACAAACCATCTTCCTGAATGGCTGT
TTACCTAAAGAAGAATAACAAAATAAAAGGTGCTAGGAAATGGAGTAGGCAGAGATCACAA
ATGTTTAATTAAAAAAAAAAAAAGTCATGTACTTTCATAGATATTCACAATCCTCTCTAGTATA
CTTTCAAATCAGTTTTAATTTCAGTTTAGTGTTTTTATGT (SEQ ID NO: 39)

Enhancer eHGT_078h Core nucleotide sequence (310 bp):
GAAAAGATCCGGGTTCACACTAATCAGGCCCAACGGAAGGCCATATTAGCAATTTGGCAG
GTACCCGAGGGCCATACCTAATCTGCATAAAATGAAGCAGATTGCAACCGCCCTCATCTTT
TTTATTTTTAAACTGGTTTTTGAAGCAGAGCATAAAATCTCAGAGGGAGAGACAGAAGATGC
TAGTGCATACATTTTCCTTCATGCCTTTATTTTCATTCTTTTTGCACAAACCATCTTCCTGAAT
GGCTGTTTACCTAAAGAAGAATAACAAAATAAAAGGTGCTAGGAAATGGAGTAGGCAGAGA
TC (SEQ ID NO: 177)

Enhancer eHGT_078h(3xCore) nucleotide sequence (980 bp):
GAAAAGATCCGGGTTCACACTAATCAGGCCCAACGGAAGGCCATATTAGCAATTTGGCAG
GTACCCGAGGGCCATACCTAATCTGCATAAAATGAAGCAGATTGCAACCGCCCTCATCTTT
TTTATTTTTAAACTGGTTTTTGAAGCAGAGCATAAAATCTCAGAGGGAGAGACAGAAGATGC
TAGTGCATACATTTTCCTTCATGCCTTTATTTTCATTCTTTTTGCACAAACCATCTTCCTGAAT
GGCTGTTTACCTAAAGAAGAATAACAAAATAAAAGGTGCTAGGAAATGGAGTAGGCAGAGA
TCGAGCAGAGCCCTCATCACACAGACTGAAAAGATCCGGGTTCACACTAATCAGGCCCAA
CGGAAGGCCATATTAGCAATTTGGCAGGTACCCGAGGGCCATACCTAATCTGCATAAAATG
AAGCAGATTGCAACCGCCCTCATCTTTTTTATTTTTAAACTGGTTTTTGAAGCAGAGCATAA
AATCTCAGAGGGAGAGACAGAAGATGCTAGTGCATACATTTTCCTTCATGCCTTTATTTTCA
TTCTTTTTGCACAAACCATCTTCCTGAATGGCTGTTTACCTAAAGAAGAATAACAAAATAAAA
GGTGCTAGGAAATGGAGTAGGCAGAGATCTGGGTGAGTAAGAGTAGGTGGCAACGAAAAG
ATCCGGGTTCACACTAATCAGGCCCAACGGAAGGCCATATTAGCAATTTGGCAGGTACCC
GAGGGCCATACCTAATCTGCATAAAATGAAGCAGATTGCAACCGCCCTCATCTTTTTTATTT
TTAAACTGGTTTTTGAAGCAGAGCATAAAATCTCAGAGGGAGAGACAGAAGATGCTAGTGC
ATACATTTTCCTTCATGCCTTTATTTTCATTCTTTTTGCACAAACCATCTTCCTGAATGGCTG
TTTACCTAAAGAAGAATAACAAAATAAAAGGTGCTAGGAAATGGAGTAGGCAGAGATC
(SEQ ID NO: 40)

FIG. 79 cont'd

Enhancer eHGT_058h nucleotide sequence (567 bp):
CAAAAGATGGAAGTTGGGAGGTTGAAGAAGTGCAGGATGGCATTCCAAGTGATGGGGGCA
ATGGCATGGAGGTAGGAAAGCATAAGGTATATTCAGGCTATAAATAATAGTTAGATTTGGCT
GGATCCTGGATTTGAGAAGCCAGGAAATGAGATAACACTGGTCACTTTCACTAAAGCTCAT
GAAAAAAAAAATACATACATATATATATATATAAAATAAATATACATATATATTTTTAAGCCCC
ATATGACTAGAGGAGGCAGCCCATCTGTTCTCTGGGCTTCACTTTTCTTGTCTGGGAAATG
AGTAGGTTGGACTGCATGGTCTTTAAGGTCTCTTTAGTATTATCTTGTTTGACTCCGTAAAG
AGAAAAACAAAGGTTCCTCCTGACATCTTGTGTTGCCTTCCAACGTCCAGTCCAGTGTGAT
TGTTTTAAGTACTCTTTGGATATTTTACTGTTATAAAAAGTGAAGAAAAAGACTGATTTTGCC
AAGTCTTATGGATCCAAATTAGTACTCATTGCACTATGGTCATTTAGTTGAGGACGATACTC
CAGCTTCAAAG (SEQ ID NO: 41)

Enhancer eHGT_058m nucleotide sequence (732 bp):
CGCGTGGTACATATTATAAGTTTGAGTCTGCAAGATGTGGCAAACCCTTCCTTTTCTCTTTA
TCTTGACAGTGGAAAACATCTAAGGAGTCTTTAAAATAACCACATCGGACTGAGCAGTGGA
GGGCAAAGAGAATGTCTGGAAGAACCTTTGTTTTTTTCGTTGGGACATCAAAGGATGTTATA
CTGAAGAGATCTCAAAGACCAGGCAGTCCAGCCTACTCGTTTCCCAGACAAGAGAAGTGA
AGCCAAGAAACAGATGGGCTGCCTCCTCTAGTCATATGGGGCTTAAAAATATATATCTCTAT
TTTTCATGAGTTTTCATGAAAGTGACCAGTGTTATCTCATTTCCTGTCTTCTCAAATTCAGGA
TCCTACCCAATCTAACTATTATTTATAGTGTGAATAAGCCCTCTACTTTCCTACCTCTACAAT
GCTCATTCTCCATTTTCCCATCATCTACTTCCATCTTGTGAAAAGTTTCCACTCTTCAGTGAT
GACCTCAAACATATCATTTCTTTTTTTTAATTCTTTTTTTATTAGATATTTTCTTTATATACATT
TCAAATGCTATCCTGAAAGTTCCCTATATCCTCCCTCTGCCCTGCTTCCCTACCCACCCACT
CCCACTTCTTGGCCCTGGCATTTCCCTGTACTGGGGCATATAAAGTTTGCAATACCAAGGG
GCCTCTCTTCACAGTGATGGCCAACTAGGCCATCTTCTGCTACGAGCT (SEQ ID NO: 42)

Enhancer eHGT_073h nucleotide sequence (756 bp):
ACTGGTCTGACTGCAGAGGAGGTCTGGGAGACCAGAGGGAGTGTGGAGAGGGTGAGGTT
AGAAGACAGGAACACCGAGCTGCATCGGCCAAATGGAGCCTTAGGGGGCCATGTGAGGC
TGAGGCAGGGAAGCAGGGATCCTGCCCTCCAGGTCCTTACAGTCAGGCGGGGACCAAAA
GCACGAGGATGCCAGCCCAATTCCCTATTAGGCAAAACGCAGCACCATCTGCACAATCCC
AGGAGCAAGAGCAGATATTTTATAACTTCCTTTTTTCTTTTTAAGTCTAAATTAAAAATAAAT
GTTCCCTTCAGCTCTCAGATGTATATCTCTGGTGCAACCTGCCCACATTCCCTCCCGCTGC
CCTTTCCAGAACATGGCAGGGGAAAGGAAGAAAGAGATGGATAGAGAGAGGGAGCCAGT
CCACCCAGCTTCAATGCCAGTGGATTGCACCTCTTCCAAGAGGGAAACGATTCAGGCGTG
GCCACGCAGACGGGTGGAGAGCGCCCAGAATGTGGCTGGTACCAAGGAAAGTGGAAGGA
GAGGGAAACAGGAGCCAACAGCTATGATTTCTAGCCCAGCCTCCACCCTATCGCGCTGCA
GGACCTTGGCCAAATCACACATCCTATCTCTGCTCCCATTTATAGTTCATAACATGGCTGAA
GTCCCCTCTGCCGCTCCAGCCCCCTGGCAGCTGTGCTCTCTGCACATCCGTCTGTACCTT
TGCTGCTCCCCTTCATTTTGGGTGTCCTACCATGG (SEQ ID NO: 43)

FIG. 79 cont'd

Enhancer eHGT_073m nucleotide sequence (670 bp):
ACTGGCCTGACTGGGAAGAATGTCCCAGACATTGACAAAAGACAATCTAGAGAGGGTAAG
GATGGGAGACCAGGGACACCAAAGAGCCCACTGGGTCCCTGTGGCCAGGCGGGGCCCA
GAGCACATGGTGCCAGCCTCGTTCCCTATTAGGCAAAGCACTGCACCATCTGTATAGTCCC
AGGAGCAGGAGCAGGAGCAGGCGTTTTATAACTTCCTTTTCTTTTTCAGTCTACATTAAAAA
TAAATGTTCCCTTCAGCTCTCAGATGTATATCTCTAGTGCAACCTGCCCACATTCCCTCCTG
CTGCCCTTTCCAGAACATGGCAGGGGAAGGGAAGGAAGAGATGGAGAGAGGGAGCCAGT
CCACCCGGCTGATGCCAGTGGATCACACCTCTTCTAAGAGGGAAGCGCGGCAGGCACGG
CCACACATGGTGGAAGGTGCCCAGAATGCATGGGGACCAGGGAAATGGAAGTGGAGGAA
ATGGGAGCCAACAGCCAGGCTTGCTTCCCACCCCCACCCTCCCGCACCGCAGGACCTTG
GCCAAATCACACATCCCATCTTTGCATTTATAGTTCATGCAGTGGCTGGAGTCCCCTCTGC
AGCTCCAGCCCTCTGGTGGCTGTCCTTGCTGCACGTCTCTCTGTACTTCCCCTTGTGTGTC
CTGCTGTGG (SEQ ID NO: 44)

Enhancer eHGT_075h nucleotide sequence (584 bp):
GAGGAACAGAACAAAACAGAACAAGCAGGTTCACTTGGGACGCCGGGAACACCCCGGGC
TTGCGCCCCTGCGCCTCCCCGCTGGCGGCCCCGCCAACTTCCCGGGGTGTCCCCTCCCT
ACCTTCTCTTCACCGCCCTGGCGCCTGGCCTGCGCGAGGTCGGGACTCGCGGGACCTCC
GCCTACCCCAGAAGCGGCTGTCTAAAGCGGGGGTGGGGGGGCGCCCCCTCCTGTCTGGT
TTTCCCTTCCAGTTGCCGGGAGAGGACTAGGCAGCCGGGAGCCGGGCCGTGCACCCGCT
GTGGCGCGCTGGCACCTCGGCCTCCGCAAACAGATTGCTCGCCCTCCTCGGGGAAAGCT
AGGAAAACAGTGCTAAGCCTCGCAAGCTGCCGCCCATTAATGCCTCTTAGCTTGCAAGATG
GGTTACTAGCTCTGAGCACGGCCCTCCCCTCGGGGCTTCTTACATTCTCCTCCCCCTCGC
CCCTTCTGTCTCCCTCCTTCTCCACGCCGCGGTACTCTCGCCTTCGCCCTCATTCTCTCCC
TCCACCTACTACCTCTTCCTTTTGTTTTCCGTTCTCCTGAATTTCCCT (SEQ ID NO: 45)

Enhancer eHGT_077h nucleotide sequence (648 bp):
GGGTCAGAGACACAGAGGATGACAGAGACCCAGAGAGAGGGAGACAGAGACCCAGAGAG
AGGGGGAGAGAGACCTAGAAATAGGGGGACAGAGACCCAGAGAGGGAAGAGATGGAAAC
CTAGAGAAGGAAGCAGACAGAGTCCCAAAGAGAGGCGGGGACAGAAACCCAGGAGATAG
AACATAGATGCAGAGAGATGAGAACAGAGATCCAGAATGCAAGAGAAAGATGGAGAGCCT
GGGAGACGGAGGATAGACAGGCTGGGGACGTGATTTGTGAGGTGCAGCCCCTCTCTGAG
GTGGGTAGGCAGCCAGGGGATCGGGCTGGATCCCAGGAAGGGGCTGGAACAGATGGAG
GCGAGGGAGACTGGGACGGGGGAGGAAGGAACAGCCAGACGGTCCAGGGGGAGGGAG
GTGGAAGAGCTGTGAGAACACAGCAACCCCTCCCCATCCTAGAACTTAAGGAGGTGGGGA
GGGGCAGTTAAGAAACAGGGGTGGGAGAAGCCAGGGAGTGGACAGAACCCAGAAGGAGT
AGGAATGAGACCCCAAGAGGAAGAAGACAGAGAGCCAGAGATAGGGGGGATTGAAGCCA
CTAGGACGAATAGTACAGGATGGCAGTAACTCCCCCCACCCATCAGAACCCATCACCCA
(SEQ ID NO: 46)

FIG. 79 cont'd

Enhancer eHGT_254h nucleotide sequence (566 bp):
GGCTTTTGGCAGAAATCAGTTCGTTGTGGTTTAAGGACTGAGGTCGCCTTTCTTTGCTGCT
AACTGTTGGCCAGGAAGTACTGTCAGCTACTACATGGTACTTGCTGGTCCTTGCACATGAC
CCCCTCCACCTTCAAACCAGGATTGACACAGTGTGTTGAGTCTTTCTTGAAGACTTTTGAAC
ATCTGACTTCCCATTCTGCCACTAGCCAGTTAAAATTCTCTAATTTTGAAGGACTCACCTGG
TTGGCCAAACCCACCCAAATAATCTCCACATCTTGAAGTCAACTGACCCAGGACTTTACATA
TGCAAAATCCCTTCACAGCAGTACCTAGATGAGTGTTTGCTTGAATAACTGGGACACAGGA
ATCTTGGGGGAGCCATCTTTAGAATTCGACCTCCTACAACCCTTCTGGAAATCTGAGAGTG
AGTCAGGGGAAGAAACCCTCTTTTGTAGTTTCCTTTTAGGGCTTTCTACTTTGCTCAAAGTT
GGGCACTATTTCACTTCAGTAGGGTCCTGCAAGCCCCATGAGGGTAGTGAGTGCTGTCCT
AGGAAACAGTAACT (SEQ ID NO: 47)

Enhancer eHGT_078m nucleotide sequence (520 bp):
CCCTGGCCTTCGAGCACATGCTCAGATGATGCTCCACCGTGGCCTGACCCACATCTTCTA
GTGGAAGCATGGTCCAGCAAAGCCTTTCTGTTCTAAAGGAAAGGATCTGAGTTGTCACCTC
CCAGGTCCGTGGAAGGCTTTTTAGCAGTTTGGCAGGTGCCTGAGGGCCACACCTCATCTG
CATAAAATGTGGCAGATTGCAACCGCCCTCGTCTTTTTTATTTTTAAACTGGTTTTTGAAACA
GAACATATATAAAAGCTCAGAGAAAGGGAAAGGAGATAGATGGCCGAGCTTCCATATCCCT
TAGTGCCTTTATTTTCATTCTTTTTCCATTTTCCTAAGTGGCTATTTACCAAGACAAAGATAA
CAAATCTGCTAGGAAAAGGAGTGGGCAGTGCTACAAAATGTTTTTTTTTTTTTAAAGAAAGT
CCTATCTTATAATAGATCTTCACCACGATGCCTCATGATGTATGCTCAAATCAGTTTTAATTG
AACTGTGTGTAGTATGCTCCTGTTTTG (SEQ ID NO: 48)

Enhancer eHGT_078m Core nucleotide sequence (401 bp):
GAAGCATGGTCCAGCAAAGCCTTTCTGTTCTAAAGGAAAGGATCTGAGTTGTCACCTCCCA
GGTCCGTGGAAGGCTTTTTAGCAGTTTGGCAGGTGCCTGAGGGCCACACCTCATCTGCAT
AAAATGTGGCAGATTGCAACCGCCCTCGTCTTTTTTATTTTTAAACTGGTTTTTGAAACAGA
ACATATATAAAAGCTCAGAGAAAGGGAAAGGAGATAGATGGCCGAGCTTCCATATCCCTTA
GTGCCTTTATTTTCATTCTTTTTCCATTTTCCTAAGTGGCTATTTACCAAGACAAAGATAACA
AATCTGCTAGGAAAAGGAGTGGGCAGTGCTACAAAATGTTTTTTTTTTTTTAAAGAAAGTCC
TATCTTATAATAGATCTTCACCACGATGCCTC (SEQ ID NO: 178)

FIG. 79 cont'd

Enhancer eHGT_078m(3xCore) nucleotide sequence (1253 bp):
GAAGCATGGTCCAGCAAAGCCTTTCTGTTCTAAAGGAAAGGATCTGAGTTGTCACCTCCCA
GGTCCGTGGAAGGCTTTTTAGCAGTTTGGCAGGTGCCTGAGGGCCACACCTCATCTGCAT
AAAATGTGGCAGATTGCAACCGCCCTCGTCTTTTTTATTTTTAAACTGGTTTTTGAAACAGA
ACATATATAAAAGCTCAGAGAAAGGGAAAGGAGATAGATGGCCGAGCTTCCATATCCCTTA
GTGCCTTTATTTTCATTCTTTTTCCATTTTCCTAAGTGGCTATTTACCAAGACAAAGATAACA
AATCTGCTAGGAAAAGGAGTGGGCAGTGCTACAAAATGTTTTTTTTTTTTTAAAGAAAGTCC
TATCTTATAATAGATCTTCACCACGATGCCTCGAGCAGAGCCCTCATCACACAGACTGAAG
CATGGTCCAGCAAAGCCTTTCTGTTCTAAAGGAAAGGATCTGAGTTGTCACCTCCCAGGTC
CGTGGAAGGCTTTTTAGCAGTTTGGCAGGTGCCTGAGGGCCACACCTCATCTGCATAAAAT
GTGGCAGATTGCAACCGCCCTCGTCTTTTTTATTTTTAAACTGGTTTTTGAAACAGAACATA
TATAAAAGCTCAGAGAAAGGGAAAGGAGATAGATGGCCGAGCTTCCATATCCCTTAGTGCC
TTTATTTTCATTCTTTTTCCATTTTCCTAAGTGGCTATTTACCAAGACAAAGATAACAAATCTG
CTAGGAAAAGGAGTGGGCAGTGCTACAAAATGTTTTTTTTTTTTTAAAGAAAGTCCTATCTT
ATAATAGATCTTCACCACGATGCCTCTGGGTGAGTAAGAGTAGGTGGCAACGAAGCATGGT
CCAGCAAAGCCTTTCTGTTCTAAAGGAAAGGATCTGAGTTGTCACCTCCCAGGTCCGTGGA
AGGCTTTTTAGCAGTTTGGCAGGTGCCTGAGGGCCACACCTCATCTGCATAAAATGTGGCA
GATTGCAACCGCCCTCGTCTTTTTTATTTTTAAACTGGTTTTTGAAACAGAACATATATAAAA
GCTCAGAGAAAGGGAAAGGAGATAGATGGCCGAGCTTCCATATCCCTTAGTGCCTTTATTT
TCATTCTTTTTCCATTTTCCTAAGTGGCTATTTACCAAGACAAAGATAACAAATCTGCTAGGA
AAAGGAGTGGGCAGTGCTACAAAATGTTTTTTTTTTTTTAAAGAAAGTCCTATCTTATAATAG
ATCTTCACCACGATGCCTC (SEQ ID NO: 49)

Enhancer eHGT_439m nucleotide sequence (386 bp):
AATTGCTGTCATTTACCTACGGTTGTCTCCAAATTTCTTCAACCAAGTAGAGAAAAATGAGA
GAGAAGGAAAGAAAAAAAGAGGTATGGGGAGAAGAGAAAGAAGGCAACTTGTTAAAAATCT
CAGTCAAACTTACATACTATATAGAACAGCATGGTGAATTTAGGGCACATGGATATAAAATG
GAAGTTTCTTATTCAGTAGCAGCAACTTGTGGGCACAGGAGTTGGCAAAGATAAAAATGTC
CAAAGTCACAAATACAATGTATAGTTAGTCATAGGTGCTGTTATTTGCCTCAAAAAATAGAC
TTTTATTTTGCCTTTCTTTTCTTTAACCACACTCAAAATTAGAGAACAGAGACAAAACCCAGC
AGGAAATAGCACAGA (SEQ ID NO: 50)

Enhancer eHGT_440h nucleotide sequence (363 bp):
AAGCCAATGACATTAGAGAAGTGTTCAAACAGTCAGCTAAATTCACTGCACTTCTCAACCAC
AGAAATATTTTCAGGTGATTCTGTTTTTGAGAAAACGTGGGAACCACAGGATCTACAACACT
TCCAGGCAAAACTCAACAGCTCTAATAATAGTGACAGAAGTGAAAGCCAATTTGGATAAAAT
AAGACATTGACTCAAAGTCCTCTGAGAGATTTTTCAAAACAAAGTTTACAAAGCTCCTTTTG
CCTTTTGGGAAATCACATTCTTCTTTGCACCTTGACTCTTTTTCTGAATTTCTTTCTGTCTGG
GAGGATCTCCTTACAGTGTTTCTTCTCCATCTGACATCATGAAATGTGATAC (SEQ ID NO:
51)

Beta-Globin Minimal promoter (pBGmin/minBGlobin/minBGprom):
GGGCTGGGCATAAAAGTCAGGGCAGAGCCATCTATTGCTTACATTTGCTTCTG (SEQ ID
NO: 52)

minCMV:
GAGGTAGGCGTGTACGGTGGGAGGCCTATATAAGCAGAGCTCGTTTAGTGAACCGTCAGA
TCGCCTGG (SEQ ID NO: 53)

FIG. 79 cont'd

Mutated minCMV promoter (SacI RE site removed):
GAGGTAGGCGTGTACGGTGGGAGGCCTATATAAGCAGAGCTGGTTTAGTGAACCGTCAGA
TCGCCTGG (SEQ ID NO: 54)

Hsp68 minimal Promoter (proHsp68):
CAGGAACATCCAAACTGAGCAGCCGGGGTCCCCCCCACCCCCCACCCCGCCCCACGCGG
CAACTTTGAGCCTGTGCTGGGACAGAGCCTCTAGTTCCTAAATTAGTCCATGAGGTCAGAG
GCAGCACTGCCATTGTAACGCGATTGGAGAGGATCACGTCACCGGACACGCCCCCAGGC
ATCTCCCTGGGTCTCCTAAACTTGGCGGGGAGAAGTTTTAGCCCTTAAGTTTTAGCCTTTAA
CCCCCATATTCAGAACTGTGCGAGTTGGCGAAACCCCACAAATCACAACAAACTGTACACA
ACACCGAGCTAGAGGTGATCTTTCTTGTCCATTCCACACAGGCCTTAGTAATGCGTCGCCA
TAGCAACAGTGTCACTAGTAGCACCAGCACTTCCCCACACCCTCCCCCTCAGGAATCCGTA
CTCTCCAGTGAACCCCAGAAACCTCTGGAGAGTTCTGGACAAGGGCGGAACCCACAACTC
CGATTACTCAAGGGAGGCGGGGAAGCTCCACCAGACGCGAAACTGCTGGAAGATTCCTG
GCCCCAAGGCCTCCTCCGGCTCGCTGATTGGCCCAGCGGAGAGTGGGCGGGGCCGGTG
AAGACTCCTTAAAGGCGCAGGGCGGCGAGCAGGTCACCAGACGCTGACAGCTACTCAGA
ACCAAATCTGGTTCCATCCAGAGACAAGCGAAGACAAGAGAAGCAGAGCGAGCGGCGCGT
TCCCGATCCTCGGCCAGGACCAGCCTTCCCCAGAGCATCCCTGCCGCGGAGCGCAACCT
TCCCAGGAGCATCCCTGCCGCGGAGCGCAACTTTCCCCGGAGCATCCACGCCGCGGAGC
GCAGCCTTCCAGAAGCAGAGCGCGGCGCC (SEQ ID NO: 55)

SYFP2:
ATGGTGAGCAAGGGCGAGGAGCTGTTCACCGGGGTGGTGCCCATCCTGGTCGAGCTGGA
CGGCGACGTAAACGGCCACAAGTTCAGCGTGTCCGGCGAGGGCGAGGGCGATGCCACCT
ACGGCAAGCTGACCCTGAAGCTGATCTGCACCACCGGCAAGCTGCCCGTGCCCTGGCCC
ACCCTCGTGACCACCCTGGGCTACGGCGTGCAGTGCTTCGCCCGCTACCCCGACCACAT
GAAGCAGCACGACTTCTTCAAGTCCGCCATGCCCGAAGGCTACGTCCAGGAGCGCACCAT
CTTCTTCAAGGACGACGGCAACTACAAGACCCGCGCCGAGGTGAAGTTCGAGGGCGACA
CCCTGGTGAACCGCATCGAGCTGAAGGGCATCGACTTCAAGGAGGACGGCAACATCCTG
GGGCACAAGCTGGAGTACAACTACAACAGCCACAACGTCTATATCACCGCCGACAAGCAG
AAGAACGGCATCAAGGCCAACTTCAAGATCCGCCACAACATCGAGGACGGCGGCGTGCA
GCTCGCCGACCACTACCAGCAGAACACCCCCATCGGCGACGGCCCCGTGCTGCTGCCCG
ACAACCACTACCTGAGCTACCAGTCCAAGCTGAGCAAAGACCCCAACGAGAAGCGCGATC
ACATGGTCCTGCTGGAGTTCGTGACCGCCGCCGGGATCACTCTCGGCATGGACGAGCTGT
ACAAGTAA (SEQ ID NO: 56)

FIG. 79 cont'd

EGFP:
ATGGTGAGCAAGGGCGAGGAGCTGTTCACCGGGGTGGTGCCCATCCTGGTCGAGCTGGA
CGGCGACGTAAACGGCCACAAGTTCAGCGTGTCCGGCGAGGGCGAGGGCGATGCCACCT
ACGGCAAGCTGACCCTGAAGTTCATCTGCACCACCGGCAAGCTGCCCGTGCCCTGGCCCA
CCCTCGTGACCACCCTGACCTACGGCGTGCAGTGCTTCAGCCGCTACCCCGACCACATGA
AGCAGCACGACTTCTTCAAGTCCGCCATGCCCGAAGGCTACGTCCAGGAGCGCACCATCT
TCTTCAAGGACGACGGCAACTACAAGACCCGCGCCGAGGTGAAGTTCGAGGGCGACACC
CTGGTGAACCGCATCGAGCTGAAGGGCATCGACTTCAAGGAGGACGGCAACATCCTGGG
GCACAAGCTGGAGTACAACTACAACAGCCACAACGTCTATATCATGGCCGACAAGCAGAA
GAACGGCATCAAGGTGAACTTCAAGATCCGCCACAACATCGAGGACGGCAGCGTGCAGCT
CGCCGACCACTACCAGCAGAACACCCCCATCGGCGACGGCCCCGTGCTGCTGCCCGACA
ACCACTACCTGAGCACCCAGTCCGCCCTGAGCAAAGACCCCAACGAGAAGCGCGATCACA
TGGTCCTGCTGGAGTTCGTGACCGCCGCCGGGATCACTCTCGGCATGGACGAGCTGTACA
AGTAA (SEQ ID NO: 57)

Optimized Flp recombinase (FlpO):
ATGGCTCCTAAGAAGAAGAGGAAGGTGATGAGCCAGTTCGACATCCTGTGCAAGACCCCC
CCCAAGGTGCTGGTGCGGCAGTTCGTGGAGAGATTCGAGAGGCCCAGCGGCGAGAAGAT
CGCCAGCTGTGCCGCCGAGCTGACCTACCTGTGCTGGATGATCACCCACAACGGCACCG
CCATCAAGAGGGCCACCTTCATGAGCTACAACACCATCATCAGCAACAGCCTGAGCTTCGA
CATCGTGAACAAGAGCCTGCAGTTCAAGTACAAGACCCAGAAGGCCACCATCCTGGAGGC
CAGCCTGAAGAAGCTGATCCCCGCCTGGGAGTTCACCATCATCCCTTACAACGGCCAGAA
GCACCAGAGCGACATCACCGACATCGTGTCCAGCCTGCAGCTGCAGTTCGAGAGCAGCG
AGGAGGCCGACAAGGGCAACAGCCACAGCAAGAAGATGCTGAAGGCCCTGCTGTCCGAG
GGCGAGAGCATCTGGGAGATCACCGAGAAGATCCTGAACAGCTTCGAGTACACCAGCAGG
TTCACCAAGACCAAGACCCTGTACCAGTTCCTGTTCCTGGCCACATTCATCAACTGCGGCA
GGTTCAGCGACATCAAGAACGTGGACCCCAAGAGCTTCAAGCTGGTGCAGAACAAGTACC
TGGGCGTGATCATTCAGTGCCTGGTGACCGAGACCAAGACAAGCGTGTCCAGGCACATCT
ACTTTTTCAGCGCCAGAGGCAGGATCGACCCCCTGGTGTACCTGGACGAGTTCCTGAGGA
ACAGCGAGCCCGTGCTGAAGAGAGTGAACAGGACCGGCAACAGCAGCAGCAACAAGCAG
GAGTACCAGCTGCTGAAGGACAACCTGGTGCGCAGCTACAACAAGGCCCTGAAGAAGAAC
GCCCCCTACCCCATCTTCGCTATCAAGAACGGCCCTAAGAGCCACATCGGCAGGCACCTG
ATGACCAGCTTTCTGAGCATGAAGGGCCTGACCGAGCTGACAAACGTGGTGGGCAACTGG
AGCGACAAGAGGGCCTCCGCCGTGGCCAGGACCACCTACACCCACCAGATCACCGCCAT
CCCCGACCACTACTTCGCCCTGGTGTCCAGGTACTACGCCTACGACCCCATCAGCAAGGA
GATGATCGCCCTGAAGGACGAGACCAACCCCATCGAGGAGTGGCAGCACATCGAGCAGC
TGAAGGGCAGCGCCGAGGGCAGCATCAGATACCCCGCCTGGAACGGCATCATCAGCCAG
GAGGTGCTGGACTACCTGAGCAGCTACATCAACAGGCGGATCTGA (SEQ ID NO: 58)

FIG. 79 cont'd

Improved Cre recombinase (iCre):
ATGGTGCCCAAGAAGAAGAGGAAAGTCTCCAACCTGCTGACTGTGCACCAAAACCTGCCT
GCCCTCCCTGTGGATGCCACCTCTGATGAAGTCAGGAAGAACCTGATGGACATGTTCAGG
GACAGGCAGGCCTTCTCTGAACACACCTGGAAGATGCTCCTGTCTGTGTGCAGATCCTGG
GCTGCCTGGTGCAAGCTGAACAACAGGAAATGGTTCCCTGCTGAACCTGAGGATGTGAGG
GACTACCTCCTGTACCTGCAAGCCAGAGGCCTGGCTGTGAAGACCATCCAACAGCACCTG
GGCCAGCTCAACATGCTGCACAGGAGATCTGGCCTGCCTCGCCCTTCTGACTCCAATGCT
GTGTCCCTGGTGATGAGGAGAATCAGAAAGGAGAATGTGGATGCTGGGGAGAGAGCCAA
GCAGGCCCTGGCCTTTGAACGCACTGACTTTGACCAAGTCAGATCCCTGATGGAGAACTC
TGACAGATGCCAGGACATCAGGAACCTGGCCTTCCTGGGCATTGCCTACAACACCCTGCT
GCGCATTGCCGAAATTGCCAGAATCAGAGTGAAGGACATCTCCCGCACCGATGGTGGGAG
AATGCTGATCCACATTGGCAGGACCAAGACCCTGGTGTCCACAGCTGGTGTGGAGAAGGC
CCTGTCCCTGGGGGTTACCAAGCTGGTGGAGAGATGGATCTCTGTGTCTGGTGTGGCTGA
TGACCCCAACAACTACCTGTTCTGCCGGGTCAGAAAGAATGGTGTGGCTGCCCCTTCTGC
CACCTCCCAACTGTCCACCCGGGCCCTGGAAGGGATCTTTGAGGCCACCCACCGCCTGAT
CTATGGTGCCAAGGATGACTCTGGGCAGAGATACCTGGCCTGGTCTGGCCACTCTGCCAG
AGTGGGTGCTGCCAGGGACATGGCCAGGGCTGGTGTGTCCATCCCTGAAATCATGCAGG
CTGGTGGCTGGACCAATGTGAACATTGTGATGAACTACATCAGAAACCTGGACTCTGAGAC
TGGGGCCATGGTGAGGCTGCTCGAGGATGGGGACTAA (SEQ ID NO: 59)

WPRE3:
ATAATCAACCTCTGGATTACAAAATTTGTGAAAGATTGACTGGTATTCTTAACTATGTTGCTC
CTTTTACGCTATGTGGATACGCTGCTTTAATGCCTTTGTATCATGCTATTGCTTCCCGTATG
GCTTTCATTTTCTCCTCCTTGTATAAATCCTGGTTGCTGTCTCTTTATGAGGAGTTGTGGCC
CGTTGTCAGGCAACGTGGCGTGGTGTGCACTGTGTTTGCTGACGCAACCCCCACTGGTTG
GGGCATTGCCACCACCTGTCAGCTCCTTTCCGGGACTTTCGCTTTCCCCCTCCCTATTGCC
ACGGCGGAACTCATCGCCGCCTGCCTTGCCCGCTGCTGGACAGGGGCTCGGCTGTTGGG
CACTGACAATTCCGTGG (SEQ ID NO: 60)

BGHpA:
CGACTGTGCCTTCTAGTTGCCAGCCATCTGTTGTTTGCCCCTCCCCCGTGCCTTCCTTGAC
CCTGGAAGGTGCCACTCCCACTGTCCTTTCCTAATAAAATGAGGAAATTGCATCGCATTGT
CTGAGTAGGTGTCATTCTATTCTGGGGGGTGGGGTGGGGCAGGACAGCAAGGGGGAGGA
TTGGGAAGACAATAGCAGGCATG (SEQ ID NO: 61)

N-terminal 3XHA tag (Protein)
MVYPYDVPDYAGSYPYDVPDYAGSYPYDVPDYA (SEQ ID NO: 62)

N-terminal 3XHA tag (DNA)
ATGGTTTACCCGTATGATGTCCCGGATTACGCTGGCAGCTACCCATACGATGTACCCGACT
ATGCCGGCAGTTATCCCTACGACGTCCCTGACTACGCA (SEQ ID NO: 63)

P2A:
GGCAGCGGCGCCACCAACTTCAGCCTGCTGAAGCAGGCCGGCGACGTGGAGGAGAACCC
CGGCCCCGGAGCTAGCGGA (SEQ ID NO: 64)

T2A:
(GSG)EGRGSLLTCGDVEENPGP (SEQ ID NO: 65)

FIG. 79 cont'd

E2A:
(GSG)QCTNYALLKLAGDVESNPGPP (SEQ ID NO: 66)

F2A:
(GSG)VKQTLNFDLLKLAGDVESNPGP (SEQ ID NO: 67)

tet-Transactivator version 2 (tTA2):
ATGTCTAGACTGGACAAGAGCAAAGTCATAAACTCTGCTCTGGAATTACTCAATGAAGTCG
GTATCGAAGGCCTGACGACAAGGAAACTCGCTCAAAAGCTGGGAGTTGAGCAGCCTACCC
TGTACTGGCACGTGAAGAACAAGCGGGCCCTGCTCGATGCCCTGGCAATCGAGATGCTGG
ACAGGCATCATACCCACTTCTGCCCCCTGGAAGGCGAGTCATGGCAAGACTTTCTGCGGA
ACAACGCCAAGTCATTCCGCTGTGCTCTCCTCTCACATCGCGACGGGGCTAAAGTGCATCT
CGGCACCCGCCCAACAGAGAAACAGTACGAAACCCTGGAAAATCAGCTCGCGTTCCTGTG
TCAGCAAGGCTTCTCCCTGGAGAACGCACTGTACGCTCTGTCCGCCGTGGGCCACTTTAC
ACTGGGCTGCGTATTGGAGGATCAGGAGCATCAAGTAGCAAAAGAGGAAAGAGAGACACC
TACCACCGATTCTATGCCCCCACTTCTGAGACAAGCAATTGAGCTGTTCGACCATCAGGGA
GCCGAACCTGCCTTCCTTTTCGGCCTGGAACTAATCATATGTGGCCTGGAGAAACAGCTAA
AGTGCGAAAGCGGCGGGCCGGCCGACGCCCTTGACGATTTTGACTTAGACATGCTCCCAG
CCGATGCCCTTGACGACTTTGACCTTGATATGCTGCCTGCTGACGCTCTTGACGATTTTGA
CCTTGACATGCTCCCCGGGTAA (SEQ ID NO: 68)

PHP.eB capsid:
MAADGYLPDWLEDNLSEGIREWWALKPGAPQPKANQQHQDNARGLVLPGYKYLGPGNGLDK
GEPVNAADAAALEHDKAYDQQLKAGDNPYLKYNHADAEFQERLKEDTSFGGNLGRAVFQAKK
RLLEPLGLVEEAAKTAPGKKRPVEQSPQEPDSSAGIGKSGAQPAKKRLNFGQTGDTESVPDP
QPIGEPPAAPSGVGSLTMASGGGAPVADNNEGADGVGSSSGNWHCDSQWLGDRVITTSTRT
WALPTYNNHLYKQISNSTSGGSSNDNAYFGYSTPWGYFDFNRFHCHFSPRDWQRLINNNWG
FRPKRLNFKLFNIQVKEVTDNNGVKTIANNLTSTVQVFTDSDYQLPYVLGSAHEGCLPPFPADV
FMIPQYGYLTLNDGSQAVGRSSFYCLEYFPSQMLRTGNNFQFSYEFENVPFHSSYAHSQSLD
RLMNPLIDQYLYYLSKTINGSGQNQQTLKFSVAGPSNMAVQGRNYIPGPSYRQQRVSTTVTQN
NNSEFAWPGASSWALNGRNSLMNPGPAMASHKEGEDRFFPLSGSLIFGKQGTGRDNVDADK
VMITNEEEIKTTNPVATESYGQVATNHQSDGTLAVPFKAQAQTGWVQNQGILPGMVWQDRDV
YLQGPIWAKIPHTDGNFHPSPLMGGFGMKHPPPQILIKNTPVPADPPTAFNKDKLNSFITQYST
GQVSVEIEWELQKENSKRWNPEIQYTSNYYKSNNVEFAVNTEGVYSEPRPIGTRYLTRNL
(SEQ ID NO: 69)

FIG. 79 cont'd

AAV9 VP1 capsid protein:
MAADGYLPDWLEDNLSEGIREWWALKPGAPQPKANQQHQDNARGLVLPGYKYLGPGNGLDK
GEPVNAADAAALEHDKAYDQQLKAGDNPYLKYNHADAEFQERLKEDTSFGGNLGRAVFQAKK
RLLEPLGLVEEAAKTAPGKKRPVEQSPQEPDSSAGIGKSGAQPAKKRLNFGQTGDTESVPDP
QPIGEPPAAPSGVGSLTMASGGGAPVADNNEGADGVGSSSGNWHCDSQWLGDRVITTSTRT
WALPTYNNHLYKQISNSTSGGSSNDNAYFGYSTPWGYFDFNRFHCHFSPRDWQRLINNNWG
FRPKRLNFKLFNIQVKEVTDNNGVKTIANNLTSTVQVFTDSDYQLPYVLGSAHEGCLPPFPADV
FMIPQYGYLTLNDGSQAVGRSSFYCLEYFPSQMLRTGNNFQFSYEFENVPFHSSYAHSQSLD
RLMNPLIDQYLYYLSKTINGSGQNQQTLKFSVAGPSNMAVQGRNYIPGPSYRQQRVSTTVTQN
NNSEFAWPGASSWALNGRNSLMNPGPAMASHKEGEDRFFPLSGSLIFGKQGTGRDNVDADK
VMITNEEEIKTTNPVATESYGQVATNHQSAQAQAQTGWVQNQGILPGMVWQDRDVYLQGPIW
AKIPHTDGNFHPSPLMGGFGMKHPPPQILIKNTPVPADPPTAFNKDKLNSFITQYSTGQVSVEIE
WELQKENSKRWNPEIQYTSNYYKSNNVEFAVNTEGVYSEPRPIGTRYLTRNL (SEQ ID NO: 70)

Plasmid backbone 1 (including ITRs; L-ITR is underlined and R-ITR is in bold; indicated sequences should be inserted into Plasmid backbone 1 directly following the L-ITR and conclude just before the start of the R-ITR):
CCTGCAGGCAGCTGCGCGCTCGCTCGCTCACTGAGGCCGCCCGGGCGTCGGGCGACCTT
TGGTCGCCCGGCCTCAGTGAGCGAGCGAGCGCGCAGAGAGGGAGTGGCCAACTCCATCA
CTAGGGGTTCCTGGCGCCTGATGCGGTATTTTCTCCTTACGCATCTGTGCGGTATTTCACA
CCGCATACGTCAAAGCAACCATAGTACGCGCCCTGTAGCGGCGCATTAAGCGCGGCGGG
TGTGGTGGTTACGCGCAGCGTGACCGCTACACTTGCCAGCGCCCTAGCGCCCGCTCCTTT
CGCTTTCTTCCCTTCCTTTCTCGCCACGTTCGCCGGCTTTCCCCGTCAAGCTCTAAATCGG
GGGCTCCCTTTAGGGTTCCGATTTAGTGCTTTACGGCACCTCGACCCCAAAAAACTTGATT
TGGGTGATGGTTCACGTAGTGGGCCATCGCCCTGATAGACGGTTTTTCGCCCTTTGACGTT
GGAGTCCACGTTCTTTAATAGTGGACTCTTGTTCCAAACTGGAACAACACTCAACCCTATCT
CGGGCTATTCTTTTGATTTATAAGGGATTTTGCCGATTTCGGCCTATTGGTTAAAAAATGAG
CTGATTTAACAAAAATTTAACGCGAATTTTAACAAAATATTAACGTTTACAATTTTATGGTGC
ACTCTCAGTACAATCTGCTCTGATGCCGCATAGTTAAGCCAGCCCCGACACCCGCCAACAC
CCGCTGACGCGCCCTGACGGGCTTGTCTGCTCCCGGCATCCGCTTACAGACAAGCTGTGA
CCGTCTCCGGGAGCTGCATGTGTCAGAGGTTTTCACCGTCATCACCGAAACGCGCGAGAC
GAAAGGGCCTCGTGATACGCCTATTTTTATAGGTTAATGTCATGATAATAATGGTTTCTTAG
ACGTCAGGTGGCACTTTTCGGGGAAATGTGCGCGGAACCCCTATTTGTTTATTTTTCTAAAT
ACATTCAAATATGTATCCGCTCATGAGACAATAACCCTGATAAATGCTTCAATAATATTGAAA
AAGGAAGAGTATGAGTATTCAACATTTCCGTGTCGCCCTTATTCCCTTTTTTGCGGCATTTT
GCCTTCCTGTTTTTGCTCACCCAGAAACGCTGGTGAAAGTAAAAGATGCTGAAGATCAGTT
GGGTGCACGAGTGGGTTACATCGAACTGGATCTCAACAGCGGTAAGATCCTTGAGAGTTTT
CGCCCCGAAGAACGTTTTCCAATGATGAGCACTTTTAAAGTTCTGCTATGTGGCGCGGTAT
TATCCCGTATTGACGCCGGGCAAGAGCAACTCGGTCGCCGCATACACTATTCTCAGAATGA
CTTGGTTGAGTACTCACCAGTCACAGAAAAGCATCTTACGGATGGCATGACAGTAAGAGAA
TTATGCAGTGCTGCCATAACCATGAGTGATAACACTGCGGCCAACTTACTTCTGACAACGA
TCGGAGGACCGAAGGAGCTAACCGCTTTTTTGCACAACATGGGGGATCATGTAACTCGCC
TTGATCGTTGGGAACCGGAGCTGAATGAAGCCATACCAAACGACGAGCGTGACACCACGA
TGCCTGTAGCAATGGCAACAACGTTGCGCAAACTATTAACTGGCGAACTACTTACTCTAGC
TTCCCGGCAACAATTAATAGACTGGATGGAGGCGGATAAAGTTGCAGGACCACTTCTGCG
CTCGGCCCTTCCGGCTGGCTGGTTTATTGCTGATAAATCTGGAGCCGGTGAGCGTGGGTC
TCGCGGTATCATTGCAGCACTGGGGCCAGATGGTAAGCCCTCCCGTATCGTAGTTATCTAC

FIG. 79 cont'd

ACGACGGGGAGTCAGGCAACTATGGATGAACGAAATAGACAGATCGCTGAGATAGGTGCC
TCACTGATTAAGCATTGGTAACTGTCAGACCAAGTTTACTCATATATACTTTAGATTGATTTA
AAACTTCATTTTTAATTTAAAAGGATCTAGGTGAAGATCCTTTTTGATAATCTCATGACCAAA
ATCCCTTAACGTGAGTTTTCGTTCCACTGAGCGTCAGACCCCGTAGAAAAGATCAAAGGAT
CTTCTTGAGATCCTTTTTTTCTGCGCGTAATCTGCTGCTTGCAAACAAAAAAACCACCGCTA
CCAGCGGTGGTTTGTTTGCCGGATCAAGAGCTACCAACTCTTTTTCCGAAGGTAACTGGCT
TCAGCAGAGCGCAGATACCAAATACTGTCCTTCTAGTGTAGCCGTAGTTAGGCCACCACTT
CAAGAACTCTGTAGCACCGCCTACATACCTCGCTCTGCTAATCCTGTTACCAGTGGCTGCT
GCCAGTGGCGATAAGTCGTGTCTTACCGGGTTGGACTCAAGACGATAGTTACCGGATAAG
GCGCAGCGGTCGGGCTGAACGGGGGGTTCGTGCACACAGCCCAGCTTGGAGCGAACGA
CCTACACCGAACTGAGATACCTACAGCGTGAGCTATGAGAAAGCGCCACGCTTCCCGAAG
GGAGAAAGGCGGACAGGTATCCGGTAAGCGGCAGGGTCGGAACAGGAGAGCGCACGAG
GGAGCTTCCAGGGGGAAACGCCTGGTATCTTTATAGTCCTGTCGGGTTTCGCCACCTCTG
ACTTGAGCGTCGATTTTTGTGATGCTCGTCAGGGGGGCGGAGCCTATGGAAAAACGCCAG
CAACGCGGCCTTTTTACGGTTCCTGGCCTTTTGCTGGCCTTTTGCTCACATGT**CCTGCAGG
CAGCTGCGCGCTCGCTCGCTCACTGAGGCCGCCCGGGCAAAGCCCGGGCGTCGGGCGA
CCTTTGGTCGCCCGGCCTCAGTGAGCGAGCGAGCGCGCAGAGAGGGAGTGGCCAACTC
CATCACTAGGGGTTCCT** (SEQ ID NO: 71)

Plasmid backbone 2 (including ITRs; R-ITR is Bold (start of sequence). L-ITR is underlined (end of sequence); indicated sequences are inserted into Plasmid backbone 2 directly following the L-ITR and conclude just before the start of the R-ITR. Thus, insertion site is the start and end of the rAAV sequence).

rAAV:

**AGGAACCCCTAGTGATGGAGTTGGCCACTCCCTCTCTGCGCGCTCGCTCGCTCACTGAG
GCCGGGCGACCAAAGGTCGCCCGACGCCCGGGCTTTGCCCGGGCGGCCTCAGTGAGCG
AGCGAGCGCGCAGCTGCCTGCAGGGGCGCCTG**ATGCGGTATTTTCTCCTTACGCATCTGT
GCGGTATTTCACACCGCATACGTCAAAGCAACCATAGTACGCGCCCTGTAGCGGCGCATT
AAGCGCGGCGGGTGTGGTGGTTACGCGCAGCGTGACCGCTACACTTGCCAGCGCCCTAG
CGCCCGCTCCTTTCGCTTTCTTCCCTTCCTTTCTCGCCACGTTCGCCGGCTTTCCCCGTCA
AGCTCTAAATCGGGGGCTCCCTTTAGGGTTCCGATTTAGTGCTTTACGGCACCTCGACCCC
AAAAAACTTGATTTGGGTGATGGTTCACGTAGTGGGCCATCGCCCTGATAGACGGTTTTTC
GCCCTTTGACGTTGGAGTCCACGTTCTTTAATAGTGGACTCTTGTTCCAAACTGGAACAAC
ACTCAACCCTATCTCGGGCTATTCTTTTGATTTATAAGGGATTTTGCCGATTTCGGCCTATT
GGTTAAAAAATGAGCTGATTTAACAAAAATTTAACGCGAATTTTAACAAAATATTAACGTTTA
CAATTTTATGGTGCACTCTCAGTACAATCTGCTCTGATGCCGCATAGTTAAGCCAGCCCCG
ACACCCGCCAACACCCGCTGACGCGCCCTGACGGGCTTGTCTGCTCCCGGCATCCGCTTA
CAGACAAGCTGTGACCGTCTCCGGGAGCTGCATGTGTCAGAGGTTTTCACCGTCATCACC
GAAACGCGCGAGACGAAAGGGCCTCGTGATACGCCTATTTTTATAGGTTAATGTCATGATA
ATAATGGTTTCTTAGACGTCAGGTGGCACTTTTCGGGGAAATGTGCGCGGAACCCCTATTT
GTTTATTTTTCTAAATACATTCAAATATGTATCCGCTCATGAGACAATAACCCTGATAAATGC
TTCAATAATATTGAAAAAGGAAGAGTATGAGTATTCAACATTTCCGTGTCGCCCTTATTCCC
TTTTTTGCGGCATTTTGCCTTCCTGTTTTTGCTCACCCAGAAACGCTGGTGAAAGTAAAAGA
TGCTGAAGATCAGTTGGGTGCACGAGTGGGTTACATCGAACTGGATCTCAACAGCGGTAA
GATCCTTGAGAGTTTTCGCCCCGAAGAACGTTTTCCAATGATGAGCACTTTTAAAGTTCTGC
TATGTGGCGCGGTATTATCCCGTATTGACGCCGGGCAAGAGCAACTCGGTCGCCGCATAC
ACTATTCTCAGAATGACTTGGTTGAGTACTCACCAGTCACAGAAAAGCATCTTACGGATGG
CATGACAGTAAGAGAATTATGCAGTGCTGCCATAACCATGAGTGATAACACTGCGGCCAAC

FIG. 79 cont'd

TTACTTCTGACAACGATCGGAGGACCGAAGGAGCTAACCGCTTTTTTGCACAACATGGGG
GATCATGTAACTCGCCTTGATCGTTGGGAACCGGAGCTGAATGAAGCCATACCAAACGAC
GAGCGTGACACCACGATGCCTGTAGCAATGGCAACAACGTTGCGCAAACTATTAACTGGC
GAACTACTTACTCTAGCTTCCCGGCAACAATTAATAGACTGGATGGAGGCGGATAAAGTTG
CAGGACCACTTCTGCGCTCGGCCCTTCCGGCTGGCTGGTTTATTGCTGATAAATCTGGAG
CCGGTGAGCGTGGGTCTCGCGGTATCATTGCAGCACTGGGGCCAGATGGTAAGCCCTCC
CGTATCGTAGTTATCTACACGACGGGGAGTCAGGCAACTATGGATGAACGAAATAGACAGA
TCGCTGAGATAGGTGCCTCACTGATTAAGCATTGGTAACTGTCAGACCAAGTTTACTCATAT
ATACTTTAGATTGATTTAAAACTTCATTTTTAATTTAAAAGGATCTAGGTGAAGATCCTTTTTG
ATAATCTCATGACCAAAATCCCTTAACGTGAGTTTTCGTTCCACTGAGCGTCAGACCCCGTA
GAAAAGATCAAAGGATCTTCTTGAGATCCTTTTTTTCTGCGCGTAATCTGCTGCTTGCAAAC
AAAAAAACCACCGCTACCAGCGGTGGTTTGTTTGCCGGATCAAGAGCTACCAACTCTTTTT
CCGAAGGTAACTGGCTTCAGCAGAGCGCAGATACCAAATACTGTCCTTCTAGTGTAGCCGT
AGTTAGGCCACCACTTCAAGAACTCTGTAGCACCGCCTACATACCTCGCTCTGCTAATCCT
GTTACCAGTGGCTGCTGCCAGTGGCGATAAGTCGTGTCTTACCGGGTTGGACTCAAGACG
ATAGTTACCGGATAAGGCGCAGCGGTCGGGCTGAACGGGGGGTTCGTGCACACAGCCCA
GCTTGGAGCGAACGACCTACACCGAACTGAGATACCTACAGCGTGAGCTATGAGAAAGCG
CCACGCTTCCCGAAGGGAGAAAGGCGGACAGGTATCCGGTAAGCGGCAGGGTCGGAACA
GGAGAGCGCACGAGGGAGCTTCCAGGGGGAAACGCCTGGTATCTTTATAGTCCTGTCGG
GTTTCGCCACCTCTGACTTGAGCGTCGATTTTTGTGATGCTCGTCAGGGGGGCGGAGCCT
ATGGAAAAACGCCAGCAACGCGGCCTTTTTACGGTTCCTGGCCTTTTGCTGGCCTTTTGCT
CACATGTCCTGCAGGCAGCTGCGCGCTCGCTCGCTCACTGAGGCCGCCCGGGCAAAGCC
CGGGCGTCGGGCGACCTTTGGTCGCCCGGCCTCAGTGAGCGAGCGAGCGCGCAGAGAG
GGAGTGGCCAACTCCATCACTAGGGGTTCCT (SEQ ID NO: 72)

Nucleotide sequences for constructs are below with enhancer sequence in bold

Construct T502-050 nucleotide sequence: rAAV_Grik1_enhScnn1a-2-Hsp68-EGFP-WPRE3-BGHpA (sequence should be inserted into Plasmid backbone 1):
GGCCGCACGCGTTCTAGACAGGAACATCCAAACTGAGCAGCCGGGGTCCCCCCCACCCC
CCACCCCGCCCCACGCGGCAACTTTGAGCCTGTGCTGGGACAGAGCCTCTAGTTCCTAAA
TTAGTCCATGAGGTCAGAGGCAGCACTGCCATTGTAACGCGATTGGAGAGGATCACGTCA
CCGGACACGCCCCCAGGCATCTCCCTGGGTCTCCTAAACTTGGCGGGGAGAAGTTTTAGC
CCTTAAGTTTTAGCCTTTAACCCCCATATTCAGAACTGTGCGAGTTGGCGAAACCCCACAA
ATCACAACAAACTGTACACAACACCGAGCTAGAGGTGATCTTTCTTGTCCATTCCACACAG
GCCTTAGTAATGCGTCGCCATAGCAACAGTGTCACTAGTAGCACCAGCACTTCCCCACACC
CTCCCCCTCAGGAATCCGTACTCTCCAGTGAACCCCAGAAACCTCTGGAGAGTTCTGGAC
AAGGGCGGAACCCACAACTCCGATTACTCAAGGGAGGCGGGGAAGCTCCACCAGACGCG
AAACTGCTGGAAGATTCCTGGCCCCAAGGCCTCCTCCGGCTCGCTGATTGGCCCAGCGGA
GAGTGGGCGGGGCCGGTGAAGACTCCTTAAAGGCGCAGGGCGGCGAGCAGGTCACCAG
ACGCTGACAGCTACTCAGAACCAAATCTGGTTCCATCCAGAGACAAGCGAAGACAAGAGA
AGCAGAGCGAGCGGCGCGTTCCCGATCCTCGGCCAGGACCAGCCTTCCCCAGAGCATCC
CTGCCGCGGAGCGCAACCTTCCCAGGAGCATCCCTGCCGCGGAGCGCAACTTTCCCCGG
AGCATCCACGCCGCGGAGCGCAGCCTTCCAGAAGCAGAGCGCGGCGCCACATATGCCGC
CGCCACCATGGTGAGCAAGGGCGAGGAGCTGTTCACCGGGGTGGTGCCCATCCTGGTCG
AGCTGGACGGCGACGTAAACGGCCACAAGTTCAGCGTGTCCGGCGAGGGCGAGGGCGAT
GCCACCTACGGCAAGCTGACCCTGAAGTTCATCTGCACCACCGGCAAGCTGCCCGTGCCC

FIG. 79 cont'd

TGGCCCACCCTCGTGACCACCCTGACCTACGGCGTGCAGTGCTTCAGCCGCTACCCCGAC
CACATGAAGCAGCACGACTTCTTCAAGTCCGCCATGCCCGAAGGCTACGTCCAGGAGCGC
ACCATCTTCTTCAAGGACGACGGCAACTACAAGACCCGCGCCGAGGTGAAGTTCGAGGGC
GACACCCTGGTGAACCGCATCGAGCTGAAGGGCATCGACTTCAAGGAGGACGGCAACATC
CTGGGGCACAAGCTGGAGTACAACTACAACAGCCACAACGTCTATATCATGGCCGACAAG
CAGAAGAACGGCATCAAGGTGAACTTCAAGATCCGCCACAACATCGAGGACGGCAGCGTG
CAGCTCGCCGACCACTACCAGCAGAACACCCCCATCGGCGACGGCCCCGTGCTGCTGCC
CGACAACCACTACCTGAGCACCCAGTCCGCCCTGAGCAAAGACCCCAACGAGAAGCGCG
ATCACATGGTCCTGCTGGAGTTCGTGACCGCCGCCGGGATCACTCTCGGCATGGACGAGC
TGTACAAGTAAGTTAATTAATCTCATAATCAACCTCTGGATTACAAAATTTGTGAAAGATTGA
CTGGTATTCTTAACTATGTTGCTCCTTTTACGCTATGTGGATACGCTGCTTTAATGCCTTTGT
ATCATGCTATTGCTTCCCGTATGGCTTTCATTTTCTCCTCCTTGTATAAATCCTGGTTAGTTC
TTGCCACGGCGGAACTCATCGCCGCCTGCCTTGCCCGCTGCTGGACAGGGGCTCGGCTG
TTGGGCACTGACAATTCCGTGGCTCGACTGTGCCTTCTAGTTGCCAGCCATCTGTTGTTTG
CCCCTCCCCCGTGCCTTCCTTGACCCTGGAAGGTGCCACTCCCACTGTCCTTTCCTAATAA
AATGAGGAAATTGCATCGCATTGTCTGAGTAGGTGTCATTCTATTCTGGGGGGTGGGGTG
GGGCAGGACAGCAAGGGGGAGGATTGGGAAGACAATAGCAGGCATGACTTGCTGCTATC
CCCTAGGTGCTGTCATTTACCTACGGTTGTCTCCAAATTTCTTCAACCAAGTAGAGAAAAA
TGAGAGAGAAGGAAAGAAAAAAAGAGGTATGGGGAGAAGAGAAAGAAGGCAACTTGTT
AAAAATCTCAGTCAAACTTACATACTATATAGAACAGCATGGTGAATTTAGGGCACATGG
ATATAAAATGGAAGTTTCTTATTCAGTAGCAGCAACTTGTGGGCACAGGAGTTGGCAAAG
ATAAAAATGTCCAAAGTCACAAATACAATGTATAGTTAGTCATAGGTGCTGTTATTTGCCT
CAAAAAATAGACTTTTATTTTGCCTTTCTTTTCTTTAACCACACTCAAAATTAGAGAACAG
AGACAAAACCCAGCAGGAAATAGCACAGAAAGCCCACAGAATCAAAGACGTGTTCAAA
CAGCCAGCTGAATTCATTGCACATTTCAACCACAGAAATATTTTCAGGTGATTCTGTTGTT
TGACAAAACGTGGGAACCACAGGATCTACAACACTTGCAAGCAAAACTCAACAGCTCTA
ATAATAGTTACAGAAGTGAAAGCCAATTTGGATAAAATAAGACATTGACTCAAGTCCTCT
CAGAAGAGTTTTGAAAGCAAAGTTTACAAAAGTCTGGTTTGTCCTTTGGGATTTACAGAC
CTTTCAGCCCCTTGATTCATTTTTTTTTTTTTGGATTTCTTCATCACTGGGAGAATTCCCAT
GCATTATTTCTCCCCTGCTTCAAAATCATCAAATGTGAAACATTTTTCACTCTTTTCTTCTG
TATATAGTGATAAAATAGCTATTGGCTTTTGGCTAAATGTGCTACTTTGAGCCCACCCACA
CAAGGGAGAAATGGGGGCAGACATGAGTTTGGGCATGAGTGAGCTCTGCCTTCTCAGAG
GTGAGCCACGTGGTGCGGACCGAGCGGCCG (SEQ ID NO: 73)

Construct T502-054 nucleotide sequence: rAAV_Grik1_enhScnn1a-2-pBGmin-EGFP-WPRE3-BGHpA (sequence includes ITRs and plasmid backbone in plain text and synthetic AAV genome sequence is underlined):
CCTGCAGGCAGCTGCGCGCTCGCTCGCTCACTGAGGCCGCCCGGGCAAAGCCCGGGCG
TCGGGCGACCTTTGGTCGCCCGGCCTCAGTGAGCGAGCGAGCGCGCAGAGAGGGAGTG
GCCAACTCCATCACTAGGGGTTCCTGCGGCCGCACGCGTTCTAGAGGGCTGGGCATAAAA
GTCAGGGCAGAGCCATCTATTGCTTACATTTGCTTCTGACATATGCCGCCGCCACCATGGT
GAGCAAGGGCGAGGAGCTGTTCACCGGGGTGGTGCCCATCCTGGTCGAGCTGGACGGC
GACGTAAACGGCCACAAGTTCAGCGTGTCCGGCGAGGGCGAGGGCGATGCCACCTACGG
CAAGCTGACCCTGAAGTTCATCTGCACCACCGGCAAGCTGCCCGTGCCCTGGCCCACCCT
CGTGACCACCCTGACCTACGGCGTGCAGTGCTTCAGCCGCTACCCCGACCACATGAAGCA
GCACGACTTCTTCAAGTCCGCCATGCCCGAAGGCTACGTCCAGGAGCGCACCATCTTCTT
CAAGGACGACGGCAACTACAAGACCCGCGCCGAGGTGAAGTTCGAGGGCGACACCCTGG
TGAACCGCATCGAGCTGAAGGGCATCGACTTCAAGGAGGACGGCAACATCCTGGGGCAC

FIG. 79 cont'd

AAGCTGGAGTACAACTACAACAGCCACAACGTCTATATCATGGCCGACAAGCAGAAGAAC
GGCATCAAGGTGAACTTCAAGATCCGCCACAACATCGAGGACGGCAGCGTGCAGCTCGCC
GACCACTACCAGCAGAACACCCCCATCGGCGACGGCCCCGTGCTGCTGCCCGACAACCA
CTACCTGAGCACCCAGTCCGCCCTGAGCAAAGACCCCAACGAGAAGCGCGATCACATGGT
CCTGCTGGAGTTCGTGACCGCCGCCGGGATCACTCTCGGCATGGACGAGCTGTACAAGTA
AGTTAATTAATCTCATAATCAACCTCTGGATTACAAAATTTGTGAAAGATTGACTGGTATTCT
TAACTATGTTGCTCCTTTTACGCTATGTGGATACGCTGCTTTAATGCCTTTGTATCATGCTAT
TGCTTCCCGTATGGCTTTCATTTTCTCCTCCTTGTATAAATCCTGGTTAGTTCTTGCCACGG
CGGAACTCATCGCCGCCTGCCTTGCCCGCTGCTGGACAGGGGCTCGGCTGTTGGGCACT
GACAATTCCGTGGCTCGACTGTGCCTTCTAGTTGCCAGCCATCTGTTGTTTGCCCCTCCCC
CGTGCCTTCCTTGACCCTGGAAGGTGCCACTCCCACTGTCCTTTCCTAATAAAATGAGGAA
ATTGCATCGCATTGTCTGAGTAGGTGTCATTCTATTCTGGGGGGTGGGGTGGGGCAGGAC
AGCAAGGGGGAGGATTGGGAAGACAATAGCAGGCATGACTTGCTGCTATCCCCTAGGTGC
TGTCATTTACCTACGGTTGTCTCCAAATTTCTTCAACCAAGTAGAGAAAAATGAGAGAGA
AGGAAAGAAAAAAAGAGGTATGGGGAGAAGAGAAAGAAGGCAACTTGTTAAAAATCTC
AGTCAAACTTACATACTATATAGAACAGCATGGTGAATTTAGGGCACATGGATATAAAAT
GGAAGTTTCTTATTCAGTAGCAGCAACTTGTGGGCACAGGAGTTGGCAAAGATAAAAAT
GTCCAAAGTCACAAATACAATGTATAGTTAGTCATAGGTGCTGTTATTTGCCTCAAAAAAT
AGACTTTTATTTTGCCTTTCTTTTCTTTAACCACACTCAAAATTAGAGAACAGAGACAAAA
CCCAGCAGGAAATAGCACAGAAAGCCCACAGAATCAAAGACGTGTTCAAACAGCCAGC
TGAATTCATTGCACATTTCAACCACAGAAATATTTTCAGGTGATTCTGTTGTTTGACAAAA
CGTGGGAACCACAGGATCTACAACACTTGCAAGCAAAACTCAACAGCTCTAATAATAGT
TACAGAAGTGAAAGCCAATTTGGATAAAATAAGACATTGACTCAAGTCCTCTCAGAAGA
GTTTTGAAAGCAAAGTTTACAAAAGTCTGGTTTGTCCTTTGGGATTTACAGACCTTTCAGC
CCCTTGATTCATTTTTTTTTTTTTGGATTTCTTCATCACTGGGAGAATTCCCATGCATTATTT
CTCCCCTGCTTCAAAATCATCAAATGTGAAACATTTTTCACTCTTTTCTTCTGTATATAGTG
ATAAAATAGCTATTGGCTTTTGGCTAAATGTGCTACTTTGAGCCCACCCACACAAGGGAG
AAATGGGGGCAGACATGAGTTTGGGCATGAGTGAGCTCTGCCTTCTCAGAGGTGAGCCA
CGTGGTGCGGACCGAGCGGCCGCAGGAACCCCTAGTGATGGAGTTGGCCACTCCCTCTC
TGCGCGCTCGCTCGCTCACTGAGGCCGGGCGACCAAAGGTCGCCCGACGCCCGGGCTTT
GCCCGGGCGGCCTCAGTGAGCGAGCGAGCGCGCAGCTGCCTGCAGGGGCGCCTGATGC
GGTATTTTCTCCTTACGCATCTGTGCGGTATTTCACACCGCATACGTCAAAGCAACCATAGT
ACGCGCCCTGTAGCGGCGCATTAAGCGCGGCGGGTGTGGTGGTTACGCGCAGCGTGACC
GCTACACTTGCCAGCGCCCTAGCGCCCGCTCCTTTCGCTTTCTTCCCTTCCTTTCTCGCCA
CGTTCGCCGGCTTTCCCCGTCAAGCTCTAAATCGGGGGCTCCCTTTAGGGTTCCGATTTAG
TGCTTTACGGCACCTCGACCCCAAAAAACTTGATTTGGGTGATGGTTCACGTAGTGGGCCA
TCGCCCTGATAGACGGTTTTTCGCCCTTTGACGTTGGAGTCCACGTTCTTTAATAGTGGAC
TCTTGTTCCAAACTGGAACAACACTCAACCCTATCTCGGGCTATTCTTTTGATTTATAAGGG
ATTTTGCCGATTTCGGCCTATTGGTTAAAAAATGAGCTGATTTAACAAAAATTTAACGCGAA
TTTTAACAAAATATTAACGTTTACAATTTTATGGTGCACTCTCAGTACAATCTGCTCTGATGC
CGCATAGTTAAGCCAGCCCCGACACCCGCCAACACCCGCTGACGCGCCCTGACGGGCTT
GTCTGCTCCCGGCATCCGCTTACAGACAAGCTGTGACCGTCTCCGGGAGCTGCATGTGTC
AGAGGTTTTCACCGTCATCACCGAAACGCGCGAGACGAAAGGGCCTCGTGATACGCCTAT
TTTTATAGGTTAATGTCATGATAATAATGGTTTCTTAGACGTCAGGTGGCACTTTTCGGGGA
AATGTGCGCGGAACCCCTATTTGTTTATTTTTCTAAATACATTCAAATATGTATCCGCTCATG
AGACAATAACCCTGATAAATGCTTCAATAATATTGAAAAAGGAAGAGTATGAGTATTCAACA
TTTCCGTGTCGCCCTTATTCCCTTTTTTGCGGCATTTTGCCTTCCTGTTTTTGCTCACCCAG
AAACGCTGGTGAAAGTAAAAGATGCTGAAGATCAGTTGGGTGCACGAGTGGGTTACATCG

FIG. 79 cont'd

AACTGGATCTCAACAGCGGTAAGATCCTTGAGAGTTTTCGCCCCGAAGAACGTTTTCCAAT
GATGAGCACTTTTAAAGTTCTGCTATGTGGCGCGGTATTATCCCGTATTGACGCCGGGCAA
GAGCAACTCGGTCGCCGCATACACTATTCTCAGAATGACTTGGTTGAGTACTCACCAGTCA
CAGAAAAGCATCTTACGGATGGCATGACAGTAAGAGAATTATGCAGTGCTGCCATAACCAT
GAGTGATAACACTGCGGCCAACTTACTTCTGACAACGATCGGAGGACCGAAGGAGCTAAC
CGCTTTTTTGCACAACATGGGGGATCATGTAACTCGCCTTGATCGTTGGGAACCGGAGCTG
AATGAAGCCATACCAAACGACGAGCGTGACACCACGATGCCTGTAGCAATGGCAACAACG
TTGCGCAAACTATTAACTGGCGAACTACTTACTCTAGCTTCCCGGCAACAATTAATAGACTG
GATGGAGGCGGATAAAGTTGCAGGACCACTTCTGCGCTCGGCCCTTCCGGCTGGCTGGTT
TATTGCTGATAAATCTGGAGCCGGTGAGCGTGGGTCTCGCGGTATCATTGCAGCACTGGG
GCCAGATGGTAAGCCCTCCCGTATCGTAGTTATCTACACGACGGGGAGTCAGGCAACTAT
GGATGAACGAAATAGACAGATCGCTGAGATAGGTGCCTCACTGATTAAGCATTGGTAACTG
TCAGACCAAGTTTACTCATATATACTTTAGATTGATTTAAAACTTCATTTTTAATTTAAAAGGA
TCTAGGTGAAGATCCTTTTTGATAATCTCATGACCAAAATCCCTTAACGTGAGTTTTCGTTC
CACTGAGCGTCAGACCCCGTAGAAAAGATCAAAGGATCTTCTTGAGATCCTTTTTTTCTGC
GCGTAATCTGCTGCTTGCAAACAAAAAAACCACCGCTACCAGCGGTGGTTTGTTTGCCGGA
TCAAGAGCTACCAACTCTTTTTCCGAAGGTAACTGGCTTCAGCAGAGCGCAGATACCAAAT
ACTGTCCTTCTAGTGTAGCCGTAGTTAGGCCACCACTTCAAGAACTCTGTAGCACCGCCTA
CATACCTCGCTCTGCTAATCCTGTTACCAGTGGCTGCTGCCAGTGGCGATAAGTCGTGTCT
TACCGGGTTGGACTCAAGACGATAGTTACCGGATAAGGCGCAGCGGTCGGGCTGAACGG
GGGGTTCGTGCACACAGCCCAGCTTGGAGCGAACGACCTACACCGAACTGAGATACCTAC
AGCGTGAGCTATGAGAAAGCGCCACGCTTCCCGAAGGGAGAAAGGCGGACAGGTATCCG
GTAAGCGGCAGGGTCGGAACAGGAGAGCGCACGAGGGAGCTTCCAGGGGGAAACGCCT
GGTATCTTTATAGTCCTGTCGGGTTTCGCCACCTCTGACTTGAGCGTCGATTTTTGTGATG
CTCGTCAGGGGGGCGGAGCCTATGGAAAAACGCCAGCAACGCGGCCTTTTTACGGTTCCT
GGCCTTTTGCTGGCCTTTTGCTCACATGT (SEQ ID NO: 179)

Construct T502-057 nucleotide sequence: scAAV_mscRE4-pBGmin-SYFP2-WPRE3-bGHpA (sequence includes ITRs and plasmid backbone in plain text and synthetic AAV genome sequence is underlined):
AAAGCTTCCCGGGGGGATCTGGGCCACTCCCTCTCTGCGCGCTCGCTCGCTCACTGAGG
CCGGGCGACCAAAGGTCGCCCGACGCCCGGGCTTTGCCCGGGCGGCCTCAGTGAGCGA
GCGAGCGCGCAGAGAGGGAGTGGCCAACTCCATCACTAGGGGTTCCTGGAGGGGTGGAG
TCGTGACCTAGGACGCGTATAAGCCTTGGGGGCAATCAAACTATTACATTGAGTCCTTGG
ATTTGCTACAAATTACATTTTAAATGCAATCATTTTATAAAAGCTTCAACACTCACACTTG
GAAGCGTTACCCTGTTGAATATCACTGACTCACTAACTTGCATTGCCATGCTAACTTGCTT
TCAGAGAGATCTCAGAACACATCATCTTCTGCTATTTCAATACATGCACATTAATTTCCTA
TCAACGTGTGCTGATCAGGAACTCTGTAATCTGGCACCGGTGTTTATTTTTATTCCTGTCT
ATTCCTGTTGGCTCACGAAAAGATTGTTTGAGCAAGTGTTTTATGGTGAGTTGTATCATAT
GTACATTGATTTAATCTGCCCACATTCAGTTCTACAAGCGGAGCCAAAAAAATAGAGACA
AGCATAATTTTCATTCAACATGAGCCCCTCAATGCAAGCCAAGTACCTCATCTGGTGCTC
AGCTAAAGCAACAGCAATCTGTTCCACCCTGGAGACACAACTGGCCACAGAAAACTTAG
TGAAAAGAGGCAATGCTATGCACAGGACAAATGAGCTCGGGCTGGGCATAAAAGTCAGG
GCAGAGCCATCTATTGCTTACATTTGCTTCTGGGATCCAGATCTTTCGAAGCTAGCGCTAC
CGGTCGCCACCATGGTGAGCAAGGGCGAGGAGCTGTTCACCGGGGTGGTGCCCATCCTG
GTCGAGCTGGACGGCGACGTAAACGGCCACAAGTTCAGCGTGTCCGGCGAGGGCGAGG
GCGATGCCACCTACGGCAAGCTGACCCTGAAGCTGATCTGCACCACCGGCAAGCTGCCC
GTGCCCTGGCCCACCCTCGTGACCACCCTGGGCTACGGCGTGCAGTGCTTCGCCCGCTA

FIG. 79 cont'd

CCCCGACCACATGAAGCAGCACGACTTCTTCAAGTCCGCCATGCCCGAAGGCTACGTCCA
GGAGCGCACCATCTTCTTCAAGGACGACGGCAACTACAAGACCCGCGCCGAGGTGAAGTT
CGAGGGCGACACCCTGGTGAACCGCATCGAGCTGAAGGGCATCGACTTCAAGGAGGACG
GCAACATCCTGGGGCACAAGCTGGAGTACAACTACAACAGCCACAACGTCTATATCACCG
CCGACAAGCAGAAGAACGGCATCAAGGCCAACTTCAAGATCCGCCACAACATCGAGGACG
GCGGCGTGCAGCTCGCCGACCACTACCAGCAGAACACCCCCATCGGCGACGGCCCCGTG
CTGCTGCCCGACAACCACTACCTGAGCTACCAGTCCAAGCTGAGCAAAGACCCCAACGAG
AAGCGCGATCACATGGTCCTGCTGGAGTTCGTGACCGCCGCCGGGATCACTCTCGGCATG
GACGAGCTGTACAAGTAAGTCGACGGCGCGCCGCGGCCGCGAATTCGATATCATAATCAA
CCTCTGGATTACAAAATTTGTGAAAGATTGACTGGTATTCTTAACTATGTTGCTCCTTTTACG
CTATGTGGATACGCTGCTTTAATGCCTTTGTATCATGCTATTGCTTCCCGTATGGCTTTCAT
TTTCTCCTCCTTGTATAAATCCTGGTTAGTTCTTGCCACGGCGGAACTCATCGCCGCCTGC
CTTGCCCGCTGCTGGACAGGGGCTCGGCTGTTGGGCACTGACAATTCCGTGGCTCGAGC
GACTGTGCCTTCTAGTTGCCAGCCATCTGTTGTTTGCCCCTCCCCCGTGCCTTCCTTGACC
CTGGAAGGTGCCACTCCCACTGTCCTTTCCTAATAAAATGAGGAAATTGCATCGCATTGTC
TGAGTAGGTGTCATTCTATTCTGGGGGGTGGGGTGGGGCAGGACAGCAAGGGGGAGGAT
TGGGAAGACAATAGCAGGCATGACTAGTCCACTCCCTCTCTGCGCGCTCGCTCGCTCACT
GAGGCCGGGCGACCAAAGGTCGCCCGACGCCCGGGCTTTGCCCGGGCGGCCTCAGTGA
GCGAGCGAGCGCGCAGAGAGGGACAGATCCGGGCCCGCATGCGTCGACAATTCACTGGC
CGTCGTTTTACAACGTCGTGACTGGGAAAACCCTGGCGTTACCCAACTTAATCGCCTTGCA
GCACATCCCCCTTTCGCCAGCTGGCGTAATAGCGAAGAGGCCCGCACCGATCGCCCTTCC
CAACAGTTGCGCAGCCTGAATGGCGAATGGCGCCTGATGCGGTATTTTCTCCTTACGCATC
TGTGCGGTATTTCACACCGCATATGGTGCACTCTCAGTACAATCTGCTCTGATGCCGCATA
GTTAAGCCAGCCCCGACACCCGCCAACACCCGCTGACGCGCCCTGACGGGCTTGTCTGC
TCCCGGCATCCGCTTACAGACAAGCTGTGACCGTCTCCGGGAGCTGCATGTGTCAGAGGT
TTTCACCGTCATCACCGAAACGCGCGAGACGAAAGGGCCTCGTGATACGCCTATTTTTATA
GGTTAATGTCATGATAATAATGGTTTCTTAGACGTCAGGTGGCACTTTTCGGGGAAATGTG
CGCGGAACCCCTATTTGTTTATTTTTCTAAATACATTCAAATATGTATCCGCTCATGAGACAA
TAACCCTGATAAATGCTTCAATAATATTGAAAAAGGAAGAGTATGAGTATTCAACATTTCCG
TGTCGCCCTTATTCCCTTTTTTGCGGCATTTTGCCTTCCTGTTTTTGCTCACCCAGAAACGC
TGGTGAAAGTAAAAGATGCTGAAGATCAGTTGGGTGCACGAGTGGGTTACATCGAACTGG
ATCTCAACAGCGGTAAGATCCTTGAGAGTTTTCGCCCCGAAGAACGTTTTCCAATGATGAG
CACTTTTAAAGTTCTGCTATGTGGCGCGGTATTATCCCGTATTGACGCCGGGCAAGAGCAA
CTCGGTCGCCGCATACACTATTCTCAGAATGACTTGGTTGAGTACTCACCAGTCACAGAAA
AGCATCTTACGGATGGCATGACAGTAAGAGAATTATGCAGTGCTGCCATAACCATGAGTGA
TAACACTGCGGCCAACTTACTTCTGACAACGATCGGAGGACCGAAGGAGCTAACCGCTTTT
TTGCACAACATGGGGGATCATGTAACTCGCCTTGATCGTTGGGAACCGGAGCTGAATGAA
GCCATACCAAACGACGAGCGTGACACCACGATGCCTGTAGCAATGGCAACAACGTTGCGC
AAACTATTAACTGGCGAACTACTTACTCTAGCTTCCCGGCAACAATTAATAGACTGGATGGA
GGCGGATAAAGTTGCAGGACCACTTCTGCGCTCGGCCCTTCCGGCTGGCTGGTTTATTGC
TGATAAATCTGGAGCCGGTGAGCGTGGGTCTCGCGGTATCATTGCAGCACTGGGGCCAGA
TGGTAAGCCCTCCCGTATCGTAGTTATCTACACGACGGGGAGTCAGGCAACTATGGATGA
ACGAAATAGACAGATCGCTGAGATAGGTGCCTCACTGATTAAGCATTGGTAACTGTCAGAC
CAAGTTTACTCATATATACTTTAGATTGATTTAAAACTTCATTTTTAATTTAAAAGGATCTAGG
TGAAGATCCTTTTTGATAATCTCATGACCAAAATCCCTTAACGTGAGTTTTCGTTCCACTGA
GCGTCAGACCCCGTAGAAAAGATCAAAGGATCTTCTTGAGATCCTTTTTTTCTGCGCGTAAT
CTGCTGCTTGCAAACAAAAAAACCACCGCTACCAGCGGTGGTTTGTTTGCCGGATCAAGAG
CTACCAACTCTTTTTCCGAAGGTAACTGGCTTCAGCAGAGCGCAGATACCAAATACTGTTC

FIG. 79 cont'd

TTCTAGTGTAGCCGTAGTTAGGCCACCACTTCAAGAACTCTGTAGCACCGCCTACATACCT
CGCTCTGCTAATCCTGTTACCAGTGGCTGCTGCCAGTGGCGATAAGTCGTGTCTTACCGG
GTTGGACTCAAGACGATAGTTACCGGATAAGGCGCAGCGGTCGGGCTGAACGGGGGGTT
CGTGCACACAGCCCAGCTTGGAGCGAACGACCTACACCGAACTGAGATACCTACAGCGTG
AGCTATGAGAAAGCGCCACGCTTCCCGAAGGGAGAAAGGCGGACAGGTATCCGGTAAGC
GGCAGGGTCGGAACAGGAGAGCGCACGAGGGAGCTTCCAGGGGGAAACGCCTGGTATCT
TTATAGTCCTGTCGGGTTTCGCCACCTCTGACTTGAGCGTCGATTTTTGTGATGCTCGTCA
GGGGGGCGGAGCCTATGGAAAAACGCCAGCAACGCGGCCTTTTTACGGTTCCTGGCCTTT
TGCTGGCCTTTTGCTCACATGTTCTTTCCTGCGTTATCCCCTGATTCTGTGGATAACCGTAT
TACCGCCTTTGAGTGAGCTGATACCGCTCGCCGCAGCCGAACGACCGAGCGCAGCGAGT
CAGTGAGCGAGGAAGCGGAAGAGCGCCCAATACGCAAACCGCCTCTCCCCGCGCGTTGG
CCGATTCATTAATGCAGCTGGCACGACAGGTTTCCCGACTGGAAAGCGGGCAGTGAGCGC
AACGCAATTAATGTGAGTTAGCTCACTCATTAGGCACCCCAGGCTTTACACTTTATGCTTCC
GGCTCGTATGTTGTGTGGAATTGTGAGCGGATAACAATTTCACACAGGAAACAGCTATGAC
CATGATTACGCCAAGCTCTCGAGATCTAG (SEQ ID NO: 74)

Construct T502-059 nucleotide sequence: rAAV_mscRE3-pBGmin-SYFP2-WPRE3-BGHpA (sequence includes ITRs and plasmid backbone in plain text and synthetic AAV genome sequence is underlined):

AAAGCTTCCCGGGGGGATCTGGGCCACTCCCTCTCTGCGCGCTCGCTCGCTCACTGAGG
CCGGGCGACCAAAGGTCGCCCGACGCCCGGGCTTTGCCCGGGCGGCCTCAGTGAGCGA
GCGAGCGCGCAGAGAGGGAGTGGCCAACTCCATCACTAGGGGTTCCTGGAGGGGTGGAG
TCGTGACCTAGGACGCGTACCTTTCCAGCCTGGCTTACAGGCTTTTTTCACCACAGTACC
AATTGCCCATGCTCTGCTCATTAATTTAAATGGCAATGACTATCTGGGTTTTAAAATAGAG
AAGTGTCAGGATGGGAACACGCAATCATTTGGCTTTTTGCGTTCCAGCACTGTTTTGAAT
AGCAGGGTTTTCACTTCCTATGAAACCTTAGCAGGAGGAAAAGCGGAAACTAAACCATA
AAGTGAGAGGGATGAGGGGAGGGAGGGACTTGAGTATTTGTAAACTCAGGGTGGCTGG
CCCTGCCTACCAGGCTGCTCTCTACCACCGGAGGCTAGGAGTGGAAAAACTTGATTTAC
GTGTTGTGCCTGCCTTTTTTTTTTCTTCTTCTTCTTCTTCTTCTTCTTCGTCTCCACACCACC
TTCTGTACACCTGACTCTGCATAAGCCTATCTGAAGCTGGCTTGGTGGCAGGGATAGCTG
GAGAACAGAAGAATGTGCGGAGGGAGGGAGGGAGGAAGGGAGGGCTGGTACTTTTCCA
TTCACATCTCCACAGTGGCTGTTCTTGTTTATTTCAACCACCGGAGCTCGGGCTGGGCAT
AAAAGTCAGGGCAGAGCCATCTATTGCTTACATTTGCTTCTGGGATCCAGATCTTTCGAAG
CTAGCGCTACCGGTCGCCACCATGGTGAGCAAGGGCGAGGAGCTGTTCACCGGGGTGGT
GCCCATCCTGGTCGAGCTGGACGGCGACGTAAACGGCCACAAGTTCAGCGTGTCCGGCG
AGGGCGAGGGCGATGCCACCTACGGCAAGCTGACCCTGAAGCTGATCTGCACCACCGGC
AAGCTGCCCGTGCCCTGGCCCACCCTCGTGACCACCCTGGGCTACGGCGTGCAGTGCTT
CGCCCGCTACCCCGACCACATGAAGCAGCACGACTTCTTCAAGTCCGCCATGCCCGAAGG
CTACGTCCAGGAGCGCACCATCTTCTTCAAGGACGACGGCAACTACAAGACCCGCGCCGA
GGTGAAGTTCGAGGGCGACACCCTGGTGAACCGCATCGAGCTGAAGGGCATCGACTTCAA
GGAGGACGGCAACATCCTGGGGCACAAGCTGGAGTACAACTACAACAGCCACAACGTCTA
TATCACCGCCGACAAGCAGAAGAACGGCATCAAGGCCAACTTCAAGATCCGCCACAACAT
CGAGGACGGCGGCGTGCAGCTCGCCGACCACTACCAGCAGAACACCCCCATCGGCGACG
GCCCCGTGCTGCTGCCCGACAACCACTACCTGAGCTACCAGTCCAAGCTGAGCAAAGACC
CCAACGAGAAGCGCGATCACATGGTCCTGCTGGAGTTCGTGACCGCCGCCGGGATCACT
CTCGGCATGGACGAGCTGTACAAGTAAGTCGACGGCGCGCCGCGGCCGCGAATTCGATA
TCATAATCAACCTCTGGATTACAAAATTTGTGAAAGATTGACTGGTATTCTTAACTATGTTGC
TCCTTTTACGCTATGTGGATACGCTGCTTTAATGCCTTTGTATCATGCTATTGCTTCCCGTA

FIG. 79 cont'd

TGGCTTTCATTTTCTCCTCCTTGTATAAATCCTGGTTAGTTCTTGCCACGGCGGAACTCATC
GCCGCCTGCCTTGCCCGCTGCTGGACAGGGGCTCGGCTGTTGGGCACTGACAATTCCGT
GGCTCGAGCGACTGTGCCTTCTAGTTGCCAGCCATCTGTTGTTTGCCCCTCCCCCGTGCC
TTCCTTGACCCTGGAAGGTGCCACTCCCACTGTCCTTTCCTAATAAAATGAGGAAATTGCAT
CGCATTGTCTGAGTAGGTGTCATTCTATTCTGGGGGGTGGGGTGGGGCAGGACAGCAAG
GGGGAGGATTGGGAAGACAATAGCAGGCATGACTAGTCCACTCCCTCTCTGCGCGCTCGC
TCGCTCACTGAGGCCGGGCGACCAAAGGTCGCCCGACGCCCGGGCTTTGCCCGGGCGG
CCTCAGTGAGCGAGCGAGCGCGCAGAGAGGGACAGATCCGGGCCCGCATGCGTCGACAA
TTCACTGGCCGTCGTTTTACAACGTCGTGACTGGGAAAACCCTGGCGTTACCCAACTTAAT
CGCCTTGCAGCACATCCCCCTTTCGCCAGCTGGCGTAATAGCGAAGAGGCCCGCACCGAT
CGCCCTTCCCAACAGTTGCGCAGCCTGAATGGCGAATGGCGCCTGATGCGGTATTTTCTC
CTTACGCATCTGTGCGGTATTTCACACCGCATATGGTGCACTCTCAGTACAATCTGCTCTG
ATGCCGCATAGTTAAGCCAGCCCCGACACCCGCCAACACCCGCTGACGCGCCCTGACGG
GCTTGTCTGCTCCCGGCATCCGCTTACAGACAAGCTGTGACCGTCTCCGGGAGCTGCATG
TGTCAGAGGTTTTCACCGTCATCACCGAAACGCGCGAGACGAAAGGGCCTCGTGATACGC
CTATTTTTATAGGTTAATGTCATGATAATAATGGTTTCTTAGACGTCAGGTGGCACTTTTCG
GGGAAATGTGCGCGGAACCCCTATTTGTTTATTTTTCTAAATACATTCAAATATGTATCCGC
TCATGAGACAATAACCCTGATAAATGCTTCAATAATATTGAAAAAGGAAGAGTATGAGTATT
CAACATTTCCGTGTCGCCCTTATTCCCTTTTTTGCGGCATTTTGCCTTCCTGTTTTTGCTCA
CCCAGAAACGCTGGTGAAAGTAAAAGATGCTGAAGATCAGTTGGGTGCACGAGTGGGTTA
CATCGAACTGGATCTCAACAGCGGTAAGATCCTTGAGAGTTTTCGCCCCGAAGAACGTTTT
CCAATGATGAGCACTTTTAAAGTTCTGCTATGTGGCGCGGTATTATCCCGTATTGACGCCG
GGCAAGAGCAACTCGGTCGCCGCATACACTATTCTCAGAATGACTTGGTTGAGTACTCACC
AGTCACAGAAAAGCATCTTACGGATGGCATGACAGTAAGAGAATTATGCAGTGCTGCCATA
ACCATGAGTGATAACACTGCGGCCAACTTACTTCTGACAACGATCGGAGGACCGAAGGAG
CTAACCGCTTTTTTGCACAACATGGGGGATCATGTAACTCGCCTTGATCGTTGGGAACCGG
AGCTGAATGAAGCCATACCAAACGACGAGCGTGACACCACGATGCCTGTAGCAATGGCAA
CAACGTTGCGCAAACTATTAACTGGCGAACTACTTACTCTAGCTTCCCGGCAACAATTAATA
GACTGGATGGAGGCGGATAAAGTTGCAGGACCACTTCTGCGCTCGGCCCTTCCGGCTGG
CTGGTTTATTGCTGATAAATCTGGAGCCGGTGAGCGTGGGTCTCGCGGTATCATTGCAGC
ACTGGGGCCAGATGGTAAGCCCTCCCGTATCGTAGTTATCTACACGACGGGGAGTCAGGC
AACTATGGATGAACGAAATAGACAGATCGCTGAGATAGGTGCCTCACTGATTAAGCATTGG
TAACTGTCAGACCAAGTTTACTCATATATACTTTAGATTGATTTAAAACTTCATTTTTAATTTA
AAAGGATCTAGGTGAAGATCCTTTTTGATAATCTCATGACCAAAATCCCTTAACGTGAGTTT
TCGTTCCACTGAGCGTCAGACCCCGTAGAAAAGATCAAAGGATCTTCTTGAGATCCTTTTTT
TCTGCGCGTAATCTGCTGCTTGCAAACAAAAAAACCACCGCTACCAGCGGTGGTTTGTTTG
CCGGATCAAGAGCTACCAACTCTTTTTCCGAAGGTAACTGGCTTCAGCAGAGCGCAGATAC
CAAATACTGTTCTTCTAGTGTAGCCGTAGTTAGGCCACCACTTCAAGAACTCTGTAGCACC
GCCTACATACCTCGCTCTGCTAATCCTGTTACCAGTGGCTGCTGCCAGTGGCGATAAGTCG
TGTCTTACCGGGTTGGACTCAAGACGATAGTTACCGGATAAGGCGCAGCGGTCGGGCTGA
ACGGGGGGTTCGTGCACACAGCCCAGCTTGGAGCGAACGACCTACACCGAACTGAGATA
CCTACAGCGTGAGCTATGAGAAAGCGCCACGCTTCCCGAAGGGAGAAAGGCGGACAGGT
ATCCGGTAAGCGGCAGGGTCGGAACAGGAGAGCGCACGAGGGAGCTTCCAGGGGGAAA
CGCCTGGTATCTTTATAGTCCTGTCGGGTTTCGCCACCTCTGACTTGAGCGTCGATTTTTG
TGATGCTCGTCAGGGGGGCGGAGCCTATGGAAAAACGCCAGCAACGCGGCCTTTTTACG
GTTCCTGGCCTTTTGCTGGCCTTTTGCTCACATGTTCTTTCCTGCGTTATCCCCTGATTCTG
TGGATAACCGTATTACCGCCTTTGAGTGAGCTGATACCGCTCGCCGCAGCCGAACGACCG
AGCGCAGCGAGTCAGTGAGCGAGGAAGCGGAAGAGCGCCCAATACGCAAACCGCCTCTC

FIG. 79 cont'd

CCCGCGCGTTGGCCGATTCATTAATGCAGCTGGCACGACAGGTTTCCCGACTGGAAAGCG
GGCAGTGAGCGCAACGCAATTAATGTGAGTTAGCTCACTCATTAGGCACCCCAGGCTTTAC
ACTTTATGCTTCCGGCTCGTATGTTGTGTGGAATTGTGAGCGGATAACAATTTCACACAGG
AAACAGCTATGACCATGATTACGCCAAGCTCTCGAGATCTAG (SEQ ID NO: 75)

Construct vAi1.0 nucleotide sequence: rAAV_mscRE1-pBGmin-SYFP2-WPRE3-BGHpA
(sequence includes ITRs and plasmid backbone in plain text and synthetic AAV genome sequence is underlined):
AAAGCTTCCCGGGGGGATCTGGGCCACTCCCTCTCTGCGCGCTCGCTCGCTCACTGAGG
CCGGGCGACCAAAGGTCGCCCGACGCCCGGGCTTTGCCCGGGCGGCCTCAGTGAGCGA
GCGAGCGCGCAGAGAGGGAGTGGCCAACTCCATCACTAGGGGTTCCTGGAGGGGTGGAG
TCGTGACCTAGGACGCGTTTCTAATCATGAATTCTTTTGTGGTATTTTAGATTTTCAGTTTG
TTCTGTATCAATTCTCTCTCATTCAAAGAATATGATAGTGAGGTAGATGAAGCTGCCTAAG
CCACAGGAAGAAACATCTTCAGTCTGTCGTAAATGCACTTCAGATACAGCACCTTGCACT
GCACATAAAAATTCATAGTCACCTAAGTGGGAATAGCTATGAAAATCTGAGTATCGCCAT
GCTGTTGACTCAGTGCTATTTATAAAACTCAGTTTTAATGTTTCCAATTTAAATTCTCTGCA
CATATCTCTCCTGCACTAAAGACTTGAGATACCAGTGCTTTACCCTAAAATATCTTGCTTT
TATATCTTGACTCTTATGTTGAGAATTTATTATTTTTAAAATATACTTTAAAACATGCATTG
GTACAAAATTAGTCAAAACAGCAACCAGTGAATTCAAAGTAAATTAGTATTATTAATGCT
GTGTATAATTTTGGTGAATTTTACTATTAAATTATAAATAAAAAGTCCTTCCAGGTAGTCAT
GTTCACTCCTGATTGGTAAGTTCAAGAACATTGAGCTCGGGCTGGGCATAAAAGTCAGGG
CAGAGCCATCTATTGCTTACATTTGCTTCTGGGATCCAGATCTTTCGAAGCTAGCGCTACC
GGTCGCCACCATGGTGAGCAAGGGCGAGGAGCTGTTCACCGGGGTGGTGCCCATCCTGG
TCGAGCTGGACGGCGACGTAAACGGCCACAAGTTCAGCGTGTCCGGCGAGGGCGAGGGC
GATGCCACCTACGGCAAGCTGACCCTGAAGCTGATCTGCACCACCGGCAAGCTGCCCGTG
CCCTGGCCCACCCTCGTGACCACCCTGGGCTACGGCGTGCAGTGCTTCGCCCGCTACCC
CGACCACATGAAGCAGCACGACTTCTTCAAGTCCGCCATGCCCGAAGGCTACGTCCAGGA
GCGCACCATCTTCTTCAAGGACGACGGCAACTACAAGACCCGCGCCGAGGTGAAGTTCGA
GGGCGACACCCTGGTGAACCGCATCGAGCTGAAGGGCATCGACTTCAAGGAGGACGGCA
ACATCCTGGGGCACAAGCTGGAGTACAACTACAACAGCCACAACGTCTATATCACCGCCG
ACAAGCAGAAGAACGGCATCAAGGCCAACTTCAAGATCCGCCACAACATCGAGGACGGCG
GCGTGCAGCTCGCCGACCACTACCAGCAGAACACCCCCATCGGCGACGGCCCCGTGCTG
CTGCCCGACAACCACTACCTGAGCTACCAGTCCAAGCTGAGCAAAGACCCCAACGAGAAG
CGCGATCACATGGTCCTGCTGGAGTTCGTGACCGCCGCCGGGATCACTCTCGGCATGGA
CGAGCTGTACAAGTAAGTCGACGGCGCGCCGCGGCCGCGAATTCGATATCATAATCAACC
TCTGGATTACAAAATTTGTGAAAGATTGACTGGTATTCTTAACTATGTTGCTCCTTTTACGCT
ATGTGGATACGCTGCTTTAATGCCTTTGTATCATGCTATTGCTTCCCGTATGGCTTTCATTTT
CTCCTCCTTGTATAAATCCTGGTTAGTTCTTGCCACGGCGGAACTCATCGCCGCCTGCCTT
GCCCGCTGCTGGACAGGGGCTCGGCTGTTGGGCACTGACAATTCCGTGGCTCGAGCGAC
TGTGCCTTCTAGTTGCCAGCCATCTGTTGTTTGCCCCTCCCCCGTGCCTTCCTTGACCCTG
GAAGGTGCCACTCCCACTGTCCTTTCCTAATAAAATGAGGAAATTGCATCGCATTGTCTGA
GTAGGTGTCATTCTATTCTGGGGGGTGGGGTGGGGCAGGACAGCAAGGGGGAGGATTGG
GAAGACAATAGCAGGCATGACTAGTCCACTCCCTCTCTGCGCGCTCGCTCGCTCACTGAG
GCCGGGCGACCAAAGGTCGCCCGACGCCCGGGCTTTGCCCGGGCGGCCTCAGTGAGCG
AGCGAGCGCGCAGAGAGGGACAGATCCGGGCCCGCATGCGTCGACAATTCACTGGCCGT
CGTTTTACAACGTCGTGACTGGGAAAACCCTGGCGTTACCCAACTTAATCGCCTTGCAGCA
CATCCCCCTTTCGCCAGCTGGCGTAATAGCGAAGAGGCCCGCACCGATCGCCCTTCCCAA
CAGTTGCGCAGCCTGAATGGCGAATGGCGCCTGATGCGGTATTTTCTCCTTACGCATCTGT

FIG. 79 cont'd

GCGGTATTTCACACCGCATATGGTGCACTCTCAGTACAATCTGCTCTGATGCCGCATAGTT
AAGCCAGCCCCGACACCCGCCAACACCCGCTGACGCGCCCTGACGGGCTTGTCTGCTCC
CGGCATCCGCTTACAGACAAGCTGTGACCGTCTCCGGGAGCTGCATGTGTCAGAGGTTTT
CACCGTCATCACCGAAACGCGCGAGACGAAAGGGCCTCGTGATACGCCTATTTTTATAGG
TTAATGTCATGATAATAATGGTTTCTTAGACGTCAGGTGGCACTTTTCGGGGAAATGTGCG
CGGAACCCCTATTTGTTTATTTTTCTAAATACATTCAAATATGTATCCGCTCATGAGACAATA
ACCCTGATAAATGCTTCAATAATATTGAAAAAGGAAGAGTATGAGTATTCAACATTTCCGTG
TCGCCCTTATTCCCTTTTTTGCGGCATTTTGCCTTCCTGTTTTTGCTCACCCAGAAACGCTG
GTGAAAGTAAAAGATGCTGAAGATCAGTTGGGTGCACGAGTGGGTTACATCGAACTGGAT
CTCAACAGCGGTAAGATCCTTGAGAGTTTTCGCCCCGAAGAACGTTTTCCAATGATGAGCA
CTTTTAAAGTTCTGCTATGTGGCGCGGTATTATCCCGTATTGACGCCGGGCAAGAGCAACT
CGGTCGCCGCATACACTATTCTCAGAATGACTTGGTTGAGTACTCACCAGTCACAGAAAAG
CATCTTACGGATGGCATGACAGTAAGAGAATTATGCAGTGCTGCCATAACCATGAGTGATA
ACACTGCGGCCAACTTACTTCTGACAACGATCGGAGGACCGAAGGAGCTAACCGCTTTTTT
GCACAACATGGGGGATCATGTAACTCGCCTTGATCGTTGGGAACCGGAGCTGAATGAAGC
CATACCAAACGACGAGCGTGACACCACGATGCCTGTAGCAATGGCAACAACGTTGCGCAA
ACTATTAACTGGCGAACTACTTACTCTAGCTTCCCGGCAACAATTAATAGACTGGATGGAG
GCGGATAAAGTTGCAGGACCACTTCTGCGCTCGGCCCTTCCGGCTGGCTGGTTTATTGCT
GATAAATCTGGAGCCGGTGAGCGTGGGTCTCGCGGTATCATTGCAGCACTGGGGCCAGAT
GGTAAGCCCTCCCGTATCGTAGTTATCTACACGACGGGGAGTCAGGCAACTATGGATGAA
CGAAATAGACAGATCGCTGAGATAGGTGCCTCACTGATTAAGCATTGGTAACTGTCAGACC
AAGTTTACTCATATATACTTTAGATTGATTTAAAACTTCATTTTTAATTTAAAAGGATCTAGGT
GAAGATCCTTTTTGATAATCTCATGACCAAAATCCCTTAACGTGAGTTTTCGTTCCACTGAG
CGTCAGACCCCGTAGAAAAGATCAAAGGATCTTCTTGAGATCCTTTTTTTCTGCGCGTAATC
TGCTGCTTGCAAACAAAAAAACCACCGCTACCAGCGGTGGTTTGTTTGCCGGATCAAGAGC
TACCAACTCTTTTTCCGAAGGTAACTGGCTTCAGCAGAGCGCAGATACCAAATACTGTTCTT
CTAGTGTAGCCGTAGTTAGGCCACCACTTCAAGAACTCTGTAGCACCGCCTACATACCTCG
CTCTGCTAATCCTGTTACCAGTGGCTGCTGCCAGTGGCGATAAGTCGTGTCTTACCGGGTT
GGACTCAAGACGATAGTTACCGGATAAGGCGCAGCGGTCGGGCTGAACGGGGGGTTCGT
GCACACAGCCCAGCTTGGAGCGAACGACCTACACCGAACTGAGATACCTACAGCGTGAGC
TATGAGAAAGCGCCACGCTTCCCGAAGGGAGAAAGGCGGACAGGTATCCGGTAAGCGGC
AGGGTCGGAACAGGAGAGCGCACGAGGGAGCTTCCAGGGGGAAACGCCTGGTATCTTTA
TAGTCCTGTCGGGTTTCGCCACCTCTGACTTGAGCGTCGATTTTTGTGATGCTCGTCAGGG
GGGCGGAGCCTATGGAAAAACGCCAGCAACGCGGCCTTTTTACGGTTCCTGGCCTTTTGC
TGGCCTTTTGCTCACATGTTCTTTCCTGCGTTATCCCCTGATTCTGTGGATAACCGTATTAC
CGCCTTTGAGTGAGCTGATACCGCTCGCCGCAGCCGAACGACCGAGCGCAGCGAGTCAG
TGAGCGAGGAAGCGGAAGAGCGCCCAATACGCAAACCGCCTCTCCCCGCGCGTTGGCCG
ATTCATTAATGCAGCTGGCACGACAGGTTTCCCGACTGGAAAGCGGGCAGTGAGCGCAAC
GCAATTAATGTGAGTTAGCTCACTCATTAGGCACCCCAGGCTTTACACTTTATGCTTCCGG
CTCGTATGTTGTGTGGAATTGTGAGCGGATAACAATTTCACACAGGAAACAGCTATGACCA
TGATTACGCCAAGCTCTCGAGATCTAG (SEQ ID NO: 76)

Construct vAi33.2 nucleotide sequence: rAAV_Grik1_enhScnn1a-2-pBGmin-EGFP-WPRE3 (sequence includes ITRs):
GCAGGCAGCTGCGCGCTCGCTCGCTCACTGAGGCCGCCCGGGCGTCGGGCGACCTTTG
GTCGCCCGGCCTCAGTGAGCGAGCGAGCGCGCAGAGAGGGAGTGGCCAACTCCATCACT
AGGGGTTCCTGCGGCCGCACGCGTTGCTGTCATTTACCTACGGTTGTCTCCAAATTTCTTC
AACCAAGTAGAGAAAAATGAGAGAGAAGGAAAGAAAAAAAGAGGTATGGGGAGAAGA

FIG. 79 cont'd

GAAAGAAGGCAACTTGTTAAAAATCTCAGTCAAACTTACATACTATATAGAACAGCATGG
TGAATTTAGGGCACATGGATATAAAATGGAAGTTTCTTATTCAGTAGCAGCAACTTGTGG
GCACAGGAGTTGGCAAAGATAAAAATGTCCAAAGTCACAAATACAATGTATAGTTAGTC
ATAGGTGCTGTTATTTGCCTCAAAAAATAGACTTTTATTTTGCCTTTCTTTTCTTTAACCAC
ACTCAAAATTAGAGAACAGAGACAAAACCCAGCAGGAAATAGCACAGAAAGCCCACAG
AATCAAAGACGTGTTCAAACAGCCAGCTGAATTCATTGCACATTTCAACCACAGAAATAT
TTTCAGGTGATTCTGTTGTTTGACAAAACGTGGGAACCACAGGATCTACAACACTTGCAA
GCAAAACTCAACAGCTCTAATAATAGTTACAGAAGTGAAAGCCAATTTGGATAAAATAAG
ACATTGACTCAAGTCCTCTCAGAAGAGTTTTGAAAGCAAAGTTTACAAAAGTCTGGTTTG
TCCTTTGGGATTTACAGACCTTTCAGCCCCTTGATTCATTTTTTTTTTTTTGGATTTCTTCAT
CACTGGGAGAATTCCCATGCATTATTTCTCCCCTGCTTCAAAATCATCAAATGTGAAACAT
TTTTCACTCTTTTCTTCTGTATATAGTGATAAAATAGCTATTGGCTTTTGGCTAAATGTGCT
ACTTTGAGCCCACCCACACAAGGGAGAAATGGGGGCAGACATGAGTTTGGGCATGAGT
CTTAAGGAGCTCGGGCTGGGCATAAAAGTCAGGGCAGAGCCATCTATTGCTTACATTTGCT
TCTGGGATCCGCCACCATGGTGAGCAAGGGCGAGGAGCTGTTCACCGGGGTGGTGCCCA
TCCTGGTCGAGCTGGACGGCGACGTAAACGGCCACAAGTTCAGCGTGTCCGGCGAGGGC
GAGGGCGATGCCACCTACGGCAAGCTGACCCTGAAGTTCATCTGCACCACCGGCAAGCTG
CCCGTGCCCTGGCCCACCCTCGTGACCACCCTGACCTACGGCGTGCAGTGCTTCAGCCG
CTACCCCGACCACATGAAGCAGCACGACTTCTTCAAGTCCGCCATGCCCGAAGGCTACGT
CCAGGAGCGCACCATCTTCTTCAAGGACGACGGCAACTACAAGACCCGCGCCGAGGTGAA
GTTCGAGGGCGACACCCTGGTGAACCGCATCGAGCTGAAGGGCATCGACTTCAAGGAGG
ACGGCAACATCCTGGGGCACAAGCTGGAGTACAACTACAACAGCCACAACGTCTATATCAT
GGCCGACAAGCAGAAGAACGGCATCAAGGTGAACTTCAAGATCCGCCACAACATCGAGGA
CGGCAGCGTGCAGCTCGCCGACCACTACCAGCAGAACACCCCCATCGGCGACGGCCCCG
TGCTGCTGCCCGACAACCACTACCTGAGCACCCAGTCCGCCCTGAGCAAAGACCCCAACG
AGAAGCGCGATCACATGGTCCTGCTGGAGTTCGTGACCGCCGCCGGGATCACTCTCGGC
ATGGACGAGCTGTACAAGTAAGAATTCGATATCAAGCTTATCGATAATCAACCTCTGGATTA
CAAAATTTGTGAAAGATTGACTGGTATTCTTAACTATGTTGCTCCTTTTACGCTATGTGGATA
CGCTGCTTTAATGCCTTTGTATCATGCTATTGCTTCCCGTATGGCTTTCATTTTCTCCTCCTT
GTATAAATCCTGGTTGCTGTCTCTTTATGAGGAGTTGTGGCCCGTTGTCAGGCAACGTGGC
GTGGTGTGCACTGTGTTTGCTGACGCAACCCCCACTGGTTGGGGCATTGCCACCACCTGT
CAGCTCCTTTCCGGGACTTTCGCTTTCCCCCTCCCTATTGCCACGGCGGAACTCATCGCC
GCCTGCCTTGCCCGCTGCTGGACAGGGGCTCGGCTGTTGGGCACTGACAATTCCGTGGT
GTTGTCGGGGAAATCATCGTCCTTTCCTTGGCTGCTCGCCTATGTTGCCACCTGGATTCTG
CGCGGGACGTCCTTCTGCTACGTCCCTTCGGCCCTCAATCCAGCGGACCTTCCTTCCCGC
GGCCTGCTGCCGGCTCTGCGGCCTCTTCCGCGTCTTCGCCTTCGCCCTCAGACGAGTCG
GATCTCCCTTTGGGCCGCCTCCCCGCATCGATACCGAGCGCTGCTCGAGAGATCTACGGG
TGGCATCCCTGTGACCCCTCCCCAGTGCCTCTCCTGGCCCTGGAAGTTGCCACTCCAGTG
CCCACCAGCCTTGTCCTAATAAAATTAAGTTGCATCATTTTGTCTGACTAGGTGTCCTTCTA
TAATATTATGGGGTGGAGGGGGGTGGTATGGAGCAAGGGGCAAGTTGGGAAGACAACCT
GTAGGGCCTGCGGGGTCTATTGGGAACCAAGCTGGAGTGCAGTGGCACAATCTTGGCTCA
CTGCAATCTCCGCCTCCTGGGTTCAAGCGATTCTCCTGCCTCAGCCTCCCGAGTTGTTGG
GATTCCAGGCATGCATGACCAGGCTCAGCTAATTTTTGTTTTTTTGGTAGAGACGGGGTTT
CACCATATTGGCCAGGCTGGTCTCCAACTCCTAATCTCAGGTGATCTACCCACCTTGGCCT
CCCAAATTGCTGGGATTACAGGCGTGAACCACTGCTCCCTTCCCTGTCCTTCTGATTTTGT
AGGTAACCACGTGCGGACCGAGCGGCCGCAGGAACCCCTAGTGATGGAGTTGGCCACTC
CCTCTCTGCGCGCTCGCTCGCTCACTGAGGCCGGGCGACCAAAGGTCGCCCGACGCCCG

FIG. 79 cont'd

GGCTTTGCCCGGGCGGCCTCAGTGAGCGAGCGAGCGCGCAGCTGCCTGCAGG (SEQ ID NO: 77)

Construct vAi34.0 nucleotide sequence: rAAV_Grik1_enhScnn1a-2-BGmin-FlpO-WPRE3 (sequence includes ITRs):
CCTGCAGGCAGCTGCGCGCTCGCTCGCTCACTGAGGCCGCCCGGGCGTCGGGCGACCTT
TGGTCGCCCGGCCTCAGTGAGCGAGCGAGCGCGCAGAGAGGGAGTGGCCAACTCCATCA
CTAGGGGTTCCTGCGGCCGCACGCGTTGCTGTCATTTACCTACGGTTGTCTCCAAATTTCT
TCAACCAAGTAGAGAAAAATGAGAGAGAAGGAAAGAAAAAAAGAGGTATGGGGAGAAG
AGAAAGAAGGCAACTTGTTAAAAATCTCAGTCAAACTTACATACTATATAGAACAGCATG
GTGAATTTAGGGCACATGGATATAAAATGGAAGTTTCTTATTCAGTAGCAGCAACTTGTG
GGCACAGGAGTTGGCAAAGATAAAAATGTCCAAAGTCACAAATACAATGTATAGTTAGT
CATAGGTGCTGTTATTTGCCTCAAAAAATAGACTTTTATTTTGCCTTTCTTTTCTTTAACCA
CACTCAAAATTAGAGAACAGAGACAAAACCCAGCAGGAAATAGCACAGAAAGCCCACA
GAATCAAAGACGTGTTCAAACAGCCAGCTGAATTCATTGCACATTTCAACCACAGAAATA
TTTTCAGGTGATTCTGTTGTTTGACAAAACGTGGGAACCACAGGATCTACAACACTTGCA
AGCAAAACTCAACAGCTCTAATAATAGTTACAGAAGTGAAAGCCAATTTGGATAAAATAA
GACATTGACTCAAGTCCTCTCAGAAGAGTTTTGAAAGCAAAGTTTACAAAAGTCTGGTTT
GTCCTTTGGGATTTACAGACCTTTCAGCCCCTTGATTCATTTTTTTTTTTTTGGATTTCTTCA
TCACTGGGAGAATTCCCATGCATTATTTCTCCCCTGCTTCAAAATCATCAAATGTGAAACA
TTTTTCACTCTTTTCTTCTGTATATAGTGATAAAATAGCTATTGGCTTTTGGCTAAATGTGC
TACTTTGAGCCCACCCACACAAGGGAGAAATGGGGGCAGACATGAGTTTGGGCATGAGT
CTTAAGGAGCTCGGGCTGGGCATAAAAGTCAGGGCAGAGCCATCTATTGCTTACATTTGCT
TCTGGCGTGGCCACCATGGCTCCTAAGAAGAAGAGGAAGGTGATGAGCCAGTTCGACATC
CTGTGCAAGACCCCCCCCAAGGTGCTGGTGCGGCAGTTCGTGGAGAGATTCGAGAGGCC
CAGCGGCGAGAAGATCGCCAGCTGTGCCGCCGAGCTGACCTACCTGTGCTGGATGATCA
CCCACAACGGCACCGCCATCAAGAGGGCCACCTTCATGAGCTACAACACCATCATCAGCA
ACAGCCTGAGCTTCGACATCGTGAACAAGAGCCTGCAGTTCAAGTACAAGACCCAGAAGG
CCACCATCCTGGAGGCCAGCCTGAAGAAGCTGATCCCCGCCTGGGAGTTCACCATCATCC
CTTACAACGGCCAGAAGCACCAGAGCGACATCACCGACATCGTGTCCAGCCTGCAGCTGC
AGTTCGAGAGCAGCGAGGAGGCCGACAAGGGCAACAGCCACAGCAAGAAGATGCTGAAG
GCCCTGCTGTCCGAGGGCGAGAGCATCTGGGAGATCACCGAGAAGATCCTGAACAGCTTC
GAGTACACCAGCAGGTTCACCAAGACCAAGACCCTGTACCAGTTCCTGTTCCTGGCCACAT
TCATCAACTGCGGCAGGTTCAGCGACATCAAGAACGTGGACCCCAAGAGCTTCAAGCTGG
TGCAGAACAAGTACCTGGGCGTGATCATTCAGTGCCTGGTGACCGAGACCAAGACAAGCG
TGTCCAGGCACATCTACTTTTTCAGCGCCAGAGGCAGGATCGACCCCCTGGTGTACCTGG
ACGAGTTCCTGAGGAACAGCGAGCCCGTGCTGAAGAGAGTGAACAGGACCGGCAACAGC
AGCAGCAACAAGCAGGAGTACCAGCTGCTGAAGGACAACCTGGTGCGCAGCTACAACAAG
GCCCTGAAGAAGAACGCCCCCTACCCCATCTTCGCTATCAAGAACGGCCCTAAGAGCCAC
ATCGGCAGGCACCTGATGACCAGCTTTCTGAGCATGAAGGGCCTGACCGAGCTGACAAAC
GTGGTGGGCAACTGGAGCGACAAGAGGGCCTCCGCCGTGGCCAGGACCACCTACACCCA
CCAGATCACCGCCATCCCCGACCACTACTTCGCCCTGGTGTCCAGGTACTACGCCTACGA
CCCCATCAGCAAGGAGATGATCGCCCTGAAGGACGAGACCAACCCCATCGAGGAGTGGC
AGCACATCGAGCAGCTGAAGGGCAGCGCCGAGGGCAGCATCAGATACCCCGCCTGGAAC
GGCATCATCAGCCAGGAGGTGCTGGACTACCTGAGCAGCTACATCAACAGGCGGATCTGA
GAATTCGATATCAAGCTTATCGATAATCAACCTCTGGATTACAAAATTTGTGAAAGATTGAC
TGGTATTCTTAACTATGTTGCTCCTTTTACGCTATGTGGATACGCTGCTTTAATGCCTTTGTA
TCATGCTATTGCTTCCCGTATGGCTTTCATTTTCTCCTCCTTGTATAAATCCTGGTTGCTGTC

FIG. 79 cont'd

TCTTTATGAGGAGTTGTGGCCCGTTGTCAGGCAACGTGGCGTGGTGTGCACTGTGTTTGC
TGACGCAACCCCCACTGGTTGGGGCATTGCCACCACCTGTCAGCTCCTTTCCGGGACTTT
CGCTTTCCCCCTCCCTATTGCCACGGCGGAACTCATCGCCGCCTGCCTTGCCCGCTGCTG
GACAGGGGCTCGGCTGTTGGGCACTGACAATTCCGTGGTGTTGTCGGGGAAATCATCGTC
CTTTCCTTGGCTGCTCGCCTATGTTGCCACCTGGATTCTGCGCGGGACGTCCTTCTGCTAC
GTCCCTTCGGCCCTCAATCCAGCGGACCTTCCTTCCCGCGGCCTGCTGCCGGCTCTGCG
GCCTCTTCCGCGTCTTCGCCTTCGCCCTCAGACGAGTCGGATCTCCCTTTGGGCCGCCTC
CCCGCATCGATACCGAGCGCTGCTCGAGAGATCTACGGGTGGCATCCCTGTGACCCCTCC
CCAGTGCCTCTCCTGGCCCTGGAAGTTGCCACTCCAGTGCCCACCAGCCTTGTCCTAATA
AAATTAAGTTGCATCATTTTGTCTGACTAGGTGTCCTTCTATAATATTATGGGGTGGAGGGG
GGTGGTATGGAGCAAGGGGCAAGTTGGGAAGACAACCTGTAGGGCCTGCGGGGTCTATT
GGGAACCAAGCTGGAGTGCAGTGGCACAATCTTGGCTCACTGCAATCTCCGCCTCCTGGG
TTCAAGCGATTCTCCTGCCTCAGCCTCCCGAGTTGTTGGGATTCCAGGCATGCATGACCAG
GCTCAGCTAATTTTTGTTTTTTTGGTAGAGACGGGGTTTCACCATATTGGCCAGGCTGGTCT
CCAACTCCTAATCTCAGGTGATCTACCCACCTTGGCCTCCCAAATTGCTGGGATTACAGGC
GTGAACCACTGCTCCCTTCCCTGTCCTTCTGATTTTGTAGGTAACCACGTGCGGACCGAGC
GGCCGCAGGAACCCCTAGTGATGGAGTTGGCCACTCCCTCTCTGCGCGCTCGCTCGCTCA
CTGAGGCCGGGCGACCAAAGGTCGCCCGACGCCCGGGCTTTGCCCGGGCGGCCTCAGT
GAGCGAGCGAGCGCGCAGCTGCCTGCA (SEQ ID NO: 78)

Construct vAi45.0 nucleotide sequence: rAAV_mscRE12-FlpO-WPRE (sequence should be inserted into Plasmid backbone 1):
GCGGCCGCACGCGTGACTGCTAAGCTTTGGGCACTACCTGGGGTCAGTCTGCATCAAAA
TGTAAGGCTCAAATGTGTAATTGTAAGTACTGTTTTGCTGAGCTGGAAGGGCTCCTTTGA
AGCCCACGTTTTAATTTTAATTTAGCCACACAGAGTGGCAAAGACAAATAGATTTATCCA
AAATACATTTGGTAACAGATTTTTTGAGTCAGTTATTAATTTTATTTGAGGGGTTCCTCTTT
TTATTTTTTATAAACTGTGAAACTCAAGAGGAAGCAGGATCCCATGCAATGCCTTTTATTG
ATGGCCTGCTATGTGCCAAGAAAGGTGTTAAATGTTTTCCAATGCTGCCTCATTTATCCTG
ATCTTACAGACAAGCAAAAGGAGGTGTGAAGAGGTGAAGTTTCTCACCCAGCTGGAAAG
TGGCAAAGTCATTCACAGATCTGCCTCCGCTCAAAAAAATTGCTTTATGCAACTCTTTGG
AAGCTAACTTCATGGGAGCTACATGCAGCTTCTGAGCTCGGGCTGGGCATAAAAGTCAGG
GCAGAGCCATCTATTGCTTACATTTGCTTCTGGCGTGGCCACCATGGCTCCTAAGAAGAAG
AGGAAGGTGATGAGCCAGTTCGACATCCTGTGCAAGACCCCCCCCAAGGTGCTGGTGCG
GCAGTTCGTGGAGAGATTCGAGAGGCCCAGCGGCGAGAAGATCGCCAGCTGTGCCGCCG
AGCTGACCTACCTGTGCTGGATGATCACCCACAACGGCACCGCCATCAAGAGGGCCACCT
TCATGAGCTACAACACCATCATCAGCAACAGCCTGAGCTTCGACATCGTGAACAAGAGCCT
GCAGTTCAAGTACAAGACCCAGAAGGCCACCATCCTGGAGGCCAGCCTGAAGAAGCTGAT
CCCCGCCTGGGAGTTCACCATCATCCCTTACAACGGCCAGAAGCACCAGAGCGACATCAC
CGACATCGTGTCCAGCCTGCAGCTGCAGTTCGAGAGCAGCGAGGAGGCCGACAAGGGCA
ACAGCCACAGCAAGAAGATGCTGAAGGCCCTGCTGTCCGAGGGCGAGAGCATCTGGGAG
ATCACCGAGAAGATCCTGAACAGCTTCGAGTACACCAGCAGGTTCACCAAGACCAAGACC
CTGTACCAGTTCCTGTTCCTGGCCACATTCATCAACTGCGGCAGGTTCAGCGACATCAAGA
ACGTGGACCCCAAGAGCTTCAAGCTGGTGCAGAACAAGTACCTGGGCGTGATCATTCAGT
GCCTGGTGACCGAGACCAAGACAAGCGTGTCCAGGCACATCTACTTTTTCAGCGCCAGAG
GCAGGATCGACCCCCTGGTGTACCTGGACGAGTTCCTGAGGAACAGCGAGCCCGTGCTG
AAGAGAGTGAACAGGACCGGCAACAGCAGCAGCAACAAGCAGGAGTACCAGCTGCTGAA
GGACAACCTGGTGCGCAGCTACAACAAGGCCCTGAAGAAGAACGCCCCCTACCCCATCTT
CGCTATCAAGAACGGCCCTAAGAGCCACATCGGCAGGCACCTGATGACCAGCTTTCTGAG

FIG. 79 cont'd

CATGAAGGGCCTGACCGAGCTGACAAACGTGGTGGGCAACTGGAGCGACAAGAGGGCCT
CCGCCGTGGCCAGGACCACCTACACCCACCAGATCACCGCCATCCCCGACCACTACTTCG
CCCTGGTGTCCAGGTACTACGCCTACGACCCCATCAGCAAGGAGATGATCGCCCTGAAGG
ACGAGACCAACCCCATCGAGGAGTGGCAGCACATCGAGCAGCTGAAGGGCAGCGCCGAG
GGCAGCATCAGATACCCCGCCTGGAACGGCATCATCAGCCAGGAGGTGCTGGACTACCT
GAGCAGCTACATCAACAGGCGGATCTGAGAATTCGATATCAAGCTTATCGATAATCAACCT
CTGGATTACAAAATTTGTGAAAGATTGACTGGTATTCTTAACTATGTTGCTCCTTTTACGCTA
TGTGGATACGCTGCTTTAATGCCTTTGTATCATGCTATTGCTTCCCGTATGGCTTTCATTTT
CTCCTCCTTGTATAAATCCTGGTTGCTGTCTCTTTATGAGGAGTTGTGGCCCGTTGTCAGG
CAACGTGGCGTGGTGTGCACTGTGTTTGCTGACGCAACCCCCACTGGTTGGGGCATTGCC
ACCACCTGTCAGCTCCTTTCCGGGACTTTCGCTTTCCCCCTCCCTATTGCCACGGCGGAAC
TCATCGCCGCCTGCCTTGCCCGCTGCTGGACAGGGGCTCGGCTGTTGGGCACTGACAATT
CCGTGGTGTTGTCGGGGAAATCATCGTCCTTTCCTTGGCTGCTCGCCTATGTTGCCACCTG
GATTCTGCGCGGGACGTCCTTCTGCTACGTCCCTTCGGCCCTCAATCCAGCGGACCTTCC
TTCCCGCGGCCTGCTGCCGGCTCTGCGGCCTCTTCCGCGTCTTCGCCTTCGCCCTCAGAC
GAGTCGGATCTCCCTTTGGGCCGCCTCCCCGCATCGATACCGAGCGCTGCTCGAGAGATC
TACGGGTGGCATCCCTGTGACCCCTCCCCAGTGCCTCTCCTGGCCCTGGAAGTTGCCACT
CCAGTGCCCACCAGCCTTGTCCTAATAAAATTAAGTTGCATCATTTTGTCTGACTAGGTGTC
CTTCTATAATATTATGGGGTGGAGGGGGGTGGTATGGAGCAAGGGGCAAGTTGGGAAGAC
AACCTGTAGGGCCTGCGGGGTCTATTGGGAACCAAGCTGGAGTGCAGTGGCACAATCTTG
GCTCACTGCAATCTCCGCCTCCTGGGTTCAAGCGATTCTCCTGCCTCAGCCTCCCGAGTT
GTTGGGATTCCAGGCATGCATGACCAGGCTCAGCTAATTTTTGTTTTTTTGGTAGAGACGG
GGTTTCACCATATTGGCCAGGCTGGTCTCCAACTCCTAATCTCAGGTGATCTACCCACCTT
GGCCTCCCAAATTGCTGGGATTACAGGCGTGAACCACTGCTCCCTTCCCTGTCCTTCTGAT
TTTGTAGGTAACCACGTGCGGACCGAGCGGCCGC (SEQ ID NO: 79)

Construct TG975 nucleotide sequence: rAAV-mscRE4-pBGmin-IRES2-FlpO-WPRE3
(sequence includes ITRs and plasmid backbone in plain text and synthetic AAV genome sequence is underlined):
CCTGCAGGCAGCTGCGCGCTCGCTCGCTCACTGAGGCCGCCCGGGCAAAGCCCGGGCG
TCGGGCGACCTTTGGTCGCCCGGCCTCAGTGAGCGAGCGAGCGCGCAGAGAGGGAGTG
GCCAACTCCATCACTAGGGGTTCCTGCGGCCGCACGCGTATA**AGCCTTGGGGGCAATCA
AACTATTACATTGAGTCCTTGGATTTGCTACAAATTACATTTTAAATGCAATCATTTTATAA
AAGCTTCAACACTCACACTTGGAAGCGTTACCCTGTTGAATATCACTGACTCACTAACTT
GCATTGCCATGCTAACTTGCTTTCAGAGAGATCTCAGAACACATCATCTTCTGCTATTTCA
ATACATGCACATTAATTTCCTATCAACGTGTGCTGATCAGGAACTCTGTAATCTGGCACC
GGTGTTTATTTTTATTCCTGTCTATTCCTGTTGGCTCACGAAAAGATTGTTTGAGCAAGTG
TTTTATGGTGAGTTGTATCATATGTACATTGATTTAATCTGCCCACATTCAGTTCTACAAG
CGGAGCCAAAAAAATAGAGACAAGCATAATTTTCATTCAACATGAGCCCCTCAATGCAA
GCCAAGTACCTCATCTGGTGCTCAGCTAAAGCAACAGCAATCTGTTCCACCCTGGAGAC
ACAACTGGCCACAGAAAACTTAGTGAAAAGAGGCAATGCTATGCACAGGACAAAT**GAGC
TCGGGCTGGGCATAAAAGTCAGGGCAGAGCCATCTATTGCTTACATTTGCTTCTGGGATCC
TTCGAAACCGGTGCTAGAGCCCCTCTCCCTCCCCCCCCCCTAACGTTACTGGCCGAAGCC
GCTTGGAATAAGGCCGGTGTGCGTTTGTCTATATGTTATTTTCCACCATATTGCCGTCTTTT
GGCAATGTGAGGGCCCGGAAACCTGGCCCTGTCTTCTTGACGAGCATTCCTAGGGGTCTT
TCCCCTCTCGCCAAAGGAATGCAAGGTCTGTTGAATGTCGTGAAGGAAGCAGTTCCTCTG
GAAGCTTCTTGAAGACAAACAACGTCTGTAGCGACCCTTTGCAGGCAGCGGAACCCCCCA
CCTGGCGACAGGTGCCTCTGCGGCCAAAAGCCACGTGTATAAGATACACCTGCAAAGGCG

FIG. 79 cont'd

GCACAACCCCAGTGCCACGTTGTGAGTTGGATAGTTGTGGAAAGAGTCAAATGGCTCTCCT
CAAGCGTATTCAACAAGGGGCTGAAGGATGCCCAGAAGGTACCCCATTGTATGGGATCTG
ATCTGGGGCCTCGGTGCACATGCTTTACATGTGTTTAGTCGAGGTTAAAAAAACGTCTAGG
CCCCCCGAACCACGGGGACGTGGTTTTCCTTTGAAAAACACGATGATAATATGGCCACATC
TAGCACCATGGCTCCTAAGAAGAAGAGGAAGGTGATGAGCCAGTTCGACATCCTGTGCAA
GACCCCCCCCAAGGTGCTGGTGCGGCAGTTCGTGGAGAGATTCGAGAGGCCCAGCGGCG
AGAAGATCGCCAGCTGTGCCGCCGAGCTGACCTACCTGTGCTGGATGATCACCCACAACG
GCACCGCCATCAAGAGGGCCACCTTCATGAGCTACAACACCATCATCAGCAACAGCCTGA
GCTTCGACATCGTGAACAAGAGCCTGCAGTTCAAGTACAAGACCCAGAAGGCCACCATCC
TGGAGGCCAGCCTGAAGAAGCTGATCCCCGCCTGGGAGTTCACCATCATCCCTTACAACG
GCCAGAAGCACCAGAGCGACATCACCGACATCGTGTCCAGCCTGCAGCTGCAGTTCGAGA
GCAGCGAGGAGGCCGACAAGGGCAACAGCCACAGCAAGAAGATGCTGAAGGCCCTGCTG
TCCGAGGGCGAGAGCATCTGGGAGATCACCGAGAAGATCCTGAACAGCTTCGAGTACACC
AGCAGGTTCACCAAGACCAAGACCCTGTACCAGTTCCTGTTCCTGGCCACATTCATCAACT
GCGGCAGGTTCAGCGACATCAAGAACGTGGACCCCAAGAGCTTCAAGCTGGTGCAGAACA
AGTACCTGGGCGTGATCATTCAGTGCCTGGTGACCGAGACCAAGACAAGCGTGTCCAGGC
ACATCTACTTTTTCAGCGCCAGAGGCAGGATCGACCCCCTGGTGTACCTGGACGAGTTCC
TGAGGAACAGCGAGCCCGTGCTGAAGAGAGTGAACAGGACCGGCAACAGCAGCAGCAAC
AAGCAGGAGTACCAGCTGCTGAAGGACAACCTGGTGCGCAGCTACAACAAGGCCCTGAAG
AAGAACGCCCCCTACCCCATCTTCGCTATCAAGAACGGCCCTAAGAGCCACATCGGCAGG
CACCTGATGACCAGCTTTCTGAGCATGAAGGGCCTGACCGAGCTGACAAACGTGGTGGGC
AACTGGAGCGACAAGAGGGCCTCCGCCGTGGCCAGGACCACCTACACCCACCAGATCAC
CGCCATCCCCGACCACTACTTCGCCCTGGTGTCCAGGTACTACGCCTACGACCCCATCAG
CAAGGAGATGATCGCCCTGAAGGACGAGACCAACCCCATCGAGGAGTGGCAGCACATCG
AGCAGCTGAAGGGCAGCGCCGAGGGCAGCATCAGATACCCCGCCTGGAACGGCATCATC
AGCCAGGAGGTGCTGGACTACCTGAGCAGCTACATCAACAGGCGGATCTGAGAATTCGAT
ATCAAGCTTATCGATAATCAACCTCTGGATTACAAAATTTGTGAAAGATTGACTGGTATTCTT
AACTATGTTGCTCCTTTTACGCTATGTGGATACGCTGCTTTAATGCCTTTGTATCATGCTATT
GCTTCCCGTATGGCTTTCATTTTCTCCTCCTTGTATAAATCCTGGTTGCTGTCTCTTTATGA
GGAGTTGTGGCCCGTTGTCAGGCAACGTGGCGTGGTGTGCACTGTGTTTGCTGACGCAAC
CCCCACTGGTTGGGGCATTGCCACCACCTGTCAGCTCCTTTCCGGGACTTTCGCTTTCCC
CCTCCCTATTGCCACGGCGGAACTCATCGCCGCCTGCCTTGCCCGCTGCTGGACAGGGG
CTCGGCTGTTGGGCACTGACAATTCCGTGGTGTTGTCGGGGAAATCATCGTCCTTTCCTTG
GCTGCTCGCCTATGTTGCCACCTGGATTCTGCGCGGGACGTCCTTCTGCTACGTCCCTTC
GGCCCTCAATCCAGCGGACCTTCCTTCCCGCGGCCTGCTGCCGGCTCTGCGGCCTCTTCC
GCGTCTTCGCCTTCGCCCTCAGACGAGTCGGATCTCCCTTTGGGCCGCCTCCCCGCATCG
ATACCGAGCGCTGCTCGAGAGATCTACGGGTGGCATCCCTGTGACCCCTCCCCAGTGCCT
CTCCTGGCCCTGGAAGTTGCCACTCCAGTGCCCACCAGCCTTGTCCTAATAAAATTAAGTT
GCATCATTTTGTCTGACTAGGTGTCCTTCTATAATATTATGGGGTGGAGGGGGGTGGTATG
GAGCAAGGGGCAAGTTGGGAAGACAACCTGTAGGGCCTGCGGGGTCTATTGGGAACCAA
GCTGGAGTGCAGTGGCACAATCTTGGCTCACTGCAATCTCCGCCTCCTGGGTTCAAGCGA
TTCTCCTGCCTCAGCCTCCCGAGTTGTTGGGATTCCAGGCATGCATGACCAGGCTCAGCT
AATTTTTGTTTTTTTGGTAGAGACGGGGTTTCACCATATTGGCCAGGCTGGTCTCCAACTCC
TAATCTCAGGTGATCTACCCACCTTGGCCTCCCAAATTGCTGGGATTACAGGCGTGAACCA
CTGCTCCCTTCCCTGTCCTTCTGATTTTGTAGGTAACCACGTGCGGACCGAGCGGCCGCA
GGAACCCCTAGTGATGGAGTTGGCCACTCCCTCTCTGCGCGCTCGCTCGCTCACTGAGGC
CGGGCGACCAAAGGTCGCCCGACGCCCGGGCTTTGCCCGGGCGGCCTCAGTGAGCGAG
CGAGCGCGCAGCTGCCTGCAGGGGCGCCTGATGCGGTATTTTCTCCTTACGCATCTGTGC

FIG. 79 cont'd

GGTATTTCACACCGCATACGTCAAAGCAACCATAGTACGCGCCCTGTAGCGGCGCATTAA
GCGCGGCGGGTGTGGTGGTTACGCGCAGCGTGACCGCTACACTTGCCAGCGCCCTAGCG
CCCGCTCCTTTCGCTTTCTTCCCTTCCTTTCTCGCCACGTTCGCCGGCTTTCCCCGTCAAG
CTCTAAATCGGGGGCTCCCTTTAGGGTTCCGATTTAGTGCTTTACGGCACCTCGACCCCAA
AAAACTTGATTTGGGTGATGGTTCACGTAGTGGGCCATCGCCCTGATAGACGGTTTTTCGC
CCTTTGACGTTGGAGTCCACGTTCTTTAATAGTGGACTCTTGTTCCAAACTGGAACAACACT
CAACCCTATCTCGGGCTATTCTTTTGATTTATAAGGGATTTTGCCGATTTCGGCCTATTGGT
TAAAAAATGAGCTGATTTAACAAAAATTTAACGCGAATTTTAACAAAATATTAACGTTTACAA
TTTTATGGTGCACTCTCAGTACAATCTGCTCTGATGCCGCATAGTTAAGCCAGCCCCGACA
CCCGCCAACACCCGCTGACGCGCCCTGACGGGCTTGTCTGCTCCCGGCATCCGCTTACA
GACAAGCTGTGACCGTCTCCGGGAGCTGCATGTGTCAGAGGTTTTCACCGTCATCACCGA
AACGCGCGAGACGAAAGGGCCTCGTGATACGCCTATTTTTATAGGTTAATGTCATGATAAT
AATGGTTTCTTAGACGTCAGGTGGCACTTTTCGGGGAAATGTGCGCGGAACCCCTATTTGT
TTATTTTTCTAAATACATTCAAATATGTATCCGCTCATGAGACAATAACCCTGATAAATGCTT
CAATAATATTGAAAAAGGAAGAGTATGAGTATTCAACATTTCCGTGTCGCCCTTATTCCCTT
TTTTGCGGCATTTTGCCTTCCTGTTTTTGCTCACCCAGAAACGCTGGTGAAAGTAAAAGATG
CTGAAGATCAGTTGGGTGCACGAGTGGGTTACATCGAACTGGATCTCAACAGCGGTAAGA
TCCTTGAGAGTTTTCGCCCCGAAGAACGTTTTCCAATGATGAGCACTTTTAAAGTTCTGCTA
TGTGGCGCGGTATTATCCCGTATTGACGCCGGGCAAGAGCAACTCGGTCGCCGCATACAC
TATTCTCAGAATGACTTGGTTGAGTACTCACCAGTCACAGAAAAGCATCTTACGGATGGCA
TGACAGTAAGAGAATTATGCAGTGCTGCCATAACCATGAGTGATAACACTGCGGCCAACTT
ACTTCTGACAACGATCGGAGGACCGAAGGAGCTAACCGCTTTTTTGCACAACATGGGGGA
TCATGTAACTCGCCTTGATCGTTGGGAACCGGAGCTGAATGAAGCCATACCAAACGACGA
GCGTGACACCACGATGCCTGTAGCAATGGCAACAACGTTGCGCAAACTATTAACTGGCGA
ACTACTTACTCTAGCTTCCCGGCAACAATTAATAGACTGGATGGAGGCGGATAAAGTTGCA
GGACCACTTCTGCGCTCGGCCCTTCCGGCTGGCTGGTTTATTGCTGATAAATCTGGAGCC
GGTGAGCGTGGGTCTCGCGGTATCATTGCAGCACTGGGGCCAGATGGTAAGCCCTCCCG
TATCGTAGTTATCTACACGACGGGGAGTCAGGCAACTATGGATGAACGAAATAGACAGATC
GCTGAGATAGGTGCCTCACTGATTAAGCATTGGTAACTGTCAGACCAAGTTTACTCATATAT
ACTTTAGATTGATTTAAAACTTCATTTTTAATTTAAAAGGATCTAGGTGAAGATCCTTTTTGAT
AATCTCATGACCAAAATCCCTTAACGTGAGTTTTCGTTCCACTGAGCGTCAGACCCCGTAG
AAAAGATCAAAGGATCTTCTTGAGATCCTTTTTTTCTGCGCGTAATCTGCTGCTTGCAAACA
AAAAAACCACCGCTACCAGCGGTGGTTTGTTTGCCGGATCAAGAGCTACCAACTCTTTTTC
CGAAGGTAACTGGCTTCAGCAGAGCGCAGATACCAAATACTGTCCTTCTAGTGTAGCCGTA
GTTAGGCCACCACTTCAAGAACTCTGTAGCACCGCCTACATACCTCGCTCTGCTAATCCTG
TTACCAGTGGCTGCTGCCAGTGGCGATAAGTCGTGTCTTACCGGGTTGGACTCAAGACGA
TAGTTACCGGATAAGGCGCAGCGGTCGGGCTGAACGGGGGGTTCGTGCACACAGCCCAG
CTTGGAGCGAACGACCTACACCGAACTGAGATACCTACAGCGTGAGCTATGAGAAAGCGC
CACGCTTCCCGAAGGGAGAAAGGCGGACAGGTATCCGGTAAGCGGCAGGGTCGGAACAG
GAGAGCGCACGAGGGAGCTTCCAGGGGGAAACGCCTGGTATCTTTATAGTCCTGTCGGGT
TTCGCCACCTCTGACTTGAGCGTCGATTTTTGTGATGCTCGTCAGGGGGGCGGAGCCTAT
GGAAAAACGCCAGCAACGCGGCCTTTTTACGGTTCCTGGCCTTTTGCTGGCCTTTTGCTCA
CATGT (SEQ ID NO: 180)

Construct TG978 nucleotide sequence: rAAV_mscRE4-pBGmin-FlpO-WPRE3 (sequence should be inserted into Plasmid backbone 1):
GCGGCCGCACGCGTATAAGCCTTGGGGGCAATCAAACTATTACATTGAGTCCTTGGATTT
GCTACAAATTACATTTTAAATGCAATCATTTTATAAAAGCTTCAACACTCACACTTGGAAG

FIG. 79 cont'd

CGTTACCCTGTTGAATATCACTGACTCACTAACTTGCATTGCCATGCTAACTTGCTTTCAG
AGAGATCTCAGAACACATCATCTTCTGCTATTTCAATACATGCACATTAATTTCCTATCAA
CGTGTGCTGATCAGGAACTCTGTAATCTGGCACCGGTGTTTATTTTTATTCCTGTCTATTC
CTGTTGGCTCACGAAAAGATTGTTTGAGCAAGTGTTTTATGGTGAGTTGTATCATATGTAC
ATTGATTTAATCTGCCCACATTCAGTTCTACAAGCGGAGCCAAAAAAATAGAGACAAGCA
TAATTTTCATTCAACATGAGCCCCTCAATGCAAGCCAAGTACCTCATCTGGTGCTCAGCT
AAAGCAACAGCAATCTGTTCCACCCTGGAGACACAACTGGCCACAGAAAACTTAGTGAA
AAGAGGCAATGCTATGCACAGGACAAATGAGCTCGGGCTGGGCATAAAAGTCAGGGCAG
AGCCATCTATTGCTTACATTTGCTTCTGGCGTGGCCACCATGGCTCCTAAGAAGAAGAGGA
AGGTGATGAGCCAGTTCGACATCCTGTGCAAGACCCCCCCCAAGGTGCTGGTGCGGCAGT
TCGTGGAGAGATTCGAGAGGCCCAGCGGCGAGAAGATCGCCAGCTGTGCCGCCGAGCTG
ACCTACCTGTGCTGGATGATCACCCACAACGGCACCGCCATCAAGAGGGCCACCTTCATG
AGCTACAACACCATCATCAGCAACAGCCTGAGCTTCGACATCGTGAACAAGAGCCTGCAGT
TCAAGTACAAGACCCAGAAGGCCACCATCCTGGAGGCCAGCCTGAAGAAGCTGATCCCCG
CCTGGGAGTTCACCATCATCCCTTACAACGGCCAGAAGCACCAGAGCGACATCACCGACA
TCGTGTCCAGCCTGCAGCTGCAGTTCGAGAGCAGCGAGGAGGCCGACAAGGGCAACAGC
CACAGCAAGAAGATGCTGAAGGCCCTGCTGTCCGAGGGCGAGAGCATCTGGGAGATCAC
CGAGAAGATCCTGAACAGCTTCGAGTACACCAGCAGGTTCACCAAGACCAAGACCCTGTA
CCAGTTCCTGTTCCTGGCCACATTCATCAACTGCGGCAGGTTCAGCGACATCAAGAACGTG
GACCCCAAGAGCTTCAAGCTGGTGCAGAACAAGTACCTGGGCGTGATCATTCAGTGCCTG
GTGACCGAGACCAAGACAAGCGTGTCCAGGCACATCTACTTTTTCAGCGCCAGAGGCAGG
ATCGACCCCCTGGTGTACCTGGACGAGTTCCTGAGGAACAGCGAGCCCGTGCTGAAGAGA
GTGAACAGGACCGGCAACAGCAGCAGCAACAAGCAGGAGTACCAGCTGCTGAAGGACAA
CCTGGTGCGCAGCTACAACAAGGCCCTGAAGAAGAACGCCCCCTACCCCATCTTCGCTAT
CAAGAACGGCCCTAAGAGCCACATCGGCAGGCACCTGATGACCAGCTTTCTGAGCATGAA
GGGCCTGACCGAGCTGACAAACGTGGTGGGCAACTGGAGCGACAAGAGGGCCTCCGCCG
TGGCCAGGACCACCTACACCCACCAGATCACCGCCATCCCCGACCACTACTTCGCCCTGG
TGTCCAGGTACTACGCCTACGACCCCATCAGCAAGGAGATGATCGCCCTGAAGGACGAGA
CCAACCCCATCGAGGAGTGGCAGCACATCGAGCAGCTGAAGGGCAGCGCCGAGGGCAGC
ATCAGATACCCCGCCTGGAACGGCATCATCAGCCAGGAGGTGCTGGACTACCTGAGCAGC
TACATCAACAGGCGGATCTGAGAATTCGATATCAAGCTTATCGATAATCAACCTCTGGATTA
CAAAATTTGTGAAAGATTGACTGGTATTCTTAACTATGTTGCTCCTTTTACGCTATGTGGATA
CGCTGCTTTAATGCCTTTGTATCATGCTATTGCTTCCCGTATGGCTTTCATTTTCTCCTCCTT
GTATAAATCCTGGTTGCTGTCTCTTTATGAGGAGTTGTGGCCCGTTGTCAGGCAACGTGGC
GTGGTGTGCACTGTGTTTGCTGACGCAACCCCCACTGGTTGGGGCATTGCCACCACCTGT
CAGCTCCTTTCCGGGACTTTCGCTTTCCCCCTCCCTATTGCCACGGCGGAACTCATCGCC
GCCTGCCTTGCCCGCTGCTGGACAGGGGCTCGGCTGTTGGGCACTGACAATTCCGTGGT
GTTGTCGGGGAAATCATCGTCCTTTCCTTGGCTGCTCGCCTATGTTGCCACCTGGATTCTG
CGCGGGACGTCCTTCTGCTACGTCCCTTCGGCCCTCAATCCAGCGGACCTTCCTTCCCGC
GGCCTGCTGCCGGCTCTGCGGCCTCTTCCGCGTCTTCGCCTTCGCCCTCAGACGAGTCG
GATCTCCCTTTGGGCCGCCTCCCCGCATCGATACCGAGCGCTGCTCGAGAGATCTACGGG
TGGCATCCCTGTGACCCCTCCCCAGTGCCTCTCCTGGCCCTGGAAGTTGCCACTCCAGTG
CCCACCAGCCTTGTCCTAATAAAATTAAGTTGCATCATTTTGTCTGACTAGGTGTCCTTCTA
TAATATTATGGGGTGGAGGGGGGTGGTATGGAGCAAGGGGCAAGTTGGGAAGACAACCT
GTAGGGCCTGCGGGGTCTATTGGGAACCAAGCTGGAGTGCAGTGGCACAATCTTGGCTCA
CTGCAATCTCCGCCTCCTGGGTTCAAGCGATTCTCCTGCCTCAGCCTCCCGAGTTGTTGG
GATTCCAGGCATGCATGACCAGGCTCAGCTAATTTTTGTTTTTTTGGTAGAGACGGGGTTT
CACCATATTGGCCAGGCTGGTCTCCAACTCCTAATCTCAGGTGATCTACCCACCTTGGCCT

FIG. 79 cont'd

CCCAAATTGCTGGGATTACAGGCGTGAACCACTGCTCCCTTCCCTGTCCTTCTGATTTTGT
AGGTAACCACGTGCGGACCGAGCGGCCGC (SEQ ID NO: 80)

Construct TG979 nucleotide sequence: rAAV-mscRE4-pBGmin-FlpO-bGHpA (sequence includes ITRs and plasmid backbone in plain text and synthetic AAV genome sequence is underlined):
CCTGCAGGCAGCTGCGCGCTCGCTCGCTCACTGAGGCCGCCCGGGCAAAGCCCGGGCG
TCGGGCGACCTTTGGTCGCCCGGCCTCAGTGAGCGAGCGAGCGCGCAGAGAGGGAGTG
GCCAACTCCATCACTAGGGGTTCCTGCGGCCGCACGCGTATA**AGCCTTGGGGGCAATCA
AACTATTACATTGAGTCCTTGGATTTGCTACAAATTACATTTTAAATGCAATCATTTTATAA
AAGCTTCAACACTCACACTTGGAAGCGTTACCCTGTTGAATATCACTGACTCACTAACTT
GCATTGCCATGCTAACTTGCTTTCAGAGAGATCTCAGAACACATCATCTTCTGCTATTTCA
ATACATGCACATTAATTTCCTATCAACGTGTGCTGATCAGGAACTCTGTAATCTGGCACC
GGTGTTTATTTTTATTCCTGTCTATTCCTGTTGGCTCACGAAAAGATTGTTTGAGCAAGTG
TTTTATGGTGAGTTGTATCATATGTACATTGATTTAATCTGCCCACATTCAGTTCTACAAG
CGGAGCCAAAAAAATAGAGACAAGCATAATTTTCATTCAACATGAGCCCCTCAATGCAA
GCCAAGTACCTCATCTGGTGCTCAGCTAAAGCAACAGCAATCTGTTCCACCCTGGAGAC
ACAACTGGCCACAGAAAACTTAGTGAAAAGAGGCAATGCTATGCACAGGACAAAT**GAGC
TCGGGCTGGGCATAAAAGTCAGGGCAGAGCCATCTATTGCTTACATTTGCTTCTGGCGTG
GCCACCATGGCTCCTAAGAAGAAGAGGAAGGTGATGAGCCAGTTCGACATCCTGTGCAAG
ACCCCCCCCAAGGTGCTGGTGCGGCAGTTCGTGGAGAGATTCGAGAGGCCCAGCGGCGA
GAAGATCGCCAGCTGTGCCGCCGAGCTGACCTACCTGTGCTGGATGATCACCCACAACGG
CACCGCCATCAAGAGGGCCACCTTCATGAGCTACAACACCATCATCAGCAACAGCCTGAG
CTTCGACATCGTGAACAAGAGCCTGCAGTTCAAGTACAAGACCCAGAAGGCCACCATCCT
GGAGGCCAGCCTGAAGAAGCTGATCCCCGCCTGGGAGTTCACCATCATCCCTTACAACGG
CCAGAAGCACCAGAGCGACATCACCGACATCGTGTCCAGCCTGCAGCTGCAGTTCGAGAG
CAGCGAGGAGGCCGACAAGGGCAACAGCCACAGCAAGAAGATGCTGAAGGCCCTGCTGT
CCGAGGGCGAGAGCATCTGGGAGATCACCGAGAAGATCCTGAACAGCTTCGAGTACACCA
GCAGGTTCACCAAGACCAAGACCCTGTACCAGTTCCTGTTCCTGGCCACATTCATCAACTG
CGGCAGGTTCAGCGACATCAAGAACGTGGACCCCAAGAGCTTCAAGCTGGTGCAGAACAA
GTACCTGGGCGTGATCATTCAGTGCCTGGTGACCGAGACCAAGACAAGCGTGTCCAGGCA
CATCTACTTTTTCAGCGCCAGAGGCAGGATCGACCCCCTGGTGTACCTGGACGAGTTCCT
GAGGAACAGCGAGCCCGTGCTGAAGAGAGTGAACAGGACCGGCAACAGCAGCAGCAACA
AGCAGGAGTACCAGCTGCTGAAGGACAACCTGGTGCGCAGCTACAACAAGGCCCTGAAGA
AGAACGCCCCCTACCCCATCTTCGCTATCAAGAACGGCCCTAAGAGCCACATCGGCAGGC
ACCTGATGACCAGCTTTCTGAGCATGAAGGGCCTGACCGAGCTGACAAACGTGGTGGGCA
ACTGGAGCGACAAGAGGGCCTCCGCCGTGGCCAGGACCACCTACACCCACCAGATCACC
GCCATCCCCGACCACTACTTCGCCCTGGTGTCCAGGTACTACGCCTACGACCCCATCAGC
AAGGAGATGATCGCCCTGAAGGACGAGACCAACCCCATCGAGGAGTGGCAGCACATCGA
GCAGCTGAAGGGCAGCGCCGAGGGCAGCATCAGATACCCCGCCTGGAACGGCATCATCA
GCCAGGAGGTGCTGGACTACCTGAGCAGCTACATCAACAGGCGGATCTGAGAATTACGGG
TGGCATCCCTGTGACCCCTCCCCAGTGCCTCTCCTGGCCCTGGAAGTTGCCACTCCAGTG
CCCACCAGCCTTGTCCTAATAAAATTAAGTTGCATCATTTTGTCTGACTAGGTGTCCTTCTA
TAATATTATGGGGTGGAGGGGGGTGGTATGGAGCAAGGGGCAAGTTGGGAAGACAACCT
GTAGGGCCTGCGGGGTCTATTGGGAACCAAGCTGGAGTGCAGTGGCACAATCTTGGCTCA
CTGCAATCTCCGCCTCCTGGGTTCAAGCGATTCTCCTGCCTCAGCCTCCCGAGTTGTTGG
GATTCCAGGCATGCATGACCAGGCTCAGCTAATTTTTGTTTTTTTGGTAGAGACGGGGTTT
CACCATATTGGCCAGGCTGGTCTCCAACTCCTAATCTCAGGTGATCTACCCACCTTGGCCT

FIG. 79 cont'd

CCCAAATTGCTGGGATTACAGGCGTGAACCACTGCTCCCTTCCCTGTCCTTCTGATTTTGT
AGGTAACCACGTGCGGACCGAGCGGCCGCAGGAACCCCTAGTGATGGAGTTGGCCACTC
CCTCTCTGCGCGCTCGCTCGCTCACTGAGGCCGGGCGACCAAAGGTCGCCCGACGCCCG
GGCTTTGCCCGGGCGGCCTCAGTGAGCGAGCGAGCGCGCAGCTGCCTGCAGGGGCGCC
TGATGCGGTATTTTCTCCTTACGCATCTGTGCGGTATTTCACACCGCATACGTCAAAGCAA
CCATAGTACGCGCCCTGTAGCGGCGCATTAAGCGCGGCGGGTGTGGTGGTTACGCGCAG
CGTGACCGCTACACTTGCCAGCGCCCTAGCGCCCGCTCCTTTCGCTTTCTTCCCTTCCTTT
CTCGCCACGTTCGCCGGCTTTCCCCGTCAAGCTCTAAATCGGGGGCTCCCTTTAGGGTTC
CGATTTAGTGCTTTACGGCACCTCGACCCCAAAAAACTTGATTTGGGTGATGGTTCACGTA
GTGGGCCATCGCCCTGATAGACGGTTTTTCGCCCTTTGACGTTGGAGTCCACGTTCTTTAA
TAGTGGACTCTTGTTCCAAACTGGAACAACACTCAACCCTATCTCGGGCTATTCTTTTGATT
TATAAGGGATTTTGCCGATTTCGGCCTATTGGTTAAAAAATGAGCTGATTTAACAAAAATTTA
ACGCGAATTTTAACAAAATATTAACGTTTACAATTTTATGGTGCACTCTCAGTACAATCTGCT
CTGATGCCGCATAGTTAAGCCAGCCCCGACACCCGCCAACACCCGCTGACGCGCCCTGA
CGGGCTTGTCTGCTCCCGGCATCCGCTTACAGACAAGCTGTGACCGTCTCCGGGAGCTGC
ATGTGTCAGAGGTTTTCACCGTCATCACCGAAACGCGCGAGACGAAAGGGCCTCGTGATA
CGCCTATTTTTATAGGTTAATGTCATGATAATAATGGTTTCTTAGACGTCAGGTGGCACTTTT
CGGGGAAATGTGCGCGGAACCCCTATTTGTTTATTTTTCTAAATACATTCAAATATGTATCC
GCTCATGAGACAATAACCCTGATAAATGCTTCAATAATATTGAAAAAGGAAGAGTATGAGTA
TTCAACATTTCCGTGTCGCCCTTATTCCCTTTTTTGCGGCATTTTGCCTTCCTGTTTTTGCTC
ACCCAGAAACGCTGGTGAAAGTAAAAGATGCTGAAGATCAGTTGGGTGCACGAGTGGGTT
ACATCGAACTGGATCTCAACAGCGGTAAGATCCTTGAGAGTTTTCGCCCCGAAGAACGTTT
TCCAATGATGAGCACTTTTAAAGTTCTGCTATGTGGCGCGGTATTATCCCGTATTGACGCC
GGGCAAGAGCAACTCGGTCGCCGCATACACTATTCTCAGAATGACTTGGTTGAGTACTCAC
CAGTCACAGAAAAGCATCTTACGGATGGCATGACAGTAAGAGAATTATGCAGTGCTGCCAT
AACCATGAGTGATAACACTGCGGCCAACTTACTTCTGACAACGATCGGAGGACCGAAGGA
GCTAACCGCTTTTTTGCACAACATGGGGGATCATGTAACTCGCCTTGATCGTTGGGAACCG
GAGCTGAATGAAGCCATACCAAACGACGAGCGTGACACCACGATGCCTGTAGCAATGGCA
ACAACGTTGCGCAAACTATTAACTGGCGAACTACTTACTCTAGCTTCCCGGCAACAATTAAT
AGACTGGATGGAGGCGGATAAAGTTGCAGGACCACTTCTGCGCTCGGCCCTTCCGGCTG
GCTGGTTTATTGCTGATAAATCTGGAGCCGGTGAGCGTGGGTCTCGCGGTATCATTGCAG
CACTGGGGCCAGATGGTAAGCCCTCCCGTATCGTAGTTATCTACACGACGGGGAGTCAGG
CAACTATGGATGAACGAAATAGACAGATCGCTGAGATAGGTGCCTCACTGATTAAGCATTG
GTAACTGTCAGACCAAGTTTACTCATATATACTTTAGATTGATTTAAAACTTCATTTTTAATTT
AAAAGGATCTAGGTGAAGATCCTTTTTGATAATCTCATGACCAAAATCCCTTAACGTGAGTT
TTCGTTCCACTGAGCGTCAGACCCCGTAGAAAAGATCAAAGGATCTTCTTGAGATCCTTTTT
TTCTGCGCGTAATCTGCTGCTTGCAAACAAAAAAACCACCGCTACCAGCGGTGGTTTGTTT
GCCGGATCAAGAGCTACCAACTCTTTTTCCGAAGGTAACTGGCTTCAGCAGAGCGCAGATA
CCAAATACTGTCCTTCTAGTGTAGCCGTAGTTAGGCCACCACTTCAAGAACTCTGTAGCAC
CGCCTACATACCTCGCTCTGCTAATCCTGTTACCAGTGGCTGCTGCCAGTGGCGATAAGTC
GTGTCTTACCGGGTTGGACTCAAGACGATAGTTACCGGATAAGGCGCAGCGGTCGGGCTG
AACGGGGGGTTCGTGCACACAGCCCAGCTTGGAGCGAACGACCTACACCGAACTGAGATA
CCTACAGCGTGAGCTATGAGAAAGCGCCACGCTTCCCGAAGGGAGAAAGGCGGACAGGT
ATCCGGTAAGCGGCAGGGTCGGAACAGGAGAGCGCACGAGGGAGCTTCCAGGGGGAAA
CGCCTGGTATCTTTATAGTCCTGTCGGGTTTCGCCACCTCTGACTTGAGCGTCGATTTTTG
TGATGCTCGTCAGGGGGGCGGAGCCTATGGAAAAACGCCAGCAACGCGGCCTTTTTACG
GTTCCTGGCCTTTTGCTGGCCTTTTGCTCACATGT (SEQ ID NO: 181)

FIG. 79 cont'd

Construct TG981 nucleotide sequence: rAAV_mscRE4-pBGmin-EGFP-WPRE3-bGHpA
(sequence should be inserted into Plasmid backbone 1):
GCGGCCGCACGCGTATA**AGCCTTGGGGGCAATCAAACTATTACATTGAGTCCTTGGATTT
GCTACAAATTACATTTTAAATGCAATCATTTTATAAAAGCTTCAACACTCACACTTGGAAG
CGTTACCCTGTTGAATATCACTGACTCACTAACTTGCATTGCCATGCTAACTTGCTTTCAG
AGAGATCTCAGAACACATCATCTTCTGCTATTTCAATACATGCACATTAATTTCCTATCAA
CGTGTGCTGATCAGGAACTCTGTAATCTGGCACCGGTGTTTATTTTTATTCCTGTCTATTC
CTGTTGGCTCACGAAAAGATTGTTTGAGCAAGTGTTTTATGGTGAGTTGTATCATATGTAC
ATTGATTTAATCTGCCCACATTCAGTTCTACAAGCGGAGCCAAAAAAATAGAGACAAGCA
TAATTTTCATTCAACATGAGCCCCTCAATGCAAGCCAAGTACCTCATCTGGTGCTCAGCT
AAAGCAACAGCAATCTGTTCCACCCTGGAGACACAACTGGCCACAGAAAACTTAGTGAA
AAGAGGCAATGCTATGCACAGGACAAAT**GAGCTCGGGCTGGGCATAAAAGTCAGGGCAG
AGCCATCTATTGCTTACATTTGCTTCTGGGATCCGCCACCATGGTGAGCAAGGGCGAGGA
GCTGTTCACCGGGGTGGTGCCCATCCTGGTCGAGCTGGACGGCGACGTAAACGGCCACA
AGTTCAGCGTGTCCGGCGAGGGCGAGGGCGATGCCACCTACGGCAAGCTGACCCTGAAG
TTCATCTGCACCACCGGCAAGCTGCCCGTGCCCTGGCCCACCCTCGTGACCACCCTGACC
TACGGCGTGCAGTGCTTCAGCCGCTACCCCGACCACATGAAGCAGCACGACTTCTTCAAG
TCCGCCATGCCCGAAGGCTACGTCCAGGAGCGCACCATCTTCTTCAAGGACGACGGCAAC
TACAAGACCCGCGCCGAGGTGAAGTTCGAGGGCGACACCCTGGTGAACCGCATCGAGCT
GAAGGGCATCGACTTCAAGGAGGACGGCAACATCCTGGGGCACAAGCTGGAGTACAACTA
CAACAGCCACAACGTCTATATCATGGCCGACAAGCAGAAGAACGGCATCAAGGTGAACTT
CAAGATCCGCCACAACATCGAGGACGGCAGCGTGCAGCTCGCCGACCACTACCAGCAGA
ACACCCCCATCGGCGACGGCCCCGTGCTGCTGCCCGACAACCACTACCTGAGCACCCAG
TCCGCCCTGAGCAAAGACCCCAACGAGAAGCGCGATCACATGGTCCTGCTGGAGTTCGTG
ACCGCCGCCGGGATCACTCTCGGCATGGACGAGCTGTACAAGTAAGAATTCGATATCAAG
CTTATCGATAATCAACCTCTGGATTACAAAATTTGTGAAAGATTGACTGGTATTCTTAACTAT
GTTGCTCCTTTTACGCTATGTGGATACGCTGCTTTAATGCCTTTGTATCATGCTATTGCTTC
CCGTATGGCTTTCATTTTCTCCTCCTTGTATAAATCCTGGTTGCTGTCTCTTTATGAGGAGT
TGTGGCCCGTTGTCAGGCAACGTGGCGTGGTGTGCACTGTGTTTGCTGACGCAACCCCCA
CTGGTTGGGGCATTGCCACCACCTGTCAGCTCCTTTCCGGGACTTTCGCTTTCCCCCTCCC
TATTGCCACGGCGGAACTCATCGCCGCCTGCCTTGCCCGCTGCTGGACAGGGGCTCGGC
TGTTGGGCACTGACAATTCCGTGGTGTTGTCGGGGAAATCATCGTCCTTTCCTTGGCTGCT
CGCCTATGTTGCCACCTGGATTCTGCGCGGGACGTCCTTCTGCTACGTCCCTTCGGCCCT
CAATCCAGCGGACCTTCCTTCCCGCGGCCTGCTGCCGGCTCTGCGGCCTCTTCCGCGTCT
TCGCCTTCGCCCTCAGACGAGTCGGATCTCCCTTTGGGCCGCCTCCCCGCATCGATACCG
AGCGCTGCTCGAGAGATCTACGGGTGGCATCCCTGTGACCCCTCCCCAGTGCCTCTCCTG
GCCCTGGAAGTTGCCACTCCAGTGCCCACCAGCCTTGTCCTAATAAAATTAAGTTGCATCA
TTTTGTCTGACTAGGTGTCCTTCTATAATATTATGGGGTGGAGGGGGGTGGTATGGAGCAA
GGGGCAAGTTGGGAAGACAACCTGTAGGGCCTGCGGGGTCTATTGGGAACCAAGCTGGA
GTGCAGTGGCACAATCTTGGCTCACTGCAATCTCCGCCTCCTGGGTTCAAGCGATTCTCCT
GCCTCAGCCTCCCGAGTTGTTGGGATTCCAGGCATGCATGACCAGGCTCAGCTAATTTTTG
TTTTTTTGGTAGAGACGGGGTTTCACCATATTGGCCAGGCTGGTCTCCAACTCCTAATCTC
AGGTGATCTACCCACCTTGGCCTCCCAAATTGCTGGGATTACAGGCGTGAACCACTGCTC
CCTTCCCTGTCCTTCTGATTTTGTAGGTAACCACGTGCGGACCGAGCGGCCGC (SEQ ID
NO: 81)

FIG. 79 cont'd

Construct TG982 nucleotide sequence: rAAV-mscRE4-pBGmin-IRES2-iCre-bGHpA
(sequence includes ITRs and plasmid backbone in plain text and synthetic AAV genome sequence is underlined):

CCTGCAGGCAGCTGCGCGCTCGCTCGCTCACTGAGGCCGCCCGGGCAAAGCCCGGGCG
TCGGGCGACCTTTGGTCGCCCGGCCTCAGTGAGCGAGCGAGCGCGCAGAGAGGGAGTG
GCCAACTCCATCACTAGGGGTTCCTGCGGCCGCACGCGTATAAGCCTTGGGGGCAATCA
AACTATTACATTGAGTCCTTGGATTTGCTACAAATTACATTTTAAATGCAATCATTTTATAA
AAGCTTCAACACTCACACTTGGAAGCGTTACCCTGTTGAATATCACTGACTCACTAACTT
GCATTGCCATGCTAACTTGCTTTCAGAGAGATCTCAGAACACATCATCTTCTGCTATTTCA
ATACATGCACATTAATTTCCTATCAACGTGTGCTGATCAGGAACTCTGTAATCTGGCACC
GGTGTTTATTTTTATTCCTGTCTATTCCTGTTGGCTCACGAAAAGATTGTTTGAGCAAGTG
TTTTATGGTGAGTTGTATCATATGTACATTGATTTAATCTGCCCACATTCAGTTCTACAAG
CGGAGCCAAAAAAATAGAGACAAGCATAATTTTCATTCAACATGAGCCCCTCAATGCAA
GCCAAGTACCTCATCTGGTGCTCAGCTAAAGCAACAGCAATCTGTTCCACCCTGGAGAC
ACAACTGGCCACAGAAAACTTAGTGAAAAGAGGCAATGCTATGCACAGGACAAATGAGC
TCGGGCTGGGCATAAAAGTCAGGGCAGAGCCATCTATTGCTTACATTTGCTTCTGGGATCC
GCCCCTCTCCCTCCCCCCCCCCTAACGTTACTGGCCGAAGCCGCTTGGAATAAGGCCGGT
GTGCGTTTGTCTATATGTTATTTTCCACCATATTGCCGTCTTTTGGCAATGTGAGGGCCCGG
AAACCTGGCCCTGTCTTCTTGACGAGCATTCCTAGGGGTCTTTCCCCTCTCGCCAAAGGAA
TGCAAGGTCTGTTGAATGTCGTGAAGGAAGCAGTTCCTCTGGAAGCTTCTTGAAGACAAAC
AACGTCTGTAGCGACCCTTTGCAGGCAGCGGAACCCCCCACCTGGCGACAGGTGCCTCT
GCGGCCAAAAGCCACGTGTATAAGATACACCTGCAAAGGCGGCACAACCCCAGTGCCACG
TTGTGAGTTGGATAGTTGTGGAAAGAGTCAAATGGCTCTCCTCAAGCGTATTCAACAAGGG
GCTGAAGGATGCCCAGAAGGTACCCCATTGTATGGGATCTGATCTGGGGCCTCGGTGCAC
ATGCTTTACATGTGTTTAGTCGAGGTTAAAAAAACGTCTAGGCCCCCCGAACCACGGGGAC
GTGGTTTTCCTTTGAAAAACACGATGATAATATGGCCACAGCTAGCACCATGGTGCCCAAG
AAGAAGAGGAAAGTCTCCAACCTGCTGACTGTGCACCAAAACCTGCCTGCCCTCCCTGTG
GATGCCACCTCTGATGAAGTCAGGAAGAACCTGATGGACATGTTCAGGGACAGGCAGGCC
TTCTCTGAACACACCTGGAAGATGCTCCTGTCTGTGTGCAGATCCTGGGCTGCCTGGTGC
AAGCTGAACAACAGGAAATGGTTCCCTGCTGAACCTGAGGATGTGAGGGACTACCTCCTG
TACCTGCAAGCCAGAGGCCTGGCTGTGAAGACCATCCAACAGCACCTGGGCCAGCTCAAC
ATGCTGCACAGGAGATCTGGCCTGCCTCGCCCTTCTGACTCCAATGCTGTGTCCCTGGTG
ATGAGGAGAATCAGAAAGGAGAATGTGGATGCTGGGGAGAGAGCCAAGCAGGCCCTGGC
CTTTGAACGCACTGACTTTGACCAAGTCAGATCCCTGATGGAGAACTCTGACAGATGCCAG
GACATCAGGAACCTGGCCTTCCTGGGCATTGCCTACAACACCCTGCTGCGCATTGCCGAA
ATTGCCAGAATCAGAGTGAAGGACATCTCCCGCACCGATGGTGGGAGAATGCTGATCCAC
ATTGGCAGGACCAAGACCCTGGTGTCCACAGCTGGTGTGGAGAAGGCCCTGTCCCTGGG
GGTTACCAAGCTGGTGGAGAGATGGATCTCTGTGTCTGGTGTGGCTGATGACCCCAACAA
CTACCTGTTCTGCCGGGTCAGAAAGAATGGTGTGGCTGCCCCTTCTGCCACCTCCCAACT
GTCCACCCGGGCCCTGGAAGGGATCTTTGAGGCCACCCACCGCCTGATCTATGGTGCCAA
GGATGACTCTGGGCAGAGATACCTGGCCTGGTCTGGCCACTCTGCCAGAGTGGGTGCTG
CCAGGGACATGGCCAGGGCTGGTGTGTCCATCCCTGAAATCATGCAGGCTGGTGGCTGG
ACCAATGTGAACATTGTGATGAACTACATCAGAAACCTGGACTCTGAGACTGGGGCCATGG
TGAGGCTGCTCGAGGATGGGGACTAATGAGGCGCGCCGCGGCCGCTGCTCGAGAGATCT
ACGGGTGGCATCCCTGTGACCCCTCCCCAGTGCCTCTCCTGGCCCTGGAAGTTGCCACTC
CAGTGCCCACCAGCCTTGTCCTAATAAAATTAAGTTGCATCATTTTGTCTGACTAGGTGTCC
TTCTATAATATTATGGGGTGGAGGGGGGTGGTATGGAGCAAGGGGCAAGTTGGGAAGACA
ACCTGTAGGGCCTGCGGGGTCTATTGGGAACCAAGCTGGAGTGCAGTGGCACAATCTTGG

FIG. 79 cont'd

CTCACTGCAATCTCCGCCTCCTGGGTTCAAGCGATTCTCCTGCCTCAGCCTCCCGAGTTGT
TGGGATTCCAGGCATGCATGACCAGGCTCAGCTAATTTTTGTTTTTTTGGTAGAGACGGGG
TTTCACCATATTGGCCAGGCTGGTCTCCAACTCCTAATCTCAGGTGATCTACCCACCTTGG
CCTCCCAAATTGCTGGGATTACAGGCGTGAACCACTGCTCCCTTCCCTGTCCTTCTGATTT
TGTAGGTAACCACGTGCGGACCGAGCGGCCGCAGGAACCCCTAGTGATGGAGTTGGCCA
CTCCCTCTCTGCGCGCTCGCTCGCTCACTGAGGCCGGGCGACCAAAGGTCGCCCGACGC
CCGGGCTTTGCCCGGGCGGCCTCAGTGAGCGAGCGAGCGCGCAGCTGCCTGCAGGGGC
GCCTGATGCGGTATTTTCTCCTTACGCATCTGTGCGGTATTTCACACCGCATACGTCAAAG
CAACCATAGTACGCGCCCTGTAGCGGCGCATTAAGCGCGGCGGGTGTGGTGGTTACGCG
CAGCGTGACCGCTACACTTGCCAGCGCCCTAGCGCCCGCTCCTTTCGCTTTCTTCCCTTC
CTTTCTCGCCACGTTCGCCGGCTTTCCCCGTCAAGCTCTAAATCGGGGGCTCCCTTTAGG
GTTCCGATTTAGTGCTTTACGGCACCTCGACCCCAAAAAACTTGATTTGGGTGATGGTTCA
CGTAGTGGGCCATCGCCCTGATAGACGGTTTTTCGCCCTTTGACGTTGGAGTCCACGTTCT
TTAATAGTGGACTCTTGTTCCAAACTGGAACAACACTCAACCCTATCTCGGGCTATTCTTTT
GATTTATAAGGGATTTTGCCGATTTCGGCCTATTGGTTAAAAAATGAGCTGATTTAACAAAA
ATTTAACGCGAATTTTAACAAAATATTAACGTTTACAATTTTATGGTGCACTCTCAGTACAAT
CTGCTCTGATGCCGCATAGTTAAGCCAGCCCCGACACCCGCCAACACCCGCTGACGCGCC
CTGACGGGCTTGTCTGCTCCCGGCATCCGCTTACAGACAAGCTGTGACCGTCTCCGGGAG
CTGCATGTGTCAGAGGTTTTCACCGTCATCACCGAAACGCGCGAGACGAAAGGGCCTCGT
GATACGCCTATTTTTATAGGTTAATGTCATGATAATAATGGTTTCTTAGACGTCAGGTGGCA
CTTTTCGGGGAAATGTGCGCGGAACCCCTATTTGTTTATTTTTCTAAATACATTCAAATATGT
ATCCGCTCATGAGACAATAACCCTGATAAATGCTTCAATAATATTGAAAAAGGAAGAGTATG
AGTATTCAACATTTCCGTGTCGCCCTTATTCCCTTTTTTGCGGCATTTTGCCTTCCTGTTTTT
GCTCACCCAGAAACGCTGGTGAAAGTAAAAGATGCTGAAGATCAGTTGGGTGCACGAGTG
GGTTACATCGAACTGGATCTCAACAGCGGTAAGATCCTTGAGAGTTTTCGCCCCGAAGAAC
GTTTTCCAATGATGAGCACTTTTAAAGTTCTGCTATGTGGCGCGGTATTATCCCGTATTGAC
GCCGGGCAAGAGCAACTCGGTCGCCGCATACACTATTCTCAGAATGACTTGGTTGAGTAC
TCACCAGTCACAGAAAAGCATCTTACGGATGGCATGACAGTAAGAGAATTATGCAGTGCTG
CCATAACCATGAGTGATAACACTGCGGCCAACTTACTTCTGACAACGATCGGAGGACCGAA
GGAGCTAACCGCTTTTTTGCACAACATGGGGGATCATGTAACTCGCCTTGATCGTTGGGAA
CCGGAGCTGAATGAAGCCATACCAAACGACGAGCGTGACACCACGATGCCTGTAGCAATG
GCAACAACGTTGCGCAAACTATTAACTGGCGAACTACTTACTCTAGCTTCCCGGCAACAAT
TAATAGACTGGATGGAGGCGGATAAAGTTGCAGGACCACTTCTGCGCTCGGCCCTTCCGG
CTGGCTGGTTTATTGCTGATAAATCTGGAGCCGGTGAGCGTGGGTCTCGCGGTATCATTG
CAGCACTGGGGCCAGATGGTAAGCCCTCCCGTATCGTAGTTATCTACACGACGGGGAGTC
AGGCAACTATGGATGAACGAAATAGACAGATCGCTGAGATAGGTGCCTCACTGATTAAGCA
TTGGTAACTGTCAGACCAAGTTTACTCATATATACTTTAGATTGATTTAAAACTTCATTTTTAA
TTTAAAAGGATCTAGGTGAAGATCCTTTTTGATAATCTCATGACCAAAATCCCTTAACGTGA
GTTTTCGTTCCACTGAGCGTCAGACCCCGTAGAAAAGATCAAAGGATCTTCTTGAGATCCT
TTTTTTCTGCGCGTAATCTGCTGCTTGCAAACAAAAAAACCACCGCTACCAGCGGTGGTTT
GTTTGCCGGATCAAGAGCTACCAACTCTTTTTCCGAAGGTAACTGGCTTCAGCAGAGCGCA
GATACCAAATACTGTCCTTCTAGTGTAGCCGTAGTTAGGCCACCACTTCAAGAACTCTGTA
GCACCGCCTACATACCTCGCTCTGCTAATCCTGTTACCAGTGGCTGCTGCCAGTGGCGAT
AAGTCGTGTCTTACCGGGTTGGACTCAAGACGATAGTTACCGGATAAGGCGCAGCGGTCG
GGCTGAACGGGGGGTTCGTGCACACAGCCCAGCTTGGAGCGAACGACCTACACCGAACT
GAGATACCTACAGCGTGAGCTATGAGAAAGCGCCACGCTTCCCGAAGGGAGAAAGGCGG
ACAGGTATCCGGTAAGCGGCAGGGTCGGAACAGGAGAGCGCACGAGGGAGCTTCCAGGG
GGAAACGCCTGGTATCTTTATAGTCCTGTCGGGTTTCGCCACCTCTGACTTGAGCGTCGAT

FIG. 79 cont'd

TTTTGTGATGCTCGTCAGGGGGGCGGAGCCTATGGAAAAACGCCAGCAACGCGGCCTTTT
TACGGTTCCTGGCCTTTTGCTGGCCTTTTGCTCACATGT (SEQ ID NO: 182)

Construct TG987 nucleotide sequence: rAAV-mscRE4-pBGmin-IRES2-tTA2-bGHpA
(sequence includes ITRs and plasmid backbone in plain text and synthetic AAV genome sequence is underlined):
CCTGCAGGCAGCTGCGCGCTCGCTCGCTCACTGAGGCCGCCCGGGCAAAGCCCGGGCG
TCGGGCGACCTTTGGTCGCCCGGCCTCAGTGAGCGAGCGAGCGCGCAGAGAGGGAGTG
GCCAACTCCATCACTAGGGGTTCCTGCGGCCGCACGCGTATA**AGCCTTGGGGGCAATCA
AACTATTACATTGAGTCCTTGGATTTGCTACAAATTACATTTTAAATGCAATCATTTTATAA
AAGCTTCAACACTCACACTTGGAAGCGTTACCCTGTTGAATATCACTGACTCACTAACTT
GCATTGCCATGCTAACTTGCTTTCAGAGAGATCTCAGAACACATCATCTTCTGCTATTTCA
ATACATGCACATTAATTTCCTATCAACGTGTGCTGATCAGGAACTCTGTAATCTGGCACC
GGTGTTTATTTTTATTCCTGTCTATTCCTGTTGGCTCACGAAAAGATTGTTTGAGCAAGTG
TTTTATGGTGAGTTGTATCATATGTACATTGATTTAATCTGCCCACATTCAGTTCTACAAG
CGGAGCCAAAAAAATAGAGACAAGCATAATTTTCATTCAACATGAGCCCCTCAATGCAA
GCCAAGTACCTCATCTGGTGCTCAGCTAAAGCAACAGCAATCTGTTCCACCCTGGAGAC
ACAACTGGCCACAGAAAACTTAGTGAAAAGAGGCAATGCTATGCACAGGACAAAT**GAGC
TCGGGCTGGGCATAAAAGTCAGGGCAGAGCCATCTATTGCTTACATTTGCTTCTGGGATCC
GCCCCTCTCCCTCCCCCCCCCCTAACGTTACTGGCCGAAGCCGCTTGGAATAAGGCCGGT
GTGCGTTTGTCTATATGTTATTTTCCACCATATTGCCGTCTTTTGGCAATGTGAGGGCCCGG
AAACCTGGCCCTGTCTTCTTGACGAGCATTCCTAGGGGTCTTTCCCCTCTCGCCAAAGGAA
TGCAAGGTCTGTTGAATGTCGTGAAGGAAGCAGTTCCTCTGGAAGCTTCTTGAAGACAAAC
AACGTCTGTAGCGACCCTTTGCAGGCAGCGGAACCCCCCACCTGGCGACAGGTGCCTCT
GCGGCCAAAAGCCACGTGTATAAGATACACCTGCAAAGGCGGCACAACCCCAGTGCCACG
TTGTGAGTTGGATAGTTGTGGAAAGAGTCAAATGGCTCTCCTCAAGCGTATTCAACAAGGG
GCTGAAGGATGCCCAGAAGGTACCCCATTGTATGGGATCTGATCTGGGGCCTCGGTGCAC
ATGCTTTACATGTGTTTAGTCGAGGTTAAAAAAACGTCTAGGCCCCCCGAACCACGGGGAC
GTGGTTTTCCTTTGAAAAACACGATGATAATATGGCCACAGCTAGCGCCACCATGTCTAGA
CTGGACAAGAGCAAAGTCATAAACTCTGCTCTGGAATTACTCAATGAAGTCGGTATCGAAG
GCCTGACGACAAGGAAACTCGCTCAAAAGCTGGGAGTTGAGCAGCCTACCCTGTACTGGC
ACGTGAAGAACAAGCGGGCCCTGCTCGATGCCCTGGCAATCGAGATGCTGGACAGGCAT
CATACCCACTTCTGCCCCCTGGAAGGCGAGTCATGGCAAGACTTTCTGCGGAACAACGCC
AAGTCATTCCGCTGTGCTCTCCTCTCACATCGCGACGGGGCTAAAGTGCATCTCGGCACC
CGCCCAACAGAGAAACAGTACGAAACCCTGGAAAATCAGCTCGCGTTCCTGTGTCAGCAA
GGCTTCTCCCTGGAGAACGCACTGTACGCTCTGTCCGCCGTGGGCCACTTTACACTGGGC
TGCGTATTGGAGGATCAGGAGCATCAAGTAGCAAAAGAGGAAAGAGAGACACCTACCACC
GATTCTATGCCCCCACTTCTGAGACAAGCAATTGAGCTGTTCGACCATCAGGGAGCCGAAC
CTGCCTTCCTTTTCGGCCTGGAACTAATCATATGTGGCCTGGAGAAACAGCTAAAGTGCGA
AAGCGGCGGGCCGGCCGACGCCCTTGACGATTTTGACTTAGACATGCTCCCAGCCGATGC
CCTTGACGACTTTGACCTTGATATGCTGCCTGCTGACGCTCTTGACGATTTTGACCTTGAC
ATGCTCCCCGGGTAAGGCGCGCCGCGGCCGCTGCTCGAGAGATCTACGGGTGGCATCCC
TGTGACCCCTCCCCAGTGCCTCTCCTGGCCCTGGAAGTTGCCACTCCAGTGCCCACCAGC
CTTGTCCTAATAAAATTAAGTTGCATCATTTTGTCTGACTAGGTGTCCTTCTATAATATTATG
GGGTGGAGGGGGGTGGTATGGAGCAAGGGGCAAGTTGGGAAGACAACCTGTAGGGCCT
GCGGGGTCTATTGGGAACCAAGCTGGAGTGCAGTGGCACAATCTTGGCTCACTGCAATCT
CCGCCTCCTGGGTTCAAGCGATTCTCCTGCCTCAGCCTCCCGAGTTGTTGGGATTCCAGG
CATGCATGACCAGGCTCAGCTAATTTTTGTTTTTTTGGTAGAGACGGGGTTTCACCATATTG

FIG. 79 cont'd

GCCAGGCTGGTCTCCAACTCCTAATCTCAGGTGATCTACCCACCTTGGCCTCCCAAATTGC
TGGGATTACAGGCGTGAACCACTGCTCCCTTCCCTGTCCTTCTGATTTTGTAGGTAACCAC
GTGCGGACCGAGCGGCCGCAGGAACCCCTAGTGATGGAGTTGGCCACTCCCTCTCTGCG
CGCTCGCTCGCTCACTGAGGCCGGGCGACCAAAGGTCGCCCGACGCCCGGGCTTTGCCC
GGGCGGCCTCAGTGAGCGAGCGAGCGCGCAGCTGCCTGCAGGGGCGCCTGATGCGGTA
TTTTCTCCTTACGCATCTGTGCGGTATTTCACACCGCATACGTCAAAGCAACCATAGTACGC
GCCCTGTAGCGGCGCATTAAGCGCGGCGGGTGTGGTGGTTACGCGCAGCGTGACCGCTA
CACTTGCCAGCGCCCTAGCGCCCGCTCCTTTCGCTTTCTTCCCTTCCTTTCTCGCCACGTT
CGCCGGCTTTCCCCGTCAAGCTCTAAATCGGGGGCTCCCTTTAGGGTTCCGATTTAGTGCT
TTACGGCACCTCGACCCCAAAAAACTTGATTTGGGTGATGGTTCACGTAGTGGGCCATCGC
CCTGATAGACGGTTTTTCGCCCTTTGACGTTGGAGTCCACGTTCTTTAATAGTGGACTCTTG
TTCCAAACTGGAACAACACTCAACCCTATCTCGGGCTATTCTTTTGATTTATAAGGGATTTT
GCCGATTTCGGCCTATTGGTTAAAAAATGAGCTGATTTAACAAAAATTTAACGCGAATTTTA
ACAAAATATTAACGTTTACAATTTTATGGTGCACTCTCAGTACAATCTGCTCTGATGCCGCA
TAGTTAAGCCAGCCCCGACACCCGCCAACACCCGCTGACGCGCCCTGACGGGCTTGTCT
GCTCCCGGCATCCGCTTACAGACAAGCTGTGACCGTCTCCGGGAGCTGCATGTGTCAGAG
GTTTTCACCGTCATCACCGAAACGCGCGAGACGAAAGGGCCTCGTGATACGCCTATTTTTA
TAGGTTAATGTCATGATAATAATGGTTTCTTAGACGTCAGGTGGCACTTTTCGGGGAAATGT
GCGCGGAACCCCTATTTGTTTATTTTTCTAAATACATTCAAATATGTATCCGCTCATGAGAC
AATAACCCTGATAAATGCTTCAATAATATTGAAAAAGGAAGAGTATGAGTATTCAACATTTCC
GTGTCGCCCTTATTCCCTTTTTTGCGGCATTTTGCCTTCCTGTTTTTGCTCACCCAGAAACG
CTGGTGAAAGTAAAAGATGCTGAAGATCAGTTGGGTGCACGAGTGGGTTACATCGAACTG
GATCTCAACAGCGGTAAGATCCTTGAGAGTTTTCGCCCCGAAGAACGTTTTCCAATGATGA
GCACTTTTAAAGTTCTGCTATGTGGCGCGGTATTATCCCGTATTGACGCCGGGCAAGAGCA
ACTCGGTCGCCGCATACACTATTCTCAGAATGACTTGGTTGAGTACTCACCAGTCACAGAA
AAGCATCTTACGGATGGCATGACAGTAAGAGAATTATGCAGTGCTGCCATAACCATGAGTG
ATAACACTGCGGCCAACTTACTTCTGACAACGATCGGAGGACCGAAGGAGCTAACCGCTTT
TTTGCACAACATGGGGGATCATGTAACTCGCCTTGATCGTTGGGAACCGGAGCTGAATGAA
GCCATACCAAACGACGAGCGTGACACCACGATGCCTGTAGCAATGGCAACAACGTTGCGC
AAACTATTAACTGGCGAACTACTTACTCTAGCTTCCCGGCAACAATTAATAGACTGGATGGA
GGCGGATAAAGTTGCAGGACCACTTCTGCGCTCGGCCCTTCCGGCTGGCTGGTTTATTGC
TGATAAATCTGGAGCCGGTGAGCGTGGGTCTCGCGGTATCATTGCAGCACTGGGGCCAGA
TGGTAAGCCCTCCCGTATCGTAGTTATCTACACGACGGGGAGTCAGGCAACTATGGATGA
ACGAAATAGACAGATCGCTGAGATAGGTGCCTCACTGATTAAGCATTGGTAACTGTCAGAC
CAAGTTTACTCATATATACTTTAGATTGATTTAAAACTTCATTTTTAATTTAAAAGGATCTAGG
TGAAGATCCTTTTTGATAATCTCATGACCAAAATCCCTTAACGTGAGTTTTCGTTCCACTGA
GCGTCAGACCCCGTAGAAAAGATCAAAGGATCTTCTTGAGATCCTTTTTTTCTGCGCGTAAT
CTGCTGCTTGCAAACAAAAAAACCACCGCTACCAGCGGTGGTTTGTTTGCCGGATCAAGAG
CTACCAACTCTTTTTCCGAAGGTAACTGGCTTCAGCAGAGCGCAGATACCAAATACTGTCC
TTCTAGTGTAGCCGTAGTTAGGCCACCACTTCAAGAACTCTGTAGCACCGCCTACATACCT
CGCTCTGCTAATCCTGTTACCAGTGGCTGCTGCCAGTGGCGATAAGTCGTGTCTTACCGG
GTTGGACTCAAGACGATAGTTACCGGATAAGGCGCAGCGGTCGGGCTGAACGGGGGGTT
CGTGCACACAGCCCAGCTTGGAGCGAACGACCTACACCGAACTGAGATACCTACAGCGTG
AGCTATGAGAAAGCGCCACGCTTCCCGAAGGGAGAAAGGCGGACAGGTATCCGGTAAGC
GGCAGGGTCGGAACAGGAGAGCGCACGAGGGAGCTTCCAGGGGGAAACGCCTGGTATCT
TTATAGTCCTGTCGGGTTTCGCCACCTCTGACTTGAGCGTCGATTTTTGTGATGCTCGTCA
GGGGGGCGGAGCCTATGGAAAAACGCCAGCAACGCGGCCTTTTTACGGTTCCTGGCCTTT
TGCTGGCCTTTTGCTCACATGT (SEQ ID NO:183)

FIG. 79 cont'd

Construct TG988 nucleotide sequence: rAAV_mscRE4-pBGmin-tTA2-bGHpA (sequence should be inserted into Plasmid backbone 1):
GCGGCCGCACGCGTATA**AGCCTTGGGGGCAATCAAACTATTACATTGAGTCCTTGGATTT
GCTACAAATTACATTTTAAATGCAATCATTTTATAAAAGCTTCAACACTCACACTTGGAAG
CGTTACCCTGTTGAATATCACTGACTCACTAACTTGCATTGCCATGCTAACTTGCTTTCAG
AGAGATCTCAGAACACATCATCTTCTGCTATTTCAATACATGCACATTAATTTCCTATCAA
CGTGTGCTGATCAGGAACTCTGTAATCTGGCACCGGTGTTTATTTTTATTCCTGTCTATTC
CTGTTGGCTCACGAAAAGATTGTTTGAGCAAGTGTTTTATGGTGAGTTGTATCATATGTAC
ATTGATTTAATCTGCCCACATTCAGTTCTACAAGCGGAGCCAAAAAAATAGAGACAAGCA
TAATTTTCATTCAACATGAGCCCCTCAATGCAAGCCAAGTACCTCATCTGGTGCTCAGCT
AAAGCAACAGCAATCTGTTCCACCCTGGAGACACAACTGGCCACAGAAAACTTAGTGAA
AAGAGGCAATGCTATGCACAGGACAAAT**GAGCTCGGGCTGGGCATAAAAGTCAGGGCAG
AGCCATCTATTGCTTACATTTGCTTCTGGGATCCGCCACCATGTCTAGACTGGACAAGAGC
AAAGTCATAAACTCTGCTCTGGAATTACTCAATGAAGTCGGTATCGAAGGCCTGACGACAA
GGAAACTCGCTCAAAAGCTGGGAGTTGAGCAGCCTACCCTGTACTGGCACGTGAAGAACA
AGCGGGCCCTGCTCGATGCCCTGGCAATCGAGATGCTGGACAGGCATCATACCCACTTCT
GCCCCCTGGAAGGCGAGTCATGGCAAGACTTTCTGCGGAACAACGCCAAGTCATTCCGCT
GTGCTCTCCTCTCACATCGCGACGGGGCTAAAGTGCATCTCGGCACCCGCCCAACAGAGA
AACAGTACGAAACCCTGGAAAATCAGCTCGCGTTCCTGTGTCAGCAAGGCTTCTCCCTGGA
GAACGCACTGTACGCTCTGTCCGCCGTGGGCCACTTTACACTGGGCTGCGTATTGGAGGA
TCAGGAGCATCAAGTAGCAAAAGAGGAAAGAGAGACACCTACCACCGATTCTATGCCCCC
ACTTCTGAGACAAGCAATTGAGCTGTTCGACCATCAGGGAGCCGAACCTGCCTTCCTTTTC
GGCCTGGAACTAATCATATGTGGCCTGGAGAAACAGCTAAAGTGCGAAAGCGGCGGGCC
GGCCGACGCCCTTGACGATTTTGACTTAGACATGCTCCCAGCCGATGCCCTTGACGACTTT
GACCTTGATATGCTGCCTGCTGACGCTCTTGACGATTTTGACCTTGACATGCTCCCCGGGT
AAGGCGCGCCGCGGCCGCTGCTCGAGAGATCTACGGGTGGCATCCCTGTGACCCCTCCC
CAGTGCCTCTCCTGGCCCTGGAAGTTGCCACTCCAGTGCCCACCAGCCTTGTCCTAATAAA
ATTAAGTTGCATCATTTTGTCTGACTAGGTGTCCTTCTATAATATTATGGGGTGGAGGGGG
GTGGTATGGAGCAAGGGGCAAGTTGGGAAGACAACCTGTAGGGCCTGCGGGGTCTATTG
GGAACCAAGCTGGAGTGCAGTGGCACAATCTTGGCTCACTGCAATCTCCGCCTCCTGGGT
TCAAGCGATTCTCCTGCCTCAGCCTCCCGAGTTGTTGGGATTCCAGGCATGCATGACCAG
GCTCAGCTAATTTTTGTTTTTTTGGTAGAGACGGGGTTTCACCATATTGGCCAGGCTGGTCT
CCAACTCCTAATCTCAGGTGATCTACCCACCTTGGCCTCCCAAATTGCTGGGATTACAGGC
GTGAACCACTGCTCCCTTCCCTGTCCTTCTGATTTTGTAGGTAACCACGTGCGGACCGAGC
GGCCGC (SEQ ID NO: 82)

Construct TG995 nucleotide sequence: rAAV_mscRE10-pBGmin-EGFP-WPRE3-BGHpA (sequence should be inserted into Plasmid backbone 1):
GCGGCCGCACGCGTATGTGTCTTTTACTCTGATCCTCCTGTTTTTACCTTCCAAGTGCTGG
AATCACAGACATATAC**CACTGTGCATAGCATCATTACAATGTTATAGTTTTTCACACTATGC
CTTGACTTTTTGGAAAGGCAAACCACCTCTTGGATTTCTCCTTCCTTCTCTATCTCTCTCTC
TCTCTCTTCCTCCCTCCGTCCCTCCATCTCTTCCTCCTTCCCATTTTCTTCTCTCCCTATTTG
GACACAATATAAAATAATTTAGATGAGGTGAGTTAAATTGTGAACAAAGTATGTGCCTAT
ACATGGTTGTAAATCAGCTTATCAAAGTGTAATATTAGAAGAATTTATAAAAATGATAAAA
TTCATACTCAAAGTTCTGTGTAAAGCAATAATAGCTTTATCTCCTTTTAGTTATCTTGAGTC
TTTCTATGACTAACAACTCCCTCATAGGCATCTTAAAGAGCAGTAAGCATAAGTAGATTC**

FIG. 79 cont'd

CAAATGGGAAGGGAGAAGTGTGAACCATCACTTTCATCCAGACTTGTAGATATATCTGCT
GCATTTTCAGAAACCAGAAACAGACAGTGTTCTTTATCTCCATTGAGTCTAGTGTAGCAAC
AGAGCTCGGGCTGGGCATAAAAGTCAGGGCAGAGCCATCTATTGCTTACATTTGCTTCTGG
GATCCGCCACCATGGTGAGCAAGGGCGAGGAGCTGTTCACCGGGGTGGTGCCCATCCTG
GTCGAGCTGGACGGCGACGTAAACGGCCACAAGTTCAGCGTGTCCGGCGAGGGCGAGG
GCGATGCCACCTACGGCAAGCTGACCCTGAAGTTCATCTGCACCACCGGCAAGCTGCCCG
TGCCCTGGCCCACCCTCGTGACCACCCTGACCTACGGCGTGCAGTGCTTCAGCCGCTACC
CCGACCACATGAAGCAGCACGACTTCTTCAAGTCCGCCATGCCCGAAGGCTACGTCCAGG
AGCGCACCATCTTCTTCAAGGACGACGGCAACTACAAGACCCGCGCCGAGGTGAAGTTCG
AGGGCGACACCCTGGTGAACCGCATCGAGCTGAAGGGCATCGACTTCAAGGAGGACGGC
AACATCCTGGGGCACAAGCTGGAGTACAACTACAACAGCCACAACGTCTATATCATGGCC
GACAAGCAGAAGAACGGCATCAAGGTGAACTTCAAGATCCGCCACAACATCGAGGACGGC
AGCGTGCAGCTCGCCGACCACTACCAGCAGAACACCCCCATCGGCGACGGCCCCGTGCT
GCTGCCCGACAACCACTACCTGAGCACCCAGTCCGCCCTGAGCAAAGACCCCAACGAGAA
GCGCGATCACATGGTCCTGCTGGAGTTCGTGACCGCCGCCGGGATCACTCTCGGCATGG
ACGAGCTGTACAAGTAAGAATTCGATATCAAGCTTATCGATAATCAACCTCTGGATTACAAA
ATTTGTGAAAGATTGACTGGTATTCTTAACTATGTTGCTCCTTTTACGCTATGTGGATACGC
TGCTTTAATGCCTTTGTATCATGCTATTGCTTCCCGTATGGCTTTCATTTTCTCCTCCTTGTA
TAAATCCTGGTTGCTGTCTCTTTATGAGGAGTTGTGGCCCGTTGTCAGGCAACGTGGCGTG
GTGTGCACTGTGTTTGCTGACGCAACCCCCACTGGTTGGGGCATTGCCACCACCTGTCAG
CTCCTTTCCGGGACTTTCGCTTTCCCCCTCCCTATTGCCACGGCGGAACTCATCGCCGCCT
GCCTTGCCCGCTGCTGGACAGGGGCTCGGCTGTTGGGCACTGACAATTCCGTGGTGTTGT
CGGGGAAATCATCGTCCTTTCCTTGGCTGCTCGCCTATGTTGCCACCTGGATTCTGCGCG
GGACGTCCTTCTGCTACGTCCCTTCGGCCCTCAATCCAGCGGACCTTCCTTCCCGCGGCC
TGCTGCCGGCTCTGCGGCCTCTTCCGCGTCTTCGCCTTCGCCCTCAGACGAGTCGGATCT
CCCTTTGGGCCGCCTCCCCGCATCGATACCGAGCGCTGCTCGAGAGATCTACGGGTGGC
ATCCCTGTGACCCCTCCCCAGTGCCTCTCCTGGCCCTGGAAGTTGCCACTCCAGTGCCCA
CCAGCCTTGTCCTAATAAAATTAAGTTGCATCATTTTGTCTGACTAGGTGTCCTTCTATAATA
TTATGGGGTGGAGGGGGGTGGTATGGAGCAAGGGGCAAGTTGGGAAGACAACCTGTAGG
GCCTGCGGGGTCTATTGGGAACCAAGCTGGAGTGCAGTGGCACAATCTTGGCTCACTGCA
ATCTCCGCCTCCTGGGTTCAAGCGATTCTCCTGCCTCAGCCTCCCGAGTTGTTGGGATTCC
AGGCATGCATGACCAGGCTCAGCTAATTTTTGTTTTTTTGGTAGAGACGGGGTTTCACCAT
ATTGGCCAGGCTGGTCTCCAACTCCTAATCTCAGGTGATCTACCCACCTTGGCCTCCCAAA
TTGCTGGGATTACAGGCGTGAACCACTGCTCCCTTCCCTGTCCTTCTGATTTTGTAGGTAA
CCACGTGCGGACCGAGCGGCCGC (SEQ ID NO: 83)

Construct TG996 nucleotide sequence: rAAV_mscRE11-pBGmin-EGFP-WPRE3-BGHpA
(sequence should be inserted into Plasmid backbone 1):
GCGGCCGCACGCGTCAGTAGTGTTAATGACAGAGTCAGATACATGAGAAATAAAGACAAA
CTGAAAATGTTCATTTTGCCAATATGATCACCAATAAAACCATTTGTGTAGACTATCCACC
TTAATCCCCCTATAATACAATAGCACAGAGGTGAGTCAGTTTGATTTTGATACTAGGTTTA
TTTTATAGGAGCTATTAAAGTTTCAGAATTTTGCTGAGTCACCAGGCTCTTCATTTTGTGG
CAAATCCATCACTACAGTTTAAGGAGAGAAGAAACAGACCCCCCCCTACCCTCTGAAAA
ATAAAAATAAAAACTTGTTTCAGGCAGGCTAGCGATTCACTAATAATGAGAAAACTCCAG
TTTTAAGACTTAATTTCACCATAAATACTCTTTCATTCTAAGCTCTGGGACATCATGAGCC
AGAGAACAGCAGAGTGAATAATACAGTTACAGAGCTGATGAGCAATGCCAGTCACTGTA
AAAAATACAGAATCCCATCCAAAGGACATCTGTAAAAGTGTCTTTAACATCTACTCAGCC
CTTCTGTGTAAAGGTCAGCACGATGGGAGTGGTTTGTCTATACTCAAGCCGAGCTCGGGC

FIG. 79 cont'd

TGGGCATAAAAGTCAGGGCAGAGCCATCTATTGCTTACATTTGCTTCTGGGATCCGCCACC
ATGGTGAGCAAGGGCGAGGAGCTGTTCACCGGGGTGGTGCCCATCCTGGTCGAGCTGGA
CGGCGACGTAAACGGCCACAAGTTCAGCGTGTCCGGCGAGGGCGAGGGCGATGCCACCT
ACGGCAAGCTGACCCTGAAGTTCATCTGCACCACCGGCAAGCTGCCCGTGCCCTGGCCCA
CCCTCGTGACCACCCTGACCTACGGCGTGCAGTGCTTCAGCCGCTACCCCGACCACATGA
AGCAGCACGACTTCTTCAAGTCCGCCATGCCCGAAGGCTACGTCCAGGAGCGCACCATCT
TCTTCAAGGACGACGGCAACTACAAGACCCGCGCCGAGGTGAAGTTCGAGGGCGACACC
CTGGTGAACCGCATCGAGCTGAAGGGCATCGACTTCAAGGAGGACGGCAACATCCTGGG
GCACAAGCTGGAGTACAACTACAACAGCCACAACGTCTATATCATGGCCGACAAGCAGAA
GAACGGCATCAAGGTGAACTTCAAGATCCGCCACAACATCGAGGACGGCAGCGTGCAGCT
CGCCGACCACTACCAGCAGAACACCCCCATCGGCGACGGCCCCGTGCTGCTGCCCGACA
ACCACTACCTGAGCACCCAGTCCGCCCTGAGCAAAGACCCCAACGAGAAGCGCGATCACA
TGGTCCTGCTGGAGTTCGTGACCGCCGCCGGGATCACTCTCGGCATGGACGAGCTGTACA
AGTAAGAATTCGATATCAAGCTTATCGATAATCAACCTCTGGATTACAAAATTTGTGAAAGA
TTGACTGGTATTCTTAACTATGTTGCTCCTTTTACGCTATGTGGATACGCTGCTTTAATGCC
TTTGTATCATGCTATTGCTTCCCGTATGGCTTTCATTTTCTCCTCCTTGTATAAATCCTGGTT
GCTGTCTCTTTATGAGGAGTTGTGGCCCGTTGTCAGGCAACGTGGCGTGGTGTGCACTGT
GTTTGCTGACGCAACCCCCACTGGTTGGGGCATTGCCACCACCTGTCAGCTCCTTTCCGG
GACTTTCGCTTTCCCCCTCCCTATTGCCACGGCGGAACTCATCGCCGCCTGCCTTGCCCG
CTGCTGGACAGGGGCTCGGCTGTTGGGCACTGACAATTCCGTGGTGTTGTCGGGGAAATC
ATCGTCCTTTCCTTGGCTGCTCGCCTATGTTGCCACCTGGATTCTGCGCGGGACGTCCTTC
TGCTACGTCCCTTCGGCCCTCAATCCAGCGGACCTTCCTTCCCGCGGCCTGCTGCCGGCT
CTGCGGCCTCTTCCGCGTCTTCGCCTTCGCCCTCAGACGAGTCGGATCTCCCTTTGGGCC
GCCTCCCCGCATCGATACCGAGCGCTGCTCGAGAGATCTACGGGTGGCATCCCTGTGACC
CCTCCCCAGTGCCTCTCCTGGCCCTGGAAGTTGCCACTCCAGTGCCCACCAGCCTTGTCC
TAATAAAATTAAGTTGCATCATTTTGTCTGACTAGGTGTCCTTCTATAATATTATGGGGTGGA
GGGGGGTGGTATGGAGCAAGGGGCAAGTTGGGAAGACAACCTGTAGGGCCTGCGGGGT
CTATTGGGAACCAAGCTGGAGTGCAGTGGCACAATCTTGGCTCACTGCAATCTCCGCCTC
CTGGGTTCAAGCGATTCTCCTGCCTCAGCCTCCCGAGTTGTTGGGATTCCAGGCATGCAT
GACCAGGCTCAGCTAATTTTTGTTTTTTTGGTAGAGACGGGGTTTCACCATATTGGCCAGG
CTGGTCTCCAACTCCTAATCTCAGGTGATCTACCCACCTTGGCCTCCCAAATTGCTGGGAT
TACAGGCGTGAACCACTGCTCCCTTCCCTGTCCTTCTGATTTTGTAGGTAACCACGTGCGG
ACCGAGCGGCCGC (SEQ ID NO: 84)

Synthetic construct TG997 nucleotide sequence: rAAV_mscRE12-pBGmin-EGFP-WPRE3-BGHpA (sequence includes ITRs and plasmid backbone in plain text and synthetic AAV genome sequence is underlined):

CCTGCAGGCAGCTGCGCGCTCGCTCGCTCACTGAGGCCGCCCGGGCAAAGCCCGGGCG
TCGGGCGACCTTTGGTCGCCCGGCCTCAGTGAGCGAGCGAGCGCGCAGAGAGGGAGTG
GCCAACTCCATCACTAGGGGTTCCTGCGGCCGCACGCGTCCTTTTCCAACCGTTCCTTCA
TGACATCAAGGCTTCAGACTGCTAAGCTTTGGGCACTACCTGGGGTCAGTCTGCATCAAA
ATGTAAGGCTCAAATGTGTAATTGTAAGTACTGTTTTGCTGAGCTGGAAGGGCTCCTTTG
AAGCCCACGTTTTAATTTTAATTTAGCCACACAGAGTGGCAAAGACAAATAGATTTATCC
AAAATACATTTGGTAACAGATTTTTTGAGTCAGTTATTAATTTTATTTGAGGGGTTCCTCTT
TTTATTTTTTATAAACTGTGAAACTCAAGAGGAAGCAGGATCCCATGCAATGCCTTTTATT
GATGGCCTGCTATGTGCCAAGAAAGGTGTTAAATGTTTTCCAATGCTGCCTCATTTATCCT
GATCTTACAGACAAGCAAAAGGAGGTGTGAAGAGGTGAAGTTTCTCACCCAGCTGGAAA
GTGGCAAAGTCATTCACAGATCTGCCTCCGCTCAAAAAAATTGCTTTATGCAACTCTTTG

FIG. 79 cont'd

GAAGCTAACTTCATGGGAGCTACATGCAGCTTCTCAATGAACCTTGTTTTGCTGGCCTGC
AGCCAGAAGTTACTACTCCTTTGGTTCCTGAGCAGAGCTCGGGCTGGGCATAAAAGTCAG
GGCAGAGCCATCTATTGCTTACATTTGCTTCTGGGATCCGCCACCATGGTGAGCAAGGGC
GAGGAGCTGTTCACCGGGGTGGTGCCCATCCTGGTCGAGCTGGACGGCGACGTAAACGG
CCACAAGTTCAGCGTGTCCGGCGAGGGCGAGGGCGATGCCACCTACGGCAAGCTGACCC
TGAAGTTCATCTGCACCACCGGCAAGCTGCCCGTGCCCTGGCCCACCCTCGTGACCACCC
TGACCTACGGCGTGCAGTGCTTCAGCCGCTACCCCGACCACATGAAGCAGCACGACTTCT
TCAAGTCCGCCATGCCCGAAGGCTACGTCCAGGAGCGCACCATCTTCTTCAAGGACGACG
GCAACTACAAGACCCGCGCCGAGGTGAAGTTCGAGGGCGACACCCTGGTGAACCGCATC
GAGCTGAAGGGCATCGACTTCAAGGAGGACGGCAACATCCTGGGGCACAAGCTGGAGTA
CAACTACAACAGCCACAACGTCTATATCATGGCCGACAAGCAGAAGAACGGCATCAAGGT
GAACTTCAAGATCCGCCACAACATCGAGGACGGCAGCGTGCAGCTCGCCGACCACTACCA
GCAGAACACCCCCATCGGCGACGGCCCCGTGCTGCTGCCCGACAACCACTACCTGAGCA
CCCAGTCCGCCCTGAGCAAAGACCCCAACGAGAAGCGCGATCACATGGTCCTGCTGGAGT
TCGTGACCGCCGCCGGGATCACTCTCGGCATGGACGAGCTGTACAAGTAAGAATTCGATA
TCAAGCTTATCGATAATCAACCTCTGGATTACAAAATTTGTGAAAGATTGACTGGTATTCTTA
ACTATGTTGCTCCTTTTACGCTATGTGGATACGCTGCTTTAATGCCTTTGTATCATGCTATT
GCTTCCCGTATGGCTTTCATTTTCTCCTCCTTGTATAAATCCTGGTTGCTGTCTCTTTATGA
GGAGTTGTGGCCCGTTGTCAGGCAACGTGGCGTGGTGTGCACTGTGTTTGCTGACGCAAC
CCCCACTGGTTGGGGCATTGCCACCACCTGTCAGCTCCTTTCCGGGACTTTCGCTTTCCC
CCTCCCTATTGCCACGGCGGAACTCATCGCCGCCTGCCTTGCCCGCTGCTGGACAGGGG
CTCGGCTGTTGGGCACTGACAATTCCGTGGTGTTGTCGGGGAAATCATCGTCCTTTCCTTG
GCTGCTCGCCTATGTTGCCACCTGGATTCTGCGCGGGACGTCCTTCTGCTACGTCCCTTC
GGCCCTCAATCCAGCGGACCTTCCTTCCCGCGGCCTGCTGCCGGCTCTGCGGCCTCTTCC
GCGTCTTCGCCTTCGCCCTCAGACGAGTCGGATCTCCCTTTGGGCCGCCTCCCCGCATCG
ATACCGAGCGCTGCTCGAGAGATCTACGGGTGGCATCCCTGTGACCCCTCCCCAGTGCCT
CTCCTGGCCCTGGAAGTTGCCACTCCAGTGCCCACCAGCCTTGTCCTAATAAAATTAAGTT
GCATCATTTTGTCTGACTAGGTGTCCTTCTATAATATTATGGGGTGGAGGGGGGTGGTATG
GAGCAAGGGGCAAGTTGGGAAGACAACCTGTAGGGCCTGCGGGGTCTATTGGGAACCAA
GCTGGAGTGCAGTGGCACAATCTTGGCTCACTGCAATCTCCGCCTCCTGGGTTCAAGCGA
TTCTCCTGCCTCAGCCTCCCGAGTTGTTGGGATTCCAGGCATGCATGACCAGGCTCAGCT
AATTTTTGTTTTTTTGGTAGAGACGGGGTTTCACCATATTGGCCAGGCTGGTCTCCAACTCC
TAATCTCAGGTGATCTACCCACCTTGGCCTCCCAAATTGCTGGGATTACAGGCGTGAACCA
CTGCTCCCTTCCCTGTCCTTCTGATTTTGTAGGTAACCACGTGCGGACCGAGCGGCCGCA
GGAACCCCTAGTGATGGAGTTGGCCACTCCCTCTCTGCGCGCTCGCTCGCTCACTGAGGC
CGGGCGACCAAAGGTCGCCCGACGCCCGGGCTTTGCCCGGGCGGCCTCAGTGAGCGAG
CGAGCGCGCAGCTGCCTGCAGGGGCGCCTGATGCGGTATTTTCTCCTTACGCATCTGTGC
GGTATTTCACACCGCATACGTCAAAGCAACCATAGTACGCGCCCTGTAGCGGCGCATTAA
GCGCGGCGGGTGTGGTGGTTACGCGCAGCGTGACCGCTACACTTGCCAGCGCCCTAGCG
CCCGCTCCTTTCGCTTTCTTCCCTTCCTTTCTCGCCACGTTCGCCGGCTTTCCCCGTCAAG
CTCTAAATCGGGGGCTCCCTTTAGGGTTCCGATTTAGTGCTTTACGGCACCTCGACCCCAA
AAAACTTGATTTGGGTGATGGTTCACGTAGTGGGCCATCGCCCTGATAGACGGTTTTTCGC
CCTTTGACGTTGGAGTCCACGTTCTTTAATAGTGGACTCTTGTTCCAAACTGGAACAACACT
CAACCCTATCTCGGGCTATTCTTTTGATTTATAAGGGATTTTGCCGATTTCGGCCTATTGGT
TAAAAAATGAGCTGATTTAACAAAAATTTAACGCGAATTTTAACAAAATATTAACGTTTACAA
TTTTATGGTGCACTCTCAGTACAATCTGCTCTGATGCCGCATAGTTAAGCCAGCCCCGACA
CCCGCCAACACCCGCTGACGCGCCCTGACGGGCTTGTCTGCTCCCGGCATCCGCTTACA
GACAAGCTGTGACCGTCTCCGGGAGCTGCATGTGTCAGAGGTTTTCACCGTCATCACCGA

FIG. 79 cont'd

AACGCGCGAGACGAAAGGGCCTCGTGATACGCCTATTTTTATAGGTTAATGTCATGATAAT
AATGGTTTCTTAGACGTCAGGTGGCACTTTTCGGGGAAATGTGCGCGGAACCCCTATTTGT
TTATTTTTCTAAATACATTCAAATATGTATCCGCTCATGAGACAATAACCCTGATAAATGCTT
CAATAATATTGAAAAAGGAAGAGTATGAGTATTCAACATTTCCGTGTCGCCCTTATTCCCTT
TTTTGCGGCATTTTGCCTTCCTGTTTTTGCTCACCCAGAAACGCTGGTGAAAGTAAAAGATG
CTGAAGATCAGTTGGGTGCACGAGTGGGTTACATCGAACTGGATCTCAACAGCGGTAAGA
TCCTTGAGAGTTTTCGCCCCGAAGAACGTTTTCCAATGATGAGCACTTTTAAAGTTCTGCTA
TGTGGCGCGGTATTATCCCGTATTGACGCCGGGCAAGAGCAACTCGGTCGCCGCATACAC
TATTCTCAGAATGACTTGGTTGAGTACTCACCAGTCACAGAAAAGCATCTTACGGATGGCA
TGACAGTAAGAGAATTATGCAGTGCTGCCATAACCATGAGTGATAACACTGCGGCCAACTT
ACTTCTGACAACGATCGGAGGACCGAAGGAGCTAACCGCTTTTTTGCACAACATGGGGGA
TCATGTAACTCGCCTTGATCGTTGGGAACCGGAGCTGAATGAAGCCATACCAAACGACGA
GCGTGACACCACGATGCCTGTAGCAATGGCAACAACGTTGCGCAAACTATTAACTGGCGA
ACTACTTACTCTAGCTTCCCGGCAACAATTAATAGACTGGATGGAGGCGGATAAAGTTGCA
GGACCACTTCTGCGCTCGGCCCTTCCGGCTGGCTGGTTTATTGCTGATAAATCTGGAGCC
GGTGAGCGTGGGTCTCGCGGTATCATTGCAGCACTGGGGCCAGATGGTAAGCCCTCCCG
TATCGTAGTTATCTACACGACGGGGAGTCAGGCAACTATGGATGAACGAAATAGACAGATC
GCTGAGATAGGTGCCTCACTGATTAAGCATTGGTAACTGTCAGACCAAGTTTACTCATATAT
ACTTTAGATTGATTTAAAACTTCATTTTTAATTTAAAAGGATCTAGGTGAAGATCCTTTTTGAT
AATCTCATGACCAAAATCCCTTAACGTGAGTTTTCGTTCCACTGAGCGTCAGACCCCGTAG
AAAAGATCAAAGGATCTTCTTGAGATCCTTTTTTTCTGCGCGTAATCTGCTGCTTGCAAACA
AAAAAACCACCGCTACCAGCGGTGGTTTGTTTGCCGGATCAAGAGCTACCAACTCTTTTTC
CGAAGGTAACTGGCTTCAGCAGAGCGCAGATACCAAATACTGTCCTTCTAGTGTAGCCGTA
GTTAGGCCACCACTTCAAGAACTCTGTAGCACCGCCTACATACCTCGCTCTGCTAATCCTG
TTACCAGTGGCTGCTGCCAGTGGCGATAAGTCGTGTCTTACCGGGTTGGACTCAAGACGA
TAGTTACCGGATAAGGCGCAGCGGTCGGGCTGAACGGGGGGTTCGTGCACACAGCCCAG
CTTGGAGCGAACGACCTACACCGAACTGAGATACCTACAGCGTGAGCTATGAGAAAGCGC
CACGCTTCCCGAAGGGAGAAAGGCGGACAGGTATCCGGTAAGCGGCAGGGTCGGAACAG
GAGAGCGCACGAGGGAGCTTCCAGGGGGAAACGCCTGGTATCTTTATAGTCCTGTCGGGT
TTCGCCACCTCTGACTTGAGCGTCGATTTTTGTGATGCTCGTCAGGGGGGCGGAGCCTAT
GGAAAAACGCCAGCAACGCGGCCTTTTTACGGTTCCTGGCCTTTTGCTGGCCTTTTGCTCA
CATGT (SEQ ID NO: 184)

Construct TG999 nucleotide sequence: rAAV_mscRE13-pBGmin-EGFP-WPRE3-BGHpA
(sequence includes ITRs and plasmid backbone in plain text and synthetic AAV genome sequence is underlined):
CCTGCAGGCAGCTGCGCGCTCGCTCGCTCACTGAGGCCGCCCGGGCAAAGCCCGGGCG
TCGGGCGACCTTTGGTCGCCCGGCCTCAGTGAGCGAGCGAGCGCGCAGAGAGGGAGTG
GCCAACTCCATCACTAGGGGTTCCTGCGGCCGCACGCGTGTCCCATAGGCAGTTTGTGGC
TGAGTGCTGGTCCAGGGGTGAGGAGGTGGGCTATGTTACTGAGGGTCTCTGGGTGTTAG
GAAAACAGGGCCCAGGAGTCTGGCTGCTCGTATGCTGGCCCAGGCTCTTGTTTTTCTTGA
GCTGACTTGCTGGAGAAGTGAGCTAAGTCAGAAACAAAATGCCACATTGCACGCCCACT
GAAGTCTGGGCTCAAGGGAAAGAAGAGAGATTGCCAGAGCGTTAGCTGTTCCCAATCCA
CTCCTGGACCTTAAGCTGTCTTGAACAGAGTTGCCAATCAGCTTGGTAGGGACTGGCCTT
TGAGGAGGGGAGGGGGTGTAGGCAGGGGAGGGGGAGAGAAGGGAGCAGTCTGCGCTC
CATCTTAATTACCTCATCAGAAACAGCTCCCTTCCCGCAAAGCTCTGGTGTCTTCTACAA
GAGGGTGAGTCTTTGGCTTTACATGTGAACTTGTGCCATTTGCCTGCGTATATAAACATG
AAGGGTCGTCTGGGTTCAGAGCTGAAATCTTTCACTTGTGACTTAGCTGGGAAATTCTTG

FIG. 79 cont'd

GCAAGATCAGAATGCAGTGGTAAGGTCTGAGCTCGGGCTGGGCATAAAAGTCAGGGCAGA
GCCATCTATTGCTTACATTTGCTTCTGGGATCCGCCACCATGGTGAGCAAGGGCGAGGAG
CTGTTCACCGGGGTGGTGCCCATCCTGGTCGAGCTGGACGGCGACGTAAACGGCCACAA
GTTCAGCGTGTCCGGCGAGGGCGAGGGCGATGCCACCTACGGCAAGCTGACCCTGAAGT
TCATCTGCACCACCGGCAAGCTGCCCGTGCCCTGGCCCACCCTCGTGACCACCCTGACCT
ACGGCGTGCAGTGCTTCAGCCGCTACCCCGACCACATGAAGCAGCACGACTTCTTCAAGT
CCGCCATGCCCGAAGGCTACGTCCAGGAGCGCACCATCTTCTTCAAGGACGACGGCAACT
ACAAGACCCGCGCCGAGGTGAAGTTCGAGGGCGACACCCTGGTGAACCGCATCGAGCTG
AAGGGCATCGACTTCAAGGAGGACGGCAACATCCTGGGGCACAAGCTGGAGTACAACTAC
AACAGCCACAACGTCTATATCATGGCCGACAAGCAGAAGAACGGCATCAAGGTGAACTTCA
AGATCCGCCACAACATCGAGGACGGCAGCGTGCAGCTCGCCGACCACTACCAGCAGAAC
ACCCCCATCGGCGACGGCCCCGTGCTGCTGCCCGACAACCACTACCTGAGCACCCAGTC
CGCCCTGAGCAAAGACCCCAACGAGAAGCGCGATCACATGGTCCTGCTGGAGTTCGTGAC
CGCCGCCGGGATCACTCTCGGCATGGACGAGCTGTACAAGTAAGAATTCGATATCAAGCT
TATCGATAATCAACCTCTGGATTACAAAATTTGTGAAAGATTGACTGGTATTCTTAACTATGT
TGCTCCTTTTACGCTATGTGGATACGCTGCTTTAATGCCTTTGTATCATGCTATTGCTTCCC
GTATGGCTTTCATTTTCTCCTCCTTGTATAAATCCTGGTTGCTGTCTCTTTATGAGGAGTTGT
GGCCCGTTGTCAGGCAACGTGGCGTGGTGTGCACTGTGTTTGCTGACGCAACCCCCACTG
GTTGGGGCATTGCCACCACCTGTCAGCTCCTTTCCGGGACTTTCGCTTTCCCCCTCCCTAT
TGCCACGGCGGAACTCATCGCCGCCTGCCTTGCCCGCTGCTGGACAGGGGCTCGGCTGT
TGGGCACTGACAATTCCGTGGTGTTGTCGGGGAAATCATCGTCCTTTCCTTGGCTGCTCGC
CTATGTTGCCACCTGGATTCTGCGCGGGACGTCCTTCTGCTACGTCCCTTCGGCCCTCAAT
CCAGCGGACCTTCCTTCCCGCGGCCTGCTGCCGGCTCTGCGGCCTCTTCCGCGTCTTCG
CCTTCGCCCTCAGACGAGTCGGATCTCCCTTTGGGCCGCCTCCCCGCATCGATACCGAGC
GCTGCTCGAGAGATCTACGGGTGGCATCCCTGTGACCCCTCCCCAGTGCCTCTCCTGGCC
CTGGAAGTTGCCACTCCAGTGCCCACCAGCCTTGTCCTAATAAAATTAAGTTGCATCATTTT
GTCTGACTAGGTGTCCTTCTATAATATTATGGGGTGGAGGGGGGTGGTATGGAGCAAGGG
GCAAGTTGGGAAGACAACCTGTAGGGCCTGCGGGGTCTATTGGGAACCAAGCTGGAGTG
CAGTGGCACAATCTTGGCTCACTGCAATCTCCGCCTCCTGGGTTCAAGCGATTCTCCTGCC
TCAGCCTCCCGAGTTGTTGGGATTCCAGGCATGCATGACCAGGCTCAGCTAATTTTTGTTT
TTTTGGTAGAGACGGGGTTTCACCATATTGGCCAGGCTGGTCTCCAACTCCTAATCTCAGG
TGATCTACCCACCTTGGCCTCCCAAATTGCTGGGATTACAGGCGTGAACCACTGCTCCCTT
CCCTGTCCTTCTGATTTTGTAGGTAACCACGTGCGGACCGAGCGGCCGCAGGAACCCCTA
GTGATGGAGTTGGCCACTCCCTCTCTGCGCGCTCGCTCGCTCACTGAGGCCGGGCGACC
AAAGGTCGCCCGACGCCCGGGCTTTGCCCGGGCGGCCTCAGTGAGCGAGCGAGCGCGC
AGCTGCCTGCAGGGGCGCCTGATGCGGTATTTTCTCCTTACGCATCTGTGCGGTATTTCAC
ACCGCATACGTCAAAGCAACCATAGTACGCGCCCTGTAGCGGCGCATTAAGCGCGGCGG
GTGTGGTGGTTACGCGCAGCGTGACCGCTACACTTGCCAGCGCCCTAGCGCCCGCTCCTT
TCGCTTTCTTCCCTTCCTTTCTCGCCACGTTCGCCGGCTTTCCCCGTCAAGCTCTAAATCG
GGGGCTCCCTTTAGGGTTCCGATTTAGTGCTTTACGGCACCTCGACCCCAAAAAACTTGAT
TTGGGTGATGGTTCACGTAGTGGGCCATCGCCCTGATAGACGGTTTTTCGCCCTTTGACGT
TGGAGTCCACGTTCTTTAATAGTGGACTCTTGTTCCAAACTGGAACAACACTCAACCCTATC
TCGGGCTATTCTTTTGATTTATAAGGGATTTTGCCGATTTCGGCCTATTGGTTAAAAAATGA
GCTGATTTAACAAAAATTTAACGCGAATTTTAACAAAATATTAACGTTTACAATTTTATGGTG
CACTCTCAGTACAATCTGCTCTGATGCCGCATAGTTAAGCCAGCCCCGACACCCGCCAACA
CCCGCTGACGCGCCCTGACGGGCTTGTCTGCTCCCGGCATCCGCTTACAGACAAGCTGTG
ACCGTCTCCGGGAGCTGCATGTGTCAGAGGTTTTCACCGTCATCACCGAAACGCGCGAGA
CGAAAGGGCCTCGTGATACGCCTATTTTTATAGGTTAATGTCATGATAATAATGGTTTCTTA

FIG. 79 cont'd

GACGTCAGGTGGCACTTTTCGGGGAAATGTGCGCGGAACCCCTATTTGTTTATTTTTCTAA
ATACATTCAAATATGTATCCGCTCATGAGACAATAACCCTGATAAATGCTTCAATAATATTGA
AAAAGGAAGAGTATGAGTATTCAACATTTCCGTGTCGCCCTTATTCCCTTTTTTGCGGCATT
TTGCCTTCCTGTTTTTGCTCACCCAGAAACGCTGGTGAAAGTAAAAGATGCTGAAGATCAG
TTGGGTGCACGAGTGGGTTACATCGAACTGGATCTCAACAGCGGTAAGATCCTTGAGAGTT
TTCGCCCCGAAGAACGTTTTCCAATGATGAGCACTTTTAAAGTTCTGCTATGTGGCGCGGT
ATTATCCCGTATTGACGCCGGGCAAGAGCAACTCGGTCGCCGCATACACTATTCTCAGAAT
GACTTGGTTGAGTACTCACCAGTCACAGAAAAGCATCTTACGGATGGCATGACAGTAAGAG
AATTATGCAGTGCTGCCATAACCATGAGTGATAACACTGCGGCCAACTTACTTCTGACAAC
GATCGGAGGACCGAAGGAGCTAACCGCTTTTTTGCACAACATGGGGGATCATGTAACTCG
CCTTGATCGTTGGGAACCGGAGCTGAATGAAGCCATACCAAACGACGAGCGTGACACCAC
GATGCCTGTAGCAATGGCAACAACGTTGCGCAAACTATTAACTGGCGAACTACTTACTCTA
GCTTCCCGGCAACAATTAATAGACTGGATGGAGGCGGATAAAGTTGCAGGACCACTTCTG
CGCTCGGCCCTTCCGGCTGGCTGGTTTATTGCTGATAAATCTGGAGCCGGTGAGCGTGGG
TCTCGCGGTATCATTGCAGCACTGGGGCCAGATGGTAAGCCCTCCCGTATCGTAGTTATCT
ACACGACGGGGAGTCAGGCAACTATGGATGAACGAAATAGACAGATCGCTGAGATAGGTG
CCTCACTGATTAAGCATTGGTAACTGTCAGACCAAGTTTACTCATATATACTTTAGATTGATT
TAAAACTTCATTTTTAATTTAAAAGGATCTAGGTGAAGATCCTTTTTGATAATCTCATGACCA
AAATCCCTTAACGTGAGTTTTCGTTCCACTGAGCGTCAGACCCCGTAGAAAAGATCAAAGG
ATCTTCTTGAGATCCTTTTTTTCTGCGCGTAATCTGCTGCTTGCAAACAAAAAAACCACCGC
TACCAGCGGTGGTTTGTTTGCCGGATCAAGAGCTACCAACTCTTTTTCCGAAGGTAACTGG
CTTCAGCAGAGCGCAGATACCAAATACTGTCCTTCTAGTGTAGCCGTAGTTAGGCCACCAC
TTCAAGAACTCTGTAGCACCGCCTACATACCTCGCTCTGCTAATCCTGTTACCAGTGGCTG
CTGCCAGTGGCGATAAGTCGTGTCTTACCGGGTTGGACTCAAGACGATAGTTACCGGATA
AGGCGCAGCGGTCGGGCTGAACGGGGGGTTCGTGCACACAGCCCAGCTTGGAGCGAAC
GACCTACACCGAACTGAGATACCTACAGCGTGAGCTATGAGAAAGCGCCACGCTTCCCGA
AGGGAGAAAGGCGGACAGGTATCCGGTAAGCGGCAGGGTCGGAACAGGAGAGCGCACG
AGGGAGCTTCCAGGGGGAAACGCCTGGTATCTTTATAGTCCTGTCGGGTTTCGCCACCTC
TGACTTGAGCGTCGATTTTTGTGATGCTCGTCAGGGGGGCGGAGCCTATGGAAAAACGCC
AGCAACGCGGCCTTTTTACGGTTCCTGGCCTTTTGCTGGCCTTTTGCTCACATGT (SEQ ID NO: 85)

Construct TG1002 nucleotide sequence: rAAV_mscRE16-pBGmin-EGFP-WPRE3-bGHpA (sequence should be inserted into Plasmid backbone 1):
GCGGCCGCACGCGTAGGGTGCAGGAGAAATGTGACCTCAAAGTCTTGTTCTATAACTGTT
GGACCTTAGGAGAGAT**CTGTGCTCAGCAATTTACCAGGACACCCCCACCCCACATGTCTT
GACCACTGTCTGGATAACTGGTATGCAGGACCACACTAGGCTTACTCACAGTGTAAACTC
TCATAACCATCACTGGAGCCCATCCTGCCTGGTAGACAAGGATTCAACCATGACTCATTG
TACTTTAGTGGTGCCATGCTTAGTCATCAGGTGCCCTGTGCTCTGACAGCCGAGGGTCAG
AGCTGGAATCACACTCTTGTTGTCTTTTAATCTCTCCCTCCCTTTCTTCCTTCTTTCTTCAC
TCTGTTGTGATTGCTCATGGAACAGATCCTAGCTGGTCTCCCTGGCAACCTACATGATTT
GAGCCCAACAGATGGATAATGGGGACATCGACTTCCAATGTCATTCAACAGAATCATTG
CCAAGGGAGTCTGATGAGCAGGCAACTGAGATGACACCCTTATCAATATAGCTTCATTTT
GGCAATCTGGAGTAGGTGTTTCAAAAGGAGAGCCCC**CACTGATGCCAGCAATACAGAAC
GTTCATGGGCAAGGAGCTCGGGCTGGGCATAAAAGTCAGGGCAGAGCCATCTATTGCTTA
CATTTGCTTCTGGGATCCGCCACCATGGTGAGCAAGGGCGAGGAGCTGTTCACCGGGGT
GGTGCCCATCCTGGTCGAGCTGGACGGCGACGTAAACGGCCACAAGTTCAGCGTGTCCG
GCGAGGGCGAGGGCGATGCCACCTACGGCAAGCTGACCCTGAAGTTCATCTGCACCACC

FIG. 79 cont'd

GGCAAGCTGCCCGTGCCCTGGCCCACCCTCGTGACCACCCTGACCTACGGCGTGCAGTG
CTTCAGCCGCTACCCCGACCACATGAAGCAGCACGACTTCTTCAAGTCCGCCATGCCCGA
AGGCTACGTCCAGGAGCGCACCATCTTCTTCAAGGACGACGGCAACTACAAGACCCGCGC
CGAGGTGAAGTTCGAGGGCGACACCCTGGTGAACCGCATCGAGCTGAAGGGCATCGACT
TCAAGGAGGACGGCAACATCCTGGGGCACAAGCTGGAGTACAACTACAACAGCCACAACG
TCTATATCATGGCCGACAAGCAGAAGAACGGCATCAAGGTGAACTTCAAGATCCGCCACAA
CATCGAGGACGGCAGCGTGCAGCTCGCCGACCACTACCAGCAGAACACCCCCATCGGCG
ACGGCCCCGTGCTGCTGCCCGACAACCACTACCTGAGCACCCAGTCCGCCCTGAGCAAA
GACCCCAACGAGAAGCGCGATCACATGGTCCTGCTGGAGTTCGTGACCGCCGCCGGGAT
CACTCTCGGCATGGACGAGCTGTACAAGTAAGAATTCGATATCAAGCTTATCGATAATCAA
CCTCTGGATTACAAAATTTGTGAAAGATTGACTGGTATTCTTAACTATGTTGCTCCTTTTACG
CTATGTGGATACGCTGCTTTAATGCCTTTGTATCATGCTATTGCTTCCCGTATGGCTTTCAT
TTTCTCCTCCTTGTATAAATCCTGGTTGCTGTCTCTTTATGAGGAGTTGTGGCCCGTTGTCA
GGCAACGTGGCGTGGTGTGCACTGTGTTTGCTGACGCAACCCCCACTGGTTGGGGCATTG
CCACCACCTGTCAGCTCCTTTCCGGGACTTTCGCTTTCCCCCTCCCTATTGCCACGGCGGA
ACTCATCGCCGCCTGCCTTGCCCGCTGCTGGACAGGGGCTCGGCTGTTGGGCACTGACA
ATTCCGTGGTGTTGTCGGGGAAATCATCGTCCTTTCCTTGGCTGCTCGCCTATGTTGCCAC
CTGGATTCTGCGCGGGACGTCCTTCTGCTACGTCCCTTCGGCCCTCAATCCAGCGGACCT
TCCTTCCCGCGGCCTGCTGCCGGCTCTGCGGCCTCTTCCGCGTCTTCGCCTTCGCCCTCA
GACGAGTCGGATCTCCCTTTGGGCCGCCTCCCCGCATCGATACCGAGCGCTGCTCGAGA
GATCTACGGGTGGCATCCCTGTGACCCCTCCCCAGTGCCTCTCCTGGCCCTGGAAGTTGC
CACTCCAGTGCCCACCAGCCTTGTCCTAATAAAATTAAGTTGCATCATTTTGTCTGACTAGG
TGTCCTTCTATAATATTATGGGGTGGAGGGGGGTGGTATGGAGCAAGGGGCAAGTTGGGA
AGACAACCTGTAGGGCCTGCGGGGTCTATTGGGAACCAAGCTGGAGTGCAGTGGCACAAT
CTTGGCTCACTGCAATCTCCGCCTCCTGGGTTCAAGCGATTCTCCTGCCTCAGCCTCCCGA
GTTGTTGGGATTCCAGGCATGCATGACCAGGCTCAGCTAATTTTTGTTTTTTTGGTAGAGAC
GGGGTTTCACCATATTGGCCAGGCTGGTCTCCAACTCCTAATCTCAGGTGATCTACCCACC
TTGGCCTCCCAAATTGCTGGGATTACAGGCGTGAACCACTGCTCCCTTCCCTGTCCTTCTG
ATTTTGTAGGTAACCACGTGCGGACCGAGCGGCCGC (SEQ ID NO: 86)

Construct TG1009 nucleotide sequence: rAAV-mscRE4-pBGmin-dgCre-WPRE3-bGHpA
(sequence includes ITRs and plasmid backbone in plain text and synthetic AAV genome sequence is underlined):
CCTGCAGGCAGCTGCGCGCTCGCTCGCTCACTGAGGCCGCCCGGGCAAAGCCCGGGCG
TCGGGCGACCTTTGGTCGCCCGGCCTCAGTGAGCGAGCGAGCGCGCAGAGAGGGAGTG
GCCAACTCCATCACTAGGGGTTCCTGCGGCCGCACGCGTATAAGCCTTGGGGGCAATCA
AACTATTACATTGAGTCCTTGGATTTGCTACAAATTACATTTTAAATGCAATCATTTTATAA
AAGCTTCAACACTCACACTTGGAAGCGTTACCCTGTTGAATATCACTGACTCACTAACTT
GCATTGCCATGCTAACTTGCTTTCAGAGAGATCTCAGAACACATCATCTTCTGCTATTTCA
ATACATGCACATTAATTTCCTATCAACGTGTGCTGATCAGGAACTCTGTAATCTGGCACC
GGTGTTTATTTTTATTCCTGTCTATTCCTGTTGGCTCACGAAAAGATTGTTTGAGCAAGTG
TTTTATGGTGAGTTGTATCATATGTACATTGATTTAATCTGCCCACATTCAGTTCTACAAG
CGGAGCCAAAAAAATAGAGACAAGCATAATTTTCATTCAACATGAGCCCCTCAATGCAA
GCCAAGTACCTCATCTGGTGCTCAGCTAAAGCAACAGCAATCTGTTCCACCCTGGAGAC
ACAACTGGCCACAGAAAACTTAGTGAAAAGAGGCAATGCTATGCACAGGACAAATGAGC
TCGGGCTGGGCATAAAAGTCAGGGCAGAGCCATCTATTGCTTACATTTGCTTCTGGGATCC
GCCACCATGATCTCTCTGATTGCCGCTCTGGCCGTGGACTACGTGATCGGGATGGAAAAC
GCTATGCCATGGAATCTGCCCGCCGATCTGGCTTGGTTCAAGAGGAACACCCTGAACAAG

FIG. 79 cont'd

CCAGTGATCATGGGCAGACACACTTGGGAGTCCATTGGACGGCCCCTGCCTGGACGCAA
GAACATCATTCTGAGCTCCCAGCCCTCTACCGACGACAGGGTGACATGGGTGAAAAGTGT
GGACGAAGCCATTGCCGCTTGCGGAGATGTGCCCGAGATCATGGTCATCGGCGGAGGGA
GAGTGATCGAGCAGTTCCTGCCTAAGGCCCAGAAACTGTACCTGACTCACATTGACGCTG
AGGTGGAAGGGGACACCCATTTTCCTGATTATGAGCCAGACGATTGGGAAAGCGTGTTCT
CCGAGTTTCACGACGCCGATGCTCAAAATTCTCATAGTTATTGCTTTGAGATCCTGGAAAG
GAGAGGCGCGCCAGTGAGCAAGGGCGAGGAGCTGTTCACCGGGGTGGTGCCCATCCTG
GTCGAGCTGGACGGCGACGTAAACGGCCACAAGTTCAGCGTGTCCGGCGAGGGCGAGG
GCGATGCCACCTACGGCAAGCTGACCCTGAAGTTCATCTGCACCACCGGCAAGCTGCCCG
TGCCCTGGCCCACCCTCGTGACCACCCTGACCTACGGCGTGCAGTGCTTCAGCCGCTACC
CCGACCACATGAAGCAGCACGACTTCTTCAAGTCCGCCATGCCCGAAGGCTACGTCCAGG
AGCGCACCATCTTCTTCAAGGACGACGGCAACTACAAGACCCGCGCCGAGGTGAAGTTCG
AGGGCGACACCCTGGTGAACCGCATCGAGCTGAAGGGCATCGACTTCAAGGAGGACGGC
AACATCCTGGGGCACAAGCTGGAGTACAACTACAACAGCCACAACGTCTATATCATGGCC
GACAAGCAGAAGAACGGCATCAAGGTGAACTTCAAGATCCGCCACAACATCGAGGACGGC
AGCGTGCAGCTCGCCGACCACTACCAGCAGAACACCCCCATCGGCGACGGCCCCGTGCT
GCTGCCCGACAACCACTACCTGAGCACCCAGTCCGCCCTGAGCAAAGACCCCAACGAGAA
GCGCGATCACATGGTCCTGCTGGAGTTCGTGACCGCCGCCGGGATCACTCTCGGCATGG
ATGAGCTGTACAAGGGCAAGAAGAAGAGGAAGGTGTCCAATTTACTGACCGTACACCAAAA
TTTGCCTGCATTACCGGTCGATGCAACGAGTGATGAGGTTCGCAAGAACCTGATGGACAT
GTTCAGGGATCGCCAGGCGTTTTCTGAGCATACCTGGAAAATGCTTCTGTCCGTTTGCCGG
TCGTGGGCGGCATGGTGCAAGTTGAATAACCGGAAATGGTTTCCCGCAGAACCTGAAGAT
GTTCGCGATTATCTTCTATATCTTCAGGCGCGCGGTCTGGCAGTAAAAACTATCCAGCAAC
ATTTGGGCCAGCTAAACATGCTTCATCGTCGGTCCGGGCTGCCACGACCAAGTGACAGCA
ATGCTGTTTCACTGGTTATGCGGCGAATCCGAAAAGAAAACGTTGATGCCGGTGAACGTGC
AAAACAGGCTCTAGCGTTCGAACGCACTGATTTCGACCAGGTTCGTTCACTCATGGAAAAT
AGCGATCGCTGCCAGGATATACGTAATCTGGCATTTCTGGGGATTGCTTATAACACCCTGT
TACGTATAGCCGAAATTGCCAGGATCAGGGTTAAAGATATCTCACGTACTGACGGTGGGAG
AATGTTAATCCATATTGGCAGAACGAAAACGCTGGTTAGCACCGCAGGTGTAGAGAAGGCA
CTTAGCCTGGGGGTAACTAAACTGGTCGAGCGATGGATTTCCGTCTCTGGTGTAGCTGAT
GATCCGAATAACTACCTGTTTTGCCGGGTCAGAAAAAATGGTGTTGCCGCGCCATCTGCCA
CCAGCCAGCTATCAACTCGCGCCCTGGAAGGGATTTTTGAAGCAACTCATCGATTGATTTA
CGGCGCTAAGGATGACTCTGGTCAGAGATACCTGGCCTGGTCTGGACACAGTGCCCGTGT
CGGAGCCGCGCGAGATATGGCCCGCGCTGGAGTTTCAATACCGGAGATCATGCAAGCTG
GTGGCTGGACCAATGTAAATATTGTCATGAACTATATCCGTAACCTGGATAGTGAAACAGG
GGCAATGGTGCGCCTGCTGGAAGATGGCGATTAGGAATTCGATATCAAGCTTATCGATAAT
CAACCTCTGGATTACAAAATTTGTGAAAGATTGACTGGTATTCTTAACTATGTTGCTCCTTTT
ACGCTATGTGGATACGCTGCTTTAATGCCTTTGTATCATGCTATTGCTTCCCGTATGGCTTT
CATTTTCTCCTCCTTGTATAAATCCTGGTTGCTGTCTCTTTATGAGGAGTTGTGGCCCGTTG
TCAGGCAACGTGGCGTGGTGTGCACTGTGTTTGCTGACGCAACCCCCACTGGTTGGGGCA
TTGCCACCACCTGTCAGCTCCTTTCCGGGACTTTCGCTTTCCCCCTCCCTATTGCCACGGC
GGAACTCATCGCCGCCTGCCTTGCCCGCTGCTGGACAGGGGCTCGGCTGTTGGGCACTG
ACAATTCCGTGGTGTTGTCGGGGAAATCATCGTCCTTTCCTTGGCTGCTCGCCTATGTTGC
CACCTGGATTCTGCGCGGGACGTCCTTCTGCTACGTCCCTTCGGCCCTCAATCCAGCGGA
CCTTCCTTCCCGCGGCCTGCTGCCGGCTCTGCGGCCTCTTCCGCGTCTTCGCCTTCGCCC
TCAGACGAGTCGGATCTCCCTTTGGGCCGCCTCCCCGCATCGATACCGAGCGCTGCTCGA
GAGATCTACGGGTGGCATCCCTGTGACCCCTCCCCAGTGCCTCTCCTGGCCCTGGAAGTT
GCCACTCCAGTGCCCACCAGCCTTGTCCTAATAAAATTAAGTTGCATCATTTTGTCTGACTA

FIG. 79 cont'd

GGTGTCCTTCTATAATATTATGGGGTGGAGGGGGGTGGTATGGAGCAAGGGGCAAGTTGG
GAAGACAACCTGTAGGGCCTGCGGGGTCTATTGGGAACCAAGCTGGAGTGCAGTGGCAC
AATCTTGGCTCACTGCAATCTCCGCCTCCTGGGTTCAAGCGATTCTCCTGCCTCAGCCTCC
CGAGTTGTTGGGATTCCAGGCATGCATGACCAGGCTCAGCTAATTTTTGTTTTTTTGGTAGA
GACGGGGTTTCACCATATTGGCCAGGCTGGTCTCCAACTCCTAATCTCAGGTGATCTACCC
ACCTTGGCCTCCCAAATTGCTGGGATTACAGGCGTGAACCACTGCTCCCTTCCCTGTCCTT
CTGATTTTGTAGGTAACCACGTGCGGACCGAGCGGCCGCAGGAACCCCTAGTGATGGAGT
TGGCCACTCCCTCTCTGCGCGCTCGCTCGCTCACTGAGGCCGGGCGACCAAAGGTCGCC
CGACGCCCGGGCTTTGCCCGGGCGGCCTCAGTGAGCGAGCGAGCGCGCAGCTGCCTGC
AGGGGCGCCTGATGCGGTATTTTCTCCTTACGCATCTGTGCGGTATTTCACACCGCATACG
TCAAAGCAACCATAGTACGCGCCCTGTAGCGGCGCATTAAGCGCGGCGGGTGTGGTGGTT
ACGCGCAGCGTGACCGCTACACTTGCCAGCGCCCTAGCGCCCGCTCCTTTCGCTTTCTTC
CCTTCCTTTCTCGCCACGTTCGCCGGCTTTCCCCGTCAAGCTCTAAATCGGGGGCTCCCTT
TAGGGTTCCGATTTAGTGCTTTACGGCACCTCGACCCCAAAAAACTTGATTTGGGTGATGG
TTCACGTAGTGGGCCATCGCCCTGATAGACGGTTTTTCGCCCTTTGACGTTGGAGTCCACG
TTCTTTAATAGTGGACTCTTGTTCCAAACTGGAACAACACTCAACCCTATCTCGGGCTATTC
TTTTGATTTATAAGGGATTTTGCCGATTTCGGCCTATTGGTTAAAAAATGAGCTGATTTAACA
AAAATTTAACGCGAATTTTAACAAAATATTAACGTTTACAATTTTATGGTGCACTCTCAGTAC
AATCTGCTCTGATGCCGCATAGTTAAGCCAGCCCCGACACCCGCCAACACCCGCTGACGC
GCCCTGACGGGCTTGTCTGCTCCCGGCATCCGCTTACAGACAAGCTGTGACCGTCTCCGG
GAGCTGCATGTGTCAGAGGTTTTCACCGTCATCACCGAAACGCGCGAGACGAAAGGGCCT
CGTGATACGCCTATTTTTATAGGTTAATGTCATGATAATAATGGTTTCTTAGACGTCAGGTG
GCACTTTTCGGGGAAATGTGCGCGGAACCCCTATTTGTTTATTTTTCTAAATACATTCAAAT
ATGTATCCGCTCATGAGACAATAACCCTGATAAATGCTTCAATAATATTGAAAAAGGAAGAG
TATGAGTATTCAACATTTCCGTGTCGCCCTTATTCCCTTTTTTGCGGCATTTTGCCTTCCTGT
TTTTGCTCACCCAGAAACGCTGGTGAAAGTAAAAGATGCTGAAGATCAGTTGGGTGCACGA
GTGGGTTACATCGAACTGGATCTCAACAGCGGTAAGATCCTTGAGAGTTTTCGCCCCGAAG
AACGTTTTCCAATGATGAGCACTTTTAAAGTTCTGCTATGTGGCGCGGTATTATCCCGTATT
GACGCCGGGCAAGAGCAACTCGGTCGCCGCATACACTATTCTCAGAATGACTTGGTTGAG
TACTCACCAGTCACAGAAAAGCATCTTACGGATGGCATGACAGTAAGAGAATTATGCAGTG
CTGCCATAACCATGAGTGATAACACTGCGGCCAACTTACTTCTGACAACGATCGGAGGACC
GAAGGAGCTAACCGCTTTTTTGCACAACATGGGGGATCATGTAACTCGCCTTGATCGTTGG
GAACCGGAGCTGAATGAAGCCATACCAAACGACGAGCGTGACACCACGATGCCTGTAGCA
ATGGCAACAACGTTGCGCAAACTATTAACTGGCGAACTACTTACTCTAGCTTCCCGGCAAC
AATTAATAGACTGGATGGAGGCGGATAAAGTTGCAGGACCACTTCTGCGCTCGGCCCTTC
CGGCTGGCTGGTTTATTGCTGATAAATCTGGAGCCGGTGAGCGTGGGTCTCGCGGTATCA
TTGCAGCACTGGGGCCAGATGGTAAGCCCTCCCGTATCGTAGTTATCTACACGACGGGGA
GTCAGGCAACTATGGATGAACGAAATAGACAGATCGCTGAGATAGGTGCCTCACTGATTAA
GCATTGGTAACTGTCAGACCAAGTTTACTCATATATACTTTAGATTGATTTAAAACTTCATTT
TTAATTTAAAAGGATCTAGGTGAAGATCCTTTTTGATAATCTCATGACCAAAATCCCTTAACG
TGAGTTTTCGTTCCACTGAGCGTCAGACCCCGTAGAAAAGATCAAAGGATCTTCTTGAGAT
CCTTTTTTTCTGCGCGTAATCTGCTGCTTGCAAACAAAAAAACCACCGCTACCAGCGGTGG
TTTGTTTGCCGGATCAAGAGCTACCAACTCTTTTTCCGAAGGTAACTGGCTTCAGCAGAGC
GCAGATACCAAATACTGTCCTTCTAGTGTAGCCGTAGTTAGGCCACCACTTCAAGAACTCT
GTAGCACCGCCTACATACCTCGCTCTGCTAATCCTGTTACCAGTGGCTGCTGCCAGTGGC
GATAAGTCGTGTCTTACCGGGTTGGACTCAAGACGATAGTTACCGGATAAGGCGCAGCGG
TCGGGCTGAACGGGGGGTTCGTGCACACAGCCCAGCTTGGAGCGAACGACCTACACCGA
ACTGAGATACCTACAGCGTGAGCTATGAGAAAGCGCCACGCTTCCCGAAGGGAGAAAGGC

FIG. 79 cont'd

GGACAGGTATCCGGTAAGCGGCAGGGTCGGAACAGGAGAGCGCACGAGGGAGCTTCCAG
GGGGAAACGCCTGGTATCTTTATAGTCCTGTCGGGTTTCGCCACCTCTGACTTGAGCGTC
GATTTTTGTGATGCTCGTCAGGGGGGCGGAGCCTATGGAAAAACGCCAGCAACGCGGCCT
TTTTACGGTTCCTGGCCTTTTGCTGGCCTTTTGCTCACATGT (SEQ ID NO: 185)

Construct TG1010 nucleotide sequence: rAAV_mscRE4-pBGmin-iCre-WPRE3-bGHpA
(sequence should be inserted into Plasmid backbone 1):
GCGGCCGCACGCGTATAAGCCTTGGGGGCAATCAAACTATTACATTGAGTCCTTGGATTT
GCTACAAATTACATTTTAAATGCAATCATTTTATAAAAGCTTCAACACTCACACTTGGAAG
CGTTACCCTGTTGAATATCACTGACTCACTAACTTGCATTGCCATGCTAACTTGCTTTCAG
AGAGATCTCAGAACACATCATCTTCTGCTATTTCAATACATGCACATTAATTTCCTATCAA
CGTGTGCTGATCAGGAACTCTGTAATCTGGCACCGGTGTTTATTTTTATTCCTGTCTATTC
CTGTTGGCTCACGAAAAGATTGTTTGAGCAAGTGTTTTATGGTGAGTTGTATCATATGTAC
ATTGATTTAATCTGCCCACATTCAGTTCTACAAGCGGAGCCAAAAAAATAGAGACAAGCA
TAATTTTCATTCAACATGAGCCCCTCAATGCAAGCCAAGTACCTCATCTGGTGCTCAGCT
AAAGCAACAGCAATCTGTTCCACCCTGGAGACACAACTGGCCACAGAAAACTTAGTGAA
AAGAGGCAATGCTATGCACAGGACAAATGAGCTCGGGCTGGGCATAAAAGTCAGGGCAG
AGCCATCTATTGCTTACATTTGCTTCTGGGATCCGCCACCATGGTGCCCAAGAAGAAGAGG
AAAGTCTCCAACCTGCTGACTGTGCACCAAAACCTGCCTGCCCTCCCTGTGGATGCCACCT
CTGATGAAGTCAGGAAGAACCTGATGGACATGTTCAGGGACAGGCAGGCCTTCTCTGAAC
ACACCTGGAAGATGCTCCTGTCTGTGTGCAGATCCTGGGCTGCCTGGTGCAAGCTGAACA
ACAGGAAATGGTTCCCTGCTGAACCTGAGGATGTGAGGGACTACCTCCTGTACCTGCAAG
CCAGAGGCCTGGCTGTGAAGACCATCCAACAGCACCTGGGCCAGCTCAACATGCTGCACA
GGAGATCTGGCCTGCCTCGCCCTTCTGACTCCAATGCTGTGTCCCTGGTGATGAGGAGAA
TCAGAAAGGAGAATGTGGATGCTGGGGAGAGAGCCAAGCAGGCCCTGGCCTTTGAACGC
ACTGACTTTGACCAAGTCAGATCCCTGATGGAGAACTCTGACAGATGCCAGGACATCAGGA
ACCTGGCCTTCCTGGGCATTGCCTACAACACCCTGCTGCGCATTGCCGAAATTGCCAGAAT
CAGAGTGAAGGACATCTCCCGCACCGATGGTGGGAGAATGCTGATCCACATTGGCAGGAC
CAAGACCCTGGTGTCCACAGCTGGTGTGGAGAAGGCCCTGTCCCTGGGGGTTACCAAGCT
GGTGGAGAGATGGATCTCTGTGTCTGGTGTGGCTGATGACCCCAACAACTACCTGTTCTG
CCGGGTCAGAAAGAATGGTGTGGCTGCCCCTTCTGCCACCTCCCAACTGTCCACCCGGGC
CCTGGAAGGGATCTTTGAGGCCACCCACCGCCTGATCTATGGTGCCAAGGATGACTCTGG
GCAGAGATACCTGGCCTGGTCTGGCCACTCTGCCAGAGTGGGTGCTGCCAGGGACATGG
CCAGGGCTGGTGTGTCCATCCCTGAAATCATGCAGGCTGGTGGCTGGACCAATGTGAACA
TTGTGATGAACTACATCAGAAACCTGGACTCTGAGACTGGGGCCATGGTGAGGCTGCTCG
AGGATGGGGACTAAGAATTCGATATCAAGCTTATCGATAATCAACCTCTGGATTACAAAATT
TGTGAAAGATTGACTGGTATTCTTAACTATGTTGCTCCTTTTACGCTATGTGGATACGCTGC
TTTAATGCCTTTGTATCATGCTATTGCTTCCCGTATGGCTTTCATTTTCTCCTCCTTGTATAA
ATCCTGGTTGCTGTCTCTTTATGAGGAGTTGTGGCCCGTTGTCAGGCAACGTGGCGTGGT
GTGCACTGTGTTTGCTGACGCAACCCCCACTGGTTGGGGCATTGCCACCACCTGTCAGCT
CCTTTCCGGGACTTTCGCTTTCCCCCTCCCTATTGCCACGGCGGAACTCATCGCCGCCTG
CCTTGCCCGCTGCTGGACAGGGGCTCGGCTGTTGGGCACTGACAATTCCGTGGTGTTGTC
GGGGAAATCATCGTCCTTTCCTTGGCTGCTCGCCTATGTTGCCACCTGGATTCTGCGCGG
GACGTCCTTCTGCTACGTCCCTTCGGCCCTCAATCCAGCGGACCTTCCTTCCCGCGGCCT
GCTGCCGGCTCTGCGGCCTCTTCCGCGTCTTCGCCTTCGCCCTCAGACGAGTCGGATCTC
CCTTTGGGCCGCCTCCCCGCATCGATACCGAGCGCTGCTCGAGAGATCTACGGGTGGCAT
CCCTGTGACCCCTCCCCAGTGCCTCTCCTGGCCCTGGAAGTTGCCACTCCAGTGCCCACC
AGCCTTGTCCTAATAAAATTAAGTTGCATCATTTTGTCTGACTAGGTGTCCTTCTATAATATT

FIG. 79 cont'd

ATGGGGTGGAGGGGGGTGGTATGGAGCAAGGGGCAAGTTGGGAAGACAACCTGTAGGGC
CTGCGGGGTCTATTGGGAACCAAGCTGGAGTGCAGTGGCACAATCTTGGCTCACTGCAAT
CTCCGCCTCCTGGGTTCAAGCGATTCTCCTGCCTCAGCCTCCCGAGTTGTTGGGATTCCA
GGCATGCATGACCAGGCTCAGCTAATTTTTGTTTTTTTGGTAGAGACGGGGTTTCACCATAT
TGGCCAGGCTGGTCTCCAACTCCTAATCTCAGGTGATCTACCCACCTTGGCCTCCCAAATT
GCTGGGATTACAGGCGTGAACCACTGCTCCCTTCCCTGTCCTTCTGATTTTGTAGGTAACC
ACGTGCGGACCGAGCGGCCGC (SEQ ID NO: 87)

Construct TG1011 nucleotide sequence: rAAV_mscRE4-pBGmin-IRES2-tTA2-WPRE3-bGHpA (sequence should be inserted into Plasmid backbone 1):
CGGCCGCACGCGTATAAGCCTTGGGGGCAATCAAACTATTACATTGAGTCCTTGGATTTG
CTACAAATTACATTTTAAATGCAATCATTTTATAAAAGCTTCAACACTCACACTTGGAAGC
GTTACCCTGTTGAATATCACTGACTCACTAACTTGCATTGCCATGCTAACTTGCTTTCAGA
GAGATCTCAGAACACATCATCTTCTGCTATTTCAATACATGCACATTAATTTCCTATCAAC
GTGTGCTGATCAGGAACTCTGTAATCTGGCACCGGTGTTTATTTTTATTCCTGTCTATTCC
TGTTGGCTCACGAAAAGATTGTTTGAGCAAGTGTTTTATGGTGAGTTGTATCATATGTACA
TTGATTTAATCTGCCCACATTCAGTTCTACAAGCGGAGCCAAAAAAATAGAGACAAGCAT
AATTTTCATTCAACATGAGCCCCTCAATGCAAGCCAAGTACCTCATCTGGTGCTCAGCTA
AAGCAACAGCAATCTGTTCCACCCTGGAGACACAACTGGCCACAGAAAACTTAGTGAAA
AGAGGCAATGCTATGCACAGGACAAATGAGCTCGGGCTGGGCATAAAAGTCAGGGCAGA
GCCATCTATTGCTTACATTTGCTTCTGGGATCCGCCACCATGTCTAGACTGGACAAGAGCA
AAGTCATAAACTCTGCTCTGGAATTACTCAATGAAGTCGGTATCGAAGGCCTGACGACAAG
GAAACTCGCTCAAAAGCTGGGAGTTGAGCAGCCTACCCTGTACTGGCACGTGAAGAACAA
GCGGGCCCTGCTCGATGCCCTGGCAATCGAGATGCTGGACAGGCATCATACCCACTTCTG
CCCCCTGGAAGGCGAGTCATGGCAAGACTTTCTGCGGAACAACGCCAAGTCATTCCGCTG
TGCTCTCCTCTCACATCGCGACGGGGCTAAAGTGCATCTCGGCACCCGCCCAACAGAGAA
ACAGTACGAAACCCTGGAAAATCAGCTCGCGTTCCTGTGTCAGCAAGGCTTCTCCCTGGA
GAACGCACTGTACGCTCTGTCCGCCGTGGGCCACTTTACACTGGGCTGCGTATTGGAGGA
TCAGGAGCATCAAGTAGCAAAAGAGGAAAGAGAGACACCTACCACCGATTCTATGCCCCC
ACTTCTGAGACAAGCAATTGAGCTGTTCGACCATCAGGGAGCCGAACCTGCCTTCCTTTTC
GGCCTGGAACTAATCATATGTGGCCTGGAGAAACAGCTAAAGTGCGAAAGCGGCGGGCC
GGCCGACGCCCTTGACGATTTTGACTTAGACATGCTCCCAGCCGATGCCCTTGACGACTTT
GACCTTGATATGCTGCCTGCTGACGCTCTTGACGATTTTGACCTTGACATGCTCCCCGGGT
AAGAATTCGATATCAAGCTTATCGATAATCAACCTCTGGATTACAAAATTTGTGAAAGATTG
ACTGGTATTCTTAACTATGTTGCTCCTTTTACGCTATGTGGATACGCTGCTTTAATGCCTTT
GTATCATGCTATTGCTTCCCGTATGGCTTTCATTTTCTCCTCCTTGTATAAATCCTGGTTGCT
GTCTCTTTATGAGGAGTTGTGGCCCGTTGTCAGGCAACGTGGCGTGGTGTGCACTGTGTT
TGCTGACGCAACCCCCACTGGTTGGGGCATTGCCACCACCTGTCAGCTCCTTTCCGGGAC
TTTCGCTTTCCCCCTCCCTATTGCCACGGCGGAACTCATCGCCGCCTGCCTTGCCCGCTG
CTGGACAGGGGCTCGGCTGTTGGGCACTGACAATTCCGTGGTGTTGTCGGGGAAATCATC
GTCCTTTCCTTGGCTGCTCGCCTATGTTGCCACCTGGATTCTGCGCGGGACGTCCTTCTGC
TACGTCCCTTCGGCCCTCAATCCAGCGGACCTTCCTTCCCGCGGCCTGCTGCCGGCTCTG
CGGCCTCTTCCGCGTCTTCGCCTTCGCCCTCAGACGAGTCGGATCTCCCTTTGGGCCGCC
TCCCCGCATCGATACCGAGCGCTGCTCGAGAGATCTACGGGTGGCATCCCTGTGACCCCT
CCCCAGTGCCTCTCCTGGCCCTGGAAGTTGCCACTCCAGTGCCCACCAGCCTTGTCCTAA
TAAAATTAAGTTGCATCATTTTGTCTGACTAGGTGTCCTTCTATAATATTATGGGGTGGAGG
GGGGTGGTATGGAGCAAGGGGCAAGTTGGGAAGACAACCTGTAGGGCCTGCGGGGTCTA
TTGGGAACCAAGCTGGAGTGCAGTGGCACAATCTTGGCTCACTGCAATCTCCGCCTCCTG

FIG. 79 cont'd

GGTTCAAGCGATTCTCCTGCCTCAGCCTCCCGAGTTGTTGGGATTCCAGGCATGCATGAC
CAGGCTCAGCTAATTTTTGTTTTTTTGGTAGAGACGGGGTTTCACCATATTGGCCAGGCTG
GTCTCCAACTCCTAATCTCAGGTGATCTACCCACCTTGGCCTCCCAAATTGCTGGGATTAC
AGGCGTGAACCACTGCTCCCTTCCCTGTCCTTCTGATTTTGTAGGTAACCACGTGCGGACC
GAGCGGCCGC (SEQ ID NO: 88)

Construct TG1022 nucleotide sequence: rAAV-mscRE4-pBGmin-Cre-i-Cre-WPRE3-bGHpA (sequence includes ITRs and plasmid backbone in plain text and synthetic AAV genome sequence is underlined):
CCTGCAGGCAGCTGCGCGCTCGCTCGCTCACTGAGGCCGCCCGGGCAAAGCCCGGGCG
TCGGGCGACCTTTGGTCGCCCGGCCTCAGTGAGCGAGCGAGCGCGCAGAGAGGGAGTG
GCCAACTCCATCACTAGGGGTTCCTGCGGCCGCACGCGTATAAGCCTTGGGGGCAATCA
AACTATTACATTGAGTCCTTGGATTTGCTACAAATTACATTTTAAATGCAATCATTTTATAA
AAGCTTCAACACTCACACTTGGAAGCGTTACCCTGTTGAATATCACTGACTCACTAACTT
GCATTGCCATGCTAACTTGCTTTCAGAGAGATCTCAGAACACATCATCTTCTGCTATTTCA
ATACATGCACATTAATTTCCTATCAACGTGTGCTGATCAGGAACTCTGTAATCTGGCACC
GGTGTTTATTTTTATTCCTGTCTATTCCTGTTGGCTCACGAAAAGATTGTTTGAGCAAGTG
TTTTATGGTGAGTTGTATCATATGTACATTGATTTAATCTGCCCACATTCAGTTCTACAAG
CGGAGCCAAAAAAATAGAGACAAGCATAATTTTCATTCAACATGAGCCCCTCAATGCAA
GCCAAGTACCTCATCTGGTGCTCAGCTAAAGCAACAGCAATCTGTTCCACCCTGGAGAC
ACAACTGGCCACAGAAAACTTAGTGAAAAGAGGCAATGCTATGCACAGGACAAATGAGC
TCGGGCTGGGCATAAAAGTCAGGGCAGAGCCATCTATTGCTTACATTTGCTTCTGTTAATT
AAGCCGCCACCATGCCCAAGAAGAAGAGGAAGGTGTCCAATTTACTGACCGTACACCAAA
ATTTGCCTGCATTACCGGTCGATGCAACGAGTGATGAGGTTCGCAAGAACCTGATGGACAT
GTTCAGGGATCGCCAGGCGTTTTCTGAGCATACCTGGAAAATGCTTCTGTCCGTTTGCCGG
TCGTGGGCGGCATGGTGCAAGTTGAATAACCGGAAATGGTTTCCCGCAGAACCTGAAGAT
GTTCGCGATTATCTTCTATATCTTCAGGCGCGCGGTCTGGCAGTAAAAACTATCCAGCAAC
ATTTGGGCCAGCTAAACATGCTTCATCGTCGGTCCGGGCTGCCACGACCAAGTGACAGCA
ATGCTGTTTCACTGGTTATGCGGCGGATCCGAAAAGAAAACGTTGATGCCGGTGAACGTG
CAAAACAGGCTCTAGCGTTCGAACGCACTGATTTCGACCAGGTTCGTTCACTCATGGAAAA
TAGCGATCGCTGCCAGGATATACGTAATCTGGCATTTCTGGGGATTGCTTATAACACCCTG
TTACGTATAGCCGAAATTGCCAGGATCAGGGTTAAAGATATCTCACGTACTGACGGTGGGA
GAATGTTAATCCATATTGGCAGAACGAAAACGCTGGTTAGCACCGCAGGTGTAGAGAAGG
CACTTAGCCTGGGGGTAACTAAACTGGTCGAGCGATGGATTTCCGTCTCTGGTGTAGCTG
ATGATCCGAATAACTACCTGTTTTGCCGGGTCAGAAAAAATGGTGTTGCCGCGCCATCTGC
CACCAGCCAGCTATCAACTCGCGCCCTGGAAGGGATTTTTGAAGCAACTCATCGATTGATT
TACGGCGCTAAGGTAAATATAAAATTTTTAAGTGTATAATGTGTTAAACTACTGATTCTAATT
GTTTGTGTATTTTAGGATGACTCTGGTCAGAGATACCTGGCCTGGTCTGGACACAGTGCCC
GTGTCGGAGCCGCGCGAGATATGGCCCGCGCTGGAGTTTCAATACCGGAGATCATGCAA
GCTGGTGGCTGGACCAATGTAAATATTGTCATGAACTATATCCGTAACCTGGATAGTGAAA
CAGGGGCAATGGTGCGCCTGCTGGAAGATGGCGATTAGGAATTCGATATCAAGCTTATCG
ATAATCAACCTCTGGATTACAAAATTTGTGAAAGATTGACTGGTATTCTTAACTATGTTGCTC
CTTTTACGCTATGTGGATACGCTGCTTTAATGCCTTTGTATCATGCTATTGCTTCCCGTATG
GCTTTCATTTTCTCCTCCTTGTATAAATCCTGGTTGCTGTCTCTTTATGAGGAGTTGTGGCC
CGTTGTCAGGCAACGTGGCGTGGTGTGCACTGTGTTTGCTGACGCAACCCCCACTGGTTG
GGGCATTGCCACCACCTGTCAGCTCCTTTCCGGGACTTTCGCTTTCCCCCTCCCTATTGCC
ACGGCGGAACTCATCGCCGCCTGCCTTGCCCGCTGCTGGACAGGGGCTCGGCTGTTGGG
CACTGACAATTCCGTGGTGTTGTCGGGGAAATCATCGTCCTTTCCTTGGCTGCTCGCCTAT

FIG. 79 cont'd

GTTGCCACCTGGATTCTGCGCGGGACGTCCTTCTGCTACGTCCCTTCGGCCCTCAATCCA
GCGGACCTTCCTTCCCGCGGCCTGCTGCCGGCTCTGCGGCCTCTTCCGCGTCTTCGCCTT
CGCCCTCAGACGAGTCGGATCTCCCTTTGGGCCGCCTCCCCGCATCGATACCGAGCGCT
GCTCGAGAGATCTACGGGTGGCATCCCTGTGACCCCTCCCCAGTGCCTCTCCTGGCCCTG
GAAGTTGCCACTCCAGTGCCCACCAGCCTTGTCCTAATAAAATTAAGTTGCATCATTTTGTC
TGACTAGGTGTCCTTCTATAATATTATGGGGTGGAGGGGGGTGGTATGGAGCAAGGGGCA
AGTTGGGAAGACAACCTGTAGGGCCTGCGGGGTCTATTGGGAACCAAGCTGGAGTGCAGT
GGCACAATCTTGGCTCACTGCAATCTCCGCCTCCTGGGTTCAAGCGATTCTCCTGCCTCAG
CCTCCCGAGTTGTTGGGATTCCAGGCATGCATGACCAGGCTCAGCTAATTTTTGTTTTTTTG
GTAGAGACGGGGTTTCACCATATTGGCCAGGCTGGTCTCCAACTCCTAATCTCAGGTGATC
TACCCACCTTGGCCTCCCAAATTGCTGGGATTACAGGCGTGAACCACTGCTCCCTTCCCTG
TCCTTCTGATTTTGTAGGTAACCACGTGCGGACCGAGCGGCCGCAGGAACCCCTAGTGAT
GGAGTTGGCCACTCCCTCTCTGCGCGCTCGCTCGCTCACTGAGGCCGGGCGACCAAAGG
TCGCCCGACGCCCGGGCTTTGCCCGGGCGGCCTCAGTGAGCGAGCGAGCGCGCAGCTG
CCTGCAGGGGCGCCTGATGCGGTATTTTCTCCTTACGCATCTGTGCGGTATTTCACACCGC
ATACGTCAAAGCAACCATAGTACGCGCCCTGTAGCGGCGCATTAAGCGCGGCGGGTGTG
GTGGTTACGCGCAGCGTGACCGCTACACTTGCCAGCGCCCTAGCGCCCGCTCCTTTCGCT
TTCTTCCCTTCCTTTCTCGCCACGTTCGCCGGCTTTCCCCGTCAAGCTCTAAATCGGGGGC
TCCCTTTAGGGTTCCGATTTAGTGCTTTACGGCACCTCGACCCCAAAAAACTTGATTTGGG
TGATGGTTCACGTAGTGGGCCATCGCCCTGATAGACGGTTTTTCGCCCTTTGACGTTGGAG
TCCACGTTCTTTAATAGTGGACTCTTGTTCCAAACTGGAACAACACTCAACCCTATCTCGGG
CTATTCTTTTGATTTATAAGGGATTTTGCCGATTTCGGCCTATTGGTTAAAAAATGAGCTGAT
TTAACAAAAATTTAACGCGAATTTTAACAAAATATTAACGTTTACAATTTTATGGTGCACTCT
CAGTACAATCTGCTCTGATGCCGCATAGTTAAGCCAGCCCCGACACCCGCCAACACCCGC
TGACGCGCCCTGACGGGCTTGTCTGCTCCCGGCATCCGCTTACAGACAAGCTGTGACCGT
CTCCGGGAGCTGCATGTGTCAGAGGTTTTCACCGTCATCACCGAAACGCGCGAGACGAAA
GGGCCTCGTGATACGCCTATTTTTATAGGTTAATGTCATGATAATAATGGTTTCTTAGACGT
CAGGTGGCACTTTTCGGGGAAATGTGCGCGGAACCCCTATTTGTTTATTTTTCTAAATACAT
TCAAATATGTATCCGCTCATGAGACAATAACCCTGATAAATGCTTCAATAATATTGAAAAAG
GAAGAGTATGAGTATTCAACATTTCCGTGTCGCCCTTATTCCCTTTTTTGCGGCATTTTGCC
TTCCTGTTTTTGCTCACCCAGAAACGCTGGTGAAAGTAAAAGATGCTGAAGATCAGTTGGG
TGCACGAGTGGGTTACATCGAACTGGATCTCAACAGCGGTAAGATCCTTGAGAGTTTTCGC
CCCGAAGAACGTTTTCCAATGATGAGCACTTTTAAAGTTCTGCTATGTGGCGCGGTATTATC
CCGTATTGACGCCGGGCAAGAGCAACTCGGTCGCCGCATACACTATTCTCAGAATGACTT
GGTTGAGTACTCACCAGTCACAGAAAAGCATCTTACGGATGGCATGACAGTAAGAGAATTA
TGCAGTGCTGCCATAACCATGAGTGATAACACTGCGGCCAACTTACTTCTGACAACGATCG
GAGGACCGAAGGAGCTAACCGCTTTTTTGCACAACATGGGGGATCATGTAACTCGCCTTG
ATCGTTGGGAACCGGAGCTGAATGAAGCCATACCAAACGACGAGCGTGACACCACGATGC
CTGTAGCAATGGCAACAACGTTGCGCAAACTATTAACTGGCGAACTACTTACTCTAGCTTC
CCGGCAACAATTAATAGACTGGATGGAGGCGGATAAAGTTGCAGGACCACTTCTGCGCTC
GGCCCTTCCGGCTGGCTGGTTTATTGCTGATAAATCTGGAGCCGGTGAGCGTGGGTCTCG
CGGTATCATTGCAGCACTGGGGCCAGATGGTAAGCCCTCCCGTATCGTAGTTATCTACAC
GACGGGGAGTCAGGCAACTATGGATGAACGAAATAGACAGATCGCTGAGATAGGTGCCTC
ACTGATTAAGCATTGGTAACTGTCAGACCAAGTTTACTCATATATACTTTAGATTGATTTAAA
ACTTCATTTTTAATTTAAAAGGATCTAGGTGAAGATCCTTTTTGATAATCTCATGACCAAAAT
CCCTTAACGTGAGTTTTCGTTCCACTGAGCGTCAGACCCCGTAGAAAAGATCAAAGGATCT
TCTTGAGATCCTTTTTTTCTGCGCGTAATCTGCTGCTTGCAAACAAAAAAACCACCGCTACC
AGCGGTGGTTTGTTTGCCGGATCAAGAGCTACCAACTCTTTTTCCGAAGGTAACTGGCTTC

FIG. 79 cont'd

AGCAGAGCGCAGATACCAAATACTGTCCTTCTAGTGTAGCCGTAGTTAGGCCACCACTTCA
AGAACTCTGTAGCACCGCCTACATACCTCGCTCTGCTAATCCTGTTACCAGTGGCTGCTGC
CAGTGGCGATAAGTCGTGTCTTACCGGGTTGGACTCAAGACGATAGTTACCGGATAAGGC
GCAGCGGTCGGGCTGAACGGGGGGTTCGTGCACACAGCCCAGCTTGGAGCGAACGACCT
ACACCGAACTGAGATACCTACAGCGTGAGCTATGAGAAAGCGCCACGCTTCCCGAAGGGA
GAAAGGCGGACAGGTATCCGGTAAGCGGCAGGGTCGGAACAGGAGAGCGCACGAGGGA
GCTTCCAGGGGGAAACGCCTGGTATCTTTATAGTCCTGTCGGGTTTCGCCACCTCTGACTT
GAGCGTCGATTTTTGTGATGCTCGTCAGGGGGGCGGAGCCTATGGAAAAACGCCAGCAAC
GCGGCCTTTTTACGGTTCCTGGCCTTTTGCTGGCCTTTTGCTCACATGT (SEQ ID NO: 186)

Construct TG1021 nucleotide sequence: rAAV_mscRE4-pBGmin-Cre-WPRE3-bGHpA
(sequence includes ITRs and plasmid backbone in plain text and synthetic AAV genome sequence is underlined):
CCTGCAGGCAGCTGCGCGCTCGCTCGCTCACTGAGGCCGCCCGGGCAAAGCCCGGGCG
TCGGGCGACCTTTGGTCGCCCGGCCTCAGTGAGCGAGCGAGCGCGCAGAGAGGGAGTG
GCCAACTCCATCACTAGGGGTTCCTGCGGCCGCACGCGTATAAGCCTTGGGGGCAATCA
AACTATTACATTGAGTCCTTGGATTTGCTACAAATTACATTTTAAATGCAATCATTTTATAA
AAGCTTCAACACTCACACTTGGAAGCGTTACCCTGTTGAATATCACTGACTCACTAACTT
GCATTGCCATGCTAACTTGCTTTCAGAGAGATCTCAGAACACATCATCTTCTGCTATTTCA
ATACATGCACATTAATTTCCTATCAACGTGTGCTGATCAGGAACTCTGTAATCTGGCACC
GGTGTTTATTTTTATTCCTGTCTATTCCTGTTGGCTCACGAAAAGATTGTTTGAGCAAGTG
TTTTATGGTGAGTTGTATCATATGTACATTGATTTAATCTGCCCACATTCAGTTCTACAAG
CGGAGCCAAAAAAATAGAGACAAGCATAATTTTCATTCAACATGAGCCCCTCAATGCAA
GCCAAGTACCTCATCTGGTGCTCAGCTAAAGCAACAGCAATCTGTTCCACCCTGGAGAC
ACAACTGGCCACAGAAAACTTAGTGAAAAGAGGCAATGCTATGCACAGGACAAATGAGC
TCGGGCTGGGCATAAAAGTCAGGGCAGAGCCATCTATTGCTTACATTTGCTTCTGTTAATT
AAGCCACCATGTCCAATTTACTGACCGTACACCAAAATTTGCCTGCATTACCGGTCGATGC
AACGAGTGATGAGGTTCGCAAGAACCTGATGGACATGTTCAGGGATCGCCAGGCGTTTTC
TGAGCATACCTGGAAAATGCTTCTGTCCGTTTGCCGGTCGTGGGCGGCATGGTGCAAGTT
GAATAACCGGAAATGGTTTCCCGCAGAACCTGAAGATGTTCGCGATTATCTTCTATATCTTC
AGGCGCGCGGTCTGGCAGTAAAAACTATCCAGCAACATTTGGGCCAGCTAAACATGCTTC
ATCGTCGGTCCGGGCTGCCACGACCAAGTGACAGCAATGCTGTTTCACTGGTTATGCGGC
GGATCCGAAAAGAAAACGTTGATGCCGGTGAACGTGCAAAACAGGCTCTAGCGTTCGAAC
GCACTGATTTCGACCAGGTTCGTTCACTCATGGAAAATAGCGATCGCTGCCAGGATATACG
TAATCTGGCATTTCTGGGGATTGCTTATAACACCCTGTTACGTATAGCCGAAATTGCCAGG
ATCAGGGTTAAAGATATCTCACGTACTGACGGTGGGAGAATGTTAATCCATATTGGCAGAA
CGAAAACGCTGGTTAGCACCGCAGGTGTAGAGAAGGCACTTAGCCTGGGGGTAACTAAAC
TGGTCGAGCGATGGATTTCCGTCTCTGGTGTAGCTGATGATCCGAATAACTACCTGTTTTG
CCGGGTCAGAAAAAATGGTGTTGCCGCGCCATCTGCCACCAGCCAGCTATCAACTCGCGC
CCTGGAAGGGATTTTTGAAGCAACTCATCGATTGATTTACGGCGCTAAGGATGACTCTGGT
CAGAGATACCTGGCCTGGTCTGGACACAGTGCCCGTGTCGGAGCCGCGCGAGATATGGC
CCGCGCTGGAGTTTCAATACCGGAGATCATGCAAGCTGGTGGCTGGACCAATGTAAATATT
GTCATGAACTATATCCGTAACCTGGATAGTGAAACAGGGGCAATGGTGCGCCTGCTGGAA
GATGGCGATTGAGAATTCGATATCAAGCTTATCGATAATCAACCTCTGGATTACAAAATTTG
TGAAAGATTGACTGGTATTCTTAACTATGTTGCTCCTTTTACGCTATGTGGATACGCTGCTT
TAATGCCTTTGTATCATGCTATTGCTTCCCGTATGGCTTTCATTTTCTCCTCCTTGTATAAAT
CCTGGTTGCTGTCTCTTTATGAGGAGTTGTGGCCCGTTGTCAGGCAACGTGGCGTGGTGT
GCACTGTGTTTGCTGACGCAACCCCCACTGGTTGGGGCATTGCCACCACCTGTCAGCTCC

FIG. 79 cont'd

TTTCCGGGACTTTCGCTTTCCCCCTCCCTATTGCCACGGCGGAACTCATCGCCGCCTGCCT
TGCCCGCTGCTGGACAGGGGCTCGGCTGTTGGGCACTGACAATTCCGTGGTGTTGTCGG
GGAAATCATCGTCCTTTCCTTGGCTGCTCGCCTATGTTGCCACCTGGATTCTGCGCGGGAC
GTCCTTCTGCTACGTCCCTTCGGCCCTCAATCCAGCGGACCTTCCTTCCCGCGGCCTGCT
GCCGGCTCTGCGGCCTCTTCCGCGTCTTCGCCTTCGCCCTCAGACGAGTCGGATCTCCCT
TTGGGCCGCCTCCCCGCATCGATACCGAGCGCTGCTCGAGAGATCTACGGGTGGCATCC
CTGTGACCCCTCCCCAGTGCCTCTCCTGGCCCTGGAAGTTGCCACTCCAGTGCCCACCAG
CCTTGTCCTAATAAAATTAAGTTGCATCATTTTGTCTGACTAGGTGTCCTTCTATAATATTAT
GGGGTGGAGGGGGGTGGTATGGAGCAAGGGGCAAGTTGGGAAGACAACCTGTAGGGCC
TGCGGGGTCTATTGGGAACCAAGCTGGAGTGCAGTGGCACAATCTTGGCTCACTGCAATC
TCCGCCTCCTGGGTTCAAGCGATTCTCCTGCCTCAGCCTCCCGAGTTGTTGGGATTCCAG
GCATGCATGACCAGGCTCAGCTAATTTTTGTTTTTTTGGTAGAGACGGGGTTTCACCATATT
GGCCAGGCTGGTCTCCAACTCCTAATCTCAGGTGATCTACCCACCTTGGCCTCCCAAATTG
CTGGGATTACAGGCGTGAACCACTGCTCCCTTCCCTGTCCTTCTGATTTTGTAGGTAACCA
CGTGCGGACCGAGCGGCCGCAGGAACCCCTAGTGATGGAGTTGGCCACTCCCTCTCTGC
GCGCTCGCTCGCTCACTGAGGCCGGGCGACCAAAGGTCGCCCGACGCCCGGGCTTTGCC
CGGGCGGCCTCAGTGAGCGAGCGAGCGCGCAGCTGCCTGCAGGGGCGCCTGATGCGGT
ATTTTCTCCTTACGCATCTGTGCGGTATTTCACACCGCATACGTCAAAGCAACCATAGTACG
CGCCCTGTAGCGGCGCATTAAGCGCGGCGGGTGTGGTGGTTACGCGCAGCGTGACCGCT
ACACTTGCCAGCGCCCTAGCGCCCGCTCCTTTCGCTTTCTTCCCTTCCTTTCTCGCCACGT
TCGCCGGCTTTCCCCGTCAAGCTCTAAATCGGGGGCTCCCTTTAGGGTTCCGATTTAGTGC
TTTACGGCACCTCGACCCCAAAAAACTTGATTTGGGTGATGGTTCACGTAGTGGGCCATCG
CCCTGATAGACGGTTTTTCGCCCTTTGACGTTGGAGTCCACGTTCTTTAATAGTGGACTCTT
GTTCCAAACTGGAACAACACTCAACCCTATCTCGGGCTATTCTTTTGATTTATAAGGGATTT
TGCCGATTTCGGCCTATTGGTTAAAAAATGAGCTGATTTAACAAAAATTTAACGCGAATTTT
AACAAAATATTAACGTTTACAATTTTATGGTGCACTCTCAGTACAATCTGCTCTGATGCCGC
ATAGTTAAGCCAGCCCCGACACCCGCCAACACCCGCTGACGCGCCCTGACGGGCTTGTCT
GCTCCCGGCATCCGCTTACAGACAAGCTGTGACCGTCTCCGGGAGCTGCATGTGTCAGAG
GTTTTCACCGTCATCACCGAAACGCGCGAGACGAAAGGGCCTCGTGATACGCCTATTTTTA
TAGGTTAATGTCATGATAATAATGGTTTCTTAGACGTCAGGTGGCACTTTTCGGGGAAATGT
GCGCGGAACCCCTATTTGTTTATTTTTCTAAATACATTCAAATATGTATCCGCTCATGAGAC
AATAACCCTGATAAATGCTTCAATAATATTGAAAAAGGAAGAGTATGAGTATTCAACATTTCC
GTGTCGCCCTTATTCCCTTTTTTGCGGCATTTTGCCTTCCTGTTTTTGCTCACCCAGAAACG
CTGGTGAAAGTAAAAGATGCTGAAGATCAGTTGGGTGCACGAGTGGGTTACATCGAACTG
GATCTCAACAGCGGTAAGATCCTTGAGAGTTTTCGCCCCGAAGAACGTTTTCCAATGATGA
GCACTTTTAAAGTTCTGCTATGTGGCGCGGTATTATCCCGTATTGACGCCGGGCAAGAGCA
ACTCGGTCGCCGCATACACTATTCTCAGAATGACTTGGTTGAGTACTCACCAGTCACAGAA
AAGCATCTTACGGATGGCATGACAGTAAGAGAATTATGCAGTGCTGCCATAACCATGAGTG
ATAACACTGCGGCCAACTTACTTCTGACAACGATCGGAGGACCGAAGGAGCTAACCGCTTT
TTTGCACAACATGGGGGATCATGTAACTCGCCTTGATCGTTGGGAACCGGAGCTGAATGAA
GCCATACCAAACGACGAGCGTGACACCACGATGCCTGTAGCAATGGCAACAACGTTGCGC
AAACTATTAACTGGCGAACTACTTACTCTAGCTTCCCGGCAACAATTAATAGACTGGATGGA
GGCGGATAAAGTTGCAGGACCACTTCTGCGCTCGGCCCTTCCGGCTGGCTGGTTTATTGC
TGATAAATCTGGAGCCGGTGAGCGTGGGTCTCGCGGTATCATTGCAGCACTGGGGCCAGA
TGGTAAGCCCTCCCGTATCGTAGTTATCTACACGACGGGGAGTCAGGCAACTATGGATGA
ACGAAATAGACAGATCGCTGAGATAGGTGCCTCACTGATTAAGCATTGGTAACTGTCAGAC
CAAGTTTACTCATATATACTTTAGATTGATTTAAAACTTCATTTTTAATTTAAAAGGATCTAGG
TGAAGATCCTTTTTGATAATCTCATGACCAAAATCCCTTAACGTGAGTTTTCGTTCCACTGA

FIG. 79 cont'd

GCGTCAGACCCCGTAGAAAAGATCAAAGGATCTTCTTGAGATCCTTTTTTTCTGCGCGTAAT
CTGCTGCTTGCAAACAAAAAAACCACCGCTACCAGCGGTGGTTTGTTTGCCGGATCAAGAG
CTACCAACTCTTTTTCCGAAGGTAACTGGCTTCAGCAGAGCGCAGATACCAAATACTGTCC
TTCTAGTGTAGCCGTAGTTAGGCCACCACTTCAAGAACTCTGTAGCACCGCCTACATACCT
CGCTCTGCTAATCCTGTTACCAGTGGCTGCTGCCAGTGGCGATAAGTCGTGTCTTACCGG
GTTGGACTCAAGACGATAGTTACCGGATAAGGCGCAGCGGTCGGGCTGAACGGGGGGTT
CGTGCACACAGCCCAGCTTGGAGCGAACGACCTACACCGAACTGAGATACCTACAGCGTG
AGCTATGAGAAAGCGCCACGCTTCCCGAAGGGAGAAAGGCGGACAGGTATCCGGTAAGC
GGCAGGGTCGGAACAGGAGAGCGCACGAGGGAGCTTCCAGGGGGAAACGCCTGGTATCT
TTATAGTCCTGTCGGGTTTCGCCACCTCTGACTTGAGCGTCGATTTTTGTGATGCTCGTCA
GGGGGGCGGAGCCTATGGAAAAACGCCAGCAACGCGGCCTTTTTACGGTTCCTGGCCTTT
TGCTGGCCTTTTGCTCACATGT (SEQ ID NO: 89)

Construct TG1036 nucleotide sequence: rAAV_mscRE10-pBGmin-FlpO-WPRE3-BGHpA
(sequence should be inserted into Plasmid backbone 1):
GCGGCCGCACGCGTATGTGTCTTTTACTCTGATCCTCCTGTTTTTACCTTCCAAGTGCTGG
AATCACAGACATATACCACTGTGCATAGCATCATTACAATGTTATAGTTTTTCACACTATGC
CTTGACTTTTTGGAAAGGCAAACCACCTCTTGGATTTCTCCTTCCTTCTCTATCTCTCTCTC
TCTCTCTTCCTCCCTCCGTCCCTCCATCTCTTCCTCCTTCCCATTTTCTTCTCTCCCTATTTG
GACACAATATAAAATAATTTAGATGAGGTGAGTTAAATTGTGAACAAAGTATGTGCCTAT
ACATGGTTGTAAATCAGCTTATCAAAGTGTAATATTAGAAGAATTTATAAAAATGATAAAA
TTCATACTCAAAGTTCTGTGTAAAGCAATAATAGCTTTATCTCCTTTTAGTTATCTTGAGTC
TTTCTATGACTAACAACTCCCTCATAGGCATCTTAAAGAGCAGTAAGCATAAGTAGATTC
CAAATGGGAAGGGAGAAGTGTGAACCATCACTTTCATCCAGACTTGTAGATATATCTGCT
GCATTTTCAGAAACCAGAAACAGACAGTGTTCTTTATCTCCATTGAGTCTAGTGTAGCAAC
AGAGCTCGGGCTGGGCATAAAAGTCAGGGCAGAGCCATCTATTGCTTACATTTGCTTCTGG
CGTGGCCACCATGGCTCCTAAGAAGAAGAGGAAGGTGATGAGCCAGTTCGACATCCTGTG
CAAGACCCCCCCCAAGGTGCTGGTGCGGCAGTTCGTGGAGAGATTCGAGAGGCCCAGCG
GCGAGAAGATCGCCAGCTGTGCCGCCGAGCTGACCTACCTGTGCTGGATGATCACCCACA
ACGGCACCGCCATCAAGAGGGCCACCTTCATGAGCTACAACACCATCATCAGCAACAGCC
TGAGCTTCGACATCGTGAACAAGAGCCTGCAGTTCAAGTACAAGACCCAGAAGGCCACCA
TCCTGGAGGCCAGCCTGAAGAAGCTGATCCCCGCCTGGGAGTTCACCATCATCCCTTACA
ACGGCCAGAAGCACCAGAGCGACATCACCGACATCGTGTCCAGCCTGCAGCTGCAGTTCG
AGAGCAGCGAGGAGGCCGACAAGGGCAACAGCCACAGCAAGAAGATGCTGAAGGCCCTG
CTGTCCGAGGGCGAGAGCATCTGGGAGATCACCGAGAAGATCCTGAACAGCTTCGAGTAC
ACCAGCAGGTTCACCAAGACCAAGACCCTGTACCAGTTCCTGTTCCTGGCCACATTCATCA
ACTGCGGCAGGTTCAGCGACATCAAGAACGTGGACCCCAAGAGCTTCAAGCTGGTGCAGA
ACAAGTACCTGGGCGTGATCATTCAGTGCCTGGTGACCGAGACCAAGACAAGCGTGTCCA
GGCACATCTACTTTTTCAGCGCCAGAGGCAGGATCGACCCCCTGGTGTACCTGGACGAGT
TCCTGAGGAACAGCGAGCCCGTGCTGAAGAGAGTGAACAGGACCGGCAACAGCAGCAGC
AACAAGCAGGAGTACCAGCTGCTGAAGGACAACCTGGTGCGCAGCTACAACAAGGCCCTG
AAGAAGAACGCCCCCTACCCCATCTTCGCTATCAAGAACGGCCCTAAGAGCCACATCGGC
AGGCACCTGATGACCAGCTTTCTGAGCATGAAGGGCCTGACCGAGCTGACAAACGTGGTG
GGCAACTGGAGCGACAAGAGGGCCTCCGCCGTGGCCAGGACCACCTACACCCACCAGAT
CACCGCCATCCCCGACCACTACTTCGCCCTGGTGTCCAGGTACTACGCCTACGACCCCAT
CAGCAAGGAGATGATCGCCCTGAAGGACGAGACCAACCCCATCGAGGAGTGGCAGCACA
TCGAGCAGCTGAAGGGCAGCGCCGAGGGCAGCATCAGATACCCCGCCTGGAACGGCATC
ATCAGCCAGGAGGTGCTGGACTACCTGAGCAGCTACATCAACAGGCGGATCTGAGAATTC

FIG. 79 cont'd

GATATCAAGCTTATCGATAATCAACCTCTGGATTACAAAATTTGTGAAAGATTGACTGGTAT
TCTTAACTATGTTGCTCCTTTTACGCTATGTGGATACGCTGCTTTAATGCCTTTGTATCATGC
TATTGCTTCCCGTATGGCTTTCATTTTCTCCTCCTTGTATAAATCCTGGTTGCTGTCTCTTTA
TGAGGAGTTGTGGCCCGTTGTCAGGCAACGTGGCGTGGTGTGCACTGTGTTTGCTGACGC
AACCCCCACTGGTTGGGGCATTGCCACCACCTGTCAGCTCCTTTCCGGGACTTTCGCTTTC
CCCCTCCCTATTGCCACGGCGGAACTCATCGCCGCCTGCCTTGCCCGCTGCTGGACAGG
GGCTCGGCTGTTGGGCACTGACAATTCCGTGGTGTTGTCGGGGAAATCATCGTCCTTTCC
TTGGCTGCTCGCCTATGTTGCCACCTGGATTCTGCGCGGGACGTCCTTCTGCTACGTCCC
TTCGGCCCTCAATCCAGCGGACCTTCCTTCCCGCGGCCTGCTGCCGGCTCTGCGGCCTCT
TCCGCGTCTTCGCCTTCGCCCTCAGACGAGTCGGATCTCCCTTTGGGCCGCCTCCCCGCA
TCGATACCGAGCGCTGCTCGAGAGATCTACGGGTGGCATCCCTGTGACCCCTCCCCAGTG
CCTCTCCTGGCCCTGGAAGTTGCCACTCCAGTGCCCACCAGCCTTGTCCTAATAAAATTAA
GTTGCATCATTTTGTCTGACTAGGTGTCCTTCTATAATATTATGGGGTGGAGGGGGGTGGT
ATGGAGCAAGGGGCAAGTTGGGAAGACAACCTGTAGGGCCTGCGGGGTCTATTGGGAAC
CAAGCTGGAGTGCAGTGGCACAATCTTGGCTCACTGCAATCTCCGCCTCCTGGGTTCAAG
CGATTCTCCTGCCTCAGCCTCCCGAGTTGTTGGGATTCCAGGCATGCATGACCAGGCTCA
GCTAATTTTTGTTTTTTTGGTAGAGACGGGGTTTCACCATATTGGCCAGGCTGGTCTCCAAC
TCCTAATCTCAGGTGATCTACCCACCTTGGCCTCCCAAATTGCTGGGATTACAGGCGTGAA
CCACTGCTCCCTTCCCTGTCCTTCTGATTTTGTAGGTAACCACGTGCGGACCGAGCGGCC
GC (SEQ ID NO: 90)

Construct TG1037 nucleotide sequence: rAAV_mscRE13-pBGmin-FlpO-WPRE3-BGHpA
(sequence should be inserted into Plasmid backbone 1):
GCGGCCGCACGCGTGTCCCATAGGCAGTTTGTGGCTGAGTGCTGGTCCAGGGGTGAGGA
GGTGGGCTATGTTACTGAGGGTCTCTGGGTGTTAGGAAAACAGGGCCCAGGAGTCTGGC
TGCTCGTATGCTGGCCCAGGCTCTTGTTTTTCTTGAGCTGACTTGCTGGAGAAGTGAGCT
AAGTCAGAAACAAAATGCCACATTGCACGCCCACTGAAGTCTGGGCTCAAGGGAAAGAA
GAGAGATTGCCAGAGCGTTAGCTGTTCCCAATCCACTCCTGGACCTTAAGCTGTCTTGAA
CAGAGTTGCCAATCAGCTTGGTAGGGACTGGCCTTTGAGGAGGGGAGGGGGTGTAGGC
AGGGGAGGGGGAGAGAAGGGAGCAGTCTGCGCTCCATCTTAATTACCTCATCAGAAAC
AGCTCCCTTCCCGCAAAGCTCTGGTGTCTTCTACAAGAGGGTGAGTCTTTGGCTTTACAT
GTGAACTTGTGCCATTTGCCTGCGTATATAAACATGAAGGGTCGTCTGGGTTCAGAGCTG
AAATCTTTCACTTGTGACTTAGCTGGGAAATTCTTGGCAAGATCAGAATGCAGTGGTAAGG
TCTGAGCTCGGGCTGGGCATAAAAGTCAGGGCAGAGCCATCTATTGCTTACATTTGCTTCT
GGCGTGGCCACCATGGCTCCTAAGAAGAAGAGGAAGGTGATGAGCCAGTTCGACATCCTG
TGCAAGACCCCCCCCAAGGTGCTGGTGCGGCAGTTCGTGGAGAGATTCGAGAGGCCCAG
CGGCGAGAAGATCGCCAGCTGTGCCGCCGAGCTGACCTACCTGTGCTGGATGATCACCC
ACAACGGCACCGCCATCAAGAGGGCCACCTTCATGAGCTACAACACCATCATCAGCAACA
GCCTGAGCTTCGACATCGTGAACAAGAGCCTGCAGTTCAAGTACAAGACCCAGAAGGCCA
CCATCCTGGAGGCCAGCCTGAAGAAGCTGATCCCCGCCTGGGAGTTCACCATCATCCCTT
ACAACGGCCAGAAGCACCAGAGCGACATCACCGACATCGTGTCCAGCCTGCAGCTGCAGT
TCGAGAGCAGCGAGGAGGCCGACAAGGGCAACAGCCACAGCAAGAAGATGCTGAAGGCC
CTGCTGTCCGAGGGCGAGAGCATCTGGGAGATCACCGAGAAGATCCTGAACAGCTTCGAG
TACACCAGCAGGTTCACCAAGACCAAGACCCTGTACCAGTTCCTGTTCCTGGCCACATTCA
TCAACTGCGGCAGGTTCAGCGACATCAAGAACGTGGACCCCAAGAGCTTCAAGCTGGTGC
AGAACAAGTACCTGGGCGTGATCATTCAGTGCCTGGTGACCGAGACCAAGACAAGCGTGT
CCAGGCACATCTACTTTTTCAGCGCCAGAGGCAGGATCGACCCCCTGGTGTACCTGGACG
AGTTCCTGAGGAACAGCGAGCCCGTGCTGAAGAGAGTGAACAGGACCGGCAACAGCAGC

FIG. 79 cont'd

AGCAACAAGCAGGAGTACCAGCTGCTGAAGGACAACCTGGTGCGCAGCTACAACAAGGCC
CTGAAGAAGAACGCCCCCTACCCCATCTTCGCTATCAAGAACGGCCCTAAGAGCCACATC
GGCAGGCACCTGATGACCAGCTTTCTGAGCATGAAGGGCCTGACCGAGCTGACAAACGTG
GTGGGCAACTGGAGCGACAAGAGGGCCTCCGCCGTGGCCAGGACCACCTACACCCACCA
GATCACCGCCATCCCCGACCACTACTTCGCCCTGGTGTCCAGGTACTACGCCTACGACCC
CATCAGCAAGGAGATGATCGCCCTGAAGGACGAGACCAACCCCATCGAGGAGTGGCAGC
ACATCGAGCAGCTGAAGGGCAGCGCCGAGGGCAGCATCAGATACCCCGCCTGGAACGGC
ATCATCAGCCAGGAGGTGCTGGACTACCTGAGCAGCTACATCAACAGGCGGATCTGAGAA
TTCGATATCAAGCTTATCGATAATCAACCTCTGGATTACAAAATTTGTGAAAGATTGACTGG
TATTCTTAACTATGTTGCTCCTTTTACGCTATGTGGATACGCTGCTTTAATGCCTTTGTATCA
TGCTATTGCTTCCCGTATGGCTTTCATTTTCTCCTCCTTGTATAAATCCTGGTTGCTGTCTCT
TTATGAGGAGTTGTGGCCCGTTGTCAGGCAACGTGGCGTGGTGTGCACTGTGTTTGCTGA
CGCAACCCCCACTGGTTGGGGCATTGCCACCACCTGTCAGCTCCTTTCCGGGACTTTCGC
TTTCCCCCTCCCTATTGCCACGGCGGAACTCATCGCCGCCTGCCTTGCCCGCTGCTGGAC
AGGGGCTCGGCTGTTGGGCACTGACAATTCCGTGGTGTTGTCGGGGAAATCATCGTCCTT
TCCTTGGCTGCTCGCCTATGTTGCCACCTGGATTCTGCGCGGGACGTCCTTCTGCTACGT
CCCTTCGGCCCTCAATCCAGCGGACCTTCCTTCCCGCGGCCTGCTGCCGGCTCTGCGGC
CTCTTCCGCGTCTTCGCCTTCGCCCTCAGACGAGTCGGATCTCCCTTTGGGCCGCCTCCC
CGCATCGATACCGAGCGCTGCTCGAGAGATCTACGGGTGGCATCCCTGTGACCCCTCCCC
AGTGCCTCTCCTGGCCCTGGAAGTTGCCACTCCAGTGCCCACCAGCCTTGTCCTAATAAAA
TTAAGTTGCATCATTTTGTCTGACTAGGTGTCCTTCTATAATATTATGGGGTGGAGGGGGGT
GGTATGGAGCAAGGGGCAAGTTGGGAAGACAACCTGTAGGGCCTGCGGGGTCTATTGGG
AACCAAGCTGGAGTGCAGTGGCACAATCTTGGCTCACTGCAATCTCCGCCTCCTGGGTTC
AAGCGATTCTCCTGCCTCAGCCTCCCGAGTTGTTGGGATTCCAGGCATGCATGACCAGGC
TCAGCTAATTTTTGTTTTTTTGGTAGAGACGGGGTTTCACCATATTGGCCAGGCTGGTCTCC
AACTCCTAATCTCAGGTGATCTACCCACCTTGGCCTCCCAAATTGCTGGGATTACAGGCGT
GAACCACTGCTCCCTTCCCTGTCCTTCTGATTTTGTAGGTAACCACGTGCGGACCGAGCG
GCCGC (SEQ ID NO: 91)

Construct TG1038 nucleotide sequence: rAAV_mscRE16- pBGmin-FlpO-WPRE3-bGHpA
(sequence should be inserted into Plasmid backbone 1):
GCGGCCGCACGCGTAGGGTGCAGGAGAAATGTGACCTCAAAGTCTTGTTCTATAACTGTT
GGACCTTAGGAGAGATCTGTGCTCAGCAATTTACCAGGACACCCCCACCCCACATGTCTT
GACCACTGTCTGGATAACTGGTATGCAGGACCACACTAGGCTTACTCACAGTGTAAACTC
TCATAACCATCACTGGAGCCCATCCTGCCTGGTAGACAAGGATTCAACCATGACTCATTG
TACTTTAGTGGTGCCATGCTTAGTCATCAGGTGCCCTGTGCTCTGACAGCCGAGGGTCAG
AGCTGGAATCACACTCTTGTTGTCTTTTAATCTCTCCCTCCCTTTCTTCCTTCTTTCTTCAC
TCTGTTGTGATTGCTCATGGAACAGATCCTAGCTGGTCTCCCTGGCAACCTACATGATTT
GAGCCCAACAGATGGATAATGGGGACATCGACTTCCAATGTCATTCAACAGAATCATTG
CCAAGGGAGTCTGATGAGCAGGCAACTGAGATGACACCCTTATCAATATAGCTTCATTTT
GGCAATCTGGAGTAGGTGTTTCAAAAGGAGAGCCCCCACTGATGCCAGCAATACAGAAC
GTTCATGGGCAAGGAGCTCGGGCTGGGCATAAAAGTCAGGGCAGAGCCATCTATTGCTTA
CATTTGCTTCTGGCGTGGCCACCATGGCTCCTAAGAAGAAGAGGAAGGTGATGAGCCAGT
TCGACATCCTGTGCAAGACCCCCCCCAAGGTGCTGGTGCGGCAGTTCGTGGAGAGATTCG
AGAGGCCCAGCGGCGAGAAGATCGCCAGCTGTGCCGCCGAGCTGACCTACCTGTGCTGG
ATGATCACCCACAACGGCACCGCCATCAAGAGGGCCACCTTCATGAGCTACAACACCATC
ATCAGCAACAGCCTGAGCTTCGACATCGTGAACAAGAGCCTGCAGTTCAAGTACAAGACC
CAGAAGGCCACCATCCTGGAGGCCAGCCTGAAGAAGCTGATCCCCGCCTGGGAGTTCAC

FIG. 79 cont'd

CATCATCCCTTACAACGGCCAGAAGCACCAGAGCGACATCACCGACATCGTGTCCAGCCT
GCAGCTGCAGTTCGAGAGCAGCGAGGAGGCCGACAAGGGCAACAGCCACAGCAAGAAGA
TGCTGAAGGCCCTGCTGTCCGAGGGCGAGAGCATCTGGGAGATCACCGAGAAGATCCTG
AACAGCTTCGAGTACACCAGCAGGTTCACCAAGACCAAGACCCTGTACCAGTTCCTGTTCC
TGGCCACATTCATCAACTGCGGCAGGTTCAGCGACATCAAGAACGTGGACCCCAAGAGCT
TCAAGCTGGTGCAGAACAAGTACCTGGGCGTGATCATTCAGTGCCTGGTGACCGAGACCA
AGACAAGCGTGTCCAGGCACATCTACTTTTTCAGCGCCAGAGGCAGGATCGACCCCCTGG
TGTACCTGGACGAGTTCCTGAGGAACAGCGAGCCCGTGCTGAAGAGAGTGAACAGGACC
GGCAACAGCAGCAGCAACAAGCAGGAGTACCAGCTGCTGAAGGACAACCTGGTGCGCAG
CTACAACAAGGCCCTGAAGAAGAACGCCCCCTACCCCATCTTCGCTATCAAGAACGGCCC
TAAGAGCCACATCGGCAGGCACCTGATGACCAGCTTTCTGAGCATGAAGGGCCTGACCGA
GCTGACAAACGTGGTGGGCAACTGGAGCGACAAGAGGGCCTCCGCCGTGGCCAGGACCA
CCTACACCCACCAGATCACCGCCATCCCCGACCACTACTTCGCCCTGGTGTCCAGGTACT
ACGCCTACGACCCCATCAGCAAGGAGATGATCGCCCTGAAGGACGAGACCAACCCCATCG
AGGAGTGGCAGCACATCGAGCAGCTGAAGGGCAGCGCCGAGGGCAGCATCAGATACCCC
GCCTGGAACGGCATCATCAGCCAGGAGGTGCTGGACTACCTGAGCAGCTACATCAACAGG
CGGATCTGAGAATTCGATATCAAGCTTATCGATAATCAACCTCTGGATTACAAAATTTGTGA
AAGATTGACTGGTATTCTTAACTATGTTGCTCCTTTTACGCTATGTGGATACGCTGCTTTAAT
GCCTTTGTATCATGCTATTGCTTCCCGTATGGCTTTCATTTTCTCCTCCTTGTATAAATCCTG
GTTGCTGTCTCTTTATGAGGAGTTGTGGCCCGTTGTCAGGCAACGTGGCGTGGTGTGCAC
TGTGTTTGCTGACGCAACCCCCACTGGTTGGGGCATTGCCACCACCTGTCAGCTCCTTTCC
GGGACTTTCGCTTTCCCCCTCCCTATTGCCACGGCGGAACTCATCGCCGCCTGCCTTGCC
CGCTGCTGGACAGGGGCTCGGCTGTTGGGCACTGACAATTCCGTGGTGTTGTCGGGGAA
ATCATCGTCCTTTCCTTGGCTGCTCGCCTATGTTGCCACCTGGATTCTGCGCGGGACGTCC
TTCTGCTACGTCCCTTCGGCCCTCAATCCAGCGGACCTTCCTTCCCGCGGCCTGCTGCCG
GCTCTGCGGCCTCTTCCGCGTCTTCGCCTTCGCCCTCAGACGAGTCGGATCTCCCTTTGG
GCCGCCTCCCCGCATCGATACCGAGCGCTGCTCGAGAGATCTACGGGTGGCATCCCTGT
GACCCCTCCCCAGTGCCTCTCCTGGCCCTGGAAGTTGCCACTCCAGTGCCCACCAGCCTT
GTCCTAATAAAATTAAGTTGCATCATTTTGTCTGACTAGGTGTCCTTCTATAATATTATGGGG
TGGAGGGGGGTGGTATGGAGCAAGGGGCAAGTTGGGAAGACAACCTGTAGGGCCTGCGG
GGTCTATTGGGAACCAAGCTGGAGTGCAGTGGCACAATCTTGGCTCACTGCAATCTCCGC
CTCCTGGGTTCAAGCGATTCTCCTGCCTCAGCCTCCCGAGTTGTTGGGATTCCAGGCATG
CATGACCAGGCTCAGCTAATTTTTGTTTTTTTGGTAGAGACGGGGTTTCACCATATTGGCCA
GGCTGGTCTCCAACTCCTAATCTCAGGTGATCTACCCACCTTGGCCTCCCAAATTGCTGGG
ATTACAGGCGTGAACCACTGCTCCCTTCCCTGTCCTTCTGATTTTGTAGGTAACCACGTGC
GGACCGAGCGGCCGC (SEQ ID NO: 92)

Synthetic construct TG1045 nucleotide sequence: rAAV_mscRE10-pBGmin-iCre-WPRE3-BGHpA (sequence includes ITRs and plasmid backbone in plain text and synthetic AAV genome sequence is underlined):

CCTGCAGGCAGCTGCGCGCTCGCTCGCTCACTGAGGCCGCCCGGGCAAAGCCCGGGCG
TCGGGCGACCTTTGGTCGCCCGGCCTCAGTGAGCGAGCGAGCGCGCAGAGAGGGAGTG
GCCAACTCCATCACTAGGGGTTCCTGCGGCCGCACGCGTATGTGTCTTTTACTCTGATCCT
CCTGTTTTTACCTTCCAAGTGCTGGAATCACAGACATATACCACTGTGCATAGCATCATTA
CAATGTTATAGTTTTTCACACTATGCCTTGACTTTTTGGAAAGGCAAACCACCTCTTGGAT
TTCTCCTTCCTTCTCTATCTCTCTCTCTCTCTTCCTCCCTCCGTCCCTCCATCTCTTCCTC
CTTCCCATTTTCTTCTCTCCCTATTTGGACACAATATAAAATAATTTAGATGAGGTGAGTT
AAATTGTGAACAAAGTATGTGCCTATACATGGTTGTAAATCAGCTTATCAAAGTGTAATAT

FIG. 79 cont'd

TAGAAGAATTTATAAAAATGATAAAATTCATACTCAAAGTTCTGTGTAAAGCAATAATAGC
TTTATCTCCTTTTAGTTATCTTGAGTCTTTCTATGACTAACAACTCCCTCATAGGCATCTTA
AAGAGCAGTAAGCATAAGTAGATTCCAAATGGGAAGGGAGAAGTGTGAACCATCACTTT
CATCCAGACTTGTAGATATATCTGCTGCATTTTCAGAAACCAGAAACAGACAGTGTTCTTT
ATCTCCATTGAGTCTAGTGTAGCAACAGAGCTCGGGCTGGGCATAAAAGTCAGGGCAGAG
CCATCTATTGCTTACATTTGCTTCTGGGATCCGCCACCATGGTGCCCAAGAAGAAGAGGAA
AGTCTCCAACCTGCTGACTGTGCACCAAAACCTGCCTGCCCTCCCTGTGGATGCCACCTCT
GATGAAGTCAGGAAGAACCTGATGGACATGTTCAGGGACAGGCAGGCCTTCTCTGAACAC
ACCTGGAAGATGCTCCTGTCTGTGTGCAGATCCTGGGCTGCCTGGTGCAAGCTGAACAAC
AGGAAATGGTTCCCTGCTGAACCTGAGGATGTGAGGGACTACCTCCTGTACCTGCAAGCC
AGAGGCCTGGCTGTGAAGACCATCCAACAGCACCTGGGCCAGCTCAACATGCTGCACAGG
AGATCTGGCCTGCCTCGCCCTTCTGACTCCAATGCTGTGTCCCTGGTGATGAGGAGAATC
AGAAAGGAGAATGTGGATGCTGGGGAGAGAGCCAAGCAGGCCCTGGCCTTTGAACGCAC
TGACTTTGACCAAGTCAGATCCCTGATGGAGAACTCTGACAGATGCCAGGACATCAGGAAC
CTGGCCTTCCTGGGCATTGCCTACAACACCCTGCTGCGCATTGCCGAAATTGCCAGAATCA
GAGTGAAGGACATCTCCCGCACCGATGGTGGGAGAATGCTGATCCACATTGGCAGGACCA
AGACCCTGGTGTCCACAGCTGGTGTGGAGAAGGCCCTGTCCCTGGGGGTTACCAAGCTG
GTGGAGAGATGGATCTCTGTGTCTGGTGTGGCTGATGACCCCAACAACTACCTGTTCTGC
CGGGTCAGAAAGAATGGTGTGGCTGCCCCTTCTGCCACCTCCCAACTGTCCACCCGGGCC
CTGGAAGGGATCTTTGAGGCCACCCACCGCCTGATCTATGGTGCCAAGGATGACTCTGGG
CAGAGATACCTGGCCTGGTCTGGCCACTCTGCCAGAGTGGGTGCTGCCAGGGACATGGC
CAGGGCTGGTGTGTCCATCCCTGAAATCATGCAGGCTGGTGGCTGGACCAATGTGAACAT
TGTGATGAACTACATCAGAAACCTGGACTCTGAGACTGGGGCCATGGTGAGGCTGCTCGA
GGATGGGGACTAAGAATTCGATATCAAGCTTATCGATAATCAACCTCTGGATTACAAAATTT
GTGAAAGATTGACTGGTATTCTTAACTATGTTGCTCCTTTTACGCTATGTGGATACGCTGCT
TTAATGCCTTTGTATCATGCTATTGCTTCCCGTATGGCTTTCATTTTCTCCTCCTTGTATAAA
TCCTGGTTGCTGTCTCTTTATGAGGAGTTGTGGCCCGTTGTCAGGCAACGTGGCGTGGTG
TGCACTGTGTTTGCTGACGCAACCCCCACTGGTTGGGGCATTGCCACCACCTGTCAGCTC
CTTTCCGGGACTTTCGCTTTCCCCCTCCCTATTGCCACGGCGGAACTCATCGCCGCCTGC
CTTGCCCGCTGCTGGACAGGGGCTCGGCTGTTGGGCACTGACAATTCCGTGGTGTTGTCG
GGGAAATCATCGTCCTTTCCTTGGCTGCTCGCCTATGTTGCCACCTGGATTCTGCGCGGG
ACGTCCTTCTGCTACGTCCCTTCGGCCCTCAATCCAGCGGACCTTCCTTCCCGCGGCCTG
CTGCCGGCTCTGCGGCCTCTTCCGCGTCTTCGCCTTCGCCCTCAGACGAGTCGGATCTCC
CTTTGGGCCGCCTCCCCGCATCGATACCGAGCGCTGCTCGAGAGATCTACGGGTGGCATC
CCTGTGACCCCTCCCCAGTGCCTCTCCTGGCCCTGGAAGTTGCCACTCCAGTGCCCACCA
GCCTTGTCCTAATAAAATTAAGTTGCATCATTTTGTCTGACTAGGTGTCCTTCTATAATATTA
TGGGGTGGAGGGGGGTGGTATGGAGCAAGGGGCAAGTTGGGAAGACAACCTGTAGGGC
CTGCGGGGTCTATTGGGAACCAAGCTGGAGTGCAGTGGCACAATCTTGGCTCACTGCAAT
CTCCGCCTCCTGGGTTCAAGCGATTCTCCTGCCTCAGCCTCCCGAGTTGTTGGGATTCCA
GGCATGCATGACCAGGCTCAGCTAATTTTTGTTTTTTTGGTAGAGACGGGGTTTCACCATAT
TGGCCAGGCTGGTCTCCAACTCCTAATCTCAGGTGATCTACCCACCTTGGCCTCCCAAATT
GCTGGGATTACAGGCGTGAACCACTGCTCCCTTCCCTGTCCTTCTGATTTTGTAGGTAACC
ACGTGCGGACCGAGCGGCCGCAGGAACCCCTAGTGATGGAGTTGGCCACTCCCTCTCTG
CGCGCTCGCTCGCTCACTGAGGCCGGGCGACCAAAGGTCGCCCGACGCCCGGGCTTTGC
CCGGGCGGCCTCAGTGAGCGAGCGAGCGCGCAGCTGCCTGCAGGGGCGCCTGATGCGG
TATTTTCTCCTTACGCATCTGTGCGGTATTTCACACCGCATACGTCAAAGCAACCATAGTAC
GCGCCCTGTAGCGGCGCATTAAGCGCGGCGGGTGTGGTGGTTACGCGCAGCGTGACCGC
TACACTTGCCAGCGCCCTAGCGCCCGCTCCTTTCGCTTTCTTCCCTTCCTTTCTCGCCACG

FIG. 79 cont'd

TTCGCCGGCTTTCCCCGTCAAGCTCTAAATCGGGGGCTCCCTTTAGGGTTCCGATTTAGTG
CTTTACGGCACCTCGACCCCAAAAAACTTGATTTGGGTGATGGTTCACGTAGTGGGCCATC
GCCCTGATAGACGGTTTTTCGCCCTTTGACGTTGGAGTCCACGTTCTTTAATAGTGGACTC
TTGTTCCAAACTGGAACAACACTCAACCCTATCTCGGGCTATTCTTTTGATTTATAAGGGAT
TTTGCCGATTTCGGCCTATTGGTTAAAAAATGAGCTGATTTAACAAAAATTTAACGCGAATTT
TAACAAAATATTAACGTTTACAATTTTATGGTGCACTCTCAGTACAATCTGCTCTGATGCCG
CATAGTTAAGCCAGCCCCGACACCCGCCAACACCCGCTGACGCGCCCTGACGGGCTTGT
CTGCTCCCGGCATCCGCTTACAGACAAGCTGTGACCGTCTCCGGGAGCTGCATGTGTCAG
AGGTTTTCACCGTCATCACCGAAACGCGCGAGACGAAAGGGCCTCGTGATACGCCTATTTT
TATAGGTTAATGTCATGATAATAATGGTTTCTTAGACGTCAGGTGGCACTTTTCGGGGAAAT
GTGCGCGGAACCCCTATTTGTTTATTTTTCTAAATACATTCAAATATGTATCCGCTCATGAG
ACAATAACCCTGATAAATGCTTCAATAATATTGAAAAAGGAAGAGTATGAGTATTCAACATTT
CCGTGTCGCCCTTATTCCCTTTTTTGCGGCATTTTGCCTTCCTGTTTTTGCTCACCCAGAAA
CGCTGGTGAAAGTAAAAGATGCTGAAGATCAGTTGGGTGCACGAGTGGGTTACATCGAAC
TGGATCTCAACAGCGGTAAGATCCTTGAGAGTTTTCGCCCCGAAGAACGTTTTCCAATGAT
GAGCACTTTTAAAGTTCTGCTATGTGGCGCGGTATTATCCCGTATTGACGCCGGGCAAGAG
CAACTCGGTCGCCGCATACACTATTCTCAGAATGACTTGGTTGAGTACTCACCAGTCACAG
AAAAGCATCTTACGGATGGCATGACAGTAAGAGAATTATGCAGTGCTGCCATAACCATGAG
TGATAACACTGCGGCCAACTTACTTCTGACAACGATCGGAGGACCGAAGGAGCTAACCGC
TTTTTTGCACAACATGGGGGATCATGTAACTCGCCTTGATCGTTGGGAACCGGAGCTGAAT
GAAGCCATACCAAACGACGAGCGTGACACCACGATGCCTGTAGCAATGGCAACAACGTTG
CGCAAACTATTAACTGGCGAACTACTTACTCTAGCTTCCCGGCAACAATTAATAGACTGGAT
GGAGGCGGATAAAGTTGCAGGACCACTTCTGCGCTCGGCCCTTCCGGCTGGCTGGTTTAT
TGCTGATAAATCTGGAGCCGGTGAGCGTGGGTCTCGCGGTATCATTGCAGCACTGGGGCC
AGATGGTAAGCCCTCCCGTATCGTAGTTATCTACACGACGGGGAGTCAGGCAACTATGGA
TGAACGAAATAGACAGATCGCTGAGATAGGTGCCTCACTGATTAAGCATTGGTAACTGTCA
GACCAAGTTTACTCATATATACTTTAGATTGATTTAAAACTTCATTTTTAATTTAAAAGGATCT
AGGTGAAGATCCTTTTTGATAATCTCATGACCAAAATCCCTTAACGTGAGTTTTCGTTCCAC
TGAGCGTCAGACCCCGTAGAAAAGATCAAAGGATCTTCTTGAGATCCTTTTTTTCTGCGCG
TAATCTGCTGCTTGCAAACAAAAAAACCACCGCTACCAGCGGTGGTTTGTTTGCCGGATCA
AGAGCTACCAACTCTTTTTCCGAAGGTAACTGGCTTCAGCAGAGCGCAGATACCAAATACT
GTCCTTCTAGTGTAGCCGTAGTTAGGCCACCACTTCAAGAACTCTGTAGCACCGCCTACAT
ACCTCGCTCTGCTAATCCTGTTACCAGTGGCTGCTGCCAGTGGCGATAAGTCGTGTCTTAC
CGGGTTGGACTCAAGACGATAGTTACCGGATAAGGCGCAGCGGTCGGGCTGAACGGGGG
GTTCGTGCACACAGCCCAGCTTGGAGCGAACGACCTACACCGAACTGAGATACCTACAGC
GTGAGCTATGAGAAAGCGCCACGCTTCCCGAAGGGAGAAAGGCGGACAGGTATCCGGTA
AGCGGCAGGGTCGGAACAGGAGAGCGCACGAGGGAGCTTCCAGGGGGAAACGCCTGGT
ATCTTTATAGTCCTGTCGGGTTTCGCCACCTCTGACTTGAGCGTCGATTTTTGTGATGCTCG
TCAGGGGGGCGGAGCCTATGGAAAAACGCCAGCAACGCGGCCTTTTTACGGTTCCTGGC
CTTTTGCTGGCCTTTTGCTCACATGT (SEQ ID NO: 187)

Construct TG1046 nucleotide sequence: rAAV_mscRE13-pBGmin-iCre-WPRE3-BGHpA
(sequence should be inserted into Plasmid backbone 1):
GCGGCCGCACGCGTGTCCCATAGGCAGTTTGTGGCTGAGTGCTGGTCCAGGGGTGAGGA
GGTGGGCTATGTTACTGAGGGTCTCTGGGTGTTAGGAAAACAGGGCCCAGGAGTCTGGC
TGCTCGTATGCTGGCCCAGGCTCTTGTTTTTCTTGAGCTGACTTGCTGGAGAAGTGAGCT
AAGTCAGAAACAAAATGCCACATTGCACGCCCACTGAAGTCTGGGCTCAAGGGAAAGAA
GAGAGATTGCCAGAGCGTTAGCTGTTCCCAATCCACTCCTGGACCTTAAGCTGTCTTGAA

FIG. 79 cont'd

CAGAGTTGCCAATCAGCTTGGTAGGGACTGGCCTTTGAGGAGGGGAGGGGGTGTAGGC
AGGGGAGGGGGAGAGAAGGGAGCAGTCTGCGCTCCATCTTAATTACCTCATCAGAAAC
AGCTCCCTTCCCGCAAAGCTCTGGTGTCTTCTACAAGAGGGTGAGTCTTTGGCTTTACAT
GTGAACTTGTGCCATTTGCCTGCGTATATAAACATGAAGGGTCGTCTGGGTTCAGAGCTG
AAATCTTTCACTTGTGACTTAGCTGGGAAATTCTTGGCAAGATCAGAATGCAGTGGTAAGG
TCTGAGCTCGGGCTGGGCATAAAAGTCAGGGCAGAGCCATCTATTGCTTACATTTGCTTCT
GGGATCCGCCACCATGGTGCCCAAGAAGAAGAGGAAAGTCTCCAACCTGCTGACTGTGCA
CCAAAACCTGCCTGCCCTCCCTGTGGATGCCACCTCTGATGAAGTCAGGAAGAACCTGAT
GGACATGTTCAGGGACAGGCAGGCCTTCTCTGAACACACCTGGAAGATGCTCCTGTCTGT
GTGCAGATCCTGGGCTGCCTGGTGCAAGCTGAACAACAGGAAATGGTTCCCTGCTGAACC
TGAGGATGTGAGGGACTACCTCCTGTACCTGCAAGCCAGAGGCCTGGCTGTGAAGACCAT
CCAACAGCACCTGGGCCAGCTCAACATGCTGCACAGGAGATCTGGCCTGCCTCGCCCTTC
TGACTCCAATGCTGTGTCCCTGGTGATGAGGAGAATCAGAAAGGAGAATGTGGATGCTGG
GGAGAGAGCCAAGCAGGCCCTGGCCTTTGAACGCACTGACTTTGACCAAGTCAGATCCCT
GATGGAGAACTCTGACAGATGCCAGGACATCAGGAACCTGGCCTTCCTGGGCATTGCCTA
CAACACCCTGCTGCGCATTGCCGAAATTGCCAGAATCAGAGTGAAGGACATCTCCCGCAC
CGATGGTGGGAGAATGCTGATCCACATTGGCAGGACCAAGACCCTGGTGTCCACAGCTGG
TGTGGAGAAGGCCCTGTCCCTGGGGGTTACCAAGCTGGTGGAGAGATGGATCTCTGTGTC
TGGTGTGGCTGATGACCCCAACAACTACCTGTTCTGCCGGGTCAGAAAGAATGGTGTGGC
TGCCCCTTCTGCCACCTCCCAACTGTCCACCCGGGCCCTGGAAGGGATCTTTGAGGCCAC
CCACCGCCTGATCTATGGTGCCAAGGATGACTCTGGGCAGAGATACCTGGCCTGGTCTGG
CCACTCTGCCAGAGTGGGTGCTGCCAGGGACATGGCCAGGGCTGGTGTGTCCATCCCTG
AAATCATGCAGGCTGGTGGCTGGACCAATGTGAACATTGTGATGAACTACATCAGAAACCT
GGACTCTGAGACTGGGGCCATGGTGAGGCTGCTCGAGGATGGGGACTAAGAATTCGATAT
CAAGCTTATCGATAATCAACCTCTGGATTACAAAATTTGTGAAAGATTGACTGGTATTCTTAA
CTATGTTGCTCCTTTTACGCTATGTGGATACGCTGCTTTAATGCCTTTGTATCATGCTATTG
CTTCCCGTATGGCTTTCATTTTCTCCTCCTTGTATAAATCCTGGTTGCTGTCTCTTTATGAG
GAGTTGTGGCCCGTTGTCAGGCAACGTGGCGTGGTGTGCACTGTGTTTGCTGACGCAACC
CCCACTGGTTGGGGCATTGCCACCACCTGTCAGCTCCTTTCCGGGACTTTCGCTTTCCCC
CTCCCTATTGCCACGGCGGAACTCATCGCCGCCTGCCTTGCCCGCTGCTGGACAGGGGC
TCGGCTGTTGGGCACTGACAATTCCGTGGTGTTGTCGGGGAAATCATCGTCCTTTCCTTGG
CTGCTCGCCTATGTTGCCACCTGGATTCTGCGCGGGACGTCCTTCTGCTACGTCCCTTCG
GCCCTCAATCCAGCGGACCTTCCTTCCCGCGGCCTGCTGCCGGCTCTGCGGCCTCTTCCG
CGTCTTCGCCTTCGCCCTCAGACGAGTCGGATCTCCCTTTGGGCCGCCTCCCCGCATCGA
TACCGAGCGCTGCTCGAGAGATCTACGGGTGGCATCCCTGTGACCCCTCCCCAGTGCCTC
TCCTGGCCCTGGAAGTTGCCACTCCAGTGCCCACCAGCCTTGTCCTAATAAAATTAAGTTG
CATCATTTTGTCTGACTAGGTGTCCTTCTATAATATTATGGGGTGGAGGGGGGTGGTATGG
AGCAAGGGGCAAGTTGGGAAGACAACCTGTAGGGCCTGCGGGGTCTATTGGGAACCAAG
CTGGAGTGCAGTGGCACAATCTTGGCTCACTGCAATCTCCGCCTCCTGGGTTCAAGCGAT
TCTCCTGCCTCAGCCTCCCGAGTTGTTGGGATTCCAGGCATGCATGACCAGGCTCAGCTA
ATTTTTGTTTTTTTGGTAGAGACGGGGTTTCACCATATTGGCCAGGCTGGTCTCCAACTCCT
AATCTCAGGTGATCTACCCACCTTGGCCTCCCAAATTGCTGGGATTACAGGCGTGAACCAC
TGCTCCCTTCCCTGTCCTTCTGATTTTGTAGGTAACCACGTGCGGACCGAGCGGCCGC
(SEQ ID NO: 93)

Construct TG1047 nucleotide sequence: rAAV_mscRE16-pBGmin-iCre-WPRE3-bGHpA
(sequence should be inserted into Plasmid backbone 1):

FIG. 79 cont'd

GCGGCCGCACGCGTAGGGTGCAGGAGAAATGTGACCTCAAAGTCTTGTTCTATAACTGTT
GGACCTTAGGAGAGATCTGTGCTCAGCAATTTACCAGGACACCCCCACCCCACATGTCTT
GACCACTGTCTGGATAACTGGTATGCAGGACCACACTAGGCTTACTCACAGTGTAAACTC
TCATAACCATCACTGGAGCCCATCCTGCCTGGTAGACAAGGATTCAACCATGACTCATTG
TACTTTAGTGGTGCCATGCTTAGTCATCAGGTGCCCTGTGCTCTGACAGCCGAGGGTCAG
AGCTGGAATCACACTCTTGTTGTCTTTTAATCTCTCCCTCCCTTTCTTCCTTCTTTCTTCAC
TCTGTTGTGATTGCTCATGGAACAGATCCTAGCTGGTCTCCCTGGCAACCTACATGATTT
GAGCCCAACAGATGGATAATGGGGACATCGACTTCCAATGTCATTCAACAGAATCATTG
CCAAGGGAGTCTGATGAGCAGGCAACTGAGATGACACCCTTATCAATATAGCTTCATTTT
GGCAATCTGGAGTAGGTGTTTCAAAAGGAGAGCCCCCACTGATGCCAGCAATACAGAAC
GTTCATGGGCAAGGAGCTCGGGCTGGGCATAAAAGTCAGGGCAGAGCCATCTATTGCTTA
CATTTGCTTCTGGGATCCGCCACCATGGTGCCCAAGAAGAAGAGGAAAGTCTCCAACCTG
CTGACTGTGCACCAAAACCTGCCTGCCCTCCCTGTGGATGCCACCTCTGATGAAGTCAGG
AAGAACCTGATGGACATGTTCAGGGACAGGCAGGCCTTCTCTGAACACACCTGGAAGATG
CTCCTGTCTGTGTGCAGATCCTGGGCTGCCTGGTGCAAGCTGAACAACAGGAAATGGTTC
CCTGCTGAACCTGAGGATGTGAGGGACTACCTCCTGTACCTGCAAGCCAGAGGCCTGGCT
GTGAAGACCATCCAACAGCACCTGGGCCAGCTCAACATGCTGCACAGGAGATCTGGCCTG
CCTCGCCCTTCTGACTCCAATGCTGTGTCCCTGGTGATGAGGAGAATCAGAAAGGAGAAT
GTGGATGCTGGGGAGAGAGCCAAGCAGGCCCTGGCCTTTGAACGCACTGACTTTGACCAA
GTCAGATCCCTGATGGAGAACTCTGACAGATGCCAGGACATCAGGAACCTGGCCTTCCTG
GGCATTGCCTACAACACCCTGCTGCGCATTGCCGAAATTGCCAGAATCAGAGTGAAGGAC
ATCTCCCGCACCGATGGTGGGAGAATGCTGATCCACATTGGCAGGACCAAGACCCTGGTG
TCCACAGCTGGTGTGGAGAAGGCCCTGTCCCTGGGGGTTACCAAGCTGGTGGAGAGATG
GATCTCTGTGTCTGGTGTGGCTGATGACCCCAACAACTACCTGTTCTGCCGGGTCAGAAA
GAATGGTGTGGCTGCCCCTTCTGCCACCTCCCAACTGTCCACCCGGGCCCTGGAAGGGAT
CTTTGAGGCCACCCACCGCCTGATCTATGGTGCCAAGGATGACTCTGGGCAGAGATACCT
GGCCTGGTCTGGCCACTCTGCCAGAGTGGGTGCTGCCAGGGACATGGCCAGGGCTGGTG
TGTCCATCCCTGAAATCATGCAGGCTGGTGGCTGGACCAATGTGAACATTGTGATGAACTA
CATCAGAAACCTGGACTCTGAGACTGGGGCCATGGTGAGGCTGCTCGAGGATGGGGACT
AAGAATTCGATATCAAGCTTATCGATAATCAACCTCTGGATTACAAAATTTGTGAAAGATTG
ACTGGTATTCTTAACTATGTTGCTCCTTTTACGCTATGTGGATACGCTGCTTTAATGCCTTT
GTATCATGCTATTGCTTCCCGTATGGCTTTCATTTTCTCCTCCTTGTATAAATCCTGGTTGCT
GTCTCTTTATGAGGAGTTGTGGCCCGTTGTCAGGCAACGTGGCGTGGTGTGCACTGTGTT
TGCTGACGCAACCCCCACTGGTTGGGGCATTGCCACCACCTGTCAGCTCCTTTCCGGGAC
TTTCGCTTTCCCCCTCCCTATTGCCACGGCGGAACTCATCGCCGCCTGCCTTGCCCGCTG
CTGGACAGGGGCTCGGCTGTTGGGCACTGACAATTCCGTGGTGTTGTCGGGGAAATCATC
GTCCTTTCCTTGGCTGCTCGCCTATGTTGCCACCTGGATTCTGCGCGGGACGTCCTTCTGC
TACGTCCCTTCGGCCCTCAATCCAGCGGACCTTCCTTCCCGCGGCCTGCTGCCGGCTCTG
CGGCCTCTTCCGCGTCTTCGCCTTCGCCCTCAGACGAGTCGGATCTCCCTTTGGGCCGCC
TCCCCGCATCGATACCGAGCGCTGCTCGAGAGATCTACGGGTGGCATCCCTGTGACCCCT
CCCCAGTGCCTCTCCTGGCCCTGGAAGTTGCCACTCCAGTGCCCACCAGCCTTGTCCTAA
TAAAATTAAGTTGCATCATTTTGTCTGACTAGGTGTCCTTCTATAATATTATGGGGTGGAGG
GGGGTGGTATGGAGCAAGGGGCAAGTTGGGAAGACAACCTGTAGGGCCTGCGGGGTCTA
TTGGGAACCAAGCTGGAGTGCAGTGGCACAATCTTGGCTCACTGCAATCTCCGCCTCCTG
GGTTCAAGCGATTCTCCTGCCTCAGCCTCCCGAGTTGTTGGGATTCCAGGCATGCATGAC
CAGGCTCAGCTAATTTTTGTTTTTTTGGTAGAGACGGGGTTTCACCATATTGGCCAGGCTG
GTCTCCAACTCCTAATCTCAGGTGATCTACCCACCTTGGCCTCCCAAATTGCTGGGATTAC

FIG. 79 cont'd

AGGCGTGAACCACTGCTCCCTTCCCTGTCCTTCTGATTTTGTAGGTAACCACGTGCGGACC
GAGCGGCCGC (SEQ ID NO: 94)

Construct TG1048 nucleotide sequence: rAAV_mscRE10-pBGmin-tTA2-WPRE3-BGHpA
(sequence includes ITRs and plasmid backbone in plain text and synthetic AAV genome sequence is underlined):
CCTGCAGGCAGCTGCGCGCTCGCTCGCTCACTGAGGCCGCCCGGGCAAAGCCCGGGCG
TCGGGCGACCTTTGGTCGCCCGGCCTCAGTGAGCGAGCGAGCGCGCAGAGAGGGAGTG
GCCAACTCCATCACTAGGGGTTCCTGCGGCCGCACGCGTATGTGTCTTTTACTCTGATCCT
CCTGTTTTTACCTTCCAAGTGCTGGAATCACAGACATATACCACTGTGCATAGCATCATTA
CAATGTTATAGTTTTTCACACTATGCCTTGACTTTTTGGAAAGGCAAACCACCTCTTGGAT
TTCTCCTTCCTTCTCTATCTCTCTCTCTCTCTCTTCCTCCCTCCGTCCCTCCATCTCTTCCTC
CTTCCCATTTTCTTCTCTCCCTATTTGGACACAATATAAAATAATTTAGATGAGGTGAGTT
AAATTGTGAACAAAGTATGTGCCTATACATGGTTGTAAATCAGCTTATCAAAGTGTAATAT
TAGAAGAATTTATAAAAATGATAAAATTCATACTCAAAGTTCTGTGTAAAGCAATAATAGC
TTTATCTCCTTTTAGTTATCTTGAGTCTTTCTATGACTAACAACTCCCTCATAGGCATCTTA
AAGAGCAGTAAGCATAAGTAGATTCCAAATGGGAAGGGAGAAGTGTGAACCATCACTTT
CATCCAGACTTGTAGATATATCTGCTGCATTTTCAGAAACCAGAAACAGACAGTGTTCTTT
ATCTCCATTGAGTCTAGTGTAGCAACAGAGCTCGGGCTGGGCATAAAAGTCAGGGCAGAG
CCATCTATTGCTTACATTTGCTTCTGGGATCCGCCACCATGTCTAGACTGGACAAGAGCAA
AGTCATAAACTCTGCTCTGGAATTACTCAATGAAGTCGGTATCGAAGGCCTGACGACAAGG
AAACTCGCTCAAAAGCTGGGAGTTGAGCAGCCTACCCTGTACTGGCACGTGAAGAACAAG
CGGGCCCTGCTCGATGCCCTGGCAATCGAGATGCTGGACAGGCATCATACCCACTTCTGC
CCCCTGGAAGGCGAGTCATGGCAAGACTTTCTGCGGAACAACGCCAAGTCATTCCGCTGT
GCTCTCCTCTCACATCGCGACGGGGCTAAAGTGCATCTCGGCACCCGCCCAACAGAGAAA
CAGTACGAAACCCTGGAAAATCAGCTCGCGTTCCTGTGTCAGCAAGGCTTCTCCCTGGAG
AACGCACTGTACGCTCTGTCCGCCGTGGGCCACTTTACACTGGGCTGCGTATTGGAGGAT
CAGGAGCATCAAGTAGCAAAAGAGGAAAGAGAGACACCTACCACCGATTCTATGCCCCCA
CTTCTGAGACAAGCAATTGAGCTGTTCGACCATCAGGGAGCCGAACCTGCCTTCCTTTTCG
GCCTGGAACTAATCATATGTGGCCTGGAGAAACAGCTAAAGTGCGAAAGCGGCGGGCCG
GCCGACGCCCTTGACGATTTTGACTTAGACATGCTCCCAGCCGATGCCCTTGACGACTTTG
ACCTTGATATGCTGCCTGCTGACGCTCTTGACGATTTTGACCTTGACATGCTCCCCGGGTA
AGAATTCGATATCAAGCTTATCGATAATCAACCTCTGGATTACAAAATTTGTGAAAGATTGA
CTGGTATTCTTAACTATGTTGCTCCTTTTACGCTATGTGGATACGCTGCTTTAATGCCTTTGT
ATCATGCTATTGCTTCCCGTATGGCTTTCATTTTCTCCTCCTTGTATAAATCCTGGTTGCTGT
CTCTTTATGAGGAGTTGTGGCCCGTTGTCAGGCAACGTGGCGTGGTGTGCACTGTGTTTG
CTGACGCAACCCCCACTGGTTGGGGCATTGCCACCACCTGTCAGCTCCTTTCCGGGACTT
TCGCTTTCCCCCTCCCTATTGCCACGGCGGAACTCATCGCCGCCTGCCTTGCCCGCTGCT
GGACAGGGGCTCGGCTGTTGGGCACTGACAATTCCGTGGTGTTGTCGGGGAAATCATCGT
CCTTTCCTTGGCTGCTCGCCTATGTTGCCACCTGGATTCTGCGCGGGACGTCCTTCTGCTA
CGTCCCTTCGGCCCTCAATCCAGCGGACCTTCCTTCCCGCGGCCTGCTGCCGGCTCTGCG
GCCTCTTCCGCGTCTTCGCCTTCGCCCTCAGACGAGTCGGATCTCCCTTTGGGCCGCCTC
CCCGCATCGATACCGAGCGCTGCTCGAGAGATCTACGGGTGGCATCCCTGTGACCCCTCC
CCAGTGCCTCTCCTGGCCCTGGAAGTTGCCACTCCAGTGCCCACCAGCCTTGTCCTAATA
AAATTAAGTTGCATCATTTTGTCTGACTAGGTGTCCTTCTATAATATTATGGGGTGGAGGGG
GGTGGTATGGAGCAAGGGGCAAGTTGGGAAGACAACCTGTAGGGCCTGCGGGGTCTATT
GGGAACCAAGCTGGAGTGCAGTGGCACAATCTTGGCTCACTGCAATCTCCGCCTCCTGGG
TTCAAGCGATTCTCCTGCCTCAGCCTCCCGAGTTGTTGGGATTCCAGGCATGCATGACCAG

FIG. 79 cont'd

GCTCAGCTAATTTTTGTTTTTTTGGTAGAGACGGGGTTTCACCATATTGGCCAGGCTGGTCT
CCAACTCCTAATCTCAGGTGATCTACCCACCTTGGCCTCCCAAATTGCTGGGATTACAGGC
GTGAACCACTGCTCCCTTCCCTGTCCTTCTGATTTTGTAGGTAACCACGTGCGGACCGAGC
GGCCGCAGGAACCCCTAGTGATGGAGTTGGCCACTCCCTCTCTGCGCGCTCGCTCGCTCA
CTGAGGCCGGGCGACCAAAGGTCGCCCGACGCCCGGGCTTTGCCCGGGCGGCCTCAGT
GAGCGAGCGAGCGCGCAGCTGCCTGCAGGGGCGCCTGATGCGGTATTTTCTCCTTACGC
ATCTGTGCGGTATTTCACACCGCATACGTCAAAGCAACCATAGTACGCGCCCTGTAGCGG
CGCATTAAGCGCGGCGGGTGTGGTGGTTACGCGCAGCGTGACCGCTACACTTGCCAGCG
CCCTAGCGCCCGCTCCTTTCGCTTTCTTCCCTTCCTTTCTCGCCACGTTCGCCGGCTTTCC
CCGTCAAGCTCTAAATCGGGGGCTCCCTTTAGGGTTCCGATTTAGTGCTTTACGGCACCTC
GACCCCAAAAAACTTGATTTGGGTGATGGTTCACGTAGTGGGCCATCGCCCTGATAGACG
GTTTTTCGCCCTTTGACGTTGGAGTCCACGTTCTTTAATAGTGGACTCTTGTTCCAAACTGG
AACAACACTCAACCCTATCTCGGGCTATTCTTTTGATTTATAAGGGATTTTGCCGATTTCGG
CCTATTGGTTAAAAAATGAGCTGATTTAACAAAAATTTAACGCGAATTTTAACAAAATATTAA
CGTTTACAATTTTATGGTGCACTCTCAGTACAATCTGCTCTGATGCCGCATAGTTAAGCCAG
CCCCGACACCCGCCAACACCCGCTGACGCGCCCTGACGGGCTTGTCTGCTCCCGGCATC
CGCTTACAGACAAGCTGTGACCGTCTCCGGGAGCTGCATGTGTCAGAGGTTTTCACCGTC
ATCACCGAAACGCGCGAGACGAAAGGGCCTCGTGATACGCCTATTTTTATAGGTTAATGTC
ATGATAATAATGGTTTCTTAGACGTCAGGTGGCACTTTTCGGGGAAATGTGCGCGGAACCC
CTATTTGTTTATTTTTCTAAATACATTCAAATATGTATCCGCTCATGAGACAATAACCCTGAT
AAATGCTTCAATAATATTGAAAAAGGAAGAGTATGAGTATTCAACATTTCCGTGTCGCCCTT
ATTCCCTTTTTTGCGGCATTTTGCCTTCCTGTTTTTGCTCACCCAGAAACGCTGGTGAAAGT
AAAAGATGCTGAAGATCAGTTGGGTGCACGAGTGGGTTACATCGAACTGGATCTCAACAG
CGGTAAGATCCTTGAGAGTTTTCGCCCCGAAGAACGTTTTCCAATGATGAGCACTTTTAAA
GTTCTGCTATGTGGCGCGGTATTATCCCGTATTGACGCCGGGCAAGAGCAACTCGGTCGC
CGCATACACTATTCTCAGAATGACTTGGTTGAGTACTCACCAGTCACAGAAAAGCATCTTAC
GGATGGCATGACAGTAAGAGAATTATGCAGTGCTGCCATAACCATGAGTGATAACACTGCG
GCCAACTTACTTCTGACAACGATCGGAGGACCGAAGGAGCTAACCGCTTTTTTGCACAACA
TGGGGGATCATGTAACTCGCCTTGATCGTTGGGAACCGGAGCTGAATGAAGCCATACCAA
ACGACGAGCGTGACACCACGATGCCTGTAGCAATGGCAACAACGTTGCGCAAACTATTAA
CTGGCGAACTACTTACTCTAGCTTCCCGGCAACAATTAATAGACTGGATGGAGGCGGATAA
AGTTGCAGGACCACTTCTGCGCTCGGCCCTTCCGGCTGGCTGGTTTATTGCTGATAAATCT
GGAGCCGGTGAGCGTGGGTCTCGCGGTATCATTGCAGCACTGGGGCCAGATGGTAAGCC
CTCCCGTATCGTAGTTATCTACACGACGGGGAGTCAGGCAACTATGGATGAACGAAATAGA
CAGATCGCTGAGATAGGTGCCTCACTGATTAAGCATTGGTAACTGTCAGACCAAGTTTACT
CATATATACTTTAGATTGATTTAAAACTTCATTTTTAATTTAAAAGGATCTAGGTGAAGATCCT
TTTTGATAATCTCATGACCAAAATCCCTTAACGTGAGTTTTCGTTCCACTGAGCGTCAGACC
CCGTAGAAAAGATCAAAGGATCTTCTTGAGATCCTTTTTTTCTGCGCGTAATCTGCTGCTTG
CAAACAAAAAAACCACCGCTACCAGCGGTGGTTTGTTTGCCGGATCAAGAGCTACCAACTC
TTTTTCCGAAGGTAACTGGCTTCAGCAGAGCGCAGATACCAAATACTGTCCTTCTAGTGTA
GCCGTAGTTAGGCCACCACTTCAAGAACTCTGTAGCACCGCCTACATACCTCGCTCTGCTA
ATCCTGTTACCAGTGGCTGCTGCCAGTGGCGATAAGTCGTGTCTTACCGGGTTGGACTCA
AGACGATAGTTACCGGATAAGGCGCAGCGGTCGGGCTGAACGGGGGGTTCGTGCACACA
GCCCAGCTTGGAGCGAACGACCTACACCGAACTGAGATACCTACAGCGTGAGCTATGAGA
AAGCGCCACGCTTCCCGAAGGGAGAAAGGCGGACAGGTATCCGGTAAGCGGCAGGGTCG
GAACAGGAGAGCGCACGAGGGAGCTTCCAGGGGGAAACGCCTGGTATCTTTATAGTCCTG
TCGGGTTTCGCCACCTCTGACTTGAGCGTCGATTTTTGTGATGCTCGTCAGGGGGGCGGA

FIG. 79 cont'd

GCCTATGGAAAAACGCCAGCAACGCGGCCTTTTTACGGTTCCTGGCCTTTTGCTGGCCTTT
TGCTCACATGT (SEQ ID NO: 95)

Construct TG1049 nucleotide sequence: rAAV_mscRE13-pBGmin-tTA2-WPRE3-BGHpA (sequence should be inserted into Plasmid backbone 1):
GCGGCCGCACGCGTGTCCCATAGGCAGTTTGTGGCTGAGTGCTGGTCCAGGGGTGAGGA
GGTGGGCTATGTTACTGAGGGTCTCTGGGTGTTAGGAAAACAGGGCCCAGGAGTCTGGC
TGCTCGTATGCTGGCCCAGGCTCTTGTTTTTCTTGAGCTGACTTGCTGGAGAAGTGAGCT
AAGTCAGAAACAAAATGCCACATTGCACGCCCACTGAAGTCTGGGCTCAAGGGAAAGAA
GAGAGATTGCCAGAGCGTTAGCTGTTCCCAATCCACTCCTGGACCTTAAGCTGTCTTGAA
CAGAGTTGCCAATCAGCTTGGTAGGGACTGGCCTTTGAGGAGGGGAGGGGGTGTAGGC
AGGGGAGGGGGAGAGAAGGGAGCAGTCTGCGCTCCATCTTAATTACCTCATCAGAAAC
AGCTCCCTTCCCGCAAAGCTCTGGTGTCTTCTACAAGAGGGTGAGTCTTTGGCTTTACAT
GTGAACTTGTGCCATTTGCCTGCGTATATAAACATGAAGGGTCGTCTGGGTTCAGAGCTG
AAATCTTTCACTTGTGACTTAGCTGGGAAATTCTTGGCAAGATCAGAATGCAGTGGTAAGG
TCTGAGCTCGGGCTGGGCATAAAAGTCAGGGCAGAGCCATCTATTGCTTACATTTGCTTCT
GGGATCCGCCACCATGTCTAGACTGGACAAGAGCAAAGTCATAAACTCTGCTCTGGAATTA
CTCAATGAAGTCGGTATCGAAGGCCTGACGACAAGGAAACTCGCTCAAAAGCTGGGAGTT
GAGCAGCCTACCCTGTACTGGCACGTGAAGAACAAGCGGGCCCTGCTCGATGCCCTGGC
AATCGAGATGCTGGACAGGCATCATACCCACTTCTGCCCCCTGGAAGGCGAGTCATGGCA
AGACTTTCTGCGGAACAACGCCAAGTCATTCCGCTGTGCTCTCCTCTCACATCGCGACGG
GGCTAAAGTGCATCTCGGCACCCGCCCAACAGAGAAACAGTACGAAACCCTGGAAAATCA
GCTCGCGTTCCTGTGTCAGCAAGGCTTCTCCCTGGAGAACGCACTGTACGCTCTGTCCGC
CGTGGGCCACTTTACACTGGGCTGCGTATTGGAGGATCAGGAGCATCAAGTAGCAAAAGA
GGAAAGAGAGACACCTACCACCGATTCTATGCCCCCACTTCTGAGACAAGCAATTGAGCTG
TTCGACCATCAGGGAGCCGAACCTGCCTTCCTTTTCGGCCTGGAACTAATCATATGTGGCC
TGGAGAAACAGCTAAAGTGCGAAAGCGGCGGGCCGGCCGACGCCCTTGACGATTTTGACT
TAGACATGCTCCCAGCCGATGCCCTTGACGACTTTGACCTTGATATGCTGCCTGCTGACGC
TCTTGACGATTTTGACCTTGACATGCTCCCCGGGTAAGAATTCGATATCAAGCTTATCGATA
ATCAACCTCTGGATTACAAAATTTGTGAAAGATTGACTGGTATTCTTAACTATGTTGCTCCTT
TTACGCTATGTGGATACGCTGCTTTAATGCCTTTGTATCATGCTATTGCTTCCCGTATGGCT
TTCATTTTCTCCTCCTTGTATAAATCCTGGTTGCTGTCTCTTTATGAGGAGTTGTGGCCCGT
TGTCAGGCAACGTGGCGTGGTGTGCACTGTGTTTGCTGACGCAACCCCCACTGGTTGGGG
CATTGCCACCACCTGTCAGCTCCTTTCCGGGACTTTCGCTTTCCCCCTCCCTATTGCCACG
GCGGAACTCATCGCCGCCTGCCTTGCCCGCTGCTGGACAGGGGCTCGGCTGTTGGGCAC
TGACAATTCCGTGGTGTTGTCGGGGAAATCATCGTCCTTTCCTTGGCTGCTCGCCTATGTT
GCCACCTGGATTCTGCGCGGGACGTCCTTCTGCTACGTCCCTTCGGCCCTCAATCCAGCG
GACCTTCCTTCCCGCGGCCTGCTGCCGGCTCTGCGGCCTCTTCCGCGTCTTCGCCTTCGC
CCTCAGACGAGTCGGATCTCCCTTTGGGCCGCCTCCCCGCATCGATACCGAGCGCTGCTC
GAGAGATCTACGGGTGGCATCCCTGTGACCCCTCCCCAGTGCCTCTCCTGGCCCTGGAAG
TTGCCACTCCAGTGCCCACCAGCCTTGTCCTAATAAAATTAAGTTGCATCATTTTGTCTGAC
TAGGTGTCCTTCTATAATATTATGGGGTGGAGGGGGGTGGTATGGAGCAAGGGGCAAGTT
GGGAAGACAACCTGTAGGGCCTGCGGGGTCTATTGGGAACCAAGCTGGAGTGCAGTGGC
ACAATCTTGGCTCACTGCAATCTCCGCCTCCTGGGTTCAAGCGATTCTCCTGCCTCAGCCT
CCCGAGTTGTTGGGATTCCAGGCATGCATGACCAGGCTCAGCTAATTTTTGTTTTTTTGGTA
GAGACGGGGTTTCACCATATTGGCCAGGCTGGTCTCCAACTCCTAATCTCAGGTGATCTAC
CCACCTTGGCCTCCCAAATTGCTGGGATTACAGGCGTGAACCACTGCTCCCTTCCCTGTCC
TTCTGATTTTGTAGGTAACCACGTGCGGACCGAGCGGCCGC (SEQ ID NO: 96)

FIG. 79 cont'd

Construct TG1050 nucleotide sequence: rAAV_mscRE16- pBGmin-tTA2-WPRE3-bGHpA
(sequence should be inserted into Plasmid backbone 1):
GCGGCCGCACGCGTAGGGTGCAGGAGAAATGTGACCTCAAAGTCTTGTTCTATAACTGTT
GGACCTTAGGAGAGATCTGTGCTCAGCAATTTACCAGGACACCCCCACCCCACATGTCTT
GACCACTGTCTGGATAACTGGTATGCAGGACCACACTAGGCTTACTCACAGTGTAAACTC
TCATAACCATCACTGGAGCCCATCCTGCCTGGTAGACAAGGATTCAACCATGACTCATTG
TACTTTAGTGGTGCCATGCTTAGTCATCAGGTGCCCTGTGCTCTGACAGCCGAGGGTCAG
AGCTGGAATCACACTCTTGTTGTCTTTTAATCTCTCCCTCCCTTTCTTCCTTCTTTCTTCAC
TCTGTTGTGATTGCTCATGGAACAGATCCTAGCTGGTCTCCCTGGCAACCTACATGATTT
GAGCCCAACAGATGGATAATGGGGACATCGACTTCCAATGTCATTCAACAGAATCATTG
CCAAGGGAGTCTGATGAGCAGGCAACTGAGATGACACCCTTATCAATATAGCTTCATTTT
GGCAATCTGGAGTAGGTGTTTCAAAAGGAGAGCCCCCACTGATGCCAGCAATACAGAAC
GTTCATGGGCAAGGAGCTCGGGCTGGGCATAAAAGTCAGGGCAGAGCCATCTATTGCTTA
CATTTGCTTCTGGGATCCGCCACCATGTCTAGACTGGACAAGAGCAAAGTCATAAACTCTG
CTCTGGAATTACTCAATGAAGTCGGTATCGAAGGCCTGACGACAAGGAAACTCGCTCAAAA
GCTGGGAGTTGAGCAGCCTACCCTGTACTGGCACGTGAAGAACAAGCGGGCCCTGCTCG
ATGCCCTGGCAATCGAGATGCTGGACAGGCATCATACCCACTTCTGCCCCCTGGAAGGCG
AGTCATGGCAAGACTTTCTGCGGAACAACGCCAAGTCATTCCGCTGTGCTCTCCTCTCACA
TCGCGACGGGGCTAAAGTGCATCTCGGCACCCGCCCAACAGAGAAACAGTACGAAACCCT
GGAAAATCAGCTCGCGTTCCTGTGTCAGCAAGGCTTCTCCCTGGAGAACGCACTGTACGC
TCTGTCCGCCGTGGGCCACTTTACACTGGGCTGCGTATTGGAGGATCAGGAGCATCAAGT
AGCAAAAGAGGAAAGAGAGACACCTACCACCGATTCTATGCCCCCACTTCTGAGACAAGC
AATTGAGCTGTTCGACCATCAGGGAGCCGAACCTGCCTTCCTTTTCGGCCTGGAACTAATC
ATATGTGGCCTGGAGAAACAGCTAAAGTGCGAAAGCGGCGGGCCGGCCGACGCCCTTGA
CGATTTTGACTTAGACATGCTCCCAGCCGATGCCCTTGACGACTTTGACCTTGATATGCTG
CCTGCTGACGCTCTTGACGATTTTGACCTTGACATGCTCCCCGGGTAAGAATTCGATATCA
AGCTTATCGATAATCAACCTCTGGATTACAAAATTTGTGAAAGATTGACTGGTATTCTTAACT
ATGTTGCTCCTTTTACGCTATGTGGATACGCTGCTTTAATGCCTTTGTATCATGCTATTGCTT
CCCGTATGGCTTTCATTTTCTCCTCCTTGTATAAATCCTGGTTGCTGTCTCTTTATGAGGAG
TTGTGGCCCGTTGTCAGGCAACGTGGCGTGGTGTGCACTGTGTTTGCTGACGCAACCCCC
ACTGGTTGGGGCATTGCCACCACCTGTCAGCTCCTTTCCGGGACTTTCGCTTTCCCCCTCC
CTATTGCCACGGCGGAACTCATCGCCGCCTGCCTTGCCCGCTGCTGGACAGGGGCTCGG
CTGTTGGGCACTGACAATTCCGTGGTGTTGTCGGGGAAATCATCGTCCTTTCCTTGGCTGC
TCGCCTATGTTGCCACCTGGATTCTGCGCGGGACGTCCTTCTGCTACGTCCCTTCGGCCC
TCAATCCAGCGGACCTTCCTTCCCGCGGCCTGCTGCCGGCTCTGCGGCCTCTTCCGCGTC
TTCGCCTTCGCCCTCAGACGAGTCGGATCTCCCTTTGGGCCGCCTCCCCGCATCGATACC
GAGCGCTGCTCGAGAGATCTACGGGTGGCATCCCTGTGACCCCTCCCCAGTGCCTCTCCT
GGCCCTGGAAGTTGCCACTCCAGTGCCCACCAGCCTTGTCCTAATAAAATTAAGTTGCATC
ATTTTGTCTGACTAGGTGTCCTTCTATAATATTATGGGGTGGAGGGGGGTGGTATGGAGCA
AGGGGCAAGTTGGGAAGACAACCTGTAGGGCCTGCGGGGTCTATTGGGAACCAAGCTGG
AGTGCAGTGGCACAATCTTGGCTCACTGCAATCTCCGCCTCCTGGGTTCAAGCGATTCTCC
TGCCTCAGCCTCCCGAGTTGTTGGGATTCCAGGCATGCATGACCAGGCTCAGCTAATTTTT
GTTTTTTTGGTAGAGACGGGGTTTCACCATATTGGCCAGGCTGGTCTCCAACTCCTAATCT
CAGGTGATCTACCCACCTTGGCCTCCCAAATTGCTGGGATTACAGGCGTGAACCACTGCT
CCCTTCCCTGTCCTTCTGATTTTGTAGGTAACCACGTGCGGACCGAGCGGCCGC (SEQ ID NO: 97)

FIG. 79 cont'd

Construct TG1052 nucleotide sequence: rAAV_4XmscRE16-pBGmin-EGFP-WPRE3-bGHpA (sequence should be inserted into Plasmid backbone 1):
GCGGCCGCACGCGTGAAATGTGACCTCAAAGTCTTGTTCTATAACTGTTGGACCTTAGGAG
AGATCTGTGCTCAGCAATTTACCAGGACACCCCCACCCCACATGTCTTGACCACTGTCTG
GATAACTGGTATGCAGGACCACACTAGGCTTACTCACAGTGTAAACTCTCATAACCATCA
CTGGAGCCCATCCTGCCTGGTAGACAAGGATTCAACCATGACTCATTGTACTTTAGTGGT
GCCATGCTTAGTCATCAGGTGCCCTGTGCTCTGACAGCCGAGGGTCAGAGCTGGAATCA
CACTCTTGTTGTCTTTTAATCTCTCCCTCCCTTTCTTCCTTCTTTCTTCACTCTGTTGTGATT
GCTCATGGAACAGATCCTAGCTGGTCTCCCTGGCAACCTACATGATTTGAGCCCAACAG
ATGGATAATGGGGACATCGACTTCCAATGTCATTCAACAGAATCATTGCCAAGGGAGTCT
GATGAGCAGGCAACTGAGATGACACCCTTATCAATATAGCTTCATTTTGGCAATCTGGAG
TAGGTGTTTCAAAAGGAGAGCCCCCACTGATGCCAGCAATACAGAACGTTCATGGGCAA
GTGACATAGCGATAGACAGATTCGACTCGGTACCAGGGTGCAGGAGAAATGTGACCTCA
AAGTCTTGTTCTATAACTGTTGGACCTTAGGAGAGATCTGTGCTCAGCAATTTACCAGGA
CACCCCCACCCCACATGTCTTGACCACTGTCTGGATAACTGGTATGCAGGACCACACTA
GGCTTACTCACAGTGTAAACTCTCATAACCATCACTGGAGCCCATCCTGCCTGGTAGACA
AGGATTCAACCATGACTCATTGTACTTTAGTGGTGCCATGCTTAGTCATCAGGTGCCCTG
TGCTCTGACAGCCGAGGGTCAGAGCTGGAATCACACTCTTGTTGTCTTTTAATCTCTCCC
TCCCTTTCTTCCTTCTTTCTTCACTCTGTTGTGATTGCTCATGGAACAGATCCTAGCTGGTC
TCCCTGGCAACCTACATGATTTGAGCCCAACAGATGGATAATGGGGACATCGACTTCCA
ATGTCATTCAACAGAATCATTGCCAAGGGAGTCTGATGAGCAGGCAACTGAGATGACAC
CCTTATCAATATAGCTTCATTTTGGCAATCTGGAGTAGGTGTTTCAAAAGGAGAGCCCCC
ACTGATGCCAGCAATACAGAACGTTCATGGGCAAGGATGATGGCATCATTGAGTAGCAT
GATCTCAATTGAGGGTGCAGGAGAAATGTGACCTCAAAGTCTTGTTCTATAACTGTTGGA
CCTTAGGAGAGATCTGTGCTCAGCAATTTACCAGGACACCCCCACCCCACATGTCTTGAC
CACTGTCTGGATAACTGGTATGCAGGACCACACTAGGCTTACTCACAGTGTAAACTCTCA
TAACCATCACTGGAGCCCATCCTGCCTGGTAGACAAGGATTCAACCATGACTCATTGTAC
TTTAGTGGTGCCATGCTTAGTCATCAGGTGCCCTGTGCTCTGACAGCCGAGGGTCAGAG
CTGGAATCACACTCTTGTTGTCTTTTAATCTCTCCCTCCCTTTCTTCCTTCTTTCTTCACTCT
GTTGTGATTGCTCATGGAACAGATCCTAGCTGGTCTCCCTGGCAACCTACATGATTTGAG
CCCAACAGATGGATAATGGGGACATCGACTTCCAATGTCATTCAACAGAATCATTGCCAA
GGGAGTCTGATGAGCAGGCAACTGAGATGACACCCTTATCAATATAGCTTCATTTTGGCA
ATCTGGAGTAGGTGTTTCAAAAGGAGAGCCCCCACTGATGCCAGCAATACAGAACGTTC
ATGGGCAAGGAGCTCAGGGTGCAGGAGAAATGTGACCTCAAAGTCTTGTTCTATAACTG
TTGGACCTTAGGAGAGATCTGTGCTCAGCAATTTACCAGGACACCCCCACCCCACATGT
CTTGACCACTGTCTGGATAACTGGTATGCAGGACCACACTAGGCTTACTCACAGTGTAAA
CTCTCATAACCATCACTGGAGCCCATCCTGCCTGGTAGACAAGGATTCAACCATGACTCA
TTGTACTTTAGTGGTGCCATGCTTAGTCATCAGGTGCCCTGTGCTCTGACAGCCGAGGGT
CAGAGCTGGAATCACACTCTTGTTGTCTTTTAATCTCTCCCTCCCTTTCTTCCTTCTTTCTT
CACTCTGTTGTGATTGCTCATGGAACAGATCCTAGCTGGTCTCCCTGGCAACCTACATGA
TTTGAGCCCAACAGATGGATAATGGGGACATCGACTTCCAATGTCATTCAACAGAATCAT
TGCCAAGGGAGTCTGATGAGCAGGCAACTGAGATGACACCCTTATCAATATAGCTTCATT
TTGGCAATCTGGAGTAGGTGTTTCAAAAGGAGAGCCCCCACTGATGCCAGCAATACAGAA
CGTTCATGGGCAAGGAGCTCGGGCTGGGCATAAAAGTCAGGGCAGAGCCATCTATTGCTT
ACATTTGCTTCTGGGATCCGCCACCATGGTGAGCAAGGGCGAGGAGCTGTTCACCGGGGT
GGTGCCCATCCTGGTCGAGCTGGACGGCGACGTAAACGGCCACAAGTTCAGCGTGTCCG
GCGAGGGCGAGGGCGATGCCACCTACGGCAAGCTGACCCTGAAGTTCATCTGCACCACC
GGCAAGCTGCCCGTGCCCTGGCCCACCCTCGTGACCACCCTGACCTACGGCGTGCAGTG

FIG. 79 cont'd

CTTCAGCCGCTACCCCGACCACATGAAGCAGCACGACTTCTTCAAGTCCGCCATGCCCGA
AGGCTACGTCCAGGAGCGCACCATCTTCTTCAAGGACGACGGCAACTACAAGACCCGCGC
CGAGGTGAAGTTCGAGGGCGACACCCTGGTGAACCGCATCGAGCTGAAGGGCATCGACT
TCAAGGAGGACGGCAACATCCTGGGGCACAAGCTGGAGTACAACTACAACAGCCACAACG
TCTATATCATGGCCGACAAGCAGAAGAACGGCATCAAGGTGAACTTCAAGATCCGCCACAA
CATCGAGGACGGCAGCGTGCAGCTCGCCGACCACTACCAGCAGAACACCCCCATCGGCG
ACGGCCCCGTGCTGCTGCCCGACAACCACTACCTGAGCACCCAGTCCGCCCTGAGCAAA
GACCCCAACGAGAAGCGCGATCACATGGTCCTGCTGGAGTTCGTGACCGCCGCCGGGAT
CACTCTCGGCATGGACGAGCTGTACAAGTAAGAATTCGATATCAAGCTTATCGATAATCAA
CCTCTGGATTACAAAATTTGTGAAAGATTGACTGGTATTCTTAACTATGTTGCTCCTTTTACG
CTATGTGGATACGCTGCTTTAATGCCTTTGTATCATGCTATTGCTTCCCGTATGGCTTTCAT
TTTCTCCTCCTTGTATAAATCCTGGTTGCTGTCTCTTTATGAGGAGTTGTGGCCCGTTGTCA
GGCAACGTGGCGTGGTGTGCACTGTGTTTGCTGACGCAACCCCCACTGGTTGGGGCATTG
CCACCACCTGTCAGCTCCTTTCCGGGACTTTCGCTTTCCCCCTCCCTATTGCCACGGCGGA
ACTCATCGCCGCCTGCCTTGCCCGCTGCTGGACAGGGGCTCGGCTGTTGGGCACTGACA
ATTCCGTGGTGTTGTCGGGGAAATCATCGTCCTTTCCTTGGCTGCTCGCCTATGTTGCCAC
CTGGATTCTGCGCGGGACGTCCTTCTGCTACGTCCCTTCGGCCCTCAATCCAGCGGACCT
TCCTTCCCGCGGCCTGCTGCCGGCTCTGCGGCCTCTTCCGCGTCTTCGCCTTCGCCCTCA
GACGAGTCGGATCTCCCTTTGGGCCGCCTCCCCGCATCGATACCGAGCGCTGCTCGAGA
GATCTACGGGTGGCATCCCTGTGACCCCTCCCCAGTGCCTCTCCTGGCCCTGGAAGTTGC
CACTCCAGTGCCCACCAGCCTTGTCCTAATAAAATTAAGTTGCATCATTTTGTCTGACTAGG
TGTCCTTCTATAATATTATGGGGTGGAGGGGGGTGGTATGGAGCAAGGGGCAAGTTGGGA
AGACAACCTGTAGGGCCTGCGGGGTCTATTGGGAACCAAGCTGGAGTGCAGTGGCACAAT
CTTGGCTCACTGCAATCTCCGCCTCCTGGGTTCAAGCGATTCTCCTGCCTCAGCCTCCCGA
GTTGTTGGGATTCCAGGCATGCATGACCAGGCTCAGCTAATTTTTGTTTTTTTGGTAGAGAC
GGGGTTTCACCATATTGGCCAGGCTGGTCTCCAACTCCTAATCTCAGGTGATCTACCCACC
TTGGCCTCCCAAATTGCTGGGATTACAGGCGTGAACCACTGCTCCCTTCCCTGTCCTTCTG
ATTTTGTAGGTAACCACGTGCGGACCGAGCGGCCGC (SEQ ID NO: 98)

Construct CN1402 nucleotide sequence: rAAV_eHGT_058h-minBglobin-SYFP2-WPRE3-BGHpA (sequence should be inserted into Plasmid backbone 2):
GCGGCCGCACGCGT**CAAAAGATGGAAGTTGGGAGGTTGAAGAAGTGCAGGATGGCATT
CCAAGTGATGGGGGCAATGGCATGGAGGTAGGAAAGCATAAGGTATATTCAGGCTATAA
ATAATAGTTAGATTTGGCTGGATCCTGGATTTGAGAAGCCAGGAAATGAGATAACACTGG
TCACTTTCACTAAAGCTCATGAAAAAAAAAATACATACATATATATATATATAAAATAAAT
ATACATATATATTTTTAAGCCCCATATGACTAGAGGAGGCAGCCCATCTGTTCTCTGGGC
TTCACTTTTCTTGTCTGGGAAATGAGTAGGTTGGACTGCATGGTCTTTAAGGTCTCTTTAG
TATTATCTTGTTTGACTCCGTAAAGAGAAAAACAAAGGTTCCTCCTGACATCTTGTGTTGC
CTTCCAACGTCCAGTCCAGTGTGATTGTTTTAAGTACTCTTTGGATATTTTACTGTTATAAA
AAGTGAAGAAAAAGACTGATTTTGCCAAGTCTTATGGATCCAAATTAGTACTCATTGCAC
TATGGTCATTTAGTTGAGGACGATACTCCAGCTTCAAAG**GAGCTCGGGCTGGGCATAAAA
GTCAGGGCAGAGCCATCTATTGCTTACATTTGCTTCTGGGATCCAGATCTTTCGAAGCTAG
CGCTACCGGTCGCCACCATGGTGAGCAAGGGCGAGGAGCTGTTCACCGGGGTGGTGCCC
ATCCTGGTCGAGCTGGACGGCGACGTAAACGGCCACAAGTTCAGCGTGTCCGGCGAGGG
CGAGGGCGATGCCACCTACGGCAAGCTGACCCTGAAGCTGATCTGCACCACCGGCAAGC
TGCCCGTGCCCTGGCCCACCCTCGTGACCACCCTGGGCTACGGCGTGCAGTGCTTCGCC
CGCTACCCCGACCACATGAAGCAGCACGACTTCTTCAAGTCCGCCATGCCCGAAGGCTAC
GTCCAGGAGCGCACCATCTTCTTCAAGGACGACGGCAACTACAAGACCCGCGCCGAGGT

FIG. 79 cont'd

GAAGTTCGAGGGCGACACCCTGGTGAACCGCATCGAGCTGAAGGGCATCGACTTCAAGG
AGGACGGCAACATCCTGGGGCACAAGCTGGAGTACAACTACAACAGCCACAACGTCTATA
TCACCGCCGACAAGCAGAAGAACGGCATCAAGGCCAACTTCAAGATCCGCCACAACATCG
AGGACGGCGGCGTGCAGCTCGCCGACCACTACCAGCAGAACACCCCCATCGGCGACGGC
CCCGTGCTGCTGCCCGACAACCACTACCTGAGCTACCAGTCCAAGCTGAGCAAAGACCCC
AACGAGAAGCGCGATCACATGGTCCTGCTGGAGTTCGTGACCGCCGCCGGGATCACTCTC
GGCATGGACGAGCTGTACAAGTAAGTCGACGGCGCGCCGCGGCCGCGAATTCGATATCA
TAATCAACCTCTGGATTACAAAATTTGTGAAAGATTGACTGGTATTCTTAACTATGTTGCTCC
TTTTACGCTATGTGGATACGCTGCTTTAATGCCTTTGTATCATGCTATTGCTTCCCGTATGG
CTTTCATTTTCTCCTCCTTGTATAAATCCTGGTTAGTTCTTGCCACGGCGGAACTCATCGCC
GCCTGCCTTGCCCGCTGCTGGACAGGGGCTCGGCTGTTGGGCACTGACAATTCCGTGGC
TCGAGAGATCTTCGACTGTGCCTTCTAGTTGCCAGCCATCTGTTGTTTGCCCCTCCCCCGT
GCCTTCCTTGACCCTGGAAGGTGCCACTCCCACTGTCCTTTCCTAATAAAATGAGGAAATT
GCATCGCATTGTCTGAGTAGGTGTCATTCTATTCTGGGGGGTGGGGTGGGGCAGGACAGC
AAGGGGGAGGATTGGGAAGACAATAGCAGGCATGCACGTGCGGACCGAGCGGCCGC
(SEQ ID NO: 99)

Construct CN1416 nucleotide sequence: rAAV_eHGT_058m-minBglobin-SYFP2-WPRE3-BGHpA (sequence should be inserted into Plasmid backbone 2):
GCGGCCGCA**CGCGTGGTACATATTATAAGTTTGAGTCTGCAAGATGTGGCAAACCCTTCC
TTTTCTCTTTATCTTGACAGTGGAAAACATCTAAGGAGTCTTTAAAATAACCACATCGGAC
TGAGCAGTGGAGGGCAAAGAGAATGTCTGGAAGAACCTTTGTTTTTTTCGTTGGGACATC
AAAGGATGTTATACTGAAGAGATCTCAAAGACCAGGCAGTCCAGCCTACTCGTTTCCCA
GACAAGAGAAGTGAAGCCAAGAAACAGATGGGCTGCCTCCTCTAGTCATATGGGGCTTA
AAAATATATATCTCTATTTTTCATGAGTTTTCATGAAAGTGACCAGTGTTATCTCATTTCCT
GTCTTCTCAAATTCAGGATCCTACCCAATCTAACTATTATTTATAGTGTGAATAAGCCCTC
TACTTTCCTACCTCTACAATGCTCATTCTCCATTTTCCCATCATCTACTTCCATCTTGTGAA
AAGTTTCCACTCTTCAGTGATGACCTCAAACATATCATTTCTTTTTTTTAATTCTTTTTTTAT
TAGATATTTTCTTTATATACATTTCAAATGCTATCCTGAAAGTTCCCTATATCCTCCCTCTG
CCCTGCTTCCCTACCCACCCACTCCCACTTCTTGGCCCTGGCATTTCCCTGTACTGGGGC
ATATAAAGTTTGCAATACCAAGGGGCCTCTCTTCACAGTGATGGCCAACTAGGCCATCTT
CTGCTACGAGCT**CGGGCTGGGCATAAAAGTCAGGGCAGAGCCATCTATTGCTTACATTTG
CTTCTGGGATCCAGATCTTTCGAAGCTAGCGCTACCGGTCGCCACCATGGTGAGCAAGGG
CGAGGAGCTGTTCACCGGGGTGGTGCCCATCCTGGTCGAGCTGGACGGCGACGTAAACG
GCCACAAGTTCAGCGTGTCCGGCGAGGGCGAGGGCGATGCCACCTACGGCAAGCTGACC
CTGAAGCTGATCTGCACCACCGGCAAGCTGCCCGTGCCCTGGCCCACCCTCGTGACCAC
CCTGGGCTACGGCGTGCAGTGCTTCGCCCGCTACCCCGACCACATGAAGCAGCACGACTT
CTTCAAGTCCGCCATGCCCGAAGGCTACGTCCAGGAGCGCACCATCTTCTTCAAGGACGA
CGGCAACTACAAGACCCGCGCCGAGGTGAAGTTCGAGGGCGACACCCTGGTGAACCGCA
TCGAGCTGAAGGGCATCGACTTCAAGGAGGACGGCAACATCCTGGGGCACAAGCTGGAG
TACAACTACAACAGCCACAACGTCTATATCACCGCCGACAAGCAGAAGAACGGCATCAAG
GCCAACTTCAAGATCCGCCACAACATCGAGGACGGCGGCGTGCAGCTCGCCGACCACTA
CCAGCAGAACACCCCCATCGGCGACGGCCCCGTGCTGCTGCCCGACAACCACTACCTGA
GCTACCAGTCCAAGCTGAGCAAAGACCCCAACGAGAAGCGCGATCACATGGTCCTGCTGG
AGTTCGTGACCGCCGCCGGGATCACTCTCGGCATGGACGAGCTGTACAAGTAAGTCGACG
GCGCGCCGCGGCCGCGAATTCGATATCATAATCAACCTCTGGATTACAAAATTTGTGAAAG
ATTGACTGGTATTCTTAACTATGTTGCTCCTTTTACGCTATGTGGATACGCTGCTTTAATGC
CTTTGTATCATGCTATTGCTTCCCGTATGGCTTTCATTTTCTCCTCCTTGTATAAATCCTGGT

FIG. 79 cont'd

TAGTTCTTGCCACGGCGGAACTCATCGCCGCCTGCCTTGCCCGCTGCTGGACAGGGGCTC
GGCTGTTGGGCACTGACAATTCCGTGGCTCGAGAGATCTTCGACTGTGCCTTCTAGTTGC
CAGCCATCTGTTGTTTGCCCCTCCCCCGTGCCTTCCTTGACCCTGGAAGGTGCCACTCCC
ACTGTCCTTTCCTAATAAAATGAGGAAATTGCATCGCATTGTCTGAGTAGGTGTCATTCTAT
TCTGGGGGGTGGGGTGGGGCAGGACAGCAAGGGGGAGGATTGGGAAGACAATAGCAGG
CATGCACGTGCGGACCGAGCGGCCGC (SEQ ID NO: 100)

Construct CN1427 nucleotide sequence: rAAV_mscRE4(4x)-minBglobin-tdTomato-WPRE3-BGHpA (sequence should be inserted into Plasmid backbone 2):
GCGGCCGCACGCGTATAGGTACCCCTTGGATTTGCTACAAATTACATTTTAAATGCAATC
ATTTTATAAAAGCTTCAACACTCACACTTGGAAGCGTTACCCTGTTGAATATCACTGACTC
ACTAACTTGCATTGCCATGCTAACTTGCTTTCAGAGAGATCTCAGAACACATCATCTTCTG
CTATTTCAATACATGCACATTAATTTCCTATCAACGTGTGCTGATCAGGAACTCTGTAATC
TGGCACCGGTGTTTATTTTTATTCCTGTCTATTCCTGTTGGCTCACGAAAAGATTGTTTGA
GCAAGTGTTTTATGGTGAGTTGTATCATATGTACATTGATTTAATCTGCCCACATTCAGTT
CTACAAGCGGAGCCAAAAAAATAGAGACAAGCATAATTTTCATTCAACATGAGCCCCTC
AATGCAAGCCAAGTACCTCATCTGGTGCTCAGCTAAAGCAACAGCAATCTGTTCCACCCT
GGAGACACAACTGGCCACAGAAAACTTAGTGAAAAGAGGCCTTGGATTTGCTACAAATT
ACATTTTAAATGCAATCATTTTATAAAAGCTTCAACACTCACACTTGGAAGCGTTACCCTG
TTGAATATCACTGACTCACTAACTTGCATTGCCATGCTAACTTGCTTTCAGAGAGATCTCA
GAACACATCATCTTCTGCTATTTCAATACATGCACATTAATTTCCTATCAACGTGTGCTGA
TCAGGAACTCTGTAATCTGGCACCGGTGTTTATTTTTATTCCTGTCTATTCCTGTTGGCTC
ACGAAAAGATTGTTTGAGCAAGTGTTTTATGGTGAGTTGTATCATATGTACATTGATTTAA
TCTGCCCACATTCAGTTCTACAAGCGGAGCCAAAAAAATAGAGACAAGCATAATTTTCAT
TCAACATGAGCCCCTCAATGCAAGCCAAGTACCTCATCTGGTGCTCAGCTAAAGCAACA
GCAATCTGTTCCACCCTGGAGACACAACTGGCCACAGAAAACTTAGTGAAAAGAGGCCT
TGGATTTGCTACAAATTACATTTTAAATGCAATCATTTTATAAAAGCTTCAACACTCACAC
TTGGAAGCGTTACCCTGTTGAATATCACTGACTCACTAACTTGCATTGCCATGCTAACTTG
CTTTCAGAGAGATCTCAGAACACATCATCTTCTGCTATTTCAATACATGCACATTAATTTC
CTATCAACGTGTGCTGATCAGGAACTCTGTAATCTGGCACCGGTGTTTATTTTTATTCCTG
TCTATTCCTGTTGGCTCACGAAAAGATTGTTTGAGCAAGTGTTTTATGGTGAGTTGTATCA
TATGTACATTGATTTAATCTGCCCACATTCAGTTCTACAAGCGGAGCCAAAAAAATAGAG
ACAAGCATAATTTTCATTCAACATGAGCCCCTCAATGCAAGCCAAGTACCTCATCTGGTG
CTCAGCTAAAGCAACAGCAATCTGTTCCACCCTGGAGACACAACTGGCCACAGAAAACT
TAGTGAAAAGAGGCCTTGGATTTGCTACAAATTACATTTTAAATGCAATCATTTTATAAAA
GCTTCAACACTCACACTTGGAAGCGTTACCCTGTTGAATATCACTGACTCACTAACTTGC
ATTGCCATGCTAACTTGCTTTCAGAGAGATCTCAGAACACATCATCTTCTGCTATTTCAAT
ACATGCACATTAATTTCCTATCAACGTGTGCTGATCAGGAACTCTGTAATCTGGCACCGG
TGTTTATTTTTATTCCTGTCTATTCCTGTTGGCTCACGAAAAGATTGTTTGAGCAAGTGTTT
TATGGTGAGTTGTATCATATGTACATTGATTTAATCTGCCCACATTCAGTTCTACAAGCGG
AGCCAAAAAAATAGAGACAAGCATAATTTTCATTCAACATGAGCCCCTCAATGCAAGCC
AAGTACCTCATCTGGTGCTCAGCTAAAGCAACAGCAATCTGTTCCACCCTGGAGACACA
ACTGGCCACAGAAAACTTAGTGAAAAGAGGGAGCTCGGGCTGGGCATAAAAGTCAGGGC
AGAGCCATCTATTGCTTACATTTGCTTCTGGGATCCTTCGAAGCTAGCGGCGCCACCATGG
TGAGCAAGGGCGAGGAGGTCATCAAAGAGTTCATGCGCTTCAAGGTGCGCATGGAGGGC
TCCATGAACGGCCACGAGTTCGAGATCGAGGGCGAGGGCGAGGGCCGCCCCTACGAGG
GCACCCAGACCGCCAAGCTGAAGGTGACCAAGGGCGGCCCCCTGCCCTTCGCCTGGGAC
ATCCTGTCCCCCCAGTTCATGTACGGCTCCAAGGCGTACGTGAAGCACCCCGCCGACATC

FIG. 79 cont'd

CCCGATTACAAGAAGCTGTCCTTCCCCGAGGGCTTCAAGTGGGAGCGCGTGATGAACTTC
GAGGACGGCGGTCTGGTGACCGTGACCCAGGACTCCTCCCTGCAGGACGGCACGCTGAT
CTACAAGGTGAAGATGCGCGGCACCAACTTCCCCCCCGACGGCCCCGTAATGCAGAAGAA
GACCATGGGCTGGGAGGCCTCCACCGAGCGCCTGTACCCCCGCGACGGCGTGCTGAAG
GGCGAGATCCACCAGGCCCTGAAGCTGAAGGACGGCGGCCACTACCTGGTGGAGTTCAA
GACCATCTACATGGCCAAGAAGCCCGTGCAACTGCCCGGCTACTACTACGTGGACACCAA
GCTGGACATCACCTCCCACAACGAGGACTACACCATCGTGGAACAGTACGAGCGCTCCGA
GGGCCGCCACCACCTGTTCCTGGGGCATGGCACCGGCAGCACCGGCAGCGGCAGCTCC
GGCACCGCCTCCTCCGAGGACAACAACATGGCCGTCATCAAAGAGTTCATGCGCTTCAAG
GTGCGCATGGAGGGCTCCATGAACGGCCACGAGTTCGAGATCGAGGGCGAGGGCGAGG
GCCGCCCCTACGAGGGCACCCAGACCGCCAAGCTGAAGGTGACCAAGGGCGGCCCCCT
GCCCTTCGCCTGGGACATCCTGTCCCCCCAGTTCATGTACGGCTCCAAGGCGTACGTGAA
GCACCCCGCCGACATCCCCGATTACAAGAAGCTGTCCTTCCCCGAGGGCTTCAAGTGGGA
GCGCGTGATGAACTTCGAGGACGGCGGTCTGGTGACCGTGACCCAGGACTCCTCCCTGC
AGGACGGCACGCTGATCTACAAGGTGAAGATGCGCGGCACCAACTTCCCCCCCGACGGC
CCCGTAATGCAGAAGAAGACCATGGGCTGGGAGGCCTCCACCGAGCGCCTGTACCCCCG
CGACGGCGTGCTGAAGGGCGAGATCCACCAGGCCCTGAAGCTGAAGGACGGCGGCCACT
ACCTGGTGGAGTTCAAGACCATCTACATGGCCAAGAAGCCCGTGCAACTGCCCGGCTACT
ACTACGTGGACACCAAGCTGGACATCACCTCCCACAACGAGGACTACACCATCGTGGAAC
AGTACGAGCGCTCCGAGGGCCGCCACCACCTGTTCCTGTACGGCATGGACGAGCTGTAC
AAGTAAGTCGACGGCGCGCCGCGGCCGCGAATTCGATATCATAATCAACCTCTGGATTAC
AAAATTTGTGAAAGATTGACTGGTATTCTTAACTATGTTGCTCCTTTTACGCTATGTGGATAC
GCTGCTTTAATGCCTTTGTATCATGCTATTGCTTCCCGTATGGCTTTCATTTTCTCCTCCTTG
TATAAATCCTGGTTAGTTCTTGCCACGGCGGAACTCATCGCCGCCTGCCTTGCCCGCTGCT
GGACAGGGGCTCGGCTGTTGGGCACTGACAATTCCGTGGCTCGAGAGATCTTCGACTGTG
CCTTCTAGTTGCCAGCCATCTGTTGTTTGCCCCTCCCCCGTGCCTTCCTTGACCCTGGAAG
GTGCCACTCCCACTGTCCTTTCCTAATAAAATGAGGAAATTGCATCGCATTGTCTGAGTAG
GTGTCATTCTATTCTGGGGGGTGGGGTGGGGCAGGACAGCAAGGGGGAGGATTGGGAAG
ACAATAGCAGGCATGCACGTGCGGACCGAGCGGCCGC (SEQ ID NO: 101)

Construct CN1452 nucleotide sequence: rAAV_eHGT_073h-minBglobin-SYFP2-WPRE3-BGHpA (sequence should be inserted into Plasmid backbone 2):
GCGGCCGCACGCGTCCGAGACAGCAGAGAGACTGGTCTGACTGCAGAGGAGGTCTGGG
AGACCAGAGGGAGTGTGGAGAGGGTGAGGTTAGAAGACAGGAACACCGAGCTGCATCG
GCCAAATGGAGCCTTAGGGGGCCATGTGAGGCTGAGGCAGGGAAGCAGGGATCCTGCC
CTCCAGGTCCTTACAGTCAGGCGGGGACCAAAAGCACGAGGATGCCAGCCCAATTCCCT
ATTAGGCAAAACGCAGCACCATCTGCACAATCCCAGGAGCAAGAGCAGATATTTTATAA
CTTCCTTTTTTCTTTTTAAGTCTAAATTAAAAATAAATGTTCCCTTCAGCTCTCAGATGTAT
ATCTCTGGTGCAACCTGCCCACATTCCCTCCCGCTGCCCTTTCCAGAACATGGCAGGGG
AAAGGAAGAAAGAGATGGATAGAGAGAGGGAGCCAGTCCACCCAGCTTCAATGCCAGT
GGATTGCACCTCTTCCAAGAGGGAAACGATTCAGGCGTGGCCACGCAGACGGGTGGAG
AGCGCCCAGAATGTGGCTGGTACCAAGGAAAGTGGAAGGAGAGGGAAACAGGAGCCA
ACAGCTATGATTTCTAGCCCAGCCTCCACCCTATCGCGCTGCAGGACCTTGGCCAAATCA
CACATCCTATCTCTGCTCCCATTTATAGTTCATAACATGGCTGAAGTCCCCTCTGCCGCTC
CAGCCCCCTGGCAGCTGTGCTCTCTGCACATCCGTCTGTACCTTTGCTGCTCCCCTTCAT
TTTGGGTGTCCTACCATGGACCTAGTGATTAACGGAGCTCGGGCTGGGCATAAAAGTCAG
GGCAGAGCCATCTATTGCTTACATTTGCTTCTGGGATCCAGATCTTTCGAAGCTAGCGCTA
CCGGTCGCCACCATGGTGAGCAAGGGCGAGGAGCTGTTCACCGGGGTGGTGCCCATCCT

FIG. 79 cont'd

GGTCGAGCTGGACGGCGACGTAAACGGCCACAAGTTCAGCGTGTCCGGCGAGGGCGAG
GGCGATGCCACCTACGGCAAGCTGACCCTGAAGCTGATCTGCACCACCGGCAAGCTGCC
CGTGCCCTGGCCCACCCTCGTGACCACCCTGGGCTACGGCGTGCAGTGCTTCGCCCGCT
ACCCCGACCACATGAAGCAGCACGACTTCTTCAAGTCCGCCATGCCCGAAGGCTACGTCC
AGGAGCGCACCATCTTCTTCAAGGACGACGGCAACTACAAGACCCGCGCCGAGGTGAAGT
TCGAGGGCGACACCCTGGTGAACCGCATCGAGCTGAAGGGCATCGACTTCAAGGAGGAC
GGCAACATCCTGGGGCACAAGCTGGAGTACAACTACAACAGCCACAACGTCTATATCACC
GCCGACAAGCAGAAGAACGGCATCAAGGCCAACTTCAAGATCCGCCACAACATCGAGGAC
GGCGGCGTGCAGCTCGCCGACCACTACCAGCAGAACACCCCCATCGGCGACGGCCCCGT
GCTGCTGCCCGACAACCACTACCTGAGCTACCAGTCCAAGCTGAGCAAAGACCCCAACGA
GAAGCGCGATCACATGGTCCTGCTGGAGTTCGTGACCGCCGCCGGGATCACTCTCGGCAT
GGACGAGCTGTACAAGTAAGTCGACGGCGCGCCGCGGCCGCGAATTCGATATCATAATCA
ACCTCTGGATTACAAAATTTGTGAAAGATTGACTGGTATTCTTAACTATGTTGCTCCTTTTAC
GCTATGTGGATACGCTGCTTTAATGCCTTTGTATCATGCTATTGCTTCCCGTATGGCTTTCA
TTTTCTCCTCCTTGTATAAATCCTGGTTAGTTCTTGCCACGGCGGAACTCATCGCCGCCTG
CCTTGCCCGCTGCTGGACAGGGGCTCGGCTGTTGGGCACTGACAATTCCGTGGCTCGAG
AGATCTTCGACTGTGCCTTCTAGTTGCCAGCCATCTGTTGTTTGCCCCTCCCCCGTGCCTT
CCTTGACCCTGGAAGGTGCCACTCCCACTGTCCTTTCCTAATAAAATGAGGAAATTGCATC
GCATTGTCTGAGTAGGTGTCATTCTATTCTGGGGGGTGGGGTGGGGCAGGACAGCAAGG
GGGAGGATTGGGAAGACAATAGCAGGCATGCACGTGCGGACCGAGCGGCCGC (SEQ ID NO: 102)

Construct CN1454 nucleotide sequence: rAAV_eHGT_075h-minBglobin-SYFP2-WPRE3-BGHpA (sequence should be inserted into Plasmid backbone 2):
GCGGCCGCACGCGTGGT**GAGGAACAGAACAAAACAGAACAAGCAGGTTCACTTGGGAC
GCCGGGAACACCCCGGGCTTGCGCCCCTGCGCCTCCCCGCTGGCGGCCCCGCCAACTT
CCCGGGGTGTCCCCTCCCTACCTTCTCTTCACCGCCCTGGCGCCTGGCCTGCGCGAGGT
CGGGACTCGCGGGACCTCCGCCTACCCCAGAAGCGGCTGTCTAAAGCGGGGGTGGGGG
GGCGCCCCCTCCTGTCTGGTTTTCCCTTCCAGTTGCCGGGAGAGGACTAGGCAGCCGGG
AGCCGGGCCGTGCACCCGCTGTGGCGCGCTGGCACCTCGGCCTCCGCAAACAGATTGC
TCGCCCTCCTCGGGGAAAGCTAGGAAAACAGTGCTAAGCCTCGCAAGCTGCCGCCCATT
AATGCCTCTTAGCTTGCAAGATGGGTTACTAGCTCTGAGCACGGCCCTCCCCTCGGGGC
TTCTTACATTCTCCTCCCCCTCGCCCCTTCTGTCTCCCTCCTTCTCCACGCCGCGGTACTC
TCGCCTTCGCCCTCATTCTCTCCCTCCACCTACTACCTCTTCCTTTTGTTTTCCGTTCTCCT
GAATTTCCCT**TTCTTTCTTTTTCGAGCTCGGGCTGGGCATAAAAGTCAGGGCAGAGCCATC
TATTGCTTACATTTGCTTCTGGGATCCAGATCTTTCGAAGCTAGCGCTACCGGTCGCCACC
ATGGTGAGCAAGGGCGAGGAGCTGTTCACCGGGGTGGTGCCCATCCTGGTCGAGCTGGA
CGGCGACGTAAACGGCCACAAGTTCAGCGTGTCCGGCGAGGGCGAGGGCGATGCCACCT
ACGGCAAGCTGACCCTGAAGCTGATCTGCACCACCGGCAAGCTGCCCGTGCCCTGGCCC
ACCCTCGTGACCACCCTGGGCTACGGCGTGCAGTGCTTCGCCCGCTACCCCGACCACAT
GAAGCAGCACGACTTCTTCAAGTCCGCCATGCCCGAAGGCTACGTCCAGGAGCGCACCAT
CTTCTTCAAGGACGACGGCAACTACAAGACCCGCGCCGAGGTGAAGTTCGAGGGCGACA
CCCTGGTGAACCGCATCGAGCTGAAGGGCATCGACTTCAAGGAGGACGGCAACATCCTG
GGGCACAAGCTGGAGTACAACTACAACAGCCACAACGTCTATATCACCGCCGACAAGCAG
AAGAACGGCATCAAGGCCAACTTCAAGATCCGCCACAACATCGAGGACGGCGGCGTGCA
GCTCGCCGACCACTACCAGCAGAACACCCCCATCGGCGACGGCCCCGTGCTGCTGCCCG
ACAACCACTACCTGAGCTACCAGTCCAAGCTGAGCAAAGACCCCAACGAGAAGCGCGATC
ACATGGTCCTGCTGGAGTTCGTGACCGCCGCCGGGATCACTCTCGGCATGGACGAGCTGT

FIG. 79 cont'd

ACAAGTAAGTCGACGGCGCGCCGCGGCCGCGAATTCGATATCATAATCAACCTCTGGATT
ACAAAATTTGTGAAAGATTGACTGGTATTCTTAACTATGTTGCTCCTTTTACGCTATGTGGAT
ACGCTGCTTTAATGCCTTTGTATCATGCTATTGCTTCCCGTATGGCTTTCATTTTCTCCTCCT
TGTATAAATCCTGGTTAGTTCTTGCCACGGCGGAACTCATCGCCGCCTGCCTTGCCCGCTG
CTGGACAGGGGCTCGGCTGTTGGGCACTGACAATTCCGTGGCTCGAGAGATCTTCGACTG
TGCCTTCTAGTTGCCAGCCATCTGTTGTTTGCCCCTCCCCCGTGCCTTCCTTGACCCTGGA
AGGTGCCACTCCCACTGTCCTTTCCTAATAAAATGAGGAAATTGCATCGCATTGTCTGAGTA
GGTGTCATTCTATTCTGGGGGGTGGGGTGGGGCAGGACAGCAAGGGGGAGGATTGGGAA
GACAATAGCAGGCATGCACGTGCGGACCGAGCGGCCGC (SEQ ID NO: 103)

Construct CN1456 nucleotide sequence: rAAV_eHGT_077h-minBglobin-SYFP2-WPRE3-BGHpA (sequence should be inserted into Plasmid backbone 2):
GCGGCCGCACGCGTCAGAGATGGAG**GGGTCAGAGACACAGAGGATGACAGAGACCCAG
AGAGAGGGAGACAGAGACCCAGAGAGAGGGGGAGAGAGACCTAGAAATAGGGGGACA
GAGACCCAGAGAGGGAAGAGATGGAAACCTAGAGAAGGAAGCAGACAGAGTCCCAAA
GAGAGGCGGGGACAGAAACCCAGGAGATAGAACATAGATGCAGAGAGATGAGAACAG
AGATCCAGAATGCAAGAGAAAGATGGAGAGCCTGGGAGACGGAGGATAGACAGGCTGG
GGACGTGATTTGTGAGGTGCAGCCCCTCTCTGAGGTGGGTAGGCAGCCAGGGGATCGG
GCTGGATCCCAGGAAGGGGCTGGAACAGATGGAGGCGAGGGAGACTGGGACGGGGGA
GGAAGGAACAGCCAGACGGTCCAGGGGGAGGGAGGTGGAAGAGCTGTGAGAACACAG
CAACCCCTCCCCATCCTAGAACTTAAGGAGGTGGGGAGGGGCAGTTAAGAAACAGGGG
TGGGAGAAGCCAGGGAGTGGACAGAACCCAGAAGGAGTAGGAATGAGACCCCAAGAG
GAAGAAGACAGAGAGCCAGAGATAGGGGGGATTGAAGCCACTAGGACGAATAGTACAG
GATGGCAGTAACTCCCCCCACCCATCAGAACCCATCACCCA**AAGAGATTAGACTGGAGC
TCGGGCTGGGCATAAAAGTCAGGGCAGAGCCATCTATTGCTTACATTTGCTTCTGGGATCC
AGATCTTTCGAAGCTAGCGCTACCGGTCGCCACCATGGTGAGCAAGGGCGAGGAGCTGTT
CACCGGGGTGGTGCCCATCCTGGTCGAGCTGGACGGCGACGTAAACGGCCACAAGTTCA
GCGTGTCCGGCGAGGGCGAGGGCGATGCCACCTACGGCAAGCTGACCCTGAAGCTGATC
TGCACCACCGGCAAGCTGCCCGTGCCCTGGCCCACCCTCGTGACCACCCTGGGCTACGG
CGTGCAGTGCTTCGCCCGCTACCCCGACCACATGAAGCAGCACGACTTCTTCAAGTCCGC
CATGCCCGAAGGCTACGTCCAGGAGCGCACCATCTTCTTCAAGGACGACGGCAACTACAA
GACCCGCGCCGAGGTGAAGTTCGAGGGCGACACCCTGGTGAACCGCATCGAGCTGAAGG
GCATCGACTTCAAGGAGGACGGCAACATCCTGGGGCACAAGCTGGAGTACAACTACAACA
GCCACAACGTCTATATCACCGCCGACAAGCAGAAGAACGGCATCAAGGCCAACTTCAAGA
TCCGCCACAACATCGAGGACGGCGGCGTGCAGCTCGCCGACCACTACCAGCAGAACACC
CCCATCGGCGACGGCCCCGTGCTGCTGCCCGACAACCACTACCTGAGCTACCAGTCCAA
GCTGAGCAAAGACCCCAACGAGAAGCGCGATCACATGGTCCTGCTGGAGTTCGTGACCGC
CGCCGGGATCACTCTCGGCATGGACGAGCTGTACAAGTAAGTCGACGGCGCGCCGCGGC
CGCGAATTCGATATCATAATCAACCTCTGGATTACAAAATTTGTGAAAGATTGACTGGTATT
CTTAACTATGTTGCTCCTTTTACGCTATGTGGATACGCTGCTTTAATGCCTTTGTATCATGCT
ATTGCTTCCCGTATGGCTTTCATTTTCTCCTCCTTGTATAAATCCTGGTTAGTTCTTGCCAC
GGCGGAACTCATCGCCGCCTGCCTTGCCCGCTGCTGGACAGGGGCTCGGCTGTTGGGCA
CTGACAATTCCGTGGCTCGAGAGATCTTCGACTGTGCCTTCTAGTTGCCAGCCATCTGTTG
TTTGCCCCTCCCCCGTGCCTTCCTTGACCCTGGAAGGTGCCACTCCCACTGTCCTTTCCTA
ATAAAATGAGGAAATTGCATCGCATTGTCTGAGTAGGTGTCATTCTATTCTGGGGGGTGGG
GTGGGGCAGGACAGCAAGGGGGAGGATTGGGAAGACAATAGCAGGCATGCACGTGCGGA
CCGAGCGGCCGC (SEQ ID NO: 104)

FIG. 79 cont'd

Construct CN1457 nucleotide sequence: rAAV_eHGT_078h-minBglobin-SYFP2-WPRE3-BGHpA (sequence should be inserted into Plasmid backbone 2):
GCGGCCGCACGCGTGAAATCATAAATGCTGAGGGTAGTCTGCCTCAGGTACACACTGAG
AAACTGCTTTAATGTAACCTGACCCACGGTTATTAGTGAAAATATCACTTTTGTTGTTACC
TTATTCCCAACAAATTCATTTCTGCTTTAATGGAAAAGATCCGGGTTCACACTAATCAGGC
CCAACGGAAGGCCATATTAGCAATTTGGCAGGTACCCGAGGGCCATACCTAATCTGCAT
AAAATGAAGCAGATTGCAACCGCCCTCATCTTTTTTATTTTTAAACTGGTTTTTGAAGCAG
AGCATAAAATCTCAGAGGGAGAGACAGAAGATGCTAGTGCATACATTTTCCTTCATGCCT
TTATTTTCATTCTTTTTGCACAAACCATCTTCCTGAATGGCTGTTTACCTAAAGAAGAATAA
CAAAATAAAAGGTGCTAGGAAATGGAGTAGGCAGAGATCACAAATGTTTAATTAAAAAA
AAAAAAAGTCATGTACTTTCATAGATATTCACAATCCTCTCTAGTATACTTTCAAATCAGT
TTTAATTTCAGTTTAGTGTTTTTATGTTTTGTGAAGATACGCGAGCTCGGGCTGGGCATAAA
AGTCAGGGCAGAGCCATCTATTGCTTACATTTGCTTCTGGGATCCAGATCTTTCGAAGCTA
GCGCTACCGGTCGCCACCATGGTGAGCAAGGGCGAGGAGCTGTTCACCGGGGTGGTGCC
CATCCTGGTCGAGCTGGACGGCGACGTAAACGGCCACAAGTTCAGCGTGTCCGGCGAGG
GCGAGGGCGATGCCACCTACGGCAAGCTGACCCTGAAGCTGATCTGCACCACCGGCAAG
CTGCCCGTGCCCTGGCCCACCCTCGTGACCACCCTGGGCTACGGCGTGCAGTGCTTCGC
CCGCTACCCCGACCACATGAAGCAGCACGACTTCTTCAAGTCCGCCATGCCCGAAGGCTA
CGTCCAGGAGCGCACCATCTTCTTCAAGGACGACGGCAACTACAAGACCCGCGCCGAGGT
GAAGTTCGAGGGCGACACCCTGGTGAACCGCATCGAGCTGAAGGGCATCGACTTCAAGG
AGGACGGCAACATCCTGGGGCACAAGCTGGAGTACAACTACAACAGCCACAACGTCTATA
TCACCGCCGACAAGCAGAAGAACGGCATCAAGGCCAACTTCAAGATCCGCCACAACATCG
AGGACGGCGGCGTGCAGCTCGCCGACCACTACCAGCAGAACACCCCCATCGGCGACGGC
CCCGTGCTGCTGCCCGACAACCACTACCTGAGCTACCAGTCCAAGCTGAGCAAAGACCCC
AACGAGAAGCGCGATCACATGGTCCTGCTGGAGTTCGTGACCGCCGCCGGGATCACTCTC
GGCATGGACGAGCTGTACAAGTAAGTCGACGGCGCGCCGCGGCCGCGAATTCGATATCA
TAATCAACCTCTGGATTACAAAATTTGTGAAAGATTGACTGGTATTCTTAACTATGTTGCTCC
TTTTACGCTATGTGGATACGCTGCTTTAATGCCTTTGTATCATGCTATTGCTTCCCGTATGG
CTTTCATTTTCTCCTCCTTGTATAAATCCTGGTTAGTTCTTGCCACGGCGGAACTCATCGCC
GCCTGCCTTGCCCGCTGCTGGACAGGGGCTCGGCTGTTGGGCACTGACAATTCCGTGGC
TCGAGAGATCTTCGACTGTGCCTTCTAGTTGCCAGCCATCTGTTGTTTGCCCCTCCCCCGT
GCCTTCCTTGACCCTGGAAGGTGCCACTCCCACTGTCCTTTCCTAATAAAATGAGGAAATT
GCATCGCATTGTCTGAGTAGGTGTCATTCTATTCTGGGGGGTGGGGTGGGGCAGGACAGC
AAGGGGGAGGATTGGGAAGACAATAGCAGGCATGCACGTGCGGACCGAGCGGCCGC
(SEQ ID NO: 105)

Construct CN1461 nucleotide sequence: rAAV_eHGT_073m-minBglobin-SYFP2-WPRE3-BGHpA (sequence should be inserted into Plasmid backbone 2):
GCGGCCGCACGCGTGTATGTGTGACAGGAGCCAGGCAGCTGAGGCAGCGGGACAACAGA
GCCACTGGCCTGACTGGGAAGAATGTCCCAGACATTGACAAAAGACAATCTAGAGAGG
GTAAGGATGGGAGACCAGGGACACCAAAGAGCCCACTGGGTCCCTGTGGCCAGGCGGG
GCCCAGAGCACATGGTGCCAGCCTCGTTCCCTATTAGGCAAAGCACTGCACCATCTGTA
TAGTCCCAGGAGCAGGAGCAGGAGCAGGCGTTTTATAACTTCCTTTTCTTTTTCAGTCTA
CATTAAAAATAAATGTTCCCTTCAGCTCTCAGATGTATATCTCTAGTGCAACCTGCCCACA
TTCCCTCCTGCTGCCCTTTCCAGAACATGGCAGGGGAAGGGAAGGAAGAGATGGAGAG
AGGGAGCCAGTCCACCCGGCTGATGCCAGTGGATCACACCTCTTCTAAGAGGGAAGCG
CGGCAGGCACGGCCACACATGGTGGAAGGTGCCCAGAATGCATGGGGACCAGGGAAAT
GGAAGTGGAGGAAATGGGAGCCAACAGCCAGGCTTGCTTCCCACCCCCACCCTCCCGC

FIG. 79 cont'd

ACCGCAGGACCTTGGCCAAATCACACATCCCATCTTTGCATTTATAGTTCATGCAGTGGC
TGGAGTCCCCTCTGCAGCTCCAGCCCTCTGGTGGCTGTCCTTGCTGCACGTCTCTCTGTA
CTTCCCCTTGTGTGTCCTGCTGTGGGAGCTCGGGCTGGGCATAAAAGTCAGGGCAGAGCC
ATCTATTGCTTACATTTGCTTCTGGGATCCAGATCTTTCGAAGCTAGCGCTACCGGTCGCC
ACCATGGTGAGCAAGGGCGAGGAGCTGTTCACCGGGGTGGTGCCCATCCTGGTCGAGCT
GGACGGCGACGTAAACGGCCACAAGTTCAGCGTGTCCGGCGAGGGCGAGGGCGATGCC
ACCTACGGCAAGCTGACCCTGAAGCTGATCTGCACCACCGGCAAGCTGCCCGTGCCCTG
GCCCACCCTCGTGACCACCCTGGGCTACGGCGTGCAGTGCTTCGCCCGCTACCCCGACC
ACATGAAGCAGCACGACTTCTTCAAGTCCGCCATGCCCGAAGGCTACGTCCAGGAGCGCA
CCATCTTCTTCAAGGACGACGGCAACTACAAGACCCGCGCCGAGGTGAAGTTCGAGGGCG
ACACCCTGGTGAACCGCATCGAGCTGAAGGGCATCGACTTCAAGGAGGACGGCAACATCC
TGGGGCACAAGCTGGAGTACAACTACAACAGCCACAACGTCTATATCACCGCCGACAAGC
AGAAGAACGGCATCAAGGCCAACTTCAAGATCCGCCACAACATCGAGGACGGCGGCGTG
CAGCTCGCCGACCACTACCAGCAGAACACCCCCATCGGCGACGGCCCCGTGCTGCTGCC
CGACAACCACTACCTGAGCTACCAGTCCAAGCTGAGCAAAGACCCCAACGAGAAGCGCGA
TCACATGGTCCTGCTGGAGTTCGTGACCGCCGCCGGGATCACTCTCGGCATGGACGAGCT
GTACAAGTAAGTCGACGGCGCGCCGCGGCCGCGAATTCGATATCATAATCAACCTCTGGA
TTACAAAATTTGTGAAAGATTGACTGGTATTCTTAACTATGTTGCTCCTTTTACGCTATGTGG
ATACGCTGCTTTAATGCCTTTGTATCATGCTATTGCTTCCCGTATGGCTTTCATTTTCTCCTC
CTTGTATAAATCCTGGTTAGTTCTTGCCACGGCGGAACTCATCGCCGCCTGCCTTGCCCGC
TGCTGGACAGGGGCTCGGCTGTTGGGCACTGACAATTCCGTGGCTCGAGAGATCTTCGAC
TGTGCCTTCTAGTTGCCAGCCATCTGTTGTTTGCCCCTCCCCCGTGCCTTCCTTGACCCTG
GAAGGTGCCACTCCCACTGTCCTTTCCTAATAAAATGAGGAAATTGCATCGCATTGTCTGA
GTAGGTGTCATTCTATTCTGGGGGGTGGGGTGGGGCAGGACAGCAAGGGGGAGGATTGG
GAAGACAATAGCAGGCATGCACGTGCGGACCGAGCGGCCGC (SEQ ID NO: 106)

Construct CN1466 nucleotide sequence: rAAV_eHGT_078m-minBglobin-SYFP2-WPRE3-BGHpA (sequence should be inserted into Plasmid backbone 2):
GCGGCCGCACGCGTCCCTGGCCTTCGAGCACATGCTCAGATGATGCTCCACCGTGGCCT
GACCCACATCTTCTAGTGGAAGCATGGTCCAGCAAAGCCTTTCTGTTCTAAAGGAAAGG
ATCTGAGTTGTCACCTCCCAGGTCCGTGGAAGGCTTTTTAGCAGTTTGGCAGGTGCCTGA
GGGCCACACCTCATCTGCATAAAATGTGGCAGATTGCAACCGCCCTCGTCTTTTTTATTTT
TAAACTGGTTTTTGAAACAGAACATATATAAAAGCTCAGAGAAAGGGAAAGGAGATAGA
TGGCCGAGCTTCCATATCCCTTAGTGCCTTTATTTTCATTCTTTTTCCATTTTCCTAAGTGG
CTATTTACCAAGACAAAGATAACAAATCTGCTAGGAAAAGGAGTGGGCAGTGCTACAAA
ATGTTTTTTTTTTTTTAAAGAAAGTCCTATCTTATAATAGATCTTCACCACGATGCCTCATG
ATGTATGCTCAAATCAGTTTTAATTGAACTGTGTGTAGTATGCTCCTGTTTTGGAGCTCGG
GCTGGGCATAAAAGTCAGGGCAGAGCCATCTATTGCTTACATTTGCTTCTGGGATCCAGAT
CTTTCGAAGCTAGCGCTACCGGTCGCCACCATGGTGAGCAAGGGCGAGGAGCTGTTCACC
GGGGTGGTGCCCATCCTGGTCGAGCTGGACGGCGACGTAAACGGCCACAAGTTCAGCGT
GTCCGGCGAGGGCGAGGGCGATGCCACCTACGGCAAGCTGACCCTGAAGCTGATCTGCA
CCACCGGCAAGCTGCCCGTGCCCTGGCCCACCCTCGTGACCACCCTGGGCTACGGCGTG
CAGTGCTTCGCCCGCTACCCCGACCACATGAAGCAGCACGACTTCTTCAAGTCCGCCATG
CCCGAAGGCTACGTCCAGGAGCGCACCATCTTCTTCAAGGACGACGGCAACTACAAGACC
CGCGCCGAGGTGAAGTTCGAGGGCGACACCCTGGTGAACCGCATCGAGCTGAAGGGCAT
CGACTTCAAGGAGGACGGCAACATCCTGGGGCACAAGCTGGAGTACAACTACAACAGCCA
CAACGTCTATATCACCGCCGACAAGCAGAAGAACGGCATCAAGGCCAACTTCAAGATCCG
CCACAACATCGAGGACGGCGGCGTGCAGCTCGCCGACCACTACCAGCAGAACACCCCCA

FIG. 79 cont'd

TCGGCGACGGCCCCGTGCTGCTGCCCGACAACCACTACCTGAGCTACCAGTCCAAGCTGA
GCAAAGACCCCAACGAGAAGCGCGATCACATGGTCCTGCTGGAGTTCGTGACCGCCGCC
GGGATCACTCTCGGCATGGACGAGCTGTACAAGTAAGTCGACGGCGCGCCGCGGCCGCG
AATTCGATATCATAATCAACCTCTGGATTACAAAATTTGTGAAAGATTGACTGGTATTCTTAA
CTATGTTGCTCCTTTTACGCTATGTGGATACGCTGCTTTAATGCCTTTGTATCATGCTATTG
CTTCCCGTATGGCTTTCATTTTCTCCTCCTTGTATAAATCCTGGTTAGTTCTTGCCACGGCG
GAACTCATCGCCGCCTGCCTTGCCCGCTGCTGGACAGGGGCTCGGCTGTTGGGCACTGA
CAATTCCGTGGCTCGAGAGATCTTCGACTGTGCCTTCTAGTTGCCAGCCATCTGTTGTTTG
CCCCTCCCCCGTGCCTTCCTTGACCCTGGAAGGTGCCACTCCCACTGTCCTTTCCTAATAA
AATGAGGAAATTGCATCGCATTGTCTGAGTAGGTGTCATTCTATTCTGGGGGGTGGGGTG
GGGCAGGACAGCAAGGGGGAGGATTGGGAAGACAATAGCAGGCATGCACGTGCGGACC
GAGCGGCCGC (SEQ ID NO: 107)

Construct CN1772 nucleotide sequence: rAAV_hsA2-eHGT_254h-minRho-SYFP2-WPRE3-BGHpA (sequence should be inserted into Plasmid backbone 2):
GCGGCCGCAACGCGTTTAGAACAATGGCTGGCCCATAGTAAATGCCGTGTTAGTGTGTTA
GTTGCTGTTCTTCCACGTCAGAAGAGGCACAGACAAATTACCACCAGGTGGCGCTCAGAG
TCTGCGGAGGCATCACAACAGCCCTGAATTTGAATCCTGCTCTGCCACTGCCTAGTTGAGA
CCTTTTACTACCTGACTAGCTGTTTGTGTATTTTAGGTGTTTGTTTCTTGCACGCTTATTCAG
GCTTTTGGCAGAAATCAGTTCGTTGTGGTTTAAGGACTGAGGTCGCCTTTCTTTGCTGCTA
ACTGTTGGCCAGGAAGTACTGTCAGCTACTACATGGTACTTGCTGGTCCTTGCACATGAC
CCCCTCCACCTTCAAACCAGGATTGACACAGTGTGTTGAGTCTTTCTTGAAGACTTTTGA
ACATCTGACTTCCCATTCTGCCACTAGCCAGTTAAAATTCTCTAATTTTGAAGGACTCACC
TGGTTGGCCAAACCCACCCAAATAATCTCCACATCTTGAAGTCAACTGACCCAGGACTTT
ACATATGCAAAATCCCTTCACAGCAGTACCTAGATGAGTGTTTGCTTGAATAACTGGGAC
ACAGGAATCTTGGGGGAGCCATCTTTAGAATTCGACCTCCTACAACCCTTCTGGAAATCT
GAGAGTGAGTCAGGGGAAGAAACCCTCTTTTGTAGTTTCCTTTTAGGGCTTTCTACTTTGC
TCAAAGTTGGGCACTATTTCACTTCAGTAGGGTCCTGCAAGCCCCATGAGGGTAGTGAGT
GCTGTCCTAGGAAACAGTAACTTAACCCTGATACCCATTTGTCCAAGAATTCGATATCATA
ATCAACCATAGGTACCGAGCTCGGGATTCAGCCGGGAGCTTAGGGAGGGGAGGTCACTTC
ATAAGGGCCTGGGGGGGGAGTTGGAGCCACGAGTCGTCCAGCCGGAGCCCCGTGTGGC
TGAGCTCCGGCCTCAGAAGCATCCCCGGGTTGGATCCTTCGAAGCTAGCGCTACCGGTCG
CCACCATGGTGAGCAAGGGCGAGGAGCTGTTCACCGGGGTGGTGCCCATCCTGGTCGAG
CTGGACGGCGACGTAAACGGCCACAAGTTCAGCGTGTCCGGCGAGGGCGAGGGCGATGC
CACCTACGGCAAGCTGACCCTGAAGCTGATCTGCACCACCGGCAAGCTGCCCGTGCCCTG
GCCCACCCTCGTGACCACCCTGGGCTACGGCGTGCAGTGCTTCGCCCGCTACCCCGACC
ACATGAAGCAGCACGACTTCTTCAAGTCCGCCATGCCCGAAGGCTACGTCCAGGAGCGCA
CCATCTTCTTCAAGGACGACGGCAACTACAAGACCCGCGCCGAGGTGAAGTTCGAGGGCG
ACACCCTGGTGAACCGCATCGAGCTGAAGGGCATCGACTTCAAGGAGGACGGCAACATCC
TGGGGCACAAGCTGGAGTACAACTACAACAGCCACAACGTCTATATCACCGCCGACAAGC
AGAAGAACGGCATCAAGGCCAACTTCAAGATCCGCCACAACATCGAGGACGGCGGCGTG
CAGCTCGCCGACCACTACCAGCAGAACACCCCCATCGGCGACGGCCCCGTGCTGCTGCC
CGACAACCACTACCTGAGCTACCAGTCCAAGCTGAGCAAAGACCCCAACGAGAAGCGCGA
TCACATGGTCCTGCTGGAGTTCGTGACCGCCGCCGGGATCACTCTCGGCATGGACGAGCT
GTACAAGTAAGTCGACATCATAATCAACCTCTGGATTACAAAATTTGTGAAAGATTGACTGG
TATTCTTAACTATGTTGCTCCTTTTACGCTATGTGGATACGCTGCTTTAATGCCTTTGTATCA
TGCTATTGCTTCCCGTATGGCTTTCATTTTCTCCTCCTTGTATAAATCCTGGTTAGTTCTTGC
CACGGCGGAACTCATCGCCGCCTGCCTTGCCCGCTGCTGGACAGGGGCTCGGCTGTTGG

FIG. 79 cont'd

GCACTGACAATTCCGTGGCTCGAGAGATCTTCGACTGTGCCTTCTAGTTGCCAGCCATCTG
TTGTTTGCCCCTCCCCCGTGCCTTCCTTGACCCTGGAAGGTGCCACTCCCACTGTCCTTTC
CTAATAAAATGAGGAAATTGCATCGCATTGTCTGAGTAGGTGTCATTCTATTCTGGGGGGT
GGGGTGGGGCAGGACAGCAAGGGGGAGGATTGGGAAGACAATAGCAGGCATGCACGTG
CGGACCGAGCGGCCGC (SEQ ID NO: 108)

Construct CN1818 nucleotide sequence: rAAV_3xCore-mscRE4-minCMV-SYFP2-WPRE3-bGHpA (sequence should be inserted into Plasmid backbone 2):
GCGGCCGCACGCGT**TTACCCTGTTGAATATCACTGACTCACTAACTTGCATTGCCATGCT
AACTTGCTTTCAGAGAGATCTCAGAACACATCATCTTCTGCTATTTCAATACATGCACATT
AATTTCCTATCAACGTGTGCTGATCAGGAACTCTGTAATCTGGCACCGTTACCCTGTTGA
ATATCACTGACTCACTAACTTGCATTGCCATGCTAACTTGCTTTCAGAGAGATCTCAGAA
CACATCATCTTCTGCTATTTCAATACATGCACATTAATTTCCTATCAACGTGTGCTGATCA
GGAACTCTGTAATCTGGCACCGTTACCCTGTTGAATATCACTGACTCACTAACTTGCATT
GCCATGCTAACTTGCTTTCAGAGAGATCTCAGAACACATCATCTTCTGCTATTTCAATACA
TGCACATTAATTTCCTATCAACGTGTGCTGATCAGGAACTCTGTAATCTGGCACCG**CTTAA
GGAGCTCAGAGGTAGGCGTGTACGGTGGGAGGCCTATATAAGCAGAGCTGGTTTAGTGAA
CCGTCAGATCGCCTGGGGATCCAGATCTTTCGAAGCTAGCGCTACCGGTCGCCACCATGG
TGAGCAAGGGCGAGGAGCTGTTCACCGGGGTGGTGCCCATCCTGGTCGAGCTGGACGGC
GACGTAAACGGCCACAAGTTCAGCGTGTCCGGCGAGGGCGAGGGCGATGCCACCTACGG
CAAGCTGACCCTGAAGCTGATCTGCACCACCGGCAAGCTGCCCGTGCCCTGGCCCACCCT
CGTGACCACCCTGGGCTACGGCGTGCAGTGCTTCGCCCGCTACCCCGACCACATGAAGC
AGCACGACTTCTTCAAGTCCGCCATGCCCGAAGGCTACGTCCAGGAGCGCACCATCTTCT
TCAAGGACGACGGCAACTACAAGACCCGCGCCGAGGTGAAGTTCGAGGGCGACACCCTG
GTGAACCGCATCGAGCTGAAGGGCATCGACTTCAAGGAGGACGGCAACATCCTGGGGCA
CAAGCTGGAGTACAACTACAACAGCCACAACGTCTATATCACCGCCGACAAGCAGAAGAA
CGGCATCAAGGCCAACTTCAAGATCCGCCACAACATCGAGGACGGCGGCGTGCAGCTCG
CCGACCACTACCAGCAGAACACCCCCATCGGCGACGGCCCCGTGCTGCTGCCCGACAAC
CACTACCTGAGCTACCAGTCCAAGCTGAGCAAAGACCCCAACGAGAAGCGCGATCACATG
GTCCTGCTGGAGTTCGTGACCGCCGCCGGGATCACTCTCGGCATGGACGAGCTGTACAA
GTAAGTCGACGGCGCGCCGCGGCCGCGAATTCGATATCATAATCAACCTCTGGATTACAA
AATTTGTGAAAGATTGACTGGTATTCTTAACTATGTTGCTCCTTTTACGCTATGTGGATACG
CTGCTTTAATGCCTTTGTATCATGCTATTGCTTCCCGTATGGCTTTCATTTTCTCCTCCTTGT
ATAAATCCTGGTTAGTTCTTGCCACGGCGGAACTCATCGCCGCCTGCCTTGCCCGCTGCT
GGACAGGGGCTCGGCTGTTGGGCACTGACAATTCCGTGGCTCGAGAGATCTTCGACTGTG
CCTTCTAGTTGCCAGCCATCTGTTGTTTGCCCCTCCCCCGTGCCTTCCTTGACCCTGGAAG
GTGCCACTCCCACTGTCCTTTCCTAATAAAATGAGGAAATTGCATCGCATTGTCTGAGTAG
GTGTCATTCTATTCTGGGGGGTGGGGTGGGGCAGGACAGCAAGGGGGAGGATTGGGAAG
ACAATAGCAGGCATGCACGTGCGGACCGAGCGGCCGc (SEQ ID NO: 109)

Construct CN1954 nucleotide sequence: rAAV_hsA2-eHGT_078h(3xCore)-minRho-SYFP2-WPRE3-BGHpA (sequence should be inserted into Plasmid backbone 2):
GCGGCCGCAACGCGTTTAGAACAATGGCTGGCCCATAGTAAATGCCGTGTTAGTGTGTTA
GTTGCTGTTCTTCCACGTCAGAAGAGGCACAGACAAATTACCACCAGGTGGCGCTCAGAG
TCTGCGGAGGCATCACAACAGCCCTGAATTTGAATCCTGCTCTGCCACTGCCTAGTTGAGA
CCTTTTACTACCTGACTAGCTGTTTGTGTATTTTAGGTGTTTGTTT**GAAAAGATCCGGGTTC
ACACTAATCAGGCCCAACGGAAGGCCATATTAGCAATTTGGCAGGTACCCGAGGGCCAT
ACCTAATCTGCATAAAATGAAGCAGATTGCAACCGCCCTCATCTTTTTTATTTTTAAACTG**

FIG. 79 cont'd

GTTTTTGAAGCAGAGCATAAAATCTCAGAGGGAGAGACAGAAGATGCTAGTGCATACAT TTTCCTTCATGCCTTTATTTTCATTCTTTTTGCACAAACCATCTTCCTGAATGGCTGTTTAC CTAAAGAAGAATAACAAAATAAAAGGTGCTAGGAAATGGAGTAGGCAGAGATCGAGCA GAGCCCTCATCACACAGACTGAAAAGATCCGGGTTCACACTAATCAGGCCCAACGGAAG GCCATATTAGCAATTTGGCAGGTACCCGAGGGCCATACCTAATCTGCATAAAATGAAGC AGATTGCAACCGCCCTCATCTTTTTTATTTTTAAACTGGTTTTTGAAGCAGAGCATAAAAT CTCAGAGGGAGAGACAGAAGATGCTAGTGCATACATTTTCCTTCATGCCTTTATTTTCATT CTTTTTGCACAAACCATCTTCCTGAATGGCTGTTTACCTAAAGAAGAATAACAAAATAAA AGGTGCTAGGAAATGGAGTAGGCAGAGATCTGGGTGAGTAAGAGTAGGTGGCAACGAA AAGATCCGGGTTCACACTAATCAGGCCCAACGGAAGGCCATATTAGCAATTTGGCAGGT ACCCGAGGGCCATACCTAATCTGCATAAAATGAAGCAGATTGCAACCGCCCTCATCTTTT TTATTTTTAAACTGGTTTTTGAAGCAGAGCATAAAATCTCAGAGGGAGAGACAGAAGATG CTAGTGCATACATTTTCCTTCATGCCTTTATTTTCATTCTTTTTGCACAAACCATCTTCCTG AATGGCTGTTTACCTAAAGAAGAATAACAAAATAAAAGGTGCTAGGAAATGGAGTAGGC AGAGATCGAATTCGATATCATAATCAACCATAGGTACCGAGCTCGGGATTCAGCCGGGAG CTTAGGGAGGGGAGGTCACTTCATAAGGGCCTGGGGGGGGAGTTGGAGCCACGAGTCGT CCAGCCGGAGCCCCGTGTGGCTGAGCTCCGGCCTCAGAAGCATCCCCGGGTTGGATCCT TCGAAGCTAGCGCTACCGGTCGCCACCATGGTGAGCAAGGGCGAGGAGCTGTTCACCGG GGTGGTGCCCATCCTGGTCGAGCTGGACGGCGACGTAAACGGCCACAAGTTCAGCGTGT CCGGCGAGGGCGAGGGCGATGCCACCTACGGCAAGCTGACCCTGAAGCTGATCTGCACC ACCGGCAAGCTGCCCGTGCCCTGGCCCACCCTCGTGACCACCCTGGGCTACGGCGTGCA GTGCTTCGCCCGCTACCCCGACCACATGAAGCAGCACGACTTCTTCAAGTCCGCCATGCC CGAAGGCTACGTCCAGGAGCGCACCATCTTCTTCAAGGACGACGGCAACTACAAGACCCG CGCCGAGGTGAAGTTCGAGGGCGACACCCTGGTGAACCGCATCGAGCTGAAGGGCATCG ACTTCAAGGAGGACGGCAACATCCTGGGGCACAAGCTGGAGTACAACTACAACAGCCACA ACGTCTATATCACCGCCGACAAGCAGAAGAACGGCATCAAGGCCAACTTCAAGATCCGCC ACAACATCGAGGACGGCGGCGTGCAGCTCGCCGACCACTACCAGCAGAACACCCCCATC GGCGACGGCCCCGTGCTGCTGCCCGACAACCACTACCTGAGCTACCAGTCCAAGCTGAG CAAAGACCCCAACGAGAAGCGCGATCACATGGTCCTGCTGGAGTTCGTGACCGCCGCCG GGATCACTCTCGGCATGGACGAGCTGTACAAGTAAGTCGACATCATAATCAACCTCTGGAT TACAAAATTTGTGAAAGATTGACTGGTATTCTTAACTATGTTGCTCCTTTTACGCTATGTGGA TACGCTGCTTTAATGCCTTTGTATCATGCTATTGCTTCCCGTATGGCTTTCATTTTCTCCTCC TTGTATAAATCCTGGTTAGTTCTTGCCACGGCGGAACTCATCGCCGCCTGCCTTGCCCGCT GCTGGACAGGGGCTCGGCTGTTGGGCACTGACAATTCCGTGGCTCGAGAGATCTTCGACT GTGCCTTCTAGTTGCCAGCCATCTGTTGTTTGCCCCTCCCCCGTGCCTTCCTTGACCCTGG AAGGTGCCACTCCCACTGTCCTTTCCTAATAAAATGAGGAAATTGCATCGCATTGTCTGAGT AGGTGTCATTCTATTCTGGGGGGTGGGGTGGGGCAGGACAGCAAGGGGGAGGATTGGGA AGACAATAGCAGGCATGCACGTGCGGACCGAGCGGCCGC (SEQ ID NO: 110)

Construct CN1955 nucleotide sequence: rAAV_hsA2-eHGT_078m(3xCore)-minRho-SYFP2-WPRE3-BGHpA (sequence should be inserted into Plasmid backbone 2):
GCGGCCGCAACGCGTTTAGAACAATGGCTGGCCCATAGTAAATGCCGTGTTAGTGTGTTA GTTGCTGTTCTTCCACGTCAGAAGAGGCACAGACAAATTACCACCAGGTGGCGCTCAGAG TCTGCGGAGGCATCACAACAGCCCTGAATTTGAATCCTGCTCTGCCACTGCCTAGTTGAGA CCTTTTACTACCTGACTAGCTGTTTGTGTATTTTAGGTGTTTGTTTGAAGCATGGTCCAGCA AAGCCTTTCTGTTCTAAAGGAAAGGATCTGAGTTGTCACCTCCCAGGTCCGTGGAAGGCT TTTTAGCAGTTTGGCAGGTGCCTGAGGGCCACACCTCATCTGCATAAAATGTGGCAGATT GCAACCGCCCTCGTCTTTTTTATTTTTAAACTGGTTTTTGAAACAGAACATATATAAAAGC

FIG. 79 cont'd

**TCAGAGAAAGGGAAAGGAGATAGATGGCCGAGCTTCCATATCCCTTAGTGCCTTTATTTT
CATTCTTTTTCCATTTTCCTAAGTGGCTATTTACCAAGACAAAGATAACAAATCTGCTAGG
AAAAGGAGTGGGCAGTGCTACAAAATGTTTTTTTTTTTTTAAAGAAAGTCCTATCTTATAA
TAGATCTTCACCACGATGCCTCGAGCAGAGCCCTCATCACACAGACTGAAGCATGGTCC
AGCAAAGCCTTTCTGTTCTAAAGGAAAGGATCTGAGTTGTCACCTCCCAGGTCCGTGGAA
GGCTTTTTAGCAGTTTGGCAGGTGCCTGAGGGCCACACCTCATCTGCATAAAATGTGGCA
GATTGCAACCGCCCTCGTCTTTTTTATTTTTAAACTGGTTTTTGAAACAGAACATATATAA
AAGCTCAGAGAAAGGGAAAGGAGATAGATGGCCGAGCTTCCATATCCCTTAGTGCCTTT
ATTTTCATTCTTTTTCCATTTTCCTAAGTGGCTATTTACCAAGACAAAGATAACAAATCTGC
TAGGAAAAGGAGTGGGCAGTGCTACAAAATGTTTTTTTTTTTTTAAAGAAAGTCCTATCTT
ATAATAGATCTTCACCACGATGCCTCTGGGTGAGTAAGAGTAGGTGGCAACGAAGCATG
GTCCAGCAAAGCCTTTCTGTTCTAAAGGAAAGGATCTGAGTTGTCACCTCCCAGGTCCGT
GGAAGGCTTTTTAGCAGTTTGGCAGGTGCCTGAGGGCCACACCTCATCTGCATAAAATGT
GGCAGATTGCAACCGCCCTCGTCTTTTTTATTTTTAAACTGGTTTTTGAAACAGAACATAT
ATAAAAGCTCAGAGAAAGGGAAAGGAGATAGATGGCCGAGCTTCCATATCCCTTAGTGC
CTTTATTTTCATTCTTTTTCCATTTTCCTAAGTGGCTATTTACCAAGACAAAGATAACAAAT
CTGCTAGGAAAAGGAGTGGGCAGTGCTACAAAATGTTTTTTTTTTTTTAAAGAAAGTCCTA
TCTTATAATAGATCTTCACCACGATGCCTC**GAATTCGATATCATAATCAACCATAGGTACC
GAGCTCGGGATTCAGCCGGGAGCTTAGGGAGGGGAGGTCACTTCATAAGGGCCTGGGGG
GGGAGTTGGAGCCACGAGTCGTCCAGCCGGAGCCCCGTGTGGCTGAGCTCCGGCCTCAG
AAGCATCCCCGGGTTGGATCCTTCGAAGCTAGCGCTACCGGTCGCCACCATGGTGAGCAA
GGGCGAGGAGCTGTTCACCGGGGTGGTGCCCATCCTGGTCGAGCTGGACGGCGACGTAA
ACGGCCACAAGTTCAGCGTGTCCGGCGAGGGCGAGGGCGATGCCACCTACGGCAAGCTG
ACCCTGAAGCTGATCTGCACCACCGGCAAGCTGCCCGTGCCCTGGCCCACCCTCGTGAC
CACCCTGGGCTACGGCGTGCAGTGCTTCGCCCGCTACCCCGACCACATGAAGCAGCACG
ACTTCTTCAAGTCCGCCATGCCCGAAGGCTACGTCCAGGAGCGCACCATCTTCTTCAAGG
ACGACGGCAACTACAAGACCCGCGCCGAGGTGAAGTTCGAGGGCGACACCCTGGTGAAC
CGCATCGAGCTGAAGGGCATCGACTTCAAGGAGGACGGCAACATCCTGGGGCACAAGCT
GGAGTACAACTACAACAGCCACAACGTCTATATCACCGCCGACAAGCAGAAGAACGGCAT
CAAGGCCAACTTCAAGATCCGCCACAACATCGAGGACGGCGGCGTGCAGCTCGCCGACC
ACTACCAGCAGAACACCCCCATCGGCGACGGCCCCGTGCTGCTGCCCGACAACCACTAC
CTGAGCTACCAGTCCAAGCTGAGCAAAGACCCCAACGAGAAGCGCGATCACATGGTCCTG
CTGGAGTTCGTGACCGCCGCCGGGATCACTCTCGGCATGGACGAGCTGTACAAGTAAGTC
GACATCATAATCAACCTCTGGATTACAAAATTTGTGAAAGATTGACTGGTATTCTTAACTATG
TTGCTCCTTTTACGCTATGTGGATACGCTGCTTTAATGCCTTTGTATCATGCTATTGCTTCC
CGTATGGCTTTCATTTTCTCCTCCTTGTATAAATCCTGGTTAGTTCTTGCCACGGCGGAACT
CATCGCCGCCTGCCTTGCCCGCTGCTGGACAGGGGCTCGGCTGTTGGGCACTGACAATT
CCGTGGCTCGAGAGATCTTCGACTGTGCCTTCTAGTTGCCAGCCATCTGTTGTTTGCCCCT
CCCCCGTGCCTTCCTTGACCCTGGAAGGTGCCACTCCCACTGTCCTTTCCTAATAAAATGA
GGAAATTGCATCGCATTGTCTGAGTAGGTGTCATTCTATTCTGGGGGGTGGGGTGGGGCA
GGACAGCAAGGGGGAGGATTGGGAAGACAATAGCAGGCATGCACGTGCGGACCGAGCG
GCCGC (SEQ ID NO: 111)

Construct CN2014 nucleotide sequence: rAAV_mscRE4-minCMV-SYFP2-WPRE3-BGHpA
(sequence should be inserted into Plasmid backbone 2):
GCGGCCGCACGCGTCGCGTATA**AGCCTTGGGGGCAATCAAACTATTACATTGAGTCCTT
GGATTTGCTACAAATTACATTTTAAATGCAATCATTTTATAAAAGCTTCAACACTCACACT
TGGAAGCGTTACCCTGTTGAATATCACTGACTCACTAACTTGCATTGCCATGCTAACTTG**

FIG. 79 cont'd

CTTTCAGAGAGATCTCAGAACACATCATCTTCTGCTATTTCAATACATGCACATTAATTTC CTATCAACGTGTGCTGATCAGGAACTCTGTAATCTGGCACCGGTGTTTATTTTTATTCCTG TCTATTCCTGTTGGCTCACGAAAAGATTGTTTGAGCAAGTGTTTTATGGTGAGTTGTATCA TATGTACATTGATTTAATCTGCCCACATTCAGTTCTACAAGCGGAGCCAAAAAAATAGAG ACAAGCATAATTTTCATTCAACATGAGCCCCTCAATGCAAGCCAAGTACCTCATCTGGTG CTCAGCTAAAGCAACAGCAATCTGTTCCACCCTGGAGACACAACTGGCCACAGAAAACT TAGTGAAAAGAGGCAATGCTATGCACAGGACAAATGAGCTCAGAGGTAGGCGTGTACGG TGGGAGGCCTATATAAGCAGAGCTGGTTTAGTGAACCGTCAGATCGCCTGGGATCCAGA TCTTTCGAAGCTAGCGCTACCGGTCGCCACCATGGTGAGCAAGGGCGAGGAGCTGTTCAC CGGGGTGGTGCCCATCCTGGTCGAGCTGGACGGCGACGTAAACGGCCACAAGTTCAGCG TGTCCGGCGAGGGCGAGGGCGATGCCACCTACGGCAAGCTGACCCTGAAGCTGATCTGC ACCACCGGCAAGCTGCCCGTGCCCTGGCCCACCCTCGTGACCACCCTGGGCTACGGCGT GCAGTGCTTCGCCCGCTACCCCGACCACATGAAGCAGCACGACTTCTTCAAGTCCGCCAT GCCCGAAGGCTACGTCCAGGAGCGCACCATCTTCTTCAAGGACGACGGCAACTACAAGAC CCGCGCCGAGGTGAAGTTCGAGGGCGACACCCTGGTGAACCGCATCGAGCTGAAGGGCA TCGACTTCAAGGAGGACGGCAACATCCTGGGGCACAAGCTGGAGTACAACTACAACAGCC ACAACGTCTATATCACCGCCGACAAGCAGAAGAACGGCATCAAGGCCAACTTCAAGATCC GCCACAACATCGAGGACGGCGGCGTGCAGCTCGCCGACCACTACCAGCAGAACACCCCC ATCGGCGACGGCCCCGTGCTGCTGCCCGACAACCACTACCTGAGCTACCAGTCCAAGCTG AGCAAAGACCCCAACGAGAAGCGCGATCACATGGTCCTGCTGGAGTTCGTGACCGCCGC CGGGATCACTCTCGGCATGGACGAGCTGTACAAGTAAGTCGACGGCGCGCCGCGGCCGC GAATTCGATATCATAATCAACCTCTGGATTACAAAATTTGTGAAAGATTGACTGGTATTCTTA ACTATGTTGCTCCTTTTACGCTATGTGGATACGCTGCTTTAATGCCTTTGTATCATGCTATT GCTTCCCGTATGGCTTTCATTTTCTCCTCCTTGTATAAATCCTGGTTAGTTCTTGCCACGGC GGAACTCATCGCCGCCTGCCTTGCCCGCTGCTGGACAGGGGCTCGGCTGTTGGGCACTG ACAATTCCGTGGCTCGAGAGATCTTCGACTGTGCCTTCTAGTTGCCAGCCATCTGTTGTTT GCCCCTCCCCCGTGCCTTCCTTGACCCTGGAAGGTGCCACTCCCACTGTCCTTTCCTAATA AAATGAGGAAATTGCATCGCATTGTCTGAGTAGGTGTCATTCTATTCTGGGGGGTGGGGTG GGGCAGGACAGCAAGGGGGAGGATTGGGAAGACAATAGCAGGCATGCACGTGCGGACC GAGCGGCCGC (SEQ ID NO: 112)

Construct CN2137 nucleotide sequence: rAAV_eHGT_440h-minBglobin-SYFP2-WPRE3-BGHpA (sequence should be inserted into Plasmid backbone 2):
GCGGCCGCACGCGTAAGCCAATGACATTAGAGAAGTGTTCAAACAGTCAGCTAAATTCA CTGCACTTCTCAACCACAGAAATATTTTCAGGTGATTCTGTTTTTGAGAAAACGTGGGAA CCACAGGATCTACAACACTTCCAGGCAAAACTCAACAGCTCTAATAATAGTGACAGAAG TGAAAGCCAATTTGGATAAAATAAGACATTGACTCAAAGTCCTCTGAGAGATTTTTCAAA ACAAAGTTTACAAAGCTCCTTTTGCCTTTTGGGAAATCACATTCTTCTTTGCACCTTGACT CTTTTTCTGAATTTCTTTCTGTCTGGGAGGATCTCCTTACAGTGTTTCTTCTCCATCTGACA TCATGAAATGTGATACGAGCTCGGGCTGGGCATAAAAGTCAGGGCAGAGCCATCTATTGC TTACATTTGCTTCTGGGATCCAGATCTTTCGAAGCTAGCGCTACCGGTCGCCACCATGGTG AGCAAGGGCGAGGAGCTGTTCACCGGGGTGGTGCCCATCCTGGTCGAGCTGGACGGCGA CGTAAACGGCCACAAGTTCAGCGTGTCCGGCGAGGGCGAGGGCGATGCCACCTACGGCA AGCTGACCCTGAAGCTGATCTGCACCACCGGCAAGCTGCCCGTGCCCTGGCCCACCCTC GTGACCACCCTGGGCTACGGCGTGCAGTGCTTCGCCCGCTACCCCGACCACATGAAGCA GCACGACTTCTTCAAGTCCGCCATGCCCGAAGGCTACGTCCAGGAGCGCACCATCTTCTT CAAGGACGACGGCAACTACAAGACCCGCGCCGAGGTGAAGTTCGAGGGCGACACCCTGG TGAACCGCATCGAGCTGAAGGGCATCGACTTCAAGGAGGACGGCAACATCCTGGGGCAC

FIG. 79 cont'd

AAGCTGGAGTACAACTACAACAGCCACAACGTCTATATCACCGCCGACAAGCAGAAGAAC
GGCATCAAGGCCAACTTCAAGATCCGCCACAACATCGAGGACGGCGGCGTGCAGCTCGC
CGACCACTACCAGCAGAACACCCCCATCGGCGACGGCCCCGTGCTGCTGCCCGACAACC
ACTACCTGAGCTACCAGTCCAAGCTGAGCAAAGACCCCAACGAGAAGCGCGATCACATGG
TCCTGCTGGAGTTCGTGACCGCCGCCGGGATCACTCTCGGCATGGACGAGCTGTACAAGT
AAGTCGACGGCGCGCCGCGGCCGCGAATTCGATATCATAATCAACCTCTGGATTACAAAAT
TTGTGAAAGATTGACTGGTATTCTTAACTATGTTGCTCCTTTTACGCTATGTGGATACGCTG
CTTTAATGCCTTTGTATCATGCTATTGCTTCCCGTATGGCTTTCATTTTCTCCTCCTTGTATA
AATCCTGGTTAGTTCTTGCCACGGCGGAACTCATCGCCGCCTGCCTTGCCCGCTGCTGGA
CAGGGGCTCGGCTGTTGGGCACTGACAATTCCGTGGCTCGAGAGATCTTCGACTGTGCCT
TCTAGTTGCCAGCCATCTGTTGTTTGCCCCTCCCCCGTGCCTTCCTTGACCCTGGAAGGTG
CCACTCCCACTGTCCTTTCCTAATAAAATGAGGAAATTGCATCGCATTGTCTGAGTAGGTGT
CATTCTATTCTGGGGGGTGGGGTGGGGCAGGACAGCAAGGGGGAGGATTGGGAAGACAA
TAGCAGGCATGAGATCTCACGTGCGGACCGAGCGGCCGC (SEQ ID NO: 113)

Construct CN2139 nucleotide sequence: rAAV_eHGT_439m-minBglobin-SYFP2-WPRE3-BGHpA (sequence should be inserted into Plasmid backbone 2):
GCGGCCGCACGCGTAATTGCTGTCATTTACCTACGGTTGTCTCCAAATTTCTTCAACCAA
GTAGAGAAAAATGAGAGAGAAGGAAAGAAAAAAAGAGGTATGGGGAGAAGAGAAAGA
AGGCAACTTGTTAAAAATCTCAGTCAAACTTACATACTATATAGAACAGCATGGTGAATT
TAGGGCACATGGATATAAAATGGAAGTTTCTTATTCAGTAGCAGCAACTTGTGGGCACAG
GAGTTGGCAAAGATAAAAATGTCCAAAGTCACAAATACAATGTATAGTTAGTCATAGGTG
CTGTTATTTGCCTCAAAAAATAGACTTTTATTTTGCCTTTCTTTTCTTTAACCACACTCAAA
ATTAGAGAACAGAGACAAAACCCAGCAGGAAATAGCACAGAGAGCTCGGGCTGGGCAT
AAAAGTCAGGGCAGAGCCATCTATTGCTTACATTTGCTTCTGGGATCCAGATCTTTCGAAG
CTAGCGCTACCGGTCGCCACCATGGTGAGCAAGGGCGAGGAGCTGTTCACCGGGGTGGT
GCCCATCCTGGTCGAGCTGGACGGCGACGTAAACGGCCACAAGTTCAGCGTGTCCGGCG
AGGGCGAGGGCGATGCCACCTACGGCAAGCTGACCCTGAAGCTGATCTGCACCACCGGC
AAGCTGCCCGTGCCCTGGCCCACCCTCGTGACCACCCTGGGCTACGGCGTGCAGTGCTT
CGCCCGCTACCCCGACCACATGAAGCAGCACGACTTCTTCAAGTCCGCCATGCCCGAAGG
CTACGTCCAGGAGCGCACCATCTTCTTCAAGGACGACGGCAACTACAAGACCCGCGCCGA
GGTGAAGTTCGAGGGCGACACCCTGGTGAACCGCATCGAGCTGAAGGGCATCGACTTCAA
GGAGGACGGCAACATCCTGGGGCACAAGCTGGAGTACAACTACAACAGCCACAACGTCTA
TATCACCGCCGACAAGCAGAAGAACGGCATCAAGGCCAACTTCAAGATCCGCCACAACAT
CGAGGACGGCGGCGTGCAGCTCGCCGACCACTACCAGCAGAACACCCCCATCGGCGACG
GCCCCGTGCTGCTGCCCGACAACCACTACCTGAGCTACCAGTCCAAGCTGAGCAAAGACC
CCAACGAGAAGCGCGATCACATGGTCCTGCTGGAGTTCGTGACCGCCGCCGGGATCACT
CTCGGCATGGACGAGCTGTACAAGTAAGTCGACGGCGCGCCGCGGCCGCGAATTCGATA
TCATAATCAACCTCTGGATTACAAAATTTGTGAAAGATTGACTGGTATTCTTAACTATGTTGC
TCCTTTTACGCTATGTGGATACGCTGCTTTAATGCCTTTGTATCATGCTATTGCTTCCCGTA
TGGCTTTCATTTTCTCCTCCTTGTATAAATCCTGGTTAGTTCTTGCCACGGCGGAACTCATC
GCCGCCTGCCTTGCCCGCTGCTGGACAGGGGCTCGGCTGTTGGGCACTGACAATTCCGT
GGCTCGAGAGATCTTCGACTGTGCCTTCTAGTTGCCAGCCATCTGTTGTTTGCCCCTCCCC
CGTGCCTTCCTTGACCCTGGAAGGTGCCACTCCCACTGTCCTTTCCTAATAAAATGAGGAA
ATTGCATCGCATTGTCTGAGTAGGTGTCATTCTATTCTGGGGGGTGGGGTGGGGCAGGAC
AGCAAGGGGGAGGATTGGGAAGACAATAGCAGGCATGAGATCTCACGTGCGGACCGAGC
GGCCGC (SEQ ID NO: 114)

FIG. 79 cont'd

Myosin light chain kinase, Green fluorescent protein, Calmodulin chimera (Chain A) [synthetic construct], PDB: 3EKJ_A:
MRGSHHHHHHGMASMTGGQQMGRDLYDDDDKDLATMVDSSRRKWNKTGHAVRAIGRLSSL
ENVYIMADKQKNGIKANFKIRHNIEDGGVQLAYHYQQNTPIGDGPVLLPDNHYLSTQSKLSKDP
NEKRDHMVLLEFVTAAGITLGMDELYKGGTGGSMVSKGEELFTGVVPILVELDGDVNGHKFSV
SGEGEGDATYGKLTLKFICTTGKLPVPWPTLVTTLXVQCFSRYPDHMKQHDFFKSAMPEGYIQ
ERTIFFKDDGNYKTRAEVKFEGDTLVNRIELKGIDFKEDGNILGHKLEYNTRDQLTEEQIAEFKE
AFSLFDKDGDGGITTKQLGTVMRSLGQNPTEAELQDMINEVGADGNGTIDFPQFLTMMARKMK
DTDSEEEIREAFRVFGKDGNGYISAAQLRHVMTNLGEKLTDEEVDEMIREAGIDGDGQVNYEQ
FVQMMTAK (SEQ ID NO: 115)

Genetically-encoded green calcium indicator NTnC (chain A) [synthetic construct], PDB: 5MWC_A:
MVSKGEEDNMASLPATHELHIFGSINGVDFDMVGQGSGNPNVGYEELNLKSTKGDLQFSPWIL
VPHIXFHQYLPYPDGMSPFQAAMVDGSGYQVHRTVQFEDGASLTVNYRYTYEGSHIKGEAQV
KGTGFPADGPVMANSLTAMVPSEEELSECFRTFDKDGDGFIDREEFGGIIRLTGEQLTDEDPD
EIFGDSDTDKNGRIDFDEFLKMVENVQLSMADWCRSKMACPNDKTLISTLKWSYTTGNGKRYR
STARTTYTFAKPMAANYLKNQPMYVFRKTELKHSKTELNFKEWQKAFTDVMGMDELYK (SEQ ID NO: 116)

Calcium indicator TN-XXL [synthetic construct], GenBank: ACF93133.1:
MVSKGEELFTGVVPILVELDGDVNGHKFSVRGEGEGDATNGKLTLKFICTTGKLPVPWPTLVTT
LTWGVQCFSRYPDHMKQHDFFKSAMPEGYVQERTIFFKDDGNYKTRAEVKFEGDTLVNRIELK
GIDFKEDGNILGHKLEYNYISHNVYITADKQKNGIKAHFKIRHNIEDGSVQLADHYQQNTPIGDG
PVLLPDNHYLSTQSKLSKDPNEKRDHMVLLEFVTAARMLSEEELANCFRIFDKDANGFIDIEELG
EILRATGEHVTEEDIEDLMKDSDKNNDGRIDFDEFLKMMEGVQGTSEEELANCFRIFDKDANGF
IDIEELGEILRATGEHVTEEDIEDLMKDSDKNNDGRIDFDEFLKMMEGVQELMGGVQLADHYQQ
NTPIGDGPVLLPDNHYLSYQSKLSKDPNEKRDHMVLLEFVTAAGITLGMDELYKGGTGGSMVS
KGEELFTGVVPILVELDGDVNGHKFSVRGEGEGDATNGKLTLKFICTTGKLPVPWPTLVTTLGY
GLMCFARYPDHMKQHDFFKSAMPEGYVQERTIFFKDDGNYKTRAEVKFEGDTLVNRIELKGID
FKEDGNILGHKLEYNYNSHNVYIMADKQKNGIKANFKIRHNIED (SEQ ID NO: 117)

BRET-based auto-luminescent calcium indicator [synthetic construct], GenBank: ADF42668.1:
MVSKGEELFTGVVPILVELDGDVNGHKFSVSGEGEGDATYGKLTLKLICTTGKLPVPWPTLVTT
LGYGLQCFARYPDHMKQHDFFKSAMPEGYVQERTIFFKDDGNYKTRAEVKFEGDTLVNRIELK
GIDFKEDGNILGHKLEYNYNSHNVYITADKQKNGIKANFKIRHNIEDGGVQLADHYQQNTPIGDG
PVLLPDNHYLSYQSKLSKDPNEKRDHMVLLEFVTAAGITLGMDELYKRMHDQLTEEQIAEFKEA
FSLFDKDGDGTITTKELGTVMRSLGQNPTEAELQDMINEVDADGNGTIYFPEFLTMMARKMKD
TDSEEEIREAFRVFDKDGNGYISAAQLRHVMTNLGEKLTDEEVDEMIREADIDGDGQVNYEEFV
QMMTAKGGKRRWKKNFIAVSAANRFKKISSSGALELMTSKVYDPEQRKRMITGPQWWARCK
QMNVLDSFINYYDSEKHAENAVIFLHGNATSSYLWRHVVPHIEPVARCIIPDLIGMGKSGKSGN
GSYRLLDHYKYLTAWFELLNLPKKIIFVGHDWGAALAFHYAYEHQDRIKAIVHMESVVDVIESW
DEWPDIEEDIALIKSEEGEKMVLENNFFVETVLPSKIMRKLEPEEFAAYLEPFKEKGEVRRPTLS
WPREIPLVKGGKPDVVQIVRNYNAYLRASDDLPKLFIESDPGFFSNAIVEGAKKFPNTEFVKVK
GLHFLQEDAPDEMGKYIKSFVERVLKNEQ (SEQ ID NO: 118)

Calcium indicator protein OeNL(Ca2+)-18u [synthetic construct], GenBank: BBB18812.1:

FIG. 79 cont'd

MVSVIKPEMKMRYYMDGSVNGHEFTIEGEGTGRPYEGHQEMTLRVTMAEGGPMPFAFDLVS
HVFCYGHRVFTKYPEEIPDYFKQAFPEGLSWERSLEFEDGGSASVSAHISLRGNTFYHKSKFT
GVNFPADGPIMQNQSVDWEPSTEKITASDGVLKGDVTMYLKLEGGGNHKCQFKTTYKAAKEIL
EMPGDHYIGHRLVRKTEGNITEQVEDAVAHSGTLEDFVGDWRQTAGYNLDQVLEQGGVSSLF
QNLGVSVTPIQRIVLSGENGLKIDIHVIIPYEGPWMHDQLTEEQIAEFKEAFSLFDKDGDGTITTK
ELGTVMRSLGQNPTEAELQDMINEVDADGNGTIYFPDFLTMMARKMKDTDSEEEIREAFRVFD
KDGNGYISAADLRHVMTNLGEKLTDEEVDEMIREADIDGEGQVNYEEFVQMMTAKGGKRRWK
KNFIAVSAANRFKKISSSGALELLSGDQMGQIEKIFKVVYPVDDHHFKVILHYGTLVIDGVTPNMI
DYFGRPYEGIAVFDGKKITVTGTLWNGNKIIDERLINPDGSLLFRVTINGVTGWRLCERILA (SEQ
ID NO: 119)

GCaMP6m
ATGGGTTCTCATCATCATCATCATCATGGTATGGCTAGCATGACTGGTGGACAGCAAATGG
GTCGGGATCTGTACGACGATGACGATAAGGATCTCGCCACCATGGTCGACTCATCACGTC
GTAAGTGGAATAAGACAGGTCACGCAGTCAGAGCTATAGGTCGGCTGAGCTCACTCGAGA
ACGTCTATATCAAGGCCGACAAGCAGAAGAACGGCATCAAGGCGAACTTCAAGATCCGCC
ACAACATCGAGGACGGCGGCGTGCAGCTCGCCTACCACTACCAGCAGAACACCCCCATC
GGCGACGGCCCCGTGCTGCTGCCCGACAACCACTACCTGAGCGTGCAGTCCAAACTTTCG
AAAGACCCCAACGAGAAGCGCGATCACATGGTCCTGCTGGAGTTCGTGACCGCCGCCGG
GATCACTCTCGGCATGGACGAGCTGTACAAGGGCGGTACCGGAGGGAGCATGGTGAGCA
AGGGCGAGGAGCTGTTCACCGGGGTGGTGCCCATCCTGGTCGAGCTGGACGGCGACGTA
AACGGCCACAAGTTCAGCGTGTCCGGCGAGGGTGAGGGCGATGCCACCTACGGCAAGCT
GACCCTGAAGTTCATCTGCACCACCGGCAAGCTGCCCGTGCCCTGGCCCACCCTCGTGAC
CACCCTGACCTACGGCGTGCAGTGCTTCAGCCGCTACCCCGACCACATGAAGCAGCACGA
CTTCTTCAAGTCCGCCATGCCCGAAGGCTACATCCAGGAGCGCACCATCTTCTTCAAGGAC
GACGGCAACTACAAGACCCGCGCCGAGGTGAAGTTCGAGGGCGACACCCTGGTGAACCG
CATCGAGCTGAAGGGCATCGACTTCAAGGAGGACGGCAACATCCTGGGGCACAAGCTGG
AGTACAACCTGCCGGACCAACTGACTGAAGAGCAGATCGCAGAATTTAAAGAGGCTTTCTC
CCTATTTGACAAGGACGGGGATGGGACAATAACAACCAAGGAGCTGGGGACGGTGATGC
GGTCTCTGGGGCAGAACCCCACAGAAGCAGAGCTGCAGGACATGATCAATGAAGTAGATG
CCGACGGTGACGGCACAATCGACTTCCCTGAGTTCCTGACAATGATGGCAAGAAAAGGGA
GCTACAGGGACACGGAAGAAGAAATTAGAGAAGCGTTCGGTGTGTTTGATAAGGATGGCA
ATGGCTACATCAGTGCAGCAGAGCTTCGCCACGTGATGACAAACCTTGGAGAGAAGTTAA
CAGATGAAGAGGTTGATGAAATGATCAGGGAAGCAGACATCGATGGGGATGGTCAGGTAA
ACTACGAAGAGTTTGTACAAATGATGACAGCGAAGTGA (SEQ ID NO: 120)

GCaMP6s
ATGGGTTCTCATCATCATCATCATCATGGTATGGCTAGCATGACTGGTGGACAGCAAATGG
GTCGGGATCTGTACGACGATGACGATAAGGATCTCGCCACCATGGTCGACTCATCACGTC
GTAAGTGGAATAAGACAGGTCACGCAGTCAGAGCTATAGGTCGGCTGAGCTCACTCGAGA
ACGTCTATATCAAGGCCGACAAGCAGAAGAACGGCATCAAGGCGAACTTCCACATCCGCC
ACAACATCGAGGACGGCGGCGTGCAGCTCGCCTACCACTACCAGCAGAACACCCCCATC
GGCGACGGCCCCGTGCTGCTGCCCGACAACCACTACCTGAGCGTGCAGTCCAAACTTTCG
AAAGACCCCAACGAGAAGCGCGATCACATGGTCCTGCTGGAGTTCGTGACCGCCGCCGG
GATCACTCTCGGCATGGACGAGCTGTACAAGGGCGGTACCGGAGGGAGCATGGTGAGCA
AGGGCGAGGAGCTGTTCACCGGGGTGGTGCCCATCCTGGTCGAGCTGGACGGCGACGTA
AACGGCCACAAGTTCAGCGTGTCCGGCGAGGGTGAGGGCGATGCCACCTACGGCAAGCT
GACCCTGAAGTTCATCTGCACCACCGGCAAGCTGCCCGTGCCCTGGCCCACCCTCGTGAC

FIG. 79 cont'd

CACCCTGACCTACGGCGTGCAGTGCTTCAGCCGCTACCCCGACCACATGAAGCAGCACGA
CTTCTTCAAGTCCGCCATGCCCGAAGGCTACATCCAGGAGCGCACCATCTTCTTCAAGGAC
GACGGCAACTACAAGACCCGCGCCGAGGTGAAGTTCGAGGGCGACACCCTGGTGAACCG
CATCGAGCTGAAGGGCATCGACTTCAAGGAGGACGGCAACATCCTGGGGCACAAGCTGG
AGTACAACCTGCCGGACCAACTGACTGAAGAGCAGATCGCAGAATTTAAAGAGGCTTTCTC
CCTATTTGACAAGGACGGGGATGGGACAATAACAACCAAGGAGCTGGGGACGGTGATGC
GGTCTCTGGGGCAGAACCCCACAGAAGCAGAGCTGCAGGACATGATCAATGAAGTAGATG
CCGACGGTGACGGCACAATCGACTTCCCTGAGTTCCTGACAATGATGGCAAGAAAAATGA
AATACAGGGACACGGAAGAAGAAATTAGAGAAGCGTTCGGTGTGTTTGATAAGGATGGCA
ATGGCTACATCAGTGCAGCAGAGCTTCGCCACGTGATGACAAACCTTGGAGAGAAGTTAA
CAGATGAAGAGGTTGATGAAATGATCAGGGAAGCAGACATCGATGGGGATGGTCAGGTAA
ACTACGAAGAGTTTGTACAAATGATGACAGCGAAGTGA (SEQ ID NO: 121)

GCaMP6f
ATGGGTTCTCATCATCATCATCATCATGGTATGGCTAGCATGACTGGTGGACAGCAAATGG
GTCGGGATCTGTACGACGATGACGATAAGGATCTCGCCACCATGGTCGACTCATCACGTC
GTAAGTGGAATAAGACAGGTCACGCAGTCAGAGCTATAGGTCGGCTGAGCTCACTCGAGA
ACGTCTATATCAAGGCCGACAAGCAGAAGAACGGCATCAAGGCGAACTTCAAGATCCGCC
ACAACATCGAGGACGGCGGCGTGCAGCTCGCCTACCACTACCAGCAGAACACCCCCATC
GGCGACGGCCCCGTGCTGCTGCCCGACAACCACTACCTGAGCGTGCAGTCCAAACTTTCG
AAAGACCCCAACGAGAAGCGCGATCACATGGTCCTGCTGGAGTTCGTGACCGCCGCCGG
GATCACTCTCGGCATGGACGAGCTGTACAAGGGCGGTACCGGAGGGAGCATGGTGAGCA
AGGGCGAGGAGCTGTTCACCGGGGTGGTGCCCATCCTGGTCGAGCTGGACGGCGACGTA
AACGGCCACAAGTTCAGCGTGTCCGGCGAGGGTGAGGGCGATGCCACCTACGGCAAGCT
GACCCTGAAGTTCATCTGCACCACCGGCAAGCTGCCCGTGCCCTGGCCCACCCTCGTGAC
CACCCTGACCTACGGCGTGCAGTGCTTCAGCCGCTACCCCGACCACATGAAGCAGCACGA
CTTCTTCAAGTCCGCCATGCCCGAAGGCTACATCCAGGAGCGCACCATCTTCTTCAAGGAC
GACGGCAACTACAAGACCCGCGCCGAGGTGAAGTTCGAGGGCGACACCCTGGTGAACCG
CATCGAGCTGAAGGGCATCGACTTCAAGGAGGACGGCAACATCCTGGGGCACAAGCTGG
AGTACAACCTGCCGGACCAACTGACTGAAGAGCAGATCGCAGAATTTAAAGAGGAATTCTC
CCTATTTGACAAGGACGGGGATGGGACAATAACAACCAAGGAGCTGGGGACGGTGATGC
GGTCTCTGGGGCAGAACCCCACAGAAGCAGAGCTGCAGGACATGATCAATGAAGTAGATG
CCGACGGTGACGGCACAATCGACTTCCCTGAGTTCCTGACAATGATGGCAAGAAAAATGA
AATACAGGGACACGGAAGAAGAAATTAGAGAAGCGTTCGGTGTGTTTGATAAGGATGGCA
ATGGCTACATCAGTGCAGCAGAGCTTCGCCACGTGATGACAAACCTTGGAGAGAAGTTAA
CAGATGAAGAGGTTGATGAAATGATCAGGGAAGCAGACATCGATGGGGATGGTCAGGTAA
ACTACGAAGAGTTTGTACAAATGATGACAGCGAAGTGA (SEQ ID NO: 122)

**Channelopsin *1 [Mesostigma viride], UniProt*KB - F8UVI5:**
MSPPTSPTPDTGHDTPDTGHDTGGHGAVEICFAPCEEDCVTIRYFVENDFEGCIPGHFDQYSS
HGSLHDIVKAALYICMVISILQILFYGFQWWRKTCGWEVWFVACIETSIYIIAITSEADSPFTLYLT
NGQISPQLRYMEWLMTCPVILIALSNITGMAEEYNKRTMTLLTSDVCCIVLGMMSAASKPRLKGI
LYAVGWAFGAWTYWTALQVYRDAHKAVPKPLAWYVRAMGYVFFTSWLTFPGWFLLGPEGLE
VVTGTVSTLMHACSDLISKNLWGFMDWHLRVLVARHHRKLFKAEEEHALKKGQTLEPGMPRS
TSFVRGLGDDVEIDPSYELYRLKRQNHPEYFLSPAQTPRRGPSFDKRTSFEMDGGKNGMLQM
MPVTGMGMGMGMGMGGGKTVLFLDYTGGGYVSFFEQQLSNMGVNVTKCWSDDDMYNTAG
VANVKQLFHFAMIPNNALGGQMVMDLRGTGLLVVAYGPEPPMPGMGQDEFVPLQMPGVPYD

FIG. 79 cont'd

ESILHNLVMRHAITQGLGMNGMQGNMGQQQQMMGMQGNMNGMQGNMNGMQGNMNGMQ
GNMSGMQGNMNGMQGNSGMNQGWNNQGFTNTGAFGY (SEQ ID NO: 123)

Channelopsin 1 [Chlamydomonas yellowstonensis], GenBank: AER58217.1
MDTLAWVARELLSSGHGTDTATDSGHGTDTSGGHDSSHDAVAHNVTLLIAPPHAGGHAGPTD
TSQQITGIDGWIAIPAGDCYCAGWYVSHGSSFEATFAHVCQWSIFAVCVLSLLWYAYQYWKAT
CGWEEVYVCCIELVFICFELYHEFDSPCSLYLSTSNVVNWLRYSEWLLCCPVILIHLSNVTGLSD
DYGRRTMGLLVSDIATIVFGVTAAMLVNWPKIIFYLIGFTMCCYTFFLAAKVLIESFHQVPKGICR
HLVKAMAITYFVGWSFFPLIFLFGQSGFKKISPYADVIASSFGDLISKNAFGMLGHFLRVKIHEHIL
KHGDIRKTTHLRIAGEEKEVETFVEEEDEDTAKHSTKELANRGSFIVMRDKMKEQGIDVRASLD
MDEDEEARTGKGKGAGATSLVPGRVILAVPDISMVDFFHDHFAHLGASIELVPALGVENTLLLV
QQAMQLGGLDFVLVHPEFLRDRSQNGLVSRLKMTGHGVCAFGWVPSGPMREIIESAGVDGW
LDGPSFGTGIDQEQLIELIGYMQAKRKFGMRFGGGGASKAGYSSDGGFGGKGMLEMQPSMS
QGSGVPLLQQNNSMMRAPPSPMGNMANNGMMNPMMSMNNPMMGGGAVMMTSMGSMQQ
AANPLYGAPPSPLSSQPGAGMYGAPAQPQMGSQGSMHGSMYGGSQQQHQQPQQAAAAPA
AADGGSEAEMLKQLMSEINRLKAELGES (SEQ ID NO: 124)

Channelrhodopsin-2 [Volvox carteri f. nagariensis], UniProtKB - B4Y105:
MDHPVARSLIGSSYTNLNNGSIVIPSDACFCMKWLKSKGSPVALKMANALQWAAFALSVIILIYY
AYATWRTTCGWEEVYVCCVELTKVVIEFFHEFDEPGMLYLANGNRVLWLRYGEWLLTCPVILI
HLSNLTGLKDDYNKRTMRLLVSDVGTIVWGATAAMSTGYIKVIFFLLGCMYGANTFFHAAKVYIE
SYHTVPKGLCRQLVRAMAWLFFVSWGMFPVLFLLGPEGFGHLSVYGSTIGHTIIDLLSKNCWG
LLGHFLRLKIHEHILLYGDIRKVQKIRVAGEELEVETLMTEEAPDTVKKSTAQYANRESFLTMRD
KLKEKGFEVRASLDNSGIDAVINHNNNYNNALANAAAAVGKPGMELSKLDHVAANAAGMGGIA
DHVATTSGAISPGRVILAVPDISMVDYFREQFAQLPVQYEVVPALGADNAVQLVVQAAGLGGC
DFVLLHPEFLRDKSSTSLPARLRSIGQRVAAFGWSPVGPVRDLIESAGLDGWLEGPSFGLGISL
PNLASLVLRMQHARKMAAMLGGMGGMLGSNLMSGSGGVGLMGAGSPGGGGGAMGVGMTG
MGMVGTNAMGRGAVGNSVANASMGGGSAGMGMGMMGMVGAGVGGQQQMGANGMGPTS
FQLGSNPLYNTAPSPLSSQPGGDASAAAAAAAAAAATGAASNSMNAMQAGGSVRNSGILAGG
LGSMMGPPGAPAAPTAAATAAPAVTMGAPGGGGAAASEAEMLQQLMAEINRLKSELGE (SEQ
ID NO: 125)

Channel rhodopsin 2 [synthetic construct], GenBank: ABO64386.1
MDYGGALSAVGRELLFVTNPVVVNGSVLVPEDQCYCAGWIESRGTNGAQTASNVLQWLAAGF
SILLLMFYAYQTWKSTCGWEEIYVCAIEMVKVILEFFFEFKNPSMLYLATGHRVQWLRYAEWLL
TCPVILIHLSNLTGLSNDYSRRTMGLLVSDIGTIVWGATSAMATGYVKVIFFCLGLCYGANTFFH
AAKAYIEGYHTVPKGRCRQVVTGMAWLFFVSWGMFPILFILGPEGFGVLSVYGSTVGHTIIDLM
SKNCWGLLGHYLRVLIHEHILIHGDIRKTTKLNIGGTEIEVETLVEDEAEAGAVP (SEQ ID NO:
126)

CRISPR-associated protein (Cas) [Streptococcus pyogenes], GenBank: AKG27598.1:
MLEHKIDFMVTLEVKEANANGDPLNGNMPRTDAKGYGVMSDVSIKRKIRNRLQDMGKSIFVQA
NERIEDDFRSLEKRFSQHFTAKTPDKEIEEKANALWFDVRAFGQVFTYLKKSIGVRGPVSISMA
KSLEPIVISSLQITRSTNGMEAKNNSGRSSDTMGTKHFVDYGVYVLKGSINAYFAEKTGFSQED
AEAIKEVLVSLFENDASSARPEGSMRVCEVFWFTHSSKLGNVSSARVFDLLEYHQSIEEKSTYD
AYQIHLNQEKLAKYEAKGLTLEILEGL (SEQ ID NO: 127)

Cas9 [synthetic construct], GenBank: AST09977.1:

FIG. 79 cont'd

MDKKYSIGLDIGTNSVGWAVITDEYKVPSKKFKVLGNTDRHSIKKNLIGALLFDSGETAEATRLK
RTARRRYTRRKNRICYLQEIFSNEMAKVDDSFFHRLEESFLVEEDKKHERHPIFGNIVDEVAYH
EKYPTIYHLRKKLVDSTDKADLRLIYLALAHMIKFRGHFLIEGDLNPDNSDVDKLFIQLVQTYNQL
FEENPINASGVDAKAILSARLSKSRRLENLIAQLPGEKKNGLFGNLIALSLGLTPNFKSNFDLAED
AKLQLSKDTYDDDLDNLLAQIGDQYADLFLAAKNLSDAILLSDILRVNTEITKAPLSASMIKRYDE
HHQDLTLLKALVRQQLPEKYKEIFFDQSKNGYAGYIDGGASQEEFYKFIKPILEKMDGTEELLVK
LNREDLLRKQRTFDNGSIPHQIHLGELHAILRRQEDFYPFLKDNREKIEKILTFRIPYYVGPLARG
NSRFAWMTRKSEETITPWNFEEVVDKGASAQSFIERMTNFDKNLPNEKVLPKHSLLYEYFTVY
NELTKVKYVTEGMRKPAFLSGEQKKAIVDLLFKTNRKVTVKQLKEDYFKKIECFDSVEISGVEDR
FNASLGTYHDLLKIIKDKDFLDNEENEDILEDIVLTLTLFEDREMIEERLKTYAHLFDDKVMKQLK
RRRYTGWGRLSRKLINGIRDKQSGKTILDFLKSDGFANRNFMQLIHDDSLTFKEDIQKAQVSGQ
GDSLHEHIANLAGSPAIKKGILQTVKVVDELVKVMGRHKPENIVIEMARENQTTQKGQKNSRER
MKRIEEGIKELGSQILKEHPVENTQLQNEKLYLYYLQNGRDMYVDQELDINRLSDYDVDHIVPQ
SFLKDDSIDNKVLTRSDKNRGKSDNVPSEEVVKKMKNYWRQLLNAKLITQRKFDNLTKAERGG
LSELDKAGFIKRQLVETRQITKHVAQILDSRMNTKYDENDKLIREVKVITLKSKLVSDFRKDFQFY
KVREINNYHHAHDAYLNAVVGTALIKKYPKLESEFVYGDYKVYDVRKMIAKSEQEIGKATAKYFF
YSNIMNFFKTEITLANGEIRKRPLIETNGETGEIVWDKGRDFATVRKVLSMPQVNIVKKTEVQTG
GFSKESILPKRNSDKLIARKKDWDPKKYGGFDSPTVAYSVLVVAKVEKGKSKKLKSVKELLGITI
MERSSFEKNPIDFLEAKGYKEVKKDLIIKLPKYSLFELENGRKRMLASAGELQKGNELALPSKYV
NFLYLASHYEKLKGSPEDNEQKQLFVEQHKHYLDEIIEQISEFSKRVILADANLDKVLSAYNKHR
DKPIREQAENIIHLFTLTNLGAPAAFKYFDTTIDRKRYTSTKEVLDATLIHQSITGLYETRIDLSQLG
GD (SEQ ID NO: 128)

CRISPR-associated endonuclease Cpf1 [Acidaminococcus sp. BV3L6], UniProtKB/Swiss-Prot: U2UMQ6.1:
MTQFEGFTNLYQVSKTLRFELIPQGKTLKHIQEQGFIEEDKARNDHYKELKPIIDRIYKTYADQCL
QLVQLDWENLSAAIDSYRKEKTEETRNALIEEQATYRNAIHDYFIGRTDNLTDAINKRHAEIYKGL
FKAELFNGKVLKQLGTVTTTEHENALLRSFDKFTTYFSGFYENRKNVFSAEDISTAIPHRIVQDN
FPKFKENCHIFTRLITAVPSLREHFENVKKAIGIFVSTSIEEVFSFPFYNQLLTQTQIDLYNQLLGGI
SREAGTEKIKGLNEVLNLAIQKNDETAHIIASLPHRFIPLFKQILSDRNTLSFILEEFKSDEEVIQSF
CKYKTLLRNENVLETAEALFNELNSIDLTHIFISHKKLETISSALCDHWDTLRNALYERRISELTGK
ITKSAKEKVQRSLKHEDINLQEIISAAGKELSEAFKQKTSEILSHAHAALDQPLPTTLKKQEEKEIL
KSQLDSLLGLYHLLDWFAVDESNEVDPEFSARLTGIKLEMEPSLSFYNKARNYATKKPYSVEKF
KLNFQMPTLASGWDVNKEKNNGAILFVKNGLYYLGIMPKQKGRYKALSFEPTEKTSEGFDKMY
YDYFPDAAKMIPKCSTQLKAVTAHFQTHTTPILLSNNFIEPLEITKEIYDLNNPEKEPKKFQTAYA
KKTGDQKGYREALCKWIDFTRDFLSKYTKTTSIDLSSLRPSSQYKDLGEYYAELNPLLYHISFQR
IAEKEIMDAVETGKLYLFQIYNKDFAKGHHGKPNLHTLYWTGLFSPENLAKTSIKLNGQAELFYR
PKSRMKRMAHRLGEKMLNKKLKDQKTPIPDTLYQELYDYVNHRLSHDLSDEARALLPNVITKEV
SHEIIKDRRFTSDKFFFHVPITLNYQAANSPSKFNQRVNAYLKEHPETPIIGIDRGERNLIYITVIDS
TGKILEQRSLNTIQQFDYQKKLDNREKERVAARQAWSVVGTIKDLKQGYLSQVIHEIVDLMIHYQ
AVVVLENLNFGFKSKRTGIAEKAVYQQFEKMLIDKLNCLVLKDYPAEKVGGVLNPYQLTDQFTS
FAKMGTQSGFLFYVPAPYTSKIDPLTGFVDPFVWKTIKNHESRKHFLEGFDFLHYDVKTGDFIL
HFKMNRNLSFQRGLPGFMPAWDIVFEKNETQFDAKGTPFIAGKRIVPVIENHRFTGRYRDLYPA
NELIALLEEKGIVFRDGSNILPKLLENDDSHAIDTMVALIRSVLQMRNSNAATGEDYINSPVRDLN
GVCFDSRFQNPEWPMDADANGAYHIALKGQLLLNHLKESKDLKLQNGISNQDWLAYIQELRN
(SEQ ID NO: 129)

Ribonuclease 4 or Ribonuclease L [Homo sapiens], UniProtKB/Swiss-Prot: Q05823.2:

FIG. 79 cont'd

MESRDHNNPQEGPTSSSGRRAAVEDNHLLIKAVQNEDVDLVQQLLEGGANVNFQEEEGGWT
PLHNAVQMSREDIVELLLRHGADPVLRKKNGATPFILAAIAGSVKLLKLFLSKGADVNECDFYGF
TAFMEAAVYGKVKALKFLYKRGANVNLRRKTKEDQERLRKGGATALMDAAEKGHVEVLKILLD
EMGADVNACDNMGRNALIHALLSSDDSDVEAITHLLLDHGADVNVRGERGKTPLILAVEKKHLG
LVQRLLEQEHIEINDTDSDGKTALLLAVELKLKKIAELLCKRGASTDCGDLVMTARRNYDHSLVK
VLLSHGAKEDFHPPAEDWKPQSSHWGAALKDLHRIYRPMIGKLKFFIDEKYKIADTSEGGIYLG
FYEKQEVAVKTFCEGSPRAQREVSCLQSSRENSHLVTFYGSESHRGHLFVCVTLCEQTLEACL
DVHRGEDVENEEDEFARNVLSSIFKAVQELHLSCGYTHQDLQPQNILIDSKKAAHLADFDKSIK
WAGDPQEVKRDLEDLGRLVLYVVKKGSISFEDLKAQSNEEVVQLSPDEETKDLIHRLFHPGEH
VRDCLSDLLGHPFFWTWESRYRTLRNVGNESDIKTRKSESEILRLLQPGPSEHSKSFDKWTTKI
NECVMKKMNKFYEKRGNFYQNTVGDLLKFIRNLGEHIDEEKHKKMKLKIGDPSLYFQKTFPDLV
IYVYTKLQNTEYRKHFPQTHSPNKPQCDGAGGASGLASPGC (SEQ ID NO: 130)

Deoxyribonuclease II beta [Homo sapiens], GenBank: AAF76893.1:
MMARLLRTSFALLFLGLFGVLGAATISCRNEEGKAVDWFTFYKLPKRQNKESGETGLEYLYLDS
TTRSWRKSEQLMNDTKSVLGRTLQQLYEAYASKSNNTAYLIYNDGVPKPVNYSRKYGHTKGLL
LWNRVQGFWLIHSIPQFPPIPEEGYDYPPTGRRNGQSGICITFKYNQYEAIDSQLLVCNPNVYS
CSIPATFHQELIHMPQLCTRASSSEIPGRLLTTLQSAQGQKFLHFAKSDSFLDDIFAAWMAQRLK
THLLTETWQRKRQELPSNCSLPYHVYNIKAIKLSRHSYFSSYQDHAKWCISQKGTKNRWTCIG
DLNRSPHQAFRSGGFICTQNWQIYQAFQGLVLYYESCK (SEQ ID NO: 131)

Sodium channel protein type 1 subunit alpha [Homo sapiens], UniProtKB - P35498
MEQTVLVPPGPDSFNFFTRESLAAIERRIAEEKAKNPKPDKKDDDENGPKPNSDLEAGKNLPFI
YGDIPPEMVSEPLEDLDPYYINKKTFIVLNKGKAIFRFSATSALYILTPFNPLRKIAIKILVHSLFSML
IMCTILTNCVFMTMSNPPDWTKNVEYTFTGIYTFESLIKIIARGFCLEDFTFLRDPWNWLDFTVIT
FAYVTEFVDLGNVSALRTFRVLRALKTISVIPGLKTIVGALIQSVKKLSDVMILTVFCLSVFALIGLQ
LFMGNLRNKCIQWPPTNASLEEHSIEKNITVNYNGTLINETVFEFDWKSYIQDSRYHYFLEGFLD
ALLCGNSSDAGQCPEGYMCVKAGRNPNYGYTSFDTFSWAFLSLFRLMTQDFWENLYQLTLRA
AGKTYMIFFVLVIFLGSFYLINLILAVVAMAYEEQNQATLEEAEQKEAEFQQMIEQLKKQQEAAQ
QAATATASEHSREPSAAGRLSDSSSEASKLSSKSAKERRNRRKKRKQKEQSGGEEKDEDEFQ
KSESEDSIRRKGFRFSIEGNRLTYEKRYSSPHQSLLSIRGSLFSPRRNSRTSLFSFRGRAKDVG
SENDFADDEHSTFEDNESRRDSLFVPRRHGERRNSNLSQTSRSSRMLAVFPANGKMHSTVD
CNGVVSLVGGPSVPTSPVGQLLPEVIIDKPATDDNGTTTETEMRKRRSSSFHVSMDFLEDPSQ
RQRAMSIASILTNTVEELEESRQKCPPCWYKFSNIFLIWDCSPYWLKVKHVVNLVVMDPFVDLA
ITICIVLNTLFMAMEHYPMTDHFNNVLTVGNLVFTGIFTAEMFLKIIAMDPYYYFQEGWNIFDGFIV
TLSLVELGLANVEGLSVLRSFRLLRVFKLAKSWPTLNMLIKIIGNSVGALGNLTLVLAIIVFIFAVVG
MQLFGKSYKDCVCKIASDCQLPRWHMNDFFHSFLIVFRVLCGEWIETMWDCMEVAGQAMCLT
VFMMVMVIGNLVVLNLFLALLLSSFSADNLAATDDDNEMNNLQIAVDRMHKGVAYVKRKIYEFI
QQSFIRKQKILDEIKPLDDLNNKKDSCMSNHTAEIGKDLDYLKDVNGTTSGIGTGSSVEKYIIDES
DYMSFINNPSLTVTVPIAVGESDFENLNTEDFSSESDLEESKEKLNESSSSSEGSTVDIGAPVEE
QPVVEPEETLEPEACFTEGCVQRFKCCQINVEEGRGKQWWNLRRTCFRIVEHNWFETFIVFMI
LLSSGALAFEDIYIDQRKTIKTMLEYADKVFTYIFILEMLLKWVAYGYQTYFTNAWCWLDFLIVDV
SLVSLTANALGYSELGAIKSLRTLRALRPLRALSRFEGMRVVVNALLGAIPSIMNVLLVCLIFWLIF
SIMGVNLFAGKFYHCINTTTGDRFDIEDVNNHTDCLKLIERNETARWKNVKVNFDNVGFGYLSL
LQVATFKGWMDIMYAAVDSRNVELQPKYEESLYMYLYFVIFIIFGSFFTLNLFIGVIIDNFNQQKK
KFGGQDIFMTEEQKKYYNAMKKLGSKKPQKPIPRPGNKFQGMVFDFVTRQVFDISIMILICLNM
VTMMVETDDQSEYVTTILSRINLVFIVLFTGECVLKLISLRHYYFTIGWNIFDFVVVILSIVGMFLAE
LIEKYFVSPTLFRVIRLARIGRILRLIKGAKGIRTLLFALMMSLPALFNIGLLLFLVMFIYAIFGMSNF

FIG. 79 cont'd

AYVKREVGIDDMFNFETFGNSMICLFQITTSAGWDGLLAPILNSKPPDCDPNKVNPGSSVKGDC
GNPSVGIFFFVSYIIISFLVVVNMYIAVILENFSVATEESAEPLSEDDFEMFYEVWEKFDPDATQF
MEFEKLSQFAAALEPPLNLPQPNKLQLIAMDLPMVSGDRIHCLDILFAFTKRVLGESGEMDALRI
QMEERFMASNPSKVSYQPITTTLKRKQEEVSAVIIQRAYRRHLLKRTVKQASFTYNKNKIKGGA
NLLIKEDMIIDRINENSITEKTDLTMSTAACPPSYDRVTKPIVEKHEQEGKDEKAKGK (SEQ ID NO: 132)

Potassium voltage-gated channel subfamily KQT member 2 [Homo sapiens], UniProtKB - O43526

MVQKSRNGGVYPGPSGEKKLKVGFVGLDPGAPDSTRDGALLIAGSEAPKRGSILSKPRAGGA
GAGKPPKRNAFYRKLQNFLYNVLERPRGWAFIYHAYVFLLVFSCLVLSVFSTIKEYEKSSEGAL
YILEIVTIVVFGVEYFVRIWAAGCCCRYRGWRGRLKFARKPFCVIDIMVLIASIAVLAAGSQGNVF
ATSALRSLRFLQILRMIRMDRRGGTWKLLGSVVYAHSKELVTAWYIGFLCLILASFLVYLAEKGE
NDHFDTYADALWWGLITLTTIGYGDKYPQTWNGRLLAATFTLIGVSFFALPAGILGSGFALKVQE
QHRQKHFEKRRNPAAGLIQSAWRFYATNLSRTDLHSTWQYYERTVTVPMYSSQTQTYGASRL
IPPLNQLELLRNLKSKSGLAFRKDPPPEPSPSKGSPCRGPLCGCCPGRSSQKVSLKDRVFSSP
RGVAAKGKGSPQAQTVRRSPSADQSLEDSPSKVPKSWSFGDRSRARQAFRIKGAASRQNSE
EASLPGEDIVDDKSCPCEFVTEDLTPGLKVSIRAVCVMRFLVSKRKFKESLRPYDVMDVIEQYS
AGHLDMLSRIKSLQSRVDQIVGRGPAITDKDRTKGPAEAELPEDPSMMGRLGKVEKQVLSMEK
KLDFLVNIYMQRMGIPPTETEAYFGAKEPEPAPPYHSPEDSREHVDRHGCIVKIVRSSSSTGQK
NFSAPPAAPPVQCPPSTSWQPQSHPRQGHGTSPVGDHGSLVRIPPPPAHERSLSAYGGGNR
ASMEFLRQEDTPGCRPPEGNLRDSDTSISIPSVDHEELERSFSGFSISQSKENLDALNSCYAAV
APCAKVRPYIAEGESDTDSDLCTPCGPPPRSATGEGPFGDVGWAGPRK (SEQ ID NO: 133)

Voltage-dependent L-type calcium channel subunit alpha-1C [Homo sapiens], UniProtKB - Q13936

MVNENTRMYIPEENHQGSNYGSPRPAHANMNANAAAGLAPEHIPTPGAALSWQAAIDAARQA
KLMGSAGNATISTVSSTQRKRQQYGKPKKQGSTTATRPPRALLCLTLKNPIRRACISIVEWKPF
EIIILLTIFANCVALAIYIPFPEDDSNATNSNLERVEYLFLIIFTVEAFLKVIAYGLLFHPNAYLRNGW
NLLDFIIVVVGLFSAILEQATKADGANALGGKGAGFDVKALRAFRVLRPLRLVSGVPSLQVVLNSI
IKAMVPLLHIALLVLFVIIIYAIIGLELFMGKMHKTCYNQEGIADVPAEDDPSPCALETGHGRQCQN
GTVCKPGWDGPKHGITNFDNFAFAMLTVFQCITMEGWTDVLYWVNDAVGRDWPWIYFVTLIII
GSFFVLNLVLGVLSGEFSKEREKAKARGDFQKLREKQQLEEDLKGYLDWITQAEDIDPENEDE
GMDEEKPRNMSMPTSETESVNTENVAGGDIEGENCGARLAHRISKSKFSRYWRRWNRFCRR
KCRAAVKSNVFYWLVIFLVFLNTLTIASEHYNQPNWLTEVQDTANKALLALFTAEMLLKMYSLGL
QAYFVSLFNRFDCFVVCGGILETILVETKIMSPLGISVLRCVRLLRIFKITRYWNSLSNLVASLLNS
VRSIASLLLLLFLFIIIFSLLGMQLFGGKFNFDEMQTRRSTFDNFPQSLLTVFQILTGEDWNSVMY
DGIMAYGGPSFPGMLVCIYFIILFICGNYILLNVFLAIAVDNLADAESLTSAQKEEEEEKERKKLAR
TASPEKKQELVEKPAVGESKEEKIELKSITADGESPPATKINMDDLQPNENEDKSPYPNPETTG
EEDEEEPEMPVGPRPRPLSELHLKEKAVPMPEASAFFIFSSNNRFRLQCHRIVNDTIFTNLILFFI
LLSSISLAAEDPVQHTSFRNHILFYFDIVFTTIFTIEIALKILGNADYVFTSIFTLEIILKMTAYGAFLH
KGSFCRNYFNILDLLVVSVSLISFGIQSSAINVVKILRVLRVLRPLRAINRAKGLKHVVQCVFVAIR
TIGNIVIVTTLLQFMFACIGVQLFKGKLYTCSDSSKQTEAECKGNYITYKDGEVDHPIIQPRSWEN
SKFDFDNVLAAMMALFTVSTFEGWPELLYRSIDSHTEDKGPIYNYRVEISIFFIIYIIIIAFFMMNIFV
GFVIVTFQEQGEQEYKNCELDKNQRQCVEYALKARPLRRYIPKNQHQYKVWYVVNSTYFEYL
MFVLILLNTICLAMQHYGQSCLFKIAMNILNMLFTGLFTVEMILKLIAFKPKGYFSDPWNVFDFLIV
IGSIIDVILSETNHYFCDAWNTFDALIVVGSIVDIAITEVNPAEHTQCSPSMNAEENSRISITFFRLF
RVMRLVKLLSRGEGIRTLLWTFIKSFQALPYVALLIVMLFFIYAVIGMQVFGKIALNDTTEINRNNN

FIG. 79 cont'd

FQTFPQAVLLLFRCATGEAWQDIMLACMPGKKCAPESEPSNSTEGETPCGSSFAVFYFISFYM
LCAFLIINLFVAVIMDNFDYLTRDWSILGPHHLDEFKRIWAEYDPEAKGRIKHLDVVTLLRRIQPPL
GFGKLCPHRVACKRLVSMNMPLNSDGTVMFNATLFALVRTALRIKTEGNLEQANEELRAIIKKI
WKRTSMKLLDQVVPPAGDDEVTVGKFYATFLIQEYFRKFKKRKEQGLVGKPSQRNALSLQAGL
RTLHDIGPEIRRAISGDLTAEEELDKAMKEAVSAASEDDIFRRAGGLFGNHVSYYQSDGRSAFP
QTFTTQRPLHINKAGSSQGDTESPSHEKLVDSTFTPSSYSSTGSNANINNANNTALGRLPRPA
GYPSTVSTVEGHGPPLSPAIRVQEVAWKLSSNRERHVPMCEDLELRRDSGSAGTQAHCLLLR
KANPSRCHSRESQAAMAGQEETSQDETYEVKMNHDTEACSEPSLLSTEMLSYQDDENRQLTL
PEEDKRDIRQSPKRGFLRSASLGRRASFHLECLKRQKDRGGDISQKTVLPLHLVHHQALAVAG
LSPLLQRSHSPASFPRPFATPPATPGSRGWPPQPVPTLRLEGVESSEKLNSSFPSIHCGSWAE
TTPGGGGSSAARRVRPVSLMVPSQAGAPGRQFHGSASSLVEAVLISEGLGQFAQDPKFIEVTT
QELADACDMTIEEMESAADNILSGGAPQSPNGALLPFVNCRDAGQDRAGGEEDAGCVRARGR
PSEEELQDSRVYVSSL (SEQ ID NO: 134)

Lactase [Homo sapiens], GenBank: EAX11622.1:
MELSWHVVFIALLSFSCWGSDWESDRNFISTAGPLTNDLLHNLSGLLGDQSSNFVAGDKDMYV
CHQPLPTFLPEYFSSLHASQITHYKVFLSWAQLLPAGSTQNPDEKTVQCYRRLLKALKTARLQP
MVILHHQTLPASTLRRTEAFADLFADYATFAFHSFGDLVGIWFTFSDLEEVIKELPHQESRASQL
QTLSDAHRKAYEIYHESYAFQGGKLSVVLRAEDIPELLLEPPISALAQDTVDFLSLDLSYECQNE
ASLRQKLSKLQTIEPKVKVFIFNLKLPDCPSTMKNPASLLFSLFEAINKDQVLTIGFDINEFLSCSS
SSKKSMSCSLTGSLALQPDQQQDHETTDSSPASAYQRVWEAFANQSRAERDAFLQDTFPEGF
LWGASTGAFNVEGGWAEGGRGVSIWDPRRPLNTTEGQATLEVASDSYHKVASDVALLCGLR
AQVYKFSISWSRIFPMGHGSSPSLPGVAYYNKLIDRLQDAGIEPMATLFHWDLPQALQDHGGW
QNESVVDAFLDYAAFCFSTFGDRVKLWVTFHEPWVMSYAGYGTGQHPPGISDPGVASFKVAH
LVLKAHARTWHHYNSHHRPQQQGHVGIVLNSDWAEPLSPERPEDLRASERFLHFMLGWFAH
PVFVDGDYPATLRTQIQQMNRQCSHPVAQLPEFTEAEKQLLKGSADFLGLSHYTSRLISNAPQ
NTCIPSYDTIGGFSQHVNHVWPQTSSSWIRVVPWGIRRLLQFVSLEYTRGKVPIYLAGNGMPIG
ESENLFDDSLRVDYFNQYINEVLKAIKEDSVDVRSYIARSLIDGFEGPSGYSQRFGLHHVNFSD
SSKSRTPRKSAYFFTSIIEKNGFLTKGAKRLLPPNTVNLPSKVRAFTFPSEVPSKAKVVWEKFSS
QPKFERDLFYHGTFRDDFLWGVSSSAYQIEGAWDADGKGPSIWDNFTHTPGSNVKDNATGDI
ACDSYHQLDADLNMLRALKVKAYRFSISWSRIFPTGRNSSINSHGVDYYNRLINGLVASNIFPM
VTLFHWDLPQALQDIGGWENPALIDLFDSYADFCFQTFGDRVKFWMTFNEPMYLAWLGYGSG
EFPPGVKDPGWAPYRIAHAVIKAHARVYHTYDEKYRQEQKGVISLSLSTHWAEPKSPGVPRDV
EAADRMLQFSLGWFAHPIFRNGDYPDTMKWKVGNRSELQHLATSRLPSFTEEEKRFIRATADV
FCLNTYYSRIVQHKTPRLNPPSYEDDQEMAEEEDPSWPSTAMNRAAPWGTRRLLNWIKEEYG
DIPIYITENGVGLTNPNTEDTDRIFYHKTYINEALKAYRLDGIDLRGYVAWSLMDNFEWLNGYTV
KFGLYHVDFNNTNRPRTARASARYYTEVITNNGMPLAREDEFLYGRFPEGFIWSAASAAYQIE
GAWRADGKGLSIWDTFSHTPLRVENDAIGDVACDSYHKIAEDLVTLQNLGVSHYRFSISWSRIL
PDGTTRYINEAGLNYYVRLIDTLLAASIQPQVTIYHWDLPQTLQDVGGWENETIVQRFKEYADVL
FQRLGDKVKFWITLNEPFVIAYQGYGYGTAAPGVSNRPGTAPYIVGHNLIKAHAEAWHLYNDVY
RASQGGVISITISSDWAEPRDPSNQEDVEAARRYVQFMGGWFAHPIFKNGDYNEVMKTRIRDR
SLAAGLNKSRLPEFTESEKRRINGTYDFFGFNHYTTVLAYNLNYATAISSFDADRGVASIADRS
WPDSGSFWLKMTPFGFRRILNWLKEEYNDPPIYVTENGVSQREETDLNDTARIYYLRTYINEAL
KAVQDKVDLRGYTVWSAMDNFEWATGFSERFGLHFVNYSDPSLPRIPKASAKFYASVVRCNG
FPDPATGPHACLHQPDAGPTISPVRQEEVQFLGLMLGTTEAQTALYVLFSLVLLGVCGLAFLSY
KYCKRSKQGKTQRSQQELSPVSSF (SEQ ID NO: 135)

Lipase [Homo sapiens], GenBank: AAA60129.1:

FIG. 79 cont'd

MLPLWTLSLLLGAVAGKEVCYERLGCFSDDSPWSGITERPLHILPWSPKDVNTRFLLYTNENPN
NFQEVAADSSSISGSNFKTNRKTRFIIHGFIDKGEENWLANVCKNLFKVESVNCICVDWKGGSR
TGYTQASQNIRIVGAEVAYFVEFLQSAFGYSPSNVHVIGHSLGAHAAGEAGRRTNGTIGRITGL
DPAEPCFQGTPELVRLDPSDAKFVDVIHTDGAPIVPNLGFGMSQVVGHLDFFPNGGVEMPGC
KKNILSQIVDIDGIWEGTRDFAACNHLRSYKYYTDSIVNPDGFAGFPCASYNVFTANKCFPCPS
GGCPQMGHYADRYPGKTNDVGQKFYLDTGDASNFARWRYKVSVTLSGKKVTGHILVSLFGNK
GNSKQYEIFKGTLKPDSTHSNEFDSDVDVGDLQMVKFIWYNNVINPTLPRVGASKIIVETNVGK
QFNFCSPETVREEVLLTLTPC (SEQ ID NO: 136)

Helicase [Homo sapiens], GenBank: AMD82207.1:
MSISSLFGGRYDNKFLLNMSSAPKIELIVDKVASLSEGRLEGRLPEDWFRHIMDPETEFNSEFA
DALCIGIDEFAQPLPFLPFKALLVTGTAGAGKTNSIQTLAANLDCIVTATTSIAAQNLSVVLNRSKS
AQVKTIFKTFGFNSSHVSMSERQSYIANDERSIQIQQKQDLSIYWNVISDIADRALGAVACKTKE
LPDLCESSVIVIDEAGVILRHILHTVVFFYWFYNALYKTPLYEDGIVPCIVCVGSPTQSNALVTSFN
PLTQNKDVKRGIDVLSALICDDVLSKYCEVDNNWIIFVNNKRCADHAFGDFLKHIEFGLPLKPELI
EYVDQFVKPASYIRNPMNEIETTRLFLSHNEVKNYFRSLHEQVEVTNRNNLFVFPVYFLIKNKTF
EDYKSEIGNFSLEIEPWFKSNIHRLNTYSQFADQDLSKTVQLEEIVLEDGSVEETLITCHLKHIRN
SSIGVTSKIKASTVGFSGTYEKFVELLQSDLFIEKTSCDQTIHAYSFLSGLMFGGMYSFCCSKFT
TPEVLMEIKNIKMPSIEFLESEMSRMSPDVQTVETDERYDFGLVDDGLSDVDLLEIDPCGDPFFT
RYSKLPLTNSLSFEEISLLYTTFKDIFISRFAILQKHTKGKFGKTLLVTYNRNNVSRKQCGEIYSHL
KSFYGMLTYAIPANNYTLEGYTNDNVVHLGTDKQLPQILYKKGLPRLVIKDEMGFISVLDNNVSK
FIDVVNGQSFHLCTTVDYATVSKVSMTITKSQGLSIQKVAIDFGSDPKNLKLSSIYVGMSRVTDP
NNLIMNVNPLRLNYENDNFIAPHIVKALKNENTMLIF (SEQ ID NO: 137)

Amylase [Homo sapiens], GenBank: AAA51724.1:
MKFFLLLFTIGFCWAQYSPNTQQGRTSIVHLFEWRWVDIALECERYLAPKGFGGVQVSPPNEN
VAIYNPFRPWWERYQPVSYKLCTRSGNEDEFRNMVTRCNNVGVRIYVDAVINHMCGNAVSAG
TSSTCGSYFNPGSRDFPAVPYSGWDFNDGKCKTGSGDIENYNDATQVRDCRLTGLLDLALEK
DYVRSKIAEYMNHLIDIGVAGFRLDASKHMWPGDIKAILDKLHNLNSNWFPAGSKPFIYQEVIDL
GGEPIKSSDYFGNGRVTEFKYGAKLGTVIRKWNGEKMSYLKNWGEGWGFVPSDRALVFVDN
HDNQRGHGAGGASILTFWDARLYKMAVGFMLAHPYGFTRVMSSYRWPRQFQNGNDVNDWV
GPPNNNGVIKEVTINPDTTCGNDWVCEHRWRQIRNMVIFRNVVDGQPFTNWYDNGSNQVAF
GRGNRGFIVFNNDDWSFSLTLQTGLPAGTYCDVISGDKINGNCTGIKIYVSDDGKAHFSISNSA
EDPFIAIHAESKL (SEQ ID NO: 138)

Alpha-glucosidase [Homo sapiens], GenBank: ABI53718.1:
MGVRHPPCSHRLLAVCALVSLATAALLGHILLHDFLLVPRELSGSSPVLEETHPAHQQGASRPG
PRDAQAHPGRPRAVPTQCDVPPNSRFDCAPDKAITQEQCEARGCCYIPAKQGLQGAQMGQP
WCFFPPSYPSYKLENLSSSEMGYTATLTRTTPTFFPKDILTLRLDVMMETENRLHFTIKDPANR
RYEVPLETPRVHSRAPSPLYSVEFSEEPFGVIVHRQLDGRVLLNTTVAPLFFADQFLQLSTSLP
SQYITGLAEHLSPLMLSTSWTRITLWNRDLAPTPGANLYGSHPFYLALEDGGSAHGVFLLNSNA
MDVVLQPSPALSWRSTGGILDVYIFLGPEPKSVVQQYLDVVGYPFMPPYWGLGFHLCRWGYS
STAITRQVVENMTRAHFPLDVQWNDLDYMDSRRDFTFNKDGFRDFPAMVQELHQGGRRYMM
IVDPAISSSGPAGSYRLYDEGLRRGVFITNETGQPLIGKVWPGSTAFPDFTNPTALAWWEDMV
AEFHDQVPFDGMWIDMNEPSNFIRGSEDGCPNNELENPPYVPGVVGGTLQAATICASSHQFL
STHYNLHNLYGLTEAIASHRALVKARGTRPFVISRSTFAGHGRYAGHWTGDVWSSWEQLASS
VPEILQFNLLGVPLVGADVCGFLGNTSEELCVRWTQLGAFYPFMRNHNSLLSLPQEPYSFSEP
AQQAMRKALTLRYALLPHLYTLFHQAHVAGETVARPLFLEFPKDSSTWTVDHQLLWGEALLITP

FIG. 79 cont'd

VLQAGKAEVTGYFPLGTWYDLQTVPIEALGSLPPPPAAPREPAIHSEGQWVTLPAPLDTINVHL
RAGYIIPLQGPGLTTTESRQQPMALAVALTKGGEARGELFWDDGESLEVLERGAYTQVIFLARN
NTIVNELVRVTSEGAGLQLQKVTVLGVATAPQQVLSNGVPVSNFTYSPDTKVLDICVSLLMGEQ
FLVSWC (SEQ ID NO: 139)

Transcription factor SP1 [Homo sapiens], UniProtKB/Swiss-Prot: P08047.3:
MSDQDHSMDEMTAVVKIEKGVGGNNGGNGNGGGAFSQARSSSTGSSSSTGGGGQESQPSP
LALLAATCSRIESPNENSNNSQGPSQSGGTGELDLTATQLSQGANGWQIISSSSGATPTSKEQ
SGSSTNGSNGSESSKNRTVSGGQYVVAAAPNLQNQQVLTGLPGVMPNIQYQVIPQFQTVDGQ
QLQFAATGAQVQQDGSGQIQIIPGANQQIITNRGSGGNIIAAMPNLLQQAVPLQGLANNVLSGQ
TQYVTNVPVALNGNITLLPVNSVSAATLTPSSQAVTISSSGSQESGSQPVTSGTTISSASLVSSQ
ASSSSFFTNANSYSTTTTTSNMGIMNFTTSGSSGTNSQGQTPQRVSGLQGSDALNIQQNQTS
GGSLQAGQQKEGEQNQQTQQQQILIQPQLVQGGQALQALQAAPLSGQTFTTQAISQETLQNL
QLQAVPNSGPIIIRTPTVGPNGQVSWQTLQLQNLQVQNPQAQTITLAPMQGVSLGQTSSSNTT
LTPIASAASIPAGTVTVNAAQLSSMPGLQTINLSALGTSGIQVHPIQGLPLAIANAPGDHGAQLGL
HGAGGDGIHDDTAGGEEGENSPDAQPQAGRRTRREACTCPYCKDSEGRGSGDPGKKKQHIC
HIQGCGKVYGKTSHLRAHLRWHTGERPFMCTWSYCGKRFTRSDELQRHKRTHTGEKKFACP
ECPKRFMRSDHLSKHIKTHQNKKGGPGVALSVGTLPLDSGAGSEGSGTATPSALITTNMVAME
AICPEGIARLANSGINVMQVADLQSINISGNGF (SEQ ID NO: 140)

Transcription factor AP-1 [Homo sapiens], NP_002219.1:
MTAKMETTFYDDALNASFLPSESGPYGYSNPKILKQSMTLNLADPVGSLKPHLRAKNSDLLTSP
DVGLLKLASPELERLIIQSSNGHITTTPTPTQFLCPKNVTDEQEGFAEGFVRALAELHSQNTLPS
VTSAAQPVNGAGMVAPAVASVAGGSGSGGFSASLHSEPPVYANLSNFNPGALSSGGGAPSY
GAAGLAFPAQPQQQQQPPHHLPQQMPVQHPRLQALKEEPQTVPEMPGETPPLSPIDMESQE
RIKAERKRMRNRIAASKCRKRKLERIARLEEKVKTLKAQNSELASTANMLREQVAQLKQKVMN
HVNSGCQLMLTQQLQTF (SEQ ID NO: 141)

Heat shock factor protein 1, UniProtKB/Swiss-Prot: Q00613.1:
MDLPVGPGAAGPSNVPAFLTKLWTLVSDPDTDALICWSPSGNSFHVFDQGQFAKEVLPKYFK
HNNMASFVRQLNMYGFRKVVHIEQGGLVKPERDDTEFQHPCFLRGQEQLLENIKRKVTSVSTL
KSEDIKIRQDSVTKLLTDVQLMKGKQECMDSKLLAMKHENEALWREVASLRQKHAQQQKVVN
KLIQFLISLVQSNRILGVKRKIPLMLNDSGSAHSMPKYSRQFSLEHVHGSGPYSAPSPAYSSSSL
YAPDAVASSGPIISDITELAPASPMASPGGSIDERPLSSSPLVRVKEEPPSPPQSPRVEEASPGR
PSSVDTLLSPTALIDSILRESEPAPASVTALTDARGHTDTEGRPPSPPPTSTPEKCLSVACLDKN
ELSDHLDAMDSNLDNLQTMLSSHGFSVDTSALLDLFSPSVTVPDMSLPDLDSSLASIQELLSPQ
EPPRPPEAENSSPDSGKQLVHYTAQPLFLLDPGSVDTGSNDLPVLFELGEGSYFSEGDGFAED
PTISLLTGSEPPKAKDPTVS (SEQ ID NO: 142)

CCAAT/enhancer-binding protein (C/EBP) beta isoform a [Homo sapiens], NP_005185.2:
MQRLVAWDPACLPLPPPPPAFKSMEVANFYYEADCLAAAYGGKAAPAAPPAARPGPRPPAGE
LGSIGDHERAIDFSPYLEPLGAPQAPAPATATDTFEAAPPAPAPAPASSGQHHDFLSDLFSDDY
GGKNCKKPAEYGYVSLGRLGAAKGALHPGCFAPLHPPPPPPPPPAELKAEPGFEPADCKRKE
EAGAPGGGAGMAAGFPYALRAYLGYQAVPSGSSGSLSTSSSSSPPGTPSPADAKAPPTACYA
GAAPAPSQVKSKAKKTVDKHSDEYKIRRERNNIAVRKSRDKAKMRNLETQHKVLELTAENERL
QKKVEQLSRELSTLRNLFKQLPEPLLASSGHC (SEQ ID NO: 143)

Octamer-binding protein 1 (Oct-1), UniProtKB/Swiss-Prot: P14859.2:

FIG. 79 cont'd

MNNPSETSKPSMESGDGNTGTQTNGLDFQKQPVPVGGAISTAQAQAFLGHLHQVQLAGTSLQ
AAAQSLNVQSKSNEESGDSQQPSQPSQQPSVQAAIPQTQLMLAGGQITGLTLTPAQQQLLLQ
QAQAQAQLLAAAVQQHSASQQHSAAGATISASAATPMTQIPLSQPIQIAQDLQQLQQLQQQNL
NLQQFVLVHPTTNLQPAQFIISQTPQGQQGLLQAQNLLTQLPQQSQANLLQSQPSITLTSQPAT
PTRTIAATPIQTLPQSQSTPKRIDTPSLEEPSDLEELEQFAKTFKQRRIKLGFTQGDVGLAMGKL
YGNDFSQTTISRFEALNLSFKNMCKLKPLLEKWLNDAENLSSDSSLSSPSALNSPGIEGLSRRR
KKRTSIETNIRVALEKSFLENQKPTSEEITMIADQLNMEKEVIRVWFCNRRQKEKRINPPSSGGT
SSSPIKAIFPSPTSLVATTPSLVTSSAATTLTVSPVLPLTSAAVTNLSVTGTSDTTSNNTATVISTA
PPASSAVTSPSLSPSPSASASTSEASSASETSTTQTTSTPLSSPLGTSQVMVTASGLQTAAAAA
LQGAAQLPANASLAAMAAAAGLNPSLMAPSQFAAGGALLSLNPGTLSGALSPALMSNSTLATI
QALASGGSLPITSLDATGNLVFANAGGAPNIVTAPLFLNPQNLSLLTSNPVSLVSAAAASAGNSA
PVASLHATSTSAESIQNSLFTVASASGAASTTTTASKAQ (SEQ ID NO: 144)

Transforming growth factor receptor beta 1 [Homo sapiens], GenBank: CAF02096.2:
MEAAVAAPRPRLLLLVLAAAAAAAAALLPGATALQCFCHLCTKDNFTCVTDGLCFVSVTETTDK
VIHNSMCIAEIDLIPRDRPFVCAPSSKTGSVTTTYCCNQDHCNKIELPTTGPFSVKSSPGLGPVE
LAAVIAGPVCFVCISLMLMVYICHNRTVIHHRVPNEEDPSLDRPFISEGTTLKDLIYDMTTSGSGS
GLPLLVQRTIARTIVLQESIGKGRFGEVWRGKWRGEEVAVKIFSSREERSWFREAEIYQTVMLR
HENILGFIAADNKDNGTWTQLWLVSDYHEHGSLFDYLNRYTVTVEGMIKLALSTASGLAHLHME
IVGTQGKPAIAHRDLKSKNILVKKNGTCCIADLGLAVRHDSATDTIDIAPNHRVGTKRYMAPEVL
DDSINMKHFESFKRADIYAMGLVFWEIARRCSIGGIHEDYQLPYYDLVPSDPSVEEMRKVVCEQ
KLRPNIPNRWQSCEALRVMAKIMRECWYANGAARLTALRIKKTLSQLSQQEGIKM (SEQ ID
NO: 145)

Platelet-derived growth factor receptor [Homo sapiens], GenBank: AAA60049.1:
MRLPGAMPALALKGELLLLSLLLLLEPQISQGLVVTPPGPELVLNVSSTFVLTCSGSAPVVWER
MSQEPPQEMAKAQDGTFSSVLTLTNLTGLDTGEYFCTHNDSRGLETDERKRLYIFVPDPTVGF
LPNDAEELFIFLTEITEITIPCRVTDPQLVVTLHEKKGDVALPVPYDHQRGFSGIFEDRSYICKTTI
GDREVDSDAYYVYRLQVSSINVSVNAVQTVVRQGENITLMCIVIGNEVVNFEWTYPRKESGRL
VEPVTDFLLDMPYHIRSILHIPSAELEDSGTYTCNVTESVNDHQDEKAINITVVESGYVRLLGEV
GTLQFAELHRSRTLQVVFEAYPPPTVLWFKDNRTLGDSSAGEIALSTRNVSETRYVSELTLVRV
KVAEAGHYTMRAFHEDAEVQLSFQLQINVPVRVLELSESHPDSGEQTVRCRGRGMPQPNIIWS
ACRDLKRCPRELPPTLLGNSSEEESQLETNVTYWEEEQEFEVVSTLRLQHVDRPLSVRCTLRN
AVGQDTQEVIVVPHSLPFKVVVISAILALVVLTIISLIILIMLWQKKPRYEIRWKVIESVSSDGHEYIY
VDPMQLPYDSTWELPRDQLVLGRTLGSGAFGQVVEATAHGLSHSQATMKVAVKMLKSTARSS
EKQALMSELKIMSHLGPHLNVVNLLGACTKGGPIYIITEYCRYGDLVDYLHRNKHTFLQHHSDK
RRPPSAELYSNALPVGLPLPSHVSLTGESDGGYMDMSKDESVDYVPMLDMKGDVKYADIESS
NYMAPYDNYVPSAPERTCRATLINESPVLSYMDLVGFSYQVANGMEFLASKNCVHRDLAARN
VLICEGKLVKICDFGLARDIMRDSNYISKGSTFLPLKWMAPESIFNSLYTTLSDVWSFGILLWEIF
TLGGTPYPELPMNEQFYNAIKRGYRMAQPAHASDEIYEIMQKCWEEKFEIRPPFSQLVLLLERL
LGEGYKKKYQQVDEEFLRSDHPAILRSQARLPGFHGLRSPLDTSSVLYTAVQPNEGDNDYIIPL
PDPKPEVADEGPLEGSPSLASSTLNEVNTSSTISCDSPLEPQDEPEPEPQLELQVEPEPELEQL
PDSGCPAPRAEAEDSFL (SEQ ID NO: 146)

Epidermal growth factor receptor [Homo sapiens], GenBank: CAA25240.1:
MRPSGTAGAALLALLAALCPASRALEEKKVCQGTSNKLTQLGTFEDHFLSLQRMFNNCEVVLG
NLEITYVQRNYDLSFLKTIQEVAGYVLIALNTVERIPLENLQIIRGNMYYENSYALAVLSNYDANKT
GLKELPMRNLQEILHGAVRFSNNPALCNVESIQWRDIVSSDFLSNMSMDFQNHLGSCQKCDPS

FIG. 79 cont'd

CPNGSCWGAGEENCQKLTKIICAQQCSGRCRGKSPSDCCHNQCAAGCTGPRESDCLVCRKF
RDEATCKDTCPPLMLYNPTTYQMDVNPEGKYSFGATCVKKCPRNYVVTDHGSCVRACGADS
YEMEEDGVRKCKKCEGPCRKVCNGIGIGEFKDSLSINATNIKHFKNCTSISGDLHILPVAFRGDS
FTHTPPLDPQELDILKTVKEITGFLLIQAWPENRTDLHAFENLEIIRGRTKQHGQFSLAVVSLNITS
LGLRSLKEISDGDVIISGNKNLCYANTINWKKLFGTSGQKTKIISNRGENSCKATGQVCHALCSP
EGCWGPEPRDCVSCRNVSRGRECVDKCKLLEGEPREFVENSECIQCHPECLPQAMNITCTGR
GPDNCIQCAHYIDGPHCVKTCPAGVMGENNTLVWKYADAGHVCHLCHPNCTYGCTGPGLEG
CPTNGPKIPSIATGMVGALLLLLVVALGIGLFMRRRHIVRKRTLRRLLQERELVEPLTPSGEAPN
QALLRILKETEFKKIKVLGSGAFGTVYKGLWIPEGEKVKIPVAIKELREATSPKANKEILDEAYVM
ASVDNPHVCRLLGICLTSTVQLITQLMPFGCLLDYVREHKDNIGSQYLLNWCVQIAKGMNYLED
RRLVHRDLAARNVLVKTPQHVKITDFGLAKLLGAEEKEYHAEGGKVPIKWMALESILHRIYTHQS
DVWSYGVTVWELMTFGSKPYDGIPASEISSILEKGERLPQPPICTIDVYMIMVKCWMIDADSRP
KFRELIIEFSKMARDPQRYLVIQGDERMHLPSPTDSNFYRALMDEEDMDDVVDADEYLIPQQGF
FSSPSTSRTPLLSSLSATSNNSTVACIDRNGLQSCPIKEDSFLQRYSSDPTGALTEDSIDDTFLP
VPEYINQSVPKRPAGSVQNPVYHNQPLNPAPSRDPHYQDPHSTAVGNPEYLNTVQPTCVNST
FDSPAHWAQKGSHQISLDNPDYQQDFFPKEAKPNGIFKGSTAENAEYLRVAPQSSEFIGA
(SEQ ID NO: 147)

Vascular endothelial growth factor receptor [Homo sapiens], GenBank: AAC16449.2:
MVSYWDTGVLLCALLSCLLLTGSSSGSKLKDPELSLKGTQHIMQAGQTLHLQCRGEAAHKWSL
PEMVSKESERLSITKSACGRNGKQFCSTLTLNTAQANHTGFYSCKYLAVPTSKKKETESAIYIFI
SDTGRPFVEMYSEIPEIIHMTEGRELVIPCRVTSPNITVTLKKFPLDTLIPDGKRIIWDSRKGFIISN
ATYKEIGLLTCEATVNGHLYKTNYLTHRQTNTIIDVQISTPRPVKLLRGHTLVLNCTATTPLNTRV
QMTWSYPDEKNKRASVRRRIDQSNSHANIFYSVLTIDKMQNKDKGLYTCRVRSGPSFKSVNTS
VHIYDKAFITVKHRKQQVLETVAGKRSYRLSMKVKAFPSPEVVWLKDGLPATEKSARYLTRGYS
LIIKDVTEEDAGNYTILLSIKQSNVFKNLTATLIVNVKPQIYEKAVSSFPDPALYPLGSRQILTCTAY
GIPQPTIKWFWHPCNHNHSEARCDFCSNNEESSILDADSNMGNRIESITQRMAIIEGKNKMAST
LVVADSRISGIYICIASNKVGTVGRNISFYITDVPNGFHVNLEKMPTEGEDLKLSCTVNKFLYRDV
TWILLRTVNNRTMHYSISKQKMAITKEHSITLNLTIMNVSLQDSGTYACRARNVYTGEEILQKKEI
TIRDQEAPYLLRNLSDHTVAISSSTTLDCHANGVPEPQITWFKNNHKIQQEPGIILGPGSSTLFIE
RVTEEDEGVYHCKATNQKGSVESSAYLTVQGTSDKSNLELITLTCTCVAATLFWLLLTLFIRKMK
RSSSEIKTDYLSIIMDPDEVPLDEQCERLPYDASKWEFARERLKLGKSLGRGAFGKVVQASAFG
IKKSPTCRTVAVKMLKEGATASEYKALMTELKILTHIGHHLNVVNLLGACTKQGGPLMVIVEYCK
YGNLSNYLKSKRDLFFLNKDAALHMEPKKEKMEPGLEQGKKPRLDSVTSSESFASSGFQEDKS
LSDVEEEEDSDGFYKEPITMEDLISYSFQVARGMEFLSSRKCIHRDLAARNILLSENNVVKICDF
GLARDIYKNPDYVRKGDTRLPLKWMAPESIFDKIYSTKSDVWSYGVLLWEIFSLGGSPYPGVQ
MDEDFCSRLREGMRMRAPEYSTPEIYQIMLDCWHRDPKERPRFAELVEKLGDLLQANVQQDG
KDYIPINAILTGNSGFTYSTPAFSEDFFKESISAPKFNSGSSDDVRYVNAFKFMSLERIKTFEELL
PNATSMFDDYQGDSSTLLASPMLKRFTWTDSKPKASLKIDLRVTSKSKESGLSDVSRPSFCHS
SCGHVSEGKRRFTYDHAELERKIACCSPPPDYNSVVLYSTPPI (SEQ ID NO: 148)

Interleukin 8 receptor alpha [Homo sapiens], GenBank: AAB59436.1:
MSNITDPQMWDFDDLNFTGMPPADEDYSPCMLETETLNKYVVIIAYALVFLLSLLGNSLVMLVIL
YSRVGRSVTDVYLLNLALADLLFALTLPIWAASKVNGWIFGTFLCKVVSLLKEVNFYSGILLLACI
SVDRYLAIVHATRTLTQKRHLVKFVCLGCWGLSMNLSLPFFLFRQAYHPNNSSPVCYEVLGND
TAKWRMVLRILPHTFGFIVPLFVMLFCYGFTLRTLFKAHMGQKHRAMRVIFAVVLIFLLCWLPYN
LVLLADTLMRTQVIQESCERRNNIGRALDATEILGFLHSCLNPIIYAFIGQNFRHGFLKILAMHGLV
SKEFLARHRVTSYTSSSVNVSSNL (SEQ ID NO: 149)

FIG. 79 cont'd

Caveolin [Homo sapiens], GenBank: CAA79476.1:
MSGGKYVDSEGHLYTVPIREQGNIYKPNNKAMADELSEKQVYDAHTKEIDLVNRDPKHLNDDV
VKIDFEDVIAEPEGTHSFHGIWKASFTTFTVTKYWFYRLLSALFGIPMALIWGIYFAILSFLHIWAV
VPCIKSFLIEIQCTSRVYSIYVHTVCDPLFEAVGKIFSNVRINLQKEI (SEQ ID NO: 150)

Dynamin [Homo sapiens], GenBank: AAA88025.1:
MGNRGMEELIPLVNKLQDAFSSIGQSCHLDLPQIAVVGGQSAGKSSVLENFVGRDFLPRGSGI
VTRRPLILQLIFSKTEHAEFLHCKSKKFTDFDEVRQEIEAETDRVTGTNKGISPVPINLRVYSPHV
LNLTLIDLPGITKVPVGDQPPDIEYRVKDMILQFISRESSLILAVTPANMDLANSDALKLAKEVDP
QGLRTIGVITKLDLMDEGTDARDVLENKLLPLRRGYIGVVNRSQKDIEGKKDIRAALAAERKFFL
SHPAYRHMADRMGTPHLQKTLNQQLTNHIRESLPALRSKLQSQLLSLEKEVEEYKIFRPDDPTP
KTKALLQMVQQFGVDFEKRIEGSGDQVDTLELSGGARINRIFHERFPFELVKMEFDEKDLRREI
SYAIKNIHGVRTGLFTPDLAFEAIVKKQVVKLKEPCLKCVDLVIQELINTVRQCTSKLSSYPRLRE
ETERIVTTYIREREGRTKDQILLLIDIEQSYINTNHEDFIGFANAQQRSTQLNKKRAIPNQVIRRGW
LTINNISLMKGGSKEYWFVLTAESLSWYKDEEEKEKKYMLPLDNLKIRDVEKGFMSNKHVFAIF
NTEQRNVYKDLRQIELACDSQEDVDSWKASFLRAGVYPEKDQAENEDGAQENTFSMDPQLER
QVETIRNLVDSYVAIINKSIRDLMPKTIMHLMINNTKAFIHHELLAYLYSSADQSSLMEESADQAQ
RRDDMLRMYHALKEALNIIGDISTSTVSTPVPPPVDDTWLQSASSHSPTPQRRPVSSIHPPGRP
PAVRGPTPGPPLIPVPVGAAASFSAPPIPSRPGPQSVFANSDLFPAPPQIPSRPVRIPPGIPPGV
PSRRPPAAPSRPTIIRPAEPSLLD (SEQ ID NO: 151)

Clathrin heavy chain 1 isoform 1 [Homo sapiens], NP_004850.1:
MAQILPIRFQEHLQLQNLGINPANIGFSTLTMESDKFICIREKVGEQAQVVIIDMNDPSNPIRRPIS
ADSAIMNPASKVIALKAGKTLQIFNIEMKSKMKAHTMTDDVTFWKWISLNTVALVTDNAVYHWS
MEGESQPVKMFDRHSSLAGCQIINYRTDAKQKWLLLTGISAQQNRVVGAMQLYSVDRKVSQPI
EGHAASFAQFKMEGNAEESTLFCFAVRGQAGGKLHIIEVGTPPTGNQPFPKKAVDVFFPPEAQ
NDFPVAMQISEKHDVVFLITKYGYIHLYDLETGTCIYMNRISGETIFVTAPHEATAGIIGVNRKGQ
VLSVCVEEENIIPYITNVLQNPDLALRMAVRNNLAGAEELFARKFNALFAQGNYSEAAKVAANAP
KGILRTPDTIRRFQSVPAQPGQTSPLLQYFGILLDQGQLNKYESLELCRPVLQQGRKQLLEKWL
KEDKLECSEELGDLVKSVDPTLALSVYLRANVPNKVIQCFAETGQVQKIVLYAKKVGYTPDWIFL
LRNVMRISPDQGQQFAQMLVQDEEPLADITQIVDVFMEYNLIQQCTAFLLDALKNNRPSEGPLQ
TRLLEMNLMHAPQVADAILGNQMFTHYDRAHIAQLCEKAGLLQRALEHFTDLYDIKRAVVHTHL
LNPEWLVNYFGSLSVEDSLECLRAMLSANIRQNLQICVQVASKYHEQLSTQSLIELFESFKSFE
GLFYFLGSIVNFSQDPDVHFKYIQAACKTGQIKEVERICRESNCYDPERVKNFLKEAKLTDQLPL
IIVCDRFDFVHDLVLYLYRNNLQKYIEIYVQKVNPSRLPVVIGGLLDVDCSEDVIKNLILVVRGQFS
TDELVAEVEKRNRLKLLLPWLEARIHEGCEEPATHNALAKIYIDSNNNPERFLRENPYYDSRVV
GKYCEKRDPHLACVAYERGQCDLELINVCNENSLFKSLSRYLVRRKDPELWGSVLLESNPYRR
PLIDQVVQTALSETQDPEEVSVTVKAFMTADLPNELIELLEKIVLDNSVFSEHRNLQNLLILTAIKA
DRTRVMEYINRLDNYDAPDIANIAISNELFEEAFAIFRKFDVNTSAVQVLIEHIGNLDRAYEFAER
CNEPAVWSQLAKAQLQKGMVKEAIDSYIKADDPSSYMEVVQAANTSGNWEELVKYLQMARKK
ARESYVETELIFALAKTNRLAELEEFINGPNNAHIQQVGDRCYDEKMYDAAKLLYNNVSNFGRL
ASTLVHLGEYQAAVDGARKANSTRTWKEVCFACVDGKEFRLAQMCGLHIVVHADELEELINYY
QDRGYFEELITMLEAALGLERAHMGMFTELAILYSKFKPQKMREHLELFWSRVNIPKVLRAAEQ
AHLWAELVFLYDKYEEYDNAIITMMNHPTDAWKEGQFKDIITKVANVELYYRAIQFYLEFKPLLL
NDLLMVLSPRLDHTRAVNYFSKVKQLPLVKPYLRSVQNHNNKSVNESLNNLFITEEDYQALRTS
IDAYDNFDNISLAQRLEKHELIEFRRIAAYLFKGNNRWKQSVELCKKDSLYKDAMQYASESKDT
ELAEELLQWFLQEEKRECFGACLFTCYDLLRPDVVLETAWRHNIMDFAMPYFIQVMKEYLTKV

FIG. 79 cont'd

DKLDASESLRKEEEQATETQPIVYGQPQLMLTAGPSVAVPPQAPFGYGYTAPPYGQPQPGFG
YSM (SEQ ID NO: 152)

Clathrin heavy chain 2 isoform 1 [Homo sapiens], NP_009029.3:
MAQILPVRFQEHFQLQNLGINPANIGFSTLTMESDKFICIREKVGEQAQVTIIDMSDPMAPIRRPI
SAESAIMNPASKVIALKAGKTLQIFNIEMKSKMKAHTMAEEVIFWKWVSVNTVALVTETAVYHW
SMEGDSQPMKMFDRHTSLVGCQVIHYRTDEYQKWLLLVGISAQQNRVVGAMQLYSVDRKVS
QPIEGHAAAFAEFKMEGNAKPATLFCFAVRNPTGGKLHIIEVGQPAAGNQPFVKKAVDVFFPPE
AQNDFPVAMQIGAKHGVIYLITKYGYLHLYDLESGVCICMNRISADTIFVTAPHKPTSGIIGVNKK
GQVLSVCVEEDNIVNYATNVLQNPDLGLRLAVRSNLAGAEKLFVRKFNTLFAQGSYAEAAKVA
ASAPKGILRTRETVQKFQSIPAQSGQASPLLQYFGILLDQGQLNKLESLELCHLVLQQGRKQLL
EKWLKEDKLECSEELGDLVKTTDPMLALSVYLRANVPSKVIQCFAETGQFQKIVLYAKKVGYTP
DWIFLLRGVMKISPEQGLQFSRMLVQDEEPLANISQIVDIFMENSLIQQCTSFLLDALKNNRPAE
GLLQTWLLEMNLVHAPQVADAILGNKMFTHYDRAHIAQLCEKAGLLQQALEHYTDLYDIKRAVV
HTHLLNPEWLVNFFGSLSVEDSVECLHAMLSANIRQNLQLCVQVASKYHEQLGTQALVELFES
FKSYKGLFYFLGSIVNFSQDPDVHLKYIQAACKTGQIKEVERICRESSCYNPERVKNFLKEAKLT
DQLPLIIVCDRFGFVHDLVLYLYRNNLQRYIEIYVQKVNPSRTPAVIGGLLDVDCSEEVIKHLIMAV
RGQFSTDELVAEVEKRNRLKLLLPWLESQIQEGCEEPATHNALAKIYIDSNNSPECFLRENAYY
DSSVVGRYCEKRDPHLACVAYERGQCDLELIKVCNENSLFKSEARYLVCRKDPELWAHVLEET
NPSRRQLIDQVVQTALSETRDPEEISVTVKAFMTADLPNELIELLEKIVLDNSVFSEHRNLQNLLI
LTAIKADRTRVMEYISRLDNYDALDIASIAVSSALYEEAFTVFHKFDMNASAIQVLIEHIGNLDRAY
EFAERCNEPAVWSQLAQAQLQKDLVKEAINSYIRGDDPSSYLEVVQSASRSNNWEDLVKFLQ
MARKKGRESYIETELIFALAKTSRVSELEDFINGPNNAHIQQVGDRCYEEGMYEAAKLLYSNVS
NFARLASTLVHLGEYQAAVDNSRKASSTRTWKEVCFACMDGQEFRFAQLCGLHIVIHADELEE
LMCYYQDRGYFEELILLLEAALGLERAHMGMFTELAILYSKFKPQKMLEHLELFWSRVNIPKVLR
AAEQAHLWAELVFLYDKYEEYDNAVLTMMSHPTEAWKEGQFKDIITKVANVELCYRALQFYLD
YKPLLINDLLLVLSPRLDHTWTVSFFSKAGQLPLVKPYLRSVQSHNNKSVNEALNHLLTEEEDY
QGLRASIDAYDNFDNISLAQQLEKHQLMEFRCIAAYLYKGNNWWAQSVELCKKDHLYKDAMQ
HAAESRDAELAQKLLQWFLEEGKRECFAACLFTCYDLLRPDMVLELAWRHNLVDLAMPYFIQV
MREYLSKVDKLDALESLRKQEEHVTEPAPLVFDFDGHE (SEQ ID NO: 153)

Clathrin light chain A isoform a [Homo sapiens], NP_001824.1:
MAELDPFGAPAGAPGGPALGNGVAGAGEEDPAAAFLAQQESEIAGIENDEAFAILDGGAPGPQ
PHGEPPGGPDAVDGVMNGEYYQESNGPTDSYAAISQVDRLQSEPESIRKWREEQMERLEAL
DANSRKQEAEWKEKAIKELEEWYARQDEQLQKTKANNRAAEEAFVNDIDESSPGTEWERVAR
LCDFNPKSSKQAKDVSRMRSVLISLKQAPLVH (SEQ ID NO: 154)

Clathrin light chain B isoform a [Homo sapiens], NP_001825.1:
MADDFGFFSSSESGAPEAAEEDPAAAFLAQQESEIAGIENDEGFGAPAGSHAAPAQPGPTSGA
GSEDMGTTVNGDVFQEANGPADGYAAIAQADRLTQEPESIRKWREEQRKRLQELDAASKVTE
QEWREKAKKDLEEWNQRQSEQVEKNKINNRASEEAFVKESKEETPGTEWEKVAQLCDFNPK
SSKQCKDVSRLRSVLMSLKQTPLSR (SEQ ID NO: 155)

Ras-related protein Rab-4A isoform 1 [Homo sapiens], NP_004569.2:
MSQTAMSETYDFLFKFLVIGNAGTGKSCLLHQFIEKKFKDDSNHTIGVEFGSKIINVGGKYVKLQI
WDTAGQERFRSVTRSYYRGAAGALLVYDITSRETYNALTNWLTDARMLASQNIVIILCGNKKDL
DADREVTFLEASRFAQENELMFLETSALTGENVEEAFVQCARKILNKIESGELDPERMGSGIQY
GDAALRQLRSPRRAQAPNAQECGC (SEQ ID NO: 156)

FIG. 79 cont'd

Ras-related protein Rab-11A, UniProtKB/Swiss-Prot: P62491.3:
MGTRDDEYDYLFKVVLIGDSGVGKSNLLSRFTRNEFNLESKSTIGVEFATRSIQVDGKTIKAQIW
DTAGQERYRAITSAYYRGAVGALLVYDIAKHLTYENVERWLKELRDHADSNIVIMLVGNKSDLR
HLRAVPTDEARAFAEKNGLSFIETSALDSTNVEAAFQTILTEIYRIVSQKQMSDRRENDMSPSNN
VVPIHVPPTTENKPKVQCCQNI (SEQ ID NO: 157)

Platelet-derived growth factor [Homo sapiens], GenBank: AAA60552.1:
MNRCWALFLSLCCYLRLVSAEGDPIPEELYEMLSDHSIRSFDDLQRLLHGDPGEEDGAELDLN
MTRSHSGGELESLARGRRSLGSLTIAEPAMIAECKTRTEVFEISRRLIDRTNANFLVWPPCVEV
QRCSGCCNNRNVQCRPTQVQLRPVQVRKIEIVRKKPIFKKATVTLEDHLACKCETVAAARPVT
RSPGGSQEQRAKTPQTRVTIRTVRVRRPPKGKHRKFKHTHDKTALKETLGA (SEQ ID NO: 158)

Transforming growth factor-beta3 [Homo sapiens], GenBank: AAA61161.1:
MKMHLQRALVVLALLNFATVSLSLSTCTTLDFGHIKKKRVEAIRGQILSKLRLTSPPEPTVMTHV
PYQVLALYNSTRELLEEMHGEREEGCTQENTESEYYAKEIHKFDMIQGLAEHNELAVCPKGITS
KVFRFNVSSVEKNRTNLFRAEFRVLRVPNPSSKRNEQRIELFQILRPDEHIAKQRYIGGKNLPTR
GTAEWLSFDVTDTVREWLLRRESNLGLEISIHCPCHTFQPNGDILENIHEVMEIKFKGVDNEDD
HGRGDLGRLKKQKDHHNPHLILMMIPPHRLDNPGQGGQRKKRALDTNYCFRNLEENCCVRPL
YIDFRQDLGWKWVHEPKGYYANFCSGPCPYLRSADTTHSTVLGLYNTLNPEASASPCCVPQD
LEPLTILYYVGRTPKVEQLSNMVVKSCKCS (SEQ ID NO: 159)

Nerve growth factor [Homo sapiens], GenBank: CAA37703.1:
MSILFYVIFLAYLRGIQGNNMDQRSLPEDSLNSLIIKLIQADILKNKLSKQMVDVKENYQSTLPKA
EAPREPERGGPAKSAFQPVIAMDTELLRQQRRYNSPRVLLSDSTPLEPPPLYLMEDYVGSPVV
ANRTSRRKRYAEHKSHRGEYSVCDSESLWVTDKSSAIDIRGHQVTVLGEIKTGNSPVKQYFYE
TRCKEARPVKNGCRGIDDKHWNSQCKTSQTYVRALTSENNKLVGWRWIRIDTSCVCALSRKIG
RT (SEQ ID NO: 160)

Epidermal growth factor (EGF) [Homo sapiens], GenBank: CAA34902.2:
MRPSGTAGAALLALLAALCPASRALEEKKGKGVSRRLPRRPRIAPRTPQPAQPRTGAPARARA
PARPFLFP (SEQ ID NO: 161)

GTPase HRas [Homo sapiens]:
MTEYKLVVVGAGGVGKSALTIQLIQNHFVDEYDPTIEDSYRKQVVIDGETCLLDILDTAGQEEYS
AMRDQYMRTGEGFLCVFAINNTKSFEDIHQYREQIKRVKDSDDVPMVLVGNKCDLAARTVESR
QAQDLARSYGIPYIETSAKTRQGVEDAFYTLVREIRQHKLRKLNPPDESGPGCMSCKCVLS
(SEQ ID NO: 162)

Cocaine And Amphetamine Regulated Transcript (Chain A) [Homo sapiens], PDB: 1HY9_A:
YGQVPMCDAGEQCAVRKGARIGKLCDCPRGTSCNSFLLKCL (SEQ ID NO: 163)

Protachykinin-1 [Homo sapiens], UniProtKB - P20366:
MKILVALAVFFLVSTQLFAEEIGANDDLNYWSDWYDSDQIKEELPEPFEHLLQRIARRPKPQQFF
GLMGKRDADSSIEKQVALLKALYGHGQISHKRHKTDSFVGLMGKRALNSVAYERSAMQNYER
RR (SEQ ID NO: 164)

FIG. 79 cont'd

Substance P is position 58-68 of Protachykinin-1 [Homo sapiens]:
RPKPQQFFGLM (SEQ ID NO: 165)

Oxytocin-neurophysin 1 [Homo sapiens], UniProtKB - P01178:
MAGPSLACCLLGLLALTSACYIQNCPLGGKRAAPDLDVRKCLPCGPGGKGRCFGPNICCAEEL
GCFVGTAEALRCQEENYLPSPCQSGQKACGSGGRCAVLGLCCSPDGCHADPACDAEATFSQ
R (SEQ ID NO: 166)

Oxytocin is position 20-28 of Oxytocin-neurophysin 1 [Homo sapiens]:
CYIQNCPLG (SEQ ID NO: 167)

Somatostatin [Homo sapiens], GenBank: AAH32625.1:
MLSCRLQCALAALSIVLALGCVTGAPSDPRLRQFLQKSLAAAAGKQELAKYFLAELLSEPNQTE
NDALEPEDLSQAAEQDEMRLELQRSANSNPAMAPRERKAGCKNFFWKTFTSC (SEQ ID NO: 168)

SEQUENCE LISTING

```
<160> NUMBER OF SEQ ID NOS: 188

<210> SEQ ID NO 1
<211> LENGTH: 49
<212> TYPE: DNA
<213> ORGANISM: Artificial Sequence
<220> FEATURE:
<223> OTHER INFORMATION: 5' Cloning Primer

<400> SEQUENCE: 1

ggtggagtcg tgacctagga cgcgtttcta atcatgaatt cttttgtgg          49
```

<210> SEQ ID NO 2
<211> LENGTH: 46
<212> TYPE: DNA
<213> ORGANISM: Artificial Sequence
<220> FEATURE:
<223> OTHER INFORMATION: 5' Cloning Primer

<400> SEQUENCE: 2
ggtggagtcg tgacctagga cgcgtctgat tgtacagcag gcactc 46

<210> SEQ ID NO 3
<211> LENGTH: 45
<212> TYPE: DNA
<213> ORGANISM: Artificial Sequence
<220> FEATURE:
<223> OTHER INFORMATION: 5' Cloning Primer

<400> SEQUENCE: 3
ggtggagtcg tgacctagga cgcgtacctt tccagcctgg cttac 45

<210> SEQ ID NO 4
<211> LENGTH: 44
<212> TYPE: DNA
<213> ORGANISM: Artificial Sequence
<220> FEATURE:
<223> OTHER INFORMATION: 5' Cloning Primer

<400> SEQUENCE: 4
ggtggagtcg tgacctagga cgcgtataag ccttgggggc aatc 44

<210> SEQ ID NO 5
<211> LENGTH: 35
<212> TYPE: DNA
<213> ORGANISM: Artificial Sequence
<220> FEATURE:
<223> OTHER INFORMATION: 5' Cloning Primer

<400> SEQUENCE: 5
cgtacacgcg tatgtgtctt ttactctgat cctcc 35

<210> SEQ ID NO 6
<211> LENGTH: 35
<212> TYPE: DNA
<213> ORGANISM: Artificial Sequence
<220> FEATURE:
<223> OTHER INFORMATION: 5' Cloning Primer

<400> SEQUENCE: 6
cgtacacgcg tcagtagtgt taatgacaga gtcag 35

<210> SEQ ID NO 7
<211> LENGTH: 31
<212> TYPE: DNA
<213> ORGANISM: Artificial Sequence
<220> FEATURE:
<223> OTHER INFORMATION: 5' Cloning Primer

<400> SEQUENCE: 7
cgtacacgcg tccttttcca accgttcctt c 31

<210> SEQ ID NO 8
<211> LENGTH: 31
<212> TYPE: DNA
<213> ORGANISM: Artificial Sequence
<220> FEATURE:
<223> OTHER INFORMATION: 5' Cloning Primer

<400> SEQUENCE: 8
cgtacacgcg tgtcccatag gcagtttgtg g 31

<210> SEQ ID NO 9
<211> LENGTH: 31
<212> TYPE: DNA
<213> ORGANISM: Artificial Sequence
<220> FEATURE:
<223> OTHER INFORMATION: 5' Cloning Primer

<400> SEQUENCE: 9
cgtacacgcg tagccgctct caccttctat a 31

<210> SEQ ID NO 10
<211> LENGTH: 31
<212> TYPE: DNA
<213> ORGANISM: Artificial Sequence
<220> FEATURE:
<223> OTHER INFORMATION: 5' Cloning Primer

<400> SEQUENCE: 10
cgtacacgcg tgagctgggc atcatcacat c 31

<210> SEQ ID NO 11
<211> LENGTH: 31
<212> TYPE: DNA
<213> ORGANISM: Artificial Sequence
<220> FEATURE:
<223> OTHER INFORMATION: 5' Cloning Primer

<400> SEQUENCE: 11
cgtacacgcg tagggtgcag gagaaatgtg a 31

<210> SEQ ID NO 12
<211> LENGTH: 47
<212> TYPE: DNA
<213> ORGANISM: Artificial Sequence
<220> FEATURE:
<223> OTHER INFORMATION: 3' Cloning Primer

<400> SEQUENCE: 12
cttttatgcc cagcccgagc tcaatgttct tgaacttacc aatcagg 47

<210> SEQ ID NO 13
<211> LENGTH: 43
<212> TYPE: DNA
<213> ORGANISM: Artificial Sequence
<220> FEATURE:
<223> OTHER INFORMATION: 3' Cloning Primer

<400> SEQUENCE: 13
cttttatgcc cagcccgagc tcatgccgtg aagtaatcca gtg 43

<210> SEQ ID NO 14
<211> LENGTH: 45
<212> TYPE: DNA
<213> ORGANISM: Artificial Sequence
<220> FEATURE:
<223> OTHER INFORMATION: 3' Cloning Primer

<400> SEQUENCE: 14
cttttatgcc cagcccgagc tccggtggtt gaaataaaca agaac 45

<210> SEQ ID NO 15

<211> LENGTH: 44
<212> TYPE: DNA
<213> ORGANISM: Artificial Sequence
<220> FEATURE:
<223> OTHER INFORMATION: 3' Cloning Primer

<400> SEQUENCE: 15
cttttatgcc cagcccgagc tcatttgtcc tgtgcatagc attg 44

<210> SEQ ID NO 16
<211> LENGTH: 34
<212> TYPE: DNA
<213> ORGANISM: Artificial Sequence
<220> FEATURE:
<223> OTHER INFORMATION: 3' Cloning Primer

<400> SEQUENCE: 16
cgtacgagct ctgttgctac actagactca atgg 34

<210> SEQ ID NO 17
<211> LENGTH: 35
<212> TYPE: DNA
<213> ORGANISM: Artificial Sequence
<220> FEATURE:
<223> OTHER INFORMATION: 3' Cloning Primer

<400> SEQUENCE: 17
cgtacgagct cggcttgagt atagacaaac cactc 35

<210> SEQ ID NO 18
<211> LENGTH: 30
<212> TYPE: DNA
<213> ORGANISM: Artificial Sequence
<220> FEATURE:
<223> OTHER INFORMATION: 3' Cloning Primer

<400> SEQUENCE: 18
cgtacgagct ctgctcagga accaaaggag 30

<210> SEQ ID NO 19
<211> LENGTH: 33
<212> TYPE: DNA
<213> ORGANISM: Artificial Sequence
<220> FEATURE:
<223> OTHER INFORMATION: 3' Cloning Primer

<400> SEQUENCE: 19
cgtacgagct cagaccttac cactgcattc tga 33

<210> SEQ ID NO 20
<211> LENGTH: 32
<212> TYPE: DNA
<213> ORGANISM: Artificial Sequence
<220> FEATURE:
<223> OTHER INFORMATION: 3' Cloning Primer

<400> SEQUENCE: 20
cgtacgagct cctgggatga acggaattgt gt 32

<210> SEQ ID NO 21
<211> LENGTH: 31
<212> TYPE: DNA
<213> ORGANISM: Artificial Sequence
<220> FEATURE:
<223> OTHER INFORMATION: 3' Cloning Primer

<400> SEQUENCE: 21
cgtacgagct ctgccgtctg atttgcatac t 31

<210> SEQ ID NO 22
<211> LENGTH: 31
<212> TYPE: DNA
<213> ORGANISM: Artificial Sequence
<220> FEATURE:
<223> OTHER INFORMATION: 3' Cloning Primer

<400> SEQUENCE: 22
cgtacgagct ccttgcccat gaacgttctg t 31

<210> SEQ ID NO 23
<211> LENGTH: 4712
<212> TYPE: DNA
<213> ORGANISM: Artificial Sequence
<220> FEATURE:
<223> OTHER INFORMATION: CN1818 top strand

<400> SEQUENCE: 23
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccgca cgcgtttacc ctgttgaata tcactgactc 180
actaacttgc attgccatgc taacttgctt tcagagagat ctcagaacac atcatcttct 240
gctatttcaa tacatgcaca ttaatttcct atcaacgtgt gctgatcagg aactctgtaa 300
tctggcaccg ttaccctgtt gaatatcact gactcactaa cttgcattgc catgctaact 360
tgctttcaga gagatctcag aacacatcat cttctgctat ttcaatacat gcacattaat 420
ttcctatcaa cgtgtgctga tcaggaactc tgtaatctgg caccgttacc ctgttgaata 480
tcactgactc actaacttgc attgccatgc taacttgctt tcagagagat ctcagaacac 540
atcatcttct gctatttcaa tacatgcaca ttaatttcct atcaacgtgt gctgatcagg 600
aactctgtaa tctggcaccg cttaaggagc tcagaggtag gcgtgtacgg tgggaggcct 660
atataagcag agctggttta gtgaaccgtc agatcgcctg gggatccttc gaagctagcg 720
ctaccggtcg ccaccatggt gagcaagggc gaggagctgt tcaccggggt ggtgcccatc 780
ctggtcgagc tggacggcga cgtaaacggc cacaagttca gcgtgtccgg cgagggcgag 840
ggcgatgcca cctacggcaa gctgaccctg aagctgatct gcaccaccgg caagctgccc 900
gtgccctggc ccaccctcgt gaccaccctg ggctacggcg tgcagtgctt cgcccgctac 960
cccgaccaca tgaagcagca cgacttcttc aagtccgcca tgcccgaagg ctacgtccag 1020
gagcgcacca tcttcttcaa ggacgacggc aactacaaga cccgcgccga ggtgaagttc 1080
gagggcgaca ccctggtgaa ccgcatcgag ctgaagggca tcgacttcaa ggaggacggc 1140
aacatcctgg ggcacaagct ggagtacaac tacaacagcc acaacgtcta tatcaccgcc 1200
gacaagcaga agaacggcat caaggccaac ttcaagatcc gccacaacat cgaggacggc 1260
ggcgtgcagc tcgccgacca ctaccagcag aacaccccca tcggcgacgg ccccgtgctg 1320
ctgcccgaca accactacct gagctaccag tccaagctga gcaaagaccc caacgagaag 1380
cgcgatcaca tggtcctgct ggagttcgtg accgccgccg ggatcactct cggcatggac 1440
gagctgtaca agtaagtcga cggcgcgccg cggccgcgaa ttcgatatca taatcaacct 1500
ctggattaca aaatttgtga aagattgact ggtattctta actatgttgc tccttttacg 1560
ctatgtggat acgctgcttt aatgcctttg tatcatgcta ttgcttcccg tatggctttc 1620

-continued

```
atttctcct ccttgtataa atcctggtta gttcttgcca cggcggaact catcgccgcc   1680
tgccttgccc gctgctggac aggggctcgg ctgttgggca ctgacaattc cgtggctcga   1740
gagatcttcg actgtgcctt ctagttgcca gccatctgtt gtttgcccct cccccgtgcc   1800
ttccttgacc ctggaaggtg ccactcccac tgtcctttcc taataaaatg aggaaattgc   1860
atcgcattgt ctgagtaggt gtcattctat tctggggggt ggggtggggc aggacagcaa   1920
gggggaggat tgggaagaca atagcaggca tgcacgtgcg gaccgagcgg ccgcaggaac   1980
ccctagtgat ggagttggcc actccctctc tgcgcgctcg ctcgctcact gaggccgggc   2040
gaccaaaggt cgcccgacgc ccgggctttg cccgggcggc ctcagtgagc gagcgagcgc   2100
gcagctgcct gcaggggcgc ctgatgcggt attttctcct tacgcatctg tgcggtattt   2160
cacaccgcat acgtcaaagc aaccatagta cgcgccctgt agcggcgcat taagcgcggc   2220
gggtgtggtg gttacgcgca gcgtgaccgc tacacttgcc agcgccctag cgcccgctcc   2280
tttcgctttc ttcccttcct ttctcgccac gttcgccggc tttccccgtc aagctctaaa   2340
tcgggggctc cctttagggt tccgatttag tgctttacgg cacctcgacc ccaaaaaact   2400
tgatttgggt gatggttcac gtagtgggcc atcgccctga tagacggttt ttcgcccttt   2460
gacgttggag tccacgttct ttaatagtgg actcttgttc caaactggaa caacactcaa   2520
ccctatctcg ggctattctt ttgatttata agggattttg ccgatttcgg cctattggtt   2580
aaaaaatgag ctgatttaac aaaaatttaa cgcgaatttt aacaaaatat taacgtttac   2640
aattttatgg tgcactctca gtacaatctg ctctgatgcc gcatagttaa gccagccccg   2700
acacccgcca acacccgctg acgcgccctg acgggcttgt ctgctcccgg catccgctta   2760
cagacaagct gtgaccgtct ccgggagctg catgtgtcag aggttttcac cgtcatcacc   2820
gaaacgcgcg agacgaaagg gcctcgtgat acgcctattt ttataggtta atgtcatgat   2880
aataatggtt tcttagacgt caggtggcac ttttcgggga aatgtgcgcg gaacccctat   2940
ttgtttattt ttctaaatac attcaaatat gtatccgctc atgagacaat aaccctgata   3000
aatgcttcaa taatattgaa aaaggaagag tatgagtatt caacatttcc gtgtcgccct   3060
tattcccttt tttgcggcat tttgccttcc tgtttttgct cacccagaaa cgctggtgaa   3120
agtaaaagat gctgaagatc agttgggtgc acgagtgggt tacatcgaac tggatctcaa   3180
cagcggtaag atccttgaga gttttcgccc cgaagaacgt tttccaatga tgagcacttt   3240
taaagttctg ctatgtggcg cggtattatc ccgtattgac gccgggcaag agcaactcgg   3300
tcgccgcata cactattctc agaatgactt ggttgagtac tcaccagtca cagaaaagca   3360
tcttacggat ggcatgacag taagagaatt atgcagtgct gccataacca tgagtgataa   3420
cactgcggcc aacttacttc tgacaacgat cggaggaccg aaggagctaa ccgctttttt   3480
gcacaacatg ggggatcatg taactcgcct tgatcgttgg gaaccggagc tgaatgaagc   3540
cataccaaac gacgagcgtg acaccacgat gcctgtagca atggcaacaa cgttgcgcaa   3600
actattaact ggcgaactac ttactctagc ttcccggcaa caattaatag actggatgga   3660
ggcggataaa gttgcaggac cacttctgcg ctcggccctt ccggctggct ggtttattgc   3720
tgataaatct ggagccggtg agcgtgggtc tcgcggtatc attgcagcac tggggccaga   3780
tggtaagccc tcccgtatcg tagttatcta cacgacgggg agtcaggcaa ctatggatga   3840
acgaaataga cagatcgctg agataggtgc ctcactgatt aagcattggt aactgtcaga   3900
ccaagtttac tcatatatac tttagattga tttaaaactt catttttaat ttaaaaggat   3960
ctaggtgaag atcctttttg ataatctcat gaccaaaatc ccttaacgtg agttttcgtt   4020
```

```
ccactgagcg tcagaccccg tagaaaagat caaaggatct tcttgagatc cttttttttct   4080

gcgcgtaatc tgctgcttgc aaacaaaaaa accaccgcta ccagcggtgg tttgtttgcc   4140

ggatcaagag ctaccaactc tttttccgaa ggtaactggc ttcagcagag cgcagatacc   4200

aaatactgtc cttctagtgt agccgtagtt aggccaccac ttcaagaact ctgtagcacc   4260

gcctacatac ctcgctctgc taatcctgtt accagtggct gctgccagtg gcgataagtc   4320

gtgtcttacc gggttggact caagacgata gttaccggat aaggcgcagc ggtcgggctg   4380

aacggggggt tcgtgcacac agcccagctt ggagcgaacg acctacaccg aactgagata   4440

cctacagcgt gagctatgag aaagcgccac gcttcccgaa gggagaaagg cggacaggta   4500

tccggtaagc ggcagggtcg gaacaggaga gcgcacgagg gagcttccag ggggaaacgc   4560

ctggtatctt tatagtcctg tcgggtttcg ccacctctga cttgagcgtc gatttttgtg   4620

atgctcgtca ggggggcgga gcctatggaa aaacgccagc aacgcggcct ttttacggtt   4680

cctggccttt tgctggcctt ttgctcacat gt                                 4712
```

<210> SEQ ID NO 24
<211> LENGTH: 4712
<212> TYPE: DNA
<213> ORGANISM: Artificial Sequence
<220> FEATURE:
<223> OTHER INFORMATION: CN1818 bottom strand

<400> SEQUENCE: 24

```
acatgtgagc aaaaggccag caaaaggcca ggaaccgtaa aaaggccgcg ttgctggcgt     60

ttttccatag gctccgcccc cctgacgagc atcacaaaaa tcgacgctca agtcagaggt    120

ggcgaaaccc gacaggacta taaagatacc aggcgtttcc ccctggaagc tccctcgtgc    180

gctctcctgt tccgaccctg ccgcttaccg gatacctgtc cgcctttctc ccttcgggaa    240

gcgtggcgct ttctcatagc tcacgctgta ggtatctcag ttcggtgtag gtcgttcgct    300

ccaagctggg ctgtgtgcac gaaccccccg ttcagcccga ccgctgcgcc ttatccggta    360

actatcgtct tgagtccaac ccggtaagac acgacttatc gccactggca gcagccactg    420

gtaacaggat tagcagagcg aggtatgtag gcggtgctac agagttcttg aagtggtggc    480

ctaactacgg ctacactaga aggacagtat ttggtatctg cgctctgctg aagccagtta    540

ccttcggaaa aagagttggt agctcttgat ccggcaaaca aaccaccgct ggtagcggtg    600

gtttttttgt ttgcaagcag cagattacgc gcagaaaaaa aggatctcaa gaagatcctt    660

tgatcttttc tacggggtct gacgctcagt ggaacgaaaa ctcacgttaa gggattttgg    720

tcatgagatt atcaaaaagg atcttcacct agatcctttt aaattaaaaa tgaagtttta    780

aatcaatcta aagtatatat gagtaaactt ggtctgacag ttaccaatgc ttaatcagtg    840

aggcacctat ctcagcgatc tgtctatttc gttcatccat agttgcctga ctccccgtcg    900

tgtagataac tacgatacgg gagggcttac catctggccc cagtgctgca atgataccgc    960

gagacccacg ctcaccggct ccagatttat cagcaataaa ccagccagcc ggaagggccg   1020

agcgcagaag tggtcctgca actttatccg cctccatcca gtctattaat tgttgccggg   1080

aagctagagt aagtagttcg ccagttaata gtttgcgcaa cgttgttgcc attgctacag   1140

gcatcgtggt gtcacgctcg tcgtttggta tggcttcatt cagctccggt tcccaacgat   1200

caaggcgagt tacatgatcc cccatgttgt gcaaaaaagc ggttagctcc ttcggtcctc   1260

cgatcgttgt cagaagtaag ttggccgcag tgttatcact catggttatg gcagcactgc   1320
```

-continued

```
ataattctct tactgtcatg ccatccgtaa gatgcttttc tgtgactggt gagtactcaa   1380
ccaagtcatt ctgagaatag tgtatgcggc gaccgagttg ctcttgcccg gcgtcaatac   1440
gggataatac cgcgccacat agcagaactt taaaagtgct catcattgga aaacgttctt   1500
cggggcgaaa actctcaagg atcttaccgc tgttgagatc cagttcgatg taacccactc   1560
gtgcacccaa ctgatcttca gcatctttta ctttcaccag cgtttctggg tgagcaaaaa   1620
caggaaggca aaatgccgca aaaaagggaa taagggcgac acggaaatgt tgaatactca   1680
tactcttcct ttttcaatat tattgaagca tttatcaggg ttattgtctc atgagcggat   1740
acatatttga atgtatttag aaaaataaac aaataggggt tccgcgcaca tttccccgaa   1800
aagtgccacc tgacgtctaa gaaaccatta ttatcatgac attaacctat aaaaataggc   1860
gtatcacgag gccctttcgt ctcgcgcgtt tcggtgatga cggtgaaaac ctctgacaca   1920
tgcagctccc ggagacggtc acagcttgtc tgtaagcgga tgccgggagc agacaagccc   1980
gtcagggcgc gtcagcgggt gttggcgggt gtcggggctg gcttaactat gcggcatcag   2040
agcagattgt actgagagtg caccataaaa ttgtaaacgt taatattttg ttaaaattcg   2100
cgttaaattt ttgttaaatc agctcatttt ttaaccaata ggccgaaatc ggcaaaatcc   2160
cttataaatc aaaagaatag cccgagatag ggttgagtgt tgttccagtt tggaacaaga   2220
gtccactatt aaagaacgtg gactccaacg tcaaagggcg aaaaaccgtc tatcagggcg   2280
atggcccact acgtgaacca tcacccaaat caagtttttt ggggtcgagg tgccgtaaag   2340
cactaaatcg gaaccctaaa gggagccccc gatttagagc ttgacgggga aagccggcga   2400
acgtggcgag aaaggaaggg aagaaagcga aaggagcggg cgctagggcg ctggcaagtg   2460
tagcggtcac gctgcgcgta accaccacac ccgccgcgct taatgcgccg ctacagggcg   2520
cgtactatgg ttgctttgac gtatgcggtg tgaaataccg cacagatgcg taaggagaaa   2580
ataccgcatc aggcgcccct gcaggcagct gcgcgctcgc tcgctcactg aggccgcccg   2640
ggcaaagccc gggcgtcggg cgacctttgg tcgcccggcc tcagtgagcg agcgagcgcg   2700
cagagaggga gtggccaact ccatcactag gggttcctgc ggccgctcgg tccgcacgtg   2760
catgcctgct attgtcttcc caatcctccc ccttgctgtc ctgccccacc ccacccccca   2820
gaatagaatg acacctactc agacaatgcg atgcaatttc ctcattttat taggaaagga   2880
cagtgggagt ggcaccttcc agggtcaagg aaggcacggg ggaggggcaa acaacagatg   2940
gctggcaact agaaggcaca gtcgaagatc tctcgagcca cggaattgtc agtgcccaac   3000
agccgagccc ctgtccagca gcgggcaagg caggcggcga tgagttccgc cgtggcaaga   3060
actaaccagg atttatacaa ggaggagaaa atgaaagcca tacgggaagc aatagcatga   3120
tacaaaggca ttaaagcagc gtatccacat agcgtaaaag gagcaacata gttaagaata   3180
ccagtcaatc tttcacaaat tttgtaatcc agaggttgat tatgatatcg aattcgcggc   3240
cgcggcgcgc cgtcgactta cttgtacagc tcgtccatgc cgagagtgat cccggcggcg   3300
gtcacgaact ccagcaggac catgtgatcg cgcttctcgt tggggtcttt gctcagcttg   3360
gactggtagc tcaggtagtg gttgtcgggc agcagcacgg ggccgtcgcc gatgggggtg   3420
ttctgctggt agtggtcggc gagctgcacg ccgccgtcct cgatgttgtg gcggatcttg   3480
aagttggcct tgatgccgtt cttctgcttg tcggcggtga tatagacgtt gtggctgttg   3540
tagttgtact ccagcttgtg ccccaggatg ttgccgtcct ccttgaagtc gatgcccttc   3600
agctcgatgc ggttcaccag ggtgtcgccc tcgaacttca cctcggcgcg ggtcttgtag   3660
ttgccgtcgt ccttgaagaa gatggtgcgc tcctggacgt agccttcggg catggcggac   3720
```

ttgaagaagt cgtgctgctt catgtggtcg gggtagcggg cgaagcactg cacgccgtag 3780
cccagggtgg tcacgagggt gggccagggc acgggcagct tgccggtggt gcagatcagc 3840
ttcagggtca gcttgccgta ggtggcatcg ccctcgccct cgccggacac gctgaacttg 3900
tggccgttta cgtcgccgtc cagctcgacc aggatgggca ccaccccggt gaacagctcc 3960
tcgcccttgc tcaccatggt ggcgaccggt agcgctagct tcgaaggatc cccaggcgat 4020
ctgacggttc actaaaccag ctctgcttat ataggcctcc caccgtacac gcctacctct 4080
gagctcctta agcggtgcca gattacagag ttcctgatca gcacacgttg ataggaaatt 4140
aatgtgcatg tattgaaata gcagaagatg atgtgttctg agatctctct gaaagcaagt 4200
tagcatggca atgcaagtta gtgagtcagt gatattcaac agggtaacgg tgccagatta 4260
cagagttcct gatcagcaca cgttgatagg aaattaatgt gcatgtattg aaatagcaga 4320
agatgatgtg ttctgagatc tctctgaaag caagttagca tggcaatgca agttagtgag 4380
tcagtgatat tcaacagggt aacggtgcca gattacagag ttcctgatca gcacacgttg 4440
ataggaaatt aatgtgcatg tattgaaata gcagaagatg atgtgttctg agatctctct 4500
gaaagcaagt tagcatggca atgcaagtta gtgagtcagt gatattcaac agggtaaacg 4560
cgtgcggccg caggaacccc tagtgatgga gttggccact ccctctctgc gcgctcgctc 4620
gctcactgag gccgggcgac caaaggtcgc ccgacgcccg ggctttgccc gggcggcctc 4680
agtgagcgag cgagcgcgca gctgcctgca gg 4712

<210> SEQ ID NO 25
<211> LENGTH: 854
<212> TYPE: DNA
<213> ORGANISM: Mus musculus

<400> SEQUENCE: 25
ctccaaattt cttcaaccaa gtagagaaaa atgagagaga aggaaagaaa aaaagaggta 60
tggggagaag agaaagaagg caacttgtta aaaatctcag tcaaacttac atactatata 120
gaacagcatg gtgaatttag ggcacatgga tataaaatgg aagtttctta ttcagtagca 180
gcaacttgtg ggcacaggag ttggcaaaga taaaaatgtc caaagtcaca aatacaatgt 240
atagttagtc ataggtgctg ttatttgcct caaaaaatag acttttattt tgcctttctt 300
ttctttaacc acactcaaaa ttagagaaca gagacaaaac ccagcaggaa atagcacaga 360
aagcccacag aatcaaagac gtgttcaaac agccagctga attcattgca catttcaacc 420
acagaaatat tttcaggtga ttctgttgtt tgacaaaacg tgggaaccac aggatctaca 480
acacttgcaa gcaaaactca acagctctaa taatagttac agaagtgaaa gccaatttgg 540
ataaaataag acattgactc aagtcctctc agaagagttt tgaaagcaaa gtttacaaaa 600
gtctggtttg tcctttggga tttacagacc tttcagcccc ttgattcatt tttttttttt 660
tggatttctt catcactggg agaattccca tgcattattt ctcccctgct tcaaaatcat 720
caaatgtgaa acatttttca ctcttttctt ctgtatatag tgataaaata gctattggct 780
tttggctaaa tgtgctactt tgagcccacc cacacaaggg agaaatgggg gcagacatga 840
gtttgggcat gagt 854

<210> SEQ ID NO 26
<211> LENGTH: 564
<212> TYPE: DNA
<213> ORGANISM: Mus musculus

<400> SEQUENCE: 26
ttctaatcat gaattctttt gtggtatttt agattttcag tttgttctgt atcaattctc 60
tctcattcaa agaatatgat agtgaggtag atgaagctgc ctaagccaca ggaagaaaca 120
tcttcagtct gtcgtaaatg cacttcagat acagcacctt gcactgcaca taaaaattca 180
tagtcaccta agtgggaata gctatgaaaa tctgagtatc gccatgctgt tgactcagtg 240
ctatttataa aactcagttt taatgtttcc aatttaaatt ctctgcacat atctctcctg 300
cactaaagac ttgagatacc agtgctttac cctaaaatat cttgctttta tatcttgact 360
cttatgttga gaatttatta tttttaaaat atactttaaa acatgcattg gtacaaaatt 420
agtcaaaaca gcaaccagtg aattcaaagt aaattagtat tattaatgct gtgtataatt 480
ttggtgaatt ttactattaa attataaata aaaagtcctt ccaggtagtc atgttcactc 540
ctgattggta agttcaagaa catt 564

<210> SEQ ID NO 27
<211> LENGTH: 562
<212> TYPE: DNA
<213> ORGANISM: Mus musculus

<400> SEQUENCE: 27
cctttccagc ctggcttaca ggcttttttc accacagtac caattgccca tgctctgctc 60
attaatttaa atggcaatga ctatctgggt tttaaaatag agaagtgtca ggatgggaac 120
acgcaatcat ttggcttttt gcgttccagc actgttttga atagcagggt tttcacttcc 180
tatgaaacct tagcaggagg aaaagcggaa actaaaccat aaagtgagag ggatgagggg 240
agggagggac ttgagtattt gtaaactcag ggtggctggc cctgcctacc aggctgctct 300
ctaccaccgg aggctaggag tggaaaaact tgatttacgt gttgtgcctg cctttttttt 360
ttcttcttct tcttcttctt cttcttcgtc tccacaccac cttctgtaca cctgactctg 420
cataagccta tctgaagctg gcttggtggc agggatagct ggagaacaga agaatgtgcg 480
gagggaggga gggaggaagg gagggctggt acttttccat tcacatctcc acagtggctg 540
ttcttgttta tttcaaccac cg 562

<210> SEQ ID NO 28
<211> LENGTH: 555
<212> TYPE: DNA
<213> ORGANISM: Mus musculus

<400> SEQUENCE: 28
agccttgggg gcaatcaaac tattacattg agtccttgga tttgctacaa attacatttt 60
aaatgcaatc attttataaa agcttcaaca ctcacacttg gaagcgttac cctgttgaat 120
atcactgact cactaacttg cattgccatg ctaacttgct ttcagagaga tctcagaaca 180
catcatcttc tgctatttca atacatgcac attaatttcc tatcaacgtg tgctgatcag 240
gaactctgta atctggcacc ggtgtttatt tttattcctg tctattcctg ttggctcacg 300
aaaagattgt ttgagcaagt gttttatggt gagttgtatc atatgtacat tgatttaatc 360
tgcccacatt cagttctaca agcggagcca aaaaaataga gacaagcata attttcattc 420
aacatgagcc cctcaatgca agccaagtac ctcatctggt gctcagctaa agcaacagca 480
atctgttcca ccctggagac acaactggcc acagaaaact tagtgaaaag aggcaatgct 540
atgcacagga caaat 555

<210> SEQ ID NO 29
<211> LENGTH: 155
<212> TYPE: DNA
<213> ORGANISM: Mus musculus

<400> SEQUENCE: 29
ttaccctgtt gaatatcact gactcactaa cttgcattgc catgctaact tgctttcaga 60
gagatctcag aacacatcat cttctgctat ttcaatacat gcacattaat ttcctatcaa 120
cgtgtgctga tcaggaactc tgtaatctgg caccg 155

<210> SEQ ID NO 30
<211> LENGTH: 465
<212> TYPE: DNA
<213> ORGANISM: Artificial Sequence
<220> FEATURE:
<223> OTHER INFORMATION: concatemer of Mus musculus core enhancer

<400> SEQUENCE: 30
ttaccctgtt gaatatcact gactcactaa cttgcattgc catgctaact tgctttcaga 60
gagatctcag aacacatcat cttctgctat ttcaatacat gcacattaat ttcctatcaa 120
cgtgtgctga tcaggaactc tgtaatctgg caccgttacc ctgttgaata tcactgactc 180
actaacttgc attgccatgc taacttgctt tcagagagat ctcagaacac atcatcttct 240
gctatttcaa tacatgcaca ttaatttcct atcaacgtgt gctgatcagg aactctgtaa 300
tctggcaccg ttaccctgtt gaatatcact gactcactaa cttgcattgc catgctaact 360
tgctttcaga gagatctcag aacacatcat cttctgctat ttcaatacat gcacattaat 420
ttcctatcaa cgtgtgctga tcaggaactc tgtaatctgg caccg 465

<210> SEQ ID NO 31
<211> LENGTH: 2000
<212> TYPE: DNA
<213> ORGANISM: Artificial Sequence
<220> FEATURE:
<223> OTHER INFORMATION: concatamer of Mus musculus enhancer

<400> SEQUENCE: 31
ccttggattt gctacaaatt acattttaaa tgcaatcatt ttataaaagc ttcaacactc 60
acacttggaa gcgttaccct gttgaatatc actgactcac taacttgcat tgccatgcta 120
acttgctttc agagagatct cagaacacat catcttctgc tatttcaata catgcacatt 180
aatttcctat caacgtgtgc tgatcaggaa ctctgtaatc tggcaccggt gtttattttt 240
attcctgtct attcctgttg gctcacgaaa agattgtttg agcaagtgtt ttatggtgag 300
ttgtatcata tgtacattga tttaatctgc ccacattcag ttctacaagc ggagccaaaa 360
aaatagagac aagcataatt ttcattcaac atgagcccct caatgcaagc caagtacctc 420
atctggtgct cagctaaagc aacagcaatc tgttccaccc tggagacaca actggccaca 480
gaaaacttag tgaaaagagg ccttggattt gctacaaatt acattttaaa tgcaatcatt 540
ttataaaagc ttcaacactc acacttggaa gcgttaccct gttgaatatc actgactcac 600
taacttgcat tgccatgcta acttgctttc agagagatct cagaacacat catcttctgc 660
tatttcaata catgcacatt aatttcctat caacgtgtgc tgatcaggaa ctctgtaatc 720
tggcaccggt gtttattttt attcctgtct attcctgttg gctcacgaaa agattgtttg 780
agcaagtgtt ttatggtgag ttgtatcata tgtacattga tttaatctgc ccacattcag 840
ttctacaagc ggagccaaaa aaatagagac aagcataatt ttcattcaac atgagcccct 900
caatgcaagc caagtacctc atctggtgct cagctaaagc aacagcaatc tgttccaccc 960
tggagacaca actggccaca gaaaacttag tgaaaagagg ccttggattt gctacaaatt 1020
acattttaaa tgcaatcatt ttataaaagc ttcaacactc acacttggaa gcgttaccct 1080
gttgaatatc actgactcac taacttgcat tgccatgcta acttgctttc agagagatct 1140
cagaacacat catcttctgc tatttcaata catgcacatt aatttcctat caacgtgtgc 1200
tgatcaggaa ctctgtaatc tggcaccggt gtttattttt attcctgtct attcctgttg 1260
gctcacgaaa agattgtttg agcaagtgtt ttatggtgag ttgtatcata tgtacattga 1320
tttaatctgc ccacattcag ttctacaagc ggagccaaaa aaatagagac aagcataatt 1380
ttcattcaac atgagcccct caatgcaagc caagtacctc atctggtgct cagctaaagc 1440
aacagcaatc tgttccaccc tggagacaca actggccaca gaaaacttag tgaaaagagg 1500
ccttggattt gctacaaatt acattttaaa tgcaatcatt ttataaaagc ttcaacactc 1560
acacttggaa gcgttaccct gttgaatatc actgactcac taacttgcat tgccatgcta 1620
acttgctttc agagagatct cagaacacat catcttctgc tatttcaata catgcacatt 1680
aatttcctat caacgtgtgc tgatcaggaa ctctgtaatc tggcaccggt gtttattttt 1740
attcctgtct attcctgttg gctcacgaaa agattgtttg agcaagtgtt ttatggtgag 1800
ttgtatcata tgtacattga tttaatctgc ccacattcag ttctacaagc ggagccaaaa 1860
aaatagagac aagcataatt ttcattcaac atgagcccct caatgcaagc caagtacctc 1920
atctggtgct cagctaaagc aacagcaatc tgttccaccc tggagacaca actggccaca 1980
gaaaacttag tgaaaagagg 2000

<210> SEQ ID NO 32
<211> LENGTH: 501
<212> TYPE: DNA
<213> ORGANISM: Mus musculus

<400> SEQUENCE: 32
cactgtgcat agcatcatta caatgttata gtttttcaca ctatgccttg actttttgga 60
aaggcaaacc acctcttgga tttctccttc cttctctatc tctctctctc tctcttcctc 120
cctccgtccc tccatctctt cctccttccc attttcttct ctccctattt ggacacaata 180
taaaataatt tagatgaggt gagttaaatt gtgaacaaag tatgtgccta tacatggttg 240
taaatcagct tatcaaagtg taatattaga agaatttata aaaatgataa aattcatact 300
caaagttctg tgtaaagcaa taatagcttt atctcctttt agttatcttg agtctttcta 360
tgactaacaa ctccctcata ggcatcttaa agagcagtaa gcataagtag attccaaatg 420
ggaagggaga agtgtgaacc atcactttca tccagacttg tagatatatc tgctgcattt 480
tcagaaacca gaaacagaca g 501

<210> SEQ ID NO 33
<211> LENGTH: 501
<212> TYPE: DNA
<213> ORGANISM: Mus musculus

<400> SEQUENCE: 33
aaaatgttca ttttgccaat atgatcacca ataaaaccat ttgtgtagac tatccacctt 60
aatcccccta taatacaata gcacagaggt gagtcagttt gattttgata ctaggtttat 120
tttataggag ctattaaagt ttcagaattt tgctgagtca ccaggctctt cattttgtgg 180
caaatccatc actacagttt aaggagagaa gaaacagacc ccccccctacc ctctgaaaaa 240

```
taaaaataaa aacttgtttc aggcaggcta gcgattcact aataatgaga aaactccagt    300

tttaagactt aatttcacca taaatactct ttcattctaa gctctgggac atcatgagcc    360

agagaacagc agagtgaata atacagttac agagctgatg agcaatgcca gtcactgtaa    420

aaaatacaga atcccatcca aaggacatct gtaaaagtgt ctttaacatc tactcagccc    480

ttctgtgtaa aggtcagcac g                                              501
```

<210> SEQ ID NO 34
<211> LENGTH: 598
<212> TYPE: DNA
<213> ORGANISM: Mus musculus

<400> SEQUENCE: 34

```
ccttttccaa ccgttccttc atgacatcaa ggcttcagac tgctaagctt tgggcactac     60

ctggggtcag tctgcatcaa aatgtaaggc tcaaatgtgt aattgtaagt actgttttgc    120

tgagctggaa gggctccttt gaagcccacg ttttaatttt aatttagcca cacagagtgg    180

caaagacaaa tagatttatc caaaatacat ttggtaacag atttttgag tcagttatta     240

attttatttg aggggttcct ctttttattt tttataaact gtgaaactca agaggaagca    300

ggatcccatg caatgccttt tattgatggc ctgctatgtg ccaagaaagg tgttaaatgt    360

tttccaatgc tgcctcattt atcctgatct tacagacaag caaaaggagg tgtgaagagg    420

tgaagtttct cacccagctg gaaagtggca aagtcattca cagatctgcc tccgctcaaa    480

aaaattgctt tatgcaactc tttggaagct aacttcatgg gagctacatg cagcttctca    540

atgaaccttg ttttgctggc ctgcagccag aagttactac tcctttggtt cctgagca      598
```

<210> SEQ ID NO 35
<211> LENGTH: 501
<212> TYPE: DNA
<213> ORGANISM: Mus musculus

<400> SEQUENCE: 35

```
gactgctaag ctttgggcac tacctggggt cagtctgcat caaaatgtaa ggctcaaatg     60

tgtaattgta agtactgttt tgctgagctg gaagggctcc tttgaagccc acgttttaat    120

tttaatttag ccacacagag tggcaaagac aaatagattt atccaaaata catttggtaa    180

cagatttttt gagtcagtta ttaattttat ttgaggggtt cctcttttta tttttataa     240

actgtgaaac tcaagaggaa gcaggatccc atgcaatgcc ttttattgat ggcctgctat    300

gtgccaagaa aggtgttaaa tgttttccaa tgctgcctca tttatcctga tcttacagac    360

aagcaaaagg aggtgtgaag aggtgaagtt tctcacccag ctggaaagtg gcaaagtcat    420

tcacagatct gcctccgctc aaaaaaattg ctttatgcaa ctctttggaa gctaacttca    480

tgggagctac atgcagcttc t                                              501
```

<210> SEQ ID NO 36
<211> LENGTH: 501
<212> TYPE: DNA
<213> ORGANISM: Mus musculus

<400> SEQUENCE: 36

```
ggtgggctat gttactgagg gtctctgggt gttaggaaaa cagggcccag gagtctggct     60

gctcgtatgc tggcccaggc tcttgttttt cttgagctga cttgctggag aagtgagcta    120

agtcagaaac aaaatgccac attgcacgcc cactgaagtc tgggctcaag ggaaagaaga    180
```

gagattgcca gagcgttagc tgttcccaat ccactcctgg accttaagct gtcttgaaca 240
gagttgccaa tcagcttggt agggactggc ctttgaggag gggagggggt gtaggcaggg 300
gagggggaga gaagggagca gtctgcgctc catcttaatt acctcatcag aaacagctcc 360
cttcccgcaa agctctggtg tcttctacaa gagggtgagt ctttggcttt acatgtgaac 420
ttgtgccatt tgcctgcgta tataaacatg aagggtcgtc tgggttcaga gctgaaatct 480
ttcacttgtg acttagctgg g 501

<210> SEQ ID NO 37
<211> LENGTH: 501
<212> TYPE: DNA
<213> ORGANISM: Mus musculus

<400> SEQUENCE: 37
ctgtgctcag caatttacca ggacaccccc accccacatg tcttgaccac tgtctggata 60
actggtatgc aggaccacac taggcttact cacagtgtaa actctcataa ccatcactgg 120
agcccatcct gcctggtaga caaggattca accatgactc attgtacttt agtggtgcca 180
tgcttagtca tcaggtgccc tgtgctctga cagccgaggg tcagagctgg aatcacactc 240
ttgttgtctt ttaatctctc cctccctttc ttccttcttt cttcactctg ttgtgattgc 300
tcatggaaca gatcctagct ggtctccctg gcaacctaca tgatttgagc ccaacagatg 360
gataatgggg acatcgactt ccaatgtcat tcaacagaat cattgccaag ggagtctgat 420
gagcaggcaa ctgagatgac acccttatca atatagcttc attttggcaa tctggagtag 480
gtgtttcaaa aggagagccc c 501

<210> SEQ ID NO 38
<211> LENGTH: 2372
<212> TYPE: DNA
<213> ORGANISM: Artificial Sequence
<220> FEATURE:
<223> OTHER INFORMATION: concatamer of Mus musculus enhancer

<400> SEQUENCE: 38
ctgtgctcag caatttacca ggacaccccc accccacatg tcttgaccac tgtctggata 60
actggtatgc aggaccacac taggcttact cacagtgtaa actctcataa ccatcactgg 120
agcccatcct gcctggtaga caaggattca accatgactc attgtacttt agtggtgcca 180
tgcttagtca tcaggtgccc tgtgctctga cagccgaggg tcagagctgg aatcacactc 240
ttgttgtctt ttaatctctc cctccctttc ttccttcttt cttcactctg ttgtgattgc 300
tcatggaaca gatcctagct ggtctccctg gcaacctaca tgatttgagc ccaacagatg 360
gataatgggg acatcgactt ccaatgtcat tcaacagaat cattgccaag ggagtctgat 420
gagcaggcaa ctgagatgac acccttatca atatagcttc attttggcaa tctggagtag 480
gtgtttcaaa aggagagccc ccactgatgc cagcaataca gaacgttcat gggcaagtga 540
catagcgata gacagattcg actcggtacc agggtgcagg agaaatgtga cctcaaagtc 600
ttgttctata actgttggac cttaggagag atctgtgctc agcaatttac caggacaccc 660
ccaccccaca tgtcttgacc actgtctgga taactggtat gcaggaccac actaggctta 720
ctcacagtgt aaactctcat aaccatcact ggagcccatc ctgcctggta gacaaggatt 780
caaccatgac tcattgtact ttagtggtgc catgcttagt catcaggtgc cctgtgctct 840
gacagccgag ggtcagagct ggaatcacac tcttgttgtc ttttaatctc tccctccctt 900
tcttccttct ttcttcactc tgttgtgatt gctcatggaa cagatcctag ctggtctccc 960

```
tggcaaccta catgatttga gcccaacaga tggataatgg ggacatcgac ttccaatgtc   1020

attcaacaga atcattgcca agggagtctg atgagcaggc aactgagatg acacccttat   1080

caatatagct tcattttggc aatctggagt aggtgtttca aaggagagc ccccactgat    1140

gccagcaata cagaacgttc atgggcaagg atgatggcat cattgagtag catgatctca   1200

attgagggtg caggagaaat gtgacctcaa agtcttgttc tataactgtt ggaccttagg   1260

agagatctgt gctcagcaat ttaccaggac acccccaccc cacatgtctt gaccactgtc   1320

tggataactg gtatgcagga ccacactagg cttactcaca gtgtaaactc tcataaccat   1380

cactggagcc catcctgcct ggtagacaag gattcaacca tgactcattg tactttagtg   1440

gtgccatgct tagtcatcag gtgccctgtg ctctgacagc cgagggtcag agctggaatc   1500

acactcttgt tgtcttttaa tctctccctc cctttcttcc ttctttcttc actctgttgt   1560

gattgctcat ggaacagatc ctagctggtc tccctggcaa cctacatgat ttgagcccaa   1620

cagatggata atggggacat cgacttccaa tgtcattcaa cagaatcatt gccaagggag   1680

tctgatgagc aggcaactga gatgacaccc ttatcaatat agcttcattt tggcaatctg   1740

gagtaggtgt ttcaaaagga gagcccccac tgatgccagc aatacagaac gttcatgggc   1800

aaggagctca gggtgcagga gaaatgtgac ctcaaagtct tgttctataa ctgttggacc   1860

ttaggagaga tctgtgctca gcaatttacc aggacacccc caccccacat gtcttgacca   1920

ctgtctggat aactggtatg caggaccaca ctaggcttac tcacagtgta aactctcata   1980

accatcactg gagcccatcc tgcctggtag acaaggattc aaccatgact cattgtactt   2040

tagtggtgcc atgcttagtc atcaggtgcc ctgtgctctg acagccgagg gtcagagctg   2100

gaatcacact cttgttgtct tttaatctct ccctcccttt cttccttctt tcttcactct   2160

gttgtgattg ctcatggaac agatcctagc tggtctccct ggcaacctac atgatttgag   2220

cccaacagat ggataatggg gacatcgact tccaatgtca ttcaacagaa tcattgccaa   2280

gggagtctga tgagcaggca actgagatga cacccttatc aatatagctt cattttggca   2340

atctggagta ggtgtttcaa aaggagagcc cc                                 2372
```

<210> SEQ ID NO 39
<211> LENGTH: 536
<212> TYPE: DNA
<213> ORGANISM: Homo sapiens

<400> SEQUENCE: 39

```
tagtctgcct caggtacaca ctgagaaact gctttaatgt aacctgaccc acggttatta     60

gtgaaaatat cacttttgtt gttaccttat tcccaacaaa ttcatttctg ctttaatgga    120

aaagatccgg gttcacacta atcaggccca acggaaggcc atattagcaa tttggcaggt    180

acccgagggc catacctaat ctgcataaaa tgaagcagat tgcaaccgcc ctcatctttt    240

ttatttttaa actggttttt gaagcagagc ataaaatctc agagggagag acagaagatg    300

ctagtgcata cattttcctt catgccttta ttttcattct ttttgcacaa accatcttcc    360

tgaatggctg tttacctaaa gaagaataac aaaataaaag gtgctaggaa atggagtagg    420

cagagatcac aaatgtttaa ttaaaaaaaa aaaaagtcat gtactttcat agatattcac    480

aatcctctct agtatacttt caaatcagtt ttaatttcag tttagtgttt ttatgt        536
```

<210> SEQ ID NO 40
<211> LENGTH: 980
<212> TYPE: DNA

<213> ORGANISM: Artificial Sequence
<220> FEATURE:
<223> OTHER INFORMATION: concatamer of Homo sapiens enhancer core

<400> SEQUENCE: 40
gaaaagatcc gggttcacac taatcaggcc caacggaagg ccatattagc aatttggcag 60
gtacccgagg gccataccta atctgcataa aatgaagcag attgcaaccg ccctcatctt 120
ttttattttt aaactggttt ttgaagcaga gcataaaatc tcagagggag agacagaaga 180
tgctagtgca tacattttcc ttcatgcctt tattttcatt ctttttgcac aaaccatctt 240
cctgaatggc tgtttaccta aagaagaata acaaaataaa aggtgctagg aaatggagta 300
ggcagagatc gagcagagcc ctcatcacac agactgaaaa gatccgggtt cacactaatc 360
aggcccaacg gaaggccata ttagcaattt ggcaggtacc cgagggccat acctaatctg 420
cataaaatga agcagattgc aaccgccctc atctttttta tttttaaact ggtttttgaa 480
gcagagcata aaatctcaga gggagagaca gaagatgcta gtgcatacat tttccttcat 540
gcctttattt tcattctttt tgcacaaacc atcttcctga atggctgttt acctaaagaa 600
gaataacaaa ataaaaggtg ctaggaaatg gagtaggcag agatctgggt gagtaagagt 660
aggtggcaac gaaaagatcc gggttcacac taatcaggcc caacggaagg ccatattagc 720
aatttggcag gtacccgagg gccataccta atctgcataa aatgaagcag attgcaaccg 780
ccctcatctt ttttattttt aaactggttt ttgaagcaga gcataaaatc tcagagggag 840
agacagaaga tgctagtgca tacattttcc ttcatgcctt tattttcatt ctttttgcac 900
aaaccatctt cctgaatggc tgtttaccta aagaagaata acaaaataaa aggtgctagg 960
aaatggagta ggcagagatc 980

<210> SEQ ID NO 41
<211> LENGTH: 567
<212> TYPE: DNA
<213> ORGANISM: Homo sapiens

<400> SEQUENCE: 41
caaaagatgg aagttgggag gttgaagaag tgcaggatgg cattccaagt gatgggggca 60
atggcatgga ggtaggaaag cataaggtat attcaggcta taaataatag ttagatttgg 120
ctggatcctg gatttgagaa gccaggaaat gagataacac tggtcacttt cactaaagct 180
catgaaaaaa aaaatacata catatatata tatataaaat aaatatacat atatattttt 240
aagccccata tgactagagg aggcagccca tctgttctct gggcttcact tttcttgtct 300
gggaaatgag taggttggac tgcatggtct ttaaggtctc tttagtatta tcttgtttga 360
ctccgtaaag agaaaaacaa aggttcctcc tgacatcttg tgttgccttc caacgtccag 420
tccagtgtga ttgttttaag tactctttgg atattttact gttataaaaa gtgaagaaaa 480
agactgattt tgccaagtct tatggatcca aattagtact cattgcacta tggtcattta 540
gttgaggacg atactccagc ttcaaag 567

<210> SEQ ID NO 42
<211> LENGTH: 732
<212> TYPE: DNA
<213> ORGANISM: Mus musculus

<400> SEQUENCE: 42
cgcgtggtac atattataag tttgagtctg caagatgtgg caaacccttc cttttctctt 60
tatcttgaca gtggaaaaca tctaaggagt ctttaaaata accacatcgg actgagcagt 120
ggagggcaaa gagaatgtct ggaagaacct ttgttttttt cgttgggaca tcaaaggatg 180
ttatactgaa gagatctcaa agaccaggca gtccagccta ctcgtttccc agacaagaga 240
agtgaagcca agaaacagat gggctgcctc ctctagtcat atggggctta aaaatatata 300
tctctatttt tcatgagttt tcatgaaagt gaccagtgtt atctcatttc ctgtcttctc 360
aaattcagga tcctacccaa tctaactatt atttatagtg tgaataagcc ctctactttc 420
ctacctctac aatgctcatt ctccattttc ccatcatcta cttccatctt gtgaaaagtt 480
tccactcttc agtgatgacc tcaaacatat catttctttt ttttaattct ttttttatta 540
gatattttct ttatatacat ttcaaatgct atcctgaaag ttccctatat cctccctctg 600
ccctgcttcc ctacccaccc actcccactt cttggccctg gcatttccct gtactggggc 660
atataaagtt tgcaatacca aggggcctct cttcacagtg atggccaact aggccatctt 720
ctgctacgag ct 732

<210> SEQ ID NO 43
<211> LENGTH: 756
<212> TYPE: DNA
<213> ORGANISM: Homo sapiens

<400> SEQUENCE: 43
actggtctga ctgcagagga ggtctgggag accagaggga gtgtggagag ggtgaggtta 60
gaagacagga acaccgagct gcatcggcca aatggagcct tagggggcca tgtgaggctg 120
aggcagggaa gcagggatcc tgccctccag gtccttacag tcaggcgggg accaaaagca 180
cgaggatgcc agcccaattc cctattaggc aaaacgcagc accatctgca caatcccagg 240
agcaagagca gatattttat aacttccttt tttcttttta agtctaaatt aaaaataaat 300
gttcccttca gctctcagat gtatatctct ggtgcaacct gcccacattc cctcccgctg 360
ccctttccag aacatggcag gggaaaggaa gaaagagatg gatagagaga gggagccagt 420
ccacccagct tcaatgccag tggattgcac ctcttccaag agggaaacga ttcaggcgtg 480
gccacgcaga cgggtggaga gcgcccagaa tgtggctggt accaaggaaa gtggaaggag 540
agggaaacag gagccaacag ctatgatttc tagcccagcc tccaccctat cgcgctgcag 600
gaccttggcc aaatcacaca tcctatctct gctcccattt atagttcata acatggctga 660
agtcccctct gccgctccag ccccctggca gctgtgctct ctgcacatcc gtctgtacct 720
ttgctgctcc ccttcatttt gggtgtccta ccatgg 756

<210> SEQ ID NO 44
<211> LENGTH: 670
<212> TYPE: DNA
<213> ORGANISM: Mus musculus

<400> SEQUENCE: 44
actggcctga ctgggaagaa tgtcccagac attgacaaaa gacaatctag agagggtaag 60
gatgggagac cagggacacc aaagagccca ctgggtccct gtggccaggc ggggcccaga 120
gcacatggtg ccagcctcgt tccctattag gcaaagcact gcaccatctg tatagtccca 180
ggagcaggag caggagcagg cgttttataa cttccttttc tttttcagtc tacattaaaa 240
ataaatgttc ccttcagctc tcagatgtat atctctagtg caacctgccc acattccctc 300
ctgctgccct ttccagaaca tggcagggga agggaaggaa gagatggaga gagggagcca 360
gtccacccgg ctgatgccag tggatcacac ctcttctaag agggaagcgc ggcaggcacg 420

-continued

```
gccacacatg gtggaaggtg cccagaatgc atggggacca gggaaatgga agtggaggaa    480

atgggagcca acagccaggc ttgcttccca cccccaccct cccgcaccgc aggaccttgg    540

ccaaatcaca catcccatct ttgcatttat agttcatgca gtggctggag tcccctctgc    600

agctccagcc ctctggtggc tgtccttgct gcacgtctct ctgtacttcc ccttgtgtgt    660

cctgctgtgg                                                           670
```

```
<210> SEQ ID NO 45
<211> LENGTH: 584
<212> TYPE: DNA
<213> ORGANISM: Homo sapiens

<400> SEQUENCE: 45

gaggaacaga acaaaacaga acaagcaggt tcacttggga cgccgggaac accccgggct     60

tgcgcccctg cgcctccccg ctggcggccc cgccaacttc ccggggtgtc ccctccctac    120

cttctcttca ccgccctggc gcctggcctg cgcgaggtcg ggactcgcgg gacctccgcc    180

taccccagaa gcggctgtct aaagcggggg tgggggggcg ccccctcctg tctggttttc    240

ccttccagtt gccgggagag gactaggcag ccgggagccg ggccgtgcac ccgctgtggc    300

gcgctggcac ctcggcctcc gcaaacagat tgctcgccct cctcggggaa agctaggaaa    360

acagtgctaa gcctcgcaag ctgccgccca ttaatgcctc ttagcttgca agatgggtta    420

ctagctctga gcacggccct cccctcgggg cttcttacat tctcctcccc ctcgcccctt    480

ctgtctccct ccttctccac gccgcggtac tctcgccttc gccctcattc tctccctcca    540

cctactacct cttccttttg ttttccgttc tcctgaattt ccct                     584
```

```
<210> SEQ ID NO 46
<211> LENGTH: 648
<212> TYPE: DNA
<213> ORGANISM: Homo sapiens

<400> SEQUENCE: 46

gggtcagaga cacagaggat gacagagacc cagagagagg gagacagaga cccagagaga     60

gggggagaga gacctagaaa tagggggaca gagacccaga gagggaagag atggaaacct    120

agagaaggaa gcagacagag tcccaaagag aggcggggac agaaacccag gagatagaac    180

atagatgcag agagatgaga acagagatcc agaatgcaag agaaagatgg agagcctggg    240

agacggagga tagacaggct ggggacgtga tttgtgaggt gcagcccctc tctgaggtgg    300

gtaggcagcc aggggatcgg gctggatccc aggaaggggc tggaacagat ggaggcgagg    360

gagactggga cgggggagga aggaacagcc agacggtcca gggggaggga ggtggaagag    420

ctgtgagaac acagcaaccc ctccccatcc tagaacttaa ggaggtgggg aggggcagtt    480

aagaaacagg ggtgggagaa gccagggagt ggacagaacc cagaaggagt aggaatgaga    540

ccccaagagg aagaagacag agagccagag ataggggga ttgaagccac taggacgaat     600

agtacaggat ggcagtaact ccccccaccc atcagaaccc atcaccca                 648
```

```
<210> SEQ ID NO 47
<211> LENGTH: 566
<212> TYPE: DNA
<213> ORGANISM: Homo sapiens

<400> SEQUENCE: 47

ggcttttggc agaaatcagt tcgttgtggt ttaaggactg aggtcgcctt tctttgctgc     60

taactgttgg ccaggaagta ctgtcagcta ctacatggta cttgctggtc cttgcacatg    120
```

```
acccctcca ccttcaaacc aggattgaca cagtgtgttg agtctttctt gaagactttt    180

gaacatctga cttcccattc tgccactagc cagttaaaat tctctaattt tgaaggactc    240

acctggttgg ccaaacccac ccaaataatc tccacatctt gaagtcaact gacccaggac    300

tttacatatg caaaatccct tcacagcagt acctagatga gtgtttgctt gaataactgg    360

gacacaggaa tcttggggga gccatcttta gaattcgacc tcctacaacc cttctggaaa    420

tctgagagtg agtcagggga agaaaccctc ttttgtagtt tccttttagg gctttctact    480

ttgctcaaag ttgggcacta tttcacttca gtagggtcct gcaagcccca tgagggtagt    540

gagtgctgtc ctaggaaaca gtaact                                         566

<210> SEQ ID NO 48
<211> LENGTH: 520
<212> TYPE: DNA
<213> ORGANISM: Mus musculus

<400> SEQUENCE: 48

ccctggcctt cgagcacatg ctcagatgat gctccaccgt ggcctgaccc acatcttcta     60

gtggaagcat ggtccagcaa agcctttctg ttctaaagga aaggatctga gttgtcacct    120

cccaggtccg tggaaggctt tttagcagtt tggcaggtgc ctgagggcca cacctcatct    180

gcataaaatg tggcagattg caaccgccct cgtctttttt atttttaaac tggtttttga    240

aacagaacat atataaaagc tcagagaaag ggaaaggaga tagatggccg agcttccata    300

tcccttagtg cctttatttt cattcttttt ccattttcct aagtggctat ttaccaagac    360

aaagataaca aatctgctag gaaaaggagt gggcagtgct acaaaatgtt tttttttttt    420

taaagaaagt cctatcttat aatagatctt caccacgatg cctcatgatg tatgctcaaa    480

tcagttttaa ttgaactgtg tgtagtatgc tcctgttttg                          520

<210> SEQ ID NO 49
<211> LENGTH: 1253
<212> TYPE: DNA
<213> ORGANISM: Artificial Sequence
<220> FEATURE:
<223> OTHER INFORMATION: concatamer of Mus musculus enhancer core

<400> SEQUENCE: 49

gaagcatggt ccagcaaagc ctttctgttc taaaggaaag gatctgagtt gtcacctccc     60

aggtccgtgg aaggcttttt agcagtttgg caggtgcctg agggccacac ctcatctgca    120

taaaatgtgg cagattgcaa ccgccctcgt ctttttttatt tttaaactgg tttttgaaac    180

agaacatata taaaagctca gagaaaggga aaggagatag atggccgagc ttccatatcc    240

cttagtgcct ttattttcat tctttttcca ttttcctaag tggctattta ccaagacaaa    300

gataacaaat ctgctaggaa aaggagtggg cagtgctaca aaatgttttt tttttttttaa    360

agaaagtcct atcttataat agatcttcac cacgatgcct cgagcagagc cctcatcaca    420

cagactgaag catggtccag caaagccttt ctgttctaaa ggaaaggatc tgagttgtca    480

cctcccaggt ccgtggaagg ctttttagca gtttggcagg tgcctgaggg ccacacctca    540

tctgcataaa atgtggcaga ttgcaaccgc cctcgtcttt tttatttttta aactggtttt    600

tgaaacagaa catatataaa agctcagaga aagggaaagg agatagatgg ccgagcttcc    660

atatccctta gtgcctttat tttcattctt tttccatttt cctaagtggc tatttaccaa    720

gacaaagata acaaatctgc taggaaaagg agtgggcagt gctacaaaat gttttttttt    780
```

```
ttttaaagaa agtcctatct tataatagat cttcaccacg atgcctctgg gtgagtaaga    840

gtaggtggca acgaagcatg gtccagcaaa gcctttctgt tctaaaggaa aggatctgag    900

ttgtcacctc ccaggtccgt ggaaggcttt ttagcagttt ggcaggtgcc tgagggccac    960

acctcatctg cataaaatgt ggcagattgc aaccgccctc gtcttttta tttttaaact   1020

ggtttttgaa acagaacata tataaaagct cagagaaagg gaaaggagat agatggccga   1080

gcttccatat cccttagtgc ctttatttc attcttttc cattttccta agtggctatt   1140

taccaagaca aagataacaa atctgctagg aaaaggagtg ggcagtgcta caaaatgttt   1200

ttttttttt aaagaaagtc ctatcttata atagatcttc accacgatgc ctc            1253
```

<210> SEQ ID NO 50
<211> LENGTH: 386
<212> TYPE: DNA
<213> ORGANISM: Mus musculus

<400> SEQUENCE: 50

```
aattgctgtc atttacctac ggttgtctcc aaatttcttc aaccaagtag agaaaaatga     60

gagagaagga aagaaaaaaa gaggtatggg gagaagagaa agaaggcaac ttgttaaaaa    120

tctcagtcaa acttacatac tatatagaac agcatggtga atttagggca catggatata    180

aaatggaagt ttcttattca gtagcagcaa cttgtgggca caggagttgg caaagataaa    240

aatgtccaaa gtcacaaata caatgtatag ttagtcatag gtgctgttat ttgcctcaaa    300

aaatagactt ttattttgcc tttcttttct ttaaccacac tcaaaattag agaacagaga    360

caaaacccag caggaaatag cacaga                                          386
```

<210> SEQ ID NO 51
<211> LENGTH: 363
<212> TYPE: DNA
<213> ORGANISM: Homo sapiens

<400> SEQUENCE: 51

```
aagccaatga cattagagaa gtgttcaaac agtcagctaa attcactgca cttctcaacc     60

acagaaatat tttcaggtga ttctgttttt gagaaaacgt gggaaccaca ggatctacaa    120

cacttccagg caaaactcaa cagctctaat aatagtgaca gaagtgaaag ccaatttgga    180

taaaataaga cattgactca aagtcctctg agagattttt caaaacaaag tttacaaagc    240

tccttttgcc ttttgggaaa tcacattctt ctttgcacct tgactctttt tctgaatttc    300

tttctgtctg ggaggatctc cttacagtgt ttcttctcca tctgacatca tgaaatgtga    360

tac                                                                   363
```

<210> SEQ ID NO 52
<211> LENGTH: 53
<212> TYPE: DNA
<213> ORGANISM: Artificial Sequence
<220> FEATURE:
<223> OTHER INFORMATION: beta globin minimal promoter

<400> SEQUENCE: 52

```
gggctgggca taaaagtcag ggcagagcca tctattgctt acatttgctt ctg            53
```

<210> SEQ ID NO 53
<211> LENGTH: 68
<212> TYPE: DNA
<213> ORGANISM: Artificial Sequence
<220> FEATURE:
<223> OTHER INFORMATION: minCMV

<400> SEQUENCE: 53
gaggtaggcg tgtacggtgg gaggcctata taagcagagc tcgtttagtg aaccgtcaga 60
tcgcctgg 68

<210> SEQ ID NO 54
<211> LENGTH: 68
<212> TYPE: DNA
<213> ORGANISM: Artificial Sequence
<220> FEATURE:
<223> OTHER INFORMATION: mutated minCMV promoter

<400> SEQUENCE: 54
gaggtaggcg tgtacggtgg gaggcctata taagcagagc tggtttagtg aaccgtcaga 60
tcgcctgg 68

<210> SEQ ID NO 55
<211> LENGTH: 867
<212> TYPE: DNA
<213> ORGANISM: Artificial Sequence
<220> FEATURE:
<223> OTHER INFORMATION: Hsp68 minimal Promoter

<400> SEQUENCE: 55
caggaacatc caaactgagc agccggggtc ccccccaccc cccaccccgc cccacgcggc 60
aactttgagc ctgtgctggg acagagcctc tagttcctaa attagtccat gaggtcagag 120
gcagcactgc cattgtaacg cgattggaga ggatcacgtc accggacacg cccccaggca 180
tctccctggg tctcctaaac ttggcgggga gaagttttag cccttaagtt ttagccttta 240
acccccatat tcagaactgt gcgagttggc gaaaccccac aaatcacaac aaactgtaca 300
caacaccgag ctagaggtga tctttcttgt ccattccaca caggccttag taatgcgtcg 360
ccatagcaac agtgtcacta gtagcaccag cacttcccca caccctcccc ctcaggaatc 420
cgtactctcc agtgaacccc agaaacctct ggagagttct ggacaagggc ggaacccaca 480
actccgatta ctcaagggag gcggggaagc tccaccagac gcgaaactgc tggaagattc 540
ctggccccaa ggcctcctcc ggctcgctga ttggcccagc ggagagtggg cggggccggt 600
gaagactcct taaaggcgca gggcggcgag caggtcacca gacgctgaca gctactcaga 660
accaaatctg gttccatcca gagacaagcg aagacaagag aagcagagcg agcggcgcgt 720
tcccgatcct cggccaggac cagccttccc cagagcatcc ctgccgcgga gcgcaacctt 780
cccaggagca tccctgccgc ggagcgcaac tttccccgga gcatccacgc cgcggagcgc 840
agccttccag aagcagagcg cggcgcc 867

<210> SEQ ID NO 56
<211> LENGTH: 720
<212> TYPE: DNA
<213> ORGANISM: Artificial Sequence
<220> FEATURE:
<223> OTHER INFORMATION: SYFP2

<400> SEQUENCE: 56
atggtgagca agggcgagga gctgttcacc ggggtggtgc ccatcctggt cgagctggac 60
ggcgacgtaa acggccacaa gttcagcgtg tccggcgagg gcgagggcga tgccacctac 120
ggcaagctga ccctgaagct gatctgcacc accggcaagc tgcccgtgcc ctggcccacc 180
ctcgtgacca ccctgggcta cggcgtgcag tgcttcgccc gctaccccga ccacatgaag 240
cagcacgact tcttcaagtc cgccatgccc gaaggctacg tccaggagcg caccatcttc 300
ttcaaggacg acggcaacta caagacccgc gccgaggtga agttcgaggg cgacaccctg 360
gtgaaccgca tcgagctgaa gggcatcgac ttcaaggagg acggcaacat cctggggcac 420
aagctggagt acaactacaa cagccacaac gtctatatca ccgccgacaa gcagaagaac 480
ggcatcaagg ccaacttcaa gatccgccac aacatcgagg acggcggcgt gcagctcgcc 540
gaccactacc agcagaacac ccccatcggc gacggccccg tgctgctgcc cgacaaccac 600
tacctgagct accagtccaa gctgagcaaa gaccccaacg agaagcgcga tcacatggtc 660
ctgctggagt tcgtgaccgc cgccgggatc actctcggca tggacgagct gtacaagtaa 720

<210> SEQ ID NO 57
<211> LENGTH: 720
<212> TYPE: DNA
<213> ORGANISM: Artificial Sequence
<220> FEATURE:
<223> OTHER INFORMATION: EGFP

<400> SEQUENCE: 57
atggtgagca agggcgagga gctgttcacc ggggtggtgc ccatcctggt cgagctggac 60
ggcgacgtaa acggccacaa gttcagcgtg tccggcgagg gcgagggcga tgccacctac 120
ggcaagctga ccctgaagtt catctgcacc accggcaagc tgcccgtgcc ctggcccacc 180
ctcgtgacca ccctgaccta cggcgtgcag tgcttcagcc gctaccccga ccacatgaag 240
cagcacgact tcttcaagtc cgccatgccc gaaggctacg tccaggagcg caccatcttc 300
ttcaaggacg acggcaacta caagacccgc gccgaggtga agttcgaggg cgacaccctg 360
gtgaaccgca tcgagctgaa gggcatcgac ttcaaggagg acggcaacat cctggggcac 420
aagctggagt acaactacaa cagccacaac gtctatatca tggccgacaa gcagaagaac 480
ggcatcaagg tgaacttcaa gatccgccac aacatcgagg acggcagcgt gcagctcgcc 540
gaccactacc agcagaacac ccccatcggc gacggccccg tgctgctgcc cgacaaccac 600
tacctgagca cccagtccgc cctgagcaaa gaccccaacg agaagcgcga tcacatggtc 660
ctgctggagt tcgtgaccgc cgccgggatc actctcggca tggacgagct gtacaagtaa 720

<210> SEQ ID NO 58
<211> LENGTH: 1299
<212> TYPE: DNA
<213> ORGANISM: Artificial Sequence
<220> FEATURE:
<223> OTHER INFORMATION: Optimized Flp recombinase

<400> SEQUENCE: 58
atggctccta agaagaagag gaaggtgatg agccagttcg acatcctgtg caagaccccc 60
cccaaggtgc tggtgcggca gttcgtggag agattcgaga ggcccagcgg cgagaagatc 120
gccagctgtg ccgccgagct gacctacctg tgctggatga tcacccacaa cggcaccgcc 180
atcaagaggg ccaccttcat gagctacaac accatcatca gcaacagcct gagcttcgac 240
atcgtgaaca agagcctgca gttcaagtac aagacccaga aggccaccat cctggaggcc 300
agcctgaaga agctgatccc cgcctgggag ttcaccatca tcccttacaa cggccagaag 360
caccagagcg acatcaccga catcgtgtcc agcctgcagc tgcagttcga gagcagcgag 420
gaggccgaca agggcaacag ccacagcaag aagatgctga aggccctgct gtccgagggc 480
gagagcatct gggagatcac cgagaagatc ctgaacagct tcgagtacac cagcaggttc 540
accaagacca agaccctgta ccagttcctg ttcctggcca cattcatcaa ctgcggcagg 600

```
ttcagcgaca tcaagaacgt ggaccccaag agcttcaagc tggtgcagaa caagtacctg    660

ggcgtgatca ttcagtgcct ggtgaccgag accaagacaa gcgtgtccag gcacatctac    720

tttttcagcg ccagaggcag gatcgacccc ctggtgtacc tggacgagtt cctgaggaac    780

agcgagcccg tgctgaagag agtgaacagg accggcaaca gcagcagcaa caagcaggag    840

taccagctgc tgaaggacaa cctggtgcgc agctacaaca aggccctgaa gaagaacgcc    900

ccctacccca tcttcgctat caagaacggc cctaagagcc acatcggcag gcacctgatg    960

accagctttc tgagcatgaa gggcctgacc gagctgacaa acgtggtggg caactggagc   1020

gacaagaggg cctccgccgt ggccaggacc acctacaccc accagatcac cgccatcccc   1080

gaccactact tcgccctggt gtccaggtac tacgcctacg accccatcag caaggagatg   1140

atcgccctga aggacgagac caaccccatc gaggagtggc agcacatcga gcagctgaag   1200

ggcagcgccg agggcagcat cagatacccc gcctggaacg gcatcatcag ccaggaggtg   1260

ctggactacc tgagcagcta catcaacagg cggatctga                          1299
```

<210> SEQ ID NO 59
<211> LENGTH: 1056
<212> TYPE: DNA
<213> ORGANISM: Artificial Sequence
<220> FEATURE:
<223> OTHER INFORMATION: Improved Cre recombinase

<400> SEQUENCE: 59

```
atggtgccca agaagaagag gaaagtctcc aacctgctga ctgtgcacca aaacctgcct     60

gccctccctg tggatgccac ctctgatgaa gtcaggaaga acctgatgga catgttcagg    120

gacaggcagg ccttctctga acacacctgg aagatgctcc tgtctgtgtg cagatcctgg    180

gctgcctggt gcaagctgaa caacaggaaa tggttccctg ctgaacctga ggatgtgagg    240

gactacctcc tgtacctgca agccagaggc ctggctgtga agaccatcca acagcacctg    300

ggccagctca acatgctgca caggagatct ggcctgcctc gcccttctga ctccaatgct    360

gtgtccctgg tgatgaggag aatcagaaag gagaatgtgg atgctgggga gagagccaag    420

caggccctgg cctttgaacg cactgacttt gaccaagtca gatccctgat ggagaactct    480

gacagatgcc aggacatcag gaacctggcc ttcctgggca ttgcctacaa caccctgctg    540

cgcattgccg aaattgccag aatcagagtg aaggacatct cccgcaccga tggtgggaga    600

atgctgatcc acattggcag gaccaagacc ctggtgtcca cagctggtgt ggagaaggcc    660

ctgtccctgg gggttaccaa gctggtggag agatggatct ctgtgtctgg tgtggctgat    720

gaccccaaca actacctgtt ctgccgggtc agaaagaatg gtgtggctgc cccttctgcc    780

acctcccaac tgtccacccg ggccctggaa gggatctttg aggccaccca ccgcctgatc    840

tatggtgcca aggatgactc tgggcagaga tacctggcct ggtctggcca ctctgccaga    900

gtgggtgctg ccagggacat ggccagggct ggtgtgtcca tccctgaaat catgcaggct    960

ggtggctgga ccaatgtgaa cattgtgatg aactacatca gaaacctgga ctctgagact   1020

ggggccatgg tgaggctgct cgaggatggg gactaa                             1056
```

<210> SEQ ID NO 60
<211> LENGTH: 384
<212> TYPE: DNA
<213> ORGANISM: Artificial Sequence
<220> FEATURE:
<223> OTHER INFORMATION: WPRE3

<400> SEQUENCE: 60
ataatcaacc tctggattac aaaatttgtg aaagattgac tggtattctt aactatgttg 60
ctccttttac gctatgtgga tacgctgctt taatgccttt gtatcatgct attgcttccc 120
gtatggcttt cattttctcc tccttgtata aatcctggtt gctgtctctt tatgaggagt 180
tgtggcccgt tgtcaggcaa cgtggcgtgg tgtgcactgt gtttgctgac gcaaccccca 240
ctggttgggg cattgccacc acctgtcagc tcctttccgg gactttcgct ttccccctcc 300
ctattgccac ggcggaactc atcgccgcct gccttgcccg ctgctggaca ggggctcggc 360
tgttgggcac tgacaattcc gtgg 384

<210> SEQ ID NO 61
<211> LENGTH: 204
<212> TYPE: DNA
<213> ORGANISM: Artificial Sequence
<220> FEATURE:
<223> OTHER INFORMATION: BGHpA

<400> SEQUENCE: 61
cgactgtgcc ttctagttgc cagccatctg ttgtttgccc ctcccccgtg ccttccttga 60
ccctggaagg tgccactccc actgtccttt cctaataaaa tgaggaaatt gcatcgcatt 120
gtctgagtag gtgtcattct attctggggg gtggggtggg gcaggacagc aagggggagg 180
attgggaaga caatagcagg catg 204

<210> SEQ ID NO 62
<211> LENGTH: 33
<212> TYPE: PRT
<213> ORGANISM: Artificial Sequence
<220> FEATURE:
<223> OTHER INFORMATION: HA tag

<400> SEQUENCE: 62

Met Val Tyr Pro Tyr Asp Val Pro Asp Tyr Ala Gly Ser Tyr Pro Tyr
1               5                   10                  15

Asp Val Pro Asp Tyr Ala Gly Ser Tyr Pro Tyr Asp Val Pro Asp Tyr
            20                  25                  30

Ala

<210> SEQ ID NO 63
<211> LENGTH: 99
<212> TYPE: DNA
<213> ORGANISM: Artificial Sequence
<220> FEATURE:
<223> OTHER INFORMATION: HA tag

<400> SEQUENCE: 63
atggtttacc cgtatgatgt cccggattac gctggcagct acccatacga tgtacccgac 60
tatgccggca gttatcccta cgacgtccct gactacgca 99

<210> SEQ ID NO 64
<211> LENGTH: 78
<212> TYPE: DNA
<213> ORGANISM: Artificial Sequence
<220> FEATURE:
<223> OTHER INFORMATION: P2A

<400> SEQUENCE: 64
ggcagcggcg ccaccaactt cagcctgctg aagcaggccg gcgacgtgga ggagaacccc 60
ggccccggag ctagcgga 78

<210> SEQ ID NO 65
<211> LENGTH: 21
<212> TYPE: PRT
<213> ORGANISM: Artificial Sequence
<220> FEATURE:
<223> OTHER INFORMATION: T2A
<220> FEATURE:
<221> NAME/KEY: MISC_FEATURE
<222> LOCATION: (1)..(3)
<223> OTHER INFORMATION: (GlySerGly) residues can be added to the 5' end
of the peptide to improve cleavage efficiency

<400> SEQUENCE: 65

Gly Ser Gly Glu Gly Arg Gly Ser Leu Leu Thr Cys Gly Asp Val Glu
1 5 10 15

Glu Asn Pro Gly Pro
20

<210> SEQ ID NO 66
<211> LENGTH: 24
<212> TYPE: PRT
<213> ORGANISM: Artificial Sequence
<220> FEATURE:
<223> OTHER INFORMATION: E2A
<220> FEATURE:
<221> NAME/KEY: MISC_FEATURE
<222> LOCATION: (1)..(3)
<223> OTHER INFORMATION: (GlySerGly) residues can be added to the 5' end
of the peptide to improve cleavage efficiency

<400> SEQUENCE: 66

Gly Ser Gly Gln Cys Thr Asn Tyr Ala Leu Leu Lys Leu Ala Gly Asp
1 5 10 15

Val Glu Ser Asn Pro Gly Pro Pro
20

<210> SEQ ID NO 67
<211> LENGTH: 25
<212> TYPE: PRT
<213> ORGANISM: Artificial Sequence
<220> FEATURE:
<223> OTHER INFORMATION: F2A
<220> FEATURE:
<221> NAME/KEY: MISC_FEATURE
<222> LOCATION: (1)..(3)
<223> OTHER INFORMATION: (GlySerGly) residues can be added to the 5' end
of the peptide to improve cleavage efficiency

<400> SEQUENCE: 67

Gly Ser Gly Val Lys Gln Thr Leu Asn Phe Asp Leu Leu Lys Leu Ala
1 5 10 15

Gly Asp Val Glu Ser Asn Pro Gly Pro
20 25

<210> SEQ ID NO 68
<211> LENGTH: 747
<212> TYPE: DNA
<213> ORGANISM: Artificial Sequence
<220> FEATURE:
<223> OTHER INFORMATION: tet-Transactivator

<400> SEQUENCE: 68
atgtctagac tggacaagag caaagtcata aactctgctc tggaattact caatgaagtc 60
ggtatcgaag gcctgacgac aaggaaactc gctcaaaagc tgggagttga gcagcctacc 120
ctgtactggc acgtgaagaa caagcgggcc ctgctcgatg ccctggcaat cgagatgctg 180

-continued

```
gacaggcatc atacccactt ctgccccctg gaaggcgagt catggcaaga ctttctgcgg    240

aacaacgcca agtcattccg ctgtgctctc ctctcacatc gcgacggggc taaagtgcat    300

ctcggcaccc gcccaacaga gaaacagtac gaaaccctgg aaaatcagct cgcgttcctg    360

tgtcagcaag gcttctccct ggagaacgca ctgtacgctc tgtccgccgt gggccacttt    420

acactgggct gcgtattgga ggatcaggag catcaagtag caaaagagga aagagagaca    480

cctaccaccg attctatgcc cccacttctg agacaagcaa ttgagctgtt cgaccatcag    540

ggagccgaac ctgccttcct tttcggcctg gaactaatca tatgtggcct ggagaaacag    600

ctaaagtgcg aaagcggcgg gccggccgac gcccttgacg attttgactt agacatgctc    660

ccagccgatg cccttgacga ctttgacctt gatatgctgc ctgctgacgc tcttgacgat    720

tttgaccttg acatgctccc cgggtaa                                        747


<210> SEQ ID NO 69
<211> LENGTH: 743
<212> TYPE: PRT
<213> ORGANISM: Artificial Sequence
<220> FEATURE:
<223> OTHER INFORMATION: PHP.eB capsid

<400> SEQUENCE: 69

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255
```

-continued

```
Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Asp Gly Thr Leu Ala Val
            580                 585                 590

Pro Phe Lys Ala Gln Ala Gln Thr Gly Trp Val Gln Asn Gln Gly Ile
        595                 600                 605

Leu Pro Gly Met Val Trp Gln Asp Arg Asp Val Tyr Leu Gln Gly Pro
    610                 615                 620

Ile Trp Ala Lys Ile Pro His Thr Asp Gly Asn Phe His Pro Ser Pro
625                 630                 635                 640

Leu Met Gly Gly Phe Gly Met Lys His Pro Pro Pro Gln Ile Leu Ile
                645                 650                 655

Lys Asn Thr Pro Val Pro Ala Asp Pro Pro Thr Ala Phe Asn Lys Asp
            660                 665                 670

Lys Leu Asn Ser Phe Ile Thr Gln Tyr Ser Thr Gly Gln Val Ser Val
```

```
        675                 680                 685

Glu Ile Glu Trp Glu Leu Gln Lys Glu Asn Ser Lys Arg Trp Asn Pro
    690                 695                 700

Glu Ile Gln Tyr Thr Ser Asn Tyr Tyr Lys Ser Asn Asn Val Glu Phe
705                 710                 715                 720

Ala Val Asn Thr Glu Gly Val Tyr Ser Glu Pro Arg Pro Ile Gly Thr
                725                 730                 735

Arg Tyr Leu Thr Arg Asn Leu
            740


<210> SEQ ID NO 70
<211> LENGTH: 736
<212> TYPE: PRT
<213> ORGANISM: Adeno-associated virus

<400> SEQUENCE: 70

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300
```

-continued

```
Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
```

725 730 735

<210> SEQ ID NO 71
<211> LENGTH: 2868
<212> TYPE: DNA
<213> ORGANISM: Artificial Sequence
<220> FEATURE:
<223> OTHER INFORMATION: Plasmid backbone

<400> SEQUENCE: 71

```
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcact    120
aggggttcct ggcgcctgat gcggtatttt ctccttacgc atctgtgcgg tatttcacac    180
cgcatacgtc aaagcaacca tagtacgcgc cctgtagcgg cgcattaagc gcggcgggtg    240
tggtggttac gcgcagcgtg accgctacac ttgccagcgc cctagcgccc gctcctttcg    300
ctttcttccc ttcctttctc gccacgttcg ccggctttcc ccgtcaagct ctaaatcggg    360
ggctcccttt agggttccga tttagtgctt tacggcacct cgaccccaaa aaacttgatt    420
tgggtgatgg ttcacgtagt gggccatcgc cctgatagac ggtttttcgc cctttgacgt    480
tggagtccac gttctttaat agtggactct tgttccaaac tggaacaaca ctcaacccta    540
tctcgggcta ttcttttgat ttataaggga ttttgccgat ttcggcctat tggttaaaaa    600
atgagctgat ttaacaaaaa tttaacgcga attttaacaa aatattaacg tttacaattt    660
tatggtgcac tctcagtaca atctgctctg atgccgcata gttaagccag ccccgacacc    720
cgccaacacc cgctgacgcg ccctgacggg cttgtctgct cccggcatcc gcttacagac    780
aagctgtgac cgtctccggg agctgcatgt gtcagaggtt ttcaccgtca tcaccgaaac    840
gcgcgagacg aaagggcctc gtgatacgcc tatttttata ggttaatgtc atgataataa    900
tggtttctta gacgtcaggt ggcacttttc ggggaaatgt gcgcggaacc cctatttgtt    960
tatttttcta aatacattca aatatgtatc cgctcatgag acaataaccc tgataaatgc   1020
ttcaataata ttgaaaaagg aagagtatga gtattcaaca tttccgtgtc gcccttattc   1080
ccttttttgc ggcattttgc cttcctgttt ttgctcaccc agaaacgctg gtgaaagtaa   1140
aagatgctga agatcagttg ggtgcacgag tgggttacat cgaactggat ctcaacagcg   1200
gtaagatcct tgagagtttt cgccccgaag aacgttttcc aatgatgagc acttttaaag   1260
ttctgctatg tggcgcggta ttatcccgta ttgacgccgg gcaagagcaa ctcggtcgcc   1320
gcatacacta ttctcagaat gacttggttg agtactcacc agtcacagaa aagcatctta   1380
cggatggcat gacagtaaga gaattatgca gtgctgccat aaccatgagt gataacactg   1440
cggccaactt acttctgaca acgatcggag gaccgaagga gctaaccgct tttttgcaca   1500
acatggggga tcatgtaact cgccttgatc gttgggaacc ggagctgaat gaagccatac   1560
caaacgacga gcgtgacacc acgatgcctg tagcaatggc aacaacgttg cgcaaactat   1620
taactggcga actacttact ctagcttccc ggcaacaatt aatagactgg atggaggcgg   1680
ataaagttgc aggaccactt ctgcgctcgg cccttccggc tggctggttt attgctgata   1740
aatctggagc cggtgagcgt gggtctcgcg gtatcattgc agcactgggg ccagatggta   1800
agccctcccg tatcgtagtt atctacacga cggggagtca ggcaactatg gatgaacgaa   1860
atagacagat cgctgagata ggtgcctcac tgattaagca ttggtaactg tcagaccaag   1920
tttactcata tatactttag attgatttaa aacttcattt ttaatttaaa aggatctagg   1980
tgaagatcct ttttgataat ctcatgacca aaatccctta acgtgagttt tcgttccact   2040
```

gagcgtcaga ccccgtagaa aagatcaaag gatcttcttg agatcctttt tttctgcgcg 2100
taatctgctg cttgcaaaca aaaaaaccac cgctaccagc ggtggtttgt ttgccggatc 2160
aagagctacc aactcttttt ccgaaggtaa ctggcttcag cagagcgcag ataccaaata 2220
ctgtccttct agtgtagccg tagttaggcc accacttcaa gaactctgta gcaccgccta 2280
catacctcgc tctgctaatc ctgttaccag tggctgctgc cagtggcgat aagtcgtgtc 2340
ttaccgggtt ggactcaaga cgatagttac cggataaggc gcagcggtcg ggctgaacgg 2400
ggggttcgtg cacacagccc agcttggagc gaacgaccta caccgaactg agatacctac 2460
agcgtgagct atgagaaagc gccacgcttc ccgaagggag aaaggcggac aggtatccgg 2520
taagcggcag ggtcggaaca ggagagcgca cgagggagct tccaggggga aacgcctggt 2580
atctttatag tcctgtcggg tttcgccacc tctgacttga gcgtcgattt ttgtgatgct 2640
cgtcaggggg gcggagccta tggaaaaacg ccagcaacgc ggccttttta cggttcctgg 2700
ccttttgctg gccttttgct cacatgtcct gcaggcagct gcgcgctcgc tcgctcactg 2760
aggccgcccg ggcaaagccc gggcgtcggg cgacctttgg tcgcccggcc tcagtgagcg 2820
agcgagcgcg cagagaggga gtggccaact ccatcactag gggttcct 2868

<210> SEQ ID NO 72
<211> LENGTH: 2879
<212> TYPE: DNA
<213> ORGANISM: Artificial Sequence
<220> FEATURE:
<223> OTHER INFORMATION: Plasmid backbone

<400> SEQUENCE: 72
aggaacccct agtgatggag ttggccactc cctctctgcg cgctcgctcg ctcactgagg 60
ccgggcgacc aaaggtcgcc cgacgcccgg gctttgcccg ggcggcctca gtgagcgagc 120
gagcgcgcag ctgcctgcag gggcgcctga tgcggtattt tctccttacg catctgtgcg 180
gtatttcaca ccgcatacgt caaagcaacc atagtacgcg ccctgtagcg gcgcattaag 240
cgcggcgggt gtggtggtta cgcgcagcgt gaccgctaca cttgccagcg ccctagcgcc 300
cgctcctttc gctttcttcc cttcctttct cgccacgttc gccggctttc cccgtcaagc 360
tctaaatcgg gggctccctt tagggttccg atttagtgct ttacggcacc tcgaccccaa 420
aaaacttgat ttgggtgatg gttcacgtag tgggccatcg ccctgataga cggtttttcg 480
ccctttgacg ttggagtcca cgttctttaa tagtggactc ttgttccaaa ctggaacaac 540
actcaaccct atctcgggct attcttttga tttataaggg attttgccga tttcggccta 600
ttggttaaaa aatgagctga tttaacaaaa atttaacgcg aattttaaca aaatattaac 660
gtttacaatt ttatggtgca ctctcagtac aatctgctct gatgccgcat agttaagcca 720
gccccgacac ccgccaacac ccgctgacgc gccctgacgg gcttgtctgc tcccggcatc 780
cgcttacaga caagctgtga ccgtctccgg gagctgcatg tgtcagaggt tttcaccgtc 840
atcaccgaaa cgcgcgagac gaaagggcct cgtgatacgc ctatttttat aggttaatgt 900
catgataata atggtttctt agacgtcagg tggcactttt cggggaaatg tgcgcggaac 960
ccctatttgt ttatttttct aaatacattc aaatatgtat ccgctcatga gacaataacc 1020
ctgataaatg cttcaataat attgaaaaag gaagagtatg agtattcaac atttccgtgt 1080
cgcccttatt cccttttttg cggcattttg ccttcctgtt tttgctcacc cagaaacgct 1140
ggtgaaagta aaagatgctg aagatcagtt gggtgcacga gtgggttaca tcgaactgga 1200

```
tctcaacagc ggtaagatcc ttgagagttt tcgccccgaa gaacgttttc caatgatgag   1260
cacttttaaa gttctgctat gtggcgcggt attatcccgt attgacgccg ggcaagagca   1320
actcggtcgc cgcatacact attctcagaa tgacttggtt gagtactcac cagtcacaga   1380
aaagcatctt acggatggca tgacagtaag agaattatgc agtgctgcca taaccatgag   1440
tgataacact gcggccaact tacttctgac aacgatcgga ggaccgaagg agctaaccgc   1500
tttttgcac aacatggggg atcatgtaac tcgccttgat cgttgggaac cggagctgaa   1560
tgaagccata ccaaacgacg agcgtgacac cacgatgcct gtagcaatgg caacaacgtt   1620
gcgcaaacta ttaactggcg aactacttac tctagcttcc cggcaacaat taatagactg   1680
gatggaggcg gataaagttg caggaccact tctgcgctcg gcccttccgg ctggctggtt   1740
tattgctgat aaatctggag ccggtgagcg tgggtctcgc ggtatcattg cagcactggg   1800
gccagatggt aagccctccc gtatcgtagt tatctacacg acggggagtc aggcaactat   1860
ggatgaacga aatagacaga tcgctgagat aggtgcctca ctgattaagc attggtaact   1920
gtcagaccaa gtttactcat atatacttta gattgattta aaacttcatt tttaatttaa   1980
aaggatctag gtgaagatcc tttttgataa tctcatgacc aaaatccctt aacgtgagtt   2040
ttcgttccac tgagcgtcag accccgtaga aaagatcaaa ggatcttctt gagatccttt   2100
ttttctgcgc gtaatctgct gcttgcaaac aaaaaaacca ccgctaccag cggtggtttg   2160
tttgccggat caagagctac caactctttt tccgaaggta actggcttca gcagagcgca   2220
gataccaaat actgtccttc tagtgtagcc gtagttaggc caccacttca agaactctgt   2280
agcaccgcct acatacctcg ctctgctaat cctgttacca gtggctgctg ccagtggcga   2340
taagtcgtgt cttaccgggt tggactcaag acgatagtta ccggataagg cgcagcggtc   2400
gggctgaacg gggggttcgt gcacacagcc cagcttggag cgaacgacct acaccgaact   2460
gagataccta cagcgtgagc tatgagaaag cgccacgctt cccgaaggga gaaaggcgga   2520
caggtatccg gtaagcggca gggtcggaac aggagagcgc acgagggagc ttccaggggg   2580
aaacgcctgg tatctttata gtcctgtcgg gtttcgccac ctctgacttg agcgtcgatt   2640
tttgtgatgc tcgtcagggg ggcggagcct atggaaaaac gccagcaacg cggccttttt   2700
acggttcctg gccttttgct ggccttttgc tcacatgtcc tgcaggcagc tgcgcgctcg   2760
ctcgctcact gaggccgccc gggcaaagcc cgggcgtcgg gcgacctttg gtcgcccggc   2820
ctcagtgagc gagcgagcgc gcagagaggg agtggccaac tccatcacta ggggttcct    2879
```

<210> SEQ ID NO 73
<211> LENGTH: 3034
<212> TYPE: DNA
<213> ORGANISM: Artificial Sequence
<220> FEATURE:
<223> OTHER INFORMATION: synthetic construct

<400> SEQUENCE: 73

```
ggccgcacgc gttctagaca ggaacatcca aactgagcag ccggggtccc ccccaccccc     60
caccccgccc cacgcggcaa ctttgagcct gtgctgggac agagcctcta gttcctaaat    120
tagtccatga ggtcagaggc agcactgcca ttgtaacgcg attggagagg atcacgtcac    180
cggacacgcc cccaggcatc tccctgggtc tcctaaactt ggcggggaga agttttagcc    240
cttaagtttt agcctttaac cccatattc agaactgtgc gagttggcga aaccccacaa    300
atcacaacaa actgtacaca acaccgagct agaggtgatc tttcttgtcc attccacaca    360
ggccttagta atgcgtcgcc atagcaacag tgtcactagt agcaccagca cttccccaca    420
```

```
ccctccccct caggaatccg tactctccag tgaaccccag aaacctctgg agagttctgg    480
acaagggcgg aacccacaac tccgattact caagggaggc ggggaagctc caccagacgc    540
gaaactgctg gaagattcct ggccccaagg cctcctccgg ctcgctgatt ggcccagcgg    600
agagtgggcg gggccggtga agactcctta aaggcgcagg gcggcgagca ggtcaccaga    660
cgctgacagc tactcagaac caaatctggt tccatccaga gacaagcgaa gacaagagaa    720
gcagagcgag cggcgcgttc ccgatcctcg gccaggacca gccttcccca gagcatccct    780
gccgcggagc gcaaccttcc caggagcatc cctgccgcgg agcgcaactt tccccggagc    840
atccacgccg cggagcgcag ccttccagaa gcagagcgcg gcgccacata tgccgccgcc    900
accatggtga gcaagggcga ggagctgttc accggggtgg tgcccatcct ggtcgagctg    960
gacggcgacg taaacggcca caagttcagc gtgtccggcg agggcgaggg cgatgccacc   1020
tacggcaagc tgaccctgaa gttcatctgc accaccggca agctgcccgt gccctggccc   1080
accctcgtga ccaccctgac ctacggcgtg cagtgcttca gccgctaccc cgaccacatg   1140
aagcagcacg acttcttcaa gtccgccatg cccgaaggct acgtccagga gcgcaccatc   1200
ttcttcaagg acgacggcaa ctacaagacc cgcgccgagg tgaagttcga gggcgacacc   1260
ctggtgaacc gcatcgagct gaagggcatc gacttcaagg aggacggcaa catcctgggg   1320
cacaagctgg agtacaacta caacagccac aacgtctata tcatggccga caagcagaag   1380
aacggcatca aggtgaactt caagatccgc cacaacatcg aggacggcag cgtgcagctc   1440
gccgaccact accagcagaa cacccccatc ggcgacggcc ccgtgctgct gcccgacaac   1500
cactacctga gcacccagtc cgccctgagc aaagacccca acgagaagcg cgatcacatg   1560
gtcctgctgg agttcgtgac cgccgccggg atcactctcg gcatggacga gctgtacaag   1620
taagttaatt aatctcataa tcaacctctg gattacaaaa tttgtgaaag attgactggt   1680
attcttaact atgttgctcc ttttacgcta tgtggatacg ctgctttaat gcctttgtat   1740
catgctattg cttcccgtat ggctttcatt ttctcctcct tgtataaatc ctggttagtt   1800
cttgccacgg cggaactcat cgccgcctgc cttgcccgct gctggacagg ggctcggctg   1860
ttgggcactg acaattccgt ggctcgactg tgccttctag ttgccagcca tctgttgttt   1920
gcccctcccc cgtgccttcc ttgaccctgg aaggtgccac tcccactgtc ctttcctaat   1980
aaaatgagga aattgcatcg cattgtctga gtaggtgtca ttctattctg gggggtgggg   2040
tggggcagga cagcaagggg gaggattggg aagacaatag caggcatgac ttgctgctat   2100
cccctaggtg ctgtcattta cctacggttg tctccaaatt tcttcaacca agtagagaaa   2160
aatgagagag aaggaaagaa aaaaagaggt atggggagaa gagaaagaag gcaacttgtt   2220
aaaaatctca gtcaaactta catactatat agaacagcat ggtgaattta gggcacatgg   2280
atataaaatg gaagtttctt attcagtagc agcaacttgt gggcacagga gttggcaaag   2340
ataaaaatgt ccaaagtcac aaatacaatg tatagttagt cataggtgct gttatttgcc   2400
tcaaaaaata gacttttatt ttgcctttct tttctttaac cacactcaaa attagagaac   2460
agagacaaaa cccagcagga aatagcacag aaagcccaca gaatcaaaga cgtgttcaaa   2520
cagccagctg aattcattgc acatttcaac cacagaaata ttttcaggtg attctgttgt   2580
ttgacaaaac gtgggaacca caggatctac aacacttgca agcaaaactc aacagctcta   2640
ataatagtta cagaagtgaa agccaatttg gataaaataa gacattgact caagtcctct   2700
cagaagagtt ttgaaagcaa agtttacaaa agtctggttt gtcctttggg atttacagac   2760
```

ctttcagccc cttgattcat tttttttttt ttggatttct tcatcactgg gagaattccc 2820
atgcattatt tctcccctgc ttcaaaatca tcaaatgtga aacatttttc actcttttct 2880
tctgtatata gtgataaaat agctattggc ttttggctaa atgtgctact ttgagcccac 2940
ccacacaagg gagaaatggg ggcagacatg agtttgggca tgagtgagct ctgccttctc 3000
agaggtgagc cacgtggtgc ggaccgagcg gccg 3034

<210> SEQ ID NO 74
<211> LENGTH: 4856
<212> TYPE: DNA
<213> ORGANISM: Artificial Sequence
<220> FEATURE:
<223> OTHER INFORMATION: synthetic construct

<400> SEQUENCE: 74
aaagcttccc ggggggatct gggccactcc ctctctgcgc gctcgctcgc tcactgaggc 60
cgggcgacca aaggtcgccc gacgcccggg ctttgcccgg gcggcctcag tgagcgagcg 120
agcgcgcaga gagggagtgg ccaactccat cactaggggt tcctggaggg gtggagtcgt 180
gacctaggac gcgtataagc cttgggggca atcaaactat tacattgagt ccttggattt 240
gctacaaatt acattttaaa tgcaatcatt ttataaaagc ttcaacactc acacttggaa 300
gcgttaccct gttgaatatc actgactcac taacttgcat tgccatgcta acttgctttc 360
agagagatct cagaacacat catcttctgc tatttcaata catgcacatt aatttcctat 420
caacgtgtgc tgatcaggaa ctctgtaatc tggcaccggt gtttattttt attcctgtct 480
attcctgttg gctcacgaaa agattgtttg agcaagtgtt ttatggtgag ttgtatcata 540
tgtacattga tttaatctgc ccacattcag ttctacaagc ggagccaaaa aaatagagac 600
aagcataatt ttcattcaac atgagcccct caatgcaagc caagtacctc atctggtgct 660
cagctaaagc aacagcaatc tgttccaccc tggagacaca actggccaca gaaaacttag 720
tgaaaagagg caatgctatg cacaggacaa atgagctcgg gctgggcata aaagtcaggg 780
cagagccatc tattgcttac atttgcttct gggatccaga tctttcgaag ctagcgctac 840
cggtcgccac catggtgagc aagggcgagg agctgttcac cggggtggtg cccatcctgg 900
tcgagctgga cggcgacgta aacggccaca agttcagcgt gtccggcgag ggcgagggcg 960
atgccaccta cggcaagctg accctgaagc tgatctgcac caccggcaag ctgcccgtgc 1020
cctggcccac cctcgtgacc accctgggct acggcgtgca gtgcttcgcc cgctaccccg 1080
accacatgaa gcagcacgac ttcttcaagt ccgccatgcc cgaaggctac gtccaggagc 1140
gcaccatctt cttcaaggac gacggcaact acaagacccg cgccgaggtg aagttcgagg 1200
gcgacaccct ggtgaaccgc atcgagctga agggcatcga cttcaaggag gacggcaaca 1260
tcctggggca caagctggag tacaactaca acagccacaa cgtctatatc accgccgaca 1320
agcagaagaa cggcatcaag gccaacttca agatccgcca caacatcgag gacggcggcg 1380
tgcagctcgc cgaccactac cagcagaaca cccccatcgg cgacggcccc gtgctgctgc 1440
ccgacaacca ctacctgagc taccagtcca agctgagcaa agaccccaac gagaagcgcg 1500
atcacatggt cctgctggag ttcgtgaccg ccgccgggat cactctcggc atggacgagc 1560
tgtacaagta agtcgacggc gcgccgcggc cgcgaattcg atatcataat caacctctgg 1620
attacaaaat ttgtgaaaga ttgactggta ttcttaacta tgttgctcct tttacgctat 1680
gtggatacgc tgctttaatg cctttgtatc atgctattgc ttcccgtatg gctttcattt 1740
tctcctcctt gtataaatcc tggttagttc ttgccacggc ggaactcatc gccgcctgcc 1800

-continued

```
ttgcccgctg ctggacaggg gctcggctgt tgggcactga caattccgtg gctcgagcga   1860
ctgtgccttc tagttgccag ccatctgttg tttgcccctc ccccgtgcct tccttgaccc   1920
tggaaggtgc cactcccact gtcctttcct aataaaatga ggaaattgca tcgcattgtc   1980
tgagtaggtg tcattctatt ctggggggtg gggtggggca ggacagcaag ggggaggatt   2040
gggaagacaa tagcaggcat gactagtcca ctccctctct gcgcgctcgc tcgctcactg   2100
aggccgggcg accaaaggtc gcccgacgcc cgggctttgc ccgggcggcc tcagtgagcg   2160
agcgagcgcg cagagaggga cagatccggg cccgcatgcg tcgacaattc actggccgtc   2220
gttttacaac gtcgtgactg ggaaaaccct ggcgttaccc aacttaatcg ccttgcagca   2280
catccccctt tcgccagctg gcgtaatagc gaagaggccc gcaccgatcg cccttcccaa   2340
cagttgcgca gcctgaatgg cgaatggcgc ctgatgcggt attttctcct tacgcatctg   2400
tgcggtattt cacaccgcat atggtgcact ctcagtacaa tctgctctga tgccgcatag   2460
ttaagccagc cccgacaccc gccaacaccc gctgacgcgc cctgacgggc ttgtctgctc   2520
ccggcatccg cttacagaca agctgtgacc gtctccggga gctgcatgtg tcagaggttt   2580
tcaccgtcat caccgaaacg cgcgagacga aagggcctcg tgatacgcct atttttatag   2640
gttaatgtca tgataataat ggtttcttag acgtcaggtg gcacttttcg gggaaatgtg   2700
cgcggaaccc ctatttgttt atttttctaa atacattcaa atatgtatcc gctcatgaga   2760
caataaccct gataaatgct tcaataatat tgaaaaagga agagtatgag tattcaacat   2820
ttccgtgtcg cccttattcc cttttttgcg gcattttgcc ttcctgtttt tgctcaccca   2880
gaaacgctgg tgaaagtaaa agatgctgaa gatcagttgg gtgcacgagt gggttacatc   2940
gaactggatc tcaacagcgg taagatcctt gagagttttc gccccgaaga acgttttcca   3000
atgatgagca cttttaaagt tctgctatgt ggcgcggtat tatcccgtat tgacgccggg   3060
caagagcaac tcggtcgccg catacactat tctcagaatg acttggttga gtactcacca   3120
gtcacagaaa agcatcttac ggatggcatg acagtaagag aattatgcag tgctgccata   3180
accatgagtg ataacactgc ggccaactta cttctgacaa cgatcggagg accgaaggag   3240
ctaaccgctt ttttgcacaa catgggggat catgtaactc gccttgatcg ttgggaaccg   3300
gagctgaatg aagccatacc aaacgacgag cgtgacacca cgatgcctgt agcaatggca   3360
acaacgttgc gcaaactatt aactggcgaa ctacttactc tagcttcccg gcaacaatta   3420
atagactgga tggaggcgga taaagttgca ggaccacttc tgcgctcggc ccttccggct   3480
ggctggttta ttgctgataa atctggagcc ggtgagcgtg ggtctcgcgg tatcattgca   3540
gcactggggc cagatggtaa gccctcccgt atcgtagtta tctacacgac ggggagtcag   3600
gcaactatgg atgaacgaaa tagacagatc gctgagatag gtgcctcact gattaagcat   3660
tggtaactgt cagaccaagt ttactcatat atactttaga ttgatttaaa acttcatttt   3720
taatttaaaa ggatctaggt gaagatcctt tttgataatc tcatgaccaa aatcccttaa   3780
cgtgagtttt cgttccactg agcgtcagac cccgtagaaa agatcaaagg atcttcttga   3840
gatccttttt ttctgcgcgt aatctgctgc ttgcaaacaa aaaaaccacc gctaccagcg   3900
gtggtttgtt tgccggatca agagctacca actctttttc cgaaggtaac tggcttcagc   3960
agagcgcaga taccaaatac tgttcttcta gtgtagccgt agttaggcca ccacttcaag   4020
aactctgtag caccgcctac atacctcgct ctgctaatcc tgttaccagt ggctgctgcc   4080
agtggcgata agtcgtgtct taccgggttg gactcaagac gatagttacc ggataaggcg   4140
```

```
cagcggtcgg gctgaacggg gggttcgtgc acacagccca gcttggagcg aacgacctac   4200

accgaactga gatacctaca gcgtgagcta tgagaaagcg ccacgcttcc cgaagggaga   4260

aaggcggaca ggtatccggt aagcggcagg gtcggaacag gagagcgcac gagggagctt   4320

ccagggggaa acgcctggta tctttatagt cctgtcgggt ttcgccacct ctgacttgag   4380

cgtcgatttt tgtgatgctc gtcagggggg cggagcctat ggaaaaacgc cagcaacgcg   4440

gcctttttac ggttcctggc cttttgctgg ccttttgctc acatgttctt tcctgcgtta   4500

tcccctgatt ctgtggataa ccgtattacc gcctttgagt gagctgatac cgctcgccgc   4560

agccgaacga ccgagcgcag cgagtcagtg agcgaggaag cggaagagcg cccaatacgc   4620

aaaccgcctc tccccgcgcg ttggccgatt cattaatgca gctggcacga caggtttccc   4680

gactggaaag cgggcagtga gcgcaacgca attaatgtga gttagctcac tcattaggca   4740

ccccaggctt tacactttat gcttccggct cgtatgttgt gtggaattgt gagcggataa   4800

caatttcaca caggaaacag ctatgaccat gattacgcca agctctcgag atctag       4856
```

<210> SEQ ID NO 75
<211> LENGTH: 4861
<212> TYPE: DNA
<213> ORGANISM: Artificial Sequence
<220> FEATURE:
<223> OTHER INFORMATION: synthetic construct

<400> SEQUENCE: 75

```
aaagcttccc ggggggatct gggccactcc ctctctgcgc gctcgctcgc tcactgaggc     60

cgggcgacca aaggtcgccc gacgcccggg ctttgcccgg gcggcctcag tgagcgagcg    120

agcgcgcaga gagggagtgg ccaactccat cactaggggt tcctggaggg gtggagtcgt    180

gacctaggac gcgtaccttt ccagcctggc ttacaggctt ttttcaccac agtaccaatt    240

gcccatgctc tgctcattaa tttaaatggc aatgactatc tgggttttaa aatagagaag    300

tgtcaggatg ggaacacgca atcatttggc tttttgcgtt ccagcactgt tttgaatagc    360

agggttttca cttcctatga aaccttagca ggaggaaaag cggaaactaa accataaagt    420

gagagggatg aggggaggga gggacttgag tatttgtaaa ctcagggtgg ctggccctgc    480

ctaccaggct gctctctacc accggaggct aggagtggaa aaacttgatt tacgtgttgt    540

gcctgccttt tttttttctt cttcttcttc ttcttcttct tcgtctccac accaccttct    600

gtacacctga ctctgcataa gcctatctga agctggcttg gtggcaggga tagctggaga    660

acagaagaat gtgcggaggg agggagggag gaagggaggg ctggtacttt tccattcaca    720

tctccacagt ggctgttctt gtttatttca accaccggag ctcgggctgg gcataaaagt    780

cagggcagag ccatctattg cttacatttg cttctgggat ccagatcttt cgaagctagc    840

gctaccggtc gccaccatgg tgagcaaggg cgaggagctg ttcaccgggg tggtgcccat    900

cctggtcgag ctggacggcg acgtaaacgg ccacaagttc agcgtgtccg gcgagggcga    960

gggcgatgcc acctacggca agctgaccct gaagctgatc tgcaccaccg gcaagctgcc   1020

cgtgccctgg cccaccctcg tgaccaccct gggctacggc gtgcagtgct tcgcccgcta   1080

ccccgaccac atgaagcagc acgacttctt caagtccgcc atgcccgaag gctacgtcca   1140

ggagcgcacc atcttcttca aggacgacgg caactacaag acccgcgccg aggtgaagtt   1200

cgagggcgac accctggtga accgcatcga gctgaagggc atcgacttca aggaggacgg   1260

caacatcctg gggcacaagc tggagtacaa ctacaacagc cacaacgtct atatcaccgc   1320

cgacaagcag aagaacggca tcaaggccaa cttcaagatc cgccacaaca tcgaggacgg   1380
```

-continued

```
cggcgtgcag ctcgccgacc actaccagca gaacaccccc atcggcgacg gccccgtgct   1440
gctgcccgac aaccactacc tgagctacca gtccaagctg agcaaagacc ccaacgagaa   1500
gcgcgatcac atggtcctgc tggagttcgt gaccgccgcc gggatcactc tcggcatgga   1560
cgagctgtac aagtaagtcg acggcgcgcc gcggccgcga attcgatatc ataatcaacc   1620
tctggattac aaaatttgtg aaagattgac tggtattctt aactatgttg ctccttttac   1680
gctatgtgga tacgctgctt taatgccttt gtatcatgct attgcttccc gtatggcttt   1740
cattttctcc tccttgtata aatcctggtt agttcttgcc acggcggaac tcatcgccgc   1800
ctgccttgcc cgctgctgga caggggctcg gctgttgggc actgacaatt ccgtggctcg   1860
agcgactgtg ccttctagtt gccagccatc tgttgtttgc ccctcccccg tgccttcctt   1920
gaccctggaa ggtgccactc ccactgtcct ttcctaataa aatgaggaaa ttgcatcgca   1980
ttgtctgagt aggtgtcatt ctattctggg gggtggggtg gggcaggaca gcaaggggga   2040
ggattgggaa gacaatagca ggcatgacta gtccactccc tctctgcgcg ctcgctcgct   2100
cactgaggcc gggcgaccaa aggtcgcccg acgcccgggc tttgcccggg cggcctcagt   2160
gagcgagcga gcgcgcagag agggacagat ccgggcccgc atgcgtcgac aattcactgg   2220
ccgtcgtttt acaacgtcgt gactgggaaa accctggcgt tacccaactt aatcgccttg   2280
cagcacatcc ccctttcgcc agctggcgta atagcgaaga ggcccgcacc gatcgccctt   2340
cccaacagtt gcgcagcctg aatggcgaat ggcgcctgat gcggtatttt ctccttacgc   2400
atctgtgcgg tatttcacac cgcatatggt gcactctcag tacaatctgc tctgatgccg   2460
catagttaag ccagccccga cacccgccaa cacccgctga cgcgccctga cgggcttgtc   2520
tgctcccggc atccgcttac agacaagctg tgaccgtctc cgggagctgc atgtgtcaga   2580
ggttttcacc gtcatcaccg aaacgcgcga gacgaaaggg cctcgtgata cgcctatttt   2640
tataggttaa tgtcatgata ataatggttt cttagacgtc aggtggcact tttcggggaa   2700
atgtgcgcgg aacccctatt tgtttatttt tctaaataca ttcaaatatg tatccgctca   2760
tgagacaata accctgataa atgcttcaat aatattgaaa aaggaagagt atgagtattc   2820
aacatttccg tgtcgccctt attccctttt ttgcggcatt ttgccttcct gtttttgctc   2880
acccagaaac gctggtgaaa gtaaaagatg ctgaagatca gttgggtgca cgagtgggtt   2940
acatcgaact ggatctcaac agcggtaaga tccttgagag ttttcgcccc gaagaacgtt   3000
ttccaatgat gagcactttt aaagttctgc tatgtggcgc ggtattatcc cgtattgacg   3060
ccgggcaaga gcaactcggt cgccgcatac actattctca gaatgacttg gttgagtact   3120
caccagtcac agaaaagcat cttacggatg gcatgacagt aagagaatta tgcagtgctg   3180
ccataaccat gagtgataac actgcggcca acttacttct gacaacgatc ggaggaccga   3240
aggagctaac cgcttttttg cacaacatgg gggatcatgt aactcgcctt gatcgttggg   3300
aaccggagct gaatgaagcc ataccaaacg acgagcgtga caccacgatg cctgtagcaa   3360
tggcaacaac gttgcgcaaa ctattaactg gcgaactact tactctagct tcccggcaac   3420
aattaataga ctggatggag gcggataaag ttgcaggacc acttctgcgc tcggcccttc   3480
cggctggctg gtttattgct gataaatctg gagccggtga gcgtgggtct cgcggtatca   3540
ttgcagcact ggggccagat ggtaagccct cccgtatcgt agttatctac acgacgggga   3600
gtcaggcaac tatggatgaa cgaaatagac agatcgctga gataggtgcc tcactgatta   3660
agcattggta actgtcagac caagtttact catatatact ttagattgat ttaaaacttc   3720
```

-continued atttttaatt taaaaggatc taggtgaaga tcctttttga taatctcatg accaaaatcc 3780
cttaacgtga gttttcgttc cactgagcgt cagaccccgt agaaaagatc aaaggatctt 3840
cttgagatcc tttttttctg cgcgtaatct gctgcttgca aacaaaaaaa ccaccgctac 3900
cagcggtggt ttgtttgccg gatcaagagc taccaactct ttttccgaag gtaactggct 3960
tcagcagagc gcagatacca aatactgttc ttctagtgta gccgtagtta ggccaccact 4020
tcaagaactc tgtagcaccg cctacatacc tcgctctgct aatcctgtta ccagtggctg 4080
ctgccagtgg cgataagtcg tgtcttaccg ggttggactc aagacgatag ttaccggata 4140
aggcgcagcg gtcgggctga acggggggtt cgtgcacaca gcccagcttg gagcgaacga 4200
cctacaccga actgagatac ctacagcgtg agctatgaga aagcgccacg cttcccgaag 4260
ggagaaaggc ggacaggtat ccggtaagcg gcagggtcgg aacaggagag cgcacgaggg 4320
agcttccagg gggaaacgcc tggtatcttt atagtcctgt cgggtttcgc cacctctgac 4380
ttgagcgtcg atttttgtga tgctcgtcag gggggcggag cctatggaaa aacgccagca 4440
acgcggcctt tttacggttc ctggcctttt gctggccttt tgctcacatg ttctttcctg 4500
cgttatcccc tgattctgtg gataaccgta ttaccgcctt tgagtgagct gataccgctc 4560
gccgcagccg aacgaccgag cgcagcgagt cagtgagcga ggaagcggaa gagcgcccaa 4620
tacgcaaacc gcctctcccc gcgcgttggc cgattcatta atgcagctgg cacgacaggt 4680
ttcccgactg gaaagcgggc agtgagcgca acgcaattaa tgtgagttag ctcactcatt 4740
aggcacccca ggctttacac tttatgcttc cggctcgtat gttgtgtgga attgtgagcg 4800
gataacaatt tcacacagga aacagctatg accatgatta cgccaagctc tcgagatcta 4860
g 4861

<210> SEQ ID NO 76
<211> LENGTH: 4862
<212> TYPE: DNA
<213> ORGANISM: Artificial Sequence
<220> FEATURE:
<223> OTHER INFORMATION: synthetic construct

<400> SEQUENCE: 76
aaagcttccc ggggggatct gggccactcc ctctctgcgc gctcgctcgc tcactgaggc 60
cgggcgacca aaggtcgccc gacgcccggg ctttgcccgg gcggcctcag tgagcgagcg 120
agcgcgcaga gagggagtgg ccaactccat cactaggggt tcctggaggg gtggagtcgt 180
gacctaggac gcgtttctaa tcatgaattc ttttgtggta ttttagattt tcagtttgtt 240
ctgtatcaat tctctctcat tcaaagaata tgatagtgag gtagatgaag ctgcctaagc 300
cacaggaaga aacatcttca gtctgtcgta aatgcacttc agatacagca ccttgcactg 360
cacataaaaa ttcatagtca cctaagtggg aatagctatg aaaatctgag tatcgccatg 420
ctgttgactc agtgctattt ataaaactca gttttaatgt ttccaattta aattctctgc 480
acatatctct cctgcactaa agacttgaga taccagtgct ttaccctaaa atatcttgct 540
tttatatctt gactcttatg ttgagaattt attattttta aaatatactt taaaacatgc 600
attggtacaa aattagtcaa aacagcaacc agtgaattca aagtaaatta gtattattaa 660
tgctgtgtat aattttggtg aattttacta ttaaattata aataaaaagt ccttccaggt 720
agtcatgttc actcctgatt ggtaagttca agaacattga gctcgggctg ggcataaaag 780
tcagggcaga gccatctatt gcttacattt gcttctggga tccagatctt tcgaagctag 840
cgctaccggt cgccaccatg gtgagcaagg gcgaggagct gttcaccggg gtggtgccca 900

-continued

```
tcctggtcga gctggacggc gacgtaaacg gccacaagtt cagcgtgtcc ggcgagggcg    960
agggcgatgc cacctacggc aagctgaccc tgaagctgat ctgcaccacc ggcaagctgc   1020
ccgtgccctg gcccaccctc gtgaccaccc tgggctacgg cgtgcagtgc ttcgcccgct   1080
accccgacca catgaagcag cacgacttct tcaagtccgc catgcccgaa ggctacgtcc   1140
aggagcgcac catcttcttc aaggacgacg gcaactacaa gacccgcgcc gaggtgaagt   1200
tcgagggcga caccctggtg aaccgcatcg agctgaaggg catcgacttc aaggaggacg   1260
gcaacatcct ggggcacaag ctggagtaca actacaacag ccacaacgtc tatatcaccg   1320
ccgacaagca gaagaacggc atcaaggcca acttcaagat ccgccacaac atcgaggacg   1380
gcggcgtgca gctcgccgac cactaccagc agaacacccc catcggcgac ggccccgtgc   1440
tgctgcccga caaccactac ctgagctacc agtccaagct gagcaaagac cccaacgaga   1500
agcgcgatca catggtcctg ctggagttcg tgaccgccgc cgggatcact ctcggcatgg   1560
acgagctgta caagtaagtc gacggcgcgc cgcggccgcg aattcgatat cataatcaac   1620
ctctggatta caaaatttgt gaaagattga ctggtattct taactatgtt gctcctttta   1680
cgctatgtgg atacgctgct ttaatgcctt tgtatcatgc tattgcttcc cgtatggctt   1740
tcattttctc ctccttgtat aaatcctggt tagttcttgc cacggcggaa ctcatcgccg   1800
cctgccttgc ccgctgctgg acaggggctc ggctgttggg cactgacaat tccgtggctc   1860
gagcgactgt gccttctagt tgccagccat ctgttgtttg cccctccccc gtgccttcct   1920
tgaccctgga aggtgccact cccactgtcc tttcctaata aaatgaggaa attgcatcgc   1980
attgtctgag taggtgtcat tctattctgg ggggtggggt ggggcaggac agcaaggggg   2040
aggattggga agacaatagc aggcatgact agtccactcc ctctctgcgc gctcgctcgc   2100
tcactgaggc cgggcgacca aaggtcgccc gacgcccggg ctttgcccgg gcggcctcag   2160
tgagcgagcg agcgcgcaga gagggacaga tccgggcccg catgcgtcga caattcactg   2220
gccgtcgttt tacaacgtcg tgactgggaa aaccctggcg ttacccaact taatcgcctt   2280
gcagcacatc ccccttcgc cagctggcgt aatagcgaag aggcccgcac cgatcgccct   2340
tcccaacagt tgcgcagcct gaatggcgaa tggcgcctga tgcggtattt tctccttacg   2400
catctgtgcg gtatttcaca ccgcatatgg tgcactctca gtacaatctg ctctgatgcc   2460
gcatagttaa gccagccccg acacccgcca acacccgctg acgcgccctg acgggcttgt   2520
ctgctcccgg catccgctta cagacaagct gtgaccgtct ccgggagctg catgtgtcag   2580
aggttttcac cgtcatcacc gaaacgcgcg agacgaaagg gcctcgtgat acgcctattt   2640
ttataggtta atgtcatgat aataatggtt tcttagacgt caggtggcac ttttcgggga   2700
aatgtgcgcg gaacccctat ttgtttattt ttctaaatac attcaaatat gtatccgctc   2760
atgagacaat aaccctgata aatgcttcaa taatattgaa aaaggaagag tatgagtatt   2820
caacatttcc gtgtcgccct tattcccttt tttgcggcat tttgccttcc tgtttttgct   2880
cacccagaaa cgctggtgaa agtaaaagat gctgaagatc agttgggtgc acgagtgggt   2940
tacatcgaac tggatctcaa cagcggtaag atccttgaga gttttcgccc cgaagaacgt   3000
tttccaatga tgagcacttt taaagttctg ctatgtggcg cggtattatc ccgtattgac   3060
gccgggcaag agcaactcgg tcgccgcata cactattctc agaatgactt ggttgagtac   3120
tcaccagtca cagaaaagca tcttacggat ggcatgacag taagagaatt atgcagtgct   3180
gccataacca tgagtgataa cactgcggcc aacttacttc tgacaacgat cggaggaccg   3240
```

aaggagctaa ccgctttttt gcacaacatg ggggatcatg taactcgcct tgatcgttgg 3300
gaaccggagc tgaatgaagc cataccaaac gacgagcgtg acaccacgat gcctgtagca 3360
atggcaacaa cgttgcgcaa actattaact ggcgaactac ttactctagc ttcccggcaa 3420
caattaatag actggatgga ggcggataaa gttgcaggac cacttctgcg ctcggccctt 3480
ccggctggct ggtttattgc tgataaatct ggagccggtg agcgtgggtc tcgcggtatc 3540
attgcagcac tggggccaga tggtaagccc tcccgtatcg tagttatcta cacgacgggg 3600
agtcaggcaa ctatggatga acgaaataga cagatcgctg agataggtgc ctcactgatt 3660
aagcattggt aactgtcaga ccaagtttac tcatatatac tttagattga tttaaaactt 3720
catttttaat ttaaaaggat ctaggtgaag atcctttttg ataatctcat gaccaaaatc 3780
ccttaacgtg agttttcgtt ccactgagcg tcagaccccg tagaaaagat caaaggatct 3840
tcttgagatc ctttttttct gcgcgtaatc tgctgcttgc aaacaaaaaa accaccgcta 3900
ccagcggtgg tttgtttgcc ggatcaagag ctaccaactc tttttccgaa ggtaactggc 3960
ttcagcagag cgcagatacc aaatactgtt cttctagtgt agccgtagtt aggccaccac 4020
ttcaagaact ctgtagcacc gcctacatac ctcgctctgc taatcctgtt accagtggct 4080
gctgccagtg gcgataagtc gtgtcttacc gggttggact caagacgata gttaccggat 4140
aaggcgcagc ggtcgggctg aacggggggt tcgtgcacac agcccagctt ggagcgaacg 4200
acctacaccg aactgagata cctacagcgt gagctatgag aaagcgccac gcttcccgaa 4260
gggagaaagg cggacaggta tccggtaagc ggcagggtcg gaacaggaga gcgcacgagg 4320
gagcttccag ggggaaacgc ctggtatctt tatagtcctg tcgggtttcg ccacctctga 4380
cttgagcgtc gatttttgtg atgctcgtca ggggggcgga gcctatggaa aaacgccagc 4440
aacgcggcct ttttacggtt cctggccttt tgctggcctt ttgctcacat gttctttcct 4500
gcgttatccc ctgattctgt ggataaccgt attaccgcct ttgagtgagc tgataccgct 4560
cgccgcagcc gaacgaccga gcgcagcgag tcagtgagcg aggaagcgga agagcgccca 4620
atacgcaaac cgcctctccc cgcgcgttgg ccgattcatt aatgcagctg gcacgacagg 4680
tttcccgact ggaaagcggg cagtgagcgc aacgcaatta atgtgagtta gctcactcat 4740
taggcacccc aggctttaca ctttatgctt ccggctcgta tgttgtgtgg aattgtgagc 4800
ggataacaat ttcacacagg aaacagctat gaccatgatt acgccaagct ctcgagatct 4860
ag 4862

<210> SEQ ID NO 77
<211> LENGTH: 3116
<212> TYPE: DNA
<213> ORGANISM: Artificial Sequence
<220> FEATURE:
<223> OTHER INFORMATION: synthetic construct

<400> SEQUENCE: 77
gcaggcagct gcgcgctcgc tcgctcactg aggccgcccg ggcgtcgggc gacctttggt 60
cgcccggcct cagtgagcga gcgagcgcgc agagagggag tggccaactc catcactagg 120
ggttcctgcg gccgcacgcg ttgctgtcat ttacctacgg ttgtctccaa atttcttcaa 180
ccaagtagag aaaaatgaga gagaaggaaa gaaaaaaaga ggtatgggga gaagagaaag 240
aaggcaactt gttaaaaatc tcagtcaaac ttacatacta tatagaacag catggtgaat 300
ttagggcaca tggatataaa atggaagttt cttattcagt agcagcaact tgtgggcaca 360
ggagttggca aagataaaaa tgtccaaagt cacaaataca atgtatagtt agtcataggt 420
gctgttattt gcctcaaaaa atagactttt attttgcctt tcttttcttt aaccacactc 480
aaaattagag aacagagaca aaacccagca ggaaatagca cagaaagccc acagaatcaa 540
agacgtgttc aaacagccag ctgaattcat tgcacatttc aaccacagaa atattttcag 600
gtgattctgt tgtttgacaa aacgtgggaa ccacaggatc tacaacactt gcaagcaaaa 660
ctcaacagct ctaataatag ttacagaagt gaaagccaat ttggataaaa taagacattg 720
actcaagtcc tctcagaaga gttttgaaag caaagtttac aaaagtctgg tttgtccttt 780
gggatttaca gacctttcag ccccttgatt catttttttt tttttggatt tcttcatcac 840
tgggagaatt cccatgcatt atttctcccc tgcttcaaaa tcatcaaatg tgaaacattt 900
ttcactcttt tcttctgtat atagtgataa aatagctatt ggcttttggc taaatgtgct 960
actttgagcc cacccacaca agggagaaat gggggcagac atgagtttgg gcatgagtct 1020
taaggagctc gggctgggca taaaagtcag ggcagagcca tctattgctt acatttgctt 1080
ctgggatccg ccaccatggt gagcaagggc gaggagctgt tcaccggggt ggtgcccatc 1140
ctggtcgagc tggacggcga cgtaaacggc cacaagttca gcgtgtccgg cgagggcgag 1200
ggcgatgcca cctacggcaa gctgaccctg aagttcatct gcaccaccgg caagctgccc 1260
gtgccctggc ccaccctcgt gaccaccctg acctacggcg tgcagtgctt cagccgctac 1320
cccgaccaca tgaagcagca cgacttcttc aagtccgcca tgcccgaagg ctacgtccag 1380
gagcgcacca tcttcttcaa ggacgacggc aactacaaga cccgcgccga ggtgaagttc 1440
gagggcgaca ccctggtgaa ccgcatcgag ctgaagggca tcgacttcaa ggaggacggc 1500
aacatcctgg ggcacaagct ggagtacaac tacaacagcc acaacgtcta tatcatggcc 1560
gacaagcaga agaacggcat caaggtgaac ttcaagatcc gccacaacat cgaggacggc 1620
agcgtgcagc tcgccgacca ctaccagcag aacaccccca tcggcgacgg ccccgtgctg 1680
ctgcccgaca accactacct gagcacccag tccgccctga gcaaagaccc caacgagaag 1740
cgcgatcaca tggtcctgct ggagttcgtg accgccgccg ggatcactct cggcatggac 1800
gagctgtaca agtaagaatt cgatatcaag cttatcgata atcaacctct ggattacaaa 1860
atttgtgaaa gattgactgg tattcttaac tatgttgctc cttttacgct atgtggatac 1920
gctgctttaa tgcctttgta tcatgctatt gcttcccgta tggctttcat tttctcctcc 1980
ttgtataaat cctggttgct gtctctttat gaggagttgt ggcccgttgt caggcaacgt 2040
ggcgtggtgt gcactgtgtt tgctgacgca acccccactg gttggggcat tgccaccacc 2100
tgtcagctcc tttccgggac tttcgctttc cccctcccta ttgccacggc ggaactcatc 2160
gccgcctgcc ttgcccgctg ctggacaggg gctcggctgt tgggcactga caattccgtg 2220
gtgttgtcgg ggaaatcatc gtcctttcct tggctgctcg cctatgttgc cacctggatt 2280
ctgcgcggga cgtccttctg ctacgtccct tcggccctca atccagcgga ccttccttcc 2340
cgcggcctgc tgccggctct gcggcctctt ccgcgtcttc gccttcgccc tcagacgagt 2400
cggatctccc tttgggccgc ctccccgcat cgataccgag cgctgctcga gagatctacg 2460
ggtggcatcc ctgtgacccc tccccagtgc ctctcctggc cctggaagtt gccactccag 2520
tgcccaccag ccttgtccta ataaaattaa gttgcatcat tttgtctgac taggtgtcct 2580
tctataatat tatggggtgg aggggggtgg tatggagcaa ggggcaagtt gggaagacaa 2640
cctgtagggc ctgcggggtc tattgggaac caagctggag tgcagtggca caatcttggc 2700
tcactgcaat ctccgcctcc tgggttcaag cgattctcct gcctcagcct cccgagttgt 2760
tgggattcca ggcatgcatg accaggctca gctaattttt gttttttttgg tagagacggg 2820 gtttcaccat attggccagg ctggtctcca actcctaatc tcaggtgatc tacccacctt 2880
ggcctcccaa attgctggga ttacaggcgt gaaccactgc tcccttccct gtccttctga 2940
ttttgtaggt aaccacgtgc ggaccgagcg gccgcaggaa cccctagtga tggagttggc 3000
cactccctct ctgcgcgctc gctcgctcac tgaggccggg cgaccaaagg tcgcccgacg 3060
cccgggcttt gcccgggcgg cctcagtgag cgagcgagcg cgcagctgcc tgcagg 3116

<210> SEQ ID NO 78
<211> LENGTH: 3695
<212> TYPE: DNA
<213> ORGANISM: Artificial Sequence
<220> FEATURE:
<223> OTHER INFORMATION: synthetic construct

<400> SEQUENCE: 78
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct gcggccgcac gcgttgctgt catttaccta cggttgtctc caaatttctt 180
caaccaagta gagaaaaatg agagagaagg aaagaaaaaa agaggtatgg ggagaagaga 240
aagaaggcaa cttgttaaaa atctcagtca aacttacata ctatatagaa cagcatggtg 300
aatttagggc acatggatat aaaatggaag tttcttattc agtagcagca acttgtgggc 360
acaggagttg gcaaagataa aaatgtccaa agtcacaaat acaatgtata gttagtcata 420
ggtgctgtta tttgcctcaa aaaatagact tttattttgc ctttcttttc tttaaccaca 480
ctcaaaatta gagaacagag acaaaaccca gcaggaaata gcacagaaag cccacagaat 540
caaagacgtg ttcaaacagc cagctgaatt cattgcacat ttcaaccaca gaaatatttt 600
caggtgattc tgttgtttga caaaacgtgg gaaccacagg atctacaaca cttgcaagca 660
aaactcaaca gctctaataa tagttacaga agtgaaagcc aatttggata aaataagaca 720
ttgactcaag tcctctcaga agagttttga aagcaaagtt tacaaaagtc tggtttgtcc 780
tttgggattt acagaccttt cagccccttg attcattttt tttttttgg atttcttcat 840 cactgggaga attcccatgc attatttctc ccctgcttca aaatcatcaa atgtgaaaca 900
tttttcactc ttttcttctg tatatagtga taaaatagct attggctttt ggctaaatgt 960
gctactttga gcccacccac acaagggaga aatgggggca gacatgagtt tgggcatgag 1020
tcttaaggag ctcgggctgg gcataaaagt cagggcagag ccatctattg cttacatttg 1080
cttctggcgt ggccaccatg gctcctaaga agaagaggaa ggtgatgagc cagttcgaca 1140
tcctgtgcaa gacccccccc aaggtgctgg tgcggcagtt cgtggagaga ttcgagaggc 1200
ccagcggcga gaagatcgcc agctgtgccg ccgagctgac ctacctgtgc tggatgatca 1260
cccacaacgg caccgccatc aagagggcca ccttcatgag ctacaacacc atcatcagca 1320
acagcctgag cttcgacatc gtgaacaaga gcctgcagtt caagtacaag acccagaagg 1380
ccaccatcct ggaggccagc ctgaagaagc tgatccccgc ctgggagttc accatcatcc 1440
cttacaacgg ccagaagcac cagagcgaca tcaccgacat cgtgtccagc ctgcagctgc 1500
agttcgagag cagcgaggag gccgacaagg gcaacagcca cagcaagaag atgctgaagg 1560
ccctgctgtc cgagggcgag agcatctggg agatcaccga gaagatcctg aacagcttcg 1620
agtacaccag caggttcacc aagaccaaga ccctgtacca gttcctgttc ctggccacat 1680
tcatcaactg cggcaggttc agcgacatca agaacgtgga ccccaagagc ttcaagctgg 1740
tgcagaacaa gtacctgggc gtgatcattc agtgcctggt gaccgagacc aagacaagcg 1800
tgtccaggca catctacttt ttcagcgcca gaggcaggat cgaccccctg gtgtacctgg 1860
acgagttcct gaggaacagc gagcccgtgc tgaagagagt gaacaggacc ggcaacagca 1920
gcagcaacaa gcaggagtac cagctgctga aggacaacct ggtgcgcagc tacaacaagg 1980
ccctgaagaa gaacgccccc taccccatct tcgctatcaa gaacggccct aagagccaca 2040
tcggcaggca cctgatgacc agctttctga gcatgaaggg cctgaccgag ctgacaaacg 2100
tggtgggcaa ctggagcgac aagagggcct ccgccgtggc caggaccacc tacacccacc 2160
agatcaccgc catccccgac cactacttcg ccctggtgtc caggtactac gcctacgacc 2220
ccatcagcaa ggagatgatc gccctgaagg acgagaccaa ccccatcgag gagtggcagc 2280
acatcgagca gctgaagggc agcgccgagg gcagcatcag ataccccgcc tggaacggca 2340
tcatcagcca ggaggtgctg gactacctga gcagctacat caacaggcgg atctgagaat 2400
tcgatatcaa gcttatcgat aatcaacctc tggattacaa aatttgtgaa agattgactg 2460
gtattcttaa ctatgttgct ccttttacgc tatgtggata cgctgcttta atgcctttgt 2520
atcatgctat tgcttcccgt atggctttca ttttctcctc cttgtataaa tcctggttgc 2580
tgtctcttta tgaggagttg tggcccgttg tcaggcaacg tggcgtggtg tgcactgtgt 2640
ttgctgacgc aacccccact ggttggggca ttgccaccac ctgtcagctc ctttccggga 2700
ctttcgcttt ccccctccct attgccacgg cggaactcat cgccgcctgc cttgcccgct 2760
gctggacagg ggctcggctg ttgggcactg acaattccgt ggtgttgtcg gggaaatcat 2820
cgtcctttcc ttggctgctc gcctatgttg ccacctggat tctgcgcggg acgtccttct 2880
gctacgtccc ttcggccctc aatccagcgg accttccttc ccgcggcctg ctgccggctc 2940
tgcggcctct tccgcgtctt cgccttcgcc ctcagacgag tcggatctcc ctttgggccg 3000
cctccccgca tcgataccga gcgctgctcg agagatctac gggtggcatc cctgtgaccc 3060
ctccccagtg cctctcctgg ccctggaagt tgccactcca gtgcccacca gccttgtcct 3120
aataaaatta agttgcatca ttttgtctga ctaggtgtcc ttctataata ttatggggtg 3180
gaggggggtg gtatggagca aggggcaagt tgggaagaca acctgtaggg cctgcggggt 3240
ctattgggaa ccaagctgga gtgcagtggc acaatcttgg ctcactgcaa tctccgcctc 3300
ctgggttcaa gcgattctcc tgcctcagcc tcccgagttg ttgggattcc aggcatgcat 3360
gaccaggctc agctaatttt tgttttttttg gtagagacgg ggtttcacca tattggccag 3420
gctggtctcc aactcctaat ctcaggtgat ctacccacct tggcctccca aattgctggg 3480
attacaggcg tgaaccactg ctcccttccc tgtccttctg attttgtagg taaccacgtg 3540
cggaccgagc ggccgcagga acccctagtg atggagttgg ccactccctc tctgcgcgct 3600
cgctcgctca ctgaggccgg gcgaccaaag gtcgcccgac gcccgggctt tgcccgggcg 3660
gcctcagtga gcgagcgagc gcgcagctgc ctgca 3695

<210> SEQ ID NO 79
<211> LENGTH: 3044
<212> TYPE: DNA
<213> ORGANISM: Artificial Sequence
<220> FEATURE:
<223> OTHER INFORMATION: synthetic construct

<400> SEQUENCE: 79
gcggccgcac gcgtgactgc taagctttgg gcactacctg ggtcagtct gcatcaaaat 60

-continued

```
gtaaggctca aatgtgtaat tgtaagtact gttttgctga gctggaaggg ctcctttgaa    120
gcccacgttt taattttaat ttagccacac agagtggcaa agacaaatag atttatccaa    180
aatacatttg gtaacagatt ttttgagtca gttattaatt ttatttgagg ggttcctctt    240
tttatttttt ataaactgtg aaactcaaga ggaagcagga tcccatgcaa tgccttttat    300
tgatggcctg ctatgtgcca agaaaggtgt taaatgtttt ccaatgctgc ctcatttatc    360
ctgatcttac agacaagcaa aaggaggtgt gaagaggtga agtttctcac ccagctggaa    420
agtggcaaag tcattcacag atctgcctcc gctcaaaaaa attgctttat gcaactcttt    480
ggaagctaac ttcatgggag ctacatgcag cttctgagct cgggctgggc ataaaagtca    540
gggcagagcc atctattgct tacatttgct tctggcgtgg ccaccatggc tcctaagaag    600
aagaggaagg tgatgagcca gttcgacatc ctgtgcaaga cccccccaa ggtgctggtg    660
cggcagttcg tggagagatt cgagaggccc agcggcgaga agatcgccag ctgtgccgcc    720
gagctgacct acctgtgctg gatgatcacc cacaacggca ccgccatcaa gagggccacc    780
ttcatgagct acaacaccat catcagcaac agcctgagct tcgacatcgt gaacaagagc    840
ctgcagttca agtacaagac ccagaaggcc accatcctgg aggccagcct gaagaagctg    900
atccccgcct gggagttcac catcatccct tacaacggcc agaagcacca gagcgacatc    960
accgacatcg tgtccagcct gcagctgcag ttcgagagca gcgaggaggc cgacaagggc   1020
aacagccaca gcaagaagat gctgaaggcc ctgctgtccg agggcgagag catctgggag   1080
atcaccgaga agatcctgaa cagcttcgag tacaccagca ggttcaccaa gaccaagacc   1140
ctgtaccagt tcctgttcct ggccacattc atcaactgcg gcaggttcag cgacatcaag   1200
aacgtggacc ccaagagctt caagctggtg cagaacaagt acctgggcgt gatcattcag   1260
tgcctggtga ccgagaccaa gacaagcgtg tccaggcaca tctacttttt cagcgccaga   1320
ggcaggatcg accccctggt gtacctggac gagttcctga ggaacagcga gcccgtgctg   1380
aagagagtga acaggaccgg caacagcagc agcaacaagc aggagtacca gctgctgaag   1440
gacaacctgg tgcgcagcta caacaaggcc ctgaagaaga acgcccccta ccccatcttc   1500
gctatcaaga acggccctaa gagccacatc ggcaggcacc tgatgaccag ctttctgagc   1560
atgaagggcc tgaccgagct gacaaacgtg gtgggcaact ggagcgacaa gagggcctcc   1620
gccgtggcca ggaccaccta cacccaccag atcaccgcca tccccgacca ctacttcgcc   1680
ctggtgtcca ggtactacgc ctacgacccc atcagcaagg agatgatcgc cctgaaggac   1740
gagaccaacc ccatcgagga gtggcagcac atcgagcagc tgaagggcag cgccgagggc   1800
agcatcagat accccgcctg gaacggcatc atcagccagg aggtgctgga ctacctgagc   1860
agctacatca acaggcggat ctgagaattc gatatcaagc ttatcgataa tcaacctctg   1920
gattacaaaa tttgtgaaag attgactggt attcttaact atgttgctcc ttttacgcta   1980
tgtggatacg ctgctttaat gcctttgtat catgctattg cttcccgtat ggctttcatt   2040
ttctcctcct tgtataaatc ctggttgctg tctctttatg aggagttgtg gcccgttgtc   2100
aggcaacgtg gcgtggtgtg cactgtgttt gctgacgcaa cccccactgg ttggggcatt   2160
gccaccacct gtcagctcct ttccgggact ttcgctttcc ccctccctat tgccacggcg   2220
gaactcatcg ccgcctgcct tgcccgctgc tggacagggg ctcggctgtt gggcactgac   2280
aattccgtgg tgttgtcggg gaaatcatcg tcctttcctt ggctgctcgc ctatgttgcc   2340
acctggattc tgcgcgggac gtccttctgc tacgtccctt cggccctcaa tccagcggac   2400
cttccttccc gcggcctgct gccggctctg cggcctcttc cgcgtcttcg ccttcgccct   2460
```

```
cagacgagtc ggatctccct ttgggccgcc tccccgcatc gataccgagc gctgctcgag   2520

agatctacgg gtggcatccc tgtgacccct ccccagtgcc tctcctggcc ctggaagttg   2580

ccactccagt gcccaccagc cttgtcctaa taaaattaag ttgcatcatt ttgtctgact   2640

aggtgtcctt ctataatatt atggggtgga ggggggtggt atggagcaag gggcaagttg   2700

ggaagacaac ctgtagggcc tgcggggtct attgggaacc aagctggagt gcagtggcac   2760

aatcttggct cactgcaatc tccgcctcct gggttcaagc gattctcctg cctcagcctc   2820

ccgagttgtt gggattccag gcatgcatga ccaggctcag ctaatttttg tttttttggt   2880

agagacgggg tttcaccata ttggccaggc tggtctccaa ctcctaatct caggtgatct   2940

acccaccttg gcctcccaaa ttgctgggat tacaggcgtg aaccactgct cccttccctg   3000

tccttctgat tttgtaggta accacgtgcg gaccgagcgg ccgc                    3044
```

<210> SEQ ID NO 80
<211> LENGTH: 3101
<212> TYPE: DNA
<213> ORGANISM: Artificial Sequence
<220> FEATURE:
<223> OTHER INFORMATION: synthetic construct

<400> SEQUENCE: 80

```
gcggccgcac gcgtataagc cttgggggca atcaaactat tacattgagt ccttggattt     60

gctacaaatt acattttaaa tgcaatcatt ttataaaagc ttcaacactc acacttggaa    120

gcgttaccct gttgaatatc actgactcac taacttgcat tgccatgcta acttgctttc    180

agagagatct cagaacacat catcttctgc tatttcaata catgcacatt aatttcctat    240

caacgtgtgc tgatcaggaa ctctgtaatc tggcaccggt gtttattttt attcctgtct    300

attcctgttg gctcacgaaa agattgtttg agcaagtgtt ttatggtgag ttgtatcata    360

tgtacattga tttaatctgc ccacattcag ttctacaagc ggagccaaaa aaatagagac    420

aagcataatt ttcattcaac atgagcccct caatgcaagc caagtacctc atctggtgct    480

cagctaaagc aacagcaatc tgttccaccc tggagacaca actggccaca gaaaacttag    540

tgaaaagagg caatgctatg cacaggacaa atgagctcgg gctgggcata aaagtcaggg    600

cagagccatc tattgcttac atttgcttct ggcgtggcca ccatggctcc taagaagaag    660

aggaaggtga tgagccagtt cgacatcctg tgcaagaccc cccccaaggt gctggtgcgg    720

cagttcgtgg agagattcga gaggcccagc ggcgagaaga tcgccagctg tgccgccgag    780

ctgacctacc tgtgctggat gatcacccac aacggcaccg ccatcaagag ggccaccttc    840

atgagctaca acaccatcat cagcaacagc ctgagcttcg acatcgtgaa caagagcctg    900

cagttcaagt acaagaccca gaaggccacc atcctggagg ccagcctgaa gaagctgatc    960

cccgcctggg agttcaccat catcccttac aacggccaga agcaccagag cgacatcacc   1020

gacatcgtgt ccagcctgca gctgcagttc gagagcagcg aggaggccga caagggcaac   1080

agccacagca agaagatgct gaaggccctg ctgtccgagg gcgagagcat ctgggagatc   1140

accgagaaga tcctgaacag cttcgagtac accagcaggt tcaccaagac caagaccctg   1200

taccagttcc tgttcctggc cacattcatc aactgcggca ggttcagcga catcaagaac   1260

gtggacccca agagcttcaa gctggtgcag aacaagtacc tgggcgtgat cattcagtgc   1320

ctggtgaccg agaccaagac aagcgtgtcc aggcacatct actttttcag cgccagaggc   1380

aggatcgacc ccctggtgta cctggacgag ttcctgagga acagcgagcc cgtgctgaag   1440
```

```
agagtgaaca ggaccggcaa cagcagcagc aacaagcagg agtaccagct gctgaaggac   1500

aacctggtgc gcagctacaa caaggccctg aagaagaacg cccoctaccc catcttcgct   1560

atcaagaacg gccctaagag ccacatcggc aggcacctga tgaccagctt tctgagcatg   1620

aagggcctga ccgagctgac aaacgtggtg ggcaactgga gcgacaagag ggcctccgcc   1680

gtggccagga ccacctacac ccaccagatc accgccatcc ccgaccacta cttcgccctg   1740

gtgtccaggt actacgccta cgaccccatc agcaaggaga tgatcgccct gaaggacgag   1800

accaacccca tcgaggagtg gcagcacatc gagcagctga agggcagcgc cgagggcagc   1860

atcagatacc ccgcctggaa cggcatcatc agccaggagg tgctggacta cctgagcagc   1920

tacatcaaca ggcggatctg agaattcgat atcaagctta tcgataatca acctctggat   1980

tacaaaattt gtgaaagatt gactggtatt cttaactatg ttgctccttt tacgctatgt   2040

ggatacgctg ctttaatgcc tttgtatcat gctattgctt cccgtatggc tttcattttc   2100

tcctccttgt ataaatcctg gttgctgtct ctttatgagg agttgtggcc cgttgtcagg   2160

caacgtggcg tggtgtgcac tgtgtttgct gacgcaaccc ccactggttg gggcattgcc   2220

accacctgtc agctcctttc cgggactttc gctttccccc tccctattgc cacggcggaa   2280

ctcatcgccg cctgccttgc ccgctgctgg acaggggctc ggctgttggg cactgacaat   2340

tccgtggtgt tgtcggggaa atcatcgtcc tttccttggc tgctcgccta tgttgccacc   2400

tggattctgc gcgggacgtc cttctgctac gtcccttcgg ccctcaatcc agcggacctt   2460

ccttcccgcg gcctgctgcc ggctctgcgg cctcttccgc gtcttcgcct tcgccctcag   2520

acgagtcgga tctccctttg ggccgcctcc ccgcatcgat accgagcgct gctcgagaga   2580

tctacgggtg gcatccctgt gacccctccc cagtgcctct cctggccctg gaagttgcca   2640

ctccagtgcc caccagcctt gtcctaataa aattaagttg catcattttg tctgactagg   2700

tgtccttcta taatattatg gggtggaggg gggtggtatg gagcaagggg caagttggga   2760

agacaacctg tagggcctgc ggggtctatt gggaaccaag ctggagtgca gtggcacaat   2820

cttggctcac tgcaatctcc gcctcctggg ttcaagcgat tctcctgcct cagcctcccg   2880

agttgttggg attccaggca tgcatgacca ggctcagcta atttttgttt ttttggtaga   2940

gacggggttt caccatattg gccaggctgg tctccaactc ctaatctcag gtgatctacc   3000

caccttggcc tcccaaattg ctgggattac aggcgtgaac cactgctccc ttccctgtcc   3060

ttctgatttt gtaggtaacc acgtgcggac cgagcggccg c                       3101
```

<210> SEQ ID NO 81
<211> LENGTH: 2523
<212> TYPE: DNA
<213> ORGANISM: Artificial Sequence
<220> FEATURE:
<223> OTHER INFORMATION: synthetic construct

<400> SEQUENCE: 81

```
gcggccgcac gcgtataagc cttgggggca atcaaactat tacattgagt ccttggattt     60

gctacaaatt acattttaaa tgcaatcatt ttataaaagc ttcaacactc acacttggaa    120

gcgttaccct gttgaatatc actgactcac taacttgcat tgccatgcta acttgctttc    180

agagagatct cagaacacat catcttctgc tatttcaata catgcacatt aatttcctat    240

caacgtgtgc tgatcaggaa ctctgtaatc tggcaccggt gtttattttt attcctgtct    300

attcctgttg gctcacgaaa agattgtttg agcaagtgtt ttatggtgag ttgtatcata    360

tgtacattga tttaatctgc ccacattcag ttctacaagc ggagccaaaa aaatagagac    420
```

-continued

```
aagcataatt ttcattcaac atgagcccct caatgcaagc caagtacctc atctggtgct    480
cagctaaagc aacagcaatc tgttccaccc tggagacaca actggccaca gaaaacttag    540
tgaaaagagg caatgctatg cacaggacaa atgagctcgg gctgggcata aaagtcaggg    600
cagagccatc tattgcttac atttgcttct gggatccgcc accatggtga gcaagggcga    660
ggagctgttc accggggtgg tgcccatcct ggtcgagctg gacggcgacg taaacggcca    720
caagttcagc gtgtccggcg agggcgaggg cgatgccacc tacggcaagc tgaccctgaa    780
gttcatctgc accaccggca agctgcccgt gccctggccc accctcgtga ccaccctgac    840
ctacggcgtg cagtgcttca gccgctaccc cgaccacatg aagcagcacg acttcttcaa    900
gtccgccatg cccgaaggct acgtccagga gcgcaccatc ttcttcaagg acgacggcaa    960
ctacaagacc cgcgccgagg tgaagttcga gggcgacacc ctggtgaacc gcatcgagct   1020
gaagggcatc gacttcaagg aggacggcaa catcctgggg cacaagctgg agtacaacta   1080
caacagccac aacgtctata tcatggccga caagcagaag aacggcatca aggtgaactt   1140
caagatccgc cacaacatcg aggacggcag cgtgcagctc gccgaccact accagcagaa   1200
cacccccatc ggcgacggcc ccgtgctgct gcccgacaac cactacctga gcacccagtc   1260
cgccctgagc aaagacccca acgagaagcg cgatcacatg gtcctgctgg agttcgtgac   1320
cgccgccggg atcactctcg gcatggacga gctgtacaag taagaattcg atatcaagct   1380
tatcgataat caacctctgg attacaaaat ttgtgaaaga ttgactggta ttcttaacta   1440
tgttgctcct tttacgctat gtggatacgc tgctttaatg cctttgtatc atgctattgc   1500
ttcccgtatg gctttcattt tctcctcctt gtataaatcc tggttgctgt ctctttatga   1560
ggagttgtgg cccgttgtca ggcaacgtgg cgtggtgtgc actgtgtttg ctgacgcaac   1620
ccccactggt tggggcattg ccaccacctg tcagctcctt tccgggactt tcgctttccc   1680
cctccctatt gccacggcgg aactcatcgc cgcctgcctt gcccgctgct ggacaggggc   1740
tcggctgttg ggcactgaca attccgtggt gttgtcgggg aaatcatcgt cctttccttg   1800
gctgctcgcc tatgttgcca cctggattct gcgcgggacg tccttctgct acgtcccttc   1860
ggccctcaat ccagcggacc ttccttcccg cggcctgctg ccggctctgc ggcctcttcc   1920
gcgtcttcgc cttcgccctc agacgagtcg gatctccctt tgggccgcct ccccgcatcg   1980
ataccgagcg ctgctcgaga gatctacggg tggcatccct gtgacccctc cccagtgcct   2040
ctcctggccc tggaagttgc cactccagtg cccaccagcc ttgtcctaat aaaattaagt   2100
tgcatcattt tgtctgacta ggtgtccttc tataatatta tggggtggag gggggtggta   2160
tggagcaagg ggcaagttgg gaagacaacc tgtagggcct gcggggtcta ttgggaacca   2220
agctggagtg cagtggcaca atcttggctc actgcaatct ccgcctcctg ggttcaagcg   2280
attctcctgc ctcagcctcc cgagttgttg ggattccagg catgcatgac caggctcagc   2340
taatttttgt ttttttggta gagacggggt ttcaccatat tggccaggct ggtctccaac   2400
tcctaatctc aggtgatcta cccaccttgg cctcccaaat tgctgggatt acaggcgtga   2460
accactgctc ccttccctgt ccttctgatt ttgtaggtaa ccacgtgcgg accgagcggc   2520
cgc                                                                 2523
```

<210> SEQ ID NO 82
<211> LENGTH: 1938
<212> TYPE: DNA
<213> ORGANISM: Artificial Sequence
<220> FEATURE:

-continued

<223> OTHER INFORMATION: synthetic construct

<400> SEQUENCE: 82
gcggccgcac gcgtataagc cttgggggca atcaaactat tacattgagt ccttggattt 60
gctacaaatt acattttaaa tgcaatcatt ttataaaagc ttcaacactc acacttggaa 120
gcgttaccct gttgaatatc actgactcac taacttgcat tgccatgcta acttgctttc 180
agagagatct cagaacacat catcttctgc tatttcaata catgcacatt aatttcctat 240
caacgtgtgc tgatcaggaa ctctgtaatc tggcaccggt gtttattttt attcctgtct 300
attcctgttg gctcacgaaa agattgtttg agcaagtgtt ttatggtgag ttgtatcata 360
tgtacattga tttaatctgc ccacattcag ttctacaagc ggagccaaaa aaatagagac 420
aagcataatt ttcattcaac atgagcccct caatgcaagc caagtacctc atctggtgct 480
cagctaaagc aacagcaatc tgttccaccc tggagacaca actggccaca gaaaacttag 540
tgaaaagagg caatgctatg cacaggacaa atgagctcgg gctgggcata aaagtcaggg 600
cagagccatc tattgcttac atttgcttct gggatccgcc accatgtcta gactggacaa 660
gagcaaagtc ataaactctg ctctggaatt actcaatgaa gtcggtatcg aaggcctgac 720
gacaaggaaa ctcgctcaaa agctgggagt tgagcagcct accctgtact ggcacgtgaa 780
gaacaagcgg gccctgctcg atgccctggc aatcgagatg ctggacaggc atcataccca 840
cttctgcccc ctggaaggcg agtcatggca agactttctg cggaacaacg ccaagtcatt 900
ccgctgtgct ctcctctcac atcgcgacgg ggctaaagtg catctcggca cccgcccaac 960
agagaaacag tacgaaaccc tggaaaatca gctcgcgttc ctgtgtcagc aaggcttctc 1020
cctggagaac gcactgtacg ctctgtccgc cgtgggccac tttacactgg gctgcgtatt 1080
ggaggatcag gagcatcaag tagcaaaaga ggaaagagag acacctacca ccgattctat 1140
gcccccactt ctgagacaag caattgagct gttcgaccat cagggagccg aacctgcctt 1200
ccttttcggc ctggaactaa tcatatgtgg cctggagaaa cagctaaagt gcgaaagcgg 1260
cgggccggcc gacgcccttg acgattttga cttagacatg ctcccagccg atgcccttga 1320
cgactttgac cttgatatgc tgcctgctga cgctcttgac gattttgacc ttgacatgct 1380
ccccgggtaa ggcgcgccgc ggccgctgct cgagagatct acgggtggca tccctgtgac 1440
ccctccccag tgcctctcct ggccctggaa gttgccactc cagtgcccac cagccttgtc 1500
ctaataaaat taagttgcat cattttgtct gactaggtgt ccttctataa tattatgggg 1560
tggagggggg tggtatggag caaggggcaa gttgggaaga caacctgtag ggcctgcggg 1620
gtctattggg aaccaagctg gagtgcagtg gcacaatctt ggctcactgc aatctccgcc 1680
tcctgggttc aagcgattct cctgcctcag cctcccgagt tgttgggatt ccaggcatgc 1740
atgaccaggc tcagctaatt tttgtttttt tggtagagac ggggtttcac catattggcc 1800
aggctggtct ccaactccta atctcaggtg atctacccac cttggcctcc caaattgctg 1860
ggattacagg cgtgaaccac tgctcccttc cctgtccttc tgattttgta ggtaaccacg 1920
tgcggaccga gcggccgc 1938

<210> SEQ ID NO 83
<211> LENGTH: 2564
<212> TYPE: DNA
<213> ORGANISM: Artificial Sequence
<220> FEATURE:
<223> OTHER INFORMATION: synthetic construct

<400> SEQUENCE: 83

```
gcggccgcac gcgtatgtgt cttttactct gatcctcctg tttttacctt ccaagtgctg     60
gaatcacaga catataccac tgtgcatagc atcattacaa tgttatagtt tttcacacta    120
tgccttgact ttttggaaag gcaaaccacc tcttggattt ctccttcctt ctctatctct    180
ctctctctct cttcctccct ccgtccctcc atctcttcct ccttcccatt ttcttctctc    240
cctatttgga cacaatataa aataatttag atgaggtgag ttaaattgtg aacaaagtat    300
gtgcctatac atggttgtaa atcagcttat caaagtgtaa tattagaaga atttataaaa    360
atgataaaat tcatactcaa agttctgtgt aaagcaataa tagctttatc tccttttagt    420
tatcttgagt ctttctatga ctaacaactc cctcataggc atcttaaaga gcagtaagca    480
taagtagatt ccaaatggga agggagaagt gtgaaccatc actttcatcc agacttgtag    540
atatatctgc tgcattttca gaaaccagaa acagacagtg ttctttatct ccattgagtc    600
tagtgtagca acagagctcg ggctgggcat aaaagtcagg gcagagccat ctattgctta    660
catttgcttc tgggatccgc caccatggtg agcaagggcg aggagctgtt caccggggtg    720
gtgcccatcc tggtcgagct ggacggcgac gtaaacggcc acaagttcag cgtgtccggc    780
gagggcgagg gcgatgccac ctacggcaag ctgaccctga agttcatctg caccaccggc    840
aagctgcccg tgccctggcc caccctcgtg accaccctga cctacggcgt gcagtgcttc    900
agccgctacc ccgaccacat gaagcagcac gacttcttca agtccgccat gcccgaaggc    960
tacgtccagg agcgcaccat cttcttcaag gacgacggca actacaagac ccgcgccgag   1020
gtgaagttcg agggcgacac cctggtgaac cgcatcgagc tgaagggcat cgacttcaag   1080
gaggacggca acatcctggg gcacaagctg gagtacaact acaacagcca caacgtctat   1140
atcatggccg acaagcagaa gaacggcatc aaggtgaact tcaagatccg ccacaacatc   1200
gaggacggca gcgtgcagct cgccgaccac taccagcaga acacccccat cggcgacggc   1260
cccgtgctgc tgcccgacaa ccactacctg agcacccagt ccgccctgag caaagacccc   1320
aacgagaagc gcgatcacat ggtcctgctg gagttcgtga ccgccgccgg gatcactctc   1380
ggcatggacg agctgtacaa gtaagaattc gatatcaagc ttatcgataa tcaacctctg   1440
gattacaaaa tttgtgaaag attgactggt attcttaact atgttgctcc ttttacgcta   1500
tgtggatacg ctgctttaat gcctttgtat catgctattg cttcccgtat ggctttcatt   1560
ttctcctcct tgtataaatc ctggttgctg tctctttatg aggagttgtg gcccgttgtc   1620
aggcaacgtg gcgtggtgtg cactgtgttt gctgacgcaa cccccactgg ttggggcatt   1680
gccaccacct gtcagctcct ttccgggact ttcgctttcc ccctccctat tgccacggcg   1740
gaactcatcg ccgcctgcct tgcccgctgc tggacagggg ctcggctgtt gggcactgac   1800
aattccgtgg tgttgtcggg gaaatcatcg tcctttcctt ggctgctcgc ctatgttgcc   1860
acctggattc tgcgcgggac gtccttctgc tacgtccctt cggccctcaa tccagcggac   1920
cttccttccc gcggcctgct gccggctctg cggcctcttc cgcgtcttcg ccttcgccct   1980
cagacgagtc ggatctccct ttgggccgcc tccccgcatc gataccgagc gctgctcgag   2040
agatctacgg gtggcatccc tgtgacccct ccccagtgcc tctcctggcc ctggaagttg   2100
ccactccagt gcccaccagc cttgtcctaa taaaattaag ttgcatcatt ttgtctgact   2160
aggtgtcctt ctataatatt atggggtgga ggggggtggt atggagcaag gggcaagttg   2220
ggaagacaac ctgtagggcc tgcggggtct attgggaacc aagctggagt gcagtggcac   2280
aatcttggct cactgcaatc tccgcctcct gggttcaagc gattctcctg cctcagcctc   2340
```

-continued ccgagttgtt gggattccag gcatgcatga ccaggctcag ctaatttttg ttttttggt 2400 agagacgggg tttcaccata ttggccaggc tggtctccaa ctcctaatct caggtgatct 2460
acccaccttg gcctcccaaa ttgctgggat tacaggcgtg aaccactgct cccttccctg 2520
tccttctgat tttgtaggta accacgtgcg gaccgagcgg ccgc 2564

<210> SEQ ID NO 84
<211> LENGTH: 2543
<212> TYPE: DNA
<213> ORGANISM: Artificial Sequence
<220> FEATURE:
<223> OTHER INFORMATION: synthetic construct

<400> SEQUENCE: 84
gcggccgcac gcgtcagtag tgttaatgac agagtcagat acatgagaaa taaagacaaa 60
ctgaaaatgt tcattttgcc aatatgatca ccaataaaac catttgtgta gactatccac 120
cttaatcccc ctataataca atagcacaga ggtgagtcag tttgattttg atactaggtt 180
tattttatag gagctattaa agtttcagaa ttttgctgag tcaccaggct cttcattttg 240
tggcaaatcc atcactacag tttaaggaga gaagaaacag acccccccct accctctgaa 300
aaataaaaat aaaaacttgt ttcaggcagg ctagcgattc actaataatg agaaaactcc 360
agttttaaga cttaatttca ccataaatac tctttcattc taagctctgg gacatcatga 420
gccagagaac agcagagtga ataatacagt tacagagctg atgagcaatg ccagtcactg 480
taaaaaatac agaatcccat ccaaaggaca tctgtaaaag tgtctttaac atctactcag 540
cccttctgtg taaaggtcag cacgatggga gtggtttgtc tatactcaag ccgagctcgg 600
gctgggcata aaagtcaggg cagagccatc tattgcttac atttgcttct gggatccgcc 660
accatggtga gcaagggcga ggagctgttc accggggtgg tgcccatcct ggtcgagctg 720
gacggcgacg taaacggcca caagttcagc gtgtccggcg agggcgaggg cgatgccacc 780
tacggcaagc tgaccctgaa gttcatctgc accaccggca agctgcccgt gccctggccc 840
accctcgtga ccaccctgac ctacggcgtg cagtgcttca gccgctaccc cgaccacatg 900
aagcagcacg acttcttcaa gtccgccatg cccgaaggct acgtccagga gcgcaccatc 960
ttcttcaagg acgacggcaa ctacaagacc cgcgccgagg tgaagttcga gggcgacacc 1020
ctggtgaacc gcatcgagct gaagggcatc gacttcaagg aggacggcaa catcctgggg 1080
cacaagctgg agtacaacta caacagccac aacgtctata tcatggccga caagcagaag 1140
aacggcatca aggtgaactt caagatccgc cacaacatcg aggacggcag cgtgcagctc 1200
gccgaccact accagcagaa cacccccatc ggcgacggcc ccgtgctgct gcccgacaac 1260
cactacctga gcacccagtc cgccctgagc aaagacccca acgagaagcg cgatcacatg 1320
gtcctgctgg agttcgtgac cgccgccggg atcactctcg gcatggacga gctgtacaag 1380
taagaattcg atatcaagct tatcgataat caacctctgg attacaaaat ttgtgaaaga 1440
ttgactggta ttcttaacta tgttgctcct tttacgctat gtggatacgc tgctttaatg 1500
cctttgtatc atgctattgc ttcccgtatg gctttcattt tctcctcctt gtataaatcc 1560
tggttgctgt ctctttatga ggagttgtgg cccgttgtca ggcaacgtgg cgtggtgtgc 1620
actgtgtttg ctgacgcaac ccccactggt tggggcattg ccaccacctg tcagctcctt 1680
tccgggactt tcgctttccc cctccctatt gccacggcgg aactcatcgc cgcctgcctt 1740
gcccgctgct ggacaggggc tcggctgttg ggcactgaca attccgtggt gttgtcgggg 1800
aaatcatcgt cctttccttg gctgctcgcc tatgttgcca cctggattct gcgcgggacg 1860
tccttctgct acgtcccttc ggccctcaat ccagcggacc ttccttcccg cggcctgctg 1920
ccggctctgc ggcctcttcc gcgtcttcgc cttcgccctc agacgagtcg gatctccctt 1980
tgggccgcct ccccgcatcg ataccgagcg ctgctcgaga gatctacggg tggcatccct 2040
gtgacccctc cccagtgcct ctcctggccc tggaagttgc cactccagtg cccaccagcc 2100
ttgtcctaat aaaattaagt tgcatcattt tgtctgacta ggtgtccttc tataatatta 2160
tggggtggag gggggtggta tggagcaagg ggcaagttgg gaagacaacc tgtagggcct 2220
gcggggtcta ttgggaacca agctggagtg cagtggcaca atcttggctc actgcaatct 2280
ccgcctcctg ggttcaagcg attctcctgc ctcagcctcc cgagttgttg ggattccagg 2340
catgcatgac caggctcagc taatttttgt ttttttggta gagacggggt ttcaccatat 2400
tggccaggct ggtctccaac tcctaatctc aggtgatcta cccaccttgg cctcccaaat 2460
tgctgggatt acaggcgtga accactgctc ccttccctgt ccttctgatt ttgtaggtaa 2520
ccacgtgcgg accgagcggc cgc 2543

<210> SEQ ID NO 85
<211> LENGTH: 5427
<212> TYPE: DNA
<213> ORGANISM: Artificial Sequence
<220> FEATURE:
<223> OTHER INFORMATION: synthetic construct

<400> SEQUENCE: 85
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccgca cgcgtgtccc ataggcagtt tgtggctgag 180
tgctggtcca ggggtgagga ggtgggctat gttactgagg gtctctgggt gttaggaaaa 240
cagggcccag gagtctggct gctcgtatgc tggcccaggc tcttgttttt cttgagctga 300
cttgctggag aagtgagcta agtcagaaac aaaatgccac attgcacgcc cactgaagtc 360
tgggctcaag ggaaagaaga gagattgcca gagcgttagc tgttcccaat ccactcctgg 420
accttaagct gtcttgaaca gagttgccaa tcagcttggt agggactggc ctttgaggag 480
gggagggggt gtaggcaggg gagggggaga gaagggagca gtctgcgctc catcttaatt 540
acctcatcag aaacagctcc cttcccgcaa agctctggtg tcttctacaa gagggtgagt 600
ctttggcttt acatgtgaac ttgtgccatt tgcctgcgta tataaacatg aagggtcgtc 660
tgggttcaga gctgaaatct ttcacttgtg acttagctgg gaaattcttg gcaagatcag 720
aatgcagtgg taaggtctga gctcgggctg ggcataaaag tcagggcaga gccatctatt 780
gcttacattt gcttctggga tccgccacca tggtgagcaa gggcgaggag ctgttcaccg 840
gggtggtgcc catcctggtc gagctggacg gcgacgtaaa cggccacaag ttcagcgtgt 900
ccggcgaggg cgagggcgat gccacctacg gcaagctgac cctgaagttc atctgcacca 960
ccggcaagct gcccgtgccc tggcccaccc tcgtgaccac cctgacctac ggcgtgcagt 1020
gcttcagccg ctaccccgac cacatgaagc agcacgactt cttcaagtcc gccatgcccg 1080
aaggctacgt ccaggagcgc accatcttct tcaaggacga cggcaactac aagacccgcg 1140
ccgaggtgaa gttcgagggc gacaccctgg tgaaccgcat cgagctgaag ggcatcgact 1200
tcaaggagga cggcaacatc ctggggcaca agctggagta caactacaac agccacaacg 1260
tctatatcat ggccgacaag cagaagaacg gcatcaaggt gaacttcaag atccgccaca 1320

-continued

```
acatcgagga cggcagcgtg cagctcgccg accactacca gcagaacacc cccatcggcg   1380
acggccccgt gctgctgccc gacaaccact acctgagcac ccagtccgcc ctgagcaaag   1440
accccaacga gaagcgcgat cacatggtcc tgctggagtt cgtgaccgcc gccgggatca   1500
ctctcggcat ggacgagctg tacaagtaag aattcgatat caagcttatc gataatcaac   1560
ctctggatta caaaatttgt gaaagattga ctggtattct taactatgtt gctcctttta   1620
cgctatgtgg atacgctgct ttaatgcctt tgtatcatgc tattgcttcc cgtatggctt   1680
tcattttctc ctccttgtat aaatcctggt tgctgtctct ttatgaggag ttgtggcccg   1740
ttgtcaggca acgtggcgtg gtgtgcactg tgtttgctga cgcaaccccc actggttggg   1800
gcattgccac cacctgtcag ctcctttccg ggactttcgc tttccccctc cctattgcca   1860
cggcggaact catcgccgcc tgccttgccc gctgctggac aggggctcgg ctgttgggca   1920
ctgacaattc cgtggtgttg tcggggaaat catcgtcctt tccttggctg ctcgcctatg   1980
ttgccacctg gattctgcgc gggacgtcct tctgctacgt cccttcggcc ctcaatccag   2040
cggaccttcc ttcccgcggc ctgctgccgg ctctgcggcc tcttccgcgt cttcgccttc   2100
gccctcagac gagtcggatc tccctttggg ccgcctcccc gcatcgatac cgagcgctgc   2160
tcgagagatc tacgggtggc atccctgtga cccctcccca gtgcctctcc tggccctgga   2220
agttgccact ccagtgccca ccagccttgt cctaataaaa ttaagttgca tcattttgtc   2280
tgactaggtg tccttctata atattatggg gtggaggggg gtggtatgga gcaaggggca   2340
agttgggaag acaacctgta gggcctgcgg ggtctattgg gaaccaagct ggagtgcagt   2400
ggcacaatct tggctcactg caatctccgc ctcctgggtt caagcgattc tcctgcctca   2460
gcctcccgag ttgttgggat tccaggcatg catgaccagg ctcagctaat ttttgttttt   2520
ttggtagaga cggggtttca ccatattggc caggctggtc tccaactcct aatctcaggt   2580
gatctaccca ccttggcctc ccaaattgct gggattacag gcgtgaacca ctgctccctt   2640
ccctgtcctt ctgattttgt aggtaaccac gtgcggaccg agcggccgca ggaaccccta   2700
gtgatggagt tggccactcc ctctctgcgc gctcgctcgc tcactgaggc cgggcgacca   2760
aaggtcgccc gacgcccggg ctttgcccgg gcggcctcag tgagcgagcg agcgcgcagc   2820
tgcctgcagg ggcgcctgat gcggtatttt ctccttacgc atctgtgcgg tatttcacac   2880
cgcatacgtc aaagcaacca tagtacgcgc cctgtagcgg cgcattaagc gcggcgggtg   2940
tggtggttac gcgcagcgtg accgctacac ttgccagcgc cctagcgccc gctcctttcg   3000
ctttcttccc ttcctttctc gccacgttcg ccggctttcc ccgtcaagct ctaaatcggg   3060
ggctcccttt agggttccga tttagtgctt tacggcacct cgaccccaaa aaacttgatt   3120
tgggtgatgg ttcacgtagt gggccatcgc cctgatagac ggtttttcgc cctttgacgt   3180
tggagtccac gttctttaat agtggactct tgttccaaac tggaacaaca ctcaacccta   3240
tctcgggcta ttcttttgat ttataaggga ttttgccgat ttcggcctat tggttaaaaa   3300
atgagctgat ttaacaaaaa tttaacgcga attttaacaa aatattaacg tttacaattt   3360
tatggtgcac tctcagtaca atctgctctg atgccgcata gttaagccag ccccgacacc   3420
cgccaacacc cgctgacgcg ccctgacggg cttgtctgct cccggcatcc gcttacagac   3480
aagctgtgac cgtctccggg agctgcatgt gtcagaggtt ttcaccgtca tcaccgaaac   3540
gcgcgagacg aaagggcctc gtgatacgcc tatttttata ggttaatgtc atgataataa   3600
tggtttctta gacgtcaggt ggcacttttc ggggaaatgt gcgcggaacc cctatttgtt   3660
tatttttcta aatacattca aatatgtatc cgctcatgag acaataaccc tgataaatgc   3720
```

ttcaataata ttgaaaaagg aagagtatga gtattcaaca tttccgtgtc gcccttattc 3780 cctttttgc ggcattttgc cttcctgttt ttgctcaccc agaaacgctg gtgaaagtaa 3840
aagatgctga agatcagttg ggtgcacgag tgggttacat cgaactggat ctcaacagcg 3900
gtaagatcct tgagagtttt cgccccgaag aacgttttcc aatgatgagc acttttaaag 3960
ttctgctatg tggcgcggta ttatcccgta ttgacgccgg gcaagagcaa ctcggtcgcc 4020
gcatacacta ttctcagaat gacttggttg agtactcacc agtcacagaa aagcatctta 4080
cggatggcat gacagtaaga gaattatgca gtgctgccat aaccatgagt gataacactg 4140
cggccaactt acttctgaca acgatcggag gaccgaagga gctaaccgct tttttgcaca 4200
acatggggga tcatgtaact cgccttgatc gttgggaacc ggagctgaat gaagccatac 4260
caaacgacga gcgtgacacc acgatgcctg tagcaatggc aacaacgttg cgcaaactat 4320
taactggcga actacttact ctagcttccc ggcaacaatt aatagactgg atggaggcgg 4380
ataaagttgc aggaccactt ctgcgctcgg cccttccggc tggctggttt attgctgata 4440
aatctggagc cggtgagcgt gggtctcgcg gtatcattgc agcactgggg ccagatggta 4500
agccctcccg tatcgtagtt atctacacga cggggagtca ggcaactatg gatgaacgaa 4560
atagacagat cgctgagata ggtgcctcac tgattaagca ttggtaactg tcagaccaag 4620
tttactcata tatactttag attgatttaa aacttcattt ttaatttaaa aggatctagg 4680
tgaagatcct ttttgataat ctcatgacca aaatccctta acgtgagttt tcgttccact 4740
gagcgtcaga ccccgtagaa aagatcaaag gatcttcttg agatcctttt tttctgcgcg 4800
taatctgctg cttgcaaaca aaaaaaccac cgctaccagc ggtggtttgt ttgccggatc 4860
aagagctacc aactcttttt ccgaaggtaa ctggcttcag cagagcgcag ataccaaata 4920
ctgtccttct agtgtagccg tagttaggcc accacttcaa gaactctgta gcaccgccta 4980
catacctcgc tctgctaatc ctgttaccag tggctgctgc cagtggcgat aagtcgtgtc 5040
ttaccgggtt ggactcaaga cgatagttac cggataaggc gcagcggtcg ggctgaacgg 5100
ggggttcgtg cacacagccc agcttggagc gaacgaccta caccgaactg agatacctac 5160
agcgtgagct atgagaaagc gccacgcttc ccgaagggag aaaggcggac aggtatccgg 5220
taagcggcag ggtcggaaca ggagagcgca cgagggagct tccaggggga aacgcctggt 5280
atctttatag tcctgtcggg tttcgccacc tctgacttga gcgtcgattt ttgtgatgct 5340
cgtcaggggg gcggagccta tggaaaaacg ccagcaacgc ggccttttta cggttcctgg 5400
ccttttgctg gccttttgct cacatgt 5427

<210> SEQ ID NO 86
<211> LENGTH: 2564
<212> TYPE: DNA
<213> ORGANISM: Artificial Sequence
<220> FEATURE:
<223> OTHER INFORMATION: synthetic construct

<400> SEQUENCE: 86
gcggccgcac gcgtagggtg caggagaaat gtgacctcaa agtcttgttc tataactgtt 60
ggaccttagg agagatctgt gctcagcaat ttaccaggac acccccaccc cacatgtctt 120
gaccactgtc tggataactg gtatgcagga ccacactagg cttactcaca gtgtaaactc 180
tcataaccat cactggagcc catcctgcct ggtagacaag gattcaacca tgactcattg 240
tactttagtg gtgccatgct tagtcatcag gtgccctgtg ctctgacagc cgagggtcag 300

-continued

```
agctggaatc acactcttgt tgtcttttaa tctctccctc cctttcttcc ttctttcttc    360
actctgttgt gattgctcat ggaacagatc ctagctggtc tccctggcaa cctacatgat    420
ttgagcccaa cagatggata atggggacat cgacttccaa tgtcattcaa cagaatcatt    480
gccaagggag tctgatgagc aggcaactga gatgacaccc ttatcaatat agcttcattt    540
tggcaatctg gagtaggtgt ttcaaaagga gagcccccac tgatgccagc aatacagaac    600
gttcatgggc aaggagctcg ggctgggcat aaaagtcagg gcagagccat ctattgctta    660
catttgcttc tgggatccgc caccatggtg agcaagggcg aggagctgtt caccggggtg    720
gtgcccatcc tggtcgagct ggacggcgac gtaaacggcc acaagttcag cgtgtccggc    780
gagggcgagg gcgatgccac ctacggcaag ctgaccctga agttcatctg caccaccggc    840
aagctgcccg tgccctggcc caccctcgtg accaccctga cctacggcgt gcagtgcttc    900
agccgctacc ccgaccacat gaagcagcac gacttcttca agtccgccat gcccgaaggc    960
tacgtccagg agcgcaccat cttcttcaag gacgacggca actacaagac ccgcgccgag   1020
gtgaagttcg agggcgacac cctggtgaac cgcatcgagc tgaagggcat cgacttcaag   1080
gaggacggca acatcctggg gcacaagctg gagtacaact acaacagcca caacgtctat   1140
atcatggccg acaagcagaa gaacggcatc aaggtgaact tcaagatccg ccacaacatc   1200
gaggacggca gcgtgcagct cgccgaccac taccagcaga acacccccat cggcgacggc   1260
cccgtgctgc tgcccgacaa ccactacctg agcacccagt ccgccctgag caaagacccc   1320
aacgagaagc gcgatcacat ggtcctgctg gagttcgtga ccgccgccgg gatcactctc   1380
ggcatggacg agctgtacaa gtaagaattc gatatcaagc ttatcgataa tcaacctctg   1440
gattacaaaa tttgtgaaag attgactggt attcttaact atgttgctcc ttttacgcta   1500
tgtggatacg ctgctttaat gcctttgtat catgctattg cttcccgtat ggctttcatt   1560
ttctcctcct tgtataaatc ctggttgctg tctctttatg aggagttgtg gcccgttgtc   1620
aggcaacgtg gcgtggtgtg cactgtgttt gctgacgcaa cccccactgg ttggggcatt   1680
gccaccacct gtcagctcct ttccgggact ttcgctttcc ccctccctat tgccacggcg   1740
gaactcatcg ccgcctgcct tgcccgctgc tggacagggg ctcggctgtt gggcactgac   1800
aattccgtgg tgttgtcggg gaaatcatcg tcctttcctt ggctgctcgc ctatgttgcc   1860
acctggattc tgcgcgggac gtccttctgc tacgtccctt cggccctcaa tccagcggac   1920
cttccttccc gcggcctgct gccggctctg cggcctcttc cgcgtcttcg ccttcgccct   1980
cagacgagtc ggatctccct ttgggccgcc tccccgcatc gataccgagc gctgctcgag   2040
agatctacgg gtggcatccc tgtgacccct ccccagtgcc tctcctggcc ctggaagttg   2100
ccactccagt gcccaccagc cttgtcctaa taaaattaag ttgcatcatt ttgtctgact   2160
aggtgtcctt ctataatatt atggggtgga ggggggtggt atggagcaag gggcaagttg   2220
ggaagacaac ctgtagggcc tgcggggtct attgggaacc aagctggagt gcagtggcac   2280
aatcttggct cactgcaatc tccgcctcct gggttcaagc gattctcctg cctcagcctc   2340
ccgagttgtt gggattccag gcatgcatga ccaggctcag ctaatttttg tttttttggt   2400
agagacgggg tttcaccata ttggccaggc tggtctccaa ctcctaatct caggtgatct   2460
acccaccttg gcctcccaaa ttgctgggat tacaggcgtg aaccactgct cccttccctg   2520
tccttctgat tttgtaggta accacgtgcg gaccgagcgg ccgc                    2564
```

<210> SEQ ID NO 87
<211> LENGTH: 2859

<212> TYPE: DNA
<213> ORGANISM: Artificial Sequence
<220> FEATURE:
<223> OTHER INFORMATION: synthetic construct

<400> SEQUENCE: 87
gcggccgcac gcgtataagc cttgggggca atcaaactat tacattgagt ccttggattt 60
gctacaaatt acattttaaa tgcaatcatt ttataaaagc ttcaacactc acacttggaa 120
gcgttaccct gttgaatatc actgactcac taacttgcat tgccatgcta acttgctttc 180
agagagatct cagaacacat catcttctgc tatttcaata catgcacatt aatttcctat 240
caacgtgtgc tgatcaggaa ctctgtaatc tggcaccggt gtttattttt attcctgtct 300
attcctgttg gctcacgaaa agattgtttg agcaagtgtt ttatggtgag ttgtatcata 360
tgtacattga tttaatctgc ccacattcag ttctacaagc ggagccaaaa aaatagagac 420
aagcataatt ttcattcaac atgagcccct caatgcaagc caagtacctc atctggtgct 480
cagctaaagc aacagcaatc tgttccaccc tggagacaca actggccaca gaaaacttag 540
tgaaaagagg caatgctatg cacaggacaa atgagctcgg gctgggcata aaagtcaggg 600
cagagccatc tattgcttac atttgcttct gggatccgcc accatggtgc ccaagaagaa 660
gaggaaagtc tccaacctgc tgactgtgca ccaaaacctg cctgccctcc ctgtggatgc 720
cacctctgat gaagtcagga agaacctgat ggacatgttc agggacaggc aggccttctc 780
tgaacacacc tggaagatgc tcctgtctgt gtgcagatcc tgggctgcct ggtgcaagct 840
gaacaacagg aaatggttcc ctgctgaacc tgaggatgtg agggactacc tcctgtacct 900
gcaagccaga ggcctggctg tgaagaccat ccaacagcac ctgggccagc tcaacatgct 960
gcacaggaga tctggcctgc ctcgcccttc tgactccaat gctgtgtccc tggtgatgag 1020
gagaatcaga aaggagaatg tggatgctgg ggagagagcc aagcaggccc tggcctttga 1080
acgcactgac tttgaccaag tcagatccct gatggagaac tctgacagat gccaggacat 1140
caggaacctg gccttcctgg gcattgccta caacaccctg ctgcgcattg ccgaaattgc 1200
cagaatcaga gtgaaggaca tctcccgcac cgatggtggg agaatgctga tccacattgg 1260
caggaccaag accctggtgt ccacagctgg tgtggagaag gccctgtccc tgggggttac 1320
caagctggtg gagagatgga tctctgtgtc tggtgtggct gatgacccca acaactacct 1380
gttctgccgg gtcagaaaga atggtgtggc tgccccttct gccacctccc aactgtccac 1440
ccgggccctg gaagggatct ttgaggccac ccaccgcctg atctatggtg ccaaggatga 1500
ctctgggcag agatacctgg cctggtctgg ccactctgcc agagtgggtg ctgccaggga 1560
catggccagg gctggtgtgt ccatccctga aatcatgcag gctggtggct ggaccaatgt 1620
gaacattgtg atgaactaca tcagaaacct ggactctgag actggggcca tggtgaggct 1680
gctcgaggat ggggactaag aattcgatat caagcttatc gataatcaac ctctggatta 1740
caaaatttgt gaaagattga ctggtattct taactatgtt gctcctttta cgctatgtgg 1800
atacgctgct ttaatgcctt tgtatcatgc tattgcttcc cgtatggctt tcattttctc 1860
ctccttgtat aaatcctggt tgctgtctct ttatgaggag ttgtggcccg ttgtcaggca 1920
acgtggcgtg gtgtgcactg tgtttgctga cgcaaccccc actggttggg gcattgccac 1980
cacctgtcag ctcctttccg ggactttcgc tttccccctc cctattgcca cggcggaact 2040
catcgccgcc tgccttgccc gctgctggac aggggctcgg ctgttgggca ctgacaattc 2100
cgtggtgttg tcggggaaat catcgtcctt tccttggctg ctcgcctatg ttgccacctg 2160

-continued

```
gattctgcgc gggacgtcct tctgctacgt cccttcggcc ctcaatccag cggaccttcc   2220

ttcccgcggc ctgctgccgg ctctgcggcc tcttccgcgt cttcgccttc gccctcagac   2280

gagtcggatc tccctttggg ccgcctcccc gcatcgatac cgagcgctgc tcgagagatc   2340

tacgggtggc atccctgtga cccctcccca gtgcctctcc tggccctgga agttgccact   2400

ccagtgccca ccagccttgt cctaataaaa ttaagttgca tcattttgtc tgactaggtg   2460

tccttctata atattatggg gtggaggggg gtggtatgga gcaaggggca agttgggaag   2520

acaacctgta gggcctgcgg ggtctattgg gaaccaagct ggagtgcagt ggcacaatct   2580

tggctcactg caatctccgc ctcctgggtt caagcgattc tcctgcctca gcctcccgag   2640

ttgttgggat tccaggcatg catgaccagg ctcagctaat ttttgttttt ttggtagaga   2700

cggggtttca ccatattggc caggctggtc tccaactcct aatctcaggt gatctaccca   2760

ccttggcctc ccaaattgct gggattacag gcgtgaacca ctgctccctt ccctgtcctt   2820

ctgattttgt aggtaaccac gtgcggaccg agcggccgc                          2859


<210> SEQ ID NO 88
<211> LENGTH: 2549
<212> TYPE: DNA
<213> ORGANISM: Artificial Sequence
<220> FEATURE:
<223> OTHER INFORMATION: synthetic construct

<400> SEQUENCE: 88

cggccgcacg cgtataagcc ttgggggcaa tcaaactatt acattgagtc cttggatttg     60

ctacaaatta cattttaaat gcaatcattt tataaaagct tcaacactca cacttggaag    120

cgttaccctg ttgaatatca ctgactcact aacttgcatt gccatgctaa cttgctttca    180

gagagatctc agaacacatc atcttctgct atttcaatac atgcacatta atttcctatc    240

aacgtgtgct gatcaggaac tctgtaatct ggcaccggtg tttattttta ttcctgtcta    300

ttcctgttgg ctcacgaaaa gattgtttga gcaagtgttt tatggtgagt tgtatcatat    360

gtacattgat ttaatctgcc cacattcagt tctacaagcg gagccaaaaa aatagagaca    420

agcataattt tcattcaaca tgagcccctc aatgcaagcc aagtacctca tctggtgctc    480

agctaaagca acagcaatct gttccaccct ggagacacaa ctggccacag aaaacttagt    540

gaaaagaggc aatgctatgc acaggacaaa tgagctcggg ctgggcataa aagtcagggc    600

agagccatct attgcttaca tttgcttctg ggatccgcca ccatgtctag actggacaag    660

agcaaagtca taaactctgc tctggaatta ctcaatgaag tcggtatcga aggcctgacg    720

acaaggaaac tcgctcaaaa gctgggagtt gagcagccta ccctgtactg gcacgtgaag    780

aacaagcggg ccctgctcga tgccctggca atcgagatgc tggacaggca tcatacccac    840

ttctgccccc tggaaggcga gtcatggcaa gactttctgc ggaacaacgc caagtcattc    900

cgctgtgctc tcctctcaca tcgcgacggg gctaaagtgc atctcggcac ccgcccaaca    960

gagaaacagt acgaaaccct ggaaaatcag ctcgcgttcc tgtgtcagca aggcttctcc   1020

ctggagaacg cactgtacgc tctgtccgcc gtgggccact ttacactggg ctgcgtattg   1080

gaggatcagg agcatcaagt agcaaaagag gaaagagaga cacctaccac cgattctatg   1140

cccccacttc tgagacaagc aattgagctg ttcgaccatc agggagccga acctgccttc   1200

cttttcggcc tggaactaat catatgtggc ctggagaaac agctaaagtg cgaaagcggc   1260

gggccggccg acgcccttga cgattttgac ttagacatgc tcccagccga tgcccttgac   1320

gactttgacc ttgatatgct gcctgctgac gctcttgacg attttgacct tgacatgctc   1380
```

```
cccgggtaag aattcgatat caagcttatc gataatcaac ctctggatta caaaatttgt   1440
gaaagattga ctggtattct taactatgtt gctcctttta cgctatgtgg atacgctgct   1500
ttaatgcctt tgtatcatgc tattgcttcc cgtatggctt tcattttctc ctccttgtat   1560
aaatcctggt tgctgtctct ttatgaggag ttgtggcccg ttgtcaggca acgtggcgtg   1620
gtgtgcactg tgtttgctga cgcaaccccc actggttggg gcattgccac cacctgtcag   1680
ctcctttccg ggactttcgc tttccccctc cctattgcca cggcggaact catcgccgcc   1740
tgccttgccc gctgctggac aggggctcgg ctgttgggca ctgacaattc cgtggtgttg   1800
tcggggaaat catcgtcctt tccttggctg ctcgcctatg ttgccacctg gattctgcgc   1860
gggacgtcct tctgctacgt cccttcggcc ctcaatccag cggaccttcc ttcccgcggc   1920
ctgctgccgg ctctgcggcc tcttccgcgt cttcgccttc gccctcagac gagtcggatc   1980
tccctttggg ccgcctcccc gcatcgatac cgagcgctgc tcgagagatc tacgggtggc   2040
atccctgtga cccctcccca gtgcctctcc tggccctgga agttgccact ccagtgccca   2100
ccagccttgt cctaataaaa ttaagttgca tcattttgtc tgactaggtg tccttctata   2160
atattatggg gtggaggggg gtggtatgga gcaaggggca agttgggaag acaacctgta   2220
gggcctgcgg ggtctattgg gaaccaagct ggagtgcagt ggcacaatct tggctcactg   2280
caatctccgc ctcctgggtt caagcgattc tcctgcctca gcctcccgag ttgttgggat   2340
tccaggcatg catgaccagg ctcagctaat ttttgttttt ttggtagaga cggggtttca   2400
ccatattggc caggctggtc tccaactcct aatctcaggt gatctaccca ccttggcctc   2460
ccaaattgct gggattacag gcgtgaacca ctgctccctt ccctgtcctt ctgattttgt   2520
aggtaaccac gtgcggaccg agcggccgc                                      2549
```

```
<210> SEQ ID NO 89
<211> LENGTH: 5716
<212> TYPE: DNA
<213> ORGANISM: Artificial Sequence
<220> FEATURE:
<223> OTHER INFORMATION: synthetic construct

<400> SEQUENCE: 89
```

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc tgcggccgca cgcgtataag ccttgggggc aatcaaacta    180
ttacattgag tccttggatt tgctacaaat tacattttaa atgcaatcat tttataaaag    240
cttcaacact cacacttgga agcgttaccc tgttgaatat cactgactca ctaacttgca    300
ttgccatgct aacttgcttt cagagagatc tcagaacaca tcatcttctg ctatttcaat    360
acatgcacat taatttccta tcaacgtgtg ctgatcagga actctgtaat ctggcaccgg    420
tgtttatttt tattcctgtc tattcctgtt ggctcacgaa aagattgttt gagcaagtgt    480
tttatggtga gttgtatcat atgtacattg atttaatctg cccacattca gttctacaag    540
cggagccaaa aaaatagaga caagcataat tttcattcaa catgagcccc tcaatgcaag    600
ccaagtacct catctggtgc tcagctaaag caacagcaat ctgttccacc ctggagacac    660
aactggccac agaaaactta gtgaaaagag gcaatgctat gcacaggaca aatgagctcg    720
ggctgggcat aaaagtcagg gcagagccat ctattgctta catttgcttc tgttaattaa    780
gccaccatgt ccaatttact gaccgtacac caaaatttgc ctgcattacc ggtcgatgca    840
```

-continued

```
acgagtgatg aggttcgcaa gaacctgatg gacatgttca gggatcgcca ggcgttttct    900
gagcatacct ggaaaatgct tctgtccgtt tgccggtcgt gggcggcatg gtgcaagttg    960
aataaccgga aatggtttcc cgcagaacct gaagatgttc gcgattatct tctatatctt   1020
caggcgcgcg gtctggcagt aaaaactatc cagcaacatt tgggccagct aaacatgctt   1080
catcgtcggt ccgggctgcc acgaccaagt gacagcaatg ctgtttcact ggttatgcgg   1140
cggatccgaa aagaaaacgt tgatgccggt gaacgtgcaa aacaggctct agcgttcgaa   1200
cgcactgatt tcgaccaggt tcgttcactc atggaaaata gcgatcgctg ccaggatata   1260
cgtaatctgg catttctggg gattgcttat aacaccctgt tacgtatagc cgaaattgcc   1320
aggatcaggg ttaaagatat ctcacgtact gacggtggga gaatgttaat ccatattggc   1380
agaacgaaaa cgctggttag caccgcaggt gtagagaagg cacttagcct gggggtaact   1440
aaactggtcg agcgatggat ttccgtctct ggtgtagctg atgatccgaa taactacctg   1500
ttttgccggg tcagaaaaaa tggtgttgcc gcgccatctg ccaccagcca gctatcaact   1560
cgcgccctgg aagggatttt tgaagcaact catcgattga tttacggcgc taaggatgac   1620
tctggtcaga gatacctggc ctggtctgga cacagtgccc gtgtcggagc cgcgcgagat   1680
atggcccgcg ctggagtttc aataccggag atcatgcaag ctggtggctg gaccaatgta   1740
aatattgtca tgaactatat ccgtaacctg gatagtgaaa caggggcaat ggtgcgcctg   1800
ctggaagatg gcgattgaga attcgatatc aagcttatcg ataatcaacc tctggattac   1860
aaaatttgtg aaagattgac tggtattctt aactatgttg ctccttttac gctatgtgga   1920
tacgctgctt taatgccttt gtatcatgct attgcttccc gtatggcttt cattttctcc   1980
tccttgtata aatcctggtt gctgtctctt tatgaggagt tgtggcccgt tgtcaggcaa   2040
cgtggcgtgg tgtgcactgt gtttgctgac gcaaccccca ctggttgggg cattgccacc   2100
acctgtcagc tcctttccgg gactttcgct ttccccctcc ctattgccac ggcggaactc   2160
atcgccgcct gccttgcccg ctgctggaca ggggctcggc tgttgggcac tgacaattcc   2220
gtggtgttgt cggggaaatc atcgtccttt ccttggctgc tcgcctatgt tgccacctgg   2280
attctgcgcg ggacgtcctt ctgctacgtc ccttcggccc tcaatccagc ggaccttcct   2340
tcccgcggcc tgctgccggc tctgcggcct cttccgcgtc ttcgccttcg ccctcagacg   2400
agtcggatct ccctttgggc cgcctccccg catcgatacc gagcgctgct cgagagatct   2460
acgggtggca tccctgtgac ccctccccag tgcctctcct ggccctggaa gttgccactc   2520
cagtgcccac cagccttgtc ctaataaaat taagttgcat cattttgtct gactaggtgt   2580
ccttctataa tattatgggg tggagggggg tggtatggag caaggggcaa gttgggaaga   2640
caacctgtag ggcctgcggg gtctattggg aaccaagctg gagtgcagtg gcacaatctt   2700
ggctcactgc aatctccgcc tcctgggttc aagcgattct cctgcctcag cctcccgagt   2760
tgttgggatt ccaggcatgc atgaccaggc tcagctaatt tttgtttttt tggtagagac   2820
ggggtttcac catattggcc aggctggtct ccaactccta atctcaggtg atctacccac   2880
cttggcctcc caaattgctg ggattacagg cgtgaaccac tgctcccttc cctgtccttc   2940
tgattttgta ggtaaccacg tgcggaccga gcggccgcag gaacccctag tgatggagtt   3000
ggccactccc tctctgcgcg ctcgctcgct cactgaggcc gggcgaccaa aggtcgcccg   3060
acgcccgggc tttgcccggg cggcctcagt gagcgagcga gcgcgcagct gcctgcaggg   3120
gcgcctgatg cggtattttc tccttacgca tctgtgcggt atttcacacc gcatacgtca   3180
aagcaaccat agtacgcgcc ctgtagcggc gcattaagcg cggcgggtgt ggtggttacg   3240
```

-continued

```
cgcagcgtga ccgctacact tgccagcgcc ctagcgcccg ctcctttcgc tttcttccct   3300
tcctttctcg ccacgttcgc cggctttccc cgtcaagctc taaatcgggg gctcccttta   3360
gggttccgat ttagtgcttt acggcacctc gaccccaaaa aacttgattt gggtgatggt   3420
tcacgtagtg ggccatcgcc ctgatagacg gtttttcgcc ctttgacgtt ggagtccacg   3480
ttctttaata gtggactctt gttccaaact ggaacaacac tcaaccctat ctcgggctat   3540
tcttttgatt tataagggat tttgccgatt tcggcctatt ggttaaaaaa tgagctgatt   3600
taacaaaaat ttaacgcgaa ttttaacaaa atattaacgt ttacaatttt atggtgcact   3660
ctcagtacaa tctgctctga tgccgcatag ttaagccagc cccgacaccc gccaacaccc   3720
gctgacgcgc cctgacgggc ttgtctgctc ccggcatccg cttacagaca agctgtgacc   3780
gtctccggga gctgcatgtg tcagaggttt tcaccgtcat caccgaaacg cgcgagacga   3840
aagggcctcg tgatacgcct atttttatag gttaatgtca tgataataat ggtttcttag   3900
acgtcaggtg gcacttttcg gggaaatgtg cgcggaaccc ctatttgttt atttttctaa   3960
atacattcaa atatgtatcc gctcatgaga caataaccct gataaatgct tcaataatat   4020
tgaaaaagga agagtatgag tattcaacat ttccgtgtcg cccttattcc cttttttgcg   4080
gcattttgcc ttcctgtttt tgctcaccca gaaacgctgg tgaaagtaaa agatgctgaa   4140
gatcagttgg gtgcacgagt gggttacatc gaactggatc tcaacagcgg taagatcctt   4200
gagagttttc gccccgaaga acgttttcca atgatgagca cttttaaagt tctgctatgt   4260
ggcgcggtat tatcccgtat tgacgccggg caagagcaac tcggtcgccg catacactat   4320
tctcagaatg acttggttga gtactcacca gtcacagaaa agcatcttac ggatggcatg   4380
acagtaagag aattatgcag tgctgccata accatgagtg ataacactgc ggccaactta   4440
cttctgacaa cgatcggagg accgaaggag ctaaccgctt ttttgcacaa catgggggat   4500
catgtaactc gccttgatcg ttgggaaccg gagctgaatg aagccatacc aaacgacgag   4560
cgtgacacca cgatgcctgt agcaatggca acaacgttgc gcaaactatt aactggcgaa   4620
ctacttactc tagcttcccg gcaacaatta atagactgga tggaggcgga taaagttgca   4680
ggaccacttc tgcgctcggc ccttccggct ggctggttta ttgctgataa atctggagcc   4740
ggtgagcgtg ggtctcgcgg tatcattgca gcactggggc cagatggtaa gccctcccgt   4800
atcgtagtta tctacacgac ggggagtcag gcaactatgg atgaacgaaa tagacagatc   4860
gctgagatag gtgcctcact gattaagcat tggtaactgt cagaccaagt ttactcatat   4920
atactttaga ttgatttaaa acttcatttt taatttaaaa ggatctaggt gaagatcctt   4980
tttgataatc tcatgaccaa aatcccttaa cgtgagtttt cgttccactg agcgtcagac   5040
cccgtagaaa agatcaaagg atcttcttga gatccttttt ttctgcgcgt aatctgctgc   5100
ttgcaaacaa aaaaaccacc gctaccagcg gtggtttgtt tgccggatca agagctacca   5160
actctttttc cgaaggtaac tggcttcagc agagcgcaga taccaaatac tgtccttcta   5220
gtgtagccgt agttaggcca ccacttcaag aactctgtag caccgcctac atacctcgct   5280
ctgctaatcc tgttaccagt ggctgctgcc agtggcgata agtcgtgtct taccgggttg   5340
gactcaagac gatagttacc ggataaggcg cagcggtcgg gctgaacggg gggttcgtgc   5400
acacagccca gcttggagcg aacgacctac accgaactga gatacctaca gcgtgagcta   5460
tgagaaagcg ccacgcttcc cgaagggaga aaggcggaca ggtatccggt aagcggcagg   5520
gtcggaacag gagagcgcac gagggagctt ccagggggaa acgcctggta tctttatagt   5580
```

cctgtcgggt ttcgccacct ctgacttgag cgtcgatttt tgtgatgctc gtcagggggg 5640
cggagcctat ggaaaaacgc cagcaacgcg gcctttttac ggttcctggc cttttgctgg 5700
ccttttgctc acatgt 5716

<210> SEQ ID NO 90
<211> LENGTH: 3142
<212> TYPE: DNA
<213> ORGANISM: Artificial Sequence
<220> FEATURE:
<223> OTHER INFORMATION: synthetic construct

<400> SEQUENCE: 90
gcggccgcac gcgtatgtgt cttttactct gatcctcctg tttttacctt ccaagtgctg 60
gaatcacaga catataccac tgtgcatagc atcattacaa tgttatagtt tttcacacta 120
tgccttgact ttttggaaag gcaaaccacc tcttggattt ctccttcctt ctctatctct 180
ctctctctct cttcctccct ccgtccctcc atctcttcct ccttcccatt ttcttctctc 240
cctatttgga cacaatataa aataatttag atgaggtgag ttaaattgtg aacaaagtat 300
gtgcctatac atggttgtaa atcagcttat caaagtgtaa tattagaaga atttataaaa 360
atgataaaat tcatactcaa agttctgtgt aaagcaataa tagctttatc tccttttagt 420
tatcttgagt ctttctatga ctaacaactc cctcataggc atcttaaaga gcagtaagca 480
taagtagatt ccaaatggga agggagaagt gtgaaccatc actttcatcc agacttgtag 540
atatatctgc tgcattttca gaaaccagaa acagacagtg ttctttatct ccattgagtc 600
tagtgtagca acagagctcg ggctgggcat aaaagtcagg gcagagccat ctattgctta 660
catttgcttc tggcgtggcc accatggctc ctaagaagaa gaggaaggtg atgagccagt 720
tcgacatcct gtgcaagacc ccccccaagg tgctggtgcg gcagttcgtg gagagattcg 780
agaggcccag cggcgagaag atcgccagct gtgccgccga gctgacctac ctgtgctgga 840
tgatcaccca caacggcacc gccatcaaga gggccacctt catgagctac aacaccatca 900
tcagcaacag cctgagcttc gacatcgtga acaagagcct gcagttcaag tacaagaccc 960
agaaggccac catcctggag gccagcctga agaagctgat ccccgcctgg gagttcacca 1020
tcatccctta caacggccag aagcaccaga gcgacatcac cgacatcgtg tccagcctgc 1080
agctgcagtt cgagagcagc gaggaggccg acaagggcaa cagccacagc aagaagatgc 1140
tgaaggccct gctgtccgag ggcgagagca tctgggagat caccgagaag atcctgaaca 1200
gcttcgagta caccagcagg ttcaccaaga ccaagaccct gtaccagttc ctgttcctgg 1260
ccacattcat caactgcggc aggttcagcg acatcaagaa cgtggacccc aagagcttca 1320
agctggtgca gaacaagtac ctgggcgtga tcattcagtg cctggtgacc gagaccaaga 1380
caagcgtgtc caggcacatc tactttttca gcgccagagg caggatcgac cccctggtgt 1440
acctggacga gttcctgagg aacagcgagc ccgtgctgaa gagagtgaac aggaccggca 1500
acagcagcag caacaagcag gagtaccagc tgctgaagga caacctggtg cgcagctaca 1560
acaaggccct gaagaagaac gccccctacc ccatcttcgc tatcaagaac ggccctaaga 1620
gccacatcgg caggcacctg atgaccagct ttctgagcat gaagggcctg accgagctga 1680
caaacgtggt gggcaactgg agcgacaaga gggcctccgc cgtggccagg accacctaca 1740
cccaccagat caccgccatc cccgaccact acttcgccct ggtgtccagg tactacgcct 1800
acgaccccat cagcaaggag atgatcgccc tgaaggacga gaccaacccc atcgaggagt 1860
ggcagcacat cgagcagctg aagggcagcg ccgagggcag catcagatac cccgcctgga 1920

```
acggcatcat cagccaggag gtgctggact acctgagcag ctacatcaac aggcggatct   1980
gagaattcga tatcaagctt atcgataatc aacctctgga ttacaaaatt tgtgaaagat   2040
tgactggtat tcttaactat gttgctcctt ttacgctatg tggatacgct gctttaatgc   2100
ctttgtatca tgctattgct tcccgtatgg ctttcatttt ctcctccttg tataaatcct   2160
ggttgctgtc tctttatgag gagttgtggc ccgttgtcag gcaacgtggc gtggtgtgca   2220
ctgtgtttgc tgacgcaacc cccactggtt ggggcattgc caccacctgt cagctccttt   2280
ccgggacttt cgctttcccc ctccctattg ccacggcgga actcatcgcc gcctgccttg   2340
cccgctgctg gacaggggct cggctgttgg gcactgacaa ttccgtggtg ttgtcgggga   2400
aatcatcgtc ctttccttgg ctgctcgcct atgttgccac ctggattctg cgcgggacgt   2460
ccttctgcta cgtcccttcg gccctcaatc cagcggacct tccttcccgc ggcctgctgc   2520
cggctctgcg gcctcttccg cgtcttcgcc ttcgccctca gacgagtcgg atctcccttt   2580
gggccgcctc cccgcatcga taccgagcgc tgctcgagag atctacgggt ggcatccctg   2640
tgacccctcc ccagtgcctc tcctggccct ggaagttgcc actccagtgc ccaccagcct   2700
tgtcctaata aaattaagtt gcatcatttt gtctgactag gtgtccttct ataatattat   2760
ggggtggagg ggggtggtat ggagcaaggg gcaagttggg aagacaacct gtagggcctg   2820
cggggtctat tgggaaccaa gctggagtgc agtggcacaa tcttggctca ctgcaatctc   2880
cgcctcctgg gttcaagcga ttctcctgcc tcagcctccc gagttgttgg gattccaggc   2940
atgcatgacc aggctcagct aatttttgtt tttttggtag agacggggtt tcaccatatt   3000
ggccaggctg gtctccaact cctaatctca ggtgatctac ccaccttggc ctcccaaatt   3060
gctgggatta caggcgtgaa ccactgctcc cttccctgtc cttctgattt tgtaggtaac   3120
cacgtgcgga ccgagcggcc gc                                            3142
```

<210> SEQ ID NO 91
<211> LENGTH: 3126
<212> TYPE: DNA
<213> ORGANISM: Artificial Sequence
<220> FEATURE:
<223> OTHER INFORMATION: synthetic construct

<400> SEQUENCE: 91

```
gcggccgcac gcgtgtccca taggcagttt gtggctgagt gctggtccag ggtgaggag     60
gtgggctatg ttactgaggg tctctgggtg ttaggaaaac agggcccagg agtctggctg    120
ctcgtatgct ggcccaggct cttgtttttc ttgagctgac ttgctggaga agtgagctaa    180
gtcagaaaca aaatgccaca ttgcacgccc actgaagtct gggctcaagg gaaagaagag    240
agattgccag agcgttagct gttcccaatc cactcctgga ccttaagctg tcttgaacag    300
agttgccaat cagcttggta gggactggcc tttgaggagg ggagggggtg taggcagggg    360
agggggagag aagggagcag tctgcgctcc atcttaatta cctcatcaga aacagctccc    420
ttcccgcaaa gctctggtgt cttctacaag agggtgagtc tttggcttta catgtgaact    480
tgtgccattt gcctgcgtat ataaacatga agggtcgtct gggttcagag ctgaaatctt    540
tcacttgtga cttagctggg aaattcttgg caagatcaga atgcagtggt aaggtctgag    600
ctcgggctgg gcataaaagt cagggcagag ccatctattg cttacatttg cttctggcgt    660
ggccaccatg gctcctaaga agaagaggaa ggtgatgagc cagttcgaca tcctgtgcaa    720
gacccccccc aaggtgctgg tgcggcagtt cgtggagaga ttcgagaggc ccagcggcga    780
```

-continued

```
gaagatcgcc agctgtgccg ccgagctgac ctacctgtgc tggatgatca cccacaacgg    840
caccgccatc aagagggcca ccttcatgag ctacaacacc atcatcagca acagcctgag    900
cttcgacatc gtgaacaaga gcctgcagtt caagtacaag acccagaagg ccaccatcct    960
ggaggccagc ctgaagaagc tgatccccgc ctgggagttc accatcatcc cttacaacgg   1020
ccagaagcac cagagcgaca tcaccgacat cgtgtccagc ctgcagctgc agttcgagag   1080
cagcgaggag gccgacaagg gcaacagcca cagcaagaag atgctgaagg ccctgctgtc   1140
cgagggcgag agcatctggg agatcaccga gaagatcctg aacagcttcg agtacaccag   1200
caggttcacc aagaccaaga ccctgtacca gttcctgttc ctggccacat tcatcaactg   1260
cggcaggttc agcgacatca agaacgtgga ccccaagagc ttcaagctgg tgcagaacaa   1320
gtacctgggc gtgatcattc agtgcctggt gaccgagacc aagacaagcg tgtccaggca   1380
catctacttt ttcagcgcca gaggcaggat cgaccccctg gtgtacctgg acgagttcct   1440
gaggaacagc gagcccgtgc tgaagagagt gaacaggacc ggcaacagca gcagcaacaa   1500
gcaggagtac cagctgctga aggacaacct ggtgcgcagc tacaacaagg ccctgaagaa   1560
gaacgccccc taccccatct tcgctatcaa gaacggccct aagagccaca tcggcaggca   1620
cctgatgacc agctttctga gcatgaaggg cctgaccgag ctgacaaacg tggtgggcaa   1680
ctggagcgac aagagggcct ccgccgtggc caggaccacc tacacccacc agatcaccgc   1740
catccccgac cactacttcg ccctggtgtc caggtactac gcctacgacc ccatcagcaa   1800
ggagatgatc gccctgaagg acgagaccaa ccccatcgag gagtggcagc acatcgagca   1860
gctgaagggc agcgccgagg gcagcatcag ataccccgcc tggaacggca tcatcagcca   1920
ggaggtgctg gactacctga gcagctacat caacaggcgg atctgagaat tcgatatcaa   1980
gcttatcgat aatcaacctc tggattacaa aatttgtgaa agattgactg gtattcttaa   2040
ctatgttgct ccttttacgc tatgtggata cgctgcttta atgcctttgt atcatgctat   2100
tgcttcccgt atggctttca ttttctcctc cttgtataaa tcctggttgc tgtctcttta   2160
tgaggagttg tggcccgttg tcaggcaacg tggcgtggtg tgcactgtgt ttgctgacgc   2220
aacccccact ggttggggca ttgccaccac ctgtcagctc ctttccggga ctttcgcttt   2280
ccccctccct attgccacgg cggaactcat cgccgcctgc cttgcccgct gctggacagg   2340
ggctcggctg ttgggcactg acaattccgt ggtgttgtcg gggaaatcat cgtcctttcc   2400
ttggctgctc gcctatgttg ccacctggat tctgcgcggg acgtccttct gctacgtccc   2460
ttcggccctc aatccagcgg accttccttc ccgcggcctg ctgccggctc tgcggcctct   2520
tccgcgtctt cgccttcgcc ctcagacgag tcggatctcc ctttgggccg cctccccgca   2580
tcgataccga gcgctgctcg agagatctac gggtggcatc cctgtgaccc ctccccagtg   2640
cctctcctgg ccctggaagt tgccactcca gtgcccacca gccttgtcct aataaaatta   2700
agttgcatca ttttgtctga ctaggtgtcc ttctataata ttatggggtg gaggggggtg   2760
gtatggagca aggggcaagt tgggaagaca acctgtaggg cctgcggggt ctattgggaa   2820
ccaagctgga gtgcagtggc acaatcttgg ctcactgcaa tctccgcctc ctgggttcaa   2880
gcgattctcc tgcctcagcc tcccgagttg ttgggattcc aggcatgcat gaccaggctc   2940
agctaatttt tgtttttttg gtagagacgg ggtttcacca tattggccag gctggtctcc   3000
aactcctaat ctcaggtgat ctacccacct tggcctccca aattgctggg attacaggcg   3060
tgaaccactg ctcccttccc tgtccttctg attttgtagg taaccacgtg cggaccgagc   3120
ggccgc                                                              3126
```

<210> SEQ ID NO 92
<211> LENGTH: 3142
<212> TYPE: DNA
<213> ORGANISM: Artificial Sequence
<220> FEATURE:
<223> OTHER INFORMATION: synthetic construct

<400> SEQUENCE: 92
gcggccgcac gcgtagggtg caggagaaat gtgacctcaa agtcttgttc tataactgtt 60
ggaccttagg agagatctgt gctcagcaat ttaccaggac acccccaccc cacatgtctt 120
gaccactgtc tggataactg gtatgcagga ccacactagg cttactcaca gtgtaaactc 180
tcataaccat cactggagcc catcctgcct ggtagacaag gattcaacca tgactcattg 240
tactttagtg gtgccatgct tagtcatcag gtgccctgtg ctctgacagc cgagggtcag 300
agctggaatc acactcttgt tgtcttttaa tctctccctc cctttcttcc ttctttcttc 360
actctgttgt gattgctcat ggaacagatc ctagctggtc tccctggcaa cctacatgat 420
ttgagcccaa cagatggata atggggacat cgacttccaa tgtcattcaa cagaatcatt 480
gccaagggag tctgatgagc aggcaactga gatgacaccc ttatcaatat agcttcattt 540
tggcaatctg gagtaggtgt ttcaaaagga gagcccccac tgatgccagc aatacagaac 600
gttcatgggc aaggagctcg ggctgggcat aaaagtcagg gcagagccat ctattgctta 660
catttgcttc tggcgtggcc accatggctc ctaagaagaa gaggaaggtg atgagccagt 720
tcgacatcct gtgcaagacc ccccccaagg tgctggtgcg gcagttcgtg gagagattcg 780
agaggcccag cggcgagaag atcgccagct gtgccgccga gctgacctac ctgtgctgga 840
tgatcaccca caacggcacc gccatcaaga gggccacctt catgagctac aacaccatca 900
tcagcaacag cctgagcttc gacatcgtga acaagagcct gcagttcaag tacaagaccc 960
agaaggccac catcctggag gccagcctga agaagctgat ccccgcctgg gagttcacca 1020
tcatccctta caacggccag aagcaccaga gcgacatcac cgacatcgtg tccagcctgc 1080
agctgcagtt cgagagcagc gaggaggccg acaagggcaa cagccacagc aagaagatgc 1140
tgaaggccct gctgtccgag ggcgagagca tctgggagat caccgagaag atcctgaaca 1200
gcttcgagta caccagcagg ttcaccaaga ccaagaccct gtaccagttc ctgttcctgg 1260
ccacattcat caactgcggc aggttcagcg acatcaagaa cgtggacccc aagagcttca 1320
agctggtgca gaacaagtac ctgggcgtga tcattcagtg cctggtgacc gagaccaaga 1380
caagcgtgtc caggcacatc tactttttca gcgccagagg caggatcgac cccctggtgt 1440
acctggacga gttcctgagg aacagcgagc ccgtgctgaa gagagtgaac aggaccggca 1500
acagcagcag caacaagcag gagtaccagc tgctgaagga caacctggtg cgcagctaca 1560
acaaggccct gaagaagaac gccccctacc ccatcttcgc tatcaagaac ggccctaaga 1620
gccacatcgg caggcacctg atgaccagct ttctgagcat gaagggcctg accgagctga 1680
caaacgtggt gggcaactgg agcgacaaga gggcctccgc cgtggccagg accacctaca 1740
cccaccagat caccgccatc cccgaccact acttcgccct ggtgtccagg tactacgcct 1800
acgaccccat cagcaaggag atgatcgccc tgaaggacga gaccaacccc atcgaggagt 1860
ggcagcacat cgagcagctg aagggcagcg ccgagggcag catcagatac cccgcctgga 1920
acggcatcat cagccaggag gtgctggact acctgagcag ctacatcaac aggcggatct 1980
gagaattcga tatcaagctt atcgataatc aacctctgga ttacaaaatt tgtgaaagat 2040

-continued

```
tgactggtat tcttaactat gttgctcctt ttacgctatg tggatacgct gctttaatgc   2100

ctttgtatca tgctattgct tcccgtatgg ctttcatttt ctcctccttg tataaatcct   2160

ggttgctgtc tctttatgag gagttgtggc ccgttgtcag gcaacgtggc gtggtgtgca   2220

ctgtgtttgc tgacgcaacc cccactggtt ggggcattgc caccacctgt cagctccttt   2280

ccgggacttt cgctttcccc ctccctattg ccacggcgga actcatcgcc gcctgccttg   2340

cccgctgctg gacaggggct cggctgttgg gcactgacaa ttccgtggtg ttgtcgggga   2400

aatcatcgtc ctttccttgg ctgctcgcct atgttgccac ctggattctg cgcgggacgt   2460

ccttctgcta cgtcccttcg gccctcaatc cagcggacct tccttcccgc ggcctgctgc   2520

cggctctgcg gcctcttccg cgtcttcgcc ttcgccctca gacgagtcgg atctcccttt   2580

gggccgcctc cccgcatcga taccgagcgc tgctcgagag atctacgggt ggcatccctg   2640

tgacccctcc ccagtgcctc tcctggccct ggaagttgcc actccagtgc ccaccagcct   2700

tgtcctaata aaattaagtt gcatcatttt gtctgactag gtgtccttct ataatattat   2760

ggggtggagg ggggtggtat ggagcaaggg gcaagttggg aagacaacct gtagggcctg   2820

cggggtctat tgggaaccaa gctggagtgc agtggcacaa tcttggctca ctgcaatctc   2880

cgcctcctgg gttcaagcga ttctcctgcc tcagcctccc gagttgttgg gattccaggc   2940

atgcatgacc aggctcagct aatttttgtt tttttggtag agacggggtt tcaccatatt   3000

ggccaggctg gtctccaact cctaatctca ggtgatctac ccaccttggc ctcccaaatt   3060

gctgggatta caggcgtgaa ccactgctcc cttccctgtc cttctgattt tgtaggtaac   3120

cacgtgcgga ccgagcggcc gc                                            3142
```

```
<210> SEQ ID NO 93
<211> LENGTH: 2884
<212> TYPE: DNA
<213> ORGANISM: Artificial Sequence
<220> FEATURE:
<223> OTHER INFORMATION: synthetic construct

<400> SEQUENCE: 93
```

```
gcggccgcac gcgtgtccca taggcagttt gtggctgagt gctggtccag ggtgaggag     60

gtgggctatg ttactgaggg tctctgggtg ttaggaaaac agggcccagg agtctggctg    120

ctcgtatgct ggcccaggct cttgtttttc ttgagctgac ttgctggaga agtgagctaa    180

gtcagaaaca aaatgccaca ttgcacgccc actgaagtct gggctcaagg gaaagaagag    240

agattgccag agcgttagct gttcccaatc cactcctgga ccttaagctg tcttgaacag    300

agttgccaat cagcttggta gggactggcc tttgaggagg ggagggggtg taggcagggg    360

agggggagag aagggagcag tctgcgctcc atcttaatta cctcatcaga aacagctccc    420

ttcccgcaaa gctctggtgt cttctacaag agggtgagtc tttggcttta catgtgaact    480

tgtgccattt gcctgcgtat ataaacatga agggtcgtct gggttcagag ctgaaatctt    540

tcacttgtga cttagctggg aaattcttgg caagatcaga atgcagtggt aaggtctgag    600

ctcgggctgg gcataaaagt cagggcagag ccatctattg cttacatttg cttctgggat    660

ccgccaccat ggtgcccaag aagaagagga aagtctccaa cctgctgact gtgcaccaaa    720

acctgcctgc cctccctgtg gatgccacct ctgatgaagt caggaagaac ctgatggaca    780

tgttcaggga caggcaggcc ttctctgaac acacctggaa gatgctcctg tctgtgtgca    840

gatcctgggc tgcctggtgc aagctgaaca acaggaaatg gttccctgct gaacctgagg    900

atgtgaggga ctacctcctg tacctgcaag ccagaggcct ggctgtgaag accatccaac    960
```

agcacctggg ccagctcaac atgctgcaca ggagatctgg cctgcctcgc ccttctgact 1020
ccaatgctgt gtccctggtg atgaggagaa tcagaaagga gaatgtggat gctggggaga 1080
gagccaagca ggccctggcc tttgaacgca ctgactttga ccaagtcaga tccctgatgg 1140
agaactctga cagatgccag gacatcagga acctggcctt cctgggcatt gcctacaaca 1200
ccctgctgcg cattgccgaa attgccagaa tcagagtgaa ggacatctcc cgcaccgatg 1260
gtgggagaat gctgatccac attggcagga ccaagaccct ggtgtccaca gctggtgtgg 1320
agaaggccct gtccctgggg gttaccaagc tggtggagag atggatctct gtgtctggtg 1380
tggctgatga ccccaacaac tacctgttct gccgggtcag aaagaatggt gtggctgccc 1440
cttctgccac ctcccaactg tccacccggg ccctggaagg gatctttgag gccacccacc 1500
gcctgatcta tggtgccaag gatgactctg ggcagagata cctggcctgg tctggccact 1560
ctgccagagt gggtgctgcc agggacatgg ccagggctgg tgtgtccatc cctgaaatca 1620
tgcaggctgg tggctggacc aatgtgaaca ttgtgatgaa ctacatcaga aacctggact 1680
ctgagactgg ggccatggtg aggctgctcg aggatgggga ctaagaattc gatatcaagc 1740
ttatcgataa tcaacctctg gattacaaaa tttgtgaaag attgactggt attcttaact 1800
atgttgctcc ttttacgcta tgtggatacg ctgctttaat gcctttgtat catgctattg 1860
cttcccgtat ggctttcatt ttctcctcct tgtataaatc ctggttgctg tctctttatg 1920
aggagttgtg gcccgttgtc aggcaacgtg gcgtggtgtg cactgtgttt gctgacgcaa 1980
cccccactgg ttggggcatt gccaccacct gtcagctcct ttccgggact ttcgctttcc 2040
ccctccctat tgccacggcg gaactcatcg ccgcctgcct tgcccgctgc tggacagggg 2100
ctcggctgtt gggcactgac aattccgtgg tgttgtcggg gaaatcatcg tcctttcctt 2160
ggctgctcgc ctatgttgcc acctggattc tgcgcgggac gtccttctgc tacgtccctt 2220
cggccctcaa tccagcggac cttccttccc gcggcctgct gccggctctg cggcctcttc 2280
cgcgtcttcg ccttcgccct cagacgagtc ggatctccct ttgggccgcc tccccgcatc 2340
gataccgagc gctgctcgag agatctacgg gtggcatccc tgtgacccct ccccagtgcc 2400
tctcctggcc ctggaagttg ccactccagt gcccaccagc cttgtcctaa taaaattaag 2460
ttgcatcatt ttgtctgact aggtgtcctt ctataatatt atggggtgga ggggggtggt 2520
atggagcaag gggcaagttg ggaagacaac ctgtagggcc tgcggggtct attgggaacc 2580
aagctggagt gcagtggcac aatcttggct cactgcaatc tccgcctcct gggttcaagc 2640
gattctcctg cctcagcctc ccgagttgtt gggattccag gcatgcatga ccaggctcag 2700
ctaatttttg tttttttggt agagacgggg tttcaccata ttggccaggc tggtctccaa 2760
ctcctaatct caggtgatct acccaccttg gcctcccaaa ttgctgggat tacaggcgtg 2820
aaccactgct cccttccctg tccttctgat tttgtaggta accacgtgcg gaccgagcgg 2880
ccgc 2884

<210> SEQ ID NO 94
<211> LENGTH: 2900
<212> TYPE: DNA
<213> ORGANISM: Artificial Sequence
<220> FEATURE:
<223> OTHER INFORMATION: synthetic construct

<400> SEQUENCE: 94
gcggccgcac gcgtagggtg caggagaaat gtgacctcaa agtcttgttc tataactgtt 60

-continued

```
ggaccttagg agagatctgt gctcagcaat ttaccaggac acccccaccc cacatgtctt    120
gaccactgtc tggataactg gtatgcagga ccacactagg cttactcaca gtgtaaactc    180
tcataaccat cactggagcc catcctgcct ggtagacaag gattcaacca tgactcattg    240
tactttagtg gtgccatgct tagtcatcag gtgccctgtg ctctgacagc cgagggtcag    300
agctggaatc acactcttgt tgtcttttaa tctctccctc cctttcttcc ttctttcttc    360
actctgttgt gattgctcat ggaacagatc ctagctggtc tccctggcaa cctacatgat    420
ttgagcccaa cagatggata atggggacat cgacttccaa tgtcattcaa cagaatcatt    480
gccaagggag tctgatgagc aggcaactga gatgacaccc ttatcaatat agcttcattt    540
tggcaatctg gagtaggtgt ttcaaaagga gagcccccac tgatgccagc aatacagaac    600
gttcatgggc aaggagctcg ggctgggcat aaaagtcagg gcagagccat ctattgctta    660
catttgcttc tgggatccgc caccatggtg cccaagaaga agaggaaagt ctccaacctg    720
ctgactgtgc accaaaacct gcctgccctc cctgtggatg ccacctctga tgaagtcagg    780
aagaacctga tggacatgtt cagggacagg caggccttct ctgaacacac ctggaagatg    840
ctcctgtctg tgtgcagatc ctgggctgcc tggtgcaagc tgaacaacag gaaatggttc    900
cctgctgaac ctgaggatgt gagggactac ctcctgtacc tgcaagccag aggcctggct    960
gtgaagacca tccaacagca cctgggccag ctcaacatgc tgcacaggag atctggcctg   1020
cctcgccctt ctgactccaa tgctgtgtcc ctggtgatga ggagaatcag aaaggagaat   1080
gtggatgctg gggagagagc caagcaggcc ctggcctttg aacgcactga ctttgaccaa   1140
gtcagatccc tgatggagaa ctctgacaga tgccaggaca tcaggaacct ggccttcctg   1200
ggcattgcct acaacaccct gctgcgcatt gccgaaattg ccagaatcag agtgaaggac   1260
atctcccgca ccgatggtgg gagaatgctg atccacattg gcaggaccaa gaccctggtg   1320
tccacagctg gtgtggagaa ggccctgtcc ctgggggtta ccaagctggt ggagagatgg   1380
atctctgtgt ctggtgtggc tgatgacccc aacaactacc tgttctgccg ggtcagaaag   1440
aatggtgtgg ctgccccttc tgccacctcc caactgtcca cccgggccct ggaagggatc   1500
tttgaggcca cccaccgcct gatctatggt gccaaggatg actctgggca gagatacctg   1560
gcctggtctg gccactctgc cagagtgggt gctgccaggg acatggccag ggctggtgtg   1620
tccatccctg aaatcatgca ggctggtggc tggaccaatg tgaacattgt gatgaactac   1680
atcagaaacc tggactctga gactggggcc atggtgaggc tgctcgagga tggggactaa   1740
gaattcgata tcaagcttat cgataatcaa cctctggatt acaaaatttg tgaaagattg   1800
actggtattc ttaactatgt tgctcctttt acgctatgtg gatacgctgc tttaatgcct   1860
ttgtatcatg ctattgcttc ccgtatggct ttcattttct cctccttgta taaatcctgg   1920
ttgctgtctc tttatgagga gttgtggccc gttgtcaggc aacgtggcgt ggtgtgcact   1980
gtgtttgctg acgcaacccc cactggttgg ggcattgcca ccacctgtca gctcctttcc   2040
gggactttcg ctttccccct ccctattgcc acggcggaac tcatcgccgc ctgccttgcc   2100
cgctgctgga caggggctcg gctgttgggc actgacaatt ccgtggtgtt gtcggggaaa   2160
tcatcgtcct ttccttggct gctcgcctat gttgccacct ggattctgcg cgggacgtcc   2220
ttctgctacg tcccttcggc cctcaatcca gcggaccttc cttcccgcgg cctgctgccg   2280
gctctgcggc ctcttccgcg tcttcgcctt cgccctcaga cgagtcggat ctccctttgg   2340
gccgcctccc cgcatcgata ccgagcgctg ctcgagagat ctacgggtgg catccctgtg   2400
acccctcccc agtgcctctc ctggccctgg aagttgccac tccagtgccc accagccttg   2460
```

tcctaataaa attaagttgc atcattttgt ctgactaggt gtccttctat aatattatgg 2520
ggtggagggg ggtggtatgg agcaaggggc aagttgggaa gacaacctgt agggcctgcg 2580
gggtctattg ggaaccaagc tggagtgcag tggcacaatc ttggctcact gcaatctccg 2640
cctcctgggt tcaagcgatt ctcctgcctc agcctcccga gttgttggga ttccaggcat 2700
gcatgaccag gctcagctaa tttttgtttt tttggtagag acggggtttc accatattgg 2760
ccaggctggt ctccaactcc taatctcagg tgatctaccc accttggcct cccaaattgc 2820
tgggattaca ggcgtgaacc actgctccct tccctgtcct tctgattttg taggtaacca 2880
cgtgcggacc gagcggccgc 2900

<210> SEQ ID NO 95
<211> LENGTH: 5470
<212> TYPE: DNA
<213> ORGANISM: Artificial Sequence
<220> FEATURE:
<223> OTHER INFORMATION: synthetic construct

<400> SEQUENCE: 95
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccgca cgcgtatgtg tcttttactc tgatcctcct 180
gtttttacct tccaagtgct ggaatcacag acatatacca ctgtgcatag catcattaca 240
atgttatagt ttttcacact atgccttgac tttttggaaa ggcaaaccac ctcttggatt 300
tctccttcct tctctatctc tctctctctc tcttcctccc tccgtccctc catctcttcc 360
tccttcccat tttcttctct ccctatttgg acacaatata aaataattta gatgaggtga 420
gttaaattgt gaacaaagta tgtgcctata catggttgta aatcagctta tcaaagtgta 480
atattagaag aatttataaa aatgataaaa ttcatactca aagttctgtg taaagcaata 540
atagctttat ctccttttag ttatcttgag tctttctatg actaacaact ccctcatagg 600
catcttaaag agcagtaagc ataagtagat tccaaatggg aagggagaag tgtgaaccat 660
cactttcatc cagacttgta gatatatctg ctgcattttc agaaaccaga aacagacagt 720
gttctttatc tccattgagt ctagtgtagc aacagagctc gggctgggca taaaagtcag 780
ggcagagcca tctattgctt acatttgctt ctgggatccg ccaccatgtc tagactggac 840
aagagcaaag tcataaactc tgctctggaa ttactcaatg aagtcggtat cgaaggcctg 900
acgacaagga aactcgctca aaagctggga gttgagcagc ctaccctgta ctggcacgtg 960
aagaacaagc gggccctgct cgatgccctg gcaatcgaga tgctggacag gcatcatacc 1020
cacttctgcc ccctggaagg cgagtcatgg caagactttc tgcggaacaa cgccaagtca 1080
ttccgctgtg ctctcctctc acatcgcgac ggggctaaag tgcatctcgg cacccgccca 1140
acagagaaac agtacgaaac cctggaaaat cagctcgcgt tcctgtgtca gcaaggcttc 1200
tccctggaga acgcactgta cgctctgtcc gccgtgggcc actttacact gggctgcgta 1260
ttggaggatc aggagcatca agtagcaaaa gaggaaagag agacacctac caccgattct 1320
atgcccccac ttctgagaca agcaattgag ctgttcgacc atcagggagc cgaacctgcc 1380
ttccttttcg gcctggaact aatcatatgt ggcctggaga aacagctaaa gtgcgaaagc 1440
ggcgggccgg ccgacgccct tgacgatttt gacttagaca tgctcccagc cgatgccctt 1500
gacgactttg accttgatat gctgcctgct gacgctcttg acgattttga ccttgacatg 1560

-continued

```
ctccccgggt aagaattcga tatcaagctt atcgataatc aacctctgga ttacaaaatt   1620
tgtgaaagat tgactggtat tcttaactat gttgctcctt ttacgctatg tggatacgct   1680
gctttaatgc ctttgtatca tgctattgct tcccgtatgg ctttcatttt ctcctccttg   1740
tataaatcct ggttgctgtc tctttatgag gagttgtggc ccgttgtcag gcaacgtggc   1800
gtggtgtgca ctgtgtttgc tgacgcaacc cccactggtt ggggcattgc caccacctgt   1860
cagctccttt ccgggacttt cgctttcccc ctccctattg ccacggcgga actcatcgcc   1920
gcctgccttg cccgctgctg gacaggggct cggctgttgg gcactgacaa ttccgtggtg   1980
ttgtcgggga aatcatcgtc ctttccttgg ctgctcgcct atgttgccac ctggattctg   2040
cgcgggacgt ccttctgcta cgtcccttcg gccctcaatc cagcggacct tccttcccgc   2100
ggcctgctgc cggctctgcg gcctcttccg cgtcttcgcc ttcgccctca gacgagtcgg   2160
atctcccttt gggccgcctc cccgcatcga taccgagcgc tgctcgagag atctacgggt   2220
ggcatccctg tgacccctcc ccagtgcctc tcctggccct ggaagttgcc actccagtgc   2280
ccaccagcct tgtcctaata aaattaagtt gcatcatttt gtctgactag gtgtccttct   2340
ataatattat ggggtggagg ggggtggtat ggagcaaggg gcaagttggg aagacaacct   2400
gtagggcctg cggggtctat tgggaaccaa gctggagtgc agtggcacaa tcttggctca   2460
ctgcaatctc cgcctcctgg gttcaagcga ttctcctgcc tcagcctccc gagttgttgg   2520
gattccaggc atgcatgacc aggctcagct aatttttgtt tttttggtag agacggggtt   2580
tcaccatatt ggccaggctg gtctccaact cctaatctca ggtgatctac ccaccttggc   2640
ctcccaaatt gctgggatta caggcgtgaa ccactgctcc cttccctgtc cttctgattt   2700
tgtaggtaac cacgtgcgga ccgagcggcc gcaggaaccc ctagtgatgg agttggccac   2760
tccctctctg cgcgctcgct cgctcactga ggccgggcga ccaaaggtcg cccgacgccc   2820
gggctttgcc cgggcggcct cagtgagcga gcgagcgcgc agctgcctgc aggggcgcct   2880
gatgcggtat tttctcctta cgcatctgtg cggtatttca caccgcatac gtcaaagcaa   2940
ccatagtacg cgccctgtag cggcgcatta agcgcggcgg gtgtggtggt tacgcgcagc   3000
gtgaccgcta cacttgccag cgccctagcg cccgctcctt tcgctttctt cccttccttt   3060
ctcgccacgt tcgccggctt tccccgtcaa gctctaaatc gggggctccc tttagggttc   3120
cgatttagtg ctttacggca cctcgacccc aaaaaacttg atttgggtga tggttcacgt   3180
agtgggccat cgccctgata gacggttttt cgccctttga cgttggagtc cacgttcttt   3240
aatagtggac tcttgttcca aactggaaca acactcaacc ctatctcggg ctattctttt   3300
gatttataag ggattttgcc gatttcggcc tattggttaa aaaatgagct gatttaacaa   3360
aaatttaacg cgaattttaa caaaatatta acgtttacaa ttttatggtg cactctcagt   3420
acaatctgct ctgatgccgc atagttaagc cagccccgac acccgccaac acccgctgac   3480
gcgccctgac gggcttgtct gctcccggca tccgcttaca gacaagctgt gaccgtctcc   3540
gggagctgca tgtgtcagag gttttcaccg tcatcaccga aacgcgcgag acgaaagggc   3600
ctcgtgatac gcctattttt ataggttaat gtcatgataa taatggtttc ttagacgtca   3660
ggtggcactt ttcggggaaa tgtgcgcgga acccctattt gtttattttt ctaaatacat   3720
tcaaatatgt atccgctcat gagacaataa ccctgataaa tgcttcaata atattgaaaa   3780
aggaagagta tgagtattca acatttccgt gtcgccctta ttcccttttt tgcggcattt   3840
tgccttcctg tttttgctca cccagaaacg ctggtgaaag taaaagatgc tgaagatcag   3900
ttgggtgcac gagtgggtta catcgaactg gatctcaaca gcggtaagat ccttgagagt   3960
```

```
tttcgccccg aagaacgttt tccaatgatg agcactttta aagttctgct atgtggcgcg   4020

gtattatccc gtattgacgc cgggcaagag caactcggtc gccgcataca ctattctcag   4080

aatgacttgg ttgagtactc accagtcaca gaaaagcatc ttacggatgg catgacagta   4140

agagaattat gcagtgctgc cataaccatg agtgataaca ctgcggccaa cttacttctg   4200

acaacgatcg gaggaccgaa ggagctaacc gcttttttgc acaacatggg ggatcatgta   4260

actcgccttg atcgttggga accggagctg aatgaagcca taccaaacga cgagcgtgac   4320

accacgatgc ctgtagcaat ggcaacaacg ttgcgcaaac tattaactgg cgaactactt   4380

actctagctt cccggcaaca attaatagac tggatggagg cggataaagt tgcaggacca   4440

cttctgcgct cggcccttcc ggctggctgg tttattgctg ataaatctgg agccggtgag   4500

cgtgggtctc gcggtatcat tgcagcactg gggccagatg gtaagccctc ccgtatcgta   4560

gttatctaca cgacggggag tcaggcaact atggatgaac gaaatagaca gatcgctgag   4620

ataggtgcct cactgattaa gcattggtaa ctgtcagacc aagtttactc atatatactt   4680

tagattgatt taaaacttca tttttaattt aaaaggatct aggtgaagat cctttttgat   4740

aatctcatga ccaaaatccc ttaacgtgag ttttcgttcc actgagcgtc agaccccgta   4800

gaaaagatca aaggatcttc ttgagatcct ttttttctgc gcgtaatctg ctgcttgcaa   4860

acaaaaaaac caccgctacc agcggtggtt tgtttgccgg atcaagagct accaactctt   4920

tttccgaagg taactggctt cagcagagcg cagataccaa atactgtcct tctagtgtag   4980

ccgtagttag gccaccactt caagaactct gtagcaccgc ctacatacct cgctctgcta   5040

atcctgttac cagtggctgc tgccagtggc gataagtcgt gtcttaccgg gttggactca   5100

agacgatagt taccggataa ggcgcagcgg tcgggctgaa cggggggttc gtgcacacag   5160

cccagcttgg agcgaacgac ctacaccgaa ctgagatacc tacagcgtga gctatgagaa   5220

agcgccacgc ttcccgaagg gagaaaggcg gacaggtatc cggtaagcgg cagggtcgga   5280

acaggagagc gcacgaggga gcttccaggg ggaaacgcct ggtatcttta tagtcctgtc   5340

gggtttcgcc acctctgact tgagcgtcga tttttgtgat gctcgtcagg ggggcggagc   5400

ctatggaaaa acgccagcaa cgcggccttt ttacggttcc tggccttttg ctggcctttt   5460

gctcacatgt                                                          5470
```

```
<210> SEQ ID NO 96
<211> LENGTH: 2575
<212> TYPE: DNA
<213> ORGANISM: Artificial Sequence
<220> FEATURE:
<223> OTHER INFORMATION: synthetic construct

<400> SEQUENCE: 96

gcggccgcac gcgtgtccca taggcagttt gtggctgagt gctggtccag gggtgaggag     60

gtgggctatg ttactgaggg tctctgggtg ttaggaaaac agggcccagg agtctggctg    120

ctcgtatgct ggcccaggct cttgtttttc ttgagctgac ttgctggaga agtgagctaa    180

gtcagaaaca aaatgccaca ttgcacgccc actgaagtct gggctcaagg gaaagaagag    240

agattgccag agcgttagct gttcccaatc cactcctgga ccttaagctg tcttgaacag    300

agttgccaat cagcttggta gggactggcc tttgaggagg ggagggggtg taggcagggg    360

agggggagag aagggagcag tctgcgctcc atcttaatta cctcatcaga aacagctccc    420

ttcccgcaaa gctctggtgt cttctacaag agggtgagtc tttggcttta catgtgaact    480
```

tgtgccattt gcctgcgtat ataaacatga agggtcgtct gggttcagag ctgaaatctt 540
tcacttgtga cttagctggg aaattcttgg caagatcaga atgcagtggt aaggtctgag 600
ctcgggctgg gcataaaagt cagggcagag ccatctattg cttacatttg cttctgggat 660
ccgccaccat gtctagactg gacaagagca aagtcataaa ctctgctctg gaattactca 720
atgaagtcgg tatcgaaggc ctgacgacaa ggaaactcgc tcaaaagctg ggagttgagc 780
agcctaccct gtactggcac gtgaagaaca agcgggccct gctcgatgcc ctggcaatcg 840
agatgctgga caggcatcat acccacttct gcccccctgga aggcgagtca tggcaagact 900
ttctgcggaa caacgccaag tcattccgct gtgctctcct ctcacatcgc gacggggcta 960
aagtgcatct cggcacccgc ccaacagaga aacagtacga aaccctggaa aatcagctcg 1020
cgttcctgtg tcagcaaggc ttctccctgg agaacgcact gtacgctctg tccgccgtgg 1080
gccactttac actgggctgc gtattggagg atcaggagca tcaagtagca aaagaggaaa 1140
gagagacacc taccaccgat tctatgcccc cacttctgag acaagcaatt gagctgttcg 1200
accatcaggg agccgaacct gccttccttt tcggcctgga actaatcata tgtggcctgg 1260
agaaacagct aaagtgcgaa agcggcgggc cggccgacgc ccttgacgat tttgacttag 1320
acatgctccc agccgatgcc cttgacgact ttgaccttga tatgctgcct gctgacgctc 1380
ttgacgattt tgaccttgac atgctccccg ggtaagaatt cgatatcaag cttatcgata 1440
atcaacctct ggattacaaa atttgtgaaa gattgactgg tattcttaac tatgttgctc 1500
cttttacgct atgtggatac gctgctttaa tgcctttgta tcatgctatt gcttcccgta 1560
tggctttcat tttctcctcc ttgtataaat cctggttgct gtctctttat gaggagttgt 1620
ggcccgttgt caggcaacgt ggcgtggtgt gcactgtgtt tgctgacgca acccccactg 1680
gttggggcat tgccaccacc tgtcagctcc tttccgggac tttcgctttc cccctcccta 1740
ttgccacggc ggaactcatc gccgcctgcc ttgcccgctg ctggacaggg gctcggctgt 1800
tgggcactga caattccgtg gtgttgtcgg ggaaatcatc gtcctttcct tggctgctcg 1860
cctatgttgc cacctggatt ctgcgcggga cgtccttctg ctacgtccct tcggccctca 1920
atccagcgga ccttccttcc cgcggcctgc tgccggctct gcggcctctt ccgcgtcttc 1980
gccttcgccc tcagacgagt cggatctccc tttgggccgc ctccccgcat cgataccgag 2040
cgctgctcga gagatctacg ggtggcatcc ctgtgacccc tccccagtgc ctctcctggc 2100
cctggaagtt gccactccag tgcccaccag ccttgtccta ataaaattaa gttgcatcat 2160
tttgtctgac taggtgtcct tctataatat tatggggtgg aggggggtgg tatggagcaa 2220
ggggcaagtt gggaagacaa cctgtagggc ctgcggggtc tattgggaac caagctggag 2280
tgcagtggca caatcttggc tcactgcaat ctccgcctcc tgggttcaag cgattctcct 2340
gcctcagcct cccgagttgt tgggattcca ggcatgcatg accaggctca gctaattttt 2400
gtttttttgg tagagacggg gtttcaccat attggccagg ctggtctcca actcctaatc 2460
tcaggtgatc tacccacctt ggcctcccaa attgctggga ttacaggcgt gaaccactgc 2520
tcccttccct gtccttctga ttttgtaggt aaccacgtgc ggaccgagcg gccgc 2575

<210> SEQ ID NO 97
<211> LENGTH: 2591
<212> TYPE: DNA
<213> ORGANISM: Artificial Sequence
<220> FEATURE:
<223> OTHER INFORMATION: synthetic construct

<400> SEQUENCE: 97

-continued gcggccgcac gcgtagggtg caggagaaat gtgacctcaa agtcttgttc tataactgtt 60
ggaccttagg agagatctgt gctcagcaat ttaccaggac acccccaccc cacatgtctt 120
gaccactgtc tggataactg gtatgcagga ccacactagg cttactcaca gtgtaaactc 180
tcataaccat cactggagcc catcctgcct ggtagacaag gattcaacca tgactcattg 240
tactttagtg gtgccatgct tagtcatcag gtgccctgtg ctctgacagc cgagggtcag 300
agctggaatc acactcttgt tgtcttttaa tctctccctc cctttcttcc ttctttcttc 360
actctgttgt gattgctcat ggaacagatc ctagctggtc tccctggcaa cctacatgat 420
ttgagcccaa cagatggata atggggacat cgacttccaa tgtcattcaa cagaatcatt 480
gccaagggag tctgatgagc aggcaactga gatgacaccc ttatcaatat agcttcattt 540
tggcaatctg gagtaggtgt ttcaaaagga gagcccccac tgatgccagc aatacagaac 600
gttcatgggc aaggagctcg ggctgggcat aaaagtcagg gcagagccat ctattgctta 660
catttgcttc tgggatccgc caccatgtct agactggaca agagcaaagt cataaactct 720
gctctggaat tactcaatga agtcggtatc gaaggcctga cgacaaggaa actcgctcaa 780
aagctgggag ttgagcagcc taccctgtac tggcacgtga agaacaagcg ggccctgctc 840
gatgccctgg caatcgagat gctggacagg catcataccc acttctgccc cctggaaggc 900
gagtcatggc aagactttct gcggaacaac gccaagtcat tccgctgtgc tctcctctca 960
catcgcgacg gggctaaagt gcatctcggc acccgcccaa cagagaaaca gtacgaaacc 1020
ctggaaaatc agctcgcgtt cctgtgtcag caaggcttct ccctggagaa cgcactgtac 1080
gctctgtccg ccgtgggcca ctttacactg ggctgcgtat tggaggatca ggagcatcaa 1140
gtagcaaaag aggaaagaga gacacctacc accgattcta tgcccccact tctgagacaa 1200
gcaattgagc tgttcgacca tcagggagcc gaacctgcct tccttttcgg cctggaacta 1260
atcatatgtg gcctggagaa acagctaaag tgcgaaagcg gcgggccggc cgacgccctt 1320
gacgattttg acttagacat gctcccagcc gatgcccttg acgactttga ccttgatatg 1380
ctgcctgctg acgctcttga cgattttgac cttgacatgc tccccgggta agaattcgat 1440
atcaagctta tcgataatca acctctggat tacaaaattt gtgaaagatt gactggtatt 1500
cttaactatg ttgctccttt tacgctatgt ggatacgctg ctttaatgcc tttgtatcat 1560
gctattgctt cccgtatggc tttcattttc tcctccttgt ataaatcctg gttgctgtct 1620
ctttatgagg agttgtggcc cgttgtcagg caacgtggcg tggtgtgcac tgtgtttgct 1680
gacgcaaccc ccactggttg gggcattgcc accacctgtc agctcctttc cgggactttc 1740
gctttccccc tccctattgc cacggcggaa ctcatcgccg cctgccttgc ccgctgctgg 1800
acaggggctc ggctgttggg cactgacaat tccgtggtgt tgtcggggaa atcatcgtcc 1860
tttccttggc tgctcgccta tgttgccacc tggattctgc gcgggacgtc cttctgctac 1920
gtcccttcgg ccctcaatcc agcggacctt ccttcccgcg gcctgctgcc ggctctgcgg 1980
cctcttccgc gtcttcgcct tcgccctcag acgagtcgga tctccctttg ggccgcctcc 2040
ccgcatcgat accgagcgct gctcgagaga tctacgggtg gcatccctgt gacccctccc 2100
cagtgcctct cctggccctg gaagttgcca ctccagtgcc caccagcctt gtcctaataa 2160
aattaagttg catcattttg tctgactagg tgtccttcta taatattatg gggtggaggg 2220
gggtggtatg gagcaagggg caagttggga agacaacctg tagggcctgc ggggtctatt 2280
gggaaccaag ctggagtgca gtggcacaat cttggctcac tgcaatctcc gcctcctggg 2340

```
ttcaagcgat tctcctgcct cagcctcccg agttgttggg attccaggca tgcatgacca   2400

ggctcagcta atttttgttt ttttggtaga gacggggttt caccatattg gccaggctgg   2460

tctccaactc ctaatctcag gtgatctacc caccttggcc tcccaaattg ctgggattac   2520

aggcgtgaac cactgctccc ttccctgtcc ttctgatttt gtaggtaacc acgtgcggac   2580

cgagcggccg c                                                        2591
```

<210> SEQ ID NO 98
<211> LENGTH: 4424
<212> TYPE: DNA
<213> ORGANISM: Artificial Sequence
<220> FEATURE:
<223> OTHER INFORMATION: synthetic construct

<400> SEQUENCE: 98

```
gcggccgcac gcgtgaaatg tgacctcaaa gtcttgttct ataactgttg gaccttagga     60

gagatctgtg ctcagcaatt taccaggaca cccccacccc acatgtcttg accactgtct    120

ggataactgg tatgcaggac cacactaggc ttactcacag tgtaaactct cataaccatc    180

actggagccc atcctgcctg gtagacaagg attcaaccat gactcattgt actttagtgg    240

tgccatgctt agtcatcagg tgccctgtgc tctgacagcc gagggtcaga gctggaatca    300

cactcttgtt gtcttttaat ctctccctcc ctttcttcct tctttcttca ctctgttgtg    360

attgctcatg gaacagatcc tagctggtct ccctggcaac ctacatgatt tgagcccaac    420

agatggataa tggggacatc gacttccaat gtcattcaac agaatcattg ccaagggagt    480

ctgatgagca ggcaactgag atgacaccct tatcaatata gcttcatttt ggcaatctgg    540

agtaggtgtt tcaaaaggag agcccccact gatgccagca atacagaacg ttcatgggca    600

agtgacatag cgatagacag attcgactcg gtaccagggt gcaggagaaa tgtgacctca    660

aagtcttgtt ctataactgt tggaccttag gagagatctg tgctcagcaa tttaccagga    720

cacccccacc ccacatgtct tgaccactgt ctggataact ggtatgcagg accacactag    780

gcttactcac agtgtaaact ctcataacca tcactggagc ccatcctgcc tggtagacaa    840

ggattcaacc atgactcatt gtactttagt ggtgccatgc ttagtcatca ggtgccctgt    900

gctctgacag ccgagggtca gagctggaat cacactcttg ttgtctttta atctctccct    960

ccctttcttc cttctttctt cactctgttg tgattgctca tggaacagat cctagctggt   1020

ctccctggca acctacatga tttgagccca acagatggat aatggggaca tcgacttcca   1080

atgtcattca acagaatcat tgccaaggga gtctgatgag caggcaactg agatgacacc   1140

cttatcaata tagcttcatt ttggcaatct ggagtaggtg tttcaaaagg agagccccca   1200

ctgatgccag caatacagaa cgttcatggg caaggatgat ggcatcattg agtagcatga   1260

tctcaattga gggtgcagga gaaatgtgac ctcaaagtct tgttctataa ctgttggacc   1320

ttaggagaga tctgtgctca gcaatttacc aggacacccc caccccacat gtcttgacca   1380

ctgtctggat aactggtatg caggaccaca ctaggcttac tcacagtgta aactctcata   1440

accatcactg gagcccatcc tgcctggtag acaaggattc aaccatgact cattgtactt   1500

tagtggtgcc atgcttagtc atcaggtgcc ctgtgctctg acagccgagg gtcagagctg   1560

gaatcacact cttgttgtct tttaatctct ccctcccttt cttccttctt tcttcactct   1620

gttgtgattg ctcatggaac agatcctagc tggtctccct ggcaacctac atgatttgag   1680

cccaacagat ggataatggg gacatcgact tccaatgtca ttcaacagaa tcattgccaa   1740

gggagtctga tgagcaggca actgagatga caccctta tc aatatagctt cattttggca   1800
```

-continued

```
atctggagta ggtgtttcaa aaggagagcc cccactgatg ccagcaatac agaacgttca   1860
tgggcaagga gctcagggtg caggagaaat gtgacctcaa agtcttgttc tataactgtt   1920
ggaccttagg agagatctgt gctcagcaat ttaccaggac acccccaccc cacatgtctt   1980
gaccactgtc tggataactg gtatgcagga ccacactagg cttactcaca gtgtaaactc   2040
tcataaccat cactggagcc catcctgcct ggtagacaag gattcaacca tgactcattg   2100
tactttagtg gtgccatgct tagtcatcag gtgccctgtg ctctgacagc cgagggtcag   2160
agctggaatc acactcttgt tgtcttttaa tctctccctc cctttcttcc ttctttcttc   2220
actctgttgt gattgctcat ggaacagatc ctagctggtc tccctggcaa cctacatgat   2280
ttgagcccaa cagatggata atggggacat cgacttccaa tgtcattcaa cagaatcatt   2340
gccaagggag tctgatgagc aggcaactga gatgacaccc ttatcaatat agcttcattt   2400
tggcaatctg gagtaggtgt ttcaaaagga gagcccccac tgatgccagc aatacagaac   2460
gttcatgggc aaggagctcg ggctgggcat aaaagtcagg gcagagccat ctattgctta   2520
catttgcttc tgggatccgc caccatggtg agcaagggcg aggagctgtt caccggggtg   2580
gtgcccatcc tggtcgagct ggacggcgac gtaaacggcc acaagttcag cgtgtccggc   2640
gagggcgagg gcgatgccac ctacggcaag ctgaccctga agttcatctg caccaccggc   2700
aagctgcccg tgccctggcc caccctcgtg accaccctga cctacggcgt gcagtgcttc   2760
agccgctacc ccgaccacat gaagcagcac gacttcttca agtccgccat gcccgaaggc   2820
tacgtccagg agcgcaccat cttcttcaag gacgacggca actacaagac ccgcgccgag   2880
gtgaagttcg agggcgacac cctggtgaac cgcatcgagc tgaagggcat cgacttcaag   2940
gaggacggca acatcctggg gcacaagctg gagtacaact acaacagcca caacgtctat   3000
atcatggccg acaagcagaa gaacggcatc aaggtgaact tcaagatccg ccacaacatc   3060
gaggacggca gcgtgcagct cgccgaccac taccagcaga acacccccat cggcgacggc   3120
cccgtgctgc tgcccgacaa ccactacctg agcacccagt ccgccctgag caaagacccc   3180
aacgagaagc gcgatcacat ggtcctgctg gagttcgtga ccgccgccgg gatcactctc   3240
ggcatggacg agctgtacaa gtaagaattc gatatcaagc ttatcgataa tcaacctctg   3300
gattacaaaa tttgtgaaag attgactggt attcttaact atgttgctcc ttttacgcta   3360
tgtggatacg ctgctttaat gcctttgtat catgctattg cttcccgtat ggctttcatt   3420
ttctcctcct tgtataaatc ctggttgctg tctctttatg aggagttgtg gcccgttgtc   3480
aggcaacgtg gcgtggtgtg cactgtgttt gctgacgcaa cccccactgg ttggggcatt   3540
gccaccacct gtcagctcct ttccgggact ttcgctttcc ccctccctat tgccacggcg   3600
gaactcatcg ccgcctgcct tgcccgctgc tggacagggg ctcggctgtt gggcactgac   3660
aattccgtgg tgttgtcggg gaaatcatcg tcctttcctt ggctgctcgc ctatgttgcc   3720
acctggattc tgcgcgggac gtccttctgc tacgtccctt cggccctcaa tccagcggac   3780
cttccttccc gcggcctgct gccggctctg cggcctcttc cgcgtcttcg ccttcgccct   3840
cagacgagtc ggatctccct ttgggccgcc tccccgcatc gataccgagc gctgctcgag   3900
agatctacgg gtggcatccc tgtgacccct ccccagtgcc tctcctggcc ctggaagttg   3960
ccactccagt gcccaccagc cttgtcctaa taaaattaag ttgcatcatt ttgtctgact   4020
aggtgtcctt ctataatatt atggggtgga ggggggtggt atggagcaag gggcaagttg   4080
ggaagacaac ctgtagggcc tgcggggtct attgggaacc aagctggagt gcagtggcac   4140
```

-continued

```
aatcttggct cactgcaatc tccgcctcct gggttcaagc gattctcctg cctcagcctc   4200

ccgagttgtt gggattccag gcatgcatga ccaggctcag ctaatttttg tttttttggt   4260

agagacgggg tttcaccata ttggccaggc tggtctccaa ctcctaatct caggtgatct   4320

acccaccttg gcctcccaaa ttgctgggat tacaggcgtg aaccactgct cccttccctg   4380

tccttctgat tttgtaggta accacgtgcg gaccgagcgg ccgc                    4424
```

<210> SEQ ID NO 99
<211> LENGTH: 1919
<212> TYPE: DNA
<213> ORGANISM: Artificial Sequence
<220> FEATURE:
<223> OTHER INFORMATION: synthetic construct

<400> SEQUENCE: 99

```
gcggccgcac gcgtcaaaag atggaagttg ggaggttgaa gaagtgcagg atggcattcc     60

aagtgatggg ggcaatggca tggaggtagg aaagcataag gtatattcag gctataaata    120

atagttagat ttggctggat cctggatttg agaagccagg aaatgagata acactggtca    180

ctttcactaa agctcatgaa aaaaaaaata catacatata tatatatata aaataaatat    240

acatatatat ttttaagccc catatgacta gaggaggcag cccatctgtt ctctgggctt    300

cacttttctt gtctgggaaa tgagtaggtt ggactgcatg gtctttaagg tctctttagt    360

attatcttgt ttgactccgt aaagagaaaa acaaaggttc ctcctgacat cttgtgttgc    420

cttccaacgt ccagtccagt gtgattgttt taagtactct ttggatattt tactgttata    480

aaaagtgaag aaaaagactg attttgccaa gtcttatgga tccaaattag tactcattgc    540

actatggtca tttagttgag gacgatactc cagcttcaaa ggagctcggg ctgggcataa    600

aagtcagggc agagccatct attgcttaca tttgcttctg ggatccagat ctttcgaagc    660

tagcgctacc ggtcgccacc atggtgagca agggcgagga gctgttcacc ggggtggtgc    720

ccatcctggt cgagctggac ggcgacgtaa acggccacaa gttcagcgtg tccggcgagg    780

gcgagggcga tgccacctac ggcaagctga ccctgaagct gatctgcacc accggcaagc    840

tgcccgtgcc ctggcccacc ctcgtgacca ccctgggcta cggcgtgcag tgcttcgccc    900

gctaccccga ccacatgaag cagcacgact tcttcaagtc cgccatgccc gaaggctacg    960

tccaggagcg caccatcttc ttcaaggacg acggcaacta caagacccgc gccgaggtga   1020

agttcgaggg cgacaccctg gtgaaccgca tcgagctgaa gggcatcgac ttcaaggagg   1080

acggcaacat cctggggcac aagctggagt acaactacaa cagccacaac gtctatatca   1140

ccgccgacaa gcagaagaac ggcatcaagg ccaacttcaa gatccgccac aacatcgagg   1200

acggcggcgt gcagctcgcc gaccactacc agcagaacac ccccatcggc gacggccccg   1260

tgctgctgcc cgacaaccac tacctgagct accagtccaa gctgagcaaa gaccccaacg   1320

agaagcgcga tcacatggtc ctgctggagt tcgtgaccgc cgccgggatc actctcggca   1380

tggacgagct gtacaagtaa gtcgacggcg cgccgcggcc gcgaattcga tatcataatc   1440

aacctctgga ttacaaaatt tgtgaaagat tgactggtat tcttaactat gttgctcctt   1500

ttacgctatg tggatacgct gctttaatgc ctttgtatca tgctattgct tcccgtatgg   1560

ctttcatttt ctcctccttg tataaatcct ggttagttct tgccacggcg gaactcatcg   1620

ccgcctgcct tgcccgctgc tggacagggg ctcggctgtt gggcactgac aattccgtgg   1680

ctcgagagat cttcgactgt gccttctagt tgccagccat ctgttgtttg cccctccccc   1740

gtgccttcct tgaccctgga aggtgccact cccactgtcc tttcctaata aaatgaggaa   1800
```

attgcatcgc attgtctgag taggtgtcat tctattctgg ggggtggggt ggggcaggac 1860
agcaaggggg aggattggga agacaatagc aggcatgcac gtgcggaccg agcggccgc 1919

<210> SEQ ID NO 100
<211> LENGTH: 2074
<212> TYPE: DNA
<213> ORGANISM: Artificial Sequence
<220> FEATURE:
<223> OTHER INFORMATION: synthetic construct

<400> SEQUENCE: 100
gcggccgcac gcgtggtaca tattataagt ttgagtctgc aagatgtggc aaacccttcc 60
ttttctcttt atcttgacag tggaaaacat ctaaggagtc tttaaaataa ccacatcgga 120
ctgagcagtg gagggcaaag agaatgtctg gaagaacctt tgtttttttc gttgggacat 180
caaaggatgt tatactgaag agatctcaaa gaccaggcag tccagcctac tcgtttccca 240
gacaagagaa gtgaagccaa gaaacagatg ggctgcctcc tctagtcata tggggcttaa 300
aaatatatat ctctattttt catgagtttt catgaaagtg accagtgtta tctcatttcc 360
tgtcttctca aattcaggat cctacccaat ctaactatta tttatagtgt gaataagccc 420
tctactttcc tacctctaca atgctcattc tccattttcc catcatctac ttccatcttg 480
tgaaaagttt ccactcttca gtgatgacct caaacatatc atttcttttt tttaattctt 540
tttttattag atattttctt tatatacatt tcaaatgcta tcctgaaagt tccctatatc 600
ctccctctgc cctgcttccc tacccaccca ctcccacttc ttggccctgg catttccctg 660
tactggggca tataaagttt gcaataccaa ggggcctctc ttcacagtga tggccaacta 720
ggccatcttc tgctacgagc tcgggctggg cataaaagtc agggcagagc catctattgc 780
ttacatttgc ttctgggatc cagatctttc gaagctagcg ctaccggtcg ccaccatggt 840
gagcaagggc gaggagctgt tcaccggggt ggtgcccatc ctggtcgagc tggacggcga 900
cgtaaacggc cacaagttca gcgtgtccgg cgagggcgag ggcgatgcca cctacggcaa 960
gctgaccctg aagctgatct gcaccaccgg caagctgccc gtgccctggc ccaccctcgt 1020
gaccaccctg ggctacggcg tgcagtgctt cgcccgctac cccgaccaca tgaagcagca 1080
cgacttcttc aagtccgcca tgcccgaagg ctacgtccag gagcgcacca tcttcttcaa 1140
ggacgacggc aactacaaga cccgcgccga ggtgaagttc gagggcgaca ccctggtgaa 1200
ccgcatcgag ctgaagggca tcgacttcaa ggaggacggc aacatcctgg ggcacaagct 1260
ggagtacaac tacaacagcc acaacgtcta tatcaccgcc gacaagcaga agaacggcat 1320
caaggccaac ttcaagatcc gccacaacat cgaggacggc ggcgtgcagc tcgccgacca 1380
ctaccagcag aacaccccca tcggcgacgg ccccgtgctg ctgcccgaca accactacct 1440
gagctaccag tccaagctga gcaaagaccc caacgagaag cgcgatcaca tggtcctgct 1500
ggagttcgtg accgccgccg ggatcactct cggcatggac gagctgtaca agtaagtcga 1560
cggcgcgccg cggccgcgaa ttcgatatca taatcaacct ctggattaca aaatttgtga 1620
aagattgact ggtattctta actatgttgc tccttttacg ctatgtggat acgctgcttt 1680
aatgcctttg tatcatgcta ttgcttcccg tatggctttc attttctcct ccttgtataa 1740
atcctggtta gttcttgcca cggcggaact catcgccgcc tgccttgccc gctgctggac 1800
aggggctcgg ctgttgggca ctgacaattc cgtggctcga gagatcttcg actgtgcctt 1860
ctagttgcca gccatctgtt gtttgcccct cccccgtgcc ttccttgacc ctggaaggtg 1920

```
ccactcccac tgtcctttcc taataaaatg aggaaattgc atcgcattgt ctgagtaggt   1980

gtcattctat tctggggggt ggggtggggc aggacagcaa gggggaggat tgggaagaca   2040

atagcaggca tgcacgtgcg gaccgagcgg ccgc                               2074


<210> SEQ ID NO 101
<211> LENGTH: 4059
<212> TYPE: DNA
<213> ORGANISM: Artificial Sequence
<220> FEATURE:
<223> OTHER INFORMATION: synthetic construct

<400> SEQUENCE: 101

gcggccgcac gcgtataggt accccttgga tttgctacaa attacatttt aaatgcaatc     60

attttataaa agcttcaaca ctcacacttg gaagcgttac cctgttgaat atcactgact    120

cactaacttg cattgccatg ctaacttgct ttcagagaga tctcagaaca catcatcttc    180

tgctatttca atacatgcac attaatttcc tatcaacgtg tgctgatcag gaactctgta    240

atctggcacc ggtgtttatt tttattcctg tctattcctg ttggctcacg aaaagattgt    300

ttgagcaagt gttttatggt gagttgtatc atatgtacat tgatttaatc tgcccacatt    360

cagttctaca agcggagcca aaaaaataga gacaagcata attttcattc aacatgagcc    420

cctcaatgca agccaagtac ctcatctggt gctcagctaa agcaacagca atctgttcca    480

ccctggagac acaactggcc acagaaaact tagtgaaaag aggccttgga tttgctacaa    540

attacatttt aaatgcaatc attttataaa agcttcaaca ctcacacttg gaagcgttac    600

cctgttgaat atcactgact cactaacttg cattgccatg ctaacttgct ttcagagaga    660

tctcagaaca catcatcttc tgctatttca atacatgcac attaatttcc tatcaacgtg    720

tgctgatcag gaactctgta atctggcacc ggtgtttatt tttattcctg tctattcctg    780

ttggctcacg aaaagattgt ttgagcaagt gttttatggt gagttgtatc atatgtacat    840

tgatttaatc tgcccacatt cagttctaca agcggagcca aaaaaataga gacaagcata    900

attttcattc aacatgagcc cctcaatgca agccaagtac ctcatctggt gctcagctaa    960

agcaacagca atctgttcca ccctggagac acaactggcc acagaaaact tagtgaaaag   1020

aggccttgga tttgctacaa attacatttt aaatgcaatc attttataaa agcttcaaca   1080

ctcacacttg gaagcgttac cctgttgaat atcactgact cactaacttg cattgccatg   1140

ctaacttgct ttcagagaga tctcagaaca catcatcttc tgctatttca atacatgcac   1200

attaatttcc tatcaacgtg tgctgatcag gaactctgta atctggcacc ggtgtttatt   1260

tttattcctg tctattcctg ttggctcacg aaaagattgt ttgagcaagt gttttatggt   1320

gagttgtatc atatgtacat tgatttaatc tgcccacatt cagttctaca agcggagcca   1380

aaaaaataga gacaagcata attttcattc aacatgagcc cctcaatgca agccaagtac   1440

ctcatctggt gctcagctaa agcaacagca atctgttcca ccctggagac acaactggcc   1500

acagaaaact tagtgaaaag aggccttgga tttgctacaa attacatttt aaatgcaatc   1560

attttataaa agcttcaaca ctcacacttg gaagcgttac cctgttgaat atcactgact   1620

cactaacttg cattgccatg ctaacttgct ttcagagaga tctcagaaca catcatcttc   1680

tgctatttca atacatgcac attaatttcc tatcaacgtg tgctgatcag gaactctgta   1740

atctggcacc ggtgtttatt tttattcctg tctattcctg ttggctcacg aaaagattgt   1800

ttgagcaagt gttttatggt gagttgtatc atatgtacat tgatttaatc tgcccacatt   1860

cagttctaca agcggagcca aaaaaataga gacaagcata attttcattc aacatgagcc   1920
```

```
cctcaatgca agccaagtac ctcatctggt gctcagctaa agcaacagca atctgttcca   1980
ccctggagac acaactggcc acagaaaact tagtgaaaag agggagctcg ggctgggcat   2040
aaaagtcagg gcagagccat ctattgctta catttgcttc tgggatcctt cgaagctagc   2100
ggcgccacca tggtgagcaa gggcgaggag gtcatcaaag agttcatgcg cttcaaggtg   2160
cgcatggagg gctccatgaa cggccacgag ttcgagatcg agggcgaggg cgagggccgc   2220
ccctacgagg gcacccagac cgccaagctg aaggtgacca agggcggccc cctgcccttc   2280
gcctgggaca tcctgtcccc ccagttcatg tacggctcca aggcgtacgt gaagcacccc   2340
gccgacatcc ccgattacaa gaagctgtcc ttccccgagg gcttcaagtg ggagcgcgtg   2400
atgaacttcg aggacggcgg tctggtgacc gtgacccagg actcctccct gcaggacggc   2460
acgctgatct acaaggtgaa gatgcgcggc accaacttcc cccccgacgg ccccgtaatg   2520
cagaagaaga ccatgggctg ggaggcctcc accgagcgcc tgtacccccg cgacggcgtg   2580
ctgaagggcg agatccacca ggccctgaag ctgaaggacg gcggccacta cctggtggag   2640
ttcaagacca tctacatggc caagaagccc gtgcaactgc ccggctacta ctacgtggac   2700
accaagctgg acatcacctc ccacaacgag gactacacca tcgtggaaca gtacgagcgc   2760
tccgagggcc gccaccacct gttcctgggg catggcaccg gcagcaccgg cagcggcagc   2820
tccggcaccg cctcctccga ggacaacaac atggccgtca tcaaagagtt catgcgcttc   2880
aaggtgcgca tggagggctc catgaacggc cacgagttcg agatcgaggg cgagggcgag   2940
ggccgcccct acgagggcac ccagaccgcc aagctgaagg tgaccaaggg cggccccctg   3000
cccttcgcct gggacatcct gtccccccag ttcatgtacg gctccaaggc gtacgtgaag   3060
caccccgccg acatccccga ttacaagaag ctgtccttcc ccgagggctt caagtgggag   3120
cgcgtgatga acttcgagga cggcggtctg gtgaccgtga cccaggactc ctccctgcag   3180
gacggcacgc tgatctacaa ggtgaagatg cgcggcacca acttcccccc cgacggcccc   3240
gtaatgcaga agaagaccat gggctgggag gcctccaccg agcgcctgta cccccgcgac   3300
ggcgtgctga agggcgagat ccaccaggcc ctgaagctga aggacggcgg ccactacctg   3360
gtggagttca agaccatcta catggccaag aagcccgtgc aactgcccgg ctactactac   3420
gtggacacca agctggacat cacctcccac aacgaggact acaccatcgt ggaacagtac   3480
gagcgctccg agggccgcca ccacctgttc ctgtacggca tggacgagct gtacaagtaa   3540
gtcgacggcg cgccgcggcc gcgaattcga tatcataatc aacctctgga ttacaaaatt   3600
tgtgaaagat tgactggtat tcttaactat gttgctcctt ttacgctatg tggatacgct   3660
gctttaatgc ctttgtatca tgctattgct tcccgtatgg ctttcatttt ctcctccttg   3720
tataaatcct ggttagttct tgccacggcg gaactcatcg ccgcctgcct tgcccgctgc   3780
tggacagggg ctcggctgtt gggcactgac aattccgtgg ctcgagagat cttcgactgt   3840
gccttctagt tgccagccat ctgttgtttg cccctccccc gtgccttcct tgaccctgga   3900
aggtgccact cccactgtcc tttcctaata aaatgaggaa attgcatcgc attgtctgag   3960
taggtgtcat tctattctgg ggggtggggt ggggcaggac agcaaggggg aggattggga   4020
agacaatagc aggcatgcac gtgcggaccg agcggccgc                          4059
```

<210> SEQ ID NO 102
<211> LENGTH: 2139
<212> TYPE: DNA
<213> ORGANISM: Artificial Sequence
<220> FEATURE:

-continued

<223> OTHER INFORMATION: synthetic construct

<400> SEQUENCE: 102
gcggccgcac gcgtccgaga cagcagagag actggtctga ctgcagagga ggtctgggag 60
accagaggga gtgtggagag ggtgaggtta gaagacagga acaccgagct gcatcggcca 120
aatggagcct tagggggcca tgtgaggctg aggcagggaa gcagggatcc tgccctccag 180
gtccttacag tcaggcgggg accaaaagca cgaggatgcc agcccaattc cctattaggc 240
aaaacgcagc accatctgca caatcccagg agcaagagca gatattttat aacttccttt 300
tttcttttta agtctaaatt aaaaataaat gttcccttca gctctcagat gtatatctct 360
ggtgcaacct gcccacattc cctcccgctg ccctttccag aacatggcag gggaaaggaa 420
gaaagagatg gatagagaga gggagccagt ccacccagct tcaatgccag tggattgcac 480
ctcttccaag agggaaacga ttcaggcgtg gccacgcaga cgggtggaga gcgcccagaa 540
tgtggctggt accaaggaaa gtggaaggag agggaaacag gagccaacag ctatgatttc 600
tagcccagcc tccaccctat cgcgctgcag gaccttggcc aaatcacaca tcctatctct 660
gctcccattt atagttcata acatggctga agtcccctct gccgctccag ccccctggca 720
gctgtgctct ctgcacatcc gtctgtacct ttgctgctcc ccttcatttt gggtgtccta 780
ccatggacct agtgattaac ggagctcggg ctgggcataa aagtcagggc agagccatct 840
attgcttaca tttgcttctg ggatccagat ctttcgaagc tagcgctacc ggtcgccacc 900
atggtgagca agggcgagga gctgttcacc ggggtggtgc ccatcctggt cgagctggac 960
ggcgacgtaa acggccacaa gttcagcgtg tccggcgagg gcgagggcga tgccacctac 1020
ggcaagctga ccctgaagct gatctgcacc accggcaagc tgcccgtgcc ctggcccacc 1080
ctcgtgacca ccctgggcta cggcgtgcag tgcttcgccc gctaccccga ccacatgaag 1140
cagcacgact tcttcaagtc cgccatgccc gaaggctacg tccaggagcg caccatcttc 1200
ttcaaggacg acggcaacta caagacccgc gccgaggtga agttcgaggg cgacaccctg 1260
gtgaaccgca tcgagctgaa gggcatcgac ttcaaggagg acggcaacat cctggggcac 1320
aagctggagt acaactacaa cagccacaac gtctatatca ccgccgacaa gcagaagaac 1380
ggcatcaagg ccaacttcaa gatccgccac aacatcgagg acggcggcgt gcagctcgcc 1440
gaccactacc agcagaacac ccccatcggc gacggccccg tgctgctgcc cgacaaccac 1500
tacctgagct accagtccaa gctgagcaaa gaccccaacg agaagcgcga tcacatggtc 1560
ctgctggagt tcgtgaccgc cgccgggatc actctcggca tggacgagct gtacaagtaa 1620
gtcgacggcg cgccgcggcc gcgaattcga tatcataatc aacctctgga ttacaaaatt 1680
tgtgaaagat tgactggtat tcttaactat gttgctcctt ttacgctatg tggatacgct 1740
gctttaatgc ctttgtatca tgctattgct tcccgtatgg ctttcatttt ctcctccttg 1800
tataaatcct ggttagttct tgccacggcg gaactcatcg ccgcctgcct tgcccgctgc 1860
tggacagggg ctcggctgtt gggcactgac aattccgtgg ctcgagagat cttcgactgt 1920
gccttctagt tgccagccat ctgttgtttg cccctccccc gtgccttcct tgaccctgga 1980
aggtgccact cccactgtcc tttcctaata aaatgaggaa attgcatcgc attgtctgag 2040
taggtgtcat tctattctgg ggggtggggt ggggcaggac agcaaggggg aggattggga 2100
agacaatagc aggcatgcac gtgcggaccg agcggccgc 2139

<210> SEQ ID NO 103
<211> LENGTH: 1952

<212> TYPE: DNA
<213> ORGANISM: Artificial Sequence
<220> FEATURE:
<223> OTHER INFORMATION: synthetic construct

<400> SEQUENCE: 103

```
gcggccgcac gcgtggtgag gaacagaaca aaacagaaca agcaggttca cttgggacgc     60
cgggaacacc ccgggcttgc gcccctgcgc ctccccgctg gcggccccgc caacttcccg    120
gggtgtcccc tccctacctt ctcttcaccg ccctggcgcc tggcctgcgc gaggtcggga    180
ctcgcgggac ctccgcctac cccagaagcg gctgtctaaa gcgggggtgg gggggcgccc    240
cctcctgtct ggttttccct tccagttgcc gggagaggac taggcagccg ggagccgggc    300
cgtgcacccg ctgtggcgcg ctggcacctc ggcctccgca aacagattgc tcgccctcct    360
cggggaaagc taggaaaaca gtgctaagcc tcgcaagctg ccgcccatta atgcctctta    420
gcttgcaaga tgggttacta gctctgagca cggccctccc ctcggggctt cttacattct    480
cctccccctc gccccttctg tctccctcct tctccacgcc gcggtactct cgccttcgcc    540
ctcattctct ccctccacct actacctctt ccttttgttt tccgttctcc tgaatttccc    600
tttctttctt tttcgagctc gggctgggca taaaagtcag ggcagagcca tctattgctt    660
acatttgctt ctgggatcca gatctttcga agctagcgct accggtcgcc accatggtga    720
gcaagggcga ggagctgttc accggggtgg tgcccatcct ggtcgagctg gacggcgacg    780
taaacggcca caagttcagc gtgtccggcg agggcgaggg cgatgccacc tacggcaagc    840
tgaccctgaa gctgatctgc accaccggca agctgcccgt gccctggccc accctcgtga    900
ccaccctggg ctacggcgtg cagtgcttcg cccgctaccc cgaccacatg aagcagcacg    960
acttcttcaa gtccgccatg cccgaaggct acgtccagga gcgcaccatc ttcttcaagg   1020
acgacggcaa ctacaagacc cgcgccgagg tgaagttcga gggcgacacc ctggtgaacc   1080
gcatcgagct gaagggcatc gacttcaagg aggacggcaa catcctgggg cacaagctgg   1140
agtacaacta caacagccac aacgtctata tcaccgccga caagcagaag aacggcatca   1200
aggccaactt caagatccgc cacaacatcg aggacggcgg cgtgcagctc gccgaccact   1260
accagcagaa cacccccatc ggcgacggcc ccgtgctgct gcccgacaac cactacctga   1320
gctaccagtc caagctgagc aaagacccca acgagaagcg cgatcacatg gtcctgctgg   1380
agttcgtgac cgccgccggg atcactctcg gcatggacga gctgtacaag taagtcgacg   1440
gcgcgccgcg gccgcgaatt cgatatcata atcaacctct ggattacaaa atttgtgaaa   1500
gattgactgg tattcttaac tatgttgctc cttttacgct atgtggatac gctgctttaa   1560
tgcctttgta tcatgctatt gcttcccgta tggctttcat tttctcctcc ttgtataaat   1620
cctggttagt tcttgccacg gcggaactca tcgccgcctg ccttgcccgc tgctggacag   1680
gggctcggct gttgggcact gacaattccg tggctcgaga gatcttcgac tgtgccttct   1740
agttgccagc catctgttgt ttgcccctcc cccgtgcctt ccttgaccct ggaaggtgcc   1800
actcccactg tcctttccta ataaaatgag gaaattgcat cgcattgtct gagtaggtgt   1860
cattctattc tggggggtgg ggtggggcag gacagcaagg gggaggattg ggaagacaat   1920
agcaggcatg cacgtgcgga ccgagcggcc gc                                 1952
```

<210> SEQ ID NO 104
<211> LENGTH: 2025
<212> TYPE: DNA
<213> ORGANISM: Artificial Sequence
<220> FEATURE:

<223> OTHER INFORMATION: synthetic construct

<400> SEQUENCE: 104
gcggccgcac gcgtcagaga tggaggggtc agagacacag aggatgacag agacccagag 60
agagggagac agagacccag agagaggggg agagagacct agaaataggg ggacagagac 120
ccagagaggg aagagatgga aacctagaga aggaagcaga cagagtccca aagagaggcg 180
gggacagaaa cccaggagat agaacataga tgcagagaga tgagaacaga gatccagaat 240
gcaagagaaa gatggagagc ctgggagacg gaggatagac aggctgggga cgtgatttgt 300
gaggtgcagc ccctctctga ggtgggtagg cagccagggg atcgggctgg atcccaggaa 360
ggggctggaa cagatggagg cgagggagac tgggacgggg gaggaaggaa cagccagacg 420
gtccaggggg agggaggtgg aagagctgtg agaacacagc aacccctccc catcctagaa 480
cttaaggagg tggggagggg cagttaagaa acaggggtgg gagaagccag ggagtggaca 540
gaacccagaa ggagtaggaa tgagacccca agaggaagaa gacagagagc cagagatagg 600
ggggattgaa gccactagga cgaatagtac aggatggcag taactccccc cacccatcag 660
aacccatcac ccaaagagat tagactggag ctcgggctgg gcataaaagt cagggcagag 720
ccatctattg cttacatttg cttctgggat ccagatcttt cgaagctagc gctaccggtc 780
gccaccatgg tgagcaaggg cgaggagctg ttcaccgggg tggtgcccat cctggtcgag 840
ctggacggcg acgtaaacgg ccacaagttc agcgtgtccg gcgagggcga gggcgatgcc 900
acctacggca agctgaccct gaagctgatc tgcaccaccg gcaagctgcc cgtgccctgg 960
cccaccctcg tgaccaccct gggctacggc gtgcagtgct tcgcccgcta ccccgaccac 1020
atgaagcagc acgacttctt caagtccgcc atgcccgaag gctacgtcca ggagcgcacc 1080
atcttcttca aggacgacgg caactacaag acccgcgccg aggtgaagtt cgagggcgac 1140
accctggtga accgcatcga gctgaagggc atcgacttca aggaggacgg caacatcctg 1200
gggcacaagc tggagtacaa ctacaacagc cacaacgtct atatcaccgc cgacaagcag 1260
aagaacggca tcaaggccaa cttcaagatc cgccacaaca tcgaggacgg cggcgtgcag 1320
ctcgccgacc actaccagca gaacaccccc atcggcgacg gccccgtgct gctgcccgac 1380
aaccactacc tgagctacca gtccaagctg agcaaagacc ccaacgagaa gcgcgatcac 1440
atggtcctgc tggagttcgt gaccgccgcc gggatcactc tcggcatgga cgagctgtac 1500
aagtaagtcg acggcgcgcc gcggccgcga attcgatatc ataatcaacc tctggattac 1560
aaaatttgtg aaagattgac tggtattctt aactatgttg ctccttttac gctatgtgga 1620
tacgctgctt taatgccttt gtatcatgct attgcttccc gtatggcttt cattttctcc 1680
tccttgtata aatcctggtt agttcttgcc acggcggaac tcatcgccgc ctgccttgcc 1740
cgctgctgga caggggctcg gctgttgggc actgacaatt ccgtggctcg agagatcttc 1800
gactgtgcct tctagttgcc agccatctgt tgtttgcccc tcccccgtgc cttccttgac 1860
cctggaaggt gccactccca ctgtcctttc ctaataaaat gaggaaattg catcgcattg 1920
tctgagtagg tgtcattcta ttctgggggg tggggtgggg caggacagca agggggagga 1980
ttgggaagac aatagcaggc atgcacgtgc ggaccgagcg gccgc 2025

<210> SEQ ID NO 105
<211> LENGTH: 1923
<212> TYPE: DNA
<213> ORGANISM: Artificial Sequence
<220> FEATURE:
<223> OTHER INFORMATION: synthetic construct

<400> SEQUENCE: 105
gcggccgcac gcgtgaaatc ataaatgctg agggtagtct gcctcaggta cacactgaga 60
aactgcttta atgtaacctg acccacggtt attagtgaaa atatcacttt tgttgttacc 120
ttattcccaa caaattcatt tctgctttaa tggaaaagat ccgggttcac actaatcagg 180
cccaacggaa ggccatatta gcaatttggc aggtacccga gggccatacc taatctgcat 240
aaaatgaagc agattgcaac cgccctcatc ttttttattt ttaaactggt ttttgaagca 300
gagcataaaa tctcagaggg agagacagaa gatgctagtg catacatttt ccttcatgcc 360
tttattttca ttctttttgc acaaaccatc ttcctgaatg gctgtttacc taaagaagaa 420
taacaaaata aaaggtgcta ggaaatggag taggcagaga tcacaaatgt ttaattaaaa 480
aaaaaaaaag tcatgtactt tcatagatat tcacaatcct ctctagtata ctttcaaatc 540
agttttaatt tcagtttagt gtttttatgt tttgtgaaga tacgcgagct cgggctgggc 600
ataaaagtca gggcagagcc atctattgct tacatttgct tctgggatcc agatctttcg 660
aagctagcgc taccggtcgc caccatggtg agcaagggcg aggagctgtt caccggggtg 720
gtgcccatcc tggtcgagct ggacggcgac gtaaacggcc acaagttcag cgtgtccggc 780
gagggcgagg gcgatgccac ctacggcaag ctgaccctga agctgatctg caccaccggc 840
aagctgcccg tgccctggcc caccctcgtg accaccctgg gctacggcgt gcagtgcttc 900
gcccgctacc ccgaccacat gaagcagcac gacttcttca agtccgccat gcccgaaggc 960
tacgtccagg agcgcaccat cttcttcaag gacgacggca actacaagac ccgcgccgag 1020
gtgaagttcg agggcgacac cctggtgaac cgcatcgagc tgaagggcat cgacttcaag 1080
gaggacggca acatcctggg gcacaagctg gagtacaact acaacagcca caacgtctat 1140
atcaccgccg acaagcagaa gaacggcatc aaggccaact tcaagatccg ccacaacatc 1200
gaggacggcg gcgtgcagct cgccgaccac taccagcaga acacccccat cggcgacggc 1260
cccgtgctgc tgcccgacaa ccactacctg agctaccagt ccaagctgag caaagacccc 1320
aacgagaagc gcgatcacat ggtcctgctg gagttcgtga ccgccgccgg gatcactctc 1380
ggcatggacg agctgtacaa gtaagtcgac ggcgcgccgc ggccgcgaat tcgatatcat 1440
aatcaacctc tggattacaa aatttgtgaa agattgactg gtattcttaa ctatgttgct 1500
ccttttacgc tatgtggata cgctgcttta atgcctttgt atcatgctat tgcttcccgt 1560
atggctttca ttttctcctc cttgtataaa tcctggttag ttcttgccac ggcggaactc 1620
atcgccgcct gccttgcccg ctgctggaca ggggctcggc tgttgggcac tgacaattcc 1680
gtggctcgag agatcttcga ctgtgccttc tagttgccag ccatctgttg tttgcccctc 1740
ccccgtgcct tccttgaccc tggaaggtgc cactcccact gtcctttcct aataaaatga 1800
ggaaattgca tcgcattgtc tgagtaggtg tcattctatt ctggggggtg gggtggggca 1860
ggacagcaag ggggaggatt gggaagacaa tagcaggcat gcacgtgcgg accgagcggc 1920
cgc 1923

<210> SEQ ID NO 106
<211> LENGTH: 2070
<212> TYPE: DNA
<213> ORGANISM: Artificial Sequence
<220> FEATURE:
<223> OTHER INFORMATION: synthetic construct

<400> SEQUENCE: 106

```
gcggccgcac gcgtgtatgt gtgacaggag ccaggcagct gaggcagcgg gacaacagag     60
ccactggcct gactgggaag aatgtcccag acattgacaa aagacaatct agagagggta    120
aggatgggag accagggaca ccaaagagcc cactgggtcc ctgtggccag gcggggccca    180
gagcacatgg tgccagcctc gttccctatt aggcaaagca ctgcaccatc tgtatagtcc    240
caggagcagg agcaggagca ggcgttttat aacttccttt tctttttcag tctacattaa    300
aaataaatgt tcccttcagc tctcagatgt atatctctag tgcaacctgc ccacattccc    360
tcctgctgcc ctttccagaa catggcaggg gaagggaagg aagagatgga gagagggagc    420
cagtccaccc ggctgatgcc agtggatcac acctcttcta agagggaagc gcggcaggca    480
cggccacaca tggtggaagg tgcccagaat gcatggggac cagggaaatg gaagtggagg    540
aaatgggagc caacagccag gcttgcttcc cacccccacc ctcccgcacc gcaggacctt    600
ggccaaatca cacatcccat ctttgcattt atagttcatg cagtggctgg agtcccctct    660
gcagctccag ccctctggtg gctgtccttg ctgcacgtct ctctgtactt ccccttgtgt    720
gtcctgctgt gggagctcgg gctgggcata aaagtcaggg cagagccatc tattgcttac    780
atttgcttct gggatccaga tctttcgaag ctagcgctac cggtcgccac catggtgagc    840
aagggcgagg agctgttcac cggggtggtg cccatcctgg tcgagctgga cggcgacgta    900
aacggccaca agttcagcgt gtccggcgag ggcgagggcg atgccaccta cggcaagctg    960
accctgaagc tgatctgcac caccggcaag ctgcccgtgc cctggcccac cctcgtgacc   1020
accctgggct acggcgtgca gtgcttcgcc cgctaccccg accacatgaa gcagcacgac   1080
ttcttcaagt ccgccatgcc cgaaggctac gtccaggagc gcaccatctt cttcaaggac   1140
gacggcaact acaagacccg cgccgaggtg aagttcgagg gcgacaccct ggtgaaccgc   1200
atcgagctga agggcatcga cttcaaggag gacggcaaca tcctggggca caagctggag   1260
tacaactaca acagccacaa cgtctatatc accgccgaca agcagaagaa cggcatcaag   1320
gccaacttca agatccgcca caacatcgag gacggcggcg tgcagctcgc cgaccactac   1380
cagcagaaca cccccatcgg cgacggcccc gtgctgctgc ccgacaacca ctacctgagc   1440
taccagtcca agctgagcaa agaccccaac gagaagcgcg atcacatggt cctgctggag   1500
ttcgtgaccg ccgccgggat cactctcggc atggacgagc tgtacaagta agtcgacggc   1560
gcgccgcggc cgcgaattcg atatcataat caacctctgg attacaaaat ttgtgaaaga   1620
ttgactggta ttcttaacta tgttgctcct tttacgctat gtggatacgc tgctttaatg   1680
cctttgtatc atgctattgc ttcccgtatg gctttcattt tctcctcctt gtataaatcc   1740
tggttagttc ttgccacggc ggaactcatc gccgcctgcc ttgcccgctg ctggacaggg   1800
gctcggctgt tgggcactga caattccgtg gctcgagaga tcttcgactg tgccttctag   1860
ttgccagcca tctgttgttt gcccctcccc cgtgccttcc ttgaccctgg aaggtgccac   1920
tcccactgtc ctttcctaat aaaatgagga aattgcatcg cattgtctga gtaggtgtca   1980
ttctattctg gggggtgggg tggggcagga cagcaagggg gaggattggg aagacaatag   2040
caggcatgca cgtgcggacc gagcggccgc                                     2070
```

<210> SEQ ID NO 107
<211> LENGTH: 1872
<212> TYPE: DNA
<213> ORGANISM: Artificial Sequence
<220> FEATURE:
<223> OTHER INFORMATION: synthetic construct

<400> SEQUENCE: 107

-continued

```
gcggccgcac gcgtccctgg ccttcgagca catgctcaga tgatgctcca ccgtggcctg     60
acccacatct tctagtggaa gcatggtcca gcaaagcctt tctgttctaa aggaaaggat    120
ctgagttgtc acctcccagg tccgtggaag gctttttagc agtttggcag gtgcctgagg    180
gccacacctc atctgcataa aatgtggcag attgcaaccg ccctcgtctt ttttattttt    240
aaactggttt ttgaaacaga acatatataa aagctcagag aaagggaaag gagatagatg    300
gccgagcttc catatccctt agtgccttta ttttcattct ttttccattt tcctaagtgg    360
ctatttacca agacaaagat aacaaatctg ctaggaaaag gagtgggcag tgctacaaaa    420
tgtttttttt tttttaaaga aagtcctatc ttataataga tcttcaccac gatgcctcat    480
gatgtatgct caaatcagtt ttaattgaac tgtgtgtagt atgctcctgt tttggagctc    540
gggctgggca taaaagtcag ggcagagcca tctattgctt acatttgctt ctgggatcca    600
gatctttcga agctagcgct accggtcgcc accatggtga gcaagggcga ggagctgttc    660
accggggtgg tgcccatcct ggtcgagctg gacggcgacg taaacggcca caagttcagc    720
gtgtccggcg agggcgaggg cgatgccacc tacggcaagc tgaccctgaa gctgatctgc    780
accaccggca agctgcccgt gccctggccc accctcgtga ccaccctggg ctacggcgtg    840
cagtgcttcg cccgctaccc cgaccacatg aagcagcacg acttcttcaa gtccgccatg    900
cccgaaggct acgtccagga gcgcaccatc ttcttcaagg acgacggcaa ctacaagacc    960
cgcgccgagg tgaagttcga gggcgacacc ctggtgaacc gcatcgagct gaagggcatc   1020
gacttcaagg aggacggcaa catcctgggg cacaagctgg agtacaacta caacagccac   1080
aacgtctata tcaccgccga caagcagaag aacggcatca aggccaactt caagatccgc   1140
cacaacatcg aggacggcgg cgtgcagctc gccgaccact accagcagaa cacccccatc   1200
ggcgacggcc ccgtgctgct gcccgacaac cactacctga gctaccagtc caagctgagc   1260
aaagacccca acgagaagcg cgatcacatg gtcctgctgg agttcgtgac cgccgccggg   1320
atcactctcg gcatggacga gctgtacaag taagtcgacg gcgcgccgcg gccgcgaatt   1380
cgatatcata atcaacctct ggattacaaa atttgtgaaa gattgactgg tattcttaac   1440
tatgttgctc cttttacgct atgtggatac gctgctttaa tgcctttgta tcatgctatt   1500
gcttcccgta tggctttcat tttctcctcc ttgtataaat cctggttagt tcttgccacg   1560
gcggaactca tcgccgcctg ccttgcccgc tgctggacag gggctcggct gttgggcact   1620
gacaattccg tggctcgaga gatcttcgac tgtgccttct agttgccagc catctgttgt   1680
ttgcccctcc cccgtgcctt ccttgaccct ggaaggtgcc actcccactg tcctttccta   1740
ataaaatgag gaaattgcat cgcattgtct gagtaggtgt cattctattc tggggggtgg   1800
ggtggggcag gacagcaagg gggaggattg ggaagacaat agcaggcatg cacgtgcgga   1860
ccgagcggcc gc                                                       1872
```

<210> SEQ ID NO 108
<211> LENGTH: 2245
<212> TYPE: DNA
<213> ORGANISM: Artificial Sequence
<220> FEATURE:
<223> OTHER INFORMATION: synthetic construct

<400> SEQUENCE: 108

```
gcggccgcaa cgcgtttaga acaatggctg gcccatagta aatgccgtgt tagtgtgtta     60
gttgctgttc ttccacgtca gaagaggcac agacaaatta ccaccaggtg gcgctcagag    120
```

-continued

```
tctgcggagg catcacaaca gccctgaatt tgaatcctgc tctgccactg cctagttgag    180

accttttact acctgactag ctgtttgtgt attttaggtg tttgtttctt gcacgcttat    240

tcaggctttt ggcagaaatc agttcgttgt ggtttaagga ctgaggtcgc ctttctttgc    300

tgctaactgt tggccaggaa gtactgtcag ctactacatg gtacttgctg gtccttgcac    360

atgaccccct ccaccttcaa accaggattg acacagtgtg ttgagtcttt cttgaagact    420

tttgaacatc tgacttccca ttctgccact agccagttaa aattctctaa ttttgaagga    480

ctcacctggt tggccaaacc cacccaaata atctccacat cttgaagtca actgacccag    540

gactttacat atgcaaaatc ccttcacagc agtacctaga tgagtgtttg cttgaataac    600

tgggacacag gaatcttggg ggagccatct ttagaattcg acctcctaca acccttctgg    660

aaatctgaga gtgagtcagg ggaagaaacc ctcttttgta gtttcctttt agggctttct    720

actttgctca aagttgggca ctatttcact tcagtagggt cctgcaagcc ccatgagggt    780

agtgagtgct gtcctaggaa acagtaactt aaccctgata cccatttgtc caagaattcg    840

atatcataat caaccatagg taccgagctc gggattcagc cgggagctta gggaggggag    900

gtcacttcat aagggcctgg ggggggagtt ggagccacga gtcgtccagc cggagccccg    960

tgtggctgag ctccggcctc agaagcatcc ccgggttgga tccttcgaag ctagcgctac   1020

cggtcgccac catggtgagc aagggcgagg agctgttcac cggggtggtg cccatcctgg   1080

tcgagctgga cggcgacgta aacggccaca agttcagcgt gtccggcgag ggcgagggcg   1140

atgccaccta cggcaagctg accctgaagc tgatctgcac caccggcaag ctgcccgtgc   1200

cctggcccac cctcgtgacc accctgggct acggcgtgca gtgcttcgcc cgctaccccg   1260

accacatgaa gcagcacgac ttcttcaagt ccgccatgcc cgaaggctac gtccaggagc   1320

gcaccatctt cttcaaggac gacggcaact acaagacccg cgccgaggtg aagttcgagg   1380

gcgacaccct ggtgaaccgc atcgagctga agggcatcga cttcaaggag gacggcaaca   1440

tcctggggca caagctggag tacaactaca acagccacaa cgtctatatc accgccgaca   1500

agcagaagaa cggcatcaag gccaacttca agatccgcca caacatcgag gacggcggcg   1560

tgcagctcgc cgaccactac cagcagaaca cccccatcgg cgacggcccc gtgctgctgc   1620

ccgacaacca ctacctgagc taccagtcca agctgagcaa agaccccaac gagaagcgcg   1680

atcacatggt cctgctggag ttcgtgaccg ccgccgggat cactctcggc atggacgagc   1740

tgtacaagta agtcgacatc ataatcaacc tctggattac aaaatttgtg aaagattgac   1800

tggtattctt aactatgttg ctccttttac gctatgtgga tacgctgctt taatgccttt   1860

gtatcatgct attgcttccc gtatggcttt cattttctcc tccttgtata aatcctggtt   1920

agttcttgcc acggcggaac tcatcgccgc ctgccttgcc cgctgctgga caggggctcg   1980

gctgttgggc actgacaatt ccgtggctcg agagatcttc gactgtgcct tctagttgcc   2040

agccatctgt tgtttgcccc tcccccgtgc cttccttgac cctggaaggt gccactccca   2100

ctgtcctttc ctaataaaat gaggaaattg catcgcattg tctgagtagg tgtcattcta   2160

ttctgggggg tggggtgggg caggacagca agggggagga ttgggaagac aatagcaggc   2220

atgcacgtgc ggaccgagcg gccgc                                         2245
```

<210> SEQ ID NO 109
<211> LENGTH: 1839
<212> TYPE: DNA
<213> ORGANISM: Artificial Sequence
<220> FEATURE:
<223> OTHER INFORMATION: synthetic construct

<400> SEQUENCE: 109
gcggccgcac gcgtttaccc tgttgaatat cactgactca ctaacttgca ttgccatgct 60
aacttgcttt cagagagatc tcagaacaca tcatcttctg ctatttcaat acatgcacat 120
taatttccta tcaacgtgtg ctgatcagga actctgtaat ctggcaccgt taccctgttg 180
aatatcactg actcactaac ttgcattgcc atgctaactt gctttcagag agatctcaga 240
acacatcatc ttctgctatt tcaatacatg cacattaatt tcctatcaac gtgtgctgat 300
caggaactct gtaatctggc accgttaccc tgttgaatat cactgactca ctaacttgca 360
ttgccatgct aacttgcttt cagagagatc tcagaacaca tcatcttctg ctatttcaat 420
acatgcacat taatttccta tcaacgtgtg ctgatcagga actctgtaat ctggcaccgc 480
ttaaggagct cagaggtagg cgtgtacggt gggaggccta tataagcaga gctggtttag 540
tgaaccgtca gatcgcctgg ggatccagat ctttcgaagc tagcgctacc ggtcgccacc 600
atggtgagca agggcgagga gctgttcacc ggggtggtgc ccatcctggt cgagctggac 660
ggcgacgtaa acggccacaa gttcagcgtg tccggcgagg gcgagggcga tgccacctac 720
ggcaagctga ccctgaagct gatctgcacc accggcaagc tgcccgtgcc ctggcccacc 780
ctcgtgacca ccctgggcta cggcgtgcag tgcttcgccc gctaccccga ccacatgaag 840
cagcacgact tcttcaagtc cgccatgccc gaaggctacg tccaggagcg caccatcttc 900
ttcaaggacg acggcaacta caagacccgc gccgaggtga agttcgaggg cgacaccctg 960
gtgaaccgca tcgagctgaa gggcatcgac ttcaaggagg acggcaacat cctggggcac 1020
aagctggagt acaactacaa cagccacaac gtctatatca ccgccgacaa gcagaagaac 1080
ggcatcaagg ccaacttcaa gatccgccac aacatcgagg acggcggcgt gcagctcgcc 1140
gaccactacc agcagaacac ccccatcggc gacggccccg tgctgctgcc cgacaaccac 1200
tacctgagct accagtccaa gctgagcaaa gaccccaacg agaagcgcga tcacatggtc 1260
ctgctggagt tcgtgaccgc cgccgggatc actctcggca tggacgagct gtacaagtaa 1320
gtcgacggcg cgccgcggcc gcgaattcga tatcataatc aacctctgga ttacaaaatt 1380
tgtgaaagat tgactggtat tcttaactat gttgctcctt ttacgctatg tggatacgct 1440
gctttaatgc ctttgtatca tgctattgct tcccgtatgg ctttcatttt ctcctccttg 1500
tataaatcct ggttagttct tgccacggcg gaactcatcg ccgcctgcct tgcccgctgc 1560
tggacagggg ctcggctgtt gggcactgac aattccgtgg ctcgagagat cttcgactgt 1620
gccttctagt tgccagccat ctgttgtttg cccctccccc gtgccttcct tgaccctgga 1680
aggtgccact cccactgtcc tttcctaata aaatgaggaa attgcatcgc attgtctgag 1740
taggtgtcat tctattctgg ggggtggggt ggggcaggac agcaaggggg aggattggga 1800
agacaatagc aggcatgcac gtgcggaccg agcggccgc 1839

<210> SEQ ID NO 110
<211> LENGTH: 2619
<212> TYPE: DNA
<213> ORGANISM: Artificial Sequence
<220> FEATURE:
<223> OTHER INFORMATION: synthetic construct

<400> SEQUENCE: 110
gcggccgcaa cgcgtttaga acaatggctg gcccatagta aatgccgtgt tagtgtgtta 60
gttgctgttc ttccacgtca gaagaggcac agacaaatta ccaccaggtg gcgctcagag 120

-continued

```
tctgcggagg catcacaaca gccctgaatt tgaatcctgc tctgccactg cctagttgag     180
acctttttact acctgactag ctgtttgtgt attttaggtg tttgtttgaa aagatccggg    240
ttcacactaa tcaggcccaa cggaaggcca tattagcaat ttggcaggta cccgagggcc     300
atacctaatc tgcataaaat gaagcagatt gcaaccgccc tcatcttttt tatttttaaa     360
ctggtttttg aagcagagca taaaatctca gagggagaga cagaagatgc tagtgcatac     420
attttccttc atgcctttat tttcattctt tttgcacaaa ccatcttcct gaatggctgt     480
ttacctaaag aagaataaca aaataaaagg tgctaggaaa tggagtaggc agagatcgag     540
cagagccctc atcacacaga ctgaaaagat ccgggttcac actaatcagg cccaacggaa     600
ggccatatta gcaatttggc aggtacccga gggccatacc taatctgcat aaaatgaagc     660
agattgcaac cgccctcatc ttttttattt ttaaactggt ttttgaagca gagcataaaa     720
tctcagaggg agagacagaa gatgctagtg catacatttt ccttcatgcc tttattttca     780
ttctttttgc acaaaccatc ttcctgaatg gctgtttacc taaagaagaa taacaaaata     840
aaaggtgcta ggaaatggag taggcagaga tctgggtgag taagagtagg tggcaacgaa     900
aagatccggg ttcacactaa tcaggcccaa cggaaggcca tattagcaat ttggcaggta     960
cccgagggcc atacctaatc tgcataaaat gaagcagatt gcaaccgccc tcatcttttt    1020
tatttttaaa ctggtttttg aagcagagca taaaatctca gagggagaga cagaagatgc    1080
tagtgcatac attttccttc atgcctttat tttcattctt tttgcacaaa ccatcttcct    1140
gaatggctgt ttacctaaag aagaataaca aaataaaagg tgctaggaaa tggagtaggc    1200
agagatcgaa ttcgatatca taatcaacca taggtaccga gctcgggatt cagccgggag    1260
cttagggagg ggaggtcact tcataagggc ctgggggggg agttggagcc acgagtcgtc    1320
cagccggagc cccgtgtggc tgagctccgg cctcagaagc atccccgggt tggatccttc    1380
gaagctagcg ctaccggtcg ccaccatggt gagcaagggc gaggagctgt tcaccggggt    1440
ggtgcccatc ctggtcgagc tggacggcga cgtaaacggc cacaagttca gcgtgtccgg    1500
cgagggcgag ggcgatgcca cctacggcaa gctgaccctg aagctgatct gcaccaccgg    1560
caagctgccc gtgccctggc ccaccctcgt gaccaccctg ggctacggcg tgcagtgctt    1620
cgcccgctac cccgaccaca tgaagcagca cgacttcttc aagtccgcca tgcccgaagg    1680
ctacgtccag gagcgcacca tcttcttcaa ggacgacggc aactacaaga cccgcgccga    1740
ggtgaagttc gagggcgaca ccctggtgaa ccgcatcgag ctgaagggca tcgacttcaa    1800
ggaggacggc aacatcctgg ggcacaagct ggagtacaac tacaacagcc acaacgtcta    1860
tatcaccgcc gacaagcaga agaacggcat caaggccaac ttcaagatcc gccacaacat    1920
cgaggacggc ggcgtgcagc tcgccgacca ctaccagcag aacaccccca tcggcgacgg    1980
ccccgtgctg ctgcccgaca accactacct gagctaccag tccaagctga gcaaagaccc    2040
caacgagaag cgcgatcaca tggtcctgct ggagttcgtg accgccgccg ggatcactct    2100
cggcatggac gagctgtaca agtaagtcga catcataatc aacctctgga ttacaaaatt    2160
tgtgaaagat tgactggtat tcttaactat gttgctcctt ttacgctatg tggatacgct    2220
gctttaatgc ctttgtatca tgctattgct tcccgtatgg ctttcatttt ctcctccttg    2280
tataaatcct ggttagttct tgccacggcg gaactcatcg ccgcctgcct tgcccgctgc    2340
tggacagggg ctcggctgtt gggcactgac aattccgtgg ctcgagagat cttcgactgt    2400
gccttctagt tgccagccat ctgttgtttg cccctccccc gtgccttcct tgaccctgga    2460
aggtgccact cccactgtcc tttcctaata aaatgaggaa attgcatcgc attgtctgag    2520
```

taggtgtcat tctattctgg ggggtggggt ggggcaggac agcaaggggg aggattggga 2580
agacaatagc aggcatgcac gtgcggaccg agcggccgc 2619

<210> SEQ ID NO 111
<211> LENGTH: 2892
<212> TYPE: DNA
<213> ORGANISM: Artificial Sequence
<220> FEATURE:
<223> OTHER INFORMATION: synthetic construct

<400> SEQUENCE: 111
gcggccgcaa cgcgtttaga acaatggctg gcccatagta aatgccgtgt tagtgtgtta 60
gttgctgttc ttccacgtca gaagaggcac agacaaatta ccaccaggtg gcgctcagag 120
tctgcggagg catcacaaca gccctgaatt tgaatcctgc tctgccactg cctagttgag 180
accttttact acctgactag ctgtttgtgt attttaggtg tttgtttgaa gcatggtcca 240
gcaaagcctt tctgttctaa aggaaaggat ctgagttgtc acctcccagg tccgtggaag 300
gctttttagc agtttggcag gtgcctgagg gccacacctc atctgcataa aatgtggcag 360
attgcaaccg ccctcgtctt ttttattttt aaactggttt ttgaaacaga acatatataa 420
aagctcagag aaagggaaag gagatagatg gccgagcttc catatccctt agtgccttta 480
ttttcattct tttttccattt tcctaagtgg ctatttacca agacaaagat aacaaatctg 540
ctaggaaaag gagtgggcag tgctacaaaa tgtttttttt tttttaaaga aagtcctatc 600
ttataataga tcttcaccac gatgcctcga gcagagccct catcacacag actgaagcat 660
ggtccagcaa agcctttctg ttctaaagga aaggatctga gttgtcacct cccaggtccg 720
tggaaggctt tttagcagtt tggcaggtgc ctgagggcca cacctcatct gcataaaatg 780
tggcagattg caaccgccct cgtctttttt atttttaaac tggtttttga aacagaacat 840
atataaaagc tcagagaaag ggaaaggaga tagatggccg agcttccata tcccttagtg 900
cctttatttt cattcttttt ccattttcct aagtggctat ttaccaagac aaagataaca 960
aatctgctag gaaaaggagt gggcagtgct acaaaatgtt tttttttttt taaagaaagt 1020
cctatcttat aatagatctt caccacgatg cctctgggtg agtaagagta ggtggcaacg 1080
aagcatggtc cagcaaagcc tttctgttct aaaggaaagg atctgagttg tcacctccca 1140
ggtccgtgga aggcttttta gcagtttggc aggtgcctga gggccacacc tcatctgcat 1200
aaaatgtggc agattgcaac cgccctcgtc ttttttattt ttaaactggt ttttgaaaca 1260
gaacatatat aaaagctcag agaaagggaa aggagataga tggccgagct tccatatccc 1320
ttagtgcctt tattttcatt ctttttccat tttcctaagt ggctatttac caagacaaag 1380
ataacaaatc tgctaggaaa aggagtgggc agtgctacaa aatgtttttt tttttttaaa 1440
gaaagtccta tcttataata gatcttcacc acgatgcctc gaattcgata tcataatcaa 1500
ccataggtac cgagctcggg attcagccgg gagcttaggg aggggaggtc acttcataag 1560
ggcctggggg gggagttgga gccacgagtc gtccagccgg agccccgtgt ggctgagctc 1620
cggcctcaga agcatccccg ggttggatcc ttcgaagcta gcgctaccgg tcgccaccat 1680
ggtgagcaag ggcgaggagc tgttcaccgg ggtggtgccc atcctggtcg agctggacgg 1740
cgacgtaaac ggccacaagt tcagcgtgtc cggcgagggc gagggcgatg ccacctacgg 1800
caagctgacc ctgaagctga tctgcaccac cggcaagctg cccgtgccct ggcccaccct 1860
cgtgaccacc ctgggctacg gcgtgcagtg cttcgcccgc taccccgacc acatgaagca 1920

-continued

```
gcacgacttc ttcaagtccg ccatgcccga aggctacgtc caggagcgca ccatcttctt   1980
caaggacgac ggcaactaca agacccgcgc cgaggtgaag ttcgagggcg acaccctggt   2040
gaaccgcatc gagctgaagg gcatcgactt caaggaggac ggcaacatcc tggggcacaa   2100
gctggagtac aactacaaca gccacaacgt ctatatcacc gccgacaagc agaagaacgg   2160
catcaaggcc aacttcaaga tccgccacaa catcgaggac ggcggcgtgc agctcgccga   2220
ccactaccag cagaacaccc ccatcggcga cggccccgtg ctgctgcccg acaaccacta   2280
cctgagctac cagtccaagc tgagcaaaga ccccaacgag aagcgcgatc acatggtcct   2340
gctggagttc gtgaccgccg ccgggatcac tctcggcatg gacgagctgt acaagtaagt   2400
cgacatcata atcaacctct ggattacaaa atttgtgaaa gattgactgg tattcttaac   2460
tatgttgctc cttttacgct atgtggatac gctgctttaa tgcctttgta tcatgctatt   2520
gcttcccgta tggctttcat tttctcctcc ttgtataaat cctggttagt tcttgccacg   2580
gcggaactca tcgccgcctg ccttgcccgc tgctggacag gggctcggct gttgggcact   2640
gacaattccg tggctcgaga gatcttcgac tgtgccttct agttgccagc catctgttgt   2700
ttgcccctcc cccgtgcctt ccttgaccct ggaaggtgcc actcccactg tcctttccta   2760
ataaaatgag gaaattgcat cgcattgtct gagtaggtgt cattctattc tggggggtgg   2820
ggtggggcag gacagcaagg gggaggattg ggaagacaat agcaggcatg cacgtgcgga   2880
ccgagcggcc gc                                                        2892
```

<210> SEQ ID NO 112
<211> LENGTH: 1931
<212> TYPE: DNA
<213> ORGANISM: Artificial Sequence
<220> FEATURE:
<223> OTHER INFORMATION: synthetic construct

<400> SEQUENCE: 112

```
gcggccgcac gcgtcgcgta taagccttgg gggcaatcaa actattacat tgagtccttg     60
gatttgctac aaattacatt ttaaatgcaa tcattttata aaagcttcaa cactcacact    120
tggaagcgtt accctgttga atatcactga ctcactaact tgcattgcca tgctaacttg    180
ctttcagaga gatctcagaa cacatcatct tctgctattt caatacatgc acattaattt    240
cctatcaacg tgtgctgatc aggaactctg taatctggca ccggtgttta tttttattcc    300
tgtctattcc tgttggctca cgaaaagatt gtttgagcaa gtgttttatg gtgagttgta    360
tcatatgtac attgatttaa tctgcccaca ttcagttcta caagcggagc caaaaaaata    420
gagacaagca taattttcat tcaacatgag cccctcaatg caagccaagt acctcatctg    480
gtgctcagct aaagcaacag caatctgttc caccctggag acacaactgg ccacagaaaa    540
cttagtgaaa agaggcaatg ctatgcacag gacaaatgag ctcagaggta ggcgtgtacg    600
gtgggaggcc tatataagca gagctggttt agtgaaccgt cagatcgcct ggggatccag    660
atctttcgaa gctagcgcta ccggtcgcca ccatggtgag caagggcgag gagctgttca    720
ccggggtggt gcccatcctg gtcgagctgg acggcgacgt aaacggccac aagttcagcg    780
tgtccggcga gggcgagggc gatgccacct acggcaagct gaccctgaag ctgatctgca    840
ccaccggcaa gctgcccgtg ccctggccca ccctcgtgac caccctgggc tacggcgtgc    900
agtgcttcgc ccgctacccc gaccacatga agcagcacga cttcttcaag tccgccatgc    960
ccgaaggcta cgtccaggag cgcaccatct tcttcaagga cgacggcaac tacaagaccc   1020
gcgccgaggt gaagttcgag ggcgacaccc tggtgaaccg catcgagctg aagggcatcg   1080
```

acttcaagga ggacggcaac atcctggggc acaagctgga gtacaactac aacagccaca 1140
acgtctatat caccgccgac aagcagaaga acggcatcaa ggccaacttc aagatccgcc 1200
acaacatcga ggacggcggc gtgcagctcg ccgaccacta ccagcagaac acccccatcg 1260
gcgacggccc cgtgctgctg cccgacaacc actacctgag ctaccagtcc aagctgagca 1320
aagaccccaa cgagaagcgc gatcacatgg tcctgctgga gttcgtgacc gccgccggga 1380
tcactctcgg catggacgag ctgtacaagt aagtcgacgg cgcgccgcgg ccgcgaattc 1440
gatatcataa tcaacctctg gattacaaaa tttgtgaaag attgactggt attcttaact 1500
atgttgctcc ttttacgcta tgtggatacg ctgctttaat gcctttgtat catgctattg 1560
cttcccgtat ggctttcatt ttctcctcct tgtataaatc ctggttagtt cttgccacgg 1620
cggaactcat cgccgcctgc cttgcccgct gctggacagg ggctcggctg ttgggcactg 1680
acaattccgt ggctcgagag atcttcgact gtgccttcta gttgccagcc atctgttgtt 1740
tgcccctccc ccgtgccttc cttgaccctg gaaggtgcca ctcccactgt cctttcctaa 1800
taaaatgagg aaattgcatc gcattgtctg agtaggtgtc attctattct ggggggtggg 1860
gtggggcagg acagcaaggg ggaggattgg gaagacaata gcaggcatgc acgtgcggac 1920
cgagcggccg c 1931

<210> SEQ ID NO 113
<211> LENGTH: 1721
<212> TYPE: DNA
<213> ORGANISM: Artificial Sequence
<220> FEATURE:
<223> OTHER INFORMATION: synthetic construct

<400> SEQUENCE: 113
gcggccgcac gcgtaagcca atgacattag agaagtgttc aaacagtcag ctaaattcac 60
tgcacttctc aaccacagaa atattttcag gtgattctgt ttttgagaaa acgtgggaac 120
cacaggatct acaacacttc caggcaaaac tcaacagctc taataatagt gacagaagtg 180
aaagccaatt tggataaaat aagacattga ctcaaagtcc tctgagagat tttcaaaac 240 aaagtttaca aagctccttt tgccttttgg gaaatcacat tcttctttgc accttgactc 300
tttttctgaa tttctttctg tctgggagga tctccttaca gtgtttcttc tccatctgac 360
atcatgaaat gtgatacgag ctcgggctgg gcataaaagt cagggcagag ccatctattg 420
cttacatttg cttctgggat ccagatcttt cgaagctagc gctaccggtc gccaccatgg 480
tgagcaaggg cgaggagctg ttcaccgggg tggtgcccat cctggtcgag ctggacggcg 540
acgtaaacgg ccacaagttc agcgtgtccg gcgagggcga gggcgatgcc acctacggca 600
agctgaccct gaagctgatc tgcaccaccg gcaagctgcc cgtgccctgg cccaccctcg 660
tgaccaccct gggctacggc gtgcagtgct tcgcccgcta ccccgaccac atgaagcagc 720
acgacttctt caagtccgcc atgcccgaag gctacgtcca ggagcgcacc atcttcttca 780
aggacgacgg caactacaag acccgcgccg aggtgaagtt cgagggcgac accctggtga 840
accgcatcga gctgaagggc atcgacttca aggaggacgg caacatcctg gggcacaagc 900
tggagtacaa ctacaacagc cacaacgtct atatcaccgc cgacaagcag aagaacggca 960
tcaaggccaa cttcaagatc cgccacaaca tcgaggacgg cggcgtgcag ctcgccgacc 1020
actaccagca gaacaccccc atcggcgacg gccccgtgct gctgcccgac aaccactacc 1080
tgagctacca gtccaagctg agcaaagacc ccaacgagaa gcgcgatcac atggtcctgc 1140

```
tggagttcgt gaccgccgcc gggatcactc tcggcatgga cgagctgtac aagtaagtcg   1200
acggcgcgcc gcggccgcga attcgatatc ataatcaacc tctggattac aaaatttgtg   1260
aaagattgac tggtattctt aactatgttg ctccttttac gctatgtgga tacgctgctt   1320
taatgccttt gtatcatgct attgcttccc gtatggcttt cattttctcc tccttgtata   1380
aatcctggtt agttcttgcc acggcggaac tcatcgccgc ctgccttgcc cgctgctgga   1440
caggggctcg gctgttgggc actgacaatt ccgtggctcg agagatcttc gactgtgcct   1500
tctagttgcc agccatctgt tgtttgcccc tcccccgtgc cttccttgac cctggaaggt   1560
gccactccca ctgtcctttc ctaataaaat gaggaaattg catcgcattg tctgagtagg   1620
tgtcattcta ttctgggggg tggggtgggg caggacagca agggggagga ttgggaagac   1680
aatagcaggc atgagatctc acgtgcggac cgagcggccg c                         1721
```

<210> SEQ ID NO 114
<211> LENGTH: 1744
<212> TYPE: DNA
<213> ORGANISM: Artificial Sequence
<220> FEATURE:
<223> OTHER INFORMATION: synthetic construct

<400> SEQUENCE: 114

```
gcggccgcac gcgtaattgc tgtcatttac ctacggttgt ctccaaattt cttcaaccaa     60
gtagagaaaa atgagagaga aggaaagaaa aaaagaggta tggggagaag agaaagaagg    120
caacttgtta aaaatctcag tcaaacttac atactatata gaacagcatg gtgaatttag    180
ggcacatgga tataaaatgg aagtttctta ttcagtagca gcaacttgtg ggcacaggag    240
ttggcaaaga taaaaatgtc caaagtcaca aatacaatgt atagttagtc ataggtgctg    300
ttatttgcct caaaaaatag acttttattt tgcctttctt ttctttaacc acactcaaaa    360
ttagagaaca gagacaaaac ccagcaggaa atagcacaga gagctcgggc tgggcataaa    420
agtcagggca gagccatcta ttgcttacat ttgcttctgg gatccagatc tttcgaagct    480
agcgctaccg gtcgccacca tggtgagcaa gggcgaggag ctgttcaccg gggtggtgcc    540
catcctggtc gagctggacg gcgacgtaaa cggccacaag ttcagcgtgt ccggcgaggg    600
cgagggcgat gccacctacg gcaagctgac cctgaagctg atctgcacca ccggcaagct    660
gcccgtgccc tggcccaccc tcgtgaccac cctgggctac ggcgtgcagt gcttcgcccg    720
ctaccccgac cacatgaagc agcacgactt cttcaagtcc gccatgcccg aaggctacgt    780
ccaggagcgc accatcttct tcaaggacga cggcaactac aagacccgcg ccgaggtgaa    840
gttcgagggc gacaccctgg tgaaccgcat cgagctgaag ggcatcgact tcaaggagga    900
cggcaacatc ctggggcaca agctggagta caactacaac agccacaacg tctatatcac    960
cgccgacaag cagaagaacg gcatcaaggc caacttcaag atccgccaca acatcgagga   1020
cggcggcgtg cagctcgccg accactacca gcagaacacc cccatcggcg acggccccgt   1080
gctgctgccc gacaaccact acctgagcta ccagtccaag ctgagcaaag accccaacga   1140
gaagcgcgat cacatggtcc tgctggagtt cgtgaccgcc gccgggatca ctctcggcat   1200
ggacgagctg tacaagtaag tcgacggcgc gccgcggccg cgaattcgat atcataatca   1260
acctctggat tacaaaattt gtgaaagatt gactggtatt cttaactatg ttgctccttt   1320
tacgctatgt ggatacgctg ctttaatgcc tttgtatcat gctattgctt cccgtatggc   1380
tttcattttc tcctccttgt ataaatcctg gttagttctt gccacggcgg aactcatcgc   1440
cgcctgcctt gcccgctgct ggacaggggc tcggctgttg ggcactgaca attccgtggc   1500
```

```
tcgagagatc ttcgactgtg ccttctagtt gccagccatc tgttgtttgc ccctcccccg   1560

tgccttcctt gaccctggaa ggtgccactc ccactgtcct ttcctaataa aatgaggaaa   1620

ttgcatcgca ttgtctgagt aggtgtcatt ctattctggg gggtggggtg gggcaggaca   1680

gcaaggggga ggattgggaa gacaatagca ggcatgagat ctcacgtgcg gaccgagcgg   1740

ccgc                                                                1744


<210> SEQ ID NO 115
<211> LENGTH: 449
<212> TYPE: PRT
<213> ORGANISM: Artificial Sequence
<220> FEATURE:
<223> OTHER INFORMATION: Myosin light chain kinase, Green fluorescent
      protein, Calmodulin chimera
<220> FEATURE:
<221> NAME/KEY: misc_feature
<222> LOCATION: (223)..(223)
<223> OTHER INFORMATION: Xaa can be any naturally occurring amino acid

<400> SEQUENCE: 115

Met Arg Gly Ser His His His His His His Gly Met Ala Ser Met Thr
1               5                   10                  15

Gly Gly Gln Gln Met Gly Arg Asp Leu Tyr Asp Asp Asp Asp Lys Asp
            20                  25                  30

Leu Ala Thr Met Val Asp Ser Ser Arg Arg Lys Trp Asn Lys Thr Gly
        35                  40                  45

His Ala Val Arg Ala Ile Gly Arg Leu Ser Ser Leu Glu Asn Val Tyr
    50                  55                  60

Ile Met Ala Asp Lys Gln Lys Asn Gly Ile Lys Ala Asn Phe Lys Ile
65                  70                  75                  80

Arg His Asn Ile Glu Asp Gly Gly Val Gln Leu Ala Tyr His Tyr Gln
                85                  90                  95

Gln Asn Thr Pro Ile Gly Asp Gly Pro Val Leu Leu Pro Asp Asn His
            100                 105                 110

Tyr Leu Ser Thr Gln Ser Lys Leu Ser Lys Asp Pro Asn Glu Lys Arg
        115                 120                 125

Asp His Met Val Leu Leu Glu Phe Val Thr Ala Ala Gly Ile Thr Leu
    130                 135                 140

Gly Met Asp Glu Leu Tyr Lys Gly Gly Thr Gly Gly Ser Met Val Ser
145                 150                 155                 160

Lys Gly Glu Glu Leu Phe Thr Gly Val Val Pro Ile Leu Val Glu Leu
                165                 170                 175

Asp Gly Asp Val Asn Gly His Lys Phe Ser Val Ser Gly Glu Gly Glu
            180                 185                 190

Gly Asp Ala Thr Tyr Gly Lys Leu Thr Leu Lys Phe Ile Cys Thr Thr
        195                 200                 205

Gly Lys Leu Pro Val Pro Trp Pro Thr Leu Val Thr Thr Leu Xaa Val
    210                 215                 220

Gln Cys Phe Ser Arg Tyr Pro Asp His Met Lys Gln His Asp Phe Phe
225                 230                 235                 240

Lys Ser Ala Met Pro Glu Gly Tyr Ile Gln Glu Arg Thr Ile Phe Phe
                245                 250                 255

Lys Asp Asp Gly Asn Tyr Lys Thr Arg Ala Glu Val Lys Phe Glu Gly
            260                 265                 270

Asp Thr Leu Val Asn Arg Ile Glu Leu Lys Gly Ile Asp Phe Lys Glu
        275                 280                 285
```

Asp Gly Asn Ile Leu Gly His Lys Leu Glu Tyr Asn Thr Arg Asp Gln
    290                 295                 300

Leu Thr Glu Glu Gln Ile Ala Glu Phe Lys Glu Ala Phe Ser Leu Phe
305                 310                 315                 320

Asp Lys Asp Gly Asp Gly Gly Ile Thr Thr Lys Gln Leu Gly Thr Val
                325                 330                 335

Met Arg Ser Leu Gly Gln Asn Pro Thr Glu Ala Glu Leu Gln Asp Met
            340                 345                 350

Ile Asn Glu Val Gly Ala Asp Gly Asn Gly Thr Ile Asp Phe Pro Gln
        355                 360                 365

Phe Leu Thr Met Met Ala Arg Lys Met Lys Asp Thr Asp Ser Glu Glu
    370                 375                 380

Glu Ile Arg Glu Ala Phe Arg Val Phe Gly Lys Asp Gly Asn Gly Tyr
385                 390                 395                 400

Ile Ser Ala Ala Gln Leu Arg His Val Met Thr Asn Leu Gly Glu Lys
                405                 410                 415

Leu Thr Asp Glu Glu Val Asp Glu Met Ile Arg Glu Ala Gly Ile Asp
            420                 425                 430

Gly Asp Gly Gln Val Asn Tyr Glu Gln Phe Val Gln Met Met Thr Ala
        435                 440                 445

Lys

<210> SEQ ID NO 116
<211> LENGTH: 309
<212> TYPE: PRT
<213> ORGANISM: Artificial Sequence
<220> FEATURE:
<223> OTHER INFORMATION: Genetically-encoded green calcium indicator
      NTnC
<220> FEATURE:
<221> NAME/KEY: misc_feature
<222> LOCATION: (68)..(68)
<223> OTHER INFORMATION: Xaa can be any naturally occurring amino acid

<400> SEQUENCE: 116

Met Val Ser Lys Gly Glu Glu Asp Asn Met Ala Ser Leu Pro Ala Thr
1               5                   10                  15

His Glu Leu His Ile Phe Gly Ser Ile Asn Gly Val Asp Phe Asp Met
            20                  25                  30

Val Gly Gln Gly Ser Gly Asn Pro Asn Val Gly Tyr Glu Glu Leu Asn
        35                  40                  45

Leu Lys Ser Thr Lys Gly Asp Leu Gln Phe Ser Pro Trp Ile Leu Val
    50                  55                  60

Pro His Ile Xaa Phe His Gln Tyr Leu Pro Tyr Pro Asp Gly Met Ser
65                  70                  75                  80

Pro Phe Gln Ala Ala Met Val Asp Gly Ser Gly Tyr Gln Val His Arg
                85                  90                  95

Thr Val Gln Phe Glu Asp Gly Ala Ser Leu Thr Val Asn Tyr Arg Tyr
            100                 105                 110

Thr Tyr Glu Gly Ser His Ile Lys Gly Glu Ala Gln Val Lys Gly Thr
        115                 120                 125

Gly Phe Pro Ala Asp Gly Pro Val Met Ala Asn Ser Leu Thr Ala Met
    130                 135                 140

Val Pro Ser Glu Glu Glu Leu Ser Glu Cys Phe Arg Thr Phe Asp Lys
145                 150                 155                 160

Asp Gly Asp Gly Phe Ile Asp Arg Glu Glu Phe Gly Gly Ile Ile Arg

```
                165                 170                 175

Leu Thr Gly Glu Gln Leu Thr Asp Glu Asp Pro Asp Glu Ile Phe Gly
            180                 185                 190

Asp Ser Asp Thr Asp Lys Asn Gly Arg Ile Asp Phe Asp Glu Phe Leu
        195                 200                 205

Lys Met Val Glu Asn Val Gln Leu Ser Met Ala Asp Trp Cys Arg Ser
    210                 215                 220

Lys Met Ala Cys Pro Asn Asp Lys Thr Leu Ile Ser Thr Leu Lys Trp
225                 230                 235                 240

Ser Tyr Thr Thr Gly Asn Gly Lys Arg Tyr Arg Ser Thr Ala Arg Thr
                245                 250                 255

Thr Tyr Thr Phe Ala Lys Pro Met Ala Ala Asn Tyr Leu Lys Asn Gln
            260                 265                 270

Pro Met Tyr Val Phe Arg Lys Thr Glu Leu Lys His Ser Lys Thr Glu
        275                 280                 285

Leu Asn Phe Lys Glu Trp Gln Lys Ala Phe Thr Asp Val Met Gly Met
    290                 295                 300

Asp Glu Leu Tyr Lys
305


<210> SEQ ID NO 117
<211> LENGTH: 619
<212> TYPE: PRT
<213> ORGANISM: Artificial Sequence
<220> FEATURE:
<223> OTHER INFORMATION: Calcium indicator TN-XXL

<400> SEQUENCE: 117

Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Arg Gly
            20                  25                  30

Glu Gly Glu Gly Asp Ala Thr Asn Gly Lys Leu Thr Leu Lys Phe Ile
        35                  40                  45

Cys Thr Thr Gly Lys Leu Pro Val Pro Trp Pro Thr Leu Val Thr Thr
    50                  55                  60

Leu Thr Trp Gly Val Gln Cys Phe Ser Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Ile Ser His Asn Val Tyr Ile Thr Ala Asp Lys Gln Lys Asn
145                 150                 155                 160

Gly Ile Lys Ala His Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Lys Leu
        195                 200                 205

Ser Lys Asp Pro Asn Glu Lys Arg Asp His Met Val Leu Leu Glu Phe
```

```
    210                 215                 220

Val Thr Ala Ala Arg Met Leu Ser Glu Glu Glu Leu Ala Asn Cys Phe
225                 230                 235                 240

Arg Ile Phe Asp Lys Asp Ala Asn Gly Phe Ile Asp Ile Glu Glu Leu
                245                 250                 255

Gly Glu Ile Leu Arg Ala Thr Gly Glu His Val Thr Glu Glu Asp Ile
            260                 265                 270

Glu Asp Leu Met Lys Asp Ser Asp Lys Asn Asn Asp Gly Arg Ile Asp
        275                 280                 285

Phe Asp Glu Phe Leu Lys Met Met Glu Gly Val Gln Gly Thr Ser Glu
    290                 295                 300

Glu Glu Leu Ala Asn Cys Phe Arg Ile Phe Asp Lys Asp Ala Asn Gly
305                 310                 315                 320

Phe Ile Asp Ile Glu Glu Leu Gly Glu Ile Leu Arg Ala Thr Gly Glu
                325                 330                 335

His Val Thr Glu Glu Asp Ile Glu Asp Leu Met Lys Asp Ser Asp Lys
            340                 345                 350

Asn Asn Asp Gly Arg Ile Asp Phe Asp Glu Phe Leu Lys Met Met Glu
        355                 360                 365

Gly Val Gln Glu Leu Met Gly Gly Val Gln Leu Ala Asp His Tyr Gln
    370                 375                 380

Gln Asn Thr Pro Ile Gly Asp Gly Pro Val Leu Leu Pro Asp Asn His
385                 390                 395                 400

Tyr Leu Ser Tyr Gln Ser Lys Leu Ser Lys Asp Pro Asn Glu Lys Arg
                405                 410                 415

Asp His Met Val Leu Leu Glu Phe Val Thr Ala Ala Gly Ile Thr Leu
            420                 425                 430

Gly Met Asp Glu Leu Tyr Lys Gly Gly Thr Gly Gly Ser Met Val Ser
        435                 440                 445

Lys Gly Glu Glu Leu Phe Thr Gly Val Val Pro Ile Leu Val Glu Leu
    450                 455                 460

Asp Gly Asp Val Asn Gly His Lys Phe Ser Val Arg Gly Glu Gly Glu
465                 470                 475                 480

Gly Asp Ala Thr Asn Gly Lys Leu Thr Leu Lys Phe Ile Cys Thr Thr
                485                 490                 495

Gly Lys Leu Pro Val Pro Trp Pro Thr Leu Val Thr Thr Leu Gly Tyr
            500                 505                 510

Gly Leu Met Cys Phe Ala Arg Tyr Pro Asp His Met Lys Gln His Asp
        515                 520                 525

Phe Phe Lys Ser Ala Met Pro Glu Gly Tyr Val Gln Glu Arg Thr Ile
    530                 535                 540

Phe Phe Lys Asp Asp Gly Asn Tyr Lys Thr Arg Ala Glu Val Lys Phe
545                 550                 555                 560

Glu Gly Asp Thr Leu Val Asn Arg Ile Glu Leu Lys Gly Ile Asp Phe
                565                 570                 575

Lys Glu Asp Gly Asn Ile Leu Gly His Lys Leu Glu Tyr Asn Tyr Asn
            580                 585                 590

Ser His Asn Val Tyr Ile Met Ala Asp Lys Gln Lys Asn Gly Ile Lys
        595                 600                 605

Ala Asn Phe Lys Ile Arg His Asn Ile Glu Asp
    610                 615
```

<210> SEQ ID NO 118

<211> LENGTH: 730
<212> TYPE: PRT
<213> ORGANISM: Artificial Sequence
<220> FEATURE:
<223> OTHER INFORMATION: BRET-based auto-luminescent calcium indicator

<400> SEQUENCE: 118

```
Met Val Ser Lys Gly Glu Glu Leu Phe Thr Gly Val Val Pro Ile Leu
1               5                   10                  15

Val Glu Leu Asp Gly Asp Val Asn Gly His Lys Phe Ser Val Ser Gly
            20                  25                  30

Glu Gly Glu Gly Asp Ala Thr Tyr Gly Lys Leu Thr Leu Lys Leu Ile
        35                  40                  45

Cys Thr Thr Gly Lys Leu Pro Val Pro Trp Pro Thr Leu Val Thr Thr
    50                  55                  60

Leu Gly Tyr Gly Leu Gln Cys Phe Ala Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Gly
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Tyr Gln Ser Lys Leu
        195                 200                 205

Ser Lys Asp Pro Asn Glu Lys Arg Asp His Met Val Leu Leu Glu Phe
    210                 215                 220

Val Thr Ala Ala Gly Ile Thr Leu Gly Met Asp Glu Leu Tyr Lys Arg
225                 230                 235                 240

Met His Asp Gln Leu Thr Glu Glu Gln Ile Ala Glu Phe Lys Glu Ala
                245                 250                 255

Phe Ser Leu Phe Asp Lys Asp Gly Asp Gly Thr Ile Thr Thr Lys Glu
            260                 265                 270

Leu Gly Thr Val Met Arg Ser Leu Gly Gln Asn Pro Thr Glu Ala Glu
        275                 280                 285

Leu Gln Asp Met Ile Asn Glu Val Asp Ala Asp Gly Asn Gly Thr Ile
    290                 295                 300

Tyr Phe Pro Glu Phe Leu Thr Met Met Ala Arg Lys Met Lys Asp Thr
305                 310                 315                 320

Asp Ser Glu Glu Glu Ile Arg Glu Ala Phe Arg Val Phe Asp Lys Asp
                325                 330                 335

Gly Asn Gly Tyr Ile Ser Ala Ala Gln Leu Arg His Val Met Thr Asn
            340                 345                 350

Leu Gly Glu Lys Leu Thr Asp Glu Glu Val Asp Glu Met Ile Arg Glu
        355                 360                 365

Ala Asp Ile Asp Gly Asp Gly Gln Val Asn Tyr Glu Glu Phe Val Gln
    370                 375                 380
```

```
Met Met Thr Ala Lys Gly Gly Lys Arg Arg Trp Lys Lys Asn Phe Ile
385                 390                 395                 400

Ala Val Ser Ala Ala Asn Arg Phe Lys Lys Ile Ser Ser Ser Gly Ala
                405                 410                 415

Leu Glu Leu Met Thr Ser Lys Val Tyr Asp Pro Glu Gln Arg Lys Arg
            420                 425                 430

Met Ile Thr Gly Pro Gln Trp Trp Ala Arg Cys Lys Gln Met Asn Val
        435                 440                 445

Leu Asp Ser Phe Ile Asn Tyr Tyr Asp Ser Glu Lys His Ala Glu Asn
    450                 455                 460

Ala Val Ile Phe Leu His Gly Asn Ala Thr Ser Ser Tyr Leu Trp Arg
465                 470                 475                 480

His Val Val Pro His Ile Glu Pro Val Ala Arg Cys Ile Ile Pro Asp
                485                 490                 495

Leu Ile Gly Met Gly Lys Ser Gly Lys Ser Gly Asn Gly Ser Tyr Arg
            500                 505                 510

Leu Leu Asp His Tyr Lys Tyr Leu Thr Ala Trp Phe Glu Leu Leu Asn
        515                 520                 525

Leu Pro Lys Lys Ile Ile Phe Val Gly His Asp Trp Gly Ala Ala Leu
    530                 535                 540

Ala Phe His Tyr Ala Tyr Glu His Gln Asp Arg Ile Lys Ala Ile Val
545                 550                 555                 560

His Met Glu Ser Val Val Asp Val Ile Glu Ser Trp Asp Glu Trp Pro
                565                 570                 575

Asp Ile Glu Glu Asp Ile Ala Leu Ile Lys Ser Glu Glu Gly Glu Lys
            580                 585                 590

Met Val Leu Glu Asn Asn Phe Phe Val Glu Thr Val Leu Pro Ser Lys
        595                 600                 605

Ile Met Arg Lys Leu Glu Pro Glu Glu Phe Ala Ala Tyr Leu Glu Pro
    610                 615                 620

Phe Lys Glu Lys Gly Glu Val Arg Arg Pro Thr Leu Ser Trp Pro Arg
625                 630                 635                 640

Glu Ile Pro Leu Val Lys Gly Gly Lys Pro Asp Val Val Gln Ile Val
                645                 650                 655

Arg Asn Tyr Asn Ala Tyr Leu Arg Ala Ser Asp Asp Leu Pro Lys Leu
            660                 665                 670

Phe Ile Glu Ser Asp Pro Gly Phe Phe Ser Asn Ala Ile Val Glu Gly
        675                 680                 685

Ala Lys Lys Phe Pro Asn Thr Glu Phe Val Lys Val Lys Gly Leu His
    690                 695                 700

Phe Leu Gln Glu Asp Ala Pro Asp Glu Met Gly Lys Tyr Ile Lys Ser
705                 710                 715                 720

Phe Val Glu Arg Val Leu Lys Asn Glu Gln
                725                 730
```

<210> SEQ ID NO 119
<211> LENGTH: 568
<212> TYPE: PRT
<213> ORGANISM: Artificial Sequence
<220> FEATURE:
<223> OTHER INFORMATION: Calcium indicator protein OeNL(Ca2+)-18u

<400> SEQUENCE: 119

```
Met Val Ser Val Ile Lys Pro Glu Met Lys Met Arg Tyr Tyr Met Asp
1               5                   10                  15
```

-continued

```
Gly Ser Val Asn Gly His Glu Phe Thr Ile Glu Gly Glu Gly Thr Gly
            20                  25                  30

Arg Pro Tyr Glu Gly His Gln Glu Met Thr Leu Arg Val Thr Met Ala
        35                  40                  45

Glu Gly Gly Pro Met Pro Phe Ala Phe Asp Leu Val Ser His Val Phe
    50                  55                  60

Cys Tyr Gly His Arg Val Phe Thr Lys Tyr Pro Glu Glu Ile Pro Asp
65                  70                  75                  80

Tyr Phe Lys Gln Ala Phe Pro Glu Gly Leu Ser Trp Glu Arg Ser Leu
                85                  90                  95

Glu Phe Glu Asp Gly Gly Ser Ala Ser Val Ser Ala His Ile Ser Leu
            100                 105                 110

Arg Gly Asn Thr Phe Tyr His Lys Ser Lys Phe Thr Gly Val Asn Phe
        115                 120                 125

Pro Ala Asp Gly Pro Ile Met Gln Asn Gln Ser Val Asp Trp Glu Pro
    130                 135                 140

Ser Thr Glu Lys Ile Thr Ala Ser Asp Gly Val Leu Lys Gly Asp Val
145                 150                 155                 160

Thr Met Tyr Leu Lys Leu Glu Gly Gly Gly Asn His Lys Cys Gln Phe
                165                 170                 175

Lys Thr Thr Tyr Lys Ala Ala Lys Glu Ile Leu Glu Met Pro Gly Asp
            180                 185                 190

His Tyr Ile Gly His Arg Leu Val Arg Lys Thr Glu Gly Asn Ile Thr
        195                 200                 205

Glu Gln Val Glu Asp Ala Val Ala His Ser Gly Thr Leu Glu Asp Phe
    210                 215                 220

Val Gly Asp Trp Arg Gln Thr Ala Gly Tyr Asn Leu Asp Gln Val Leu
225                 230                 235                 240

Glu Gln Gly Gly Val Ser Ser Leu Phe Gln Asn Leu Gly Val Ser Val
                245                 250                 255

Thr Pro Ile Gln Arg Ile Val Leu Ser Gly Glu Asn Gly Leu Lys Ile
            260                 265                 270

Asp Ile His Val Ile Ile Pro Tyr Glu Gly Pro Trp Met His Asp Gln
        275                 280                 285

Leu Thr Glu Glu Gln Ile Ala Glu Phe Lys Glu Ala Phe Ser Leu Phe
    290                 295                 300

Asp Lys Asp Gly Asp Gly Thr Ile Thr Thr Lys Glu Leu Gly Thr Val
305                 310                 315                 320

Met Arg Ser Leu Gly Gln Asn Pro Thr Glu Ala Glu Leu Gln Asp Met
                325                 330                 335

Ile Asn Glu Val Asp Ala Asp Gly Asn Gly Thr Ile Tyr Phe Pro Asp
            340                 345                 350

Phe Leu Thr Met Met Ala Arg Lys Met Lys Asp Thr Asp Ser Glu Glu
        355                 360                 365

Glu Ile Arg Glu Ala Phe Arg Val Phe Asp Lys Asp Gly Asn Gly Tyr
    370                 375                 380

Ile Ser Ala Ala Asp Leu Arg His Val Met Thr Asn Leu Gly Glu Lys
385                 390                 395                 400

Leu Thr Asp Glu Glu Val Asp Glu Met Ile Arg Glu Ala Asp Ile Asp
                405                 410                 415

Gly Glu Gly Gln Val Asn Tyr Glu Glu Phe Val Gln Met Met Thr Ala
            420                 425                 430
```

```
Lys Gly Gly Lys Arg Arg Trp Lys Lys Asn Phe Ile Ala Val Ser Ala
        435                 440                 445

Ala Asn Arg Phe Lys Lys Ile Ser Ser Ser Gly Ala Leu Glu Leu Leu
    450                 455                 460

Ser Gly Asp Gln Met Gly Gln Ile Glu Lys Ile Phe Lys Val Val Tyr
465                 470                 475                 480

Pro Val Asp Asp His His Phe Lys Val Ile Leu His Tyr Gly Thr Leu
                485                 490                 495

Val Ile Asp Gly Val Thr Pro Asn Met Ile Asp Tyr Phe Gly Arg Pro
            500                 505                 510

Tyr Glu Gly Ile Ala Val Phe Asp Gly Lys Lys Ile Thr Val Thr Gly
        515                 520                 525

Thr Leu Trp Asn Gly Asn Lys Ile Ile Asp Glu Arg Leu Ile Asn Pro
    530                 535                 540

Asp Gly Ser Leu Leu Phe Arg Val Thr Ile Asn Gly Val Thr Gly Trp
545                 550                 555                 560

Arg Leu Cys Glu Arg Ile Leu Ala
                565
```

<210> SEQ ID NO 120
<211> LENGTH: 1353
<212> TYPE: DNA
<213> ORGANISM: Artificial Sequence
<220> FEATURE:
<223> OTHER INFORMATION: GCaMP6m

<400> SEQUENCE: 120

```
atgggttctc atcatcatca tcatcatggt atggctagca tgactggtgg acagcaaatg     60

ggtcgggatc tgtacgacga tgacgataag gatctcgcca ccatggtcga ctcatcacgt    120

cgtaagtgga ataagacagg tcacgcagtc agagctatag gtcggctgag ctcactcgag    180

aacgtctata tcaaggccga caagcagaag aacggcatca aggcgaactt caagatccgc    240

cacaacatcg aggacggcgg cgtgcagctc gcctaccact accagcagaa cacccccatc    300

ggcgacggcc ccgtgctgct gcccgacaac cactacctga gcgtgcagtc caaactttcg    360

aaagacccca acgagaagcg cgatcacatg gtcctgctgg agttcgtgac cgccgccggg    420

atcactctcg gcatggacga gctgtacaag ggcggtaccg gagggagcat ggtgagcaag    480

ggcgaggagc tgttcaccgg ggtggtgccc atcctggtcg agctggacgg cgacgtaaac    540

ggccacaagt tcagcgtgtc cggcgagggt gagggcgatg ccacctacgg caagctgacc    600

ctgaagttca tctgcaccac cggcaagctg cccgtgccct ggcccaccct cgtgaccacc    660

ctgacctacg gcgtgcagtg cttcagccgc taccccgacc acatgaagca gcacgacttc    720

ttcaagtccg ccatgcccga aggctacatc caggagcgca ccatcttctt caaggacgac    780

ggcaactaca agacccgcgc cgaggtgaag ttcgagggcg acaccctggt gaaccgcatc    840

gagctgaagg gcatcgactt caaggaggac ggcaacatcc tggggcacaa gctggagtac    900

aacctgccgg accaactgac tgaagagcag atcgcagaat ttaaagaggc tttctcccta    960

tttgacaagg acggggatgg gacaataaca accaaggagc tggggacggt gatgcggtct   1020

ctggggcaga accccacaga agcagagctg caggacatga tcaatgaagt agatgccgac   1080

ggtgacggca caatcgactt ccctgagttc ctgacaatga tggcaagaaa agggagctac   1140

agggacacgg aagaagaaat tagagaagcg ttcggtgtgt ttgataagga tggcaatggc   1200

tacatcagtg cagcagagct tcgccacgtg atgacaaacc ttggagagaa gttaacagat   1260
```

gaagaggttg atgaaatgat cagggaagca gacatcgatg gggatggtca ggtaaactac 1320
gaagagtttg tacaaatgat gacagcgaag tga 1353

<210> SEQ ID NO 121
<211> LENGTH: 1353
<212> TYPE: DNA
<213> ORGANISM: Artificial Sequence
<220> FEATURE:
<223> OTHER INFORMATION: GCaMP6s

<400> SEQUENCE: 121
atgggttctc atcatcatca tcatcatggt atggctagca tgactggtgg acagcaaatg 60
ggtcgggatc tgtacgacga tgacgataag gatctcgcca ccatggtcga ctcatcacgt 120
cgtaagtgga ataagacagg tcacgcagtc agagctatag gtcggctgag ctcactcgag 180
aacgtctata tcaaggccga caagcagaag aacggcatca aggcgaactt ccacatccgc 240
cacaacatcg aggacggcgg cgtgcagctc gcctaccact accagcagaa cacccccatc 300
ggcgacggcc ccgtgctgct gcccgacaac cactacctga gcgtgcagtc caaactttcg 360
aaagacccca acgagaagcg cgatcacatg gtcctgctgg agttcgtgac cgccgccggg 420
atcactctcg gcatggacga gctgtacaag ggcggtaccg gagggagcat ggtgagcaag 480
ggcgaggagc tgttcaccgg ggtggtgccc atcctggtcg agctggacgg cgacgtaaac 540
ggccacaagt tcagcgtgtc cggcgagggt gagggcgatg ccacctacgg caagctgacc 600
ctgaagttca tctgcaccac cggcaagctg cccgtgccct ggcccaccct cgtgaccacc 660
ctgacctacg gcgtgcagtg cttcagccgc taccccgacc acatgaagca gcacgacttc 720
ttcaagtccg ccatgcccga aggctacatc caggagcgca ccatcttctt caaggacgac 780
ggcaactaca agacccgcgc cgaggtgaag ttcgagggcg acaccctggt gaaccgcatc 840
gagctgaagg gcatcgactt caaggaggac ggcaacatcc tggggcacaa gctggagtac 900
aacctgccgg accaactgac tgaagagcag atcgcagaat ttaaagaggc tttctcccta 960
tttgacaagg acggggatgg gacaataaca accaaggagc tggggacggt gatgcggtct 1020
ctggggcaga accccacaga agcagagctg caggacatga tcaatgaagt agatgccgac 1080
ggtgacggca caatcgactt ccctgagttc ctgacaatga tggcaagaaa aatgaaatac 1140
agggacacgg aagaagaaat tagagaagcg ttcggtgtgt ttgataagga tggcaatggc 1200
tacatcagtg cagcagagct tcgccacgtg atgacaaacc ttggagagaa gttaacagat 1260
gaagaggttg atgaaatgat cagggaagca gacatcgatg gggatggtca ggtaaactac 1320
gaagagtttg tacaaatgat gacagcgaag tga 1353

<210> SEQ ID NO 122
<211> LENGTH: 1353
<212> TYPE: DNA
<213> ORGANISM: Artificial Sequence
<220> FEATURE:
<223> OTHER INFORMATION: GCaMP6f

<400> SEQUENCE: 122
atgggttctc atcatcatca tcatcatggt atggctagca tgactggtgg acagcaaatg 60
ggtcgggatc tgtacgacga tgacgataag gatctcgcca ccatggtcga ctcatcacgt 120
cgtaagtgga ataagacagg tcacgcagtc agagctatag gtcggctgag ctcactcgag 180
aacgtctata tcaaggccga caagcagaag aacggcatca aggcgaactt caagatccgc 240
cacaacatcg aggacggcgg cgtgcagctc gcctaccact accagcagaa cacccccatc 300

```
ggcgacggcc ccgtgctgct gcccgacaac cactacctga gcgtgcagtc caaactttcg    360

aaagacccca acgagaagcg cgatcacatg gtcctgctgg agttcgtgac cgccgccggg    420

atcactctcg gcatggacga gctgtacaag ggcggtaccg gagggagcat ggtgagcaag    480

ggcgaggagc tgttcaccgg ggtggtgccc atcctggtcg agctggacgg cgacgtaaac    540

ggccacaagt tcagcgtgtc cggcgagggt gagggcgatg ccacctacgg caagctgacc    600

ctgaagttca tctgcaccac cggcaagctg cccgtgccct ggcccaccct cgtgaccacc    660

ctgacctacg gcgtgcagtg cttcagccgc taccccgacc acatgaagca gcacgacttc    720

ttcaagtccg ccatgcccga aggctacatc caggagcgca ccatcttctt caaggacgac    780

ggcaactaca agacccgcgc cgaggtgaag ttcgagggcg acaccctggt gaaccgcatc    840

gagctgaagg gcatcgactt caaggaggac ggcaacatcc tggggcacaa gctggagtac    900

aacctgccgg accaactgac tgaagagcag atcgcagaat ttaaagagga attctcccta    960

tttgacaagg acggggatgg gacaataaca accaaggagc tggggacggt gatgcggtct   1020

ctggggcaga accccacaga agcagagctg caggacatga tcaatgaagt agatgccgac   1080

ggtgacggca caatcgactt ccctgagttc ctgacaatga tggcaagaaa aatgaaatac   1140

agggacacgg aagaagaaat tagagaagcg ttcggtgtgt ttgataagga tggcaatggc   1200

tacatcagtg cagcagagct tcgccacgtg atgacaaacc ttggagagaa gttaacagat   1260

gaagaggttg atgaaatgat cagggaagca gacatcgatg gggatggtca ggtaaactac   1320

gaagagtttg tacaaatgat gacagcgaag tga                                1353
```

<210> SEQ ID NO 123
<211> LENGTH: 593
<212> TYPE: PRT
<213> ORGANISM: Mesostigma viride

<400> SEQUENCE: 123

```
Met Ser Pro Pro Thr Ser Pro Thr Pro Asp Thr Gly His Asp Thr Pro
1               5                   10                  15

Asp Thr Gly His Asp Thr Gly Gly His Gly Ala Val Glu Ile Cys Phe
            20                  25                  30

Ala Pro Cys Glu Glu Asp Cys Val Thr Ile Arg Tyr Phe Val Glu Asn
        35                  40                  45

Asp Phe Glu Gly Cys Ile Pro Gly His Phe Asp Gln Tyr Ser Ser His
    50                  55                  60

Gly Ser Leu His Asp Ile Val Lys Ala Ala Leu Tyr Ile Cys Met Val
65                  70                  75                  80

Ile Ser Ile Leu Gln Ile Leu Phe Tyr Gly Phe Gln Trp Trp Arg Lys
                85                  90                  95

Thr Cys Gly Trp Glu Val Trp Phe Val Ala Cys Ile Glu Thr Ser Ile
            100                 105                 110

Tyr Ile Ile Ala Ile Thr Ser Glu Ala Asp Ser Pro Phe Thr Leu Tyr
        115                 120                 125

Leu Thr Asn Gly Gln Ile Ser Pro Gln Leu Arg Tyr Met Glu Trp Leu
    130                 135                 140

Met Thr Cys Pro Val Ile Leu Ile Ala Leu Ser Asn Ile Thr Gly Met
145                 150                 155                 160

Ala Glu Glu Tyr Asn Lys Arg Thr Met Thr Leu Leu Thr Ser Asp Val
                165                 170                 175

Cys Cys Ile Val Leu Gly Met Met Ser Ala Ala Ser Lys Pro Arg Leu
```

-continued

```
            180                 185                 190

Lys Gly Ile Leu Tyr Ala Val Gly Trp Ala Phe Gly Ala Trp Thr Tyr
        195                 200                 205

Trp Thr Ala Leu Gln Val Tyr Arg Asp Ala His Lys Ala Val Pro Lys
    210                 215                 220

Pro Leu Ala Trp Tyr Val Arg Ala Met Gly Tyr Val Phe Phe Thr Ser
225                 230                 235                 240

Trp Leu Thr Phe Pro Gly Trp Phe Leu Leu Gly Pro Glu Gly Leu Glu
                245                 250                 255

Val Val Thr Gly Thr Val Ser Thr Leu Met His Ala Cys Ser Asp Leu
            260                 265                 270

Ile Ser Lys Asn Leu Trp Gly Phe Met Asp Trp His Leu Arg Val Leu
        275                 280                 285

Val Ala Arg His His Arg Lys Leu Phe Lys Ala Glu Glu Glu His Ala
    290                 295                 300

Leu Lys Lys Gly Gln Thr Leu Glu Pro Gly Met Pro Arg Ser Thr Ser
305                 310                 315                 320

Phe Val Arg Gly Leu Gly Asp Asp Val Glu Ile Asp Pro Ser Tyr Glu
                325                 330                 335

Leu Tyr Arg Leu Lys Arg Gln Asn His Pro Glu Tyr Phe Leu Ser Pro
            340                 345                 350

Ala Gln Thr Pro Arg Arg Gly Pro Ser Phe Asp Lys Arg Thr Ser Phe
        355                 360                 365

Glu Met Asp Gly Gly Lys Asn Gly Met Leu Gln Met Met Pro Val Thr
    370                 375                 380

Gly Met Gly Met Gly Met Gly Met Gly Met Gly Gly Gly Lys Thr Val
385                 390                 395                 400

Leu Phe Leu Asp Tyr Thr Gly Gly Gly Tyr Val Ser Phe Phe Glu Gln
                405                 410                 415

Gln Leu Ser Asn Met Gly Val Asn Val Thr Lys Cys Trp Ser Asp Asp
            420                 425                 430

Asp Met Tyr Asn Thr Ala Gly Val Ala Asn Val Lys Gln Leu Phe His
        435                 440                 445

Phe Ala Met Ile Pro Asn Asn Ala Leu Gly Gly Gln Met Val Met Asp
    450                 455                 460

Leu Arg Gly Thr Gly Leu Leu Val Val Ala Tyr Gly Pro Glu Pro Pro
465                 470                 475                 480

Met Pro Gly Met Gly Gln Asp Glu Phe Val Pro Leu Gln Met Pro Gly
                485                 490                 495

Val Pro Tyr Asp Glu Ser Ile Leu His Asn Leu Val Met Arg His Ala
            500                 505                 510

Ile Thr Gln Gly Leu Gly Met Asn Gly Met Gln Gly Asn Met Gly Gln
        515                 520                 525

Gln Gln Gln Met Met Gly Met Gln Gly Asn Met Asn Gly Met Gln Gly
    530                 535                 540

Asn Met Asn Gly Met Gln Gly Asn Met Asn Gly Met Gln Gly Asn Met
545                 550                 555                 560

Ser Gly Met Gln Gly Asn Met Asn Gly Met Gln Gly Asn Ser Gly Met
                565                 570                 575

Asn Gln Gly Trp Asn Asn Gln Gly Phe Thr Asn Thr Gly Ala Phe Gly
            580                 585                 590

Tyr
```

<210> SEQ ID NO 124
<211> LENGTH: 717
<212> TYPE: PRT
<213> ORGANISM: Chlamydomonas yellowstonensis

<400> SEQUENCE: 124

```
Met Asp Thr Leu Ala Trp Val Ala Arg Glu Leu Leu Ser Ser Gly His
1               5                   10                  15

Gly Thr Asp Thr Ala Thr Asp Ser Gly His Gly Thr Asp Thr Ser Gly
            20                  25                  30

Gly His Asp Ser Ser His Asp Ala Val Ala His Asn Val Thr Leu Leu
        35                  40                  45

Ile Ala Pro Pro His Ala Gly Gly His Ala Gly Pro Thr Asp Thr Ser
    50                  55                  60

Gln Gln Ile Thr Gly Ile Asp Gly Trp Ile Ala Ile Pro Ala Gly Asp
65                  70                  75                  80

Cys Tyr Cys Ala Gly Trp Tyr Val Ser His Gly Ser Ser Phe Glu Ala
                85                  90                  95

Thr Phe Ala His Val Cys Gln Trp Ser Ile Phe Ala Val Cys Val Leu
            100                 105                 110

Ser Leu Leu Trp Tyr Ala Tyr Gln Tyr Trp Lys Ala Thr Cys Gly Trp
        115                 120                 125

Glu Glu Val Tyr Val Cys Cys Ile Glu Leu Val Phe Ile Cys Phe Glu
    130                 135                 140

Leu Tyr His Glu Phe Asp Ser Pro Cys Ser Leu Tyr Leu Ser Thr Ser
145                 150                 155                 160

Asn Val Val Asn Trp Leu Arg Tyr Ser Glu Trp Leu Leu Cys Cys Pro
                165                 170                 175

Val Ile Leu Ile His Leu Ser Asn Val Thr Gly Leu Ser Asp Asp Tyr
            180                 185                 190

Gly Arg Arg Thr Met Gly Leu Leu Val Ser Asp Ile Ala Thr Ile Val
        195                 200                 205

Phe Gly Val Thr Ala Ala Met Leu Val Asn Trp Pro Lys Ile Ile Phe
    210                 215                 220

Tyr Leu Ile Gly Phe Thr Met Cys Cys Tyr Thr Phe Phe Leu Ala Ala
225                 230                 235                 240

Lys Val Leu Ile Glu Ser Phe His Gln Val Pro Lys Gly Ile Cys Arg
                245                 250                 255

His Leu Val Lys Ala Met Ala Ile Thr Tyr Phe Val Gly Trp Ser Phe
            260                 265                 270

Phe Pro Leu Ile Phe Leu Phe Gly Gln Ser Gly Phe Lys Lys Ile Ser
        275                 280                 285

Pro Tyr Ala Asp Val Ile Ala Ser Ser Phe Gly Asp Leu Ile Ser Lys
    290                 295                 300

Asn Ala Phe Gly Met Leu Gly His Phe Leu Arg Val Lys Ile His Glu
305                 310                 315                 320

His Ile Leu Lys His Gly Asp Ile Arg Lys Thr Thr His Leu Arg Ile
                325                 330                 335

Ala Gly Glu Glu Lys Glu Val Glu Thr Phe Val Glu Glu Glu Asp Glu
            340                 345                 350

Asp Thr Ala Lys His Ser Thr Lys Glu Leu Ala Asn Arg Gly Ser Phe
        355                 360                 365

Ile Val Met Arg Asp Lys Met Lys Glu Gln Gly Ile Asp Val Arg Ala
    370                 375                 380
```

```
Ser Leu Asp Met Asp Glu Asp Glu Glu Ala Arg Thr Gly Lys Gly Lys
385                 390                 395                 400

Gly Ala Gly Ala Thr Ser Leu Val Pro Gly Arg Val Ile Leu Ala Val
                405                 410                 415

Pro Asp Ile Ser Met Val Asp Phe Phe His Asp His Phe Ala His Leu
            420                 425                 430

Gly Ala Ser Ile Glu Leu Val Pro Ala Leu Gly Val Glu Asn Thr Leu
        435                 440                 445

Leu Leu Val Gln Gln Ala Met Gln Leu Gly Gly Leu Asp Phe Val Leu
    450                 455                 460

Val His Pro Glu Phe Leu Arg Asp Arg Ser Gln Asn Gly Leu Val Ser
465                 470                 475                 480

Arg Leu Lys Met Thr Gly His Gly Val Cys Ala Phe Gly Trp Val Pro
                485                 490                 495

Ser Gly Pro Met Arg Glu Ile Ile Glu Ser Ala Gly Val Asp Gly Trp
            500                 505                 510

Leu Asp Gly Pro Ser Phe Gly Thr Gly Ile Asp Gln Glu Gln Leu Ile
        515                 520                 525

Glu Leu Ile Gly Tyr Met Gln Ala Lys Arg Lys Phe Gly Met Arg Phe
    530                 535                 540

Gly Gly Gly Gly Ala Ser Lys Ala Gly Tyr Ser Ser Asp Gly Gly Phe
545                 550                 555                 560

Gly Gly Lys Gly Met Leu Glu Met Gln Pro Ser Met Ser Gln Gly Ser
                565                 570                 575

Gly Val Pro Leu Leu Gln Gln Asn Asn Ser Met Met Arg Ala Pro Pro
            580                 585                 590

Ser Pro Met Gly Asn Met Ala Asn Asn Gly Met Met Asn Pro Met Met
        595                 600                 605

Ser Met Asn Asn Pro Met Met Gly Gly Gly Ala Val Met Met Thr Ser
    610                 615                 620

Met Gly Ser Met Gln Gln Ala Ala Asn Pro Leu Tyr Gly Ala Pro Pro
625                 630                 635                 640

Ser Pro Leu Ser Ser Gln Pro Gly Ala Gly Met Tyr Gly Ala Pro Ala
                645                 650                 655

Gln Pro Gln Met Gly Ser Gln Gly Ser Met His Gly Ser Met Tyr Gly
            660                 665                 670

Gly Ser Gln Gln Gln His Gln Gln Pro Gln Gln Ala Ala Ala Ala Pro
        675                 680                 685

Ala Ala Ala Asp Gly Gly Ser Glu Ala Glu Met Leu Lys Gln Leu Met
    690                 695                 700

Ser Glu Ile Asn Arg Leu Lys Ala Glu Leu Gly Glu Ser
705                 710                 715


<210> SEQ ID NO 125
<211> LENGTH: 747
<212> TYPE: PRT
<213> ORGANISM: Volvox carteri f. nagariensis

<400> SEQUENCE: 125

Met Asp His Pro Val Ala Arg Ser Leu Ile Gly Ser Ser Tyr Thr Asn
1               5                   10                  15

Leu Asn Asn Gly Ser Ile Val Ile Pro Ser Asp Ala Cys Phe Cys Met
            20                  25                  30

Lys Trp Leu Lys Ser Lys Gly Ser Pro Val Ala Leu Lys Met Ala Asn
```

```
        35                  40                  45

Ala Leu Gln Trp Ala Ala Phe Ala Leu Ser Val Ile Ile Leu Ile Tyr
    50                  55                  60

Tyr Ala Tyr Ala Thr Trp Arg Thr Thr Cys Gly Trp Glu Glu Val Tyr
65                  70                  75                  80

Val Cys Cys Val Glu Leu Thr Lys Val Val Ile Glu Phe Phe His Glu
                85                  90                  95

Phe Asp Glu Pro Gly Met Leu Tyr Leu Ala Asn Gly Asn Arg Val Leu
            100                 105                 110

Trp Leu Arg Tyr Gly Glu Trp Leu Leu Thr Cys Pro Val Ile Leu Ile
        115                 120                 125

His Leu Ser Asn Leu Thr Gly Leu Lys Asp Asp Tyr Asn Lys Arg Thr
    130                 135                 140

Met Arg Leu Leu Val Ser Asp Val Gly Thr Ile Val Trp Gly Ala Thr
145                 150                 155                 160

Ala Ala Met Ser Thr Gly Tyr Ile Lys Val Ile Phe Phe Leu Leu Gly
                165                 170                 175

Cys Met Tyr Gly Ala Asn Thr Phe Phe His Ala Ala Lys Val Tyr Ile
            180                 185                 190

Glu Ser Tyr His Thr Val Pro Lys Gly Leu Cys Arg Gln Leu Val Arg
        195                 200                 205

Ala Met Ala Trp Leu Phe Phe Val Ser Trp Gly Met Phe Pro Val Leu
    210                 215                 220

Phe Leu Leu Gly Pro Glu Gly Phe Gly His Leu Ser Val Tyr Gly Ser
225                 230                 235                 240

Thr Ile Gly His Thr Ile Ile Asp Leu Leu Ser Lys Asn Cys Trp Gly
                245                 250                 255

Leu Leu Gly His Phe Leu Arg Leu Lys Ile His Glu His Ile Leu Leu
            260                 265                 270

Tyr Gly Asp Ile Arg Lys Val Gln Lys Ile Arg Val Ala Gly Glu Glu
        275                 280                 285

Leu Glu Val Glu Thr Leu Met Thr Glu Glu Ala Pro Asp Thr Val Lys
    290                 295                 300

Lys Ser Thr Ala Gln Tyr Ala Asn Arg Glu Ser Phe Leu Thr Met Arg
305                 310                 315                 320

Asp Lys Leu Lys Glu Lys Gly Phe Glu Val Arg Ala Ser Leu Asp Asn
                325                 330                 335

Ser Gly Ile Asp Ala Val Ile Asn His Asn Asn Asn Tyr Asn Asn Ala
            340                 345                 350

Leu Ala Asn Ala Ala Ala Ala Val Gly Lys Pro Gly Met Glu Leu Ser
        355                 360                 365

Lys Leu Asp His Val Ala Ala Asn Ala Ala Gly Met Gly Gly Ile Ala
    370                 375                 380

Asp His Val Ala Thr Thr Ser Gly Ala Ile Ser Pro Gly Arg Val Ile
385                 390                 395                 400

Leu Ala Val Pro Asp Ile Ser Met Val Asp Tyr Phe Arg Glu Gln Phe
                405                 410                 415

Ala Gln Leu Pro Val Gln Tyr Glu Val Val Pro Ala Leu Gly Ala Asp
            420                 425                 430

Asn Ala Val Gln Leu Val Val Gln Ala Ala Gly Leu Gly Gly Cys Asp
        435                 440                 445

Phe Val Leu Leu His Pro Glu Phe Leu Arg Asp Lys Ser Ser Thr Ser
    450                 455                 460
```

```
Leu Pro Ala Arg Leu Arg Ser Ile Gly Gln Arg Val Ala Ala Phe Gly
465                 470                 475                 480

Trp Ser Pro Val Gly Pro Val Arg Asp Leu Ile Glu Ser Ala Gly Leu
                485                 490                 495

Asp Gly Trp Leu Glu Gly Pro Ser Phe Gly Leu Gly Ile Ser Leu Pro
            500                 505                 510

Asn Leu Ala Ser Leu Val Leu Arg Met Gln His Ala Arg Lys Met Ala
        515                 520                 525

Ala Met Leu Gly Gly Met Gly Gly Met Leu Gly Ser Asn Leu Met Ser
    530                 535                 540

Gly Ser Gly Gly Val Gly Leu Met Gly Ala Gly Ser Pro Gly Gly Gly
545                 550                 555                 560

Gly Gly Ala Met Gly Val Gly Met Thr Gly Met Gly Met Val Gly Thr
                565                 570                 575

Asn Ala Met Gly Arg Gly Ala Val Gly Asn Ser Val Ala Asn Ala Ser
            580                 585                 590

Met Gly Gly Gly Ser Ala Gly Met Gly Met Gly Met Met Gly Met Val
        595                 600                 605

Gly Ala Gly Val Gly Gly Gln Gln Gln Met Gly Ala Asn Gly Met Gly
    610                 615                 620

Pro Thr Ser Phe Gln Leu Gly Ser Asn Pro Leu Tyr Asn Thr Ala Pro
625                 630                 635                 640

Ser Pro Leu Ser Ser Gln Pro Gly Gly Asp Ala Ser Ala Ala Ala Ala
                645                 650                 655

Ala Ala Ala Ala Ala Ala Ala Thr Gly Ala Ala Ser Asn Ser Met Asn
            660                 665                 670

Ala Met Gln Ala Gly Gly Ser Val Arg Asn Ser Gly Ile Leu Ala Gly
        675                 680                 685

Gly Leu Gly Ser Met Met Gly Pro Pro Gly Ala Pro Ala Ala Pro Thr
    690                 695                 700

Ala Ala Ala Thr Ala Ala Pro Ala Val Thr Met Gly Ala Pro Gly Gly
705                 710                 715                 720

Gly Gly Ala Ala Ala Ser Glu Ala Glu Met Leu Gln Gln Leu Met Ala
                725                 730                 735

Glu Ile Asn Arg Leu Lys Ser Glu Leu Gly Glu
            740                 745


<210> SEQ ID NO 126
<211> LENGTH: 310
<212> TYPE: PRT
<213> ORGANISM: Artificial Sequence
<220> FEATURE:
<223> OTHER INFORMATION: Channel rhodopsin 2

<400> SEQUENCE: 126

Met Asp Tyr Gly Gly Ala Leu Ser Ala Val Gly Arg Glu Leu Leu Phe
1               5                   10                  15

Val Thr Asn Pro Val Val Val Asn Gly Ser Val Leu Val Pro Glu Asp
            20                  25                  30

Gln Cys Tyr Cys Ala Gly Trp Ile Glu Ser Arg Gly Thr Asn Gly Ala
        35                  40                  45

Gln Thr Ala Ser Asn Val Leu Gln Trp Leu Ala Ala Gly Phe Ser Ile
    50                  55                  60

Leu Leu Leu Met Phe Tyr Ala Tyr Gln Thr Trp Lys Ser Thr Cys Gly
65                  70                  75                  80
```

```
Trp Glu Glu Ile Tyr Val Cys Ala Ile Glu Met Val Lys Val Ile Leu
                85                  90                  95

Glu Phe Phe Phe Glu Phe Lys Asn Pro Ser Met Leu Tyr Leu Ala Thr
            100                 105                 110

Gly His Arg Val Gln Trp Leu Arg Tyr Ala Glu Trp Leu Leu Thr Cys
        115                 120                 125

Pro Val Ile Leu Ile His Leu Ser Asn Leu Thr Gly Leu Ser Asn Asp
    130                 135                 140

Tyr Ser Arg Arg Thr Met Gly Leu Leu Val Ser Asp Ile Gly Thr Ile
145                 150                 155                 160

Val Trp Gly Ala Thr Ser Ala Met Ala Thr Gly Tyr Val Lys Val Ile
                165                 170                 175

Phe Phe Cys Leu Gly Leu Cys Tyr Gly Ala Asn Thr Phe Phe His Ala
            180                 185                 190

Ala Lys Ala Tyr Ile Glu Gly Tyr His Thr Val Pro Lys Gly Arg Cys
        195                 200                 205

Arg Gln Val Val Thr Gly Met Ala Trp Leu Phe Phe Val Ser Trp Gly
    210                 215                 220

Met Phe Pro Ile Leu Phe Ile Leu Gly Pro Glu Gly Phe Gly Val Leu
225                 230                 235                 240

Ser Val Tyr Gly Ser Thr Val Gly His Thr Ile Ile Asp Leu Met Ser
                245                 250                 255

Lys Asn Cys Trp Gly Leu Leu Gly His Tyr Leu Arg Val Leu Ile His
            260                 265                 270

Glu His Ile Leu Ile His Gly Asp Ile Arg Lys Thr Thr Lys Leu Asn
        275                 280                 285

Ile Gly Gly Thr Glu Ile Glu Val Glu Thr Leu Val Glu Asp Glu Ala
    290                 295                 300

Glu Ala Gly Ala Val Pro
305                 310


<210> SEQ ID NO 127
<211> LENGTH: 282
<212> TYPE: PRT
<213> ORGANISM: Streptococcus pyogenes

<400> SEQUENCE: 127

Met Leu Glu His Lys Ile Asp Phe Met Val Thr Leu Glu Val Lys Glu
1               5                   10                  15

Ala Asn Ala Asn Gly Asp Pro Leu Asn Gly Asn Met Pro Arg Thr Asp
            20                  25                  30

Ala Lys Gly Tyr Gly Val Met Ser Asp Val Ser Ile Lys Arg Lys Ile
        35                  40                  45

Arg Asn Arg Leu Gln Asp Met Gly Lys Ser Ile Phe Val Gln Ala Asn
    50                  55                  60

Glu Arg Ile Glu Asp Asp Phe Arg Ser Leu Glu Lys Arg Phe Ser Gln
65                  70                  75                  80

His Phe Thr Ala Lys Thr Pro Asp Lys Glu Ile Glu Glu Lys Ala Asn
                85                  90                  95

Ala Leu Trp Phe Asp Val Arg Ala Phe Gly Gln Val Phe Thr Tyr Leu
            100                 105                 110

Lys Lys Ser Ile Gly Val Arg Gly Pro Val Ser Ile Ser Met Ala Lys
        115                 120                 125

Ser Leu Glu Pro Ile Val Ile Ser Ser Leu Gln Ile Thr Arg Ser Thr
```

```
    130                 135                 140

Asn Gly Met Glu Ala Lys Asn Asn Ser Gly Arg Ser Ser Asp Thr Met
145                 150                 155                 160

Gly Thr Lys His Phe Val Asp Tyr Gly Val Tyr Val Leu Lys Gly Ser
                165                 170                 175

Ile Asn Ala Tyr Phe Ala Glu Lys Thr Gly Phe Ser Gln Glu Asp Ala
            180                 185                 190

Glu Ala Ile Lys Glu Val Leu Val Ser Leu Phe Glu Asn Asp Ala Ser
        195                 200                 205

Ser Ala Arg Pro Glu Gly Ser Met Arg Val Cys Glu Val Phe Trp Phe
    210                 215                 220

Thr His Ser Ser Lys Leu Gly Asn Val Ser Ser Ala Arg Val Phe Asp
225                 230                 235                 240

Leu Leu Glu Tyr His Gln Ser Ile Glu Glu Lys Ser Thr Tyr Asp Ala
                245                 250                 255

Tyr Gln Ile His Leu Asn Gln Glu Lys Leu Ala Lys Tyr Glu Ala Lys
            260                 265                 270

Gly Leu Thr Leu Glu Ile Leu Glu Gly Leu
        275                 280


<210> SEQ ID NO 128
<211> LENGTH: 1368
<212> TYPE: PRT
<213> ORGANISM: Artificial Sequence
<220> FEATURE:
<223> OTHER INFORMATION: Cas9

<400> SEQUENCE: 128

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
```

-continued

```
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640
```

```
His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050
```

```
Asn Gly  Glu Ile Arg Lys Arg  Pro Leu Ile Glu Thr  Asn Gly Glu
    1055                 1060                 1065

Thr Gly  Glu Ile Val Trp Asp  Lys Gly Arg Asp Phe  Ala Thr Val
    1070                 1075                 1080

Arg Lys  Val Leu Ser Met Pro  Gln Val Asn Ile Val  Lys Lys Thr
    1085                 1090                 1095

Glu Val  Gln Thr Gly Gly Phe  Ser Lys Glu Ser Ile  Leu Pro Lys
    1100                 1105                 1110

Arg Asn  Ser Asp Lys Leu Ile  Ala Arg Lys Lys Asp  Trp Asp Pro
    1115                 1120                 1125

Lys Lys  Tyr Gly Gly Phe Asp  Ser Pro Thr Val Ala  Tyr Ser Val
    1130                 1135                 1140

Leu Val  Val Ala Lys Val Glu  Lys Gly Lys Ser Lys  Lys Leu Lys
    1145                 1150                 1155

Ser Val  Lys Glu Leu Leu Gly  Ile Thr Ile Met Glu  Arg Ser Ser
    1160                 1165                 1170

Phe Glu  Lys Asn Pro Ile Asp  Phe Leu Glu Ala Lys  Gly Tyr Lys
    1175                 1180                 1185

Glu Val  Lys Lys Asp Leu Ile  Ile Lys Leu Pro Lys  Tyr Ser Leu
    1190                 1195                 1200

Phe Glu  Leu Glu Asn Gly Arg  Lys Arg Met Leu Ala  Ser Ala Gly
    1205                 1210                 1215

Glu Leu  Gln Lys Gly Asn Glu  Leu Ala Leu Pro Ser  Lys Tyr Val
    1220                 1225                 1230

Asn Phe  Leu Tyr Leu Ala Ser  His Tyr Glu Lys Leu  Lys Gly Ser
    1235                 1240                 1245

Pro Glu  Asp Asn Glu Gln Lys  Gln Leu Phe Val Glu  Gln His Lys
    1250                 1255                 1260

His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350

Gly Leu  Tyr Glu Thr Arg Ile  Asp Leu Ser Gln Leu  Gly Gly Asp
    1355                 1360                 1365
```

<210> SEQ ID NO 129
<211> LENGTH: 1307
<212> TYPE: PRT
<213> ORGANISM: Acidaminococcus sp.

<400> SEQUENCE: 129

```
Met Thr Gln Phe Glu Gly Phe Thr Asn Leu Tyr Gln Val Ser Lys Thr
1               5                   10                  15

Leu Arg Phe Glu Leu Ile Pro Gln Gly Lys Thr Leu Lys His Ile Gln
            20                  25                  30

Glu Gln Gly Phe Ile Glu Glu Asp Lys Ala Arg Asn Asp His Tyr Lys
        35                  40                  45
```

```
Glu Leu Lys Pro Ile Ile Asp Arg Ile Tyr Lys Thr Tyr Ala Asp Gln
    50                  55                  60

Cys Leu Gln Leu Val Gln Leu Asp Trp Glu Asn Leu Ser Ala Ala Ile
65                  70                  75                  80

Asp Ser Tyr Arg Lys Glu Lys Thr Glu Glu Thr Arg Asn Ala Leu Ile
                85                  90                  95

Glu Glu Gln Ala Thr Tyr Arg Asn Ala Ile His Asp Tyr Phe Ile Gly
            100                 105                 110

Arg Thr Asp Asn Leu Thr Asp Ala Ile Asn Lys Arg His Ala Glu Ile
        115                 120                 125

Tyr Lys Gly Leu Phe Lys Ala Glu Leu Phe Asn Gly Lys Val Leu Lys
    130                 135                 140

Gln Leu Gly Thr Val Thr Thr Thr Glu His Glu Asn Ala Leu Leu Arg
145                 150                 155                 160

Ser Phe Asp Lys Phe Thr Thr Tyr Phe Ser Gly Phe Tyr Glu Asn Arg
                165                 170                 175

Lys Asn Val Phe Ser Ala Glu Asp Ile Ser Thr Ala Ile Pro His Arg
            180                 185                 190

Ile Val Gln Asp Asn Phe Pro Lys Phe Lys Glu Asn Cys His Ile Phe
        195                 200                 205

Thr Arg Leu Ile Thr Ala Val Pro Ser Leu Arg Glu His Phe Glu Asn
    210                 215                 220

Val Lys Lys Ala Ile Gly Ile Phe Val Ser Thr Ser Ile Glu Glu Val
225                 230                 235                 240

Phe Ser Phe Pro Phe Tyr Asn Gln Leu Leu Thr Gln Thr Gln Ile Asp
                245                 250                 255

Leu Tyr Asn Gln Leu Leu Gly Gly Ile Ser Arg Glu Ala Gly Thr Glu
            260                 265                 270

Lys Ile Lys Gly Leu Asn Glu Val Leu Asn Leu Ala Ile Gln Lys Asn
        275                 280                 285

Asp Glu Thr Ala His Ile Ile Ala Ser Leu Pro His Arg Phe Ile Pro
    290                 295                 300

Leu Phe Lys Gln Ile Leu Ser Asp Arg Asn Thr Leu Ser Phe Ile Leu
305                 310                 315                 320

Glu Glu Phe Lys Ser Asp Glu Glu Val Ile Gln Ser Phe Cys Lys Tyr
                325                 330                 335

Lys Thr Leu Leu Arg Asn Glu Asn Val Leu Glu Thr Ala Glu Ala Leu
            340                 345                 350

Phe Asn Glu Leu Asn Ser Ile Asp Leu Thr His Ile Phe Ile Ser His
        355                 360                 365

Lys Lys Leu Glu Thr Ile Ser Ser Ala Leu Cys Asp His Trp Asp Thr
    370                 375                 380

Leu Arg Asn Ala Leu Tyr Glu Arg Arg Ile Ser Glu Leu Thr Gly Lys
385                 390                 395                 400

Ile Thr Lys Ser Ala Lys Glu Lys Val Gln Arg Ser Leu Lys His Glu
                405                 410                 415

Asp Ile Asn Leu Gln Glu Ile Ile Ser Ala Ala Gly Lys Glu Leu Ser
            420                 425                 430

Glu Ala Phe Lys Gln Lys Thr Ser Glu Ile Leu Ser His Ala His Ala
        435                 440                 445

Ala Leu Asp Gln Pro Leu Pro Thr Thr Leu Lys Lys Gln Glu Glu Lys
    450                 455                 460
```

-continued

```
Glu Ile Leu Lys Ser Gln Leu Asp Ser Leu Leu Gly Leu Tyr His Leu
465                 470                 475                 480

Leu Asp Trp Phe Ala Val Asp Glu Ser Asn Glu Val Asp Pro Glu Phe
                485                 490                 495

Ser Ala Arg Leu Thr Gly Ile Lys Leu Glu Met Glu Pro Ser Leu Ser
            500                 505                 510

Phe Tyr Asn Lys Ala Arg Asn Tyr Ala Thr Lys Lys Pro Tyr Ser Val
        515                 520                 525

Glu Lys Phe Lys Leu Asn Phe Gln Met Pro Thr Leu Ala Ser Gly Trp
    530                 535                 540

Asp Val Asn Lys Glu Lys Asn Asn Gly Ala Ile Leu Phe Val Lys Asn
545                 550                 555                 560

Gly Leu Tyr Tyr Leu Gly Ile Met Pro Lys Gln Lys Gly Arg Tyr Lys
                565                 570                 575

Ala Leu Ser Phe Glu Pro Thr Glu Lys Thr Ser Glu Gly Phe Asp Lys
            580                 585                 590

Met Tyr Tyr Asp Tyr Phe Pro Asp Ala Ala Lys Met Ile Pro Lys Cys
        595                 600                 605

Ser Thr Gln Leu Lys Ala Val Thr Ala His Phe Gln Thr His Thr Thr
    610                 615                 620

Pro Ile Leu Leu Ser Asn Asn Phe Ile Glu Pro Leu Glu Ile Thr Lys
625                 630                 635                 640

Glu Ile Tyr Asp Leu Asn Asn Pro Glu Lys Glu Pro Lys Lys Phe Gln
                645                 650                 655

Thr Ala Tyr Ala Lys Lys Thr Gly Asp Gln Lys Gly Tyr Arg Glu Ala
            660                 665                 670

Leu Cys Lys Trp Ile Asp Phe Thr Arg Asp Phe Leu Ser Lys Tyr Thr
        675                 680                 685

Lys Thr Thr Ser Ile Asp Leu Ser Ser Leu Arg Pro Ser Ser Gln Tyr
    690                 695                 700

Lys Asp Leu Gly Glu Tyr Tyr Ala Glu Leu Asn Pro Leu Leu Tyr His
705                 710                 715                 720

Ile Ser Phe Gln Arg Ile Ala Glu Lys Glu Ile Met Asp Ala Val Glu
                725                 730                 735

Thr Gly Lys Leu Tyr Leu Phe Gln Ile Tyr Asn Lys Asp Phe Ala Lys
            740                 745                 750

Gly His His Gly Lys Pro Asn Leu His Thr Leu Tyr Trp Thr Gly Leu
        755                 760                 765

Phe Ser Pro Glu Asn Leu Ala Lys Thr Ser Ile Lys Leu Asn Gly Gln
    770                 775                 780

Ala Glu Leu Phe Tyr Arg Pro Lys Ser Arg Met Lys Arg Met Ala His
785                 790                 795                 800

Arg Leu Gly Glu Lys Met Leu Asn Lys Lys Leu Lys Asp Gln Lys Thr
                805                 810                 815

Pro Ile Pro Asp Thr Leu Tyr Gln Glu Leu Tyr Asp Tyr Val Asn His
            820                 825                 830

Arg Leu Ser His Asp Leu Ser Asp Glu Ala Arg Ala Leu Leu Pro Asn
        835                 840                 845

Val Ile Thr Lys Glu Val Ser His Glu Ile Ile Lys Asp Arg Arg Phe
    850                 855                 860

Thr Ser Asp Lys Phe Phe Phe His Val Pro Ile Thr Leu Asn Tyr Gln
865                 870                 875                 880

Ala Ala Asn Ser Pro Ser Lys Phe Asn Gln Arg Val Asn Ala Tyr Leu
```

```
                885                 890                 895

Lys Glu His Pro Glu Thr Pro Ile Ile Gly Ile Asp Arg Gly Glu Arg
            900                 905                 910

Asn Leu Ile Tyr Ile Thr Val Ile Asp Ser Thr Gly Lys Ile Leu Glu
        915                 920                 925

Gln Arg Ser Leu Asn Thr Ile Gln Gln Phe Asp Tyr Gln Lys Lys Leu
    930                 935                 940

Asp Asn Arg Glu Lys Glu Arg Val Ala Ala Arg Gln Ala Trp Ser Val
945                 950                 955                 960

Val Gly Thr Ile Lys Asp Leu Lys Gln Gly Tyr Leu Ser Gln Val Ile
                965                 970                 975

His Glu Ile Val Asp Leu Met Ile His Tyr Gln Ala Val Val Val Leu
            980                 985                 990

Glu Asn Leu Asn Phe Gly Phe Lys  Ser Lys Arg Thr Gly  Ile Ala Glu
        995                 1000                1005

Lys Ala  Val Tyr Gln Gln Phe  Glu Lys Met Leu Ile  Asp Lys Leu
    1010                1015                1020

Asn Cys  Leu Val Leu Lys Asp  Tyr Pro Ala Glu Lys  Val Gly Gly
    1025                1030                1035

Val Leu  Asn Pro Tyr Gln Leu  Thr Asp Gln Phe Thr  Ser Phe Ala
    1040                1045                1050

Lys Met  Gly Thr Gln Ser Gly  Phe Leu Phe Tyr Val  Pro Ala Pro
    1055                1060                1065

Tyr Thr  Ser Lys Ile Asp Pro  Leu Thr Gly Phe Val  Asp Pro Phe
    1070                1075                1080

Val Trp  Lys Thr Ile Lys Asn  His Glu Ser Arg Lys  His Phe Leu
    1085                1090                1095

Glu Gly  Phe Asp Phe Leu His  Tyr Asp Val Lys Thr  Gly Asp Phe
    1100                1105                1110

Ile Leu  His Phe Lys Met Asn  Arg Asn Leu Ser Phe  Gln Arg Gly
    1115                1120                1125

Leu Pro  Gly Phe Met Pro Ala  Trp Asp Ile Val Phe  Glu Lys Asn
    1130                1135                1140

Glu Thr  Gln Phe Asp Ala Lys  Gly Thr Pro Phe Ile  Ala Gly Lys
    1145                1150                1155

Arg Ile  Val Pro Val Ile Glu  Asn His Arg Phe Thr  Gly Arg Tyr
    1160                1165                1170

Arg Asp  Leu Tyr Pro Ala Asn  Glu Leu Ile Ala Leu  Leu Glu Glu
    1175                1180                1185

Lys Gly  Ile Val Phe Arg Asp  Gly Ser Asn Ile Leu  Pro Lys Leu
    1190                1195                1200

Leu Glu  Asn Asp Asp Ser His  Ala Ile Asp Thr Met  Val Ala Leu
    1205                1210                1215

Ile Arg  Ser Val Leu Gln Met  Arg Asn Ser Asn Ala  Ala Thr Gly
    1220                1225                1230

Glu Asp  Tyr Ile Asn Ser Pro  Val Arg Asp Leu Asn  Gly Val Cys
    1235                1240                1245

Phe Asp  Ser Arg Phe Gln Asn  Pro Glu Trp Pro Met  Asp Ala Asp
    1250                1255                1260

Ala Asn  Gly Ala Tyr His Ile  Ala Leu Lys Gly Gln  Leu Leu Leu
    1265                1270                1275

Asn His  Leu Lys Glu Ser Lys  Asp Leu Lys Leu Gln  Asn Gly Ile
    1280                1285                1290
```

Ser Asn Gln Asp Trp Leu Ala Tyr Ile Gln Glu Leu Arg Asn
1295 1300 1305

<210> SEQ ID NO 130
<211> LENGTH: 741
<212> TYPE: PRT
<213> ORGANISM: Homo sapiens

<400> SEQUENCE: 130

Met Glu Ser Arg Asp His Asn Asn Pro Gln Glu Gly Pro Thr Ser Ser
1 5 10 15

Ser Gly Arg Arg Ala Ala Val Glu Asp Asn His Leu Leu Ile Lys Ala
20 25 30

Val Gln Asn Glu Asp Val Asp Leu Val Gln Gln Leu Leu Glu Gly Gly
35 40 45

Ala Asn Val Asn Phe Gln Glu Glu Glu Gly Gly Trp Thr Pro Leu His
50 55 60

Asn Ala Val Gln Met Ser Arg Glu Asp Ile Val Glu Leu Leu Leu Arg
65 70 75 80

His Gly Ala Asp Pro Val Leu Arg Lys Lys Asn Gly Ala Thr Pro Phe
85 90 95

Ile Leu Ala Ala Ile Ala Gly Ser Val Lys Leu Leu Lys Leu Phe Leu
100 105 110

Ser Lys Gly Ala Asp Val Asn Glu Cys Asp Phe Tyr Gly Phe Thr Ala
115 120 125

Phe Met Glu Ala Ala Val Tyr Gly Lys Val Lys Ala Leu Lys Phe Leu
130 135 140

Tyr Lys Arg Gly Ala Asn Val Asn Leu Arg Arg Lys Thr Lys Glu Asp
145 150 155 160

Gln Glu Arg Leu Arg Lys Gly Gly Ala Thr Ala Leu Met Asp Ala Ala
165 170 175

Glu Lys Gly His Val Glu Val Leu Lys Ile Leu Leu Asp Glu Met Gly
180 185 190

Ala Asp Val Asn Ala Cys Asp Asn Met Gly Arg Asn Ala Leu Ile His
195 200 205

Ala Leu Leu Ser Ser Asp Asp Ser Asp Val Glu Ala Ile Thr His Leu
210 215 220

Leu Leu Asp His Gly Ala Asp Val Asn Val Arg Gly Glu Arg Gly Lys
225 230 235 240

Thr Pro Leu Ile Leu Ala Val Glu Lys Lys His Leu Gly Leu Val Gln
245 250 255

Arg Leu Leu Glu Gln Glu His Ile Glu Ile Asn Asp Thr Asp Ser Asp
260 265 270

Gly Lys Thr Ala Leu Leu Leu Ala Val Glu Leu Lys Leu Lys Lys Ile
275 280 285

Ala Glu Leu Leu Cys Lys Arg Gly Ala Ser Thr Asp Cys Gly Asp Leu
290 295 300

Val Met Thr Ala Arg Arg Asn Tyr Asp His Ser Leu Val Lys Val Leu
305 310 315 320

Leu Ser His Gly Ala Lys Glu Asp Phe His Pro Pro Ala Glu Asp Trp
325 330 335

Lys Pro Gln Ser Ser His Trp Gly Ala Ala Leu Lys Asp Leu His Arg
340 345 350

Ile Tyr Arg Pro Met Ile Gly Lys Leu Lys Phe Phe Ile Asp Glu Lys

```
        355                 360                 365

Tyr Lys Ile Ala Asp Thr Ser Glu Gly Gly Ile Tyr Leu Gly Phe Tyr
    370                 375                 380

Glu Lys Gln Glu Val Ala Val Lys Thr Phe Cys Glu Gly Ser Pro Arg
385                 390                 395                 400

Ala Gln Arg Glu Val Ser Cys Leu Gln Ser Ser Arg Glu Asn Ser His
                405                 410                 415

Leu Val Thr Phe Tyr Gly Ser Glu Ser His Arg Gly His Leu Phe Val
            420                 425                 430

Cys Val Thr Leu Cys Glu Gln Thr Leu Glu Ala Cys Leu Asp Val His
        435                 440                 445

Arg Gly Glu Asp Val Glu Asn Glu Glu Asp Glu Phe Ala Arg Asn Val
    450                 455                 460

Leu Ser Ser Ile Phe Lys Ala Val Gln Glu Leu His Leu Ser Cys Gly
465                 470                 475                 480

Tyr Thr His Gln Asp Leu Gln Pro Gln Asn Ile Leu Ile Asp Ser Lys
                485                 490                 495

Lys Ala Ala His Leu Ala Asp Phe Asp Lys Ser Ile Lys Trp Ala Gly
            500                 505                 510

Asp Pro Gln Glu Val Lys Arg Asp Leu Glu Asp Leu Gly Arg Leu Val
        515                 520                 525

Leu Tyr Val Val Lys Lys Gly Ser Ile Ser Phe Glu Asp Leu Lys Ala
    530                 535                 540

Gln Ser Asn Glu Glu Val Val Gln Leu Ser Pro Asp Glu Glu Thr Lys
545                 550                 555                 560

Asp Leu Ile His Arg Leu Phe His Pro Gly Glu His Val Arg Asp Cys
                565                 570                 575

Leu Ser Asp Leu Leu Gly His Pro Phe Phe Trp Thr Trp Glu Ser Arg
            580                 585                 590

Tyr Arg Thr Leu Arg Asn Val Gly Asn Glu Ser Asp Ile Lys Thr Arg
        595                 600                 605

Lys Ser Glu Ser Glu Ile Leu Arg Leu Leu Gln Pro Gly Pro Ser Glu
    610                 615                 620

His Ser Lys Ser Phe Asp Lys Trp Thr Thr Lys Ile Asn Glu Cys Val
625                 630                 635                 640

Met Lys Lys Met Asn Lys Phe Tyr Glu Lys Arg Gly Asn Phe Tyr Gln
                645                 650                 655

Asn Thr Val Gly Asp Leu Leu Lys Phe Ile Arg Asn Leu Gly Glu His
            660                 665                 670

Ile Asp Glu Glu Lys His Lys Lys Met Lys Leu Lys Ile Gly Asp Pro
        675                 680                 685

Ser Leu Tyr Phe Gln Lys Thr Phe Pro Asp Leu Val Ile Tyr Val Tyr
    690                 695                 700

Thr Lys Leu Gln Asn Thr Glu Tyr Arg Lys His Phe Pro Gln Thr His
705                 710                 715                 720

Ser Pro Asn Lys Pro Gln Cys Asp Gly Ala Gly Gly Ala Ser Gly Leu
                725                 730                 735

Ala Ser Pro Gly Cys
            740
```

<210> SEQ ID NO 131
<211> LENGTH: 357
<212> TYPE: PRT
<213> ORGANISM: Homo sapiens -continued

<400> SEQUENCE: 131

Met Met Ala Arg Leu Leu Arg Thr Ser Phe Ala Leu Leu Phe Leu Gly
1               5                   10                  15

Leu Phe Gly Val Leu Gly Ala Ala Thr Ile Ser Cys Arg Asn Glu Glu
            20                  25                  30

Gly Lys Ala Val Asp Trp Phe Thr Phe Tyr Lys Leu Pro Lys Arg Gln
        35                  40                  45

Asn Lys Glu Ser Gly Glu Thr Gly Leu Glu Tyr Leu Tyr Leu Asp Ser
    50                  55                  60

Thr Thr Arg Ser Trp Arg Lys Ser Glu Gln Leu Met Asn Asp Thr Lys
65                  70                  75                  80

Ser Val Leu Gly Arg Thr Leu Gln Gln Leu Tyr Glu Ala Tyr Ala Ser
                85                  90                  95

Lys Ser Asn Asn Thr Ala Tyr Leu Ile Tyr Asn Asp Gly Val Pro Lys
            100                 105                 110

Pro Val Asn Tyr Ser Arg Lys Tyr Gly His Thr Lys Gly Leu Leu Leu
        115                 120                 125

Trp Asn Arg Val Gln Gly Phe Trp Leu Ile His Ser Ile Pro Gln Phe
    130                 135                 140

Pro Pro Ile Pro Glu Glu Gly Tyr Asp Tyr Pro Pro Thr Gly Arg Arg
145                 150                 155                 160

Asn Gly Gln Ser Gly Ile Cys Ile Thr Phe Lys Tyr Asn Gln Tyr Glu
                165                 170                 175

Ala Ile Asp Ser Gln Leu Leu Val Cys Asn Pro Asn Val Tyr Ser Cys
            180                 185                 190

Ser Ile Pro Ala Thr Phe His Gln Glu Leu Ile His Met Pro Gln Leu
        195                 200                 205

Cys Thr Arg Ala Ser Ser Ser Glu Ile Pro Gly Arg Leu Leu Thr Thr
    210                 215                 220

Leu Gln Ser Ala Gln Gly Gln Lys Phe Leu His Phe Ala Lys Ser Asp
225                 230                 235                 240

Ser Phe Leu Asp Asp Ile Phe Ala Ala Trp Met Ala Gln Arg Leu Lys
                245                 250                 255

Thr His Leu Leu Thr Glu Thr Trp Gln Arg Lys Arg Gln Glu Leu Pro
            260                 265                 270

Ser Asn Cys Ser Leu Pro Tyr His Val Tyr Asn Ile Lys Ala Ile Lys
        275                 280                 285

Leu Ser Arg His Ser Tyr Phe Ser Ser Tyr Gln Asp His Ala Lys Trp
    290                 295                 300

Cys Ile Ser Gln Lys Gly Thr Lys Asn Arg Trp Thr Cys Ile Gly Asp
305                 310                 315                 320

Leu Asn Arg Ser Pro His Gln Ala Phe Arg Ser Gly Gly Phe Ile Cys
                325                 330                 335

Thr Gln Asn Trp Gln Ile Tyr Gln Ala Phe Gln Gly Leu Val Leu Tyr
            340                 345                 350

Tyr Glu Ser Cys Lys
        355

<210> SEQ ID NO 132
<211> LENGTH: 2009
<212> TYPE: PRT
<213> ORGANISM: Homo sapiens

<400> SEQUENCE: 132

```
Met Glu Gln Thr Val Leu Val Pro Pro Gly Pro Asp Ser Phe Asn Phe
1               5                   10                  15

Phe Thr Arg Glu Ser Leu Ala Ala Ile Glu Arg Arg Ile Ala Glu Glu
            20                  25                  30

Lys Ala Lys Asn Pro Lys Pro Asp Lys Lys Asp Asp Asp Glu Asn Gly
        35                  40                  45

Pro Lys Pro Asn Ser Asp Leu Glu Ala Gly Lys Asn Leu Pro Phe Ile
    50                  55                  60

Tyr Gly Asp Ile Pro Pro Glu Met Val Ser Glu Pro Leu Glu Asp Leu
65                  70                  75                  80

Asp Pro Tyr Tyr Ile Asn Lys Lys Thr Phe Ile Val Leu Asn Lys Gly
                85                  90                  95

Lys Ala Ile Phe Arg Phe Ser Ala Thr Ser Ala Leu Tyr Ile Leu Thr
            100                 105                 110

Pro Phe Asn Pro Leu Arg Lys Ile Ala Ile Lys Ile Leu Val His Ser
        115                 120                 125

Leu Phe Ser Met Leu Ile Met Cys Thr Ile Leu Thr Asn Cys Val Phe
    130                 135                 140

Met Thr Met Ser Asn Pro Pro Asp Trp Thr Lys Asn Val Glu Tyr Thr
145                 150                 155                 160

Phe Thr Gly Ile Tyr Thr Phe Glu Ser Leu Ile Lys Ile Ile Ala Arg
                165                 170                 175

Gly Phe Cys Leu Glu Asp Phe Thr Phe Leu Arg Asp Pro Trp Asn Trp
            180                 185                 190

Leu Asp Phe Thr Val Ile Thr Phe Ala Tyr Val Thr Glu Phe Val Asp
        195                 200                 205

Leu Gly Asn Val Ser Ala Leu Arg Thr Phe Arg Val Leu Arg Ala Leu
    210                 215                 220

Lys Thr Ile Ser Val Ile Pro Gly Leu Lys Thr Ile Val Gly Ala Leu
225                 230                 235                 240

Ile Gln Ser Val Lys Lys Leu Ser Asp Val Met Ile Leu Thr Val Phe
                245                 250                 255

Cys Leu Ser Val Phe Ala Leu Ile Gly Leu Gln Leu Phe Met Gly Asn
            260                 265                 270

Leu Arg Asn Lys Cys Ile Gln Trp Pro Pro Thr Asn Ala Ser Leu Glu
        275                 280                 285

Glu His Ser Ile Glu Lys Asn Ile Thr Val Asn Tyr Asn Gly Thr Leu
    290                 295                 300

Ile Asn Glu Thr Val Phe Glu Phe Asp Trp Lys Ser Tyr Ile Gln Asp
305                 310                 315                 320

Ser Arg Tyr His Tyr Phe Leu Glu Gly Phe Leu Asp Ala Leu Leu Cys
                325                 330                 335

Gly Asn Ser Ser Asp Ala Gly Gln Cys Pro Glu Gly Tyr Met Cys Val
            340                 345                 350

Lys Ala Gly Arg Asn Pro Asn Tyr Gly Tyr Thr Ser Phe Asp Thr Phe
        355                 360                 365

Ser Trp Ala Phe Leu Ser Leu Phe Arg Leu Met Thr Gln Asp Phe Trp
    370                 375                 380

Glu Asn Leu Tyr Gln Leu Thr Leu Arg Ala Ala Gly Lys Thr Tyr Met
385                 390                 395                 400

Ile Phe Phe Val Leu Val Ile Phe Leu Gly Ser Phe Tyr Leu Ile Asn
                405                 410                 415
```

-continued

```
Leu Ile Leu Ala Val Val Ala Met Ala Tyr Glu Glu Gln Asn Gln Ala
            420                 425                 430

Thr Leu Glu Glu Ala Glu Gln Lys Glu Ala Glu Phe Gln Gln Met Ile
        435                 440                 445

Glu Gln Leu Lys Lys Gln Gln Glu Ala Ala Gln Gln Ala Ala Thr Ala
    450                 455                 460

Thr Ala Ser Glu His Ser Arg Glu Pro Ser Ala Ala Gly Arg Leu Ser
465                 470                 475                 480

Asp Ser Ser Ser Glu Ala Ser Lys Leu Ser Ser Lys Ser Ala Lys Glu
                485                 490                 495

Arg Arg Asn Arg Arg Lys Lys Arg Lys Gln Lys Glu Gln Ser Gly Gly
            500                 505                 510

Glu Glu Lys Asp Glu Asp Glu Phe Gln Lys Ser Glu Ser Glu Asp Ser
        515                 520                 525

Ile Arg Arg Lys Gly Phe Arg Phe Ser Ile Glu Gly Asn Arg Leu Thr
    530                 535                 540

Tyr Glu Lys Arg Tyr Ser Ser Pro His Gln Ser Leu Leu Ser Ile Arg
545                 550                 555                 560

Gly Ser Leu Phe Ser Pro Arg Arg Asn Ser Arg Thr Ser Leu Phe Ser
                565                 570                 575

Phe Arg Gly Arg Ala Lys Asp Val Gly Ser Glu Asn Asp Phe Ala Asp
            580                 585                 590

Asp Glu His Ser Thr Phe Glu Asp Asn Glu Ser Arg Arg Asp Ser Leu
        595                 600                 605

Phe Val Pro Arg Arg His Gly Glu Arg Arg Asn Ser Asn Leu Ser Gln
    610                 615                 620

Thr Ser Arg Ser Ser Arg Met Leu Ala Val Phe Pro Ala Asn Gly Lys
625                 630                 635                 640

Met His Ser Thr Val Asp Cys Asn Gly Val Val Ser Leu Val Gly Gly
                645                 650                 655

Pro Ser Val Pro Thr Ser Pro Val Gly Gln Leu Leu Pro Glu Val Ile
            660                 665                 670

Ile Asp Lys Pro Ala Thr Asp Asp Asn Gly Thr Thr Thr Glu Thr Glu
        675                 680                 685

Met Arg Lys Arg Arg Ser Ser Ser Phe His Val Ser Met Asp Phe Leu
    690                 695                 700

Glu Asp Pro Ser Gln Arg Gln Arg Ala Met Ser Ile Ala Ser Ile Leu
705                 710                 715                 720

Thr Asn Thr Val Glu Glu Leu Glu Glu Ser Arg Gln Lys Cys Pro Pro
                725                 730                 735

Cys Trp Tyr Lys Phe Ser Asn Ile Phe Leu Ile Trp Asp Cys Ser Pro
            740                 745                 750

Tyr Trp Leu Lys Val Lys His Val Val Asn Leu Val Val Met Asp Pro
        755                 760                 765

Phe Val Asp Leu Ala Ile Thr Ile Cys Ile Val Leu Asn Thr Leu Phe
    770                 775                 780

Met Ala Met Glu His Tyr Pro Met Thr Asp His Phe Asn Asn Val Leu
785                 790                 795                 800

Thr Val Gly Asn Leu Val Phe Thr Gly Ile Phe Thr Ala Glu Met Phe
                805                 810                 815

Leu Lys Ile Ile Ala Met Asp Pro Tyr Tyr Tyr Phe Gln Glu Gly Trp
            820                 825                 830

Asn Ile Phe Asp Gly Phe Ile Val Thr Leu Ser Leu Val Glu Leu Gly
```

-continued

```
        835                 840                 845

Leu Ala Asn Val Glu Gly Leu Ser Val Leu Arg Ser Phe Arg Leu Leu
    850                 855                 860

Arg Val Phe Lys Leu Ala Lys Ser Trp Pro Thr Leu Asn Met Leu Ile
865                 870                 875                 880

Lys Ile Ile Gly Asn Ser Val Gly Ala Leu Gly Asn Leu Thr Leu Val
                885                 890                 895

Leu Ala Ile Ile Val Phe Ile Phe Ala Val Val Gly Met Gln Leu Phe
            900                 905                 910

Gly Lys Ser Tyr Lys Asp Cys Val Cys Lys Ile Ala Ser Asp Cys Gln
        915                 920                 925

Leu Pro Arg Trp His Met Asn Asp Phe Phe His Ser Phe Leu Ile Val
    930                 935                 940

Phe Arg Val Leu Cys Gly Glu Trp Ile Glu Thr Met Trp Asp Cys Met
945                 950                 955                 960

Glu Val Ala Gly Gln Ala Met Cys Leu Thr Val Phe Met Met Val Met
                965                 970                 975

Val Ile Gly Asn Leu Val Val Leu Asn Leu Phe Leu Ala Leu Leu Leu
            980                 985                 990

Ser Ser Phe Ser Ala Asp Asn Leu  Ala Ala Thr Asp Asp  Asp Asn Glu
        995                 1000                1005

Met Asn  Asn Leu Gln Ile Ala  Val Asp Arg Met His  Lys Gly Val
    1010                 1015                1020

Ala Tyr  Val Lys Arg Lys Ile  Tyr Glu Phe Ile Gln  Gln Ser Phe
    1025                 1030                1035

Ile Arg  Lys Gln Lys Ile Leu  Asp Glu Ile Lys Pro  Leu Asp Asp
    1040                 1045                1050

Leu Asn  Asn Lys Lys Asp Ser  Cys Met Ser Asn His  Thr Ala Glu
    1055                 1060                1065

Ile Gly  Lys Asp Leu Asp Tyr  Leu Lys Asp Val Asn  Gly Thr Thr
    1070                 1075                1080

Ser Gly  Ile Gly Thr Gly Ser  Ser Val Glu Lys Tyr  Ile Ile Asp
    1085                 1090                1095

Glu Ser  Asp Tyr Met Ser Phe  Ile Asn Asn Pro Ser  Leu Thr Val
    1100                 1105                1110

Thr Val  Pro Ile Ala Val Gly  Glu Ser Asp Phe Glu  Asn Leu Asn
    1115                 1120                1125

Thr Glu  Asp Phe Ser Ser Glu  Ser Asp Leu Glu Glu  Ser Lys Glu
    1130                 1135                1140

Lys Leu  Asn Glu Ser Ser Ser  Ser Ser Glu Gly Ser  Thr Val Asp
    1145                 1150                1155

Ile Gly  Ala Pro Val Glu Glu  Gln Pro Val Val Glu  Pro Glu Glu
    1160                 1165                1170

Thr Leu  Glu Pro Glu Ala Cys  Phe Thr Glu Gly Cys  Val Gln Arg
    1175                 1180                1185

Phe Lys  Cys Cys Gln Ile Asn  Val Glu Glu Gly Arg  Gly Lys Gln
    1190                 1195                1200

Trp Trp  Asn Leu Arg Arg Thr  Cys Phe Arg Ile Val  Glu His Asn
    1205                 1210                1215

Trp Phe  Glu Thr Phe Ile Val  Phe Met Ile Leu Leu  Ser Ser Gly
    1220                 1225                1230

Ala Leu  Ala Phe Glu Asp Ile  Tyr Ile Asp Gln Arg  Lys Thr Ile
    1235                 1240                1245
```

```
Lys Thr  Met Leu Glu Tyr Ala  Asp Lys Val Phe Thr  Tyr Ile Phe
    1250                 1255                 1260

Ile Leu  Glu Met Leu Leu Lys  Trp Val Ala Tyr Gly  Tyr Gln Thr
    1265                 1270                 1275

Tyr Phe  Thr Asn Ala Trp Cys  Trp Leu Asp Phe Leu  Ile Val Asp
    1280                 1285                 1290

Val Ser  Leu Val Ser Leu Thr  Ala Asn Ala Leu Gly  Tyr Ser Glu
    1295                 1300                 1305

Leu Gly  Ala Ile Lys Ser Leu  Arg Thr Leu Arg Ala  Leu Arg Pro
    1310                 1315                 1320

Leu Arg  Ala Leu Ser Arg Phe  Glu Gly Met Arg Val  Val Val Asn
    1325                 1330                 1335

Ala Leu  Leu Gly Ala Ile Pro  Ser Ile Met Asn Val  Leu Leu Val
    1340                 1345                 1350

Cys Leu  Ile Phe Trp Leu Ile  Phe Ser Ile Met Gly  Val Asn Leu
    1355                 1360                 1365

Phe Ala  Gly Lys Phe Tyr His  Cys Ile Asn Thr Thr  Thr Gly Asp
    1370                 1375                 1380

Arg Phe  Asp Ile Glu Asp Val  Asn Asn His Thr Asp  Cys Leu Lys
    1385                 1390                 1395

Leu Ile  Glu Arg Asn Glu Thr  Ala Arg Trp Lys Asn  Val Lys Val
    1400                 1405                 1410

Asn Phe  Asp Asn Val Gly Phe  Gly Tyr Leu Ser Leu  Leu Gln Val
    1415                 1420                 1425

Ala Thr  Phe Lys Gly Trp Met  Asp Ile Met Tyr Ala  Ala Val Asp
    1430                 1435                 1440

Ser Arg  Asn Val Glu Leu Gln  Pro Lys Tyr Glu Glu  Ser Leu Tyr
    1445                 1450                 1455

Met Tyr  Leu Tyr Phe Val Ile  Phe Ile Ile Phe Gly  Ser Phe Phe
    1460                 1465                 1470

Thr Leu  Asn Leu Phe Ile Gly  Val Ile Ile Asp Asn  Phe Asn Gln
    1475                 1480                 1485

Gln Lys  Lys Lys Phe Gly Gly  Gln Asp Ile Phe Met  Thr Glu Glu
    1490                 1495                 1500

Gln Lys  Lys Tyr Tyr Asn Ala  Met Lys Lys Leu Gly  Ser Lys Lys
    1505                 1510                 1515

Pro Gln  Lys Pro Ile Pro Arg  Pro Gly Asn Lys Phe  Gln Gly Met
    1520                 1525                 1530

Val Phe  Asp Phe Val Thr Arg  Gln Val Phe Asp Ile  Ser Ile Met
    1535                 1540                 1545

Ile Leu  Ile Cys Leu Asn Met  Val Thr Met Met Val  Glu Thr Asp
    1550                 1555                 1560

Asp Gln  Ser Glu Tyr Val Thr  Thr Ile Leu Ser Arg  Ile Asn Leu
    1565                 1570                 1575

Val Phe  Ile Val Leu Phe Thr  Gly Glu Cys Val Leu  Lys Leu Ile
    1580                 1585                 1590

Ser Leu  Arg His Tyr Tyr Phe  Thr Ile Gly Trp Asn  Ile Phe Asp
    1595                 1600                 1605

Phe Val  Val Val Ile Leu Ser  Ile Val Gly Met Phe  Leu Ala Glu
    1610                 1615                 1620

Leu Ile  Glu Lys Tyr Phe Val  Ser Pro Thr Leu Phe  Arg Val Ile
    1625                 1630                 1635
```

-continued

Arg Leu Ala Arg Ile Gly Arg Ile Leu Arg Leu Ile Lys Gly Ala
1640 1645 1650

Lys Gly Ile Arg Thr Leu Leu Phe Ala Leu Met Met Ser Leu Pro
1655 1660 1665

Ala Leu Phe Asn Ile Gly Leu Leu Leu Phe Leu Val Met Phe Ile
1670 1675 1680

Tyr Ala Ile Phe Gly Met Ser Asn Phe Ala Tyr Val Lys Arg Glu
1685 1690 1695

Val Gly Ile Asp Asp Met Phe Asn Phe Glu Thr Phe Gly Asn Ser
1700 1705 1710

Met Ile Cys Leu Phe Gln Ile Thr Thr Ser Ala Gly Trp Asp Gly
1715 1720 1725

Leu Leu Ala Pro Ile Leu Asn Ser Lys Pro Pro Asp Cys Asp Pro
1730 1735 1740

Asn Lys Val Asn Pro Gly Ser Ser Val Lys Gly Asp Cys Gly Asn
1745 1750 1755

Pro Ser Val Gly Ile Phe Phe Phe Val Ser Tyr Ile Ile Ile Ser
1760 1765 1770

Phe Leu Val Val Val Asn Met Tyr Ile Ala Val Ile Leu Glu Asn
1775 1780 1785

Phe Ser Val Ala Thr Glu Glu Ser Ala Glu Pro Leu Ser Glu Asp
1790 1795 1800

Asp Phe Glu Met Phe Tyr Glu Val Trp Glu Lys Phe Asp Pro Asp
1805 1810 1815

Ala Thr Gln Phe Met Glu Phe Glu Lys Leu Ser Gln Phe Ala Ala
1820 1825 1830

Ala Leu Glu Pro Pro Leu Asn Leu Pro Gln Pro Asn Lys Leu Gln
1835 1840 1845

Leu Ile Ala Met Asp Leu Pro Met Val Ser Gly Asp Arg Ile His
1850 1855 1860

Cys Leu Asp Ile Leu Phe Ala Phe Thr Lys Arg Val Leu Gly Glu
1865 1870 1875

Ser Gly Glu Met Asp Ala Leu Arg Ile Gln Met Glu Glu Arg Phe
1880 1885 1890

Met Ala Ser Asn Pro Ser Lys Val Ser Tyr Gln Pro Ile Thr Thr
1895 1900 1905

Thr Leu Lys Arg Lys Gln Glu Glu Val Ser Ala Val Ile Ile Gln
1910 1915 1920

Arg Ala Tyr Arg Arg His Leu Leu Lys Arg Thr Val Lys Gln Ala
1925 1930 1935

Ser Phe Thr Tyr Asn Lys Asn Lys Ile Lys Gly Gly Ala Asn Leu
1940 1945 1950

Leu Ile Lys Glu Asp Met Ile Ile Asp Arg Ile Asn Glu Asn Ser
1955 1960 1965

Ile Thr Glu Lys Thr Asp Leu Thr Met Ser Thr Ala Ala Cys Pro
1970 1975 1980

Pro Ser Tyr Asp Arg Val Thr Lys Pro Ile Val Glu Lys His Glu
1985 1990 1995

Gln Glu Gly Lys Asp Glu Lys Ala Lys Gly Lys
2000 2005

<210> SEQ ID NO 133
<211> LENGTH: 872
<212> TYPE: PRT

<213> ORGANISM: Homo sapiens

<400> SEQUENCE: 133

```
Met Val Gln Lys Ser Arg Asn Gly Gly Val Tyr Pro Gly Pro Ser Gly
1               5                   10                  15

Glu Lys Lys Leu Lys Val Gly Phe Val Gly Leu Asp Pro Gly Ala Pro
            20                  25                  30

Asp Ser Thr Arg Asp Gly Ala Leu Leu Ile Ala Gly Ser Glu Ala Pro
        35                  40                  45

Lys Arg Gly Ser Ile Leu Ser Lys Pro Arg Ala Gly Gly Ala Gly Ala
    50                  55                  60

Gly Lys Pro Pro Lys Arg Asn Ala Phe Tyr Arg Lys Leu Gln Asn Phe
65                  70                  75                  80

Leu Tyr Asn Val Leu Glu Arg Pro Arg Gly Trp Ala Phe Ile Tyr His
                85                  90                  95

Ala Tyr Val Phe Leu Leu Val Phe Ser Cys Leu Val Leu Ser Val Phe
            100                 105                 110

Ser Thr Ile Lys Glu Tyr Glu Lys Ser Ser Glu Gly Ala Leu Tyr Ile
        115                 120                 125

Leu Glu Ile Val Thr Ile Val Val Phe Gly Val Glu Tyr Phe Val Arg
    130                 135                 140

Ile Trp Ala Ala Gly Cys Cys Cys Arg Tyr Arg Gly Trp Arg Gly Arg
145                 150                 155                 160

Leu Lys Phe Ala Arg Lys Pro Phe Cys Val Ile Asp Ile Met Val Leu
                165                 170                 175

Ile Ala Ser Ile Ala Val Leu Ala Ala Gly Ser Gln Gly Asn Val Phe
            180                 185                 190

Ala Thr Ser Ala Leu Arg Ser Leu Arg Phe Leu Gln Ile Leu Arg Met
        195                 200                 205

Ile Arg Met Asp Arg Arg Gly Gly Thr Trp Lys Leu Leu Gly Ser Val
    210                 215                 220

Val Tyr Ala His Ser Lys Glu Leu Val Thr Ala Trp Tyr Ile Gly Phe
225                 230                 235                 240

Leu Cys Leu Ile Leu Ala Ser Phe Leu Val Tyr Leu Ala Glu Lys Gly
                245                 250                 255

Glu Asn Asp His Phe Asp Thr Tyr Ala Asp Ala Leu Trp Trp Gly Leu
            260                 265                 270

Ile Thr Leu Thr Thr Ile Gly Tyr Gly Asp Lys Tyr Pro Gln Thr Trp
        275                 280                 285

Asn Gly Arg Leu Leu Ala Ala Thr Phe Thr Leu Ile Gly Val Ser Phe
    290                 295                 300

Phe Ala Leu Pro Ala Gly Ile Leu Gly Ser Gly Phe Ala Leu Lys Val
305                 310                 315                 320

Gln Glu Gln His Arg Gln Lys His Phe Glu Lys Arg Arg Asn Pro Ala
                325                 330                 335

Ala Gly Leu Ile Gln Ser Ala Trp Arg Phe Tyr Ala Thr Asn Leu Ser
            340                 345                 350

Arg Thr Asp Leu His Ser Thr Trp Gln Tyr Tyr Glu Arg Thr Val Thr
        355                 360                 365

Val Pro Met Tyr Ser Ser Gln Thr Gln Thr Tyr Gly Ala Ser Arg Leu
    370                 375                 380

Ile Pro Pro Leu Asn Gln Leu Glu Leu Leu Arg Asn Leu Lys Ser Lys
385                 390                 395                 400
```

```
Ser Gly Leu Ala Phe Arg Lys Asp Pro Pro Pro Glu Pro Ser Pro Ser
                405                 410                 415

Lys Gly Ser Pro Cys Arg Gly Pro Leu Cys Gly Cys Cys Pro Gly Arg
            420                 425                 430

Ser Ser Gln Lys Val Ser Leu Lys Asp Arg Val Phe Ser Ser Pro Arg
        435                 440                 445

Gly Val Ala Ala Lys Gly Lys Gly Ser Pro Gln Ala Gln Thr Val Arg
    450                 455                 460

Arg Ser Pro Ser Ala Asp Gln Ser Leu Glu Asp Ser Pro Ser Lys Val
465                 470                 475                 480

Pro Lys Ser Trp Ser Phe Gly Asp Arg Ser Arg Ala Arg Gln Ala Phe
                485                 490                 495

Arg Ile Lys Gly Ala Ala Ser Arg Gln Asn Ser Glu Glu Ala Ser Leu
            500                 505                 510

Pro Gly Glu Asp Ile Val Asp Asp Lys Ser Cys Pro Cys Glu Phe Val
        515                 520                 525

Thr Glu Asp Leu Thr Pro Gly Leu Lys Val Ser Ile Arg Ala Val Cys
    530                 535                 540

Val Met Arg Phe Leu Val Ser Lys Arg Lys Phe Lys Glu Ser Leu Arg
545                 550                 555                 560

Pro Tyr Asp Val Met Asp Val Ile Glu Gln Tyr Ser Ala Gly His Leu
                565                 570                 575

Asp Met Leu Ser Arg Ile Lys Ser Leu Gln Ser Arg Val Asp Gln Ile
            580                 585                 590

Val Gly Arg Gly Pro Ala Ile Thr Asp Lys Asp Arg Thr Lys Gly Pro
        595                 600                 605

Ala Glu Ala Glu Leu Pro Glu Asp Pro Ser Met Met Gly Arg Leu Gly
    610                 615                 620

Lys Val Glu Lys Gln Val Leu Ser Met Glu Lys Lys Leu Asp Phe Leu
625                 630                 635                 640

Val Asn Ile Tyr Met Gln Arg Met Gly Ile Pro Pro Thr Glu Thr Glu
                645                 650                 655

Ala Tyr Phe Gly Ala Lys Glu Pro Glu Pro Ala Pro Pro Tyr His Ser
            660                 665                 670

Pro Glu Asp Ser Arg Glu His Val Asp Arg His Gly Cys Ile Val Lys
        675                 680                 685

Ile Val Arg Ser Ser Ser Ser Thr Gly Gln Lys Asn Phe Ser Ala Pro
    690                 695                 700

Pro Ala Ala Pro Pro Val Gln Cys Pro Pro Ser Thr Ser Trp Gln Pro
705                 710                 715                 720

Gln Ser His Pro Arg Gln Gly His Gly Thr Ser Pro Val Gly Asp His
                725                 730                 735

Gly Ser Leu Val Arg Ile Pro Pro Pro Pro Ala His Glu Arg Ser Leu
            740                 745                 750

Ser Ala Tyr Gly Gly Gly Asn Arg Ala Ser Met Glu Phe Leu Arg Gln
        755                 760                 765

Glu Asp Thr Pro Gly Cys Arg Pro Pro Glu Gly Asn Leu Arg Asp Ser
    770                 775                 780

Asp Thr Ser Ile Ser Ile Pro Ser Val Asp His Glu Glu Leu Glu Arg
785                 790                 795                 800

Ser Phe Ser Gly Phe Ser Ile Ser Gln Ser Lys Glu Asn Leu Asp Ala
                805                 810                 815

Leu Asn Ser Cys Tyr Ala Ala Val Ala Pro Cys Ala Lys Val Arg Pro
```

```
            820                 825                 830

Tyr Ile Ala Glu Gly Glu Ser Asp Thr Asp Ser Asp Leu Cys Thr Pro
        835                 840                 845

Cys Gly Pro Pro Pro Arg Ser Ala Thr Gly Glu Gly Pro Phe Gly Asp
    850                 855                 860

Val Gly Trp Ala Gly Pro Arg Lys
865                 870


<210> SEQ ID NO 134
<211> LENGTH: 2221
<212> TYPE: PRT
<213> ORGANISM: Homo sapiens

<400> SEQUENCE: 134

Met Val Asn Glu Asn Thr Arg Met Tyr Ile Pro Glu Glu Asn His Gln
1               5                   10                  15

Gly Ser Asn Tyr Gly Ser Pro Arg Pro Ala His Ala Asn Met Asn Ala
            20                  25                  30

Asn Ala Ala Ala Gly Leu Ala Pro Glu His Ile Pro Thr Pro Gly Ala
        35                  40                  45

Ala Leu Ser Trp Gln Ala Ala Ile Asp Ala Ala Arg Gln Ala Lys Leu
    50                  55                  60

Met Gly Ser Ala Gly Asn Ala Thr Ile Ser Thr Val Ser Ser Thr Gln
65                  70                  75                  80

Arg Lys Arg Gln Gln Tyr Gly Lys Pro Lys Lys Gln Gly Ser Thr Thr
                85                  90                  95

Ala Thr Arg Pro Pro Arg Ala Leu Leu Cys Leu Thr Leu Lys Asn Pro
            100                 105                 110

Ile Arg Arg Ala Cys Ile Ser Ile Val Glu Trp Lys Pro Phe Glu Ile
        115                 120                 125

Ile Ile Leu Leu Thr Ile Phe Ala Asn Cys Val Ala Leu Ala Ile Tyr
    130                 135                 140

Ile Pro Phe Pro Glu Asp Asp Ser Asn Ala Thr Asn Ser Asn Leu Glu
145                 150                 155                 160

Arg Val Glu Tyr Leu Phe Leu Ile Ile Phe Thr Val Glu Ala Phe Leu
                165                 170                 175

Lys Val Ile Ala Tyr Gly Leu Leu Phe His Pro Asn Ala Tyr Leu Arg
            180                 185                 190

Asn Gly Trp Asn Leu Leu Asp Phe Ile Ile Val Val Val Gly Leu Phe
        195                 200                 205

Ser Ala Ile Leu Glu Gln Ala Thr Lys Ala Asp Gly Ala Asn Ala Leu
    210                 215                 220

Gly Gly Lys Gly Ala Gly Phe Asp Val Lys Ala Leu Arg Ala Phe Arg
225                 230                 235                 240

Val Leu Arg Pro Leu Arg Leu Val Ser Gly Val Pro Ser Leu Gln Val
                245                 250                 255

Val Leu Asn Ser Ile Ile Lys Ala Met Val Pro Leu Leu His Ile Ala
            260                 265                 270

Leu Leu Val Leu Phe Val Ile Ile Ile Tyr Ala Ile Ile Gly Leu Glu
        275                 280                 285

Leu Phe Met Gly Lys Met His Lys Thr Cys Tyr Asn Gln Glu Gly Ile
    290                 295                 300

Ala Asp Val Pro Ala Glu Asp Asp Pro Ser Pro Cys Ala Leu Glu Thr
305                 310                 315                 320
```

-continued

```
Gly His Gly Arg Gln Cys Gln Asn Gly Thr Val Cys Lys Pro Gly Trp
                325                 330                 335

Asp Gly Pro Lys His Gly Ile Thr Asn Phe Asp Asn Phe Ala Phe Ala
            340                 345                 350

Met Leu Thr Val Phe Gln Cys Ile Thr Met Glu Gly Trp Thr Asp Val
        355                 360                 365

Leu Tyr Trp Val Asn Asp Ala Val Gly Arg Asp Trp Pro Trp Ile Tyr
    370                 375                 380

Phe Val Thr Leu Ile Ile Ile Gly Ser Phe Phe Val Leu Asn Leu Val
385                 390                 395                 400

Leu Gly Val Leu Ser Gly Glu Phe Ser Lys Glu Arg Glu Lys Ala Lys
                405                 410                 415

Ala Arg Gly Asp Phe Gln Lys Leu Arg Glu Lys Gln Gln Leu Glu Glu
            420                 425                 430

Asp Leu Lys Gly Tyr Leu Asp Trp Ile Thr Gln Ala Glu Asp Ile Asp
        435                 440                 445

Pro Glu Asn Glu Asp Glu Gly Met Asp Glu Glu Lys Pro Arg Asn Met
    450                 455                 460

Ser Met Pro Thr Ser Glu Thr Glu Ser Val Asn Thr Glu Asn Val Ala
465                 470                 475                 480

Gly Gly Asp Ile Glu Gly Glu Asn Cys Gly Ala Arg Leu Ala His Arg
                485                 490                 495

Ile Ser Lys Ser Lys Phe Ser Arg Tyr Trp Arg Arg Trp Asn Arg Phe
            500                 505                 510

Cys Arg Arg Lys Cys Arg Ala Ala Val Lys Ser Asn Val Phe Tyr Trp
        515                 520                 525

Leu Val Ile Phe Leu Val Phe Leu Asn Thr Leu Thr Ile Ala Ser Glu
    530                 535                 540

His Tyr Asn Gln Pro Asn Trp Leu Thr Glu Val Gln Asp Thr Ala Asn
545                 550                 555                 560

Lys Ala Leu Leu Ala Leu Phe Thr Ala Glu Met Leu Leu Lys Met Tyr
                565                 570                 575

Ser Leu Gly Leu Gln Ala Tyr Phe Val Ser Leu Phe Asn Arg Phe Asp
            580                 585                 590

Cys Phe Val Val Cys Gly Gly Ile Leu Glu Thr Ile Leu Val Glu Thr
        595                 600                 605

Lys Ile Met Ser Pro Leu Gly Ile Ser Val Leu Arg Cys Val Arg Leu
    610                 615                 620

Leu Arg Ile Phe Lys Ile Thr Arg Tyr Trp Asn Ser Leu Ser Asn Leu
625                 630                 635                 640

Val Ala Ser Leu Leu Asn Ser Val Arg Ser Ile Ala Ser Leu Leu Leu
                645                 650                 655

Leu Leu Phe Leu Phe Ile Ile Ile Phe Ser Leu Leu Gly Met Gln Leu
            660                 665                 670

Phe Gly Gly Lys Phe Asn Phe Asp Glu Met Gln Thr Arg Arg Ser Thr
        675                 680                 685

Phe Asp Asn Phe Pro Gln Ser Leu Leu Thr Val Phe Gln Ile Leu Thr
    690                 695                 700

Gly Glu Asp Trp Asn Ser Val Met Tyr Asp Gly Ile Met Ala Tyr Gly
705                 710                 715                 720

Gly Pro Ser Phe Pro Gly Met Leu Val Cys Ile Tyr Phe Ile Ile Leu
                725                 730                 735

Phe Ile Cys Gly Asn Tyr Ile Leu Leu Asn Val Phe Leu Ala Ile Ala
```

-continued

```
            740                 745                 750

Val Asp Asn Leu Ala Asp Ala Glu Ser Leu Thr Ser Ala Gln Lys Glu
        755                 760                 765

Glu Glu Glu Glu Lys Glu Arg Lys Lys Leu Ala Arg Thr Ala Ser Pro
    770                 775                 780

Glu Lys Lys Gln Glu Leu Val Glu Lys Pro Ala Val Gly Glu Ser Lys
785                 790                 795                 800

Glu Glu Lys Ile Glu Leu Lys Ser Ile Thr Ala Asp Gly Glu Ser Pro
            805                 810                 815

Pro Ala Thr Lys Ile Asn Met Asp Asp Leu Gln Pro Asn Glu Asn Glu
            820                 825                 830

Asp Lys Ser Pro Tyr Pro Asn Pro Glu Thr Thr Gly Glu Glu Asp Glu
        835                 840                 845

Glu Glu Pro Glu Met Pro Val Gly Pro Arg Pro Arg Pro Leu Ser Glu
    850                 855                 860

Leu His Leu Lys Glu Lys Ala Val Pro Met Pro Glu Ala Ser Ala Phe
865                 870                 875                 880

Phe Ile Phe Ser Ser Asn Asn Arg Phe Arg Leu Gln Cys His Arg Ile
            885                 890                 895

Val Asn Asp Thr Ile Phe Thr Asn Leu Ile Leu Phe Phe Ile Leu Leu
            900                 905                 910

Ser Ser Ile Ser Leu Ala Ala Glu Asp Pro Val Gln His Thr Ser Phe
        915                 920                 925

Arg Asn His Ile Leu Phe Tyr Phe Asp Ile Val Phe Thr Thr Ile Phe
    930                 935                 940

Thr Ile Glu Ile Ala Leu Lys Ile Leu Gly Asn Ala Asp Tyr Val Phe
945                 950                 955                 960

Thr Ser Ile Phe Thr Leu Glu Ile Ile Leu Lys Met Thr Ala Tyr Gly
            965                 970                 975

Ala Phe Leu His Lys Gly Ser Phe Cys Arg Asn Tyr Phe Asn Ile Leu
            980                 985                 990

Asp Leu Leu Val Val Ser Val Ser  Leu Ile Ser Phe Gly  Ile Gln Ser
        995                 1000                1005

Ser Ala  Ile Asn Val Val Lys  Ile Leu Arg Val Leu  Arg Val Leu
    1010                 1015                 1020

Arg Pro  Leu Arg Ala Ile Asn  Arg Ala Lys Gly Leu  Lys His Val
    1025                 1030                 1035

Val Gln  Cys Val Phe Val Ala  Ile Arg Thr Ile Gly  Asn Ile Val
    1040                 1045                 1050

Ile Val  Thr Thr Leu Leu Gln  Phe Met Phe Ala Cys  Ile Gly Val
    1055                 1060                 1065

Gln Leu  Phe Lys Gly Lys Leu  Tyr Thr Cys Ser Asp  Ser Ser Lys
    1070                 1075                 1080

Gln Thr  Glu Ala Glu Cys Lys  Gly Asn Tyr Ile Thr  Tyr Lys Asp
    1085                 1090                 1095

Gly Glu  Val Asp His Pro Ile  Ile Gln Pro Arg Ser  Trp Glu Asn
    1100                 1105                 1110

Ser Lys  Phe Asp Phe Asp Asn  Val Leu Ala Ala Met  Met Ala Leu
    1115                 1120                 1125

Phe Thr  Val Ser Thr Phe Glu  Gly Trp Pro Glu Leu  Leu Tyr Arg
    1130                 1135                 1140

Ser Ile  Asp Ser His Thr Glu  Asp Lys Gly Pro Ile  Tyr Asn Tyr
    1145                 1150                 1155
```

-continued

```
Arg Val  Glu Ile Ser Ile Phe  Phe Ile Ile Tyr Ile  Ile Ile Ile
    1160                 1165                 1170

Ala Phe  Phe Met Met Asn Ile  Phe Val Gly Phe Val  Ile Val Thr
    1175                 1180                 1185

Phe Gln  Glu Gln Gly Glu Gln  Glu Tyr Lys Asn Cys  Glu Leu Asp
    1190                 1195                 1200

Lys Asn  Gln Arg Gln Cys Val  Glu Tyr Ala Leu Lys  Ala Arg Pro
    1205                 1210                 1215

Leu Arg  Arg Tyr Ile Pro Lys  Asn Gln His Gln Tyr  Lys Val Trp
    1220                 1225                 1230

Tyr Val  Val Asn Ser Thr Tyr  Phe Glu Tyr Leu Met  Phe Val Leu
    1235                 1240                 1245

Ile Leu  Leu Asn Thr Ile Cys  Leu Ala Met Gln His  Tyr Gly Gln
    1250                 1255                 1260

Ser Cys  Leu Phe Lys Ile Ala  Met Asn Ile Leu Asn  Met Leu Phe
    1265                 1270                 1275

Thr Gly  Leu Phe Thr Val Glu  Met Ile Leu Lys Leu  Ile Ala Phe
    1280                 1285                 1290

Lys Pro  Lys Gly Tyr Phe Ser  Asp Pro Trp Asn Val  Phe Asp Phe
    1295                 1300                 1305

Leu Ile  Val Ile Gly Ser Ile  Ile Asp Val Ile Leu  Ser Glu Thr
    1310                 1315                 1320

Asn His  Tyr Phe Cys Asp Ala  Trp Asn Thr Phe Asp  Ala Leu Ile
    1325                 1330                 1335

Val Val  Gly Ser Ile Val Asp  Ile Ala Ile Thr Glu  Val Asn Pro
    1340                 1345                 1350

Ala Glu  His Thr Gln Cys Ser  Pro Ser Met Asn Ala  Glu Glu Asn
    1355                 1360                 1365

Ser Arg  Ile Ser Ile Thr Phe  Phe Arg Leu Phe Arg  Val Met Arg
    1370                 1375                 1380

Leu Val  Lys Leu Leu Ser Arg  Gly Glu Gly Ile Arg  Thr Leu Leu
    1385                 1390                 1395

Trp Thr  Phe Ile Lys Ser Phe  Gln Ala Leu Pro Tyr  Val Ala Leu
    1400                 1405                 1410

Leu Ile  Val Met Leu Phe Phe  Ile Tyr Ala Val Ile  Gly Met Gln
    1415                 1420                 1425

Val Phe  Gly Lys Ile Ala Leu  Asn Asp Thr Thr Glu  Ile Asn Arg
    1430                 1435                 1440

Asn Asn  Asn Phe Gln Thr Phe  Pro Gln Ala Val Leu  Leu Leu Phe
    1445                 1450                 1455

Arg Cys  Ala Thr Gly Glu Ala  Trp Gln Asp Ile Met  Leu Ala Cys
    1460                 1465                 1470

Met Pro  Gly Lys Lys Cys Ala  Pro Glu Ser Glu Pro  Ser Asn Ser
    1475                 1480                 1485

Thr Glu  Gly Glu Thr Pro Cys  Gly Ser Ser Phe Ala  Val Phe Tyr
    1490                 1495                 1500

Phe Ile  Ser Phe Tyr Met Leu  Cys Ala Phe Leu Ile  Ile Asn Leu
    1505                 1510                 1515

Phe Val  Ala Val Ile Met Asp  Asn Phe Asp Tyr Leu  Thr Arg Asp
    1520                 1525                 1530

Trp Ser  Ile Leu Gly Pro His  His Leu Asp Glu Phe  Lys Arg Ile
    1535                 1540                 1545
```

```
Trp Ala  Glu Tyr Asp Pro Glu  Ala Lys Gly Arg Ile  Lys His Leu
    1550                 1555                 1560

Asp Val  Val Thr Leu Leu Arg  Arg Ile Gln Pro Pro  Leu Gly Phe
    1565                 1570                 1575

Gly Lys  Leu Cys Pro His Arg  Val Ala Cys Lys Arg  Leu Val Ser
    1580                 1585                 1590

Met Asn  Met Pro Leu Asn Ser  Asp Gly Thr Val Met  Phe Asn Ala
    1595                 1600                 1605

Thr Leu  Phe Ala Leu Val Arg  Thr Ala Leu Arg Ile  Lys Thr Glu
    1610                 1615                 1620

Gly Asn  Leu Glu Gln Ala Asn  Glu Glu Leu Arg Ala  Ile Ile Lys
    1625                 1630                 1635

Lys Ile  Trp Lys Arg Thr Ser  Met Lys Leu Leu Asp  Gln Val Val
    1640                 1645                 1650

Pro Pro  Ala Gly Asp Asp Glu  Val Thr Val Gly Lys  Phe Tyr Ala
    1655                 1660                 1665

Thr Phe  Leu Ile Gln Glu Tyr  Phe Arg Lys Phe Lys  Lys Arg Lys
    1670                 1675                 1680

Glu Gln  Gly Leu Val Gly Lys  Pro Ser Gln Arg Asn  Ala Leu Ser
    1685                 1690                 1695

Leu Gln  Ala Gly Leu Arg Thr  Leu His Asp Ile Gly  Pro Glu Ile
    1700                 1705                 1710

Arg Arg  Ala Ile Ser Gly Asp  Leu Thr Ala Glu Glu  Glu Leu Asp
    1715                 1720                 1725

Lys Ala  Met Lys Glu Ala Val  Ser Ala Ala Ser Glu  Asp Asp Ile
    1730                 1735                 1740

Phe Arg  Arg Ala Gly Gly Leu  Phe Gly Asn His Val  Ser Tyr Tyr
    1745                 1750                 1755

Gln Ser  Asp Gly Arg Ser Ala  Phe Pro Gln Thr Phe  Thr Thr Gln
    1760                 1765                 1770

Arg Pro  Leu His Ile Asn Lys  Ala Gly Ser Ser Gln  Gly Asp Thr
    1775                 1780                 1785

Glu Ser  Pro Ser His Glu Lys  Leu Val Asp Ser Thr  Phe Thr Pro
    1790                 1795                 1800

Ser Ser  Tyr Ser Ser Thr Gly  Ser Asn Ala Asn Ile  Asn Asn Ala
    1805                 1810                 1815

Asn Asn  Thr Ala Leu Gly Arg  Leu Pro Arg Pro Ala  Gly Tyr Pro
    1820                 1825                 1830

Ser Thr  Val Ser Thr Val Glu  Gly His Gly Pro Pro  Leu Ser Pro
    1835                 1840                 1845

Ala Ile  Arg Val Gln Glu Val  Ala Trp Lys Leu Ser  Ser Asn Arg
    1850                 1855                 1860

Glu Arg  His Val Pro Met Cys  Glu Asp Leu Glu Leu  Arg Arg Asp
    1865                 1870                 1875

Ser Gly  Ser Ala Gly Thr Gln  Ala His Cys Leu Leu  Leu Arg Lys
    1880                 1885                 1890

Ala Asn  Pro Ser Arg Cys His  Ser Arg Glu Ser Gln  Ala Ala Met
    1895                 1900                 1905

Ala Gly  Gln Glu Glu Thr Ser  Gln Asp Glu Thr Tyr  Glu Val Lys
    1910                 1915                 1920

Met Asn  His Asp Thr Glu Ala  Cys Ser Glu Pro Ser  Leu Leu Ser
    1925                 1930                 1935

Thr Glu  Met Leu Ser Tyr Gln  Asp Asp Glu Asn Arg  Gln Leu Thr
```

```
    1940                1945                1950

Leu Pro  Glu Glu Asp Lys Arg  Asp Ile Arg Gln Ser  Pro Lys Arg
    1955                1960                1965

Gly Phe  Leu Arg Ser Ala Ser  Leu Gly Arg Arg Ala  Ser Phe His
    1970                1975                1980

Leu Glu  Cys Leu Lys Arg Gln  Lys Asp Arg Gly Gly  Asp Ile Ser
    1985                1990                1995

Gln Lys  Thr Val Leu Pro Leu  His Leu Val His His  Gln Ala Leu
    2000                2005                2010

Ala Val  Ala Gly Leu Ser Pro  Leu Leu Gln Arg Ser  His Ser Pro
    2015                2020                2025

Ala Ser  Phe Pro Arg Pro Phe  Ala Thr Pro Pro Ala  Thr Pro Gly
    2030                2035                2040

Ser Arg  Gly Trp Pro Pro Gln  Pro Val Pro Thr Leu  Arg Leu Glu
    2045                2050                2055

Gly Val  Glu Ser Ser Glu Lys  Leu Asn Ser Ser Phe  Pro Ser Ile
    2060                2065                2070

His Cys  Gly Ser Trp Ala Glu  Thr Thr Pro Gly Gly  Gly Gly Ser
    2075                2080                2085

Ser Ala  Ala Arg Arg Val Arg  Pro Val Ser Leu Met  Val Pro Ser
    2090                2095                2100

Gln Ala  Gly Ala Pro Gly Arg  Gln Phe His Gly Ser  Ala Ser Ser
    2105                2110                2115

Leu Val  Glu Ala Val Leu Ile  Ser Glu Gly Leu Gly  Gln Phe Ala
    2120                2125                2130

Gln Asp  Pro Lys Phe Ile Glu  Val Thr Thr Gln Glu  Leu Ala Asp
    2135                2140                2145

Ala Cys  Asp Met Thr Ile Glu  Glu Met Glu Ser Ala  Ala Asp Asn
    2150                2155                2160

Ile Leu  Ser Gly Gly Ala Pro  Gln Ser Pro Asn Gly  Ala Leu Leu
    2165                2170                2175

Pro Phe  Val Asn Cys Arg Asp  Ala Gly Gln Asp Arg  Ala Gly Gly
    2180                2185                2190

Glu Glu  Asp Ala Gly Cys Val  Arg Ala Arg Gly Arg  Pro Ser Glu
    2195                2200                2205

Glu Glu  Leu Gln Asp Ser Arg  Val Tyr Val Ser Ser  Leu
    2210                2215                2220


<210> SEQ ID NO 135
<211> LENGTH: 1927
<212> TYPE: PRT
<213> ORGANISM: Homo sapiens

<400> SEQUENCE: 135

Met Glu Leu Ser Trp His Val Val Phe Ile Ala Leu Leu Ser Phe Ser
1               5                   10                  15

Cys Trp Gly Ser Asp Trp Glu Ser Asp Arg Asn Phe Ile Ser Thr Ala
            20                  25                  30

Gly Pro Leu Thr Asn Asp Leu Leu His Asn Leu Ser Gly Leu Leu Gly
        35                  40                  45

Asp Gln Ser Ser Asn Phe Val Ala Gly Asp Lys Asp Met Tyr Val Cys
    50                  55                  60

His Gln Pro Leu Pro Thr Phe Leu Pro Glu Tyr Phe Ser Ser Leu His
65                  70                  75                  80
```

-continued

```
Ala Ser Gln Ile Thr His Tyr Lys Val Phe Leu Ser Trp Ala Gln Leu
                85                  90                  95

Leu Pro Ala Gly Ser Thr Gln Asn Pro Asp Glu Lys Thr Val Gln Cys
            100                 105                 110

Tyr Arg Arg Leu Leu Lys Ala Leu Lys Thr Ala Arg Leu Gln Pro Met
        115                 120                 125

Val Ile Leu His His Gln Thr Leu Pro Ala Ser Thr Leu Arg Arg Thr
    130                 135                 140

Glu Ala Phe Ala Asp Leu Phe Ala Asp Tyr Ala Thr Phe Ala Phe His
145                 150                 155                 160

Ser Phe Gly Asp Leu Val Gly Ile Trp Phe Thr Phe Ser Asp Leu Glu
                165                 170                 175

Glu Val Ile Lys Glu Leu Pro His Gln Glu Ser Arg Ala Ser Gln Leu
            180                 185                 190

Gln Thr Leu Ser Asp Ala His Arg Lys Ala Tyr Glu Ile Tyr His Glu
        195                 200                 205

Ser Tyr Ala Phe Gln Gly Gly Lys Leu Ser Val Val Leu Arg Ala Glu
    210                 215                 220

Asp Ile Pro Glu Leu Leu Leu Glu Pro Pro Ile Ser Ala Leu Ala Gln
225                 230                 235                 240

Asp Thr Val Asp Phe Leu Ser Leu Asp Leu Ser Tyr Glu Cys Gln Asn
                245                 250                 255

Glu Ala Ser Leu Arg Gln Lys Leu Ser Lys Leu Gln Thr Ile Glu Pro
            260                 265                 270

Lys Val Lys Val Phe Ile Phe Asn Leu Lys Leu Pro Asp Cys Pro Ser
        275                 280                 285

Thr Met Lys Asn Pro Ala Ser Leu Leu Phe Ser Leu Phe Glu Ala Ile
    290                 295                 300

Asn Lys Asp Gln Val Leu Thr Ile Gly Phe Asp Ile Asn Glu Phe Leu
305                 310                 315                 320

Ser Cys Ser Ser Ser Ser Lys Lys Ser Met Ser Cys Ser Leu Thr Gly
                325                 330                 335

Ser Leu Ala Leu Gln Pro Asp Gln Gln Gln Asp His Glu Thr Thr Asp
            340                 345                 350

Ser Ser Pro Ala Ser Ala Tyr Gln Arg Val Trp Glu Ala Phe Ala Asn
        355                 360                 365

Gln Ser Arg Ala Glu Arg Asp Ala Phe Leu Gln Asp Thr Phe Pro Glu
    370                 375                 380

Gly Phe Leu Trp Gly Ala Ser Thr Gly Ala Phe Asn Val Glu Gly Gly
385                 390                 395                 400

Trp Ala Glu Gly Gly Arg Gly Val Ser Ile Trp Asp Pro Arg Arg Pro
                405                 410                 415

Leu Asn Thr Thr Glu Gly Gln Ala Thr Leu Glu Val Ala Ser Asp Ser
            420                 425                 430

Tyr His Lys Val Ala Ser Asp Val Ala Leu Leu Cys Gly Leu Arg Ala
        435                 440                 445

Gln Val Tyr Lys Phe Ser Ile Ser Trp Ser Arg Ile Phe Pro Met Gly
    450                 455                 460

His Gly Ser Ser Pro Ser Leu Pro Gly Val Ala Tyr Tyr Asn Lys Leu
465                 470                 475                 480

Ile Asp Arg Leu Gln Asp Ala Gly Ile Glu Pro Met Ala Thr Leu Phe
                485                 490                 495

His Trp Asp Leu Pro Gln Ala Leu Gln Asp His Gly Gly Trp Gln Asn
```

-continued

```
            500                 505                 510

Glu Ser Val Val Asp Ala Phe Leu Asp Tyr Ala Ala Phe Cys Phe Ser
        515                 520                 525

Thr Phe Gly Asp Arg Val Lys Leu Trp Val Thr Phe His Glu Pro Trp
    530                 535                 540

Val Met Ser Tyr Ala Gly Tyr Gly Thr Gly Gln His Pro Pro Gly Ile
545                 550                 555                 560

Ser Asp Pro Gly Val Ala Ser Phe Lys Val Ala His Leu Val Leu Lys
                565                 570                 575

Ala His Ala Arg Thr Trp His His Tyr Asn Ser His His Arg Pro Gln
            580                 585                 590

Gln Gln Gly His Val Gly Ile Val Leu Asn Ser Asp Trp Ala Glu Pro
        595                 600                 605

Leu Ser Pro Glu Arg Pro Glu Asp Leu Arg Ala Ser Glu Arg Phe Leu
    610                 615                 620

His Phe Met Leu Gly Trp Phe Ala His Pro Val Phe Val Asp Gly Asp
625                 630                 635                 640

Tyr Pro Ala Thr Leu Arg Thr Gln Ile Gln Gln Met Asn Arg Gln Cys
                645                 650                 655

Ser His Pro Val Ala Gln Leu Pro Glu Phe Thr Glu Ala Glu Lys Gln
            660                 665                 670

Leu Leu Lys Gly Ser Ala Asp Phe Leu Gly Leu Ser His Tyr Thr Ser
        675                 680                 685

Arg Leu Ile Ser Asn Ala Pro Gln Asn Thr Cys Ile Pro Ser Tyr Asp
    690                 695                 700

Thr Ile Gly Gly Phe Ser Gln His Val Asn His Val Trp Pro Gln Thr
705                 710                 715                 720

Ser Ser Ser Trp Ile Arg Val Val Pro Trp Gly Ile Arg Arg Leu Leu
                725                 730                 735

Gln Phe Val Ser Leu Glu Tyr Thr Arg Gly Lys Val Pro Ile Tyr Leu
            740                 745                 750

Ala Gly Asn Gly Met Pro Ile Gly Glu Ser Glu Asn Leu Phe Asp Asp
        755                 760                 765

Ser Leu Arg Val Asp Tyr Phe Asn Gln Tyr Ile Asn Glu Val Leu Lys
    770                 775                 780

Ala Ile Lys Glu Asp Ser Val Asp Val Arg Ser Tyr Ile Ala Arg Ser
785                 790                 795                 800

Leu Ile Asp Gly Phe Glu Gly Pro Ser Gly Tyr Ser Gln Arg Phe Gly
                805                 810                 815

Leu His His Val Asn Phe Ser Asp Ser Ser Lys Ser Arg Thr Pro Arg
            820                 825                 830

Lys Ser Ala Tyr Phe Phe Thr Ser Ile Ile Glu Lys Asn Gly Phe Leu
        835                 840                 845

Thr Lys Gly Ala Lys Arg Leu Leu Pro Pro Asn Thr Val Asn Leu Pro
    850                 855                 860

Ser Lys Val Arg Ala Phe Thr Phe Pro Ser Glu Val Pro Ser Lys Ala
865                 870                 875                 880

Lys Val Val Trp Glu Lys Phe Ser Ser Gln Pro Lys Phe Glu Arg Asp
                885                 890                 895

Leu Phe Tyr His Gly Thr Phe Arg Asp Asp Phe Leu Trp Gly Val Ser
            900                 905                 910

Ser Ser Ala Tyr Gln Ile Glu Gly Ala Trp Asp Ala Asp Gly Lys Gly
        915                 920                 925
```

-continued

```
Pro Ser Ile Trp Asp Asn Phe Thr His Thr Pro Gly Ser Asn Val Lys
    930                 935                 940

Asp Asn Ala Thr Gly Asp Ile Ala Cys Asp Ser Tyr His Gln Leu Asp
945                 950                 955                 960

Ala Asp Leu Asn Met Leu Arg Ala Leu Lys Val Lys Ala Tyr Arg Phe
                965                 970                 975

Ser Ile Ser Trp Ser Arg Ile Phe Pro Thr Gly Arg Asn Ser Ser Ile
            980                 985                 990

Asn Ser His Gly Val Asp Tyr Tyr  Asn Arg Leu Ile Asn  Gly Leu Val
        995                 1000                1005

Ala Ser  Asn Ile Phe Pro Met  Val Thr Leu Phe His  Trp Asp Leu
    1010                1015                1020

Pro Gln  Ala Leu Gln Asp Ile  Gly Gly Trp Glu Asn  Pro Ala Leu
    1025                1030                1035

Ile Asp  Leu Phe Asp Ser Tyr  Ala Asp Phe Cys Phe  Gln Thr Phe
    1040                1045                1050

Gly Asp  Arg Val Lys Phe Trp  Met Thr Phe Asn Glu  Pro Met Tyr
    1055                1060                1065

Leu Ala  Trp Leu Gly Tyr Gly  Ser Gly Glu Phe Pro  Pro Gly Val
    1070                1075                1080

Lys Asp  Pro Gly Trp Ala Pro  Tyr Arg Ile Ala His  Ala Val Ile
    1085                1090                1095

Lys Ala  His Ala Arg Val Tyr  His Thr Tyr Asp Glu  Lys Tyr Arg
    1100                1105                1110

Gln Glu  Gln Lys Gly Val Ile  Ser Leu Ser Leu Ser  Thr His Trp
    1115                1120                1125

Ala Glu  Pro Lys Ser Pro Gly  Val Pro Arg Asp Val  Glu Ala Ala
    1130                1135                1140

Asp Arg  Met Leu Gln Phe Ser  Leu Gly Trp Phe Ala  His Pro Ile
    1145                1150                1155

Phe Arg  Asn Gly Asp Tyr Pro  Asp Thr Met Lys Trp  Lys Val Gly
    1160                1165                1170

Asn Arg  Ser Glu Leu Gln His  Leu Ala Thr Ser Arg  Leu Pro Ser
    1175                1180                1185

Phe Thr  Glu Glu Glu Lys Arg  Phe Ile Arg Ala Thr  Ala Asp Val
    1190                1195                1200

Phe Cys  Leu Asn Thr Tyr Tyr  Ser Arg Ile Val Gln  His Lys Thr
    1205                1210                1215

Pro Arg  Leu Asn Pro Pro Ser  Tyr Glu Asp Asp Gln  Glu Met Ala
    1220                1225                1230

Glu Glu  Glu Asp Pro Ser Trp  Pro Ser Thr Ala Met  Asn Arg Ala
    1235                1240                1245

Ala Pro  Trp Gly Thr Arg Arg  Leu Leu Asn Trp Ile  Lys Glu Glu
    1250                1255                1260

Tyr Gly  Asp Ile Pro Ile Tyr  Ile Thr Glu Asn Gly  Val Gly Leu
    1265                1270                1275

Thr Asn  Pro Asn Thr Glu Asp  Thr Asp Arg Ile Phe  Tyr His Lys
    1280                1285                1290

Thr Tyr  Ile Asn Glu Ala Leu  Lys Ala Tyr Arg Leu  Asp Gly Ile
    1295                1300                1305

Asp Leu  Arg Gly Tyr Val Ala  Trp Ser Leu Met Asp  Asn Phe Glu
    1310                1315                1320
```

```
Trp Leu  Asn Gly Tyr Thr Val  Lys Phe Gly Leu Tyr  His Val Asp
    1325                 1330                 1335

Phe Asn  Asn Thr Asn Arg Pro  Arg Thr Ala Arg Ala  Ser Ala Arg
    1340                 1345                 1350

Tyr Tyr  Thr Glu Val Ile Thr  Asn Asn Gly Met Pro  Leu Ala Arg
    1355                 1360                 1365

Glu Asp  Glu Phe Leu Tyr Gly  Arg Phe Pro Glu Gly  Phe Ile Trp
    1370                 1375                 1380

Ser Ala  Ala Ser Ala Ala Tyr  Gln Ile Glu Gly Ala  Trp Arg Ala
    1385                 1390                 1395

Asp Gly  Lys Gly Leu Ser Ile  Trp Asp Thr Phe Ser  His Thr Pro
    1400                 1405                 1410

Leu Arg  Val Glu Asn Asp Ala  Ile Gly Asp Val Ala  Cys Asp Ser
    1415                 1420                 1425

Tyr His  Lys Ile Ala Glu Asp  Leu Val Thr Leu Gln  Asn Leu Gly
    1430                 1435                 1440

Val Ser  His Tyr Arg Phe Ser  Ile Ser Trp Ser Arg  Ile Leu Pro
    1445                 1450                 1455

Asp Gly  Thr Thr Arg Tyr Ile  Asn Glu Ala Gly Leu  Asn Tyr Tyr
    1460                 1465                 1470

Val Arg  Leu Ile Asp Thr Leu  Leu Ala Ala Ser Ile  Gln Pro Gln
    1475                 1480                 1485

Val Thr  Ile Tyr His Trp Asp  Leu Pro Gln Thr Leu  Gln Asp Val
    1490                 1495                 1500

Gly Gly  Trp Glu Asn Glu Thr  Ile Val Gln Arg Phe  Lys Glu Tyr
    1505                 1510                 1515

Ala Asp  Val Leu Phe Gln Arg  Leu Gly Asp Lys Val  Lys Phe Trp
    1520                 1525                 1530

Ile Thr  Leu Asn Glu Pro Phe  Val Ile Ala Tyr Gln  Gly Tyr Gly
    1535                 1540                 1545

Tyr Gly  Thr Ala Ala Pro Gly  Val Ser Asn Arg Pro  Gly Thr Ala
    1550                 1555                 1560

Pro Tyr  Ile Val Gly His Asn  Leu Ile Lys Ala His  Ala Glu Ala
    1565                 1570                 1575

Trp His  Leu Tyr Asn Asp Val  Tyr Arg Ala Ser Gln  Gly Gly Val
    1580                 1585                 1590

Ile Ser  Ile Thr Ile Ser Ser  Asp Trp Ala Glu Pro  Arg Asp Pro
    1595                 1600                 1605

Ser Asn  Gln Glu Asp Val Glu  Ala Ala Arg Arg Tyr  Val Gln Phe
    1610                 1615                 1620

Met Gly  Gly Trp Phe Ala His  Pro Ile Phe Lys Asn  Gly Asp Tyr
    1625                 1630                 1635

Asn Glu  Val Met Lys Thr Arg  Ile Arg Asp Arg Ser  Leu Ala Ala
    1640                 1645                 1650

Gly Leu  Asn Lys Ser Arg Leu  Pro Glu Phe Thr Glu  Ser Glu Lys
    1655                 1660                 1665

Arg Arg  Ile Asn Gly Thr Tyr  Asp Phe Phe Gly Phe  Asn His Tyr
    1670                 1675                 1680

Thr Thr  Val Leu Ala Tyr Asn  Leu Asn Tyr Ala Thr  Ala Ile Ser
    1685                 1690                 1695

Ser Phe  Asp Ala Asp Arg Gly  Val Ala Ser Ile Ala  Asp Arg Ser
    1700                 1705                 1710

Trp Pro  Asp Ser Gly Ser Phe  Trp Leu Lys Met Thr  Pro Phe Gly
```

-continued

```
    1715                1720                1725

Phe Arg  Arg Ile Leu Asn Trp  Leu Lys Glu Glu Tyr  Asn Asp Pro
    1730                1735                1740

Pro Ile  Tyr Val Thr Glu Asn  Gly Val Ser Gln Arg  Glu Glu Thr
    1745                1750                1755

Asp Leu  Asn Asp Thr Ala Arg  Ile Tyr Tyr Leu Arg  Thr Tyr Ile
    1760                1765                1770

Asn Glu  Ala Leu Lys Ala Val  Gln Asp Lys Val Asp  Leu Arg Gly
    1775                1780                1785

Tyr Thr  Val Trp Ser Ala Met  Asp Asn Phe Glu Trp  Ala Thr Gly
    1790                1795                1800

Phe Ser  Glu Arg Phe Gly Leu  His Phe Val Asn Tyr  Ser Asp Pro
    1805                1810                1815

Ser Leu  Pro Arg Ile Pro Lys  Ala Ser Ala Lys Phe  Tyr Ala Ser
    1820                1825                1830

Val Val  Arg Cys Asn Gly Phe  Pro Asp Pro Ala Thr  Gly Pro His
    1835                1840                1845

Ala Cys  Leu His Gln Pro Asp  Ala Gly Pro Thr Ile  Ser Pro Val
    1850                1855                1860

Arg Gln  Glu Glu Val Gln Phe  Leu Gly Leu Met Leu  Gly Thr Thr
    1865                1870                1875

Glu Ala  Gln Thr Ala Leu Tyr  Val Leu Phe Ser Leu  Val Leu Leu
    1880                1885                1890

Gly Val  Cys Gly Leu Ala Phe  Leu Ser Tyr Lys Tyr  Cys Lys Arg
    1895                1900                1905

Ser Lys  Gln Gly Lys Thr Gln  Arg Ser Gln Gln Glu  Leu Ser Pro
    1910                1915                1920

Val Ser  Ser Phe
    1925


<210> SEQ ID NO 136
<211> LENGTH: 465
<212> TYPE: PRT
<213> ORGANISM: Homo sapiens

<400> SEQUENCE: 136

Met Leu Pro Leu Trp Thr Leu Ser Leu Leu Leu Gly Ala Val Ala Gly
1               5                   10                  15

Lys Glu Val Cys Tyr Glu Arg Leu Gly Cys Phe Ser Asp Asp Ser Pro
            20                  25                  30

Trp Ser Gly Ile Thr Glu Arg Pro Leu His Ile Leu Pro Trp Ser Pro
        35                  40                  45

Lys Asp Val Asn Thr Arg Phe Leu Leu Tyr Thr Asn Glu Asn Pro Asn
    50                  55                  60

Asn Phe Gln Glu Val Ala Ala Asp Ser Ser Ser Ile Ser Gly Ser Asn
65                  70                  75                  80

Phe Lys Thr Asn Arg Lys Thr Arg Phe Ile Ile His Gly Phe Ile Asp
                85                  90                  95

Lys Gly Glu Glu Asn Trp Leu Ala Asn Val Cys Lys Asn Leu Phe Lys
            100                 105                 110

Val Glu Ser Val Asn Cys Ile Cys Val Asp Trp Lys Gly Gly Ser Arg
        115                 120                 125

Thr Gly Tyr Thr Gln Ala Ser Gln Asn Ile Arg Ile Val Gly Ala Glu
    130                 135                 140
```

-continued

Val Ala Tyr Phe Val Glu Phe Leu Gln Ser Ala Phe Gly Tyr Ser Pro
145 150 155 160

Ser Asn Val His Val Ile Gly His Ser Leu Gly Ala His Ala Ala Gly
165 170 175

Glu Ala Gly Arg Arg Thr Asn Gly Thr Ile Gly Arg Ile Thr Gly Leu
180 185 190

Asp Pro Ala Glu Pro Cys Phe Gln Gly Thr Pro Glu Leu Val Arg Leu
195 200 205

Asp Pro Ser Asp Ala Lys Phe Val Asp Val Ile His Thr Asp Gly Ala
210 215 220

Pro Ile Val Pro Asn Leu Gly Phe Gly Met Ser Gln Val Val Gly His
225 230 235 240

Leu Asp Phe Phe Pro Asn Gly Gly Val Glu Met Pro Gly Cys Lys Lys
245 250 255

Asn Ile Leu Ser Gln Ile Val Asp Ile Asp Gly Ile Trp Glu Gly Thr
260 265 270

Arg Asp Phe Ala Ala Cys Asn His Leu Arg Ser Tyr Lys Tyr Tyr Thr
275 280 285

Asp Ser Ile Val Asn Pro Asp Gly Phe Ala Gly Phe Pro Cys Ala Ser
290 295 300

Tyr Asn Val Phe Thr Ala Asn Lys Cys Phe Pro Cys Pro Ser Gly Gly
305 310 315 320

Cys Pro Gln Met Gly His Tyr Ala Asp Arg Tyr Pro Gly Lys Thr Asn
325 330 335

Asp Val Gly Gln Lys Phe Tyr Leu Asp Thr Gly Asp Ala Ser Asn Phe
340 345 350

Ala Arg Trp Arg Tyr Lys Val Ser Val Thr Leu Ser Gly Lys Lys Val
355 360 365

Thr Gly His Ile Leu Val Ser Leu Phe Gly Asn Lys Gly Asn Ser Lys
370 375 380

Gln Tyr Glu Ile Phe Lys Gly Thr Leu Lys Pro Asp Ser Thr His Ser
385 390 395 400

Asn Glu Phe Asp Ser Asp Val Asp Val Gly Asp Leu Gln Met Val Lys
405 410 415

Phe Ile Trp Tyr Asn Asn Val Ile Asn Pro Thr Leu Pro Arg Val Gly
420 425 430

Ala Ser Lys Ile Ile Val Glu Thr Asn Val Gly Lys Gln Phe Asn Phe
435 440 445

Cys Ser Pro Glu Thr Val Arg Glu Glu Val Leu Leu Thr Leu Thr Pro
450 455 460

Cys
465

<210> SEQ ID NO 137
<211> LENGTH: 824
<212> TYPE: PRT
<213> ORGANISM: Homo sapiens

<400> SEQUENCE: 137

Met Ser Ile Ser Ser Leu Phe Gly Gly Arg Tyr Asp Asn Lys Phe Leu
1 5 10 15

Leu Asn Met Ser Ser Ala Pro Lys Ile Glu Leu Ile Val Asp Lys Val
20 25 30

Ala Ser Leu Ser Glu Gly Arg Leu Glu Gly Arg Leu Pro Glu Asp Trp
35 40 45

```
Phe Arg His Ile Met Asp Pro Glu Thr Glu Phe Asn Ser Glu Phe Ala
    50                  55                  60

Asp Ala Leu Cys Ile Gly Ile Asp Glu Phe Ala Gln Pro Leu Pro Phe
65                  70                  75                  80

Leu Pro Phe Lys Ala Leu Leu Val Thr Gly Thr Ala Gly Ala Gly Lys
                85                  90                  95

Thr Asn Ser Ile Gln Thr Leu Ala Ala Asn Leu Asp Cys Ile Val Thr
            100                 105                 110

Ala Thr Thr Ser Ile Ala Ala Gln Asn Leu Ser Val Val Leu Asn Arg
        115                 120                 125

Ser Lys Ser Ala Gln Val Lys Thr Ile Phe Lys Thr Phe Gly Phe Asn
    130                 135                 140

Ser Ser His Val Ser Met Ser Glu Arg Gln Ser Tyr Ile Ala Asn Asp
145                 150                 155                 160

Glu Arg Ser Ile Gln Ile Gln Gln Lys Gln Asp Leu Ser Ile Tyr Trp
                165                 170                 175

Asn Val Ile Ser Asp Ile Ala Asp Arg Ala Leu Gly Ala Val Ala Cys
            180                 185                 190

Lys Thr Lys Glu Leu Pro Asp Leu Cys Glu Ser Ser Val Ile Val Ile
        195                 200                 205

Asp Glu Ala Gly Val Ile Leu Arg His Ile Leu His Thr Val Val Phe
    210                 215                 220

Phe Tyr Trp Phe Tyr Asn Ala Leu Tyr Lys Thr Pro Leu Tyr Glu Asp
225                 230                 235                 240

Gly Ile Val Pro Cys Ile Val Cys Val Gly Ser Pro Thr Gln Ser Asn
                245                 250                 255

Ala Leu Val Thr Ser Phe Asn Pro Leu Thr Gln Asn Lys Asp Val Lys
            260                 265                 270

Arg Gly Ile Asp Val Leu Ser Ala Leu Ile Cys Asp Asp Val Leu Ser
        275                 280                 285

Lys Tyr Cys Glu Val Asp Asn Asn Trp Ile Ile Phe Val Asn Asn Lys
    290                 295                 300

Arg Cys Ala Asp His Ala Phe Gly Asp Phe Leu Lys His Ile Glu Phe
305                 310                 315                 320

Gly Leu Pro Leu Lys Pro Glu Leu Ile Glu Tyr Val Asp Gln Phe Val
                325                 330                 335

Lys Pro Ala Ser Tyr Ile Arg Asn Pro Met Asn Glu Ile Glu Thr Thr
            340                 345                 350

Arg Leu Phe Leu Ser His Asn Glu Val Lys Asn Tyr Phe Arg Ser Leu
        355                 360                 365

His Glu Gln Val Glu Val Thr Asn Arg Asn Asn Leu Phe Val Phe Pro
    370                 375                 380

Val Tyr Phe Leu Ile Lys Asn Lys Thr Phe Glu Asp Tyr Lys Ser Glu
385                 390                 395                 400

Ile Gly Asn Phe Ser Leu Glu Ile Glu Pro Trp Phe Lys Ser Asn Ile
                405                 410                 415

His Arg Leu Asn Thr Tyr Ser Gln Phe Ala Asp Gln Asp Leu Ser Lys
            420                 425                 430

Thr Val Gln Leu Glu Glu Ile Val Leu Glu Asp Gly Ser Val Glu Glu
        435                 440                 445

Thr Leu Ile Thr Cys His Leu Lys His Ile Arg Asn Ser Ser Ile Gly
    450                 455                 460
```

-continued

Val Thr Ser Lys Ile Lys Ala Ser Thr Val Gly Phe Ser Gly Thr Tyr
465 470 475 480

Glu Lys Phe Val Glu Leu Leu Gln Ser Asp Leu Phe Ile Glu Lys Thr
485 490 495

Ser Cys Asp Gln Thr Ile His Ala Tyr Ser Phe Leu Ser Gly Leu Met
500 505 510

Phe Gly Gly Met Tyr Ser Phe Cys Cys Ser Lys Phe Thr Thr Pro Glu
515 520 525

Val Leu Met Glu Ile Lys Asn Ile Lys Met Pro Ser Ile Glu Phe Leu
530 535 540

Glu Ser Glu Met Ser Arg Met Ser Pro Asp Val Gln Thr Val Glu Thr
545 550 555 560

Asp Glu Arg Tyr Asp Phe Gly Leu Val Asp Asp Gly Leu Ser Asp Val
565 570 575

Asp Leu Leu Glu Ile Asp Pro Cys Gly Asp Pro Phe Phe Thr Arg Tyr
580 585 590

Ser Lys Leu Pro Leu Thr Asn Ser Leu Ser Phe Glu Glu Ile Ser Leu
595 600 605

Leu Tyr Thr Thr Phe Lys Asp Ile Phe Ile Ser Arg Phe Ala Ile Leu
610 615 620

Gln Lys His Thr Lys Gly Lys Phe Gly Lys Thr Leu Leu Val Thr Tyr
625 630 635 640

Asn Arg Asn Asn Val Ser Arg Lys Gln Cys Gly Glu Ile Tyr Ser His
645 650 655

Leu Lys Ser Phe Tyr Gly Met Leu Thr Tyr Ala Ile Pro Ala Asn Asn
660 665 670

Tyr Thr Leu Glu Gly Tyr Thr Asn Asp Asn Val Val His Leu Gly Thr
675 680 685

Asp Lys Gln Leu Pro Gln Ile Leu Tyr Lys Lys Gly Leu Pro Arg Leu
690 695 700

Val Ile Lys Asp Glu Met Gly Phe Ile Ser Val Leu Asp Asn Asn Val
705 710 715 720

Ser Lys Phe Ile Asp Val Val Asn Gly Gln Ser Phe His Leu Cys Thr
725 730 735

Thr Val Asp Tyr Ala Thr Val Ser Lys Val Ser Met Thr Ile Thr Lys
740 745 750

Ser Gln Gly Leu Ser Ile Gln Lys Val Ala Ile Asp Phe Gly Ser Asp
755 760 765

Pro Lys Asn Leu Lys Leu Ser Ser Ile Tyr Val Gly Met Ser Arg Val
770 775 780

Thr Asp Pro Asn Asn Leu Ile Met Asn Val Asn Pro Leu Arg Leu Asn
785 790 795 800

Tyr Glu Asn Asp Asn Phe Ile Ala Pro His Ile Val Lys Ala Leu Lys
805 810 815

Asn Glu Asn Thr Met Leu Ile Phe
820

<210> SEQ ID NO 138
<211> LENGTH: 511
<212> TYPE: PRT
<213> ORGANISM: Homo sapiens

<400> SEQUENCE: 138

Met Lys Phe Phe Leu Leu Leu Phe Thr Ile Gly Phe Cys Trp Ala Gln
1 5 10 15

-continued

```
Tyr Ser Pro Asn Thr Gln Gln Gly Arg Thr Ser Ile Val His Leu Phe
            20                  25                  30

Glu Trp Arg Trp Val Asp Ile Ala Leu Glu Cys Glu Arg Tyr Leu Ala
        35                  40                  45

Pro Lys Gly Phe Gly Gly Val Gln Val Ser Pro Pro Asn Glu Asn Val
    50                  55                  60

Ala Ile Tyr Asn Pro Phe Arg Pro Trp Trp Glu Arg Tyr Gln Pro Val
65                  70                  75                  80

Ser Tyr Lys Leu Cys Thr Arg Ser Gly Asn Glu Asp Glu Phe Arg Asn
                85                  90                  95

Met Val Thr Arg Cys Asn Asn Val Gly Val Arg Ile Tyr Val Asp Ala
            100                 105                 110

Val Ile Asn His Met Cys Gly Asn Ala Val Ser Ala Gly Thr Ser Ser
        115                 120                 125

Thr Cys Gly Ser Tyr Phe Asn Pro Gly Ser Arg Asp Phe Pro Ala Val
    130                 135                 140

Pro Tyr Ser Gly Trp Asp Phe Asn Asp Gly Lys Cys Lys Thr Gly Ser
145                 150                 155                 160

Gly Asp Ile Glu Asn Tyr Asn Asp Ala Thr Gln Val Arg Asp Cys Arg
                165                 170                 175

Leu Thr Gly Leu Leu Asp Leu Ala Leu Glu Lys Asp Tyr Val Arg Ser
            180                 185                 190

Lys Ile Ala Glu Tyr Met Asn His Leu Ile Asp Ile Gly Val Ala Gly
        195                 200                 205

Phe Arg Leu Asp Ala Ser Lys His Met Trp Pro Gly Asp Ile Lys Ala
    210                 215                 220

Ile Leu Asp Lys Leu His Asn Leu Asn Ser Asn Trp Phe Pro Ala Gly
225                 230                 235                 240

Ser Lys Pro Phe Ile Tyr Gln Glu Val Ile Asp Leu Gly Gly Glu Pro
                245                 250                 255

Ile Lys Ser Ser Asp Tyr Phe Gly Asn Gly Arg Val Thr Glu Phe Lys
            260                 265                 270

Tyr Gly Ala Lys Leu Gly Thr Val Ile Arg Lys Trp Asn Gly Glu Lys
        275                 280                 285

Met Ser Tyr Leu Lys Asn Trp Gly Glu Gly Trp Gly Phe Val Pro Ser
    290                 295                 300

Asp Arg Ala Leu Val Phe Val Asp Asn His Asp Asn Gln Arg Gly His
305                 310                 315                 320

Gly Ala Gly Gly Ala Ser Ile Leu Thr Phe Trp Asp Ala Arg Leu Tyr
                325                 330                 335

Lys Met Ala Val Gly Phe Met Leu Ala His Pro Tyr Gly Phe Thr Arg
            340                 345                 350

Val Met Ser Ser Tyr Arg Trp Pro Arg Gln Phe Gln Asn Gly Asn Asp
        355                 360                 365

Val Asn Asp Trp Val Gly Pro Pro Asn Asn Asn Gly Val Ile Lys Glu
    370                 375                 380

Val Thr Ile Asn Pro Asp Thr Thr Cys Gly Asn Asp Trp Val Cys Glu
385                 390                 395                 400

His Arg Trp Arg Gln Ile Arg Asn Met Val Ile Phe Arg Asn Val Val
                405                 410                 415

Asp Gly Gln Pro Phe Thr Asn Trp Tyr Asp Asn Gly Ser Asn Gln Val
            420                 425                 430
```

```
Ala Phe Gly Arg Gly Asn Arg Gly Phe Ile Val Phe Asn Asn Asp Asp
        435                 440                 445

Trp Ser Phe Ser Leu Thr Leu Gln Thr Gly Leu Pro Ala Gly Thr Tyr
    450                 455                 460

Cys Asp Val Ile Ser Gly Asp Lys Ile Asn Gly Asn Cys Thr Gly Ile
465                 470                 475                 480

Lys Ile Tyr Val Ser Asp Asp Gly Lys Ala His Phe Ser Ile Ser Asn
                485                 490                 495

Ser Ala Glu Asp Pro Phe Ile Ala Ile His Ala Glu Ser Lys Leu
            500                 505                 510


<210> SEQ ID NO 139
<211> LENGTH: 952
<212> TYPE: PRT
<213> ORGANISM: Homo sapiens

<400> SEQUENCE: 139

Met Gly Val Arg His Pro Pro Cys Ser His Arg Leu Leu Ala Val Cys
1               5                   10                  15

Ala Leu Val Ser Leu Ala Thr Ala Ala Leu Leu Gly His Ile Leu Leu
            20                  25                  30

His Asp Phe Leu Leu Val Pro Arg Glu Leu Ser Gly Ser Ser Pro Val
        35                  40                  45

Leu Glu Glu Thr His Pro Ala His Gln Gln Gly Ala Ser Arg Pro Gly
    50                  55                  60

Pro Arg Asp Ala Gln Ala His Pro Gly Arg Pro Arg Ala Val Pro Thr
65                  70                  75                  80

Gln Cys Asp Val Pro Pro Asn Ser Arg Phe Asp Cys Ala Pro Asp Lys
                85                  90                  95

Ala Ile Thr Gln Glu Gln Cys Glu Ala Arg Gly Cys Cys Tyr Ile Pro
            100                 105                 110

Ala Lys Gln Gly Leu Gln Gly Ala Gln Met Gly Gln Pro Trp Cys Phe
        115                 120                 125

Phe Pro Pro Ser Tyr Pro Ser Tyr Lys Leu Glu Asn Leu Ser Ser Ser
    130                 135                 140

Glu Met Gly Tyr Thr Ala Thr Leu Thr Arg Thr Thr Pro Thr Phe Phe
145                 150                 155                 160

Pro Lys Asp Ile Leu Thr Leu Arg Leu Asp Val Met Met Glu Thr Glu
                165                 170                 175

Asn Arg Leu His Phe Thr Ile Lys Asp Pro Ala Asn Arg Arg Tyr Glu
            180                 185                 190

Val Pro Leu Glu Thr Pro Arg Val His Ser Arg Ala Pro Ser Pro Leu
        195                 200                 205

Tyr Ser Val Glu Phe Ser Glu Glu Pro Phe Gly Val Ile Val His Arg
    210                 215                 220

Gln Leu Asp Gly Arg Val Leu Leu Asn Thr Thr Val Ala Pro Leu Phe
225                 230                 235                 240

Phe Ala Asp Gln Phe Leu Gln Leu Ser Thr Ser Leu Pro Ser Gln Tyr
                245                 250                 255

Ile Thr Gly Leu Ala Glu His Leu Ser Pro Leu Met Leu Ser Thr Ser
            260                 265                 270

Trp Thr Arg Ile Thr Leu Trp Asn Arg Asp Leu Ala Pro Thr Pro Gly
        275                 280                 285

Ala Asn Leu Tyr Gly Ser His Pro Phe Tyr Leu Ala Leu Glu Asp Gly
    290                 295                 300
```

-continued

```
Gly Ser Ala His Gly Val Phe Leu Leu Asn Ser Asn Ala Met Asp Val
305                 310                 315                 320

Val Leu Gln Pro Ser Pro Ala Leu Ser Trp Arg Ser Thr Gly Gly Ile
                325                 330                 335

Leu Asp Val Tyr Ile Phe Leu Gly Pro Glu Pro Lys Ser Val Val Gln
            340                 345                 350

Gln Tyr Leu Asp Val Val Gly Tyr Pro Phe Met Pro Pro Tyr Trp Gly
        355                 360                 365

Leu Gly Phe His Leu Cys Arg Trp Gly Tyr Ser Ser Thr Ala Ile Thr
    370                 375                 380

Arg Gln Val Val Glu Asn Met Thr Arg Ala His Phe Pro Leu Asp Val
385                 390                 395                 400

Gln Trp Asn Asp Leu Asp Tyr Met Asp Ser Arg Arg Asp Phe Thr Phe
                405                 410                 415

Asn Lys Asp Gly Phe Arg Asp Phe Pro Ala Met Val Gln Glu Leu His
            420                 425                 430

Gln Gly Gly Arg Arg Tyr Met Met Ile Val Asp Pro Ala Ile Ser Ser
        435                 440                 445

Ser Gly Pro Ala Gly Ser Tyr Arg Leu Tyr Asp Glu Gly Leu Arg Arg
    450                 455                 460

Gly Val Phe Ile Thr Asn Glu Thr Gly Gln Pro Leu Ile Gly Lys Val
465                 470                 475                 480

Trp Pro Gly Ser Thr Ala Phe Pro Asp Phe Thr Asn Pro Thr Ala Leu
                485                 490                 495

Ala Trp Trp Glu Asp Met Val Ala Glu Phe His Asp Gln Val Pro Phe
            500                 505                 510

Asp Gly Met Trp Ile Asp Met Asn Glu Pro Ser Asn Phe Ile Arg Gly
        515                 520                 525

Ser Glu Asp Gly Cys Pro Asn Asn Glu Leu Glu Asn Pro Pro Tyr Val
    530                 535                 540

Pro Gly Val Val Gly Gly Thr Leu Gln Ala Ala Thr Ile Cys Ala Ser
545                 550                 555                 560

Ser His Gln Phe Leu Ser Thr His Tyr Asn Leu His Asn Leu Tyr Gly
                565                 570                 575

Leu Thr Glu Ala Ile Ala Ser His Arg Ala Leu Val Lys Ala Arg Gly
            580                 585                 590

Thr Arg Pro Phe Val Ile Ser Arg Ser Thr Phe Ala Gly His Gly Arg
        595                 600                 605

Tyr Ala Gly His Trp Thr Gly Asp Val Trp Ser Ser Trp Glu Gln Leu
    610                 615                 620

Ala Ser Ser Val Pro Glu Ile Leu Gln Phe Asn Leu Leu Gly Val Pro
625                 630                 635                 640

Leu Val Gly Ala Asp Val Cys Gly Phe Leu Gly Asn Thr Ser Glu Glu
                645                 650                 655

Leu Cys Val Arg Trp Thr Gln Leu Gly Ala Phe Tyr Pro Phe Met Arg
            660                 665                 670

Asn His Asn Ser Leu Leu Ser Leu Pro Gln Glu Pro Tyr Ser Phe Ser
        675                 680                 685

Glu Pro Ala Gln Gln Ala Met Arg Lys Ala Leu Thr Leu Arg Tyr Ala
    690                 695                 700

Leu Leu Pro His Leu Tyr Thr Leu Phe His Gln Ala His Val Ala Gly
705                 710                 715                 720
```

```
Glu Thr Val Ala Arg Pro Leu Phe Leu Glu Phe Pro Lys Asp Ser Ser
                725                 730                 735

Thr Trp Thr Val Asp His Gln Leu Leu Trp Gly Glu Ala Leu Leu Ile
            740                 745                 750

Thr Pro Val Leu Gln Ala Gly Lys Ala Glu Val Thr Gly Tyr Phe Pro
        755                 760                 765

Leu Gly Thr Trp Tyr Asp Leu Gln Thr Val Pro Ile Glu Ala Leu Gly
    770                 775                 780

Ser Leu Pro Pro Pro Pro Ala Ala Pro Arg Glu Pro Ala Ile His Ser
785                 790                 795                 800

Glu Gly Gln Trp Val Thr Leu Pro Ala Pro Leu Asp Thr Ile Asn Val
                805                 810                 815

His Leu Arg Ala Gly Tyr Ile Ile Pro Leu Gln Gly Pro Gly Leu Thr
            820                 825                 830

Thr Thr Glu Ser Arg Gln Gln Pro Met Ala Leu Ala Val Ala Leu Thr
        835                 840                 845

Lys Gly Gly Glu Ala Arg Gly Glu Leu Phe Trp Asp Asp Gly Glu Ser
    850                 855                 860

Leu Glu Val Leu Glu Arg Gly Ala Tyr Thr Gln Val Ile Phe Leu Ala
865                 870                 875                 880

Arg Asn Asn Thr Ile Val Asn Glu Leu Val Arg Val Thr Ser Glu Gly
                885                 890                 895

Ala Gly Leu Gln Leu Gln Lys Val Thr Val Leu Gly Val Ala Thr Ala
            900                 905                 910

Pro Gln Gln Val Leu Ser Asn Gly Val Pro Val Ser Asn Phe Thr Tyr
        915                 920                 925

Ser Pro Asp Thr Lys Val Leu Asp Ile Cys Val Ser Leu Leu Met Gly
    930                 935                 940

Glu Gln Phe Leu Val Ser Trp Cys
945                 950
```

<210> SEQ ID NO 140
<211> LENGTH: 785
<212> TYPE: PRT
<213> ORGANISM: Homo sapiens

<400> SEQUENCE: 140

```
Met Ser Asp Gln Asp His Ser Met Asp Glu Met Thr Ala Val Val Lys
1               5                   10                  15

Ile Glu Lys Gly Val Gly Gly Asn Asn Gly Gly Asn Gly Asn Gly Gly
            20                  25                  30

Gly Ala Phe Ser Gln Ala Arg Ser Ser Ser Thr Gly Ser Ser Ser Ser
        35                  40                  45

Thr Gly Gly Gly Gly Gln Glu Ser Gln Pro Ser Pro Leu Ala Leu Leu
    50                  55                  60

Ala Ala Thr Cys Ser Arg Ile Glu Ser Pro Asn Glu Asn Ser Asn Asn
65                  70                  75                  80

Ser Gln Gly Pro Ser Gln Ser Gly Gly Thr Gly Glu Leu Asp Leu Thr
                85                  90                  95

Ala Thr Gln Leu Ser Gln Gly Ala Asn Gly Trp Gln Ile Ile Ser Ser
            100                 105                 110

Ser Ser Gly Ala Thr Pro Thr Ser Lys Glu Gln Ser Gly Ser Ser Thr
        115                 120                 125

Asn Gly Ser Asn Gly Ser Glu Ser Ser Lys Asn Arg Thr Val Ser Gly
    130                 135                 140
```

```
Gly Gln Tyr Val Val Ala Ala Ala Pro Asn Leu Gln Asn Gln Gln Val
145                 150                 155                 160

Leu Thr Gly Leu Pro Gly Val Met Pro Asn Ile Gln Tyr Gln Val Ile
                165                 170                 175

Pro Gln Phe Gln Thr Val Asp Gly Gln Gln Leu Gln Phe Ala Ala Thr
            180                 185                 190

Gly Ala Gln Val Gln Gln Asp Gly Ser Gly Gln Ile Gln Ile Ile Pro
        195                 200                 205

Gly Ala Asn Gln Gln Ile Ile Thr Asn Arg Gly Ser Gly Gly Asn Ile
    210                 215                 220

Ile Ala Ala Met Pro Asn Leu Leu Gln Gln Ala Val Pro Leu Gln Gly
225                 230                 235                 240

Leu Ala Asn Asn Val Leu Ser Gly Gln Thr Gln Tyr Val Thr Asn Val
                245                 250                 255

Pro Val Ala Leu Asn Gly Asn Ile Thr Leu Leu Pro Val Asn Ser Val
            260                 265                 270

Ser Ala Ala Thr Leu Thr Pro Ser Ser Gln Ala Val Thr Ile Ser Ser
        275                 280                 285

Ser Gly Ser Gln Glu Ser Gly Ser Gln Pro Val Thr Ser Gly Thr Thr
    290                 295                 300

Ile Ser Ser Ala Ser Leu Val Ser Ser Gln Ala Ser Ser Ser Ser Phe
305                 310                 315                 320

Phe Thr Asn Ala Asn Ser Tyr Ser Thr Thr Thr Thr Thr Ser Asn Met
                325                 330                 335

Gly Ile Met Asn Phe Thr Thr Ser Gly Ser Ser Gly Thr Asn Ser Gln
            340                 345                 350

Gly Gln Thr Pro Gln Arg Val Ser Gly Leu Gln Gly Ser Asp Ala Leu
        355                 360                 365

Asn Ile Gln Gln Asn Gln Thr Ser Gly Gly Ser Leu Gln Ala Gly Gln
    370                 375                 380

Gln Lys Glu Gly Glu Gln Asn Gln Gln Thr Gln Gln Gln Gln Ile Leu
385                 390                 395                 400

Ile Gln Pro Gln Leu Val Gln Gly Gly Gln Ala Leu Gln Ala Leu Gln
                405                 410                 415

Ala Ala Pro Leu Ser Gly Gln Thr Phe Thr Thr Gln Ala Ile Ser Gln
            420                 425                 430

Glu Thr Leu Gln Asn Leu Gln Leu Gln Ala Val Pro Asn Ser Gly Pro
        435                 440                 445

Ile Ile Ile Arg Thr Pro Thr Val Gly Pro Asn Gly Gln Val Ser Trp
    450                 455                 460

Gln Thr Leu Gln Leu Gln Asn Leu Gln Val Gln Asn Pro Gln Ala Gln
465                 470                 475                 480

Thr Ile Thr Leu Ala Pro Met Gln Gly Val Ser Leu Gly Gln Thr Ser
                485                 490                 495

Ser Ser Asn Thr Thr Leu Thr Pro Ile Ala Ser Ala Ala Ser Ile Pro
            500                 505                 510

Ala Gly Thr Val Thr Val Asn Ala Ala Gln Leu Ser Ser Met Pro Gly
        515                 520                 525

Leu Gln Thr Ile Asn Leu Ser Ala Leu Gly Thr Ser Gly Ile Gln Val
    530                 535                 540

His Pro Ile Gln Gly Leu Pro Leu Ala Ile Ala Asn Ala Pro Gly Asp
545                 550                 555                 560
```

```
His Gly Ala Gln Leu Gly Leu His Gly Ala Gly Gly Asp Gly Ile His
                565                 570                 575

Asp Asp Thr Ala Gly Gly Glu Glu Gly Glu Asn Ser Pro Asp Ala Gln
            580                 585                 590

Pro Gln Ala Gly Arg Arg Thr Arg Arg Glu Ala Cys Thr Cys Pro Tyr
        595                 600                 605

Cys Lys Asp Ser Glu Gly Arg Gly Ser Gly Asp Pro Gly Lys Lys Lys
    610                 615                 620

Gln His Ile Cys His Ile Gln Gly Cys Gly Lys Val Tyr Gly Lys Thr
625                 630                 635                 640

Ser His Leu Arg Ala His Leu Arg Trp His Thr Gly Glu Arg Pro Phe
                645                 650                 655

Met Cys Thr Trp Ser Tyr Cys Gly Lys Arg Phe Thr Arg Ser Asp Glu
            660                 665                 670

Leu Gln Arg His Lys Arg Thr His Thr Gly Glu Lys Lys Phe Ala Cys
        675                 680                 685

Pro Glu Cys Pro Lys Arg Phe Met Arg Ser Asp His Leu Ser Lys His
    690                 695                 700

Ile Lys Thr His Gln Asn Lys Lys Gly Gly Pro Gly Val Ala Leu Ser
705                 710                 715                 720

Val Gly Thr Leu Pro Leu Asp Ser Gly Ala Gly Ser Glu Gly Ser Gly
                725                 730                 735

Thr Ala Thr Pro Ser Ala Leu Ile Thr Thr Asn Met Val Ala Met Glu
            740                 745                 750

Ala Ile Cys Pro Glu Gly Ile Ala Arg Leu Ala Asn Ser Gly Ile Asn
        755                 760                 765

Val Met Gln Val Ala Asp Leu Gln Ser Ile Asn Ile Ser Gly Asn Gly
    770                 775                 780

Phe
785


<210> SEQ ID NO 141
<211> LENGTH: 331
<212> TYPE: PRT
<213> ORGANISM: Homo sapiens

<400> SEQUENCE: 141

Met Thr Ala Lys Met Glu Thr Thr Phe Tyr Asp Asp Ala Leu Asn Ala
1               5                   10                  15

Ser Phe Leu Pro Ser Glu Ser Gly Pro Tyr Gly Tyr Ser Asn Pro Lys
            20                  25                  30

Ile Leu Lys Gln Ser Met Thr Leu Asn Leu Ala Asp Pro Val Gly Ser
        35                  40                  45

Leu Lys Pro His Leu Arg Ala Lys Asn Ser Asp Leu Leu Thr Ser Pro
    50                  55                  60

Asp Val Gly Leu Leu Lys Leu Ala Ser Pro Glu Leu Glu Arg Leu Ile
65                  70                  75                  80

Ile Gln Ser Ser Asn Gly His Ile Thr Thr Thr Pro Thr Pro Thr Gln
                85                  90                  95

Phe Leu Cys Pro Lys Asn Val Thr Asp Glu Gln Glu Gly Phe Ala Glu
            100                 105                 110

Gly Phe Val Arg Ala Leu Ala Glu Leu His Ser Gln Asn Thr Leu Pro
        115                 120                 125

Ser Val Thr Ser Ala Ala Gln Pro Val Asn Gly Ala Gly Met Val Ala
    130                 135                 140
```

-continued

```
Pro Ala Val Ala Ser Val Ala Gly Gly Ser Gly Ser Gly Gly Phe Ser
145                 150                 155                 160

Ala Ser Leu His Ser Glu Pro Pro Val Tyr Ala Asn Leu Ser Asn Phe
                165                 170                 175

Asn Pro Gly Ala Leu Ser Ser Gly Gly Gly Ala Pro Ser Tyr Gly Ala
            180                 185                 190

Ala Gly Leu Ala Phe Pro Ala Gln Pro Gln Gln Gln Gln Gln Pro Pro
        195                 200                 205

His His Leu Pro Gln Gln Met Pro Val Gln His Pro Arg Leu Gln Ala
    210                 215                 220

Leu Lys Glu Glu Pro Gln Thr Val Pro Glu Met Pro Gly Glu Thr Pro
225                 230                 235                 240

Pro Leu Ser Pro Ile Asp Met Glu Ser Gln Glu Arg Ile Lys Ala Glu
                245                 250                 255

Arg Lys Arg Met Arg Asn Arg Ile Ala Ala Ser Lys Cys Arg Lys Arg
            260                 265                 270

Lys Leu Glu Arg Ile Ala Arg Leu Glu Glu Lys Val Lys Thr Leu Lys
        275                 280                 285

Ala Gln Asn Ser Glu Leu Ala Ser Thr Ala Asn Met Leu Arg Glu Gln
    290                 295                 300

Val Ala Gln Leu Lys Gln Lys Val Met Asn His Val Asn Ser Gly Cys
305                 310                 315                 320

Gln Leu Met Leu Thr Gln Gln Leu Gln Thr Phe
                325                 330


<210> SEQ ID NO 142
<211> LENGTH: 529
<212> TYPE: PRT
<213> ORGANISM: Homo sapiens

<400> SEQUENCE: 142

Met Asp Leu Pro Val Gly Pro Gly Ala Ala Gly Pro Ser Asn Val Pro
1               5                   10                  15

Ala Phe Leu Thr Lys Leu Trp Thr Leu Val Ser Asp Pro Asp Thr Asp
            20                  25                  30

Ala Leu Ile Cys Trp Ser Pro Ser Gly Asn Ser Phe His Val Phe Asp
        35                  40                  45

Gln Gly Gln Phe Ala Lys Glu Val Leu Pro Lys Tyr Phe Lys His Asn
    50                  55                  60

Asn Met Ala Ser Phe Val Arg Gln Leu Asn Met Tyr Gly Phe Arg Lys
65                  70                  75                  80

Val Val His Ile Glu Gln Gly Gly Leu Val Lys Pro Glu Arg Asp Asp
                85                  90                  95

Thr Glu Phe Gln His Pro Cys Phe Leu Arg Gly Gln Glu Gln Leu Leu
            100                 105                 110

Glu Asn Ile Lys Arg Lys Val Thr Ser Val Ser Thr Leu Lys Ser Glu
        115                 120                 125

Asp Ile Lys Ile Arg Gln Asp Ser Val Thr Lys Leu Leu Thr Asp Val
    130                 135                 140

Gln Leu Met Lys Gly Lys Gln Glu Cys Met Asp Ser Lys Leu Leu Ala
145                 150                 155                 160

Met Lys His Glu Asn Glu Ala Leu Trp Arg Glu Val Ala Ser Leu Arg
                165                 170                 175

Gln Lys His Ala Gln Gln Gln Lys Val Val Asn Lys Leu Ile Gln Phe
```

180 185 190

Leu Ile Ser Leu Val Gln Ser Asn Arg Ile Leu Gly Val Lys Arg Lys
195 200 205

Ile Pro Leu Met Leu Asn Asp Ser Gly Ser Ala His Ser Met Pro Lys
210 215 220

Tyr Ser Arg Gln Phe Ser Leu Glu His Val His Gly Ser Gly Pro Tyr
225 230 235 240

Ser Ala Pro Ser Pro Ala Tyr Ser Ser Ser Ser Leu Tyr Ala Pro Asp
245 250 255

Ala Val Ala Ser Ser Gly Pro Ile Ile Ser Asp Ile Thr Glu Leu Ala
260 265 270

Pro Ala Ser Pro Met Ala Ser Pro Gly Gly Ser Ile Asp Glu Arg Pro
275 280 285

Leu Ser Ser Ser Pro Leu Val Arg Val Lys Glu Glu Pro Pro Ser Pro
290 295 300

Pro Gln Ser Pro Arg Val Glu Glu Ala Ser Pro Gly Arg Pro Ser Ser
305 310 315 320

Val Asp Thr Leu Leu Ser Pro Thr Ala Leu Ile Asp Ser Ile Leu Arg
325 330 335

Glu Ser Glu Pro Ala Pro Ala Ser Val Thr Ala Leu Thr Asp Ala Arg
340 345 350

Gly His Thr Asp Thr Glu Gly Arg Pro Pro Ser Pro Pro Pro Thr Ser
355 360 365

Thr Pro Glu Lys Cys Leu Ser Val Ala Cys Leu Asp Lys Asn Glu Leu
370 375 380

Ser Asp His Leu Asp Ala Met Asp Ser Asn Leu Asp Asn Leu Gln Thr
385 390 395 400

Met Leu Ser Ser His Gly Phe Ser Val Asp Thr Ser Ala Leu Leu Asp
405 410 415

Leu Phe Ser Pro Ser Val Thr Val Pro Asp Met Ser Leu Pro Asp Leu
420 425 430

Asp Ser Ser Leu Ala Ser Ile Gln Glu Leu Leu Ser Pro Gln Glu Pro
435 440 445

Pro Arg Pro Pro Glu Ala Glu Asn Ser Ser Pro Asp Ser Gly Lys Gln
450 455 460

Leu Val His Tyr Thr Ala Gln Pro Leu Phe Leu Leu Asp Pro Gly Ser
465 470 475 480

Val Asp Thr Gly Ser Asn Asp Leu Pro Val Leu Phe Glu Leu Gly Glu
485 490 495

Gly Ser Tyr Phe Ser Glu Gly Asp Gly Phe Ala Glu Asp Pro Thr Ile
500 505 510

Ser Leu Leu Thr Gly Ser Glu Pro Pro Lys Ala Lys Asp Pro Thr Val
515 520 525

Ser

<210> SEQ ID NO 143
<211> LENGTH: 345
<212> TYPE: PRT
<213> ORGANISM: Homo sapiens

<400> SEQUENCE: 143

Met Gln Arg Leu Val Ala Trp Asp Pro Ala Cys Leu Pro Leu Pro Pro
1 5 10 15

Pro Pro Pro Ala Phe Lys Ser Met Glu Val Ala Asn Phe Tyr Tyr Glu

```
            20                  25                  30

Ala Asp Cys Leu Ala Ala Ala Tyr Gly Gly Lys Ala Ala Pro Ala Ala
        35                  40                  45

Pro Pro Ala Ala Arg Pro Gly Pro Arg Pro Pro Ala Gly Glu Leu Gly
    50                  55                  60

Ser Ile Gly Asp His Glu Arg Ala Ile Asp Phe Ser Pro Tyr Leu Glu
65                  70                  75                  80

Pro Leu Gly Ala Pro Gln Ala Pro Ala Pro Ala Thr Ala Thr Asp Thr
                85                  90                  95

Phe Glu Ala Ala Pro Pro Ala Pro Ala Pro Ala Pro Ala Ser Ser Gly
            100                 105                 110

Gln His His Asp Phe Leu Ser Asp Leu Phe Ser Asp Asp Tyr Gly Gly
        115                 120                 125

Lys Asn Cys Lys Lys Pro Ala Glu Tyr Gly Tyr Val Ser Leu Gly Arg
    130                 135                 140

Leu Gly Ala Ala Lys Gly Ala Leu His Pro Gly Cys Phe Ala Pro Leu
145                 150                 155                 160

His Pro Pro Pro Pro Pro Pro Pro Pro Pro Ala Glu Leu Lys Ala Glu
                165                 170                 175

Pro Gly Phe Glu Pro Ala Asp Cys Lys Arg Lys Glu Glu Ala Gly Ala
            180                 185                 190

Pro Gly Gly Gly Ala Gly Met Ala Ala Gly Phe Pro Tyr Ala Leu Arg
        195                 200                 205

Ala Tyr Leu Gly Tyr Gln Ala Val Pro Ser Gly Ser Ser Gly Ser Leu
    210                 215                 220

Ser Thr Ser Ser Ser Ser Ser Pro Pro Gly Thr Pro Ser Pro Ala Asp
225                 230                 235                 240

Ala Lys Ala Pro Pro Thr Ala Cys Tyr Ala Gly Ala Ala Pro Ala Pro
                245                 250                 255

Ser Gln Val Lys Ser Lys Ala Lys Lys Thr Val Asp Lys His Ser Asp
            260                 265                 270

Glu Tyr Lys Ile Arg Arg Glu Arg Asn Asn Ile Ala Val Arg Lys Ser
        275                 280                 285

Arg Asp Lys Ala Lys Met Arg Asn Leu Glu Thr Gln His Lys Val Leu
    290                 295                 300

Glu Leu Thr Ala Glu Asn Glu Arg Leu Gln Lys Lys Val Glu Gln Leu
305                 310                 315                 320

Ser Arg Glu Leu Ser Thr Leu Arg Asn Leu Phe Lys Gln Leu Pro Glu
                325                 330                 335

Pro Leu Leu Ala Ser Ser Gly His Cys
            340                 345


<210> SEQ ID NO 144
<211> LENGTH: 743
<212> TYPE: PRT
<213> ORGANISM: Homo sapiens

<400> SEQUENCE: 144

Met Asn Asn Pro Ser Glu Thr Ser Lys Pro Ser Met Glu Ser Gly Asp
1               5                   10                  15

Gly Asn Thr Gly Thr Gln Thr Asn Gly Leu Asp Phe Gln Lys Gln Pro
            20                  25                  30

Val Pro Val Gly Gly Ala Ile Ser Thr Ala Gln Ala Gln Ala Phe Leu
        35                  40                  45
```

```
Gly His Leu His Gln Val Gln Leu Ala Gly Thr Ser Leu Gln Ala Ala
    50                  55                  60

Ala Gln Ser Leu Asn Val Gln Ser Lys Ser Asn Glu Glu Ser Gly Asp
65                  70                  75                  80

Ser Gln Gln Pro Ser Gln Pro Ser Gln Gln Pro Ser Val Gln Ala Ala
                85                  90                  95

Ile Pro Gln Thr Gln Leu Met Leu Ala Gly Gly Gln Ile Thr Gly Leu
            100                 105                 110

Thr Leu Thr Pro Ala Gln Gln Gln Leu Leu Leu Gln Gln Ala Gln Ala
        115                 120                 125

Gln Ala Gln Leu Leu Ala Ala Ala Val Gln Gln His Ser Ala Ser Gln
    130                 135                 140

Gln His Ser Ala Ala Gly Ala Thr Ile Ser Ala Ser Ala Ala Thr Pro
145                 150                 155                 160

Met Thr Gln Ile Pro Leu Ser Gln Pro Ile Gln Ile Ala Gln Asp Leu
                165                 170                 175

Gln Gln Leu Gln Gln Leu Gln Gln Gln Asn Leu Asn Leu Gln Gln Phe
            180                 185                 190

Val Leu Val His Pro Thr Thr Asn Leu Gln Pro Ala Gln Phe Ile Ile
        195                 200                 205

Ser Gln Thr Pro Gln Gly Gln Gln Gly Leu Leu Gln Ala Gln Asn Leu
    210                 215                 220

Leu Thr Gln Leu Pro Gln Gln Ser Gln Ala Asn Leu Leu Gln Ser Gln
225                 230                 235                 240

Pro Ser Ile Thr Leu Thr Ser Gln Pro Ala Thr Pro Thr Arg Thr Ile
                245                 250                 255

Ala Ala Thr Pro Ile Gln Thr Leu Pro Gln Ser Gln Ser Thr Pro Lys
            260                 265                 270

Arg Ile Asp Thr Pro Ser Leu Glu Glu Pro Ser Asp Leu Glu Glu Leu
        275                 280                 285

Glu Gln Phe Ala Lys Thr Phe Lys Gln Arg Arg Ile Lys Leu Gly Phe
    290                 295                 300

Thr Gln Gly Asp Val Gly Leu Ala Met Gly Lys Leu Tyr Gly Asn Asp
305                 310                 315                 320

Phe Ser Gln Thr Thr Ile Ser Arg Phe Glu Ala Leu Asn Leu Ser Phe
                325                 330                 335

Lys Asn Met Cys Lys Leu Lys Pro Leu Leu Glu Lys Trp Leu Asn Asp
            340                 345                 350

Ala Glu Asn Leu Ser Ser Asp Ser Ser Leu Ser Ser Pro Ser Ala Leu
        355                 360                 365

Asn Ser Pro Gly Ile Glu Gly Leu Ser Arg Arg Arg Lys Lys Arg Thr
    370                 375                 380

Ser Ile Glu Thr Asn Ile Arg Val Ala Leu Glu Lys Ser Phe Leu Glu
385                 390                 395                 400

Asn Gln Lys Pro Thr Ser Glu Glu Ile Thr Met Ile Ala Asp Gln Leu
                405                 410                 415

Asn Met Glu Lys Glu Val Ile Arg Val Trp Phe Cys Asn Arg Arg Gln
            420                 425                 430

Lys Glu Lys Arg Ile Asn Pro Pro Ser Ser Gly Gly Thr Ser Ser Ser
        435                 440                 445

Pro Ile Lys Ala Ile Phe Pro Ser Pro Thr Ser Leu Val Ala Thr Thr
    450                 455                 460

Pro Ser Leu Val Thr Ser Ser Ala Ala Thr Thr Leu Thr Val Ser Pro
```

465 470 475 480

Val Leu Pro Leu Thr Ser Ala Ala Val Thr Asn Leu Ser Val Thr Gly
485 490 495

Thr Ser Asp Thr Thr Ser Asn Asn Thr Ala Thr Val Ile Ser Thr Ala
500 505 510

Pro Pro Ala Ser Ser Ala Val Thr Ser Pro Ser Leu Ser Pro Ser Pro
515 520 525

Ser Ala Ser Ala Ser Thr Ser Glu Ala Ser Ser Ala Ser Glu Thr Ser
530 535 540

Thr Thr Gln Thr Thr Ser Thr Pro Leu Ser Ser Pro Leu Gly Thr Ser
545 550 555 560

Gln Val Met Val Thr Ala Ser Gly Leu Gln Thr Ala Ala Ala Ala Ala
565 570 575

Leu Gln Gly Ala Ala Gln Leu Pro Ala Asn Ala Ser Leu Ala Ala Met
580 585 590

Ala Ala Ala Ala Gly Leu Asn Pro Ser Leu Met Ala Pro Ser Gln Phe
595 600 605

Ala Ala Gly Gly Ala Leu Leu Ser Leu Asn Pro Gly Thr Leu Ser Gly
610 615 620

Ala Leu Ser Pro Ala Leu Met Ser Asn Ser Thr Leu Ala Thr Ile Gln
625 630 635 640

Ala Leu Ala Ser Gly Gly Ser Leu Pro Ile Thr Ser Leu Asp Ala Thr
645 650 655

Gly Asn Leu Val Phe Ala Asn Ala Gly Gly Ala Pro Asn Ile Val Thr
660 665 670

Ala Pro Leu Phe Leu Asn Pro Gln Asn Leu Ser Leu Leu Thr Ser Asn
675 680 685

Pro Val Ser Leu Val Ser Ala Ala Ala Ala Ser Ala Gly Asn Ser Ala
690 695 700

Pro Val Ala Ser Leu His Ala Thr Ser Thr Ser Ala Glu Ser Ile Gln
705 710 715 720

Asn Ser Leu Phe Thr Val Ala Ser Ala Ser Gly Ala Ala Ser Thr Thr
725 730 735

Thr Thr Ala Ser Lys Ala Gln
740

<210> SEQ ID NO 145
<211> LENGTH: 507
<212> TYPE: PRT
<213> ORGANISM: Homo sapiens

<400> SEQUENCE: 145

Met Glu Ala Ala Val Ala Ala Pro Arg Pro Arg Leu Leu Leu Leu Val
1 5 10 15

Leu Ala Ala Ala Ala Ala Ala Ala Ala Ala Leu Leu Pro Gly Ala Thr
20 25 30

Ala Leu Gln Cys Phe Cys His Leu Cys Thr Lys Asp Asn Phe Thr Cys
35 40 45

Val Thr Asp Gly Leu Cys Phe Val Ser Val Thr Glu Thr Thr Asp Lys
50 55 60

Val Ile His Asn Ser Met Cys Ile Ala Glu Ile Asp Leu Ile Pro Arg
65 70 75 80

Asp Arg Pro Phe Val Cys Ala Pro Ser Ser Lys Thr Gly Ser Val Thr
85 90 95

-continued

```
Thr Thr Tyr Cys Cys Asn Gln Asp His Cys Asn Lys Ile Glu Leu Pro
            100                 105                 110

Thr Thr Gly Pro Phe Ser Val Lys Ser Ser Pro Gly Leu Gly Pro Val
        115                 120                 125

Glu Leu Ala Ala Val Ile Ala Gly Pro Val Cys Phe Val Cys Ile Ser
    130                 135                 140

Leu Met Leu Met Val Tyr Ile Cys His Asn Arg Thr Val Ile His His
145                 150                 155                 160

Arg Val Pro Asn Glu Glu Asp Pro Ser Leu Asp Arg Pro Phe Ile Ser
                165                 170                 175

Glu Gly Thr Thr Leu Lys Asp Leu Ile Tyr Asp Met Thr Thr Ser Gly
            180                 185                 190

Ser Gly Ser Gly Leu Pro Leu Leu Val Gln Arg Thr Ile Ala Arg Thr
        195                 200                 205

Ile Val Leu Gln Glu Ser Ile Gly Lys Gly Arg Phe Gly Glu Val Trp
    210                 215                 220

Arg Gly Lys Trp Arg Gly Glu Glu Val Ala Val Lys Ile Phe Ser Ser
225                 230                 235                 240

Arg Glu Glu Arg Ser Trp Phe Arg Glu Ala Glu Ile Tyr Gln Thr Val
                245                 250                 255

Met Leu Arg His Glu Asn Ile Leu Gly Phe Ile Ala Ala Asp Asn Lys
            260                 265                 270

Asp Asn Gly Thr Trp Thr Gln Leu Trp Leu Val Ser Asp Tyr His Glu
        275                 280                 285

His Gly Ser Leu Phe Asp Tyr Leu Asn Arg Tyr Thr Val Thr Val Glu
    290                 295                 300

Gly Met Ile Lys Leu Ala Leu Ser Thr Ala Ser Gly Leu Ala His Leu
305                 310                 315                 320

His Met Glu Ile Val Gly Thr Gln Gly Lys Pro Ala Ile Ala His Arg
                325                 330                 335

Asp Leu Lys Ser Lys Asn Ile Leu Val Lys Lys Asn Gly Thr Cys Cys
            340                 345                 350

Ile Ala Asp Leu Gly Leu Ala Val Arg His Asp Ser Ala Thr Asp Thr
        355                 360                 365

Ile Asp Ile Ala Pro Asn His Arg Val Gly Thr Lys Arg Tyr Met Ala
    370                 375                 380

Pro Glu Val Leu Asp Asp Ser Ile Asn Met Lys His Phe Glu Ser Phe
385                 390                 395                 400

Lys Arg Ala Asp Ile Tyr Ala Met Gly Leu Val Phe Trp Glu Ile Ala
                405                 410                 415

Arg Arg Cys Ser Ile Gly Gly Ile His Glu Asp Tyr Gln Leu Pro Tyr
            420                 425                 430

Tyr Asp Leu Val Pro Ser Asp Pro Ser Val Glu Glu Met Arg Lys Val
        435                 440                 445

Val Cys Glu Gln Lys Leu Arg Pro Asn Ile Pro Asn Arg Trp Gln Ser
    450                 455                 460

Cys Glu Ala Leu Arg Val Met Ala Lys Ile Met Arg Glu Cys Trp Tyr
465                 470                 475                 480

Ala Asn Gly Ala Ala Arg Leu Thr Ala Leu Arg Ile Lys Lys Thr Leu
                485                 490                 495

Ser Gln Leu Ser Gln Gln Glu Gly Ile Lys Met
            500                 505
```

<210> SEQ ID NO 146
<211> LENGTH: 1106
<212> TYPE: PRT
<213> ORGANISM: Homo sapiens

<400> SEQUENCE: 146

```
Met Arg Leu Pro Gly Ala Met Pro Ala Leu Ala Leu Lys Gly Glu Leu
1               5                   10                  15

Leu Leu Leu Ser Leu Leu Leu Leu Leu Glu Pro Gln Ile Ser Gln Gly
            20                  25                  30

Leu Val Val Thr Pro Pro Gly Pro Glu Leu Val Leu Asn Val Ser Ser
        35                  40                  45

Thr Phe Val Leu Thr Cys Ser Gly Ser Ala Pro Val Val Trp Glu Arg
    50                  55                  60

Met Ser Gln Glu Pro Pro Gln Glu Met Ala Lys Ala Gln Asp Gly Thr
65                  70                  75                  80

Phe Ser Ser Val Leu Thr Leu Thr Asn Leu Thr Gly Leu Asp Thr Gly
                85                  90                  95

Glu Tyr Phe Cys Thr His Asn Asp Ser Arg Gly Leu Glu Thr Asp Glu
            100                 105                 110

Arg Lys Arg Leu Tyr Ile Phe Val Pro Asp Pro Thr Val Gly Phe Leu
        115                 120                 125

Pro Asn Asp Ala Glu Glu Leu Phe Ile Phe Leu Thr Glu Ile Thr Glu
    130                 135                 140

Ile Thr Ile Pro Cys Arg Val Thr Asp Pro Gln Leu Val Val Thr Leu
145                 150                 155                 160

His Glu Lys Lys Gly Asp Val Ala Leu Pro Val Pro Tyr Asp His Gln
                165                 170                 175

Arg Gly Phe Ser Gly Ile Phe Glu Asp Arg Ser Tyr Ile Cys Lys Thr
            180                 185                 190

Thr Ile Gly Asp Arg Glu Val Asp Ser Asp Ala Tyr Tyr Val Tyr Arg
        195                 200                 205

Leu Gln Val Ser Ser Ile Asn Val Ser Val Asn Ala Val Gln Thr Val
    210                 215                 220

Val Arg Gln Gly Glu Asn Ile Thr Leu Met Cys Ile Val Ile Gly Asn
225                 230                 235                 240

Glu Val Val Asn Phe Glu Trp Thr Tyr Pro Arg Lys Glu Ser Gly Arg
                245                 250                 255

Leu Val Glu Pro Val Thr Asp Phe Leu Leu Asp Met Pro Tyr His Ile
            260                 265                 270

Arg Ser Ile Leu His Ile Pro Ser Ala Glu Leu Glu Asp Ser Gly Thr
        275                 280                 285

Tyr Thr Cys Asn Val Thr Glu Ser Val Asn Asp His Gln Asp Glu Lys
    290                 295                 300

Ala Ile Asn Ile Thr Val Val Glu Ser Gly Tyr Val Arg Leu Leu Gly
305                 310                 315                 320

Glu Val Gly Thr Leu Gln Phe Ala Glu Leu His Arg Ser Arg Thr Leu
                325                 330                 335

Gln Val Val Phe Glu Ala Tyr Pro Pro Pro Thr Val Leu Trp Phe Lys
            340                 345                 350

Asp Asn Arg Thr Leu Gly Asp Ser Ser Ala Gly Glu Ile Ala Leu Ser
        355                 360                 365

Thr Arg Asn Val Ser Glu Thr Arg Tyr Val Ser Glu Leu Thr Leu Val
    370                 375                 380
```

```
Arg Val Lys Val Ala Glu Ala Gly His Tyr Thr Met Arg Ala Phe His
385                 390                 395                 400

Glu Asp Ala Glu Val Gln Leu Ser Phe Gln Leu Gln Ile Asn Val Pro
                405                 410                 415

Val Arg Val Leu Glu Leu Ser Glu Ser His Pro Asp Ser Gly Glu Gln
            420                 425                 430

Thr Val Arg Cys Arg Gly Arg Gly Met Pro Gln Pro Asn Ile Ile Trp
        435                 440                 445

Ser Ala Cys Arg Asp Leu Lys Arg Cys Pro Arg Glu Leu Pro Pro Thr
    450                 455                 460

Leu Leu Gly Asn Ser Ser Glu Glu Glu Ser Gln Leu Glu Thr Asn Val
465                 470                 475                 480

Thr Tyr Trp Glu Glu Glu Gln Glu Phe Glu Val Val Ser Thr Leu Arg
                485                 490                 495

Leu Gln His Val Asp Arg Pro Leu Ser Val Arg Cys Thr Leu Arg Asn
            500                 505                 510

Ala Val Gly Gln Asp Thr Gln Glu Val Ile Val Val Pro His Ser Leu
        515                 520                 525

Pro Phe Lys Val Val Val Ile Ser Ala Ile Leu Ala Leu Val Val Leu
    530                 535                 540

Thr Ile Ile Ser Leu Ile Ile Leu Ile Met Leu Trp Gln Lys Lys Pro
545                 550                 555                 560

Arg Tyr Glu Ile Arg Trp Lys Val Ile Glu Ser Val Ser Ser Asp Gly
                565                 570                 575

His Glu Tyr Ile Tyr Val Asp Pro Met Gln Leu Pro Tyr Asp Ser Thr
            580                 585                 590

Trp Glu Leu Pro Arg Asp Gln Leu Val Leu Gly Arg Thr Leu Gly Ser
        595                 600                 605

Gly Ala Phe Gly Gln Val Val Glu Ala Thr Ala His Gly Leu Ser His
    610                 615                 620

Ser Gln Ala Thr Met Lys Val Ala Val Lys Met Leu Lys Ser Thr Ala
625                 630                 635                 640

Arg Ser Ser Glu Lys Gln Ala Leu Met Ser Glu Leu Lys Ile Met Ser
                645                 650                 655

His Leu Gly Pro His Leu Asn Val Val Asn Leu Leu Gly Ala Cys Thr
            660                 665                 670

Lys Gly Gly Pro Ile Tyr Ile Ile Thr Glu Tyr Cys Arg Tyr Gly Asp
        675                 680                 685

Leu Val Asp Tyr Leu His Arg Asn Lys His Thr Phe Leu Gln His His
    690                 695                 700

Ser Asp Lys Arg Arg Pro Pro Ser Ala Glu Leu Tyr Ser Asn Ala Leu
705                 710                 715                 720

Pro Val Gly Leu Pro Leu Pro Ser His Val Ser Leu Thr Gly Glu Ser
                725                 730                 735

Asp Gly Gly Tyr Met Asp Met Ser Lys Asp Glu Ser Val Asp Tyr Val
            740                 745                 750

Pro Met Leu Asp Met Lys Gly Asp Val Lys Tyr Ala Asp Ile Glu Ser
        755                 760                 765

Ser Asn Tyr Met Ala Pro Tyr Asp Asn Tyr Val Pro Ser Ala Pro Glu
    770                 775                 780

Arg Thr Cys Arg Ala Thr Leu Ile Asn Glu Ser Pro Val Leu Ser Tyr
785                 790                 795                 800

Met Asp Leu Val Gly Phe Ser Tyr Gln Val Ala Asn Gly Met Glu Phe
```

```
                805                 810                 815

Leu Ala Ser Lys Asn Cys Val His Arg Asp Leu Ala Ala Arg Asn Val
            820                 825                 830

Leu Ile Cys Glu Gly Lys Leu Val Lys Ile Cys Asp Phe Gly Leu Ala
        835                 840                 845

Arg Asp Ile Met Arg Asp Ser Asn Tyr Ile Ser Lys Gly Ser Thr Phe
    850                 855                 860

Leu Pro Leu Lys Trp Met Ala Pro Glu Ser Ile Phe Asn Ser Leu Tyr
865                 870                 875                 880

Thr Thr Leu Ser Asp Val Trp Ser Phe Gly Ile Leu Leu Trp Glu Ile
                885                 890                 895

Phe Thr Leu Gly Gly Thr Pro Tyr Pro Glu Leu Pro Met Asn Glu Gln
            900                 905                 910

Phe Tyr Asn Ala Ile Lys Arg Gly Tyr Arg Met Ala Gln Pro Ala His
        915                 920                 925

Ala Ser Asp Glu Ile Tyr Glu Ile Met Gln Lys Cys Trp Glu Glu Lys
    930                 935                 940

Phe Glu Ile Arg Pro Pro Phe Ser Gln Leu Val Leu Leu Leu Glu Arg
945                 950                 955                 960

Leu Leu Gly Glu Gly Tyr Lys Lys Lys Tyr Gln Gln Val Asp Glu Glu
                965                 970                 975

Phe Leu Arg Ser Asp His Pro Ala Ile Leu Arg Ser Gln Ala Arg Leu
            980                 985                 990

Pro Gly Phe His Gly Leu Arg Ser  Pro Leu Asp Thr Ser  Ser Val Leu
        995                 1000                1005

Tyr Thr  Ala Val Gln Pro Asn  Glu Gly Asp Asn Asp  Tyr Ile Ile
    1010                1015                1020

Pro Leu  Pro Asp Pro Lys Pro  Glu Val Ala Asp Glu  Gly Pro Leu
    1025                1030                1035

Glu Gly  Ser Pro Ser Leu Ala  Ser Ser Thr Leu Asn  Glu Val Asn
    1040                1045                1050

Thr Ser  Ser Thr Ile Ser Cys  Asp Ser Pro Leu Glu  Pro Gln Asp
    1055                1060                1065

Glu Pro  Glu Pro Glu Pro Gln  Leu Glu Leu Gln Val  Glu Pro Glu
    1070                1075                1080

Pro Glu  Leu Glu Gln Leu Pro  Asp Ser Gly Cys Pro  Ala Pro Arg
    1085                1090                1095

Ala Glu  Ala Glu Asp Ser Phe  Leu
    1100                1105


<210> SEQ ID NO 147
<211> LENGTH: 1210
<212> TYPE: PRT
<213> ORGANISM: Homo sapiens

<400> SEQUENCE: 147

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60
```

-continued

```
Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
```

-continued

```
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Lys Leu Leu Glu Gly
    530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910
```

```
Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro
            980                 985                 990

Thr Asp Ser Asn Phe Tyr Arg Ala  Leu Met Asp Glu Glu  Asp Met Asp
        995                 1000                1005

Asp Val  Val Asp Ala Asp Glu  Tyr Leu Ile Pro Gln  Gln Gly Phe
    1010                1015                1020

Phe Ser  Ser Pro Ser Thr Ser  Arg Thr Pro Leu Leu  Ser Ser Leu
    1025                1030                1035

Ser Ala  Thr Ser Asn Asn Ser  Thr Val Ala Cys Ile  Asp Arg Asn
    1040                1045                1050

Gly Leu  Gln Ser Cys Pro Ile  Lys Glu Asp Ser Phe  Leu Gln Arg
    1055                1060                1065

Tyr Ser  Ser Asp Pro Thr Gly  Ala Leu Thr Glu Asp  Ser Ile Asp
    1070                1075                1080

Asp Thr  Phe Leu Pro Val Pro  Glu Tyr Ile Asn Gln  Ser Val Pro
    1085                1090                1095

Lys Arg  Pro Ala Gly Ser Val  Gln Asn Pro Val Tyr  His Asn Gln
    1100                1105                1110

Pro Leu  Asn Pro Ala Pro Ser  Arg Asp Pro His Tyr  Gln Asp Pro
    1115                1120                1125

His Ser  Thr Ala Val Gly Asn  Pro Glu Tyr Leu Asn  Thr Val Gln
    1130                1135                1140

Pro Thr  Cys Val Asn Ser Thr  Phe Asp Ser Pro Ala  His Trp Ala
    1145                1150                1155

Gln Lys  Gly Ser His Gln Ile  Ser Leu Asp Asn Pro  Asp Tyr Gln
    1160                1165                1170

Gln Asp  Phe Phe Pro Lys Glu  Ala Lys Pro Asn Gly  Ile Phe Lys
    1175                1180                1185

Gly Ser  Thr Ala Glu Asn Ala  Glu Tyr Leu Arg Val  Ala Pro Gln
    1190                1195                1200

Ser Ser  Glu Phe Ile Gly Ala
    1205                1210


<210> SEQ ID NO 148
<211> LENGTH: 1338
<212> TYPE: PRT
<213> ORGANISM: Homo sapiens

<400> SEQUENCE: 148

Met Val Ser Tyr Trp Asp Thr Gly Val Leu Leu Cys Ala Leu Leu Ser
1               5                   10                  15

Cys Leu Leu Leu Thr Gly Ser Ser Ser Gly Ser Lys Leu Lys Asp Pro
            20                  25                  30

Glu Leu Ser Leu Lys Gly Thr Gln His Ile Met Gln Ala Gly Gln Thr
        35                  40                  45

Leu His Leu Gln Cys Arg Gly Glu Ala Ala His Lys Trp Ser Leu Pro
```

```
    50                  55                  60

Glu Met Val Ser Lys Glu Ser Glu Arg Leu Ser Ile Thr Lys Ser Ala
65                  70                  75                  80

Cys Gly Arg Asn Gly Lys Gln Phe Cys Ser Thr Leu Thr Leu Asn Thr
                85                  90                  95

Ala Gln Ala Asn His Thr Gly Phe Tyr Ser Cys Lys Tyr Leu Ala Val
            100                 105                 110

Pro Thr Ser Lys Lys Lys Glu Thr Glu Ser Ala Ile Tyr Ile Phe Ile
        115                 120                 125

Ser Asp Thr Gly Arg Pro Phe Val Glu Met Tyr Ser Glu Ile Pro Glu
    130                 135                 140

Ile Ile His Met Thr Glu Gly Arg Glu Leu Val Ile Pro Cys Arg Val
145                 150                 155                 160

Thr Ser Pro Asn Ile Thr Val Thr Leu Lys Lys Phe Pro Leu Asp Thr
                165                 170                 175

Leu Ile Pro Asp Gly Lys Arg Ile Ile Trp Asp Ser Arg Lys Gly Phe
            180                 185                 190

Ile Ile Ser Asn Ala Thr Tyr Lys Glu Ile Gly Leu Leu Thr Cys Glu
        195                 200                 205

Ala Thr Val Asn Gly His Leu Tyr Lys Thr Asn Tyr Leu Thr His Arg
    210                 215                 220

Gln Thr Asn Thr Ile Ile Asp Val Gln Ile Ser Thr Pro Arg Pro Val
225                 230                 235                 240

Lys Leu Leu Arg Gly His Thr Leu Val Leu Asn Cys Thr Ala Thr Thr
                245                 250                 255

Pro Leu Asn Thr Arg Val Gln Met Thr Trp Ser Tyr Pro Asp Glu Lys
            260                 265                 270

Asn Lys Arg Ala Ser Val Arg Arg Arg Ile Asp Gln Ser Asn Ser His
        275                 280                 285

Ala Asn Ile Phe Tyr Ser Val Leu Thr Ile Asp Lys Met Gln Asn Lys
    290                 295                 300

Asp Lys Gly Leu Tyr Thr Cys Arg Val Arg Ser Gly Pro Ser Phe Lys
305                 310                 315                 320

Ser Val Asn Thr Ser Val His Ile Tyr Asp Lys Ala Phe Ile Thr Val
                325                 330                 335

Lys His Arg Lys Gln Gln Val Leu Glu Thr Val Ala Gly Lys Arg Ser
            340                 345                 350

Tyr Arg Leu Ser Met Lys Val Lys Ala Phe Pro Ser Pro Glu Val Val
        355                 360                 365

Trp Leu Lys Asp Gly Leu Pro Ala Thr Glu Lys Ser Ala Arg Tyr Leu
    370                 375                 380

Thr Arg Gly Tyr Ser Leu Ile Ile Lys Asp Val Thr Glu Glu Asp Ala
385                 390                 395                 400

Gly Asn Tyr Thr Ile Leu Leu Ser Ile Lys Gln Ser Asn Val Phe Lys
                405                 410                 415

Asn Leu Thr Ala Thr Leu Ile Val Asn Val Lys Pro Gln Ile Tyr Glu
            420                 425                 430

Lys Ala Val Ser Ser Phe Pro Asp Pro Ala Leu Tyr Pro Leu Gly Ser
        435                 440                 445

Arg Gln Ile Leu Thr Cys Thr Ala Tyr Gly Ile Pro Gln Pro Thr Ile
    450                 455                 460

Lys Trp Phe Trp His Pro Cys Asn His Asn His Ser Glu Ala Arg Cys
465                 470                 475                 480
```

Asp Phe Cys Ser Asn Asn Glu Glu Ser Ser Ile Leu Asp Ala Asp Ser
485 490 495

Asn Met Gly Asn Arg Ile Glu Ser Ile Thr Gln Arg Met Ala Ile Ile
500 505 510

Glu Gly Lys Asn Lys Met Ala Ser Thr Leu Val Val Ala Asp Ser Arg
515 520 525

Ile Ser Gly Ile Tyr Ile Cys Ile Ala Ser Asn Lys Val Gly Thr Val
530 535 540

Gly Arg Asn Ile Ser Phe Tyr Ile Thr Asp Val Pro Asn Gly Phe His
545 550 555 560

Val Asn Leu Glu Lys Met Pro Thr Glu Gly Glu Asp Leu Lys Leu Ser
565 570 575

Cys Thr Val Asn Lys Phe Leu Tyr Arg Asp Val Thr Trp Ile Leu Leu
580 585 590

Arg Thr Val Asn Asn Arg Thr Met His Tyr Ser Ile Ser Lys Gln Lys
595 600 605

Met Ala Ile Thr Lys Glu His Ser Ile Thr Leu Asn Leu Thr Ile Met
610 615 620

Asn Val Ser Leu Gln Asp Ser Gly Thr Tyr Ala Cys Arg Ala Arg Asn
625 630 635 640

Val Tyr Thr Gly Glu Glu Ile Leu Gln Lys Lys Glu Ile Thr Ile Arg
645 650 655

Asp Gln Glu Ala Pro Tyr Leu Leu Arg Asn Leu Ser Asp His Thr Val
660 665 670

Ala Ile Ser Ser Ser Thr Thr Leu Asp Cys His Ala Asn Gly Val Pro
675 680 685

Glu Pro Gln Ile Thr Trp Phe Lys Asn Asn His Lys Ile Gln Gln Glu
690 695 700

Pro Gly Ile Ile Leu Gly Pro Gly Ser Ser Thr Leu Phe Ile Glu Arg
705 710 715 720

Val Thr Glu Glu Asp Glu Gly Val Tyr His Cys Lys Ala Thr Asn Gln
725 730 735

Lys Gly Ser Val Glu Ser Ser Ala Tyr Leu Thr Val Gln Gly Thr Ser
740 745 750

Asp Lys Ser Asn Leu Glu Leu Ile Thr Leu Thr Cys Thr Cys Val Ala
755 760 765

Ala Thr Leu Phe Trp Leu Leu Leu Thr Leu Phe Ile Arg Lys Met Lys
770 775 780

Arg Ser Ser Ser Glu Ile Lys Thr Asp Tyr Leu Ser Ile Ile Met Asp
785 790 795 800

Pro Asp Glu Val Pro Leu Asp Glu Gln Cys Glu Arg Leu Pro Tyr Asp
805 810 815

Ala Ser Lys Trp Glu Phe Ala Arg Glu Arg Leu Lys Leu Gly Lys Ser
820 825 830

Leu Gly Arg Gly Ala Phe Gly Lys Val Val Gln Ala Ser Ala Phe Gly
835 840 845

Ile Lys Lys Ser Pro Thr Cys Arg Thr Val Ala Val Lys Met Leu Lys
850 855 860

Glu Gly Ala Thr Ala Ser Glu Tyr Lys Ala Leu Met Thr Glu Leu Lys
865 870 875 880

Ile Leu Thr His Ile Gly His His Leu Asn Val Val Asn Leu Leu Gly
885 890 895

-continued

```
Ala Cys Thr Lys Gln Gly Gly Pro Leu Met Val Ile Val Glu Tyr Cys
            900                 905                 910

Lys Tyr Gly Asn Leu Ser Asn Tyr Leu Lys Ser Lys Arg Asp Leu Phe
        915                 920                 925

Phe Leu Asn Lys Asp Ala Ala Leu His Met Glu Pro Lys Lys Glu Lys
    930                 935                 940

Met Glu Pro Gly Leu Glu Gln Gly Lys Lys Pro Arg Leu Asp Ser Val
945                 950                 955                 960

Thr Ser Ser Glu Ser Phe Ala Ser Ser Gly Phe Gln Glu Asp Lys Ser
                965                 970                 975

Leu Ser Asp Val Glu Glu Glu Glu Asp Ser Asp Gly Phe Tyr Lys Glu
            980                 985                 990

Pro Ile Thr Met Glu Asp Leu Ile  Ser Tyr Ser Phe Gln  Val Ala Arg
        995                 1000                 1005

Gly Met  Glu Phe Leu Ser Ser  Arg Lys Cys Ile His  Arg Asp Leu
    1010                 1015                 1020

Ala Ala  Arg Asn Ile Leu Leu  Ser Glu Asn Asn Val  Val Lys Ile
    1025                 1030                 1035

Cys Asp  Phe Gly Leu Ala Arg  Asp Ile Tyr Lys Asn  Pro Asp Tyr
    1040                 1045                 1050

Val Arg  Lys Gly Asp Thr Arg  Leu Pro Leu Lys Trp  Met Ala Pro
    1055                 1060                 1065

Glu Ser  Ile Phe Asp Lys Ile  Tyr Ser Thr Lys Ser  Asp Val Trp
    1070                 1075                 1080

Ser Tyr  Gly Val Leu Leu Trp  Glu Ile Phe Ser Leu  Gly Gly Ser
    1085                 1090                 1095

Pro Tyr  Pro Gly Val Gln Met  Asp Glu Asp Phe Cys  Ser Arg Leu
    1100                 1105                 1110

Arg Glu  Gly Met Arg Met Arg  Ala Pro Glu Tyr Ser  Thr Pro Glu
    1115                 1120                 1125

Ile Tyr  Gln Ile Met Leu Asp  Cys Trp His Arg Asp  Pro Lys Glu
    1130                 1135                 1140

Arg Pro  Arg Phe Ala Glu Leu  Val Glu Lys Leu Gly  Asp Leu Leu
    1145                 1150                 1155

Gln Ala  Asn Val Gln Gln Asp  Gly Lys Asp Tyr Ile  Pro Ile Asn
    1160                 1165                 1170

Ala Ile  Leu Thr Gly Asn Ser  Gly Phe Thr Tyr Ser  Thr Pro Ala
    1175                 1180                 1185

Phe Ser  Glu Asp Phe Phe Lys  Glu Ser Ile Ser Ala  Pro Lys Phe
    1190                 1195                 1200

Asn Ser  Gly Ser Ser Asp Asp  Val Arg Tyr Val Asn  Ala Phe Lys
    1205                 1210                 1215

Phe Met  Ser Leu Glu Arg Ile  Lys Thr Phe Glu Glu  Leu Leu Pro
    1220                 1225                 1230

Asn Ala  Thr Ser Met Phe Asp  Asp Tyr Gln Gly Asp  Ser Ser Thr
    1235                 1240                 1245

Leu Leu  Ala Ser Pro Met Leu  Lys Arg Phe Thr Trp  Thr Asp Ser
    1250                 1255                 1260

Lys Pro  Lys Ala Ser Leu Lys  Ile Asp Leu Arg Val  Thr Ser Lys
    1265                 1270                 1275

Ser Lys  Glu Ser Gly Leu Ser  Asp Val Ser Arg Pro  Ser Phe Cys
    1280                 1285                 1290

His Ser  Ser Cys Gly His Val  Ser Glu Gly Lys Arg  Arg Phe Thr
```

```
    1295                1300                1305

Tyr Asp  His Ala Glu Leu Glu  Arg Lys Ile Ala Cys  Cys Ser Pro
    1310                1315                1320

Pro Pro  Asp Tyr Asn Ser Val  Val Leu Tyr Ser Thr  Pro Pro Ile
    1325                1330                1335


<210> SEQ ID NO 149
<211> LENGTH: 350
<212> TYPE: PRT
<213> ORGANISM: Homo sapiens

<400> SEQUENCE: 149

Met Ser Asn Ile Thr Asp Pro Gln Met Trp Asp Phe Asp Asp Leu Asn
1               5                   10                  15

Phe Thr Gly Met Pro Pro Ala Asp Glu Asp Tyr Ser Pro Cys Met Leu
            20                  25                  30

Glu Thr Glu Thr Leu Asn Lys Tyr Val Val Ile Ile Ala Tyr Ala Leu
        35                  40                  45

Val Phe Leu Leu Ser Leu Leu Gly Asn Ser Leu Val Met Leu Val Ile
    50                  55                  60

Leu Tyr Ser Arg Val Gly Arg Ser Val Thr Asp Val Tyr Leu Leu Asn
65                  70                  75                  80

Leu Ala Leu Ala Asp Leu Leu Phe Ala Leu Thr Leu Pro Ile Trp Ala
                85                  90                  95

Ala Ser Lys Val Asn Gly Trp Ile Phe Gly Thr Phe Leu Cys Lys Val
            100                 105                 110

Val Ser Leu Leu Lys Glu Val Asn Phe Tyr Ser Gly Ile Leu Leu Leu
        115                 120                 125

Ala Cys Ile Ser Val Asp Arg Tyr Leu Ala Ile Val His Ala Thr Arg
    130                 135                 140

Thr Leu Thr Gln Lys Arg His Leu Val Lys Phe Val Cys Leu Gly Cys
145                 150                 155                 160

Trp Gly Leu Ser Met Asn Leu Ser Leu Pro Phe Phe Leu Phe Arg Gln
                165                 170                 175

Ala Tyr His Pro Asn Asn Ser Ser Pro Val Cys Tyr Glu Val Leu Gly
            180                 185                 190

Asn Asp Thr Ala Lys Trp Arg Met Val Leu Arg Ile Leu Pro His Thr
        195                 200                 205

Phe Gly Phe Ile Val Pro Leu Phe Val Met Leu Phe Cys Tyr Gly Phe
    210                 215                 220

Thr Leu Arg Thr Leu Phe Lys Ala His Met Gly Gln Lys His Arg Ala
225                 230                 235                 240

Met Arg Val Ile Phe Ala Val Val Leu Ile Phe Leu Leu Cys Trp Leu
                245                 250                 255

Pro Tyr Asn Leu Val Leu Leu Ala Asp Thr Leu Met Arg Thr Gln Val
            260                 265                 270

Ile Gln Glu Ser Cys Glu Arg Arg Asn Asn Ile Gly Arg Ala Leu Asp
        275                 280                 285

Ala Thr Glu Ile Leu Gly Phe Leu His Ser Cys Leu Asn Pro Ile Ile
    290                 295                 300

Tyr Ala Phe Ile Gly Gln Asn Phe Arg His Gly Phe Leu Lys Ile Leu
305                 310                 315                 320

Ala Met His Gly Leu Val Ser Lys Glu Phe Leu Ala Arg His Arg Val
                325                 330                 335
```

```
Thr Ser Tyr Thr Ser Ser Ser Val Asn Val Ser Ser Asn Leu
            340                 345                 350


<210> SEQ ID NO 150
<211> LENGTH: 178
<212> TYPE: PRT
<213> ORGANISM: Homo sapiens

<400> SEQUENCE: 150

Met Ser Gly Gly Lys Tyr Val Asp Ser Glu Gly His Leu Tyr Thr Val
1               5                   10                  15

Pro Ile Arg Glu Gln Gly Asn Ile Tyr Lys Pro Asn Asn Lys Ala Met
            20                  25                  30

Ala Asp Glu Leu Ser Glu Lys Gln Val Tyr Asp Ala His Thr Lys Glu
        35                  40                  45

Ile Asp Leu Val Asn Arg Asp Pro Lys His Leu Asn Asp Asp Val Val
    50                  55                  60

Lys Ile Asp Phe Glu Asp Val Ile Ala Glu Pro Glu Gly Thr His Ser
65                  70                  75                  80

Phe His Gly Ile Trp Lys Ala Ser Phe Thr Thr Phe Thr Val Thr Lys
                85                  90                  95

Tyr Trp Phe Tyr Arg Leu Leu Ser Ala Leu Phe Gly Ile Pro Met Ala
            100                 105                 110

Leu Ile Trp Gly Ile Tyr Phe Ala Ile Leu Ser Phe Leu His Ile Trp
        115                 120                 125

Ala Val Val Pro Cys Ile Lys Ser Phe Leu Ile Glu Ile Gln Cys Thr
    130                 135                 140

Ser Arg Val Tyr Ser Ile Tyr Val His Thr Val Cys Asp Pro Leu Phe
145                 150                 155                 160

Glu Ala Val Gly Lys Ile Phe Ser Asn Val Arg Ile Asn Leu Gln Lys
                165                 170                 175

Glu Ile


<210> SEQ ID NO 151
<211> LENGTH: 866
<212> TYPE: PRT
<213> ORGANISM: Homo sapiens

<400> SEQUENCE: 151

Met Gly Asn Arg Gly Met Glu Glu Leu Ile Pro Leu Val Asn Lys Leu
1               5                   10                  15

Gln Asp Ala Phe Ser Ser Ile Gly Gln Ser Cys His Leu Asp Leu Pro
            20                  25                  30

Gln Ile Ala Val Val Gly Gly Gln Ser Ala Gly Lys Ser Ser Val Leu
        35                  40                  45

Glu Asn Phe Val Gly Arg Asp Phe Leu Pro Arg Gly Ser Gly Ile Val
    50                  55                  60

Thr Arg Arg Pro Leu Ile Leu Gln Leu Ile Phe Ser Lys Thr Glu His
65                  70                  75                  80

Ala Glu Phe Leu His Cys Lys Ser Lys Lys Phe Thr Asp Phe Asp Glu
                85                  90                  95

Val Arg Gln Glu Ile Glu Ala Glu Thr Asp Arg Val Thr Gly Thr Asn
            100                 105                 110

Lys Gly Ile Ser Pro Val Pro Ile Asn Leu Arg Val Tyr Ser Pro His
        115                 120                 125

Val Leu Asn Leu Thr Leu Ile Asp Leu Pro Gly Ile Thr Lys Val Pro
```

```
    130                 135                 140

Val Gly Asp Gln Pro Pro Asp Ile Glu Tyr Arg Val Lys Asp Met Ile
145                 150                 155                 160

Leu Gln Phe Ile Ser Arg Glu Ser Ser Leu Ile Leu Ala Val Thr Pro
                165                 170                 175

Ala Asn Met Asp Leu Ala Asn Ser Asp Ala Leu Lys Leu Ala Lys Glu
            180                 185                 190

Val Asp Pro Gln Gly Leu Arg Thr Ile Gly Val Ile Thr Lys Leu Asp
        195                 200                 205

Leu Met Asp Glu Gly Thr Asp Ala Arg Asp Val Leu Glu Asn Lys Leu
    210                 215                 220

Leu Pro Leu Arg Arg Gly Tyr Ile Gly Val Val Asn Arg Ser Gln Lys
225                 230                 235                 240

Asp Ile Glu Gly Lys Lys Asp Ile Arg Ala Ala Leu Ala Ala Glu Arg
                245                 250                 255

Lys Phe Phe Leu Ser His Pro Ala Tyr Arg His Met Ala Asp Arg Met
            260                 265                 270

Gly Thr Pro His Leu Gln Lys Thr Leu Asn Gln Gln Leu Thr Asn His
        275                 280                 285

Ile Arg Glu Ser Leu Pro Ala Leu Arg Ser Lys Leu Gln Ser Gln Leu
    290                 295                 300

Leu Ser Leu Glu Lys Glu Val Glu Glu Tyr Lys Ile Phe Arg Pro Asp
305                 310                 315                 320

Asp Pro Thr Pro Lys Thr Lys Ala Leu Leu Gln Met Val Gln Gln Phe
                325                 330                 335

Gly Val Asp Phe Glu Lys Arg Ile Glu Gly Ser Gly Asp Gln Val Asp
            340                 345                 350

Thr Leu Glu Leu Ser Gly Gly Ala Arg Ile Asn Arg Ile Phe His Glu
        355                 360                 365

Arg Phe Pro Phe Glu Leu Val Lys Met Glu Phe Asp Glu Lys Asp Leu
    370                 375                 380

Arg Arg Glu Ile Ser Tyr Ala Ile Lys Asn Ile His Gly Val Arg Thr
385                 390                 395                 400

Gly Leu Phe Thr Pro Asp Leu Ala Phe Glu Ala Ile Val Lys Lys Gln
                405                 410                 415

Val Val Lys Leu Lys Glu Pro Cys Leu Lys Cys Val Asp Leu Val Ile
            420                 425                 430

Gln Glu Leu Ile Asn Thr Val Arg Gln Cys Thr Ser Lys Leu Ser Ser
        435                 440                 445

Tyr Pro Arg Leu Arg Glu Glu Thr Glu Arg Ile Val Thr Thr Tyr Ile
    450                 455                 460

Arg Glu Arg Glu Gly Arg Thr Lys Asp Gln Ile Leu Leu Leu Ile Asp
465                 470                 475                 480

Ile Glu Gln Ser Tyr Ile Asn Thr Asn His Glu Asp Phe Ile Gly Phe
                485                 490                 495

Ala Asn Ala Gln Gln Arg Ser Thr Gln Leu Asn Lys Lys Arg Ala Ile
            500                 505                 510

Pro Asn Gln Val Ile Arg Arg Gly Trp Leu Thr Ile Asn Asn Ile Ser
        515                 520                 525

Leu Met Lys Gly Gly Ser Lys Glu Tyr Trp Phe Val Leu Thr Ala Glu
    530                 535                 540

Ser Leu Ser Trp Tyr Lys Asp Glu Glu Glu Lys Glu Lys Lys Tyr Met
545                 550                 555                 560
```

Leu Pro Leu Asp Asn Leu Lys Ile Arg Asp Val Glu Lys Gly Phe Met
565 570 575

Ser Asn Lys His Val Phe Ala Ile Phe Asn Thr Glu Gln Arg Asn Val
580 585 590

Tyr Lys Asp Leu Arg Gln Ile Glu Leu Ala Cys Asp Ser Gln Glu Asp
595 600 605

Val Asp Ser Trp Lys Ala Ser Phe Leu Arg Ala Gly Val Tyr Pro Glu
610 615 620

Lys Asp Gln Ala Glu Asn Glu Asp Gly Ala Gln Glu Asn Thr Phe Ser
625 630 635 640

Met Asp Pro Gln Leu Glu Arg Gln Val Glu Thr Ile Arg Asn Leu Val
645 650 655

Asp Ser Tyr Val Ala Ile Ile Asn Lys Ser Ile Arg Asp Leu Met Pro
660 665 670

Lys Thr Ile Met His Leu Met Ile Asn Asn Thr Lys Ala Phe Ile His
675 680 685

His Glu Leu Leu Ala Tyr Leu Tyr Ser Ser Ala Asp Gln Ser Ser Leu
690 695 700

Met Glu Glu Ser Ala Asp Gln Ala Gln Arg Arg Asp Asp Met Leu Arg
705 710 715 720

Met Tyr His Ala Leu Lys Glu Ala Leu Asn Ile Ile Gly Asp Ile Ser
725 730 735

Thr Ser Thr Val Ser Thr Pro Val Pro Pro Pro Val Asp Asp Thr Trp
740 745 750

Leu Gln Ser Ala Ser Ser His Ser Pro Thr Pro Gln Arg Arg Pro Val
755 760 765

Ser Ser Ile His Pro Pro Gly Arg Pro Pro Ala Val Arg Gly Pro Thr
770 775 780

Pro Gly Pro Pro Leu Ile Pro Val Pro Val Gly Ala Ala Ala Ser Phe
785 790 795 800

Ser Ala Pro Pro Ile Pro Ser Arg Pro Gly Pro Gln Ser Val Phe Ala
805 810 815

Asn Ser Asp Leu Phe Pro Ala Pro Pro Gln Ile Pro Ser Arg Pro Val
820 825 830

Arg Ile Pro Pro Gly Ile Pro Pro Gly Val Pro Ser Arg Arg Pro Pro
835 840 845

Ala Ala Pro Ser Arg Pro Thr Ile Ile Arg Pro Ala Glu Pro Ser Leu
850 855 860

Leu Asp
865

<210> SEQ ID NO 152
<211> LENGTH: 1675
<212> TYPE: PRT
<213> ORGANISM: Homo sapiens

<400> SEQUENCE: 152

Met Ala Gln Ile Leu Pro Ile Arg Phe Gln Glu His Leu Gln Leu Gln
1 5 10 15

Asn Leu Gly Ile Asn Pro Ala Asn Ile Gly Phe Ser Thr Leu Thr Met
20 25 30

Glu Ser Asp Lys Phe Ile Cys Ile Arg Glu Lys Val Gly Glu Gln Ala
35 40 45

Gln Val Val Ile Ile Asp Met Asn Asp Pro Ser Asn Pro Ile Arg Arg

```
    50                  55                  60

Pro Ile Ser Ala Asp Ser Ala Ile Met Asn Pro Ala Ser Lys Val Ile
65                  70                  75                  80

Ala Leu Lys Ala Gly Lys Thr Leu Gln Ile Phe Asn Ile Glu Met Lys
                85                  90                  95

Ser Lys Met Lys Ala His Thr Met Thr Asp Asp Val Thr Phe Trp Lys
            100                 105                 110

Trp Ile Ser Leu Asn Thr Val Ala Leu Val Thr Asp Asn Ala Val Tyr
        115                 120                 125

His Trp Ser Met Glu Gly Glu Ser Gln Pro Val Lys Met Phe Asp Arg
    130                 135                 140

His Ser Ser Leu Ala Gly Cys Gln Ile Ile Asn Tyr Arg Thr Asp Ala
145                 150                 155                 160

Lys Gln Lys Trp Leu Leu Leu Thr Gly Ile Ser Ala Gln Gln Asn Arg
                165                 170                 175

Val Val Gly Ala Met Gln Leu Tyr Ser Val Asp Arg Lys Val Ser Gln
            180                 185                 190

Pro Ile Glu Gly His Ala Ala Ser Phe Ala Gln Phe Lys Met Glu Gly
        195                 200                 205

Asn Ala Glu Glu Ser Thr Leu Phe Cys Phe Ala Val Arg Gly Gln Ala
    210                 215                 220

Gly Gly Lys Leu His Ile Ile Glu Val Gly Thr Pro Pro Thr Gly Asn
225                 230                 235                 240

Gln Pro Phe Pro Lys Lys Ala Val Asp Val Phe Phe Pro Pro Glu Ala
                245                 250                 255

Gln Asn Asp Phe Pro Val Ala Met Gln Ile Ser Glu Lys His Asp Val
            260                 265                 270

Val Phe Leu Ile Thr Lys Tyr Gly Tyr Ile His Leu Tyr Asp Leu Glu
        275                 280                 285

Thr Gly Thr Cys Ile Tyr Met Asn Arg Ile Ser Gly Glu Thr Ile Phe
    290                 295                 300

Val Thr Ala Pro His Glu Ala Thr Ala Gly Ile Ile Gly Val Asn Arg
305                 310                 315                 320

Lys Gly Gln Val Leu Ser Val Cys Val Glu Glu Glu Asn Ile Ile Pro
                325                 330                 335

Tyr Ile Thr Asn Val Leu Gln Asn Pro Asp Leu Ala Leu Arg Met Ala
            340                 345                 350

Val Arg Asn Asn Leu Ala Gly Ala Glu Glu Leu Phe Ala Arg Lys Phe
        355                 360                 365

Asn Ala Leu Phe Ala Gln Gly Asn Tyr Ser Glu Ala Ala Lys Val Ala
    370                 375                 380

Ala Asn Ala Pro Lys Gly Ile Leu Arg Thr Pro Asp Thr Ile Arg Arg
385                 390                 395                 400

Phe Gln Ser Val Pro Ala Gln Pro Gly Gln Thr Ser Pro Leu Leu Gln
                405                 410                 415

Tyr Phe Gly Ile Leu Leu Asp Gln Gly Gln Leu Asn Lys Tyr Glu Ser
            420                 425                 430

Leu Glu Leu Cys Arg Pro Val Leu Gln Gln Gly Arg Lys Gln Leu Leu
        435                 440                 445

Glu Lys Trp Leu Lys Glu Asp Lys Leu Glu Cys Ser Glu Glu Leu Gly
    450                 455                 460

Asp Leu Val Lys Ser Val Asp Pro Thr Leu Ala Leu Ser Val Tyr Leu
465                 470                 475                 480
```

```
Arg Ala Asn Val Pro Asn Lys Val Ile Gln Cys Phe Ala Glu Thr Gly
                485                 490                 495

Gln Val Gln Lys Ile Val Leu Tyr Ala Lys Lys Val Gly Tyr Thr Pro
            500                 505                 510

Asp Trp Ile Phe Leu Leu Arg Asn Val Met Arg Ile Ser Pro Asp Gln
        515                 520                 525

Gly Gln Gln Phe Ala Gln Met Leu Val Gln Asp Glu Glu Pro Leu Ala
    530                 535                 540

Asp Ile Thr Gln Ile Val Asp Val Phe Met Glu Tyr Asn Leu Ile Gln
545                 550                 555                 560

Gln Cys Thr Ala Phe Leu Leu Asp Ala Leu Lys Asn Asn Arg Pro Ser
                565                 570                 575

Glu Gly Pro Leu Gln Thr Arg Leu Leu Glu Met Asn Leu Met His Ala
            580                 585                 590

Pro Gln Val Ala Asp Ala Ile Leu Gly Asn Gln Met Phe Thr His Tyr
        595                 600                 605

Asp Arg Ala His Ile Ala Gln Leu Cys Glu Lys Ala Gly Leu Leu Gln
    610                 615                 620

Arg Ala Leu Glu His Phe Thr Asp Leu Tyr Asp Ile Lys Arg Ala Val
625                 630                 635                 640

Val His Thr His Leu Leu Asn Pro Glu Trp Leu Val Asn Tyr Phe Gly
                645                 650                 655

Ser Leu Ser Val Glu Asp Ser Leu Glu Cys Leu Arg Ala Met Leu Ser
            660                 665                 670

Ala Asn Ile Arg Gln Asn Leu Gln Ile Cys Val Gln Val Ala Ser Lys
        675                 680                 685

Tyr His Glu Gln Leu Ser Thr Gln Ser Leu Ile Glu Leu Phe Glu Ser
    690                 695                 700

Phe Lys Ser Phe Glu Gly Leu Phe Tyr Phe Leu Gly Ser Ile Val Asn
705                 710                 715                 720

Phe Ser Gln Asp Pro Asp Val His Phe Lys Tyr Ile Gln Ala Ala Cys
                725                 730                 735

Lys Thr Gly Gln Ile Lys Glu Val Glu Arg Ile Cys Arg Glu Ser Asn
            740                 745                 750

Cys Tyr Asp Pro Glu Arg Val Lys Asn Phe Leu Lys Glu Ala Lys Leu
        755                 760                 765

Thr Asp Gln Leu Pro Leu Ile Ile Val Cys Asp Arg Phe Asp Phe Val
    770                 775                 780

His Asp Leu Val Leu Tyr Leu Tyr Arg Asn Asn Leu Gln Lys Tyr Ile
785                 790                 795                 800

Glu Ile Tyr Val Gln Lys Val Asn Pro Ser Arg Leu Pro Val Val Ile
                805                 810                 815

Gly Gly Leu Leu Asp Val Asp Cys Ser Glu Asp Val Ile Lys Asn Leu
            820                 825                 830

Ile Leu Val Val Arg Gly Gln Phe Ser Thr Asp Glu Leu Val Ala Glu
        835                 840                 845

Val Glu Lys Arg Asn Arg Leu Lys Leu Leu Leu Pro Trp Leu Glu Ala
    850                 855                 860

Arg Ile His Glu Gly Cys Glu Glu Pro Ala Thr His Asn Ala Leu Ala
865                 870                 875                 880

Lys Ile Tyr Ile Asp Ser Asn Asn Asn Pro Glu Arg Phe Leu Arg Glu
                885                 890                 895
```

-continued

```
Asn Pro Tyr Tyr Asp Ser Arg Val Val Gly Lys Tyr Cys Glu Lys Arg
            900                 905                 910

Asp Pro His Leu Ala Cys Val Ala Tyr Glu Arg Gly Gln Cys Asp Leu
        915                 920                 925

Glu Leu Ile Asn Val Cys Asn Glu Asn Ser Leu Phe Lys Ser Leu Ser
    930                 935                 940

Arg Tyr Leu Val Arg Arg Lys Asp Pro Glu Leu Trp Gly Ser Val Leu
945                 950                 955                 960

Leu Glu Ser Asn Pro Tyr Arg Arg Pro Leu Ile Asp Gln Val Val Gln
                965                 970                 975

Thr Ala Leu Ser Glu Thr Gln Asp Pro Glu Glu Val Ser Val Thr Val
            980                 985                 990

Lys Ala Phe Met Thr Ala Asp Leu  Pro Asn Glu Leu Ile  Glu Leu Leu
        995                 1000                1005

Glu Lys  Ile Val Leu Asp Asn  Ser Val Phe Ser Glu  His Arg Asn
    1010                 1015                 1020

Leu Gln  Asn Leu Leu Ile Leu  Thr Ala Ile Lys Ala  Asp Arg Thr
    1025                 1030                 1035

Arg Val  Met Glu Tyr Ile Asn  Arg Leu Asp Asn Tyr  Asp Ala Pro
    1040                 1045                 1050

Asp Ile  Ala Asn Ile Ala Ile  Ser Asn Glu Leu Phe  Glu Glu Ala
    1055                 1060                 1065

Phe Ala  Ile Phe Arg Lys Phe  Asp Val Asn Thr Ser  Ala Val Gln
    1070                 1075                 1080

Val Leu  Ile Glu His Ile Gly  Asn Leu Asp Arg Ala  Tyr Glu Phe
    1085                 1090                 1095

Ala Glu  Arg Cys Asn Glu Pro  Ala Val Trp Ser Gln  Leu Ala Lys
    1100                 1105                 1110

Ala Gln  Leu Gln Lys Gly Met  Val Lys Glu Ala Ile  Asp Ser Tyr
    1115                 1120                 1125

Ile Lys  Ala Asp Asp Pro Ser  Ser Tyr Met Glu Val  Val Gln Ala
    1130                 1135                 1140

Ala Asn  Thr Ser Gly Asn Trp  Glu Glu Leu Val Lys  Tyr Leu Gln
    1145                 1150                 1155

Met Ala  Arg Lys Lys Ala Arg  Glu Ser Tyr Val Glu  Thr Glu Leu
    1160                 1165                 1170

Ile Phe  Ala Leu Ala Lys Thr  Asn Arg Leu Ala Glu  Leu Glu Glu
    1175                 1180                 1185

Phe Ile  Asn Gly Pro Asn Asn  Ala His Ile Gln Gln  Val Gly Asp
    1190                 1195                 1200

Arg Cys  Tyr Asp Glu Lys Met  Tyr Asp Ala Ala Lys  Leu Leu Tyr
    1205                 1210                 1215

Asn Asn  Val Ser Asn Phe Gly  Arg Leu Ala Ser Thr  Leu Val His
    1220                 1225                 1230

Leu Gly  Glu Tyr Gln Ala Ala  Val Asp Gly Ala Arg  Lys Ala Asn
    1235                 1240                 1245

Ser Thr  Arg Thr Trp Lys Glu  Val Cys Phe Ala Cys  Val Asp Gly
    1250                 1255                 1260

Lys Glu  Phe Arg Leu Ala Gln  Met Cys Gly Leu His  Ile Val Val
    1265                 1270                 1275

His Ala  Asp Glu Leu Glu Glu  Leu Ile Asn Tyr Tyr  Gln Asp Arg
    1280                 1285                 1290

Gly Tyr  Phe Glu Glu Leu Ile  Thr Met Leu Glu Ala  Ala Leu Gly
```

```
    1295                1300                1305

Leu Glu  Arg Ala His Met Gly  Met Phe Thr Glu Leu  Ala Ile Leu
    1310                1315                1320

Tyr Ser  Lys Phe Lys Pro Gln  Lys Met Arg Glu His  Leu Glu Leu
    1325                1330                1335

Phe Trp  Ser Arg Val Asn Ile  Pro Lys Val Leu Arg  Ala Ala Glu
    1340                1345                1350

Gln Ala  His Leu Trp Ala Glu  Leu Val Phe Leu Tyr  Asp Lys Tyr
    1355                1360                1365

Glu Glu  Tyr Asp Asn Ala Ile  Ile Thr Met Met Asn  His Pro Thr
    1370                1375                1380

Asp Ala  Trp Lys Glu Gly Gln  Phe Lys Asp Ile Ile  Thr Lys Val
    1385                1390                1395

Ala Asn  Val Glu Leu Tyr Tyr  Arg Ala Ile Gln Phe  Tyr Leu Glu
    1400                1405                1410

Phe Lys  Pro Leu Leu Leu Asn  Asp Leu Leu Met Val  Leu Ser Pro
    1415                1420                1425

Arg Leu  Asp His Thr Arg Ala  Val Asn Tyr Phe Ser  Lys Val Lys
    1430                1435                1440

Gln Leu  Pro Leu Val Lys Pro  Tyr Leu Arg Ser Val  Gln Asn His
    1445                1450                1455

Asn Asn  Lys Ser Val Asn Glu  Ser Leu Asn Asn Leu  Phe Ile Thr
    1460                1465                1470

Glu Glu  Asp Tyr Gln Ala Leu  Arg Thr Ser Ile Asp  Ala Tyr Asp
    1475                1480                1485

Asn Phe  Asp Asn Ile Ser Leu  Ala Gln Arg Leu Glu  Lys His Glu
    1490                1495                1500

Leu Ile  Glu Phe Arg Arg Ile  Ala Ala Tyr Leu Phe  Lys Gly Asn
    1505                1510                1515

Asn Arg  Trp Lys Gln Ser Val  Glu Leu Cys Lys Lys  Asp Ser Leu
    1520                1525                1530

Tyr Lys  Asp Ala Met Gln Tyr  Ala Ser Glu Ser Lys  Asp Thr Glu
    1535                1540                1545

Leu Ala  Glu Glu Leu Leu Gln  Trp Phe Leu Gln Glu  Glu Lys Arg
    1550                1555                1560

Glu Cys  Phe Gly Ala Cys Leu  Phe Thr Cys Tyr Asp  Leu Leu Arg
    1565                1570                1575

Pro Asp  Val Val Leu Glu Thr  Ala Trp Arg His Asn  Ile Met Asp
    1580                1585                1590

Phe Ala  Met Pro Tyr Phe Ile  Gln Val Met Lys Glu  Tyr Leu Thr
    1595                1600                1605

Lys Val  Asp Lys Leu Asp Ala  Ser Glu Ser Leu Arg  Lys Glu Glu
    1610                1615                1620

Glu Gln  Ala Thr Glu Thr Gln  Pro Ile Val Tyr Gly  Gln Pro Gln
    1625                1630                1635

Leu Met  Leu Thr Ala Gly Pro  Ser Val Ala Val Pro  Pro Gln Ala
    1640                1645                1650

Pro Phe  Gly Tyr Gly Tyr Thr  Ala Pro Pro Tyr Gly  Gln Pro Gln
    1655                1660                1665

Pro Gly  Phe Gly Tyr Ser Met
    1670                1675
```

<210> SEQ ID NO 153

<211> LENGTH: 1640
<212> TYPE: PRT
<213> ORGANISM: Homo sapiens

<400> SEQUENCE: 153

```
Met Ala Gln Ile Leu Pro Val Arg Phe Gln Glu His Phe Gln Leu Gln
1               5                   10                  15

Asn Leu Gly Ile Asn Pro Ala Asn Ile Gly Phe Ser Thr Leu Thr Met
            20                  25                  30

Glu Ser Asp Lys Phe Ile Cys Ile Arg Glu Lys Val Gly Glu Gln Ala
        35                  40                  45

Gln Val Thr Ile Ile Asp Met Ser Asp Pro Met Ala Pro Ile Arg Arg
    50                  55                  60

Pro Ile Ser Ala Glu Ser Ala Ile Met Asn Pro Ala Ser Lys Val Ile
65                  70                  75                  80

Ala Leu Lys Ala Gly Lys Thr Leu Gln Ile Phe Asn Ile Glu Met Lys
                85                  90                  95

Ser Lys Met Lys Ala His Thr Met Ala Glu Glu Val Ile Phe Trp Lys
            100                 105                 110

Trp Val Ser Val Asn Thr Val Ala Leu Val Thr Glu Thr Ala Val Tyr
        115                 120                 125

His Trp Ser Met Glu Gly Asp Ser Gln Pro Met Lys Met Phe Asp Arg
    130                 135                 140

His Thr Ser Leu Val Gly Cys Gln Val Ile His Tyr Arg Thr Asp Glu
145                 150                 155                 160

Tyr Gln Lys Trp Leu Leu Leu Val Gly Ile Ser Ala Gln Gln Asn Arg
                165                 170                 175

Val Val Gly Ala Met Gln Leu Tyr Ser Val Asp Arg Lys Val Ser Gln
            180                 185                 190

Pro Ile Glu Gly His Ala Ala Ala Phe Ala Glu Phe Lys Met Glu Gly
        195                 200                 205

Asn Ala Lys Pro Ala Thr Leu Phe Cys Phe Ala Val Arg Asn Pro Thr
    210                 215                 220

Gly Gly Lys Leu His Ile Ile Glu Val Gly Gln Pro Ala Ala Gly Asn
225                 230                 235                 240

Gln Pro Phe Val Lys Lys Ala Val Asp Val Phe Phe Pro Pro Glu Ala
                245                 250                 255

Gln Asn Asp Phe Pro Val Ala Met Gln Ile Gly Ala Lys His Gly Val
            260                 265                 270

Ile Tyr Leu Ile Thr Lys Tyr Gly Tyr Leu His Leu Tyr Asp Leu Glu
        275                 280                 285

Ser Gly Val Cys Ile Cys Met Asn Arg Ile Ser Ala Asp Thr Ile Phe
    290                 295                 300

Val Thr Ala Pro His Lys Pro Thr Ser Gly Ile Ile Gly Val Asn Lys
305                 310                 315                 320

Lys Gly Gln Val Leu Ser Val Cys Val Glu Glu Asp Asn Ile Val Asn
                325                 330                 335

Tyr Ala Thr Asn Val Leu Gln Asn Pro Asp Leu Gly Leu Arg Leu Ala
            340                 345                 350

Val Arg Ser Asn Leu Ala Gly Ala Glu Lys Leu Phe Val Arg Lys Phe
        355                 360                 365

Asn Thr Leu Phe Ala Gln Gly Ser Tyr Ala Glu Ala Ala Lys Val Ala
    370                 375                 380

Ala Ser Ala Pro Lys Gly Ile Leu Arg Thr Arg Glu Thr Val Gln Lys
```

```
385                 390                 395                 400

Phe Gln Ser Ile Pro Ala Gln Ser Gly Gln Ala Ser Pro Leu Leu Gln
                405                 410                 415

Tyr Phe Gly Ile Leu Leu Asp Gln Gly Gln Leu Asn Lys Leu Glu Ser
            420                 425                 430

Leu Glu Leu Cys His Leu Val Leu Gln Gln Gly Arg Lys Gln Leu Leu
        435                 440                 445

Glu Lys Trp Leu Lys Glu Asp Lys Leu Glu Cys Ser Glu Glu Leu Gly
    450                 455                 460

Asp Leu Val Lys Thr Thr Asp Pro Met Leu Ala Leu Ser Val Tyr Leu
465                 470                 475                 480

Arg Ala Asn Val Pro Ser Lys Val Ile Gln Cys Phe Ala Glu Thr Gly
                485                 490                 495

Gln Phe Gln Lys Ile Val Leu Tyr Ala Lys Lys Val Gly Tyr Thr Pro
            500                 505                 510

Asp Trp Ile Phe Leu Leu Arg Gly Val Met Lys Ile Ser Pro Glu Gln
        515                 520                 525

Gly Leu Gln Phe Ser Arg Met Leu Val Gln Asp Glu Glu Pro Leu Ala
    530                 535                 540

Asn Ile Ser Gln Ile Val Asp Ile Phe Met Glu Asn Ser Leu Ile Gln
545                 550                 555                 560

Gln Cys Thr Ser Phe Leu Leu Asp Ala Leu Lys Asn Asn Arg Pro Ala
                565                 570                 575

Glu Gly Leu Leu Gln Thr Trp Leu Leu Glu Met Asn Leu Val His Ala
            580                 585                 590

Pro Gln Val Ala Asp Ala Ile Leu Gly Asn Lys Met Phe Thr His Tyr
        595                 600                 605

Asp Arg Ala His Ile Ala Gln Leu Cys Glu Lys Ala Gly Leu Leu Gln
    610                 615                 620

Gln Ala Leu Glu His Tyr Thr Asp Leu Tyr Asp Ile Lys Arg Ala Val
625                 630                 635                 640

Val His Thr His Leu Leu Asn Pro Glu Trp Leu Val Asn Phe Phe Gly
                645                 650                 655

Ser Leu Ser Val Glu Asp Ser Val Glu Cys Leu His Ala Met Leu Ser
            660                 665                 670

Ala Asn Ile Arg Gln Asn Leu Gln Leu Cys Val Gln Val Ala Ser Lys
        675                 680                 685

Tyr His Glu Gln Leu Gly Thr Gln Ala Leu Val Glu Leu Phe Glu Ser
    690                 695                 700

Phe Lys Ser Tyr Lys Gly Leu Phe Tyr Phe Leu Gly Ser Ile Val Asn
705                 710                 715                 720

Phe Ser Gln Asp Pro Asp Val His Leu Lys Tyr Ile Gln Ala Ala Cys
                725                 730                 735

Lys Thr Gly Gln Ile Lys Glu Val Glu Arg Ile Cys Arg Glu Ser Ser
            740                 745                 750

Cys Tyr Asn Pro Glu Arg Val Lys Asn Phe Leu Lys Glu Ala Lys Leu
        755                 760                 765

Thr Asp Gln Leu Pro Leu Ile Ile Val Cys Asp Arg Phe Gly Phe Val
    770                 775                 780

His Asp Leu Val Leu Tyr Leu Tyr Arg Asn Asn Leu Gln Arg Tyr Ile
785                 790                 795                 800

Glu Ile Tyr Val Gln Lys Val Asn Pro Ser Arg Thr Pro Ala Val Ile
                805                 810                 815
```

Gly Gly Leu Leu Asp Val Asp Cys Ser Glu Glu Val Ile Lys His Leu
820 825 830

Ile Met Ala Val Arg Gly Gln Phe Ser Thr Asp Glu Leu Val Ala Glu
835 840 845

Val Glu Lys Arg Asn Arg Leu Lys Leu Leu Leu Pro Trp Leu Glu Ser
850 855 860

Gln Ile Gln Glu Gly Cys Glu Glu Pro Ala Thr His Asn Ala Leu Ala
865 870 875 880

Lys Ile Tyr Ile Asp Ser Asn Asn Ser Pro Glu Cys Phe Leu Arg Glu
885 890 895

Asn Ala Tyr Tyr Asp Ser Ser Val Val Gly Arg Tyr Cys Glu Lys Arg
900 905 910

Asp Pro His Leu Ala Cys Val Ala Tyr Glu Arg Gly Gln Cys Asp Leu
915 920 925

Glu Leu Ile Lys Val Cys Asn Glu Asn Ser Leu Phe Lys Ser Glu Ala
930 935 940

Arg Tyr Leu Val Cys Arg Lys Asp Pro Glu Leu Trp Ala His Val Leu
945 950 955 960

Glu Glu Thr Asn Pro Ser Arg Arg Gln Leu Ile Asp Gln Val Val Gln
965 970 975

Thr Ala Leu Ser Glu Thr Arg Asp Pro Glu Glu Ile Ser Val Thr Val
980 985 990

Lys Ala Phe Met Thr Ala Asp Leu Pro Asn Glu Leu Ile Glu Leu Leu
995 1000 1005

Glu Lys Ile Val Leu Asp Asn Ser Val Phe Ser Glu His Arg Asn
1010 1015 1020

Leu Gln Asn Leu Leu Ile Leu Thr Ala Ile Lys Ala Asp Arg Thr
1025 1030 1035

Arg Val Met Glu Tyr Ile Ser Arg Leu Asp Asn Tyr Asp Ala Leu
1040 1045 1050

Asp Ile Ala Ser Ile Ala Val Ser Ser Ala Leu Tyr Glu Glu Ala
1055 1060 1065

Phe Thr Val Phe His Lys Phe Asp Met Asn Ala Ser Ala Ile Gln
1070 1075 1080

Val Leu Ile Glu His Ile Gly Asn Leu Asp Arg Ala Tyr Glu Phe
1085 1090 1095

Ala Glu Arg Cys Asn Glu Pro Ala Val Trp Ser Gln Leu Ala Gln
1100 1105 1110

Ala Gln Leu Gln Lys Asp Leu Val Lys Glu Ala Ile Asn Ser Tyr
1115 1120 1125

Ile Arg Gly Asp Asp Pro Ser Ser Tyr Leu Glu Val Val Gln Ser
1130 1135 1140

Ala Ser Arg Ser Asn Asn Trp Glu Asp Leu Val Lys Phe Leu Gln
1145 1150 1155

Met Ala Arg Lys Lys Gly Arg Glu Ser Tyr Ile Glu Thr Glu Leu
1160 1165 1170

Ile Phe Ala Leu Ala Lys Thr Ser Arg Val Ser Glu Leu Glu Asp
1175 1180 1185

Phe Ile Asn Gly Pro Asn Asn Ala His Ile Gln Gln Val Gly Asp
1190 1195 1200

Arg Cys Tyr Glu Glu Gly Met Tyr Glu Ala Ala Lys Leu Leu Tyr
1205 1210 1215

```
Ser Asn  Val Ser Asn Phe Ala  Arg Leu Ala Ser Thr  Leu Val His
    1220                 1225                 1230

Leu Gly  Glu Tyr Gln Ala Ala  Val Asp Asn Ser Arg  Lys Ala Ser
    1235                 1240                 1245

Ser Thr  Arg Thr Trp Lys Glu  Val Cys Phe Ala Cys  Met Asp Gly
    1250                 1255                 1260

Gln Glu  Phe Arg Phe Ala Gln  Leu Cys Gly Leu His  Ile Val Ile
    1265                 1270                 1275

His Ala  Asp Glu Leu Glu Glu  Leu Met Cys Tyr Tyr  Gln Asp Arg
    1280                 1285                 1290

Gly Tyr  Phe Glu Glu Leu Ile  Leu Leu Leu Glu Ala  Ala Leu Gly
    1295                 1300                 1305

Leu Glu  Arg Ala His Met Gly  Met Phe Thr Glu Leu  Ala Ile Leu
    1310                 1315                 1320

Tyr Ser  Lys Phe Lys Pro Gln  Lys Met Leu Glu His  Leu Glu Leu
    1325                 1330                 1335

Phe Trp  Ser Arg Val Asn Ile  Pro Lys Val Leu Arg  Ala Ala Glu
    1340                 1345                 1350

Gln Ala  His Leu Trp Ala Glu  Leu Val Phe Leu Tyr  Asp Lys Tyr
    1355                 1360                 1365

Glu Glu  Tyr Asp Asn Ala Val  Leu Thr Met Met Ser  His Pro Thr
    1370                 1375                 1380

Glu Ala  Trp Lys Glu Gly Gln  Phe Lys Asp Ile Ile  Thr Lys Val
    1385                 1390                 1395

Ala Asn  Val Glu Leu Cys Tyr  Arg Ala Leu Gln Phe  Tyr Leu Asp
    1400                 1405                 1410

Tyr Lys  Pro Leu Leu Ile Asn  Asp Leu Leu Leu Val  Leu Ser Pro
    1415                 1420                 1425

Arg Leu  Asp His Thr Trp Thr  Val Ser Phe Phe Ser  Lys Ala Gly
    1430                 1435                 1440

Gln Leu  Pro Leu Val Lys Pro  Tyr Leu Arg Ser Val  Gln Ser His
    1445                 1450                 1455

Asn Asn  Lys Ser Val Asn Glu  Ala Leu Asn His Leu  Leu Thr Glu
    1460                 1465                 1470

Glu Glu  Asp Tyr Gln Gly Leu  Arg Ala Ser Ile Asp  Ala Tyr Asp
    1475                 1480                 1485

Asn Phe  Asp Asn Ile Ser Leu  Ala Gln Gln Leu Glu  Lys His Gln
    1490                 1495                 1500

Leu Met  Glu Phe Arg Cys Ile  Ala Ala Tyr Leu Tyr  Lys Gly Asn
    1505                 1510                 1515

Asn Trp  Trp Ala Gln Ser Val  Glu Leu Cys Lys Lys  Asp His Leu
    1520                 1525                 1530

Tyr Lys  Asp Ala Met Gln His  Ala Ala Glu Ser Arg  Asp Ala Glu
    1535                 1540                 1545

Leu Ala  Gln Lys Leu Leu Gln  Trp Phe Leu Glu Glu  Gly Lys Arg
    1550                 1555                 1560

Glu Cys  Phe Ala Ala Cys Leu  Phe Thr Cys Tyr Asp  Leu Leu Arg
    1565                 1570                 1575

Pro Asp  Met Val Leu Glu Leu  Ala Trp Arg His Asn  Leu Val Asp
    1580                 1585                 1590

Leu Ala  Met Pro Tyr Phe Ile  Gln Val Met Arg Glu  Tyr Leu Ser
    1595                 1600                 1605

Lys Val  Asp Lys Leu Asp Ala  Leu Glu Ser Leu Arg  Lys Gln Glu
```

```
    1610                1615                1620

Glu His  Val Thr Glu Pro Ala  Pro Leu Val Phe Asp  Phe Asp Gly
    1625                1630                1635

His Glu
    1640


<210> SEQ ID NO 154
<211> LENGTH: 218
<212> TYPE: PRT
<213> ORGANISM: Homo sapiens

<400> SEQUENCE: 154

Met Ala Glu Leu Asp Pro Phe Gly Ala Pro Ala Gly Ala Pro Gly Gly
1               5                   10                  15

Pro Ala Leu Gly Asn Gly Val Ala Gly Ala Gly Glu Glu Asp Pro Ala
            20                  25                  30

Ala Ala Phe Leu Ala Gln Gln Glu Ser Glu Ile Ala Gly Ile Glu Asn
        35                  40                  45

Asp Glu Ala Phe Ala Ile Leu Asp Gly Gly Ala Pro Gly Pro Gln Pro
    50                  55                  60

His Gly Glu Pro Pro Gly Gly Pro Asp Ala Val Asp Gly Val Met Asn
65                  70                  75                  80

Gly Glu Tyr Tyr Gln Glu Ser Asn Gly Pro Thr Asp Ser Tyr Ala Ala
                85                  90                  95

Ile Ser Gln Val Asp Arg Leu Gln Ser Glu Pro Glu Ser Ile Arg Lys
            100                 105                 110

Trp Arg Glu Glu Gln Met Glu Arg Leu Glu Ala Leu Asp Ala Asn Ser
        115                 120                 125

Arg Lys Gln Glu Ala Glu Trp Lys Glu Lys Ala Ile Lys Glu Leu Glu
    130                 135                 140

Glu Trp Tyr Ala Arg Gln Asp Glu Gln Leu Gln Lys Thr Lys Ala Asn
145                 150                 155                 160

Asn Arg Ala Ala Glu Glu Ala Phe Val Asn Asp Ile Asp Glu Ser Ser
                165                 170                 175

Pro Gly Thr Glu Trp Glu Arg Val Ala Arg Leu Cys Asp Phe Asn Pro
            180                 185                 190

Lys Ser Ser Lys Gln Ala Lys Asp Val Ser Arg Met Arg Ser Val Leu
        195                 200                 205

Ile Ser Leu Lys Gln Ala Pro Leu Val His
    210                 215


<210> SEQ ID NO 155
<211> LENGTH: 211
<212> TYPE: PRT
<213> ORGANISM: Homo sapiens

<400> SEQUENCE: 155

Met Ala Asp Asp Phe Gly Phe Phe Ser Ser Ser Glu Ser Gly Ala Pro
1               5                   10                  15

Glu Ala Ala Glu Glu Asp Pro Ala Ala Ala Phe Leu Ala Gln Gln Glu
            20                  25                  30

Ser Glu Ile Ala Gly Ile Glu Asn Asp Glu Gly Phe Gly Ala Pro Ala
        35                  40                  45

Gly Ser His Ala Ala Pro Ala Gln Pro Gly Pro Thr Ser Gly Ala Gly
    50                  55                  60

Ser Glu Asp Met Gly Thr Thr Val Asn Gly Asp Val Phe Gln Glu Ala
```

65 70 75 80

Asn Gly Pro Ala Asp Gly Tyr Ala Ala Ile Ala Gln Ala Asp Arg Leu
85 90 95

Thr Gln Glu Pro Glu Ser Ile Arg Lys Trp Arg Glu Glu Gln Arg Lys
100 105 110

Arg Leu Gln Glu Leu Asp Ala Ala Ser Lys Val Thr Glu Gln Glu Trp
115 120 125

Arg Glu Lys Ala Lys Lys Asp Leu Glu Glu Trp Asn Gln Arg Gln Ser
130 135 140

Glu Gln Val Glu Lys Asn Lys Ile Asn Asn Arg Ala Ser Glu Glu Ala
145 150 155 160

Phe Val Lys Glu Ser Lys Glu Glu Thr Pro Gly Thr Glu Trp Glu Lys
165 170 175

Val Ala Gln Leu Cys Asp Phe Asn Pro Lys Ser Ser Lys Gln Cys Lys
180 185 190

Asp Val Ser Arg Leu Arg Ser Val Leu Met Ser Leu Lys Gln Thr Pro
195 200 205

Leu Ser Arg
210

<210> SEQ ID NO 156
<211> LENGTH: 218
<212> TYPE: PRT
<213> ORGANISM: Homo sapiens

<400> SEQUENCE: 156

Met Ser Gln Thr Ala Met Ser Glu Thr Tyr Asp Phe Leu Phe Lys Phe
1 5 10 15

Leu Val Ile Gly Asn Ala Gly Thr Gly Lys Ser Cys Leu Leu His Gln
20 25 30

Phe Ile Glu Lys Lys Phe Lys Asp Asp Ser Asn His Thr Ile Gly Val
35 40 45

Glu Phe Gly Ser Lys Ile Ile Asn Val Gly Gly Lys Tyr Val Lys Leu
50 55 60

Gln Ile Trp Asp Thr Ala Gly Gln Glu Arg Phe Arg Ser Val Thr Arg
65 70 75 80

Ser Tyr Tyr Arg Gly Ala Ala Gly Ala Leu Leu Val Tyr Asp Ile Thr
85 90 95

Ser Arg Glu Thr Tyr Asn Ala Leu Thr Asn Trp Leu Thr Asp Ala Arg
100 105 110

Met Leu Ala Ser Gln Asn Ile Val Ile Ile Leu Cys Gly Asn Lys Lys
115 120 125

Asp Leu Asp Ala Asp Arg Glu Val Thr Phe Leu Glu Ala Ser Arg Phe
130 135 140

Ala Gln Glu Asn Glu Leu Met Phe Leu Glu Thr Ser Ala Leu Thr Gly
145 150 155 160

Glu Asn Val Glu Glu Ala Phe Val Gln Cys Ala Arg Lys Ile Leu Asn
165 170 175

Lys Ile Glu Ser Gly Glu Leu Asp Pro Glu Arg Met Gly Ser Gly Ile
180 185 190

Gln Tyr Gly Asp Ala Ala Leu Arg Gln Leu Arg Ser Pro Arg Arg Ala
195 200 205

Gln Ala Pro Asn Ala Gln Glu Cys Gly Cys
210 215

<210> SEQ ID NO 157
<211> LENGTH: 216
<212> TYPE: PRT
<213> ORGANISM: Homo sapiens

<400> SEQUENCE: 157

```
Met Gly Thr Arg Asp Asp Glu Tyr Asp Tyr Leu Phe Lys Val Val Leu
1               5                   10                  15

Ile Gly Asp Ser Gly Val Gly Lys Ser Asn Leu Leu Ser Arg Phe Thr
            20                  25                  30

Arg Asn Glu Phe Asn Leu Glu Ser Lys Ser Thr Ile Gly Val Glu Phe
        35                  40                  45

Ala Thr Arg Ser Ile Gln Val Asp Gly Lys Thr Ile Lys Ala Gln Ile
    50                  55                  60

Trp Asp Thr Ala Gly Gln Glu Arg Tyr Arg Ala Ile Thr Ser Ala Tyr
65                  70                  75                  80

Tyr Arg Gly Ala Val Gly Ala Leu Leu Val Tyr Asp Ile Ala Lys His
                85                  90                  95

Leu Thr Tyr Glu Asn Val Glu Arg Trp Leu Lys Glu Leu Arg Asp His
            100                 105                 110

Ala Asp Ser Asn Ile Val Ile Met Leu Val Gly Asn Lys Ser Asp Leu
        115                 120                 125

Arg His Leu Arg Ala Val Pro Thr Asp Glu Ala Arg Ala Phe Ala Glu
    130                 135                 140

Lys Asn Gly Leu Ser Phe Ile Glu Thr Ser Ala Leu Asp Ser Thr Asn
145                 150                 155                 160

Val Glu Ala Ala Phe Gln Thr Ile Leu Thr Glu Ile Tyr Arg Ile Val
                165                 170                 175

Ser Gln Lys Gln Met Ser Asp Arg Arg Glu Asn Asp Met Ser Pro Ser
            180                 185                 190

Asn Asn Val Val Pro Ile His Val Pro Pro Thr Thr Glu Asn Lys Pro
        195                 200                 205

Lys Val Gln Cys Cys Gln Asn Ile
    210                 215
```

<210> SEQ ID NO 158
<211> LENGTH: 241
<212> TYPE: PRT
<213> ORGANISM: Homo sapiens

<400> SEQUENCE: 158

```
Met Asn Arg Cys Trp Ala Leu Phe Leu Ser Leu Cys Cys Tyr Leu Arg
1               5                   10                  15

Leu Val Ser Ala Glu Gly Asp Pro Ile Pro Glu Glu Leu Tyr Glu Met
            20                  25                  30

Leu Ser Asp His Ser Ile Arg Ser Phe Asp Asp Leu Gln Arg Leu Leu
        35                  40                  45

His Gly Asp Pro Gly Glu Glu Asp Gly Ala Glu Leu Asp Leu Asn Met
    50                  55                  60

Thr Arg Ser His Ser Gly Gly Glu Leu Glu Ser Leu Ala Arg Gly Arg
65                  70                  75                  80

Arg Ser Leu Gly Ser Leu Thr Ile Ala Glu Pro Ala Met Ile Ala Glu
                85                  90                  95

Cys Lys Thr Arg Thr Glu Val Phe Glu Ile Ser Arg Arg Leu Ile Asp
            100                 105                 110
```

-continued

```
Arg Thr Asn Ala Asn Phe Leu Val Trp Pro Pro Cys Val Glu Val Gln
        115                 120                 125

Arg Cys Ser Gly Cys Cys Asn Asn Arg Asn Val Gln Cys Arg Pro Thr
    130                 135                 140

Gln Val Gln Leu Arg Pro Val Gln Val Arg Lys Ile Glu Ile Val Arg
145                 150                 155                 160

Lys Lys Pro Ile Phe Lys Lys Ala Thr Val Thr Leu Glu Asp His Leu
                165                 170                 175

Ala Cys Lys Cys Glu Thr Val Ala Ala Ala Arg Pro Val Thr Arg Ser
            180                 185                 190

Pro Gly Gly Ser Gln Glu Gln Arg Ala Lys Thr Pro Gln Thr Arg Val
        195                 200                 205

Thr Ile Arg Thr Val Arg Val Arg Arg Pro Pro Lys Gly Lys His Arg
    210                 215                 220

Lys Phe Lys His Thr His Asp Lys Thr Ala Leu Lys Glu Thr Leu Gly
225                 230                 235                 240

Ala


<210> SEQ ID NO 159
<211> LENGTH: 412
<212> TYPE: PRT
<213> ORGANISM: Homo sapiens

<400> SEQUENCE: 159

Met Lys Met His Leu Gln Arg Ala Leu Val Val Leu Ala Leu Leu Asn
1               5                   10                  15

Phe Ala Thr Val Ser Leu Ser Leu Ser Thr Cys Thr Thr Leu Asp Phe
            20                  25                  30

Gly His Ile Lys Lys Lys Arg Val Glu Ala Ile Arg Gly Gln Ile Leu
        35                  40                  45

Ser Lys Leu Arg Leu Thr Ser Pro Pro Glu Pro Thr Val Met Thr His
    50                  55                  60

Val Pro Tyr Gln Val Leu Ala Leu Tyr Asn Ser Thr Arg Glu Leu Leu
65                  70                  75                  80

Glu Glu Met His Gly Glu Arg Glu Glu Gly Cys Thr Gln Glu Asn Thr
                85                  90                  95

Glu Ser Glu Tyr Tyr Ala Lys Glu Ile His Lys Phe Asp Met Ile Gln
            100                 105                 110

Gly Leu Ala Glu His Asn Glu Leu Ala Val Cys Pro Lys Gly Ile Thr
        115                 120                 125

Ser Lys Val Phe Arg Phe Asn Val Ser Ser Val Glu Lys Asn Arg Thr
    130                 135                 140

Asn Leu Phe Arg Ala Glu Phe Arg Val Leu Arg Val Pro Asn Pro Ser
145                 150                 155                 160

Ser Lys Arg Asn Glu Gln Arg Ile Glu Leu Phe Gln Ile Leu Arg Pro
                165                 170                 175

Asp Glu His Ile Ala Lys Gln Arg Tyr Ile Gly Gly Lys Asn Leu Pro
            180                 185                 190

Thr Arg Gly Thr Ala Glu Trp Leu Ser Phe Asp Val Thr Asp Thr Val
        195                 200                 205

Arg Glu Trp Leu Leu Arg Arg Glu Ser Asn Leu Gly Leu Glu Ile Ser
    210                 215                 220

Ile His Cys Pro Cys His Thr Phe Gln Pro Asn Gly Asp Ile Leu Glu
225                 230                 235                 240
```

Asn Ile His Glu Val Met Glu Ile Lys Phe Lys Gly Val Asp Asn Glu
245 250 255

Asp Asp His Gly Arg Gly Asp Leu Gly Arg Leu Lys Lys Gln Lys Asp
260 265 270

His His Asn Pro His Leu Ile Leu Met Met Ile Pro Pro His Arg Leu
275 280 285

Asp Asn Pro Gly Gln Gly Gly Gln Arg Lys Lys Arg Ala Leu Asp Thr
290 295 300

Asn Tyr Cys Phe Arg Asn Leu Glu Glu Asn Cys Cys Val Arg Pro Leu
305 310 315 320

Tyr Ile Asp Phe Arg Gln Asp Leu Gly Trp Lys Trp Val His Glu Pro
325 330 335

Lys Gly Tyr Tyr Ala Asn Phe Cys Ser Gly Pro Cys Pro Tyr Leu Arg
340 345 350

Ser Ala Asp Thr Thr His Ser Thr Val Leu Gly Leu Tyr Asn Thr Leu
355 360 365

Asn Pro Glu Ala Ser Ala Ser Pro Cys Cys Val Pro Gln Asp Leu Glu
370 375 380

Pro Leu Thr Ile Leu Tyr Tyr Val Gly Arg Thr Pro Lys Val Glu Gln
385 390 395 400

Leu Ser Asn Met Val Val Lys Ser Cys Lys Cys Ser
405 410

<210> SEQ ID NO 160
<211> LENGTH: 257
<212> TYPE: PRT
<213> ORGANISM: Homo sapiens

<400> SEQUENCE: 160

Met Ser Ile Leu Phe Tyr Val Ile Phe Leu Ala Tyr Leu Arg Gly Ile
1 5 10 15

Gln Gly Asn Asn Met Asp Gln Arg Ser Leu Pro Glu Asp Ser Leu Asn
20 25 30

Ser Leu Ile Ile Lys Leu Ile Gln Ala Asp Ile Leu Lys Asn Lys Leu
35 40 45

Ser Lys Gln Met Val Asp Val Lys Glu Asn Tyr Gln Ser Thr Leu Pro
50 55 60

Lys Ala Glu Ala Pro Arg Glu Pro Glu Arg Gly Gly Pro Ala Lys Ser
65 70 75 80

Ala Phe Gln Pro Val Ile Ala Met Asp Thr Glu Leu Leu Arg Gln Gln
85 90 95

Arg Arg Tyr Asn Ser Pro Arg Val Leu Leu Ser Asp Ser Thr Pro Leu
100 105 110

Glu Pro Pro Pro Leu Tyr Leu Met Glu Asp Tyr Val Gly Ser Pro Val
115 120 125

Val Ala Asn Arg Thr Ser Arg Arg Lys Arg Tyr Ala Glu His Lys Ser
130 135 140

His Arg Gly Glu Tyr Ser Val Cys Asp Ser Glu Ser Leu Trp Val Thr
145 150 155 160

Asp Lys Ser Ser Ala Ile Asp Ile Arg Gly His Gln Val Thr Val Leu
165 170 175

Gly Glu Ile Lys Thr Gly Asn Ser Pro Val Lys Gln Tyr Phe Tyr Glu
180 185 190

Thr Arg Cys Lys Glu Ala Arg Pro Val Lys Asn Gly Cys Arg Gly Ile
195 200 205

```
Asp Asp Lys His Trp Asn Ser Gln Cys Lys Thr Ser Gln Thr Tyr Val
    210                 215                 220

Arg Ala Leu Thr Ser Glu Asn Asn Lys Leu Val Gly Trp Arg Trp Ile
225                 230                 235                 240

Arg Ile Asp Thr Ser Cys Val Cys Ala Leu Ser Arg Lys Ile Gly Arg
                245                 250                 255

Thr


<210> SEQ ID NO 161
<211> LENGTH: 71
<212> TYPE: PRT
<213> ORGANISM: Homo sapiens

<400> SEQUENCE: 161

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Gly Lys Gly
            20                  25                  30

Val Ser Arg Arg Leu Pro Arg Arg Pro Arg Ile Ala Pro Arg Thr Pro
        35                  40                  45

Gln Pro Ala Gln Pro Arg Thr Gly Ala Pro Ala Arg Ala Arg Ala Pro
    50                  55                  60

Ala Arg Pro Phe Leu Phe Pro
65                  70


<210> SEQ ID NO 162
<211> LENGTH: 189
<212> TYPE: PRT
<213> ORGANISM: Homo sapiens

<400> SEQUENCE: 162

Met Thr Glu Tyr Lys Leu Val Val Val Gly Ala Gly Gly Val Gly Lys
1               5                   10                  15

Ser Ala Leu Thr Ile Gln Leu Ile Gln Asn His Phe Val Asp Glu Tyr
            20                  25                  30

Asp Pro Thr Ile Glu Asp Ser Tyr Arg Lys Gln Val Val Ile Asp Gly
        35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
            100                 105                 110

Leu Val Gly Asn Lys Cys Asp Leu Ala Ala Arg Thr Val Glu Ser Arg
        115                 120                 125

Gln Ala Gln Asp Leu Ala Arg Ser Tyr Gly Ile Pro Tyr Ile Glu Thr
    130                 135                 140

Ser Ala Lys Thr Arg Gln Gly Val Glu Asp Ala Phe Tyr Thr Leu Val
145                 150                 155                 160

Arg Glu Ile Arg Gln His Lys Leu Arg Lys Leu Asn Pro Pro Asp Glu
                165                 170                 175

Ser Gly Pro Gly Cys Met Ser Cys Lys Cys Val Leu Ser
            180                 185
```

<210> SEQ ID NO 163
<211> LENGTH: 41
<212> TYPE: PRT
<213> ORGANISM: Homo sapiens

<400> SEQUENCE: 163

Tyr Gly Gln Val Pro Met Cys Asp Ala Gly Glu Gln Cys Ala Val Arg
1               5                   10                  15

Lys Gly Ala Arg Ile Gly Lys Leu Cys Asp Cys Pro Arg Gly Thr Ser
            20                  25                  30

Cys Asn Ser Phe Leu Leu Lys Cys Leu
        35                  40

<210> SEQ ID NO 164
<211> LENGTH: 129
<212> TYPE: PRT
<213> ORGANISM: Homo sapiens

<400> SEQUENCE: 164

Met Lys Ile Leu Val Ala Leu Ala Val Phe Phe Leu Val Ser Thr Gln
1               5                   10                  15

Leu Phe Ala Glu Glu Ile Gly Ala Asn Asp Asp Leu Asn Tyr Trp Ser
            20                  25                  30

Asp Trp Tyr Asp Ser Asp Gln Ile Lys Glu Glu Leu Pro Glu Pro Phe
        35                  40                  45

Glu His Leu Leu Gln Arg Ile Ala Arg Arg Pro Lys Pro Gln Gln Phe
    50                  55                  60

Phe Gly Leu Met Gly Lys Arg Asp Ala Asp Ser Ser Ile Glu Lys Gln
65                  70                  75                  80

Val Ala Leu Leu Lys Ala Leu Tyr Gly His Gly Gln Ile Ser His Lys
                85                  90                  95

Arg His Lys Thr Asp Ser Phe Val Gly Leu Met Gly Lys Arg Ala Leu
            100                 105                 110

Asn Ser Val Ala Tyr Glu Arg Ser Ala Met Gln Asn Tyr Glu Arg Arg
        115                 120                 125

Arg

<210> SEQ ID NO 165
<211> LENGTH: 11
<212> TYPE: PRT
<213> ORGANISM: Homo sapiens

<400> SEQUENCE: 165

Arg Pro Lys Pro Gln Gln Phe Phe Gly Leu Met
1               5                   10

<210> SEQ ID NO 166
<211> LENGTH: 125
<212> TYPE: PRT
<213> ORGANISM: Homo sapiens

<400> SEQUENCE: 166

Met Ala Gly Pro Ser Leu Ala Cys Cys Leu Leu Gly Leu Leu Ala Leu
1               5                   10                  15

Thr Ser Ala Cys Tyr Ile Gln Asn Cys Pro Leu Gly Gly Lys Arg Ala
            20                  25                  30

Ala Pro Asp Leu Asp Val Arg Lys Cys Leu Pro Cys Gly Pro Gly Gly
        35                  40                  45

```
Lys Gly Arg Cys Phe Gly Pro Asn Ile Cys Cys Ala Glu Glu Leu Gly
    50                  55                  60

Cys Phe Val Gly Thr Ala Glu Ala Leu Arg Cys Gln Glu Glu Asn Tyr
65                  70                  75                  80

Leu Pro Ser Pro Cys Gln Ser Gly Gln Lys Ala Cys Gly Ser Gly Gly
                85                  90                  95

Arg Cys Ala Val Leu Gly Leu Cys Cys Ser Pro Asp Gly Cys His Ala
            100                 105                 110

Asp Pro Ala Cys Asp Ala Glu Ala Thr Phe Ser Gln Arg
        115                 120                 125


<210> SEQ ID NO 167
<211> LENGTH: 9
<212> TYPE: PRT
<213> ORGANISM: Homo sapiens

<400> SEQUENCE: 167

Cys Tyr Ile Gln Asn Cys Pro Leu Gly
1               5


<210> SEQ ID NO 168
<211> LENGTH: 116
<212> TYPE: PRT
<213> ORGANISM: Homo sapiens

<400> SEQUENCE: 168

Met Leu Ser Cys Arg Leu Gln Cys Ala Leu Ala Ala Leu Ser Ile Val
1               5                   10                  15

Leu Ala Leu Gly Cys Val Thr Gly Ala Pro Ser Asp Pro Arg Leu Arg
            20                  25                  30

Gln Phe Leu Gln Lys Ser Leu Ala Ala Ala Ala Gly Lys Gln Glu Leu
        35                  40                  45

Ala Lys Tyr Phe Leu Ala Glu Leu Leu Ser Glu Pro Asn Gln Thr Glu
    50                  55                  60

Asn Asp Ala Leu Glu Pro Glu Asp Leu Ser Gln Ala Ala Glu Gln Asp
65                  70                  75                  80

Glu Met Arg Leu Glu Leu Gln Arg Ser Ala Asn Ser Asn Pro Ala Met
                85                  90                  95

Ala Pro Arg Glu Arg Lys Ala Gly Cys Lys Asn Phe Phe Trp Lys Thr
            100                 105                 110

Phe Thr Ser Cys
        115


<210> SEQ ID NO 169
<211> LENGTH: 4
<212> TYPE: PRT
<213> ORGANISM: Artificial Sequence
<220> FEATURE:
<223> OTHER INFORMATION: AAV9 residues at residue 586

<400> SEQUENCE: 169

Ser Ala Gln Ala
1


<210> SEQ ID NO 170
<211> LENGTH: 11
<212> TYPE: PRT
<213> ORGANISM: Artificial Sequence
<220> FEATURE:
<223> OTHER INFORMATION: Substitution at residue 586 to form PHP.eB
      capsid
```

<400> SEQUENCE: 170

Ser Asp Gly Thr Leu Ala Val Pro Phe Lys Ala
1 5 10

<210> SEQ ID NO 171
<211> LENGTH: 7
<212> TYPE: PRT
<213> ORGANISM: Artificial Sequence
<220> FEATURE:
<223> OTHER INFORMATION: AAV-BR1

<400> SEQUENCE: 171

Asn Arg Gly Thr Glu Trp Asp
1 5

<210> SEQ ID NO 172
<211> LENGTH: 7
<212> TYPE: PRT
<213> ORGANISM: Artificial Sequence
<220> FEATURE:
<223> OTHER INFORMATION: AAV-PHP.S

<400> SEQUENCE: 172

Gln Ala Val Arg Thr Ser Leu
1 5

<210> SEQ ID NO 173
<211> LENGTH: 7
<212> TYPE: PRT
<213> ORGANISM: Artificial Sequence
<220> FEATURE:
<223> OTHER INFORMATION: AAV-PHP.B

<400> SEQUENCE: 173

Thr Leu Ala Val Pro Phe Lys
1 5

<210> SEQ ID NO 174
<211> LENGTH: 7
<212> TYPE: PRT
<213> ORGANISM: Artificial Sequence
<220> FEATURE:
<223> OTHER INFORMATION: AAV-PPS

<400> SEQUENCE: 174

Asp Ser Pro Ala His Pro Ser
1 5

<210> SEQ ID NO 175
<211> LENGTH: 21
<212> TYPE: DNA
<213> ORGANISM: Artificial Sequence
<220> FEATURE:
<223> OTHER INFORMATION: forward primer

<400> SEQUENCE: 175
ggaaccccta gtgatggagt t 21

<210> SEQ ID NO 176
<211> LENGTH: 16
<212> TYPE: DNA
<213> ORGANISM: Artificial Sequence
<220> FEATURE:
<223> OTHER INFORMATION: reverse primer

<400> SEQUENCE: 176
cggcctcagt gagcga 16

<210> SEQ ID NO 177
<211> LENGTH: 310
<212> TYPE: DNA
<213> ORGANISM: Homo sapiens

<400> SEQUENCE: 177
gaaaagatcc gggttcacac taatcaggcc caacggaagg ccatattagc aatttggcag 60
gtacccgagg gccataccta atctgcataa aatgaagcag attgcaaccg ccctcatctt 120
ttttattttt aaactggttt ttgaagcaga gcataaaatc tcagagggag agacagaaga 180
tgctagtgca tacattttcc ttcatgcctt tattttcatt ctttttgcac aaaccatctt 240
cctgaatggc tgtttaccta aagaagaata acaaaataaa aggtgctagg aaatggagta 300
ggcagagatc 310

<210> SEQ ID NO 178
<211> LENGTH: 401
<212> TYPE: DNA
<213> ORGANISM: Mus musculus

<400> SEQUENCE: 178
gaagcatggt ccagcaaagc ctttctgttc taaaggaaag gatctgagtt gtcacctccc 60
aggtccgtgg aaggcttttt agcagtttgg caggtgcctg agggccacac ctcatctgca 120
taaaatgtgg cagattgcaa ccgccctcgt ctttttttatt tttaaactgg tttttgaaac 180
agaacatata taaaagctca gagaaaggga aaggagatag atggccgagc ttccatatcc 240
cttagtgcct ttattttcat tctttttcca ttttcctaag tggctattta ccaagacaaa 300
gataacaaat ctgctaggaa aaggagtggg cagtgctaca aaatgttttt ttttttttaa 360
agaaagtcct atcttataat agatcttcac cacgatgcct c 401

<210> SEQ ID NO 179
<211> LENGTH: 5102
<212> TYPE: DNA
<213> ORGANISM: Artificial Sequence
<220> FEATURE:
<223> OTHER INFORMATION: synthetic construct

<400> SEQUENCE: 179
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccgca cgcgttctag agggctgggc ataaaagtca 180
gggcagagcc atctattgct tacatttgct tctgacatat gccgccgcca ccatggtgag 240
caagggcgag gagctgttca ccggggtggt gcccatcctg gtcgagctgg acggcgacgt 300
aaacggccac aagttcagcg tgtccggcga gggcgagggc gatgccacct acggcaagct 360
gaccctgaag ttcatctgca ccaccggcaa gctgcccgtg ccctggccca ccctcgtgac 420
caccctgacc tacggcgtgc agtgcttcag ccgctacccc gaccacatga agcagcacga 480
cttcttcaag tccgccatgc ccgaaggcta cgtccaggag cgcaccatct tcttcaagga 540
cgacggcaac tacaagaccc gcgccgaggt gaagttcgag ggcgacaccc tggtgaaccg 600
catcgagctg aagggcatcg acttcaagga ggacggcaac atcctggggc acaagctgga 660
gtacaactac aacagccaca acgtctatat catggccgac aagcagaaga acggcatcaa 720

```
ggtgaacttc aagatccgcc acaacatcga ggacggcagc gtgcagctcg ccgaccacta    780
ccagcagaac acccccatcg gcgacggccc cgtgctgctg cccgacaacc actacctgag    840
cacccagtcc gccctgagca aagaccccaa cgagaagcgc gatcacatgg tcctgctgga    900
gttcgtgacc gccgccggga tcactctcgg catggacgag ctgtacaagt aagttaatta    960
atctcataat caacctctgg attacaaaat ttgtgaaaga ttgactggta ttcttaacta   1020
tgttgctcct tttacgctat gtggatacgc tgctttaatg cctttgtatc atgctattgc   1080
ttcccgtatg gctttcattt tctcctcctt gtataaatcc tggttagttc ttgccacggc   1140
ggaactcatc gccgcctgcc ttgcccgctg ctggacaggg gctcggctgt tgggcactga   1200
caattccgtg gctcgactgt gccttctagt tgccagccat ctgttgtttg cccctccccc   1260
gtgccttcct tgaccctgga aggtgccact cccactgtcc tttcctaata aaatgaggaa   1320
attgcatcgc attgtctgag taggtgtcat tctattctgg ggggtggggt ggggcaggac   1380
agcaaggggg aggattggga agacaatagc aggcatgact tgctgctatc ccctaggtgc   1440
tgtcatttac ctacggttgt ctccaaattt cttcaaccaa gtagagaaaa atgagagaga   1500
aggaaagaaa aaaagaggta tggggagaag agaaagaagg caacttgtta aaaatctcag   1560
tcaaacttac atactatata gaacagcatg gtgaatttag ggcacatgga tataaaatgg   1620
aagtttctta ttcagtagca gcaacttgtg ggcacaggag ttggcaaaga taaaaatgtc   1680
caaagtcaca aatacaatgt atagttagtc ataggtgctg ttatttgcct caaaaaatag   1740
acttttattt tgcctttctt ttctttaacc acactcaaaa ttagagaaca gagacaaaac   1800
ccagcaggaa atagcacaga aagcccacag aatcaaagac gtgttcaaac agccagctga   1860
attcattgca catttcaacc acagaaatat tttcaggtga ttctgttgtt tgacaaaacg   1920
tgggaaccac aggatctaca acacttgcaa gcaaaactca acagctctaa taatagttac   1980
agaagtgaaa gccaatttgg ataaaataag acattgactc aagtcctctc agaagagttt   2040
tgaaagcaaa gtttacaaaa gtctggtttg tcctttggga tttacagacc tttcagcccc   2100
ttgattcatt tttttttttt tggatttctt catcactggg agaattccca tgcattattt   2160
ctcccctgct tcaaaatcat caaatgtgaa acatttttca ctcttttctt ctgtatatag   2220
tgataaaata gctattggct tttggctaaa tgtgctactt tgagcccacc cacacaaggg   2280
agaaatgggg gcagacatga gtttgggcat gagtgagctc tgccttctca gaggtgagcc   2340
acgtggtgcg gaccgagcgg ccgcaggaac ccctagtgat ggagttggcc actccctctc   2400
tgcgcgctcg ctcgctcact gaggccgggc gaccaaaggt cgcccgacgc ccgggctttg   2460
cccgggcggc ctcagtgagc gagcgagcgc gcagctgcct gcaggggcgc ctgatgcggt   2520
attttctcct tacgcatctg tgcggtattt cacaccgcat acgtcaaagc aaccatagta   2580
cgcgccctgt agcggcgcat taagcgcggc gggtgtggtg gttacgcgca gcgtgaccgc   2640
tacacttgcc agcgccctag cgcccgctcc tttcgctttc ttcccttcct ttctcgccac   2700
gttcgccggc tttccccgtc aagctctaaa tcgggggctc cctttagggt tccgatttag   2760
tgctttacgg cacctcgacc ccaaaaaact tgatttgggt gatggttcac gtagtgggcc   2820
atcgccctga tagacggttt ttcgcccttt gacgttggag tccacgttct ttaatagtgg   2880
actcttgttc caaactggaa caacactcaa ccctatctcg ggctattctt ttgatttata   2940
agggattttg ccgatttcgg cctattggtt aaaaaatgag ctgatttaac aaaaatttaa   3000
cgcgaatttt aacaaaatat taacgtttac aattttatgg tgcactctca gtacaatctg   3060
ctctgatgcc gcatagttaa gccagccccg acacccgcca acacccgctg acgcgccctg   3120
```

```
acgggcttgt ctgctcccgg catccgctta cagacaagct gtgaccgtct ccgggagctg   3180
catgtgtcag aggttttcac cgtcatcacc gaaacgcgcg agacgaaagg gcctcgtgat   3240
acgcctattt ttataggtta atgtcatgat aataatggtt tcttagacgt caggtggcac   3300
ttttcgggga aatgtgcgcg gaacccctat ttgtttattt ttctaaatac attcaaatat   3360
gtatccgctc atgagacaat aaccctgata aatgcttcaa taatattgaa aaaggaagag   3420
tatgagtatt caacatttcc gtgtcgccct tattcccttt tttgcggcat tttgccttcc   3480
tgtttttgct cacccagaaa cgctggtgaa agtaaaagat gctgaagatc agttgggtgc   3540
acgagtgggt tacatcgaac tggatctcaa cagcggtaag atccttgaga gttttcgccc   3600
cgaagaacgt tttccaatga tgagcacttt taaagttctg ctatgtggcg cggtattatc   3660
ccgtattgac gccgggcaag agcaactcgg tcgccgcata cactattctc agaatgactt   3720
ggttgagtac tcaccagtca cagaaaagca tcttacggat ggcatgacag taagagaatt   3780
atgcagtgct gccataacca tgagtgataa cactgcggcc aacttacttc tgacaacgat   3840
cggaggaccg aaggagctaa ccgctttttt gcacaacatg ggggatcatg taactcgcct   3900
tgatcgttgg gaaccggagc tgaatgaagc cataccaaac gacgagcgtg acaccacgat   3960
gcctgtagca atggcaacaa cgttgcgcaa actattaact ggcgaactac ttactctagc   4020
ttcccggcaa caattaatag actggatgga ggcggataaa gttgcaggac cacttctgcg   4080
ctcggccctt ccggctggct ggtttattgc tgataaatct ggagccggtg agcgtgggtc   4140
tcgcggtatc attgcagcac tggggccaga tggtaagccc tcccgtatcg tagttatcta   4200
cacgacgggg agtcaggcaa ctatggatga acgaaataga cagatcgctg agataggtgc   4260
ctcactgatt aagcattggt aactgtcaga ccaagtttac tcatatatac tttagattga   4320
tttaaaactt catttttaat ttaaaaggat ctaggtgaag atcctttttg ataatctcat   4380
gaccaaaatc ccttaacgtg agttttcgtt ccactgagcg tcagaccccg tagaaaagat   4440
caaaggatct tcttgagatc ctttttttct gcgcgtaatc tgctgcttgc aaacaaaaaa   4500
accaccgcta ccagcggtgg tttgtttgcc ggatcaagag ctaccaactc tttttccgaa   4560
ggtaactggc ttcagcagag cgcagatacc aaatactgtc cttctagtgt agccgtagtt   4620
aggccaccac ttcaagaact ctgtagcacc gcctacatac ctcgctctgc taatcctgtt   4680
accagtggct gctgccagtg gcgataagtc gtgtcttacc gggttggact caagacgata   4740
gttaccggat aaggcgcagc ggtcgggctg aacggggggt tcgtgcacac agcccagctt   4800
ggagcgaacg acctacaccg aactgagata cctacagcgt gagctatgag aaagcgccac   4860
gcttcccgaa gggagaaagg cggacaggta tccggtaagc ggcagggtcg gaacaggaga   4920
gcgcacgagg gagcttccag ggggaaacgc ctggtatctt tatagtcctg tcgggtttcg   4980
ccacctctga cttgagcgtc gatttttgtg atgctcgtca ggggggcgga gcctatggaa   5040
aaacgccagc aacgcggcct ttttacggtt cctggccttt tgctggcctt ttgctcacat   5100
gt                                                                  5102
```

<210> SEQ ID NO 180
<211> LENGTH: 6587
<212> TYPE: DNA
<213> ORGANISM: Artificial Sequence
<220> FEATURE:
<223> OTHER INFORMATION: synthetic construct

<400> SEQUENCE: 180

-continued

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc tgcggccgca cgcgtataag ccttgggggc aatcaaacta    180
ttacattgag tccttggatt tgctacaaat tacattttaa atgcaatcat tttataaaag    240
cttcaacact cacacttgga agcgttaccc tgttgaatat cactgactca ctaacttgca    300
ttgccatgct aacttgcttt cagagagatc tcagaacaca tcatcttctg ctatttcaat    360
acatgcacat taatttccta tcaacgtgtg ctgatcagga actctgtaat ctggcaccgg    420
tgtttatttt tattcctgtc tattcctgtt ggctcacgaa aagattgttt gagcaagtgt    480
tttatggtga gttgtatcat atgtacattg atttaatctg cccacattca gttctacaag    540
cggagccaaa aaaatagaga caagcataat tttcattcaa catgagcccc tcaatgcaag    600
ccaagtacct catctggtgc tcagctaaag caacagcaat ctgttccacc ctggagacac    660
aactggccac agaaaactta gtgaaaagag gcaatgctat gcacaggaca aatgagctcg    720
ggctgggcat aaaagtcagg gcagagccat ctattgctta catttgcttc tgggatcctt    780
cgaaaccggt gctagagccc ctctccctcc cccccccta acgttactgg ccgaagccgc    840
ttggaataag gccggtgtgc gtttgtctat atgttatttt ccaccatatt gccgtctttt    900
ggcaatgtga gggcccggaa acctggccct gtcttcttga cgagcattcc taggggtctt    960
tcccctctcg ccaaaggaat gcaaggtctg ttgaatgtcg tgaaggaagc agttcctctg   1020
gaagcttctt gaagacaaac aacgtctgta gcgacccttt gcaggcagcg gaacccccca   1080
cctggcgaca ggtgcctctg cggccaaaag ccacgtgtat aagatacacc tgcaaaggcg   1140
gcacaacccc agtgccacgt tgtgagttgg atagttgtgg aaagagtcaa atggctctcc   1200
tcaagcgtat tcaacaaggg gctgaaggat gcccagaagg taccccattg tatgggatct   1260
gatctggggc ctcggtgcac atgctttaca tgtgtttagt cgaggttaaa aaaacgtcta   1320
ggccccccga accacgggga cgtggttttc ctttgaaaaa cacgatgata atatggccac   1380
atctagcacc atggctccta agaagaagag gaaggtgatg agccagttcg acatcctgtg   1440
caagaccccc cccaaggtgc tggtgcggca gttcgtggag agattcgaga ggcccagcgg   1500
cgagaagatc gccagctgtg ccgccgagct gacctacctg tgctggatga tcacccacaa   1560
cggcaccgcc atcaagaggg ccaccttcat gagctacaac accatcatca gcaacagcct   1620
gagcttcgac atcgtgaaca agagcctgca gttcaagtac aagacccaga aggccaccat   1680
cctggaggcc agcctgaaga agctgatccc cgcctgggag ttcaccatca tcccttacaa   1740
cggccagaag caccagagcg acatcaccga catcgtgtcc agcctgcagc tgcagttcga   1800
gagcagcgag gaggccgaca agggcaacag ccacagcaag aagatgctga aggccctgct   1860
gtccgagggc gagagcatct gggagatcac cgagaagatc ctgaacagct tcgagtacac   1920
cagcaggttc accaagacca agaccctgta ccagttcctg ttcctggcca cattcatcaa   1980
ctgcggcagg ttcagcgaca tcaagaacgt ggaccccaag agcttcaagc tggtgcagaa   2040
caagtacctg ggcgtgatca ttcagtgcct ggtgaccgag accaagacaa gcgtgtccag   2100
gcacatctac tttttcagcg ccagaggcag gatcgacccc ctggtgtacc tggacgagtt   2160
cctgaggaac agcgagcccg tgctgaagag agtgaacagg accggcaaca gcagcagcaa   2220
caagcaggag taccagctgc tgaaggacaa cctggtgcgc agctacaaca aggccctgaa   2280
gaagaacgcc ccctacccca tcttcgctat caagaacggc cctaagagcc acatcggcag   2340
gcacctgatg accagctttc tgagcatgaa gggcctgacc gagctgacaa acgtggtggg   2400
```

caactggagc gacaagaggg cctccgccgt ggccaggacc acctacaccc accagatcac 2460
cgccatcccc gaccactact tcgccctggt gtccaggtac tacgcctacg accccatcag 2520
caaggagatg atcgccctga aggacgagac caaccccatc gaggagtggc agcacatcga 2580
gcagctgaag ggcagcgccg agggcagcat cagatacccc gcctggaacg gcatcatcag 2640
ccaggaggtg ctggactacc tgagcagcta catcaacagg cggatctgag aattcgatat 2700
caagcttatc gataatcaac ctctggatta caaaatttgt gaaagattga ctggtattct 2760
taactatgtt gctcctttta cgctatgtgg atacgctgct ttaatgcctt tgtatcatgc 2820
tattgcttcc cgtatggctt tcattttctc ctccttgtat aaatcctggt tgctgtctct 2880
ttatgaggag ttgtggcccg ttgtcaggca acgtggcgtg gtgtgcactg tgtttgctga 2940
cgcaaccccc actggttggg gcattgccac cacctgtcag ctcctttccg ggactttcgc 3000
tttccccctc cctattgcca cggcggaact catcgccgcc tgccttgccc gctgctggac 3060
aggggctcgg ctgttgggca ctgacaattc cgtggtgttg tcggggaaat catcgtcctt 3120
tccttggctg ctcgcctatg ttgccacctg gattctgcgc gggacgtcct tctgctacgt 3180
cccttcggcc ctcaatccag cggaccttcc ttcccgcggc ctgctgccgg ctctgcggcc 3240
tcttccgcgt cttcgccttc gccctcagac gagtcggatc tccctttggg ccgcctcccc 3300
gcatcgatac cgagcgctgc tcgagagatc tacgggtggc atccctgtga cccctcccca 3360
gtgcctctcc tggccctgga agttgccact ccagtgccca ccagccttgt cctaataaaa 3420
ttaagttgca tcattttgtc tgactaggtg tccttctata atattatggg gtggaggggg 3480
gtggtatgga gcaaggggca agttgggaag acaacctgta gggcctgcgg ggtctattgg 3540
gaaccaagct ggagtgcagt ggcacaatct tggctcactg caatctccgc ctcctgggtt 3600
caagcgattc tcctgcctca gcctcccgag ttgttgggat tccaggcatg catgaccagg 3660
ctcagctaat ttttgttttt ttggtagaga cggggtttca ccatattggc caggctggtc 3720
tccaactcct aatctcaggt gatctaccca ccttggcctc ccaaattgct gggattacag 3780
gcgtgaacca ctgctccctt ccctgtcctt ctgattttgt aggtaaccac gtgcggaccg 3840
agcggccgca ggaaccccta gtgatggagt tggccactcc ctctctgcgc gctcgctcgc 3900
tcactgaggc cgggcgacca aaggtcgccc gacgcccggg ctttgcccgg gcggcctcag 3960
tgagcgagcg agcgcgcagc tgcctgcagg ggcgcctgat gcggtatttt ctccttacgc 4020
atctgtgcgg tatttcacac cgcatacgtc aaagcaacca tagtacgcgc cctgtagcgg 4080
cgcattaagc gcggcgggtg tggtggttac gcgcagcgtg accgctacac ttgccagcgc 4140
cctagcgccc gctcctttcg ctttcttccc ttcctttctc gccacgttcg ccggctttcc 4200
ccgtcaagct ctaaatcggg ggctcccttt agggttccga tttagtgctt tacggcacct 4260
cgaccccaaa aaacttgatt tgggtgatgg ttcacgtagt gggccatcgc cctgatagac 4320
ggtttttcgc cctttgacgt tggagtccac gttctttaat agtggactct tgttccaaac 4380
tggaacaaca ctcaacccta tctcgggcta ttcttttgat ttataaggga ttttgccgat 4440
ttcggcctat tggttaaaaa atgagctgat ttaacaaaaa tttaacgcga attttaacaa 4500
aatattaacg tttacaattt tatggtgcac tctcagtaca atctgctctg atgccgcata 4560
gttaagccag ccccgacacc cgccaacacc cgctgacgcg ccctgacggg cttgtctgct 4620
cccggcatcc gcttacagac aagctgtgac cgtctccggg agctgcatgt gtcagaggtt 4680
ttcaccgtca tcaccgaaac gcgcgagacg aaagggcctc gtgatacgcc tattttata 4740

```
ggttaatgtc atgataataa tggtttctta gacgtcaggt ggcacttttc ggggaaatgt   4800
gcgcggaacc cctatttgtt tatttttcta aatacattca aatatgtatc cgctcatgag   4860
acaataaccc tgataaatgc ttcaataata ttgaaaaagg aagagtatga gtattcaaca   4920
tttccgtgtc gcccttattc ccttttttgc ggcattttgc cttcctgttt ttgctcaccc   4980
agaaacgctg gtgaaagtaa aagatgctga agatcagttg ggtgcacgag tgggttacat   5040
cgaactggat ctcaacagcg gtaagatcct tgagagtttt cgccccgaag aacgttttcc   5100
aatgatgagc acttttaaag ttctgctatg tggcgcggta ttatcccgta ttgacgccgg   5160
gcaagagcaa ctcggtcgcc gcatacacta ttctcagaat gacttggttg agtactcacc   5220
agtcacagaa aagcatctta cggatggcat gacagtaaga gaattatgca gtgctgccat   5280
aaccatgagt gataacactg cggccaactt acttctgaca acgatcggag gaccgaagga   5340
gctaaccgct tttttgcaca acatggggga tcatgtaact cgccttgatc gttgggaacc   5400
ggagctgaat gaagccatac caaacgacga gcgtgacacc acgatgcctg tagcaatggc   5460
aacaacgttg cgcaaactat taactggcga actacttact ctagcttccc ggcaacaatt   5520
aatagactgg atggaggcgg ataaagttgc aggaccactt ctgcgctcgg cccttccggc   5580
tggctggttt attgctgata aatctggagc cggtgagcgt gggtctcgcg gtatcattgc   5640
agcactgggg ccagatggta agccctcccg tatcgtagtt atctacacga cggggagtca   5700
ggcaactatg gatgaacgaa atagacagat cgctgagata ggtgcctcac tgattaagca   5760
ttggtaactg tcagaccaag tttactcata tatactttag attgatttaa aacttcattt   5820
ttaatttaaa aggatctagg tgaagatcct ttttgataat ctcatgacca aaatccctta   5880
acgtgagttt tcgttccact gagcgtcaga ccccgtagaa aagatcaaag gatcttcttg   5940
agatcctttt tttctgcgcg taatctgctg cttgcaaaca aaaaaaccac cgctaccagc   6000
ggtggtttgt ttgccggatc aagagctacc aactcttttt ccgaaggtaa ctggcttcag   6060
cagagcgcag ataccaaata ctgtccttct agtgtagccg tagttaggcc accacttcaa   6120
gaactctgta gcaccgccta catacctcgc tctgctaatc ctgttaccag tggctgctgc   6180
cagtggcgat aagtcgtgtc ttaccgggtt ggactcaaga cgatagttac cggataaggc   6240
gcagcggtcg ggctgaacgg ggggttcgtg cacacagccc agcttggagc gaacgaccta   6300
caccgaactg agatacctac agcgtgagct atgagaaagc gccacgcttc ccgaagggag   6360
aaaggcggac aggtatccgg taagcggcag ggtcggaaca ggagagcgca cgagggagct   6420
tccaggggga aacgcctggt atctttatag tcctgtcggg tttcgccacc tctgacttga   6480
gcgtcgattt ttgtgatgct cgtcaggggg gcggagccta tggaaaaacg ccagcaacgc   6540
ggccttttta cggttcctgg ccttttgctg gccttttgct cacatgt                 6587
```

<210> SEQ ID NO 181
<211> LENGTH: 5343
<212> TYPE: DNA
<213> ORGANISM: Artificial Sequence
<220> FEATURE:
<223> OTHER INFORMATION: synthetic construct

<400> SEQUENCE: 181

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc tgcggccgca cgcgtataag ccttgggggc aatcaaacta    180
ttacattgag tccttggatt tgctacaaat tacattttaa atgcaatcat tttataaaag    240
```

```
cttcaacact cacacttgga agcgttaccc tgttgaatat cactgactca ctaacttgca    300
ttgccatgct aacttgcttt cagagagatc tcagaacaca tcatcttctg ctatttcaat    360
acatgcacat taatttccta tcaacgtgtg ctgatcagga actctgtaat ctggcaccgg    420
tgtttatttt tattcctgtc tattcctgtt ggctcacgaa aagattgttt gagcaagtgt    480
tttatggtga gttgtatcat atgtacattg atttaatctg cccacattca gttctacaag    540
cggagccaaa aaaatagaga caagcataat tttcattcaa catgagcccc tcaatgcaag    600
ccaagtacct catctggtgc tcagctaaag caacagcaat ctgttccacc ctggagacac    660
aactggccac agaaaactta gtgaaaagag gcaatgctat gcacaggaca aatgagctcg    720
ggctgggcat aaaagtcagg gcagagccat ctattgctta catttgcttc tggcgtggcc    780
accatggctc ctaagaagaa gaggaaggtg atgagccagt tcgacatcct gtgcaagacc    840
ccccccaagg tgctggtgcg gcagttcgtg gagagattcg agaggcccag cggcgagaag    900
atcgccagct gtgccgccga gctgacctac ctgtgctgga tgatcaccca caacggcacc    960
gccatcaaga gggccacctt catgagctac aacaccatca tcagcaacag cctgagcttc   1020
gacatcgtga acaagagcct gcagttcaag tacaagaccc agaaggccac catcctggag   1080
gccagcctga agaagctgat ccccgcctgg gagttcacca tcatccctta caacggccag   1140
aagcaccaga gcgacatcac cgacatcgtg tccagcctgc agctgcagtt cgagagcagc   1200
gaggaggccg acaagggcaa cagccacagc aagaagatgc tgaaggccct gctgtccgag   1260
ggcgagagca tctgggagat caccgagaag atcctgaaca gcttcgagta caccagcagg   1320
ttcaccaaga ccaagaccct gtaccagttc ctgttcctgg ccacattcat caactgcggc   1380
aggttcagcg acatcaagaa cgtggacccc aagagcttca agctggtgca gaacaagtac   1440
ctgggcgtga tcattcagtg cctggtgacc gagaccaaga caagcgtgtc caggcacatc   1500
tactttttca gcgccagagg caggatcgac cccctggtgt acctggacga gttcctgagg   1560
aacagcgagc ccgtgctgaa gagagtgaac aggaccggca acagcagcag caacaagcag   1620
gagtaccagc tgctgaagga caacctggtg cgcagctaca acaaggccct gaagaagaac   1680
gcccccctacc ccatcttcgc tatcaagaac ggccctaaga gccacatcgg caggcacctg   1740
atgaccagct ttctgagcat gaagggcctg accgagctga caaacgtggt gggcaactgg   1800
agcgacaaga gggcctccgc cgtggccagg accacctaca cccaccagat caccgccatc   1860
cccgaccact acttcgccct ggtgtccagg tactacgcct acgaccccat cagcaaggag   1920
atgatcgccc tgaaggacga gaccaacccc atcgaggagt ggcagcacat cgagcagctg   1980
aagggcagcg ccgagggcag catcagatac cccgcctgga acggcatcat cagccaggag   2040
gtgctggact acctgagcag ctacatcaac aggcggatct gagaattacg ggtggcatcc   2100
ctgtgacccc tccccagtgc ctctcctggc cctggaagtt gccactccag tgcccaccag   2160
ccttgtccta ataaaattaa gttgcatcat tttgtctgac taggtgtcct tctataatat   2220
tatggggtgg aggggggtgg tatggagcaa ggggcaagtt gggaagacaa cctgtagggc   2280
ctgcggggtc tattgggaac caagctggag tgcagtggca caatcttggc tcactgcaat   2340
ctccgcctcc tgggttcaag cgattctcct gcctcagcct cccgagttgt tgggattcca   2400
ggcatgcatg accaggctca gctaattttt gtttttttgg tagagacggg gtttcaccat   2460
attggccagg ctggtctcca actcctaatc tcaggtgatc tacccacctt ggcctcccaa   2520
attgctggga ttacaggcgt gaaccactgc tcccttccct gtccttctga ttttgtaggt   2580
```

-continued

```
aaccacgtgc ggaccgagcg gccgcaggaa cccctagtga tggagttggc cactccctct   2640
ctgcgcgctc gctcgctcac tgaggccggg cgaccaaagg tcgcccgacg cccgggcttt   2700
gcccgggcgg cctcagtgag cgagcgagcg cgcagctgcc tgcaggggcg cctgatgcgg   2760
tattttctcc ttacgcatct gtgcggtatt tcacaccgca tacgtcaaag caaccatagt   2820
acgcgccctg tagcggcgca ttaagcgcgg cgggtgtggt ggttacgcgc agcgtgaccg   2880
ctacacttgc cagcgcccta gcgcccgctc ctttcgcttt cttcccttcc tttctcgcca   2940
cgttcgccgg ctttccccgt caagctctaa atcgggggct ccctttaggg ttccgattta   3000
gtgctttacg gcacctcgac cccaaaaaac ttgatttggg tgatggttca cgtagtgggc   3060
catcgccctg atagacggtt tttcgccctt tgacgttgga gtccacgttc tttaatagtg   3120
gactcttgtt ccaaactgga acaacactca accctatctc gggctattct tttgatttat   3180
aagggatttt gccgatttcg gcctattggt taaaaaatga gctgatttaa caaaaattta   3240
acgcgaattt taacaaaata ttaacgttta caattttatg gtgcactctc agtacaatct   3300
gctctgatgc cgcatagtta agccagcccc gacacccgcc aacacccgct gacgcgccct   3360
gacgggcttg tctgctcccg gcatccgctt acagacaagc tgtgaccgtc tccgggagct   3420
gcatgtgtca gaggttttca ccgtcatcac cgaaacgcgc gagacgaaag ggcctcgtga   3480
tacgcctatt tttataggtt aatgtcatga taataatggt ttcttagacg tcaggtggca   3540
cttttcgggg aaatgtgcgc ggaaccccta tttgtttatt tttctaaata cattcaaata   3600
tgtatccgct catgagacaa taaccctgat aaatgcttca ataatattga aaaaggaaga   3660
gtatgagtat tcaacatttc cgtgtcgccc ttattccctt ttttgcggca ttttgccttc   3720
ctgtttttgc tcacccagaa acgctggtga aagtaaaaga tgctgaagat cagttgggtg   3780
cacgagtggg ttacatcgaa ctggatctca acagcggtaa gatccttgag agttttcgcc   3840
ccgaagaacg ttttccaatg atgagcactt ttaaagttct gctatgtggc gcggtattat   3900
cccgtattga cgccgggcaa gagcaactcg gtcgccgcat acactattct cagaatgact   3960
tggttgagta ctcaccagtc acagaaaagc atcttacgga tggcatgaca gtaagagaat   4020
tatgcagtgc tgccataacc atgagtgata acactgcggc caacttactt ctgacaacga   4080
tcggaggacc gaaggagcta accgcttttt tgcacaacat gggggatcat gtaactcgcc   4140
ttgatcgttg ggaaccggag ctgaatgaag ccataccaaa cgacgagcgt gacaccacga   4200
tgcctgtagc aatggcaaca acgttgcgca aactattaac tggcgaacta cttactctag   4260
cttcccggca acaattaata gactggatgg aggcggataa agttgcagga ccacttctgc   4320
gctcggccct tccggctggc tggtttattg ctgataaatc tggagccggt gagcgtgggt   4380
ctcgcggtat cattgcagca ctggggccag atggtaagcc ctcccgtatc gtagttatct   4440
acacgacggg gagtcaggca actatggatg aacgaaatag acagatcgct gagataggtg   4500
cctcactgat taagcattgg taactgtcag accaagttta ctcatatata ctttagattg   4560
atttaaaact tcatttttaa tttaaaagga tctaggtgaa gatccttttt gataatctca   4620
tgaccaaaat cccttaacgt gagttttcgt tccactgagc gtcagacccc gtagaaaaga   4680
tcaaaggatc ttcttgagat cctttttttc tgcgcgtaat ctgctgcttg caaacaaaaa   4740
aaccaccgct accagcggtg gtttgtttgc cggatcaaga gctaccaact ctttttccga   4800
aggtaactgg cttcagcaga gcgcagatac caaatactgt ccttctagtg tagccgtagt   4860
taggccacca cttcaagaac tctgtagcac cgcctacata cctcgctctg ctaatcctgt   4920
taccagtggc tgctgccagt ggcgataagt cgtgtcttac cgggttggac tcaagacgat   4980
```

agttaccgga taaggcgcag cggtcgggct gaacgggggg ttcgtgcaca cagcccagct 5040
tggagcgaac gacctacacc gaactgagat acctacagcg tgagctatga gaaagcgcca 5100
cgcttcccga agggagaaag gcggacaggt atccggtaag cggcagggtc ggaacaggag 5160
agcgcacgag ggagcttcca gggggaaacg cctggtatct ttatagtcct gtcgggtttc 5220
gccacctctg acttgagcgt cgatttttgt gatgctcgtc aggggggcgg agcctatgga 5280
aaaacgccag caacgcggcc tttttacggt tcctggcctt ttgctggcct tttgctcaca 5340
tgt 5343

<210> SEQ ID NO 182
<211> LENGTH: 5717
<212> TYPE: DNA
<213> ORGANISM: Artificial Sequence
<220> FEATURE:
<223> OTHER INFORMATION: synthetic construct

<400> SEQUENCE: 182
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccgca cgcgtataag ccttggggc aatcaaacta 180 ttacattgag tccttggatt tgctacaaat tacattttaa atgcaatcat tttataaaag 240
cttcaacact cacacttgga agcgttaccc tgttgaatat cactgactca ctaacttgca 300
ttgccatgct aacttgcttt cagagagatc tcagaacaca tcatcttctg ctatttcaat 360
acatgcacat taatttccta tcaacgtgtg ctgatcagga actctgtaat ctggcaccgg 420
tgtttatttt tattcctgtc tattcctgtt ggctcacgaa aagattgttt gagcaagtgt 480
tttatggtga gttgtatcat atgtacattg atttaatctg cccacattca gttctacaag 540
cggagccaaa aaaatagaga caagcataat tttcattcaa catgagcccc tcaatgcaag 600
ccaagtacct catctggtgc tcagctaaag caacagcaat ctgttccacc ctggagacac 660
aactggccac agaaaactta gtgaaaagag gcaatgctat gcacaggaca aatgagctcg 720
ggctgggcat aaaagtcagg gcagagccat ctattgctta catttgcttc tgggatccgc 780
ccctctccct cccccccccc taacgttact ggccgaagcc gcttggaata aggccggtgt 840
gcgtttgtct atatgttatt ttccaccata ttgccgtctt ttggcaatgt gagggcccgg 900
aaacctggcc ctgtcttctt gacgagcatt cctaggggtc tttcccctct cgccaaagga 960
atgcaaggtc tgttgaatgt cgtgaaggaa gcagttcctc tggaagcttc ttgaagacaa 1020
acaacgtctg tagcgaccct ttgcaggcag cggaaccccc cacctggcga caggtgcctc 1080
tgcggccaaa agccacgtgt ataagataca cctgcaaagg cggcacaacc ccagtgccac 1140
gttgtgagtt ggatagttgt ggaaagagtc aaatggctct cctcaagcgt attcaacaag 1200
gggctgaagg atgcccagaa ggtaccccat tgtatgggat ctgatctggg gcctcggtgc 1260
acatgcttta catgtgttta gtcgaggtta aaaaaacgtc taggcccccc gaaccacggg 1320
gacgtggttt tcctttgaaa aacacgatga taatatggcc acagctagca ccatggtgcc 1380
caagaagaag aggaaagtct ccaacctgct gactgtgcac caaaacctgc ctgccctccc 1440
tgtggatgcc acctctgatg aagtcaggaa gaacctgatg gacatgttca gggacaggca 1500
ggccttctct gaacacacct ggaagatgct cctgtctgtg tgcagatcct gggctgcctg 1560
gtgcaagctg aacaacagga aatggttccc tgctgaacct gaggatgtga gggactacct 1620

-continued

```
cctgtacctg caagccagag gcctggctgt gaagaccatc caacagcacc tgggccagct   1680
caacatgctg cacaggagat ctggcctgcc tcgcccttct gactccaatg ctgtgtccct   1740
ggtgatgagg agaatcagaa aggagaatgt ggatgctggg gagagagcca agcaggccct   1800
ggcctttgaa cgcactgact ttgaccaagt cagatccctg atggagaact ctgacagatg   1860
ccaggacatc aggaacctgg ccttcctggg cattgcctac aacaccctgc tgcgcattgc   1920
cgaaattgcc agaatcagag tgaaggacat ctcccgcacc gatggtggga gaatgctgat   1980
ccacattggc aggaccaaga ccctggtgtc cacagctggt gtggagaagg ccctgtccct   2040
gggggttacc aagctggtgg agagatggat ctctgtgtct ggtgtggctg atgaccccaa   2100
caactacctg ttctgccggg tcagaaagaa tggtgtggct gccccttctg ccacctccca   2160
actgtccacc cgggccctgg aagggatctt tgaggccacc caccgcctga tctatggtgc   2220
caaggatgac tctgggcaga gatacctggc ctggtctggc cactctgcca gagtgggtgc   2280
tgccagggac atggccaggg ctggtgtgtc catccctgaa atcatgcagg ctggtggctg   2340
gaccaatgtg aacattgtga tgaactacat cagaaacctg gactctgaga ctggggccat   2400
ggtgaggctg ctcgaggatg gggactaatg aggcgcgccg cggccgctgc tcgagagatc   2460
tacgggtggc atccctgtga cccctcccca gtgcctctcc tggccctgga agttgccact   2520
ccagtgccca ccagccttgt cctaataaaa ttaagttgca tcattttgtc tgactaggtg   2580
tccttctata atattatggg gtggaggggg gtggtatgga gcaaggggca agttgggaag   2640
acaacctgta gggcctgcgg ggtctattgg gaaccaagct ggagtgcagt ggcacaatct   2700
tggctcactg caatctccgc ctcctgggtt caagcgattc tcctgcctca gcctcccgag   2760
ttgttgggat tccaggcatg catgaccagg ctcagctaat tttgtttttt ttggtagaga   2820
cggggtttca ccatattggc caggctggtc tccaactcct aatctcaggt gatctaccca   2880
ccttggcctc ccaaattgct gggattacag gcgtgaacca ctgctccctt ccctgtcctt   2940
ctgattttgt aggtaaccac gtgcggaccg agcggccgca ggaaccccta gtgatggagt   3000
tggccactcc ctctctgcgc gctcgctcgc tcactgaggc cgggcgacca aaggtcgccc   3060
gacgcccggg ctttgcccgg gcggcctcag tgagcgagcg agcgcgcagc tgcctgcagg   3120
ggcgcctgat gcggtatttt ctccttacgc atctgtgcgg tatttcacac cgcatacgtc   3180
aaagcaacca tagtacgcgc cctgtagcgg cgcattaagc gcggcgggtg tggtggttac   3240
gcgcagcgtg accgctacac ttgccagcgc cctagcgccc gctcctttcg ctttcttccc   3300
ttcctttctc gccacgttcg ccggctttcc ccgtcaagct ctaaatcggg ggctcccttt   3360
agggttccga tttagtgctt tacggcacct cgaccccaaa aaacttgatt tgggtgatgg   3420
ttcacgtagt gggccatcgc cctgatagac ggtttttcgc cctttgacgt tggagtccac   3480
gttctttaat agtggactct tgttccaaac tggaacaaca ctcaacccta tctcgggcta   3540
ttcttttgat ttataaggga ttttgccgat ttcggcctat tggttaaaaa atgagctgat   3600
ttaacaaaaa tttaacgcga attttaacaa aatattaacg tttacaattt tatggtgcac   3660
tctcagtaca atctgctctg atgccgcata gttaagccag ccccgacacc cgccaacacc   3720
cgctgacgcg ccctgacggg cttgtctgct cccggcatcc gcttacagac aagctgtgac   3780
cgtctccggg agctgcatgt gtcagaggtt ttcaccgtca tcaccgaaac gcgcgagacg   3840
aaagggcctc gtgatacgcc tatttttata ggttaatgtc atgataataa tggtttctta   3900
gacgtcaggt ggcacttttc ggggaaatgt gcgcggaacc cctatttgtt tatttttcta   3960
aatacattca aatatgtatc cgctcatgag acaataaccc tgataaatgc ttcaataata   4020
```

ttgaaaaagg aagagtatga gtattcaaca tttccgtgtc gcccttattc ccttttttgc 4080
ggcattttgc cttcctgttt ttgctcaccc agaaacgctg gtgaaagtaa aagatgctga 4140
agatcagttg ggtgcacgag tgggttacat cgaactggat ctcaacagcg gtaagatcct 4200
tgagagtttt cgccccgaag aacgttttcc aatgatgagc acttttaaag ttctgctatg 4260
tggcgcggta ttatcccgta ttgacgccgg gcaagagcaa ctcggtcgcc gcatacacta 4320
ttctcagaat gacttggttg agtactcacc agtcacagaa aagcatctta cggatggcat 4380
gacagtaaga gaattatgca gtgctgccat aaccatgagt gataacactg cggccaactt 4440
acttctgaca acgatcggag gaccgaagga gctaaccgct tttttgcaca acatggggga 4500
tcatgtaact cgccttgatc gttgggaacc ggagctgaat gaagccatac caaacgacga 4560
gcgtgacacc acgatgcctg tagcaatggc aacaacgttg cgcaaactat taactggcga 4620
actacttact ctagcttccc ggcaacaatt aatagactgg atggaggcgg ataaagttgc 4680
aggaccactt ctgcgctcgg cccttccggc tggctggttt attgctgata aatctggagc 4740
cggtgagcgt gggtctcgcg gtatcattgc agcactgggg ccagatggta agccctcccg 4800
tatcgtagtt atctacacga cggggagtca ggcaactatg gatgaacgaa atagacagat 4860
cgctgagata ggtgcctcac tgattaagca ttggtaactg tcagaccaag tttactcata 4920
tatactttag attgatttaa aacttcattt ttaatttaaa aggatctagg tgaagatcct 4980
ttttgataat ctcatgacca aaatccctta acgtgagttt tcgttccact gagcgtcaga 5040
ccccgtagaa aagatcaaag gatcttcttg agatcctttt tttctgcgcg taatctgctg 5100
cttgcaaaca aaaaaaccac cgctaccagc ggtggtttgt ttgccggatc aagagctacc 5160
aactcttttt ccgaaggtaa ctggcttcag cagagcgcag ataccaaata ctgtccttct 5220
agtgtagccg tagttaggcc accacttcaa gaactctgta gcaccgccta catacctcgc 5280
tctgctaatc ctgttaccag tggctgctgc cagtggcgat aagtcgtgtc ttaccgggtt 5340
ggactcaaga cgatagttac cggataaggc gcagcggtcg ggctgaacgg ggggttcgtg 5400
cacacagccc agcttggagc gaacgaccta caccgaactg agatacctac agcgtgagct 5460
atgagaaagc gccacgcttc ccgaagggag aaaggcggac aggtatccgg taagcggcag 5520
ggtcggaaca ggagagcgca cgagggagct tccaggggga aacgcctggt atctttatag 5580
tcctgtcggg tttcgccacc tctgacttga gcgtcgattt ttgtgatgct cgtcaggggg 5640
gcggagccta tggaaaaacg ccagcaacgc ggccttttta cggttcctgg ccttttgctg 5700
gccttttgct cacatgt 5717

<210> SEQ ID NO 183
<211> LENGTH: 5408
<212> TYPE: DNA
<213> ORGANISM: Artificial Sequence
<220> FEATURE:
<223> OTHER INFORMATION: synthetic construct

<400> SEQUENCE: 183
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccgca cgcgtataag ccttgggggc aatcaaacta 180
ttacattgag tccttggatt tgctacaaat tacattttaa atgcaatcat tttataaaag 240
cttcaacact cacacttgga agcgttaccc tgttgaatat cactgactca ctaacttgca 300

```
ttgccatgct aacttgcttt cagagagatc tcagaacaca tcatcttctg ctatttcaat    360
acatgcacat taatttccta tcaacgtgtg ctgatcagga actctgtaat ctggcaccgg    420
tgtttatttt tattcctgtc tattcctgtt ggctcacgaa aagattgttt gagcaagtgt    480
tttatggtga gttgtatcat atgtacattg atttaatctg cccacattca gttctacaag    540
cggagccaaa aaaatagaga caagcataat tttcattcaa catgagcccc tcaatgcaag    600
ccaagtacct catctggtgc tcagctaaag caacagcaat ctgttccacc ctggagacac    660
aactggccac agaaaactta gtgaaaagag gcaatgctat gcacaggaca aatgagctcg    720
ggctgggcat aaaagtcagg gcagagccat ctattgctta catttgcttc tgggatccgc    780
ccctctccct cccccccccc taacgttact ggccgaagcc gcttggaata aggccggtgt    840
gcgtttgtct atatgttatt ttccaccata ttgccgtctt ttggcaatgt gagggcccgg    900
aaacctggcc ctgtcttctt gacgagcatt cctaggggtc tttcccctct cgccaaagga    960
atgcaaggtc tgttgaatgt cgtgaaggaa gcagttcctc tggaagcttc ttgaagacaa   1020
acaacgtctg tagcgaccct ttgcaggcag cggaaccccc cacctggcga caggtgcctc   1080
tgcggccaaa agccacgtgt ataagataca cctgcaaagg cggcacaacc ccagtgccac   1140
gttgtgagtt ggatagttgt ggaaagagtc aaatggctct cctcaagcgt attcaacaag   1200
gggctgaagg atgcccagaa ggtaccccat tgtatgggat ctgatctggg gcctcggtgc   1260
acatgcttta catgtgttta gtcgaggtta aaaaaacgtc taggcccccc gaaccacggg   1320
gacgtggttt tcctttgaaa aacacgatga taatatggcc acagctagcg ccaccatgtc   1380
tagactggac aagagcaaag tcataaactc tgctctggaa ttactcaatg aagtcggtat   1440
cgaaggcctg acgacaagga aactcgctca aaagctggga gttgagcagc ctaccctgta   1500
ctggcacgtg aagaacaagc gggccctgct cgatgccctg gcaatcgaga tgctggacag   1560
gcatcatacc cacttctgcc ccctggaagg cgagtcatgg caagactttc tgcggaacaa   1620
cgccaagtca ttccgctgtg ctctcctctc acatcgcgac ggggctaaag tgcatctcgg   1680
cacccgccca acagagaaac agtacgaaac cctggaaaat cagctcgcgt tcctgtgtca   1740
gcaaggcttc tccctggaga acgcactgta cgctctgtcc gccgtgggcc actttacact   1800
gggctgcgta ttggaggatc aggagcatca agtagcaaaa gaggaaagag agacacctac   1860
caccgattct atgcccccac ttctgagaca agcaattgag ctgttcgacc atcagggagc   1920
cgaacctgcc ttccttttcg gcctggaact aatcatatgt ggcctggaga aacagctaaa   1980
gtgcgaaagc ggcgggccgg ccgacgccct tgacgatttt gacttagaca tgctcccagc   2040
cgatgccctt gacgactttg accttgatat gctgcctgct gacgctcttg acgattttga   2100
ccttgacatg ctccccgggt aaggcgcgcc gcggccgctg ctcgagagat ctacgggtgg   2160
catccctgtg acccctcccc agtgcctctc ctggccctgg aagttgccac tccagtgccc   2220
accagccttg tcctaataaa attaagttgc atcattttgt ctgactaggt gtccttctat   2280
aatattatgg ggtggagggg ggtggtatgg agcaaggggc aagttgggaa gacaacctgt   2340
agggcctgcg gggtctattg ggaaccaagc tggagtgcag tggcacaatc ttggctcact   2400
gcaatctccg cctcctgggt tcaagcgatt ctcctgcctc agcctcccga gttgttggga   2460
ttccaggcat gcatgaccag gctcagctaa tttttgtttt tttggtagag acggggtttc   2520
accatattgg ccaggctggt ctccaactcc taatctcagg tgatctaccc accttggcct   2580
cccaaattgc tgggattaca ggcgtgaacc actgctccct tccctgtcct tctgattttg   2640
taggtaacca cgtgcggacc gagcggccgc aggaacccct agtgatggag ttggccactc   2700
```

cctctctgcg cgctcgctcg ctcactgagg ccgggcgacc aaaggtcgcc cgacgcccgg 2760
gctttgcccg ggcggcctca gtgagcgagc gagcgcgcag ctgcctgcag gggcgcctga 2820
tgcggtattt tctccttacg catctgtgcg gtatttcaca ccgcatacgt caaagcaacc 2880
atagtacgcg ccctgtagcg gcgcattaag cgcggcgggt gtggtggtta cgcgcagcgt 2940
gaccgctaca cttgccagcg ccctagcgcc cgctcctttc gctttcttcc cttcctttct 3000
cgccacgttc gccggctttc cccgtcaagc tctaaatcgg gggctccctt tagggttccg 3060
atttagtgct ttacggcacc tcgaccccaa aaaacttgat ttgggtgatg gttcacgtag 3120
tgggccatcg ccctgataga cggtttttcg ccctttgacg ttggagtcca cgttctttaa 3180
tagtggactc ttgttccaaa ctggaacaac actcaaccct atctcgggct attcttttga 3240
tttataaggg attttgccga tttcggccta ttggttaaaa aatgagctga tttaacaaaa 3300
atttaacgcg aattttaaca aaatattaac gtttacaatt ttatggtgca ctctcagtac 3360
aatctgctct gatgccgcat agttaagcca gccccgacac ccgccaacac ccgctgacgc 3420
gccctgacgg gcttgtctgc tcccggcatc cgcttacaga caagctgtga ccgtctccgg 3480
gagctgcatg tgtcagaggt tttcaccgtc atcaccgaaa cgcgcgagac gaaagggcct 3540
cgtgatacgc ctatttttat aggttaatgt catgataata atggtttctt agacgtcagg 3600
tggcactttt cggggaaatg tgcgcggaac ccctatttgt ttatttttct aaatacattc 3660
aaatatgtat ccgctcatga gacaataacc ctgataaatg cttcaataat attgaaaaag 3720
gaagagtatg agtattcaac atttccgtgt cgcccttatt cccttttttg cggcattttg 3780
ccttcctgtt tttgctcacc cagaaacgct ggtgaaagta aaagatgctg aagatcagtt 3840
gggtgcacga gtgggttaca tcgaactgga tctcaacagc ggtaagatcc ttgagagttt 3900
tcgccccgaa gaacgttttc caatgatgag cacttttaaa gttctgctat gtggcgcggt 3960
attatcccgt attgacgccg ggcaagagca actcggtcgc cgcatacact attctcagaa 4020
tgacttggtt gagtactcac cagtcacaga aaagcatctt acggatggca tgacagtaag 4080
agaattatgc agtgctgcca taaccatgag tgataacact gcggccaact tacttctgac 4140
aacgatcgga ggaccgaagg agctaaccgc ttttttgcac aacatggggg atcatgtaac 4200
tcgccttgat cgttgggaac cggagctgaa tgaagccata ccaaacgacg agcgtgacac 4260
cacgatgcct gtagcaatgg caacaacgtt gcgcaaacta ttaactggcg aactacttac 4320
tctagcttcc cggcaacaat taatagactg gatggaggcg gataaagttg caggaccact 4380
tctgcgctcg gcccttccgg ctggctggtt tattgctgat aaatctggag ccggtgagcg 4440
tgggtctcgc ggtatcattg cagcactggg gccagatggt aagccctccc gtatcgtagt 4500
tatctacacg acggggagtc aggcaactat ggatgaacga aatagacaga tcgctgagat 4560
aggtgcctca ctgattaagc attggtaact gtcagaccaa gtttactcat atatacttta 4620
gattgattta aaacttcatt tttaatttaa aaggatctag gtgaagatcc tttttgataa 4680
tctcatgacc aaaatccctt aacgtgagtt ttcgttccac tgagcgtcag accccgtaga 4740
aaagatcaaa ggatcttctt gagatccttt ttttctgcgc gtaatctgct gcttgcaaac 4800
aaaaaaacca ccgctaccag cggtggtttg tttgccggat caagagctac caactctttt 4860
tccgaaggta actggcttca gcagagcgca gataccaaat actgtccttc tagtgtagcc 4920
gtagttaggc caccacttca agaactctgt agcaccgcct acatacctcg ctctgctaat 4980
cctgttacca gtggctgctg ccagtggcga taagtcgtgt cttaccgggt tggactcaag 5040
acgatagtta ccggataagg cgcagcggtc gggctgaacg gggggttcgt gcacacagcc 5100
cagcttggag cgaacgacct acaccgaact gagataccta cagcgtgagc tatgagaaag 5160
cgccacgctt cccgaaggga gaaaggcgga caggtatccg gtaagcggca gggtcggaac 5220
aggagagcgc acgagggagc ttccaggggg aaacgcctgg tatctttata gtcctgtcgg 5280
gtttcgccac ctctgacttg agcgtcgatt tttgtgatgc tcgtcagggg ggcggagcct 5340
atggaaaaac gccagcaacg cggccttttt acggttcctg gccttttgct ggccttttgc 5400
tcacatgt 5408

<210> SEQ ID NO 184
<211> LENGTH: 5442
<212> TYPE: DNA
<213> ORGANISM: Artificial Sequence
<220> FEATURE:
<223> OTHER INFORMATION: synthetic construct

<400> SEQUENCE: 184
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccgca cgcgtccttt tccaaccgtt ccttcatgac 180
atcaaggctt cagactgcta agctttgggc actacctggg gtcagtctgc atcaaaatgt 240
aaggctcaaa tgtgtaattg taagtactgt tttgctgagc tggaagggct cctttgaagc 300
ccacgtttta attttaattt agccacacag agtggcaaag acaaatagat ttatccaaaa 360
tacatttggt aacagatttt ttgagtcagt tattaatttt atttgagggg ttcctctttt 420
tattttttat aaactgtgaa actcaagagg aagcaggatc ccatgcaatg ccttttattg 480
atggcctgct atgtgccaag aaaggtgtta aatgttttcc aatgctgcct catttatcct 540
gatcttacag acaagcaaaa ggaggtgtga agaggtgaag tttctcaccc agctggaaag 600
tggcaaagtc attcacagat ctgcctccgc tcaaaaaaat tgctttatgc aactctttgg 660
aagctaactt catgggagct acatgcagct tctcaatgaa ccttgttttg ctggcctgca 720
gccagaagtt actactcctt tggttcctga gcagagctcg ggctgggcat aaaagtcagg 780
gcagagccat ctattgctta catttgcttc tgggatccgc caccatggtg agcaagggcg 840
aggagctgtt caccggggtg gtgcccatcc tggtcgagct ggacggcgac gtaaacggcc 900
acaagttcag cgtgtccggc gagggcgagg gcgatgccac ctacggcaag ctgaccctga 960
agttcatctg caccaccggc aagctgcccg tgccctggcc caccctcgtg accaccctga 1020
cctacggcgt gcagtgcttc agccgctacc ccgaccacat gaagcagcac gacttcttca 1080
agtccgccat gcccgaaggc tacgtccagg agcgcaccat cttcttcaag gacgacggca 1140
actacaagac ccgcgccgag gtgaagttcg agggcgacac cctggtgaac cgcatcgagc 1200
tgaagggcat cgacttcaag gaggacggca acatcctggg gcacaagctg gagtacaact 1260
acaacagcca caacgtctat atcatggccg acaagcagaa gaacggcatc aaggtgaact 1320
tcaagatccg ccacaacatc gaggacggca gcgtgcagct cgccgaccac taccagcaga 1380
acacccccat cggcgacggc cccgtgctgc tgcccgacaa ccactacctg agcacccagt 1440
ccgccctgag caaagacccc aacgagaagc gcgatcacat ggtcctgctg gagttcgtga 1500
ccgccgccgg gatcactctc ggcatggacg agctgtacaa gtaagaattc gatatcaagc 1560
ttatcgataa tcaacctctg gattacaaaa tttgtgaaag attgactggt attcttaact 1620
atgttgctcc ttttacgcta tgtggatacg ctgctttaat gcctttgtat catgctattg 1680

-continued

```
cttcccgtat ggctttcatt ttctcctcct tgtataaatc ctggttgctg tctctttatg   1740
aggagttgtg gcccgttgtc aggcaacgtg gcgtggtgtg cactgtgttt gctgacgcaa   1800
cccccactgg ttggggcatt gccaccacct gtcagctcct ttccgggact ttcgctttcc   1860
ccctccctat tgccacggcg gaactcatcg ccgcctgcct tgcccgctgc tggacagggg   1920
ctcggctgtt gggcactgac aattccgtgg tgttgtcggg gaaatcatcg tcctttcctt   1980
ggctgctcgc ctatgttgcc acctggattc tgcgcgggac gtccttctgc tacgtccctt   2040
cggccctcaa tccagcggac cttccttccc gcggcctgct gccggctctg cggcctcttc   2100
cgcgtcttcg ccttcgccct cagacgagtc ggatctccct ttgggccgcc tccccgcatc   2160
gataccgagc gctgctcgag agatctacgg gtggcatccc tgtgacccct ccccagtgcc   2220
tctcctggcc ctggaagttg ccactccagt gcccaccagc cttgtcctaa taaaattaag   2280
ttgcatcatt ttgtctgact aggtgtcctt ctataatatt atggggtgga ggggggtggt   2340
atggagcaag gggcaagttg ggaagacaac ctgtagggcc tgcggggtct attgggaacc   2400
aagctggagt gcagtggcac aatcttggct cactgcaatc tccgcctcct gggttcaagc   2460
gattctcctg cctcagcctc ccgagttgtt gggattccag gcatgcatga ccaggctcag   2520
ctaatttttg tttttttggt agagacgggg tttcaccata ttggccaggc tggtctccaa   2580
ctcctaatct caggtgatct acccaccttg gcctcccaaa ttgctgggat tacaggcgtg   2640
aaccactgct cccttccctg tccttctgat tttgtaggta accacgtgcg gaccgagcgg   2700
ccgcaggaac ccctagtgat ggagttggcc actccctctc tgcgcgctcg ctcgctcact   2760
gaggccgggc gaccaaaggt cgcccgacgc ccgggctttg cccgggcggc ctcagtgagc   2820
gagcgagcgc gcagctgcct gcaggggcgc ctgatgcggt attttctcct tacgcatctg   2880
tgcggtattt cacaccgcat acgtcaaagc aaccatagta cgcgccctgt agcggcgcat   2940
taagcgcggc gggtgtggtg gttacgcgca gcgtgaccgc tacacttgcc agcgccctag   3000
cgcccgctcc tttcgctttc ttcccttcct ttctcgccac gttcgccggc tttccccgtc   3060
aagctctaaa tcgggggctc cctttagggt tccgatttag tgctttacgg cacctcgacc   3120
ccaaaaaact tgatttgggt gatggttcac gtagtgggcc atcgccctga tagacggttt   3180
ttcgcccttt gacgttggag tccacgttct ttaatagtgg actcttgttc caaactggaa   3240
caacactcaa ccctatctcg ggctattctt ttgatttata agggattttg ccgatttcgg   3300
cctattggtt aaaaaatgag ctgatttaac aaaaatttaa cgcgaatttt aacaaaatat   3360
taacgtttac aattttatgg tgcactctca gtacaatctg ctctgatgcc gcatagttaa   3420
gccagccccg acacccgcca acacccgctg acgcgccctg acgggcttgt ctgctcccgg   3480
catccgctta cagacaagct gtgaccgtct ccgggagctg catgtgtcag aggttttcac   3540
cgtcatcacc gaaacgcgcg agacgaaagg gcctcgtgat acgcctattt ttataggtta   3600
atgtcatgat aataatggtt tcttagacgt caggtggcac ttttcgggga aatgtgcgcg   3660
gaacccctat ttgtttattt ttctaaatac attcaaatat gtatccgctc atgagacaat   3720
aaccctgata aatgcttcaa taatattgaa aaaggaagag tatgagtatt caacatttcc   3780
gtgtcgccct tattcccttt tttgcggcat tttgccttcc tgtttttgct cacccagaaa   3840
cgctggtgaa agtaaaagat gctgaagatc agttgggtgc acgagtgggt tacatcgaac   3900
tggatctcaa cagcggtaag atccttgaga gttttcgccc cgaagaacgt tttccaatga   3960
tgagcacttt taaagttctg ctatgtggcg cggtattatc ccgtattgac gccgggcaag   4020
```

agcaactcgg tcgccgcata cactattctc agaatgactt ggttgagtac tcaccagtca 4080
cagaaaagca tcttacggat ggcatgacag taagagaatt atgcagtgct gccataacca 4140
tgagtgataa cactgcggcc aacttacttc tgacaacgat cggaggaccg aaggagctaa 4200
ccgctttttt gcacaacatg ggggatcatg taactcgcct tgatcgttgg gaaccggagc 4260
tgaatgaagc cataccaaac gacgagcgtg acaccacgat gcctgtagca atggcaacaa 4320
cgttgcgcaa actattaact ggcgaactac ttactctagc ttcccggcaa caattaatag 4380
actggatgga ggcggataaa gttgcaggac cacttctgcg ctcggccctt ccggctggct 4440
ggtttattgc tgataaatct ggagccggtg agcgtgggtc tcgcggtatc attgcagcac 4500
tggggccaga tggtaagccc tcccgtatcg tagttatcta cacgacgggg agtcaggcaa 4560
ctatggatga acgaaataga cagatcgctg agataggtgc ctcactgatt aagcattggt 4620
aactgtcaga ccaagtttac tcatatatac tttagattga tttaaaactt catttttaat 4680
ttaaaaggat ctaggtgaag atcctttttg ataatctcat gaccaaaatc ccttaacgtg 4740
agttttcgtt ccactgagcg tcagaccccg tagaaaagat caaaggatct tcttgagatc 4800
cttttttctt gcgcgtaatc tgctgcttgc aaacaaaaaa accaccgcta ccagcggtgg 4860
tttgtttgcc ggatcaagag ctaccaactc tttttccgaa ggtaactggc ttcagcagag 4920
cgcagatacc aaatactgtc cttctagtgt agccgtagtt aggccaccac ttcaagaact 4980
ctgtagcacc gcctacatac ctcgctctgc taatcctgtt accagtggct gctgccagtg 5040
gcgataagtc gtgtcttacc gggttggact caagacgata gttaccggat aaggcgcagc 5100
ggtcgggctg aacggggggt tcgtgcacac agcccagctt ggagcgaacg acctacaccg 5160
aactgagata cctacagcgt gagctatgag aaagcgccac gcttcccgaa gggagaaagg 5220
cggacaggta tccggtaagc ggcagggtcg gaacaggaga gcgcacgagg gagcttccag 5280
ggggaaacgc ctggtatctt tatagtcctg tcgggtttcg ccacctctga cttgagcgtc 5340
gatttttgtg atgctcgtca ggggggcgga gcctatggaa aaacgccagc aacgcggcct 5400
ttttacggtt cctggccttt tgctggcctt ttgctcacat gt 5442

<210> SEQ ID NO 185
<211> LENGTH: 6932
<212> TYPE: DNA
<213> ORGANISM: Artificial Sequence
<220> FEATURE:
<223> OTHER INFORMATION: synthetic construct

<400> SEQUENCE: 185
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccgca cgcgtataag ccttgggggc aatcaaacta 180
ttacattgag tccttggatt tgctacaaat tacattttaa atgcaatcat tttataaaag 240
cttcaacact cacacttgga agcgttaccc tgttgaatat cactgactca ctaacttgca 300
ttgccatgct aacttgcttt cagagagatc tcagaacaca tcatcttctg ctatttcaat 360
acatgcacat taatttccta tcaacgtgtg ctgatcagga actctgtaat ctggcaccgg 420
tgtttatttt tattcctgtc tattcctgtt ggctcacgaa aagattgttt gagcaagtgt 480
tttatggtga gttgtatcat atgtacattg atttaatctg cccacattca gttctacaag 540
cggagccaaa aaaatagaga caagcataat tttcattcaa catgagcccc tcaatgcaag 600
ccaagtacct catctggtgc tcagctaaag caacagcaat ctgttccacc ctggagacac 660

```
aactggccac agaaaactta gtgaaaagag gcaatgctat gcacaggaca aatgagctcg    720
ggctgggcat aaaagtcagg gcagagccat ctattgctta catttgcttc tgggatccgc    780
caccatgatc tctctgattg ccgctctggc cgtggactac gtgatcggga tggaaaacgc    840
tatgccatgg aatctgcccg ccgatctggc ttggttcaag aggaacaccc tgaacaagcc    900
agtgatcatg ggcagacaca cttgggagtc cattggacgg cccctgcctg gacgcaagaa    960
catcattctg agctcccagc cctctaccga cgacagggtg acatgggtga aaagtgtgga   1020
cgaagccatt gccgcttgcg gagatgtgcc cgagatcatg gtcatcggcg gagggagagt   1080
gatcgagcag ttcctgccta aggcccagaa actgtacctg actcacattg acgctgaggt   1140
ggaaggggac acccattttc ctgattatga gccagacgat tgggaaagcg tgttctccga   1200
gtttcacgac gccgatgctc aaaattctca tagttattgc tttgagatcc tggaaaggag   1260
aggcgcgcca gtgagcaagg gcgaggagct gttcaccggg gtggtgccca tcctggtcga   1320
gctggacggc gacgtaaacg gccacaagtt cagcgtgtcc ggcgagggcg agggcgatgc   1380
cacctacggc aagctgaccc tgaagttcat ctgcaccacc ggcaagctgc ccgtgccctg   1440
gcccaccctc gtgaccaccc tgacctacgg cgtgcagtgc ttcagccgct accccgacca   1500
catgaagcag cacgacttct tcaagtccgc catgcccgaa ggctacgtcc aggagcgcac   1560
catcttcttc aaggacgacg gcaactacaa gacccgcgcc gaggtgaagt tcgagggcga   1620
caccctggtg aaccgcatcg agctgaaggg catcgacttc aaggaggacg gcaacatcct   1680
ggggcacaag ctggagtaca actacaacag ccacaacgtc tatatcatgg ccgacaagca   1740
gaagaacggc atcaaggtga acttcaagat ccgccacaac atcgaggacg gcagcgtgca   1800
gctcgccgac cactaccagc agaacacccc catcggcgac ggccccgtgc tgctgcccga   1860
caaccactac ctgagcaccc agtccgccct gagcaaagac cccaacgaga agcgcgatca   1920
catggtcctg ctggagttcg tgaccgccgc cgggatcact ctcggcatgg atgagctgta   1980
caagggcaag aagaagagga aggtgtccaa tttactgacc gtacaccaaa atttgcctgc   2040
attaccggtc gatgcaacga gtgatgaggt tcgcaagaac ctgatggaca tgttcaggga   2100
tcgccaggcg ttttctgagc atacctggaa aatgcttctg tccgtttgcc ggtcgtgggc   2160
ggcatggtgc aagttgaata accggaaatg gtttcccgca gaacctgaag atgttcgcga   2220
ttatcttcta tatcttcagg cgcgcggtct ggcagtaaaa actatccagc aacatttggg   2280
ccagctaaac atgcttcatc gtcggtccgg gctgccacga ccaagtgaca gcaatgctgt   2340
ttcactggtt atgcggcgaa tccgaaaaga aaacgttgat gccggtgaac gtgcaaaaca   2400
ggctctagcg ttcgaacgca ctgatttcga ccaggttcgt tcactcatgg aaaatagcga   2460
tcgctgccag gatatacgta atctggcatt tctggggatt gcttataaca ccctgttacg   2520
tatagccgaa attgccagga tcagggttaa agatatctca cgtactgacg gtgggagaat   2580
gttaatccat attggcagaa cgaaaacgct ggttagcacc gcaggtgtag agaaggcact   2640
tagcctgggg gtaactaaac tggtcgagcg atggatttcc gtctctggtg tagctgatga   2700
tccgaataac tacctgtttt gccgggtcag aaaaaatggt gttgccgcgc catctgccac   2760
cagccagcta tcaactcgcg ccctggaagg gatttttgaa gcaactcatc gattgattta   2820
cggcgctaag gatgactctg gtcagagata cctggcctgg tctggacaca gtgcccgtgt   2880
cggagccgcg cgagatatgg cccgcgctgg agtttcaata ccggagatca tgcaagctgg   2940
tggctggacc aatgtaaata ttgtcatgaa ctatatccgt aacctggata gtgaaacagg   3000
```

-continued

```
ggcaatggtg cgcctgctgg aagatggcga ttaggaattc gatatcaagc ttatcgataa   3060
tcaacctctg gattacaaaa tttgtgaaag attgactggt attcttaact atgttgctcc   3120
ttttacgcta tgtggatacg ctgctttaat gcctttgtat catgctattg cttcccgtat   3180
ggctttcatt ttctcctcct tgtataaatc ctggttgctg tctctttatg aggagttgtg   3240
gcccgttgtc aggcaacgtg gcgtggtgtg cactgtgttt gctgacgcaa cccccactgg   3300
ttggggcatt gccaccacct gtcagctcct ttccgggact ttcgctttcc ccctccctat   3360
tgccacggcg gaactcatcg ccgcctgcct tgcccgctgc tggacagggg ctcggctgtt   3420
gggcactgac aattccgtgg tgttgtcggg gaaatcatcg tcctttcctt ggctgctcgc   3480
ctatgttgcc acctggattc tgcgcgggac gtccttctgc tacgtccctt cggccctcaa   3540
tccagcggac cttccttccc gcggcctgct gccggctctg cggcctcttc cgcgtcttcg   3600
ccttcgccct cagacgagtc ggatctccct ttgggccgcc tccccgcatc gataccgagc   3660
gctgctcgag agatctacgg gtggcatccc tgtgacccct ccccagtgcc tctcctggcc   3720
ctggaagttg ccactccagt gcccaccagc cttgtcctaa taaaattaag ttgcatcatt   3780
ttgtctgact aggtgtcctt ctataatatt atggggtgga ggggggtggt atggagcaag   3840
gggcaagttg ggaagacaac ctgtagggcc tgcggggtct attgggaacc aagctggagt   3900
gcagtggcac aatcttggct cactgcaatc tccgcctcct gggttcaagc gattctcctg   3960
cctcagcctc ccgagttgtt gggattccag gcatgcatga ccaggctcag ctaatttttg   4020
tttttttggt agagacgggg tttcaccata ttggccaggc tggtctccaa ctcctaatct   4080
caggtgatct acccaccttg gcctcccaaa ttgctgggat tacaggcgtg aaccactgct   4140
cccttccctg tccttctgat tttgtaggta accacgtgcg gaccgagcgg ccgcaggaac   4200
ccctagtgat ggagttggcc actccctctc tgcgcgctcg ctcgctcact gaggccgggc   4260
gaccaaaggt cgcccgacgc ccgggctttg cccgggcggc ctcagtgagc gagcgagcgc   4320
gcagctgcct gcaggggcgc ctgatgcggt attttctcct tacgcatctg tgcggtattt   4380
cacaccgcat acgtcaaagc aaccatagta cgcgccctgt agcggcgcat taagcgcggc   4440
gggtgtggtg gttacgcgca gcgtgaccgc tacacttgcc agcgccctag cgcccgctcc   4500
tttcgctttc ttcccttcct ttctcgccac gttcgccggc tttccccgtc aagctctaaa   4560
tcgggggctc cctttagggt tccgatttag tgctttacgg cacctcgacc ccaaaaaact   4620
tgatttgggt gatggttcac gtagtgggcc atcgccctga tagacggttt ttcgcccttt   4680
gacgttggag tccacgttct ttaatagtgg actcttgttc caaactggaa caacactcaa   4740
ccctatctcg ggctattctt ttgatttata agggattttg ccgatttcgg cctattggtt   4800
aaaaaatgag ctgatttaac aaaaatttaa cgcgaatttt aacaaaatat taacgtttac   4860
aattttatgg tgcactctca gtacaatctg ctctgatgcc gcatagttaa gccagccccg   4920
acacccgcca acacccgctg acgcgccctg acgggcttgt ctgctcccgg catccgctta   4980
cagacaagct gtgaccgtct ccgggagctg catgtgtcag aggttttcac cgtcatcacc   5040
gaaacgcgcg agacgaaagg gcctcgtgat acgcctattt ttataggtta atgtcatgat   5100
aataatggtt tcttagacgt caggtggcac ttttcgggga aatgtgcgcg gaacccctat   5160
ttgtttattt ttctaaatac attcaaatat gtatccgctc atgagacaat aaccctgata   5220
aatgcttcaa taatattgaa aaaggaagag tatgagtatt caacatttcc gtgtcgccct   5280
tattcccttt tttgcggcat tttgccttcc tgtttttgct cacccagaaa cgctggtgaa   5340
agtaaaagat gctgaagatc agttgggtgc acgagtgggt tacatcgaac tggatctcaa   5400
```

```
cagcggtaag atccttgaga gttttcgccc cgaagaacgt tttccaatga tgagcacttt   5460
taaagttctg ctatgtggcg cggtattatc ccgtattgac gccgggcaag agcaactcgg   5520
tcgccgcata cactattctc agaatgactt ggttgagtac tcaccagtca cagaaaagca   5580
tcttacggat ggcatgacag taagagaatt atgcagtgct gccataacca tgagtgataa   5640
cactgcggcc aacttacttc tgacaacgat cggaggaccg aaggagctaa ccgctttttt   5700
gcacaacatg ggggatcatg taactcgcct tgatcgttgg gaaccggagc tgaatgaagc   5760
cataccaaac gacgagcgtg acaccacgat gcctgtagca atggcaacaa cgttgcgcaa   5820
actattaact ggcgaactac ttactctagc ttcccggcaa caattaatag actggatgga   5880
ggcggataaa gttgcaggac cacttctgcg ctcggccctt ccggctggct ggtttattgc   5940
tgataaatct ggagccggtg agcgtgggtc tcgcggtatc attgcagcac tggggccaga   6000
tggtaagccc tcccgtatcg tagttatcta cacgacgggg agtcaggcaa ctatggatga   6060
acgaaataga cagatcgctg agataggtgc ctcactgatt aagcattggt aactgtcaga   6120
ccaagtttac tcatatatac tttagattga tttaaaactt catttttaat ttaaaaggat   6180
ctaggtgaag atcctttttg ataatctcat gaccaaaatc ccttaacgtg agttttcgtt   6240
ccactgagcg tcagaccccg tagaaaagat caaaggatct tcttgagatc cttttttct    6300
gcgcgtaatc tgctgcttgc aaacaaaaaa accaccgcta ccagcggtgg tttgtttgcc   6360
ggatcaagag ctaccaactc tttttccgaa ggtaactggc ttcagcagag cgcagatacc   6420
aaatactgtc cttctagtgt agccgtagtt aggccaccac ttcaagaact ctgtagcacc   6480
gcctacatac ctcgctctgc taatcctgtt accagtggct gctgccagtg gcgataagtc   6540
gtgtcttacc gggttggact caagacgata gttaccggat aaggcgcagc ggtcgggctg   6600
aacggggggt tcgtgcacac agcccagctt ggagcgaacg acctacaccg aactgagata   6660
cctacagcgt gagctatgag aaagcgccac gcttcccgaa gggagaaagg cggacaggta   6720
tccggtaagc ggcagggtcg gaacaggaga gcgcacgagg gagcttccag ggggaaacgc   6780
ctggtatctt tatagtcctg tcgggtttcg ccacctctga cttgagcgtc gatttttgtg   6840
atgctcgtca ggggggcgga gcctatggaa aaacgccagc aacgcggcct ttttacggtt   6900
cctggccttt tgctggcctt ttgctcacat gt                                6932
```

<210> SEQ ID NO 186
<211> LENGTH: 5806
<212> TYPE: DNA
<213> ORGANISM: Artificial Sequence
<220> FEATURE:
<223> OTHER INFORMATION: synthetic construct

<400> SEQUENCE: 186

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc tgcggccgca cgcgtataag ccttgggggc aatcaaacta    180
ttacattgag tccttggatt tgctacaaat tacattttaa atgcaatcat tttataaaag    240
cttcaacact cacacttgga agcgttaccc tgttgaatat cactgactca ctaacttgca    300
ttgccatgct aacttgcttt cagagagatc tcagaacaca tcatcttctg ctatttcaat    360
acatgcacat taatttccta tcaacgtgtg ctgatcagga actctgtaat ctggcaccgg    420
tgtttatttt tattcctgtc tattcctgtt ggctcacgaa aagattgttt gagcaagtgt    480
```

-continued

```
tttatggtga gttgtatcat atgtacattg atttaatctg cccacattca gttctacaag    540
cggagccaaa aaaatagaga caagcataat tttcattcaa catgagcccc tcaatgcaag    600
ccaagtacct catctggtgc tcagctaaag caacagcaat ctgttccacc ctggagacac    660
aactggccac agaaaactta gtgaaaagag gcaatgctat gcacaggaca aatgagctcg    720
ggctgggcat aaaagtcagg gcagagccat ctattgctta catttgcttc tgttaattaa    780
gccgccacca tgcccaagaa gaagaggaag gtgtccaatt tactgaccgt acaccaaaat    840
ttgcctgcat taccggtcga tgcaacgagt gatgaggttc gcaagaacct gatggacatg    900
ttcagggatc gccaggcgtt ttctgagcat acctggaaaa tgcttctgtc cgtttgccgg    960
tcgtgggcgg catggtgcaa gttgaataac cggaaatggt ttcccgcaga acctgaagat   1020
gttcgcgatt atcttctata tcttcaggcg cgcggtctgg cagtaaaaac tatccagcaa   1080
catttgggcc agctaaacat gcttcatcgt cggtccgggc tgccacgacc aagtgacagc   1140
aatgctgttt cactggttat gcggcggatc cgaaaagaaa acgttgatgc cggtgaacgt   1200
gcaaaacagg ctctagcgtt cgaacgcact gatttcgacc aggttcgttc actcatggaa   1260
aatagcgatc gctgccagga tatacgtaat ctggcatttc tggggattgc ttataacacc   1320
ctgttacgta tagccgaaat tgccaggatc agggttaaag atatctcacg tactgacggt   1380
gggagaatgt taatccatat tggcagaacg aaaacgctgg ttagcaccgc aggtgtagag   1440
aaggcactta gcctgggggt aactaaactg gtcgagcgat ggatttccgt ctctggtgta   1500
gctgatgatc cgaataacta cctgttttgc cgggtcagaa aaaatggtgt tgccgcgcca   1560
tctgccacca gccagctatc aactcgcgcc ctggaaggga tttttgaagc aactcatcga   1620
ttgatttacg gcgctaaggt aaatataaaa tttttaagtg tataatgtgt taaactactg   1680
attctaattg tttgtgtatt ttaggatgac tctggtcaga gatacctggc ctggtctgga   1740
cacagtgccc gtgtcggagc cgcgcgagat atggcccgcg ctggagtttc aataccggag   1800
atcatgcaag ctggtggctg gaccaatgta aatattgtca tgaactatat ccgtaacctg   1860
gatagtgaaa caggggcaat ggtgcgcctg ctggaagatg gcgattagga attcgatatc   1920
aagcttatcg ataatcaacc tctggattac aaaatttgtg aaagattgac tggtattctt   1980
aactatgttg ctccttttac gctatgtgga tacgctgctt taatgccttt gtatcatgct   2040
attgcttccc gtatggcttt cattttctcc tccttgtata aatcctggtt gctgtctctt   2100
tatgaggagt tgtggcccgt tgtcaggcaa cgtggcgtgg tgtgcactgt gtttgctgac   2160
gcaaccccca ctggttgggg cattgccacc acctgtcagc tcctttccgg gactttcgct   2220
ttccccctcc ctattgccac ggcggaactc atcgccgcct gccttgcccg ctgctggaca   2280
ggggctcggc tgttgggcac tgacaattcc gtggtgttgt cggggaaatc atcgtccttt   2340
ccttggctgc tcgcctatgt tgccacctgg attctgcgcg ggacgtcctt ctgctacgtc   2400
ccttcggccc tcaatccagc ggaccttcct tcccgcggcc tgctgccggc tctgcggcct   2460
cttccgcgtc ttcgccttcg ccctcagacg agtcggatct ccctttgggc cgcctccccg   2520
catcgatacc gagcgctgct cgagagatct acgggtggca tccctgtgac ccctccccag   2580
tgcctctcct ggccctggaa gttgccactc cagtgcccac cagccttgtc ctaataaaat   2640
taagttgcat cattttgtct gactaggtgt ccttctataa tattatgggg tggagggggg   2700
tggtatggag caaggggcaa gttgggaaga caacctgtag ggcctgcggg gtctattggg   2760
aaccaagctg gagtgcagtg gcacaatctt ggctcactgc aatctccgcc tcctgggttc   2820
aagcgattct cctgcctcag cctcccgagt tgttgggatt ccaggcatgc atgaccaggc   2880
```

```
tcagctaatt tttgtttttt tggtagagac ggggtttcac catattggcc aggctggtct   2940
ccaactccta atctcaggtg atctacccac cttggcctcc caaattgctg ggattacagg   3000
cgtgaaccac tgctcccttc cctgtccttc tgattttgta ggtaaccacg tgcggaccga   3060
gcggccgcag gaacccctag tgatggagtt ggccactccc tctctgcgcg ctcgctcgct   3120
cactgaggcc gggcgaccaa aggtcgcccg acgcccgggc tttgcccggg cggcctcagt   3180
gagcgagcga gcgcgcagct gcctgcaggg gcgcctgatg cggtattttc tccttacgca   3240
tctgtgcggt atttcacacc gcatacgtca aagcaaccat agtacgcgcc ctgtagcggc   3300
gcattaagcg cggcgggtgt ggtggttacg cgcagcgtga ccgctacact tgccagcgcc   3360
ctagcgcccg ctcctttcgc tttcttccct tcctttctcg ccacgttcgc cggctttccc   3420
cgtcaagctc taaatcgggg gctcccttta gggttccgat ttagtgcttt acggcacctc   3480
gaccccaaaa aacttgattt gggtgatggt tcacgtagtg ggccatcgcc ctgatagacg   3540
gtttttcgcc ctttgacgtt ggagtccacg ttctttaata gtggactctt gttccaaact   3600
ggaacaacac tcaaccctat ctcgggctat tcttttgatt tataagggat tttgccgatt   3660
tcggcctatt ggttaaaaaa tgagctgatt taacaaaaat ttaacgcgaa ttttaacaaa   3720
atattaacgt ttacaatttt atggtgcact ctcagtacaa tctgctctga tgccgcatag   3780
ttaagccagc cccgacaccc gccaacaccc gctgacgcgc cctgacgggc ttgtctgctc   3840
ccggcatccg cttacagaca agctgtgacc gtctccggga gctgcatgtg tcagaggttt   3900
tcaccgtcat caccgaaacg cgcgagacga aagggcctcg tgatacgcct atttttatag   3960
gttaatgtca tgataataat ggtttcttag acgtcaggtg gcacttttcg gggaaatgtg   4020
cgcggaaccc ctatttgttt atttttctaa atacattcaa atatgtatcc gctcatgaga   4080
caataaccct gataaatgct tcaataatat tgaaaaagga agagtatgag tattcaacat   4140
ttccgtgtcg cccttattcc cttttttgcg gcattttgcc ttcctgtttt tgctcaccca   4200
gaaacgctgg tgaaagtaaa agatgctgaa gatcagttgg gtgcacgagt gggttacatc   4260
gaactggatc tcaacagcgg taagatcctt gagagttttc gccccgaaga acgttttcca   4320
atgatgagca cttttaaagt tctgctatgt ggcgcggtat tatcccgtat tgacgccggg   4380
caagagcaac tcggtcgccg catacactat tctcagaatg acttggttga gtactcacca   4440
gtcacagaaa agcatcttac ggatggcatg acagtaagag aattatgcag tgctgccata   4500
accatgagtg ataacactgc ggccaactta cttctgacaa cgatcggagg accgaaggag   4560
ctaaccgctt ttttgcacaa catgggggat catgtaactc gccttgatcg ttgggaaccg   4620
gagctgaatg aagccatacc aaacgacgag cgtgacacca cgatgcctgt agcaatggca   4680
acaacgttgc gcaaactatt aactggcgaa ctacttactc tagcttcccg gcaacaatta   4740
atagactgga tggaggcgga taaagttgca ggaccacttc tgcgctcggc ccttccggct   4800
ggctggttta ttgctgataa atctggagcc ggtgagcgtg ggtctcgcgg tatcattgca   4860
gcactggggc cagatggtaa gccctcccgt atcgtagtta tctacacgac ggggagtcag   4920
gcaactatgg atgaacgaaa tagacagatc gctgagatag gtgcctcact gattaagcat   4980
tggtaactgt cagaccaagt ttactcatat atactttaga ttgatttaaa acttcatttt   5040
taatttaaaa ggatctaggt gaagatcctt tttgataatc tcatgaccaa aatcccttaa   5100
cgtgagtttt cgttccactg agcgtcagac cccgtagaaa agatcaaagg atcttcttga   5160
gatccttttt ttctgcgcgt aatctgctgc ttgcaaacaa aaaaaccacc gctaccagcg   5220
```

```
gtggtttgtt tgccggatca agagctacca actctttttc cgaaggtaac tggcttcagc   5280

agagcgcaga taccaaatac tgtccttcta gtgtagccgt agttaggcca ccacttcaag   5340

aactctgtag caccgcctac atacctcgct ctgctaatcc tgttaccagt ggctgctgcc   5400

agtggcgata agtcgtgtct taccgggttg gactcaagac gatagttacc ggataaggcg   5460

cagcggtcgg gctgaacggg gggttcgtgc acacagccca gcttggagcg aacgacctac   5520

accgaactga gatacctaca gcgtgagcta tgagaaagcg ccacgcttcc cgaagggaga   5580

aaggcggaca ggtatccggt aagcggcagg gtcggaacag gagagcgcac gagggagctt   5640

ccagggggaa acgcctggta tctttatagt cctgtcgggt ttcgccacct ctgacttgag   5700

cgtcgatttt tgtgatgctc gtcagggggg cggagcctat ggaaaaacgc cagcaacgcg   5760

gcctttttac ggttcctggc cttttgctgg ccttttgctc acatgt                  5806
```

<210> SEQ ID NO 187
<211> LENGTH: 5779
<212> TYPE: DNA
<213> ORGANISM: Artificial Sequence
<220> FEATURE:
<223> OTHER INFORMATION: synthetic construct

<400> SEQUENCE: 187

```
cctgcaggca gctgcgcgct cgctcgctca ctgaggccgc ccgggcaaag cccgggcgtc     60

gggcgacctt tggtcgcccg gcctcagtga gcgagcgagc gcgcagagag ggagtggcca    120

actccatcac taggggttcc tgcggccgca cgcgtatgtg tcttttactc tgatcctcct    180

gtttttacct tccaagtgct ggaatcacag acatatacca ctgtgcatag catcattaca    240

atgttatagt tttcacact atgccttgac tttttggaaa ggcaaaccac ctcttggatt    300

tctccttcct tctctatctc tctctctctc tcttcctccc tccgtccctc catctcttcc    360

tccttcccat tttcttctct ccctatttgg acacaatata aaataattta gatgaggtga    420

gttaaattgt gaacaaagta tgtgcctata catggttgta aatcagctta tcaaagtgta    480

atattagaag aatttataaa aatgataaaa ttcatactca aagttctgtg taaagcaata    540

atagctttat ctccttttag ttatcttgag tctttctatg actaacaact ccctcatagg    600

catcttaaag agcagtaagc ataagtagat tccaaatggg aagggagaag tgtgaaccat    660

cactttcatc cagacttgta gatatatctg ctgcattttc agaaaccaga aacagacagt    720

gttctttatc tccattgagt ctagtgtagc aacagagctc gggctgggca taaaagtcag    780

ggcagagcca tctattgctt acatttgctt ctgggatccg ccaccatggt gcccaagaag    840

aagaggaaag tctccaacct gctgactgtg caccaaaacc tgcctgccct ccctgtggat    900

gccacctctg atgaagtcag gaagaacctg atggacatgt tcagggacag gcaggccttc    960

tctgaacaca cctggaagat gctcctgtct gtgtgcagat cctgggctgc ctggtgcaag   1020

ctgaacaaca ggaaatggtt ccctgctgaa cctgaggatg tgagggacta cctcctgtac   1080

ctgcaagcca gaggcctggc tgtgaagacc atccaacagc acctgggcca gctcaacatg   1140

ctgcacagga gatctggcct gcctcgccct tctgactcca atgctgtgtc cctggtgatg   1200

aggagaatca gaaaggagaa tgtggatgct ggggagagag ccaagcaggc cctggccttt   1260

gaacgcactg actttgacca agtcagatcc ctgatggaga actctgacag atgccaggac   1320

atcaggaacc tggccttcct gggcattgcc tacaacaccc tgctgcgcat tgccgaaatt   1380

gccagaatca gagtgaagga catctcccgc accgatggtg ggagaatgct gatccacatt   1440

ggcaggacca agaccctggt gtccacagct ggtgtggaga aggccctgtc cctgggggtt   1500
```

-continued

```
accaagctgg tggagagatg gatctctgtg tctggtgtgg ctgatgaccc caacaactac   1560
ctgttctgcc gggtcagaaa gaatggtgtg gctgcccctt ctgccacctc ccaactgtcc   1620
acccgggccc tggaagggat ctttgaggcc acccaccgcc tgatctatgg tgccaaggat   1680
gactctgggc agagatacct ggcctggtct ggccactctg ccagagtggg tgctgccagg   1740
gacatggcca gggctggtgt gtccatccct gaaatcatgc aggctggtgg ctggaccaat   1800
gtgaacattg tgatgaacta catcagaaac ctggactctg agactggggc catggtgagg   1860
ctgctcgagg atggggacta agaattcgat atcaagctta tcgataatca acctctggat   1920
tacaaaattt gtgaaagatt gactggtatt cttaactatg ttgctccttt tacgctatgt   1980
ggatacgctg ctttaatgcc tttgtatcat gctattgctt cccgtatggc tttcattttc   2040
tcctccttgt ataaatcctg gttgctgtct ctttatgagg agttgtggcc cgttgtcagg   2100
caacgtggcg tggtgtgcac tgtgtttgct gacgcaaccc ccactggttg gggcattgcc   2160
accacctgtc agctcctttc cgggactttc gctttccccc tccctattgc cacggcggaa   2220
ctcatcgccg cctgccttgc ccgctgctgg acaggggctc ggctgttggg cactgacaat   2280
tccgtggtgt tgtcggggaa atcatcgtcc tttccttggc tgctcgccta tgttgccacc   2340
tggattctgc gcgggacgtc cttctgctac gtcccttcgg ccctcaatcc agcggacctt   2400
ccttcccgcg gcctgctgcc ggctctgcgg cctcttccgc gtcttcgcct tcgccctcag   2460
acgagtcgga tctccctttg ggccgcctcc ccgcatcgat accgagcgct gctcgagaga   2520
tctacgggtg gcatccctgt gacccctccc cagtgcctct cctggccctg gaagttgcca   2580
ctccagtgcc caccagcctt gtcctaataa aattaagttg catcattttg tctgactagg   2640
tgtccttcta taatattatg gggtggaggg gggtggtatg gagcaagggg caagttggga   2700
agacaacctg tagggcctgc ggggtctatt gggaaccaag ctggagtgca gtggcacaat   2760
cttggctcac tgcaatctcc gcctcctggg ttcaagcgat tctcctgcct cagcctcccg   2820
agttgttggg attccaggca tgcatgacca ggctcagcta atttttgttt ttttggtaga   2880
gacggggttt caccatattg gccaggctgg tctccaactc ctaatctcag gtgatctacc   2940
caccttggcc tcccaaattg ctgggattac aggcgtgaac cactgctccc ttccctgtcc   3000
ttctgatttt gtaggtaacc acgtgcggac cgagcggccg caggaacccc tagtgatgga   3060
gttggccact ccctctctgc gcgctcgctc gctcactgag gccgggcgac caaaggtcgc   3120
ccgacgcccg ggctttgccc gggcggcctc agtgagcgag cgagcgcgca gctgcctgca   3180
ggggcgcctg atgcggtatt ttctccttac gcatctgtgc ggtatttcac accgcatacg   3240
tcaaagcaac catagtacgc gccctgtagc ggcgcattaa gcgcggcggg tgtggtggtt   3300
acgcgcagcg tgaccgctac acttgccagc gccctagcgc ccgctccttt cgctttcttc   3360
ccttcctttc tcgccacgtt cgccggcttt ccccgtcaag ctctaaatcg ggggctccct   3420
ttagggttcc gatttagtgc tttacggcac ctcgacccca aaaaacttga tttgggtgat   3480
ggttcacgta gtgggccatc gccctgatag acggtttttc gccctttgac gttggagtcc   3540
acgttcttta atagtggact cttgttccaa actggaacaa cactcaaccc tatctcgggc   3600
tattcttttg atttataagg gattttgccg atttcggcct attggttaaa aaatgagctg   3660
atttaacaaa aatttaacgc gaattttaac aaaatattaa cgtttacaat tttatggtgc   3720
actctcagta caatctgctc tgatgccgca tagttaagcc agccccgaca cccgccaaca   3780
cccgctgacg cgccctgacg ggcttgtctg ctcccggcat ccgcttacag acaagctgtg   3840
```

```
accgtctccg ggagctgcat gtgtcagagg ttttcaccgt catcaccgaa acgcgcgaga   3900
cgaaagggcc tcgtgatacg cctattttta taggttaatg tcatgataat aatggtttct   3960
tagacgtcag gtggcacttt tcggggaaat gtgcgcggaa cccctatttg tttatttttc   4020
taaatacatt caaatatgta tccgctcatg agacaataac cctgataaat gcttcaataa   4080
tattgaaaaa ggaagagtat gagtattcaa catttccgtg tcgcccttat tccctttttt   4140
gcggcatttt gccttcctgt ttttgctcac ccagaaacgc tggtgaaagt aaaagatgct   4200
gaagatcagt tgggtgcacg agtgggttac atcgaactgg atctcaacag cggtaagatc   4260
cttgagagtt ttcgccccga agaacgtttt ccaatgatga gcacttttaa agttctgcta   4320
tgtggcgcgg tattatcccg tattgacgcc gggcaagagc aactcggtcg ccgcatacac   4380
tattctcaga atgacttggt tgagtactca ccagtcacag aaaagcatct tacggatggc   4440
atgacagtaa gagaattatg cagtgctgcc ataaccatga gtgataacac tgcggccaac   4500
ttacttctga caacgatcgg aggaccgaag gagctaaccg cttttttgca caacatgggg   4560
gatcatgtaa ctcgccttga tcgttgggaa ccggagctga atgaagccat accaaacgac   4620
gagcgtgaca ccacgatgcc tgtagcaatg gcaacaacgt tgcgcaaact attaactggc   4680
gaactactta ctctagcttc ccggcaacaa ttaatagact ggatggaggc ggataaagtt   4740
gcaggaccac ttctgcgctc ggcccttccg gctggctggt ttattgctga taaatctgga   4800
gccggtgagc gtgggtctcg cggtatcatt gcagcactgg ggccagatgg taagccctcc   4860
cgtatcgtag ttatctacac gacggggagt caggcaacta tggatgaacg aaatagacag   4920
atcgctgaga taggtgcctc actgattaag cattggtaac tgtcagacca agtttactca   4980
tatatacttt agattgattt aaaacttcat ttttaattta aaaggatcta ggtgaagatc   5040
ctttttgata atctcatgac caaaatccct taacgtgagt tttcgttcca ctgagcgtca   5100
gaccccgtag aaaagatcaa aggatcttct tgagatcctt tttttctgcg cgtaatctgc   5160
tgcttgcaaa caaaaaaacc accgctacca gcggtggttt gtttgccgga tcaagagcta   5220
ccaactcttt ttccgaaggt aactggcttc agcagagcgc agataccaaa tactgtcctt   5280
ctagtgtagc cgtagttagg ccaccacttc aagaactctg tagcaccgcc tacatacctc   5340
gctctgctaa tcctgttacc agtggctgct gccagtggcg ataagtcgtg tcttaccggg   5400
ttggactcaa gacgatagtt accggataag gcgcagcggt cgggctgaac ggggggttcg   5460
tgcacacagc ccagcttgga gcgaacgacc tacaccgaac tgagatacct acagcgtgag   5520
ctatgagaaa gcgccacgct tcccgaaggg agaaaggcgg acaggtatcc ggtaagcggc   5580
agggtcggaa caggagagcg cacgagggag cttccagggg gaaacgcctg gtatctttat   5640
agtcctgtcg ggtttcgcca cctctgactt gagcgtcgat ttttgtgatg ctcgtcaggg   5700
gggcggagcc tatggaaaaa cgccagcaac gcggcctttt tacggttcct ggccttttgc   5760
tggccttttg ctcacatgt                                                5779
```

<210> SEQ ID NO 188
<211> LENGTH: 255
<212> TYPE: DNA
<213> ORGANISM: Mus musculus

<400> SEQUENCE: 188

```
ctccaaattt cttcaaccaa gtagagaaaa atgagagaga aggaaagaaa aaaagaggta     60
tggggagaag agaaagaagg caacttgtta aaaatctcag tcaaacttac atactatata    120
gaacagcatg gtgaatttag ggcacatgga tataaaatgg aagtttctta ttcagtagca    180
```

-continued

```
gcaacttgtg ggcacaggag ttggcaaaga taaaaatgtc caaagtcaca aatacaatgt    240

atagttagtc atagg                                                     255
```

ARTIFICIAL EXPRESSION CONSTRUCTS FOR SELECTIVELY MODULATING GENE EXPRESSION IN EXCITATORY CORTICAL NEURONS

CROSS-REFERENCE TO RELATED APPLICATIONS

This application is a U.S. National Phase Applications based on International Patent Application No. PCT/US2019/059927, filed Nov. 5, 2019, which claims priority to U.S. Provisional Patent Application Nos. 62/755,988 filed Nov. 5, 2018; 62/806,600 filed Feb. 15, 2019; 62/806,684 filed Feb. 15, 2019; and 62/872,021 filed Jul. 9, 2019; each of which is incorporated herein by reference in its entirety as if fully set forth herein.

STATEMENT REGARDING FEDERALLY SPONSORED RESEARCH OR DEVELOPMENT

This invention was made with government support under grant 1R01-DA036909 awarded by the National Institutes of Health. The government has certain rights in the invention.

REFERENCE TO SEQUENCE LISTING

The Sequence Listing associated with this application is provided in text format in lieu of a paper copy and is hereby incorporated by reference into the specification. The name of the text file containing the Sequence Listing is 2GE2196 ST25.txt. The text file is 600 KB, was created on Mar. 10, 2021, and is being submitted electronically via EFS-Web

FIELD OF THE DISCLOSURE

The current disclosure provides artificial expression constructs for selectively driving gene expression in excitatory cortical neurons. The artificial expression constructs can be used to selectively express synthetic genes or modify gene expression in excitatory cortical neurons, such as primarily within cortical layers 2/3, 4, 5, and 6 and including those with extratelencephalic (ET) projections, intratelencephalic (IT) projections, and pyramidal tract (PT) projections, among others.

BACKGROUND OF THE DISCLOSURE

To fully understand the biology of the brain, different cell types need to be distinguished and defined and, to further study them, vectors that can selectively label and perturb them need to be identified. In mouse, recombinase driver lines have been used to great effect to label cell populations that share marker gene expression. However, the creation, maintenance, and use of such lines that label cell types with high specificity can be costly, frequently requiring triple transgenic crosses, which yield a low frequency of experimental animals. Furthermore, those tools require germline transgenic animals and thus are not applicable to humans.

Recent advances in single-cell profiling, such as single-cell RNA-seq and surveys of neural electrophysiology and morphology, have revealed that many recombinant driver lines label heterogeneous mixtures of cell types, and often include cells from multiple subclasses. For example, the Rbp4-Cre mouse driver line, which is commonly used to label layer 5 (L5) neurons, labels cells with drastically different connectivity patterns: L5 intratelencephalic (IT, also called cortico-cortical) and pyramidal tract (PT, also called cortico-subcortical) neurons.

SUMMARY OF THE DISCLOSURE

The current disclosure provides artificial expression constructs that selectively drive gene expression in targeted central nervous system cell populations. Targeted central nervous system cell populations include excitatory cortical neurons, such as those primarily within cortical layers (L) 2/3, 4, 5, and/or 6 and including those with extratelencephalic (ET) projections, intratelencephalic (IT) projections, and/or pyramidal tract (PT) projections. Particular artificial expression constructs disclosed herein target specific excitatory cell types, while others selectively drive gene expression across numerous excitatory neuron types.

For example, artificial expression constructs including a promoter, the eHGT_075 h enhancer, and a gene encoding an expression product can lead to selective gene expression in L2/3 IT excitatory cortical neurons.

Artificial expression constructs including a promoter; the Grik1_enhScnn1a-2, eHGT_058 h, eHGT_058 m, eHGT_439 m, and/or eHGT_254 h enhancer; and a gene encoding an expression product can lead to selective gene expression in L4 IT excitatory cortical neurons.

Particular examples of artificial expression constructs including a promoter; the mscRE4 enhancer, a concatenated mscRE4, and/or a concatenated mscRE16 enhancer; and a gene encoding an expression product can lead to selective gene expression in L5 PT excitatory cortical neurons. Examples of these expression constructs include T502-057 (vAi3.0), 981 (vAi5.0), 1052 (vAi10.0), CN1818 (vAi128.0), CN2014 (vAi129.0) and vAi130.0.

Artificial expression constructs including a promoter, a concatenated core of the mscRE4 enhancer, and a gene encoding an expression product can lead to selective gene expression in L5 PT and L5 ET excitatory cortical neurons.

Artificial expression constructs including a promoter; the mscRE1, mscRE11, and/or mscRE16 enhancer; and a gene encoding an expression product can lead to selective gene expression in L5 PT and L5 IT excitatory cortical neurons.

Artificial expression constructs including a promoter, the mscRE13 enhancer, and a gene encoding an expression product can lead to selective gene expression in L6 IT excitatory cortical neurons.

Particular examples of artificial expression constructs including a promoter, the mscRE10 enhancer, and a gene encoding an expression product can lead to selective gene expression in L6 CT excitatory cortical neurons. An example includes 995 (vAi15.0).

Artificial expression constructs including a promoter, the eHGT_440 h enhancer, and a gene encoding an expression product can lead to selective gene expression in subtypes of L6b excitatory cortical neurons.

Artificial expression constructs including a promoter, the eHGT_078 h enhancer; and a gene encoding an expression product can lead to selective gene expression in L2/3 IT, L4 IT, L5 IT, L5 NP, and L5 PT excitatory cortical neurons.

Selective expression of a gene encoding an expression product can be achieved in L2/3 IT, L5 IT, and L6b neurons utilizing the 1036 (vAi16.0) artificial expression construct described herein. This construct includes the mscRE10 enhancer.

Selective expression of a gene encoding an expression product can be achieved in L2/3 IT, L5 PT, L6 CT, and L6b neurons utilizing the 988 (vAi7.1), 1010 (vAi6.1), and/or 1011 (vAi7.2) artificial expression constructs described herein. These constructs include the mscRE4 enhancer.

Pan excitatory and/or broad expression in excitatory cortical neurons can be selectively achieved utilizing artificial expression constructs including a promoter; the eHGT_073 h, eHGT_073 m, eHGT_077 h, and/or eHGT_078 m enhancer; and a gene encoding an expression product. In particular embodiments, pan excitatory expression refers to expression in at least four types of cortical excitatory cells with limited to no expression in inhibitory cells and glial cells.

Artificial expression constructs described herein can additionally label other discrete cell types. For example, in addition to L5 PT cells, artificial expression constructs including a promoter, the mscRE4 enhancer, and a gene encoding an expression product can lead to gene expression in subcortical populations in the CEAc, the substantia nigra, compact part (or pars *compacta*, SNc), and (ProS). Similarly, in addition to L5 PT cells, artificial expression constructs including a promoter, a concatenated core of the mscRE4 enhancer, and a gene encoding an expression product can lead to gene expression in the subiculum, CA1 pyramidal neurons, a subset of dentate gyrus granule cells, scattered striatal neurons, and sparse cerebellar Purkinje cells.

As indicated by the proceeding discussion, certain artificial expression constructs disclosed herein include engineered enhancers, for example, concatenated cores of the mscRE4, eHGT_078 h, and eHGT_078 m enhancers and concatemers of the mscRE4 and mscRE16 enhancers. In relation to mscRE4, a functional 155 base pair (bp) core of the mscRE4 enhancer (SEQ ID NO: 29) was concatenated (SEQ ID NO: 30) to minimize the size required to drive gene expression. Despite being a 3× concatemer, SEQ ID NO: 30 is shorter in length than the original mscRE4 enhancer (SEQ ID NO: 28, which includes 555 bp). When used to construct an artificial expression construct, such as an rAAV, such concatemers allow more room for cargo genes linked to the enhancer, which is highly desirable, for example, in gene therapy vectors. For instance, many therapeutic cargo genes are too big to fit in an AAV vector design, so space (length of sequence) is at a premium.

As will be described in more detail throughout the disclosure, particular artificial expression constructs disclosed herein include T502-050, T502-054, vAi34.0, vAi33.2, vAi45.0, vAi1.0, T502-057, T502-059, TG978, TG981, TG988, TG995, TG996, TG999, TG1002, TG1010, TG1011, TG1021, TG1036, TG1037, TG1038, TG1046, TG1047, TG1048, TG1049, TG1050, TG1052, CN1402, CN1457, CN1818, CN1416, CN1452, CN1461, CN1454, CN1456, CN1772, CN1427, CN1466, CN1954, CN1955, CN2137, CN2139, and CN2014.

BRIEF DESCRIPTION OF THE FIGURES

Many of the drawings submitted herein are better understood in color. Applicant considers the color versions of the drawings as part of the original submission and reserves the right to present color images of the drawings in later proceedings.

FIGS. 13A, 13B. TG1037 (vAi22.0) Enhancer mscRE13 (eAi9.0). (13A) Representative epifluorescence image of mscre13-FlpO-WPRE virus induced expression in the brain of a Ai65F reporter mouse (13B) single cell RNA sequencing analysis of tdTomato positive cells isolated from primary visual cortex (V1) of an mscre13-FlpO-WPRE infected Ai65F mouse. The Cell types from top to bottom include: Lamp5 Pich2 Dock5, Lamp5 Lsp1, Vip Chat Htr1f, Sst Tac1 Htr1d, Sst Calb2 Pdlm5, Sst Nr2f2 Necab, Pvalb Sema3e Kank4, Pvalb Rein Itm2a, L2/3 IT VISp Rred, L2/3 IT VISp Adamts2, L2/3 IT VISp Agmat, L2/3 IT ALM Sla, L6 IT VISp Penk Col27a1, L6 IT VISp Penk Fst, L6 IT VISp Col18a1, L5 IT VISp Hsd11b1 Endou, L5 IT VISp Whrn Tox2, L5 IT VISp Col27a1, L5 PT VISp C1qI2 Cdh13, L5 PT VISp Krt80, L6 IT VISp Car3, L4 IT VISp Rspo1, High Intronic VISp L5 Endou, L6 CT VISp Gpr139, L6 CT VISp Ctxn3 Brinp3, L6 CT VISp Ctxn3 Sla, and L6b VISp Mup5.

FIG. 45. Samples were clustered in t-SNE space using the Phenograph implementation of Louvain clustering. To identify the cell types within these clusters, cells from each cluster were pooled, and the number of fragments within 20 kb of each TSS were counted. Then, marker genes for transcriptomic clusters from Tasic et al., Nature 563, 72-78 (2018) were selected, and correlations between TSS accessibility scores and log-transformed gene expression were performed. The scRNA-seq cluster with the highest correlation score was assigned as the identity for each Phenograph cluster, and clusters with the same transcriptomic mapping were combined for downstream analyses. The cluster with the highest correlation score was assigned as the identity for each cluster, and clusters with the same transcriptomic mapping were combined for downstream analyses.

FIG. 47. mscRE locations and cloning primers.

FIGS. 57A-57C. Enhancer-driven recombinase viruses as drivers for cell labeling. (57A) Full-section imaging of a mscRE4-FlpO injection shows labeling throughout L5 of the posterior cortex. Inset region on the right corresponds to the white box on the left. Layer overlays from the Allen Brain Reference Atlas shows labeling restricted primarily to L5. tdTomato+ cells were dissected from the full cortical depth and were collected by FACS for scRNA-seq. Transcriptomic profiles were mapped to reference cell types from Tasic, et al. (2018). 87.5% of cells (28 of 32) mapped to L5 PT cell types. (57B) Full-section imaging of mscRE10-FlpO injection shows labeling in layer 6 (L6) of the cortex. Inset region on the right corresponds to the white box on the left. scRNA-seq of tdTomato+ cells shows that layer 6 corticothalamic (L6 CT) and L6b cell types are the most frequently labeled subclasses of neurons at 75% (n=36 of 48). (57C) Full-section imaging of mscRE16-FlpO injection shows labeling in L5 of the cortex. Inset region on the right corresponds to the white box on the left. scRNA-seq of tdTomato+ cells shows that L5 IT cell types are the most frequently labeled subclass of neurons at 42% (n=20 of 48), but other subclasses are also labeled at this titer (Lamp5, 27%; L6 IT, 6%; L5 PT, 15%).

FIG. 62. Annotated sequence of CN1818

FIG. 70. Enhancer ID, labeled cell types, and validation methods.

FIG. 71. Summary of vector components. Sequence names, associated length, enhancer, promoter, product class, primary product and other components of expression constructs described herein.

FIG. 72. Taxonomy and clustering of selected central nervous system cells.

FIGS. 73A, 73B. (73A) Enhancer targeting validation data. FM stands for fluorescence microscopy. (73B) Cell type specificity of enhancers and vectors described herein. S=subset of types in group; A=all types in group; *=validated in mouse, RNA-seq, and a third modality; ~=validated in mouse, RNA-seq, primate/human, and a fourth modality.

FIG. 79. Sequences supporting the disclosure. Sequences for Enhancer Grik1-enhScnn1a-1 short form (SEQ ID NO: 188), Enhancer Grik1-enhScnn1a-1 (eAi14.0) (SEQ ID NO: 25), Enhancer mscRE1 (eAi1.0) (SEQ ID NO: 26), Enhancer mscRE3 (eAi2.0) (SEQ ID NO: 27), Enhancer mscRE4 (eAi3.0) (SEQ ID NO: 28), Enhancer mscRE4 core (SEQ ID NO: 29), Enhancer 3× mscRE4 core (eAi3.2) (SEQ ID NO: 30), Enhancer mscRE4 (4×) (eAi3.1) (SEQ ID NO: 31), Enhancer mscRE10 (eAi6.0) (SEQ ID NO: 32), Enhancer mscRE11 (eAi7.0) (SEQ ID NO: 33), Enhancer mscRE12 long form (SEQ ID NO: 34), Enhancer mscre12 (eAi8.0) (SEQ ID NO: 35), Enhancer mscRE13 (eAi9.0) (SEQ ID NO: 36), Enhancer mscRE16 (eAi11.0) (SEQ ID NO: 37), Enhancer 4XmscRE16 (eAi11.1) (SEQ ID NO: 38), Enhancer eHGT_078 h (eAi107.0) (SEQ ID NO: 39), Enhancer eHGT_078 h Core (SEQ ID NO: 177), Enhancer eHGT_078 h (3×Core) (eAi129.0) (SEQ ID NO: 40), Enhancer eHGT_058 h (eAi106.0) (SEQ ID NO: 41), Enhancer eHGT_058 m (eAi108.0) (SEQ ID NO: 42), Enhancer eHGT_073 h (eAi111.0) (SEQ ID NO: 43), Enhancer eHGT_073 m (eAi112.0) (SEQ ID NO: 44), Enhancer eHGT_075 h (eAi113.0) (SEQ ID NO: 45), Enhancer eHGT_077 h (eAi114.0) (SEQ ID NO: 46), Enhancer eHGT_254 h (eAi127.0) (SEQ ID NO: 47), Enhancer eHGT_078 m (eAi128.0) (SEQ ID NO: 48), Enhancer eHGT_078 m Core (SEQ ID NO: 178), Enhancer eHGT_078 m (3×Core) (eAi130.0) (SEQ ID NO: 49), Enhancer eHGT_439 m (eAi131.0) (SEQ ID NO: 50), Enhancer eHGT_440 h (eAi132.0) (SEQ ID NO: 51), Beta-globin minimal promoter (SEQ ID NO: 52), minCMV (SEQ ID NO: 53), mutated minCMV promoter (SEQ ID NO: 54), Hsp68 minimal Promoter (SEQ ID NO: 55), SYFP2 (SEQ ID NO: 56), EGFP (SEQ ID NO: 57), Optimized Flp recombinase (SEQ ID NO: 58), Improved Cre recombinase (SEQ ID NO: 59), WPRE3 (SEQ ID NO: 60), BGHpA (SEQ ID NO: 61), HA tag (SEQ ID NO: 62), HA tag (SEQ ID NO: 63), P2A (SEQ ID NO: 64), T2A (SEQ ID NO: 65), E2A (SEQ ID NO: 66), F2A (SEQ ID NO: 67), tet-Transactivator (SEQ ID NO: 68), PHP.eB capsid (SEQ ID NO: 69), AAV9 VP1 capsid (SEQ ID NO: 70), Plasmid backbone 1 (SEQ ID NO: 71), Plasmid backbone 2 (SEQ ID NO: 72), T502-050 (vAi33.0) (SEQ ID NO: 73), T502-054 (vAi33.1) (SEQ ID NO: 179), T502-057 (vAi3.0) (SEQ ID NO: 74), T502-059 (vAi2.0) (SEQ ID NO: 75), vAi1.0 (SEQ ID NO: 76), vAi33.2 (TG1114) (SEQ ID NO: 77), vAi34.0 (TG1108) (SEQ ID NO: 78), vAi45.0 (TG1109) (SEQ ID NO: 79), TG975 (vAi4.0) (SEQ ID NO: 180), TG978 (vAi4.1) (SEQ ID NO: 80), TG979 (vAi4.2) (SEQ ID NO: 181), TG981 (vAi5.0) (SEQ ID NO: 81), TG982 (vAi6.0) (SEQ ID NO: 182), TG987 (vAi7.0) (SEQ ID NO: 183), TG988 (vAi7.1) (SEQ ID NO: 82), TG995 (vAi15.0) (SEQ ID NO: 83), TG996 (vAi19.0) (SEQ ID NO: 84), TG997(vAi20.0) (SEQ ID NO: 184), TG999 (vAi21.0) (SEQ ID NO: 85), TG1002 (vAi26.0) (SEQ ID NO: 86), TG1009 (vAi8.0dgCre) (SEQ ID NO: 185), TG1010 (vAi6.1) (SEQ ID NO: 87), TG1011 (vAi7.2) (SEQ ID NO: 88), TG1021 (vAi8.0Cre) (SEQ ID NO: 89), TG1022 (vAi9.0) (SEQ ID NO: 186), TG1036 (vAi16.0) (SEQ ID NO: 90), TG1037 (vAi22.0) (SEQ ID NO: 91), TG1038 (vAi27.0) (SEQ ID NO: 92), TG1045 (vAi17.0) (SEQ ID NO: 187), TG1046 (vAi23.0) (SEQ ID NO: 93), TG1047 (vAi28.0) (SEQ ID NO: 94), TG1048 (vAi18.0) (SEQ ID NO: 95), TG1049 (vAi24.0) (SEQ ID NO: 96), TG1050 (vAi29.0) (SEQ ID NO: 97), TG1052 (vAi10.0) (SEQ ID NO: 98), CN1402 (vAi106.0) (SEQ ID NO: 99), CN1416 (vAi108.0) (SEQ ID NO: 100), CN1427 (vAi130.0) (SEQ ID NO: 101), CN1452 (vAi111.0) (SEQ ID NO: 102), CN1454 (vAi113.0) (SEQ ID NO: 103), CN1456 (vAi114.0) (SEQ ID NO: 104), CN1457 (vAi107.0) (SEQ ID NO: 105), CN1461 (vAi112.0) (SEQ ID NO: 106), CN1466 (vAi131.0) (SEQ ID NO: 107), CN1772 (vAi127.0) (SEQ ID NO: 108), CN1818 (vAi128.0) (SEQ ID NO: 109), CN1954 (vAi132.0) (SEQ ID NO: 110), CN1955 (vAi133.0) (SEQ ID NO: 111), CN2014 (vAi129.0) (SEQ ID NO: 112), CN2137 (vAi135.0) (SEQ ID NO: 113), CN2139 (vAi134.0) (SEQ ID NO: 114), Myosin light chain kinase, Green fluorescent protein, Calmodulin chimera (SEQ ID NO: 115), Genetically-encoded green calcium indicator NTnC (SEQ ID NO: 116), Calcium indicator TN-XXL (SEQ ID NO: 117), BRET-based auto-luminescent calcium indicator (SEQ ID NO: 118), Calcium indicator protein OeNL(Ca2+)-18u (SEQ ID NO: 119), GCaMP6m (SEQ ID NO: 120), GCaMP6s (SEQ ID NO: 121), GCaMP6f (SEQ ID NO: 122), Channelopsin 1 (SEQ ID NOs: 123 and 124), Channelrhodopsin-2 (SEQ ID NOs: 125 and 126), CRISPR-associated protein (Cas) (SEQ ID NO: 127), Cas9 (SEQ ID NO: 128), CRISPR-associated endonuclease Cpf1 (SEQ ID NO: 129), Ribonuclease 4 or Ribonuclease L (SEQ ID NO:

Figure 1A:
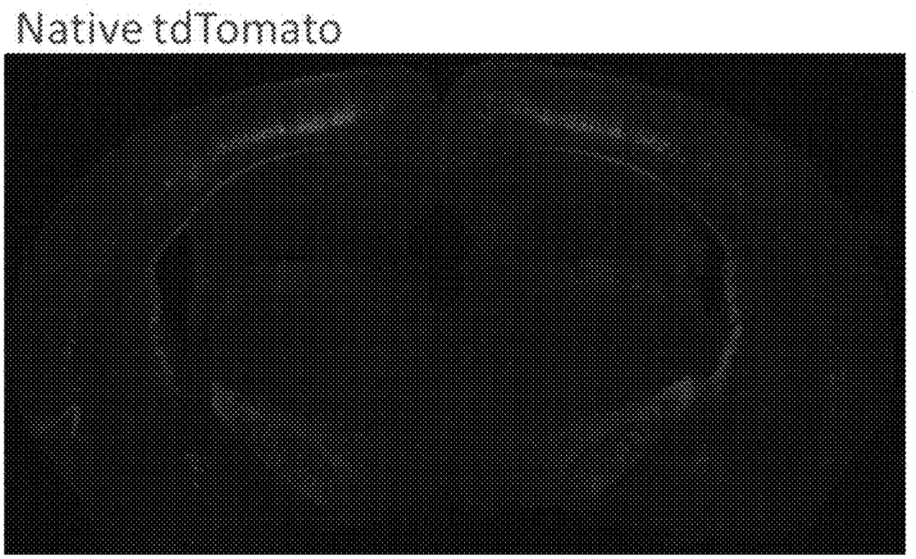
FIGS. 1A-1C. TG978 (vAi4.1). Enhancer mscRE4 (eAi3.0). (1A, 1B) Representative epifluorescence images of mscre4-FlpO-WPRE virus induced expression in the brain of a Ai65F reporter mouse (IC) single cell RNA sequencing analysis of tdTomato-positive cells isolated from primary visual cortex (V1) of an mscre4-FlpO infected Ai65F mouse. L2/3, layer 2/3; L5, layer 5; wm, white matter.
Figure 1B:
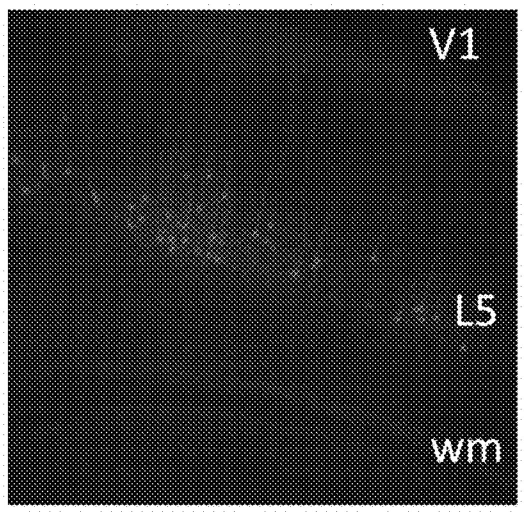
Figure 1C:
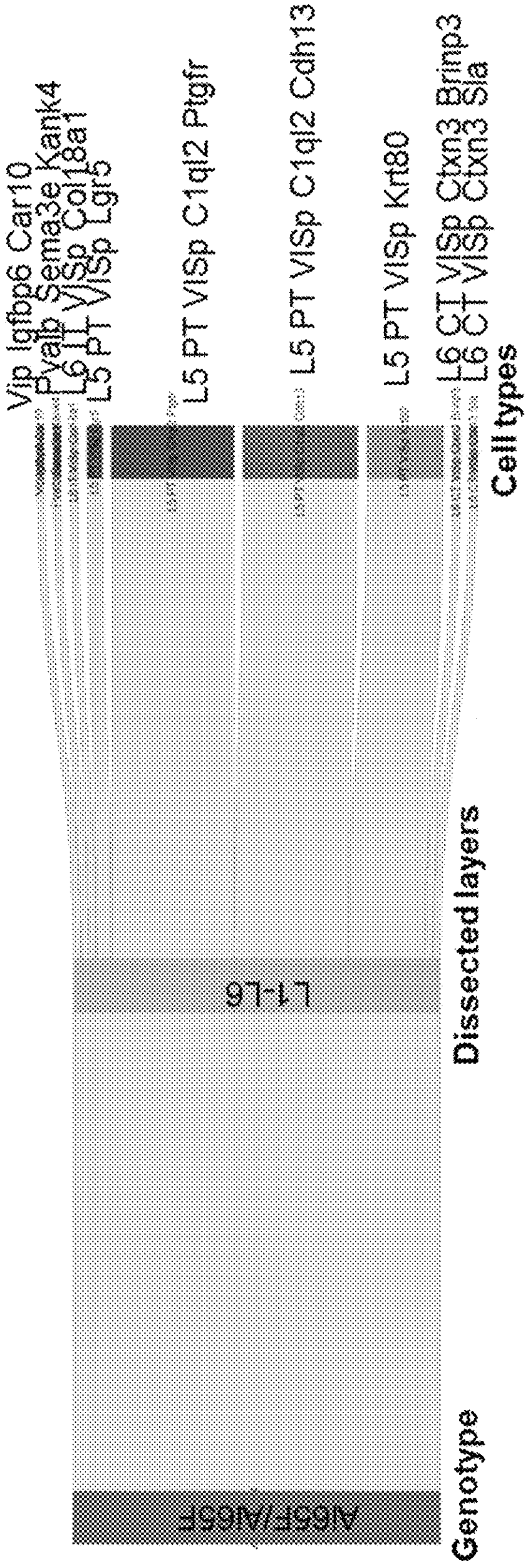
Figure 2:
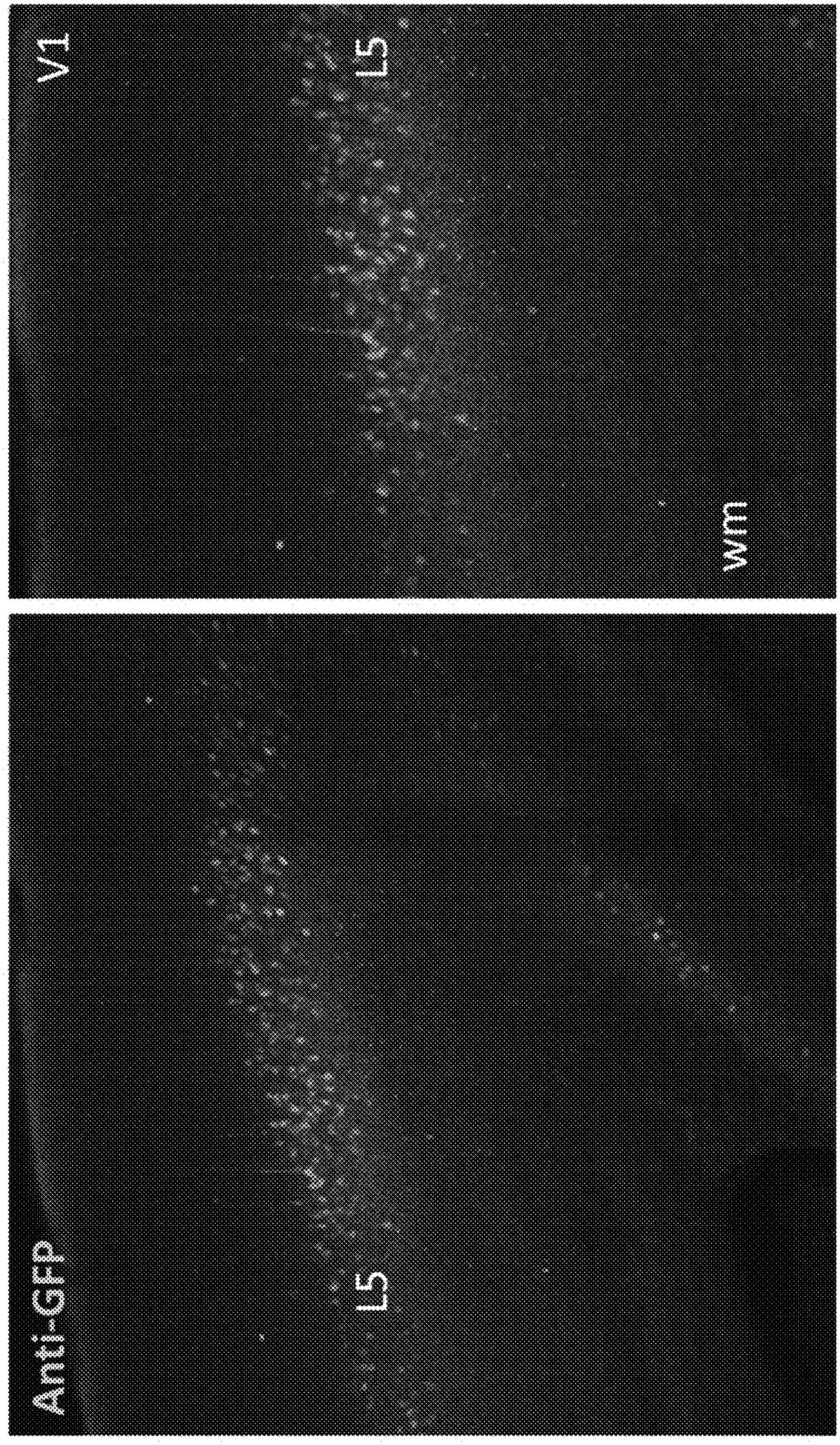
FIG. 2. TG981 (vAi5.0) Enhancer mscRE4 (eAi3.0). Representative epifluorescence images of mscre4-EGFP-WPRE virus expression in the brain of a wild type mouse. Brain sections were stained with an anti-GFP antibody to visualize GFP fluorescence.
Figure 3A:
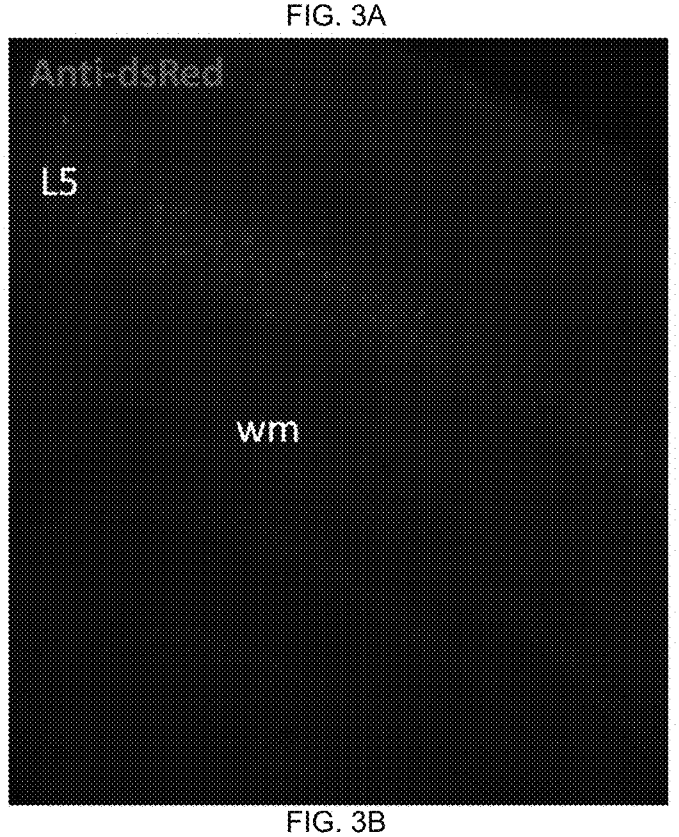
FIGS. 3A, 3B. TG988 (vAi7.1) Enhancer mscRE4 (eAi3.0). (3A) Representative epifluorescence images of mscre4-tTA2 virus induced expression in the brain of a Ai63 reporter mouse. Brain sections were stained with an anti-dsred antibody to reveal tdTomato fluorescence. (3B) The mscre4-tTA2 virus was directly injected into the brain of an Ai63 mouse and native tdTomato fluorescence was imaged within primary visual cortex (V1 or VISp). Note that imaging parameters between the two images may be different. L2/3, layer 2/3; L5, layer 5; wm, white matter.
Figure 3B:
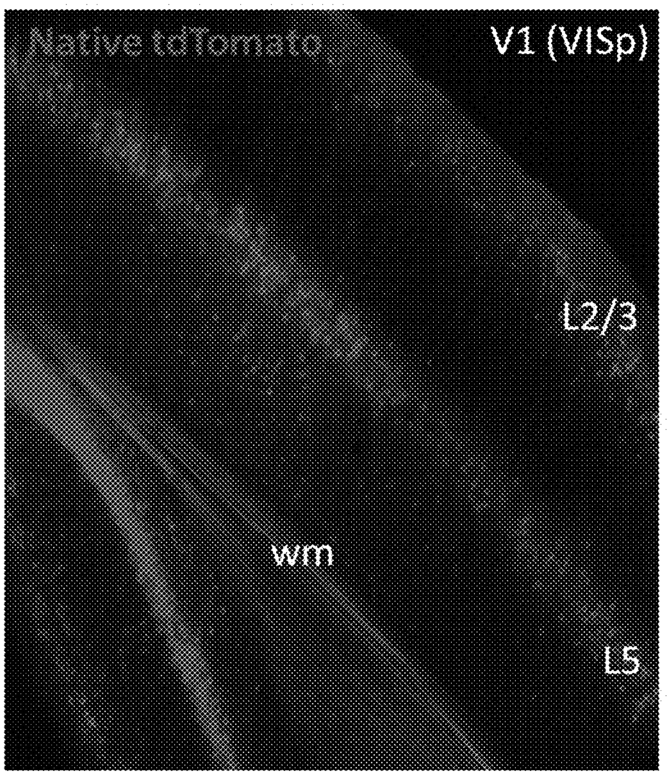
Figure 4A:
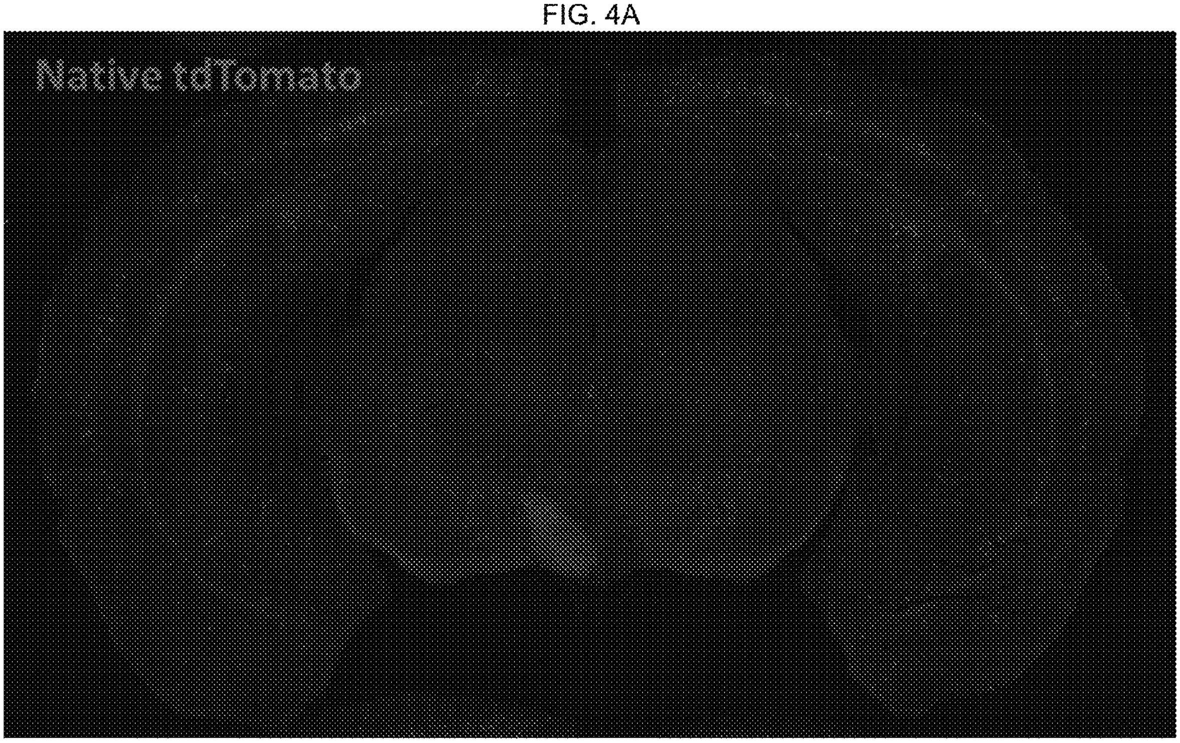
FIGS. 4A, 4B. TG1010 (vAi6.1) Enhancer mscRE4 (eAi3.0). Representative epifluorescence images of mscre4-iCre virus induced expression in the brain of a Ai14 reporter mouse. L5, layer 5; L6, layer 6; wm, white matter.
Figure 4B:
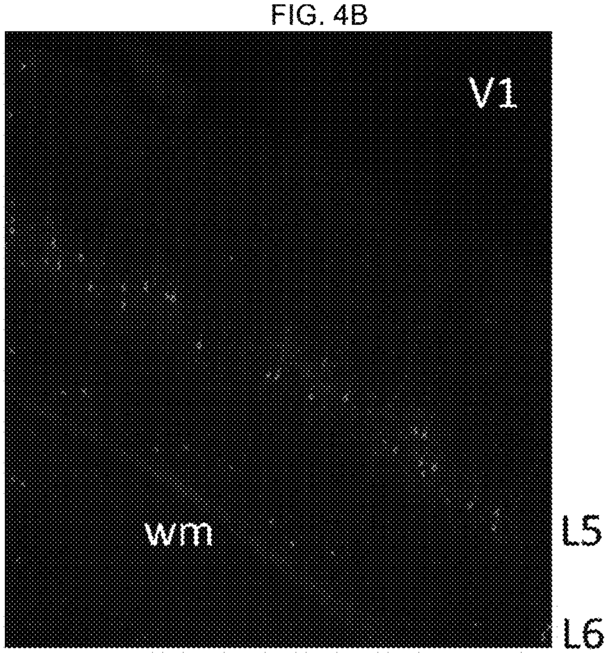
Figure 5A:
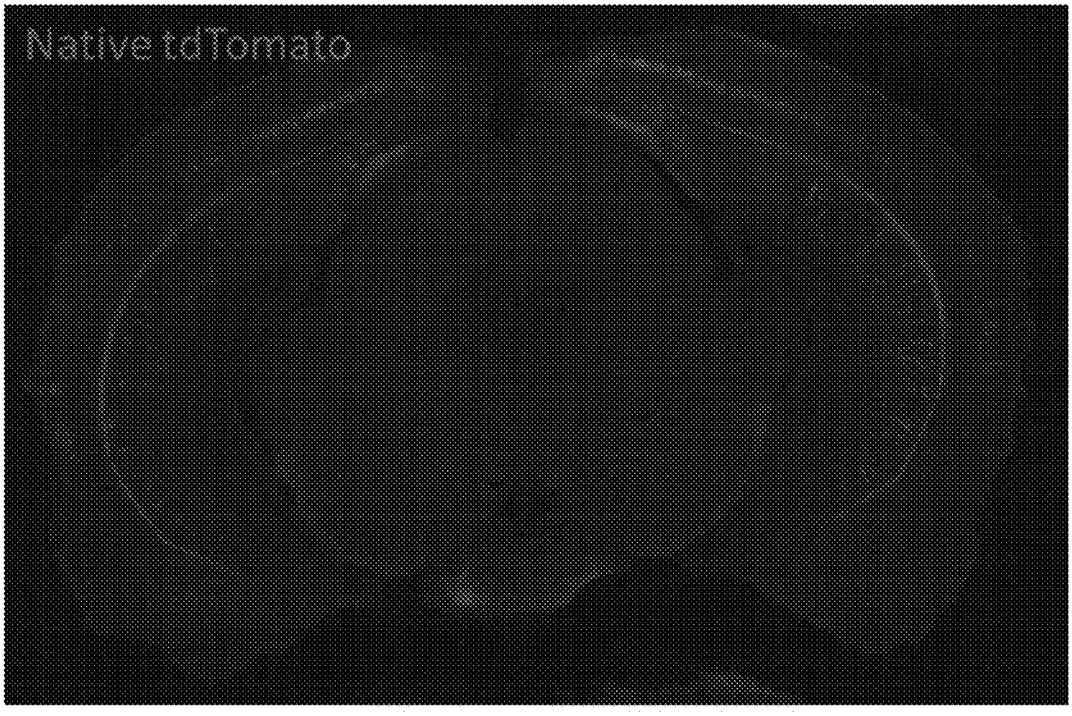
FIGS. 5A, 5B. TG1011 (vAi7.2) Enhancer mscRE4 (eAi3.0). Representative epifluorescence images of mscre4-tTA2 virus induced expression in the brain of a Ai63 reporter mouse.
Figure 5B:
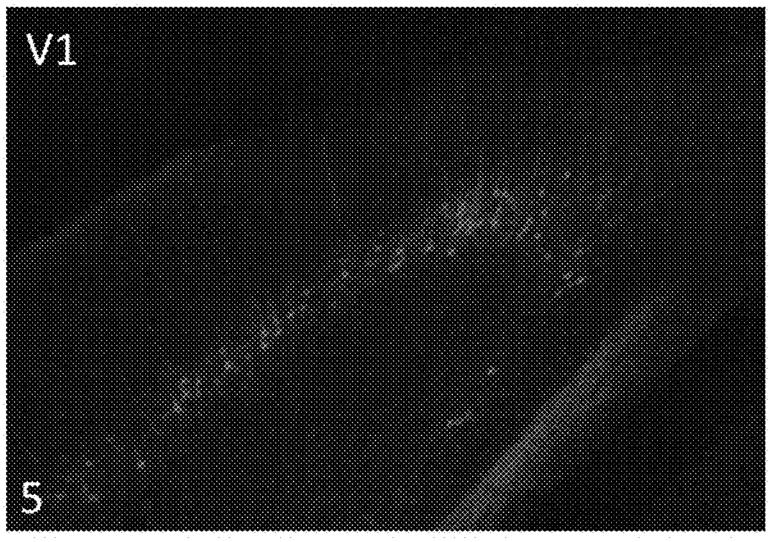
Figure 6:
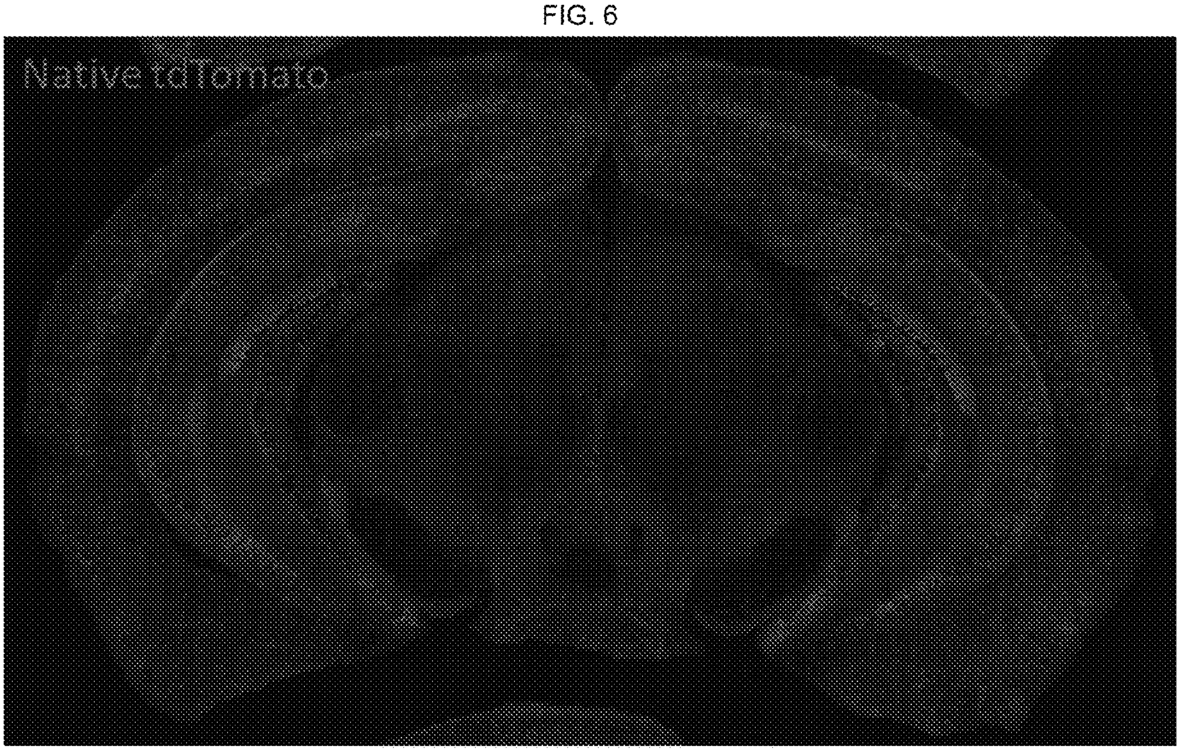
FIG. 6 TG1021 (vAi8.0Cre) Enhancer mscRE4 (eAi3.0). Representative epifluorescence image of mscre4-Cre-WPRE virus induced expression in the brain of a Ai14 reporter mouse.
Figure 7:
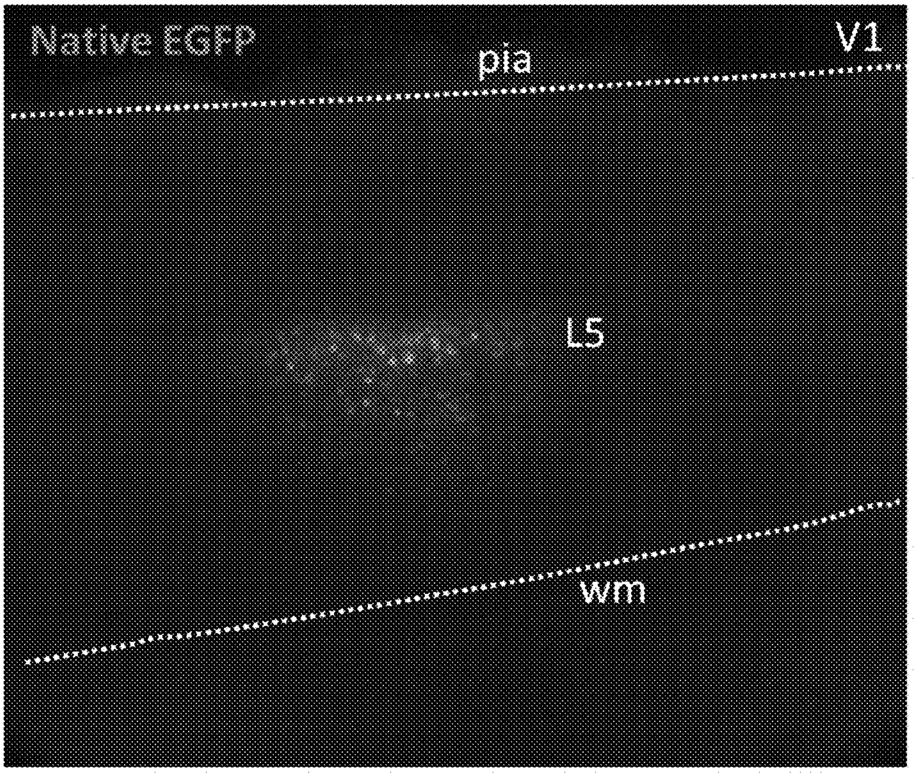
FIG. 7. TG1052 (vAi10.0) Enhancer 4XmscRE16 (eAi11.1). Representative epifluorescence image of 4Xmscre16-EGFP-WPRE virus expression in the brain of a wild type mouse. Virus was delivered by stereotaxic injection directly into the brain.
Figure 8A:
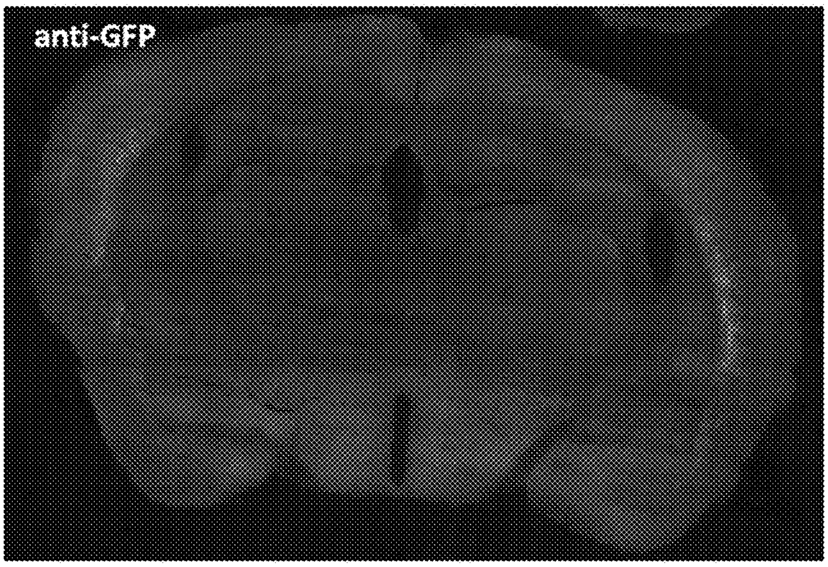
FIGS. 8A, 8B. TG995 (vAi15.0) Enhancer mscRE10 (eAi6.0). Representative epifluorescence images of mscre10-EGFP-WPRE virus expression in the brain of a wild-type mouse.
Figure 8B:
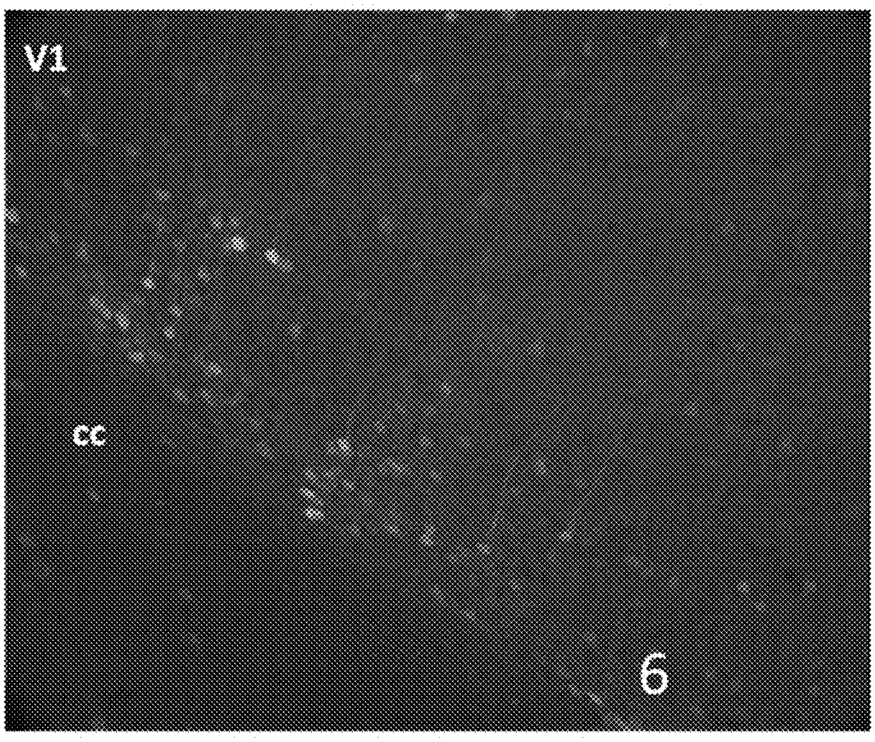
Figure 9A:
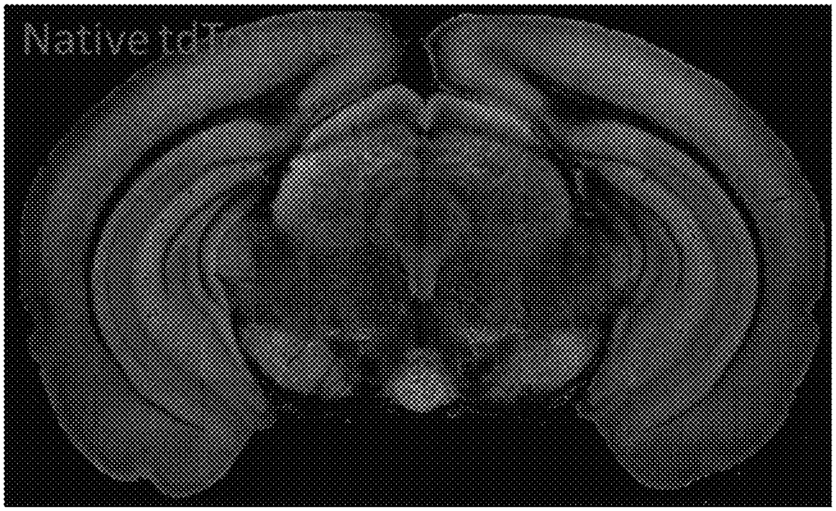
FIGS. 9A-9C. TG1036 (vAi16.0) Enhancer mscRE10 (eAi6.0). (9A, 9B) Representative epifluorescence images of mscre10-FlpO-WPRE virus induced expression in the brain of a Ai65F reporter mouse (9C) single cell RNA sequencing analysis of tdTomato positive cells isolated from primary visual cortex (V1) of an mscre10-FlpO-WPRE infected Ai65F mouse FIGS. 10A, 10B. TG1048 (vAi18.0) Enhancer mscRE10 (eAi6.0). Representative epifluorescence images of mscre10-tTA2-WPRE virus induced expression in the brain of a Ai63 reporter mouse.
Figure 9B:
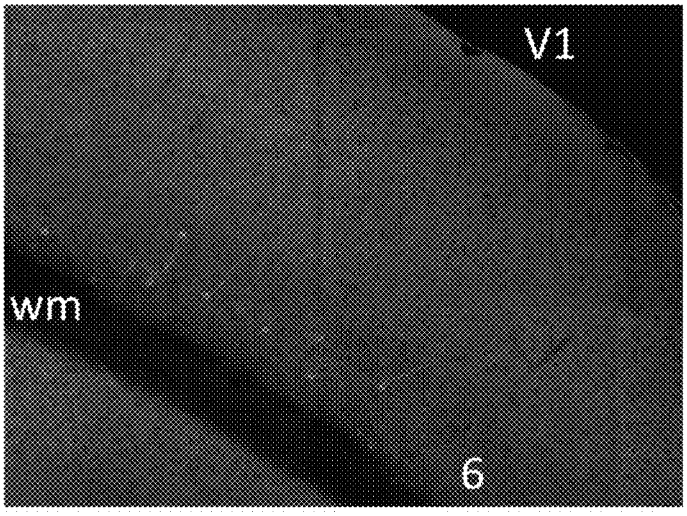
Figure 9C:
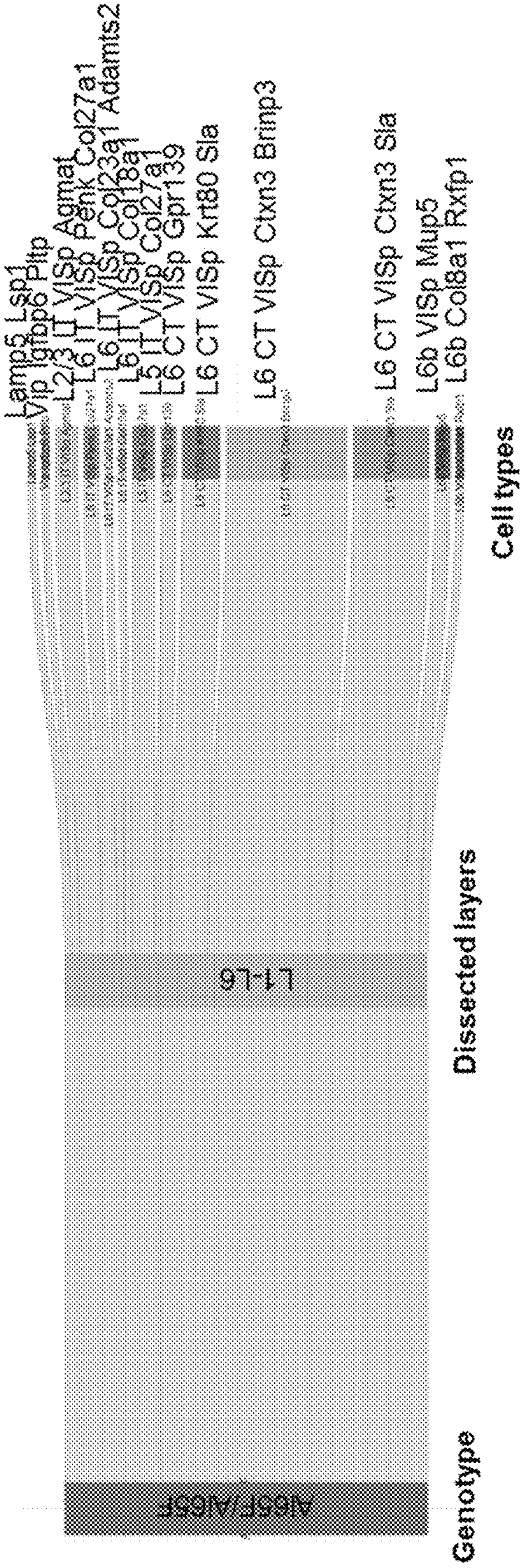
Figure 10A:
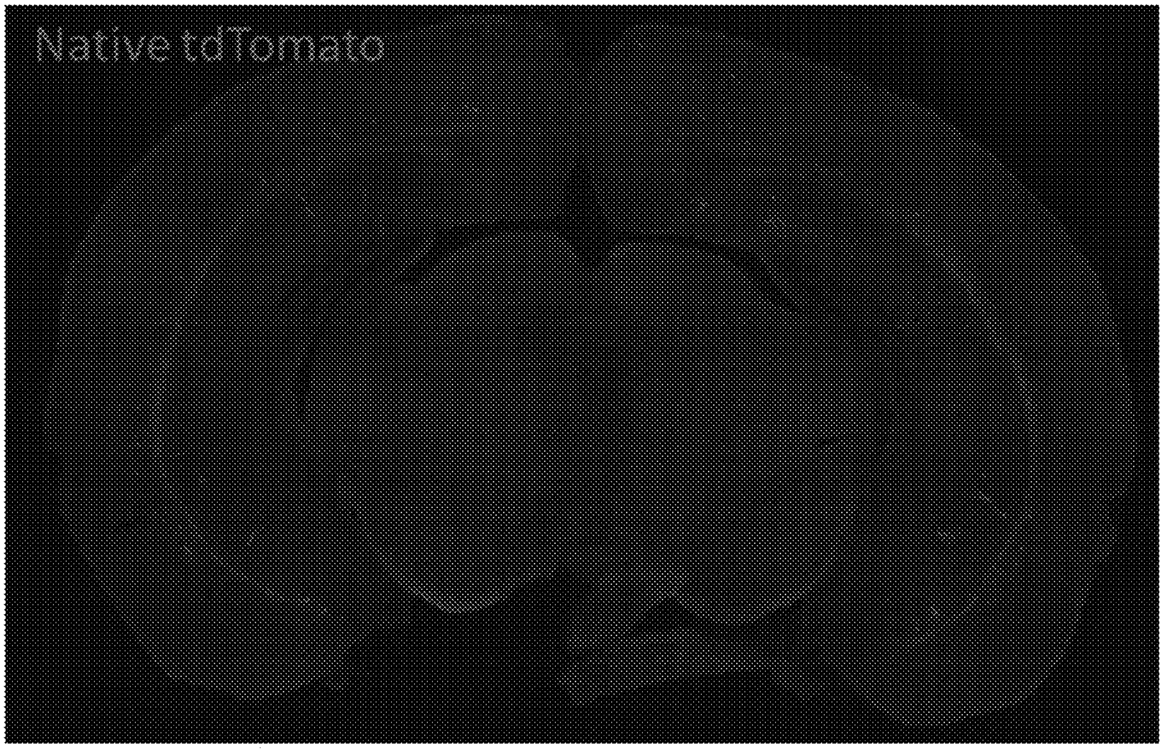
Figure 10B:
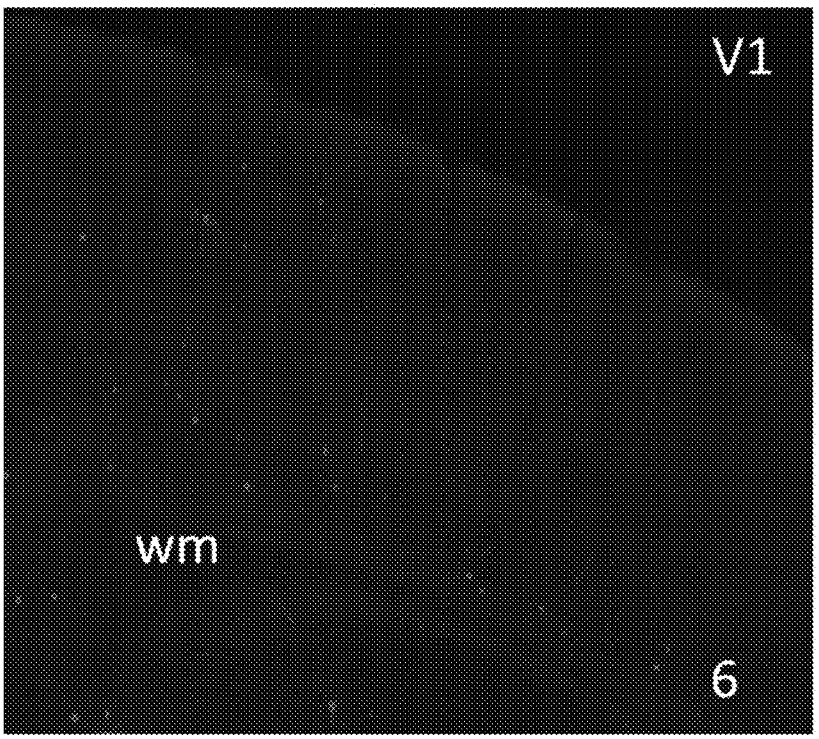
Figure 11:
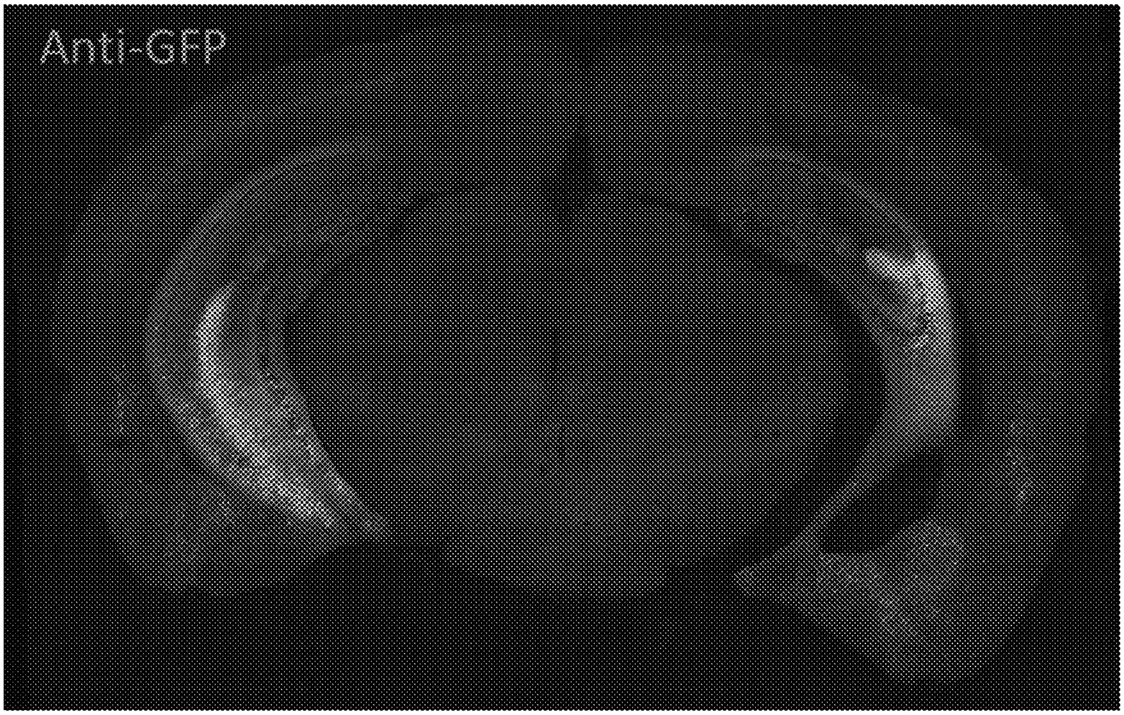
FIG. 11. TG996 (vAi19.0) Enhancer mscRE11 (eAi7.0). Representative epifluorescence images of mscre11-EGFP-WPRE virus in the brain of a wild-type mouse. Brain sections were stained with an anti-GFP antibody to reveal GFP fluorescence.
Figure 12A:
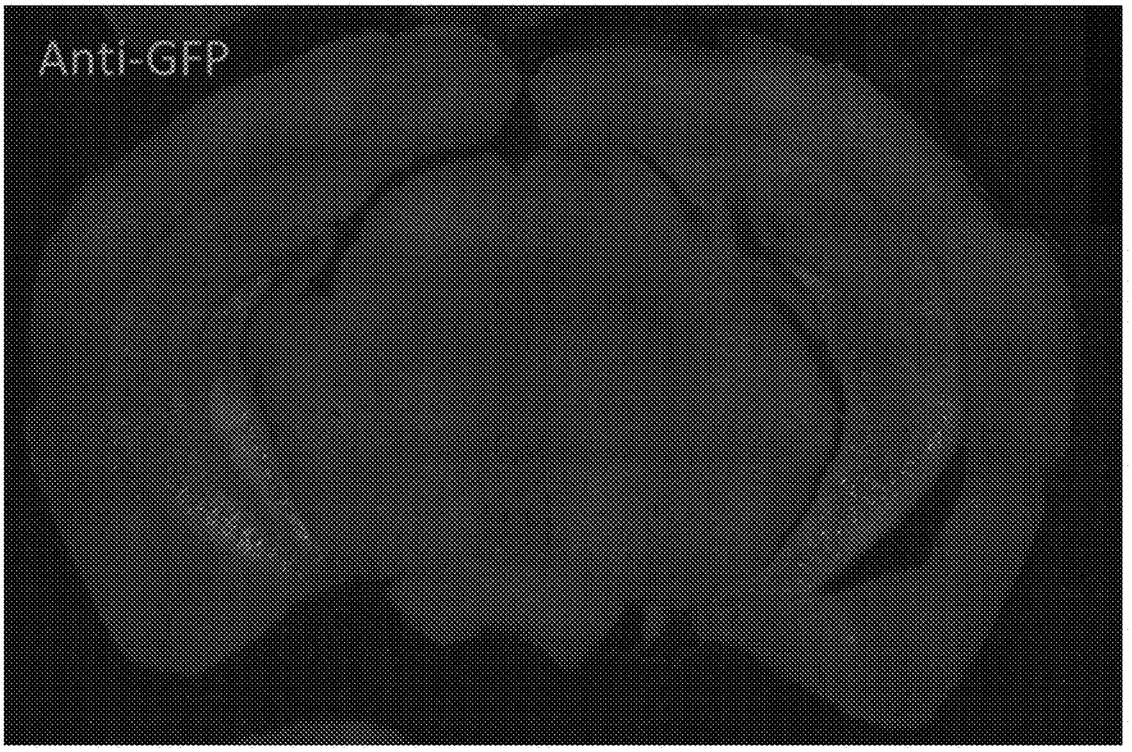
FIGS. 12A, 12B. TG999 (vAi21.0) Enhancer mscRE13 (eAi9.0). Representative epifluorescence images of mscre13-EGFP-WPRE virus in the brain of a wild-type mouse. Brain sections were stained with an anti-GFP antibody to reveal GFP fluorescence.
Figure 12B:
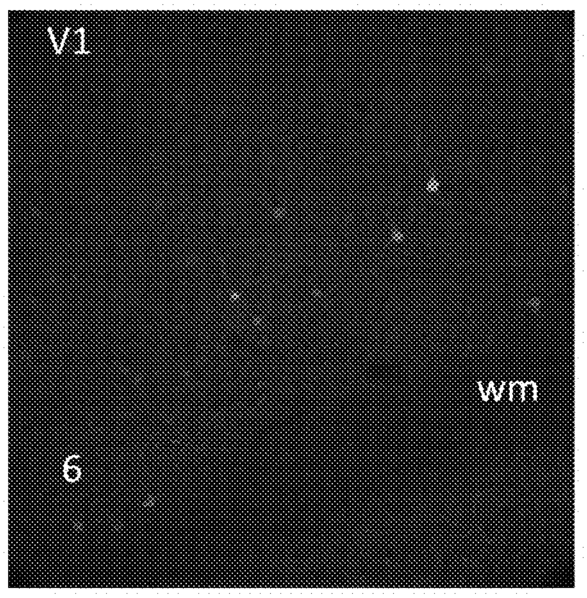
Figure 13A:
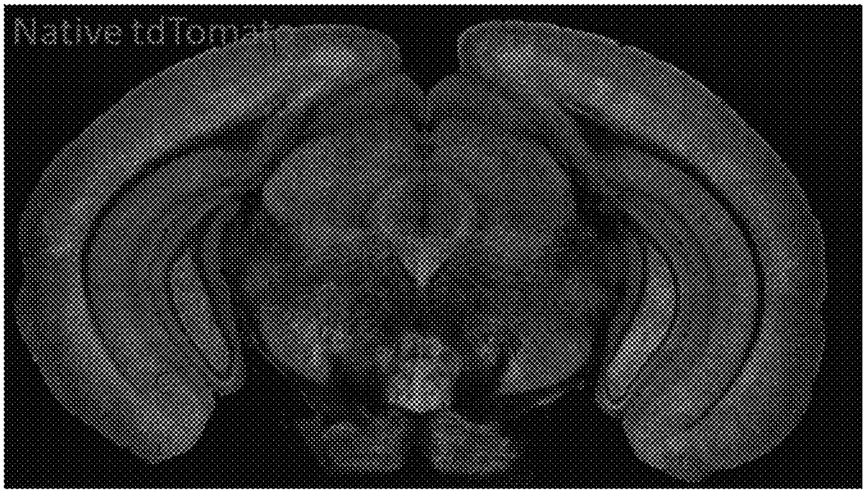
Figure 14:
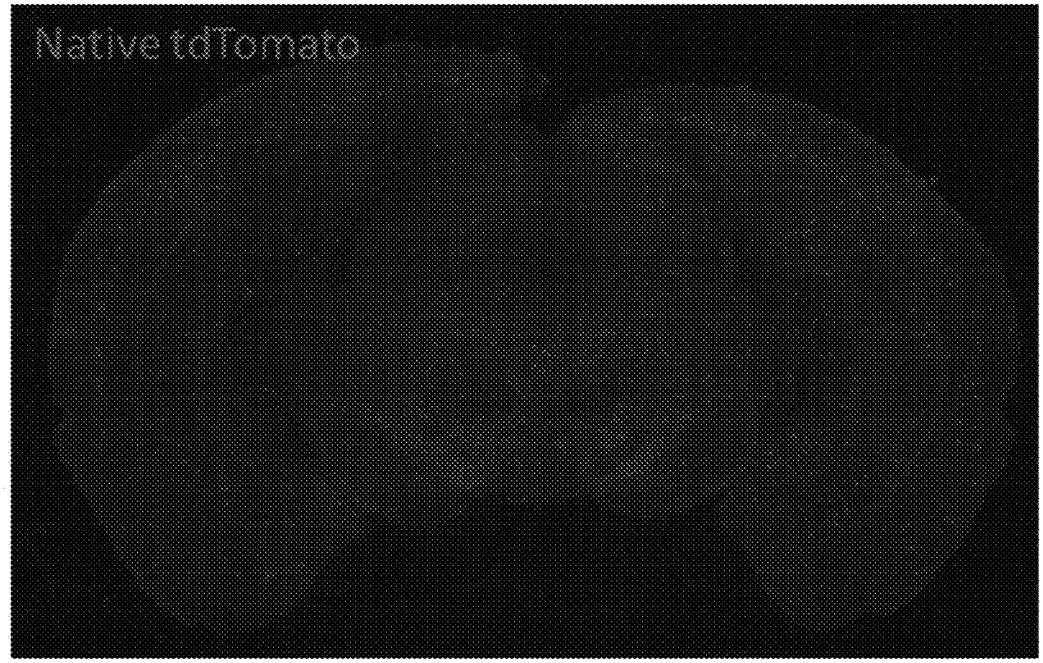
FIG. 14. TG1046 (vAi23.0) Enhancer mscRE13 (eAi9.0). Representative epifluorescence image of mscre13-iCre-WPRE virus induced expression in the brain of a Ai14 reporter mouse.
Figure 15:
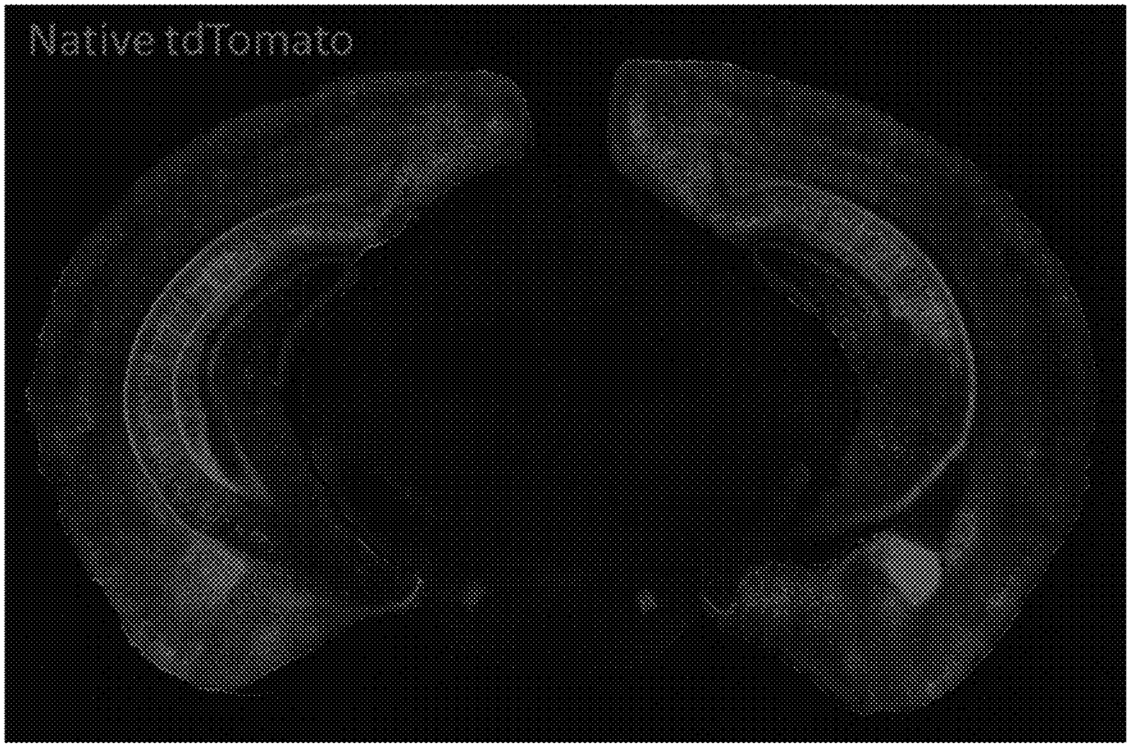
FIG. 15. TG1049 (vAi24.0) Enhancer mscRE13 (eAi9.0). Representative epifluorescence image of mscre13-tTA2-WPRE virus induced expression in the brain of a Ai63 reporter mouse.
Figure 16A:
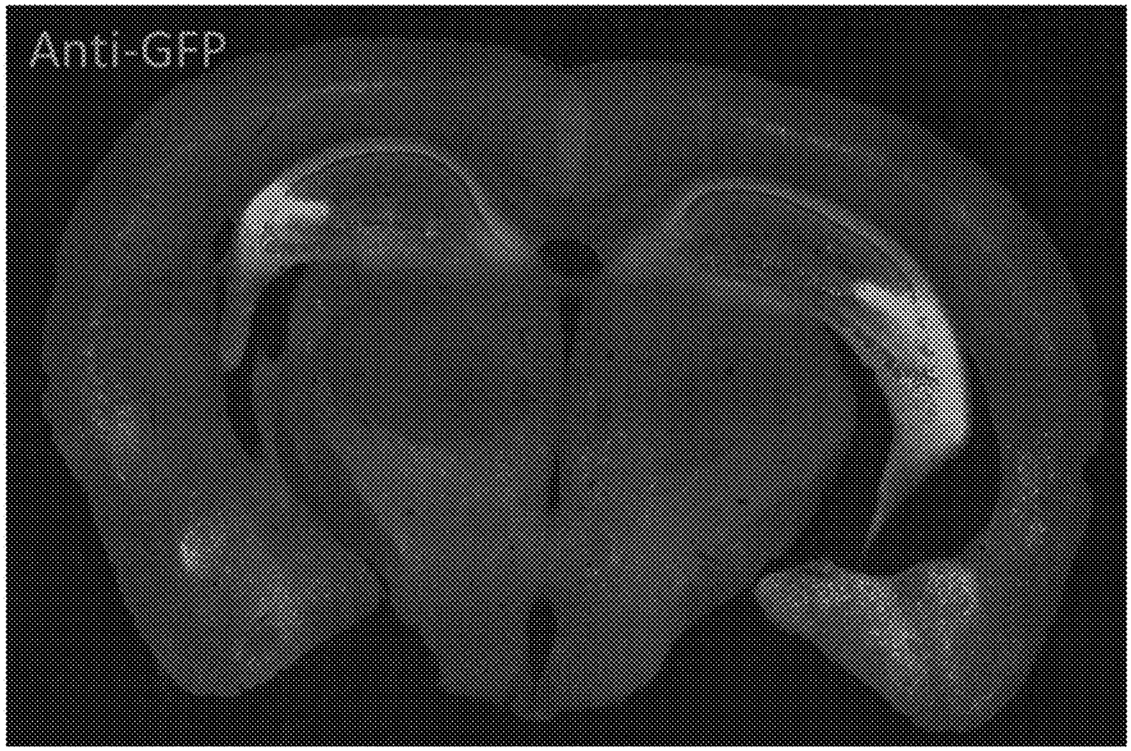
FIGS. 16A, 16B. TG1002 (vAi26.0) Enhancer mscRE16 (eAi11.0). Representative epifluorescence images of mscre16-EGFP-WPRE virus in the brain of a wild-type mouse. Brain sections were stained with an anti-GFP antibody to reveal GFP fluorescence.
Figure 16B:
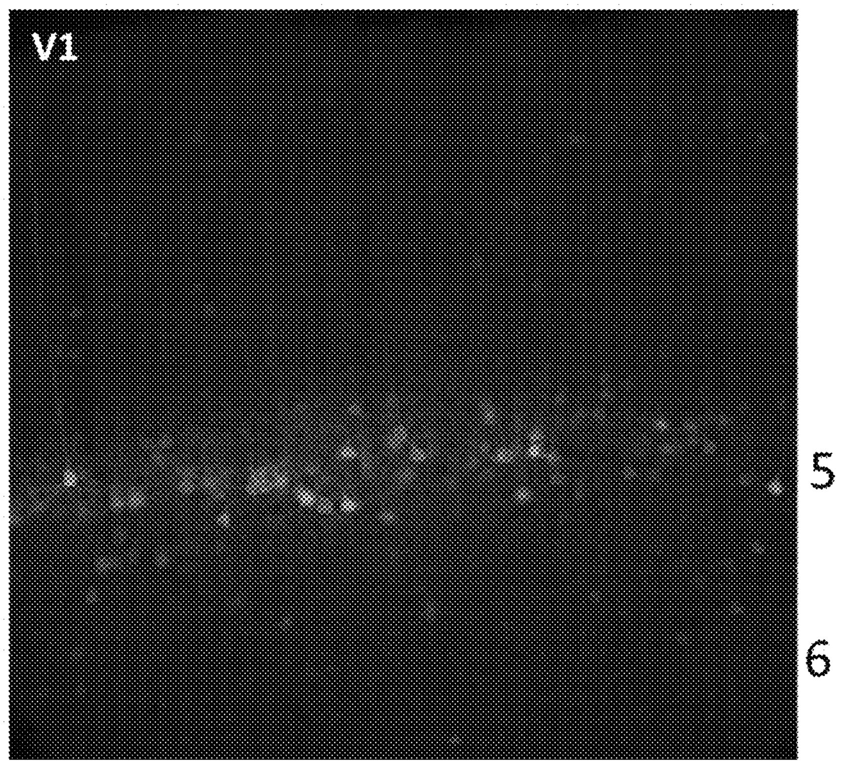
Figure 17A:
FIGS. 17A-17C. TG1038 (vAi27.0) Enhancer mscRE16 (eAi11.0). (17A, 17B) Representative epifluorescence images of mscre16-FlpO-WPRE virus induced expression in the brain of a Ai65F reporter mouse (17C) single cell RNA sequencing analysis of tdTomato positive cells isolated from primary visual cortex (V1) of an mscre16-FlpO-WPRE infected Ai65F mouse. The Cell types from top to bottom include: Lamp5 Pich2 Dock5, Lamp5 Lsp1, Sst Mme Fam114a1, L2/3 IT VISp Agmat, L6 IT VISp Agmat, L6 IT VISp Penk Fst, L6 IT VISp Col23a1, Adamts2, L6 IT VISp Col18a1, L5 IT VISp Hsd11b1 Endou, L5 IT VISp Whrn Tox2, L5 IT VISp Batf3, L5 IT VISp Col6a1 Fezf2, L5 IT ALM Tmem163 Arhgap25, L5 IT ALM Cpa6 Gpr88, L5 PT VISp C1qqI2 Cdh13, L5 PT VISp Krt80, High Intronic VISp L5 Endou, L6 CT VISp Ctxn3 Brinp3, L6CT VISp Ctxn3 Sla, and LowAqp4.
Figure 17B:
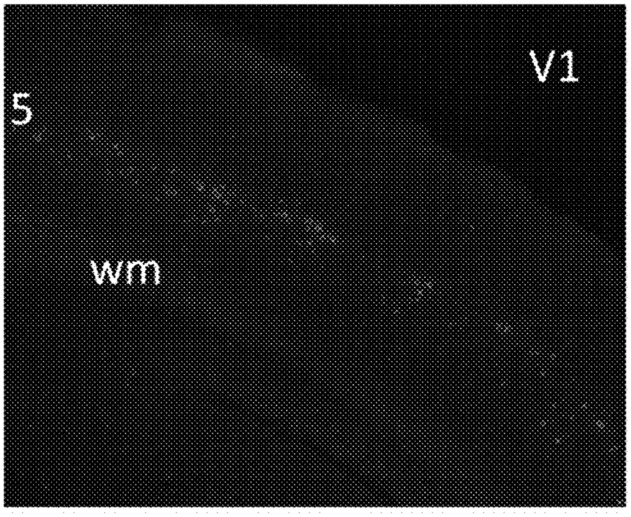
Figure 17C:
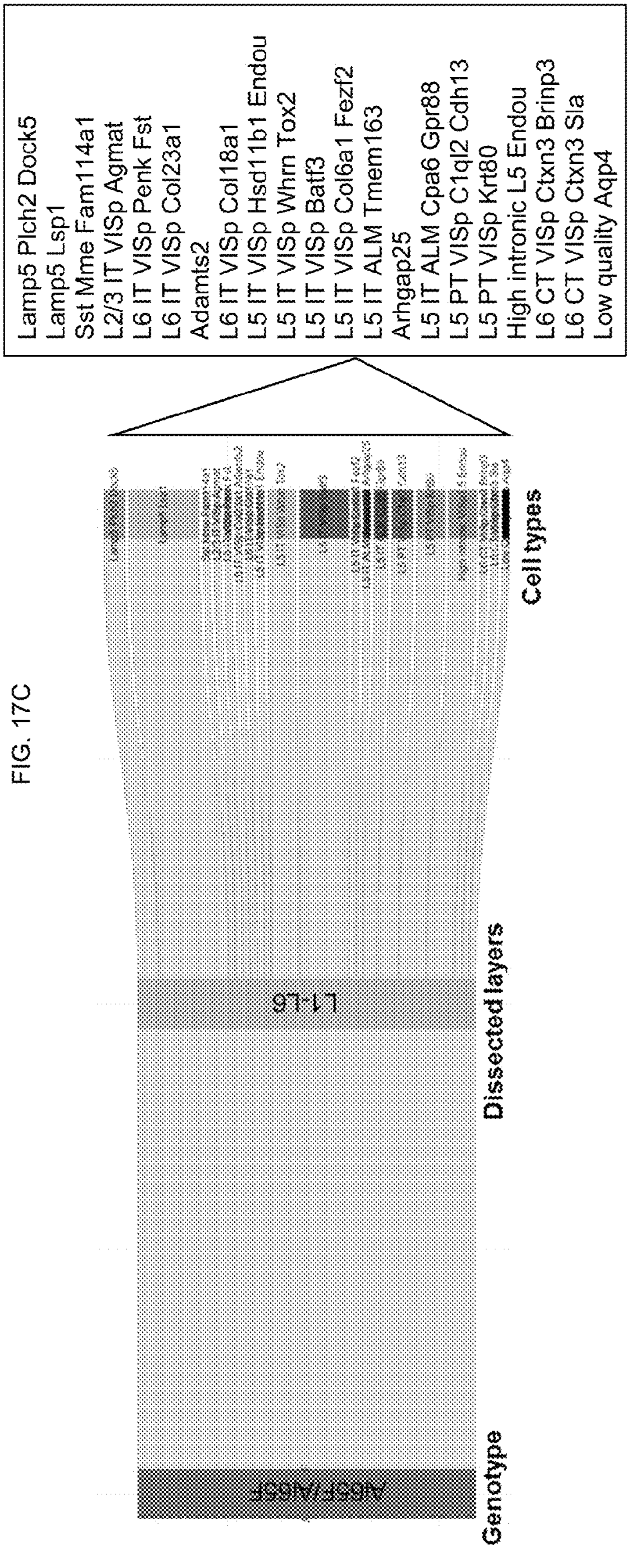
Figure 18:
FIG. 18. TG1047 (vAi28.0) Enhancer (mscRE16 (eAi11.0). Representative epifluorescence image of mscre16-iCre-WPRE virus induced expression in the brain of a Ai14 reporter mouse.
Figure 19A:
FIGS. 19A, 19B. TG1050 (vAi29.0) Enhancer mscRE16 (eAi11.0). Representative epifluorescence images of mscre16-tTA2-WPRE virus induced expression in the brain of a Ai63 reporter mouse.
Figure 19B:
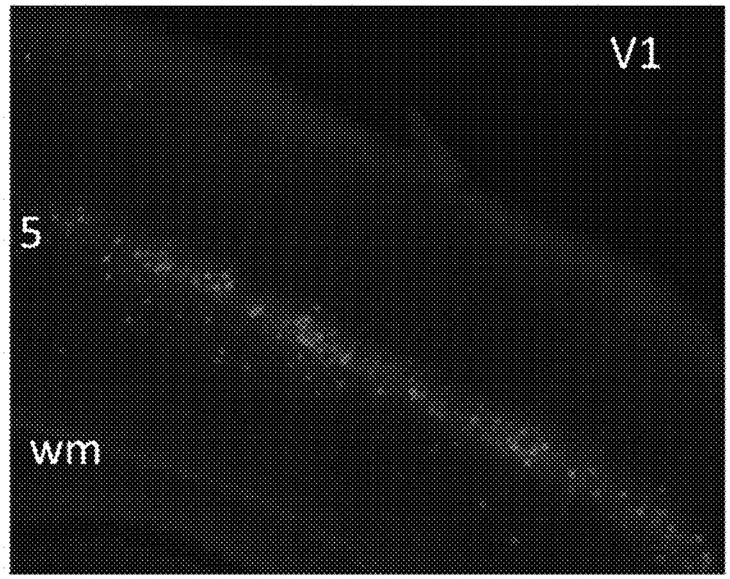
Figure 20:
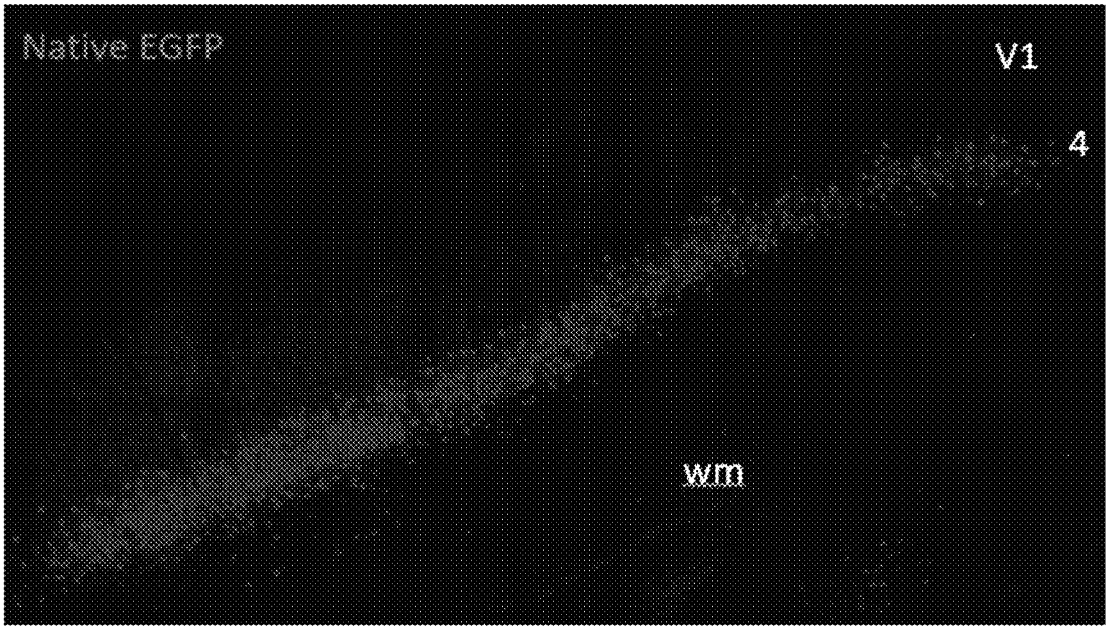
FIG. 20. TG1149/(T502-050; vAi33.0) Enhancer Grik1-enhScnn1a-2 (eAi14.0). Representative confocal image of Hsp68-EGFP-WPRE-Grik1-enhScnn1a-2 virus induced expression in the brain of a wild type mouse.
Figure 21A:
FIGS. 21A, 21B. TG1108 (vAi34.0) Enhancer Scnn1a (Grik1) (eAi14.0). Representative confocal images of Scnn1a(Grik1)-FlpO-WPRE virus induced expression in the brain of a Ai65 reporter mouse.
Figure 21B:
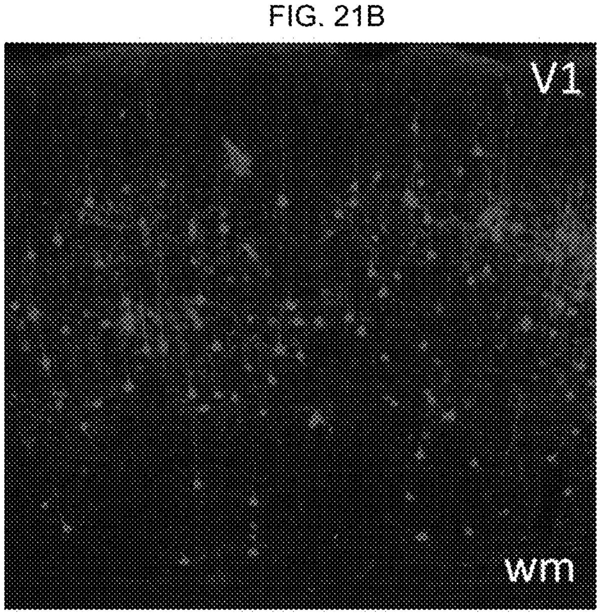
Figure 22A:
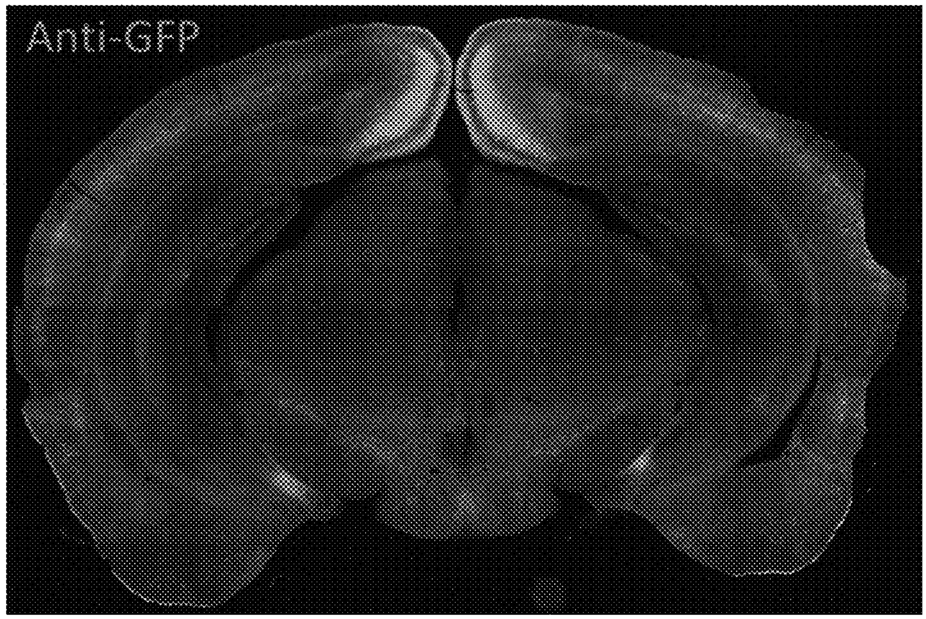
FIGS. 22A, 22B. TG1114 (vAi33.2) Enhancer Scnn1a (Grik1) (eAi14.0). Representative epifluorescence images of Scnn1a(Grik1)-EGFP-WPRE virus in the brain of a wild-type mouse. Brain sections were stained with an anti-GFP antibody to reveal GFP fluorescence.
Figure 22B:
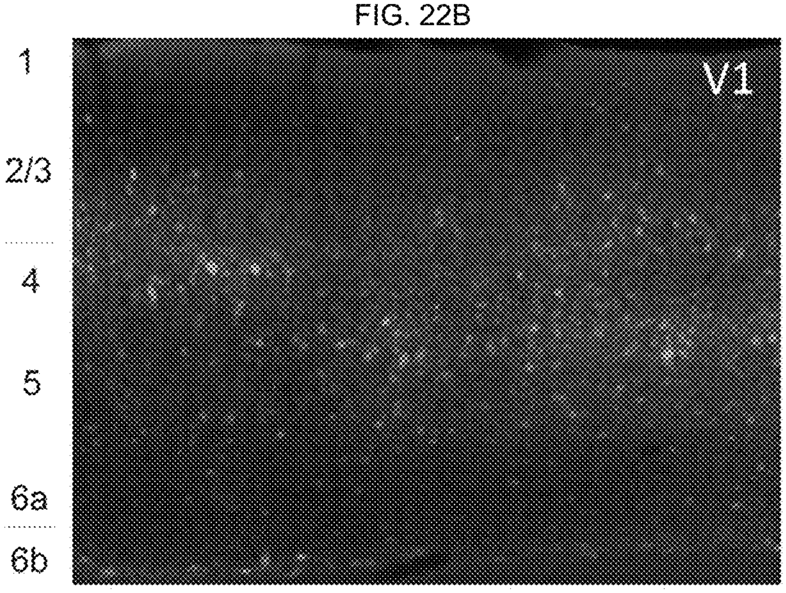
Figure 23:
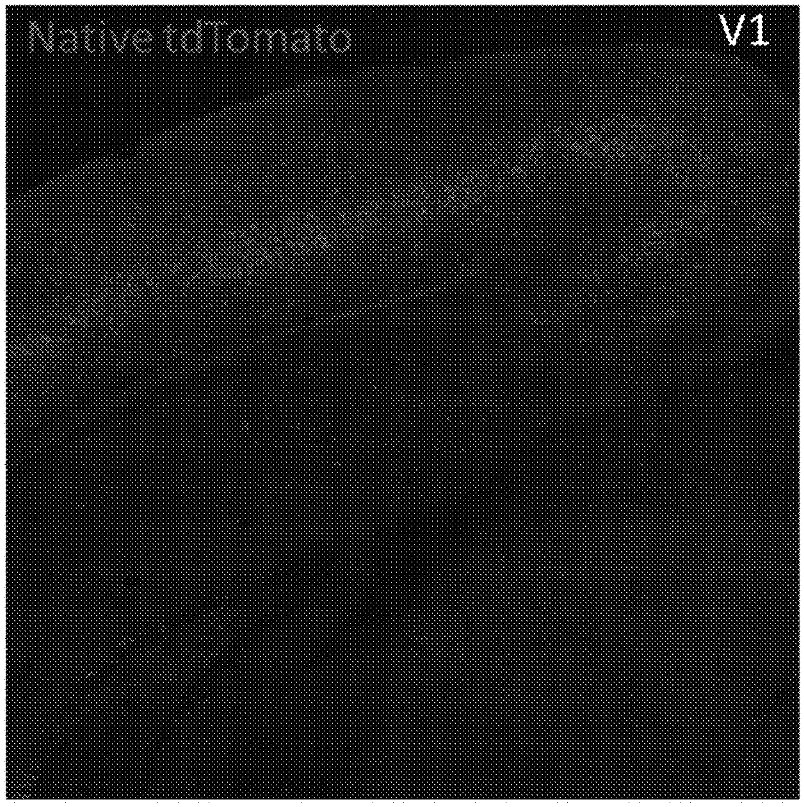
FIG. 23. TG1109 (vAi45.0) Enhancer mscRE12 (eAi8.0). Representative epifluorescence image of mscre12-FlpO-WPRE virus induced expression in the brain of a Ai65F reporter mouse.
Figure 24A:
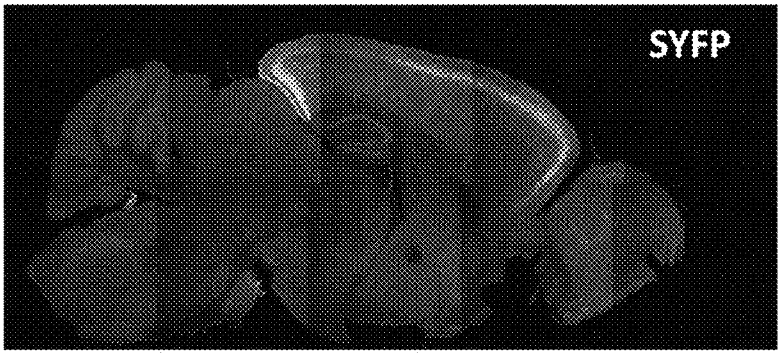
FIGS. 24A-24D. CN1402 (vAi106.0) Enhancer eHGT_058 h (eAi106.0). (24A) Fluorescence expression of CN1402 shown in whole mouse brain in sagittal section. (24B) High resolution image (left) showing non-overlap of CN1402 SYFP fluorescence (red) and inhibitory marker Gad1 mRNA expression (white). Image on the right shows near compete overlap of CN1402 SYFP fluorescence (red) and cortical excitatory marker Slc17a7 mRNA expression (white). (24C) Quantification of specificity of CN1402 SYFP fluorescence in ALM and V1 mouse cortical areas based on multiplexed FISH data. Single cell transcriptomic characterization of SYFP fluorescent cells isolated from mouse V1. (24D) After single cell gene expression analysis, cells were mapped to an existing taxonomy of mouse cell types. Blue circle location reflects extent of single cell mapping (toward the final leaf), while size of the blue circle reflects the number of single cells that mapped to that point in the hierarchy. Bars projecting down reflect the number of cells that map to that terminal branch of the cell type taxonomy. The cells listed from left to right include: 169 L2/3 IT VISp Rrad, 168 L2/3 IT VISp Adamts2, 167 L2/3 IT VISp Agmat, 164 L4 IT VISp Rspo1, 163 L5 IT VISp Hsd11b1 Endou, 162 L5 IT VISp Whrn Tox2, 160 L5 IT VISp Batf3, 158 L5 IT VISp Col6a1 Fezf2, 157 L5 IT VISp Col27a1, 154 L6 IT VISp Penk Col27a1, 153 L6 IT VISp Penk Fst, 152 L6 IT VISp Col23a1 Adamts2, 149 L6 IT VISp Col18a1, 146 L6 IT VISp Car3, 144 L5 PT VISp Chrna6, 143 L5 PT VISp Lgr5, 142 L5 PT VISp C1qI2 PTgfr, 141 L5 PT VISp C1qI2 Cdh13, 140 L5 PT VISp Krt80, 134 L5 NP VISp Trhr Cpne7, 133 L5 NP VISp Trhr Met, 131 L6 CT Nxph2 Sla, 130 L6 CT VISp Krt80 Sla, 128 L6 CT VISp Nxph2 Wls, 127 L6 CT VISp Ctxn3 Brinp3, 126 L6 CT VISp Ctxn3 Sla, 122 L6 CT VISp Gpr139, 120 L6b Col8a1 Rprm, 119 L6b VISp Mup5, 118 L6b VISp Col8a1 Rxfp1, 115 L6b P2ry12, 114 L6b VISp Crh, 110 Lamp5 Krt73, 109 Lamp5 Fam19a1 Pax6, 108 Lamp5 Fam19a1 Tmem182, 106 Lamp5 Ntn1 Npy2r, 105 Lamp5 Plch2 Dock5, 101 Lamp5 Lsp1, 100 Lamp5 Lhx6, 97 Sncg Slc17a8, 96 Sncg Vip Nptx2, 95 Sncg Gpr50, 93 Vip Itih5, 90 Serpinf1 Clrn1, 89 Serpinf1 Aqp5 Vip, 85 Vip Igfbp6 Car10, 84 Vip Igfbp6 Pltp, 82 Vip Lmo1 Fam159b, 81 Vip Lmo1 Myl1, 79 Vip Igfbp6 Mab21I1, 78 Vip Arhgap36 Hmcn1, 77 Vip Gpc3 Slc18a3, 74 Vip Ptprt Pkp2, 73 Vip Rspo4 Rxfp1 Chat, 71 Vip Lect1 Oxtr, 70 Vip Rspo1 Itga4, 67 Vip Chat Htr1f, 66 Vip Pygm C1qI1, 61 Vip CrispId2 Htr2c, 60 Vip CrispId2 Kcne4, 58 Vip Col15a1 Pde1a, 54 Sst Chodl, 53 Sst Mme Fam114a1, 52 Sst Tac1 Htr1d, 50 Sst Tac1 Tacr3, 49 Sst Calb2 Necab1, 48 Sst Calb2 Pdlim5, 46 Sst Nr2f2 Necab1, 45 Sst Myh8 Etv1, 44 Sst Chrna2 Glra3, 42 Sst Myh8 Pibin, 40 Sst Chrna2 Ptgdr, 39 Sst Tac2 Myh4, 37 Sst Hpse Sema3c, 36 Sst Hpse Cbln4, 34 Sst Crhr2 Efemp1, 33 Sst Crh 4930553C11Rik, 31 Sst Esrn1, 29 Sst Tac2 Tacstd2, 28 Sst Rxfp1 Eya1, 27 Sst Rsfp1 Prdm8, 23 Sst Nts, 21 Pvalb Gabrg1, 20 Pvalb Th Sst, 18 Pvalb Calb1 Sst, 17 Pvalb Akr1c18 Ntf3, 16 Pvalb Sema3e Kank4, 14 Pvalb Gpr149 Islr, 11 Pvalb Reln Itm2a, 10 Pvalb Reln Tact 9 Pvalb Tpbg, 4 Pvalb Vipr2, 1 Meis2 Adamts19, 170 Astro Aqp4, 171 OPC Pdgfra Grm5, 173 Oligo Serpinb1a, 174 Oligo Synpr, 175 VLMC Osr1 Cd74, 176 VLMC Osr1 Mc5r, 177 VLMC Spp1 Col15a1, 178 Peri Kcni8, 179 SMC Acta2, 180 Endo Ctla2a, and 181 Microglia Siglech.
Figure 24B:
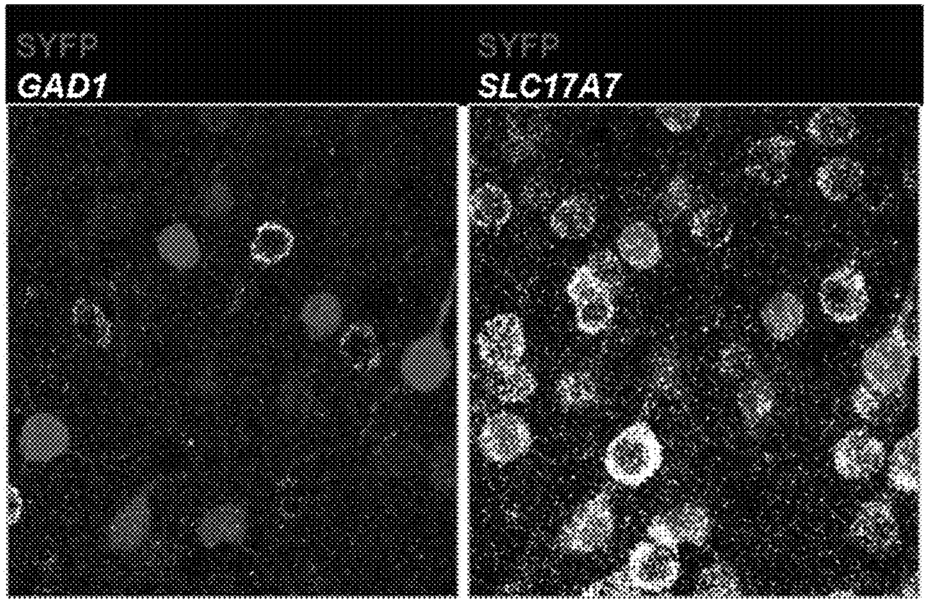
Figure 24C:
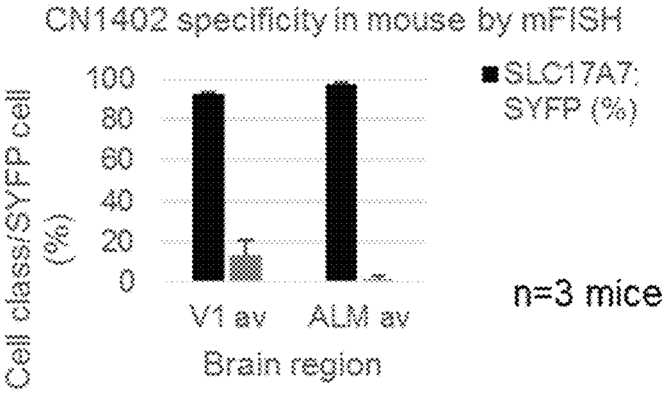
Figure 24D:
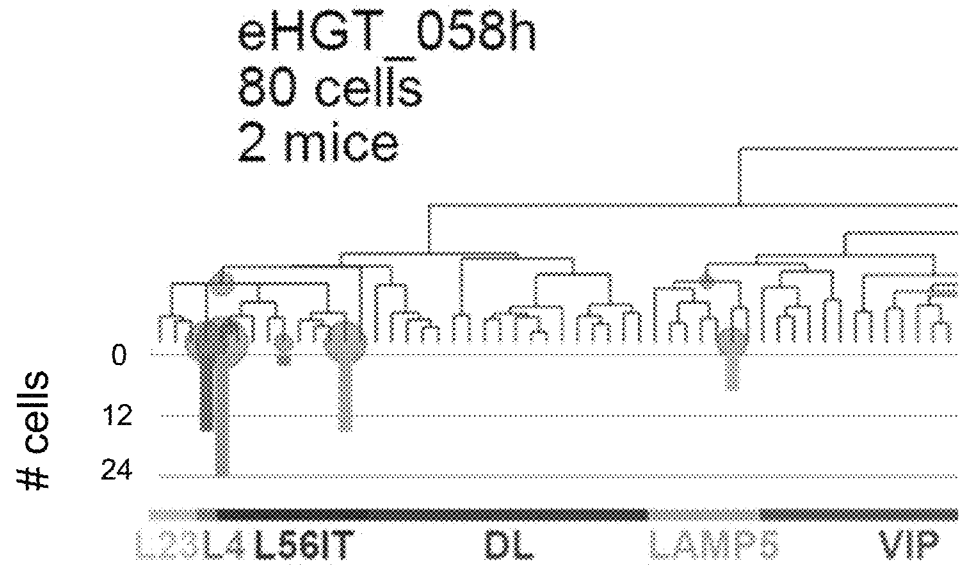
Figure 24D:
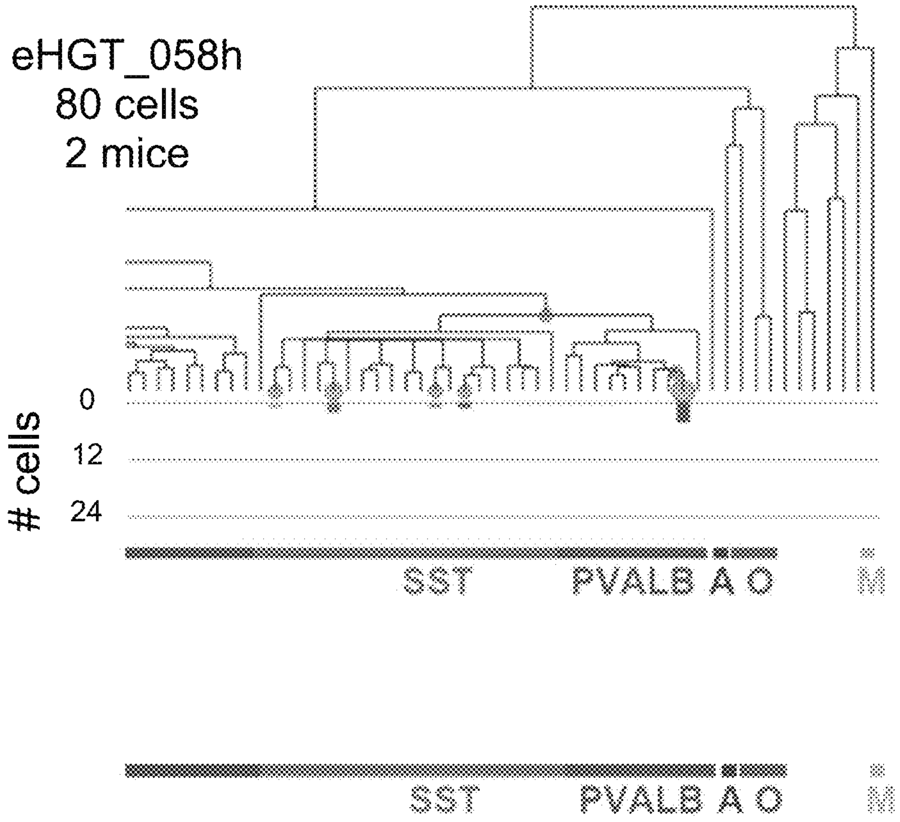
Figure 25A:
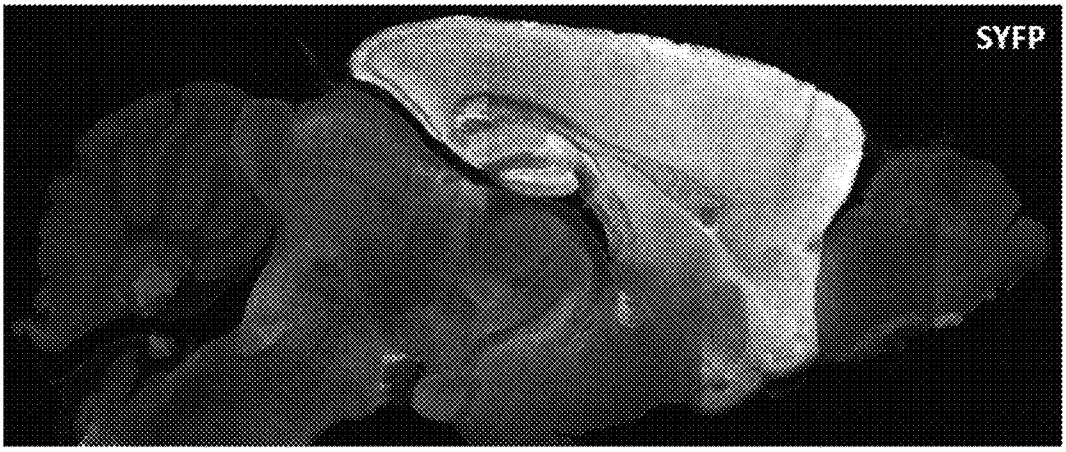
FIGS. 25A-25D. CN1457 (vAi107.0) Enhancer eHGT_078 h (eAi107.0). (25A) Fluorescence expression of CN1457 shown in whole mouse brain in sagittal section. (25B) High resolution image (left) showing non-overlap of CN1457 SYFP fluorescence (red) and inhibitory marker Gad1 mRNA expression (white). Image on the right shows near compete overlap of CN1457 SYFP fluorescence (red) and cortical excitatory marker Slc17a7 mRNA expression (white). (25C) Quantification of specificity of CN1457 SYFP fluorescence in ALM and V1 mouse cortical areas based on multiplexed FISH data. (25D) Single cell transcriptomic characterization of SYFP fluorescent cells isolated from mouse V1. After single cell gene expression analysis, cells were mapped to an existing taxonomy of mouse cell types. Blue circle location reflects extent of single cell mapping (toward the final leaf), while size of the blue circle reflects the number of single cells that mapped to that point in the hierarchy. Bars projecting down reflect the number of cells that map to that terminal branch of the cell type taxonomy. The cells are the same as the cells listed in the Brief Description of the Figures of FIG. 24D.
Figure 25B:
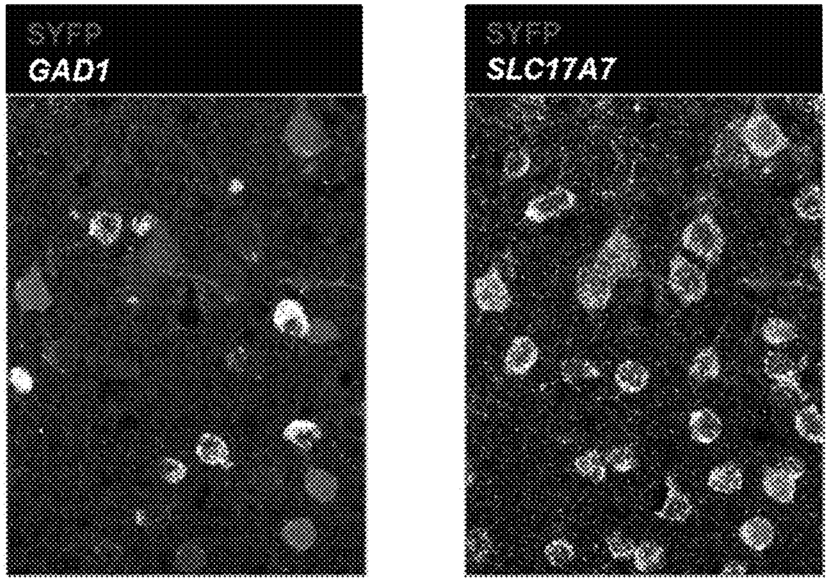
Figure 25C:
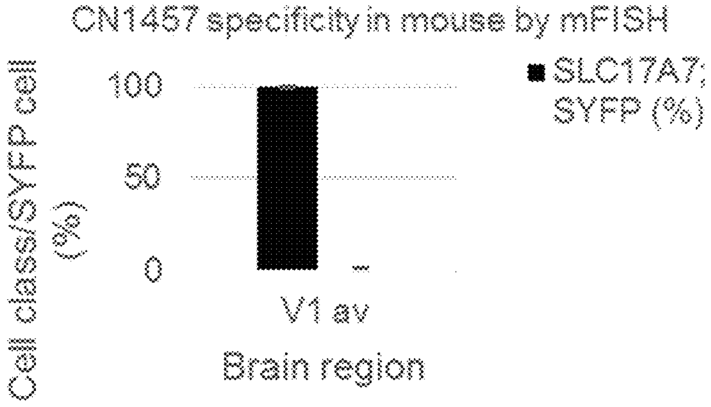
Figure 25D:
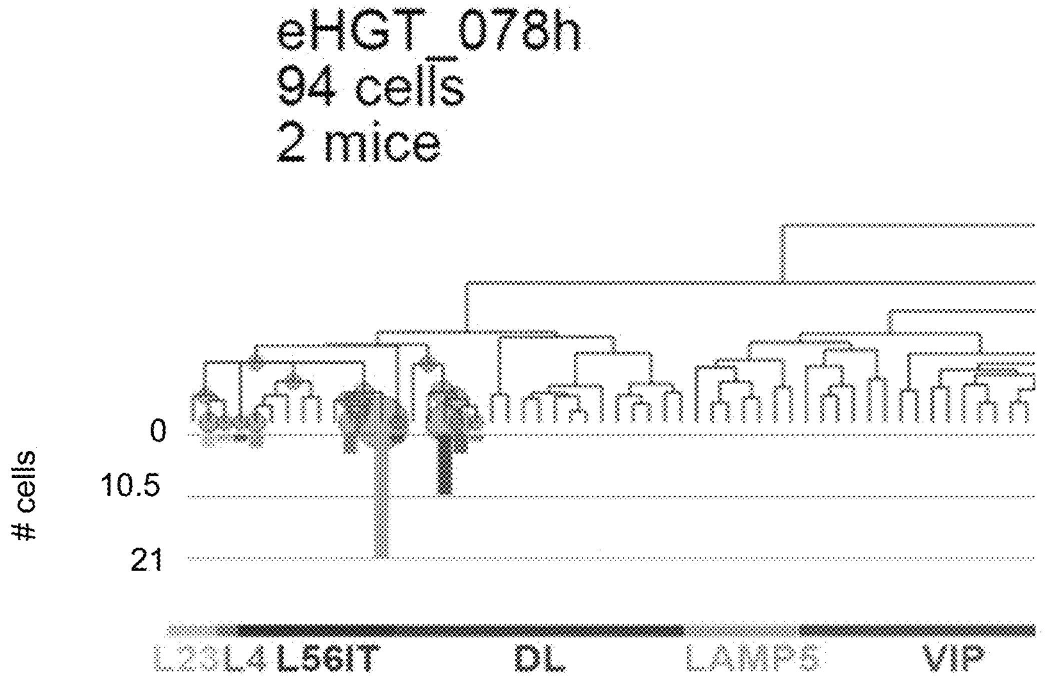
Figure 25D:
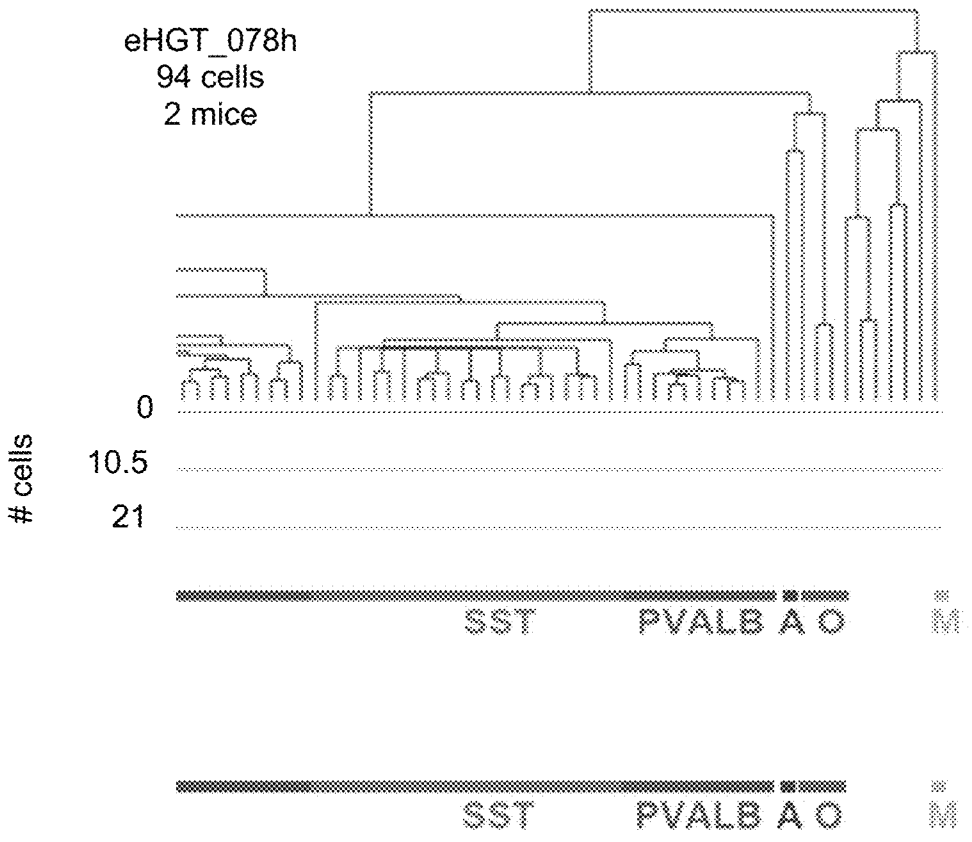
Figure 26A:
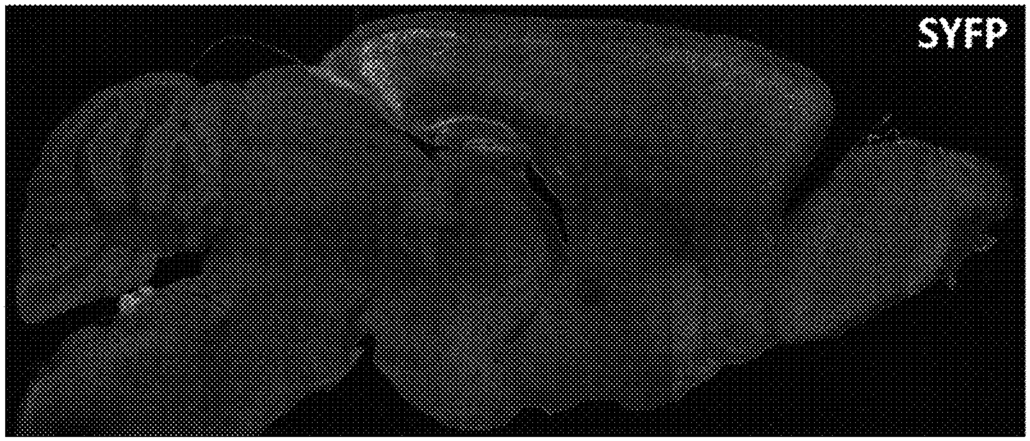
FIGS. 26A-26C. CN1416 (vAi108.0) Enhancer eHGT_058 m (eAi108.0). (26A) Fluorescence expression of CN1416 shown in whole mouse brain in sagittal section. (26B) High resolution image (left) showing non-overlap of CN1416 SYFP fluorescence (red) and inhibitory marker Gad1 mRNA expression (white). Image on the right shows near compete overlap of CN1416 SYFP fluorescence (red) and cortical excitatory marker Slc17a7 mRNA expression (white). (26C) Quantification of specificity of CN1416 SYFP fluorescence in ALM and V1 mouse cortical areas based on multiplexed FISH data.
Figure 26B:
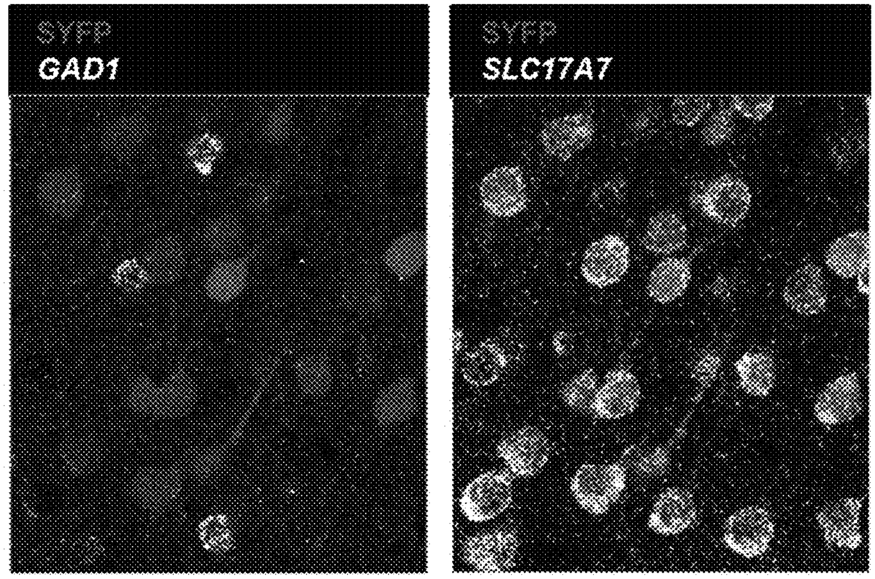
Figure 26C:
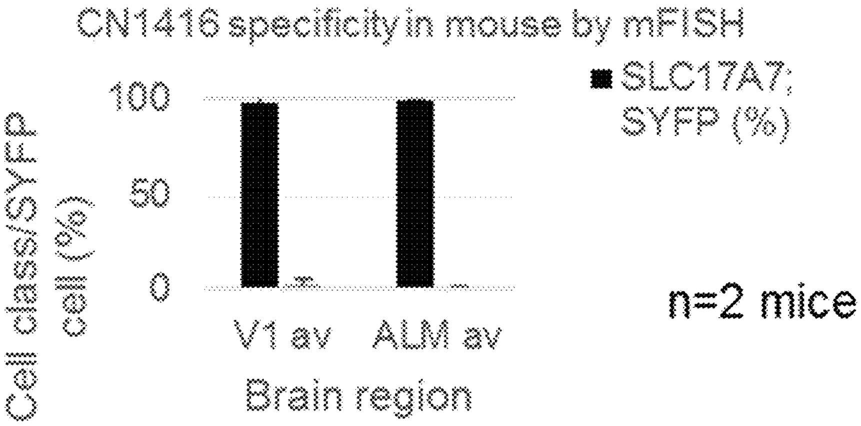
Figure 27A:
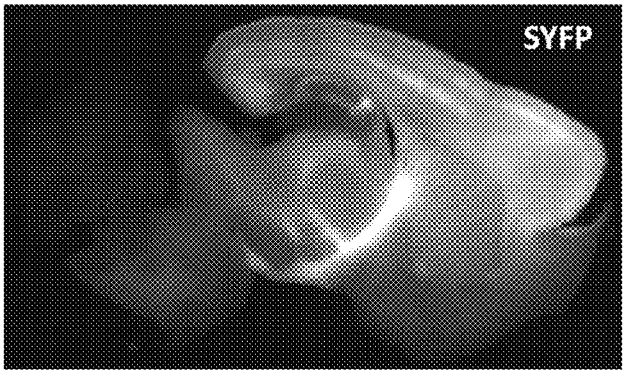
FIGS. 27A-27C. CN1452 (vAi111.0) Enhancer eHGT_073 h (eAi111.0). (27A) Fluorescence expression of CN1452 shown in whole mouse brain in sagittal section. (27B) Grayscale fluorescent images of DAPI, and mFISH images of Gad1, Pvalb, Sst, SYFP (CN1452) and Vip mRNA in mouse visual cortex. (27C) Co-staining of SYFP (CN1452) and Gad1 showing that only 7% of Gad1+ cells overlap with SYFP. N=43 cells from one animal.
Figure 27B:
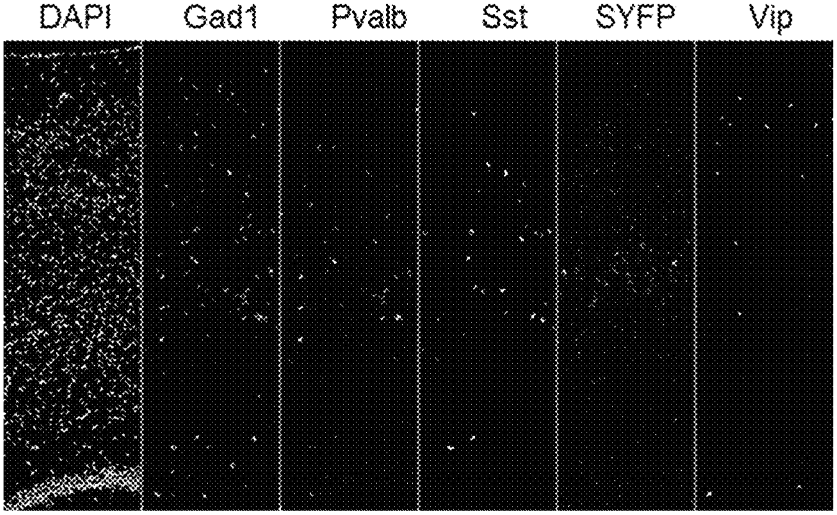
Figure 27C:
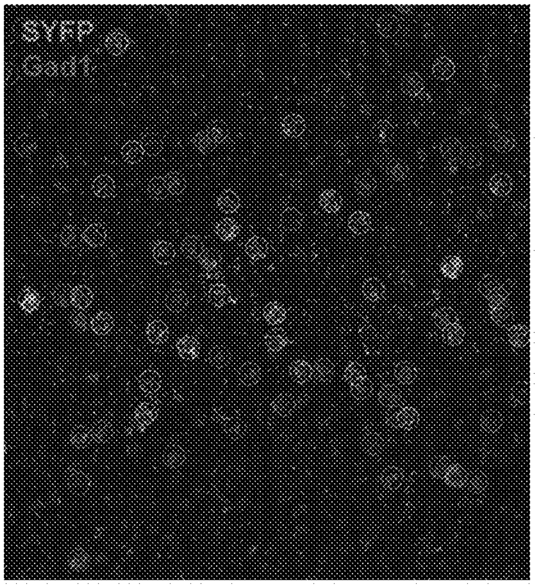
Figure 28A:
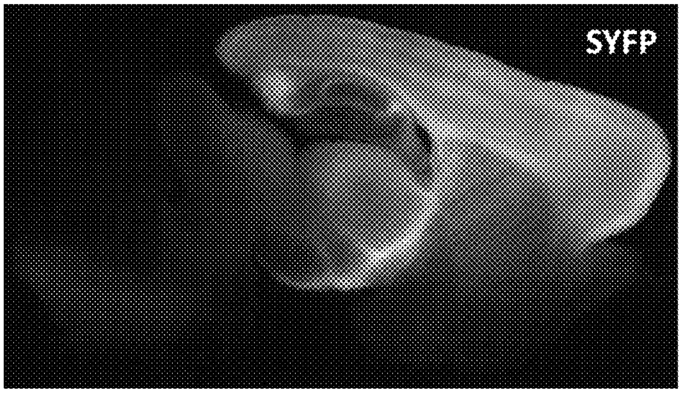
FIGS. 28A-28C. CN1461 (vAi112.0) Enhancer eHGT_073 m (eAi112.0). (28A) Fluorescence expression of CN1461 shown in whole mouse brain in sagittal section. (28B) Grayscale fluorescent images of DAPI, and mFISH images of Gad1, Pvalb, Sst, SYFP (CN1461), and Vip mRNA in mouse visual cortex. (28C) Co-staining of SYFP (CN1461) and Gad1 showing that only 1.5% of Gad1+ cells overlap with SYFP. N=130 cells from one animal.
Figure 28B:
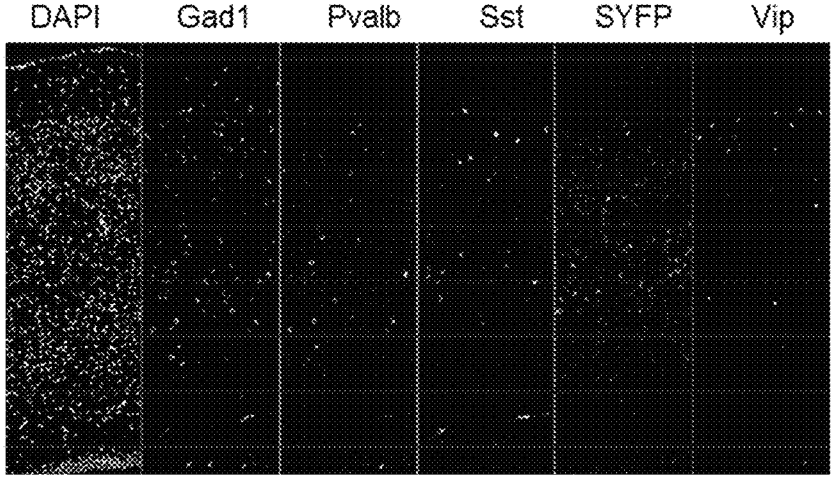
Figure 28C:
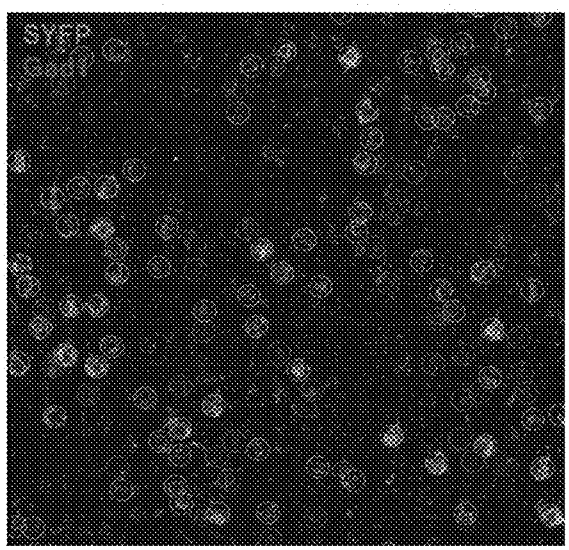
Figure 29A:
FIGS. 29A-29C. CN1454 (vAi113.0) Enhancer eHGT_075 h (eAi113.0). (29A) Fluorescence expression of CN1454 shown in whole mouse brain in sagittal section. (29B) High resolution image (left) showing non-overlap of CN1454 SYFP fluorescence (red) and inhibitory marker Gad1 mRNA expression (white). Image on the right shows near compete overlap of CN1454 SYFP fluorescence (red) and cortical excitatory marker Slc17a7 mRNA expression (white). (29C) Quantification of specificity of CN1454 SYFP fluorescence in V1 mouse cortical areas based on multiplexed FISH data.
Figure 29B:
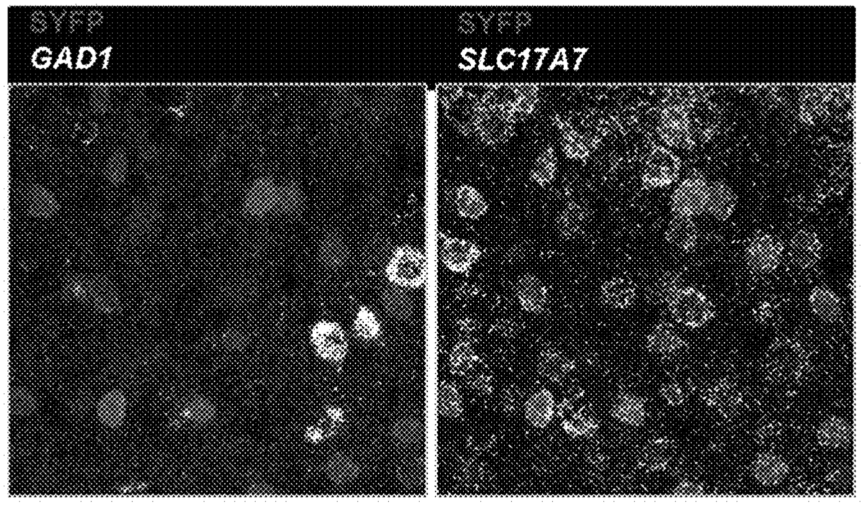
Figure 29C:
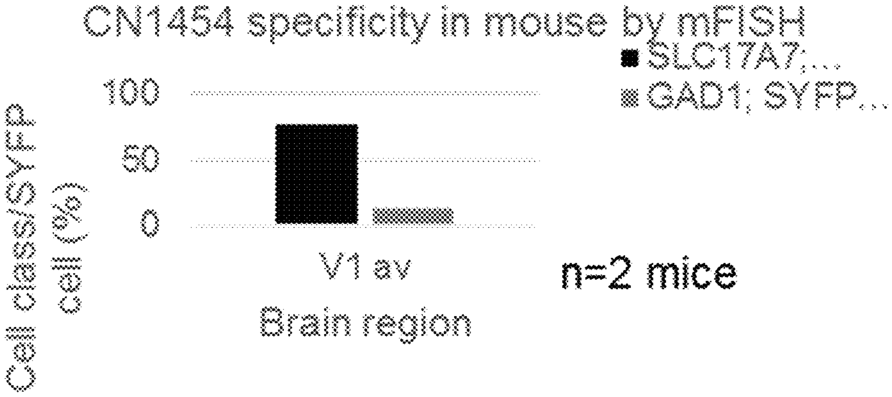
Figure 30A:
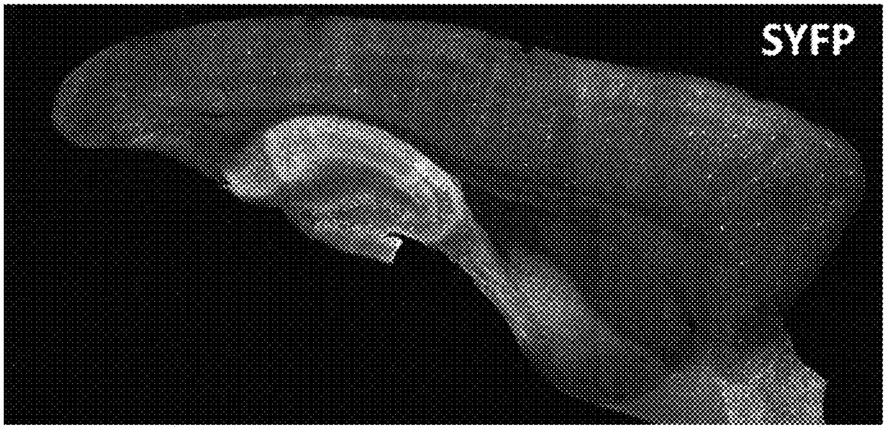
FIGS. 30A-30C. CN1456 (vAi114.0) Enhancer eHGT_077 h (eAi114.0). (30A) Fluorescence expression of CN1402 shown in whole mouse brain in sagittal section. (30B) High resolution image (left) showing non-overlap of CN1402 SYFP fluorescence (red) and inhibitory marker Gad1 mRNA expression (white). Image on the right shows near compete overlap of CN1402 SYFP fluorescence (red) and cortical excitatory marker Slc17a7 mRNA expression (white). (30C) Quantification of specificity of CN1402 SYFP fluorescence in ALM and V1 mouse cortical areas based on multiplexed FISH data. Single cell transcriptomic characterization of SYFP fluorescent cells isolated from mouse V1.
Figure 30B:
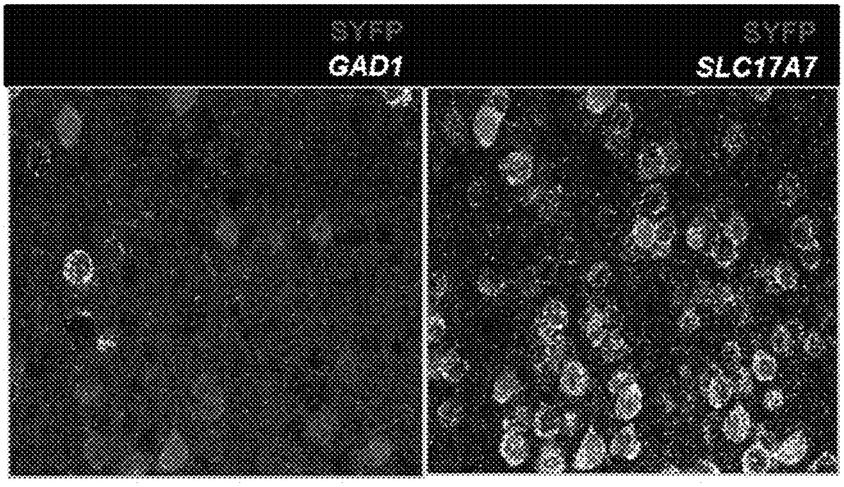
Figure 30C:
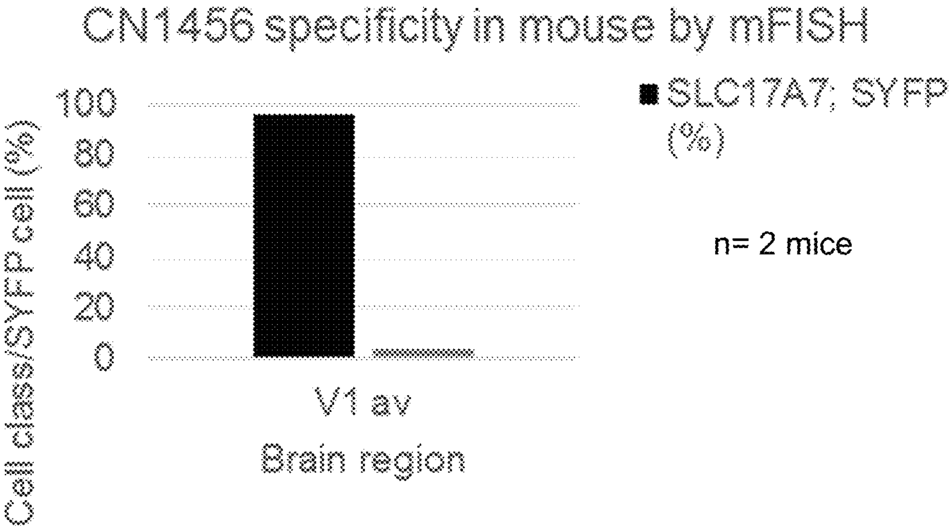
Figure 31A:
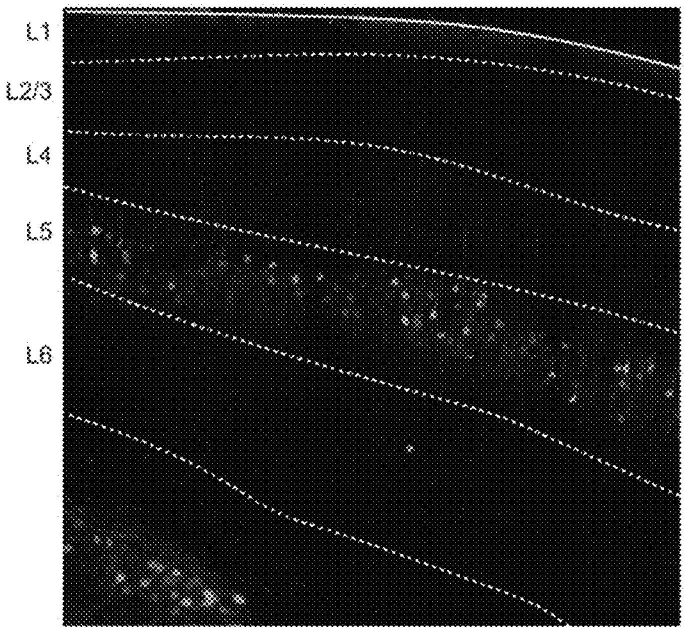
FIGS. 31A, 31B. CN1818 (vAi128.0) Enhancer mscRE4 (3×Core) (eAi3.2). Expression of construct CN1818 tested by (31A) Native fluorescence microscopy of cells labeled by retro-orbital injection, (31B) Hairpin Chain Reaction (HCR) RNA FISH targeting SYFP2 (from viral expression), Fam84b (expressed in L5 ET cells) and Rorb (expressed in L4 IT and L5 IT cells). FISH revealed a specificity rate of 78% in situ (62 Fam84b+ and SYFP2+/80 total SYFP2+).
Figure 31B:
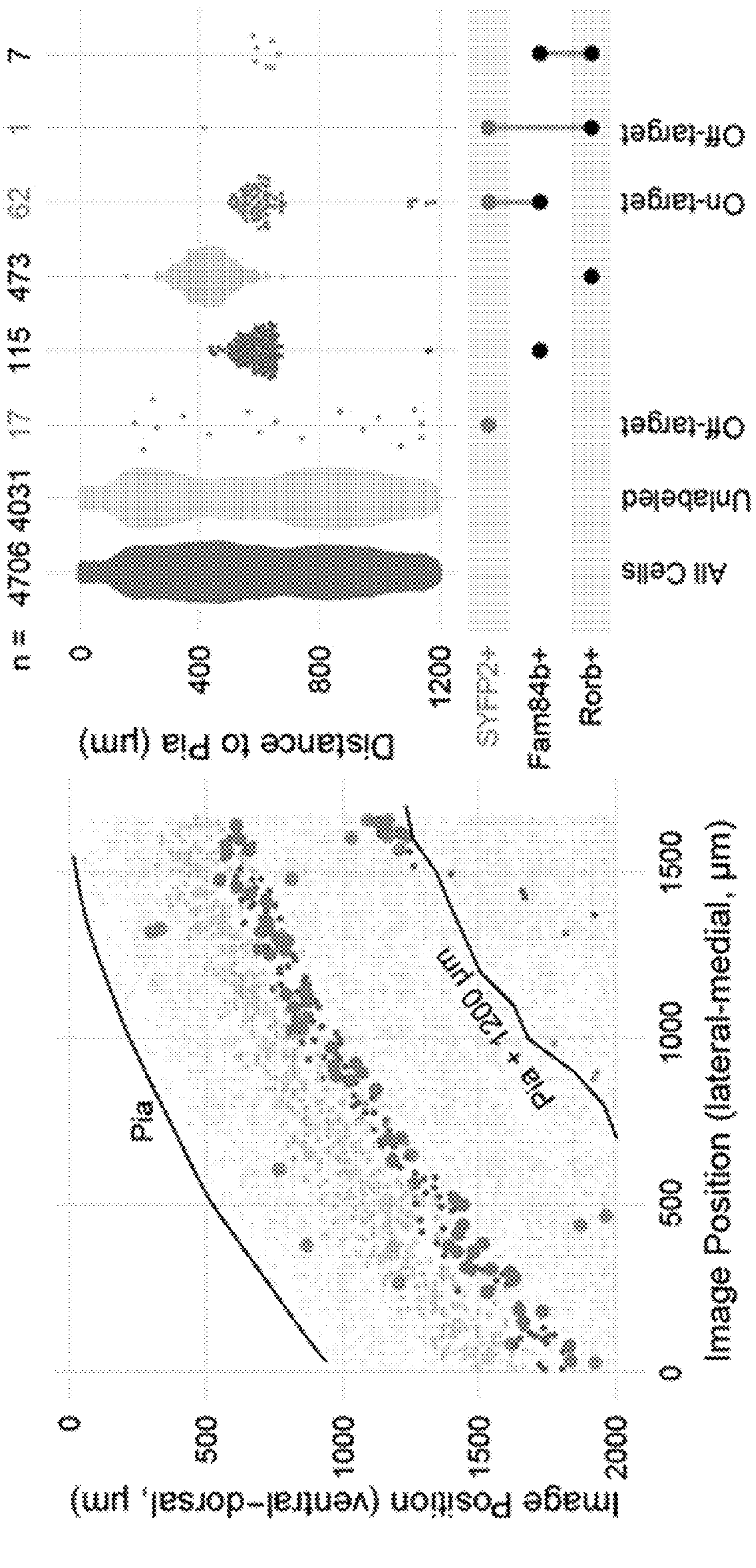
Figure 32A:
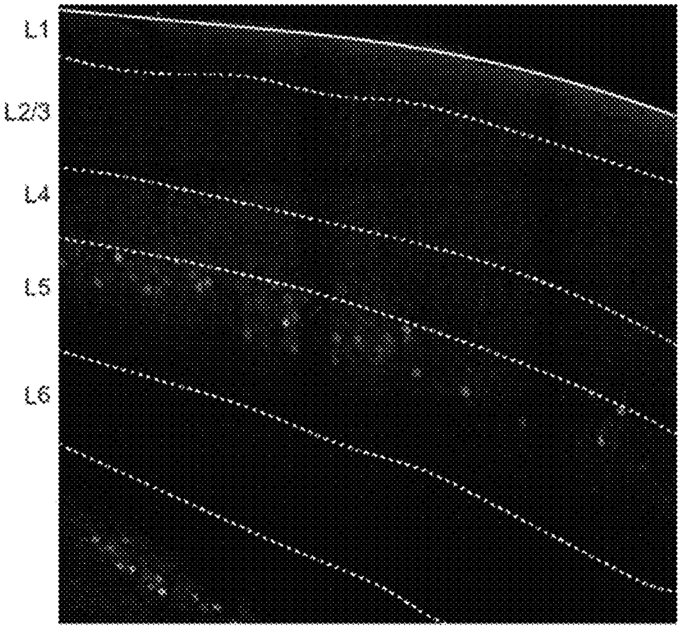
FIG. 32A, 32B. CN2014 (vAi129.0) Enhancer mscRE4 (eAi3.0). Expression of construct CN2014 tested by (32A) Native fluorescence microscopy of cells labeled by retro-orbital injection, (32B) Hairpin Chain Reaction (HCR) RNA FISH targeting SYFP2 (from viral expression), Fam84b (expressed in L5 ET cells) and Rorb (expressed in L4 IT and L5 IT cells). FISH revealed a specificity rate of 85% in situ (45 Fam84b+ and SYFP2+/53 total SYFP2+).
Figure 32B:
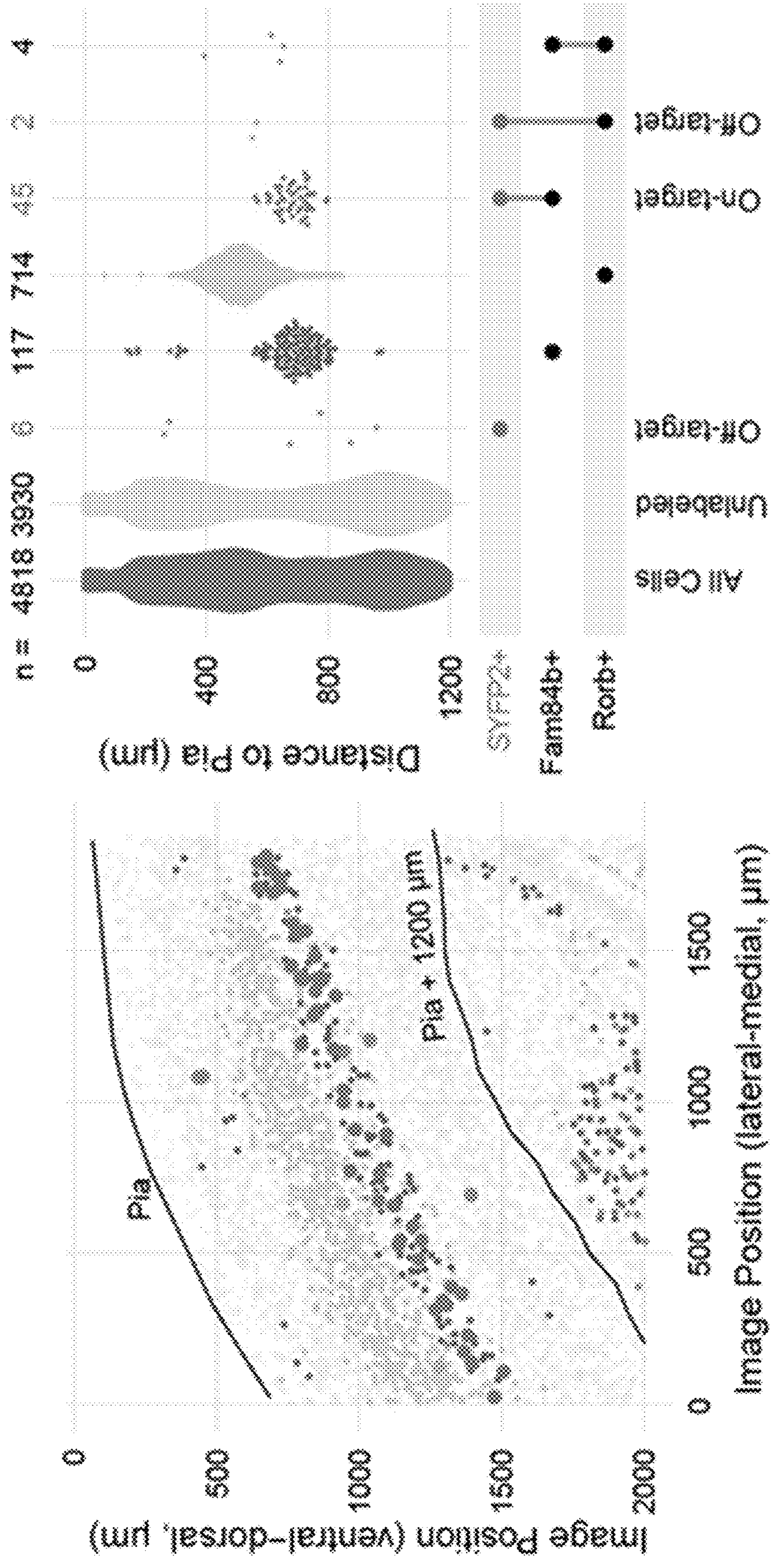
Figure 33:
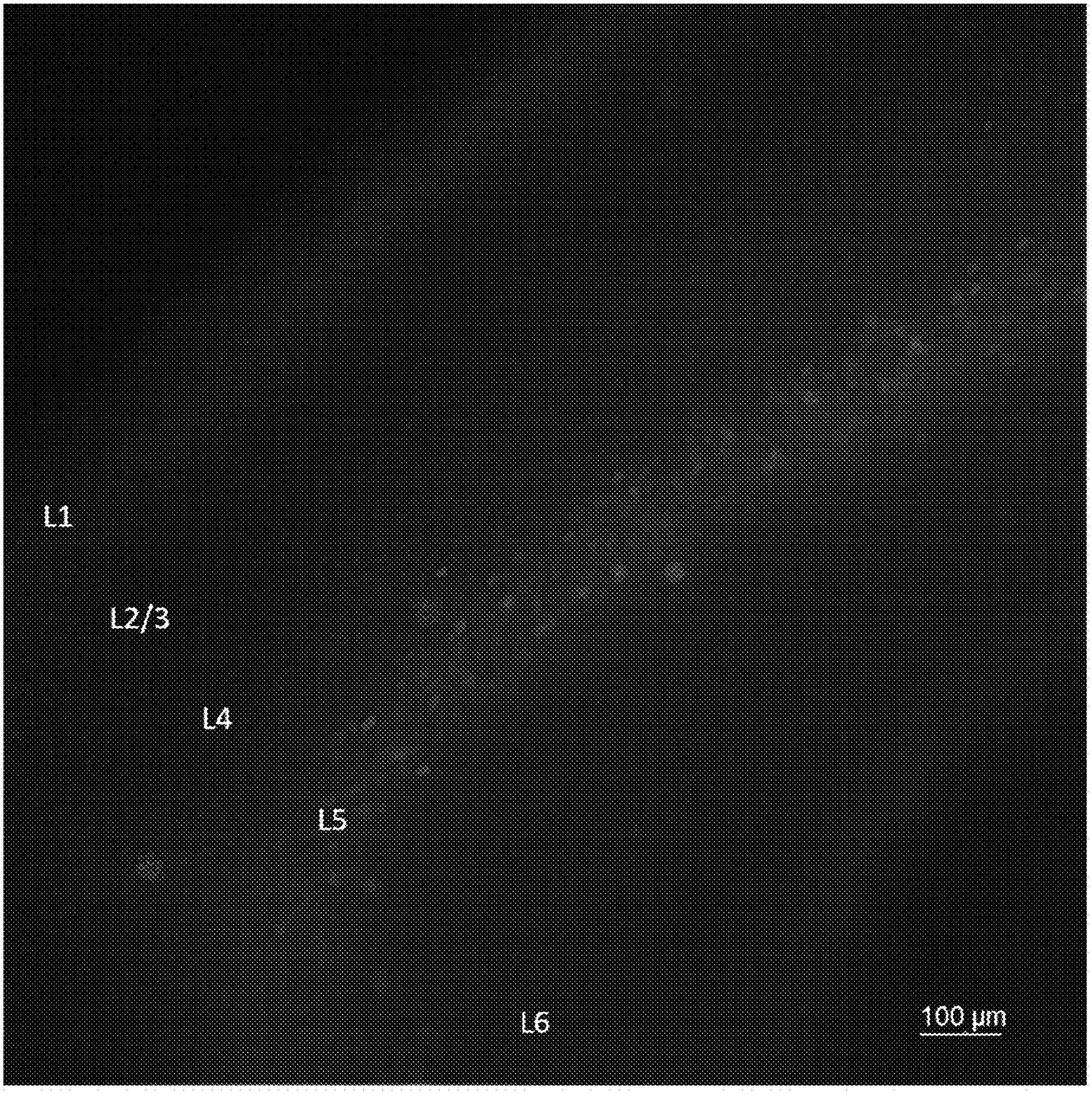
FIG. 33. CN1427 (vAi130.0) Enhancer mscRE4(4×) (eAi3.1). A Native tdTomato fluorescence expression in V1 region of a mouse brain slice. CN1427 serotype PHPeB virus was delivered by retroorbital injection, with analysis of reporter transgene expression at 40 days post injection.
Figure 34A:
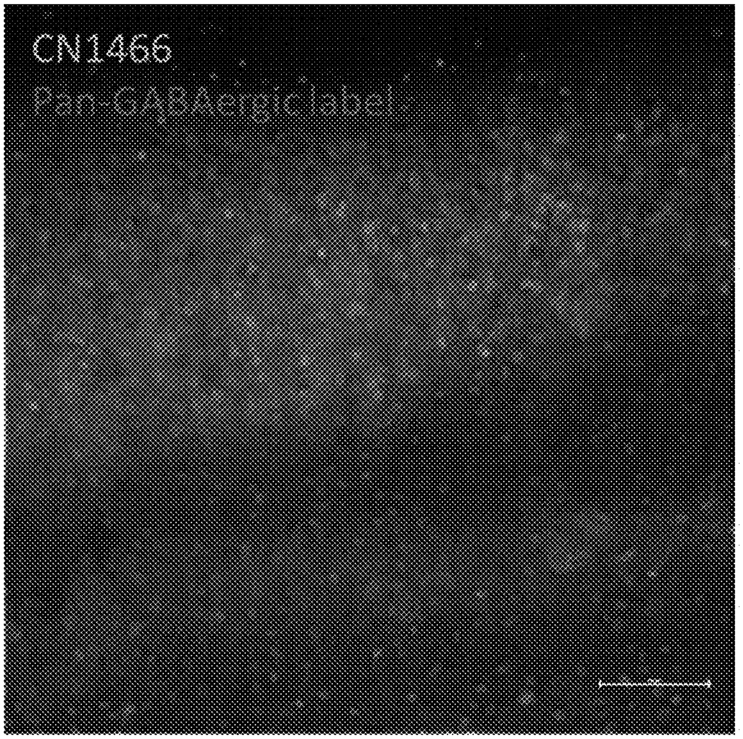
FIGS. 34A, 34B. CN1466 (vAi131.0) Enhancer eHGT_078 m (eAi128.0). (34A) Expression of vector CN1466 (green) in mouse neocortical brain slice culture at 25 days in vitro and 15 days post infection. Mutually exclusive labeling CN1466-labeled neurons (green) and GABAergic neurons (red). (34B) Expression of vector CN1466 in human neocortical brain slice cultures at 9 days in vitro and 9 days post infection. Extensive pyramidal neuron labeling is observed.
Figure 34B:
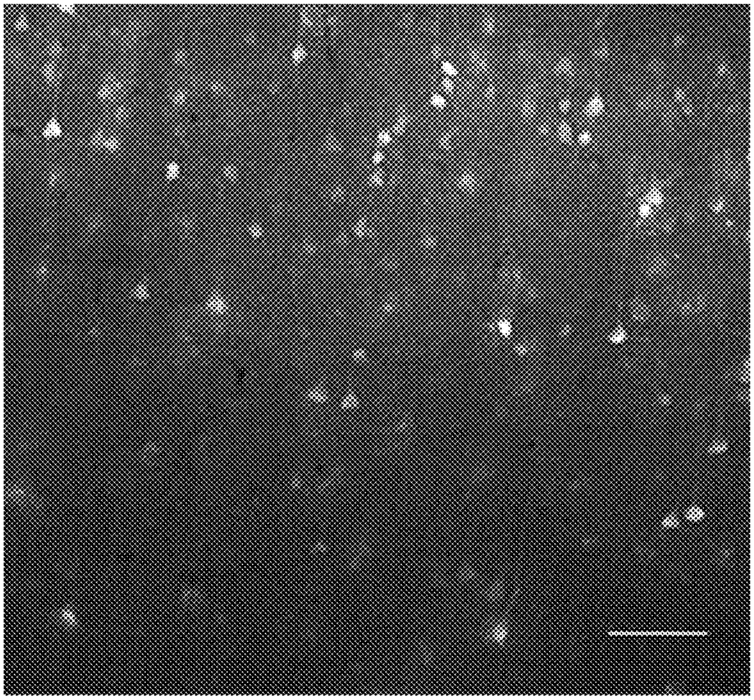
Figure 35:
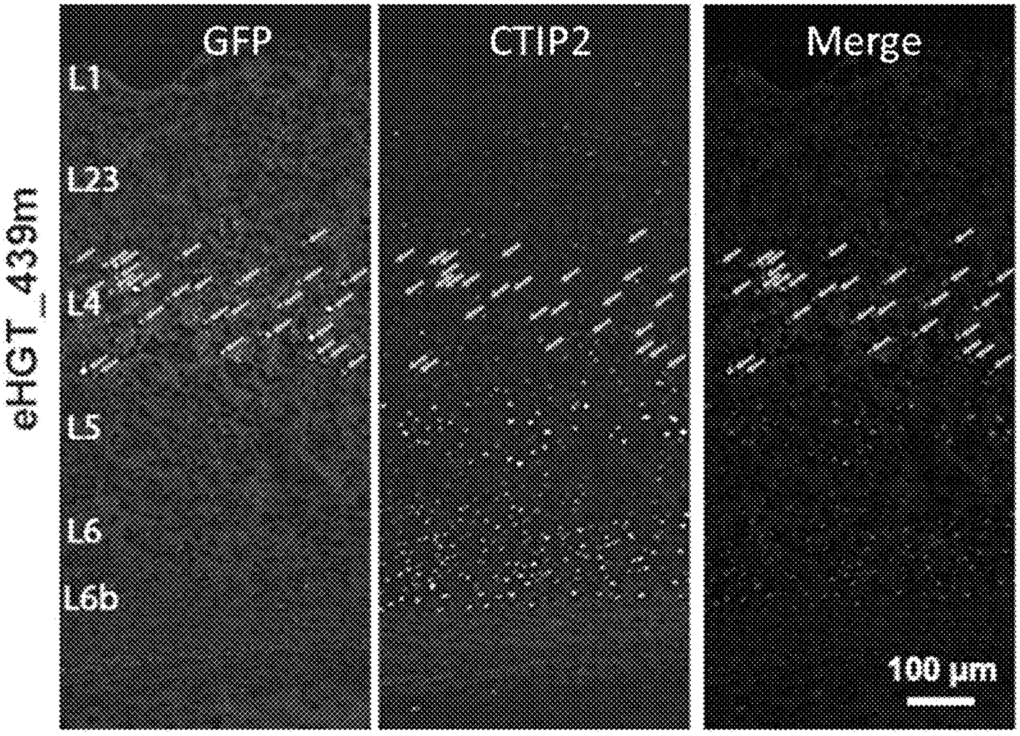
FIG. 35. CN2139 (vAi134.0) Enhancer eHGT_439 m (eAi131.0). Expression of vector CN2139 by retroorbital delivery in mouse brain. Brain slices were subjected to fixed tissue immunohistochemistry with anti-GFP and anti-CTIP2 antibodies. Virus labeled cells were observed in L4 of neocortex.
Figure 36:
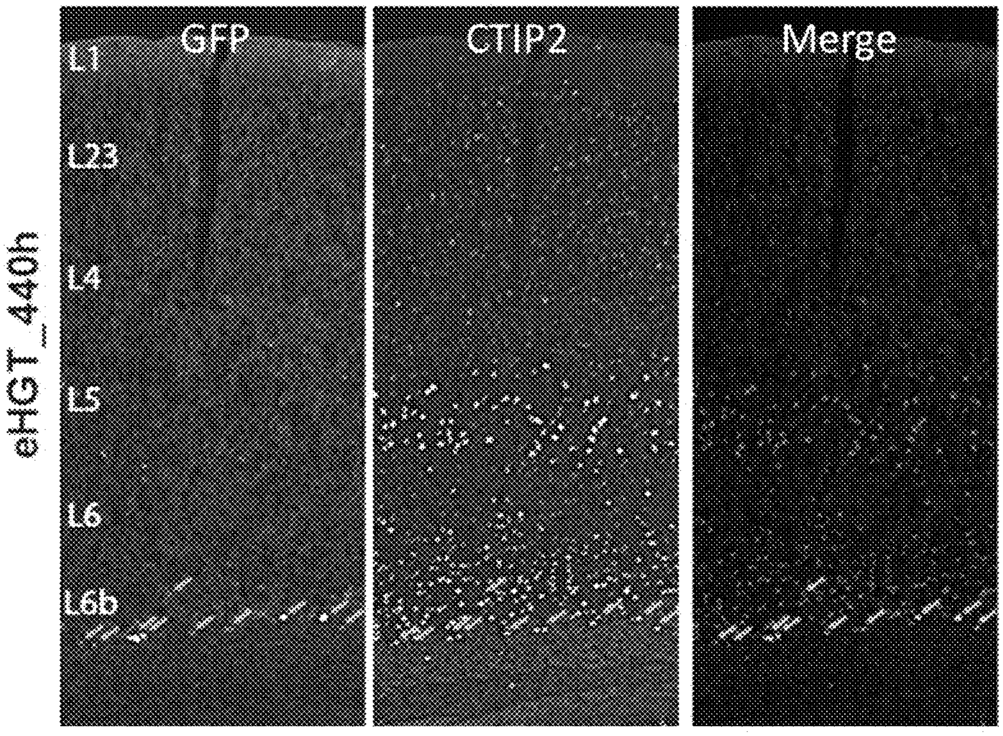
FIG. 36. CN2137 (vAi135.0) Enhancer eHGT_440 h (eAi132.0). Expression of vector CN2137 by retroorbital delivery in mouse brain. Brain slices were subjected to fixed tissue immunohistochemistry with anti-GFP and anti-CTIP2 antibodies. Virus labeled cells were observed in L6b of neocortex.
Figure 37A:
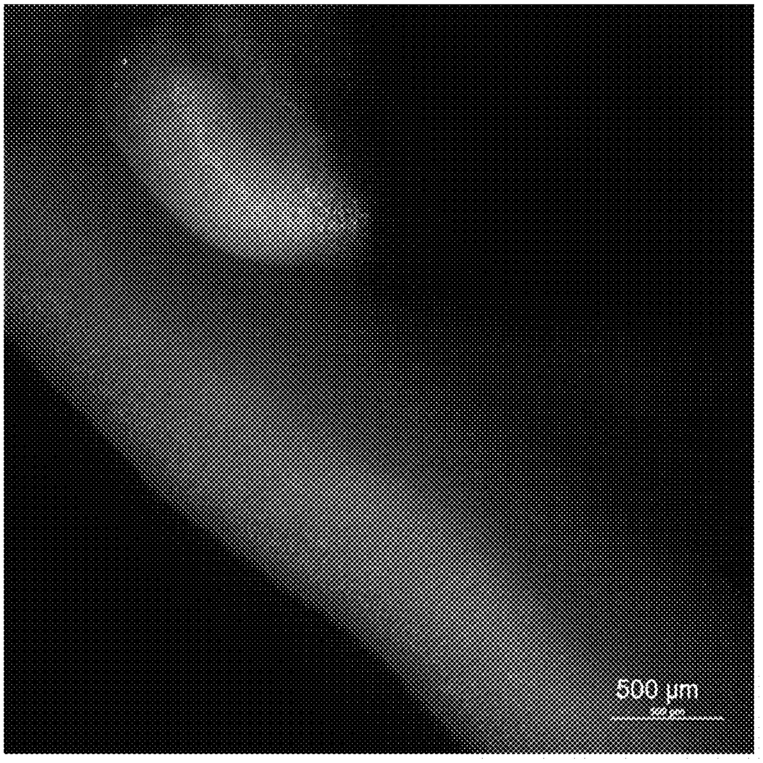
FIGS. 37A, 37B. (37A) CN1954 (vAi132.0) Enhancer eHGT_078h(3×Core) (eAi129.0). Expression of vector CN1954 in mouse neocortical brain slice culture at 27 days in vitro and 20 days post infection. (37B) CN1955 (vAi133.0) Enhancer eHGT_078m(3×Core) (eAi130.0). Expression of vector CN1955 in mouse neocortical brain slice culture at 27 days in vitro and 20 days post infection.
Figure 37B:
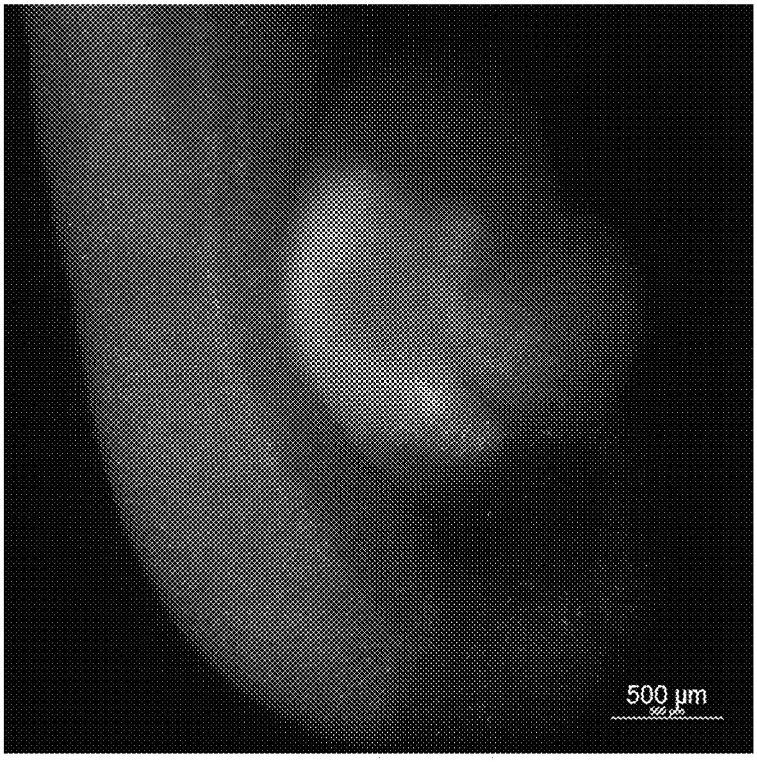
Figure 38A:
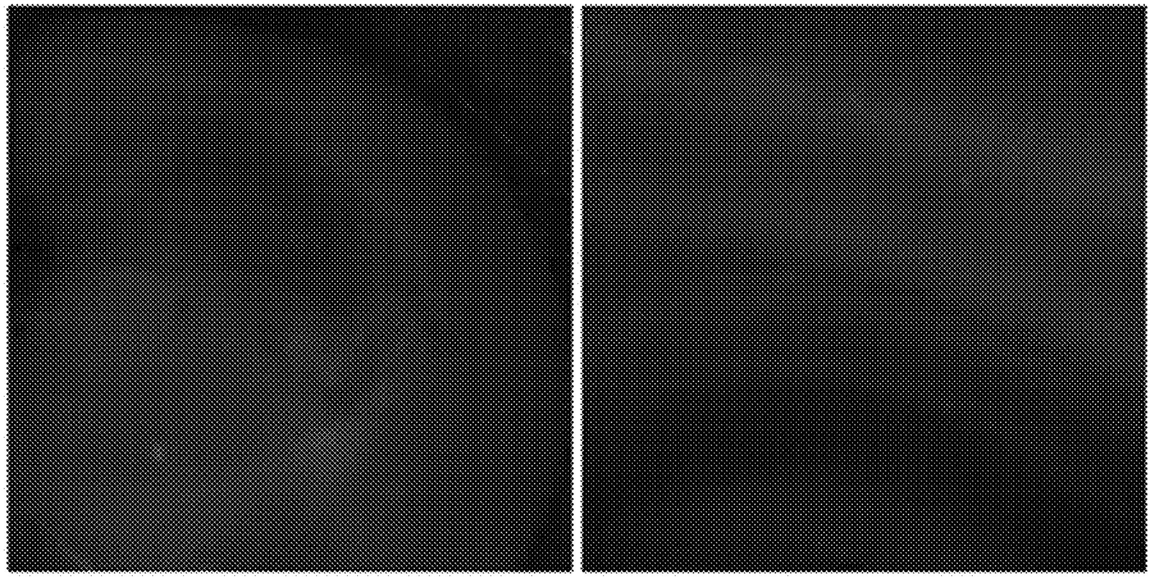
FIGS. 38A, 38B. (38A) vAi1.0 Enhancer mscRE1 (eAi1.0). Expression of construct mscRE1-SYFP2 tested by A) Native fluorescence imaging of retro-orbital injection. (38B) T502-059 (vAi2.0) Enhancer mscRE1 (eAi2.0). Expression of construct mscRE3-SYFP2 tested by A) Native fluorescence imaging of retro-orbital injection.
Figure 38B:
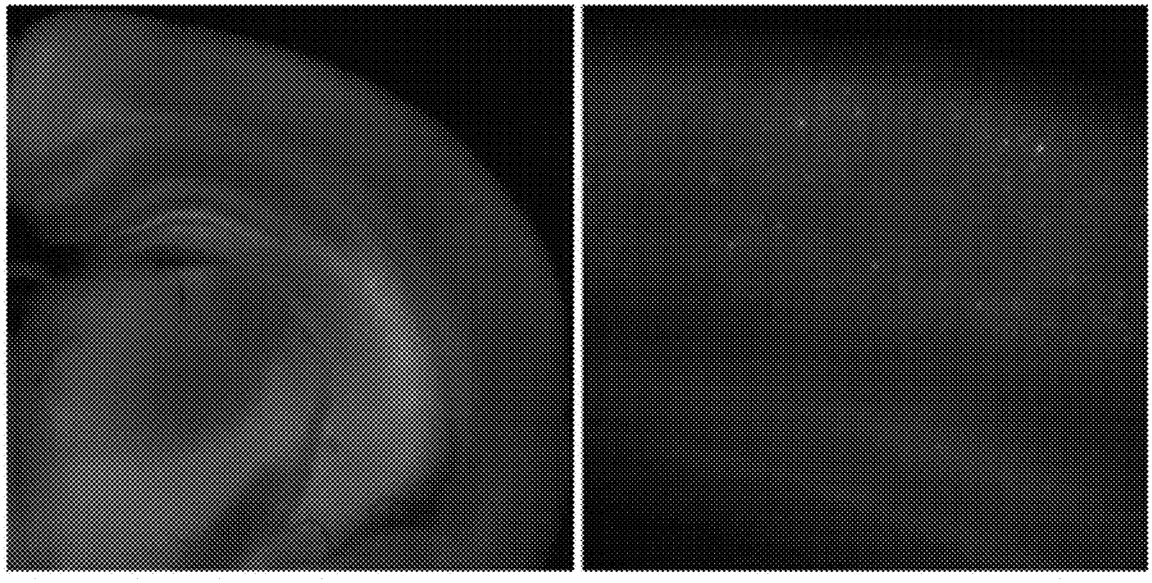
Figure 39:
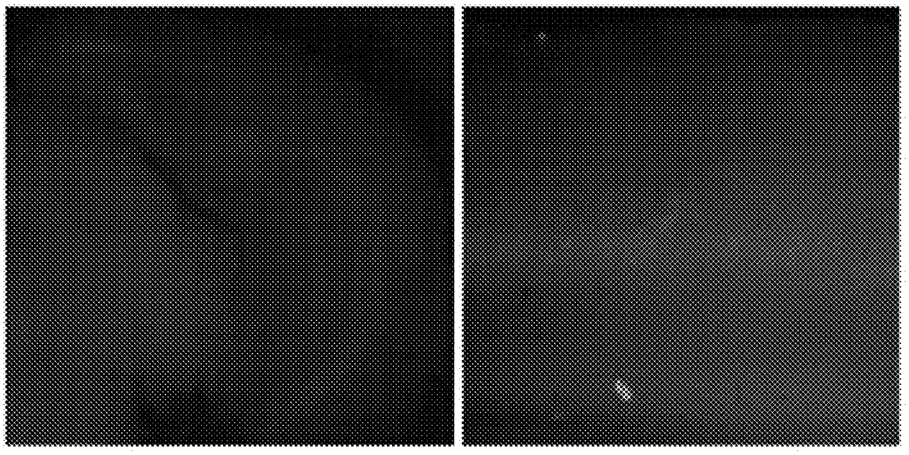
FIG. 39. T502-057 (vAi3.0) Enhancer mscRE4 (eAi3.0). Expression of construct mscRE4-SYFP2 tested by native fluorescence imaging of retro-orbital injection.
Figure 40:
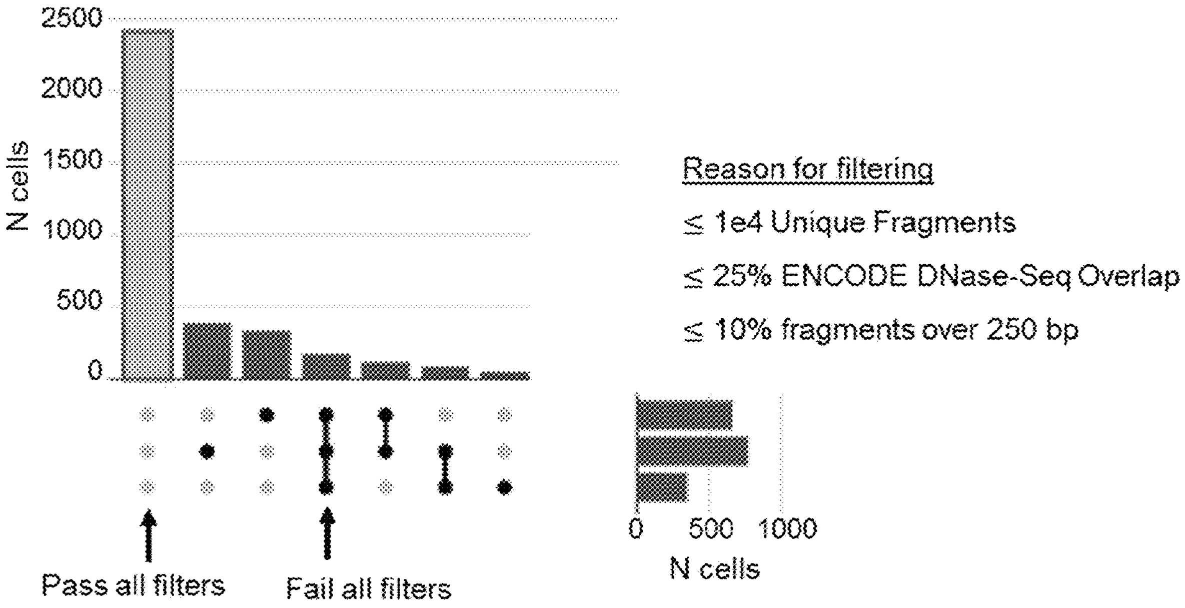
FIG. 40. Cell sources and Quality Control (QC Statistics). Barplot showing how many cells were flagged with each combination of QC criteria. N, number of cells collected. Unique fragments is the number of uniquely mapped fragments used for analysis, and was used for the first QC cutoff of >1e4 unique fragments. Fraction of fragments overlapping Encyclopedia of DNA Elements (ENCODE) DNase-seq peaks were computed using uniquely mapped fragments and were used for the second QC cutoff of >0.25. Fraction of fragments with length>250 bp was computed using unique fragments and provides the third QC cutoff of >0.1.
Figure 41:
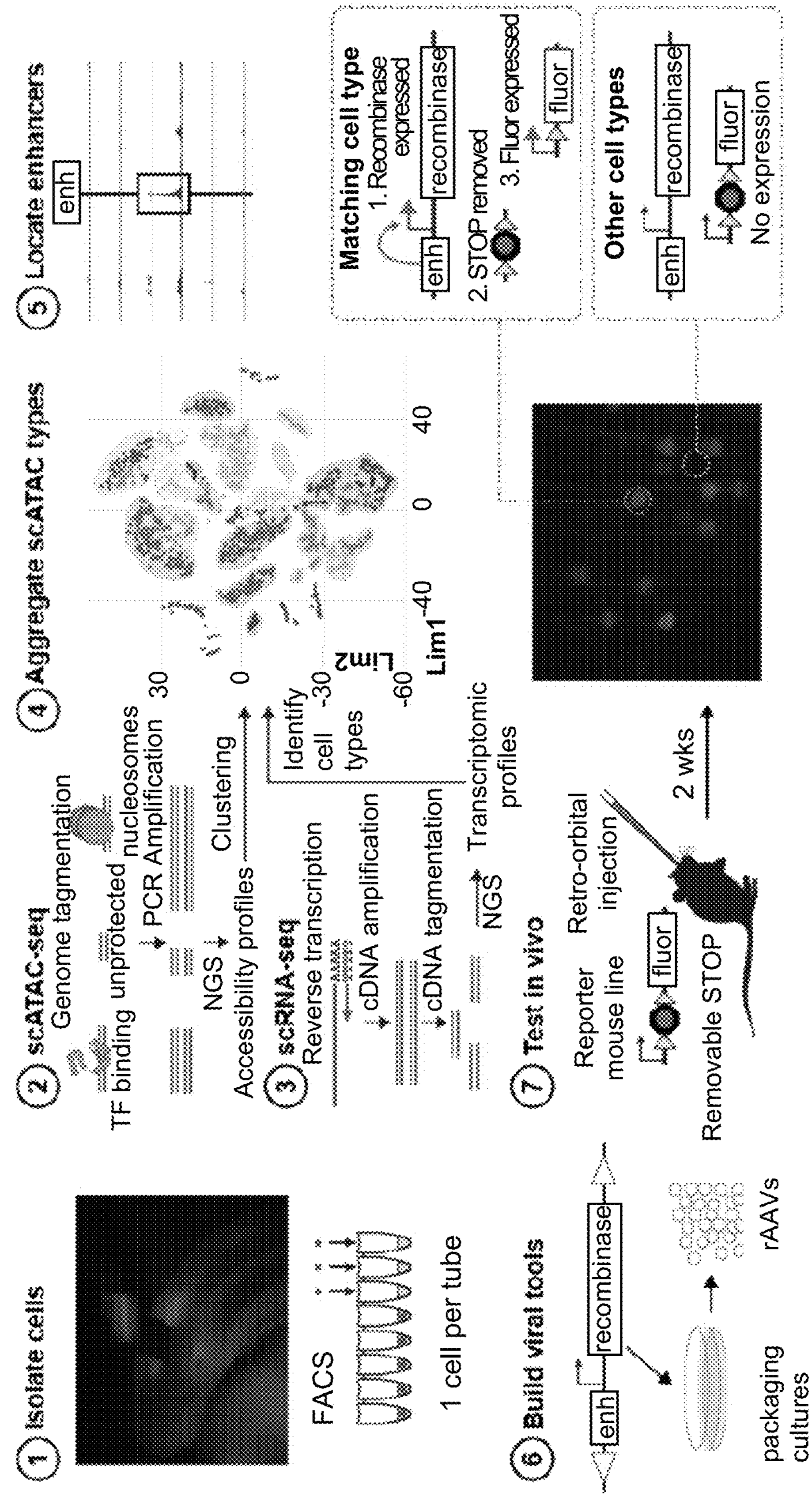
FIG. 41. Overview of enhancer discovery for viral tools. To build cell type-specific labeling tools, cells from adult mouse cortex were isolated and a single cell assay for transposase-accessible chromatin using sequencing (scATAC-seq) was performed. Samples were clustered and compared to single cell RNA sequencing (scRNA-seq) datasets to identify the clusters. Single cells matching the same transcriptomic types were then pooled and the genome was searched for type-specific putative enhancers. These regions were cloned upstream of a minimal promoter in an adeno-associated virus (AAV) genomic backbone, which was used to generate self-complementary adeno-associated viral vectors (scAAVs) or recombinant adeno-associated viral vectors (rAAVs). These viral tools were delivered retro-orbitally or stereotaxically to label specific cortical populations. In cells with a matching cell type, enhancers recruit their cognate transcription factors to drive cell type-specific expression. In other cells, viral genomes are present, but transcripts are not expressed. However, it is necessary to test the enhancer constructs for specificity, as not all enhancers behave as expected.

130), Deoxyribonuclease II beta (SEQ ID NO: 131), Sodium channel protein type 1 subunit alpha (SEQ ID NO: 132), Potassium voltage-gated channel subfamily KQT member 2 (SEQ ID NO: 133), Voltage-dependent L-type calcium channel subunit alpha-1C (SEQ ID NO: 134), Lactase (SEQ ID NO: 135), Lipase (SEQ ID NO: 136), Helicase (SEQ ID NO: 137), Amylase (SEQ ID NO: 138), Alpha-glucosidase (SEQ ID NO: 139), Transcription factor SP1 (SEQ ID NO: 140), Transcription factor AP-1 (SEQ ID NO: 141), Heat shock factor protein 1 (SEQ ID NO: 142), CCAAT/enhancer-binding protein (C/EBP) beta isoform a (SEQ ID NO: 143), Octamer-binding protein 1 (Oct-1) (SEQ ID NO: 144), Transforming growth factor receptor beta 1 (SEQ ID NO: 145), Platelet-derived growth factor receptor (SEQ ID NO: 146), Epidermal growth factor receptor (SEQ ID NO: 147), Vascular endothelial growth factor receptor (SEQ ID NO: 148), Interleukin 8 receptor alpha (SEQ ID NO: 149), Caveolin (SEQ ID NO: 150), Dynamin (SEQ ID NO: 151), Clathrin heavy chain 1 isoform 1 (SEQ ID NO: 152), Clathrin heavy chain 2 isoform 1 (SEQ ID NO: 153), Clathrin light chain A isoform a (SEQ ID NO: 154), Clathrin light chain B isoform a (SEQ ID NO: 155), Ras-related protein Rab-4A isoform 1 (SEQ ID NO: 156), Ras-related protein Rab-11A (SEQ ID NO: 157), Platelet-derived growth factor (SEQ ID NO: 158), Transforming growth factor-beta3 (SEQ ID NO: 159), Nerve growth factor (SEQ ID NO: 160), Epidermal growth factor (EGF) (SEQ ID NO: 161), GTPase HRas (SEQ ID NO: 162), Cocaine And Amphetamine Regulated Transcript (Chain A) (SEQ ID NO: 163), Protachykinin-1 (SEQ ID NO: 164), Substance P is position 58-68 of Protachykinin-1 (SEQ ID NO: 165), Oxytocin-neurophysin 1 (SEQ ID NO: 166), Oxytocin is position 20-28 of Oxytocin-neurophysin 1 (SEQ ID NO: 167), and Somatostatin (SEQ ID NO: 168). The nucleic acid sequences described herein are shown using standard letter abbreviations for nucleotide bases, as defined in 37 C.F.R. § 1.822. Only one strand of each nucleic acid sequence is shown, but the complementary strand is understood as included in embodiments where it would be appropriate.

DETAILED DESCRIPTION

To fully understand the biology of the brain, different cell types need to be distinguished and defined and, to further study them, vectors that can selectively label and perturb them need to be identified. Tasic, Curr. Opin. Neurobiol. 50, 242-249 (2018); Zeng & Sanes, Nat. Rev. Neurosci. 18, 530-546 (2017). In mouse, recombinase driver lines have been used to great effect to label cell populations that share marker gene expression. Daigle et al., Cell 174, 465-480.e22 (2018); Taniguchi, et al., Neuron 71, 995-1013 (2011); Gong et al., J. Neurosci. 27, 9817-9823 (2007). However, the creation, maintenance, and use of such lines that label cell types with high specificity can be costly, frequently requiring triple transgenic crosses, which yield a low frequency of experimental animals. Furthermore, those tools require germline transgenic animals and thus are not applicable to humans.

Recent advances in single-cell profiling, such as single-cell RNA-seq (Tasic et al., Nature 563, 72-78 (2018); Tasic 2016, Nat Neurosci 19, 335-346) and surveys of neural electrophysiology and morphology (Gouwens 2019, Nat Neurosci 22, 1182-1195), have revealed that many recombinant driver lines label heterogeneous mixtures of cell types, and often include cells from multiple subclasses. For example, the Rbp4-Cre mouse driver line, which is commonly used to label layer 5 (L5) neurons, also labels cells with drastically different connectivity patterns: L5 intratelencephalic (IT, also called cortico-cortical) and pyramidal tract (PT, also called cortico-subcortical) neurons.

The current disclosure provides artificial expression constructs that selectively drive gene expression in targeted central nervous system cell populations. Targeted central nervous system cell populations include: L2/3 IT excitatory cortical neurons; L4 IT excitatory cortical neurons; L5 PT excitatory cortical neurons; L5 PT and L5 ET excitatory cortical neurons; L5 PT and L5 IT excitatory cortical neurons; L6 IT excitatory cortical neurons; L6 CT excitatory cortical neurons; L2/3 and 5 excitatory cortical neurons; L2/3 IT, L4 IT, L5 IT, L5 NP, L5 PT, and CR excitatory cortical neurons; pan excitatory and/or broad expression in excitatory cortical neurons; L5 PT excitatory cortical neurons in combination with subcortical populations in the CEAc, the substantia nigra, compact part (or pars compacta, SNc), and (ProS); and L5 PT excitatory cortical neurons in combination with cells within the subiculum, CA1 pyramidal neurons, a subset of dentate gyrus granule cells, scattered striatal neurons, and sparse cerebellar Purkinje cells.

Artificial expression constructs including a promoter; the Grik1_enhScnn1a-2, eHGT_058 h, eHGT_058 m, eHGT_439 m, and/or eHGT_254 h enhancer; and a gene encoding an expression product can lead to selective gene expression in L4 IT excitatory cortical neurons.

Particular examples of artificial expression constructs including a promoter; the mscRE4 enhancer, a concatenated mscRE4, and/or a concatenated mscRE16 enhancer; and a gene encoding an expression product can lead to selective gene expression in L5 PT excitatory cortical neurons. Examples of these expression constructs include T502-057 (vAi3.0), 981 (vAi5.0), 1052 (vAi10.0), CN1818 (vAi128.0), CN2014 (vAi129.0) and vAi130.0.

Artificial expression constructs including a promoter, a concatenated core of the mscRE4 enhancer, and a gene encoding an expression product can lead to selective gene expression in L5 PT and L5 ET excitatory cortical neurons.

Artificial expression constructs including a promoter; the mscRE1, mscRE11, and/or mscRE16 enhancer; and a gene encoding an expression product can lead to selective gene expression in L5 PT and L5 IT excitatory cortical neurons.

Artificial expression constructs including a promoter, the mscRE13 enhancer, and a gene encoding an expression product can lead to selective gene expression in L6 IT excitatory cortical neurons.

Particular examples of artificial expression constructs including a promoter, the mscRE10 enhancer, and a gene encoding an expression product can lead to selective gene expression in L6 CT excitatory cortical neurons. An example includes 995 (vAi15.0).

Artificial expression constructs including a promoter, the eHGT_440 h enhancer, and a gene encoding an expression product can lead to selective gene expression in subtypes of L6b excitatory cortical neurons.

Artificial expression constructs including a promoter, the eHGT_078 h enhancer; and a gene encoding an expression product can lead to selective gene expression in L2/3 IT, L4 IT, L5 IT, L5 NP, and L5 PT excitatory cortical neurons.

Selective expression of a gene encoding an expression product can be achieved in L2/3 IT, L5 IT, and L6b neurons utilizing the 1036 (vAi16.0) artificial expression construct described herein. This construct includes the mscRE10 enhancer.

Selective expression of a gene encoding an expression product can be achieved in L2/3 IT, L5 PT, L6 CT, and L6b neurons utilizing the 988 (vAi7.1), 1010 (vAi6.1), and/or 1011 (vAi7.2) artificial expression constructs described herein. These constructs include the mscRE4 enhancer.

Pan excitatory and/or broad expression in excitatory cortical neurons can be selectively achieved utilizing artificial expression constructs including a promoter; the eHGT_073 h, eHGT_073 m, eHGT_077 h, and/or eHGT_078 m enhancer; and a gene encoding an expression product. In particular embodiments, pan excitatory expression refers to expression in at least four types of cortical excitatory cells with limited to no expression in inhibitory cells and glial cells.

Artificial expression constructs described herein can additionally label other discrete cell types. For example, in addition to L5 PT cells, artificial expression constructs including a promoter, the mscRE4 enhancer, and a gene encoding an expression product can lead to gene expression in subcortical populations in the CEAc, the substantia nigra, compact part (or pars *compacta*, SNc), and (ProS). Similarly, in addition to L5 PT cells, artificial expression constructs including a promoter, a concatenated core of the mscRE4 enhancer, and a gene encoding an expression product can lead to gene expression in the subiculum, CA1 pyramidal neurons, a subset of dentate gyrus granule cells, scattered striatal neurons, and sparse cerebellar Purkinje cells.

As indicated by the proceeding discussion, certain artificial expression constructs disclosed herein include engineered enhancers, for example, concatenated cores of the mscRE4, eHGT_078 h, and eHGT_078 m enhancers as well as concatemers of the mscRE4 and mscRE16 enhancers. In relation to mscRE4, a functional 155 base pair (bp) core of the mscRE4 enhancer (SEQ ID NO: 29) was concatenated (SEQ ID NO: 30) to minimize the size required to drive gene expression. Despite being a 3× concatemer, SEQ ID NO: 30 is shorter in length than the original mscRE4 enhancer (SEQ ID NO: 28, which includes 555 bp). When used to construct an artificial expression construct, such as an rAAV, such concatemers allow more room for cargo genes linked to the enhancer, which is highly desirable, for example, in gene therapy vectors. For instance, many therapeutic cargo genes are too big to fit in an AAV vector design, so space (length of sequence) is at a premium.

As will be described in more detail throughout the disclosure, particular artificial expression constructs disclosed herein include T502-050, T502-054, vAi34.0, vAi33.2, vAi45.0, vAi1.0, T502-057, T502-059, TG978, TG981, TG988, TG995, TG996, TG997, TG999, TG1002, TG1010, TG1011, TG1021, TG1036, TG1037, TG1038, TG1046, TG1047, TG1048, TG1049, TG1050, TG1052, CN1402, CN1457, CN1818, CN1416, CN1452, CN1461, CN1454, CN1456, CN1772, CN1427, CN1466, CN1954, CN1955, CN2137, CN2139, and CN2014.

Aspects of the disclosure are now described with the following additional options and detail: (i) Artificial Expression Constructs & Vectors for Selective Expression of Genes in Selected Cell Types; (ii) Compositions for Administration (iii) Cell Lines Including Artificial Expression Constructs; (iv) Transgenic Animals; (v) Methods of Use; (vi) Kits and Commercial Packages; (vii) Exemplary Embodiments; (viii) Experimental Examples; and (ix) Closing Paragraphs.

(i) ARTIFICIAL EXPRESSION CONSTRUCTS & VECTORS FOR SELECTIVE EXPRESSION OF GENES IN SELECTED Cell Types Artificial expression constructs disclosed herein include (i) an enhancer sequence that leads to selective expression of a coding sequence within a targeted central nervous system cell type, (ii) a coding sequence that is expressed, and (iii) a promoter. The expression construct can also include other regulatory elements if necessary or beneficial.

In particular embodiments, an "enhancer" or an "enhancer element" is a cis-acting sequence that increases the level of transcription associated with a promoter and can function in either orientation relative to the promoter and the coding sequence that is to be transcribed and can be located upstream or downstream relative to the promoter or the coding sequence to be transcribed. There are art-recognized methods and techniques for measuring function(s) of enhancer element sequences. Particular examples of enhancer sequences utilized within artificial expression constructs disclosed herein include mscRE1, mscRE3, mscRE4, a concatemer of the mscRE4 core, mscRE10, mscRE11, mscRE12, mscRE13, mscRE16, a concatemer of mscRE16, Grik1_enhScnn1a-2, eHGT_058 h, eHGT_058 m, eHGT_073 h, eHGT_073 m, eHGT_075 h, eHGT_077 h, eHGT_078 h, a concatemer of eHGT_078 h core, eHGT_078 m, a concatemer of eHGT_078 m core, eHGT_439 m, eHGT_440 h, and eHGT_254 h.

In particular embodiments, a targeted central nervous system cell type enhancer is an enhancer that is uniquely or predominantly utilized by the targeted central nervous system cell type. A targeted central nervous system cell type enhancer enhances expression of a gene in the targeted central nervous system cell type but does not substantially direct expression of genes in other non-targeted cell types, thus having neural specific transcriptional activity.

When a coding sequence is selectively expressed in selected neural cells and is not substantially expressed in other neural cell types, the product of the coding sequence is preferentially expressed in the selected cell type. In particular embodiments, preferential expression is greater than 50% expression as compared to a reference cell type; greater than 60% expression as compared to a reference cell type; greater than 70% expression as compared to a reference cell type; greater than 80% expression as compared to a reference cell type; or greater than 90% expression as compared to a reference cell type. In particular embodiments, a reference cell type refers to non-targeted neural cells. The non-targeted neural cells can be within the same anatomical structure as the targeted cells and/or can project to a common anatomical area. In particular embodiments, a reference cell type is within an anatomical structure that is adjacent to an anatomical structure that includes the targeted cell type. In particular embodiments, a reference cell type is a non-targeted neural cell with a different gene expression profile than the targeted cells.

In particular embodiments, the product of the coding sequence may be expressed at low levels in non-selected cell types, for example at less than 1% or 1%, 2%, 3%, 5%, 10%, 15% or 20% of the levels at which the product is expressed in selected neural cells. In particular embodiments, the targeted central nervous system cell type is the only cell type that expresses the right combination of transcription factors that bind an enhancer disclosed herein to drive gene expression. Thus, in particular embodiments, expression occurs exclusively within the targeted cell type.

In particular embodiments, targeted cell types (e.g. neural, neuronal, and/or non-neuronal) can be identified based on transcriptional profiles, such as those described in Tasic et al., 2018 Nature, and Hodge et al., Nature 573, 61-68 (2019). Human cell types are further defined in an ontological framework defined at bioontology.org. For reference, the following description of neural cell types and distinguishing features is also provided:

The cortical glutamatergic neuron class. Glutamatergic neurons (also called excitatory neurons) generate the neurotransmitter glutamate, which is excitatory (promotes firing) when received by neurons with ionotropic receptors and is modulatory when received by neurons expressing metabotropic receptors. Most cortical glutamatergic neurons project outside of their resident area (defined as the location of the primary cell body, including the nucleus), and genetic markers have been correlated with these projection properties.

Cortical glutamatergic neuron subclasses. Subclasses of glutamatergic neurons are defined both by the layer in which the neuronal cell body (including the nucleus) resides, as well as the major projection pattern of these neurons. In mouse, glutamatergic neurons are found in layer (L) 1, L2/3, L4, L5, L6, and in the cortical subplate (also called L6b). In human, glutamatergic neurons are found in L2, L3, L4, L5, L6, and L6b. In mouse, L2/3 is often considered a single layer, while in the human cortex layers 2 and 3 are distinct. Intratelencephalic (IT, also called cortico-cortical) neurons project primarily from cortical cell bodies to other adjacent or distant cortical regions. Corticothalamic (CT) neurons project primarily from the cortex to the thalamus. Pyramidal tract (PT, also called corticofugal or extratelencephalic neurons) project primarily from cortex to a variety of subcortical targets, usually from Layer 5 of the cortex. Near-projecting (NP) neurons appear to have only local projections within their cortical region of residence.

In the mouse, the projection and layer categories intersect in specific patterns that define glutamatergic neuron subclasses: For IT neurons: L2/3 IT, L4 IT, L5 IT, L6 IT; for CT neurons, L6 CT; for PT neurons, L5 PT; and for NP neurons, L5/6 NP (found in both layers in some regions). Projections of the L6b subclass of cells are not yet clearly defined, although projections from L6b to local targets as well as cortico-cortical projections to the anterior cingulate and subcortical projections to the thalamus have been observed. In mouse, there is also a highly distinct type of neurons that stands on its own: CR-Lhx5 cells correspond to Cajal-Retzius (CR) cells based on their location in L1 and expression of known Cajal-Retzius markers, such as Trp73, Lhx5 and Reln.

In the human cortex, long range cortical and subcortical projections are difficult to ascertain directly. However, similar patterns of cell types are observed based on layer position and molecular correspondence to the projection classes seen in the mouse. Layer 4 cells tend to receive input from other cortical structures through the expression of specific genes such as RORB, by the lack of projection neurons, and through a granular cytoarchitecture usually visualized by nuclear markers such as DAPI.

Summary of Cortical Glutamatergic Subclasses:

- All: Express glutamate transmitters Slc17a6 and/or Slc17a7. They all express Snap25 and lack expression of Gad1/Gad2 and lack expression of Slc1A3.
- L2/3 IT: Primarily reside in Layer 2/3 and have mainly intratelencephalic (cortico-cortical) projections.
- L4 IT: Primarily reside in Layer 4 and mainly have either local or intratelencephalic (cortico-cortical) projections.
- L5 IT: Primarily reside in Layer 5 and have mainly intratelencephalic (cortico-cortical) projections. Also called L5a.
- L5 PT: Primarily reside in Layer 5 and have mainly cortico-subcortical (pyramidal tract or corticofugal) projections. Also called L5b or L5 CF (corticofugal) or L5 ET (extratelencephalic). This subclass includes cells that are located in the primary motor cortex and neighboring areas and are corticospinal projection neurons, which are associated with motor neuron/movement disorders, such as ALS. This subclass includes thick-tufted pyramidal neurons, including distinctive subtypes found only in specialized regions, e.g. Betz cells, Meynert cells, and von Economo cells.
- L5 NP: Primarily reside in Layer 5 and have mainly nearby projections.
- L6 CT: Primarily reside in Layer 6 and have mainly cortico-thalamic projections.
- L6 IT: Primarily reside in Layer 6 and have mainly intratelencephalic (cortico-cortical) projections. Included in this subclass are L6 IT Car3 cells, which are highly similar to intracortical-projecting cells in the claustrum.
- L6b: Primarily reside in the cortical subplate (L6b), with local (near the cell body) projections and some cortico-cortical projections from VISp to anterior cingulate, and cortico-subcortical projections to the thalamus.
- CR: A distinct subclass defined by a single type in L1, Cajal-Retzius cells express distinct molecular markers Lhx5 and Trp73.

Within each subclass, differentially expressed genes define multiple distinct and experimentally targetable cell types. For example, within L2/3 IT cells in the primary visual cortex, 3 distinct cell types have been observed: L2/3 IT VISp Rrad, L2/3 IT VISp Adamts2, and L2/3 IT VISp Agmat, which are identified by the expression of the Rrad, Adamts2, and Agmat genes, respectively. These gene labels are mainly used to distinguish each cell type from related cell types within the cell subclass (in this case, L2/3 IT), and may not represent a single gene that distinguishes the cell type from all other cells in the cortex. Marker genes may need to be applied in a combinatorial fashion to uniquely identify a given cell type.

The cortical GABAergic neuron class. GABAergic neurons (also called inhibitory neurons) generate the neurotransmitter gamma aminobutyric acid (GABA), which inhibits firing of downstream neurons. All cortical GABAergic neurons except one (called Meis2-Adamts19) share many gene expression markers including Thy1 and Scn2b. Meis2-Adamts19 type corresponds to the Meis2-expressing GABAergic neuronal type largely confined to white matter that originates from the embryonic pallial-subpallial boundary. Among GABAergic types, this is the only type that reliably expresses the transcription factor Meis2 mRNA, transcribes the smallest number of genes, and does not express Thy1 and Scn2b.

Summary of Cortical GABAergic Subclasses:

- All: Express GABA synthesis genes Gad1/GAD1 and Gad2/GAD2.
- Lamp5, Sncg, Serpinf1, and Vip: Developmentally derived from neuronal progenitors from the caudal ganglionic eminence (CGE) or preoptic area (POA).
- Sst and Pvalb: Developmentally derived from neuronal progenitors in the medial ganglionic eminence (MGE).
- Lamp5: Found in many cortical layers, especially upper (L1-L2/3), and have mainly neurogliaform and single bouquet morphology.
- Sncg: Found in many cortical layers, and have molecular overlaps with Lamp5 and Vip cells, but inconsistent expression of Lamp5 or Vip, with more consistent expression of Sncg.

Serpinf1: Found in many cortical layers, and have molecular overlaps with Sncg and Vip cells, but inconsistent expression of Sncg or Vip, with more consistent expression of Serpinf1.

Vip: Found in many cortical layers, but especially frequent in upper layers (L1-L4), and highly express the neurotransmitter vasoactive intestinal peptide (Vip).

Sst: Found in many cortical layers, but especially frequent in lower layers (L5-L6). They highly express the neurotransmitter somatostatin (Sst), and frequently block dendritic inputs to postsynaptic neurons. Included in this subclass are sleep-active Sst Chodl neurons (which also express Nos1 and Tacr1) that are highly distinct from other Sst neurons but express some shared marker genes including Sst. In human, SST gene expression is often detected in layer 1 LAMP5+ cells.

Pvalb: Found in many cortical layers, but especially frequent in lower layers (L5-L6). They highly express the calcium-binding protein parvalbumin (Pvalb), express neuropeptide Tact, and frequently dampen the output of postsynaptic neurons. Most fast-spiking inhibitory cells express Pvalb strongly. Included in this subclass are chandelier cells, which have distinct, chandelier-like morphology and express the markers Cpne5 and Vipr2 in mouse, and NOG and UNC5B in human.

Meis2: A distinct subclass defined by a single type, only cortical GABAergic type that expresses Meis2 gene, and does not express some other genes that are expressed by all other cortical GABAergic types (for example, Thy1 and Scn2b). This type is found in L6b and subcortical white matter.

Cells located in the central nucleus of the amygdala (CEA, which includes CEAc) are involved in pain, anxiety, and fear processing. Cells in the substantia nigra compact part (SNc, also called pars compacta) are located in the midbrain, are involved in motor control, and are adversely affected in Parkinson's disease. Cells in the prosubiculum (ProS) are located between the hippocampus CA1 region and the subiculum.

The subiculum is the most inferior component of the hippocampal formation. It lies between the entorhinal cortex and the CA1 subfield of the hippocampus proper. CA1 pyramidal neurons send their axons to the subiculum and deep layers of the entorhinal cortex. Granule cells within the dentate gyrus receive excitatory neuron input from the entorhinal cortex and send excitatory output to the hippocampal CA3 region via mossy fibers. Cell bodies of striatal neurons are located within the subcortical basal ganglia of the forebrain. Purkinje cells send inhibitory projections to the deep cerebellar nuclei, and constitute the dominant, if not sole output of all motor coordination in the cerebellar cortex.

Non-neuronal Subclasses:

Astrocytes: Neuroectoderm-derived glial cells which express the marker Aqp4 and often GFAP, but do not express neuronal marker SNAP25. They can have a distinct star-shaped morphology and are involved in metabolic support of other cells in the brain. Multiple astrocyte morphologies are observed in mouse and human Oligodendrocytes: Neuroectoderm-derived glial cells, which express the marker Sox10. This category includes oligodendrocyte precursor cells (OPCs). Oligodendrocytes are the subclass that is primarily responsible for myelination of neurons.

VLMCs: Vascular leptomeningeal cells (VLMCs) are part of the meninges that surround the outer layer of the cortex and express the marker genes Lum and Col1a1.

Pericytes: Blood vessel-associated cells, also called mural cells, that express the marker genes Kcnj8 and Abcc9. Pericytes wrap around endothelial cells and are important for regulation of capillary blood flow and are involved in blood-brain barrier permeability.

SMCs: Specialized smooth-muscle cells, also called mural cells, which are blood vessel-associated cells that express the marker gene Acta2. SMCs cover arterioles in the brain and are involved in blood-brain barrier permeability.

Endothelial: Cells that line blood vessels of the brain. Endothelial cells express the markers Tek and PDGF-B.

Microglia: hematopoietic-derived immune cells, which are brain-resident macrophages, and perivascular macrophages (PVMs) that may be transitionally associated with brain tissue, or included as a biproduct of brain dissection methods. Microglia are known to express Cx3cr1, Tmem119, and PTPRC (CD45).

In particular embodiments, a coding sequence is a heterologous coding sequence that encodes an effector element. An effector element is a sequence that is expressed to achieve, and that in fact achieves, an intended effect. Examples of effector elements include reporter genes/proteins and functional genes/proteins.

Exemplary reporter genes/proteins include those expressed by Addgene ID #s 83894 (pAAV-hDlx-Flex-dTomato-Fishell_7), 83895 (pAAV-hDlx-Flex-GFP-Fishell_6), 83896 (pAAV-hDlx-GiDREADD-dTomato-Fishell-5), 83898 (pAAV-mDlx-ChR2-mCherry-Fishell-3), 83899 (pAAV-mDlx-GCaMP6f-Fishell-2), 83900 (pAAV-mDlx-GFP-Fishell-1), and 89897 (pcDNA3-FLAG-mTET2 (N500)). Exemplary reporter genes particularly can include those which encode an expressible fluorescent protein, or expressible biotin; blue fluorescent proteins (e.g. eBFP, eBFP2, Azurite, mKalamal, GFPuv, Sapphire, T-sapphire); cyan fluorescent proteins (e.g. eCFP, Cerulean, CyPet, AmCyanl, Midoriishi-Cyan, mTurquoise); green fluorescent proteins (e.g. GFP, GFP-2, tagGFP, turboGFP, EGFP, Emerald, Azami Green, Monomeric Azami Green (mAzami-green), CopGFP, AceGFP, avGFP, ZsGreenl, Oregon Green™ (Thermo Fisher Scientific)); Luciferase; orange fluorescent proteins (mOrange, mKO, Kusabira-Orange, Monomeric Kusabira-Orange, mTangerine, tdTomato, dTomato); red fluorescent proteins (mKate, mKate2, mPlum, DsRed monomer, mCherry, mRuby, mRFP1, DsRed-Express, DsRed2, DsRed-Monomer, HcRed-Tandem, HcRedl, AsRed2, eqFP611, mRaspberry, mStrawberry, Jred, Texas Red™ (Thermo Fisher Scientific)); far red fluorescent proteins (e.g., mPlum and mNeptune); yellow fluorescent proteins (e.g., YFP, eYFP, Citrine, SYFP2, Venus, YPet, PhiYFP, ZsYellowl); and tandem conjugates.

GFP is composed of 238 amino acids (26.9 kDa), originally isolated from the jellyfish *Aequorea victoria/Aequorea aequorea/Aequorea forskalea* that fluoresces green when exposed to blue light. The GFP from *A. victoria* has a major excitation peak at a wavelength of 395 nm and a minor one at 475 nm. Its emission peak is at 509 nm which is in the lower green portion of the visible spectrum. The GFP from the sea pansy (*Renilla reniformis*) has a single major excitation peak at 498 nm. Due to the potential for widespread usage and the evolving needs of researchers, many different mutants of GFP have been engineered. The first major improvement was a single point mutation (S65T) reported in 1995 in Nature by Roger Tsien. This mutation dramatically improved the spectral characteristics of GFP, resulting in increased fluorescence, photostability and a shift of the major excitation peak to 488 nm with the peak emission kept at 509 nm. The addition of the 37° C. folding efficiency (F64L) point mutant to this scaffold yielded enhanced GFP (EGFP). EGFP has an extinction coefficient (denoted ε), also known as its optical cross section of 9.13x10-21 $m^2$/molecule, also quoted as 55,000 L/(mol·cm). Superfolder GFP, a series of mutations that allow GFP to rapidly fold and mature even when fused to poorly folding peptides, was reported in 2006.

The "yellow fluorescent protein" (YFP) is a genetic mutant of green fluorescent protein, derived from *Aequorea victoria*. Its excitation peak is 514 nm and its emission peak is 527 nm.

Exemplary functional molecules include functioning ion transporters, cellular trafficking proteins, enzymes, transcription factors, neurotransmitters, calcium reporters, channel rhodopsins, guide RNA, nucleases, or designer receptors exclusively activated by designer drugs (DREADDs).

Ion transporters are transmembrane proteins that mediate transport of ions across cell membranes. These transporters are pervasive throughout most cell types and important for regulating cellular excitability and homeostasis. Ion transporters participate in numerous cellular processes such as action potentials, synaptic transmission, hormone secretion, and muscle contraction. Many important biological processes in living cells involve the translocation of cations, such as calcium (Ca2+), potassium (K+), and sodium (Na+) ions, through such ion channels. In particular embodiments, ion transporters include voltage gated sodium channels (e.g., SCN1A), potassium channels (e.g., KCNQ2), and calcium channels (e.g. CACNA1C)).

Exemplary enzymes, transcription factors, receptors, membrane proteins, cellular trafficking proteins, signaling molecules, and neurotransmitters include enzymes such as lactase, lipase, helicase, alpha-glucosidase, amylase; transcription factors such as SP1, AP-1, Heat shock factor protein 1, C/EBP (CCAA-T/enhancer binding protein), and Oct-1; receptors such as transforming growth factor receptor beta 1, platelet-derived growth factor receptor, epidermal growth factor receptor, vascular endothelial growth factor receptor, and interleukin 8 receptor alpha; membrane proteins, cellular trafficking proteins such as clathrin, dynamin, caveolin, Rab-4A, and Rab-11A; signaling molecules such as nerve growth factor (NGF), platelet-derived growth factor (PDGF), transforming growth factor β (TGFβ), epidermal growth factor (EGF), GTPase and HRas; and neurotransmitters such as cocaine and amphetamine regulated transcript, substance P, oxytocin, and somatostatin.

In particular embodiments, functional molecules include reporters of neural function and states such as calcium reporters. Intracellular calcium concentration is an important predictor of numerous cellular activities, which include neuronal activation, muscle cell contraction and second messenger signaling. A sensitive and convenient technique to monitor the intracellular calcium levels is through the genetically encoded calcium indicator (GECI). Among the GECIs, green fluorescent protein (GFP) based calcium sensors named GCaMPs are efficient and widely used tools. The GCaMPs are formed by fusion of M13 and calmodulin protein to N- and C-termini of circularly permutated GFP. Some GCaMPs yield distinct fluorescence emission spectra (Zhao et al., Science, 2011, 333(6051): 1888-1891). Exemplary GECIs with green fluorescence include GCaMP3, GCaMP5G, GCaMP6s, GCaMP6m, GCaMP6f, jGCaMP7s, jGCaMP7c, jGCaMP7b, and jGCaMP7f. Furthermore, GECIs with red fluorescence include jRGECO1a and jRGECO1b. AAV products containing GECIs are commercially available. For example, Vigene Biosciences provides AAV products including AAV8-CAG-GCaMP3 (Cat. No:BS4-CX3AAV8), AAV8-Syn-FLEX-GCaMP6s-WPRE (Cat. No: BS1-NXSAAV8), AAV8-Syn-FLEX-GCaMP6s-WPRE (Cat. No: BS1-NXSAAV8), AAV9-CAG-FLEX-GCaMP6m-WPRE (Cat. No: BS2-CXMAAV9), AAV9-Syn-FLEX-jGCaMP7s-WPRE (Cat. No: BS12-NXSAAV9), AAV9-CAG-FLEX-jGCaMP7f-WPRE (Cat. No: BS12-CXFAAV9), AAV9-Syn-FLEX-jGCaMP7b-WPRE (Cat. No: BS12-NXBAAV9), AAV9-Syn-FLEX-jGCaMP7c-WPRE (Cat. No: BS12-NXCAAV9), AAV9-Syn-FLEX-NES-jRGECO1a-WPRE (Cat. No: BS8-NXAAAV9), and AAV8-Syn-FLEX-NES-jRCaMP1b-WPRE (Cat. No: BS7-NXBAAV8).

In particular embodiments calcium reporters include the genetically encoded calcium indicators GECI, NTnC; Myosin light chain kinase, GFP, Calmodulin chimera; Calcium indicator TN-XXL; BRET-based auto-luminescent calcium indicator; and/or Calcium indicator protein OeNL(Ca2+)-18u).

In particular embodiments, functional molecules include modulators of neuronal activity like channel rhodopsins (e.g., channelopsin-1, channelrhodopsin-2, and variants thereof). Channelrhodopsins are a subfamily of retinylidene proteins (rhodopsins) that function as light-gated ion channels. In addition to channelrhodopsin 1 (ChR1) and channelrhodopsin 2 (ChR2), several variants of channelrhodopsins have been developed. For example, Lin et al. (*Biophys J,* 2009, 96(5): 1803-14) describe making chimeras of the transmembrane domains of ChR1 and ChR2, combined with site-directed mutagenesis. Zhang et al. (*Nat Neurosci,* 2008, 11(6): 631-3) describe VChR1, which is a red-shifted channelrhodopsin variant. VChR1 has lower light sensitivity and poor membrane trafficking and expression. Other known channelrhodopsin variants include the ChR2 variant described in Nagel, et al., *Proc Natl Acad Sci USA,* 2003, 100(24): 13940-5), ChR2/H134R (Nagel, G., et al., *Curr Biol,* 2005, 15(24): 2279-84), and ChD/ChEF/ChIEF (Lin, J. Y., et al., *Biophys J,* 2009, 96(5): 1803-14), which are activated by blue light (470 nm) but show no sensitivity to orange/red light. Additional variants are described in Lin, *Experimental Physiology,* 2010, 96.1: 19-25 and Knopfel et al., *The Journal of Neuroscience,* 2010, 30(45): 14998-15004).

In particular embodiments, functional molecules include DNA and RNA editing tools such CRISPR/CAS (e.g., guide RNA and a nuclease, such as Cas, Cas9 or cpf1). Functional molecules can also include engineered Cpf1s such as those described in US 2018/0030425, US 2016/0208243, WO/2017/184768 and Zetsche et al. (2015) *Cell* 163: 759-771; single gRNA (see e.g., Jinek et al. (2012) Science 337:816-821; Jinek et al. (2013) eLife 2:e00471; Segal (2013) eLife 2:e00563) or editase, guide RNA molecules or homologous recombination donor cassettes.

Additional effector elements include Cre, iCre, dgCre, FlpO, and tTA2. iCre refers to a codon-improved Cre. dgCre refers to an enhanced GFP/Cre recombinase fusion gene with an N terminal fusion of the first 159 amino acids of the *Escherichia coli* K-12 strain chromosomal dihydrofolate reductase gene (DHFR or folA) harboring a G67S mutation and modified to also include the R12Y/Y100I destabilizing domain mutation. FlpO refers to a codon-optimized form of FLPe that greatly increases protein expression and FRT recombination efficiency in mouse cells. Like the Cre/LoxP system, the FLP/FRT system has been widely used for gene expression (and generating conditional knockout mice, mediated by the FLP/FRT system). tTA2 refers to tetracycline transactivator.

Exemplary expressible elements are expression products that do not include effector elements, for example, a non-functioning or defective protein. In particular embodiments, expressible elements can provide methods to study the effects of their functioning counterparts. In particular embodiments, expressible elements are non-functioning or defective based on an engineered mutation that renders them non-functioning. In these aspects, non-expressible elements are as similar in structure as possible to their functioning counterparts.

Exemplary self-cleaving peptides include the 2A peptides which lead to the production of two proteins from one mRNA. The 2A sequences are short (e.g., 20 amino acids), allowing more use in size-limited constructs. Particular examples include P2A, T2A, E2A, and F2A. In particular embodiments, the expression constructs include an internal ribosome entry site (IRES) sequence. IRES allow ribosomes to initiate translation at a second internal site on a mRNA molecule, leading to production of two proteins from one mRNA.

Coding sequences encoding molecules (e.g., RNA, proteins) described herein can be obtained from publicly available databases and publications. Coding sequences can further include various sequence polymorphisms, mutations, and/or sequence variants wherein such alterations do not affect the function of the encoded molecule. The term "encode" or "encoding" refers to a property of sequences of nucleic acids, such as a vector, a plasmid, a gene, cDNA, mRNA, to serve as templates for synthesis of other molecules such as proteins.

The term "gene" may include not only coding sequences but also regulatory regions such as promoters, enhancers, and termination regions. The term further can include all introns and other DNA sequences spliced from the mRNA transcript, along with variants resulting from alternative splice sites. The sequences can also include degenerate codons of a reference sequence or sequences that may be introduced to provide codon preference in a specific organism or cell type.

Promoters can include general promoters, tissue-specific promoters, cell-specific promoters, and/or promoters specific for the cytoplasm. Promoters may include strong promoters, weak promoters, constitutive expression promoters, and/or inducible promoters. Inducible promoters direct expression in response to certain conditions, signals or cellular events. For example, the promoter may be an inducible promoter that requires a particular ligand, small molecule, transcription factor or hormone protein in order to effect transcription from the promoter. Particular examples of promoters include minBglobin, CMV, minCMV, a mutated minCMV, SV40 immediately early promoter, the Hsp68 minimal promoter (proHSP68), and the Rous Sarcoma Virus (RSV) long-terminal repeat (LTR) promoter. Minimal promoters have no activity to drive gene expression on their own but can be activated to drive gene expression when linked to a proximal enhancer element.

In particular embodiments, expression constructs are provided within vectors. The term vector refers to a nucleic acid molecule capable of transferring or transporting another nucleic acid molecule, such as an expression construct. The transferred nucleic acid is generally linked to, e.g., inserted into, the vector nucleic acid molecule. A vector may include sequences that direct autonomous replication in a cell or may include sequences that permit integration into host cell DNA. Useful vectors include, for example, plasmids (e.g., DNA plasmids or RNA plasmids), transposons, cosmids, bacterial artificial chromosomes, and viral vectors.

Viral vector is widely used to refer to a nucleic acid molecule that includes virus-derived nucleic acid elements that facilitate transfer and expression of non-native nucleic acid molecules within a cell. The term adeno-associated viral vector refers to a viral vector or plasmid containing structural and functional genetic elements, or portions thereof, that are primarily derived from AAV. The term "retroviral vector" refers to a viral vector or plasmid containing structural and functional genetic elements, or portions thereof, that are primarily derived from a retrovirus. The term "lentiviral vector" refers to a viral vector or plasmid containing structural and functional genetic elements, or portions thereof, that are primarily derived from a lentivirus, and so on. The term "hybrid vector" refers to a vector including structural and/or functional genetic elements from more than one virus type.

Adenovirus. "Adenovirus vectors" refer to those constructs containing adenovirus sequences sufficient to (a) support packaging of an expression construct and (b) to express a coding sequence that has been cloned therein in a sense or antisense orientation. A recombinant Adenovirus vector includes a genetically engineered form of an adenovirus. Knowledge of the genetic organization of adenovirus, a 36 kb, linear, double-stranded DNA virus, allows substitution of large pieces of adenoviral DNA with foreign sequences up to 7 kb. In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification.

Adenovirus is particularly suitable for use as a gene transfer vector because of its mid-sized genome, ease of manipulation, high titer, wide target-cell range, and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut-off. The products of the late genes, including the majority of the viral capsid proteins, are expressed only after significant processing of a single primary transcript issued by the major late promoter (MLP). The MLP is particularly efficient during the late phase of infection, and all the mRNAs issued from this promoter possess a 5'-tripartite leader (TPL) sequence which makes them preferred mRNAs for translation.

Other than the requirement that an adenovirus vector be replication defective, or at least conditionally defective, the nature of the adenovirus vector is not believed to be crucial to the successful practice of particular embodiments disclosed herein. The adenovirus may be of any of the 42 different known serotypes or subgroups A-F. In particular embodiments, adenovirus type 5 of subgroup C is the preferred starting material in order to obtain a conditional replication-defective adenovirus vector for use in particular embodiments, since Adenovirus type 5 is a human adenovirus about which a great deal of biochemical and genetic information is known, and it has historically been used for most constructions employing adenovirus as a vector.

As indicated, the typical vector is replication defective and will not have an adenovirus E1 region. Thus, it will be most convenient to introduce the polynucleotide encoding the gene of interest at the position from which the E1-coding sequences have been removed. However, the position of insertion of the construct within the adenovirus sequences is not critical. The polynucleotide encoding the gene of interest may also be inserted in lieu of a deleted E3 region in E3 replacement vectors or in the E4 region where a helper cell line or helper virus complements the E4 defect.

Adeno-Associated Virus (AAV) is a parvovirus, discovered as a contamination of adenoviral stocks. It is a ubiquitous virus (antibodies are present in 85% of the US human population) that has not been linked to any disease. It is also classified as a dependovirus, because its replication is dependent on the presence of a helper virus, such as adenovirus. Various serotypes have been isolated, of which AAV-2 is the best characterized. AAV has a single-stranded linear DNA that is encapsidated into capsid proteins VP1, VP2 and VP3 to form an icosahedral virion of 20 to 24 nm in diameter.

The AAV DNA is 4.7 kilobases long. It contains two open reading frames and is flanked by two ITRs. There are two major genes in the AAV genome: rep and cap. The rep gene codes for proteins responsible for viral replications, whereas cap codes for capsid protein VP1-3. Each ITR forms a T-shaped hairpin structure. These terminal repeats are the only essential cis components of the AAV for chromosomal integration. Therefore, the AAV can be used as a vector with all viral coding sequences removed and replaced by the cassette of genes for delivery. Three AAV viral promoters have been identified and named p5, p19, and p40, according to their map position. Transcription from p5 and p19 results in production of rep proteins, and transcription from p40 produces the capsid proteins.

AAVs stand out for use within the current disclosure because of their superb safety profile and because their capsids and genomes can be tailored to allow expression in selected cell populations. scAAV refers to a self-complementary AAV. pAAV refers to a plasmid adeno-associated virus. rAAV refers to a recombinant adeno-associated virus.

Other viral vectors may also be employed. For example, vectors derived from viruses such as vaccinia virus, polioviruses and herpes viruses may be employed. They offer several attractive features for various mammalian cells.

Retrovirus. Retroviruses are a common tool for gene delivery. "Retrovirus" refers to an RNA virus that reverse transcribes its genomic RNA into a linear double-stranded DNA copy and subsequently covalently integrates its genomic DNA into a host genome. Once the virus is integrated into the host genome, it is referred to as a "provirus." The provirus serves as a template for RNA polymerase II and directs the expression of RNA molecules which encode the structural proteins and enzymes needed to produce new viral particles.

Illustrative retroviruses suitable for use in particular embodiments, include: Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV) and lentivirus.

"Lentivirus" refers to a group (or genus) of complex retroviruses. Illustrative lentiviruses include: HIV (human immunodeficiency virus; including HIV type 1, and HIV type 2); visna-maedi virus (VMV); the caprine arthritis-encephalitis virus (CAEV); equine infectious anemia virus (EIAV); feline immunodeficiency virus (FIV); bovine immune deficiency virus (BIV); and simian immunodeficiency virus (SIV). In particular embodiments, HIV based vector backbones (i.e., HIV cis-acting sequence elements) can be used.

A safety enhancement for the use of some vectors can be provided by replacing the U3 region of the 5' LTR with a heterologous promoter to drive transcription of the viral genome during production of viral particles. Examples of heterologous promoters which can be used for this purpose include, for example, viral simian virus 40 (SV40) (e.g., early or late), cytomegalovirus (CMV) (e.g., immediate early), Moloney murine leukemia virus (MoMLV), Rous sarcoma virus (RSV), and herpes simplex virus (HSV) (thymidine kinase) promoters. Typical promoters are able to drive high levels of transcription in a Tat-independent manner. This replacement reduces the possibility of recombination to generate replication-competent virus because there is no complete U3 sequence in the virus production system. In particular embodiments, the heterologous promoter has additional advantages in controlling the manner in which the viral genome is transcribed. For example, the heterologous promoter can be inducible, such that transcription of all or part of the viral genome will occur only when the induction factors are present. Induction factors include one or more chemical compounds or the physiological conditions such as temperature or pH, in which the host cells are cultured.

In particular embodiments, viral vectors include a TAR element. The term "TAR" refers to the "trans-activation response" genetic element located in the R region of lentiviral LTRs. This element interacts with the lentiviral trans-activator (tat) genetic element to enhance viral replication. However, this element is not required in embodiments wherein the U3 region of the 5' LTR is replaced by a heterologous promoter.

The "R region" refers to the region within retroviral LTRs beginning at the start of the capping group (i.e., the start of transcription) and ending immediately prior to the start of the poly(A) tract. The R region is also defined as being flanked by the U3 and U5 regions. The R region plays a role during reverse transcription in permitting the transfer of nascent DNA from one end of the genome to the other.

In particular embodiments, expression of heterologous sequences in viral vectors is increased by incorporating posttranscriptional regulatory elements, efficient polyadenylation sites, and optionally, transcription termination signals into the vectors. A variety of posttranscriptional regulatory elements can increase expression of a heterologous nucleic acid. Examples include the woodchuck hepatitis virus posttranscriptional regulatory element (WPRE; Zufferey et al., 1999, J. Virol., 73:2886); the posttranscriptional regulatory element present in hepatitis B virus (HPRE) (Smith et al., Nucleic Acids Res. 26(21):4818-4827, 1998); and the like (Liu et al., 1995, Genes Dev., 9:1766). In particular embodiments, vectors include a posttranscriptional regulatory element such as a WPRE or HPRE. In particular embodiments, vectors lack or do not include a posttranscriptional regulatory element such as a WPRE or HPRE.

Elements directing the efficient termination and polyadenylation of a heterologous nucleic acid transcript can increase heterologous gene expression. Transcription termination signals are generally found downstream of the polyadenylation signal. In particular embodiments, vectors include a polyadenylation sequence 3' of a polynucleotide encoding a molecule (e.g., protein) to be expressed. The term "poly(A) site" or "poly(A) sequence" denotes a DNA sequence which directs both the termination and polyadenylation of the nascent RNA transcript by RNA polymerase II. Polyadenylation sequences can promote mRNA stability by addition of a poly(A) tail to the 3' end of the coding sequence and thus, contribute to increased translational efficiency. Particular embodiments may utilize BGHpA or SV40 pA. In particular embodiments, a preferred embodiment of an expression construct includes a terminator element. These elements can serve to enhance transcript levels and to minimize read through from the construct into other plasmid sequences.

In particular embodiments, a viral vector further includes one or more insulator elements. Insulators elements may contribute to protecting viral vector-expressed sequences, e.g., effector elements or expressible elements, from integration site effects, which may be mediated by cis-acting elements present in genomic DNA and lead to deregulated expression of transferred sequences (i.e., position effect; see, e.g., Burgess-Beusse et al., *PNAS., USA,* 99:16433, 2002; and Zhan et al., *Hum. Genet.,* 109:471, 2001). In particular embodiments, viral transfer vectors include one or more insulator elements at the 3' LTR and upon integration of the provirus into the host genome, the provirus includes the one or more insulators at both the 5' LTR and 3' LTR, by virtue of duplicating the 3' LTR. Suitable insulators for use in particular embodiments include the chicken β-globin insulator (see Chung et al., *Cell* 74:505, 1993; Chung et al., *PNAS USA* 94:575, 1997; and Bell et al., *Cell* 98:387, 1999), SP10 insulator (Abhyankar et al., *JBC* 282:36143, 2007), or other small CTCF recognition sequences that function as enhancer blocking insulators (Liu et al., *Nature Biotechnology,* 33:198, 2015).

Beyond the foregoing description, a wide range of suitable expression vector types will be known to a person of ordinary skill in the art. These can include commercially available expression vectors designed for general recombinant procedures, for example plasmids that contain one or more reporter genes and regulatory elements required for expression of the reporter gene in cells. Numerous vectors are commercially available, e.g., from Invitrogen, Stratagene, Clontech, etc., and are described in numerous associated guides. In particular embodiments, suitable expression vectors include any plasmid, cosmid or phage construct that is capable of supporting expression of encoded genes in mammalian cell, such as pUC or Bluescript plasmid series.

TABLE 1

Particular embodiments of vectors disclosed herein include:

| Expression Construct Name | Features |
|---|---|
| T502-050 | rAAV: Grik1_enhScnn1a-2-Hsp68-EGFP-WPRE3-BGHpA |
| T502-054 | rAAV: Grik1_enhScnn1a-2-pBGmin-EGFP-WPRE3-BGHpA |
| vAi34.0 | rAAV: Grik1_enhScnn1a-2-pBGmin-FlpO-WPRE3 |
| vAi33.2 | rAAV: Grik1_enhScnn1a-2-pBGmin-EGFP-WPRE3 |
| vAi45.0 | rAAV: mscRE12-pBGmin-FlpO-WPRE-BGHpA |
| vAi1.0 | rAAV: mscRE1-pBGmin-SYFP2-WPRE3-BGHpA |
| T502-057 | scAAV: mscRE4-pBGmin-SYFP2-WPRE3-bGHpA |
| T502-059 | rAAV: mscRE3-pBGmin-SYFP2-WPRE3-BGHpA |
| TG975 | rAAV: mscRE4-pBGmin-IRES2-FlpO-WPRE3 |
| TG978 | rAAV: mscRE4-pBGmin-FlpO-WPRE3 |
| TG979 | rAAV: mscRE4-pBGmin-FlpO-bGHpA |
| TG981 | rAAV: mscRE4-pBGmin-EGFP-WPRE3-bGHpA |
| TG982 | rAAV: mscRE4-pBGmin-IRES2-iCre-bGHpA |
| TG987 | rAAV: mscRE4-pBGmin-IRES2-tTA2-bGHpA |
| TG988 | rAAV: mscRE4-pBGmin-tTA2-bGHpA |
| TG995 | rAAV: mscRE10-pBGmin-EGFP-WPRE3-BGHpA |
| TG996 | rAAV: mscRE11-pBGmin-EGFP-WPRE3-BGHp |
| TG997 | rAAV: mscRE12-pBGmin-EGFP-WPRE3-BGHpA |
| TG999 | rAAV: mscRE13-pBGmin-EGFP-WPRE3-BGHpA |
| TG1002 | rAAV: mscRE16-pBGmin-EGFP-WPRE3-bGHpA |
| TG1009 | rAAV: mscRE4-pBGmin-dgCre-WPRE3-bGHpA |
| TG1010 | rAAV: mscRE4-pBGmin-iCre-WPRE3-bGHpA |
| TG1011 | rAAV: mscRE4-pBGmin-IRES2-tTA2-WPRE3-bGHpA |
| TG1021 | rAAV: mscRE4-pBGmin-Cre-WPRE3-bGHpA |
| TG1022 | rAAV: mscRE4-pBGmin-Cre-i-Cre-WPRE3-bGHpA |
| TG1036 | rAAV: mscRE10-pBGmin-FlpO-WPRE3-BGHpA |
| TG1037 | rAAV: mscRE13-pBGmin-FlpO-WPRE3-BGHpA |
| TG1038 | rAAV_mscRE16- pBGmin-FlpO-WPRE3-bGHpA |
| TG1045 | rAAV: mscRE10-pBGmin-iCre-WPRE3-BGHpA |
| TG1046 | rAAV: mscRE13-pBGmin-iCre-WPRE3-BGHpA |
| TG1047 | rAAV: mscRE16-pBGmin-iCre-WPRE3-bGHpA |
| TG1048 | rAAV: mscRE10-pBGmin-tTA2-WPRE3-BGHpA |
| TG1049 | rAAV: mscRE13-pBGmin-tTA2-WPRE3-BGHpA |
| TG1050 | rAAV: mscRE16- pBGmin-tTA2-WPRE3-bGHpA |
| TG1052 | rAAV: 4XmscRE16-pBGmin-EGFP-WPRE3-bGHpA |
| CN1402 | rAAV: eHGT_058h-minBglobin-SYFP2-WPRE3-BGHpA |
| CN1416 | rAAV: eHGT_058m-minBglobin-SYFP2-WPRE3-BGHpA |
| CN1427 | rAAV: mscRE4(4x)-minBglobin-tdTomato-WPRE3-BGHpA |
| CN1452 | rAAV: eHGT_073h-minBglobin-SYFP2-WPRE3-BGHpA |
| CN1454 | rAAV: eHGT_075h-minBglobin-SYFP2-WPRE3-BGHpA |
| CN1456 | rAAV: eHGT_077h-minBglobin-SYFP2-WPRE3-BGHpA |
| CN1457 | rAAV: eHGT_078h-minBglobin-SYFP2-WPRE3-BGHpA |
| CN1461 | rAAV: eHGT_073m-minBglobin-SYFP2-WPRE3-BGHpA |
| CN1466 | rAAV: eHGT_078m-minBglobin-SYFP2-WPRE3-BGHpA |
| CN1772 | rAAV: hsA2-eHGT_254h-minRho-SYFP2-WPRE3-BGHpA |

TABLE 1-continued

| Particular embodiments of vectors disclosed herein include: | |
|---|---|
| Expression Construct Name | Features |
| CN1818 | rAAV: 3xCore-mscRE4-minCMV-SYFP2-WPRE3-bGHpA |
| CN1954 | rAAV: hsA2-eHGT 078h(3xCore)-minRho-SYFP2-WPRE3-BGHpA |
| CN1955 | rAAV: hsA2-eHGT 078m(3xCore)-minRho-SYFP2-WPRE3-BGHpA |
| CN2014 | rAAV: mscRE4-minCMV-SYFP2-WPRE3-BGHpA |
| CN2137 | rAAV: eHGT__440h-minBglobin-SYFP2-WPRE3-BGHpAv |
| CN2139 | rAAV: eHGT__439m-minBglobin-SYFP2-WPRE3-BGHpA |

In particular embodiments vectors (e.g., AAV) with capsids that cross the blood-brain barrier (BBB) are selected. In particular embodiments, vectors are modified to include capsids that cross the BBB. Examples of AAV with viral capsids that cross the blood brain barrier include AAV9 (Gombash et al., Front Mol Neurosci. 2014; 7:81), AAVrh.10 (Yang, et al., Mol Ther. 2014; 22(7): 1299-1309), AAV1R6, AAV1R7 (Albright et al., Mol Ther. 2018; 26(2): 510), rAAVrh.8 (Yang, et al., supra), AAV-BR1 (Marchio et al., EMBO Mol Med. 2016; 8(6): 592), AAV-PHP.S (Chan et al., Nat Neurosci. 2017; 20(8): 1172), AAV-PHP.B (Deverman et al., Nat Biotechnol. 2016; 34(2): 204), AAV-PPS (Chen et al., Nat Med. 2009; 15: 1215), and the PHP.eB capsid. The PHP.eB capsid differs from AAV9 such that, using AAV9 as a reference, amino acids starting at residue 586: S-AQ-A (SEQ ID NO: 169) are changed to S-DGT-LAVPFK-A (SEQ ID NO: 170).

AAV9 is a naturally occurring AAV serotype that, unlike many other naturally occurring serotypes, can cross the BBB following intravenous injection. It transduces large sections of the central nervous system (CNS), thus permitting minimally invasive treatments (Naso et al., BioDrugs. 2017; 31(4): 317), for example, as described in relation to clinical trials for the treatment of spinal muscular atrophy (SMA) syndrome by AveXis (AVXS-101, NCT03505099) and the treatment of CLN3 gene-Related Neuronal Ceroid-Lipofuscinosis (NCT03770572).

AAVrh.10, was originally isolated from rhesus macaques and shows low seropositivity in humans when compared with other common serotypes used for gene delivery applications (Selot et al., Front Pharmacol. 2017; 8: 441) and has been evaluated in clinical trials LYS-SAF302, LYSOGENE, and NCT03612869.

AAV1R6 and AAV1R7, two variants isolated from a library of chimeric AAV vectors (AAV1 capsid domains swapped into AAVrh.10), retain the ability to cross the BBB and transduce the CNS while showing significantly reduced hepatic and vascular endothelial transduction.

rAAVrh.8, also isolated from rhesus macaques, shows a global transduction of glial and neuronal cell types in regions of clinical importance following peripheral administration and also displays reduced peripheral tissue tropism compared to other vectors.

AAV-BR1 is an AAV2 variant displaying the NRGTEWD (SEQ ID NO: 171) epitope that was isolated during in vivo screening of a random AAV display peptide library. It shows high specificity accompanied by high transgene expression in the brain with minimal off-target affinity (including for the liver) (Körbelin et al., EMBO Mol Med. 2016; 8(6): 609).

AAV-PHP.S (Addgene, Watertown, MA) is a variant of AAV9 generated with the CREATE method that encodes the 7-mer sequence QAVRTSL (SEQ ID NO: 172), transduces neurons in the enteric nervous system, and strongly transduces peripheral sensory afferents entering the spinal cord and brain stem.

AAV-PHP.B (Addgene, Watertown, MA) is a variant of AAV9 generated with the CREATE method that encodes the 7-mer sequence TLAVPFK (SEQ ID NO: 173). It transfers genes throughout the CNS with higher efficiency than AAV9 and transduces the majority of astrocytes and neurons across multiple CNS regions.

AAV-PPS, an AAV2 variant crated by insertion of the DSPAHPS (SEQ ID NO: 174) epitope into the capsid of AAV2, shows a dramatically improved brain tropism relative to AAV2.

For additional information regarding capsids that cross the blood brain barrier, see Chan et al., Nat. Neurosci. 2017 August: 20(8): 1172-1179.

(ii) COMPOSITIONS FOR ADMINISTRATION

Artificial expression constructs and vectors of the present disclosure (referred to herein as physiologically active components) can be formulated with a carrier that is suitable for administration to a cell, tissue slice, animal (e.g., mouse, non-human primate), or human. Physiologically active components within compositions described herein can be prepared in neutral forms, as freebases, or as pharmacologically acceptable salts.

Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Carriers of physiologically active components can include solvents, dispersion media, vehicles, coatings, diluents, isotonic and absorption delaying agents, buffers, solutions, suspensions, colloids, and the like. The use of such carriers for physiologically active components is well known in the art. Except insofar as any conventional media or agent is incompatible with the physiologically active components, it can be used with compositions as described herein.

The phrase "pharmaceutically-acceptable carriers" refer to carriers that do not produce an allergic or similar untoward reaction when administered to a human, and in particular embodiments, when administered intravenously (e.g. at the retro-orbital plexus).

In particular embodiments, compositions can be formulated for intravenous, intraparenchymal, intraocular, intravitreal, parenteral, subcutaneous, intracerebro-ventricular, intramuscular, intrathecal, intraspinal, intraperitoneal, oral or nasal inhalation, or by direct injection in or application to one or more cells, tissues, or organs.

Compositions may include liposomes, lipids, lipid complexes, microspheres, microparticles, nanospheres, and/or nanoparticles.

The formation and use of liposomes is generally known to those of skill in the art. Liposomes have been developed with improved serum stability and circulation half-times (see, for instance, U.S. Pat. No. 5,741,516). Further, various methods of liposome and liposome like preparations as potential drug carriers have been described (see, for instance U.S. Pat. Nos. 5,567,434; 5,552,157; 5,565,213; 5,738,868; and 5,795,587).

The disclosure also provides for pharmaceutically acceptable nanocapsule formulations of the physiologically active components. Nanocapsules can generally entrap compounds in a stable and reproducible way (Quintanar-Guerrero et al., *Drug Dev Ind Pharm* 24(12):1113-1128, 1998; Quintanar-Guerrero et al., *Pharm Res.* 15(7):1056-1062, 1998; Quintanar-Guerrero et al., *J. Microencapsul.* 15(1):107-119, 1998; Douglas et al., *Crit Rev Ther Drug Carrier Syst* 3(3):233-261, 1987). To avoid side effects due to intracellular polymeric overloading, such ultrafine particles can be designed using polymers able to be degraded in vivo. Biodegradable polyalkyl-cyanoacrylate nanoparticles that meet these requirements are contemplated for use in the present disclosure. Such particles can be easily made, as described in Couvreur et al., *J Pharm Sci* 69(2):199-202, 1980; Couvreur et al., *Crit Rev Ther Drug Carrier Syst.* 5(1)1-20, 1988; zur Muhlen et al., *Eur J Pharm Biopharm,* 45(2):149-155, 1998; Zambaux et al., *J Control Release* 50(1-3):31-40, 1998; and U.S. Pat. No. 5,145,684.

Injectable compositions can include sterile aqueous solutions or dispersions and sterile powders for the extemporaneous preparation of sterile injectable solutions or dispersions (U.S. Pat. No. 5,466,468). For delivery via injection, the form is sterile and fluid to the extent that it can be delivered by syringe. In particular embodiments, it is stable under the conditions of manufacture and storage, and optionally contains one or more preservative compounds against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion, and/or by the use of surfactants. The prevention of the action of microorganisms can be brought about by various antibacterial and/or antifungal agents, for example, parabens, chlorobutanol, phenol, sorbic acid, thimerosal, and the like. In various embodiments, the preparation will include an isotonic agent(s), for example, sugar(s) or sodium chloride. Prolonged absorption of the injectable compositions can be accomplished by including in the compositions of agents that delay absorption, for example, aluminum monostearate and gelatin. Injectable compositions can be suitably buffered, if necessary, and the liquid diluent first rendered isotonic with sufficient saline or glucose.

Dispersions may also be prepared in glycerol, liquid polyethylene glycols, and mixtures thereof and in oils. As indicated, under ordinary conditions of storage and use, these preparations can contain a preservative to prevent the growth of microorganisms.

Sterile compositions can be prepared by incorporating the physiologically active component in an appropriate amount of a solvent with other optional ingredients (e.g., as enumerated above), followed by filtered sterilization. Generally, dispersions are prepared by incorporating the various sterilized physiologically active components into a sterile vehicle that contains the basic dispersion medium and the required other ingredients (e.g., from those enumerated above). In the case of sterile powders for the preparation of sterile injectable solutions, preferred methods of preparation can be vacuum-drying and freeze-drying techniques which yield a powder of the physiologically active components plus any additional desired ingredient from a previously sterile-filtered solution thereof.

Oral compositions may be in liquid form, for example, as solutions, syrups or suspensions, or may be presented as a drug product for reconstitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, or fractionated vegetable oils); and preservatives (e.g., methyl or propyl-p-hydroxybenzoates or sorbic acid). The compositions may take the form of, for example, tablets or capsules prepared by conventional means with pharmaceutically acceptable excipients such as binding agents (e.g., pregelatinized maize starch, polyvinyl pyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). Tablets may be coated by methods well-known in the art.

Inhalable compositions can be delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch.

Compositions can also include microchip devices (U.S. Pat. No. 5,797,898), ophthalmic formulations (Bourlais et al., *Prog Retin Eye Res,* 17(1):33-58, 1998), transdermal matrices (U.S. Pat. Nos. 5,770,219 and 5,783,208) and feedback-controlled delivery (U.S. Pat. No. 5,697,899).

Supplementary active ingredients can also be incorporated into the compositions.

Typically, compositions can include at least 0.1% of the physiologically active components or more, although the percentage of the physiologically active components may, of course, be varied and may conveniently be between 1 or 2% and 70% or 80% or more or 0.5-99% of the weight or volume of the total composition. Naturally, the amount of physiologically active components in each physiologically-useful composition may be prepared in such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of compositions and dosages may be desirable.

In particular embodiments, for administration to humans, compositions should meet sterility, pyrogenicity, and the general safety and purity standards as required by United States Food and Drug Administration (FDA) or other applicable regulatory agencies in other countries.

(iii) CELL LINES INCLUDING ARTIFICIAL EXPRESSION CONSTRUCTS

The present disclosure includes cells including an artificial expression construct described herein. A cell that has been transformed with an artificial expression construct can be used for many purposes, including in neuroanatomical studies, assessments of functioning and/or non-functioning proteins, and drug screens that assess the regulatory properties of enhancers.

A variety of host cell lines can be used, but in particular embodiments, the cell is a mammalian neural cell. In particular embodiments, the enhancer sequence of the artificial expression construct is mscRE1, mscRE3, mscRE4, a concatemer of the mscRE4 core, mscRE10, mscRE11, mscRE12, mscRE13, mscRE16, a concatemer of mscRE16, Grik1_enhScnn1a-2, eHGT_058 h, eHGT_058 m, eHGT_073 h, eHGT_073 m, eHGT_075 h, eHGT_077 h, eHGT_078 h, a concatemer of eHGT_078 h core, eHGT_078 m, a concatemer of eHGT_078 m core, eHGT_439 m, eHGT_440 h, and eHGT_254 h and/or the artificial expression construct includes T502-050, T502-054, vAi34.0, vAi33.2, vAi45.0, vAi1.0, T502-057, T502-059, TG975, TG978, TG979, TG981, TG982, TG987, TG988, TG995, TG996, TG997, TG999, TG1002, TG1009, TG1010, TG1011, TG1021, TG1022, TG1036, TG1037, TG1038, TG1045, TG1046, TG1047, TG1048, TG1049, TG1050, TG1052, CN1402, CN1457, CN1818, CN1416, CN1452, CN1461, CN1454, CN1456, CN1772, CN1427, CN1466, CN1954, CN1955, CN2137, CN2139, and/or CN2014., and the cell line is a human, primate, or murine neural cell. Cell lines which can be utilized for transgenesis in the present disclosure also include primary cell lines derived from living tissue such as rat or mouse brains and organotypic cell cultures, including brain slices from animals such as rats or mice. The PC12 cell line (available from the American Type Culture Collection, ATCC, Manassas, VA) has been shown to express a number of neuronal marker proteins in response to Neuronal Growth Factor (NGF). The PC12 cell line is considered to be a neuronal cell line and is applicable for use with this disclosure. JAR cells (available from ATCC) are a platelet derived cell-line that express some neuronal genes, such as the serotonin transporter gene, and may be used with embodiments described herein.

WO 91/13150 describes a variety of cell lines, including neuronal cell lines, and methods of producing them. Similarly, WO 97/39117 describes a neuronal cell line and methods of producing such cell lines. The neuronal cell lines disclosed in these patent applications are applicable for use in the present disclosure.

In particular embodiments, a "neural cell" refers to a cell or cells located within the central nervous system, and includes neurons and glia, and cells derived from neurons and glia, including neoplastic and tumor cells derived from neurons or glia. A "cell derived from a neural cell" refers to a cell which is derived from or originates or is differentiated from a neural cell.

In particular embodiments, "neuronal" describes something that is of, related to, or includes, neuronal cells. Neuronal cells are defined by the presence of an axon and dendrites. The term "neuronal-specific" refers to something that is found, or an activity that occurs, in neuronal cells or cells derived from neuronal cells, but is not found in or occur in, or is not found substantially in or occur substantially in, non-neuronal cells or cells not derived from neuronal cells, for example glial cells such as astrocytes or oligodendrocytes.

In particular embodiments, non-neuronal cell lines may be used, including mouse embryonic stem cells. Cultured mouse embryonic stem cells can be used to analyze expression of genetic constructs using transient transfection with plasmid constructs. Mouse embryonic stem cells are pluripotent and undifferentiated. These cells can be maintained in this undifferentiated state by Leukemia Inhibitory Factor (LIF). Withdrawal of LIF induces differentiation of the embryonic stem cells. In culture, the stem cells form a variety of differentiated cell types. Differentiation is caused by the expression of tissue specific transcription factors, allowing the function of an enhancer sequence to be evaluated. (See for example Fiskerstrand et al., *FEBS Lett* 458: 171-174, 1999.)

Methods to differentiate stem cells into neuronal cells include replacing a stem cell culture media with a media including basic fibroblast growth factor (bFGF) heparin, an N2 supplement (e.g., transferrin, insulin, progesterone, putrescine, and selenite), laminin and polyornithine. A process to produce myelinating oligodendrocytes from stem cells is described in Hu, et al., 2009, Nat. Protoc. 4:1614-22. Bibel, et al., 2007, *Nat. Protoc.* 2:1034-43 describes a protocol to produce glutamatergic neurons from stem cells while Chatzi, et al., 2009, *Exp. Neurol* 217:407-16 describes a procedure to produce GABAergic neurons. This procedure includes exposing stem cells to all-trans-RA for three days. After subsequent culture in serum-free neuronal induction medium including Neurobasal medium supplemented with B27, bFGF and EGF, 95% GABA neurons develop U.S. Publication No, 2012/0329714 describes use of prolactin to increase neural stem cell numbers while U.S. Publication No. 2012/0308530 describes a culture surface with amino groups that promotes neuronal differentiation into neurons, astrocytes and oligodendrocytes. Thus, the fate of neural stem cells can be controlled by a variety of extracellular factors. Commonly used factors include brain derived growth factor (BDNF; Shetty and Turner, 1998, *J. Neurobiol.* 35:395-425); fibroblast growth factor (bFGF; U.S. Pat. No. 5,766,948; FGF-1, FGF-2); Neurotrophin-3 (NT-3) and Neurotrophin-4 (NT-4); Caldwell, et al., 2001, *Nat. Biotechnol.* 1; 19:475-9); ciliary neurotrophic factor (CNTF); BMP-2 (U.S. Pat. Nos. 5,948,428 and 6,001,654); isobutyl 3-methylxanthine; leukemia inhibitory growth factor (LIF; U.S. Pat. No. 6,103,530); somatostatin; amphiregulin; neurotrophins (e.g., cyclic adenosine monophosphate; epidermal growth factor (EGF); dexamethasone (glucocorticoid hormone); forskolin; GDNF family receptor ligands; potassium; retinoic acid (U.S. Pat. No. 6,395,546); tetanus toxin; and transforming growth factor-α and TGF-β (U.S. Pat. Nos. 5,851,832 and 5,753,506).

In particular embodiments, yeast one-hybrid systems may also be used to identify compounds that inhibit specific protein/DNA interactions, such as transcription factors for the mscRE1, mscRE3, mscRE4, mscRE10, mscRE11, mscRE12, mscRE13, mscRE16, Grik1_enhScnn1a-2, eHGT_058 h, eHGT_058 m, eHGT_073 h, eHGT_073 m, eHGT_075 h, eHGT_077 h, eHGT_078 h, a concatemer of eHGT_078 h core, eHGT_078 m, a concatemer of eHGT_078 m core, eHGT_439 m, eHGT_440 h, and/or eHGT_254 h enhancer.

Transgenic animals are described below. Cell lines may also be derived from such transgenic animals. For example, primary tissue culture from transgenic mice (e.g., also as described below) can provide cell lines with the expression construct already integrated into the genome. (for an example see MacKenzie & Quinn, *Proc Natl Acad Sci USA* 96: 15251-15255, 1999).

(iv) TRANSGENIC ANIMALS

Another aspect of the disclosure includes transgenic animals, the genome or cells of which contain an artificial expression construct including mscRE1, mscRE3, mscRE4, a concatemer of the mscRE4 core, mscRE10, mscRE11, mscRE12, mscRE13, mscRE16, a concatemer of mscRE16, Grik1_enhScnn1a-2, eHGT_058 h, eHGT_058 m, eHGT_073 h, eHGT_073 m, eHGT_075 h, eHGT_077 h, eHGT_078 h, a concatemer of eHGT_078 h core, eHGT_078 m, a concatemer of eHGT_078 m core, eHGT_439 m, eHGT_440 h, and/or eHGT_254 h operatively linked to a heterologous coding sequence. In particular embodiments, the genome or cells of a transgenic animal includes an artificial expression construct including T502-050, T502-054, vAi34.0, vAi33.2, vAi45.0, vAi1.0, T502-057, T502-059, TG975, TG978, TG979, TG981, TG982, TG987, TG988, TG995, TG996, TG997, TG999, TG1002, TG1009, TG1010, TG1011, TG1021, TG1022, TG1036, TG1037, TG1038, TG1045, TG1046, TG1047, TG1048, TG1049, TG1050, TG1052, CN1402, CN1457, CN1818, CN1416, CN1452, CN1461, CN1454, CN1456, CN1772, CN1427, CN1466, CN1954, CN1955, CN2137, CN2139, and/or CN2014.In particular embodiments, when a non-integrating vector is utilized, a transgenic animal includes an artificial expression construct including mscRE1, mscRE3, mscRE4, a concatemer of the mscRE4 core, mscRE10, mscRE11, mscRE12, mscRE13, mscRE16, a concatemer of mscRE16, Grik1_enhScnn1a-2, eHGT_058 h, eHGT_058 m, eHGT_073 h, eHGT_073 m, eHGT_075 h, eHGT_077 h, eHGT_078 h, a concatemer of eHGT_078 h core, eHGT_078 m, a concatemer of eHGT_078 m core, eHGT_439 m, eHGT_440 h, eHGT_254 h and/or T502-050, T502-054, vAi34.0, vAi33.2, vAi45.0, vAi1.0, T502-057, T502-059, TG975, TG978, TG979, TG981, TG982, TG987, TG988, TG995, TG996, TG997, TG999, TG1002, TG1009, TG1010, TG1011, TG1021, TG1022, TG1036, TG1037, TG1038, TG1045, TG1046, TG1047, TG1048, TG1049, TG1050, TG1052, CN1402, CN1457, CN1818, CN1416, CN1452, CN1461, CN1454, CN1456, CN1772, CN1427, CN1466, CN1954, CN1955, CN2137, CN2139, and/or CN2014 within one or more of its cells.

Detailed methods for producing transgenic animals are described in U.S. Pat. No. 4,736,866. Transgenic animals may be of any nonhuman species, but preferably include nonhuman primates (NHPs), sheep, horses, cattle, pigs, goats, dogs, cats, rabbits, chickens, and rodents such as guinea pigs, hamsters, gerbils, rats, mice, and ferrets.

In particular embodiments, construction of a transgenic animal results in an organism that has an engineered construct present in all cells in the same genomic integration site. Thus, cell lines derived from such transgenic animals will be consistent in as much as the engineered construct will be in the same genomic integration site in all cells and hence will suffer the same position effect variegation. In contrast, introducing genes into cell lines or primary cell cultures can give rise to heterologous expression of the construct. A disadvantage of this approach is that the expression of the introduced DNA may be affected by the specific genetic background of the host animal.

As indicated above in relation to cell lines, the artificial expression constructs of this disclosure can be used to genetically modify mouse embryonic stem cells using techniques known in the art. Typically, the artificial expression construct is introduced into cultured murine embryonic stem cells. Transformed ES cells are then injected into a blastocyst from a host mother and the host embryo re-implanted into the mother. This results in a chimeric mouse whose tissues are composed of cells derived from both the embryonic stem cells present in the cultured cell line and the embryonic stem cells present in the host embryo. Usually the mice from which the cultured ES cells used for transgenesis are derived are chosen to have a different coat color from the host mouse into whose embryos the transformed cells are to be injected. Chimeric mice will then have a variegated coat color. As long as the germ-line tissue is derived, at least in part, from the genetically modified cells, then the chimeric mice be crossed with an appropriate strain to produce offspring that will carry the transgene.

In addition to the methods of delivery described above, the following techniques are also contemplated as alternative methods of delivering artificial expression constructs to target cells or selected tissues and organs of an animal, and in particular, to cells, organs, or tissues of a vertebrate mammal: sonophoresis (e.g., ultrasound, as described in U.S. Pat. No. 5,656,016); intraosseous injection (U.S. Pat. No. 5,779,708); microchip devices (U.S. Pat. No. 5,797,898); ophthalmic formulations (Bourlais et al., *Prog Retin Eye Res,* 17(1):33-58, 1998); transdermal matrices (U.S. Pat. Nos. 5,770,219 and 5,783,208); and feedback-controlled delivery (U.S. Pat. No. 5,697,899).

(v) Methods of Use. In particular embodiments, a composition including a physiologically active component described herein is administered to a subject to result in a physiological effect.

In particular embodiments, the disclosure includes the use of the artificial expression constructs described herein to modulate expression of a heterologous gene which is either partially or wholly encoded in a location downstream to that enhancer in an engineered sequence. Thus, there are provided herein methods of use of the disclosed artificial expression constructs in the research, study, and potential development of medicaments for preventing, treating or ameliorating the symptoms of a disease, dysfunction, or disorder.

Particular embodiments include methods of administering to a subject an artificial expression construct that includes SEQ ID NOs: 25-51, 177-178, and/or 188 and/or SEQ ID NOs: 73-114, and/or 179-187 as described herein to drive selective expression of a gene in a selected neural cell type.

Particular embodiments include methods of administering to a subject an artificial expression construct that includes SEQ ID NOs: 25-51, 177-178, and/or 188 and/or SEQ ID NOs: 73-114, and/or 179-187 as described herein to drive selective expression of a gene in a selected neural cell type wherein the subject can be an isolated cell, a network of cells, a tissue slice, an experimental animal, a veterinary animal, or a human.

As is well known in the medical arts, dosages for any one subject depends upon many factors, including the subject's size, surface area, age, the particular compound to be administered, sex, time and route of administration, general health, and other drugs being administered concurrently. Dosages for the compounds of the disclosure will vary, but, in particular embodiments, a dose could be from $10^5$ to $10^{100}$ copies of an artificial expression construct of the disclosure. In particular embodiments, a patient receiving intravenous, intraparenchymal, intraspinal, retro-orbital, or intrathecal administration can be infused with from $10^6$ to $10^{22}$ copies of the artificial expression construct.

An "effective amount" is the amount of a composition necessary to result in a desired physiological change in the subject. Effective amounts are often administered for research purposes. Effective amounts disclosed herein can cause a statistically-significant effect in an animal model or in vitro assay.

The amount of expression constructs and time of administration of such compositions will be within the purview of the skilled artisan having benefit of the present teachings. It is likely, however, that the administration of effective amounts of the disclosed compositions may be achieved by a single administration, such as for example, a single injection of sufficient numbers of infectious particles to provide an effect in the subject. Alternatively, in some circumstances, it may be desirable to provide multiple, or successive administrations of the artificial expression construct compositions or other genetic constructs, either over a relatively short, or a relatively prolonged period of time, as may be determined by the individual overseeing the administration of such compositions. For example, the number of infectious particles administered to a mammal may be $10^7$, $10^8$, $10^9$, $10^{10}$, $10^{11}$, $10^{12}$, $10^{13}$, or even higher, infectious particles/ml given either as a single dose or divided into two or more administrations as may be required to achieve an intended effect. In fact, in certain embodiments, it may be desirable to administer two or more different expression constructs in combination to achieve a desired effect.

In certain circumstances it will be desirable to deliver the artificial expression construct in suitably formulated compositions disclosed herein either by pipette, retro-orbital injection, subcutaneously, intraocularly, intravitreally, parenterally, subcutaneously, intravenously, intraparenchymally, intracerebro-ventricularly, intramuscularly, intrathecally, intraspinally, orally, by oral or nasal inhalation, intraperitoneally, or by direct application or injection to one or more cells, tissues, or organs. The methods of administration may also include those modalities as described in U.S. Pat. Nos. 5,543,158; 5,641,515 and 5,399,363.

(vi) KITS AND COMMERCIAL PACKAGES

Kits and commercial packages contain an artificial expression construct described herein. The expression construct can be isolated. In particular embodiments, the components of an expression product can be isolated from each other. In particular embodiments, the expression product can be within a vector, within a viral vector, within a cell, within a tissue slice or sample, and/or within a transgenic animal. Such kits may further include one or more reagents, restriction enzymes, peptides, therapeutics, pharmaceutical compounds, or means for delivery of the compositions such as syringes, injectables, and the like.

Embodiments of a kit or commercial package will also contain instructions regarding use of the included components, for example, in basic research, electrophysiological research, neuroanatomical research, and/or the research and/or treatment of a disorder, disease or condition.

The Exemplary Embodiments and Experimental Examples below are included to demonstrate particular embodiments of the disclosure. Those of ordinary skill in the art should recognize in light of the present disclosure that many changes can be made to the specific embodiments disclosed herein and still obtain a like or similar result without departing from the spirit and scope of the disclosure.

(vii) EXEMPLARY EMBODIMENTS

1. A concatenated core of an enhancer disclosed herein.
2. A concatenated core of embodiment 1, wherein the core is selected from SEQ ID NOs: 29, 177, and/or 178.
3. The concatenated core of embodiment 1 or 2, wherein the concatenated core includes 2, 3, 4, 5, 6, 7, 8, 9, or 10 copies of SEQ ID NOs: 29, 177, and/or 178.
4. The concatenated core of embodiment 3, including 3 copies of SEQ ID NO: 29.
5. The concatenated core of embodiment 4, including SEQ ID NO: 30.
6. The concatenated core of embodiment 3, including 3 copies of SEQ ID NO: 177.
7. The concatenated core of embodiment 6 including SEQ ID NO: 40.
8. The concatenated core of embodiment 3, including 3 copies of SEQ ID NO: 178.
9. The concatenated core of embodiment 8 including SEQ ID NO: 49.
10. An artificial expression construct including (i) an enhancer selected from mscRE1, mscRE3, mscRE4, mscRE10, mscRE11, mscRE12, mscRE13, mscRE16, Grik1_enhScnn1a-2, eHGT_058 h, eHGT_058 m, eHGT_073 h, eHGT_073 m, eHGT_075 h, eHGT_077 h, eHGT_078 h, eHGT_078 m, eHGT_439 m, eHGT_440 h, eHGT_254 h, and/or a concatemer of any of embodiments 1-8; (ii) a promoter; and (iii) a heterologous encoding sequence.
11. The artificial expression construct of embodiment 10, wherein the heterologous encoding sequence encodes an effector element or an expressible element.
12. The artificial expression construct of embodiment 11, wherein the effector element includes a reporter protein or a functional molecule.
13. The artificial expression construct of embodiment 12, wherein the reporter protein includes a fluorescent protein.
14. The artificial expression construct of embodiment 12, wherein the functional molecule includes a functional ion transporter, enzyme, transcription factor, receptor, membrane protein, cellular trafficking protein, signaling molecule, neurotransmitter, calcium reporter, channel rhodopsin, CRISPR/CAS molecule, editase, guide RNA molecule, homologous recombination donor cassette, or a designer receptor exclusively activated by designer drug (DREADD).
15. The artificial expression construct of embodiment 11, wherein the expressible element includes a non-functional molecule.
16. The artificial expression construct of embodiment 15, wherein the non-functional molecule includes a non-functional ion transporter, enzyme, transcription factor, receptor, membrane protein, cellular trafficking protein, signaling molecule, neurotransmitter, calcium reporter, channel rhodopsin, CRISPR/CAS molecule, editase, guide RNA molecule, homologous recombination donor cassette, or a DREADD.
17. The artificial expression construct of any of embodiments 10-16 including a concatemer of an enhancer selected from mscRE1, mscRE3, mscRE4, mscRE10, mscRE11, mscRE12, mscRE13, mscRE16, Grik1_enhScnn1a-2, eHGT_058 h, eHGT_058 m, eHGT_073 h, eHGT_073 m, eHGT_075 h, eHGT_077 h, eHGT_078 h, eHGT_078 m, eHGT_439 m, eHGT_440 h, and eHGT_254 h.

18. The artificial expression construct of embodiment 17 wherein the concatemer includes 2, 3, 4, 5, 6, 7, 8, 9, or 10 copies of the selected enhancer.
19. The artificial expression construct of embodiment 18 wherein the concatemer includes 3 or 4 copies of mscRE4 or 3 or 4 copies of mscRE16.
20. The artificial expression construct of any of embodiments 10-19, wherein the artificial expression construct is associated with a capsid that crosses the blood brain barrier.
21. The artificial expression construct of embodiment 20, wherein the capsid includes PHP.eB, AAV-BR1, AAV-PHP.S, AAV-PHP.B, or AAV-PPS.
22. The artificial expression construct of any of embodiments 10-21, wherein the expression construct includes or encodes a skipping element.
23. The artificial expression construct of embodiment 22, wherein the skipping element includes a 2A peptide and/or an internal ribosome entry site (IRES).
24. The artificial expression construct of embodiment 23, wherein the 2A peptide includes selected from T2A, P2A, E2A, or F2A.
25. The artificial expression construct of any of embodiments 10-24, wherein the artificial expression construct includes a set of features selected from: an enhancer selected from mscRE1, mscRE3, mscRE4, mscRE10, mscRE11, mscRE12, mscRE13, mscRE16, Grik1_enhScnn1a-2, eHGT_058 h, eHGT_058 m, eHGT_073 h, eHGT_073 m, eHGT_075 h, eHGT_077 h, eHGT_078 h, eHGT_078 m, eHGT_439 m, eHGT_440 h, or eHGT_254 h, and/or a concatemer of any of embodiments 1-9; a promoter selected from pBGmin or minBglobin; an expression product selected from EGFP, SYFP2, IRES2, FlpO, Cre, iCre, dgCre, or tTA2; and a post-regulatory element selected from WPRE3 and/or BGHpA
26. A vector including a concatenated core and/or artificial expression construct of any of embodiments 1-25.
27. A vector including features selected from T502-050, T502-054, vAi34.0, vAi33.2, vAi45.0, vAi1.0, T502-057, T502-059, TG975, TG978, TG979, TG981, TG982, TG987, TG988, TG995, TG996, TG997, TG999, TG1002, TG1009, TG1010, TG1011, TG1021, TG1022, TG1036, TG1037, TG1038, TG1045, TG1046, TG1047, TG1048, TG1049, TG1050, TG1052, 0N1402, CN1457, CN1818, CN1416, CN1452, CN1461, CN1454, CN1456, CN1772, CN1427, CN1466, CN1954, CN1955, CN2137, CN2139, and CN2014.
28. The vector of embodiment 27, wherein the vector includes a viral vector.
29. The vector of embodiment 28, wherein the viral vector includes a recombinant adeno-associated viral (AAV) vector.
30. An adeno-associated viral (AAV) vector including at least one heterologous encoding sequence, wherein the heterologous encoding sequence is under control of a promoter and an enhancer selected from mscRE1, mscRE3, mscRE4, mscRE10, mscRE11, mscRE12, mscRE13, mscRE16, Grik1_enhScnn1a-2, eHGT_058 h, eHGT_058 m, eHGT_073 h, eHGT_073 m, eHGT_075 h, eHGT_077 h, eHGT_078 h, eHGT_078 m, eHGT_439 m, eHGT_440 h, eHGT_254 h, and/or a concatemer of any of embodiments 1-9.
31. The AAV vector of embodiment 30, wherein the AAV vector is replication-competent.
32. A transgenic cell including a concatenated core, artificial expression construct and/or vector of any of the preceding embodiments.
33. The transgenic cell of embodiment 32, wherein the transgenic cell is an excitatory cortical neuron.
34. The transgenic cell of embodiment 32 or 33, wherein the transgenic cell is a layer (L) 2, L3, L4, L5, or L6 excitatory cortical neuron.
35. The transgenic cell of any of embodiments 32-34, wherein the transgenic cell is an L4 IT excitatory cortical neuron, an L5 PT excitatory cortical neuron, an L5 ET excitatory cortical neuron, an L5 IT excitatory cortical neuron, an L5 NP excitatory cortical neuron, an L6 IT excitatory cortical neuron, an L6 CT excitatory cortical neuron, or a CR excitatory cortical neuron.
36. The transgenic cell of embodiment 32, wherein the transgenic cell is derived from a subcortical population in the CEAc, the substantia nigra, compact part, the subiculum, or the prosubiculum (ProS).
37. The transgenic cell of embodiment 32, wherein the transgenic cell is a CA1 pyramidal neuron, a dentate gyrus granule cell, a striatal neuron, or a cerebellar Purkinje cell.
38. A non-human transgenic animal including a concatenated core enhancer, an artificial expression construct, vector, and/or transgenic cell of any of the preceding embodiments.
39. The non-human transgenic animal of embodiment 38, wherein the non-human transgenic animal is a mouse or a non-human primate.
40. An administrable composition including a concatenated core, an artificial expression construct, vector, or transgenic cell of any of the preceding embodiments.
41. A kit including a concatenated core, an artificial expression construct, vector, transgenic cell, transgenic animal, and/or administrable compositions of any of the preceding embodiments.
42. A method for selectively expressing a heterologous gene within a population of neural cells in vivo or in vitro, the method including providing the administrable composition of embodiment 40 in a sufficient dosage and for a sufficient time to a sample or subject including the population of neural cells thereby selectively expressing the gene within the population of neural cells.
43. The method of embodiment 42, wherein the heterologous gene encodes an effector element or an expressible element.
44. The method of embodiment 43, wherein the effector element includes a reporter protein or a functional molecule.
45. The method of embodiment 44, wherein the reporter protein includes a fluorescent protein.
46. The method of embodiment 44, wherein the functional molecule includes a functional ion transporter, enzyme, transcription factor, receptor, membrane protein, cellular trafficking protein, signaling molecule, neurotransmitter, calcium reporter, channel rhodopsin, CRISPR/CAS molecule, editase, guide RNA molecule, homologous recombination donor cassette, or a DREADD.
47. The method of embodiment 43, wherein the expressible element includes a non-functional molecule.
48. The method of embodiment 47, wherein the non-functional molecule includes a non-functional ion transporter, enzyme, transcription factor, receptor, membrane protein, cellular trafficking protein, signaling molecule, neurotransmitter, calcium reporter, channel rhodopsin, CRISPR/CAS molecule, editase, guide RNA molecule, homologous recombination donor cassette, or DREADD.

49. The method of any of embodiments 42-48, wherein the providing includes pipetting.
50. The method of embodiment 49, wherein the pipetting is to a brain slice.
51. The method of embodiment 50, wherein the brain slice includes an excitatory neuron.
52. The method of embodiment 50 or 51, wherein the brain slice includes a layer (L) 2, L3, L4, L5, and/or a L6 excitatory cortical neuron.
53. The method of any of embodiments 50-52, wherein the brain slice includes an L4 IT excitatory cortical neuron, an L5 PT excitatory cortical neuron, an L5 ET excitatory cortical neuron, an L5 IT excitatory cortical neuron, an L5 NP excitatory cortical neuron, an L6 IT excitatory cortical neuron, an L6 CT excitatory cortical neuron, and/or a CR excitatory cortical neuron.
54. The method of any of embodiments 50-53, wherein the brain slice includes a subcortical population in the CEAc, the substantia nigra, compact part, the subiculum, and/or the prosubiculum (ProS).
55. The method of any of embodiments 50-54, wherein the brain slice includes a CA1 pyramidal neuron, a dentate gyrus granule cell, a striatal neuron, and/or a cerebellar Purkinje cell.
56. The method of any of embodiments 50-55, wherein the brain slice is murine, human, or non-human primate.
57. The method of embodiment 48, wherein the providing includes administering to a living subject.
58. The method of embodiment 57, wherein the living subject is a human, non-human primate, or a mouse.
59. The method of embodiments 56 or 57, wherein the administering to a living subject is through injection.
60. The method of embodiment 59, wherein the injection includes intravenous injection, intraparenchymal injection, intracerebroventricular (ICV) injection, intra-cisterna *magna* (ICM) injection, or intrathecal injection.
61. An artificial expression construct including T502-050, T502-054, vAi34.0, vAi33.2, vAi45.0, vAi1.0, T502-057, T502-059, TG975, TG978, TG979, TG981, TG982, TG987, TG988, TG995, TG996, TG997, TG999, TG1002, TG1009, TG1010, TG1011, TG1021, TG1022, TG1036, TG 1037, TG1038, TG 1045, TG1046, TG 1047, TG1048, TG 1049, TG1050, TG1052, CN 1402, CN1457, CN1818, CN1416, CN1452, CN1461, CN1454, CN1456, CN1772, CN1427, CN1466, CN1954, CN1955, CN2137, CN2139, and CN2014.

(viii) EXPERIMENTAL EXAMPLES

Example 1. Individual neuronal or non-neuronal cells were isolated from the mouse cortex by FACS and examined using the Assay for Transposase-Accessible Chromatin with next generation sequencing (ATAC-seq). This strategy allowed interrogation of both abundant and very rare cell types with the same method. 25 individual or combinatorial Cre or Flp-driver lines were utilized in combination with reporter lines, many of which have been characterized using single-cell RNA-seq (Tasic, et al., 2018, Nature 563: 72-78), as well as retrograde labeling to selectively sample cell populations in adult mouse brain. Shared GABAergic cell types across two distant poles of mouse cortex, but divergent glutamatergic cell types from different cortical regions have been observed (Tasic, et al., 2018, Nature 563: 72-78). Therefore, dissections focused on visual cortex for glutamatergic cell types, but allowed broader cortical sampling for GABAergic cell types. Retrogradely labeled cells were collected only from visual cortex. In total, 3,381 single cells from 25 driver-reporter combinations in 60 mice, 126 retrogradely labeled cells from injections into 3 targets across 7 donors, and 96 samples labeled in 1 retro-orbital injection from a viral tool generated were collected. After FACS, individual cells were subjected to ATAC-seq, and were sequenced in 60-96 sample batches using a MiSeq (Materials and Methods of Example 1). Quality control filtering was performed to select 2,416 samples with >10,000 uniquely mapped paired-end fragments, >10% of which had a fragment size longer than 250 bp, and with >25% of fragments overlapping high-depth cortical DNAse-seq peaks generated by ENCODE (Yue, et al., 2014, Nature, 515: 355-364).

Previous studies have shown that most recombinase driver lines label more than one transcriptomic cell type (Tasic, et al., 2018, Nature 563: 72-78; and Tasic, et al., 2016, Nat Neurosci 19: 335-346). To increase the resolution of chromatin accessibility profiles beyond that provided by driver lines, the scATAC-seq data was clustered using a novel feature-free method for computation of pairwise Jaccard distances. These distances were used for clustering by t-stochastic neighborhood embedding (t-SNE), followed by phenograph clustering (FIG. 45). Cluster identity was then assigned by comparison of accessibility near transcription start sites (TSS±20 kb) to scRNA-seq dataset for VISp (Tasic, et al., 2018, Nature 563: 72-78) using median correlation.

Layer 5 of visual cortex contains L5 IT neurons that project to other cortical regions, near-projecting (L5 NP) neurons that have only local projections, and L5 PT neurons that have long axonic projections to subcortical brain regions such as thalamus (Tasic, et al., 2018, Nature 563: 72-78; Harris, et al., 2018, biorXiv, 292961). The driver line Rbp4-Cre labels both L5 IT and L5 PT neurons in cortex (Tasic, et al., 2016, Nat Neurosci 19: 335-346). To deconvolute these populations, L5 PT and L5 IT neurons were identified in the scATAC-seq dataset based on correlation with scRNA-seq cell types, labeling of these cells by Rbp4-Cre, and by retrograde labeling from a known L5 PT target region, the lateral posterior nucleus of the thalamus (LP). Populations of L5 PT and L5 IT scATAC-seq samples were pooled into subclass-specific tracks, and searches were performed near transcriptomic marker genes for 500 bp putative enhancer elements that were specific to L5 PT or L5 IT cells, and which had strong sequence conservation. These regions are referred to as mouse single-cell regulatory elements (mscREs).

Figure 48A:
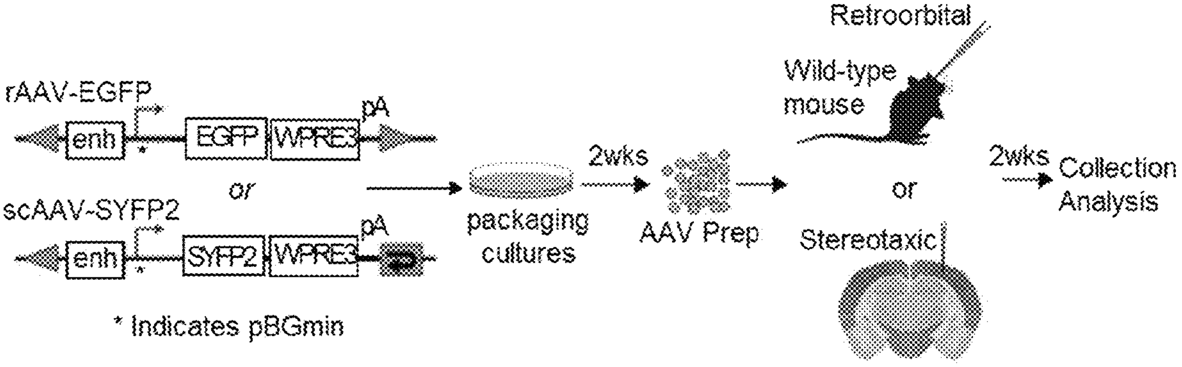
FIGS. 48A-48C. (48A) Direct enhancer-driven expression of a fluorophore was tested by cloning the putative mscRE4 or mscRE16 enhancer in an scAAV construct with a minimal promoter driving a fluorophore-WPRE3. After packaging, purification, and titering scAAVs were retro-orbitally injected into a wild-type mouse. (48B) Two weeks after retro-orbital injection of an rAAV with mscRE16 driving expression of EGFP (TG1002), cells are selectively labeled in L5 of the mouse cortex by EGFP expression, which is amplified here using antibody staining by immunohistochemistry (IHC). (48C) Two weeks after retro-orbital injection of an scAAV with mscRE4 driving expression of SYFP (T502-057), dim but distinct labeling was seen in L5 PT cells by native fluorescence without antibody amplification.

Putative mscREs were cloned upstream of a minimal beta-globin promoter driving SYFP2 or EGFP expression in a viral construct to generate AAVs (FIG. 48A). These constructs were packaged for retro-orbital injection into wild-type mice in a PHP.eB-serotype virus, which can cross the blood-brain barrier (Chan, et al., 2017, Nat. Neurosci 20: 1172-1179). In total, 4 mscREs for L5 PT cells, and 2 mscREs for L5 IT were screened. Two weeks after retro-orbital injection, brains of infected mice were collected and screened expression by visual inspection of native fluorescence and immunohistochemistry to enhance SYFP2 and EGFP signal. Three of the enhancers provided labeling of cells in L5, while others showed off-target or no detectable labeling.

Figure 48B:
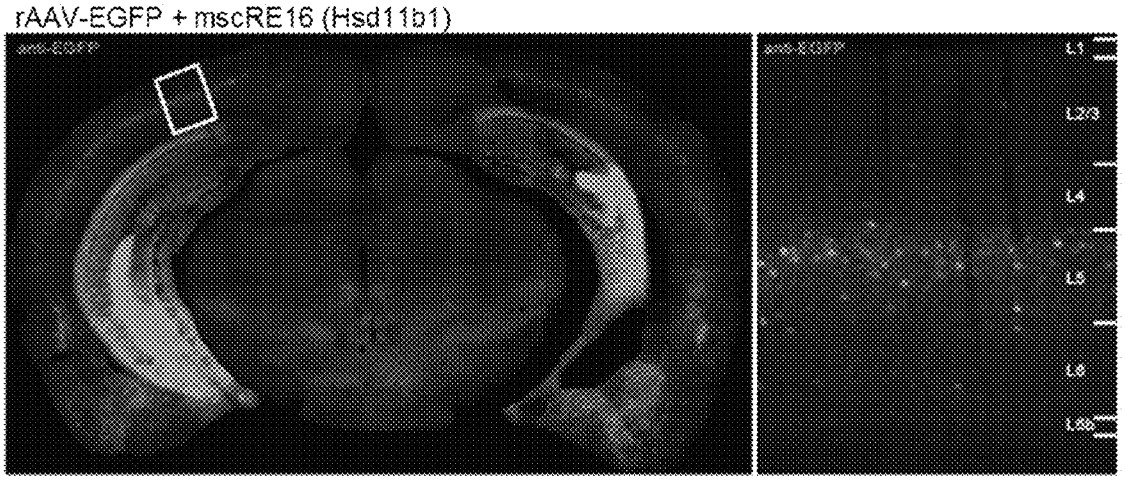
Figure 49A:
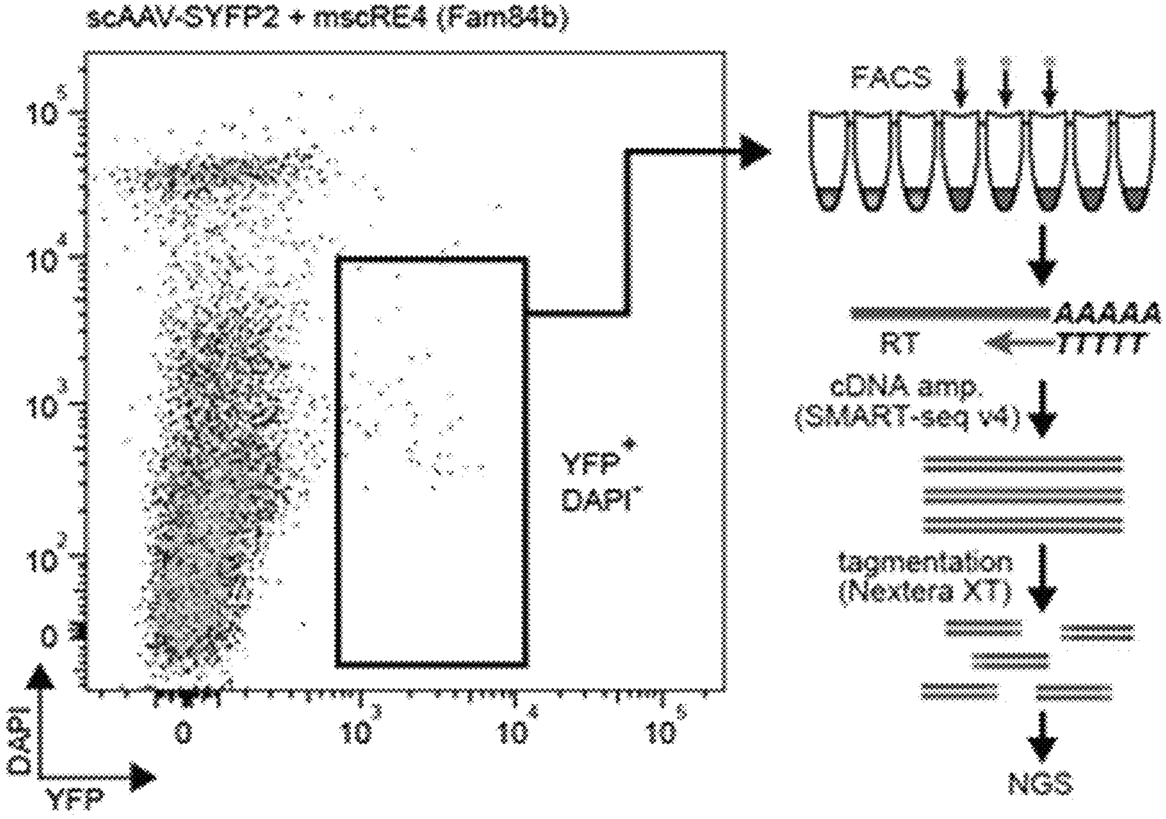
FIGS. 49A, 49B. Validation of cell type targeting of scAAV-mscRE4-SYFP2 viruses by scRNA-seq. (49A) Enhancer-driven recombinase expression was tested using a scAAV construct with a minimal promoter driving EGFP-WPRE3. After packaging, mice were given retro-orbital injections. After 2 weeks, SYFP-expressing cells were visible in the cortex, which could be isolated by FACS and used for scRNA-seq. (49B) Centroid classifier mapping of labeled cells onto data from Tasic, et al. (2018, Nature) revealed that 91.8% of the cells mapped to L5 PT transcriptomic cell types.

To assess the specificity of cell type labeling, stereotaxic injection of these viruses in VISp was performed, labeled cells were sorted by FACS, and scRNA-seq was performed as described previously (Tasic, et al., 2018, Nature 563: 72-78). scRNA-seq expression profiles were compared to a VISp reference dataset using centroid classification of cell types (Materials and Methods of Example 1). The mscRE4 element yielded specificity for L5 PT cells, (FIG. 48B), mscRE1 yielded specificity for L5 PT cells, and mscRE16 yielded specificity for L5 IT cells. scRNA-seq of FACS-sorted cells was also performed from retro-orbital labeling of the mscRE4 and mscRE1 viruses, with similarly specific results (>92% for mscRE4). Direct labeling of cells by stereotaxic injection induced an innate immune response similar to anterograde labeling, but retrograde injections caused no significant upregulation of immune-related pathways at the time of collection. For mscRE4, labeling of L5 PT cells was confirmed by electrophysiological characterization of labeled vs unlabeled cells in the cortex. Cells labeled by mscRE4 had characteristics of L5 PT neurons, whereas cells that were label-negative did not (FIG. 49A). This demonstrates the utility of these viral tools for electrophysiology experiments targeted to specific subclasses for which driver lines are not available.

L5 PT cells are often difficult to isolate from single-cell suspensions when in a heterogeneous mixture with other cell types due to differential cell survival (Tasic, et al., 2016, Nat Neurosci 19: 335-346; and Tasic, et al., 2018, Nature 563: 72-78). Retro-orbital injection of the mscRE4-driven virus (T502-057) was used to bootstrap the scATAC-seq dataset by sorting cells labeled by mscRE4 for FACS. As expected, based on scRNA-seq analysis, 55 of 61 high-quality mscRE4 scATAC-seq profiles clustered together with other L5 PT samples (90.2%).

Although the direct fluorophore labeling provided enough signal to sort cells by FACS or perform patch-clamp experiments, use of an enhancer to drive expression of a recombinase could allow for expression of previously generated mouse reporter lines that drive fluorophores, activity reporters, opsins, or genes that are too large to package in AAVs (Daigle, et al., 2018, Cell 174(2): 465-480 and Madisen, et al., 2015, Neuron 85(5): 942-958). To test the specificity of enhancer-driven recombinase expression, mscRE4 was cloned into constructs containing a minimal beta-globin enhancer driving dgCre (TG1009), iCre (TG1010), FlpO (TG978) or tTA2 (TG1011), and packaged them in PHP.eB viruses. These viruses were delivered by retro-orbital injection into mice with genetically encoded reporters for each recombinase (Ai14 for dgCre and iCre; Ai65F for FlpO; and Ai63 for tTA2). Labeling was characterized by sectioning and microscopy of native fluorescence (Materials and Methods of Example 1). FlpO, dgCre, and tTA2 yielded highly specific labeling of cells in L5 of the mouse cortex. For the FlpO virus, whole-brain microscopy was also performed using a TissueCyte system, and strong, specific labeling of L5 cells was found throughout the cortex, with bright labeling of pyramidal tract projections to subcortical targets. Finally, brain-wide colabeling of both L5 IT and L5 PT populations by retro-orbital injection of mscRE4-FlpO (to label L5 PT cells, red, TG978) and mscRE16-EGFP (to label L5 IT cells, green, TG1002) was tested in the same Ai65F animal. Distinct labeling of these two cell populations in L5 by microscopy was found, demonstrating that multiple enhancer-driven viruses can be used to simultaneously label populations of transcriptomically defined cell types in the same animal.

Materials and Methods of Example 1. Mouse breeding and husbandry. Mice were housed under Institutional Care and Use Committee protocols 1508 and 1802 at the Allen Institute for Brain Science, with no more than five animals per cage, maintained on a 12 hr day/night cycle, with food and water provided ad libitum. Animals with anophthalmia or microphthalmia were excluded from experiments. Animals were maintained on a C57BL/6J genetic background.

Retrograde labeling. Stereotaxic injection of CAV-Cre (Hnasko et al., 2006, Proc. Natl. Acad. Sci. USA 103: 8858-8863) was performed into brains of heterozygous or homozygous Ai14 mice using coordinates obtained from Paxinos adult mouse brain atlas (Paxinos & Franklin, The Mouse Brain in Stereotaxic Coordinates Compact $3^{rd}$ Ed., Academic Press, N Y, 2008}. TdT+ single cells were isolated from VISp by FACS.

Single cell ATAC. Single-cell suspensions of cortical neurons were generated as described previously (Gray, et al., 2017, eLife 6: e21883}, with the exception of use of Papain in place of Proteinase K for dissociation of some samples. Individual cells with high fluorophore labeling (tdTomato or SYFP2) were then sorted for neuronal sorting or low fluorophore labeling for non-neuronal cell labeling, and low DAPI into 200 μL 8-well strip tubes containing 1.5 μL tagmentation reaction mix (0.75 μL Nextera Reaction Buffer, 0.2 μL Nextera Tn5 Enzyme, 0.55 μL water). After collection, cells were briefly spun down in a bench-top centrifuge, then immediately tagmented at 3TC for 30 minutes in a PCR machine. After tagmentation, 0.6 μL Proteinase K stop solution was added to each tube (5 mg/mL Proteinase K solution (Qiagen), 50 mM EDTA, 5 mM NaCl, 1.25% SDS) followed by incubation at 40° C. for 30 minutes in a PCR machine. The tagmented DNA was then purified using AM Pure XP beads (Beckman Coulter) at a ratio of 1.8:1 resuspended beads to reaction volume (3.8 μL added to 2.1 μL), with a final elution volume of 11 μL. Libraries were indexed and amplified by the addition of 15 uL 2× Kapa HiFi HotStart ReadyMix and 2 uL Nextera i5 and i7 indexes to each tube, followed by incubation at 72° C. for 3 minutes and PCR (95° C. for 1 min, 22 cycles of 98° C. for 20 sec, 65° C. for 15 sec, and 72° C. for 15 sec, then final extension at 72° C. for 1 min). After amplification, sample concentrations were measured using a Quant-iT PicoGreen assay (Thermo Fisher) in duplicate. For each sample, the mean concentration was calculated by comparison to a standard curve, and the mean and standard deviation of concentrations was calculated for all samples. Samples with a concentration greater than 2 standard deviations above the mean were not used for downstream steps, as these were found in early experiments to dominate sequencing runs. All other samples were pooled by combining 5 μL of each sample in a 1.5 mL tube. The combined library was then purified by adding Ampure XP beads in a 1.8:1 ratio, with final elution in 50 μL. The mixed library was then quantified using a BioAnalyzer High Sensitivity DNA kit (Agilent).

scATAC sequencing, alignment, and filtering. Mixed libraries, containing 60 to 96 samples each, were sequenced on an Illumina MiSeq at a final concentration of 20-30 pM. After sequencing, raw FASTQ files were aligned to the GRCm38 (mm10) mouse genome using Bowtie v1.1.0 as described previously (Gray, et al., 2017, eLife 6: e21883). After alignment, duplicate reads were removed using samtools rmdup, which yielded only single copies of uniquely mapped paired reads in BAM format. For analysis, samples were filtered to remove the ones with fewer than 10,000 paired-end fragments (20,000 reads), and with at least 10% of sequenced fragments longer than 250 bp. An additional filter was created using ENCODE whole cortex DNase-seq HotSpot peaks (sample ID ENCFF651EAU from experiment ID ENCSR00COF). Samples with less than 25% of paired-end fragments that overlapped DNase-seq peaks were removed from downstream analysis. Cells passing these criteria both had sufficient unique reads for downstream analysis and had high-quality chromatin accessibility profiles as assessed by fragment size analysis. As an additional QC check, aggregate scATAC-seq data was compared to bulk ATAC-seq data from matching Cre-driver lines, where available. Aggregate single-cell datasets were found to match well to previously published bulk datasets.

Jaccard distance calculation, PCA and tSNE embedding, and density-based clustering. To compare scATAC-seq samples, all cells were downsampled to an equal number of uniquely aligned fragments (10,000 per sample). These fragments were extended to a length of 10 kb, then any overlapping fragments within each sample were collapsed into regions based on the outer boundaries of overlapping fragments. Then, the number of overlapping regions between every pair of samples was counted and divided by the total number of regions in both samples to obtain a Jaccard similarity score. These scores were converted to Jaccard distances (1—Jaccard similarity), and the resulting matrix was used as input for t-stochastic neighbor embedding (t-SNE). After t-SNE, samples were clustered in t-SNE space using the RPhenograph package with settings that yielded >100 clusters to obtain small groups of similar neighbors (Levine, et al., 2015, Cell 162: 184-197).

Correlation with single-cell transcriptomics. Phenograph-defined neighborhoods were assigned to cell subclasses and clusters by comparison of accessibility scores of regions within 20 kb of each transcription start site (TSS) to median expression values of scRNA-seq clusters from mouse primary visual cortex (Tasic, et al., 2018, Nature 563: 72-78) (Materials and Methods of Example 1). This strategy of neighbor assignment and correlation allowed resolution of cell types within the scATAC-seq data close to the resolution of the scRNA-seq data, as types that were split too far would resolve to the same transcriptomic type by correlation. To assess the robustness of these assignments, a bootstrapped clustering method was used, in which 20% of the scATAC-seq samples were randomly discarded, t-SNE was performed, clusters assigned, and comparison to scRNA-seq clusters were performed 100 times. As an alternative to Phenograph clustering, these analyses were also performed by selecting the 5 nearest neighbors of each sample in t-SNE space and performing the same count and correlation analysis described above.

Merging cell classes and peak calling. Aligned reads from single cell subclasses/clusters were used to create Tag Directories and call chromatin accessible peaks using HOMER (findPeaks-region-o auto). The resulting peaks were transformed to BED format and used as input for DiffBind/differential enrichment analyses.

Viral genome cloning. Enhancers were cloned from C57BI/6J genomic DNA using enhancer-specific primers and Phusion high-fidelity polymerase (M0530S; NEB). Individual enhancers were then inserted into an rAAV or self-complementary adeno-associated virus (scAAV) backbone that contained a minimal beta-globin promoter, gene, and bovine growth hormone polyA using standard molecular cloning approaches. Plasmid integrity was verified via Sanger sequencing and restriction digests to confirm intact inverted terminal repeat (ITR) sites.

Viral packaging and tittering. Before transfection, $10^5$ μg of AAV viral genome plasmid, 190 μg pHelper, and 105 μg AAV-PHP.eB were mixed with 5 mL of Opti-MEM I media (Reduced Serum, GlutaMAX; ThermoFisher Scientific) and 1.1 mL of a solution of 1 mg/mL 25 kDa linear Polyethylenimine (Polysciences) in PBS at pH 4-5. This cotransfection mixture was incubated at room temperature for 10 minutes. Recombinant AAV of the PHP.eB serotype was generated by adding 0.61 mL of this cotransfection mixture to each of ten 15-cm dishes of HEK293T cells (ATCC) at 70-80% confluence. 24 hours post-transfection, cell medium was replaced with DMEM (with high glucose, L-glutamine and sodium pyruvate; ThermoFisher Scientific) with 4% FBS (Hyclone) and 1% Antibiotic-Antimycotic solution. Cells were collected 72 hours post transfection by scraping in 5 mL of medium, and were pelleted at 1500 rpm at 4° C. for 15 minutes. Pellets were suspended in a buffer containing 150 mM NaCl, 10 mM Tris, and 10 mM MgCl2, pH 7.6, and were frozen in dry ice. Cell pellets were thawed quickly in a 37° C. water bath, then passed through a syringe with a 21-23G needle 5 times, followed by 3 more rounds of freeze/thaw, and 30 minutes of incubation with 50 U/ml Benzonase (Sigma-Aldrich) at 37° C. The suspension was then centrifuged at 3,000×g and purified using a layered iodixanol step gradient (15%, 25%, 40%, and 60%) by centrifugation at 58,000 rpm in a Beckman 70Ti rotor for 90 minutes at 18° C. by extraction of a volume below the 40-60% gradient layer interface. Viruses were concentrated using Amicon Ultra-15 centrifugal filter unit by centrifugation at 3,000 rpm at 4° C., and reconstituted in PBS with 5% glycerol and 35 mM NaCl before storage at −80° C.

Retro-orbital injections. To introduce AAV viruses into the blood stream, 21 day old or older C57BI/6J, Ai14, Ai65F, or Ai63 mice (Madisen, et al., 2015, Neuron 85(5): 942-958) were briefly anesthetized by isoflurane and $1\times10^{10}$-$1\times10^{11}$ viral genome copies (gc) was delivered into the retro-orbital sinus in a maximum volume of 50 μL or less. This approach has been utilized previously to deliver AAV viruses across the blood brain barrier and into the murine brain with high efficiency (Chan., et al., 2017, Nat Neurosci 20(8): 1172-1179). For delivery of multiple AAVs, the viruses were mixed beforehand and then delivered simultaneously into the retro-orbital sinus. Animals were allowed to recover and then sacrificed 1-3 weeks post-infection in order to analyze virally-introduced transgenes within the brain.

Stereotaxic injections and tissue processing. Viral DNA was packaged in a PHP.eB serotype to produce recombinant adeno-associated virus (rAAV) for mscRE4-minBGprom-EGFP-WPRE3 (TG981), mscRE4-minBGprom-IRES2-tTa2-WPRE3 (TG1011), and mscRE4-minBGprom-FlpO-WPRE3 (TG978) viruses (titers: 1.64×1014, 5.11×1013, 6.00×1013, respectively), or self-complementary AAV (scAAV) for mscRE4-minBGprom-SYFP2-WPRE3-BGHpA (T502-057) virus (titer $1.34\times10^{13}$) (Chan, et al., Nat. Neurosci 20: 1172-1170, 2017). Each virus was delivered bilaterally at 250 nL and 50 nL into the primary visual cortex (VISp; coordinates: A/P: −3.8, ML: −2.5, DV: 0.6) of male and female C57Bl6/J and wild-type transgenic mice (Htr2a-Cre (−), SST-IRES-Cre; Ai67(−), Cck-IRES-Cre (−)) for rAAV-mscRE4-minBGprom-EGFP-WPRE3 and scAAV-mscRE4-minBGprom-SYFP2-WPRE3 viruses, or heterozygous Ai65F and Ai63 mice for rAAV-mscRE4-minBGprom-FlpO-WPRE3 and rAAV-mscRE4-minBGprom-tTa2-WPRE3 viruses, respectively, using a pressure injection system (Nanoject II, Drummond Scientific Company, Catalog #3-000-204). To mark the injection site, rAAV-EF1a-tdTomato or rAAV-EF1a-EGFP was co-injected at a dilution of 1:10 with experimental virus. The expression for all viruses was analyzed at 14 days post-injection. For tissue processing, mice were transcardially perfused with 4% paraformaldehyde (PFA) and post-fixed in 30% sucrose for 1-2 days. 50 μm sections were prepared using a freezing microtome and fluorescent images of the injections were captured from mounted sections using a Nikon Eclipse TI epi-fluorescent microscope.

Immunohistochemistry. Mice were transcardially perfused with 0.1M phosphate buffered saline (PBS) followed by 4% paraformaldehyde (PFA). Brains were removed, post-fixed in PFA overnight, followed by an additional incubation overnight in 30% sucrose. Coronal sections (50 μm) were cut using a freezing microtome and native fluorescence or antibody-antibody enhanced was analyzed in mounted sections. To enhance the Enhanced Green Fluorescent Protein (EGFP) fluorescence, a rabbit anti-GFP antibody was used to stain free floating brain sections. Briefly, sections were rinsed three times in PBS, blocked for 1 hour in phosphate buffered saline (PBS) containing 5% donor donkey serum, 2% bovine serum albumin (BSA) and 0.2% Triton X-100, and incubated overnight at 4° C. in the anti-GFP primary antibody (1:2000; Abcam ab6556). The following day, sections were washed three times in PBS and incubated in blocking solution containing an Alexa® 488 conjugated secondary antibody (1:1500; Invitrogen), washed in PBS, and mounted in Vectashield containing DAPI (H-1500, Vector Labs). Epifluorescence images of native or antibody-enhanced fluorescence were acquired on a Nikon Eclipse Ti microscope or on a TissueCyte 1000 (Tissue Vision) system.

Virus titers were measured using quantitative PCR (qPCR) with a primer pair that recognizes a region of 117 bp in the AAV2 ITRs (Forward: GGAACCCCTAGTGATGGAGTT (SEQ ID NO: 175); Reverse: CGGCCTCAGTGAGCGA (SEQ ID NO: 176)). QPCR reactions were performed using QuantiTect SYBR Green PCR Master Mix (Qiagen) and 500 nM primers. To determine virus titers, a positive control AAV with known titer and newly produced viruses with unknown titers were treated with DNAse I. Serial dilutions (1/10, 1/100, 1/500, 1/2500, 1/12500, and 1/62500) of both positive control and newly generated viruses were loaded on the same qPCR plate. A standard curve of virus particle concentrations vs Cq values was generated based on the positive control virus, and the titers of the new viruses were calculated based on the standard curve.

Single cell RNA sequencing and cell type mapping. scRNA-seq was performed using the SMART-Seq v4 kit (Takara Cat #634894) as described previously (Tasic, et al., 2018, Nature 563: 72-78). In brief, single cells were sorted into 8-well strips containing SMART-Seq lysis buffer with RNase inhibitor (0.17 U/μL), and were immediately frozen on dry ice for storage at −80 C. SMART-Seq reagents were used for reverse transcription and cDNA amplification. Samples were tagmented and indexed using a NexteraXT DNA Library Preparation kit (Illumina FC-131-1096) with NexteraXT Index Kit V2 Set A (FC-131-2001) according to manufacturer's instructions except for decreases in volumes of all reagents, including cDNA, to 0.4× recommended volume. Full documentation for the scRNA-seq procedure is available in the 'Documentation' section of the Allen Institute data portal at http://celltypes.brain-map.org/. Samples were sequenced on an Illumina HiSeq 2500 or Illumina MiSeq as 50 bp paired-end reads to a median depth of XX reads per cell. Reads were aligned to GRCm38 (mm10) using STAR v2.5.3 (Dobin, et al., 2013, Bioinformatics 29: 15-21) in towpassMode, and exonic read counts were quantified using the GenomicRanges package for R as described in Tasic, et al., (2018, Nature 563: 72-78). To determine the corresponding cell type for each scRNA-seq dataset, the scrattch.hicat package for R was utilized (Tasic, et al., 2018, Nature 563: 72-78). Marker genes that distinguished each cluster were selected, then this panel of genes was used in a bootstrapped centroid classifier which performed 100 rounds of correlation using 80% of the marker panel selected at random in each round.

Physiology. Coronal mouse brain slices were prepared using the NMDG protective recovery method (Ting, et al., 2014, Methods Mol. Biol. 1183: 221-242). Mice were deeply anesthetized by intraperitoneal administration of Advertin (20 mg/kg) and were perfused through the heart with an artificial cerebral spinal (ACSF) solution containing (in mM): 92 NMDG, 2.5 KCl, 1.25 $NaH_2PO_4$, 30 $NaHCO_3$, 20 HEPES, 25 glucose, 2 thiourea, 5 Na-ascorbate, 3 Na-pyruvate, 0.5 $CaCl_2.4H_2O$ and 10 $MgSO_4.7H_2O$. Slices (300 μm) were sectioned on a Compresstome VF-200 (Precisionary Instruments) using a zirconium ceramic blade (EF-INZ10, Cadence). After sectioning, slices were transferred to a warmed (32-34° C.) recovery chamber filled with NMDG ACSF under constant carbogenation. After 12 minutes, slices were transferred to a holding chamber containing an ACSF made of (in mM) 92 NaCl, 2.5 KCl, 1.25 $NaH_2PO_4$, 30 $NaHCO_3$, 20 HEPES, 25 glucose, 2 thiourea, 5 Na-ascorbate, 3 Na-pyruvate, 128 $CaCl_2.4H_2O$ and 2 $MgSO_4.7H_2O$ continuously bubbled with 95/5 $O_2/CO_2$.

For patch clamp recordings, slices were placed in a submerged, heated (32-34° C.) recording chamber that was continuously perfused with ACSF under constant carbogenation containing (in mM): 119 NaCl, 2.5 KCl, 1.25 $NaH_2PO_4$, 24 $NaHCO_3$, 12.5 glucose, 2 $CaCl_2.4H_2O$ and 2 $MgSO_4.7H_2O$ (pH 7.3-7.4). Neurons were viewed with an Olympus BX51WI microscope and infrared differential contrast optics and a 40× water immersion objective. Patch pipettes (3-6 MO) were pulled from borosilicate glass using a horizontal pipette puller (P1000, Sutter Instruments). Electrical signals were acquired using a Multiclamp 700B amplifier and PClamp 10 data acquisition software (Molecular Devices). Signals were digitized (Axon Digidata 1550B) at 10-50 kHz and filtered at 2-10 kHz. Pipette capacitance was compensated and the bridge balanced throughout whole-cell current clamp recordings. Access resistance was 8-25 MO).

Data was analyzed using custom scripts written in Igor Pro (Wavemetrics). All measurements were made at resting membrane potential. Input resistance ($R_N$) was calculated from the linear portion of the voltage-current relationship generated in response to a series of 1s current injections. The maximum and steady state voltage deflections were used to determine the maximum and steady state of $R_N$, respectively. Voltage sag was fined as the ratio of maximum to steady-state $R_N$. Resonance frequency ($f_R$) was determined from the voltage response to a constant amplitude sinusoidal current injection that either linearly increased from 1-15 Hz over 15 seconds or increased logarithmically from 0.2-40 Hz over 20 seconds. Impedance amplitude profiles were constructed from the ratio of the fast Fourier transform of the voltage response to the fast Fourier transform of the current injection. $f_R$ corresponded to the frequency at which maximum impedance was measured. While the majority of neurons included in the examples currently described were located in primary visual cortex (n=10 YFP+, 10 YFP−), recordings from motor cortex (n=1 YFP+) and primary somatosensory cortex (n=4 YFP) were also made. For illustrative purposes, the properties of YFP+ and YFP− neurons to 32 L5 pyramidal neurons located in somatosensory cortex from an uninfected mouse were also compared. To classify these neurons as IT-like or PT-like, Divisive Analysis of Clustering (diana) from the cluster package in R was used (Maechler and Rousseeuw, 2012, R package version 1(2), 56). In-related membrane properties are known to differentiate IT and PT neurons across many brain regions (Baker, et al., 2018, J. Neurosci. 38: 5441-5455. As such, features included in clustering were restricted to the Ih—related membrane properties—sag ratio, $R_N$ and $f_R$. To assess statistical significance of clustering, the sigclust package in R (Huang, et al., 2015, J Comput Graph Stat 24(4): 975-993) was used.

Figure 42:
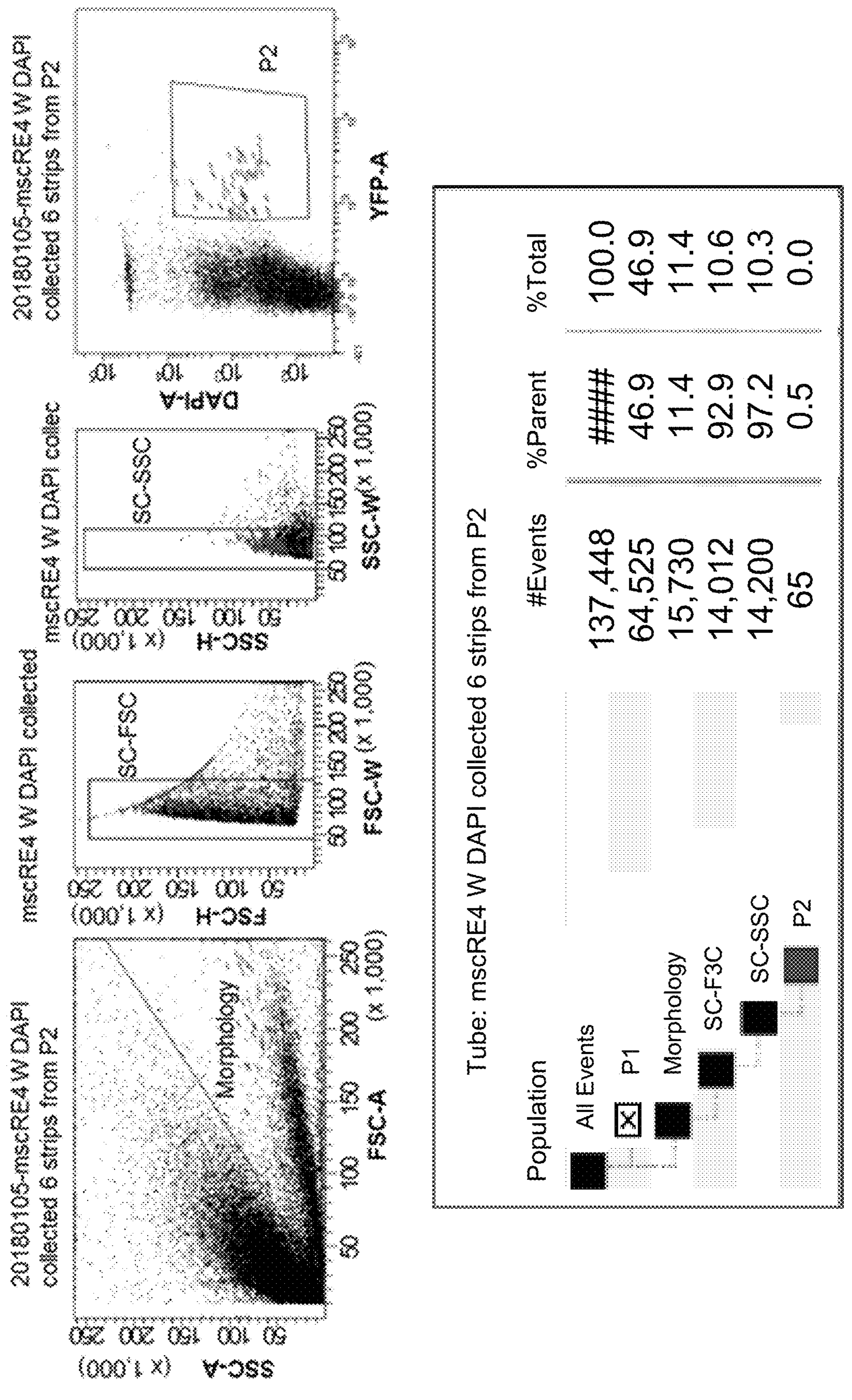
FIG. 42. Fluorescence-activated cell sorting (FACS) Gating examples. (4A) All FACS sorts followed a similar gating strategy: Morphology and debris removal using Forward Scatter Area (FSC-A) and Side Scatter Area (SSC-A); Removal of doublets/multiplets using Forward Scatter Width (FSC-W)×Forward Scatter Height (FSC-H) and Side Scatter Width (SSC-W)×Side Scatter Height (SSC-H) gating; and selection of live cells with or without fluorescent labels using 4',6-diamidino-2-phenylindole (DAPI) and fluorophore signals. This panel shows example shows gating for direct fluorophore labeling of cells from injection of mscRE4-SYFP2.
Figure 43:
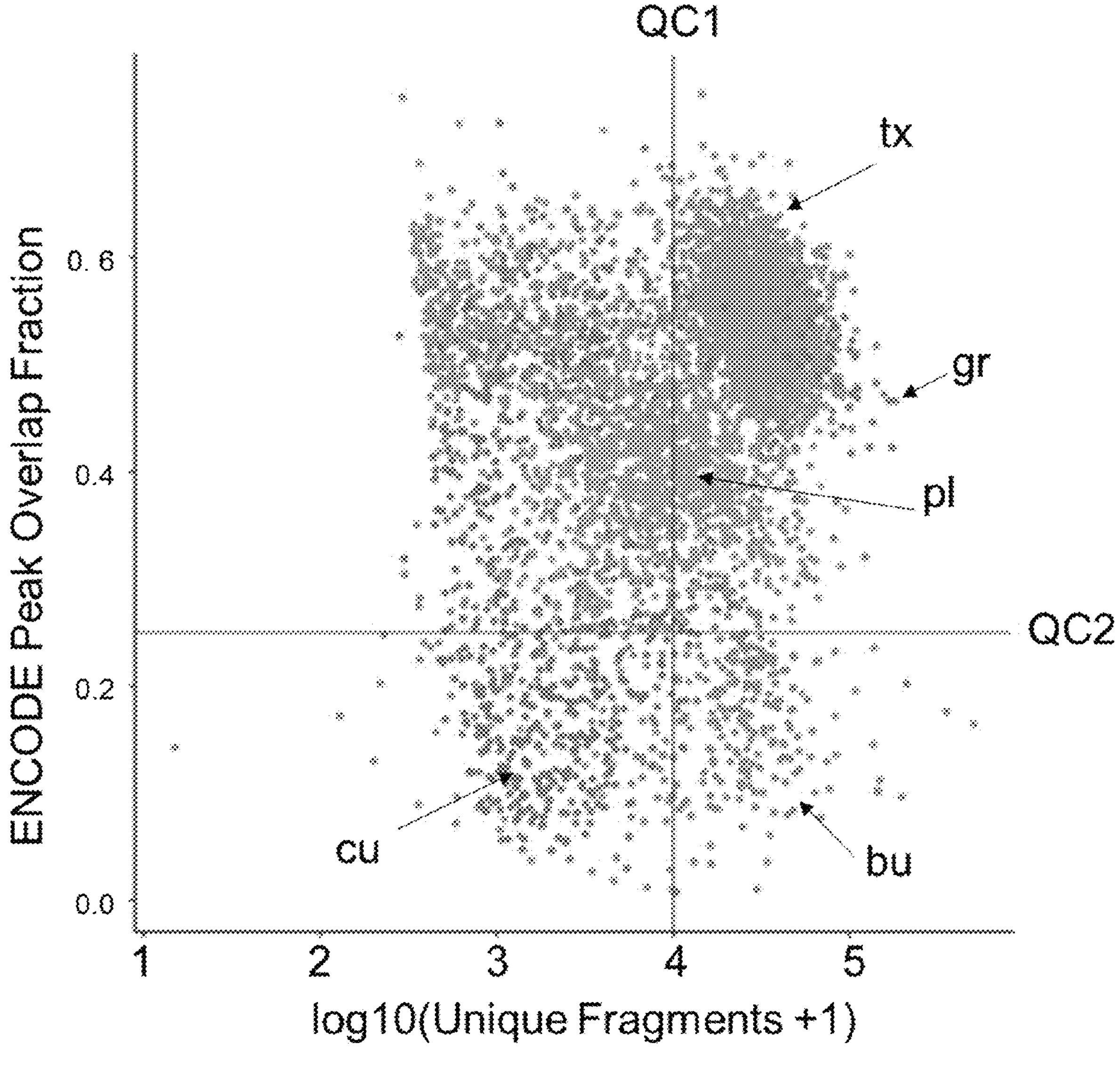
FIG. 43. Gm12878 platform comparisons. Comparison of FACS-sorted scATAC-seq libraries to those previously generated using Fluidigm C1 (Buenrostro, et al., Nature 523 (2015)) sci-ATAC-seq (Cusanovich, et al., Science 348 (2015) and Pliner, et al., Mol. Cell 71 (2018)) or droplet-based indexing (10× Genomics) for which data using the common cell line of human Gm12878 cells is available. To use in these comparisons, scATAC-seq data was generated using a FACS-based method for 60 Gm12878 cells. For each published dataset, raw data was obtained from GEO and was aligned and analyzed using the same methods. For 10× Genomics, aligned fragment locations and metadata were obtained from the 10× genomics website. Abbreviations used throughout the plots: bu, Buenrostro, et al., Nature 523 (2015) Fluidigm C1 ATAC-seq; cu, Cusanovich, et al., Science 348 (2015) sci-ATAC-seq (2015); gr, Graybuck, et al. (the data described herein) FACS scATAC-seq; pl, Pliner, et al., Mol. Cell 71 (2018) sci-ATAC-seq (2018), and tx, 10× Genomics, 5 k cells 10×ATAC-seq. Gray et al., Elife 1-30 (2017). Two-axis QC criteria plot, showing the QC1 and QC2 cutoffs used for mouse cortical scATAC-seq data.
Figure 44:
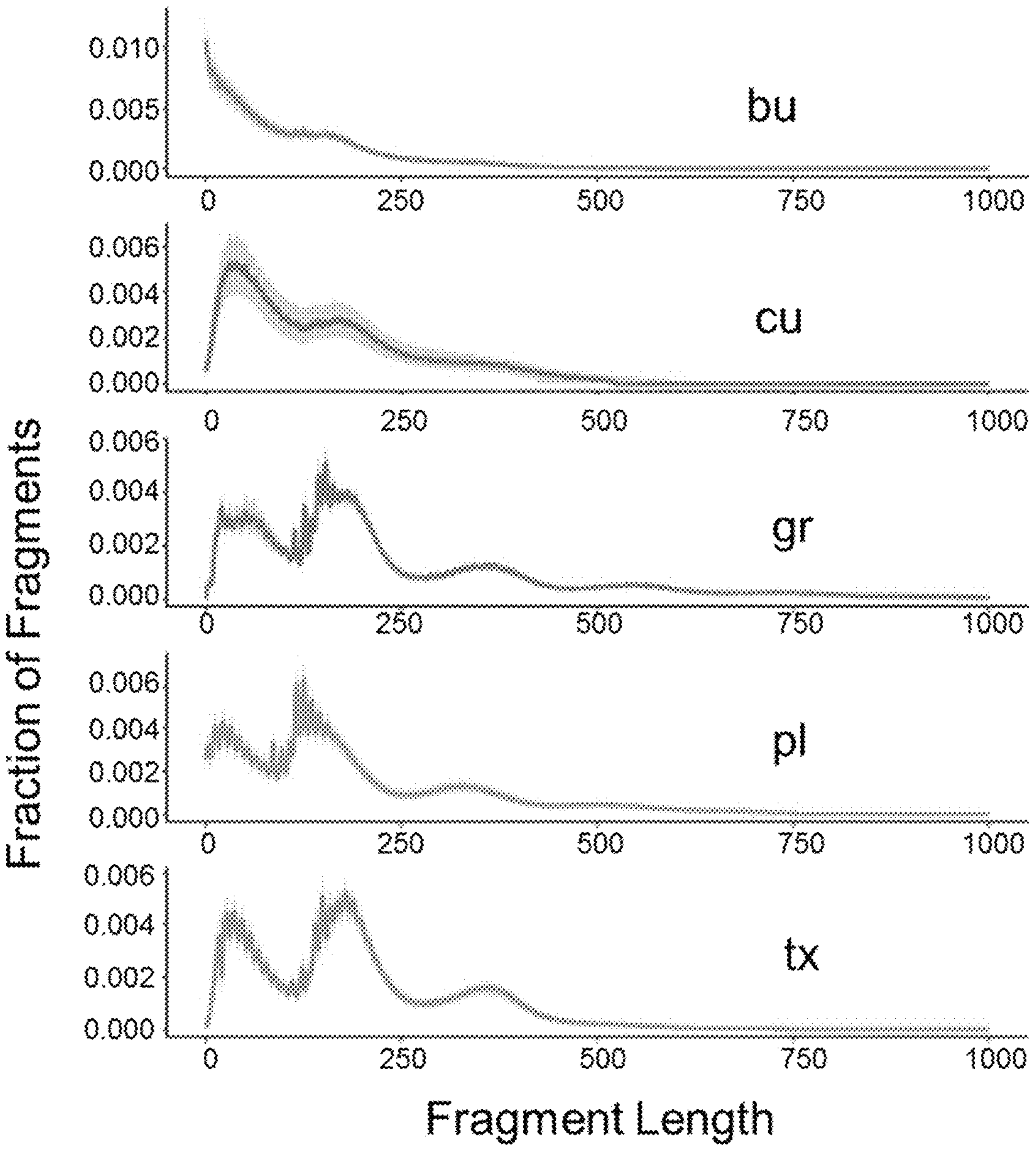
FIG. 44. Gm12878 platform comparisons. Aggregate fragment length frequency plots. Fragment length is shown on the x-axis, and the fraction of reads with fragments of each bp size was calculated for each sample in each dataset. For this analysis, the median fraction at each fragment size is shown as a solid line, with $25^{th}$ and $75^{th}$ percentiles shown in the shaded regions. Abbreviations used throughout the plots: bu, Buenrostro, et al., Nature 523 (2015) Fluidigm C1 ATAC-seq; cu, Cusanovich, et al., Science 348 (2015) sci-ATAC-seq (2015); gr, Graybuck, et al. (the data described herein)
Figure 46A:
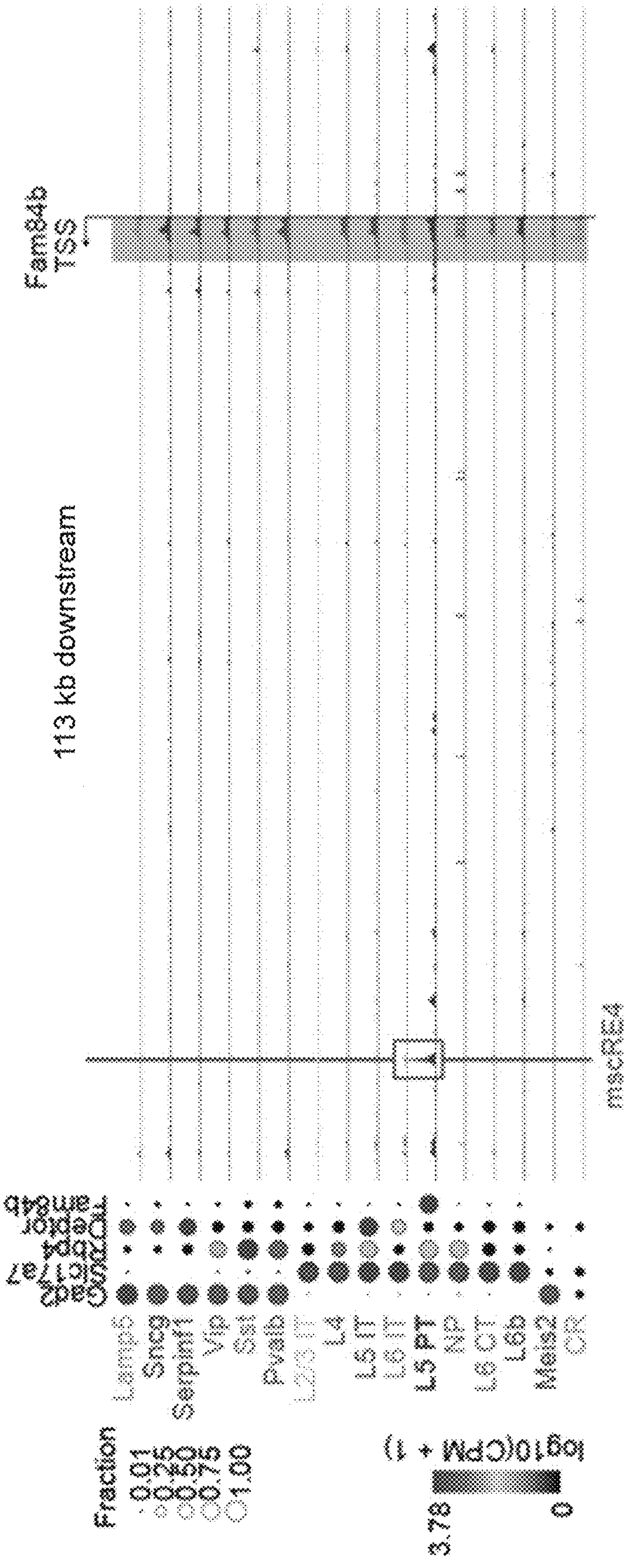
FIGS. 46A-46D. scATAC-seq data. The dotplot shows both the fraction of cells in each subclass that express each gene (size of points), and the median expression level within each subclass (color of points). scATAC-seq data were grouped by subclass based on transcriptomic mapping, and aggregated fragment overlaps were plotted near the gene of interest after normalization for fragment count (track plots, right panel). (46A) Subclass-level gene expression profiles (dot-plots, left panel) from Tasic, et al. (2018, Nature) show highly specific expression of the Fam84b gene in the L5 PT subclass. Fam84b (family with sequence similarity 74, member B) is a transcription factor gene that was recently shown to be a highly selective marker gene for L5 PT neurons across two regions of the mouse cortex (Tasic, et al. (2018) Nature). A peak of accessibility specific to L5 PT samples (mscRE4) was identified 113 kb downstream from the Fam84b TSS. (46B) Subclass-level gene expression profiles (dot-plots, left panel) from Tasic, et al. (2018) show enrichment of Hsd11b1 expression in L5 IT and L5 PT cell types. Hsd11b1 (hydroxysteroid 11-beta dehydrogenase 1) is a gene involved in corticosteroid biosynthesis. It has been shown to be selectively expressed in L5 cells, with higher expression in some L5 IT types than in L5 PT cells {Tasic, et al. (2018) Nature}. A peak of accessibility enriched in L5 IT cells but absent in L5 PT cells (mscRE16) was identified 34 kb upstream of the Hsd11b1 TSS. The cell types listed along the side of FIGS. 46A and 46B are (from top to bottom) Lamp5, Sncg, Serpinf1, Vip, Sst Pvalb, L2/3 IT, L4, L5 IT, L6 IT, L5 PT, NP, L6 CT, L6b, Meis2, and CR. (46C) scATAC-seq data showed a peak of accessibility specific to mscRE10 located 34 kb upstream of Car3. (46D) scATAC-seq data showed a peak of accessibility specific to mscRE13 located 86 kb upstream of Osr1.
Figure 46B:
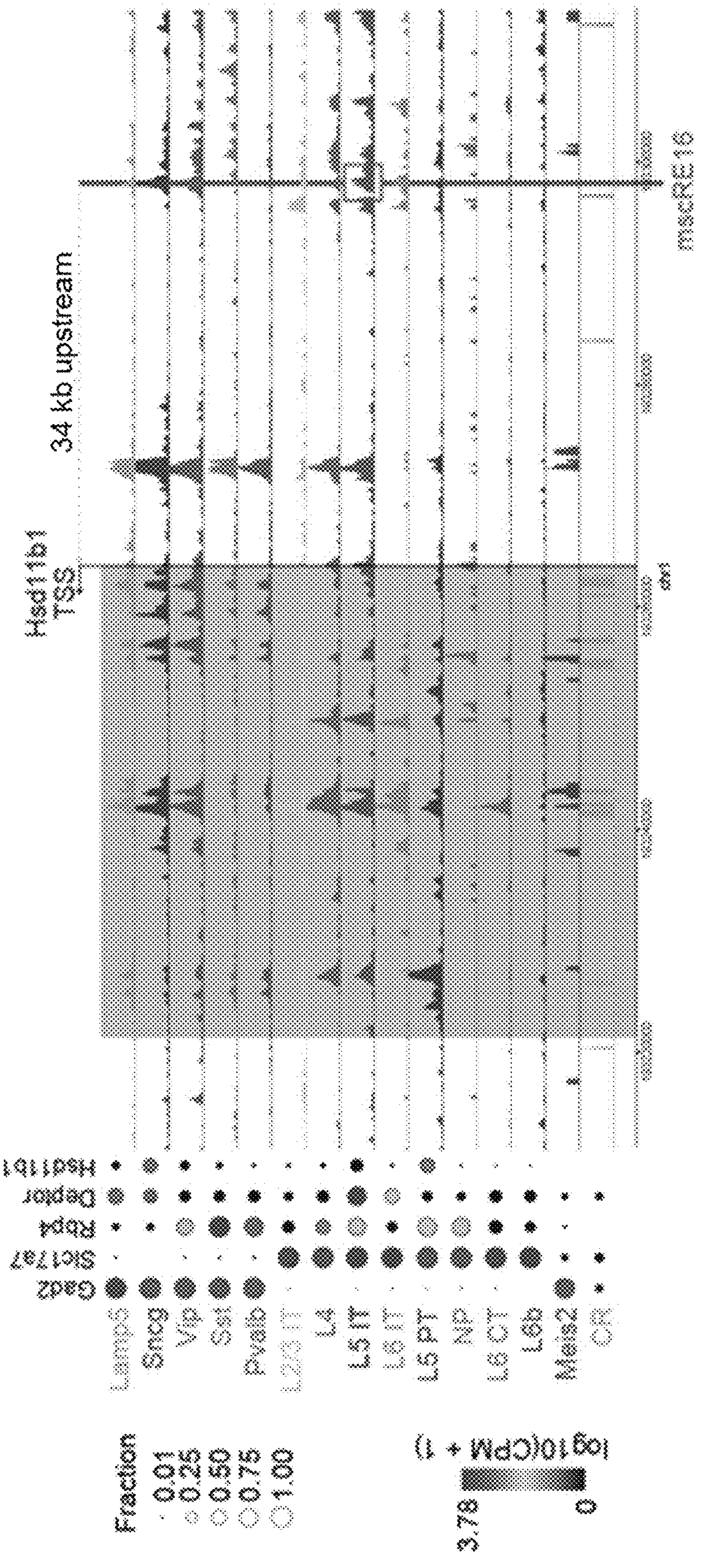
Figure 46C:
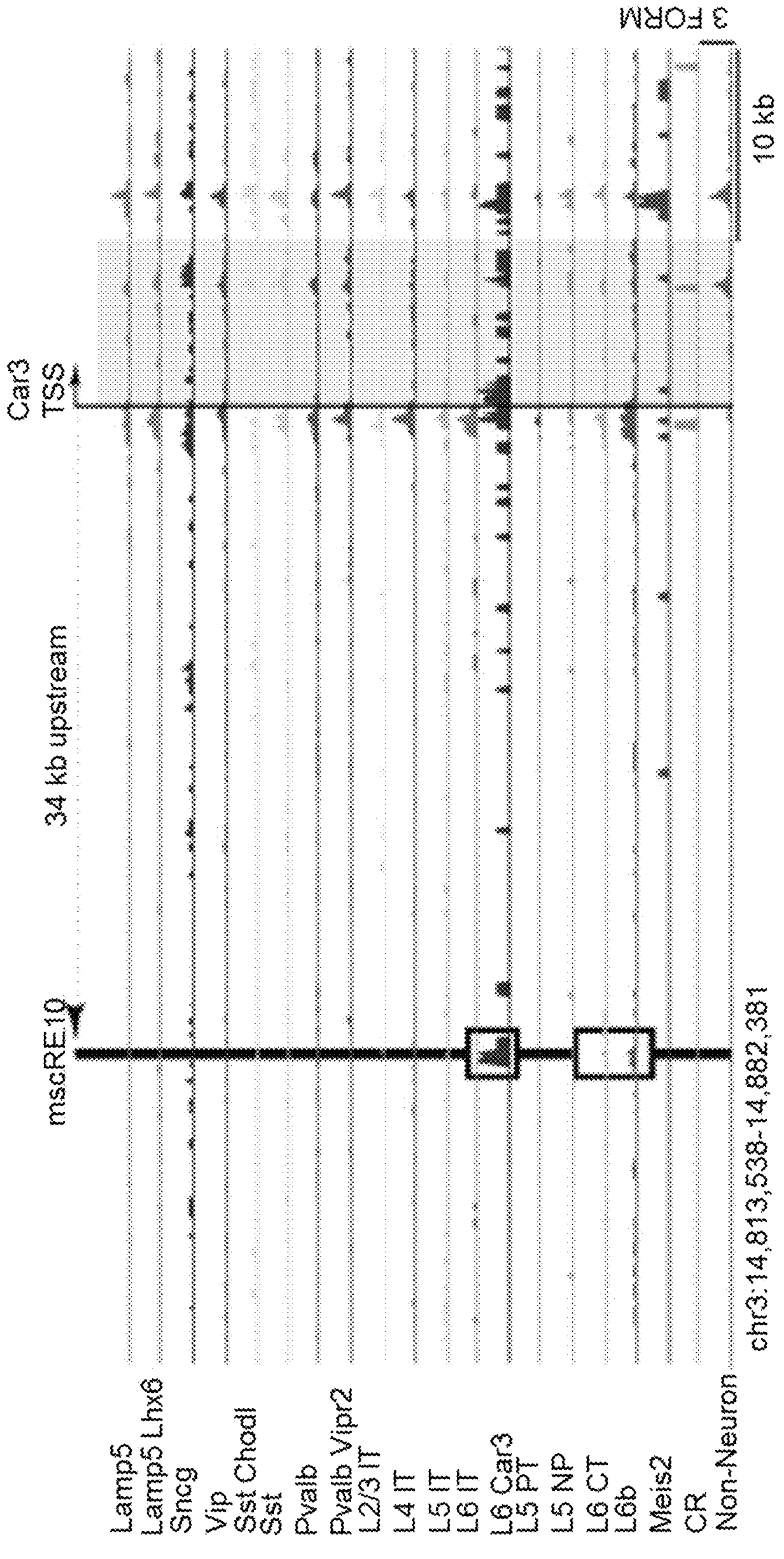
Figure 46D:
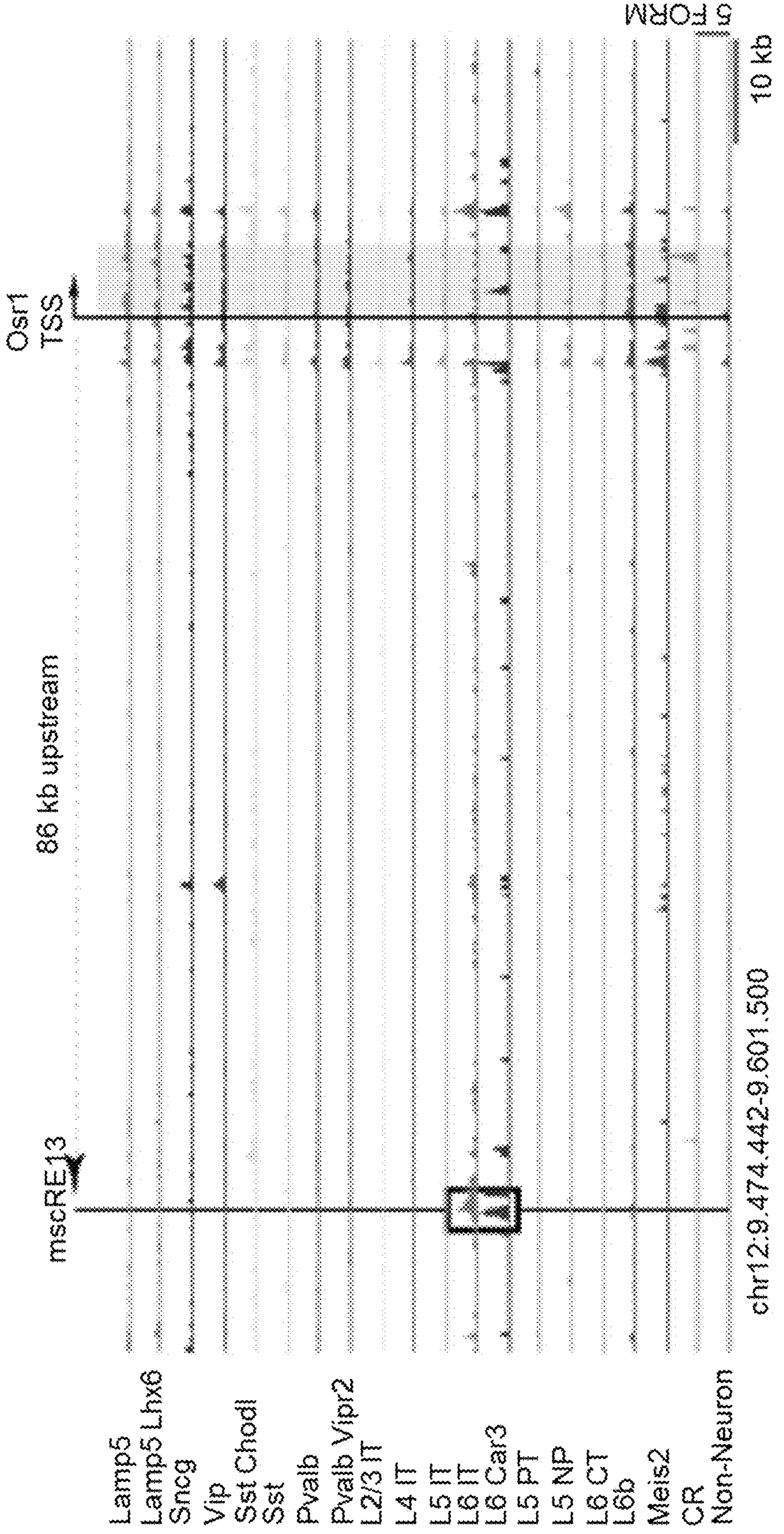

Example 2. Prospective, brain-wide labeling of neuronal subclasses with enhancer-driven adeno-associated virus (AAVs). Individual neuronal and non-neuronal cells from transgenically-labeled mouse cortex were isolated by Fluorescent Activated Cell Sorting (FACS) and examined using the Assay for Transposase-Accessible Chromatin with next generation sequencing (scATAC-seq). Buenrostro, et al., 2015, Nature 523: 486-90); Cusanovich, et al., 2015, Science (80): 348, 910-914. This strategy allows for interrogation of both abundant (e.g. layer 4 intratelencephalic L4 IT neurons, 17% of primary visual area of the cortex, VISp, neurons) and very rare cell types (e.g. Sst Chodl neurons, 0.1% of VISp neurons) with the same method. To sample cells both broadly and specifically in the mouse brain, 25 different Cre or Flp-driver lines, or their combinations crossed to appropriate reporter lines, were utilized (FIG. 42). Many of the same lines were previously characterized by single-cell RNA-seq. Tasic, et al., 2018, Nature 563, 72-78. In addition, retrograde labeling by recombinase-expressing viruses was employed to selectively sample cells with specific projections (Retro-ATAC-seq). This method yielded scATAC-seq libraries of comparable quality to previously published scATAC-seq studies (FIGS. 43, 44). Buenrostro, et al., 2015, Nature 523, 486-90; Pliner et al., 2018, Mol. Cell 71, 858-871.e8; Cusanovich, et al., 2015, Science 348, 910-4.

To generate scATAC-seq data that would be directly comparable to the scRNA-seq dataset (Tasic, et al., 2018, Nature 563: 72-78), the dissections were focused on visual cortex for glutamatergic cell types, but allowing broader cortical sampling for GABAergic cell types. This strategy is rooted in the observation that GABAergic cell types are shared across two distant poles of mouse cortex, whereas the glutamatergic cell types are distinct among different cortical regions. Tasic, et al., 2018, Nature 563: 72-78. Retro-ATAC-seq cells were collected only from the visual cortex. In total, 3,381 single cells from 25 driver-reporter combinations in 60 mice, 126 retrogradely labeled cells from injections into 3 targets across 7 donors, and 96 samples labeled by one retro-orbital injection of a viral tool generated according to the current disclosure were collected. After FACS, individual cells were processed using ATAC-seq, and were sequenced in 60-96 sample batches using a MiSeq (Materials and Methods of Example 2). Quality control (QC) was performed by filtering to select 2,416 samples with >10,000 uniquely mapped paired-end fragments, >10% of which had a fragment size longer than 250 bp, and with >25% of fragments overlapping high-depth cortical DNAse-seq peaks generated by Encyclopedia of DNA Elements (ENCODE) (FIG. 42). Yue, et al., 2014, Nature 515: 355-64.

Previous studies have shown that most recombinase driver lines label more than one transcriptomic cell type. Tasic, et al., 2018, Nature 563: 72-78; Tasic, et al., 2016, Nat. Neurosci. 19, 335-346. To increase the cell type resolution of chromatin accessibility profiles beyond that provided by driver lines, the scATAC-seq data was clustered using a novel, feature-free method for computation of pairwise Jaccard distances. These distances were used for principal component analysis (PCA) and t-stochastic neighbor embedding (t-SNE), followed by Phenograph clustering (FIG. 45, Materials and Methods of Example 2). Levine, et al., 2015, Cell 162: 184-197. This clustering method clearly grouped cells from class-specific driver lines together, and segregated them into multiple clusters as expected based on transcriptomic analyses. Cluster identity was then assigned by comparison of accessibility near transcription start sites (TSS±20 kb) to the scRNA-seq dataset generated for VISp using median correlation (FIG. 45, Materials and Methods of Example 2). Tasic, et al., 2018, Nature 563: 72-78. Subclass-level assignments for each driver line were found to match closely with those observed for the same driver lines by scRNA-seq. Once assigned, clusters from the same subclass (e.g. Vip or layer 5, L5, IT) or distinct cell type (e.g. Pvalb Vipr2) were aggregated for peak calling and examination of accessibility patterns (FIGS. 46A-46D). Comparisons of these scATAC-seq aggregate profiles to previously published ATAC-seq from cortical populations showed strong correspondence between aggregate profiles and populations, and comparisons to previously published cortical scATAC-seq data demonstrate an increase in cell type resolution using the current dataset generated by this lab. Cusanovich, et al., 2018, Cell 174, 1309-1324.e18; Preissl, et al., 2018, Nat. Neurosci. 21: 432-439.

L5 of mouse cortex contains three major subclasses of excitatory neurons: intertelencephalic (IT) neurons that project to other cortical regions, near-projecting (L5 NP) neurons that have mostly local projections, and cortico-fugal (a subset of which is called pyramidal tract, L5 PT) neurons that project to subcortical brain regions such as the thalamus. Tasic, et al., 2018, Nature 563: 72-78; Harris et al., bioRxiv, 2018 doi:10.1101/292961. The driver line Rbp4-Cre labels both L5 IT and L5 PT neurons in cortex, but not L5 NP. Tasic, et al., 2018, Nature 563: 72-78. The scATAC-seq clustering identified L5 PT and L5 IT neurons in the generated dataset based on correlation with scRNA-seq cell types (FIG. 45). Labeling of these cells by Rbp4-Cre and retrograde labeling from a known L5 PT target region, the lateral posterior nucleus of the thalamus (LP), validated that these cells are likely L5 IT (Rbp4-Cre+ only) and L5 PT neurons (Rbp4 and LP Retro-ATAC-seq). A search was performed near transcriptomic marker genes for 500 bp putative enhancer regions that were specific to L5 PT or L5 IT cells, and which had strong sequence conservation (FIG. 46A-46D). These regions are referred to as mouse single-cell regulatory elements (mscREs, FIG. 47).

Figure 48C:
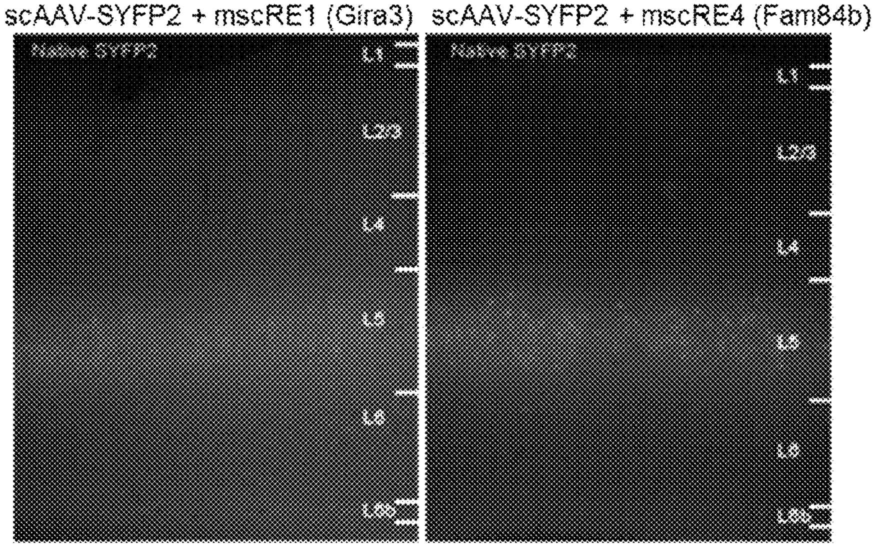

To functionally test mscREs, their genomic sequences were cloned upstream of a minimal beta-globin promoter driving fluorescent proteins SYFP2 or EGFP in a recombinant adeno-associated virus (rAAV) genome (FIG. 48A). These constructs were packaged using a PHP.eB serotype, which can cross the blood-brain barrier, to enable delivery by retro-orbital injection. Four mscREs were screened for L5 PT cells and two for L5 IT (FIG. 47). Chan, et al., 2017, Nat. Neurosci. 20: 1172-1179. Two weeks after retro-orbital injection, the brains of infected mice were collected and screened for expression by visual inspection of native fluorescence and immunohistochemistry to enhance SYFP2 and EGFP signal. Two of these enhancers provided specific labeling of cells in L5 (FIG. 48C, right) and were selected for further validation.

Figure 49B:
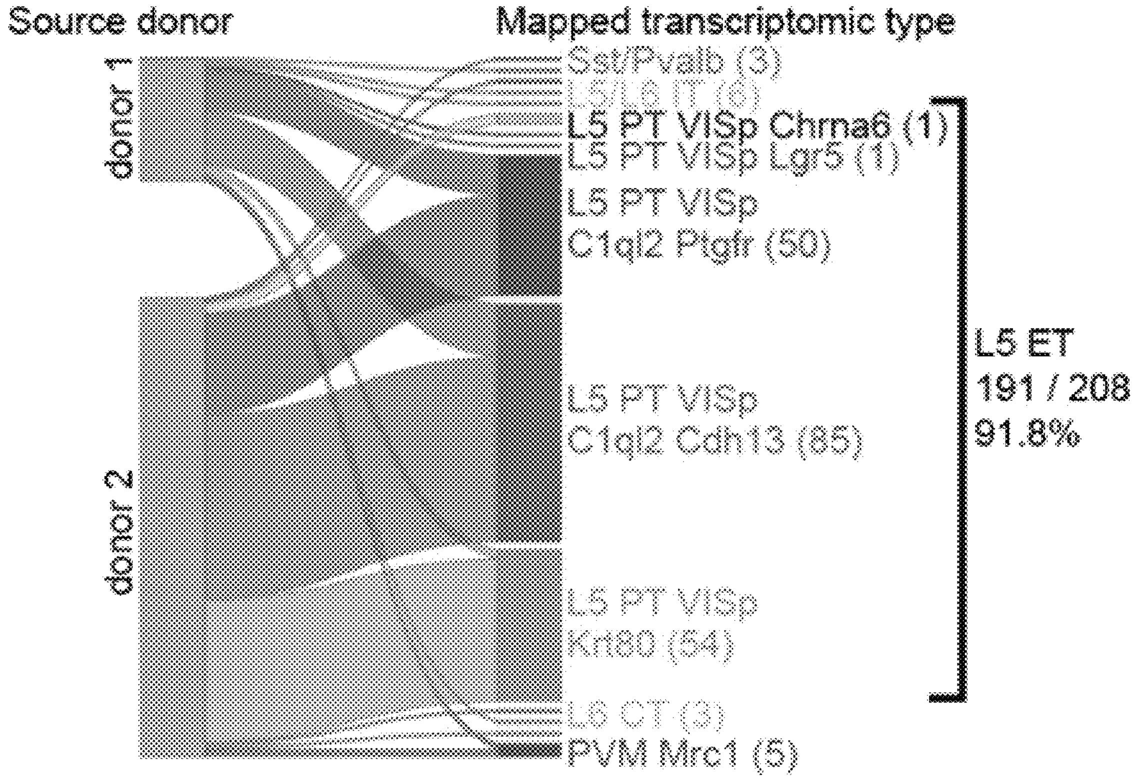
Figure 50A:
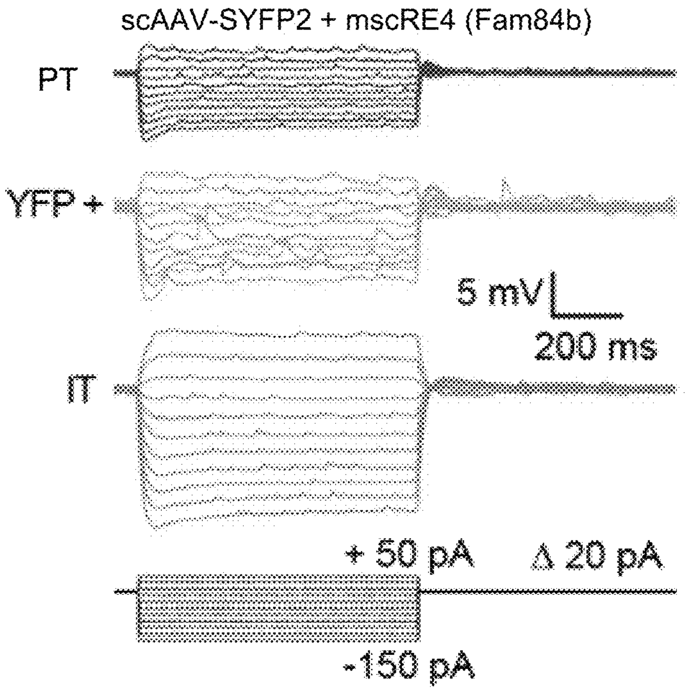
FIGS. 50A-50C. Electrophysiological characterization of mscRE4-labeled cells and demonstration of utility for electrophysiological recording of labeled neurons. (50A) Cortical slices from an animal labeled with the scAAV-mscRE4-SYPF2 (T502-057) virus were used for electrophysiological characterization. Example impedance amplitude profiles obtained from a (Yellow Fluorescent Protein) YFP+ and a YFP− neuron in VISp. For comparison, impedance amplitude profiles from an unlabeled PT-like and an IT-like neuron from somatosensory cortex are also shown. Resonance frequency is plotted as a function of input resistance. (50B) Example voltage responses to a series of hyperpolarizing and depolarizing current injections for a YFP+ and a YFP− neuron. Example voltage responses obtained from unlabeled PT-like and IT-like neurons are also shown for reference. (50C) Input resistance, sag ratio and resonance frequency for three experimental conditions.
Figure 50B:
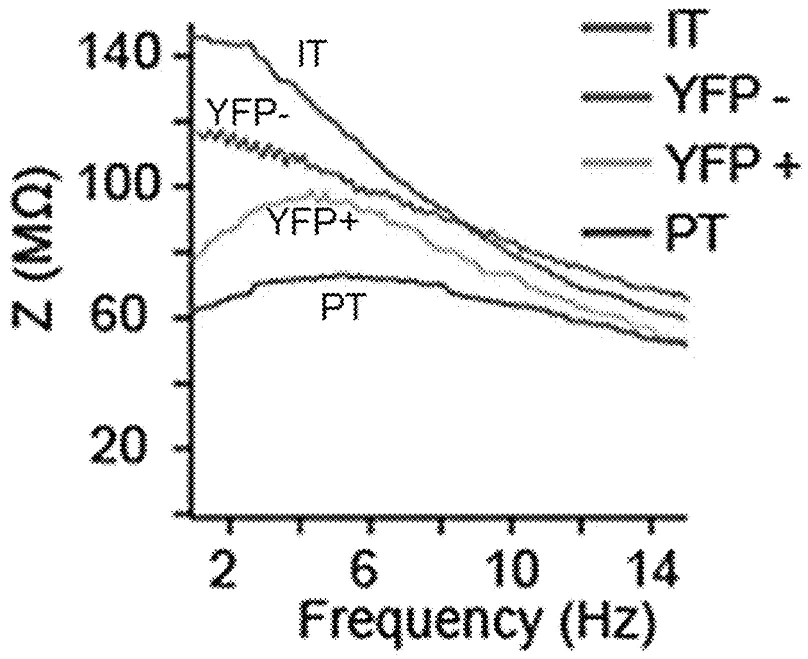
Figure 50C:
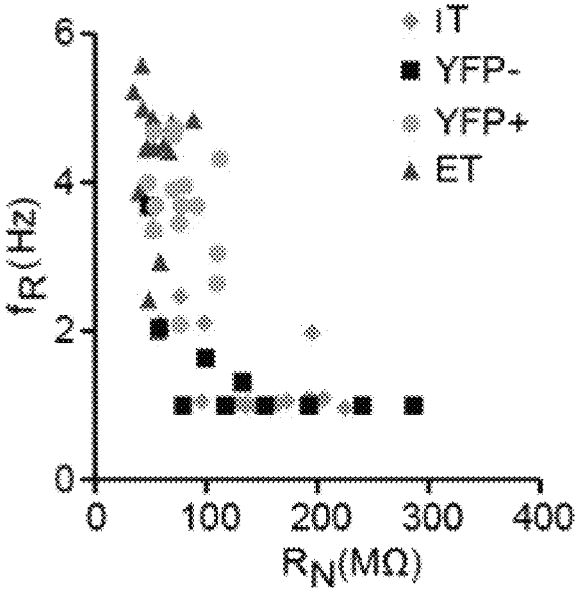
Figure 51A:
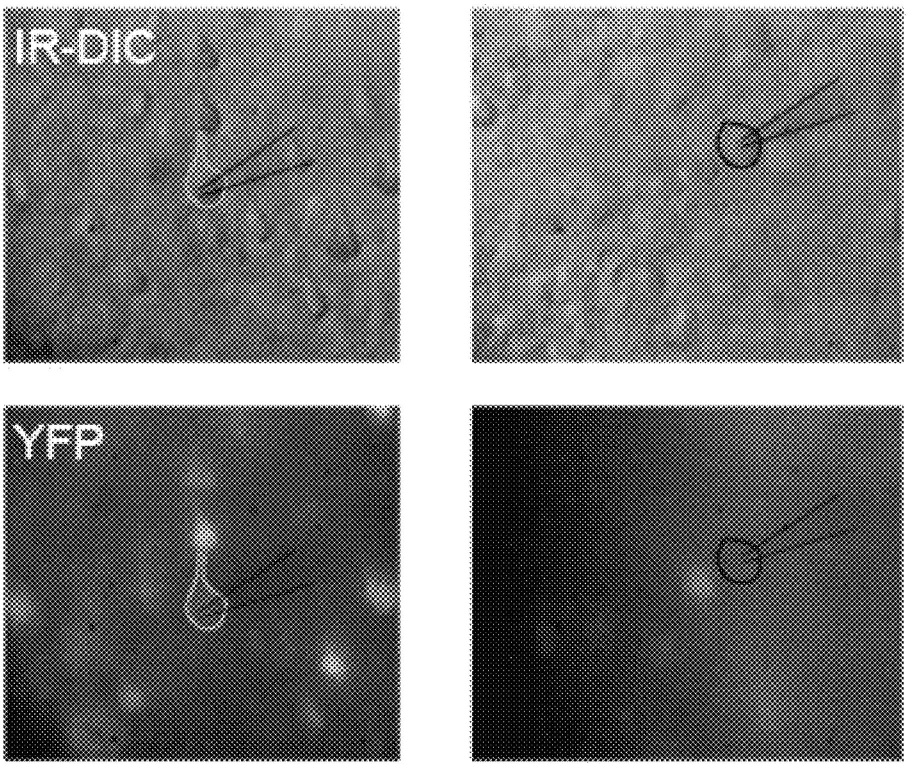
FIGS. 51A, 51B. Additional eletrophysiological characteristics of mscRE4-SYFP2 labeled cells. (51A) Microscopy of example cells characterized by patch electrophysiology. Left, a SYFP2-positive cell; right, a SFYP2-negative cell. (51B) Input resistance, sag ratio, and resonance frequency for the four experimental conditions: IT, YFP−, YFP+, and PT.
Figure 51B:
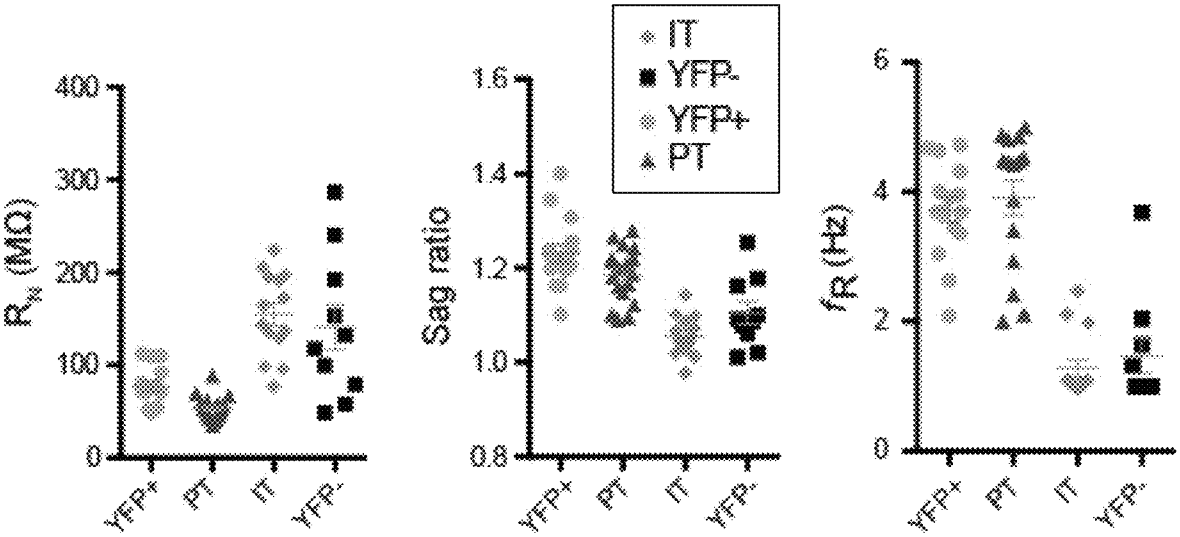
Figure 52A:
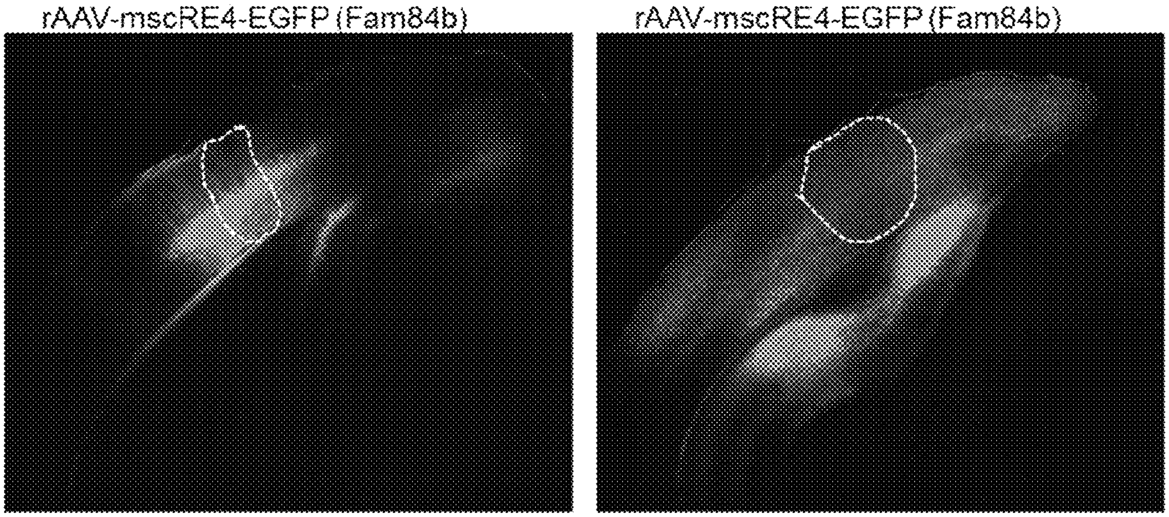
FIGS. 52A, 52B. Stereotaxic labeling using enhancer-driven viruses. (52A) Native fluorescence imaging of animals with stereotaxic injection of mscRE4-EGFP in primary visual cortex. Enhancer-driven viruses were co-injected with a constitutive dTomato virus, rAAVDJ-EF1a-dTomato at 0.1× of the volumes of the mscRE viruses, to provide injection site location (dotted outlines). (52B) Native fluorescence imaging of animals with stereotaxic injection of mscRE4-SYFP2 into primary visual cortex at the indicated volumes.
Figure 52B:
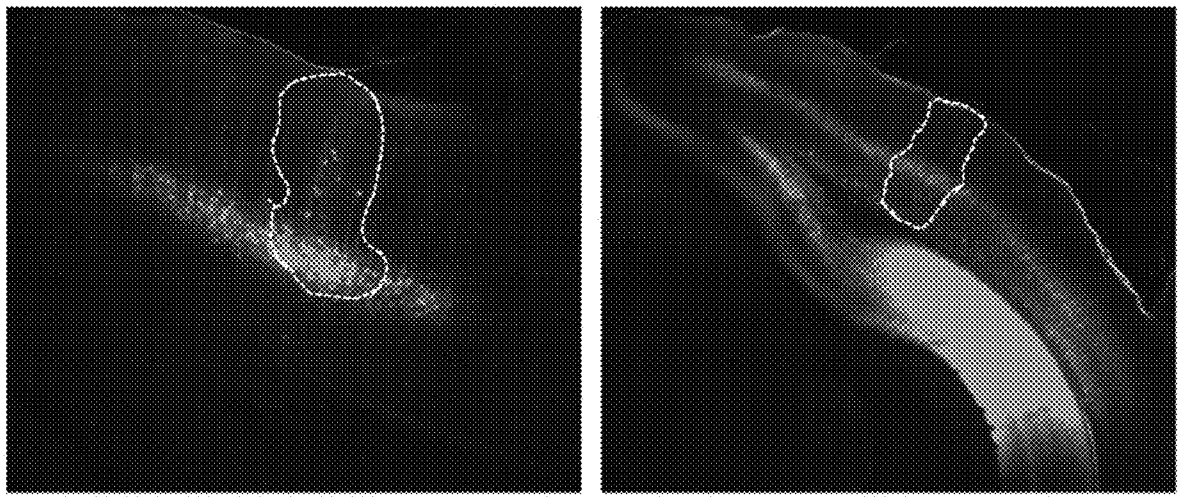

To assess the utility of enhancer-driven fluorophores as viral tools, a retro-orbital injection of the mscRE4-SYFP2 virus was performed in additional animals. From two of these, L5 of VISp was dissected, labeled cells were sorted by FACS, and scRNA-seq was performed as described previously. Tasic, et al., 2018, Nature 563: 72-78. scRNA-seq expression profiles were compared to a VISp reference dataset using centroid classification of cell types (Materials and Methods of Example 2). Tasic, et al., 2018, Nature 563: 72-78. The mscRE4-SYFP2 virus was found to yield>91% specificity for L5 PT cells within L5 (FIG. 49B). Labeling of L5 PT cells was confirmed by electrophysiological characterization of labeled vs unlabeled cells in the cortex (FIGS. 49B, 50A, 51). Cells labeled by mscRE4 had characteristics of L5 PT neurons, whereas cells that were label-negative more closely matched L5 IT neurons. Baker, et al., J. Neurosci. 38, 5441-5455, 2018. This experiment demonstrates the utility of these viral tools for electrophysiology experiments targeted to specific neuronal subclasses for which driver lines are not available. Finally, stereotaxic injection of the mscRE4 fluorophore viruses directly into VISp was tested. It was found that an extremely bright and specific labeling could be achieved by using stereotaxic injection, although the specificity depended on the volume of injection, likely reflecting a loss of specificity at high numbers of viral genome copies per cell (FIGS. 52A, 52B).

L5 PT cells are often difficult to isolate from single-cell suspensions when in a heterogeneous mixture with other cell types due to differential cell survival, and there is currently no reliable driver line to selectively label L5 PT cells. Tasic, et al., 2018, Nature 563: 72-78; Tasic, et al., Nat. Neurosci. 19, 335-346, 2016. Retro-orbital injection of the mscRE4-SYFP2 virus was used to enhance the scATAC-seq generated dataset by sorting cells labeled by mscRE4 for FACS. As expected based on scRNA-seq analysis, 55 of 61 high-quality mscRE4 scATAC-seq profiles clustered together with other L5 PT samples (90.2%).

Figure 53:
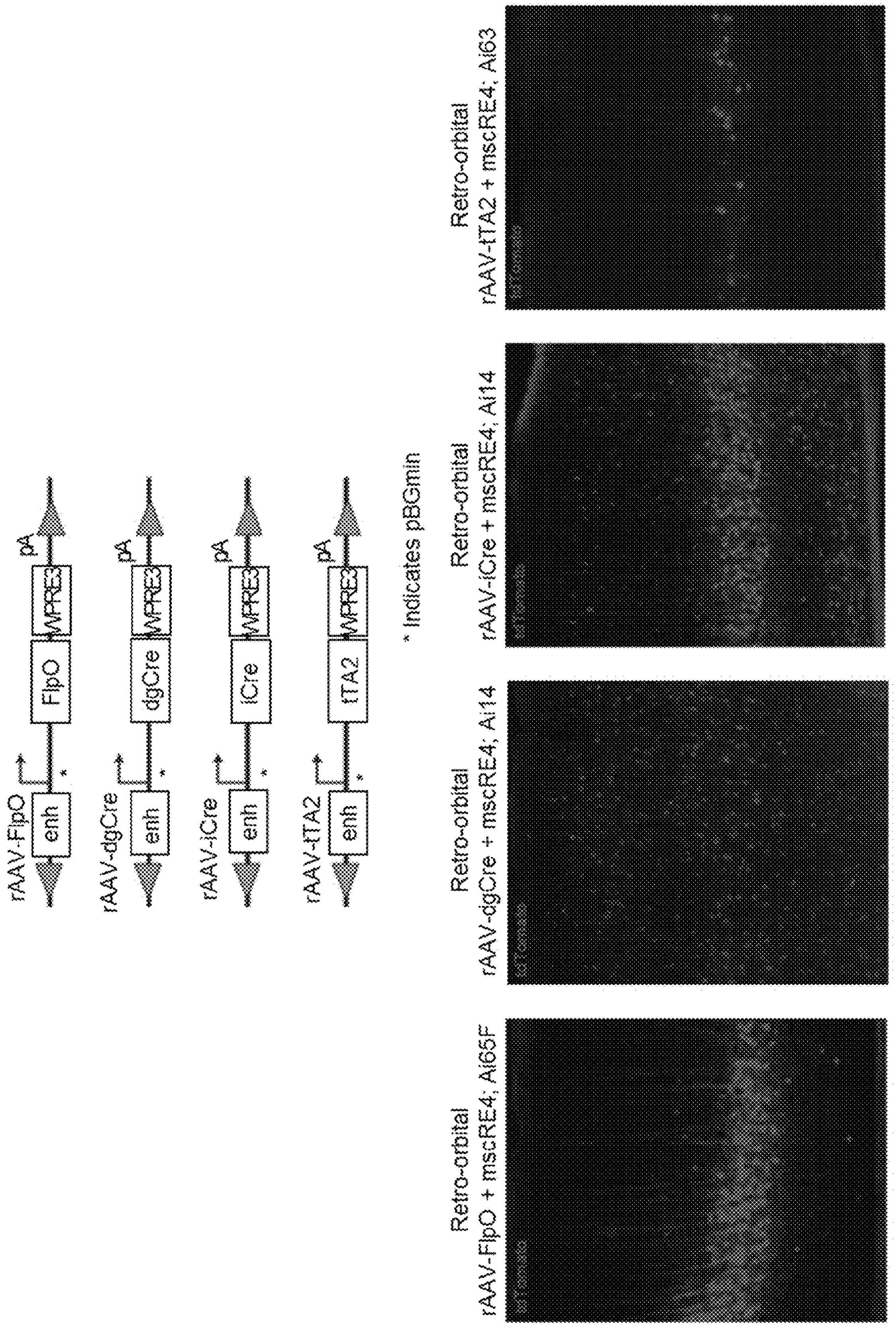
FIG. 53. Some enhancer-driven recombinase viruses provide specific, binary labeling. Three different recombinases and one transactivator were inserted downstream of mscRE4 and a promoter in viral constructs. After retro-orbital injection, labeling of L5 was found with various degrees of specificity using tTA2 (TG1011, SEQ ID NO: 88) in an Ai63 reporter mouse (most sparse, most specific), FlpO (TG978, SEQ ID NO: 80) in an Ai65F reporter mouse (most complete and specific), iCre (TG1010, SEQ ID NO: 87) in an Ai14 reporter mouse (complete, but with background in L6), and dgCre in an Ai14 reporter mouse (least specific). Images show native fluorescence in visual cortex 2 weeks post-injection. See FIGS. 68A-68G for depictions.
Figure 54:
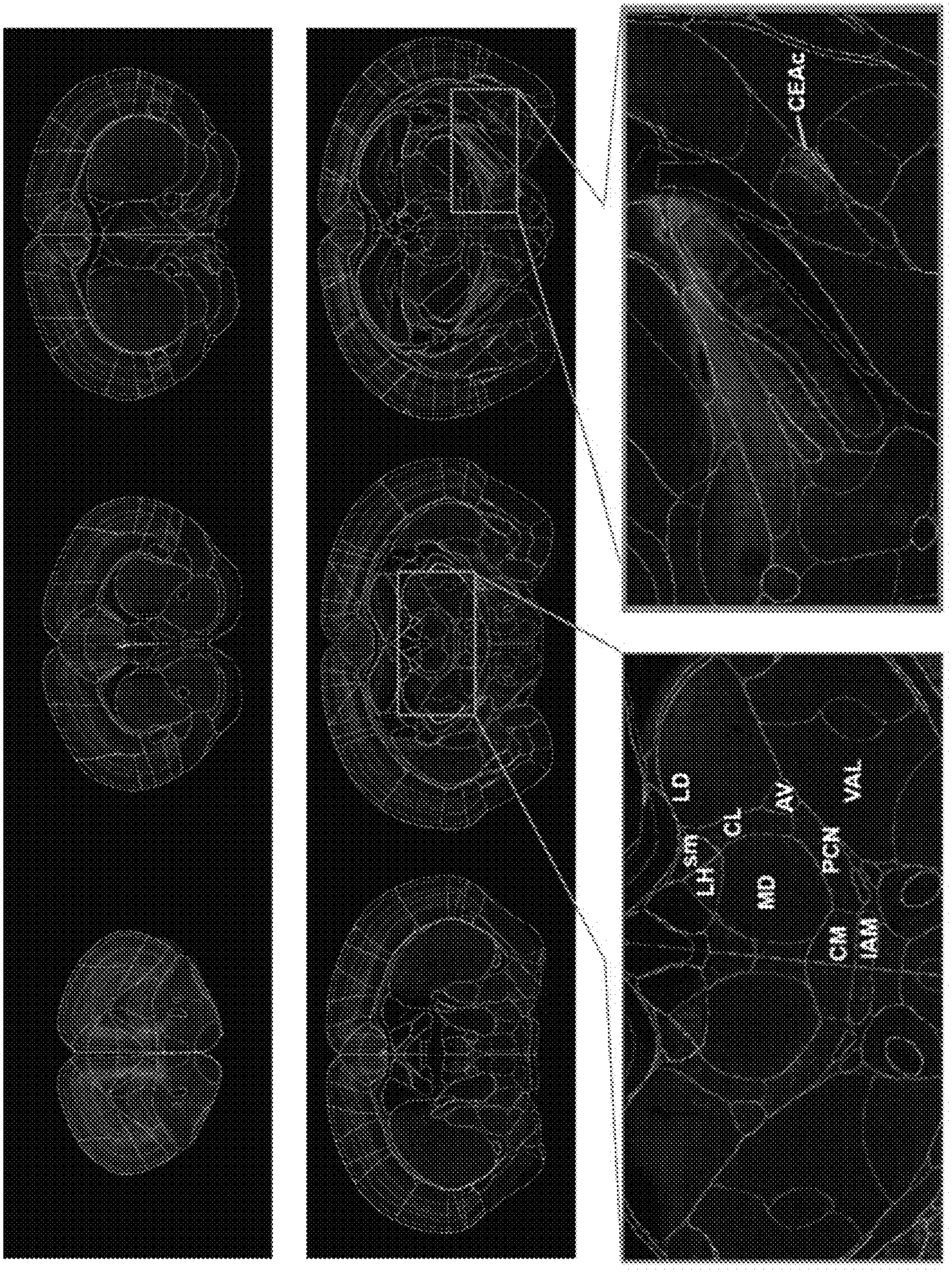
FIG. 54. Brain-wide imaging of retro-orbitally delivered mscRE4-FlpO-WPRE3 (TG978, SEQ ID NO: 80) viral labeling reveals specific, L5-restricted labeling throughout the cortex, and labeling of specific subcortical populations in the central amygdalar nucleus, capsular part (CEAc), a portion of the CeA, which receives and processes pain signals; the substantia nigra, compact part (or pars compacta, SNc), which is involved in movement control and is affected by Parkinson's disease; and prosubiculum (ProS).
Figure 54:
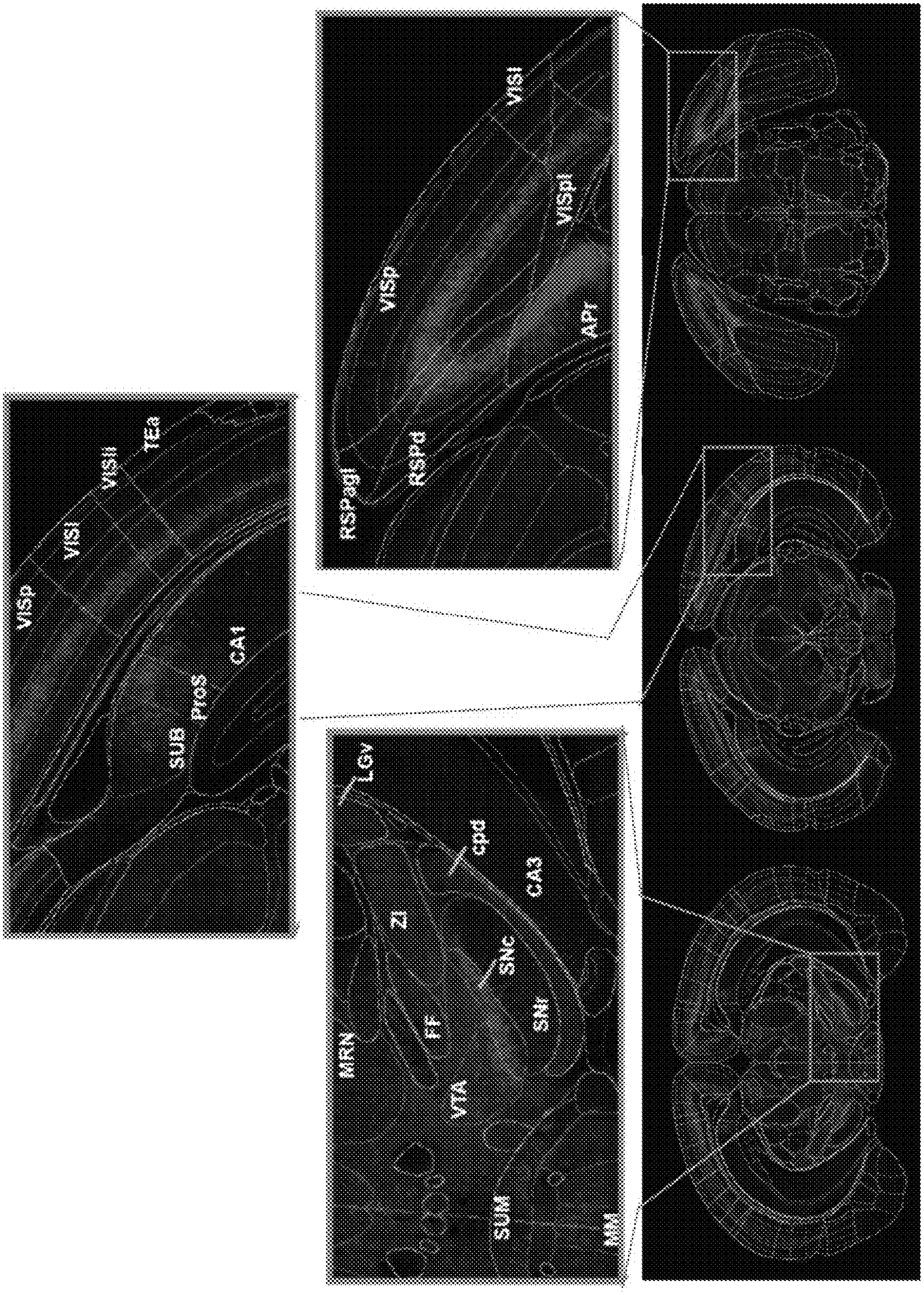
Figure 55A:
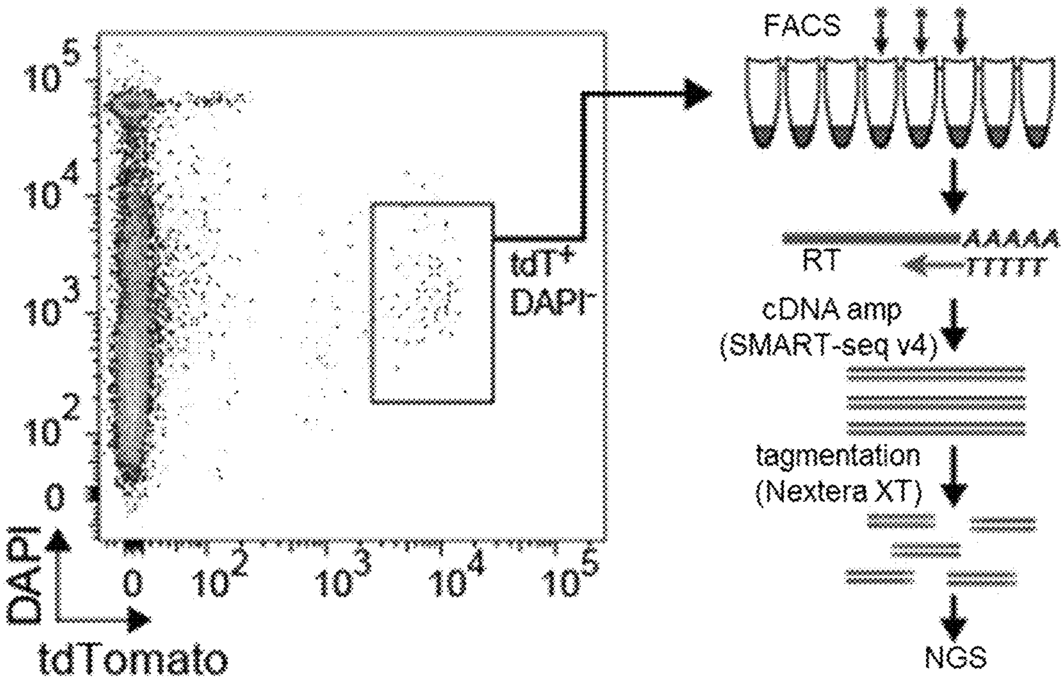
FIGS. 55A, 55B. Validation of cell type targeting of mscRE4-FlpO-WPRE3 viruses by scRNA-seq. (55A) Enhancer-driven recombinase expression was tested using an rAAV construct with a minimal promoter driving FlpO-WPRE3. After packaging, Ai65F mice were given retro-orbital injections. After 2 weeks, tdTomato-expressing cells were visible in the cortex, which could be isolated from L5 dissection, and were sorted by FACS and used for scRNA-seq. (55B) Centroid classifier mapping of labeled cells onto data from Tasic, et al. (2018, Nature) revealed that 90.6% of the cells mapped to L5 PT transcriptomic cell types. The list of cell types along the right, from top to bottom, are: Sst Hpse Cbln4 (3), L5 IT VISp Hsd11b1 Endou (2), L5 PT VISp Chrna6 (2), LSPT VISp Lgr5 (2), L5 PT VISp C1qI2 Ptgfr (40), L5 PT VISp C1qI2 Cdh13 (40), and L5 PT VISp Krt80 (7).
Figure 55B:
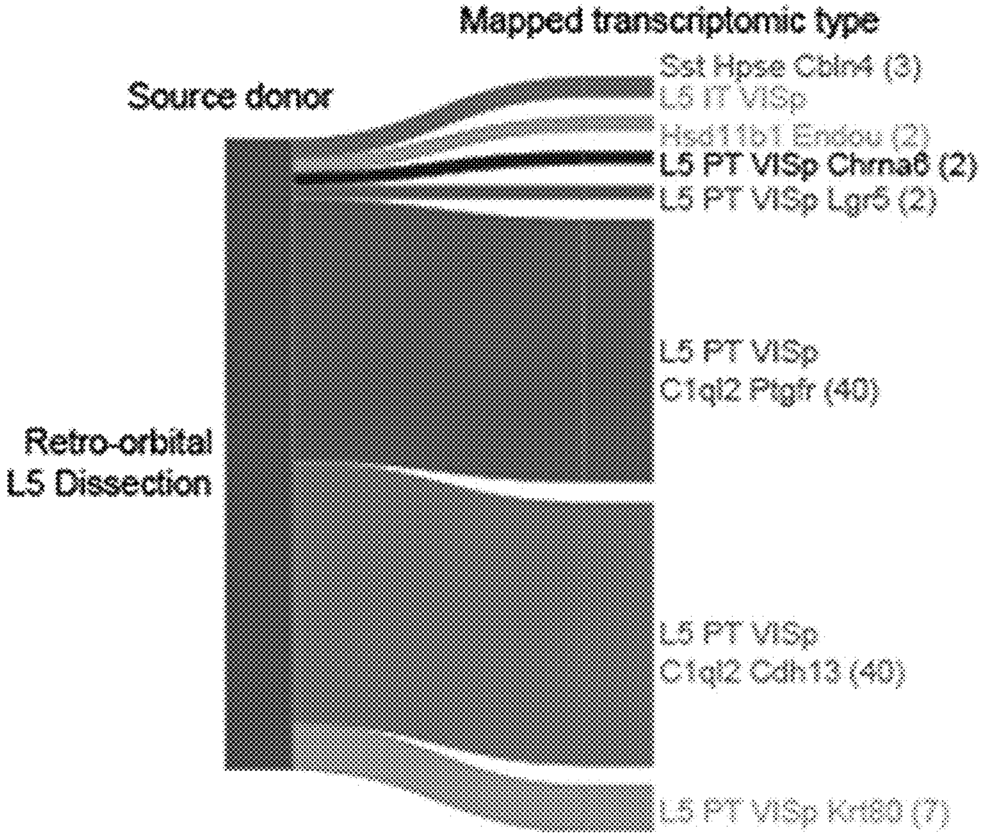
Figure 56A:
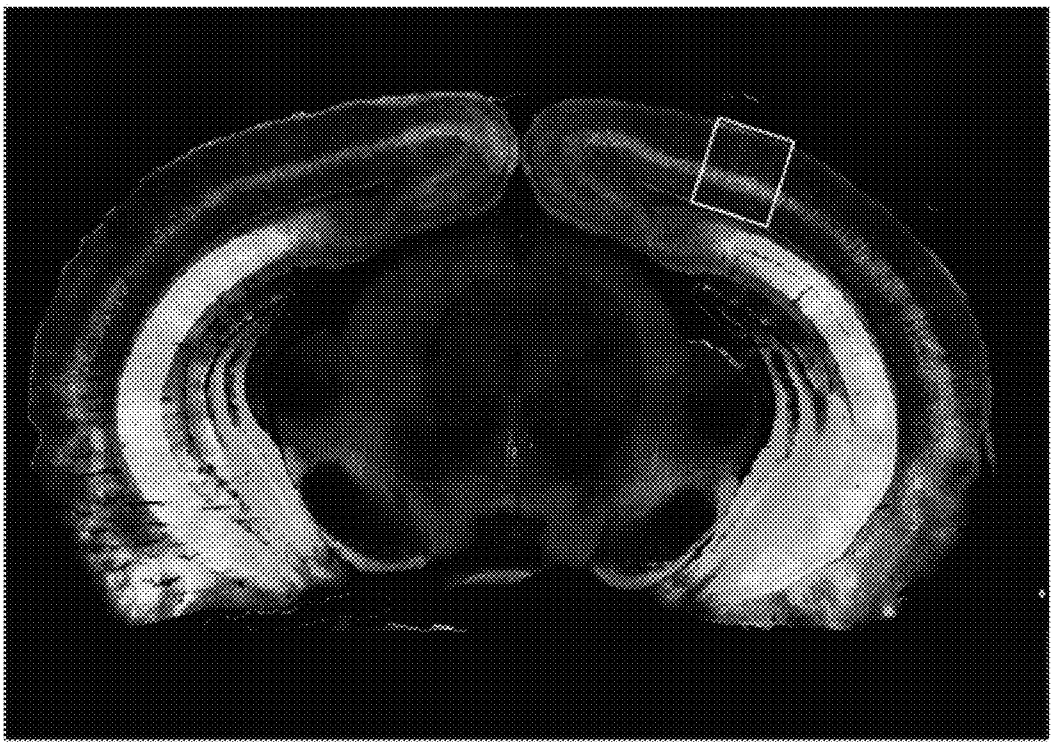
FIGS. 56A-56C. Dual labeling and titration of viral copy number to achieve broad, intersectional labeling (56A, 56B) at high titer, and specific, exclusive labeling (56C) at low titer. These experiments were performed by retro-orbital coinjection of mscRE4-FlpO (TG978, SEQ ID NO: 80) and mscRE16-EGFP (TG1002, SEQ ID NO: 86) viruses into Flp-dependent tdTomato reporter mice (Ai65F). See FIG. 68 for depictions of this dual-labeling strategy. Corner of fluorescence image identifies the fluorophore (Anti-GFP, Native tdTomato, and merge).
Figure 56B:
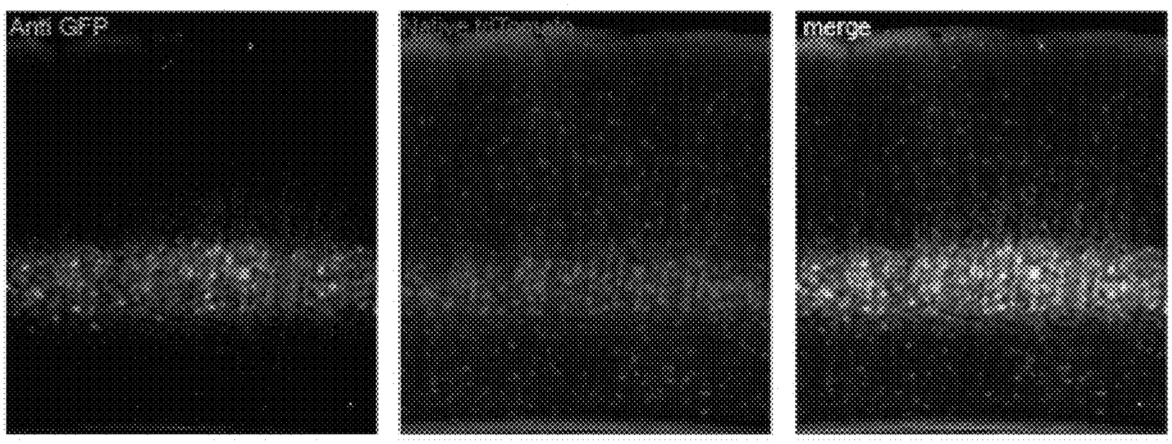
Figure 56C:
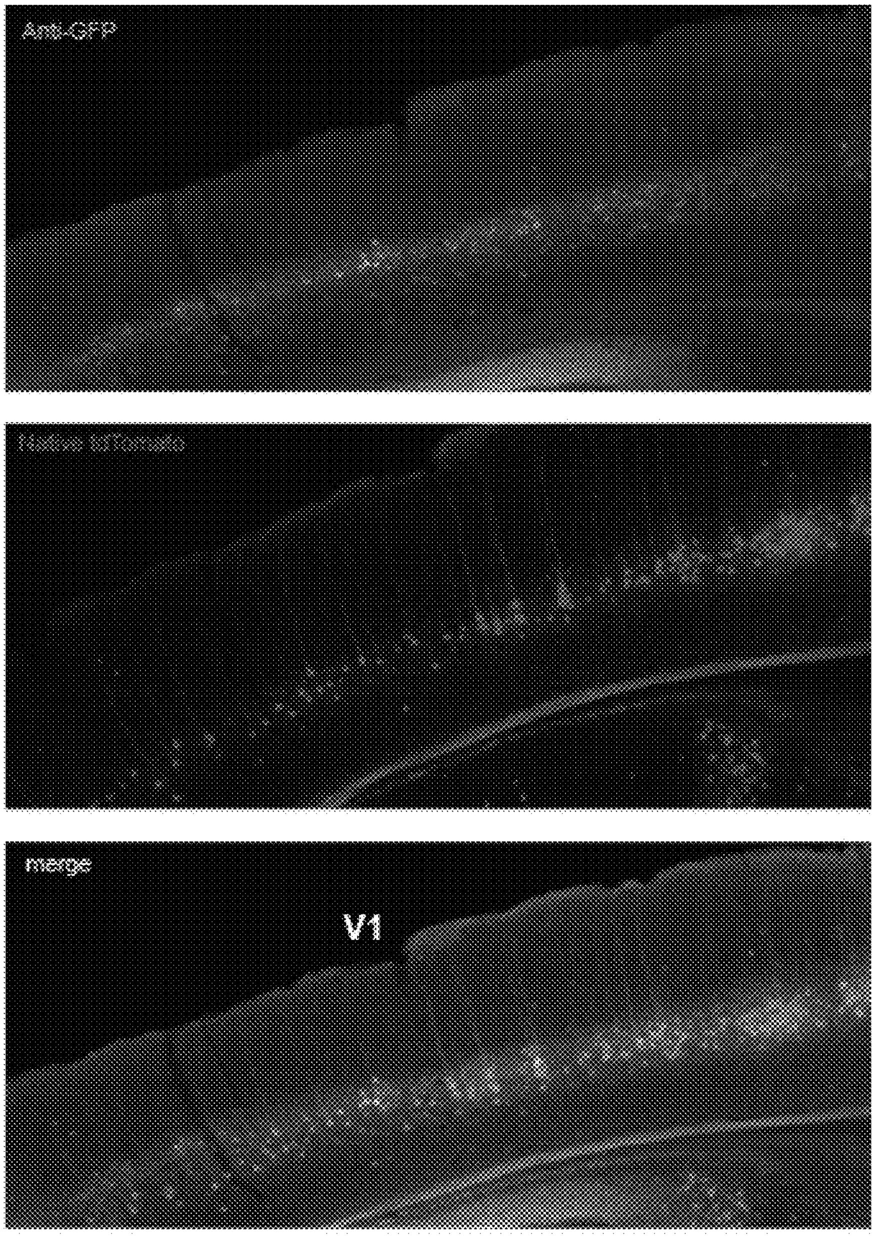
Figure 57B:
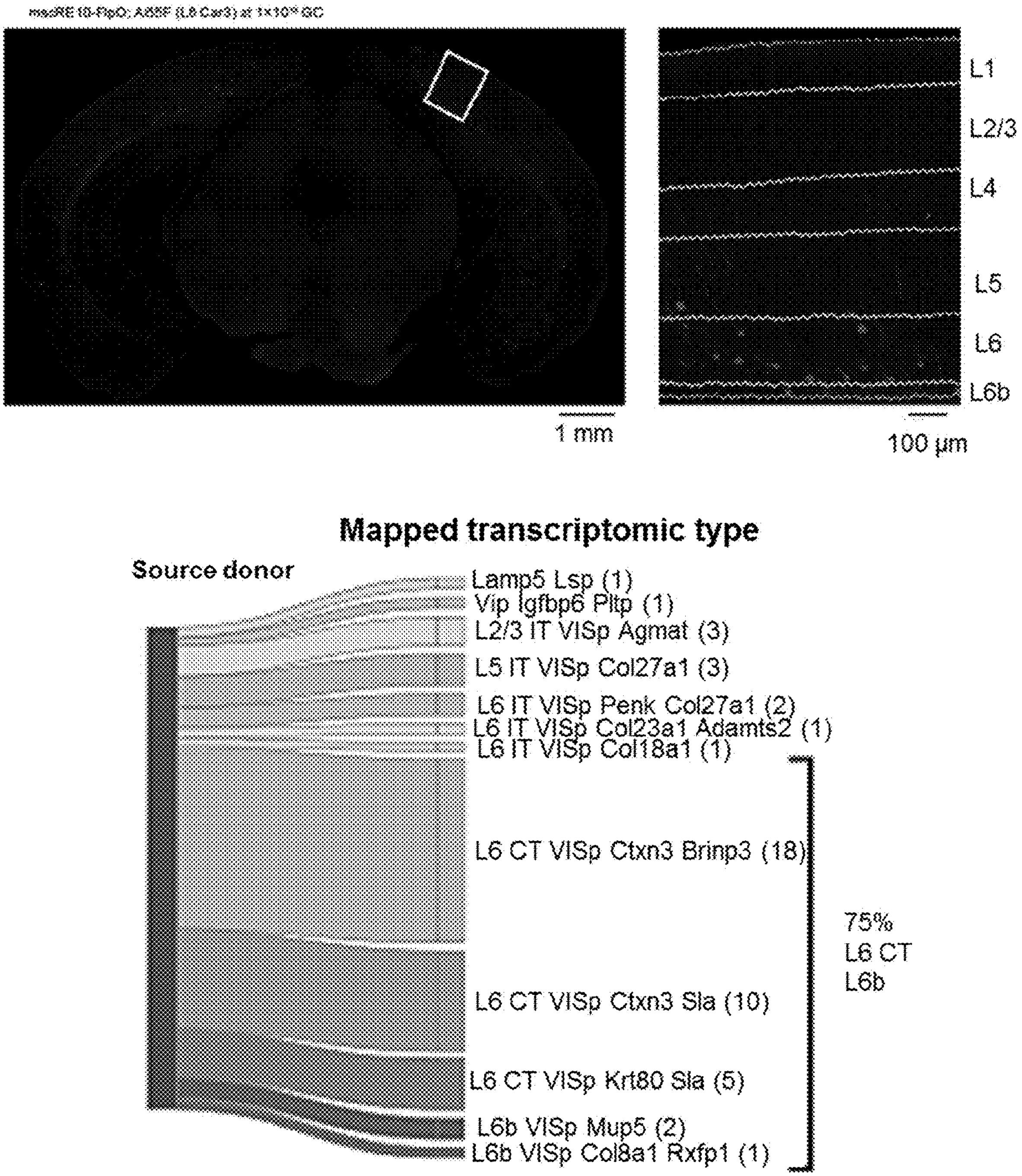
Figure 58:
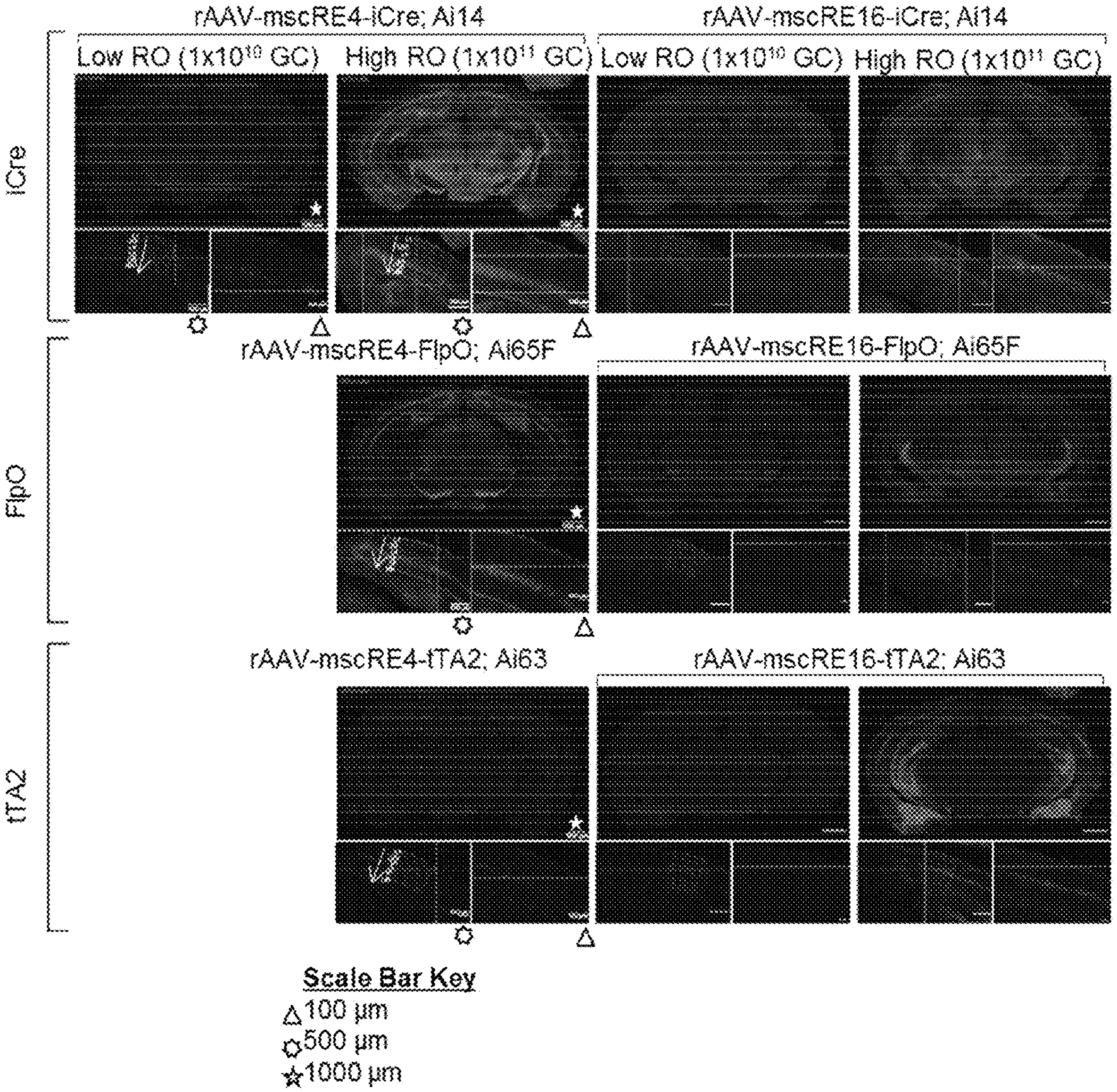
FIG. 58. Retro-orbital mscRE driver screening at multiple titers. Native fluorescence images for reporter mice retro-orbitally (RO) injected with enhancer-driven recombinase viruses at two titers: Low RO, $1\times10^{10}$ genome copies, GC; High RO, $1\times10^{11}$ GC. Fluorescence is tdTomato. Scale bar sizes can be determined by Scale Bar Key where a triangle indicates a scale of 100 μm, the 7-point star indicates a scale of 500 μm, and the 5-point star indicates a scale of 1000 μm. The arrows show where layers are labeled where, in the direction of the arrow, the layers are labeled L1, L2/3, L4, L5, L6, and L6b.

Although fluorophore expression provided enough signal to sort cells by FACS or perform patch-clamp experiments, expression of a recombinase from a specific enhancer virus would expand the utility of these tools as drivers for reporter lines that express fluorophores, activity reporters, opsins, or other genes that are too large to package in AAVs. Daigle, et al., 2018, Cell 174(2): 465-480; Madisen, et al., Neuron 85, 942-958, 2015. To test the specificity of enhancer-driven recombinase expression, mscRE4 was cloned into constructs containing a minimal beta-globin promoter driving destabilized Cre (dgCre), iCre, FlpO, or tTA2, and the constructs were packaged into PHP.eB viruses (FIG. 53). These viruses were delivered by retro-orbital injection into mice with genetically encoded reporters for each recombinase (Ai14 for dgCre and iCre; Ai65F for FlpO; and Ai63 for tTA2). Madisen, et al., Nat. Neurosci. 13, 133-40, 2010; Madisen, et al., Neuron 85, 942-958, 2015; Daigle, et al., Cell 174, 465-480.e22, 2018. Labeling was assessed by sectioning and microscopy of native fluorescence (FIG. 53). FlpO, iCre, and tTA2 viral constructs yielded labeling of cells in L5 of the mouse cortex with varying levels of specificity, while dgCre showed non-specific labeling of cortical layers. The same strategy was applied to screen both mscRE4 and mscRE16 drivers of FlpO, iCre, and/or tTA2 by retro-orbital injection at two different titers ($1\times10^{10}$ and $1\times10^{11}$ total genome copies, GC). The specificity and completeness of labeling was found to depend heavily on both the injected titer and the recombinase-reporter combination used in these experiments (FIG. 58). Based on these experiments, a single titer for each FlpO virus was chosen for in-depth characterization, and additional animals were injected for scRNA-seq and whole-brain two-photon tomography by TissueCyte (FIGS. 57A-57C, 59A, 59B, and 60). Each of these viruses was found to have a high degree of layer and subclass specificity in the cortex, with 87.5% of cells labeled by mscRE4-FlpO corresponding to L5 PT cells (FIG. 57A) and 42% of cells labeled by mscRE16-FlpO corresponding to L5 IT cells (FIG. 57C), with little overlap. TissueCyte imaging revealed that two viruses labeled additional subcortical populations (mscRE4 in APr, CEa, and HIP, FIG. 59A; and mscRE16 in pons, BLA, and HIP, FIG. 60).

Figure 59A:
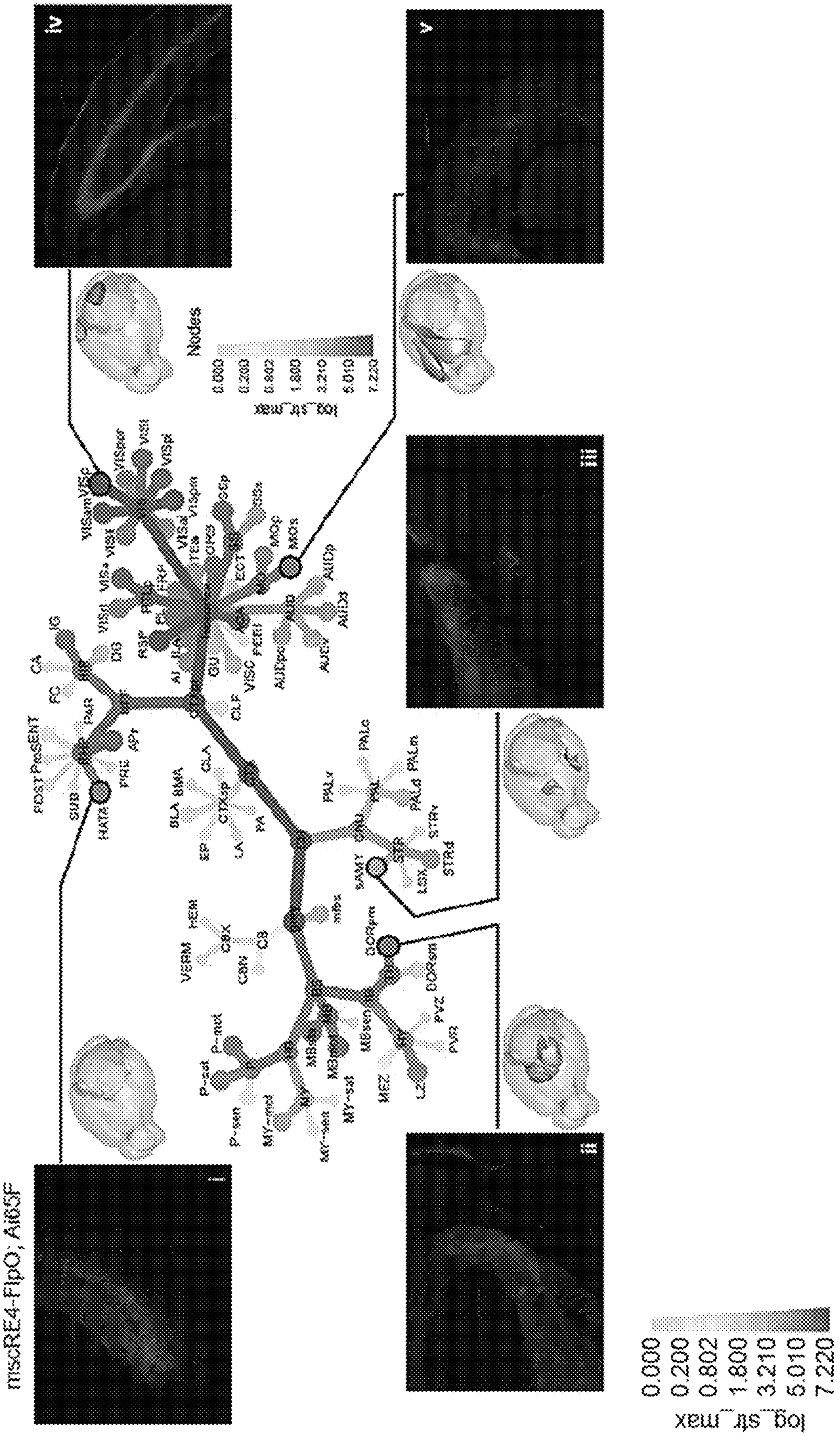
FIGS. 59A-59E. Brain-wide and intersectional labeling of cell type. (59A) Results from full-brain imaging using TissueCyte. Sections throughout the whole brain of an Ai65F mouse after retro-orbital injection of mscRE-FlpO were aligned to the Allen Institute Common Coordinate Framework (CCF) and mapped to the Allen Brain Atlas structural ontology. A high-level overview of cell labeling throughout the structural ontology is represented by the taxonomic plot. "Grey" is the root of the plot, representing all grey-matter regions, and each branching of nodes shows child structures within each region. The size and color of nodes represents the maximum signal found among all children of the nodes, which allows one to follow the tree to the source of high signal within each structure. Insets display selected regions of high or specific signal. Region acronyms correspond to the Allen Brain Adult Mouse Atlas. (59B) Further division of the isocortical regions in the TissueCyte dataset to the level of cortical layers allows brain-wide quantification of layer-specific signal. Representative cortical sections from the TissueCyte dataset are shown along the top, from most anterior to most posterior (left to right). The heatmap shows quantification of the signal in each region and layer. Agranular regions, which lack layer 4, have hashing in the L4 row. From Anterior to Posterior the regions are FRP, ORBv1, ORBm, ORBI, PL, ILA, Aid, Mos, Alv, Mop, SSp-m, GU, ACAd, SSp-n, SSp-un, ACAv, SSp-ul, SSp-II, VISC, Aip, SSs, SSp-bfd, SSp-tr, AUDv, AUDd, AUDp, PTLp, RSPv, RSPd, PERI, VISam, TE, ECT, AUDpo, VISI, VISpm, and VISpl. (59C) Diagrams showing the use of co-injected recombinase viruses in a dual-reporter system for co-labeling or intersectional labeling of cell types. In this experiment, one virus driving FlpO and a second driving iCre are co-injected into a mouse with genetically-encoded Flp-dependent and Cre-dependent reporters. In target cell types, enhancers will drive the recombinases, which will permanently label their target cell types. If the enhancers selected are mutually exclusive, distinct populations will be labeled. If they overlap, intersectional labeling is possible. (59D) Native fluorescence imaging of an Ai65F; Ai140 dual-reporter mouse line retro-orbitally injected with mscRE16-FlpO (red fluorescence) and mscRE4-iCre (green fluorescence). These enhancers are expected to label mutually-exclusive cell types in L5 of the cortex. The region in the white box corresponds the inset image, showing strong labeling of cells in L5. (59E) Cell counts within each layer for all cortical regions labeled with EGFP (mscRE4; L5 PT), tdTomato (mscre16; L5 IT), or both in the image in (59D).
Figure 59B:
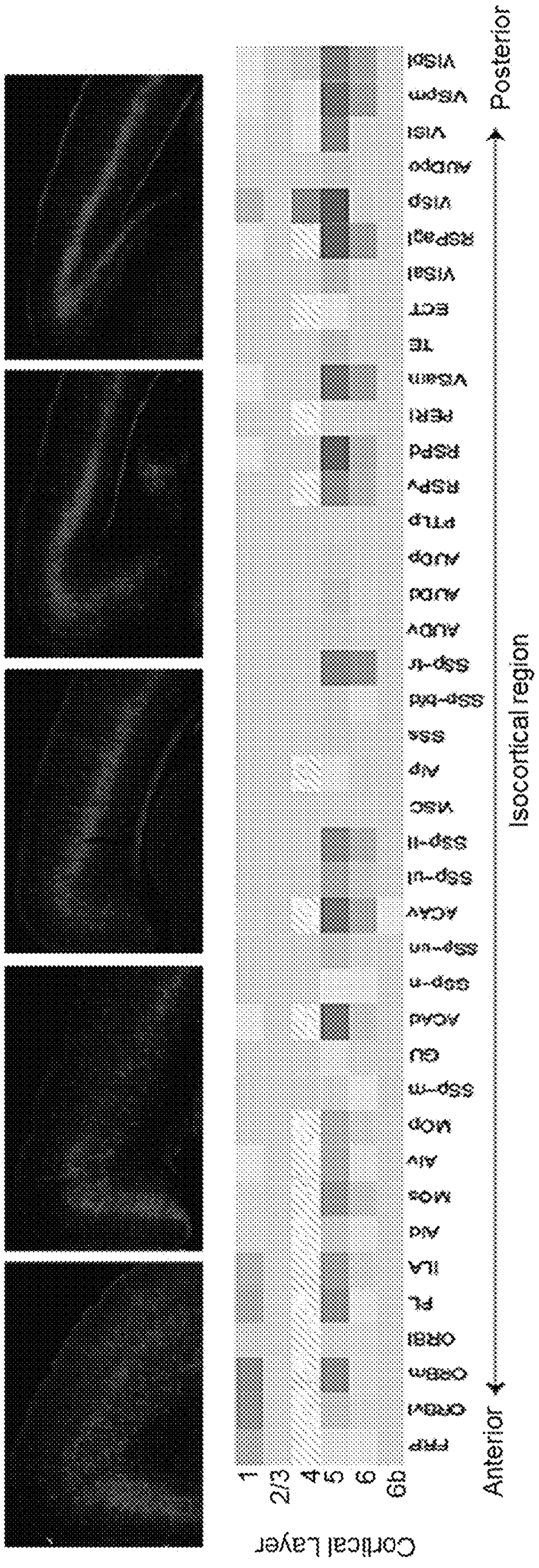
Figure 59C:
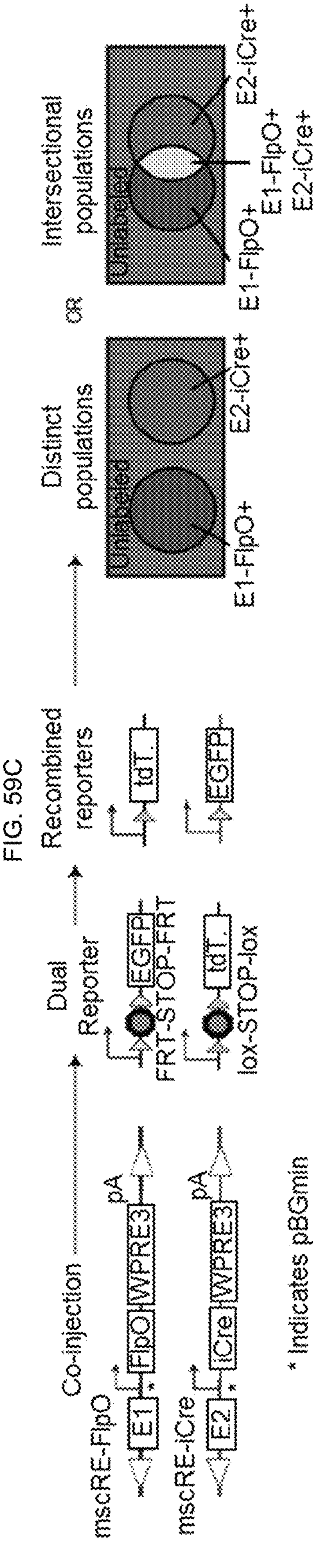
Figure 59D:
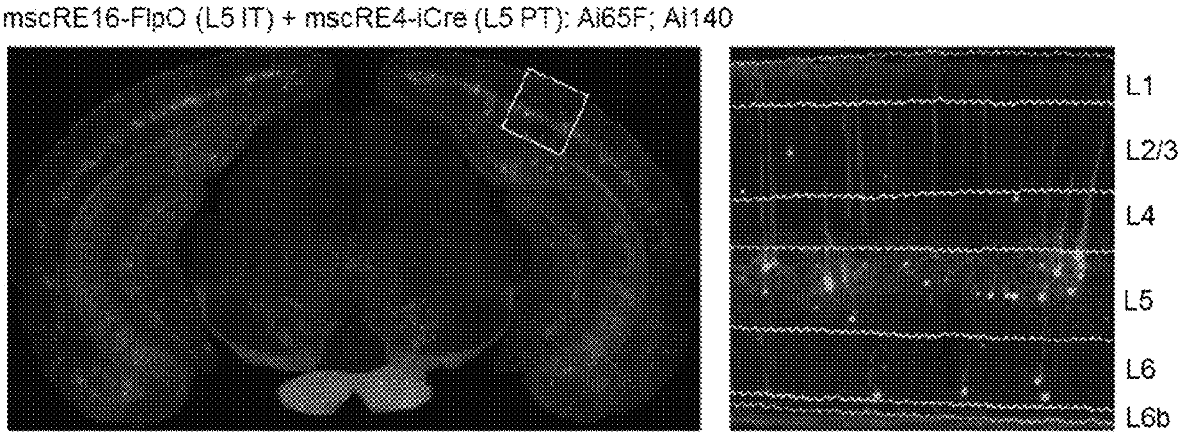
Figure 59E:
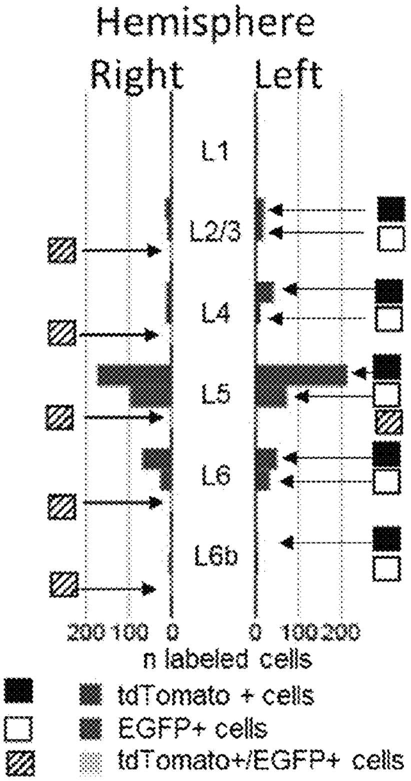
Figure 60A:
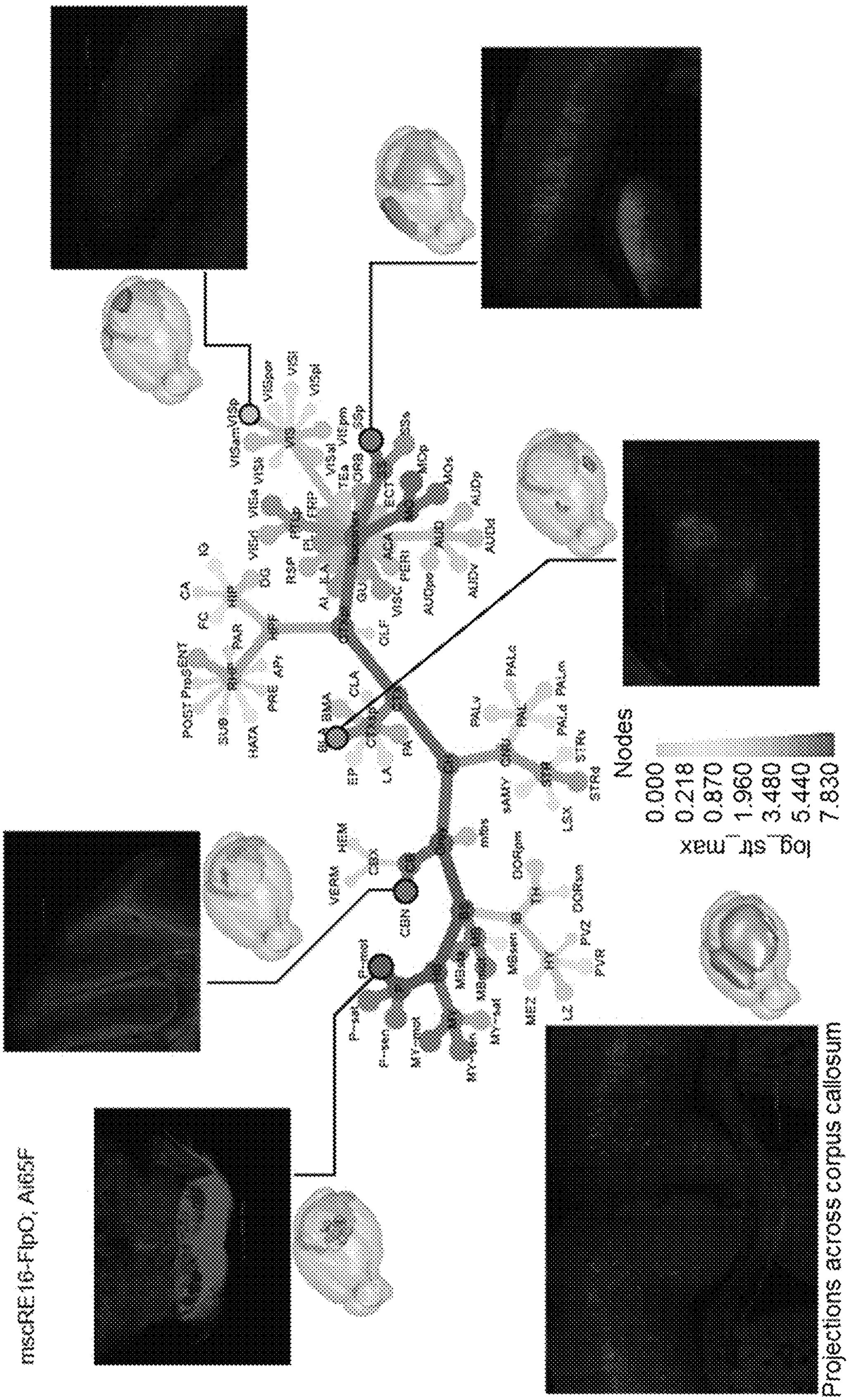
FIGS. 60A, 60B. Whole-brain characterization of mscRE16-FlpO. (60A) TissueCyte imaging of an mscRE16-FlpO; Ai65F mouse 2 weeks after retro-orbital injection was registered to the Allen Institute Common Coordinate Framework (CCF), and each structure in the adult mouse structural ontology was scored. As for FIGS. 59A-59E, these panels provide a high-level overview of cell labeling throughout the structural ontology. The size and color of nodes represents the maximum signal found among all children of the nodes, which allows one to follow the tree to the source of high signal within each structure. Insets display selected regions of high or specific signal. The inset at the bottom-left shows projection of IT neurons across the corpus callosum. (60B) Layer quantification for the same TissueCyte image registered to the CCF for all isocortical regions. Agranular regions that lack L4 are shown with a white box in the L4 row. All acronyms correspond to the Allen Institute for Brain Science Adult Mouse 3D atlas.
Figure 60B:
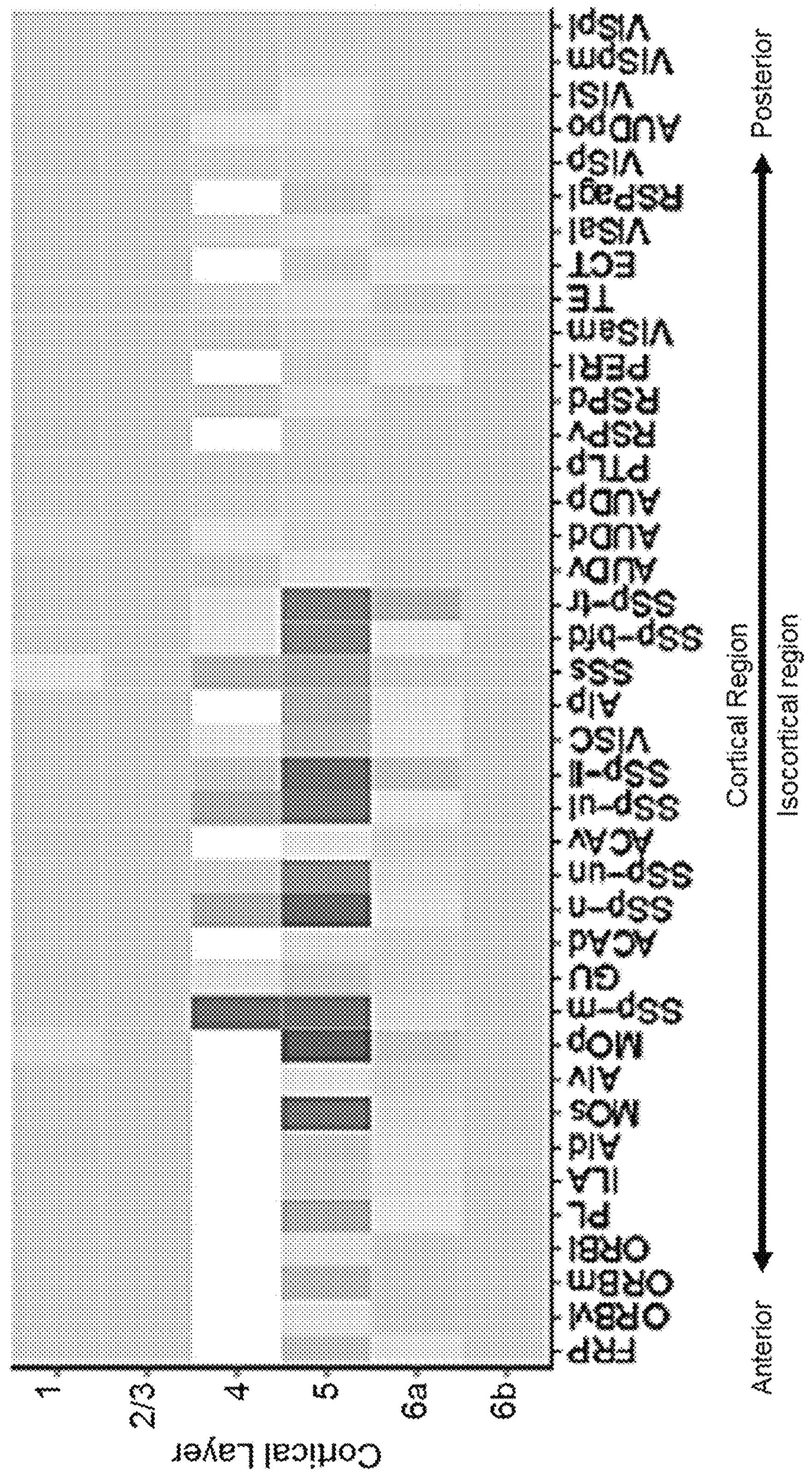
Figure 61A:
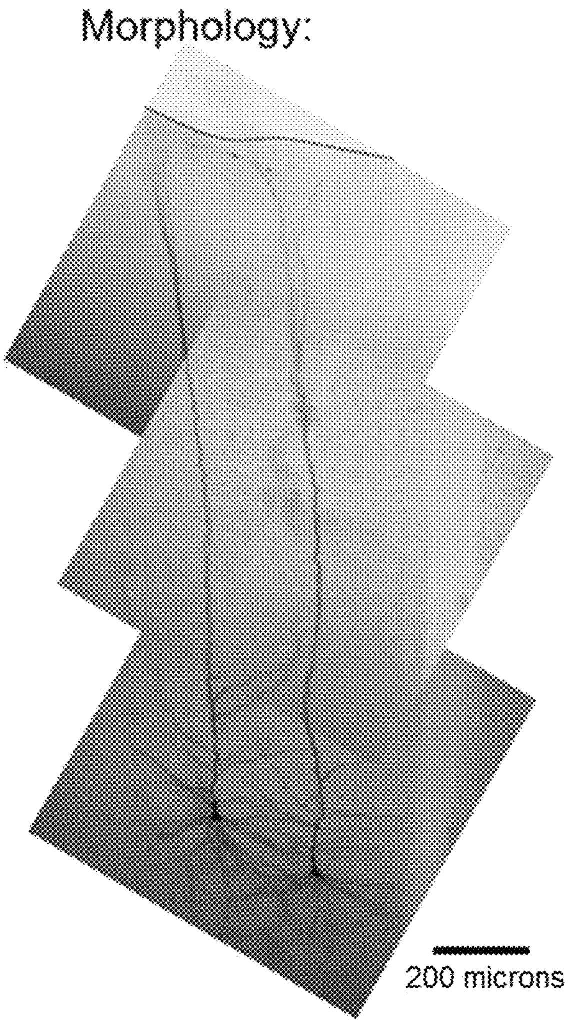
FIGS. 61A-61D. mscRE4 AAV vectors target rare L5 PT neurons in the human cortex. Human acute slice cultures resected from the middle temporal gyrus (MTG) were infected with a quartet of viruses: two mscRE4-driven rAAVs expressing Cre or Flp recombinase and two fluorescent reporter viruses, one expressing SYFP and the other expressing an RFP. This strategy enables high specificity by selection of only colabeled neurons. (61A) Biocytin fills of colabeled cells that were used for patch electrophysiology reveals morphology consistent with human L5 PT neurons; (61B) dual fluorescent labeling of a L5 PT neuron in human cortex (scale bar is 100 microns); (61C) transcriptomic validation was performed by mapping RNA extracted from a labeled cell using Patch-seq. The RNA was reverse-transcribed, amplified, sequenced, and mapped to a human MTG reference dataset, and matched the human L4/5 PT cell type in 100 of 100 trials using a bootstrapped centroid classifier; (61D) electrophysiology of a colabeled human L5 PT cell is consistent with previous studies of L5 PT cells, and demonstrates the utility of this method for selective electrophysiological targeting.
Figure 61B:
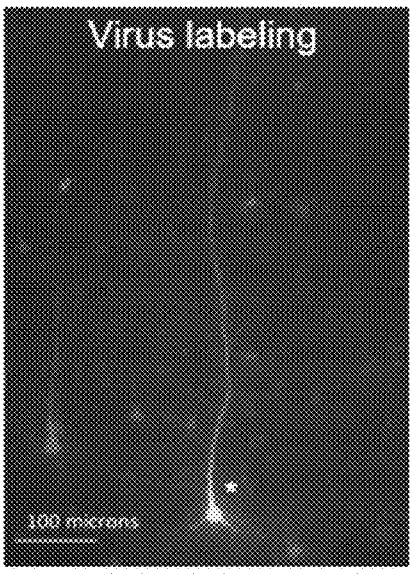
Figure 61C:
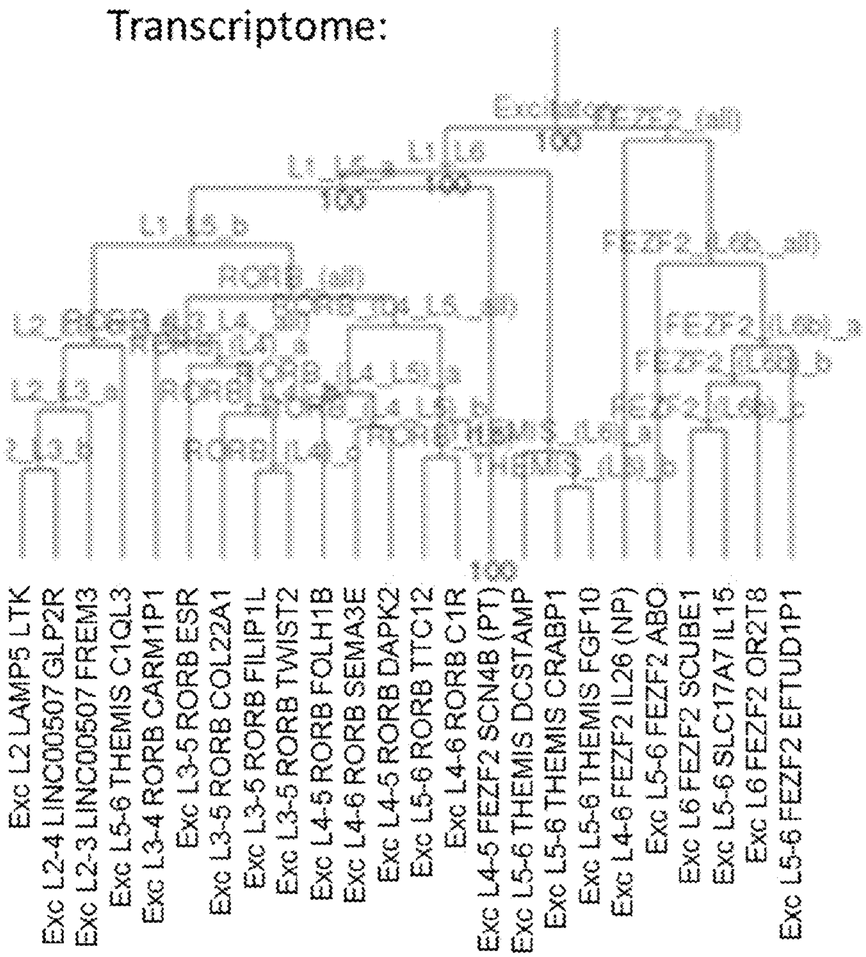
Figure 61D:
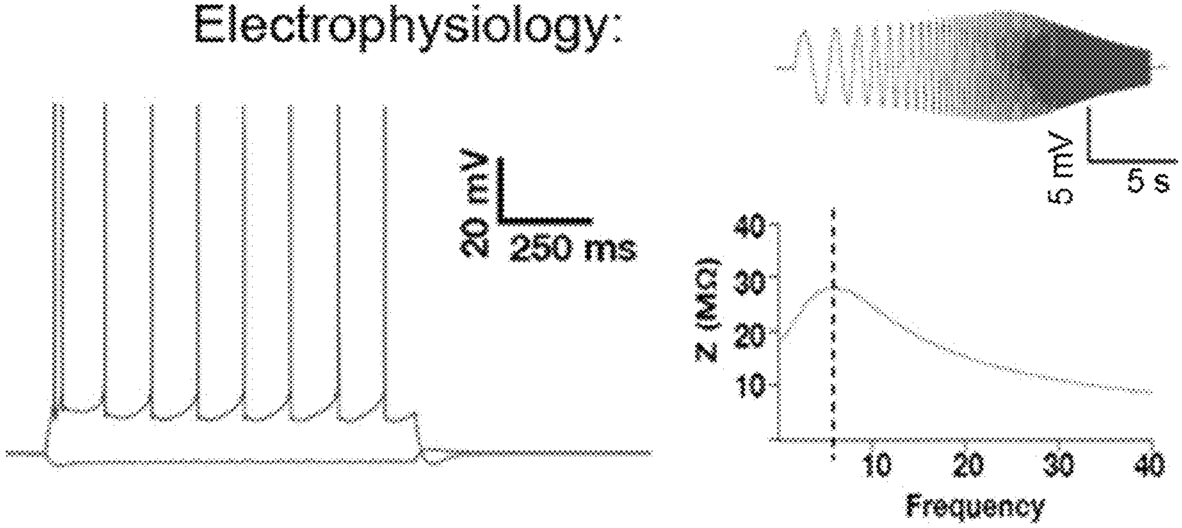
Figure 63:
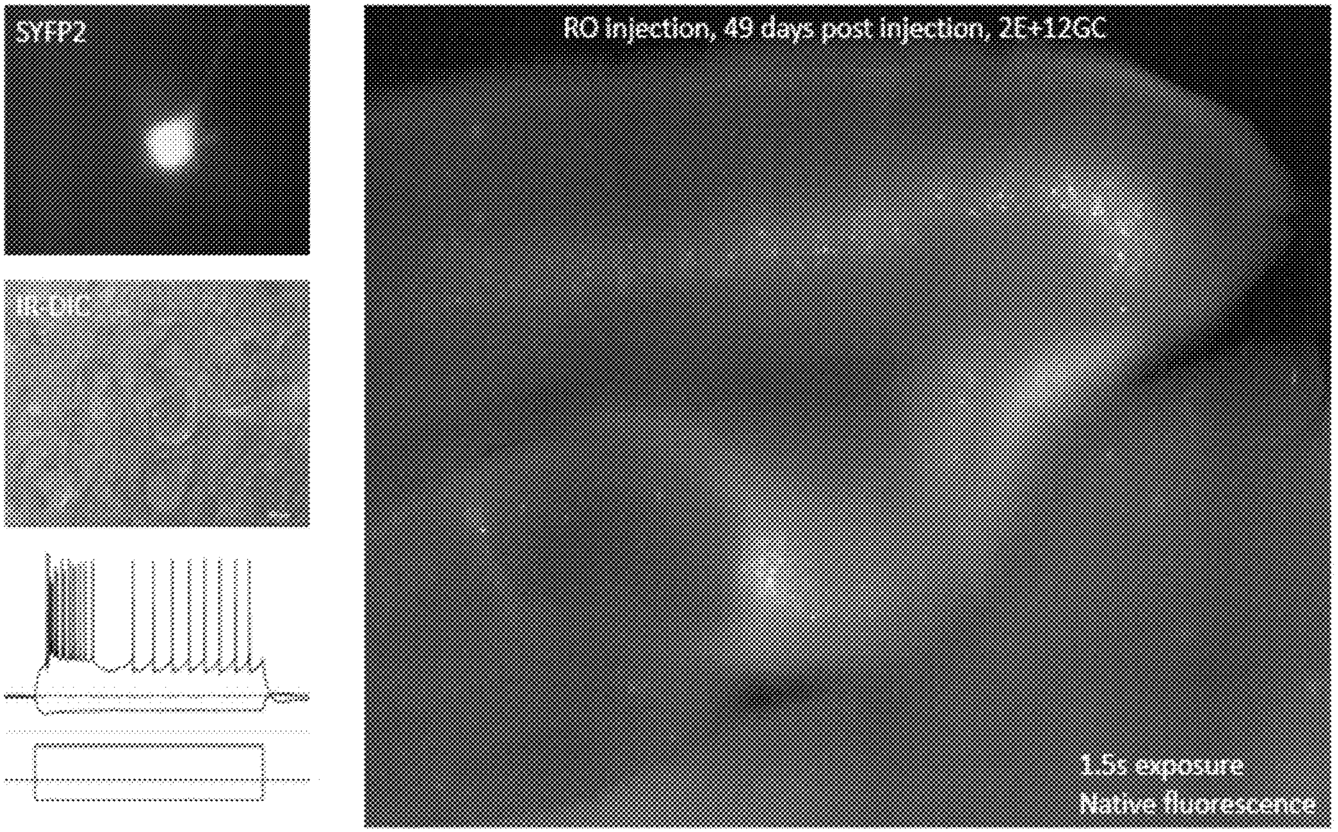
FIG. 63. 3×Core-mscRE4-SYFP2 viruses (CN1818, SEQ ID NO: 109) were injected retro-orbitally into adult mice. 3 weeks after injection, brains from injected mice were sectioned and imaged to assess targeted expression of SYFP2 fluorophore labeling. Robust expression of SYFP2 reporter gene in the adult mouse brain was observed following retroorbital injection of CN1818. Labeled cells are predominantly in layer 5 and have electrophysiological properties consistent with L5 PT neurons.
Figure 64A:
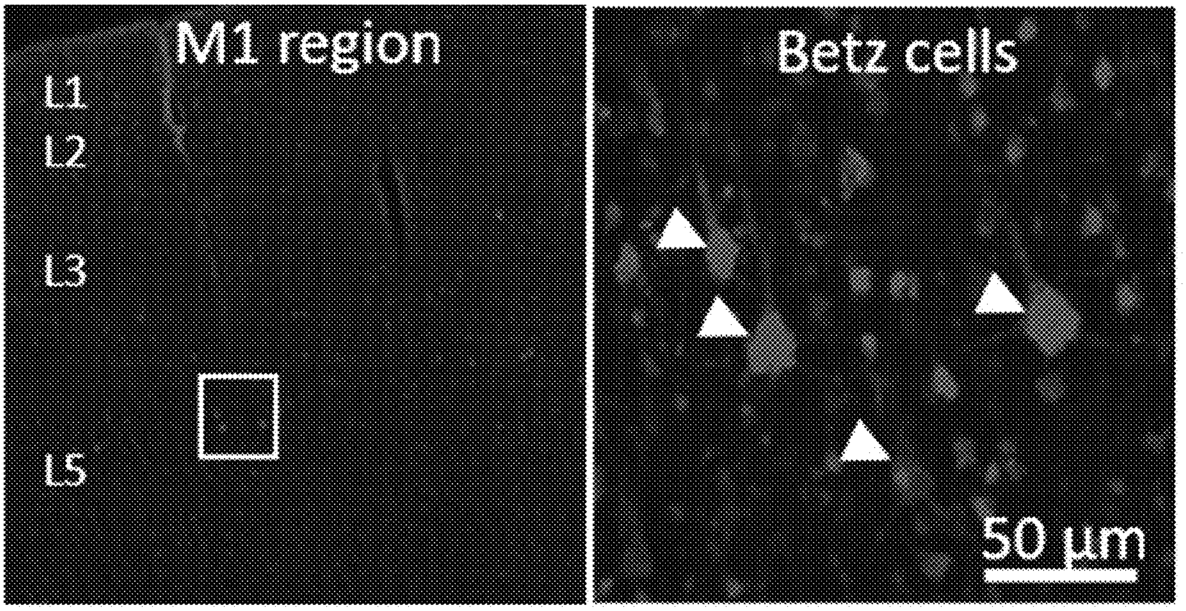
FIGS. 64A, 64B. (64A) Nissl stain of the M1 region in a macaque brain slice showing neocortical layers, and higher magnification view of the boxed region showing numerous magnopyramidal Betz cells (white arrows). (64B) Native YFP expression detected in a Betz cell (white arrow) 4 days post infection with CN1818, and corresponding Nissl stain of the same field of view.
Figure 64B:
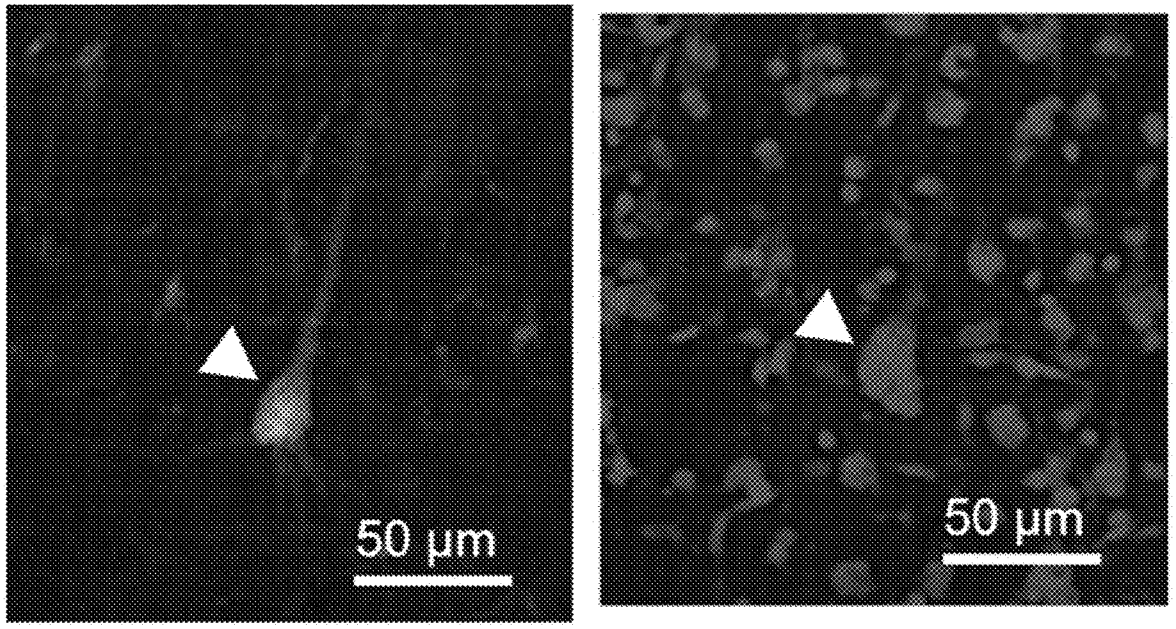
Figure 65A:
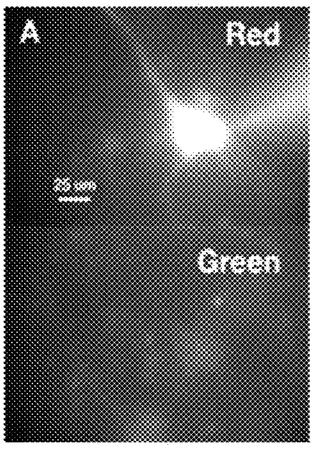
FIGS. 65A-65C. (66A) Prospective viral labeling (green) and targeted patch clamp recording of a putative Betz cell in a cultured macaque M1 brain slice infected with CN1818, with Alexa dye filling from the patch pipette (red). (66B) Firing in response to a 1s, 3 nA current injection step, showing narrow action potential width. (66C) Summary plot showing high firing rate in response to escalating current injection steps.
Figure 65B:
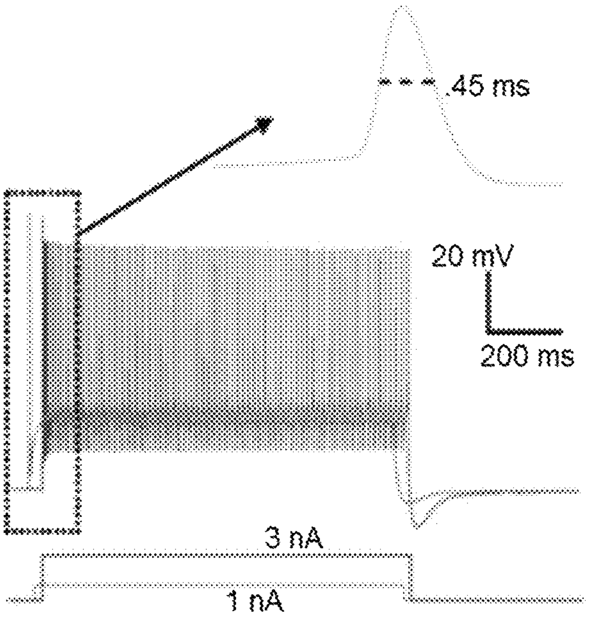
Figure 65C:
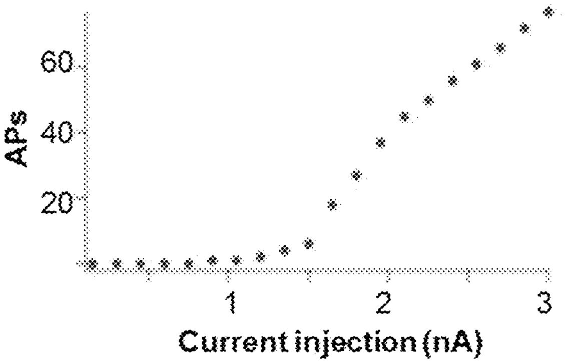
Figure 66A:
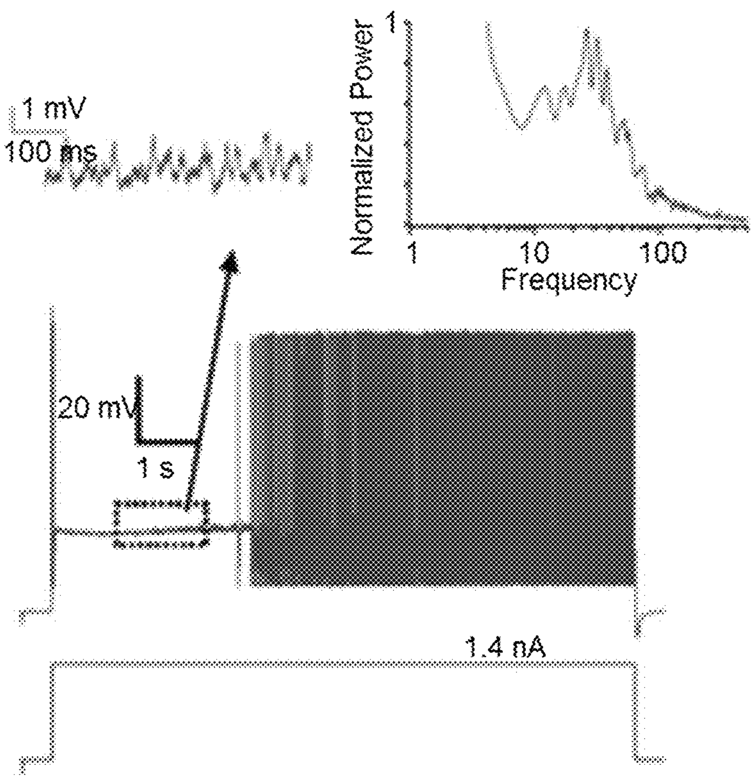
FIGS. 66A-66C. (66A) Spike frequency acceleration and subthreshold membrane potential oscillations in the gamma band shown for a CN1818 virus labeled macaque M1 putative Betz cell. (66B) Prominent fast sag, low input resistance (19MOhms) and (66C) subthreshold membrane resonance with a peak resonance frequency of 5.3 Hz.
Figure 66B:
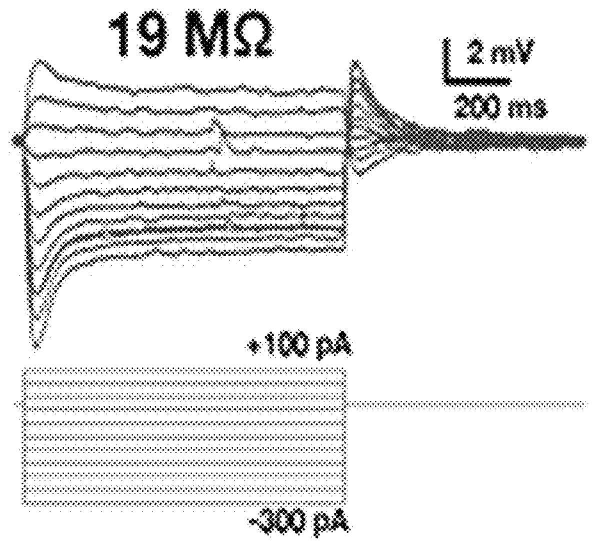
Figure 66C:
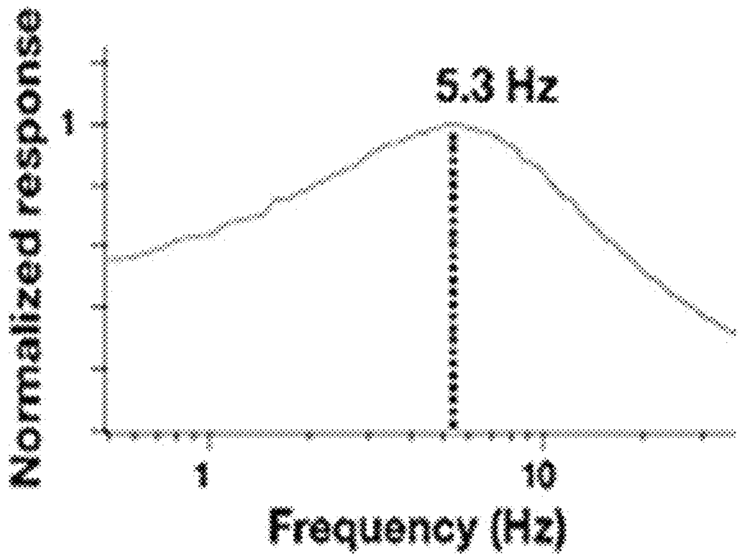
Figure 67:
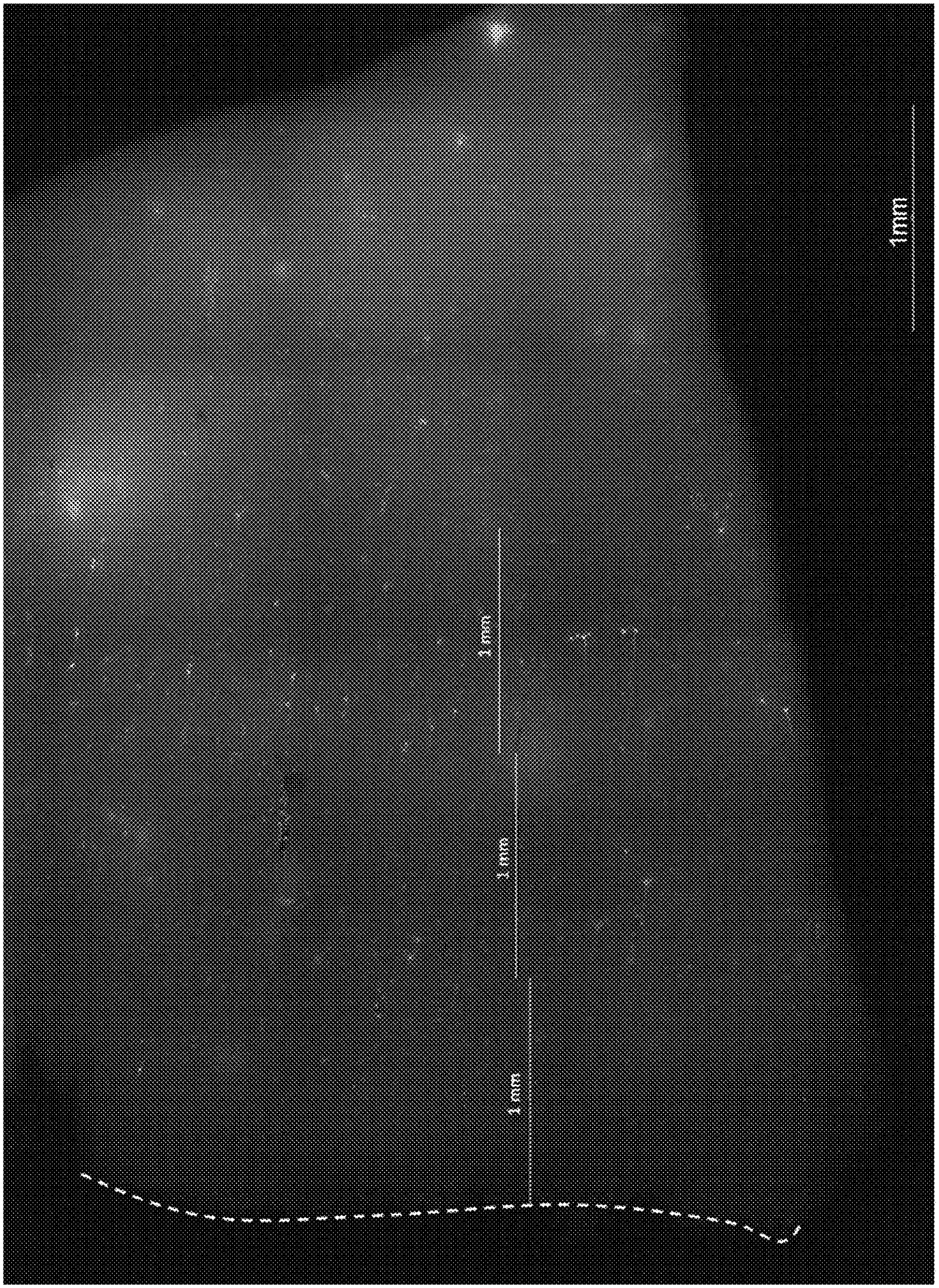
FIG. 67. 3×Core-mscRE4-SYFP2 viruses (CN1818, SEQ ID NO: 109) was applied to human surgical ex vivo cortical slice cultures. After incubation, the cortical slices were imaged by microscopy to assess targeted expression of SYFP2 fluorophore labeling. It was found that CN1818 labels L5 PT neurons in human ex vivo neocortical brain slice cultures. Scale bars are 1 mm in length.
Figure 68A:
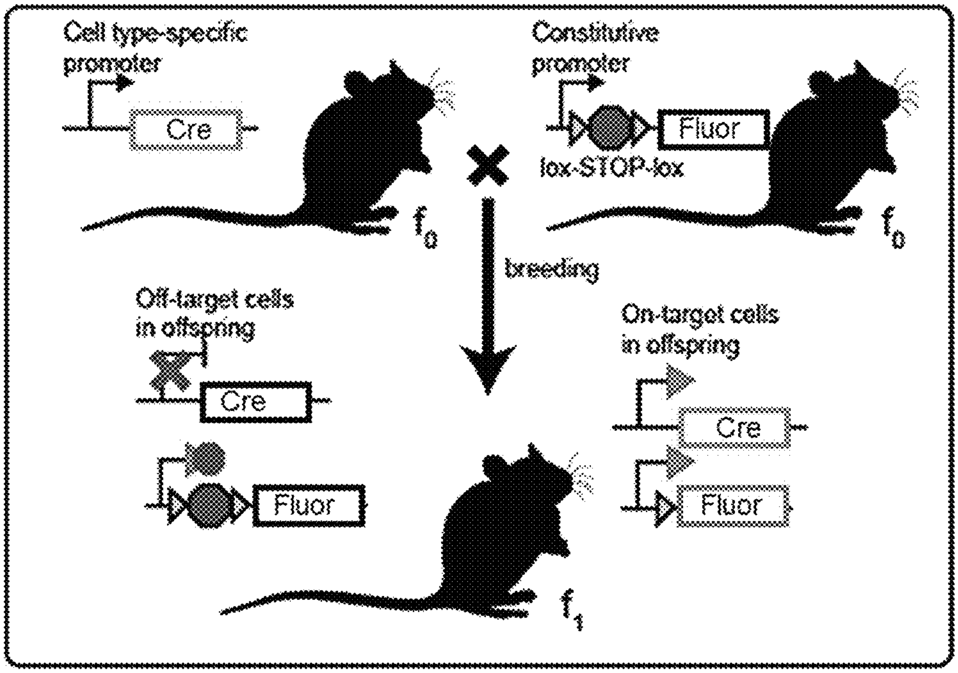
FIGS. 68A-68G. (68A) and (68B) show the traditional Cre/lox and Flp/FRT systems, respectively, to generate cell type-specific labels by breeding. (68C) Shows the traditional TET Transactivator/TET Responsive element (tTA2/TRE) system used to generate cell type-specific labels. (68D), (68E), and (68F) show mechanisms to bypass breeding by substituting a viral Cre, Flp, or tTA driver. (68F) also shows an additional layer of regulation via doxycycline treatment, which can reduce or inactivate tTA2 activity. (68G) shows bypassing these systems altogether for direct labeling. A strong advantage of the Cre or Flp-dependent reporters is that they can be much brighter and are permanently on after recombination to remove the STOP sites. The tTA2/TRE system is an additional mechanism for selective labeling that may also be tunable by doxycycline treatment.
Figure 68B:
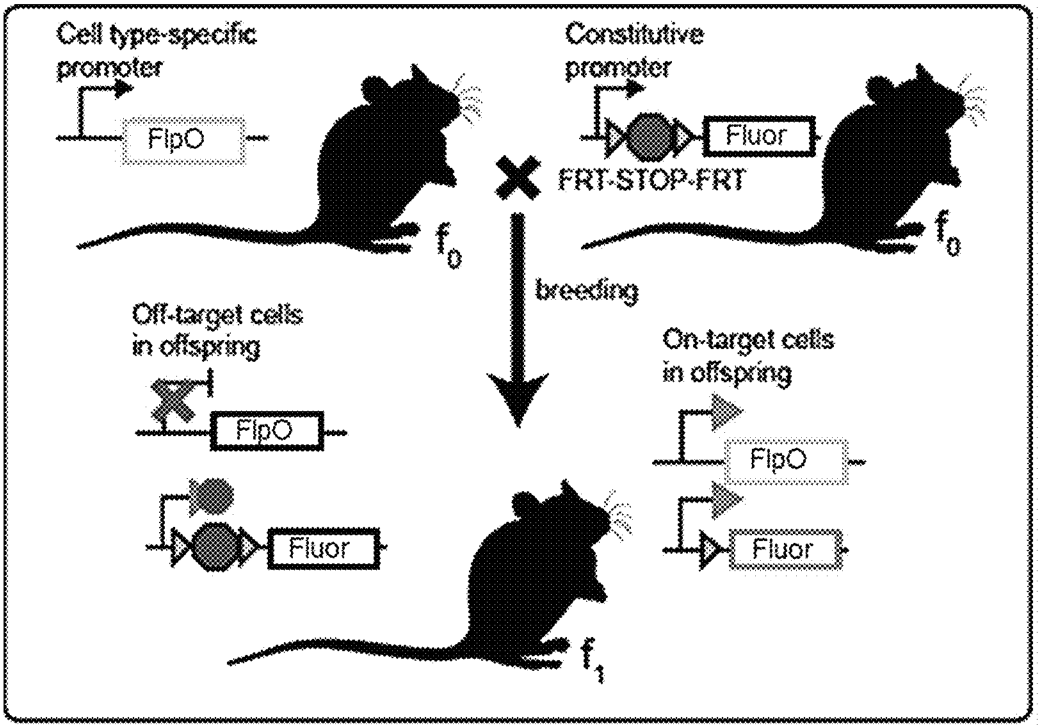
Figure 68C:
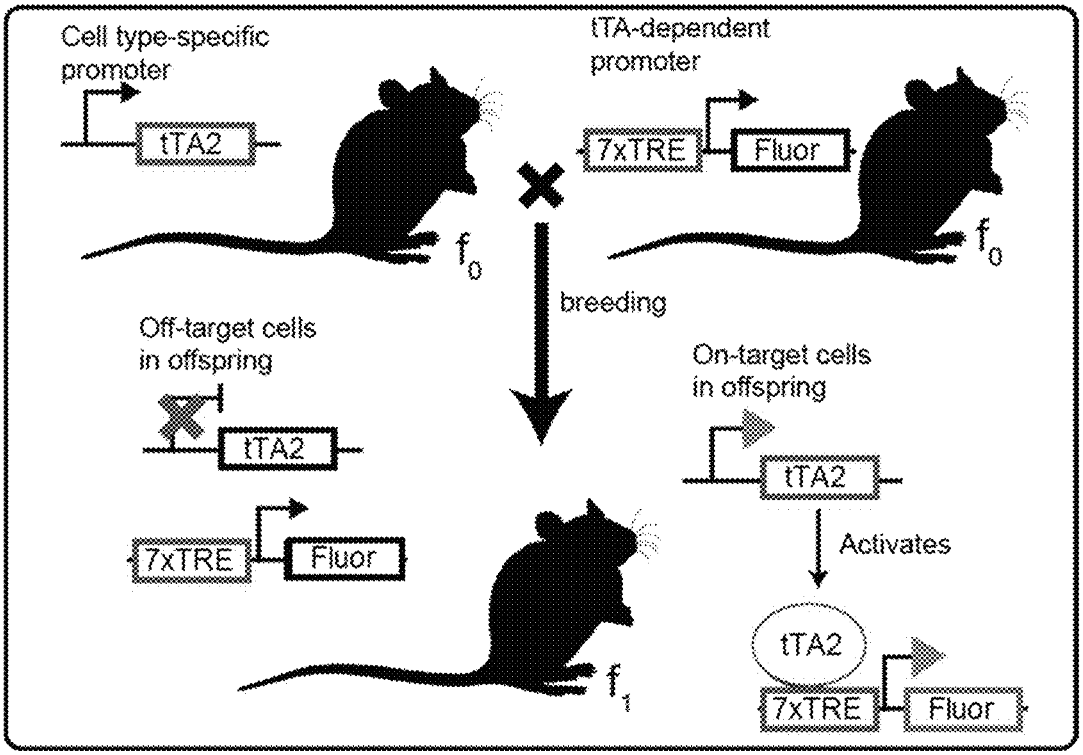
Figure 68D:
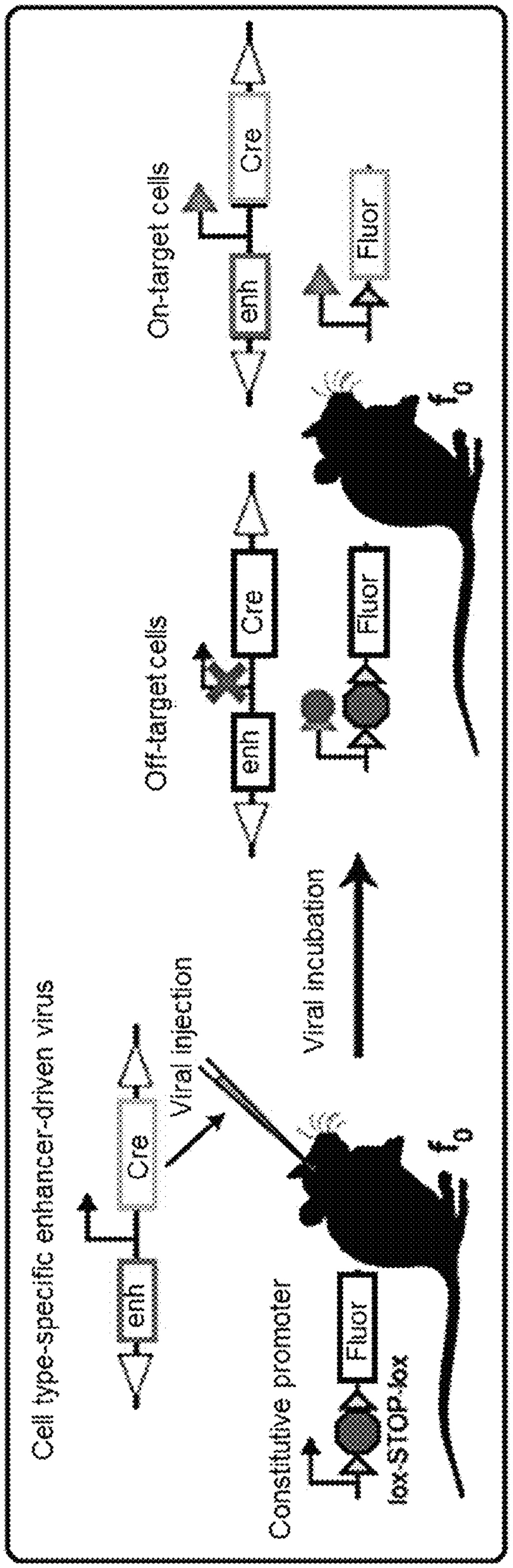
Figure 68E:
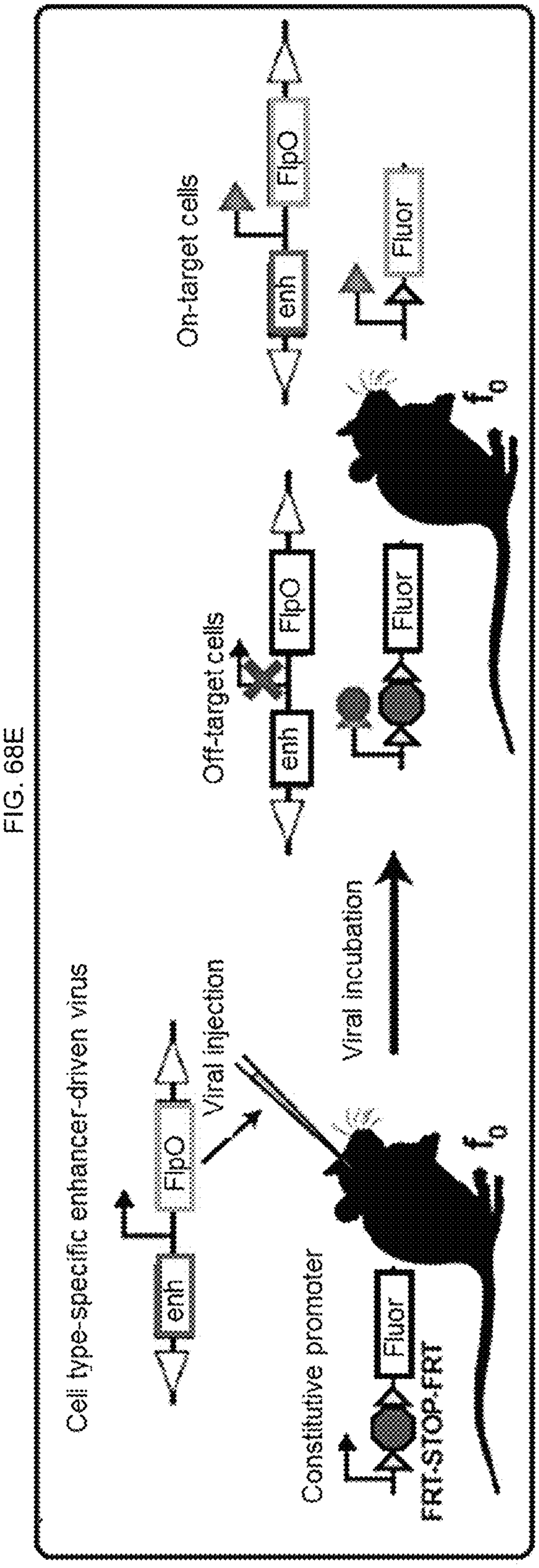
Figure 68F:
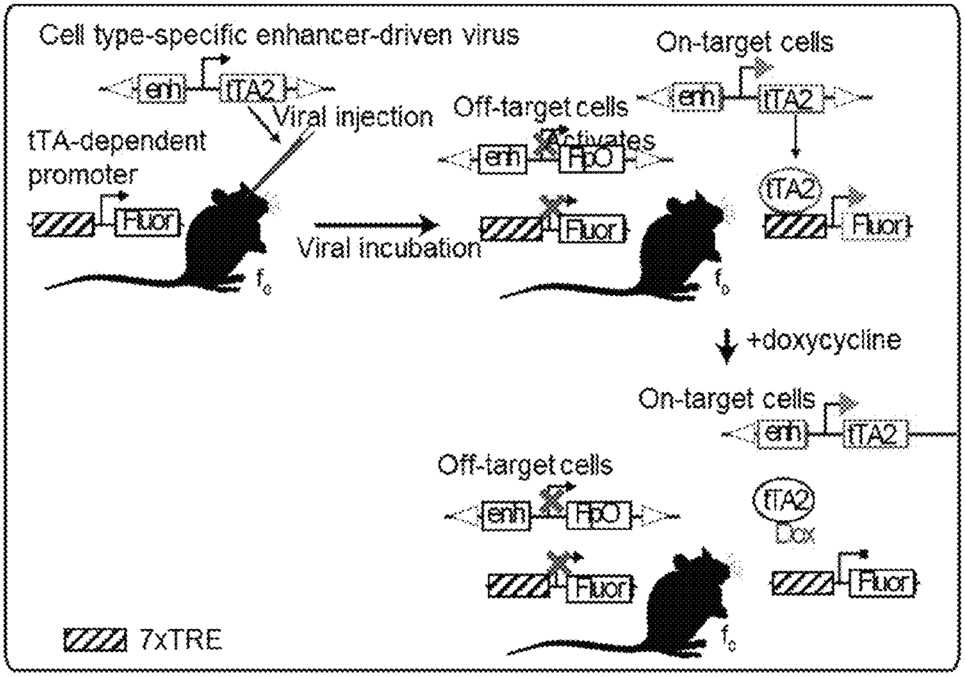
Figure 68G:
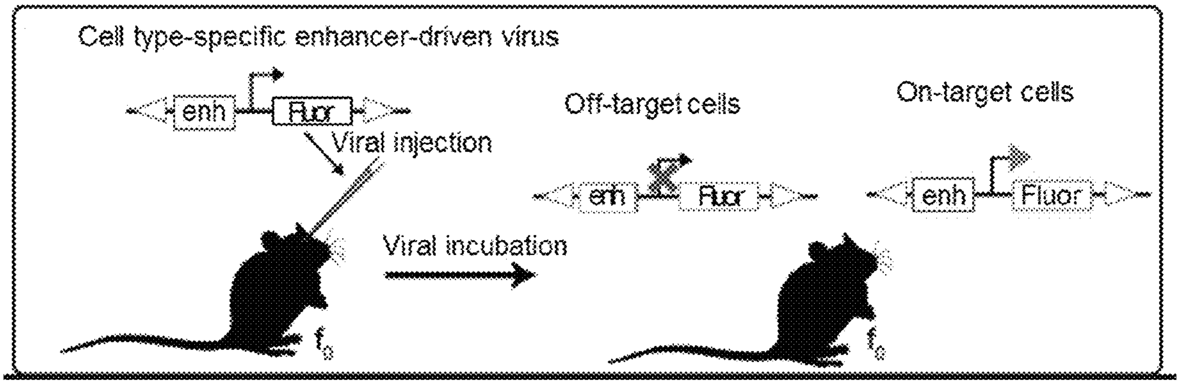
Figure 69:
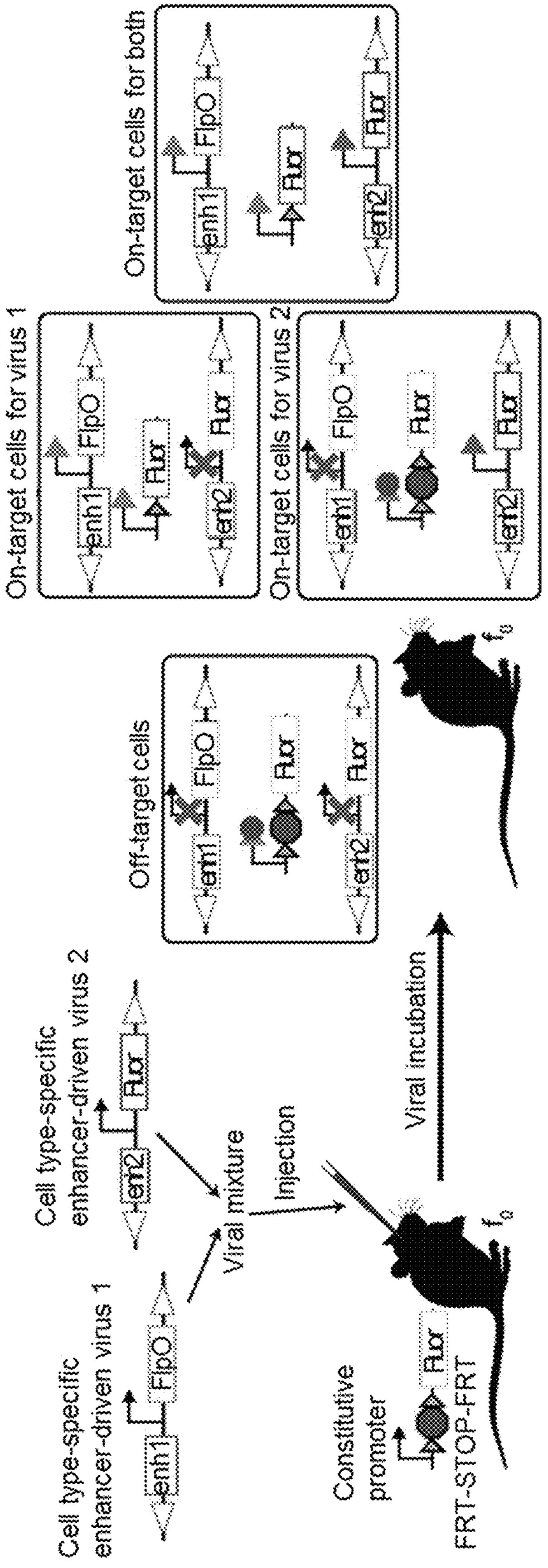
FIG. 69. Diagrammatic overview of a multi-virus labeling system. Here, two different viruses driven by the same or different enhancers drive either a recombinase or a fluorophore. If injected into a reporter mouse, enhancer-driven recombinases will cause excision of a STOP site in the target cell type, and the enhancer-driven fluorophore will be expressed directly in another target cell type. If these cell types overlap in their use of the viral enhancer elements, intersectional colabeling can be observed.
Figure 74:
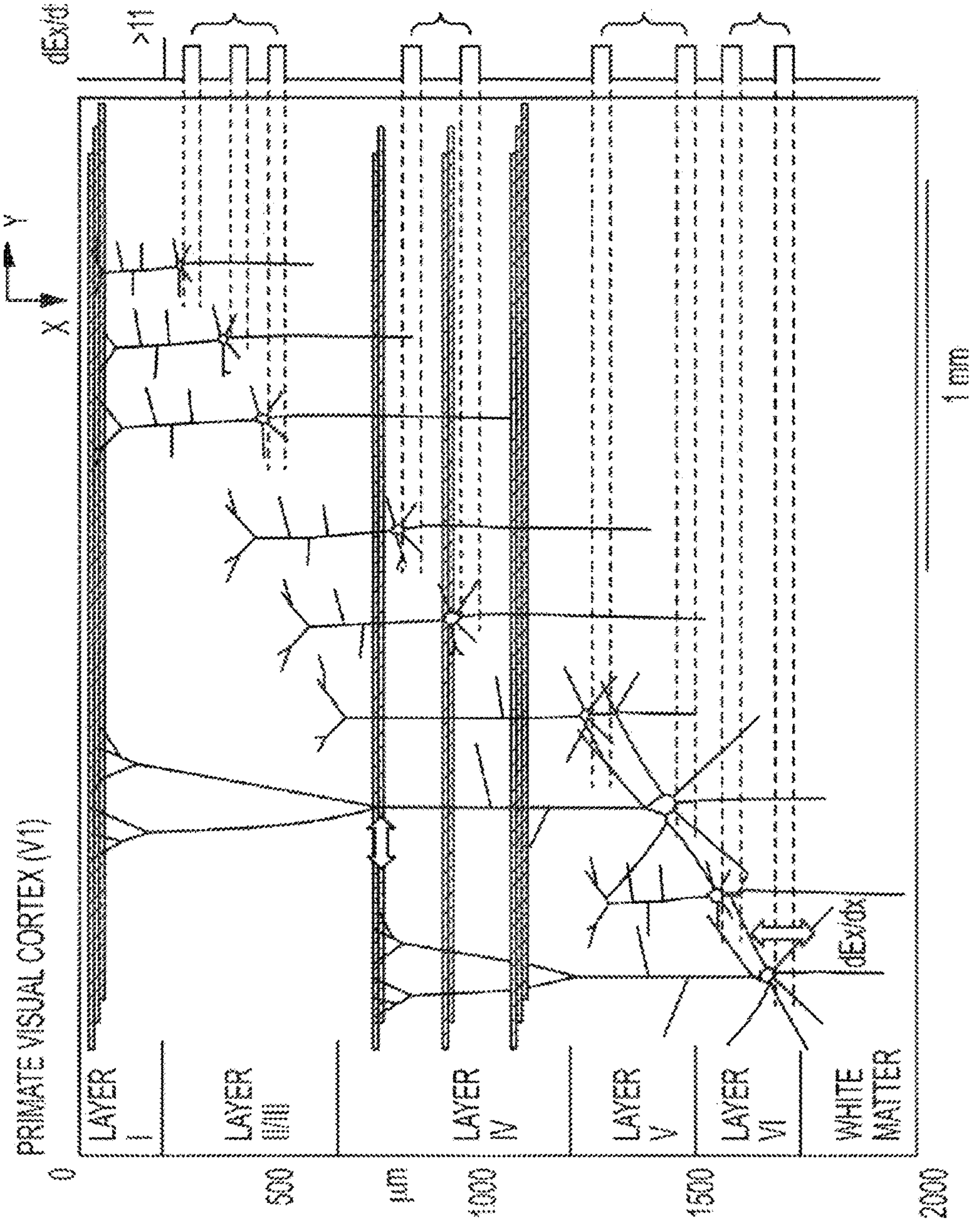
FIG. 74. Schematic of cortical layers, with particular relevance to the primate visual cortex. This schematic is provided as an illustration of intracortical layers.

Viruses can also be co-administered to label multiple populations of cells, either exclusively or intersectionally (FIG. 59C). This strategy reduces the need for triple- or quadruple crosses to obtain co-labeled populations of cells. Brain-wide co-labeling of both L5 IT and L5 PT populations was tested by retro-orbital injection of mscRE4-iCre (to label L5 PT cells, green) and mscRE16-FlpO (to label L5 IT cells, red) in the same Ai65F; Ai140 animal (FIG. 59D). Distinct labeling of these two cell populations was found in L5 by microscopy (FIG. 59E), demonstrating that multiple enhancer-driven viruses can be used to simultaneously label or perturb populations of prospectively defined subclasses in the same animal.

Materials and Methods of Example 2. Mouse breeding and husbandry and retrograde labeling were performed as described in the Materials and Methods section of Example 1.

Single cell ATAC. Single-cell suspensions of cortical neurons were generated as described previously, with the exception of use of papain in place of pronase for some samples, and the addition of trehalose to the dissociation and sorting medium for some samples. Gray, et al., Elife 1-30, 2017 doi:10.7554/eLife.21883. Then individual cells were sorted using FACS with gating of negative-DAPI (and positive-fluorophore labeling (tdTomato, EGFP, or SYFP2) to select for live neuronal cells or negative-DAPI and negative-fluorophore labeling for live non-neuronal cells.

For GM12878 scATAC, cells were obtained from Coriell Institute, and were grown in T25 culture flasks in RPMI 1640 Medium (Gibco, Thermo Fisher Cat #11875093) supplemented with 10% fetal bovine serum (FBS) and Penn/Strep. At 80% confluence, cells were transferred to a 15 mL conical tube, centrifuged, and washed with PBS containing 1% FBS. Cells were then resuspended in PBS with 1% FBS and 2 ng/mL DAPI (DAPI*2HCl, Life Technologies Cat #D1306) for FACS sorting.

Single cells were sorted into 200 μL 8-well strip tubes containing 1.5 μL tagmentation reaction mix (0.75 μL Nextera Reaction Buffer, 0.2 μL Nextera Tn5 Enzyme, 0.55 μL water). After collection, cells were briefly spun down in a bench-top centrifuge, then immediately tagmented at 37° C. for 30 minutes in a thermocycler. After tagmentation, 0.6 μL of Proteinase K stop solution was added to each tube (5 mg/mL Proteinase K solution (Qiagen), 50 mM EDTA, 5 mM NaCl, 1.25% SDS) followed by incubation at 40° C. for 30 minutes in a thermocycler. Then, the tagmented DNA was purified using AMPure XP beads (Beckman Coulter) at a ratio of 1.8:1 resuspended beads to reaction volume (3.8 μL added to 2.1 μL), with a final elution volume of 11 μL. Libraries were indexed and amplified by the addition of 15 uL 2× Kapa HiFi HotStart ReadyMix and 2 uL Nextera i5 and i7 indexes to each tube, followed by incubation at 72° C. for 3 minutes and PCR (95° C. for 1 minute, 22 cycles of 98° C. for 20 seconds, 65° C. for 15 seconds, and 72° C. for 15 seconds, then final extension at 72° C. for 1 minute). After amplification, sample concentrations were measured using a Quant-iT PicoGreen assay (Thermo Fisher) in duplicate. For each sample, the mean concentration was calculated by comparison to a standard curve, and the mean and standard deviation of concentrations was calculated for each batch of samples. Samples with a concentration greater than 2 standard deviations above the mean were not used for downstream steps, as these were found in early experiments to dominate sequencing runs. All other samples were pooled by combining 5 μL of each sample in a 1.5 mL tube. Then, the combined library was purified by adding Ampure XP beads in a 1.8:1 ratio, with final elution in 50 μL. The mixed library was then quantified using a BioAnalyzer High Sensitivity DNA kit (Agilent).

scATAC sequencing, alignment, and filtering was performed as described in the Materials and Methods section of Example 1. Jaccard distance calculation, PCA and tSNE embedding, and density-based clustering were also performed as described in the Materials and Methods section of Example 1, except that in comparing scATAC-seq samples, fragments were extended to a length of 1 kb and samples were clustered in t-SNE space using the RPhenograph package with k=6.

Correlation with single-cell transcriptomics. Phenograph-defined neighborhoods were assigned to cell subclasses and clusters by comparison of accessibility near transcription start site (TSS) to median expression values of scRNA-seq clusters at the cell type (e.g. L5 PT Chrna6) and at the subclass level (e.g. Sst) from mouse primary visual cortex. Tasic, et al., Nature 563, 72-78, 2018. To score each transcription start site (TSS), TSS locations were retrieved from the RefSeq Gene annotations provided by the UCSC Genome Browser database, and windows from TSS+/−20 kb were generated. Then, the number of fragments for all samples within each cluster that overlapped these windows were counted. For comparison, differentially expressed marker genes were selected from the Tasic, et al., Nature 563, 72-78, 2018 scRNA-seq dataset using the scrattch.hicat package for R. Then, Phenograph cluster scores were correlated with the log-transformed median exon read count values for this set of marker genes for each scRNA-seq cluster from primary visual cortex, and the transcriptomic cell type with the highest-scoring correlation was assigned. This strategy of neighbor assignment and correlation allowed resolution of cell types within the scATAC-seq data close to the resolution of the scRNA-seq data, as types that were split too far would resolve to the same transcriptomic subclass or type by correlation.

scATAC-seq grouping and peak calling. For downstream analysis, cell type assignments were grouped to the subclass level, with the exception of highly distinct cell types (Lamp5 Lhx6, Sst Chodl, Pvalb Vipr2, L6 IT Car3, CR, and Meis2). Unique fragments for all cells within each of these subclass/distinct type groups were aggregated to BAM files for analysis. Aligned reads from single cell subclasses/clusters were used to create Tag Directories and peaks of chromatin accessibility were called using HOMER with settings "findPeaks -region -o auto". The resulting peaks were converted to BED format. Heinz, et al., Mol. Cell 38, 576-589, 2010.

Population ATAC of Sst neurons. Population ATAC-seq of neurons from Sst-IRES2-Cre; Ai14 mice was performed as described previously. Gray, et al., Elife 1-30, 2017. doi: 10.7554/eLife.21883. Briefly, cells from the visual cortex of an adult mouse were microdissected and FACS sorted into 8-well strips as described above, but with 500 cells per well instead of single cells as for scATAC-seq. Cell membranes were lysed, and nuclei were pelleted before resuspension in the same tagmentation buffer described above at a higher volume (25 μL). Tagmentation was carried out at 37 C for 1 hour, followed by addition of 5 μL of Cleanup Buffer (900 mM NaCl, 300 mM EDTA), 2 μL 5% SDS, and 2 μL Proteinase K and incubation at 40° C. for 30 minutes, and cleanup with AM Pure XP beads (Beckman Coulter) at a ratio of 1.8:1 beads to reaction volume. Samples were amplified using KAPA HotStart Ready Mix (Kapa Biosystems, Cat #KK2602) and 2 uL each of Nextera i5 and i7 primers (Illumina), quantified using a Bioanalyzer, and sequenced on an Illumina MiSeq.

Comparisons to bulk ATAC-seq data. For comparison to previously published studies, data was used from GEO accession GSE63137 from Mo, et al., Neuron 86, 1369-1384, 2015 for Camk2a, Pvalb, and Vip neuron populations, GEO accession GSE87548 from Gray, et al. (Elife 1-30, 2017) for Cux2, Scnn1a-Tg3, Rbp4, Ntsr1, Gad2, mES, and genomic controls. Mo, et al., Neuron 86, 1369-1384, 2015; Gray et al., Elife 1-30, 2017 doi:10.7554/eLife.21883. For these comparisons, population ATAC-seq of Sst neurons, described above, were also included. For each population, reads from all replicates were merged and each region was downsampled to 6.4 million reads. Then, peaks were called using HOMER as described above for aggregated scATAC-seq. The BED-formatted peaks for scATAC-seq aggregates with or without bulk ATAC-seq datasets were used as input for comparisons using the DiffBind package for R as described previously. Gray, et al., Elife 1-30, 2017 doi: 10.7554/eLife.21883.

Identification of mouse single-cell regulatory elements. A targeted search for mouse single cell regulatory elements (mscREs) was done by performing pairwise differential expression analysis of scRNA-seq clusters to identify uniquely expressed genes in L5 PT and L5 IT subclasses across all glutamatergic subclasses. Then, unique peaks were searched for within 1 Mbp of each marker gene, and these peaks were manually inspected for low or no accessibility in off-target cell types and for conservation. If a region of high conservation overlapped the peak region, but the peak was not centered on the highly conserved region, the peak selection was adjusted to include neighboring highly conserved sequence. For cloning, primer search was centered on 500 bp regions centered at the middle of the selected peak regions and included up to 100 bp on either side. Final region selections and PCR primers are shown in FIG. 47.

The following techniques were performed as described in the Materials and Methods Section of Example 1: viral genome cloning; viral packaging, titering, and titer measurement; retro-orbital injections; stereotaxic injections (except that each virus was delivered bilaterally at 250 nL, 50 nL, and 25 nL); immunohistochemistry; and single cell RNA sequencing and cell type mapping.

Comparisons to previous scATAC-seq studies. For comparisons to GM 12878 datasets, raw data from Cusanovich, et al. (Science 348, 910-4, 2015) was downloaded from GEO accession GSE67446, Salav, et al. (2015) from GEO accession GSE65360, and Pliner, et al. (Mol. Cell 71, 858-871.e8, 2018) from GEO accession GSE109828. Buenrostro et al., Nature 523, 486-90, 2015. Processed 10× Genomics data was retrieved from the 10× Genomics website. Samples from Buenrostro, Cusanovich, Pliner, and the Gm12878 from this lab were aligned to the hg38 human genome using the same bowtie pipeline described above for mouse samples to obtain per-cell fragment locations. 10× Genomics samples were analyzed using fragment locations provided by 10× Genomics. For comparison to TSS regions, the RefSeq Genes tables provided by the UCSC Genome Browser database for hg19 (for 10× data) and for hg38 (for other datasets) were used. To compare to ENCODE peaks, ENCODE Gm12878 DNA-seq HotSpot results from ENCODE experiment ID ENCSR000EJD aligned to hg19 (ENCODE file ID ENCFF206HYT) or hg38 (ENCODE file ID ENCFF773SPT) were used.

For comparisons to previously published mouse cortex datasets, raw FASTQ files were downloaded from GEO accession GSE111586 for Cusanovich, et al. (Cell 174, 1309-1324.e18, 2018) and from GEO accession GSE100033 for Preissl, et al. Nat. Neurosci. 21, 1, 2018. Multiplexed files were aligned to the mm10 genome using Bowtie v1.1.0 and were demultiplexed using an R script prior to removal of duplicate location alignments. Only barcodes with >1,000 mapped reads were retained for analysis. Per-barcode statistics were computed using the same algorithms used for per-cell statistics from the dataset generated by this lab, and samples from the Cusanovich, et al., Cell 174, 2018 dataset that passed the established QC criteria, were subjected to the same analysis pipeline as the data generated by this lab after demultiplexing and duplicate read removal. Metadata from Cusanovich, et al., (Cell 174, 2018) were obtained from the Mouse sci-ATAC-seq Atlas website at http://atlas.gs.washington.edu/mouse-atac/.

Physiology, patch clamp recordings, and data analysis was performed as described in the Materials and Methods section of Example 1.

TissueCyte imaging and analysis. TissueCyte images were collected, registered, and segmented as described previously. Oh et al., (Nature 508, 207-214, 2014). After registration, 3D arrays of signal binned to 25 um voxels were analyzed in R by subtraction of background, and averaging the signal in the finest structure in the Allen Brain Atlas structural ontology. To propagate signals from fine to coarse structure in the ontology, hierarchical calculations that assigned the maximum value of child nodes in the ontology to each parent from the bottom to the top of the ontology were performed. Then, the ontology was filtered to remove very fine structures, and the taxa and metacodeR packages for R were used to display the resulting ontological relationships and structure scores. Foster et al., bioRxiv 071019, 2016 doi:10.1101/071019.

Software for analysis and visualization. Analysis and visualization of scATAC-seq and transcriptomic datasets were performed using R v.3.5.0 and greater in the Rstudio IDE (Integrated Development Environment for R) or using the Rstudio Server Open Source Edition as well as the following packages: for general data analysis and manipulation, data.table, dplyr, Matrix, matrixStats, purrr, and reshape2; for analysis of genomic data, GenomicAlignments, GenomicRanges, and rtracklayer; for plotting and visualization, cowplot, ggbeeswarm, ggExtra, ggplot2, and rgl; for clustering and dimensionality reduction, Rphenograph and Rtsne; for analysis of transcriptomic datasets: scrattch.hicat and scrattch.io; for taxonomic analysis and visualization, metacodeR and taxa; and plater for management of plate-based experimental results and metadata.

Example 3. Human single neuron epigenetic evaluation of neocortical cell classes. The primate and especially human neocortex is greatly expanded in size and complexity relative to that of other mammals like the rodent (Zeng, et al., Cell. 149, 483-496, 2012; Rakic, *Nat Rev Neurosci.* 10, 724-735, 2009). Neocortical expansion enables human-centric abilities such as language and reasoning, which are disrupted in human diseases like schizophrenia and autism (King, et al., *JAMA Netw Open.* 1, e184777-e184777, 2018; van den Heuvel et al., *JAMA Psychiatry.* 70, 783-792, 2013). This structure contains of billions of cells, grouped into dozens if not hundreds of molecularly defined cell types (Zeisel, et al., *Science.* 347, 1138-1142, 2015; Tasic, et al., *Nat Neurosci.* 19, 335-346, 2016; Tasic et al., *Nature.* 563, 72, 2018; Hodge, et al., bioRxiv, 384826, 2018).

Figure 75A:
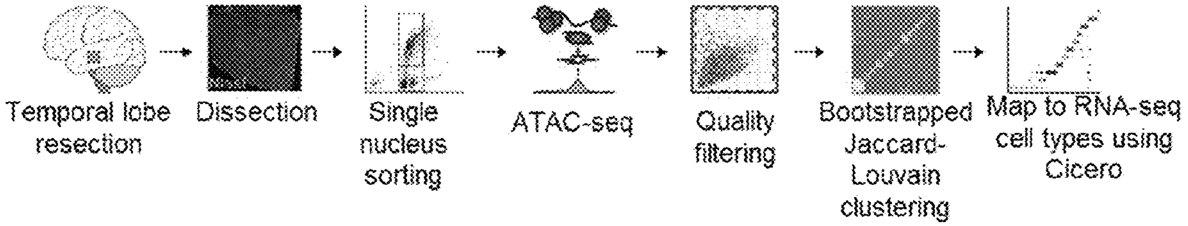
FIGS. 75A, 75B. A database of human neocortical cell subclass-specific accessible chromatin elements. (75A) Workflow for human neocortical epigenetic characterization. (75B-75D) High-quality nuclei (2858 from 14 specimens) visualized by tSNE and colored according to mapped transcriptomic cell type (75B), sort strategy (775C), or specimen (75D). L, layer. (75E) Transcriptomic abundances of eleven known cell subclass-specific marker genes across 75 cell types identified in human temporal cortex middle temporal gyrus (Hodge et al., bioRxiv, 384826, 2018).
Figure 75B:
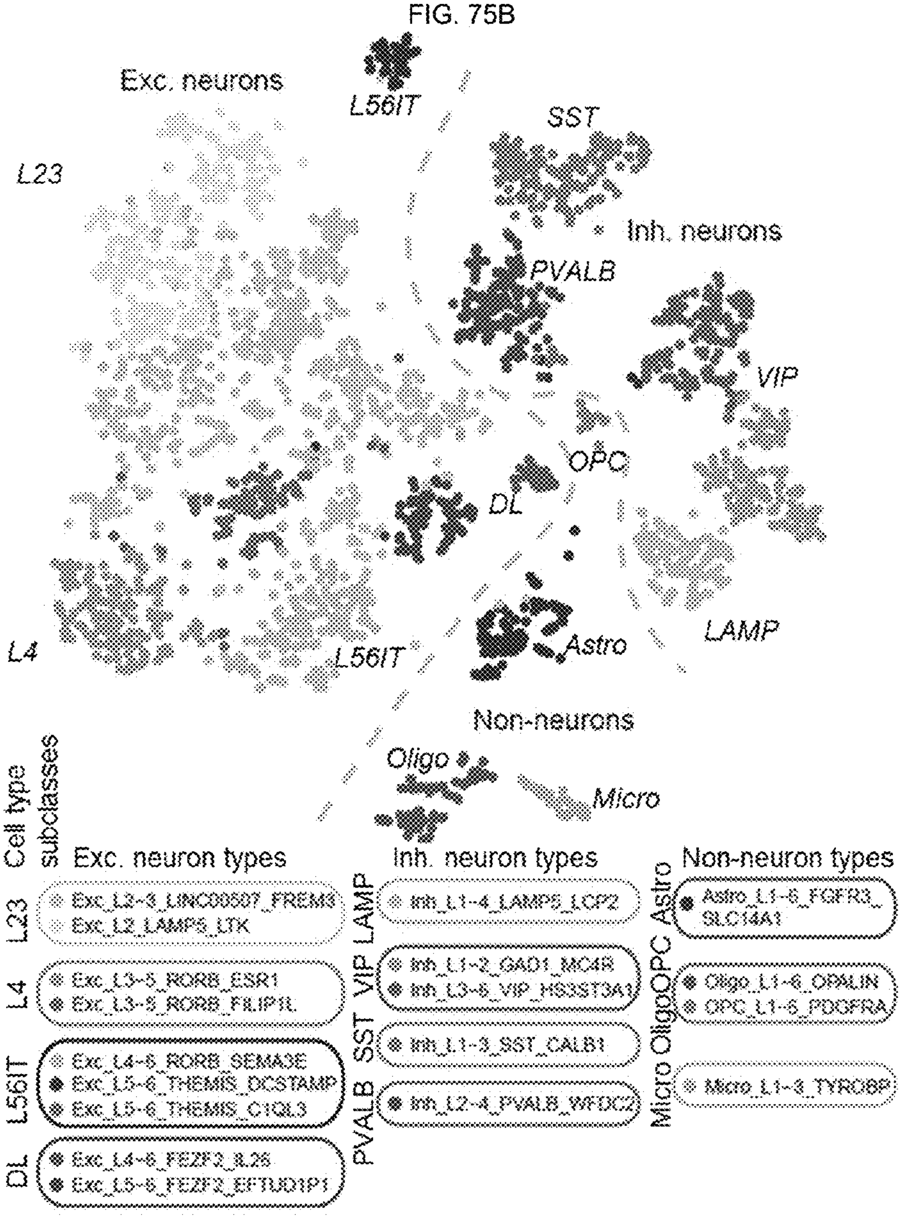

To understand these cells and their regulation, from multiple fresh neurosurgical specimens (bulk n=5, single n=14) a high-quality dataset of accessible chromatin was generated using both bulk and single human brain nuclei via ATAC-seq (Buenrostro et al., *Nature.* 523, 486-490, 2015; Graybuck et al., bioRxiv, 525014, 2019; Gray et al., *eLife Sciences.* 6, e21883, 2017). 3660 single nucleus ATAC-seq libraries (median 48542 unique mapped reads) were prepared and 2858 quality-filtered nuclei were used for clustering and mapping (FIG. 75A, and Materials and Methods of Example 3). 27 ATAC-seq clusters were identified that mapped to 18 human brain temporal lobe transcriptomically defined cell types (Hodge et al., bioRxiv, 384826, 2018) (FIG. 75B). These cell types spanned three major classes of brain cell types: excitatory, inhibitory, and non-neurons; and eleven cell type subclasses: excitatory layer 2/3 (L23), layer 4 (L4), layer 5/6 intra-telencephalic (L56I T), and deep layer non-intratelencephalic neurons (DL); inhibitory LAMPS, VIP, SST, and PVALB neurons, and non-neuronal Astrocytes, Microglia, and Oligodendrocytes/OPCs. The identified cell types were typically identified in the expected sort strategy (FIG. 75B), and all cell types were populated by multiple specimens.

To identify putative regulatory elements within each subclass, data was aggregated for all nuclei within each subclass, and subclass-specific peaks were called with Homer (Heinz et al., Molecular Cell. 38, 576-589, 2010), revealing peaks proximal to recently identified transcriptomic subclass-specific marker genes (Hodge et al., bioRxiv, 384826, 2018), confirming the clustering and mapping strategy. Furthermore, within peaks chromVAR (Schep et al., Nature Methods. 14, 975-978, 2017) identified expected cell type-distinguishing transcription factor motifs, including DLX1 in inhibitory neurons and NEUROD6 in lower-layer excitatory neurons, whose accessibilities correlated with their transcript abundances (Hodge et al., bioRxiv, 384826, 2018) across subclasses (paired t-tests for correlation; DLX1 $t=3.0$ $p<0.01$; NEUROD6 $t=5.4$ $p<0.001$). These observations indicate strong concordance between RNA-seq and ATAC-seq data modalities.

To assess the correspondence among accessibility and epigenetic modifications and primary sequence, the overlap between subclass snATAC-seq peaks and differentially methylated regions (DMRs) as previously identified (Lister, et al., *Science.* 341, 1237905, 2013; Luo, et al., *Science.* 357, 600-604, 2017) was calculated and aggregated by subclass. For every cell subclass, a greater overlap of ATAC-seq peaks was observed with DMRs than would be expected by chance alone (FIG. 77E), furnishing thousands of independently validated human neocortical cell subclass epigenetic elements.

To explore the relationships of these elements to genes, cell subclass peaks were also subset to sets of all peaks, subclass-specific peaks, transcription start site (TSS)-distal peaks (farther than 20 kb from any RefSeq TSS), and the intersection of subclass-specific and TSS-distal peaks; this analysis revealed a particularly strong DMR overlap in TSS-distal peaks (ANOVA $F=3.6$; all peaks versus TSS-distal $p<0.05$; all peaks versus TSS-distal and subclass-specific; $p<0.01$ [Sidak post-hoc corrected probabilities]). To further characterize ATAC-seq peaks, their primary sequence conservation was next calculated by phyloP scores (Pollard et al., *Genome Res.* 20, 110-121, 2010). All cell subclass peak sets were on average more conserved than random DNA stretches. In particular, it was observed that TSS-distal peaks have greater conservation scores than all peaks (paired t-test, $p<0.001$, $t=5.4$, $df=10$), and inhibitory neuron subclass peaks had significantly greater conservation than those of excitatory neuron subclasses (heteroscedastic t-test, $p<0.05$, $t=2.6$, $df=5.6$ for the all peak sets; $p<0.05$, $t=2.5$, $df=5.9$ for the TSS-distal peak sets), agreeing with previous observations by Luo et al. (*Science.* 357, 600-604, 2017).

Taken as a whole, high conservation and confirmation via molecularly independent techniques together suggest that ATAC-seq identifies authentic functional genomic elements that bestow human neocortical cell type identity.

In order to count human accessible chromatin regions shared with mouse ("conserved"), and those unique to human ("divergent"), Jaccard similarity coefficients among human peaks and human genome-mapped mouse peaks were computed for all cell subclasses. All mouse subclasses display highest Jaccard similarity enrichment to their orthologous human subclasses, and all but one human subclass map as expected reciprocally. In addition, non-neurons displayed the strongest cross-species epigenetic similarities, followed by inhibitory neurons, and excitatory neurons displayed the weakest but still greater than random similarities. Quantifying conserved and divergent peaks in each species revealed thousands in each category, with many more conserved peaks than expected by chance alone. Furthermore, much greater primary sequence conservation is observed in conserved peaks than divergent peaks in both species (heteroscedastic t-test; human $t=10.3$, $p<0.001$; mouse $t=6.6$, $p<0.001$), suggesting that these elements perform important evolutionarily shared functions. Across 11 cortical subclasses, it was observed that 34±10% (mean±sd) of all human accessible chromatin elements are conservedly detected in mouse. In conclusion, many functional genomic elements are conserved between human and mouse, across all major neocortical cell subclasses.

Having established a high-quality and high-resolution catalog of human neocortical accessible genomic elements, these data were used as a tool to associate cell subclasses with brain diseases and traits. Linkage disequilibrium score regression (LDSC; Bulik-Sullivan et al., *Nature Genetics.* 47, 291-295, 2015; Finucane et al., *Nat Genet.* 47, 1228-1235, 2015) was used to find significant associations between human brain cell subclass ATAC-seq peaks and SNPs identified in 15 genome-wide association study brain diseases or traits with sufficient power (see Materials and Methods of Example 3). Overall similar association patterns were observed using either ATAC-seq peaks or DMRs (Lister et al., *Science.* 341, 1237905, 2013; Luo et al., *Science.* 357, 600-604, 2017), and generally weak associations for the outgroup trait (Crohn's disease) and outgroup peakset (The ENCODE Project Consortium, *Nature.* 489, 57-74, 2012), together suggesting that these analyses are robust to experimental technique.

Subclass peaksets were split into conserved and divergent subsets, and generally stronger associations between brain diseases/traits and conserved peaks were found. Significant associations (passing Bonferroni-corrected p-value significance cutoffs) between multiple neuronal (but not non-neuronal) subclass peaksets and educational attainment and schizophrenia were observed, similar to previous analyses of RNA-seq data (Skene et al., *Nature Genetics.* 50, 825, 2018; Girdhar et al., *Nature Neuroscience.* 21, 1126-1136, 2018; Cusanovich et al., *Cell.* 174, 1309-1324.e18, 2018), and it was found that these associations are stronger in conserved regions than in divergent regions. The strongest association was also observed between microglial peaks and Alzheimer's disease as in previous reports (Skene et al., *Nature Genetics.* 50, 825, 2018; Girdhar et al., *Nature Neuroscience.* 21, 1126-1136, 2018; Cusanovich et al., *Cell.* 174, 1309-1324.e18, 2018), although these results did not pass significance cutoffs, possibly due to low overall total heritability and hence power in Alzheimer's studies. Interestingly, this microglial-Alzheimer's association is stronger in divergent peaks than in conserved peaks, suggesting human-specific modes of microglial gene expression contribute to Alzheimer's pathology.

Since human divergent peaks outnumber conserved peaks, it was speculated whether overall heritability of neuron-associated traits (educational attainment and schizophrenia) is largely conserved or divergent. Summing total subclass-associated heritabilities revealed that the conserved peaks contain the majority of heritability, and significantly more than divergent peaks. Taken as a whole, these analyses suggest that that cross-species epigenetic analysis enables the discovery of conserved functional genomic elements that illuminate human health and disease.

Figure 78:
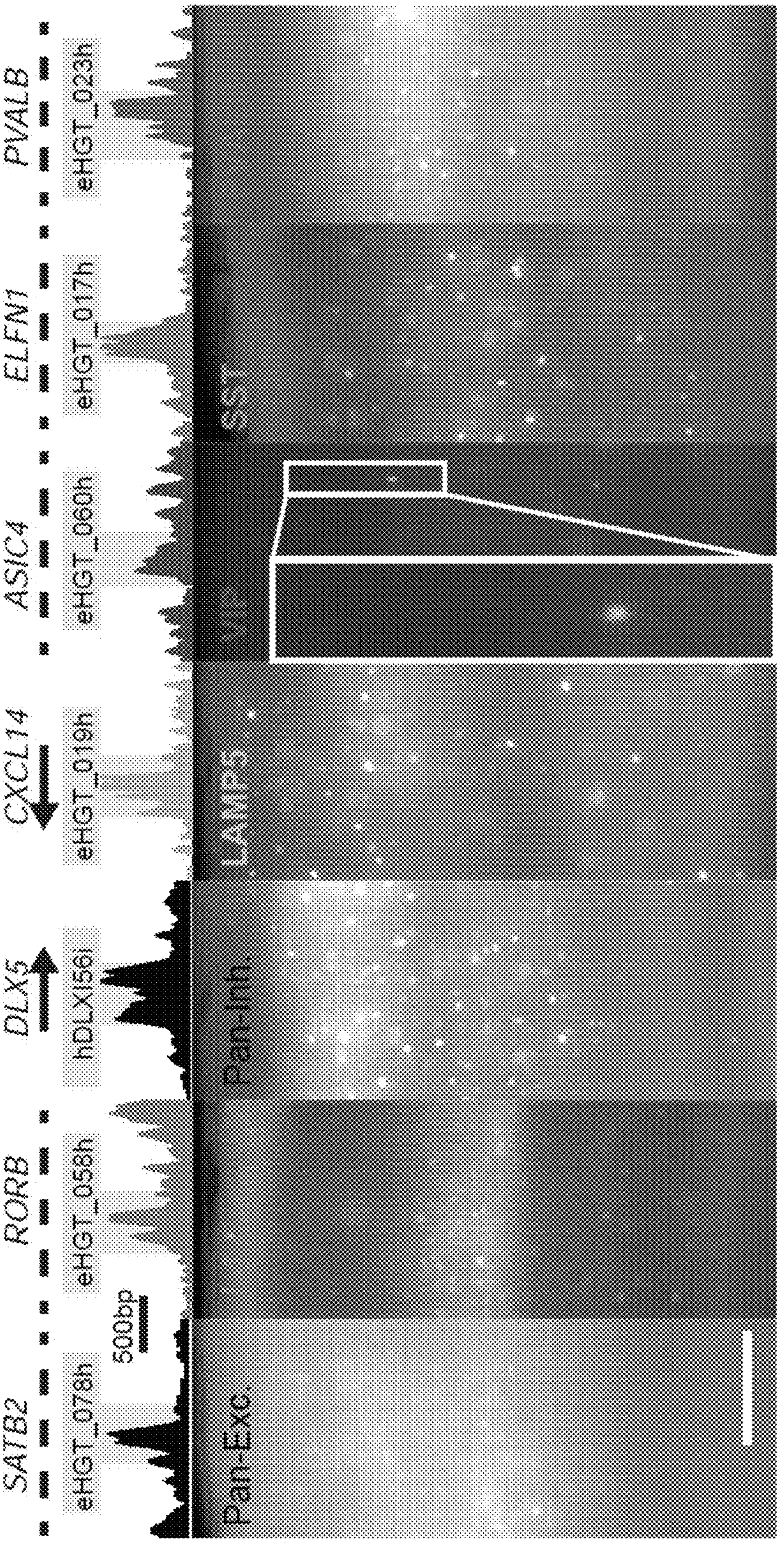

To determine whether these functional genomic elements could furnish useful genetic tools, several subclass-specific peaks were cloned into an adeno-associated virus (AAV) reporter expression vector to test for subclass-specific enhancer activity (Dimidschstein et al., Nature *Neuroscience.* 19, 1743-1749, 2016). Peaks were chosen to be nearby known subclass-specific marker genes from RNA-seq (Hodge et al., bioRxiv, 384826, 2018) and to exhibit subclass-specific accessibility. Several enhancers that drive distinct reporter expression patterns in mouse consistent with their expected subclass-specific accessibility profiles (Zerucha et al., *J. Neurosci.* 20, 709-721, 2000) were discovered (FIG. 78), suggesting that the herein described ATAC-seq enhancer discovery is a generalizable strategy to identify cell class-/type-specific genetic tools.

Since these tools are non-species restricted, research was focused on eHGT_022 near the LAMPS/VIP cell marker CXCL14, and which is conservedly accessible in LAMPS and VIP neuron subclasses in human and mouse. It was found that AAV vectors driving either the human or mouse ortholog of eHGT_022 are both sufficient to drive expression in upper-layer-enriched interneurons in both mouse and human, and these reporter-positive cells specifically correspond to LAMP5 and VIP neurons in both mouse and human. These observations, coupled with those of the companion manuscript (Graybuck et al., bioRxiv, 525014, 2019), suggest that ATAC-seq can identify specific cell type and subclass enhancers that enable genetic tools useful in human and other species.

Human brain functions and diseases are often difficult to study because model organisms do not recapitulate human brain circuitry or display clear clinically relevant phenotypes. In particular, the functionally relevant cell types are unknown for many conditions, which leads to undertreatment of many debilitating brain disorders. It is thus critical to understand human brain-specific circuit components and their regulatory apparatus to furnish avenues for therapeutic intervention. In this work, human neocortical functional genomic elements were catalogued with cell type precision, furnishing the most high-resolution dataset of human brain chromatin accessibility so far. This deepens knowledge of human brain chromatin structure and uncovers a cell type-specific logic in gene regulation. It is expected that this knowledge will not only guide models of human cognitive circuitry, but also fuel gene therapy for unmet clinical needs.

Materials and Methods of Example 3. Neurosurgical tissue acquisition. From a network of surgeons in Seattle WA, a pipeline was established for regular delivery of fresh neurosurgical brain tissue to the Allen Institute for processing. These samples are excised as a matter of course to access the epileptic focus or tumor. Experiments are confined to temporal cortex, most frequently middle temporal gyrus. These samples are immersed in pre-carbogenated ACSF.7 (recipe in Table 3), transported to the Institute rapidly with carbogenation, and sliced on a vibratome into 350 μm slices, and continuously carbogenated in ACSF.7 until dissociation.

Bulk tissue ATAC-seq. MTG tissue slices were harvested after bubbling in ACSF.7 for up to 16 hours, and they were treated with NeuroTrace 500/525 (catalog #N21480 from ThermoFisher Scientific, 1/100 in ACSF.7) to highlight layered cortex structure. With fine forceps, white matter and meningeal tissues were trimmed away, and then layers 1-6 were dissected into six different low-binding Eppendorf 1.5 mL tubes (MilliporeSigma catalog #Z666548) under a fluorescence microscope as in Hodge et al. (bioRxiv, 384826, 2018) The supernatant was discarded and replaced with 50-100 μL of Nextera DNA library reaction (#FC-121-1031 from Illumina) containing 0.1% IGEPAL-630 (NP-40 alternative), then it was pipetted up and down vigorously 25-50 times using a P200 pipette, and then incubated at 37° C. for one hour for transposition. Then, 1 mL of ice-cold nuclear isolation medium was added to quench the reaction, samples were pelleted at 1000 g for 5 minutes at 4° C., and resuspended in 1 mL fresh Homogenization Buffer (recipe in Table 3), nuclei were released from samples using 10-15 strokes of a loose-fitting dounce pestle followed by 10-15 strokes of a tight-fitting dounce pestle, then nuclei were filtered with a 70 μm nylon mesh strainer, and nuclei were pelleted at 1000 g for 10 minutes at 4° C. To stain, nuclei were resuspended in 500 μL of ice-cold Blocking Buffer (recipe in Table 3) containing 1/500 PE-NeuN antibody (MilliporeSigma catalog #FCMAB317PE) and 1 μg/mL 4'-diamino-phenylindazole (DAPI, MilliporeSigma catalog #D9542), samples were rocked for 30 minutes at 4° C., then pelleted at 1000 g for 5 minutes at 4° C., and finally samples were resuspended in 500 μL fresh ice-cold blocking buffer before sorting cells on a FacsARIA III.

Using scatter profiles to eliminate debris and doublets, bulk samples were sorted as DAPI+NeuN+ from layers 1-6, or as DAPI+NeuN− from layer 1 and layer 5 samples, at 5000-10000 cells per sample, into 200 μL of blocking buffer in low-binding Eppendorf 1.5 mL tubes. Sorted nuclei were pelleted at 1000 g for 10 minutes at 4° C., followed by resuspension in 50 μL Proteinase K Cleanup Buffer (recipe in Table 3) and 37° C. incubation for 30 minutes, and then freezing at −20° C. until library prep and sequencing.

For library prep, tagmented DNA was purified with 1.8× vol/vol Ampure XP beads (Beckman-Coulter catalog #A63881), eluted in 11 μL of water, and then PCR-amplified with Nextera Index kit primers (#FC-121-1012 from Illumina) using KAPA HiFi HotStart ReadyMix (KAPA Biosystems #KK2602) in a 30 μL reaction (72° 3:00, 95° 1:00, cycle 17×[98°:20, 65°:15, 72°:15], 72° 1:00). PCR products were purified using 1.8× Ampure XP beads, and libraries were quantified using Agilent BioAnalyzer High Sensitivity DNA Chips (catalog #5067-4626). Then sample libraries were pooled evenly and sequenced with paired-end 50 bp reads either on Illumina MiSeq (Allen Institute) or NextSeq machines (SeqMatic, Fremont CA USA). Fastq files were processed as described below.

Single Cell ATAC-seq. The single cell ATAC-seq workflow was modified from the bulk sample workflow in several ways, most notably performing transposition reactions following sorting rather than prior to sorting, and omitting DAPI except for non-neuronal samples (due to the uncertainty of DAPI possibly interfering with transposition).

Specific MTG tissue layers were collected and dissected as for bulk samples, but the layers were immediately dounced to release nuclei, and then stained in blocking buffer containing PE-NeuN antibody but not DAPI. Single NeuN+ nuclei from each layer were sorted into each well of a 96-well plate, using scatter profiles to exclude debris and doublets. Single nucleus-to-event correspondence was confirmed by test-sorting single NeuN+ events into flat-bottom 96 well plates with 40 μL blocking buffer containing DAPI followed by pelleting 1 min at 3000 g and microscopic examination. These tests routinely yielded >95% single nucleus-filled wells and undetectable doublets. In the cases where glial cells were sorted, neurons were first sorted from the sample using PE-NeuN+ staining, and then treated with DAPI (1 μg/μL) for 1-2 minutes prior to sorting glial cells as DAPI+NeuN− events.

Single NeuN+ cells were sorted into 1.5 μL of Nextera Tn5 transposition reaction (0.6 μL Tn5 enzyme, 0.75 μL tagmentation buffer, 0.15 μL 1% IGEPAL CA-630) in Eppendorf semi-skirted 96-well plates (MilliporeSigma catalog #EP0030129504). Immediately following sorting, plates were briefly spun down, briefly vortexed, spun down again, and then incubated at 37° C. for 30 minutes for transposition. After transposition 0.6 μL Proteinase K Cleanup Buffer were added, sample was briefly vortexed and spun down, and incubated at 40° C. for an additional 30 minutes, then plates were frozen until library prep. Library prep for single cell samples was the same as for bulk samples, except the number of amplification cycles was increased from 17 to 22 cycles due to the lower input DNA content.

Bulk ATAC-seq sample clustering. Peaks were called on all 39 bulk samples from 5 independent specimens using MACS2 (Zhang et al., *Genome Biology.* 9, R137, 2008), and then DiffBind (Ross-Innes et al., *Nature.* 481, 389-393, 2012) was used to identify 73742 differential peaks for all contrasts among the sample types (sort strategies and specimens). Of these, 1524 distinguished experimental specimens and were discarded for clustering. With 72218 remaining peaks found specifically to discriminate any pairwise combinations of sort strategies, correlation among bulk samples was reanalyzed using reads in these peaks. A correlation matrix revealed grouping of non-neuronal samples, upper layer neuronal samples, and lower layer neuronal samples. One sample was omitted from this analysis (H17.03.009 L1 NeuN+) because this sample appeared intermediate between NeuN+ and NeuN− cells, likely due to a sorting error.

ATAC-seq data preprocessing and quality control. Sample-specific fastq files were retrieved using standard built-in Illumina deindexing protocols. Each fastq file was mapped to human genome reference hg38 patch 7 using bowtie2 and the flags—no-mixed—no-discordant-×2000 to generate sample-specific bam files, which were then filtered for low-quality mappings, secondary mappings, and unmapped reads using samtools view -q 10 -F 256 -F 4, and then filtered for duplicate reads using samtools rmdup. Then, these filtered reads bam files were converted to bed files using bedTools bamToBed for quality control calculations of mean ENCODE overlap and TSS enrichment score. For mean ENCODE overlap bed files were converted to fragment format, the percentage of unique fragments that overlap with ENCODE project DNaseI hypersensitivity peaks from adult human frontal cortex (studies ENCSR000EIK and ENCSR000EIY; The ENCODE Project Consortium,

*Nature.* 489, 57-74, 2012; Sloan et al., *Nucleic Acids Res.* 44, D726-D732, 2016) was assessed using bedTools intersectBed (Quinlan & Hall, *Bioinformatics.* 26, 841-842, 2010), and the mean of these two numbers was taken. For TSS enrichment score, the published technique of Chen et al (Chen et al., *Nat Meth.* 13, 1013-1020, 2016) was used. This technique sums the overlap of reads in 2 kb windows surrounding all human TSSs, then segments this 2 kb window into 40 50-bp bins, then normalizes the summed read counts to the outside four bins (first and last two), and finally reports the TSS enrichment score as the maximum height of that normalized read count graph. It was noticed that this technique worked well for all bulk samples but gave spurious abnormally high scores for some single cells having low read count; as a result a modification was made to set TSS enrichment score to 1 (no enrichment) for single cells having fewer than 500 reads or TSSs calculated to be greater than 20 (likely spurious events).

These quality control metrics were used to filter out low quality cells (ENCODE overlap<15% AND TSS score<4). Additionally, cells having fewer than 10000 unique read pairs were filtered out, since these many reads are required for the clustering approach. Of 3660 initial cells, analysis was confined to 2858 high quality nuclei for clustering.

Clustering single cells: bootstrapped clustering. Single cells were clustered using extended fragment Jaccard distance calculations among cells as implemented by the lowcat package (Graybuck et al., bioRxiv, 525014, 2019). To accomplish this, first, reads on chromosomes X, Y, and M were excluded to prevent differential chromosome-biased clustering. Then, it was randomly downsampled as described in Materials and Methods of Example 1 with fragments extended to a regularized length of 1000 bp with the same center. Then, Jaccard distances were calculated as described in Materials and Methods of Example 1.

Finally, this 2858×2858 Jaccard distance matrix was dimensionality reduced to a 2858×29 matrix of principal component scores 2 through 30 using princomp in R. Principal component 1 was omitted because it was highly correlated to quality control metrics, suggesting that this axis primarily reflected cell library quality. Principal components beyond 30 contain little cell type information, so excluding them represents a de-noising step. These resulting 29 PCs are used to call cell clusters and to visualize them using tSNE.

To call cell clusters on this 2858×29 principal component matrix, an iterated Jaccard-Louvain clustering technique was bootstrapped using k=15 nearest neighbors. Each bootstrapping round was repeated 200 times, each time including only 80% (2286) of the cells, and the frequency with which each cell co-clusters with every other cell was tabulated. This co-clustering frequency matrix was then hierarchically clustered by Euclidean distances, and 27 cell type clusters were called by cutting the tree to represent visually apparent co-clustered blocks of cells. Repeating this process with more stringent variable 50-90% cell inclusion resulted in similar cluster structure with similar cluster memberships, but randomizing the Jaccard distance matrix prior to principal component analysis and bootstrapped clustering yielded no clusters in the dataset. Together these analyses suggest that the identified clusters represent real and reproducible cell groups.

Clustering single cells: comparing choice of feature set. Clustering cells using other feature sets besides Jaccard distances among cells was also attempted. These feature sets included: 1) the list of all detected peaks from the entire aggregated dataset (236588 peaks called using Homer findPeaks (Heinz et al., *Molecular Cell.* 38, 576-589, 2010) with -region flag), 2) the list of all RefSeq gene TSS regions, extended +/−10 kb (27021 regions), 3) all 321184 non-overlapping 10 kb bins across the human genome, and 4) the list of "GeneBins" defined as the genomic region for each gene between the boundaries of midpoints between each RefSeq gene transcribed region. For each feature set, counts in regions for each cell were computed, then principal components were identified, and cell groupings were visualized by tSNE of principal components 2:50 in order to observe cell groupings. Jaccard distances disclosed the qualitatively cleanest separation among cells, and among cell clusters. Furthermore, a wide range of tSNE perplexity values maintained these separations.

Mapping clusters to transcriptomic cell types: assimilating epigenetic and transcriptomic information. The goal was to map the 2858 high quality ATAC-seq profiled cells to human brain cell types discovered by large-scale RNA-seq studies (Hodge et al., bioRxiv, 384826, 2018). To do this, first, the best technique to manufacture gene-level information from the ATAC-seq data was sought, in order to correlate with RNA-seq transcript counts. Four techniques were tried: 1) read counts in RefSeq gene bins, 2) read counts in RefSeq gene bodies, 3) read counts in RefSeg gene TSS regions extended +/−10 kb, and 4) Cicero gene activity scores (Cusanovich et al., *Cell.* 174, 1309-1324.e18, 2018; Pliner et al., *Molecular Cell.* 71, 858-871.e8, 2018). With these four sets of gene-level information computed for each cell, single cells were mapped to RNA-seq cell types using as the best correlated RNA-seq cluster median gene counts per million (CPM) with each epigenetic feature set (using a subset of 831 marker genes), resulting in four distinct mappings for each cell.

The 831 marker genes were chosen to be both informative marker genes for RNA-seq clustering and to contain abundant epigenetic information. This was accomplished by using the select markers function with default parameters from the scrattch.hicat R package (Tasic et al., *Nature.* 563, 72, 2018) which yielded 2791 transcriptomic marker genes, which was further filtered by intersecting with the top ten percent of genes with the highest summed Cicero gene activity scores across all 2858 cells, to yield 831 combined transcriptomic and epigenetic marker genes for mapping.

The four sets of cellwise mappings yielded four tables of cell type abundances within the dataset. Next, taking the RNA-seq dataset as a true gold standard, the four cell type abundance tables were compared with the 'expected' cell type abundances, which were calculated as the sum of numbers of cells sorted in each sort strategy, times the expected cell type frequencies in each sort strategy. Correlating the four cell type abundance tables with the expected abundance table (Pearson correlations of log-transformed abundance values plus one) revealed that Cicero gene activity scores supply the most dependable gene-level information for the purpose of epigenetic to transcriptomic mapping.

Mapping clusters to transcriptomic cell types: bootstrapping mapping for final mapping calls. Using Cicero gene activity scores, the cellwise mapping procedure was bootstrapped 100 times with retention of a variable 50-90% of genes each round, and the most frequently mapped transcriptomic cell type was applied to each single ATAC-seq cell. Then, the percentage of each cluster's constituent cells mapping to each cell type was reported and summed by cell type subclass.

Figure 76:
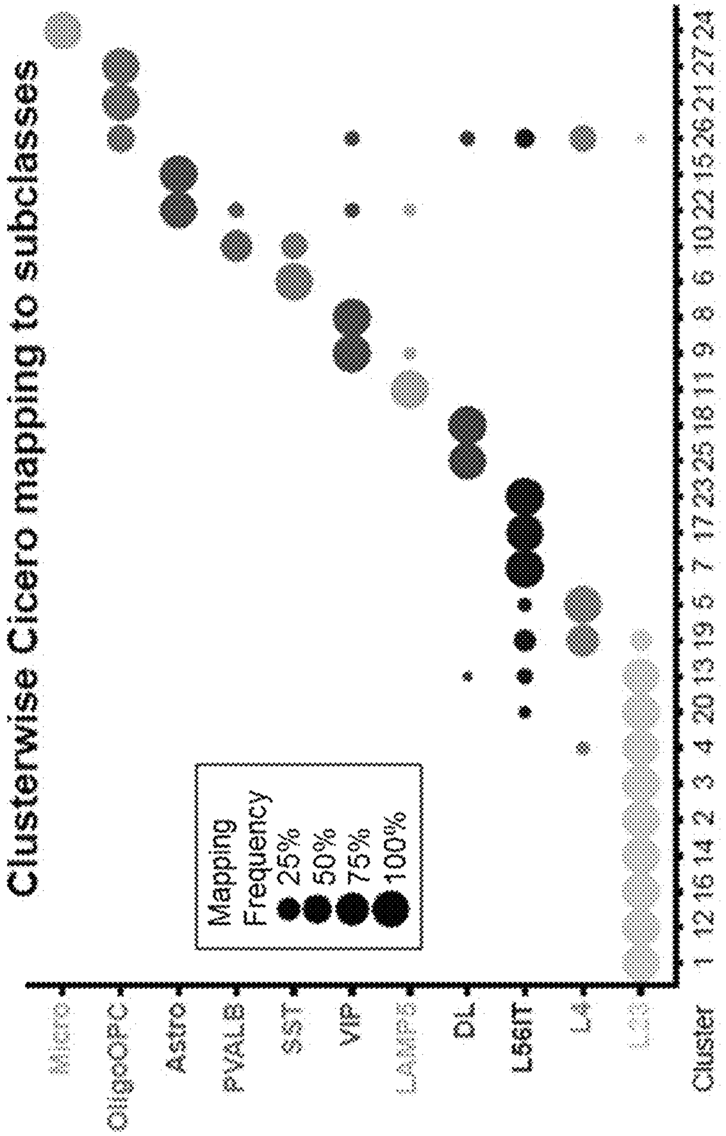
FIG. 76. Mapping ATAC-seq clusters to RNA-seq cell types. Transcriptomic cell types within subclasses were summed across for clusterwise mapping, to yield clusterwise mapping to subclasses. This plot represents the final mapped subclass assigned as the most frequent mapping for each cluster, and these subclass identities are used for the pileups and calculations in FIGS. 75B, 77, and 78.

Clusterwise mapping was also performed for each of the 27 ATAC-seq clusters using the same bootstrapped mapping procedure, except that Cicero gene activity scores were aggregated by mean across cells within each cluster prior to mapping. The number of 100 times that each cluster is mapped to each cell type was reportedand summed by transcriptomic subclass in FIG. 76.

Clusterwise mapping was observed to largely agree with, but to be cleaner than, cellwise mapping (FIG. 76); hence clusterwise mapping was elected as the final mapping procedure. Each cell is thus assigned a final mapped transcriptomic cell type and cell type subclass (shown in FIG. 76) as a result of its ATAC-seq cluster membership.

Peak calling. Peaks were called on both bulk and aggregated single-cell data using Homer findPeaks with -region flag (Heinz et al., *Molecular Cell.* 38, 576-589, 2010). This program was found to be superior to Hotspot, MACS2, and SICER to identify small regions corresponding to likely enhancers, while still capturing the peak boundaries. Peak sizes are median 400-500 bp across subclasses.

Identifying transcription factor motifs using chromVAR. ChromVAR (Schep et al., *Nature Methods.* 14, 975-978, 2017) was used to identify transcription factor motif accessibilities in the cells. Using Homer findPeaks, peaks were called on the aggregation of all single cell and bulk libraries (236588 peaks), and then they were resized to a standard 150 bp size with the same center. 452 transcription factor motifs from JASPAR (using JASPAR2018 R package; Tan, JASPAR2018: Data package for JASPAR 2018., 2017) and 1764 from cisBP (as included in the R package chromVARmotifs; Schep et al., *Nature Methods.* 14, 975-978, 2017) were downloaded, and chromVAR was used to aggregate and quantify motif accessibilities in all 2858 single cells. Cell type subclass-distinguishing motifs across were found by ranking subclass-averaged motif accessibilities by standard deviation across subclasses (including DLX1 and NEUROD6).

Global peak characterization by conservation. With peaks called for each subclass, peaks were subset into four sets. 1) All peaks (no subsetting). 2) Subclass-specific peaks which were detected in only that subclass and not in an outgroup subset of human keratinocyte or mouse E16.5 kidney ATAC-seq data downloaded from ENCODE (The ENCODE Project Consortium, *Nature.* 489, 57-74, 2012). 3) TSS-distal peaks which were not located less than 20 kb from any of 27021 RefSeq gene TSS sites, downloaded from UCSC table browser (Karolchik et al., *Nucleic Acids Res.* 32:D493-D496, 2004). 4) Subclass-specific AND TSS-distal peaks. Overlaps were calculated using bedtools intersectBed. In analyses that shuffle peak positions, for TSS-distal peaks randomly generated comparator peak positions were restricted to the same TSS-distal genomic regions.

For peak phyloP scores, bigWigSummary was used to lookup phyloP values from hg38.phyloP4way.bw or mm10.phyloP4way.bw. These files quantify the basepair conservation across four mammals: *Homo sapiens, Mus musculus, Galeopterus variegatus* (Malayan flying lemur), and *Tupaia chinensis* (Chinese tree shrew). Ten values distributed across each peak were returned, and the maximum mean of eight three-consecutive-value sets was calculated. This is done to find smaller regions on the order of 100 bp highly conserved regions within each peak and yields greater deviations between real and random phyloP scores than taking a single peak-wise average alone. Peak-wise phyloP scores were compared to those of randomly distributed peak regions throughout the genome by subtracting real peak phyloP mean minus random peak phyloP mean.

Identifying transcriptomic cell type matches for methylation data. Using the dataset of Luo et al. (*Science.* 357, 600-604, 2017 (Supplementary Table 3 containing 1012 human and 1016 mouse methylation marker genes)), the published mCH gene body marker genes were correlated with cluster-wise medians for transcriptomic human cell types identified by Hodge et al. (bioRxiv, 384826, 2018) and for mouse cell types by Tasic et al. (*Nature.* 563, 72, 2018). Pearson correlation coefficients were calculated between normalized gene body mCH and RNA-seq clusterwise median FPKM, and the best-correlated transcriptomic cell type was assigned to each methylation cell type. Specificity of matches was calculated as the difference between the best correlation and the second-best correlation. Importantly, all transcriptomic cell type assignments agree with the predicted subclasses by the original authors.

Figure 77:
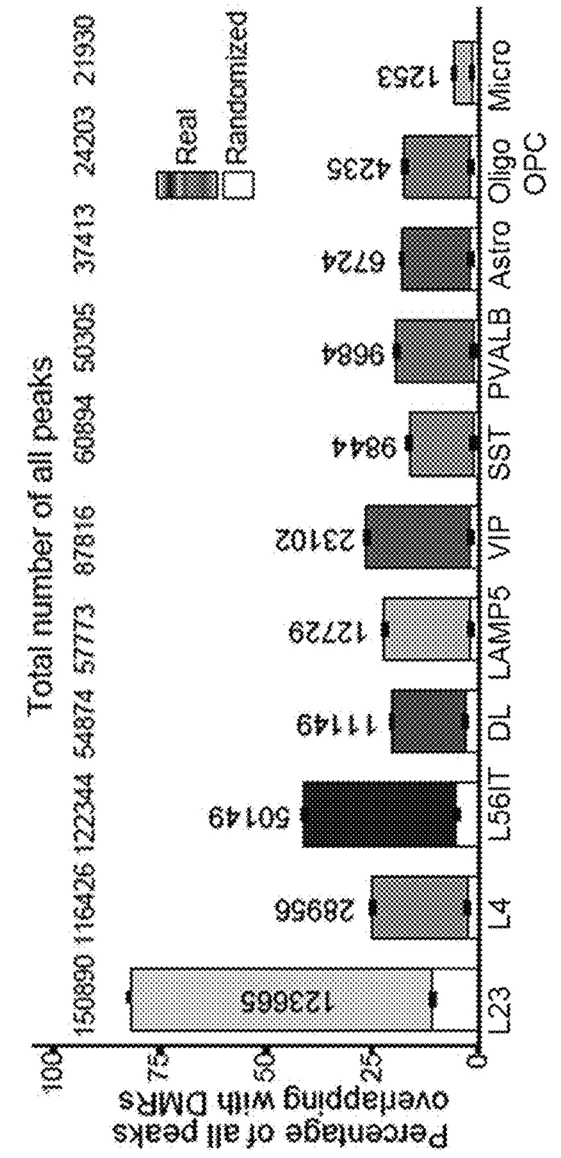
FIG. 77. Properties of human neocortical cell subclass-specific accessible genomic elements. Percent overlap of ATAC-seq peaks with previously identified DMRs (Lister et al., Science. 341, 1237905, 2013, Luo et al., *Science*. 357, 600-604, 2017), comparing real peaks to randomized peak positions. Absolute numbers of detected peaks and peak-DMR overlaps are shown FIG. 78. Accessible chromatin elements furnish human genetic tools. Multiple enhancer-AAV vectors yield distinct subclass selectivities. Seven gene loci and ATAC-seq read pileups are shown, as well as expression pattern in mouse V1 for those seven AAV reporter vectors. Scale 200 μm.

Quantifying ATAC-seq peak overlaps with DMRs. First, human DMRs from Luo et al. (*Science.* 341, 1237905, 2013) and Lister et al. (*Science.* 357, 600-604, 2017) were aggregated. For neuron types, DMRs were downloaded as calculated by the authors and then these DMRs were merged using bedtools mergeBed. For non-neuron types, raw fastq files were downloaded from the GEO submission of Lister et al corresponding to bulk NeuN-negative cells from two human replicates (GSM1173774 and GSM1173777) and converted these to allc files using the pipeline analysis method of Luo et al. (*Science.* 357, 600-604, 2017). These allc files were aggregated and used to find DMRs with methylpy DMRfind against allc files for all human subclasses from Luo et al., and an outgroup of human H1 cells from ENCODE (The ENCODE Project Consortium, *Nature.* 489, 57-74, 2012). The same set of bulk non-neuronal DMRs were used as one for comparison to Astrocytes, Oligodendrocytes/OPCs, and Microglia ATAC-seq classes (FIG. 77).

With bed files corresponding to each subclass ATAC-seq peakset and to each subclass DMR set, bedtools intersectbed were used to quantify the overlap between peaks and DMRs. Calculation of real peak overlaps 100× was bootstrapped by removing 20 percent of peaks each time and calculating percentage overlap, and the mean of these 100 measurements is reported.

Similarly, peak positions were randomized throughout the genome 100× using bedtools shuffleBed, percentage overlap was calculated each time, and the mean of these 100 measurements is reported. By definition, disjoint ranges of real versus randomized peak overlap percentages established false discovery rate<0.01. Enrichment of DMR overlaps for ATAC-seq peaksets, defined as the ratio of real peak-DMR overlap percentage to the overlap percentage of randomized peak positions, was also calculated.

Mouse to human cross-species comparisons. The sets of subclass-specific peaks were used to map between human and mouse subclasses, which are uniquely identified in only that subclass. First subclass-specific mouse peaks were mapped to hg38 using liftOver. Then calculation of human peak overlap was bootstrapped 100× against all mouse peaks with random retention of 80% of human peaks each time, and the mean of Jaccard similarity coefficients (intersection over union) over 100 runs was taken. In addition, genomic peak positions were shuffled 100×, and mean Jaccard similarity coefficients were calculated each time. The enrichment of Jaccard similarity coefficients was determined as the ratio of the real over random.

Characterization of human conserved and divergent peaks began with all human peaks and subset to those intersecting ("Conserved") or not intersecting ("Divergent") with mouse peaks identified within the same homologous subclass and mapped to hg38 by liftOver. To characterize mouse conserved and divergent peaks, all mouse peaks were intersected with reciprocal mm10-mapped human peaks. Then phyloP scores were calculated as above for these four sets of peaks.

Cloning enhancers. Enhancers were manually chosen from ATAC-seq and RNA-seq data for cloning by the following criteria: 1) adjacent to known subclass marker gene, and 2) specifically accessible peak in only the subclass of interest, and 3) contains region of high primary sequence conservation by phyloP score.

Chosen enhancers were cloned into AAV expression vectors that are derivatives of either pscAAV-MCS (Cell Biolabs catalog #VPK-430), including eHGT_019 h, eHGT_017 h, eHGT_022 h, eHGT_022 m, and eHGT_023 h; or pAAV-GFP (Cell Biolabs catalog #VPK-410), including eHGT_078 h, eHGT_058 h, eHGT_060 h, and hDLXl56i (Dimidschstein et al., Nature *Neuroscience.* 19, 1743-1749, 2016; Zerucha et al., *J. Neurosci.* 20, 709-721, 2000). Enhancers were inserted by standard Gibson assembly approaches, upstream of a minimal beta-globin promoter and SYFP2, a brighter EGFP alternative that is well tolerated in neurons (Kremers, et al., *Biochemistry.* 45, 6570-6580, 2006). NEB Stable cells (New England Biolabs #C30401) were used for transformations. scAAV plasmids were monitored by restriction analysis and sanger sequencing for occasional (10%) recombination of the left ITR.

Virus production. Enhancer AAV plasmids were maxiprepped and transfected with polyethylimine max into 1 plate of AAV-293 cells (Cell Biolabs catalog #AAV-100), along with helper plasmid and PHP.eB rep/cap packaging vector. The next day medium was changed to 1% FBS, and then after 5 days cells and supernatant were harvested and AAV particles released by three freeze-thaw cycles. Lysate was treated with benzonase after freeze thaw to degrade free DNA (2 μL benzonase, 30 min at 37 degrees, MilliporeSigma catalog #E8263-25KU), and then cell debris was precleared with low-speed spin (1500 g 10 min), and finally the crude virus was concentrated over a 100 kDa molecular weight cutoff Centricon column (MilliporeSigma catalog #Z648043) to a final volume of 150 μL. This crude virus prep was useful in both mouse and human virus testing.

Mouse virus testing. Mice were retro-orbitally injected at P42-P49 with 10 μL (1E11 genome copies) of crude virus prep diluted with 100 μL PBS, then sacrificed at 18-28 days post infection. For live epifluorescence, mice were perfused with ACSF.7 and live 350 μm physiology sections were cut with a compresstome from one hemisphere to analyze reporter expression. For antibody staining the other hemisphere was drop-fixed in 4% PFA in PBS for 4-6 hours at 4 degrees, then cryoprotected in 30% sucrose in PBS 48-72 hours, then embedded in OCT for 3 hours at room temperature, then frozen on dry ice and sectioned at 10 μm thickness, prior to antibody stain using standard practice. Single-cell RNA-seq was accomplished as described previously (Tasic et al., *Nat Neurosci.* 19, 335-346, 2016; Tasic et al., *Nature.* 563, 72, 2018).

Human virus testing. Temporal cortex neurosurgical samples were bubbled in cold ACSF.7 and kept sterile throughout processing. Blocks of tissue were sliced at 350 μm thickness and then white matter and pial membranes were dissected away. Typically all layers are represented in a good cortical slice. Slices then underwent warm recovery (bubbled ACSF.7 at 30 degrees for 15 minutes) followed by reintroduction of sodium (bubbled ACSF.8 at room temperature for 30 minutes, recipe in Table 2; Ting et al., *Scientific Reports.* 8, 8407, 2018). Slices were then plated at the gas interface on Millicell PTFE cell culture inserts (MilliporeSigma #PICM03050) in a 6-well dish on 1 mL of Slice Culture Medium (recipe in Table 3). After 30 minutes, slices were infected by direct application of high-titer AAV2/PHP.eB viral prep to the surface of the slice, 1 μL per slice. Slice Culture Medium was replenished every 2 days and reporter expression was monitored.

Single cell RNA-seq was accomplished on human virus-infected neurons by 1 hr digestion at 30 degrees in carbogenated ACSF.1/trehalose+blockers+papain (recipes in Table 3), followed by gentle trituration in Low-BSA Quench buffer, shallow spin gradient centrifugation (100 g 10 minutes at room temperature) into High-BSA Quench buffer, and resuspension into Cell Resuspension Buffer. Also, Myelin Bead Removal Kit II (Miltenyi catalog #130-096-733) at 1/20 was employed to remove myelin debris, and PE-anti CD9 clone eBioSN4 (Thermo Fisher catalog #12-0098-42) at 1/40 to sort away contaminating glial cells. Then, single SYFP2+ labeled human neurons were sorted for sequencing using SMARTer V4 as previously described (Tasic et al., *Nat Neurosci.* 19, 335-346, 2016; Tasic et al., *Nature.* 563, 72, 2018).

Inferring GWAS-cell subclass associations. Linkage disequilibrium score regression (LDSC; Bulik-Sullivan et al., Nature Genetics. 47, 291-295, 2015; Finucane et al., Nat Genet. 47, 1228-1235, 2015) was used to partition heritability of various brain conditions to regions associated with accessible chromatin in eleven human cortical cell subclasses, whose peaks are partitioned into Conserved and Divergent subsets. As outgroup comparators, heritability associated with outgroup populations of human keratinocytes downloaded from ENCODE was also investigated.

Summary statistics from 21 Genome Wide Association Studies (GWAS) were downloaded, including expected brain-related (schizophrenia, major depressive disorder, autism spectrum disorder, ADHD, Alzheimer's disease, Tourette's syndrome, bipolar disorder, eating disorder, obsessive-compulsive disorder, loneliness, BM I, PTSD) and expected non-brain-related diseases (Crohn's disease and asthma) from the PGC and EMBL/EBI GWAS repositories (see Table 2). Studies with $\log^{10}(N*h^2)<3.6$ were excluded, where N is number of patients in the study and $h^2$ represents the sum of heritability across SNPs within the study, the effective power of the study (Finucane et al., *Nat Genet.* 47, 1228-1235, 2015). This exclusion removed asthma (Demenais et al., *Nat. Genet.* 50, 42-53, 2018; $\log^{10}(N*h^2)=3.5$, PTSD (Duncan et al., *Mol. Psychiatry.* 23, 666-673, 2018 $\log^{10}(N*h^2)=2.9$), eating disorder (Duncan et al., *Am J Psychiatry.* 174, 850-858, 2017; $\log^{10}N*h^2)=3.5$), loneliness (Gao et al., *Neuropsychopharmacology.* 42, 811-821, 2017; $\log^{10}(N*h^2)=3.3$), obsessive-compulsive disorder (IOCDF-GC & OCGAS, *Mol. Psychiatry.* 23, 1181-1188, 2018; $\log^{10}(N*h^2)=3.5$), and one major depressive disorder study (Major Depressive Disorder Working Group of the Psychiatric GWAS Consortium et al., *Mol. Psychiatry.* 18, 497-511, 2013; $\log^{10}(N*h^2)=3.3$). All 15 included studies were performed on a European descent population. Within these datasets, the analysis was confined to 1389227 high-confidence SNPs present in the HapMap3 list, and using linkage disequilibrium maps from the 1000 Genomes European descent individuals, the trait and disease enrichments of cell subclass-associated chromatin were analyzed along with the LDSC baseline model LDv2.0 with 75 enumerated genomic feature categories. For statistical testing to identify significant enrichments Bonferroni multiple hypothesis testing correction of LDSC's block jackknife-estimated p-values was used, as previously suggested (Skene et al., Nature Genetics. 50, 825, 2018). This correction is 0.05/345 disease/subclass combinations$=1.45e^{-4}$ significance cutoff, and similarly 180 and 150 tests were used.

TABLE 2

| Citations for GWAS studies | |
|---|---|
| Citation | Disease(s)/Condition(s) |
| Anney et al., *Molecular Autism.* 8, 21, 2017 | Autism |
| Autism Spectrum Disorder Working Group of the Psychiatry Genomics Consortium, PGC- ASD summary statistics from a meta-analysis of 5,305 ASD-diagnosed cases and 5,305 pseudocontrols of European descent. (2015), (available online at med.unc.edu/pgc/results-and-downloads). | Autism spectrum disorder |
| de Lange et al., *Nat. Genet.* 49, 256-261, 2017 | Inflammatory Bowel Disease |
| Demenais et al., *Nat. Genet.* 50, 42-53, 2018 | Asthma |
| Duncan et al., *Mol. Psychiatry.* 23, 666-673, 2018 | PTSD |
| Duncan et al., *Am J Psychiatry.* 174, 850-858, 2017 | Eating disorder |
| Gao et al., *Neuropsychopharmacology.* 42, 811-821, 2017 | Loneliness |
| International Obsessive Compulsive Disorder Foundation Genetics Collaborative (IOCDF-GC) and OCD Collaborative Genetics Association Studies (OCGAS), *Mol. Psychiatry.* 23, 1181-1188, 2018 | OCD |
| Lambert et al., *Nat. Genet.* 45, 1452-1458, 2013 | Alzheimer's |
| Lee et al., *Nat. Genet.* 50, 1112-1121, 2018 | Educational Attainment |
| Liu et al., *Nat. Genet.* 47, 979-986, 2015 | Inflammatory Bowel Disease |
| Major Depressive Disorder Working Group of the Psychiatric GWAS Consortium et al., *Mol. Psychiatry.* 18, 497-511, 2013 | Major Depressive Disorder |
| Marioni et al., *Transl Psychiatry.* 8, 99, 2018 | Alzheimer's |
| Okbay et al., *Nature.* 533, 539-542, 2016 | Educational Attainment |
| Psychiatric GWAS Consortium Bipolar Disorder Working Group, *Nat. Genet.* 43, 977-983, 2011 | Bipolar Disorder |
| Schizophrenia Psychiatric Genome-Wide Association Study (GWAS) Consortium, *Nat. Genet.* 43, 969-976, 2011 | Schizophrenia |
| Schizophrenia Working Group of the Psychiatric Genomics Consortium, *Nature.* 511, 421-427, 2014 | Schizophrenia |
| Tourette Association of America International Consortium for Genetics (TAAICG, Interrogating the genetic determinants of Tourette syndrome and other tic disorders through genome-wide association studies, 2018 | Tourette |
| Wray et al., *Nat. Genet.* 50, 668-681, 2018 | Major Depressive Disorder |
| Yang et al., *Nat Meth.* 14, 621-628, 2017 | |
| Demontis, Discovery Of The First Genome-Wide Significant Risk Loci For ADHD \| bioRxiv, (available online at biorxiv.org/content/10.1101/145581v1). | ADHD |

TABLE 3

| Buffer Recipes | | |
|---|---|---|
| Proteinase K Cleanup Buffer | EDTA | 50 mM |
| | Sodium chloride | 5 mM |
| | Sodium dodecyl sulfate | 1.25% (w/v) |
| | Proteinase K (Qiagen # 19131) | 5 mg/mL |
| Nuclei Isolation Medium | Sucrose | 250 mM |
| | Potassium chloride | 25 mM |
| | Magnesium chloride | 5 mM |
| | Tris-HCl | 10 mM |
| | pH to 8.0 and sterile filter. Store refrigerated. | |
| Homogenization Buffer | 10 mL Nuclei Isolation Medium | |
| | 0.1% (w/v) Triton X-100 | |
| | One pellet Roche Mini cOmplete ™ EDTA-free (Sigma catalog # 4693159001) | |
| | Prepare fresh on day of experiment. | |
| Blocking Buffer | PBS | |
| | BSA (catalog # A2058 from Millipore Sigma) | 0.5% (w/v) |
| | Triton X-100 | 0.1% (w/v) |
| ACSF.7 | HEPES | 20 mM |
| | Sodium Pyruvate | 3 mM |
| | Taurine | 10 μM |
| | Thiourea | 2 mM |
| | D-(+)-glucose | 25 mM |
| | Myo-inositol | 3 mM |
| | Sodium bicarbonate | 30 mM |
| | Calcium chloride dihydrate | 0.5 mM |

TABLE 3-continued

| Buffer Recipes | | |
|---|---|---|
| | Magnesium sulfate | 10 mM |
| | Potassium chloride | 2.5 mM |
| | Monosodium Phosphate | 1.25 mM |
| | HCl | 92 mM |
| | N-methyl-D-(+)-glucamine | 92 mM |
| | L-ascorbic acid | 5.0 mM |
| | N-acetyl-L-cysteine | 12 mM |
| | Adjust pH to 7.3-7.4 with HCl, then adjust osmolarity to 295-305. Sterile filter, and then make 100 mL aliquots and freeze them. The thawed aliquot keeps 2-3 months at 4 degrees, until it turns yellow. Bubble with carbogen at least 10-15 minutes before use, and continuously while in use. | |
| ACSF.8 | HEPES | 20 mM |
| | Taurine | 10 μM |
| | Thiourea | 2 mM |
| | D-(+)-glucose | 25 mM |
| | Myo-inositol | 3 mM |
| | Sodium bicarbonate | 30 mM |
| | Calcium chloride dihydrate | 2.0 mM |
| | Magnesium sulfate | 2.0 mM |
| | Potassium chloride | 2.5 mM |
| | Monosodium Phosphate | 1.25 mM |
| | Sodium chloride | 92 mM |
| | L-ascorbic acid | 5.0 mM |
| | N-acetyl-L-cysteine | 12 mM |
| | Adjust pH to 7.3-7.4 with HCl, then adjust osmolarity to 295-305. Sterile filter, and then make 100 mL aliquots and freeze them. The thawed aliquot keeps 2-3 months at 4 degrees, until it turns yellow. Bubble with carbogen at least 10-15 minutes before use, and continuously while in use. | |
| Slice Culture Medium | MEM Eagle medium powder (MilliporeSigma catalog # M4642) | 1680 mg |
| | L-ascorbic acid powder | 36 mg |
| | $CaCl_2$, 2.0M | 100 μL |
| | $MgSO_4$, 2.0M | 200 μL |
| | HEPES, 1.0M | 6.0 mL |
| | Sodium bicarbonate, 893 mM | 3.36 mL |
| | D-(+)-glucose, 1.11M | 2.25 mL |
| | Pen/Strep 100x (5k U/mL) (Thermo catalog # 15070063) | 1.0 mL |
| | Tris base, 1.0M | 260 μL |
| | GlutaMAX 200 mM (Thermo catalog # 35050061) | 0.5 mL |
| | Bovine Pancreas Insulin, 10 mg/mL (MilliporeSigma catalog # I0516) | 20 μL |
| | Heat-inactivated horse serum (Thermo catalog # 26050088) | 40 mL |
| | Deionized water to 250 mL Adjust pH to 7.3-7.4 with HCl, then adjust osmolarity to 300-305. Sterile filter and store refrigerated for up to 1-2 months. | |
| ACSF.1/trehalose | HEPES | 20 mM |
| | Sodium Pyruvate | 3 mM |
| | Taurine | 10 μM |
| | Thiourea | 2 mM |
| | D-(+)-glucose | 25 mM |
| | Myo-inositol | 3 mM |
| | Sodium bicarbonate | 25 mM |
| | Calcium chloride dihydrate | 0.5 mM |
| | Magnesium sulfate | 10 mM |
| | Potassium chloride | 2.5 mM |
| | Monosodium Phosphate | 1.25 mM |
| | Trehalose dihydrate | 132 mM |
| | N-methyl-D-(+)-glucamine | 30 mM |
| | L-ascorbic acid | 5.0 mM |
| | N-acetyl-L-cysteine 1 | 2 mM |
| | Adjust pH to 7.3-7.4 with HCl and adjust osmolarity to 295-305. Sterile filter, and then make 100 mL aliquots and freeze them. The thawed aliquot keeps 2-3 months at 4 degrees, until it turns yellow. | |
| ACSF.1/trehalose + blockers | ACSF.1/trehalose | 50 mL |
| | 100 μM TTX (final 0.1 μM) | 50 μL |
| | 25 mM DL-AP5 (final 50 μM) | 100 μL |
| | 60 mM DNQX (final 20 μM) | 15 μL |
| | 100 mM (+)-MK801 (final 10 μM) | 5 μL |
| ACSF.1/trehalose + blockers + papain | ACSF.1/trehalose + blockers | 15 mL |
| | One vial Worthington PAP2 reagent (150 U, final 10 U/mL) | |
| | 10 kU/mL DNase I (Roche) | 15 μL |
| Low-BSA Quench buffer | ACSF.1/trehalose + blockers | 15 mL |
| | 10 kU/mL DNase I (Roche) | 15 μL |
| | 20% BSA dissolved in water (final conc. 2 mg/mL) | 150 μL |
| | 10 mg/mL ovomucoid inhibitor (Sigma T9253, final conc. 0.1 mg/mL) | 150 μL |

TABLE 3-continued

| Buffer Recipes | | | |
|---|---|---|---|
| High-BSA Quench buffer | ACSF.1/trehalose + blockers | 15 | mL |
| | 10 kU/mL DNase I (Roche) | 15 | μL |
| | 20% BSA dissolved in water (final conc. 10 mg/mL) | 750 | μL |
| | 10 mg/mL ovomucoid inhibitor (Sigma T9253, final conc. 0.1 mg/mL) | 150 | μL |
| ACSF.1/trehalose + EDTA | HEPES | 20 | mM |
| | Sodium Pyruvate | 3 | mM |
| | Taurine | 10 | μM |
| | Thiourea | 2 | mM |
| | D-(+)-glucose | 25 | mM |
| | Myo-inositol | 3 | mM |
| | Sodium bicarbonate | 25 | mM |
| | Potassium chloride | 2.5 | mM |
| | Monosodium Phosphate | 1.25 | mM |
| | Trehalose | 132 | mM |
| | HCl | 2.9 | mM |
| | EDTA | 0.25 | mM |
| | N-methyl-D-(+)-glucamine | 30 | mM |
| | L-ascorbic acid | 5.0 | mM |
| | N-acetyl-L-cysteine | 12 | mM |
| | Adjust pH to 7.3-7.4 with HCl and adjust osmolarity to 295-305. Sterile filter, and then make 100 mL aliquots and freeze them (−20). The thawed aliquot keeps 2-3 months at 4 degrees, until it turns yellow. | | |
| Cell Resuspension Buffer | ACSF.1/trehalose + EDTA | 50 | mL |
| | 100 μM TTX (final 0.1 μM) | 50 | μL |
| | 25 mM DL-AP5 (final 50 μM) | 100 | μL |
| | 60 mM DNQX (final 20 μM) | 15 | μL |
| | 100 mM (+)-MK801 (final 10 μM) | 5 | μL |
| | 20% BSA dissolved in water (final conc. 2 mg/mL) | 150 | μL |
| | 4'-diamino-phenylindazole (DAPI) | 1 | μg/mL |

(ix) CLOSING PARAGRAPHS

Variants of the sequences disclosed and referenced herein are also included. Guidance in determining which amino acid residues can be substituted, inserted, or deleted without abolishing biological activity can be found using computer programs well known in the art, such as DNASTAR™ (Madison, Wisconsin) software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains.

In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. *Molecular Biology of the Gene,* 4th Edition, 1987, The Benjamin/Cummings Pub. Co., p. 224). Naturally occurring amino acids are generally divided into conservative substitution families as follows: Group 1: Alanine (Ala), Glycine (Gly), Serine (Ser), and Threonine (Thr); Group 2: (acidic): Aspartic acid (Asp), and Glutamic acid (Glu); Group 3: (acidic; also classified as polar, negatively charged residues and their amides): Asparagine (Asn), Glutamine (Gin), Asp, and Glu; Group 4: Gln and Asn; Group 5: (basic; also classified as polar, positively charged residues): Arginine (Arg), Lysine (Lys), and Histidine (His); Group 6 (large aliphatic, nonpolar residues): Isoleucine (Ile), Leucine (Leu), Methionine (Met), Valine (Val) and Cysteine (Cys); Group 7 (uncharged polar): Tyrosine (Tyr), Gly, Asn, Gln, Cys, Ser, and Thr; Group 8 (large aromatic residues): Phenylalanine (Phe), Tryptophan (Trp), and Tyr; Group 9 (non-polar): Proline (Pro), Ala, Val, Leu, Ile, Phe, Met, and Trp; Group 11 (aliphatic): Gly, Ala, Val, Leu, and Ile; Group 10 (small aliphatic, nonpolar or slightly polar residues): Ala, Ser, Thr, Pro, and Gly; and Group 12 (sulfur-containing): Met and Cys. Additional information can be found in Creighton (1984) Proteins, W.H. Freeman and Company.

In making such changes, the hydropathic index of amino acids may be considered. The importance of the hydropathic amino acid index in conferring interactive biologic function on a protein is generally understood in the art (Kyte and Doolittle, 1982, J. Mol. Biol. 157(1), 105-32). Each amino acid has been assigned a hydropathic index on the basis of its hydrophobicity and charge characteristics (Kyte and Doolittle, 1982). These values are: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glutamate (−3.5); Gln (−3.5); aspartate (−3.5); Asn (−3.5); Lys (−3.9); and Arg (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity.

As detailed in U.S. Pat. No. 4,554,101, the following hydrophilicity values have been assigned to amino acid residues: Arg (+3.0); Lys (+3.0); aspartate (+3.0±1); glutamate (+3.0±1); Ser (+0.3); Asn (+0.2); Gln (+0.2); Gly (0); Thr (−0.4); Pro (−0.5±1); Ala (−0.5); His (−0.5); Cys (−1.0); Met (−1.3); Val (−1.5); Leu (−1.8); Ile (−1.8); Tyr (−2.3); Phe (−2.5); Trp (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions may be based on the relative similarity of the amino acid side-chain substituents, for example, their hydrophobicity, hydrophilicity, charge, size, and the like.

As indicated elsewhere, variants of gene sequences can include codon optimized variants, sequence polymorphisms, splice variants, and/or mutations that do not affect the function of an encoded product to a statistically-significant degree.

Variants of the protein, nucleic acid, and gene sequences disclosed herein also include sequences with at least 70% sequence identity, 80% sequence identity, 85% sequence, 90% sequence identity, 95% sequence identity, 96% sequence identity, 97% sequence identity, 98% sequence identity, or 99% sequence identity to the protein, nucleic acid, or gene sequences disclosed herein.

"% sequence identity" refers to a relationship between two or more sequences, as determined by comparing the sequences. In the art, "identity" also means the degree of sequence relatedness between protein, nucleic acid, or gene sequences as determined by the match between strings of such sequences. "Identity" (often referred to as "similarity") can be readily calculated by known methods, including those described in: Computational Molecular Biology (Lesk, A. M., ed.) Oxford University Press, N Y (1988); Biocomputing: Informatics and Genome Projects (Smith, D. W., ed.) Academic Press, N Y (1994); Computer Analysis of Sequence Data, Part I (Griffin, A. M., and Griffin, H. G., eds.) Humana Press, N J (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR, Inc., Madison, Wisconsin). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wisconsin); BLASTP, BLASTN, BLASTX (Altschul, et al., J. Mol. Biol. 215:403-410 (1990); DNASTAR (DNASTAR, Inc., Madison, Wisconsin); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y. Within the context of this disclosure it will be understood that where sequence analysis software is used for analysis, the results of the analysis are based on the "default values" of the program referenced. As used herein "default values" will mean any set of values or parameters, which originally load with the software when first initialized.

Variants also include nucleic acid molecules that hybridizes under stringent hybridization conditions to a sequence disclosed herein and provide the same function as the reference sequence. Exemplary stringent hybridization conditions include an overnight incubation at 42° C. in a solution including 50% formamide, 5×SSC (750 mM NaCl, 75 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at 50° C. Changes in the stringency of hybridization and signal detection are primarily accomplished through the manipulation of formamide concentration (lower percentages of formamide result in lowered stringency); salt conditions, or temperature. For example, moderately high stringency conditions include an overnight incubation at 37° C. in a solution including 6×SSPE (20×SSPE=3M NaCl; 0.2M $NaH_2PO_4$; 0.02M EDTA, pH 7.4), 0.5% SDS, 30% formamide, 100 μg/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC). Variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

The term concatenate is broadly used to describe linking together into a chain or series. It is used to describe the linking together of nucleotide or amino acid sequences into a single nucleotide or amino acid sequence, respectively. The term "concatamerize" should be interpreted to recite: "concatenate."

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically significant reduction in selective expression in the targeted cell population as determined by scRNA-Seq and the selected artificial expression construct/targeted cell population pairing.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

What is claimed is:

1. An artificial expression construct comprising
(i) an enhancer consisting of
the sequence of SEQ ID NO: 29,
the sequence of SEQ ID NO: 177,
the sequence of SEQ ID NO: 178,
the sequence of SEQ ID NO: 188,
the sequence of SEQ ID NO: 25,
the sequence of SEQ ID NO: 26,
the sequence of SEQ ID NO: 27,
the sequence of SEQ ID NO: 28,
the sequence of SEQ ID NO: 31,
the sequence of SEQ ID NO: 32,
the sequence of SEQ ID NO: 33,
the sequence of SEQ ID NO: 34,
the sequence of SEQ ID NO: 35,
the sequence of SEQ ID NO: 36,
the sequence of SEQ ID NO: 37,
the sequence of SEQ ID NO: 38,
the sequence of SEQ ID NO: 39,
the sequence of SEQ ID NO: 41,
the sequence of SEQ ID NO: 42,
the sequence of SEQ ID NO: 43,
the sequence of SEQ ID NO: 44,
the sequence of SEQ ID NO: 45,
the sequence of SEQ ID NO: 46,
the sequence of SEQ ID NO: 47,
the sequence of SEQ ID NO: 48,
the sequence of SEQ ID NO: 50,
the sequence of SEQ ID NO: 51,
a sequence having at least 95% sequence identity to the sequence consisting of SEQ ID NO: 29,
a sequence having at least 95% sequence identity to the sequence consisting of SEQ ID NO: 177,
a sequence having at least 95% sequence identity to the sequence consisting of SEQ ID NO: 178,
a sequence having at least 95% sequence identity with the sequence consisting of SEQ ID NO: 188,
a sequence having at least 95% sequence identity with the sequence consisting of SEQ ID NO: 25,
a sequence having at least 95% sequence identity with the sequence consisting of SEQ ID NO: 26,
a sequence having at least 95% sequence identity with the sequence consisting of SEQ ID NO: 27,
a sequence having at least 95% sequence identity with the sequence consisting of SEQ ID NO: 28,
a sequence having at least 95% sequence identity with the sequence consisting of SEQ ID NO: 31,
a sequence having at least 95% sequence identity with the sequence consisting of SEQ ID NO: 32,
a sequence having at least 95% sequence identity with the sequence consisting of SEQ ID NO: 33,
a sequence having at least 95% sequence identity with the sequence consisting of SEQ ID NO: 34,
a sequence having at least 95% sequence identity with the sequence consisting of SEQ ID NO: 35,
a sequence having at least 95% sequence identity with the sequence consisting of SEQ ID NO: 36,
a sequence having at least 95% sequence identity with the sequence consisting of SEQ ID NO: 37,
a sequence having at least 95% sequence identity with the sequence consisting of SEQ ID NO: 38,
a sequence having at least 95% sequence identity with the sequence consisting of SEQ ID NO: 39,
a sequence having at least 95% sequence identity with the sequence consisting of SEQ ID NO: 41,
a sequence having at least 95% sequence identity with the sequence consisting of SEQ ID NO: 42,
a sequence having at least 95% sequence identity with the sequence consisting of SEQ ID NO: 43,
a sequence having at least 95% sequence identity with the sequence consisting of SEQ ID NO: 44,
a sequence having at least 95% sequence identity with the sequence consisting of SEQ ID NO: 45,
a sequence having at least 95% sequence identity with the sequence consisting of SEQ ID NO: 46,
a sequence having at least 95% sequence identity with the sequence consisting of SEQ ID NO: 47,
a sequence having at least 95% sequence identity with the sequence consisting of SEQ ID NO: 48,
a sequence having at least 95% sequence identity with the sequence consisting of SEQ ID NO: 50, or
a sequence having at least 95% sequence identity with the sequence consisting of SEQ ID NO: 51,
(ii) a promoter, and
(iii) a coding sequence.

2. The artificial expression construct of claim 1, wherein the artificial expression construct comprises
three copies of the enhancer consisting of SEQ ID NO: 29,
three copies of the enhancer consisting of SEQ ID NO: 177,
three copies of the enhancer consisting of SEQ ID NO: 178,
three copies of the enhancer having at least 95% sequence identity to the sequence consisting of SEQ ID NO: 29,
three copies of the enhancer having at least 95% sequence identity to the sequence consisting of SEQ ID NO: 177, or
three copies of the enhancer having at least 95% sequence identity to the sequence consisting of SEQ ID NO: 178.

3. The artificial expression construct of claim 1, wherein the enhancer comprises
the sequence of SEQ ID NO: 30,
the sequence of SEQ ID NO: 40,
the sequence of SEQ ID NO: 49,
a sequence having at least 95% sequence identity to the sequence of SEQ ID NO: 30,
a sequence having at least 95% sequence identity to the sequence of SEQ ID NO: 40, or
a sequence having at least 95% sequence identity to the sequence of SEQ ID NO: 49.

4. The artificial expression construct of claim 1, wherein the artificial expression construct comprises 2, 3, 4, 5, 6, 7, 8, 9, or 10 copies of a sequence having at least 95% sequence identity to the sequence of SEQ ID NO: 29, SEQ ID NO: 177, SEQ ID NO: 178, SEQ ID NO: 188, SEQ ID NO: 25, SEQ ID NO: 26, SEQ ID NO: 27, SEQ ID NO: 28, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 50, or SEQ ID NO: 51.

5. The artificial expression construct of claim 1, wherein the artificial expression construct comprises 2, 3, 4, 5, 6, 7, 8, 9, or 10 copies of the sequence of SEQ ID NO: 29, SEQ ID NO: 177, SEQ ID NO: 178, SEQ ID NO: 188, SEQ ID NO: 25, SEQ ID NO: 26, SEQ ID NO: 27, SEQ ID NO: 28, SEQ ID NO: 31, SEQ ID NO: 32, SEQ ID NO: 33, SEQ ID NO: 34, SEQ ID NO: 35, SEQ ID NO: 36, SEQ ID NO: 37, SEQ ID NO: 38, SEQ ID NO: 39, SEQ ID NO: 41, SEQ ID NO: 42, SEQ ID NO: 43, SEQ ID NO: 44, SEQ ID NO: 45, SEQ ID NO: 46, SEQ ID NO: 47, SEQ ID NO: 48, SEQ ID NO: 50, or SEQ ID NO: 51.

6. The artificial expression construct of claim 1, wherein the coding sequence encodes an effector element or an expressible element.

7. The artificial expression construct of claim 6, wherein the effector element comprises a reporter protein or a functional molecule.

8. The artificial expression construct of claim 7, wherein the reporter protein comprises a fluorescent protein.

9. The artificial expression construct of claim 7, wherein the functional molecule comprises a functional ion transporter, enzyme, transcription factor, receptor, membrane protein, cellular trafficking protein, signaling molecule, neurotransmitter, calcium reporter, channel rhodopsin, CRISPR/Cas molecule, editase, guide RNA molecule, homologous recombination donor cassette, or a designer receptor exclusively activated by designer drug (DREADD).

10. The artificial expression construct of claim 1, wherein the artificial expression construct is associated with a capsid that crosses the blood brain barrier.

11. The artificial expression construct of claim 10, wherein the capsid comprises PHP.eB, AAV-BR1, AAV-PHP.S, AAV-PHP.B, AAV-PPS, AAV9, or AAVrh.10.

12. The artificial expression construct of claim 1, wherein the expression construct comprises or encodes a skipping element.

13. The artificial expression construct of claim 12, wherein the skipping element comprises a 2A peptide and/or an internal ribosome entry site (IRES).

14. The artificial expression construct of claim 13, wherein the 2A peptide is selected from T2A, P2A, E2A, or F2A.

15. The artificial expression construct of claim 1, wherein the artificial expression construct is within a viral vector.

16. The artificial expression construct of claim 15, wherein the viral vector comprises a recombinant adeno-associated viral (AAV) vector.

17. The artificial expression construct of claim 16, wherein the AAV vector is replication-competent.

18. The artificial expression construct of claim 1, comprising a sequence having 95% sequence identity to the sequence of SEQ ID NO: 73, SEQ ID NO: 179, SEQ ID NO: 78, SEQ ID NO: 77, SEQ ID NO: 79, SEQ ID NO: 76, SEQ ID NO: 74, SEQ ID NO: 75, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 105, SEQ ID NO: 109, SEQ ID NO: 100, SEQ ID NO: 102, SEQ ID NO: 106, SEQ ID NO: 103, SEQ ID NO: 104, SEQ ID NO: 108, SEQ ID NO: 101, SEQ ID NO: 107, SEQ ID NO: 110, SEQ ID NO: 111, SEQ ID NO: 113, SEQ ID NO: 114, or SEQ ID NO: 112.

19. The artificial expression construct of claim 1, comprising the sequence of SEQ ID NO: 73, SEQ ID NO: 179, SEQ ID NO: 78, SEQ ID NO: 77, SEQ ID NO: 79, SEQ ID NO: 76, SEQ ID NO: 74, SEQ ID NO: 75, SEQ ID NO: 80, SEQ ID NO: 81, SEQ ID NO: 82, SEQ ID NO: 83, SEQ ID NO: 84, SEQ ID NO: 85, SEQ ID NO: 86, SEQ ID NO: 87, SEQ ID NO: 88, SEQ ID NO: 89, SEQ ID NO: 90, SEQ ID NO: 91, SEQ ID NO: 92, SEQ ID NO: 93, SEQ ID NO: 94, SEQ ID NO: 95, SEQ ID NO: 96, SEQ ID NO: 97, SEQ ID NO: 98, SEQ ID NO: 99, SEQ ID NO: 105, SEQ ID NO: 109, SEQ ID NO: 100, SEQ ID NO: 102, SEQ ID NO: 106, SEQ ID NO: 103, SEQ ID NO: 104, SEQ ID NO: 108, SEQ ID NO: 101, SEQ ID NO: 107, SEQ ID NO: 110, SEQ ID NO: 111, SEQ ID NO: 113, SEQ ID NO: 114, or SEQ ID NO: 112.

* * * * *